US009771420B2

(12) United States Patent
Ceska et al.

(10) Patent No.: US 9,771,420 B2
(45) Date of Patent: *Sep. 26, 2017

(54) METHODS OF TREATING AN IL-17A MEDIATED PATHOLOGICAL CONDITION

(71) Applicant: UCB BIOPHARMA SPRL, Brussels (BE)

(72) Inventors: Thomas Allen Ceska, Berkshire (GB); Alistar James Henry, Berkshire (GB); Jiye Shi, Rochester, NY (US)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/695,677

(22) Filed: Jun. 29, 2015

(65) Prior Publication Data

US 2015/0315272 A1    Nov. 5, 2015

Related U.S. Application Data

(63) Continuation of application No. 14/173,613, filed on Feb. 5, 2014, now Pat. No. 9,045,537, which is a continuation of application No. 12/989,373, filed as application No. PCT/GB2009/001026 on Apr. 22, 2009, now Pat. No. 8,679,494.

(30) Foreign Application Priority Data

Apr. 23, 2008 (GB) .................... 0807413.0

(51) Int. Cl.
*A61K 39/395* (2006.01)
*C07K 16/24* (2006.01)
*C07K 14/54* (2006.01)

(52) U.S. Cl.
CPC ............ *C07K 16/244* (2013.01); *C07K 14/54* (2013.01); *C07K 2299/00* (2013.01); *C07K 2317/24* (2013.01); *C07K 2317/31* (2013.01); *C07K 2317/34* (2013.01); *C07K 2317/54* (2013.01); *C07K 2317/55* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 8,303,953 | B2 | 11/2012 | Adams et al. |
| 2007/0009959 | A1 | 1/2007 | Lawson et al. |
| 2007/0160576 | A1 | 7/2007 | Arnott et al. |
| 2008/0044423 | A1 | 2/2008 | Cochrane et al. |
| 2008/0181888 | A1 | 7/2008 | Ambrose et al. |

FOREIGN PATENT DOCUMENTS

| WO | WO 00/69463 A1 | 11/2000 |
| WO | 2004106377 | 12/2004 |
| WO | WO 2004/016377 A1 | 12/2004 |
| WO | WO 2005/010044 A2 | 2/2005 |
| WO | 2005051422 | 6/2005 |
| WO | 2006013107 | 2/2006 |
| WO | WO 2006/054059 A1 | 5/2006 |
| WO | WO 2006/088833 A2 | 8/2006 |
| WO | WO 2007070750 | 6/2007 |
| WO | WO 2007106769 | 9/2007 |
| WO | WO 2007149032 | 12/2007 |
| WO | WO 2008001063 | 1/2008 |
| WO | WO 2008021156 | 2/2008 |
| WO | WO 2008047134 | 4/2008 |

OTHER PUBLICATIONS

Matsuzaki et al. Interleukin-17 as an effector molecule of innate and acquired immunity against infections. Microbiol Immunol., 2007; 51(12):1139-47.*
Benchetrit et al. Interleukin-17 inhibits tumor cell growth by means of a T-cell-dependent mechanism. Blood, Mar. 15, 2002, vol. 99, No. 6, pp. 2114-2121.*
Muranski et al. Tumor-specific Th17-polarized cells eradicate large established melanoma. Blood, 2008, 112: 362-373.*
Wróbel et al. Interleukin-17 in acute myeloid leukemia. J Cell Mol Med. Oct.-Dec. 2003;7(4):472-4.*
Fan et al. The prevalence of Th17 cells in patients with acute myeloid leukemia. Zhonghua Xue Ye Xue Za Zhi. Sep. 2010;31(9):617-620 (abstrac).*
Anti-human IL-17 Antibody, R& D Systems, Aug. 28, 2007, retrieved from internet: http://www.mdsystems, com/pdf/af317na. pdf on Mar. 27, 2008.
Boder, et al., "Direct evolution of antibody fragments with monvalent femtomolar antigen-binding affinity", Proceedings of The National Academy of Sciences of USA, vol. 97, No. 20, Sep. 26, 2000, pp. 10701-10705.
Burchill, et al., "Inhibition of interleukin-17 prevents the development of arthritis in vaccinated mice challenged with Borrelia burgdorferi", Infection and Immunity, vol. 71, No. 6, Jun. 2003, pp. 3437-3442.
Chabaud, M. et al., "Contribution of Interleukin 17 to Synovium Matrix Destruction in Rheumatoid Arthritis", Cytokine, Academic Press Ltd., vol. 12, No. 7, Jul. 2000, pp. 1092-1099.
Doo, et al., "CD4+ T cells regulate surgical and postinfection adhesion formation", The Journal of Experimental Medicine, Jun. 3, 2002, vol. 195, No. 11, Jun. 3, 2002, pp. 1471-1478.

(Continued)

*Primary Examiner* — Dong Jiang

(74) *Attorney, Agent, or Firm* — Marshall, Gerstein & Borun LLP

(57) ABSTRACT

The present invention relates neutralizing epitopes of IL-17A and IL-17F and antibodies which bind those epitopes. The present invention also relates to the therapeutic uses of the antibody molecules and methods for producing them.

7 Claims, 5 Drawing Sheets

(56) References Cited

OTHER PUBLICATIONS

Figure 2A:
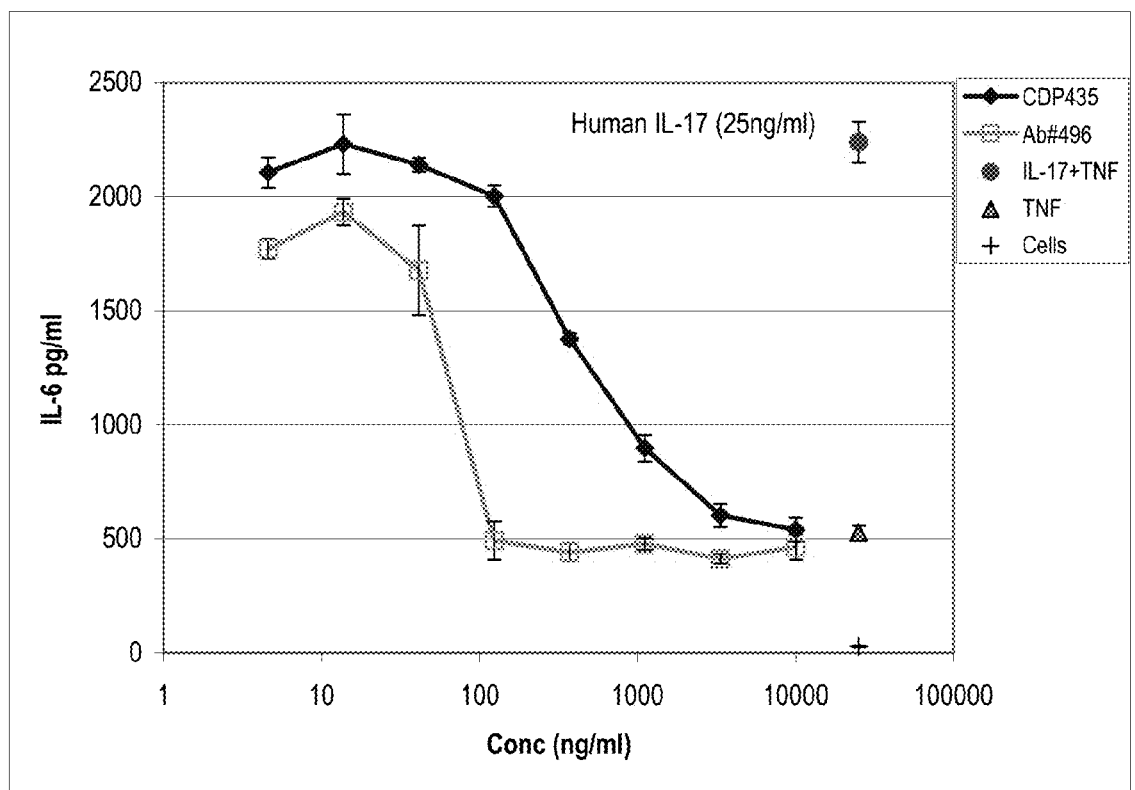

Davies, Julian, Affinity Improvement of Single Antibody VH Domains: Residues in All Three Hypervariable Regions Affect Antigen Binding, Sep. 1996, pp. 169-179, vol. 2, No. 3.

Dumont, F. J., "IL-17 cytokine/receptor families: Emerging targets for the modulation of inflammatory responses", Expert Opinion of Therapeutic Patents, Ashley Publications, GB vol. 13, No. 3, Mar. 1, 2003, pp. 287-3030.

Hellings, et al., "Interleukin-17 orchestrates the granulocyte influx into airways after allergen inhalation in a mouse model of allergic asthma", American Journal of Respiratory Cell and Molecular biology, vol. 28, No. 1, Jan. 2003, pp. 42-50.

Holt, Lucy J.: Domain Antibodies: Proteins for Therapy, Trends in Biotechnology, Nov. 2003, pp. 484-490, vol. 21, No. 11.

Kotake et al., "IL-17 in synovial fluids from patients with rheumatoid arthritis is a potent stimulator of osteoclastogenesis," The Journal of Clincial Investigation, 103(9):1345-1352 (May 1999).

Numasaki, et al., "Interleukin-17 promotes angiogenesis and tumor growth", Blood, vol. 101, No. 7, Apr. 1, 2003, pp. 2620-2627.

Pascalis, et al., "Grafting of 'abbreviated' complementary-determining regions containing specificity determining residues essential for ligand contact to engineer a less immunogenic hmanized monoclonal antibody", J. Immunol., 2002, 169:3076-3084.

Paul, "Fv Structure and Diversity in Three Dimensions", Fundamental Immunology, 3rd Edition, 1993, pp. 292-295.

R&D Systems: "Monoclonal Anti-Human IL-17 Antibody", Announcement R&D Systems, Jan. 11, 2004, pp. 1-2.

Thompson, et al., "Affinity maturation of a high-affinity human monoclonal antibody against the third hypervariable loop of human immunodeficiency virus: use of phage display to improve affiinity and broaden strain reactivity", Journal of Molecular Biology, vol. 256, No. 1, Feb. 16, 1996, pp. 77-88.

Vandamme et al.: Construction and characterization of a recombinant murine monocional antibody directed against human fibrin fragment-D dimer., J. Biochem. (1990) vol. 192, pp. 767-775.

PCT International Search Report of PCT International Application PCT/GB2007/003983 filed Oct. 18, 2007.

PCT International Search Report of PCT International Application PCT/GB2005/004392, dated Feb. 14, 2006.

PCT International Search Report of PCT International Application PCT/GB2009/001026, dated Apr. 22, 2009.

* cited by examiner

Figure 1

(a) Light Chain variable region of antibody CA028_496 (SEQ ID NO:7)
AIQLTQSPSSLSASVGDRVTITCRADESVTTLMHWYQQKPGKAPKLLIYLVSNRESGVPSRF
SGSGSGTDFTLTISSLQPEDFATYYCQQTWSDPWTFGQGTKVEIKR (b) Heavy Chain variable region of antibody CA028_496 (SEQ ID NO:9)
EVQLVESGGGLVQPGGSLRLSCAASGFTFSDYNMAWVRQAPGKGLEWVATITYEGRNTYYRD
SVKGRFTISRDNAKNSLYLQMNSLRAEDTAVYYCASPPQYYEGSIYRLWFAHWGQGTLVTVS
S (c)

| | |
|---|---|
| CDRH1: | GFTFSDYNMA (SEQ ID NO:1) |
| CDRH2: | TITYEGRNTYYRDSVKG (SEQ ID NO:2) |
| CDRH3: | PPQYYEGSIYRLWFAH (SEQ ID NO:3) |
| CDRL1: | RADESVTTLMH (SEQ ID NO:4) |
| CDRL2: | LVSNRES (SEQ ID NO:5) |
| CDRL3: | QQTWSDPWT (SEQ ID NO:6) |

(d) Light chain of antibody CA028_496 (SEQ ID NO:11)
AIQLTQSPSSLSASVGDRVTITCRADESVTTLMHWYQQKPGKAPKLLIYLVSNRESGVPSRF
SGSGSGTDFTLTISSLQPEDFATYYCQQTWSDPWTFGQGTKVEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC (e) Heavy chain of antibody CA028_496 (SEQ ID NO:15)
EVQLVESGGGLVQPGGSLRLSCAASGFTFSDYNMAWVRQAPGKGLEWVATITYEGRNTYYRD
SVKGRFTISRDNAKNSLYLQMNSLRAEDTAVYYCASPPQYYEGSIYRLWFAHWGQGTLVTVS
SASTKGPSVFPLAPCSRSTSESTAALGCLVKDYFPEPVTVSWNSGALTSGVHTFPAVLQSSG
LYSLSSVVTVPSSSLGTKTYTCNVDHKPSNTKVDKRVESKYGPPCPPCPAPEFLGGPSVFLF
PPKPKDTLMISRTPEVTCVVVDVSQEDPEVQFNWYVDGVEVHNAKTKPREEQFNSTYRVVSV
LTVLHQDWLNGKEYKCKVSNKGLPSSIEKTISKAKGQPREPQVYTLPPSQEEMTKNQVSLTC
LVKGFYPSDIAVEWESNGQPENNYKTTPPVLDSDGSFFLYSRLTVDKSRWQEGNVFSCSVMH
EALHNHYTQKSLSLSLGK (f) DNA encoding light chain of antibody CA028_496 including signal sequence (SEQ ID NO:14)
atgtcagttcccacacaggtgctgggcctgcttctgttgtggctcaccgatgctaggtgtgc
catccagctgacccagagcccttcctctctcagcgccagtgtcggagacagagtgactatta
cctgcagggctgacgaaagcgtgaccacattgatgcactggtaccaacagaagcctggcaaa
gcccccaagctcctgatctatctggtttccaatcgggagtctggagtccccagcaggttcag
cggcagtgggtctggaactgactttaccctgacaatctcctcactccagcccgaagatttcg
ccacctactattgccagcagacttggagcgaccttggacatttggacagggcacaaaagtg
gagatcaagcgtacggtagcggccccatctgtcttcatcttcccgccatctgatgagcagtt
gaaatctggaactgcctctgttgtgtgcctgctgaataacttctatcccagagaggccaaag

Figure 1 continued tacagtggaaggtggataacgccctccaatcgggtaactcccaggagagtgtcacagagcag
gacagcaaggacagcacctacagcctcagcagcaccctgacgctgagcaaagcagactacga gaaacacaaagtctacgcctgcgaagtcacccatcagggcctgagctcgcccgtcacaaaga
gcttcaacaggggagagtgttag (g) DNA encoding heavy chain of antibody CA028_496 including signal sequence (SEQ ID NO:18)
atggaatggtcctgggtcttcctgttttttcctttctgtcacaaccggggtgcacagcgaggt
tcagctcgttgaatccggaggcggactcgtgcagcctgggggctccttgcggctgagctgcg
ctgccagtggcttcactttcagcgattacaatatggcctgggtgcgccaggccccaggcaag
ggtctggagtgggtggccacaattacctatgagggcagaaacacttattaccgggattcagt
gaaagggcgatttaccatcagcagggataatgcaaagaacagtctgtacctgcagatgaact
ctctgagagctgaggacaccgctgtctactattgtgcaagcccacccagtactatgagggc
tcaatctacagattgtggtttgcccattggggccagggaacactggtgaccgtctcgagcgc
ttctacaaagggcccatccgtcttccccctggcgccctgctccaggagcacctccgagagca
cagccgccctgggctgcctggtcaaggactacttccccgaaccggtgacggtgtcgtggaac
tcaggcgccctgaccagcggcgtgcacaccttcccggctgtcctacagtcctcaggactcta
ctccctcagcagcgtggtgaccgtgccctccagcagcttgggcacgaagacctacacctgca
acgtagatcacaagcccagcaacaccaaggtggacaagagagttggtgagaggccagcacag
ggagggagggtgtctgctggaagccaggctcagccctcctgcctggacgcacccggctgtg
cagccccagcccagggcagcaaggcatgccccatctgtctcctcaccggaggcctctgacc
accccactcatgcccagggagagggtcttctggattttccaccaggctccgggcagccaca
ggctggatgcccctaccccaggccctgcgcatacaggggcaggtgctgcgctcagacctgcc
aagagccatatccgggaggaccctgcccctgacctaagccacccaaaggccaaactctcc
actccctcagctcagacaccttctctcctcccagatctgagtaactcccaatcttctctctg
cagagtccaaatatggtcccccatgccaccatgcccaggtaagccaacccaggcctcgccc
tccagctcaaggcgggacaggtgccctagagtagcctgcatccagggacaggccccagccgg
gtgctgacgcatccacctccatctcttcctcagcacctgagttcctggggggaccatcagtc
ttcctgttccccccaaaacccaaggacactctcatgatctcccggacccctgaggtcacgtg
cgtggtggtggacgtgagccaggaagaccccgaggtccagttcaactggtacgtggatggcg
tggaggtgcataatgccaagacaaagccgcgggaggagcagttcaacagcacgtaccgtgtg
gtcagcgtcctcaccgtcctgcaccaggactggctgaacggcaaggagtacaagtgcaaggt
ctccaacaaaggcctcccgtcctccatcgagaaaaccatctccaaagccaaaggtgggaccc
acggggtgcgagggccacatggacagaggtcagctcggcccaccctctgccctgggagtgac
cgctgtgccaacctctgtccctacagggcagccccgagagccacaggtgtacaccctgcccc
catcccaggaggagatgaccaagaaccaggtcagcctgacctgcctggtcaaaggcttctac
cccagcgacatcgccgtggagtgggagagcaatgggcagccggagaacaactacaagaccac
gcctcccgtgctggactccgacggctccttcttcctctacagcaggctaaccgtggacaaga
gcaggtggcaggaggggaatgtcttctcatgctccgtgatgcatgaggctctgcacaaccac
tacacacagaagagcctctccctgtctctgggtaaa

Figure 1 continued (h) Human IL-17A (SEQ ID NO:21)

GITIPRNPGCPNSEDKNFPRTVMVNLNIHNRNTNTNPKRSSDYYNRSTSPWNLHRNEDPERY
PSVIWEAKCRHLGCINADGNVDYHMNSVPIQQEILVLRREPPHCPNSFRLEKILVSVGCTCV
TPIVHHVA (i) Human IL-17F (SEQ ID NO:22)

RKIPKVGHTFFQKPESCPPVPGGSMKLDIGIINENQRVSMSRNIESRSTSPWNYTVTWDPNR
YPSEVVQAQCRNLGCINAQGKEDISMNSVPIQQETLVVRRKHQGCSVSFQLEKVLVTVGCTC
VTPVIHHVQ

METHODS OF TREATING AN IL-17A MEDIATED PATHOLOGICAL CONDITION

The present invention relates to neutralising epitopes of IL-17A and IL-17F and antibodies which bind those epitopes. The present invention also relates to the therapeutic uses of the antibody molecules and methods for producing them.

Interleukin 17 (IL-17), also known as CTLA-8 or IL-17A, is a pro-inflammatory cytokine which stimulates the secretion of a wide range of other cytokines from various non-immune cells. IL-17A is capable of inducing the secretion of IL-6, IL-8, PGE2, MCP-1 and G-CSF by adherent cells like fibroblasts, keratinocytes, epithelial and endothelial cells and is also able to induce ICAM-1 surface expression, proliferation of T cells, and growth and differentiation of CD34+ human progenitors into neutrophils when cocultured in the presence of irradiated fibroblasts (Fossiez et al., 1998, Int. Rev. Immunol. 16, 541-551). IL-17A is predominantly produced by activated memory T cells and acts by binding to a ubiquitously distributed cell surface receptor (IL-17R) (Yao et al., 1997, Cytokine, 9, 794-800). It may also act through binding to a complex of IL-17RA and IL-17RC (Toy et al., 2006, J. Immunol. 177(11); 36-39). IL-17 producing T cells called 'TH17 cells' have been implicated in the pathogenesis of certain cancers (Weaver et al., 2006, Immunity, 24, 677-688; Langowski et al., 2006, 442, 461-465; Iwakura and Ishigame, 2006, J. Clin. Invest. 116, 5, 1218-1222).

A number of homologues of IL-17 have been identified which have both similar and distinct roles in regulating inflammatory responses. For a review of IL-17 cytokine/receptor families see Dumont, 2003, Expert Opin. Ther. Patents, 13, 287-303. One such homologue is IL-17F, also known as IL-24 and ML-1, which is around 55% identical to IL-17A and is thought to share the same receptors as IL-17A (Kolls and Linden 2004, Immunity, 21, 467-476; Hymowitz, et al., 2001, EMBO J. 20(19), 5332-5341; Kuestner et al., 2007, Journal of Immunology, 179, 5462-5473).

Both IL-17A and IL-17F can form both homodimeric and heterodimeric proteins, all of which are produced by activated human CD4+ T cells (Wright et al., 2007, J Biol Chem. 282 (18), 13447-13455).

IL-17 may contribute to a number of diseases mediated by abnormal immune responses, such as rheumatoid arthritis and air-way inflammation, as well as organ transplant rejection and antitumour immunity. Inhibitors of IL-17 activity are well known in the art for example a murine IL-17R: human Fc fusion protein, a murine soluble IL-17R and an anti-IL-17 monoclonal antibody have been used to demonstrate the role of IL-17 in various models of rheumatoid arthritis (Lubberts et al., J. Immunol. 2001, 167, 1004-1013; Chabaud et al., Arthritis Res. 2001, 3, 168-177). In addition, neutralising polyclonal antibodies have been used to reduce peritoneal adhesion formation (Chung et al., 2002, J. Exp. Med., 195, 1471-1478). Rat derived anti-human IL-17A antibodies were described in WO04/106377. A humanised anti-IL-17A antibody with an affinity of around 220 pM was described in WO2006/054059. A monoclonal anti-IL-17A fully human antibody with an affinity of around 188 pM was described in WO2006/013107.

International patent application WO2008/001063 describes a high affinity neutralising anti-IL-17A antibody, CA048_497. Other neutralising antibodies which bind IL-17A have been described in WO2007/070750 and WO2007/149032.

Antibodies which bind IL-17F and IL-17A/IL-17F heterodimers were described in WO2006/088833. Antibodies which specifically bind the IL-17A/IL-17F heterodimer were described in WO2005/010044.

IL-17F antagonism has been associated with protection against asthma (Kawaguchi et al., 2006, J. Allergy Clin. Immunol. 117(4); 795-801) and IL-17F is also thought to play a role in arthritis pathology (Lubberts 2003, Current Opinion in Investigational Drugs, 4 (5), 572-577).

Accordingly dual antagonists of IL-17A and IL-17F may be more effective than a sole antagonist in treating IL-17 mediated diseases. Antibodies which bind IL-17A and IL-17F were described in WO2007/106769. International patent application PCT/GB2007/003983 (international filing date 18 Oct. 2007) describes a high affinity antibody, CA048496 which binds human IL-17A, IL-17F and IL-17A/F heterodimer, the sequence of which is provided herein below.

The present invention provides novel neutralising epitopes on IL-17A and IL-17F and antibodies which bind to, and/or interact with, those epitopes.

In one embodiment the present invention provides a neutralising epitope of IL-17A which comprises or consists of one or more of the residues, eg. two or more, e.g. three or more, e.g. four or more, selected from the group consisting of TYR44, ASN45, TRP51, ASN52 and ASP84 of human IL-17A (SEQ ID NO:21).

In one embodiment the present invention provides a neutralising epitope of IL-17A which comprises or consists of one or more of the residues selected from the group consisting of SER41, TYR44, ASN45, TRP51, ASN52, HIS54, ARG72, HIS73 and ASP84 of human IL-17A (SEQ ID NO:21).

In one embodiment, the present invention provides a neutralising epitope of IL-17A which comprises or consists of one or more of the residues selected from the group consisting of SER41, TYR44, ASN45, ARG46, TRP51, ASN52, HIS54, ARG72, HIS73, ASP84, HIS86, VAL128, HIS129 and VAL131 of human IL-17A (SEQ ID NO:21).

In one embodiment, the present invention provides a neutralising epitope of IL-17A which comprises one or more of the residues, eg. two or more, e.g. three or more, e.g. four or more selected from the group consisting of TYR44, ASN45, TRP51, ASN52 and ASP84 of human IL-17A (SEQ ID NO:21) and optionally one or more of the residues selected from the group consisting of SER41, ARG46, HIS54, ARG72, HIS73, HIS86, VAL128, HIS129 and VAL131 of human IL-17A (SEQ ID NO:21).

In one embodiment, the present invention provides a neutralising epitope of IL-17A which comprises amino acid residues TYR44, ASN45, TRP51, ASN52 and ASP84 of human IL-17A (SEQ ID NO:21) and optionally one or more of the residues selected from the group consisting of SER41, ARG46, HIS54, ARG72, HIS73, HIS86, VAL128, HIS129 and VAL131 of human IL-17A (SEQ ID NO:21).

In one embodiment, the neutralising epitope provided by the present invention does not comprise one or more of the amino acid residues selected from the group consisting of ASP80, GLY81 and ASN82 of human IL-17A (SEQ ID NO:21).

In one embodiment, the neutralising epitope provided by the present invention does not comprise one or more of the amino acid residues selected from the group consisting of ASP80, GLY81, ASN82 and VAL83 of human IL-17A (SEQ ID NO:21).

The present invention also provides a novel neutralising epitope of human IL-17F (SEQ ID NO:22) which comprises or consists of one or more e.g. three or more, e.g. five or more, e.g. ten or more of the following residues: SER39, MET40, SER41, ARG42, ARG47, ASN53, ARG73, ASN74, LEU75, LYS83, GLU84, ASP85, ILE86, SER87, MET88, ASN89, VAL91, PRO92, GLN94, THR126, PRO127, VAL128.

The present invention also provides a novel neutralising epitope of human IL-17F (SEQ ID NO:22) which comprises or consists of one or more e.g. three or more, e.g. five or more, e.g. ten or more of the following residues: SER39, MET40, SER41, ARG42, ARG47, ASN53, CYS72, ARG73, ASN74, LEU75, LYS83, GLU84, ASP85, ILE86, SER87, MET88, ASN89, SER90, VAL91, PRO92, GLN94, THR119, CYS122, VAL125, THR126, PRO127, VAL128.

In one embodiment the neutralising epitope of human IL-17F (SEQ ID NO:22) comprises or consists of one or more e.g. three or more, e.g. five or more, e.g. ten or more of the following residues: SER39, MET40, SER41, ARG42, ARG47, ASN53, ARG73, ASN74, LEU75, LYS83, GLU84, ASP85, ILE86, SER87, MET88, ASN89, VAL91, PRO92, GLN94, THR126, PRO127, VAL128.

In one embodiment the neutralising epitope of human IL-17F (SEQ ID NO:22) comprises or consists of (or further comprises or further consists of) one or more e.g. three or four of the following residues: GLN71, CYS72, ILE86, ASN89, SER90 and VAL128 for example from a first chain in an IL17f dimer.

In one embodiment the neutralising epitope of human IL-17F (SEQ ID NO:22) comprises or consists of (or further comprises or further consists of) one a residue: ARG47 for example from a second chain in an IL17f dimer.

In one embodiment the neutralising epitope of human IL-17F (SEQ ID NO:22) comprises or consists of one or more e.g. three or more, e.g. five or more, e.g. ten or more of the following residues: GLN71, CYS72, ASN74, LEU75, ILE86, ASN89, SER90, PRO92, VAL128, HIS131 and GLN133 for example from a first chain in an IL17f dimer.

In one embodiment the neutralising epitope of human IL-17F (SEQ ID NO:22) comprises or consists of (or further comprises or further consists of) one or more e.g. three or four of the following residues: ARG37, SER39, SER41 and ARG47 for example from a second chain in an IL17f dimer.

In one embodiment the neutralising epitope of human IL-17F (SEQ ID NO:22) comprises or consists of one or more e.g. three or more, e.g. five or more, e.g. ten or more of the following residues: GLN71, CYS72, ARG73, ASN74, LEU75, ILE86, SER87 ASN89, SER90, VAL91, PRO92, VAL128, HIS131 and GLN133, for example from a first chain in an IL17f dimer.

In one embodiment the neutralising epitope of human IL-17F (SEQ ID NO:22) comprises or consists of (or further comprises or further consists of) one or more e.g. three or four of the following residues: ASN33, GLN36, ARG37, SER39, SER41, ARG42, ILE44 and ARG47 for example from a second chain in an IL17f dimer.

In one embodiment the neutralising epitope of human IL-17F (SEQ ID NO:22) comprises or consists of one or more e.g. three or more, e.g. five or more, e.g. ten or more of the following residues: GLN12, LYS13, SER24, ISO32, ASN33 GLU34, ASN35, GLN36, VAL38, SER46, ASN53, TYR54, GLN69, ISO78, ASP85, SER87, MET88, ASM89, GLN94, LYS103 and THR126.

In one embodiment the neutralising epitope of human IL-17F (SEQ ID NO:22) comprises or consists of one or more e.g. three or more, e.g. five or more, e.g. ten or more of the following residues: GLN12, SER24, ASN33, GLU34, GLN36, VAL38, ASN53, TYR54, ASP85, MET88, ASM89, and THR126.

In one embodiment the neutralising epitope of human IL-17F (SEQ ID NO:22) comprises or consists of one or more e.g. three or four of the following residues: GLN12, SER24, ASN33, GLU34, ASP85 and MET88.

In one embodiment the neutralising epitope of human IL-17F (SEQ ID NO:22) comprises or consists of amino acids V33 to V38 inclusive.

In one embodiment the neutralising epitope of human IL-17F (SEQ ID NO:22) comprises or consists of amino acids V87 to Q94 inclusive.

In one embodiment the neutralising epitope of IL-17F further comprises one or more of the following residues: ILE129, HIS130, H131, V132, Q133.

In one embodiment there is provided one or more neutralising epitope of human IL-17F (SEQ ID NO:22) each independently comprises or consists of amino acids V33 to V38 inclusive and/or V87 to Q94 inclusive.

In one embodiment the epitope is defined as amino acid residues located within 4 Å, 3.5 Å or 3.0 Å of a binding entity, such as an antibody or fragment.

The present invention also provides epitopic fragments of IL-17A that can be used, if required, as an immunogen to obtain neutralising antibodies which bind to the neutralising epitope of IL-17A. For example epitopic fragments comprising one or more of the amino acid residues of IL-17A provided herein above, may be used as an immunogen.

The present invention also provides epitopic fragments of IL-17F that can be used, if required, as an immunogen to obtain neutralising antibodies which bind to the neutralising epitope of IL-17F. For example epitopic fragments comprising one or more of the amino acid residues of IL-17F provided herein above, may be used as an immunogen.

The present invention also provides antibodies which bind to, and/or interact with, a neutralising epitope provided by the present invention. It will be appreciated that an antibody can interact directly or indirectly with an epitope of the present invention, e.g. by direct binding or by allosteric interaction.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus 'CDR-H1', as used herein, comprises residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

In one embodiment the antibodies of the present invention specifically bind to IL-17A. Specifically binding means that the antibodies have a greater affinity for IL-17A polypeptides than for other polypeptides. In one embodiment the antibodies of the present invention specifically bind to IL-17F. Specifically binding means that the antibodies have a greater affinity for IL-17F polypeptides than for other polypeptides. In a preferred embodiment the antibodies of the present invention specifically bind to IL-17A and IL-17F. Specifically binding means that the antibodies have a greater affinity for IL-17A and IL-17F polypeptides (including the IL-17A/IL-17F heterodimer) than for other polypeptides. Preferably the IL-17A and IL-17F polypeptides are human. In one embodiment the antibody also binds cynomolgus IL-17A and/or IL-17F.

Where an antibody of the present invention binds human IL-17A and human IL-17F the antibody is not an antibody comprising the sequence given in SEQ ID NO:1 for CDR-H1, the sequence given in SEQ ID NO:2 for CDR-H2, the sequence given in SEQ ID NO:3 for CDR-H3, the sequence given in SEQ ID NO:4 for CDR-L1, the sequence given in SEQ ID NO:5 for CDR-L2 and the sequence given in SEQ ID NO:6 for CDR-L3.

As used herein, the term 'neutralising antibody' describes an antibody that is capable of neutralising the biological signalling activity of IL-17A and/or IL17F and/or IL-17A/F heterodimer, for example by blocking binding of IL-17A and/or IL17F to one or more of their receptors and by blocking binding of the IL-17A/IL-17F heterodimer to one or more of its receptors. It will be appreciated that the term 'neutralising' as used herein refers to a reduction in biological signalling activity which may be partial or complete. Further, it will be appreciated that the extent of neutralisation of IL-17A and IL-17F activity by an antibody which binds both IL-17A and IL-17F may be the same or different. In one embodiment the extent of neutralisation of the activity of the IL-17A/IL-17F heterodimer may be the same or different as the extent of neutralisation of IL-17A or IL-17F activity.

In one embodiment the invention provides antibodies which bind to, and/or interact with, a neutralising epitope of IL-17A provided by the present invention.

Accordingly, in one embodiment the present invention provides a neutralising antibody which binds human IL-17A that binds to, and/or interacts with, an epitope of human IL-17A comprising or consisting of one or more e.g. two or more or three or more of the residues selected from the group consisting of TYR44, ASN45, TRP51, ASN52 and ASP84 of human IL-17A (SEQ ID NO:21).

In one embodiment the present invention provides a neutralising antibody which binds human IL-17A that binds to an epitope of human IL-17A comprising ASN52 of human IL-17A (SEQ ID NO:21).

In one embodiment the present invention provides a neutralising antibody which binds human IL-17A that binds to an epitope of human IL-17A comprising ASN52 and ASP84 of human IL-17A (SEQ ID NO:21).

In one embodiment, the present invention provides a neutralising antibody which binds human IL-17A that binds to an epitope of human IL-17A which comprises or consists of one or more of the residues selected from the group consisting of SER41, ASN52, ARG72, HIS73 and ASP84 of human IL-17A (SEQ ID NO:21).

In one embodiment, the present invention provides a neutralising antibody which binds human IL-17A that binds to an epitope of human IL-17A which comprises or consists of one or more of the residues selected from the group consisting of SER41, TYR44, ASN45, ARG46, TRP51, ASN52, HIS54, ARG72, HIS73, ASP84, HIS86, VAL128, HIS129 and VAL131 of human IL-17A (SEQ ID NO:21).

In one embodiment an antibody of the present invention does not bind one or more e.g two or more of the amino acid residues selected from the group consisting of ASP80, GLY81 and ASN82 of human IL-17A (SEQ ID NO:21).

In one embodiment an antibody of the present invention does not bind one or more amino acid residues selected from the group consisting of ASP80, GLY81, ASN82 and VAL83 of human IL-17A (SEQ ID NO:21).

In one embodiment an antibody of the present invention does not bind any of the following amino acid residues, ASP80, GLY81 and ASN82 of human IL-17A (SEQ ID NO:21).

In one embodiment the invention provides antibodies which bind to, and/or interact with, a neutralising epitope of IL-17F provided by the present invention.

Accordingly, in one embodiment the present invention provides a neutralising antibody which binds human IL-17F that binds to an epitope of human IL-17F comprising one or more e.g. three or more, e.g. five or more, e.g. ten or more of the following residues: SER39, MET40, SER41, ARG42, ARG47, ASN53, ARG73, ASN74, LEU75, LYS83, GLU84, ASP85, ILE86, SER87, MET88, ASN89, VAL91, PRO92, GLN94, THR126, PRO127, VAL128 of SEQ ID NO:22 (IL-17F).

In one embodiment the present invention provides a neutralising antibody which binds human IL-17F that binds to an epitope of human IL-17F within one or more of the following regions:
(i) 39-42 (SER39, MET40, SER41, ARG42)
(ii) 47 (ARG47)
(iii) 53 (ASN53)
(iv) 72-75 (CYS72, ARG73, ASN74, LEU75)
(v) 83-92 (LYS83, GLU84, ASP85, ILE86, SER87, MET88, ASN89, SER90, VAL91, PRO92)
(vi) 94 (GLN94)
(vii) 119 (THR119)
(viii) 122 (CYS122)
(ix) 125-128 (VAL125, THR126, PRO127, VAL128).

In one embodiment an antibody of the present invention binds human IL-17A and human IL-17F.

In one embodiment an antibody of the present invention binds human IL-17A/F heterodimer.

In one embodiment, an antibody of the present invention binds human IL-17A and human IL-17A/F heterodimer. In one embodiment an antibody of the present invention binds human IL-17F and human IL-17A/F heterodimer. In a preferred embodiment, an antibody of the present invention binds human IL-17A, human IL-17F and human IL-17A/F heterodimer.

Accordingly, in one embodiment the present invention provides a neutralising antibody which binds human IL-17A and human IL-17F that binds to an epitope of human IL-17A comprising one or more of the residues selected from the group consisting of TYR44, ASN45, TRP51, ASN52 and ASP84 of SEQ ID NO:21 (IL-17A) wherein the antibody is not an antibody comprising the sequence given in SEQ ID NO:1 for CDR-H1, the sequence given in SEQ ID NO:2 for CDR-H2, the sequence given in SEQ ID NO:3 for CDR-H3, the sequence given in SEQ ID NO:4 for CDR-L1, the sequence given in SEQ ID NO:5 for CDR-L2 and the sequence given in SEQ ID NO:6 for CDR-L3.

In one embodiment the present invention provides a neutralising antibody which binds human IL-17A and human IL-17F that binds to an epitope of human IL-17A comprising ASN52 and ASP84 of SEQ ID NO:21 (IL-17A) and optionally one or more amino acid residues selected from the group consisting of SER41, TYR44, ASN45, ARG46, TRP51, HIS54, ARG72, HIS73, HIS86, VAL128, HIS129 and VAL131 wherein the antibody is not an antibody comprising the sequence given in SEQ ID NO:1 for CDR-H1, the sequence given in SEQ ID NO:2 for CDR-H2, the sequence given in SEQ ID NO:3 for CDR-H3, the sequence given in SEQ ID NO:4 for CDR-L1, the sequence given in SEQ ID NO:5 for CDR-L2 and the sequence given in SEQ ID NO:6 for CDR-L3.

In one embodiment the present invention provides a neutralising antibody which binds human IL-17A and IL-17F that binds to an epitope of human IL-17F comprising one or more of the amino acid residues selected from the group consisting of SER39, MET40, SER41, ARG42, ARG47, ASN53, ARG73, ASN74, LEU75, LYS83, GLU84, ASP85, ILE86, SER87, MET88, ASN89, VAL91, PRO92, GLN94, THR126, PRO127 and VAL128 of human IL-17F (SEQ ID NO:22) wherein the antibody is not an antibody comprising the sequence given in SEQ ID NO:1 for CDR-H1, the sequence given in SEQ ID NO:2 for CDR-H2, the sequence given in SEQ ID NO:3 for CDR-H3, the sequence given in SEQ ID NO:4 for CDR-L1, the sequence given in SEQ ID NO:5 for CDR-L2 and the sequence given in SEQ ID NO:6 for CDR-L3.

In one embodiment the present invention provides a neutralising antibody which binds human IL-17A and IL-17F that binds to an epitope of human IL-17F within one or more of the following regions:
(i) 39-42 (SER39, MET40, SER41, ARG42)
(ii) 47 (ARG47)
(iii) 53 (ASN53)
(iv) 72-75 (CYS72, ARG73, ASN74, LEU75)
(v) 83-92 (LYS83, GLU84, ASP85, ILE86, SER87, MET88, ASN89, SER90, VAL91, PRO92)
(vi) 94 (GLN94)
(vii) 119 (THR119)
(viii) 122 (CYS122)
(ix) 125-128 (VAL125, THR126, PRO127, VAL128).

wherein the antibody is not an antibody comprising the sequence given in SEQ ID NO:1 for CDR-H1, the sequence given in SEQ ID NO:2 for CDR-H2, the sequence given in SEQ ID NO:3 for CDR-H3, the sequence given in SEQ ID NO:4 for CDR-L1, the sequence given in SEQ ID NO:5 for CDR-L2 and the sequence given in SEQ ID NO:6 for CDR-L3.

In one embodiment the present invention provides a neutralising antibody which binds human IL-17A and IL-17F that binds to an epitope of human IL-17A comprising one or more of the amino acids selected from the group consisting of SER41, TYR44, ASN45, ARG46, TRP51, ASN52, HIS54, ARG72, HIS73, ASP84, HIS86, VAL128, HIS129 and VAL131 of human IL-17A (SEQ ID NO:21) and that binds to an epitope of human IL-17F comprising one or more of the amino acid residues selected from the group consisting of SER39, MET40, SER41, ARG42, ARG47, ASN53, ARG73, ASN74, LEU75, LYS83, GLU84, ASP85, ILE86, SER87, MET88, ASN89, VAL91, PRO92, GLN94, THR126, PRO127 and VAL128 of human IL-17F (SEQ ID NO:22) wherein the antibody is not an antibody comprising the sequence given in SEQ ID NO:1 for CDR-H1, the sequence given in SEQ ID NO:2 for CDR-H2, the sequence given in SEQ ID NO:3 for CDR-H3, the sequence given in SEQ ID NO:4 for CDR-L1, the sequence given in SEQ ID NO:5 for CDR-L2 and the sequence given in SEQ ID NO:6 for CDR-L3.

In one embodiment an antibody of the present invention which is capable of binding to both IL-17A and IL-17F is capable of neutralising the activity of both isoforms of IL-17. In particular, in one embodiment an antibody of the present invention is capable of specifically binding to both IL-17A and IL-17F i.e. the antibody does not bind to other isoforms of IL-17. Preferably an antibody of the present invention also binds the IL-17A/IL-17F heterodimer. Preferably, an antibody of the present invention neutralises the activity of both IL-17A and IL-17F. In one embodiment an antibody of the present invention also neutralises the activity of the IL-17A/IL-17F heterodimer. The antibodies provided by this aspect of the present invention therefore have the advantageous property that they can inhibit the biological activity of both IL-17A and IL-17F. Accordingly, the present invention also provides the use of such antibodies in the treatment of and/or prophylaxis of a disease mediated by either or both of IL-17A or IL-17F such as autoimmune or inflammatory disease or cancer.

IL-17A or IL-17F polypeptides or a mixture of the two or cells expressing one or both of said polypeptides can be used to produce antibodies which specifically recognise one or both polypeptides. The IL-17 polypeptides (IL-17A and IL-17F) may be 'mature' polypeptides or biologically active fragments or derivatives thereof which preferably include the receptor binding site. Preferably the IL-17 polypeptides are the mature polypeptides provided in SEQ ID NOs 21 and 22 for IL-17A and IL-17F respectively. IL-17 polypeptides may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The IL-17 polypeptide may in some instances be part of a larger protein such as a fusion protein for example fused to an affinity tag. Antibodies generated against these polypeptides may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows or pigs may be immunized. However, mice, rabbits, pigs and rats are generally preferred.

Antibodies for use in the present invention include whole antibodies and functionally active fragments or derivatives thereof and may be, but are not limited to, monoclonal, multi-valent, multi-specific, fully human, humanized or chimeric antibodies, domain antibodies e.g. VH, VL, VHH, single chain antibodies, Fab fragments, Fab' and F(ab')$_2$ fragments and epitope-binding fragments of any of the above. Other antibody fragments include those described in International patent applications WO2005003169, WO2005003170 and WO2005003171. Antibody fragments and methods of producing them are well known in the art, see for example Verma et al., 1998, Journal of Immunological Methods, 216, 165-181; Adair and Lawson, 2005. Therapeutic antibodies. *Drug Design Reviews—Online* 2(3):209-217.

Antibodies for use in the present invention include immunoglobulin molecules and immunologically active portions of immunoglobulin molecules, i.e. molecules that contain an antigen binding site that specifically binds an antigen. The immunoglobulin molecules of the invention can be of any class (e.g. IgG, IgE, IgM, IgD and IgA) or subclass of immunoglobulin molecule. The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply blocking IL-17 activity. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. Particularly preferred is the IgG4 constant domain comprising this change. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705: 129-134, 1995).

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93(15): 7843-78481; WO92/02551; WO2004/051268 and International Patent Application number WO2004/106377.

Humanized antibodies are antibody molecules from non-human species having one or more complementarity determining regions (CDRs) from the non-human species and a framework region from a human immunoglobulin molecule (see, e.g. U.S. Pat. No. 5,585,089; WO91/09967).

Chimeric antibodies are those antibodies encoded by immunoglobulin genes that have been genetically engineered so that the light and heavy chain genes are composed of immunoglobulin gene segments belonging to different species. These chimeric antibodies are likely to be less antigenic. Bivalent antibodies may be made by methods known in the art (Milstein et al., 1983, Nature 305:537-539; WO 93/08829, Traunecker et al., 1991, EMBO J. 10:3655-3659). Multi-valent antibodies may comprise multiple specificities or may be monospecific (see for example WO 92/22853 and WO05/113605).

The antibodies for use in the present invention can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108. Techniques for the production of single chain antibodies, such as those described in U.S. Pat. No. 4,946,778 can also be adapted to produce single chain antibodies which bind to IL-17A and IL-17F. Also, transgenic mice, or other organisms, including other mammals, may be used to express humanized antibodies.

Fully human antibodies are those antibodies in which the variable regions and the constant regions (where present) of both the heavy and the light chains are all of human origin, or substantially identical to sequences of human origin, not necessarily from the same antibody. Examples of fully human antibodies may include antibodies produced for example by the phage display methods described above and antibodies produced by mice in which the murine immunoglobulin variable and constant region genes have been replaced by their human counterparts eg. as described in general terms in EP0546073 B1, U.S. Pat. No. 5,545,806, U.S. Pat. No. 5,569,825, U.S. Pat. No. 5,625,126, U.S. Pat. No. 5,633,425, U.S. Pat. No. 5,661,016, U.S. Pat. No. 5,770,429, EP 0438474 B1 and EP0463151 B1.

Any suitable method known in the art may be used to determine the residues bound by an antibody provided by the present invention e.g. hydrogen-deuterium exchange, site-directed mutagenesis, mass spectrometry, NMR and X-ray crystallography. See for example the methods described in WO2007/149032.

The specific region or epitope of the human IL-17A polypeptide and/or the specific region or epitope of the human IL-17F polypeptide and/or the specific region or epitope of the human IL-17A/F heterodimer can be identified by any suitable epitope mapping method known in the art in combination with any one of the antibodies provided by the present invention. Examples of such methods include screening peptides of varying lengths derived from IL-17A and IL-17F for binding to the antibody of the present invention with the smallest fragment that can specifically bind to the antibody containing the sequence of the epitope recognised by the antibody. The IL-17 peptides may be produced synthetically or by proteolytic digestion of the appropriate IL-17 polypeptide. Peptides that bind the antibody can be identified by, for example, mass spectrometric analysis. In another example, NMR spectroscopy, as described in the Examples herein can be used to identify residues which interact with an antibody of the present invention.

The neutralising antibody molecules provided by the present invention preferably have a high binding affinity, preferably nanomolar, even more preferably picomolar. It will be appreciated that the binding affinity of an antibody according to the present invention for human IL-17A may be different from the binding affinity of the same antibody for human IL-17F and/or the IL-17A/F heterodimer. In one example the antibody molecule of the present invention has an affinity for IL-17A that is greater than its affinity for IL-17F. In one example the antibody molecule of the present invention has an affinity for IL-17A which is at least 10 fold greater than its binding affinity for IL-17F. In one example the antibody molecule of the present invention has an affinity for IL-17A which is at least 50 fold greater than its binding affinity for IL-17F. In one example the antibody molecule of the present invention has an affinity for IL-17A which is at least 100 fold greater than its binding affinity for IL-17F. In one example the antibody molecule of the present invention has an affinity for IL-17F that is greater than its affinity for IL-17A. In one example the antibody molecule of the present invention has an affinity for IL-17A that is the same as its affinity for IL-17F. In one example the antibody molecule of the present invention has a picomolar affinity for IL-17A and a nanomolar affinity for IL-17F. In one example the antibody molecule of the present invention has a nanomolar affinity for IL-17F and a picomolar affinity for IL-17A. In one example the antibody molecule of the present invention has a nanomolar affinity for both IL-17A and IL-17F. In one example the antibody molecule of the present invention has a picomolar affinity for both IL-17A and IL-17F.

Preferably the antibody molecule of the present invention has a binding affinity for IL-17A of better than 10 nM. In one embodiment the antibody molecule of the present invention has a binding affinity for IL-17A of better than 500 pM. In one embodiment the antibody molecule of the present invention has a binding affinity for IL-17A of better than 100 pM. In one embodiment the antibody molecule of the present invention has a binding affinity for IL-17A of better than 20 pM.

Preferably the antibody molecule of the present invention has a binding affinity for IL-17F of better than 10 nM. In one embodiment the antibody of the present invention has an affinity for IL-17F of better than 2 nM. In one embodiment the antibody of the present invention has an affinity for IL-17F of better than 500 pM. In one embodiment the antibody molecule of the present invention has a binding affinity for IL-17F of better than 100 pM.

Preferably the antibody molecule of the present invention has a binding affinity for IL-17A/F heterodimer of better than 10 nM. In one embodiment the antibody molecule of the present invention has a binding affinity for IL-17A/F heterodimer of better than 500 pM. In one embodiment the antibody molecule of the present invention has a binding affinity for IL-17A/F heterodimer of better than 100 pM.

In one embodiment the antibody molecule of the present invention has a binding affinity for cynomolgus IL-17F of better than 2 nM.

It will be appreciated that the affinity of antibodies provided by the present invention may be altered using any suitable method known in the art. The present invention therefore also relates to variants of the antibody molecules of the present invention, which have an improved affinity for IL-17A and/or IL-17F. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In one embodiment the antibody molecules of the present invention neutralise IL-17A and IL-17F activity, for example in the in vitro assays described in the Examples. In one embodiment the present invention provides a neutralising antibody having specificity for human IL-17A and IL-17F which is capable of inhibiting the activity of 0.8 nM human IL-17A by 50% at a concentration of less than 5 nM and the activity of 4.2 nM IL-17F by 50% at a concentration of less than 12 nM said inhibitory activity being measured on the IL-17A or IL-17F induced release of IL-6 from Hela cells. In one embodiment the concentration of antibody which inhibits IL-17A by 50% is less than 3 nM. In one embodiment the concentration of antibody which inhibits IL-17F by 50% is less than 11 nM. In one embodiment the human IL-17A and human IL-17F used in the assay are recombinant human IL-17A and IL-17F. In one embodiment the neutralising antibody is a humanised or fully human antibody.

If desired an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO03031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II)

(DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, *pseudomonas* exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Particular optional substituents which may be present on the above-mentioned synthetic polymers include one or more hydroxy, methyl or methoxy groups.

Particular examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Particular naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, preferably from 5000 to 40000 Da and more preferably from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. No. 5,219,996; U.S. Pat. No. 5,667,425; WO98/25971). In one example the antibody molecule of the present invention is a modified Fab fragment wherein the modification is the addition to the C-terminal end of its heavy chain one or more amino acids to allow the attachment of an effector molecule. Preferably, the additional amino acids form a modified hinge region containing one or more cysteine residues to which the effector molecule may be attached. Multiple sites can be used to attach two or more PEG molecules.

Preferably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment which is PEGylated, i.e. has PEG (poly(ethyleneglycol)) covalently attached thereto, e.g. according to the method disclosed in EP 0948544 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

In one embodiment, a neutralising antibody molecule of the present invention is a modified Fab fragment having at the C-terminal end of its heavy chain a modified hinge region containing at least one cysteine residue to which an effector molecule is attached. Preferably the effector molecule is PEG and is attached using the methods described in (WO98/25971 and WO2004072116) whereby a lysyl-maleimide group is attached to the cysteine residue at the C-terminal end of the heavy chain, and each amino group of the lysyl residue has covalently linked to it a methoxypoly (ethyleneglycol) residue having a molecular weight of about 20,000 Da. The total molecular weight of the PEG attached to the antibody is therefore approximately 40,000 Da.

In another example effector molecules may be attached to antibody fragments using the methods described in International patent applications WO2005/003169, WO2005/003170 and WO2005/003171.

The present invention also provides an isolated DNA sequence encoding the heavy and/or light chain(s) of an antibody molecule of the present invention. Preferably, the DNA sequence encodes the heavy or the light chain of an antibody molecule of the present invention. The DNA sequence of the present invention may comprise synthetic DNA, for instance produced by chemical processing, cDNA, genomic DNA or any combination thereof.

DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

The present invention also relates to a cloning or expression vector comprising one or more DNA sequences of the present invention. Accordingly, provided is a cloning or expression vector comprising one or more DNA sequences encoding an antibody of the present invention. Preferably, the cloning or expression vector comprises two DNA sequences, encoding the light chain and the heavy chain of the antibody molecule of the present invention, respectively.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example *E. coli*, and other microbial systems may be used or eukaryotic, for example mammalian, host cell expression systems may also be used. Suitable mammalian host cells include CHO, myeloma or hybridoma cells.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

As the antibodies of the present invention are useful in the treatment and/or prophylaxis of a pathological condition, the present invention also provides a pharmaceutical or diagnostic composition comprising an antibody molecule of the present invention in combination with one or more of a pharmaceutically acceptable excipient, diluent or carrier. Accordingly, provided is the use of an antibody according to the present invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody molecule of the present invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines.

The pharmaceutical compositions preferably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, preferably 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which the antibody molecule of the present invention is administered depends on the nature of the condition to be treated, the extent of the inflammation present and on whether the antibody molecule is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Preferred forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO 98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

It is also envisaged that the antibody of the present invention will be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The present invention also provides an antibody molecule for use in the control of inflammatory diseases. Preferably, the antibody molecule can be used to reduce the inflammatory process or to prevent the inflammatory process.

The present invention also provides an antibody molecule of the present invention for use in the treatment or prophylaxis of a pathological disorder that is mediated by IL-17A and/or IL-17F or is associated with an increased level of IL-17A and/or IL-17F. Preferably, the pathological condition is selected from the group consisting of infections (viral, bacterial, fungal and parasitic), endotoxic shock associated with infection, arthritis, rheumatoid arthritis, asthma, pelvic inflammatory disease, Alzheimer's Disease, Crohn's disease, inflammatory bowel disease, Ulcerative colitis, Peyronie's Disease, coeliac disease, gallbladder disease, Pilonidal disease, peritonitis, psoriasis, vasculitis, surgical adhesions, stroke, Type I Diabetes, lyme arthritis, meningoencephalitis, immune mediated inflammatory disorders of the central and peripheral nervous system such as multiple sclerosis and Guillain-Barr syndrome, other autoimmune disorders, pancreatitis, trauma (surgery), graft-versus-host disease, transplant rejection, cancer (both solid tumours such as melanomas, hepatoblastomas, sarcomas, squamous cell carcinomas, transitional cell cancers, ovarian cancers and hematologic malignancies and in particular acute myelogenous leukaemia, chronic myelogenous leukemia, gastric cancer and colon cancer), heart disease including ischaemic diseases such as myocardial infarction as well as atherosclerosis, intravascular coagulation, bone resorption, osteoporosis, periodontitis and hypochlorhydia.

The present invention also provides an antibody molecule according to the present invention for use in the treatment or prophylaxis of pain.

The present invention further provides the use of an antibody molecule according to the present invention in the manufacture of a medicament for the treatment or prophylaxis of a pathological disorder that is mediated by IL-17A and/or IL-17F or associated with an increased level of IL-17A and/or IL-17F. Preferably the pathological disorder is rheumatoid arthritis or multiple sclerosis.

The present invention further provides the use of an antibody molecule according to the present invention in the manufacture of a medicament for the treatment or prophylaxis of pain.

An antibody molecule of the present invention may be utilised in any therapy where it is desired to reduce the effects of IL-17A and/or IL-17F in the human or animal body. IL-17 A and/or IL-17F may be circulating in the body or may be present in an undesirably high level localised at a particular site in the body, for example a site of inflammation.

An antibody molecule according to the present invention is preferably used for the control of inflammatory disease, autoimmune disease or cancer.

The present invention also provides a method of treating human or animal subjects suffering from or at risk of a disorder mediated by IL-17A and/or IL-17F, the method comprising administering to the subject an effective amount of an antibody molecule of the present invention.

An antibody molecule according to the present invention may also be used in diagnosis, for example in the in vivo diagnosis and imaging of disease states involving IL-17A and/or IL-17F.

The present invention is further described by way of illustration only in the following examples, which refer to the accompanying Figures, in which:

FIG. 1
a) Light chain V region of antibody CA028_0496 (SEQ ID NO:7)
b) Heavy chain V region of antibody CA028_0496 (SEQ ID NO:9)
c) CDRH1 (SEQ ID NO:1), CDRH2 (SEQ ID NO:2), CDRH3 (SEQ ID NO:3), CDRL1 (SEQ ID NO:4), CDRL2 (SEQ ID NO:5), CDRL3 (SEQ ID NO:6) of antibody CA028_496.
d) Light chain of antibody CA028_496 (SEQ ID NO:11).
e) Heavy chain of antibody CA028_496 (SEQ ID NO:15).
f) DNA encoding light chain of antibody CA028496 including signal sequence (SEQ ID NO:14).
g) DNA encoding heavy chain of antibody CA028496 including signal sequence (SEQ ID NO:18)
h) Mature human IL-17A.
i) Mature human IL-17F.

Figure 2B:
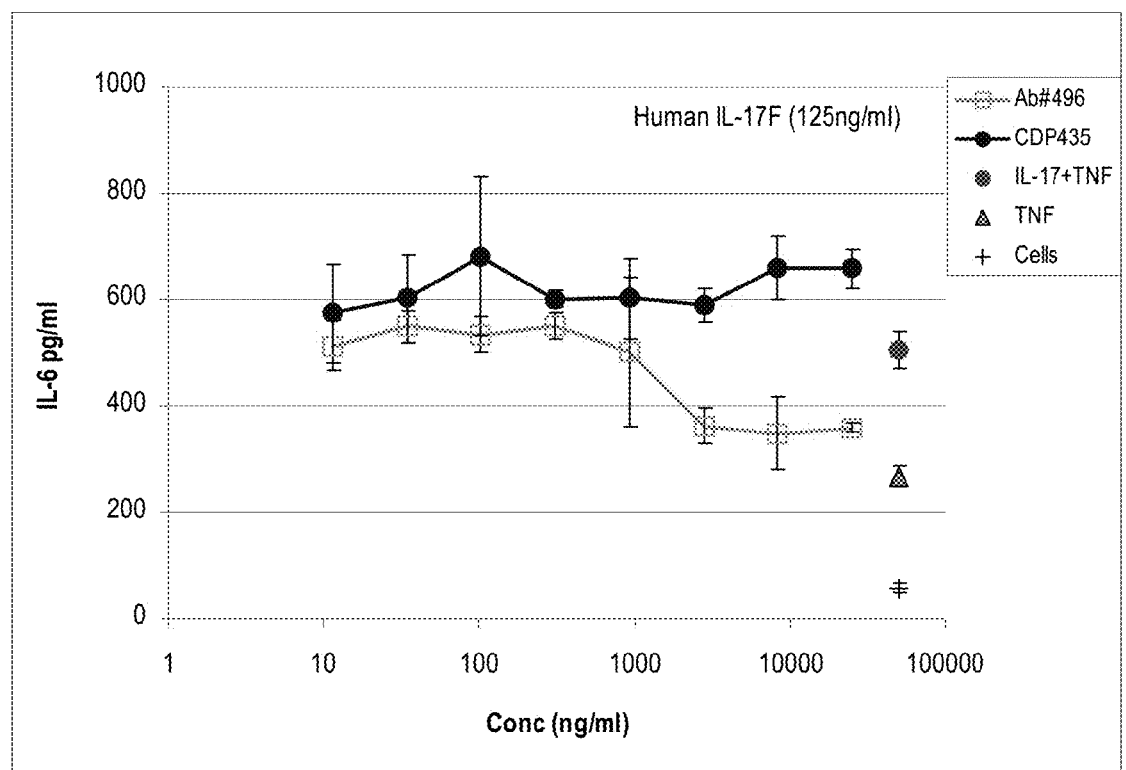

FIG. 2a) The effect of antibody CA028_0496 (designated Ab#496 in legend) on human IL-17 induced IL-6 production from Hela cells. FIG. 2b) The effect of antibody CA028_0496 (designated Ab#496 in legend) on human IL-17F induced IL-6 production from Hela cells

DNA MANIPULATIONS AND GENERAL METHODS

*E. coli* strain INVαF' (Invitrogen) was used for transformation and routine culture growth. DNA restriction and modification enzymes were obtained from Roche Diagnostics Ltd. and New England Biolabs. Plasmid preparations were performed using Maxi Plasmid purification kits (QIAGEN, catalogue No. 12165). DNA sequencing reactions were performed using the ABI Prism Big Dye terminator sequencing kit (catalogue No. 4304149) and run on an ABI 3100 automated sequencer (Applied Biosystems). Data was analysed using the program AutoAssembler (Applied Biosystems). Oligonucleotides were obtained from Invitrogen. The concentration of IgG was determined using IgG assembly ELISA.

IL-17 Isoforms

Recombinant IL-17A and IL-17F were purchased from R&D Systems.

Recombinant IL-17A/F heterodimer was produced by linking IL-17A and IL-17F using a GS linker. The heterodimer had the following sequence (SEQ ID NO:19) MGITIPRNPGCPNSEDKNFPRTVMVNLNIHNRNTNTNPKRSSDYYNRSTSPWNLHRNE DPERYPSVIWEAKCRHLGCINADGNVDYHMNSVPIQQEILVLRREPPHCPNSFRLEKIL VSVGCTCVTPIVH-HVAGGGGSGGGGSGGGGSGGGGSRKIPK-VGHTFFQKPESCPPVP GGSMKLDIGIINENQRVSM-SRNIESRSTSPWNYTVTWDPNRYPSEVVQAQCRNLGCIN AQGKEDISMNSVPIQQETLVVRRKHQGCSVSFQLEK-VLVTVGCTCVTPVIHHVQ Recombinant cynomolgus IL-17F (SEQ ID NO:20) MRKIPKVGHTFFQKPESCPPVPEGSMKLDTGIINEN-QRVSMSRNIESRSTSPWNYTVTWDPNR YPSEV-VQAQCKHLGCINAQGKEDISMNSVPIQQETLVLR-RKHQGCSVSFQLEKVLVTVGCTCV TPVIHHVQ The DNA sequence encoding IL-17A/F heterodimer was chemically synthesised by Entelechon GmbH and was subcloned into pET43.1a at the NdeI/XhoI sites.

The DNA sequence encoding cyno L-17F was amplified by PCR using primers that introduced NdeI and XhoI restriction sites. The PCR products were ligated into pCR4Blunt-TOPO and sequence verified before digestion and ligation into pET43.1a at the NdeI/XhoI sites.

pET43.1a DNA encoding IL-17 isoforms was used to transfect BL21(DE3) cells and selected carbenicillin-resistant clones were grown at 37° C. overnight in 2TY broth containing 2% glucose and 50 µg/ml carbenicillin. The cultures were then diluted and grown in the same medium to an $OD_{600}$ of 0.5-0.7, induced with 1 mM IPTG and grown at 37° C. for a further 4-5 hours.

Cells were harvested by centrifugation and inclusion bodies prepared from from the cells. Inclusion bodies were solubilised in 50 mM Tris-HCl, 5M guanidinium hydrochloride, 50 mM NaCl, 1 mM EDTA, 2 mM reduced glutathione, 0.2 mM oxidised glutathione, pH 8.5. IL-17 protein was refolded by dropwise addition of the solubilised protein to the above buffer without guanidinium hydrochloride, with vigorous stirring. The final volume was chosen such that the final protein concentration was no more than 0.1 mg/ml.

The refolded protein solution was concentrated if required, before buffer exchange with 10 mM MES pH6. The protein was then applied to a column of Sepharose SP HP equilibrated with 20 mM MES pH6. Protein was eluted with a linear gradient of 0-500 mM NaCl in MES pH6 over 10 column volumes. For IL-17F the gradient was extended to 600 mM NaCl. In order to further purify IL-17, the relevant fraction from the Sepharose SP HP column were pooled, concentrated and diluted with 20 mM CAPSO (pH10) and applied to a Mono Q column equilibrated with 20 mM CAPSO. Protein was eluted with a linear gradient of 0-250 mM NaCl in 20 mM CAPSO over 20 column volumes. Fractions containing IL-17 were pooled and neutralised using 1M MES pH6.

Example 1: Production of a Neutralising Anti-IL-17 Antibody

Female Sprague Dawly rats were immunised with recombinant human IL-17 (purchased from R & D systems). Rats received four immunisations of 20 μg IL-17 in 100 μl Freund's adjuvant. Antibody 225 which binds human IL-17 was isolated using the methods described in WO04/051268. Genes for the heavy chain variable domain (VH) and light chain variable domain (VL) of antibody 225 were isolated and sequenced following cloning via reverse transcription PCR.

A series of humanised VL and VH regions were designed using human V-region acceptor frameworks and by varying the number of donor residues in the framework regions. Eight grafted VL regions (gL1-8) and 9 grafted VH regions (gH1-9) were designed and genes were built by oligonucleotide assembly and PCR mutagenesis.

The light chain grafted sequences were sub-cloned into the human light chain expression vector pKH10.1 which contains the DNA encoding the human C-Kappa constant region (Km3 allotype). The heavy chain grafted sequences were sub-cloned into the human gamma-4 expression vector pVhg4P FL, which contains the DNA encoding the human gamma-4 constant region containing the hinge stabilising mutation S241P (Angal et al., supra). Plasmids were co-transfected into CHO cells and the antibodies produced screened for activity in IL-17 binding and neutralisation assays. Transfections of CHO cells were performed using the Lipofectamine™ 2000 procedure according to manufacturer's instructions (InVitrogen, catalogue No. 11668).

The most optimal graft based on expression, affinity and neutralisation potency (gL7gH9) was selected and named CA028_0496 (also referred to herein as 496). The V region sequences of this antibody are shown in FIG. 1(a) and (b) and in SEQ ID NOs: 7 and 9 for the light chain (gL7) and heavy chains (gH9) respectively.

The heavy chain acceptor framework is the human germline sequence VH3 1-3 3-07 with framework 4 coming from this portion of the human JH-region germline JH4. The light chain acceptor framework is the human germline sequence VK1 2-1-(1) L4, with framework 4 coming from this portion of the human JK-region germline JK1.

Example 2: Antibody CA028_0496 Neutralises IL-17 and IL-17F and IL-17a/F Heterodimer HeLa Cells The potency of antibody CA028_0496 against human recombinant IL-17 and human recombinant IL-17F in Hela cells was tested and compared to antibody CDP435 (WO06/054059). Hela cells were obtained from the cell bank at ATCC (ATCC CCL-2). Cells were grown in Dulbecco's modified Eagle's medium (DMEM) supplemented with 10% foetal calf serum, penicillin, gentamycin and glutamine. $1 \times 10^4$ cells were plated out into 96 well flat bottomed tissue culture plates. Cells were incubated overnight and washed once in assay buffer. Either human IL-17A (25 ng ml$^{-1}$) or human IL-17F (125 ng ml$^{-1}$) was incubated in the presence of a fixed concentration of human TNF-αc this mixture was preincubated with antibody CA028_0496 or antibody CDP435. Cytokine plus antibody was then added to the Hela cells which were incubated overnight. The production of IL-6 in the cell culture supernatant was proportionate to the amount of IL-17A/IL-17F added to the cells. Human IL-6 levels were measured by ELISA and quantified by comparison with known standard concentrations of human IL-6.

The data (FIGS. 2a & 2b) indicates that CA028_0496 potently neutralised human recombinant IL-17A and also had some activity against human IL-17F. The data from these experiments indicated that antibody CA028_0496 gave an $IC_{50}$ of 43 ng/ml against human recombinant IL-17 (25 ng ml$^{-1}$) & 1477 ng/ml against recombinant IL-17F (125 ng ml$^{-1}$). Accordingly, antibody CA028_0496 gave an IC50 of 0.29M against human recombinant IL-17 (0.78 nM) and 10.18 nM against human recombinant IL-17F (4.16 nM) in this assay (calculation based on per IgG assuming a molecular weight of 145,000 as an average IgG4 and assuming that IL-17A and IL-17F are dimers).

Human Microglia Cells

Human microglia cells (TCS Cellworks) were plated out in a flat bottom 96-well plate at 5,000 cells per well in a total volume of 100 μl and left for 24 hours to attach to the plastic. At this time titrations (5, 1, 0.2 and 0.04 μg/ml) of human recombinant IL-17A, human recombinant IL-17F, cynomolgus recombinant IL-17F and human recombinant IL-17A/F heterodimer in the presence and absence of 10 ng/ml human recombinant TNFα were added to wells in triplicate. Control wells contained no stimulation, IL-17A alone (100 ng/ml), TNFα alone and IL-17A and TNFα together. All cytokines were added in a total volume of 110 μl/well, making the total well volume 210 μl. In experiments involving antibodies, cells were plated out in the same way. After 24 hours antibodies and cytokines were added at the same time to give the stated final concentrations in a total final volume of 200 μl.

After a further 24 hours incubation at 37° C., supernatants were harvested and frozen at −20° C. until analysis. For analysis, supernatants were diluted 1/10 and measured for IL-6 using a human IL-6 MSD kit, according to manufacturer's instructions.

All isoforms of IL-17 tested were found to be active in the assay, particularly in the presence of TNFα.

The potency of antibody CA028_0496 against human recombinant IL-17A and human recombinant IL-17F, cynomolgus recombinant IL-17F and human recombinant IL-17A/F heterodimer in human microglia cells was tested in the presence of TNFα and compared to a control antibody and an IL-17A specific antibody using the method described above.

The control antibody had no effect on the activity of any of the cytokines tested. Antibody CA028_0496 had inhibitory activity against all three cytokines IL-17, IL-17F and IL-17A/F, including cynomolgus IL-17F while the IL-17A specific antibody only had inhibitory activity against IL-17A and IL-17A/F heterodimer.

Example 3: Affinity of Antibody CA028_0496 (Human IgG4 Constant Regions) for IL-17A and IL-17F BIA (Biamolecular Interaction Analysis) was performed using a Biacore 3000 (BiacoreAB).

All experiments were performed at 25° C. Affinipure Fc Fragment goat anti-human IgG, Fc fragment specific (Jackson ImmunoResearch) was immobilised on a CM5 Sensor Chip via amine coupling chemistry to a capture level of ≈6000 response units (RUs). HBS-EP buffer (10 mM HEPES pH 7.4, 0.15 M NaCl, 3 mM EDTA, 0.005% Surfactant P20, Biacore AB) was used as the running buffer with a flow rate of 10 μl/min. A 10 μl injection of antibody CA028_0496 (1.81 mg/ml) was used for capture by the immobilised anti-human IgG-Fc. Human IL-17A and IL-17 isoforms were titrated over the captured CA028_0496 at doubling dilutions from 50 nM to sub nM at a flow rate of 30 μL/min. The surface was regenerated by a 30 μL injections of 40 mM HCl, followed by one 5 μL injection of 5 mM NaOH.

Background subtraction binding curves were double referenced and analysed using the BIAevaluation software (version 3.2) following standard procedures. Kinetic parameters were determined from the fitting algorithm.

The affinity value determined for antibody CA028_0496 binding IL-17A was 16 pM and 1750 pM for IL-17F. Antibody CA028_0496 did not bind to the other IL-17 isoforms (IL-17 B, C, D and E). Antibody CA028_0496 therefore specifically binds IL-17A and IL-17F.

Example 4: Affinity of Antibody CA028_0496 (Murine IgG1 Constant Regions) for IL-17A, Cynomolgus IL-17F and IL-17A/F Heterodimer BIA (Biamolecular Interaction Analysis) was performed using a Biacore 3000 (Biacore AB).

All experiments were performed at 25° C. Affinipure F(ab')$_2$ fragment goat anti-mouse IgG, Fc fragment specific (Jackson ImmunoResearch) was immobilised on a CM5 Sensor Chip (Biacore AB) via amine coupling chemistry to a capture level of ≈6000 response units (RUs). HBS-EP buffer (10 mM HEPES pH 7.4, 0.15 M NaCl, 3 mM EDTA, 0.005% Surfactant P20, Biacore AB) was used as the running buffer with a flow rate of 10 μL/min. A 10 μL injection of antibody CA028_0496 at 4 ug/mL was used for capture by the immobilised anti-mouse IgG, Fc. Human IL-17A, cyno IL-17F and heterodimer A/F were titrated over the captured CA028_0496 at doubling dilutions from 25 nM to sub nM at a flow rate of 30 μL/min. The surface was regenerated at a flowrate of 10 uL/min by a 10 μL injection of 40 mM HCl, followed by a 5 μL injection of 5 mM NaOH.

Double referenced background subtracted binding curves were analysed using the BIAevaluation software (version 3.2) following standard procedures. Kinetic parameters were determined from the fitting algorithm.

Antibody CA028_0496 had an affinity of 21 pM for IL-17A, 116 pM for IL-17A/F heterodimer and 1030 pM for cynomolgus IL-17F.

Example 5: Epitope Mapping by NMR of a Fab' Fragment Comprising the Variable Regions of Antibody CA028_0496

Antibody CA028_0496 was produced as a Fab' fragment comprising '496 variable regions and murine IgG1 constant regions (SEQ ID NO:162323 and 241724).

Heavy chain sequence
(SEQ ID NO: 231623)

EVQLVESGGG LVQPGGSLRL SCAASGFTFS DYNMAWVRQA
PGKGLEWVAT ITYEGRNTYY RDSVKGRFTI SRDNAKNSLY
LQMNSLRAED TAVYYCASPP QYYEGSIYRL WFAHWGQGTL
VTVSSAKTTP PSVYPLAPGS AAQTNSMVTL GCLVKGYFPE
PVTVTWNSGS LSSGVHTFPA VLQSDLYTLS SSVTVPSSTW
PSETVTCNVA HPASSTKVDK KIVPRDCGCA AAIQLTQSPS
SLSASVGDRV TITCRADESV TTLMHWYQQK PGKAPKLLIY
LVSNRESGVP SRFSGSGSGT DFTLTISSLQ PEDFATYYCQ
QTWSDPWTFG QGTKVEIKRT DAAPTVSIFP PSSEQLTSGG
ASVVCFLNNF YPKDINVKWK IDGSERQNGV LNSWTDQDSK
DSTYSMSSTL TLTKDEYERH NSYTCEATHK TSTSPIVKSF
NRNEC

Light chain sequence
(SEQ ID NO: 172424)

AIQLTQSPSS LSASVGDRVT ITCRADESVT TLMHWYQQKP
GKAPKLLIYL VSNRESGVPS RFSGSGSGTD FTLTISSLQP
EDFATYYCQQ TWSDPWTFGQ GTKVEIK

Transient Expression of CA028_00496.g1 mFab' in a 10 L Wave Bioreactor

For the transfection of the HEK 293 F cells in a 10 L wave bag, 10 L of the in-house NM6 medium was prepared and supplemented with 2 mM Glutamax (Invitrogen). The cells were counted and seeded into the bag at a final cell density of 1×10$^6$ cells/ml. The transfection mixture was prepared in 700 ml of NM6 medium. For the preparation of the transfection mixture the NM6 medium was divided into two halves. To one half 5 mg of the heavy chain plasmid DNA and 5 mg of the light chain plasmid DNA was added and gently shaken. To the other half 37 ml of a 1 mg/ml linear 25 kD polyethylenimine (PEI) stock solution was added and gently shaken. Thereafter NM6 medium containing the DNA was slowly transferred to the NM6 medium containing the PEI. The mixture was incubated at room temperature for 20 minutes before added to the cell suspension in the wave bag. The transfected cells were cultured over 14 days at 25 rpm, a 7° angle, 37° C. and 5% CO2. Samples were taken regularly to determine the cell density and viability. On day 14 post transfection cells were harvested. The 10 L cell suspension was transferred to centrifuge bottles and spun at 4000 rpm for 45 min. The supernatant was then passed through a Sartobran (0.45 μm to 0.2 μm) filter and finally through a Millipack Gold60 (0.22 μm) sterile filter. Fab' was then purified from the sterile filtered supernatant.

Purification of CA028_00496.g1 mFab'

Transiently expressed CA028_00496.g1 mFab' was purified from mammalian host cells (HEK293F) as follows. The mammalian host cell conditioned medium containing secreted CA028_00496.g1 mFab' was concentrated 10 fold by tangential flow ultrafiltration (TFF) using a 10,000 MWCO membrane. The concentrated supernatant was passed down a GammaBind Plus Sepharose column (media supplied by GE Healthcare) which had been equilibrated with 75 mM citrate/phosphate buffer, pH6.0. After loading, the GammaBind Plus Sepharose column was washed with 75 mM citrate/phosphate buffer, pH6.0 until the absorbance at 280 nm of the flow-through returned to baseline. The CA028_00496.g1 mFab' was then eluted from the column by stepping into 0.1M glycine-HCl buffer, pH2.7. The absorbance at 280 nm of the eluate was monitored and fractions containing protein were collected. Supernatant loading and column elution were performed in two batches so as not to exceed the capacity of the column.

Fractions containing protein were combined and buffer exchanged (by diafiltration) into 0.1M sodium phosphate buffer, pH6.0+2 mM EDTA using an Amicon stirred cell and 10,000 MWCO membrane. The affinity purified CA028_00496.g1 mFab' was concentrated to 20 mg/ml prior to reduction. Disulphide bonded cysteines at the hinge region were reduced by incubating the Fab' with 5 mM β-Mercaptoethylamine at 37° C. for 30 minutes. The reduction was stopped by adding 50 mM N-Ethylmaleimide (NEM) to cap the reduced thiol groups. The capping reaction was incubated at +4° C. overnight. Excess capping agent and high molecular weight impurities were removed by preparative Gel Filtration. The reduced and capped Fab' was loaded onto a Superdex 200 column (GE Healthcare) and eluted in PBS, pH7.4. The absorbance at 280 nm of the eluate was monitored and fractions containing protein were collected. Fractions were analysed for purity by analytical SE-HPLC using a Zorbax GF250 column (Agilent) run in 0.2M sodium phosphate buffer, pH7.0. Fractions containing pure Fab' were combined, 0.22 m sterile filtered and stored at +4° C. Final purity was analysed by SE-HPLC (as above) and non-reducing and reducing SDS-PAGE.

Preparation of dN- and dCN-Labelled hIL17A

The DNA sequence encoding IL-17A was amplified by PCR using primers that introduced NdeI and XhoI restriction sites. The PCR products were ligated into pCR4Blunt-TOPO and sequence verified before digestion and ligation into pET43.1a at the NdeI/XhoI sites.

hIL17A-pET43.1a was used to transform *E. coli* strain BL21(DE3). 1 ml of LB inoculated with transformed cells. Cells incubated overnight at 37° C. Dense overnight culture used to inoculate 30% dN labelled Celltone media at 1:40 dilution. Cells incubated overnight at 37° C. Dense overnight culture then used to inoculate 30% dN- or dCN-labelled Celltone media. Culture incubated overnight at 37° C. This step was then repeated with 70% media and then finally with 100% media. 100% dN- or dCN-labelled media inoculated with dense overnight culture and grown to 0.8 OD 595 nm. Culture induced with a final concentration 1 mM IPTG and incubated for 6 hours at 37° C. Cells harvested by centrifugation.

Inclusion Bodies Extracted (for 2 L of Culture).
1) Resuspend cell pellet in 40 ml Buffer A (100 mM KCl, 2 mM DTT, 2 mM PMSF, 10 mM Tris-HCl pH 8.5, 25% (w/v) sucrose)
2) Add 10 ml Buffer B (300 mM Tris-HCl pH 8.5, 100 mM EDTA, 4 mg/ml lysozyme) Incubate on ice for 10-30 minutes with occasional swirling.
3) Add 50 ml Buffer C (1M LiCl, 20 mM EDTA, 0.5% (v/v) NP-40). Sonicate sample to homogenise. Pass sample through French Press at 20,000 psi. Pass sample through French Press again. Spin sample at 10,000 rpm for 10 minutes @ 4° C.
4) Resuspend pellet in 40 ml Buffer D (10 mM Tris-HCl pH 8.5, 0.1 mM EDTA, 0.5M LiCl, 0.5% (v/v) NP-40, 1 mM DTT, 1 mM PMSF). Sonicate to homogenise and spin at 10,000 rpm for 10 minutes @ 4° C. Repeat step.
5) Resuspend pellet in 40 ml Buffer E (10 mM Tris-HCl pH 8.5, 0.1 mM EDTA, 0.5% (v/v) NP-40, 1 mM DTT, 1 mM PMSF). Sonicate to homogenise and spin at 10,000 rpm for 10 minutes @ 4° C. Repeat step.

Resolubilisation of Pellet
6) Make up 6M Guanidine HCl, 50 mM Tris-HCl pH8.5, 50 mM NaCl. Add to pellet. Stir pellet until completely dissolved.
7) Filter sample through a 0.2 uM syringe filter.

Refolding and Dialysis
1) 2.5 ml resolubilised inclusion bodies diluted into 50 ml of 5M Guanidine-HCl, 50 mM Tris pH8.5, 50 mM NaCl, 1 mM EDTA, 2 mM reduced-Glutathione, 0.2 mM oxidised-Glutathione.
2) Diluted inclusion bodies added drop wise to 500 ml of 50 mM Tris pH8.5, 50 mM NaCl, 1 mM EDTA, 2 mM reduced-Glutathione, 0.2 mM oxidised-Glutathione.
3) Refolded protein dialyse against 20 mM MES pH6 overnight at 4° C.

Purification of Labelled Protein
1) Dialysed lysate loaded onto a Mono SP HP (cation) column equilibrated with 20 mM MES pH6
2) Protein eluted with 50% NaCl gradient over 10 column volumes.
3) Eluted protein buffer exchanged into 20 mM NaPi, 100 mM NaCl, 0.02% azide pH6 and concentrated and assayed for concentration.

Purification of Unlabelled Protein
1) Dialysed lysate loaded onto a Mono SP HP (cation) column equilibrated with 20 mM MES pH6.
2) Protein eluted with 50% gradient of 1M NaCl over 10 column volumes.
3) Eluted protein concentrated and buffer exchanged into 20 mM CAPSO buffer pH10 and loaded onto a MonoQ column equilibrated with 20 mM CAPSO buffer pH10.
4) Protein eluted with 50% gradient of 1M NaCl over 20 column volumes.
5) Eluted protein concentrated.
6) Concentrated protein injected onto a Superdex 75 16?60 column for a final polishing step. Column equilibrated with 20 mM HEPES, 50 mM NaCl pH7.4. Eluted protein collected and concentrated and assayed for concentration.

Principle of the NMR Epitope Mapping Assay

The NMR technology allows the sensitive detection of changes in the environment of paramagnetic species. In practice this means that a protein that has been uniformly $^{15}$N and $^{2}$H labelled can be mixed with an unlabelled binding partner and those amino acids in the labelled protein that interact with the unlabelled binding partner can be detected as their position within the NMR spectra change. In this case, human IL-17A was uniformly labelled and its NMR spectra recorded in the presence and absence of the Fab' fragment of an anti-IL-17A antibody. The difference between the two spectra enables the amino acids in IL-17A that are involved in the interaction with the antibody to be identified.

NMR Spectroscopy

The NMR experiments were carried out on 0.35 mL samples of the proteins and complexes in a 25 mM sodium phosphate, 100 mM sodium chloride and 0.01% (w/v) sodium azide buffer at pH 6 (95% $H_2O$ and 5% $D_2O$). The 1:2 (dimer:Fab) complex between $^{15}$N/$^{2}$H labelled IL-17A and the unlabelled Fab' fragment of antibody '496 was prepared for NMR analysis by mixing equimolar (monomer:Fab) amounts of the proteins to achieve a final concentration of 0.25 mM. The NMR data were acquired at 35° C. for free IL-17A and for the IL-17A:Fab' fragment of '496 complex on a 800 MHz Bruker Avance spectrometer equipped with a triple-resonance ($^{15}$N/$^{13}$C/$^{1}$H) cryoprobe. TROSY-based HNCACB, HN(CO)CACB and HNCO spectra (1-4) were used to make complete sequence-specific backbone resonance assignments ($^{15}$N, $^{13}$C and $^{1}$H) for free IL-17A using a 0.8 mM uniformly $^{15}$N/$^{13}$C labelled sample.

Changes in the positions of IL-17A backbone signals induced by the Fab' fragment of '496 binding were detected using a 2D $^{15}$N/$^{1}$H TROSY spectrum (5). Typical acquisition parameters for all the NMR experiments are set out below.

Basic parameters of NMR experiments.

| Experiment | Indirect dimension | Sweep width [ppm] | Carrier offset [ppm] | Acquisition time [ms] |
|---|---|---|---|---|
| TROSY-HNCACB & | $^{15}$N (F2) | 32 | 118.0 | 19.3 |
| TROSY-HN(CO)CACB | $^{13}$C (F1) | 56 | 44.0 | 8.0 |
| TROSY-HNCO | $^{15}$N (F2) | 32 | 118.5 | 20.6 |
|  | $^{13}$C (F1) | 11.5 | 175.5 | 24.8 |
| 2D $^{15}$N/$^{1}$H HSQC | $^{15}$N (F1) | 34 | 118.0 | 80 |
| 2D $^{15}$N/$^{1}$H TROSY | $^{15}$N (F1) | 34 | 117.5 | 50 |

The direct $^{1}$H dimension (F3 or F2) was acquired with a sweep width of 14 ppm and acquisition time of 90 or 60 ms.

All the spectra were processed using Topspin 2.1, with linear prediction used to extend the effective acquisition time in the $^{15}$N dimension of 3D data to about 30 ms. Mild resolution enhancement was applied in all dimensions using a shifted sine-squared function. Analysis of the spectra was carried out using Sparky (7).

Analysis of Fab' Binding Data

The minimal shift approach (Farmer, B. T. et al., (1996) *Nat Struct Mol Biol* 3(12), 995; Muskett, F. W. et al., (1998) *J Biol Chem* 273(34), 21736-21743) was used to determine the changes in the positions of IL-17A NMR signals resulting from the Fab' fragment of '496 binding to human IL-17A. Initially, all peaks in the 2D $^{15}$N/$^{1}$H HSQC spectrum of free IL-17A and 2D $^{15}$N/$^{1}$H TROSY spectrum of IL-17A bound to the Fab' fragment of '496 were picked in their centres. The $^{15}$N and $^{1}$H chemical shift values of backbone resonances were corrected for the difference in the 2D $^{15}$N/$^{1}$H TROSY and 2D $^{15}$N/$^{1}$H HSQC spectra of the complex and free protein (0.58 ppm for $^{15}$N and −0.06 ppm for $^{1}$H). The minimum change in position for peaks between free and Fab'-bound IL-17A was obtained by using Microsoft Excel to calculate the combined chemical shift difference in $^{15}$N and $^{1}$H for each assigned peak in the $^{15}$N/$^{1}$H HSQC spectrum of the free protein compared to all observed peaks in $^{15}$N/$^{1}$H TROSY spectrum of the Fab' complex. The combined amide proton and nitrogen chemical shift differences (Δδ) were defined according to the following equation (Equation 1), where $\Delta\delta_{HN}$ and $\Delta\delta_{N}$ correspond to the differences in $^{1}$H and $^{15}$N shifts between pairs of compared peaks and $\alpha_{N}$ is a scaling factor of 0.2 required to account for differences in the range of amide proton, amide nitrogen and carbon chemical shifts. For each individual peak, the minimal shift induced by Fab' binding was taken as the lowest possible combined shift value (Δδ).

$$\Delta\delta = \sqrt{(\Delta\delta_{HN})^2 + (\Delta\delta_{N} \cdot \alpha_{N})^2}$$ (Equation 1)

To identify the Fab' binding sites (epitopes) on IL-17A, a histogram of combined minimal shift versus protein sequence was used to reveal regions of IL-17A containing significantly perturbed signals. If the size of the combined chemical shift change for individual amino acids exceeded a threshold value, these residues were selected for further evaluation as possible contact residues in the Fab' binding site. It will be appreciated that these possible 'contact' residues may be involved in binding by direct or indirect (e.g. allosteric) interactions with the Fab'. The threshold values were set as +1.5×SD of all the minimal shift data, the mean minimal shift +1 SD and the mean minimal shift +2 SD. The locations of candidate binding site residues were finally examined on the high resolution structure of IL-17A and only residues positioned on the protein surface were considered to be available for Fab' binding.

Residues selected as possible 'contact' residues based on shifts>+1.5×SD of all the minimal shift data, solvent accessibility>25%:
SER41, TYR44, ASN45, ARG46, TRP51, ASN52, HIS54, ARG72, HIS73, ASP84, HIS86, VAL128, HIS129 and VAL131.

Residues selected as possible 'contact' residues based on shifts>the mean+1 SD of all minimal shift data, solvent accessibility>25%:
SER41, TYR44, ASN45, TRP51, ASN52, HIS54, ARG72, HIS73 and ASP84.

Residues selected as possible 'contact' residues based on shifts>the mean+2 SD of all minimal shift data, solvent accessibility>25%:
TYR44, ASN45, TRP51, ASN52 and ASP84.

The NMR technique described above was also used to identify the Fab' binding sites (epitopes) on IL-17F.

The threshold values were set as the mean minimal shift, the mean minimal shift +0.5 SD and the mean minimal shift +1 SD. The locations of candidate binding site residues were finally examined on the high resolution structure of IL-17F and only residues positioned on the protein surface were considered to be available for Fab' binding.

Residues selected as possible 'contact' residues based on shifts>mean of all the minimal shift data, solvent accessibility>20%:
GLN12, LYS13, SER24, ISO32, ASN33 GLU34, ASN35, GLN36, VAL38, SER46, ASN53, TYR54, GLN69, ISO78, ASP85, SER87, MET88, ASM89, GLN94, LYS103 and THR126.

Residues selected as possible 'contact' residues based on shifts>the mean+0.5 SD of all minimal shift data, solvent accessibility>20%:
GLN12, SER24, ASN33, GLU34, GLN36, VAL38, ASN53, TYR54, ASP85, MET88, ASM89, and THR126.

Residues selected as possible 'contact' residues based on shifts>the mean+1 SD of all minimal shift data, solvent accessibility>20%:
GLN12, SER24, ASN33, GLU34, ASP85 and MET88.

Example 6: Modelling of Antibody 496 Binding on IL-17F

The probable binding site for antibody 496 on human IL-17F was determined by homology modelling and docking.

MODELLER (Sali, A. & Blundell, T. L., (1993) *J. Mol. Biol.* 234(3), 779-815) was used to build a homology model of antibody 496, using the x-ray structure of antibody CA048_497 (antibody described in WO2008/001063). The overall sequence identity between the two antibodies is 82%. At such high similarity level, the homology modelling process is well understood by anyone who is skilled in the art.

The homology model of antibody 496 was then docked to the x-ray structure of IL17A/F heterodimer using Rosetta-Dock (Gray, J. J., et. al., (2003) *J. Mol. Biol.,* 331(1), 281-299) in order to build a 3D model of the complex. A global unrestricted docking process was carried out to generate 10,000 decoys (i.e., potential docking solutions). The top 10 decoys with lowest energy scores, according to RosettaDock, were selected for perturbation study to probe the energy landscape around each docking solution. The perturbation studies were again carried out using Rosetta-Dock. Decoys that had funnel-like energy landscape were promoted as potential candidates.

The potential candidates were then screened against proximity to residues ASP80, GLY81 and ASN82 of the IL17A subunit and to residues GLN81, GLY82 and LYS83 of the IL17F subunit. Candidates that had antibody 496 located within 4 angstroms from any of such residues were discarded. Note that residues ASP80, GLY81 and ASN82 of IL17A, which are structurally equivalent to residues GLN81, GLY82 and LYS83 of IL17F, were not identified as possible contact residues by the minimal shift data as shown in Example 5, but were identified as possible contact residues when the binding of antibody CA048_497 and IL17A was studied using the same technique (data not shown).

The remaining candidates were then screened for proximity to IL17F residues ARG42, GLU45, SER46, ARG47, TRP52, ASN53, THR55, ARG73, ASN74, LEU75, ASP85 and SER87 ("IL17F-496 Key Residues"), which are structurally equivalent to the possible IL17A contact residues specified in Example 5. Note that the residues that are structurally equivalent to VAL128, HIS129 and VAL131 of IL17A are not present in the x-ray structure IL17F and thus ignored. The candidate with the lowest sum of distances between "IL17F-496 Key Residues" and antibody 496 was selected as the final docking solution.

The proximity screening protocols were carried out using PyMol (DeLano, W. L. The PyMOL Molecular Graphics System (2002) on World Wide Web http://www.pymol.org). According to the final docking solution, antibody 496 is expected to bind IL-17F at one or more of the following residues: SER39, MET40, SER41, ARG42, ARG47, ASN53, CYS72, ARG73, ASN74, LEU75, LYS83, GLU84, ASP85, ILE86, SER87, MET88, ASN89, SER90, VAL91, PRO92, GLN94, THR119, CYS122, VAL125, THR126, PRO127, VAL128.

Antibody 496 is expected to bind within one or more of the following regions, comprising amino acid residues:

39-42 (SER39, MET40, SER41, ARG42) SEQ ID NO: 8
47 (ARG47)
53 (ASN53)
72-75 (CYS72, ARG73, ASN74, LEU75) SEQ ID NO: 10
83-92 (LYS83, GLU84, ASP85, ILE86, SER87, MET88, ASN89, SER90, VAL91, PRO92) SEQ ID NO: 12
94 (GLN94)
119 (THR119)
122 (CYS122)
125-128 (VAL125, THR126, PRO127, VAL128) SEQ ID NO: 13.

Note that CYS72, SER90, THR119, CYS122 and VAL125 are less than 25% solvent accessible, according to the x-ray structure of IL17F, thus may not directly interact with antibody 496. These residues, however, are likely to support surrounding residues that are making direct contacts with antibody 496.

Therefore antibody 496 is expected to bind IL-17F at one or more of the following residues: SER39, MET40, SER41, ARG42, ARG47, ASN53, ARG73, ASN74, LEU75, LYS83, GLU84, ASP85, ILE86, SER87, MET88, ASN89, VAL91, PRO92, GLN94, THR126, PRO127, VAL128.

Example 7

The interaction between 496 and IL-17f was studied by x-ray crystallography.

Crystallisation, Structure Determination and Refinement of the crystal structure of Human IL17f complexed with 496 Fab

Crystallisation

The human IL17f/496 Fab complex crystallized as pyramids from hanging drops through the vapour phase at 18.5° C. against a reservoir of 500 μl solution containing 0.85M ammonium sulfate, 0.2M sodium potassium tartrate and 0.05M Tris buffer pH 6.9 for 1-2 weeks in Hampton Research VDXm plates. The drops contained 1 μl of protein at 10 mg/ml in 20 mM Hepes pH 7.4, 50 mM NaCl, 0.02% azide, and 1 μl reservoir solution. The crystals belong to the space group H32 with cell dimensions a=b=189.4; c=490.9, and three molecules of the IL17f/496 Fab in the asymmetric unit.

X-Ray Diffraction Collection

We collected the x-ray diffraction data through a single IL17f/496 Fab crystal suspended in a litho loop and flash frozen under liquid nitrogen, after briefly passing the crystal through a cryoprotectant solution containing 1.3M ammonium sulphate, 0.2M sodium potassium tartrate and Tris buffer pH 6.9 and 30% glycerol. The diffraction data was collected on an ADSC Quantum 4 charge coupled device at the 103 beamline station at the Diamond synchrotron, Didcot, Oxfordshire, UK. The wavelength of the monochromatic x-ray beam was 0.9796 Å. The reciprocal space was sampled at 1.0° oscillation steps around the ϕ goniostat axis. The data were processed with Mosflm (Leslie, A G W, Joint CCP4+ESF-EAMCB Newsletter on Protein Crystallography, No. 26; CCP4, Collaborative Computational Project, Number 4. Acta Cryst. D50, 760-763 (1994)).

Structure Determination

The crystal structure of human IL17f/496 Fab complex was determined in two steps. First the Fab position was located with the molecular replacement program Phaser (Read, R J, Acta Cryst. D57, 1373-1382 (2001)), using the Fab with the PDB code 1L7I stripped of water molecules. The cross rotation and translation functions were carried out at 4.0 Å resolution and default settings. Three molecules of Fab were located. The searches after translation translation yielded a solution with a high R-factor of after rigid body refinement in CNX (Brunger, A et al, Science, 235, 458-460 (1997)). Although electron density for IL17f was visible in 2Fo-Fc electron density maps, a molecular replacement solution for IL17f, using IL17f (PDB code 1JPY) was not found. Instead a structure of an IL17a dimer was used to locate this molecule. A solution was found that corresponded to its location along a 2-fold axis. After selecting one half of the IL17a, and overlaying IL17f, a new search model was created that contained one Fab and one half of an IL17f dimer, with resides at the N-terminus removed that caused symmetry clashes. This search model was used to define the final molecular replacement solution for this half-complex.

Model Building and Refinement

The 496 Fab/IL17f structure was built from the rotation and translation operations found by molecular replacement. Using 2Fo-Fc and Fo-Fc electron density maps, residues in the Fab model were changed to reflect the sequence in the 496 Fab. According to these maps, one can establish the 496 Fab rough model by altering side chain conformations, replacing amino acids present in the model structure by those in the 496 Fab as well as by adding or deleting residues. Adjustments in residue conformer orientations were made for IL17f. We used the interactive computer program O (Jones, T A et al., Acta Cryst. A47, 110-119 (1991)) to perform these manipulations.

This rough model was subjected to rounds of simulated annealing, positional and B-factor refinement using CNX, followed by manual intervention. The refinement and manual rebuilding was monitored by the quality of the 2Fo-Fc and Fo-Fc electron density maps as well as the value of the crystallographic R and R-free value. The resolution used through the refinement was increased gradually from 4.0 Å to 3.2 Å as the refinement proceeded, with a bulk solvent correction used throughout. The model of IL17f/496 Fab complex encompasses residues 15 to 133 of IL17f (see SEQ ID NO. 22), residues 1 to 214 of the light chain of 496 Fab (SEQ ID NO 11) and residues 1 to 227 of the heavy chain of 496 Fab (SEQ ID NO 15). The R-factor of the model is 0.243, and R-free is 0.288 for 56128 reflections. The rms deviation from standard geometry (Engh, R et al., Acta Cryst., A47, 392-400 (1991)) is 0.009 Å for bond lengths and 1.48° for bond angles.

The Epitope

The interaction between 496 and IL-17f (which is a covalent homodimer) studied by x-ray crystallography was of a complex of 496 Fab fragments incubated with human IL-17f. The structure reveals the major contact sites between 496 Fab and IL-17f, and were identified as clustered mainly at the CDR loops of the antibody and along part of the length of IL-17f, interacting with both chains of IL-17f. According to the numbering sequence shown in SEQ ID NO. 22 for the mature IL-17f protein, i.e., the IL-17f protein from which the signal peptide has been cleaved, the residues which interact most closely with the CDR region of 496 Fab within 3.0 Å, are Gln71, Cys72, Ile86, Asn89, Ser90 and Val128 from the first chain, and Arg47 from the second chain. Major residues of IL-17f that contact 496 Fab within 3.5 Å are Gln71, Cys72, Asn74, Leu75, Ile86, Asn89, Ser90, Pro92, Val128, His131 and Gln133 from the first chain, and Arg37, Ser39, Ser41 and Arg47 from the second chain. Residues that contact 496 Fab within 4.0 Å are Gln71, Cys72, Arg73, Asn74, Leu75, Ile86, Ser87 Asn89, Ser90, Val91, Pro92, Val128, His131 and Gln133 from the first chain, and Asn33, Gln36, Arg37, Ser39, Ser41, Arg42, Ile44 and Arg47 from the second chain. These residues define the epitope of the 496 antibody.

TABLE 1

The atomic coordinates of IL17F in complex with 496 Fab
(H32; a = 189.4; b = 189.4; c = 490.9, α, β = 90°; γ = 120°)

| | | | | | | | | | | | |
|---|---|---|---|---|---|---|---|---|---|---|---|
| ATOM | 1 | CB | ALA | A | 1 | 64.135 | −69.931 | −35.658 | 1.00 | 101.85 | MOL1 | C |
| ATOM | 2 | C | ALA | A | 1 | 63.428 | −68.932 | −37.846 | 1.00 | 100.38 | MOL1 | C |
| ATOM | 3 | O | ALA | A | 1 | 63.710 | −68.947 | −39.048 | 1.00 | 103.91 | MOL1 | O |
| ATOM | 4 | N | ALA | A | 1 | 64.812 | −67.616 | −36.255 | 1.00 | 97.55 | MOL1 | N |
| ATOM | 5 | CA | ALA | A | 1 | 64.533 | −68.979 | −36.793 | 1.00 | 100.78 | MOL1 | C |
| ATOM | 6 | N | ILE | A | 2 | 62.175 | −68.869 | −37.394 | 1.00 | 93.65 | MOL1 | N |
| ATOM | 7 | CA | ILE | A | 2 | 61.034 | −68.831 | −38.303 | 1.00 | 84.13 | MOL1 | C |
| ATOM | 8 | CB | ILE | A | 2 | 59.767 | −68.352 | −37.603 | 1.00 | 84.62 | MOL1 | C |
| ATOM | 9 | CG2 | ILE | A | 2 | 58.563 | −68.791 | −38.396 | 1.00 | 85.22 | MOL1 | C |
| ATOM | 10 | CG1 | ILE | A | 2 | 59.667 | −68.961 | −36.210 | 1.00 | 89.64 | MOL1 | C |
| ATOM | 11 | CD1 | ILE | A | 2 | 59.427 | −70.445 | −36.220 | 1.00 | 98.49 | MOL1 | C |
| ATOM | 12 | C | ILE | A | 2 | 61.326 | −67.860 | −39.422 | 1.00 | 77.53 | MOL1 | C |
| ATOM | 13 | O | ILE | A | 2 | 61.538 | −66.687 | −39.176 | 1.00 | 75.73 | MOL1 | O |
| ATOM | 14 | N | GLN | A | 3 | 61.335 | −68.350 | −40.650 | 1.00 | 76.57 | MOL1 | N |
| ATOM | 15 | CA | GLN | A | 3 | 61.622 | −67.506 | −41.795 | 1.00 | 82.12 | MOL1 | C |
| ATOM | 16 | CB | GLN | A | 3 | 62.718 | −68.157 | −42.649 | 1.00 | 92.76 | MOL1 | C |
| ATOM | 17 | CG | GLN | A | 3 | 64.019 | −68.483 | −41.902 | 1.00 | 101.08 | MOL1 | C |
| ATOM | 18 | CD | GLN | A | 3 | 65.144 | −67.494 | −42.192 | 1.00 | 106.71 | MOL1 | C |
| ATOM | 19 | OE1 | GLN | A | 3 | 65.504 | −67.266 | −43.353 | 1.00 | 109.71 | MOL1 | O |
| ATOM | 20 | NE2 | GLN | A | 3 | 65.711 | −66.911 | −41.138 | 1.00 | 104.54 | MOL1 | N |
| ATOM | 21 | C | GLN | A | 3 | 60.369 | −67.277 | −42.642 | 1.00 | 81.94 | MOL1 | C |
| ATOM | 22 | O | GLN | A | 3 | 59.813 | −68.215 | −43.222 | 1.00 | 85.46 | MOL1 | O |
| ATOM | 23 | N | LEU | A | 4 | 59.929 | −66.027 | −42.718 | 1.00 | 77.54 | MOL1 | N |
| ATOM | 24 | CA | LEU | A | 4 | 58.748 | −65.707 | −43.498 | 1.00 | 76.02 | MOL1 | C |
| ATOM | 25 | CB | LEU | A | 4 | 57.995 | −64.531 | −42.867 | 1.00 | 77.03 | MOL1 | C |
| ATOM | 26 | CG | LEU | A | 4 | 57.134 | −64.833 | −41.631 | 1.00 | 77.01 | MOL1 | C |
| ATOM | 27 | CD1 | LEU | A | 4 | 58.004 | −65.184 | −40.445 | 1.00 | 72.40 | MOL1 | C |
| ATOM | 28 | CD2 | LEU | A | 4 | 56.279 | −63.620 | −41.307 | 1.00 | 75.95 | MOL1 | C |
| ATOM | 29 | C | LEU | A | 4 | 59.123 | −65.402 | −44.944 | 1.00 | 76.62 | MOL1 | C |
| ATOM | 30 | O | LEU | A | 4 | 60.057 | −64.649 | −45.220 | 1.00 | 78.44 | MOL1 | O |
| ATOM | 31 | N | THR | A | 5 | 58.379 | −65.986 | −45.872 | 1.00 | 76.08 | MOL1 | N |
| ATOM | 32 | CA | THR | A | 5 | 58.668 | −65.805 | −47.281 | 1.00 | 77.89 | MOL1 | C |
| ATOM | 33 | CB | THR | A | 5 | 59.111 | −67.158 | −47.884 | 1.00 | 86.00 | MOL1 | C |
| ATOM | 34 | OG1 | THR | A | 5 | 60.135 | −67.731 | −47.054 | 1.00 | 85.74 | MOL1 | O |
| ATOM | 35 | CG2 | THR | A | 5 | 59.642 | −66.978 | −49.307 | 1.00 | 86.71 | MOL1 | C |
| ATOM | 36 | C | THR | A | 5 | 57.485 | −65.246 | −48.068 | 1.00 | 74.23 | MOL1 | C |
| ATOM | 37 | O | THR | A | 5 | 56.634 | −65.998 | −48.559 | 1.00 | 76.11 | MOL1 | O |
| ATOM | 38 | N | GLN | A | 6 | 57.434 | −63.926 | −48.191 | 1.00 | 67.23 | MOL1 | N |
| ATOM | 39 | CA | GLN | A | 6 | 56.353 | −63.292 | −48.928 | 1.00 | 66.03 | MOL1 | C |
| ATOM | 40 | CB | GLN | A | 6 | 56.383 | −61.786 | −48.732 | 1.00 | 60.93 | MOL1 | C |
| ATOM | 41 | CG | GLN | A | 6 | 56.267 | −61.364 | −47.295 | 1.00 | 59.07 | MOL1 | C |
| ATOM | 42 | CD | GLN | A | 6 | 55.893 | −59.916 | −47.174 | 1.00 | 60.94 | MOL1 | C |
| ATOM | 43 | OE1 | GLN | A | 6 | 55.813 | −59.381 | −46.076 | 1.00 | 66.71 | MOL1 | O |
| ATOM | 44 | NE2 | GLN | A | 6 | 55.651 | −59.269 | −48.309 | 1.00 | 54.84 | MOL1 | N |
| ATOM | 45 | C | GLN | A | 6 | 56.500 | −63.599 | −50.398 | 1.00 | 67.13 | MOL1 | C |
| ATOM | 46 | O | GLN | A | 6 | 57.566 | −64.008 | −50.840 | 1.00 | 69.36 | MOL1 | O |
| ATOM | 47 | N | SER | A | 7 | 55.430 | −63.396 | −51.156 | 1.00 | 69.44 | MOL1 | N |
| ATOM | 48 | CA | SER | A | 7 | 55.450 | −63.654 | −52.591 | 1.00 | 72.19 | MOL1 | C |
| ATOM | 49 | CB | SER | A | 7 | 55.687 | −65.142 | −52.863 | 1.00 | 75.98 | MOL1 | C |
| ATOM | 50 | OG | SER | A | 7 | 54.856 | −65.954 | −52.047 | 1.00 | 81.94 | MOL1 | O |

TABLE 1-continued

The atomic coordinates of IL17F in complex with 496 Fab
(H32; a = 189.4; b = 189.4; c = 490.9, α, β = 90°; γ = 120°)

| ATOM | 51 | C | SER | A | 7 | 54.147 | −63.217 | −53.228 | 1.00 | 72.06 | MOL1 | C |
|---|---|---|---|---|---|---|---|---|---|---|---|---|
| ATOM | 52 | O | SER | A | 7 | 53.071 | −63.493 | −52.707 | 1.00 | 78.33 | MOL1 | O |
| ATOM | 53 | N | PRO | A | 8 | 54.227 | −62.516 | −54.361 | 1.00 | 69.31 | MOL1 | N |
| ATOM | 54 | CD | PRO | A | 8 | 53.099 | −62.002 | −55.147 | 1.00 | 73.31 | MOL1 | C |
| ATOM | 55 | CA | PRO | A | 8 | 55.483 | −62.155 | −55.002 | 1.00 | 70.91 | MOL1 | C |
| ATOM | 56 | CB | PRO | A | 8 | 55.025 | −61.554 | −56.323 | 1.00 | 72.80 | MOL1 | C |
| ATOM | 57 | CG | PRO | A | 8 | 53.757 | −60.910 | −55.950 | 1.00 | 72.88 | MOL1 | C |
| ATOM | 58 | C | PRO | A | 8 | 56.259 | −61.164 | −54.164 | 1.00 | 69.23 | MOL1 | C |
| ATOM | 59 | O | PRO | A | 8 | 55.781 | −60.717 | −53.132 | 1.00 | 70.34 | MOL1 | O |
| ATOM | 60 | N | SER | A | 9 | 57.467 | −60.838 | −54.601 | 1.00 | 69.17 | MOL1 | N |
| ATOM | 61 | CA | SER | A | 9 | 58.273 | −59.881 | −53.879 | 1.00 | 66.93 | MOL1 | C |
| ATOM | 62 | CB | SER | A | 9 | 59.749 | −60.210 | −54.018 | 1.00 | 73.37 | MOL1 | C |
| ATOM | 63 | OG | SER | A | 9 | 60.038 | −61.381 | −53.269 | 1.00 | 83.72 | MOL1 | O |
| ATOM | 64 | C | SER | A | 9 | 57.951 | −58.524 | −54.453 | 1.00 | 63.36 | MOL1 | C |
| ATOM | 65 | O | SER | A | 9 | 58.048 | −57.512 | −53.777 | 1.00 | 67.00 | MOL1 | O |
| ATOM | 66 | N | SER | A | 10 | 57.544 | −58.512 | −55.708 | 1.00 | 57.29 | MOL1 | N |
| ATOM | 67 | CA | SER | A | 10 | 57.151 | −57.276 | −56.358 | 1.00 | 55.01 | MOL1 | C |
| ATOM | 68 | CB | SER | A | 10 | 58.253 | −56.771 | −57.294 | 1.00 | 57.78 | MOL1 | C |
| ATOM | 69 | OG | SER | A | 10 | 57.805 | −55.674 | −58.082 | 1.00 | 62.00 | MOL1 | O |
| ATOM | 70 | C | SER | A | 10 | 55.911 | −57.621 | −57.159 | 1.00 | 55.31 | MOL1 | C |
| ATOM | 71 | O | SER | A | 10 | 55.526 | −58.787 | −57.245 | 1.00 | 56.46 | MOL1 | O |
| ATOM | 72 | N | LEU | A | 11 | 55.281 | −56.613 | −57.742 | 1.00 | 53.75 | MOL1 | N |
| ATOM | 73 | CA | LEU | A | 11 | 54.098 | −56.851 | −58.548 | 1.00 | 50.55 | MOL1 | C |
| ATOM | 74 | CB | LEU | A | 11 | 53.090 | −57.669 | −57.754 | 1.00 | 43.48 | MOL1 | C |
| ATOM | 75 | CG | LEU | A | 11 | 51.993 | −56.877 | −57.070 | 1.00 | 44.84 | MOL1 | C |
| ATOM | 76 | CD1 | LEU | A | 11 | 50.917 | −56.523 | −58.096 | 1.00 | 49.00 | MOL1 | C |
| ATOM | 77 | CD2 | LEU | A | 11 | 51.412 | −57.704 | −55.952 | 1.00 | 42.51 | MOL1 | C |
| ATOM | 78 | C | LEU | A | 11 | 53.478 | −55.536 | −59.002 | 1.00 | 50.49 | MOL1 | C |
| ATOM | 79 | O | LEU | A | 11 | 53.350 | −54.595 | −58.225 | 1.00 | 44.62 | MOL1 | O |
| ATOM | 80 | N | SER | A | 12 | 53.111 | −55.471 | −60.275 | 1.00 | 56.63 | MOL1 | N |
| ATOM | 81 | CA | SER | A | 12 | 52.491 | −54.273 | −60.825 | 1.00 | 62.24 | MOL1 | C |
| ATOM | 82 | CB | SER | A | 12 | 53.076 | −53.922 | −62.199 | 1.00 | 63.67 | MOL1 | C |
| ATOM | 83 | OG | SER | A | 12 | 54.373 | −53.355 | −62.082 | 1.00 | 74.97 | MOL1 | O |
| ATOM | 84 | C | SER | A | 12 | 51.001 | −54.519 | −60.960 | 1.00 | 62.36 | MOL1 | C |
| ATOM | 85 | O | SER | A | 12 | 50.573 | −55.593 | −61.383 | 1.00 | 66.42 | MOL1 | O |
| ATOM | 86 | N | ALA | A | 13 | 50.216 | −53.517 | −60.593 | 1.00 | 60.34 | MOL1 | N |
| ATOM | 87 | CA | ALA | A | 13 | 48.768 | −53.613 | −60.654 | 1.00 | 56.37 | MOL1 | C |
| ATOM | 88 | CB | ALA | A | 13 | 48.232 | −54.119 | −59.330 | 1.00 | 52.68 | MOL1 | C |
| ATOM | 89 | C | ALA | A | 13 | 48.196 | −52.241 | −60.964 | 1.00 | 57.76 | MOL1 | C |
| ATOM | 90 | O | ALA | A | 13 | 48.927 | −51.236 | −60.931 | 1.00 | 56.32 | MOL1 | O |
| ATOM | 91 | N | SER | A | 14 | 46.895 | −52.204 | −61.263 | 1.00 | 56.07 | MOL1 | N |
| ATOM | 92 | CA | SER | A | 14 | 46.202 | −50.957 | −61.594 | 1.00 | 58.55 | MOL1 | C |
| ATOM | 93 | CB | SER | A | 14 | 45.601 | −51.052 | −62.987 | 1.00 | 58.96 | MOL1 | C |
| ATOM | 94 | OG | SER | A | 14 | 46.285 | −52.023 | −63.759 | 1.00 | 71.46 | MOL1 | O |
| ATOM | 95 | C | SER | A | 14 | 45.089 | −50.686 | −60.596 | 1.00 | 55.27 | MOL1 | C |
| ATOM | 96 | O | SER | A | 14 | 44.547 | −51.621 | −60.008 | 1.00 | 53.63 | MOL1 | O |
| ATOM | 97 | N | VAL | A | 15 | 44.748 | −49.411 | −60.407 | 1.00 | 52.20 | MOL1 | N |
| ATOM | 98 | CA | VAL | A | 15 | 43.687 | −49.047 | −59.472 | 1.00 | 45.77 | MOL1 | C |
| ATOM | 99 | CB | VAL | A | 15 | 43.201 | −47.592 | −59.665 | 1.00 | 37.82 | MOL1 | C |
| ATOM | 100 | CG1 | VAL | A | 15 | 42.027 | −47.348 | −58.802 | 1.00 | 32.20 | MOL1 | C |
| ATOM | 101 | CG2 | VAL | A | 15 | 44.273 | −46.607 | −59.305 | 1.00 | 34.78 | MOL1 | C |
| ATOM | 102 | C | VAL | A | 15 | 42.489 | −49.966 | −59.685 | 1.00 | 48.79 | MOL1 | C |
| ATOM | 103 | O | VAL | A | 15 | 42.048 | −50.197 | −60.819 | 1.00 | 49.28 | MOL1 | O |
| ATOM | 104 | N | GLY | A | 16 | 41.973 | −50.504 | −58.592 | 1.00 | 45.79 | MOL1 | N |
| ATOM | 105 | CA | GLY | A | 16 | 40.830 | −51.373 | −58.703 | 1.00 | 52.21 | MOL1 | C |
| ATOM | 106 | C | GLY | A | 16 | 41.181 | −52.836 | −58.601 | 1.00 | 56.48 | MOL1 | C |
| ATOM | 107 | O | GLY | A | 16 | 40.444 | −53.606 | −57.979 | 1.00 | 63.88 | MOL1 | O |
| ATOM | 108 | N | ASP | A | 17 | 42.290 | −53.233 | −59.215 | 1.00 | 55.01 | MOL1 | N |
| ATOM | 109 | CA | ASP | A | 17 | 42.716 | −54.635 | −59.164 | 1.00 | 58.91 | MOL1 | C |
| ATOM | 110 | CB | ASP | A | 17 | 44.180 | −54.760 | −59.601 | 1.00 | 65.37 | MOL1 | C |
| ATOM | 111 | CG | ASP | A | 17 | 44.367 | −54.622 | −61.100 | 1.00 | 70.44 | MOL1 | C |
| ATOM | 112 | OD1 | ASP | A | 17 | 45.147 | −53.733 | −61.531 | 1.00 | 59.18 | MOL1 | O |
| ATOM | 113 | OD2 | ASP | A | 17 | 43.742 | −55.421 | −61.836 | 1.00 | 74.78 | MOL1 | O |
| ATOM | 114 | C | ASP | A | 17 | 42.575 | −55.254 | −57.761 | 1.00 | 54.18 | MOL1 | C |
| ATOM | 115 | O | ASP | A | 17 | 42.559 | −54.547 | −56.761 | 1.00 | 55.66 | MOL1 | O |
| ATOM | 116 | N | ARG | A | 18 | 42.462 | −56.571 | −57.693 | 1.00 | 48.09 | MOL1 | N |
| ATOM | 117 | CA | ARG | A | 18 | 42.366 | −57.231 | −56.411 | 1.00 | 55.61 | MOL1 | C |
| ATOM | 118 | CB | ARG | A | 18 | 41.284 | −58.316 | −56.404 | 1.00 | 69.85 | MOL1 | C |
| ATOM | 119 | CG | ARG | A | 18 | 41.140 | −59.019 | −55.033 | 1.00 | 84.25 | MOL1 | C |
| ATOM | 120 | CD | ARG | A | 18 | 40.007 | −60.048 | −54.994 | 1.00 | 96.26 | MOL1 | C |
| ATOM | 121 | NE | ARG | A | 18 | 40.377 | −61.322 | −55.613 | 1.00 | 111.22 | MOL1 | N |
| ATOM | 122 | CZ | ARG | A | 18 | 40.792 | −62.397 | −54.941 | 1.00 | 117.53 | MOL1 | C |
| ATOM | 123 | NH1 | ARG | A | 18 | 40.889 | −62.360 | −53.615 | 1.00 | 117.33 | MOL1 | N |
| ATOM | 124 | NH2 | ARG | A | 18 | 41.110 | −63.514 | −55.596 | 1.00 | 116.29 | MOL1 | N |
| ATOM | 125 | C | ARG | A | 18 | 43.710 | −57.871 | −56.135 | 1.00 | 58.76 | MOL1 | C |
| ATOM | 126 | O | ARG | A | 18 | 43.918 | −59.053 | −56.418 | 1.00 | 65.72 | MOL1 | O |
| ATOM | 127 | N | VAL | A | 19 | 44.628 | −57.086 | −55.588 | 1.00 | 56.07 | MOL1 | N |

TABLE 1-continued

The atomic coordinates of IL17F in complex with 496 Fab
(H32; a = 189.4; b = 189.4; c = 490.9, α, β = 90°; γ = 120°)

| ATOM | 128 | CA  | VAL | A | 19 | 45.966 | −57.576 | −55.268 | 1.00 | 53.63  | MOL1 | C |
|------|-----|-----|-----|---|----|--------|---------|---------|------|--------|------|---|
| ATOM | 129 | CB  | VAL | A | 19 | 46.908 | −56.394 | −54.920 | 1.00 | 55.93  | MOL1 | C |
| ATOM | 130 | CG1 | VAL | A | 19 | 48.281 | −56.927 | −54.521 | 1.00 | 55.97  | MOL1 | C |
| ATOM | 131 | CG2 | VAL | A | 19 | 47.004 | −55.420 | −56.108 | 1.00 | 42.74  | MOL1 | C |
| ATOM | 132 | C   | VAL | A | 19 | 45.964 | −58.593 | −54.112 | 1.00 | 51.70  | MOL1 | C |
| ATOM | 133 | O   | VAL | A | 19 | 45.146 | −58.511 | −53.190 | 1.00 | 49.50  | MOL1 | O |
| ATOM | 134 | N   | THR | A | 20 | 46.885 | −59.549 | −54.172 | 1.00 | 49.46  | MOL1 | N |
| ATOM | 135 | CA  | THR | A | 20 | 46.983 | −60.583 | −53.149 | 1.00 | 54.36  | MOL1 | C |
| ATOM | 136 | CB  | THR | A | 20 | 46.232 | −61.841 | −53.579 | 1.00 | 58.85  | MOL1 | C |
| ATOM | 137 | OG1 | THR | A | 20 | 44.838 | −61.542 | −53.667 | 1.00 | 70.14  | MOL1 | O |
| ATOM | 138 | CG2 | THR | A | 20 | 46.450 | −62.967 | −52.576 | 1.00 | 59.96  | MOL1 | C |
| ATOM | 139 | C   | THR | A | 20 | 48.427 | −60.973 | −52.863 | 1.00 | 53.08  | MOL1 | C |
| ATOM | 140 | O   | THR | A | 20 | 49.137 | −61.449 | −53.736 | 1.00 | 55.72  | MOL1 | O |
| ATOM | 141 | N   | ILE | A | 21 | 48.849 | −60.783 | −51.626 | 1.00 | 49.50  | MOL1 | N |
| ATOM | 142 | CA  | ILE | A | 21 | 50.201 | −61.088 | −51.217 | 1.00 | 41.41  | MOL1 | C |
| ATOM | 143 | CB  | ILE | A | 21 | 50.802 | −59.884 | −50.503 | 1.00 | 38.15  | MOL1 | C |
| ATOM | 144 | CG2 | ILE | A | 21 | 52.083 | −60.247 | −49.827 | 1.00 | 34.27  | MOL1 | C |
| ATOM | 145 | CG1 | ILE | A | 21 | 51.001 | −58.760 | −51.510 | 1.00 | 38.51  | MOL1 | C |
| ATOM | 146 | CD1 | ILE | A | 21 | 51.246 | −57.416 | −50.864 | 1.00 | 49.11  | MOL1 | C |
| ATOM | 147 | C   | ILE | A | 21 | 50.140 | −62.268 | −50.285 | 1.00 | 44.55  | MOL1 | C |
| ATOM | 148 | O   | ILE | A | 21 | 49.183 | −62.428 | −49.550 | 1.00 | 52.97  | MOL1 | O |
| ATOM | 149 | N   | THR | A | 22 | 51.169 | −63.095 | −50.310 | 1.00 | 48.57  | MOL1 | N |
| ATOM | 150 | CA  | THR | A | 22 | 51.210 | −64.278 | −49.467 | 1.00 | 52.07  | MOL1 | C |
| ATOM | 151 | CB  | THR | A | 22 | 51.296 | −65.552 | −50.308 | 1.00 | 55.40  | MOL1 | C |
| ATOM | 152 | OG1 | THR | A | 22 | 50.290 | −65.514 | −51.325 | 1.00 | 62.21  | MOL1 | O |
| ATOM | 153 | CG2 | THR | A | 22 | 51.090 | −66.788 | −49.435 | 1.00 | 58.38  | MOL1 | C |
| ATOM | 154 | C   | THR | A | 22 | 52.435 | −64.240 | −48.597 | 1.00 | 51.61  | MOL1 | C |
| ATOM | 155 | O   | THR | A | 22 | 53.390 | −63.554 | −48.912 | 1.00 | 50.06  | MOL1 | O |
| ATOM | 156 | N   | CYS | A | 23 | 52.420 | −65.001 | −47.512 | 1.00 | 56.21  | MOL1 | N |
| ATOM | 157 | CA  | CYS | A | 23 | 53.560 | −65.048 | −46.609 | 1.00 | 62.68  | MOL1 | C |
| ATOM | 158 | C   | CYS | A | 23 | 53.660 | −66.404 | −45.926 | 1.00 | 68.74  | MOL1 | C |
| ATOM | 159 | O   | CYS | A | 23 | 53.256 | −66.566 | −44.778 | 1.00 | 68.17  | MOL1 | O |
| ATOM | 160 | CB  | CYS | A | 23 | 53.441 | −63.935 | −45.571 | 1.00 | 65.09  | MOL1 | C |
| ATOM | 161 | SG  | CYS | A | 23 | 54.612 | −63.909 | −44.165 | 1.00 | 70.81  | MOL1 | S |
| ATOM | 162 | N   | ARG | A | 24 | 54.201 | −67.377 | −46.652 | 1.00 | 77.18  | MOL1 | N |
| ATOM | 163 | CA  | ARG | A | 24 | 54.379 | −68.736 | −46.147 | 1.00 | 84.44  | MOL1 | C |
| ATOM | 164 | CB  | ARG | A | 24 | 54.742 | −69.656 | −47.332 | 1.00 | 95.87  | MOL1 | C |
| ATOM | 165 | CG  | ARG | A | 24 | 54.432 | −71.160 | −47.168 | 1.00 | 108.89 | MOL1 | C |
| ATOM | 166 | CD  | ARG | A | 24 | 55.506 | −71.938 | −46.383 | 1.00 | 119.33 | MOL1 | C |
| ATOM | 167 | NE  | ARG | A | 24 | 55.120 | −73.333 | −46.140 | 1.00 | 124.33 | MOL1 | N |
| ATOM | 168 | CZ  | ARG | A | 24 | 55.845 | −74.215 | −45.452 | 1.00 | 127.65 | MOL1 | C |
| ATOM | 169 | NH1 | ARG | A | 24 | 57.012 | −73.863 | −44.927 | 1.00 | 129.22 | MOL1 | N |
| ATOM | 170 | NH2 | ARG | A | 24 | 55.397 | −75.454 | −45.277 | 1.00 | 127.95 | MOL1 | N |
| ATOM | 171 | C   | ARG | A | 24 | 55.511 | −68.687 | −45.111 | 1.00 | 84.04  | MOL1 | C |
| ATOM | 172 | O   | ARG | A | 24 | 56.466 | −67.926 | −45.271 | 1.00 | 84.20  | MOL1 | O |
| ATOM | 173 | N   | ALA | A | 25 | 55.416 | −69.484 | −44.051 | 1.00 | 83.87  | MOL1 | N |
| ATOM | 174 | CA  | ALA | A | 25 | 56.461 | −69.462 | −43.031 | 1.00 | 88.97  | MOL1 | C |
| ATOM | 175 | CB  | ALA | A | 25 | 55.987 | −68.685 | −41.807 | 1.00 | 83.58  | MOL1 | C |
| ATOM | 176 | C   | ALA | A | 25 | 57.012 | −70.808 | −42.583 | 1.00 | 93.69  | MOL1 | C |
| ATOM | 177 | O   | ALA | A | 25 | 56.280 | −71.784 | −42.408 | 1.00 | 93.21  | MOL1 | O |
| ATOM | 178 | N   | ASP | A | 26 | 58.327 | −70.813 | −42.395 | 1.00 | 98.19  | MOL1 | N |
| ATOM | 179 | CA  | ASP | A | 26 | 59.114 | −71.947 | −41.937 | 1.00 | 101.85 | MOL1 | C |
| ATOM | 180 | CB  | ASP | A | 26 | 60.324 | −71.372 | −41.202 | 1.00 | 110.27 | MOL1 | C |
| ATOM | 181 | CG  | ASP | A | 26 | 61.348 | −72.408 | −40.854 | 1.00 | 121.51 | MOL1 | C |
| ATOM | 182 | OD1 | ASP | A | 26 | 62.404 | −72.014 | −40.315 | 1.00 | 124.97 | MOL1 | O |
| ATOM | 183 | OD2 | ASP | A | 26 | 61.102 | −73.607 | −41.114 | 1.00 | 133.17 | MOL1 | O |
| ATOM | 184 | C   | ASP | A | 26 | 58.330 | −72.912 | −41.031 | 1.00 | 101.21 | MOL1 | C |
| ATOM | 185 | O   | ASP | A | 26 | 57.944 | −74.006 | −41.455 | 1.00 | 100.34 | MOL1 | O |
| ATOM | 186 | N   | GLU | A | 27 | 58.111 | −72.498 | −39.786 | 1.00 | 100.36 | MOL1 | N |
| ATOM | 187 | CA  | GLU | A | 27 | 57.378 | −73.295 | −38.808 | 1.00 | 105.27 | MOL1 | C |
| ATOM | 188 | CB  | GLU | A | 27 | 58.046 | −73.174 | −37.434 | 1.00 | 114.82 | MOL1 | C |
| ATOM | 189 | CG  | GLU | A | 27 | 59.493 | −73.679 | −37.373 | 1.00 | 130.16 | MOL1 | C |
| ATOM | 190 | CD  | GLU | A | 27 | 59.608 | −75.187 | −37.133 | 1.00 | 139.75 | MOL1 | C |
| ATOM | 191 | OE1 | GLU | A | 27 | 59.170 | −75.660 | −36.058 | 1.00 | 142.50 | MOL1 | O |
| ATOM | 192 | OE2 | GLU | A | 27 | 60.144 | −75.898 | −38.017 | 1.00 | 142.27 | MOL1 | O |
| ATOM | 193 | C   | GLU | A | 27 | 55.920 | −72.825 | −38.719 | 1.00 | 103.78 | MOL1 | C |
| ATOM | 194 | O   | GLU | A | 27 | 55.398 | −72.228 | −39.663 | 1.00 | 105.79 | MOL1 | O |
| ATOM | 195 | N   | SER | A | 28 | 55.270 | −73.097 | −37.587 | 1.00 | 98.98  | MOL1 | N |
| ATOM | 196 | CA  | SER | A | 28 | 53.876 | −72.706 | −37.377 | 1.00 | 93.29  | MOL1 | C |
| ATOM | 197 | CB  | SER | A | 28 | 53.077 | −73.882 | −36.796 | 1.00 | 94.85  | MOL1 | C |
| ATOM | 198 | OG  | SER | A | 28 | 51.722 | −73.537 | −36.538 | 1.00 | 86.40  | MOL1 | O |
| ATOM | 199 | C   | SER | A | 28 | 53.804 | −71.523 | −36.426 | 1.00 | 89.30  | MOL1 | C |
| ATOM | 200 | O   | SER | A | 28 | 54.496 | −71.499 | −35.418 | 1.00 | 88.29  | MOL1 | O |
| ATOM | 201 | N   | VAL | A | 29 | 52.960 | −70.548 | −36.742 | 1.00 | 85.47  | MOL1 | N |
| ATOM | 202 | CA  | VAL | A | 29 | 52.824 | −69.375 | −35.895 | 1.00 | 80.22  | MOL1 | C |
| ATOM | 203 | CB  | VAL | A | 29 | 53.247 | −68.131 | −36.651 | 1.00 | 79.07  | MOL1 | C |
| ATOM | 204 | CG1 | VAL | A | 29 | 54.746 | −67.943 | −36.514 | 1.00 | 74.72  | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 205 | CG2 | VAL | A | 29 | 52.870 | −68.278 | −38.111 | 1.00 | 74.69 | MOL1 | C |
|---|---|---|---|---|---|---|---|---|---|---|---|---|
| ATOM | 206 | C | VAL | A | 29 | 51.433 | −69.174 | −35.317 | 1.00 | 79.76 | MOL1 | C |
| ATOM | 207 | O | VAL | A | 29 | 51.265 | −68.406 | −34.377 | 1.00 | 81.49 | MOL1 | O |
| ATOM | 208 | N | THR | A | 30 | 50.441 | −69.854 | −35.886 | 1.00 | 78.92 | MOL1 | N |
| ATOM | 209 | CA | THR | A | 30 | 49.066 | −69.788 | −35.395 | 1.00 | 76.47 | MOL1 | C |
| ATOM | 210 | CB | THR | A | 30 | 48.880 | −70.697 | −34.149 | 1.00 | 81.34 | MOL1 | C |
| ATOM | 211 | OG1 | THR | A | 30 | 49.772 | −70.277 | −33.101 | 1.00 | 70.40 | MOL1 | O |
| ATOM | 212 | CG2 | THR | A | 30 | 49.159 | −72.154 | −34.501 | 1.00 | 88.52 | MOL1 | C |
| ATOM | 213 | C | THR | A | 30 | 48.560 | −68.414 | −34.995 | 1.00 | 72.85 | MOL1 | C |
| ATOM | 214 | O | THR | A | 30 | 48.860 | −67.931 | −33.910 | 1.00 | 77.37 | MOL1 | O |
| ATOM | 215 | N | THR | A | 31 | 47.780 | −67.792 | −35.859 | 1.00 | 65.58 | MOL1 | N |
| ATOM | 216 | CA | THR | A | 31 | 47.204 | −66.490 | −35.554 | 1.00 | 65.07 | MOL1 | C |
| ATOM | 217 | CB | THR | A | 31 | 46.132 | −66.605 | −34.447 | 1.00 | 62.31 | MOL1 | C |
| ATOM | 218 | OG1 | THR | A | 31 | 46.758 | −66.543 | −33.161 | 1.00 | 62.48 | MOL1 | O |
| ATOM | 219 | CG2 | THR | A | 31 | 45.375 | −67.912 | −34.576 | 1.00 | 59.69 | MOL1 | C |
| ATOM | 220 | C | THR | A | 31 | 48.144 | −65.340 | −35.168 | 1.00 | 63.64 | MOL1 | C |
| ATOM | 221 | O | THR | A | 31 | 47.730 | −64.175 | −35.226 | 1.00 | 69.01 | MOL1 | O |
| ATOM | 222 | N | LEU | A | 32 | 49.386 | −65.628 | −34.773 | 1.00 | 53.42 | MOL1 | N |
| ATOM | 223 | CA | LEU | A | 32 | 50.282 | −64.535 | −34.409 | 1.00 | 46.42 | MOL1 | C |
| ATOM | 224 | CB | LEU | A | 32 | 51.263 | −64.942 | −33.314 | 1.00 | 39.87 | MOL1 | C |
| ATOM | 225 | CG | LEU | A | 32 | 50.570 | −65.258 | −31.986 | 1.00 | 46.68 | MOL1 | C |
| ATOM | 226 | CD1 | LEU | A | 32 | 51.221 | −64.518 | −30.820 | 1.00 | 43.33 | MOL1 | C |
| ATOM | 227 | CD2 | LEU | A | 32 | 49.117 | −64.863 | −32.109 | 1.00 | 44.87 | MOL1 | C |
| ATOM | 228 | C | LEU | A | 32 | 51.040 | −63.975 | −35.598 | 1.00 | 46.61 | MOL1 | C |
| ATOM | 229 | O | LEU | A | 32 | 52.238 | −63.738 | −35.533 | 1.00 | 52.07 | MOL1 | O |
| ATOM | 230 | N | MET | A | 33 | 50.322 | −63.762 | −36.690 | 1.00 | 43.06 | MOL1 | N |
| ATOM | 231 | CA | MET | A | 33 | 50.889 | −63.191 | −37.889 | 1.00 | 41.75 | MOL1 | C |
| ATOM | 232 | CB | MET | A | 33 | 50.483 | −64.018 | −39.096 | 1.00 | 41.68 | MOL1 | C |
| ATOM | 233 | CG | MET | A | 33 | 51.029 | −63.483 | −40.389 | 1.00 | 51.79 | MOL1 | C |
| ATOM | 234 | SD | MET | A | 33 | 52.828 | −63.453 | −40.386 | 1.00 | 67.13 | MOL1 | S |
| ATOM | 235 | CE | MET | A | 33 | 53.193 | −64.771 | −41.526 | 1.00 | 56.01 | MOL1 | C |
| ATOM | 236 | C | MET | A | 33 | 50.293 | −61.789 | −37.983 | 1.00 | 43.97 | MOL1 | C |
| ATOM | 237 | O | MET | A | 33 | 49.131 | −61.584 | −37.651 | 1.00 | 45.70 | MOL1 | O |
| ATOM | 238 | N | HIS | A | 34 | 51.082 | −60.819 | −38.426 | 1.00 | 43.67 | MOL1 | N |
| ATOM | 239 | CA | HIS | A | 34 | 50.606 | −59.449 | −38.530 | 1.00 | 39.94 | MOL1 | C |
| ATOM | 240 | CB | HIS | A | 34 | 51.145 | −58.649 | −37.367 | 1.00 | 35.91 | MOL1 | C |
| ATOM | 241 | CG | HIS | A | 34 | 51.087 | −59.377 | −36.065 | 1.00 | 40.27 | MOL1 | C |
| ATOM | 242 | CD2 | HIS | A | 34 | 52.053 | −59.680 | −35.168 | 1.00 | 41.79 | MOL1 | C |
| ATOM | 243 | ND1 | HIS | A | 34 | 49.913 | −59.870 | −35.542 | 1.00 | 44.64 | MOL1 | N |
| ATOM | 244 | CE1 | HIS | A | 34 | 50.158 | −60.439 | −34.376 | 1.00 | 42.55 | MOL1 | C |
| ATOM | 245 | NE2 | HIS | A | 34 | 51.449 | −60.337 | −34.126 | 1.00 | 40.07 | MOL1 | N |
| ATOM | 246 | C | HIS | A | 34 | 51.081 | −58.825 | −39.825 | 1.00 | 45.33 | MOL1 | C |
| ATOM | 247 | O | HIS | A | 34 | 51.997 | −59.330 | −40.447 | 1.00 | 56.68 | MOL1 | O |
| ATOM | 248 | N | TRP | A | 35 | 50.468 | −57.728 | −40.243 | 1.00 | 46.73 | MOL1 | N |
| ATOM | 249 | CA | TRP | A | 35 | 50.897 | −57.072 | −41.468 | 1.00 | 41.10 | MOL1 | C |
| ATOM | 250 | CB | TRP | A | 35 | 49.885 | −57.289 | −42.575 | 1.00 | 44.24 | MOL1 | C |
| ATOM | 251 | CG | TRP | A | 35 | 49.856 | −58.687 | −43.087 | 1.00 | 47.88 | MOL1 | C |
| ATOM | 252 | CD2 | TRP | A | 35 | 50.552 | −59.193 | −44.232 | 1.00 | 49.52 | MOL1 | C |
| ATOM | 253 | CE2 | TRP | A | 35 | 50.216 | −60.552 | −44.354 | 1.00 | 49.33 | MOL1 | C |
| ATOM | 254 | CE3 | TRP | A | 35 | 51.430 | −58.628 | −45.162 | 1.00 | 49.53 | MOL1 | C |
| ATOM | 255 | CD1 | TRP | A | 35 | 49.156 | −59.729 | −42.574 | 1.00 | 44.24 | MOL1 | C |
| ATOM | 256 | NE1 | TRP | A | 35 | 49.360 | −60.855 | −43.329 | 1.00 | 47.22 | MOL1 | N |
| ATOM | 257 | CZ2 | TRP | A | 35 | 50.723 | −61.358 | −45.370 | 1.00 | 50.90 | MOL1 | C |
| ATOM | 258 | CZ3 | TRP | A | 35 | 51.935 | −59.428 | −46.168 | 1.00 | 52.17 | MOL1 | C |
| ATOM | 259 | CH2 | TRP | A | 35 | 51.580 | −60.781 | −46.265 | 1.00 | 52.09 | MOL1 | C |
| ATOM | 260 | C | TRP | A | 35 | 51.106 | −55.592 | −41.280 | 1.00 | 39.10 | MOL1 | C |
| ATOM | 261 | O | TRP | A | 35 | 50.346 | −54.931 | −40.592 | 1.00 | 44.85 | MOL1 | O |
| ATOM | 262 | N | TYR | A | 36 | 52.154 | −55.076 | −41.896 | 1.00 | 37.01 | MOL1 | N |
| ATOM | 263 | CA | TYR | A | 36 | 52.477 | −53.659 | −41.818 | 1.00 | 34.30 | MOL1 | C |
| ATOM | 264 | CB | TYR | A | 36 | 53.802 | −53.452 | −41.096 | 1.00 | 26.67 | MOL1 | C |
| ATOM | 265 | CG | TYR | A | 36 | 53.852 | −53.935 | −39.675 | 1.00 | 29.74 | MOL1 | C |
| ATOM | 266 | CD1 | TYR | A | 36 | 53.482 | −53.108 | −38.630 | 1.00 | 32.47 | MOL1 | C |
| ATOM | 267 | CE1 | TYR | A | 36 | 53.565 | −53.530 | −37.315 | 1.00 | 33.73 | MOL1 | C |
| ATOM | 268 | CD2 | TYR | A | 36 | 54.304 | −55.210 | −39.372 | 1.00 | 32.94 | MOL1 | C |
| ATOM | 269 | CE2 | TYR | A | 36 | 54.390 | −55.651 | −38.063 | 1.00 | 32.23 | MOL1 | C |
| ATOM | 270 | CZ | TYR | A | 36 | 54.020 | −54.805 | −37.034 | 1.00 | 39.55 | MOL1 | C |
| ATOM | 271 | OH | TYR | A | 36 | 54.109 | −55.225 | −35.718 | 1.00 | 39.71 | MOL1 | O |
| ATOM | 272 | C | TYR | A | 36 | 52.635 | −53.128 | −43.234 | 1.00 | 34.60 | MOL1 | C |
| ATOM | 273 | O | TYR | A | 36 | 52.911 | −53.882 | −44.161 | 1.00 | 39.81 | MOL1 | O |
| ATOM | 274 | N | GLN | A | 37 | 52.464 | −51.829 | −43.409 | 1.00 | 31.56 | MOL1 | N |
| ATOM | 275 | CA | GLN | A | 37 | 52.653 | −51.253 | −44.722 | 1.00 | 30.34 | MOL1 | C |
| ATOM | 276 | CB | GLN | A | 37 | 51.352 | −50.726 | −45.293 | 1.00 | 23.81 | MOL1 | C |
| ATOM | 277 | CG | GLN | A | 37 | 51.246 | −49.247 | −45.228 | 1.00 | 22.13 | MOL1 | C |
| ATOM | 278 | CD | GLN | A | 37 | 50.323 | −48.707 | −46.279 | 1.00 | 32.73 | MOL1 | C |
| ATOM | 279 | OE1 | GLN | A | 37 | 49.891 | −47.556 | −46.199 | 1.00 | 46.81 | MOL1 | O |
| ATOM | 280 | NE2 | GLN | A | 37 | 50.016 | −49.527 | −47.287 | 1.00 | 24.92 | MOL1 | N |
| ATOM | 281 | C | GLN | A | 37 | 53.647 | −50.126 | −44.581 | 1.00 | 34.22 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 282 | O | GLN | A | 37 | 53.724 | −49.490 | −43.538 | 1.00 | 41.80 | MOL1 | O |
|---|---|---|---|---|---|---|---|---|---|---|---|---|
| ATOM | 283 | N | GLN | A | 38 | 54.440 | −49.882 | −45.611 | 1.00 | 36.15 | MOL1 | N |
| ATOM | 284 | CA | GLN | A | 38 | 55.405 | −48.801 | −45.516 | 1.00 | 35.62 | MOL1 | C |
| ATOM | 285 | CB | GLN | A | 38 | 56.743 | −49.324 | −45.023 | 1.00 | 32.87 | MOL1 | C |
| ATOM | 286 | CG | GLN | A | 38 | 57.828 | −48.289 | −45.090 | 1.00 | 38.05 | MOL1 | C |
| ATOM | 287 | CD | GLN | A | 38 | 59.145 | −48.758 | −44.498 | 1.00 | 42.59 | MOL1 | C |
| ATOM | 288 | OE1 | GLN | A | 38 | 59.598 | −49.876 | −44.760 | 1.00 | 42.39 | MOL1 | O |
| ATOM | 289 | NE2 | GLN | A | 38 | 59.779 | −47.892 | −43.708 | 1.00 | 36.19 | MOL1 | N |
| ATOM | 290 | C | GLN | A | 38 | 55.588 | −48.109 | −46.839 | 1.00 | 36.42 | MOL1 | C |
| ATOM | 291 | O | GLN | A | 38 | 55.911 | −48.752 | −47.830 | 1.00 | 39.70 | MOL1 | O |
| ATOM | 292 | N | LYS | A | 39 | 55.353 | −46.800 | −46.857 | 1.00 | 37.89 | MOL1 | N |
| ATOM | 293 | CA | LYS | A | 39 | 55.509 | −46.014 | −48.078 | 1.00 | 41.72 | MOL1 | C |
| ATOM | 294 | CB | LYS | A | 39 | 54.682 | −44.722 | −48.051 | 1.00 | 37.51 | MOL1 | C |
| ATOM | 295 | CG | LYS | A | 39 | 53.216 | −44.884 | −47.725 | 1.00 | 44.18 | MOL1 | C |
| ATOM | 296 | CD | LYS | A | 39 | 52.470 | −45.653 | −48.785 | 1.00 | 42.55 | MOL1 | C |
| ATOM | 297 | CE | LYS | A | 39 | 50.969 | −45.457 | −48.626 | 1.00 | 42.83 | MOL1 | C |
| ATOM | 298 | NZ | LYS | A | 39 | 50.575 | −44.017 | −48.679 | 1.00 | 43.58 | MOL1 | N |
| ATOM | 299 | C | LYS | A | 39 | 56.967 | −45.625 | −48.097 | 1.00 | 45.26 | MOL1 | C |
| ATOM | 300 | O | LYS | A | 39 | 57.645 | −45.729 | −47.087 | 1.00 | 42.51 | MOL1 | O |
| ATOM | 301 | N | PRO | A | 40 | 57.463 | −45.152 | −49.243 | 1.00 | 50.43 | MOL1 | N |
| ATOM | 302 | CD | PRO | A | 40 | 56.783 | −45.080 | −50.543 | 1.00 | 57.17 | MOL1 | C |
| ATOM | 303 | CA | PRO | A | 40 | 58.864 | −44.749 | −49.360 | 1.00 | 50.55 | MOL1 | C |
| ATOM | 304 | CB | PRO | A | 40 | 59.011 | −44.416 | −50.834 | 1.00 | 50.04 | MOL1 | C |
| ATOM | 305 | CG | PRO | A | 40 | 57.937 | −45.247 | −51.486 | 1.00 | 65.03 | MOL1 | C |
| ATOM | 306 | C | PRO | A | 40 | 59.141 | −43.535 | −48.501 | 1.00 | 55.95 | MOL1 | C |
| ATOM | 307 | O | PRO | A | 40 | 58.425 | −42.534 | −48.591 | 1.00 | 57.59 | MOL1 | O |
| ATOM | 308 | N | GLY | A | 41 | 60.171 | −43.627 | −47.665 | 1.00 | 59.86 | MOL1 | N |
| ATOM | 309 | CA | GLY | A | 41 | 60.536 | −42.501 | −46.823 | 1.00 | 63.21 | MOL1 | C |
| ATOM | 310 | C | GLY | A | 41 | 59.937 | −42.484 | −45.434 | 1.00 | 67.58 | MOL1 | C |
| ATOM | 311 | O | GLY | A | 41 | 60.609 | −42.093 | −44.479 | 1.00 | 70.86 | MOL1 | O |
| ATOM | 312 | N | LYS | A | 42 | 58.678 | −42.894 | −45.308 | 1.00 | 66.25 | MOL1 | N |
| ATOM | 313 | CA | LYS | A | 42 | 58.036 | −42.913 | −44.005 | 1.00 | 62.93 | MOL1 | C |
| ATOM | 314 | CB | LYS | A | 42 | 56.532 | −42.646 | −44.175 | 1.00 | 74.75 | MOL1 | C |
| ATOM | 315 | CG | LYS | A | 42 | 55.962 | −41.619 | −43.159 | 1.00 | 91.14 | MOL1 | C |
| ATOM | 316 | CD | LYS | A | 42 | 55.795 | −42.209 | −41.726 | 1.00 | 87.95 | MOL1 | C |
| ATOM | 317 | CE | LYS | A | 42 | 56.220 | −41.239 | −40.612 | 1.00 | 79.63 | MOL1 | C |
| ATOM | 318 | NZ | LYS | A | 42 | 57.692 | −41.271 | −40.342 | 1.00 | 67.73 | MOL1 | N |
| ATOM | 319 | C | LYS | A | 42 | 58.321 | −44.251 | −43.273 | 1.00 | 54.36 | MOL1 | C |
| ATOM | 320 | O | LYS | A | 42 | 58.987 | −45.129 | −43.827 | 1.00 | 53.81 | MOL1 | O |
| ATOM | 321 | N | ALA | A | 43 | 57.853 | −44.398 | −42.032 | 1.00 | 41.27 | MOL1 | N |
| ATOM | 322 | CA | ALA | A | 43 | 58.090 | −45.624 | −41.269 | 1.00 | 37.44 | MOL1 | C |
| ATOM | 323 | CB | ALA | A | 43 | 58.311 | −45.298 | −39.829 | 1.00 | 31.23 | MOL1 | C |
| ATOM | 324 | C | ALA | A | 43 | 56.951 | −46.613 | −41.384 | 1.00 | 39.99 | MOL1 | C |
| ATOM | 325 | O | ALA | A | 43 | 55.837 | −46.236 | −41.720 | 1.00 | 48.24 | MOL1 | O |
| ATOM | 326 | N | PRO | A | 44 | 57.207 | −47.892 | −41.064 | 1.00 | 40.76 | MOL1 | N |
| ATOM | 327 | CD | PRO | A | 44 | 58.327 | −48.380 | −40.244 | 1.00 | 43.70 | MOL1 | C |
| ATOM | 328 | CA | PRO | A | 44 | 56.163 | −48.916 | −41.154 | 1.00 | 39.42 | MOL1 | C |
| ATOM | 329 | CB | PRO | A | 44 | 56.766 | −50.111 | −40.410 | 1.00 | 41.43 | MOL1 | C |
| ATOM | 330 | CG | PRO | A | 44 | 58.225 | −49.868 | −40.429 | 1.00 | 40.94 | MOL1 | C |
| ATOM | 331 | C | PRO | A | 44 | 54.900 | −48.418 | −40.470 | 1.00 | 39.92 | MOL1 | C |
| ATOM | 332 | O | PRO | A | 44 | 54.952 | −47.488 | −39.662 | 1.00 | 42.44 | MOL1 | O |
| ATOM | 333 | N | LYS | A | 45 | 53.773 | −49.041 | −40.792 | 1.00 | 33.97 | MOL1 | N |
| ATOM | 334 | CA | LYS | A | 45 | 52.500 | −48.663 | −40.211 | 1.00 | 29.31 | MOL1 | C |
| ATOM | 335 | CB | LYS | A | 45 | 51.802 | −47.628 | −41.110 | 1.00 | 23.93 | MOL1 | C |
| ATOM | 336 | CG | LYS | A | 45 | 50.614 | −46.938 | −40.477 | 1.00 | 49.73 | MOL1 | C |
| ATOM | 337 | CD | LYS | A | 45 | 49.426 | −47.914 | −40.236 | 1.00 | 65.12 | MOL1 | C |
| ATOM | 338 | CE | LYS | A | 45 | 48.637 | −47.640 | −38.911 | 1.00 | 69.62 | MOL1 | C |
| ATOM | 339 | NZ | LYS | A | 45 | 49.396 | −47.958 | −37.634 | 1.00 | 66.75 | MOL1 | N |
| ATOM | 340 | C | LYS | A | 45 | 51.706 | −49.954 | −40.101 | 1.00 | 25.70 | MOL1 | C |
| ATOM | 341 | O | LYS | A | 45 | 51.601 | −50.709 | −41.051 | 1.00 | 28.05 | MOL1 | O |
| ATOM | 342 | N | LEU | A | 46 | 51.168 | −50.228 | −38.925 | 1.00 | 27.60 | MOL1 | N |
| ATOM | 343 | CA | LEU | A | 46 | 50.410 | −51.452 | −38.738 | 1.00 | 28.62 | MOL1 | C |
| ATOM | 344 | CB | LEU | A | 46 | 50.121 | −51.647 | −37.252 | 1.00 | 22.22 | MOL1 | C |
| ATOM | 345 | CG | LEU | A | 46 | 49.308 | −52.852 | −36.800 | 1.00 | 29.50 | MOL1 | C |
| ATOM | 346 | CD1 | LEU | A | 46 | 49.954 | −54.157 | −37.235 | 1.00 | 34.12 | MOL1 | C |
| ATOM | 347 | CD2 | LEU | A | 46 | 49.202 | −52.805 | −35.296 | 1.00 | 32.37 | MOL1 | C |
| ATOM | 348 | C | LEU | A | 46 | 49.115 | −51.466 | −39.540 | 1.00 | 31.21 | MOL1 | C |
| ATOM | 349 | O | LEU | A | 46 | 48.347 | −50.516 | −39.528 | 1.00 | 35.06 | MOL1 | O |
| ATOM | 350 | N | LEU | A | 47 | 48.887 | −52.555 | −40.256 | 1.00 | 36.36 | MOL1 | N |
| ATOM | 351 | CA | LEU | A | 47 | 47.682 | −52.715 | −41.051 | 1.00 | 34.09 | MOL1 | C |
| ATOM | 352 | CB | LEU | A | 47 | 48.012 | −53.198 | −42.458 | 1.00 | 32.28 | MOL1 | C |
| ATOM | 353 | CG | LEU | A | 47 | 48.244 | −52.143 | −43.523 | 1.00 | 40.18 | MOL1 | C |
| ATOM | 354 | CD1 | LEU | A | 47 | 48.267 | −52.787 | −44.907 | 1.00 | 38.84 | MOL1 | C |
| ATOM | 355 | CD2 | LEU | A | 47 | 47.122 | −51.145 | −43.444 | 1.00 | 45.92 | MOL1 | C |
| ATOM | 356 | C | LEU | A | 47 | 46.761 | −53.738 | −40.416 | 1.00 | 36.98 | MOL1 | C |
| ATOM | 357 | O | LEU | A | 47 | 45.592 | −53.471 | −40.193 | 1.00 | 40.47 | MOL1 | O |
| ATOM | 358 | N | ILE | A | 48 | 47.305 | −54.909 | −40.112 | 1.00 | 35.94 | MOL1 | N |

TABLE 1-continued

The atomic coordinates of IL17F in complex with 496 Fab
(H32; a = 189.4; b = 189.4; c = 490.9, α, β = 90°; γ = 120°)

| ATOM | 359 | CA | ILE | A | 48 | 46.518 | −55.986 | −39.555 | 1.00 | 33.25 | MOL1 | C |
|---|---|---|---|---|---|---|---|---|---|---|---|---|
| ATOM | 360 | CB | ILE | A | 48 | 46.192 | −56.963 | −40.656 | 1.00 | 27.62 | MOL1 | C |
| ATOM | 361 | CG2 | ILE | A | 48 | 45.776 | −58.294 | −40.078 | 1.00 | 23.32 | MOL1 | C |
| ATOM | 362 | CG1 | ILE | A | 48 | 45.137 | −56.356 | −41.560 | 1.00 | 26.25 | MOL1 | C |
| ATOM | 363 | CD1 | ILE | A | 48 | 44.894 | −57.199 | −42.775 | 1.00 | 34.54 | MOL1 | C |
| ATOM | 364 | C | ILE | A | 48 | 47.219 | −56.757 | −38.457 | 1.00 | 37.92 | MOL1 | C |
| ATOM | 365 | O | ILE | A | 48 | 48.370 | −57.124 | −38.614 | 1.00 | 40.68 | MOL1 | O |
| ATOM | 366 | N | TYR | A | 49 | 46.530 | −57.002 | −37.347 | 1.00 | 41.14 | MOL1 | N |
| ATOM | 367 | CA | TYR | A | 49 | 47.119 | −57.786 | −36.277 | 1.00 | 46.26 | MOL1 | C |
| ATOM | 368 | CB | TYR | A | 49 | 47.159 | −57.021 | −34.949 | 1.00 | 55.74 | MOL1 | C |
| ATOM | 369 | CG | TYR | A | 49 | 45.822 | −56.547 | −34.437 | 1.00 | 62.14 | MOL1 | C |
| ATOM | 370 | CD1 | TYR | A | 49 | 45.335 | −55.306 | −34.794 | 1.00 | 65.27 | MOL1 | C |
| ATOM | 371 | CE1 | TYR | A | 49 | 44.117 | −54.869 | −34.353 | 1.00 | 67.22 | MOL1 | C |
| ATOM | 372 | CD2 | TYR | A | 49 | 45.039 | −57.345 | −33.610 | 1.00 | 58.99 | MOL1 | C |
| ATOM | 373 | CE2 | TYR | A | 49 | 43.810 | −56.909 | −33.163 | 1.00 | 58.66 | MOL1 | C |
| ATOM | 374 | CZ | TYR | A | 49 | 43.358 | −55.668 | −33.544 | 1.00 | 63.21 | MOL1 | C |
| ATOM | 375 | OH | TYR | A | 49 | 42.132 | −55.195 | −33.147 | 1.00 | 72.90 | MOL1 | O |
| ATOM | 376 | C | TYR | A | 49 | 46.337 | −59.085 | −36.104 | 1.00 | 46.52 | MOL1 | C |
| ATOM | 377 | O | TYR | A | 49 | 45.223 | −59.228 | −36.629 | 1.00 | 42.71 | MOL1 | O |
| ATOM | 378 | N | LEU | A | 50 | 46.944 | −60.025 | −35.381 | 1.00 | 41.10 | MOL1 | N |
| ATOM | 379 | CA | LEU | A | 50 | 46.345 | −61.315 | −35.135 | 1.00 | 34.80 | MOL1 | C |
| ATOM | 380 | CB | LEU | A | 50 | 45.363 | −61.201 | −33.984 | 1.00 | 32.33 | MOL1 | C |
| ATOM | 381 | CG | LEU | A | 50 | 45.893 | −61.742 | −32.653 | 1.00 | 38.66 | MOL1 | C |
| ATOM | 382 | CD1 | LEU | A | 50 | 47.319 | −62.185 | −32.829 | 1.00 | 34.22 | MOL1 | C |
| ATOM | 383 | CD2 | LEU | A | 50 | 45.771 | −60.698 | −31.568 | 1.00 | 34.17 | MOL1 | C |
| ATOM | 384 | C | LEU | A | 50 | 45.652 | −61.867 | −36.369 | 1.00 | 38.68 | MOL1 | C |
| ATOM | 385 | O | LEU | A | 50 | 44.459 | −62.128 | −36.353 | 1.00 | 44.22 | MOL1 | O |
| ATOM | 386 | N | VAL | A | 51 | 46.417 | −62.011 | −37.444 | 1.00 | 40.23 | MOL1 | N |
| ATOM | 387 | CA | VAL | A | 51 | 45.957 | −62.564 | −38.721 | 1.00 | 42.34 | MOL1 | C |
| ATOM | 388 | CB | VAL | A | 51 | 45.367 | −63.974 | −38.582 | 1.00 | 42.81 | MOL1 | C |
| ATOM | 389 | CG1 | VAL | A | 51 | 45.083 | −64.543 | −39.970 | 1.00 | 39.52 | MOL1 | C |
| ATOM | 390 | CG2 | VAL | A | 51 | 46.312 | −64.860 | −37.852 | 1.00 | 38.74 | MOL1 | C |
| ATOM | 391 | C | VAL | A | 51 | 44.954 | −61.831 | −39.560 | 1.00 | 44.05 | MOL1 | C |
| ATOM | 392 | O | VAL | A | 51 | 45.151 | −61.673 | −40.768 | 1.00 | 44.76 | MOL1 | O |
| ATOM | 393 | N | SER | A | 52 | 43.856 | −61.408 | −38.957 | 1.00 | 48.06 | MOL1 | N |
| ATOM | 394 | CA | SER | A | 52 | 42.859 | −60.755 | −39.775 | 1.00 | 51.23 | MOL1 | C |
| ATOM | 395 | CB | SER | A | 52 | 41.856 | −61.804 | −40.216 | 1.00 | 46.93 | MOL1 | C |
| ATOM | 396 | OG | SER | A | 52 | 41.328 | −61.413 | −41.467 | 1.00 | 62.81 | MOL1 | O |
| ATOM | 397 | C | SER | A | 52 | 42.136 | −59.531 | −39.227 | 1.00 | 44.79 | MOL1 | C |
| ATOM | 398 | O | SER | A | 52 | 41.180 | −59.048 | −39.821 | 1.00 | 40.87 | MOL1 | O |
| ATOM | 399 | N | ASN | A | 53 | 42.617 | −59.000 | −38.122 | 1.00 | 42.43 | MOL1 | N |
| ATOM | 400 | CA | ASN | A | 53 | 41.974 | −57.853 | −37.551 | 1.00 | 47.09 | MOL1 | C |
| ATOM | 401 | CB | ASN | A | 53 | 41.955 | −58.062 | −36.051 | 1.00 | 55.32 | MOL1 | C |
| ATOM | 402 | CG | ASN | A | 53 | 41.391 | −59.423 | −35.688 | 1.00 | 60.02 | MOL1 | C |
| ATOM | 403 | OD1 | ASN | A | 53 | 42.115 | −60.319 | −35.263 | 1.00 | 69.59 | MOL1 | O |
| ATOM | 404 | ND2 | ASN | A | 53 | 40.093 | −59.591 | −35.888 | 1.00 | 61.16 | MOL1 | N |
| ATOM | 405 | C | ASN | A | 53 | 42.667 | −56.560 | −37.968 | 1.00 | 46.67 | MOL1 | C |
| ATOM | 406 | O | ASN | A | 53 | 43.883 | −56.463 | −37.909 | 1.00 | 50.32 | MOL1 | O |
| ATOM | 407 | N | ARG | A | 54 | 41.895 | −55.572 | −38.410 | 1.00 | 43.04 | MOL1 | N |
| ATOM | 408 | CA | ARG | A | 54 | 42.470 | −54.295 | −38.838 | 1.00 | 46.76 | MOL1 | C |
| ATOM | 409 | CB | ARG | A | 54 | 41.615 | −53.661 | −39.918 | 1.00 | 51.66 | MOL1 | C |
| ATOM | 410 | CG | ARG | A | 54 | 41.349 | −54.549 | −41.074 | 1.00 | 59.02 | MOL1 | C |
| ATOM | 411 | CD | ARG | A | 54 | 40.225 | −53.990 | −41.865 | 1.00 | 56.96 | MOL1 | C |
| ATOM | 412 | NE | ARG | A | 54 | 39.479 | −55.082 | −42.452 | 1.00 | 72.58 | MOL1 | N |
| ATOM | 413 | CZ | ARG | A | 54 | 38.278 | −54.943 | −42.988 | 1.00 | 83.40 | MOL1 | C |
| ATOM | 414 | NH1 | ARG | A | 54 | 37.702 | −53.741 | −42.998 | 1.00 | 86.60 | MOL1 | N |
| ATOM | 415 | NH2 | ARG | A | 54 | 37.663 | −56.002 | −43.508 | 1.00 | 87.76 | MOL1 | N |
| ATOM | 416 | C | ARG | A | 54 | 42.621 | −53.247 | −37.746 | 1.00 | 48.10 | MOL1 | C |
| ATOM | 417 | O | ARG | A | 54 | 41.834 | −53.178 | −36.809 | 1.00 | 51.95 | MOL1 | O |
| ATOM | 418 | N | GLU | A | 55 | 43.633 | −52.404 | −37.885 | 1.00 | 52.04 | MOL1 | N |
| ATOM | 419 | CA | GLU | A | 55 | 43.851 | −51.339 | −36.921 | 1.00 | 54.69 | MOL1 | C |
| ATOM | 420 | CB | GLU | A | 55 | 45.169 | −50.607 | −37.187 | 1.00 | 59.74 | MOL1 | C |
| ATOM | 421 | CG | GLU | A | 55 | 46.197 | −50.722 | −36.093 | 1.00 | 66.74 | MOL1 | C |
| ATOM | 422 | CD | GLU | A | 55 | 45.609 | −50.484 | −34.726 | 1.00 | 71.76 | MOL1 | C |
| ATOM | 423 | OE1 | GLU | A | 55 | 46.368 | −50.556 | −33.736 | 1.00 | 77.92 | MOL1 | O |
| ATOM | 424 | OE2 | GLU | A | 55 | 44.387 | −50.234 | −34.637 | 1.00 | 76.06 | MOL1 | O |
| ATOM | 425 | C | GLU | A | 55 | 42.716 | −50.374 | −37.153 | 1.00 | 58.65 | MOL1 | C |
| ATOM | 426 | O | GLU | A | 55 | 42.017 | −50.472 | −38.166 | 1.00 | 60.22 | MOL1 | O |
| ATOM | 427 | N | SER | A | 56 | 42.550 | −49.432 | −36.232 | 1.00 | 62.90 | MOL1 | N |
| ATOM | 428 | CA | SER | A | 56 | 41.495 | −48.434 | −36.329 | 1.00 | 68.93 | MOL1 | C |
| ATOM | 429 | CB | SER | A | 56 | 41.733 | −47.342 | −35.283 | 1.00 | 73.11 | MOL1 | C |
| ATOM | 430 | OG | SER | A | 56 | 40.885 | −46.224 | −35.507 | 1.00 | 88.98 | MOL1 | O |
| ATOM | 431 | C | SER | A | 56 | 41.368 | −47.794 | −37.720 | 1.00 | 69.73 | MOL1 | C |
| ATOM | 432 | O | SER | A | 56 | 40.371 | −48.000 | −38.435 | 1.00 | 72.32 | MOL1 | O |
| ATOM | 433 | N | GLY | A | 57 | 42.379 | −47.027 | −38.107 | 1.00 | 62.78 | MOL1 | N |
| ATOM | 434 | CA | GLY | A | 57 | 42.325 | −46.353 | −39.390 | 1.00 | 62.16 | MOL1 | C |
| ATOM | 435 | C | GLY | A | 57 | 42.241 | −47.222 | −40.631 | 1.00 | 60.06 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 436 | O   | GLY | A | 57 | 41.522 | −46.887 | −41.576 | 1.00 | 62.24  | MOL1 | O |
|------|-----|-----|-----|---|----|--------|---------|---------|------|--------|------|---|
| ATOM | 437 | N   | VAL | A | 58 | 42.971 | −48.333 | −40.640 | 1.00 | 54.16  | MOL1 | N |
| ATOM | 438 | CA  | VAL | A | 58 | 42.992 | −49.222 | −41.793 | 1.00 | 46.09  | MOL1 | C |
| ATOM | 439 | CB  | VAL | A | 58 | 43.492 | −50.641 | −41.428 | 1.00 | 42.17  | MOL1 | C |
| ATOM | 440 | CG1 | VAL | A | 58 | 43.441 | −51.531 | −42.658 | 1.00 | 44.61  | MOL1 | C |
| ATOM | 441 | CG2 | VAL | A | 58 | 44.914 | −50.589 | −40.919 | 1.00 | 33.38  | MOL1 | C |
| ATOM | 442 | C   | VAL | A | 58 | 41.639 | −49.362 | −42.478 | 1.00 | 47.33  | MOL1 | C |
| ATOM | 443 | O   | VAL | A | 58 | 40.646 | −49.733 | −41.851 | 1.00 | 50.17  | MOL1 | O |
| ATOM | 444 | N   | PRO | A | 59 | 41.598 | −49.063 | −43.784 | 1.00 | 43.39  | MOL1 | N |
| ATOM | 445 | CD  | PRO | A | 59 | 42.726 | −48.444 | −44.489 | 1.00 | 50.20  | MOL1 | C |
| ATOM | 446 | CA  | PRO | A | 59 | 40.450 | −49.114 | −44.672 | 1.00 | 43.89  | MOL1 | C |
| ATOM | 447 | CB  | PRO | A | 59 | 41.041 | −48.754 | −46.013 | 1.00 | 38.01  | MOL1 | C |
| ATOM | 448 | CG  | PRO | A | 59 | 42.029 | −47.769 | −45.649 | 1.00 | 47.10  | MOL1 | C |
| ATOM | 449 | C   | PRO | A | 59 | 39.774 | −50.451 | −44.722 | 1.00 | 48.92  | MOL1 | C |
| ATOM | 450 | O   | PRO | A | 59 | 40.312 | −51.472 | −44.331 | 1.00 | 50.56  | MOL1 | O |
| ATOM | 451 | N   | SER | A | 60 | 38.571 | −50.408 | −45.254 | 1.00 | 60.71  | MOL1 | N |
| ATOM | 452 | CA  | SER | A | 60 | 37.716 | −51.560 | −45.394 | 1.00 | 62.90  | MOL1 | C |
| ATOM | 453 | CB  | SER | A | 60 | 36.349 | −51.056 | −45.920 | 1.00 | 73.59  | MOL1 | C |
| ATOM | 454 | OG  | SER | A | 60 | 36.074 | −49.695 | −45.508 | 1.00 | 70.93  | MOL1 | O |
| ATOM | 455 | C   | SER | A | 60 | 38.332 | −52.630 | −46.325 | 1.00 | 59.30  | MOL1 | C |
| ATOM | 456 | O   | SER | A | 60 | 38.222 | −53.827 | −46.047 | 1.00 | 52.16  | MOL1 | O |
| ATOM | 457 | N   | ARG | A | 61 | 39.001 | −52.194 | −47.403 | 1.00 | 57.27  | MOL1 | N |
| ATOM | 458 | CA  | ARG | A | 61 | 39.595 | −53.110 | −48.401 | 1.00 | 50.63  | MOL1 | C |
| ATOM | 459 | CB  | ARG | A | 61 | 40.135 | −52.329 | −49.615 | 1.00 | 44.86  | MOL1 | C |
| ATOM | 460 | CG  | ARG | A | 61 | 40.850 | −51.018 | −49.297 | 1.00 | 48.98  | MOL1 | C |
| ATOM | 461 | CD  | ARG | A | 61 | 41.327 | −50.284 | −50.562 | 1.00 | 38.52  | MOL1 | C |
| ATOM | 462 | NE  | ARG | A | 61 | 42.113 | −49.084 | −50.256 | 1.00 | 36.18  | MOL1 | N |
| ATOM | 463 | CZ  | ARG | A | 61 | 41.633 | −48.005 | −49.641 | 1.00 | 45.79  | MOL1 | C |
| ATOM | 464 | NH1 | ARG | A | 61 | 40.364 | −47.972 | −49.265 | 1.00 | 59.68  | MOL1 | N |
| ATOM | 465 | NH2 | ARG | A | 61 | 42.410 | −46.955 | −49.396 | 1.00 | 43.46  | MOL1 | N |
| ATOM | 466 | C   | ARG | A | 61 | 40.653 | −54.103 | −47.951 | 1.00 | 48.11  | MOL1 | C |
| ATOM | 467 | O   | ARG | A | 61 | 40.679 | −55.230 | −48.426 | 1.00 | 49.00  | MOL1 | O |
| ATOM | 468 | N   | PHE | A | 62 | 41.524 | −53.702 | −47.040 | 1.00 | 51.14  | MOL1 | N |
| ATOM | 469 | CA  | PHE | A | 62 | 42.579 | −54.595 | −46.560 | 1.00 | 50.93  | MOL1 | C |
| ATOM | 470 | CB  | PHE | A | 62 | 43.596 | −53.804 | −45.744 | 1.00 | 51.89  | MOL1 | C |
| ATOM | 471 | CG  | PHE | A | 62 | 44.446 | −52.895 | −46.561 | 1.00 | 46.54  | MOL1 | C |
| ATOM | 472 | CD1 | PHE | A | 62 | 45.569 | −53.374 | −47.197 | 1.00 | 51.00  | MOL1 | C |
| ATOM | 473 | CD2 | PHE | A | 62 | 44.117 | −51.571 | −46.702 | 1.00 | 47.30  | MOL1 | C |
| ATOM | 474 | CE1 | PHE | A | 62 | 46.351 | −52.549 | −47.957 | 1.00 | 54.48  | MOL1 | C |
| ATOM | 475 | CE2 | PHE | A | 62 | 44.894 | −50.738 | −47.465 | 1.00 | 54.48  | MOL1 | C |
| ATOM | 476 | CZ  | PHE | A | 62 | 46.016 | −51.228 | −48.094 | 1.00 | 54.72  | MOL1 | C |
| ATOM | 477 | C   | PHE | A | 62 | 42.029 | −55.724 | −45.707 | 1.00 | 50.14  | MOL1 | C |
| ATOM | 478 | O   | PHE | A | 62 | 41.314 | −55.478 | −44.741 | 1.00 | 53.36  | MOL1 | O |
| ATOM | 479 | N   | SER | A | 63 | 42.382 | −56.960 | −46.047 | 1.00 | 50.94  | MOL1 | N |
| ATOM | 480 | CA  | SER | A | 63 | 41.903 | −58.131 | −45.299 | 1.00 | 54.44  | MOL1 | C |
| ATOM | 481 | CB  | SER | A | 63 | 40.640 | −58.702 | −45.963 | 1.00 | 55.07  | MOL1 | C |
| ATOM | 482 | OG  | SER | A | 63 | 40.676 | −58.570 | −47.379 | 1.00 | 55.10  | MOL1 | O |
| ATOM | 483 | C   | SER | A | 63 | 42.937 | −59.249 | −45.147 | 1.00 | 53.22  | MOL1 | C |
| ATOM | 484 | O   | SER | A | 63 | 43.529 | −59.695 | −46.119 | 1.00 | 48.30  | MOL1 | O |
| ATOM | 485 | N   | GLY | A | 64 | 43.146 | −59.706 | −43.920 | 1.00 | 57.34  | MOL1 | N |
| ATOM | 486 | CA  | GLY | A | 64 | 44.112 | −60.766 | −43.690 | 1.00 | 60.19  | MOL1 | C |
| ATOM | 487 | C   | GLY | A | 64 | 43.429 | −62.111 | −43.737 | 1.00 | 63.57  | MOL1 | C |
| ATOM | 488 | O   | GLY | A | 64 | 42.224 | −62.166 | −43.974 | 1.00 | 70.23  | MOL1 | O |
| ATOM | 489 | N   | SER | A | 65 | 44.179 | −63.188 | −43.515 | 1.00 | 64.27  | MOL1 | N |
| ATOM | 490 | CA  | SER | A | 65 | 43.611 | −64.543 | −43.539 | 1.00 | 65.17  | MOL1 | C |
| ATOM | 491 | CB  | SER | A | 65 | 42.818 | −64.763 | −44.816 | 1.00 | 58.41  | MOL1 | C |
| ATOM | 492 | OG  | SER | A | 65 | 43.689 | −64.837 | −45.915 | 1.00 | 51.64  | MOL1 | O |
| ATOM | 493 | C   | SER | A | 65 | 44.689 | −65.612 | −43.478 | 1.00 | 68.10  | MOL1 | C |
| ATOM | 494 | O   | SER | A | 65 | 45.642 | −65.562 | −44.247 | 1.00 | 73.66  | MOL1 | O |
| ATOM | 495 | N   | GLY | A | 66 | 44.542 | −66.590 | −42.592 | 1.00 | 66.93  | MOL1 | N |
| ATOM | 496 | CA  | GLY | A | 66 | 45.564 | −67.610 | −42.522 | 1.00 | 72.19  | MOL1 | C |
| ATOM | 497 | C   | GLY | A | 66 | 45.465 | −68.652 | −41.431 | 1.00 | 78.05  | MOL1 | C |
| ATOM | 498 | O   | GLY | A | 66 | 44.768 | −68.487 | −40.431 | 1.00 | 78.15  | MOL1 | O |
| ATOM | 499 | N   | SER | A | 67 | 46.204 | −69.735 | −41.641 | 1.00 | 84.82  | MOL1 | N |
| ATOM | 500 | CA  | SER | A | 67 | 46.245 | −70.864 | −40.726 | 1.00 | 92.63  | MOL1 | C |
| ATOM | 501 | CB  | SER | A | 67 | 46.594 | −72.142 | −41.522 | 1.00 | 98.58  | MOL1 | C |
| ATOM | 502 | OG  | SER | A | 67 | 46.395 | −73.337 | −40.771 | 1.00 | 104.28 | MOL1 | O |
| ATOM | 503 | C   | SER | A | 67 | 47.292 | −70.612 | −39.646 | 1.00 | 91.84  | MOL1 | C |
| ATOM | 504 | O   | SER | A | 67 | 47.033 | −69.929 | −38.649 | 1.00 | 88.73  | MOL1 | O |
| ATOM | 505 | N   | GLY | A | 68 | 48.475 | −71.175 | −39.868 | 1.00 | 91.75  | MOL1 | N |
| ATOM | 506 | CA  | GLY | A | 68 | 49.575 | −71.034 | −38.934 | 1.00 | 91.50  | MOL1 | C |
| ATOM | 507 | C   | GLY | A | 68 | 50.883 | −71.335 | −39.640 | 1.00 | 91.39  | MOL1 | C |
| ATOM | 508 | O   | GLY | A | 68 | 51.926 | −71.482 | −39.010 | 1.00 | 90.20  | MOL1 | O |
| ATOM | 509 | N   | THR | A | 69 | 50.815 | −71.431 | −40.964 | 1.00 | 92.60  | MOL1 | N |
| ATOM | 510 | CA  | THR | A | 69 | 51.985 | −71.707 | −41.796 | 1.00 | 93.85  | MOL1 | C |
| ATOM | 511 | CB  | THR | A | 69 | 52.082 | −73.213 | −42.153 | 1.00 | 98.87  | MOL1 | C |
| ATOM | 512 | OG1 | THR | A | 69 | 52.875 | −73.372 | −43.335 | 1.00 | 101.90 | MOL1 | O |

TABLE 1-continued

The atomic coordinates of IL17F in complex with 496 Fab
(H32; a = 189.4; b = 189.4; c = 490.9, α, β = 90°; γ = 120°)

| ATOM | 513 | CG2 | THR | A | 69 | 50.694 | −73.811 | −42.391 | 1.00 | 103.36 | MOL1 | C |
|---|---|---|---|---|---|---|---|---|---|---|---|---|
| ATOM | 514 | C | THR | A | 69 | 51.913 | −70.893 | −43.088 | 1.00 | 89.96 | MOL1 | C |
| ATOM | 515 | O | THR | A | 69 | 52.928 | −70.476 | −43.642 | 1.00 | 86.26 | MOL1 | O |
| ATOM | 516 | N | ASP | A | 70 | 50.695 | −70.670 | −43.558 | 1.00 | 87.82 | MOL1 | N |
| ATOM | 517 | CA | ASP | A | 70 | 50.466 | −69.906 | −44.770 | 1.00 | 85.45 | MOL1 | C |
| ATOM | 518 | CB | ASP | A | 70 | 49.881 | −70.815 | −45.848 | 1.00 | 95.94 | MOL1 | C |
| ATOM | 519 | CG | ASP | A | 70 | 50.904 | −71.768 | −46.422 | 1.00 | 104.24 | MOL1 | C |
| ATOM | 520 | OD1 | ASP | A | 70 | 51.583 | −71.378 | −47.400 | 1.00 | 111.20 | MOL1 | O |
| ATOM | 521 | OD2 | ASP | A | 70 | 51.038 | −72.896 | −45.891 | 1.00 | 104.29 | MOL1 | O |
| ATOM | 522 | C | ASP | A | 70 | 49.491 | −68.786 | −44.463 | 1.00 | 76.70 | MOL1 | C |
| ATOM | 523 | O | ASP | A | 70 | 48.476 | −69.002 | −43.812 | 1.00 | 79.25 | MOL1 | O |
| ATOM | 524 | N | PHE | A | 71 | 49.803 | −67.591 | −44.935 | 1.00 | 65.62 | MOL1 | N |
| ATOM | 525 | CA | PHE | A | 71 | 48.947 | −66.446 | −44.712 | 1.00 | 57.28 | MOL1 | C |
| ATOM | 526 | CB | PHE | A | 71 | 49.515 | −65.591 | −43.610 | 1.00 | 55.73 | MOL1 | C |
| ATOM | 527 | CG | PHE | A | 71 | 49.677 | −66.310 | −42.327 | 1.00 | 57.16 | MOL1 | C |
| ATOM | 528 | CD1 | PHE | A | 71 | 48.666 | −66.313 | −41.394 | 1.00 | 61.41 | MOL1 | C |
| ATOM | 529 | CD2 | PHE | A | 71 | 50.851 | −66.957 | −42.034 | 1.00 | 56.82 | MOL1 | C |
| ATOM | 530 | CE1 | PHE | A | 71 | 48.833 | −66.945 | −40.190 | 1.00 | 62.74 | MOL1 | C |
| ATOM | 531 | CE2 | PHE | A | 71 | 51.019 | −67.588 | −40.833 | 1.00 | 57.76 | MOL1 | C |
| ATOM | 532 | CZ | PHE | A | 71 | 50.013 | −67.582 | −39.910 | 1.00 | 60.40 | MOL1 | C |
| ATOM | 533 | C | PHE | A | 71 | 48.861 | −65.621 | −45.969 | 1.00 | 53.97 | MOL1 | C |
| ATOM | 534 | O | PHE | A | 71 | 49.711 | −65.713 | −46.843 | 1.00 | 54.59 | MOL1 | O |
| ATOM | 535 | N | THR | A | 72 | 47.847 | −64.785 | −46.050 | 1.00 | 49.73 | MOL1 | N |
| ATOM | 536 | CA | THR | A | 72 | 47.694 | −63.975 | −47.228 | 1.00 | 52.51 | MOL1 | C |
| ATOM | 537 | CB | THR | A | 72 | 46.884 | −64.747 | −48.258 | 1.00 | 52.75 | MOL1 | C |
| ATOM | 538 | OG1 | THR | A | 72 | 45.947 | −65.587 | −47.577 | 1.00 | 64.27 | MOL1 | O |
| ATOM | 539 | CG2 | THR | A | 72 | 47.790 | −65.642 | −49.075 | 1.00 | 60.75 | MOL1 | C |
| ATOM | 540 | C | THR | A | 72 | 47.040 | −62.646 | −46.923 | 1.00 | 52.73 | MOL1 | C |
| ATOM | 541 | O | THR | A | 72 | 46.052 | −62.582 | −46.196 | 1.00 | 63.07 | MOL1 | O |
| ATOM | 542 | N | LEU | A | 73 | 47.622 | −61.575 | −47.442 | 1.00 | 46.87 | MOL1 | N |
| ATOM | 543 | CA | LEU | A | 73 | 47.058 | −60.253 | −47.244 | 1.00 | 45.65 | MOL1 | C |
| ATOM | 544 | CB | LEU | A | 73 | 48.141 | −59.220 | −46.949 | 1.00 | 41.84 | MOL1 | C |
| ATOM | 545 | CG | LEU | A | 73 | 47.623 | −57.784 | −47.007 | 1.00 | 36.88 | MOL1 | C |
| ATOM | 546 | CD1 | LEU | A | 73 | 46.384 | −57.656 | −46.159 | 1.00 | 41.11 | MOL1 | C |
| ATOM | 547 | CD2 | LEU | A | 73 | 48.678 | −56.844 | −46.521 | 1.00 | 31.94 | MOL1 | C |
| ATOM | 548 | C | LEU | A | 73 | 46.404 | −59.949 | −48.564 | 1.00 | 45.20 | MOL1 | C |
| ATOM | 549 | O | LEU | A | 73 | 46.907 | −60.347 | −49.598 | 1.00 | 47.90 | MOL1 | O |
| ATOM | 550 | N | THR | A | 74 | 45.279 | −59.255 | −48.551 | 1.00 | 47.26 | MOL1 | N |
| ATOM | 551 | CA | THR | A | 74 | 44.619 | −58.979 | −49.809 | 1.00 | 44.51 | MOL1 | C |
| ATOM | 552 | CB | THR | A | 74 | 43.712 | −60.167 | −50.198 | 1.00 | 41.06 | MOL1 | C |
| ATOM | 553 | OG1 | THR | A | 74 | 42.684 | −59.708 | −51.073 | 1.00 | 47.07 | MOL1 | O |
| ATOM | 554 | CG2 | THR | A | 74 | 43.108 | −60.828 | −48.960 | 1.00 | 35.97 | MOL1 | C |
| ATOM | 555 | C | THR | A | 74 | 43.844 | −57.672 | −49.871 | 1.00 | 43.60 | MOL1 | C |
| ATOM | 556 | O | THR | A | 74 | 43.046 | −57.345 | −48.991 | 1.00 | 46.72 | MOL1 | O |
| ATOM | 557 | N | ILE | A | 75 | 44.102 | −56.927 | −50.933 | 1.00 | 37.25 | MOL1 | N |
| ATOM | 558 | CA | ILE | A | 75 | 43.465 | −55.655 | −51.145 | 1.00 | 43.51 | MOL1 | C |
| ATOM | 559 | CB | ILE | A | 75 | 44.519 | −54.661 | −51.591 | 1.00 | 38.34 | MOL1 | C |
| ATOM | 560 | CG2 | ILE | A | 75 | 43.889 | −53.329 | −51.907 | 1.00 | 45.29 | MOL1 | C |
| ATOM | 561 | CG1 | ILE | A | 75 | 45.563 | −54.528 | −50.483 | 1.00 | 40.01 | MOL1 | C |
| ATOM | 562 | CD1 | ILE | A | 75 | 46.792 | −53.717 | −50.864 | 1.00 | 44.00 | MOL1 | C |
| ATOM | 563 | C | ILE | A | 75 | 42.360 | −55.826 | −52.191 | 1.00 | 51.76 | MOL1 | C |
| ATOM | 564 | O | ILE | A | 75 | 42.638 | −55.972 | −53.375 | 1.00 | 54.94 | MOL1 | O |
| ATOM | 565 | N | SER | A | 76 | 41.107 | −55.816 | −51.734 | 1.00 | 56.54 | MOL1 | N |
| ATOM | 566 | CA | SER | A | 76 | 39.951 | −56.004 | −52.605 | 1.00 | 57.64 | MOL1 | C |
| ATOM | 567 | CB | SER | A | 76 | 38.660 | −55.979 | −51.789 | 1.00 | 66.08 | MOL1 | C |
| ATOM | 568 | OG | SER | A | 76 | 38.509 | −54.748 | −51.105 | 1.00 | 79.00 | MOL1 | O |
| ATOM | 569 | C | SER | A | 76 | 39.831 | −55.022 | −53.751 | 1.00 | 58.33 | MOL1 | C |
| ATOM | 570 | O | SER | A | 76 | 39.343 | −55.378 | −54.819 | 1.00 | 65.75 | MOL1 | O |
| ATOM | 571 | N | SER | A | 77 | 40.266 | −53.787 | −53.553 | 1.00 | 54.83 | MOL1 | N |
| ATOM | 572 | CA | SER | A | 77 | 40.166 | −52.825 | −54.633 | 1.00 | 54.06 | MOL1 | C |
| ATOM | 573 | CB | SER | A | 77 | 38.801 | −52.148 | −54.570 | 1.00 | 51.46 | MOL1 | C |
| ATOM | 574 | OG | SER | A | 77 | 38.583 | −51.319 | −55.694 | 1.00 | 63.11 | MOL1 | O |
| ATOM | 575 | C | SER | A | 77 | 41.293 | −51.807 | −54.534 | 1.00 | 54.48 | MOL1 | C |
| ATOM | 576 | O | SER | A | 77 | 41.129 | −50.745 | −53.935 | 1.00 | 60.30 | MOL1 | O |
| ATOM | 577 | N | LEU | A | 78 | 42.432 | −52.131 | −55.139 | 1.00 | 50.14 | MOL1 | N |
| ATOM | 578 | CA | LEU | A | 78 | 43.598 | −51.257 | −55.081 | 1.00 | 51.12 | MOL1 | C |
| ATOM | 579 | CB | LEU | A | 78 | 44.644 | −51.685 | −56.099 | 1.00 | 51.48 | MOL1 | C |
| ATOM | 580 | CG | LEU | A | 78 | 46.065 | −51.361 | −55.647 | 1.00 | 45.21 | MOL1 | C |
| ATOM | 581 | CD1 | LEU | A | 78 | 46.215 | −51.714 | −54.187 | 1.00 | 49.93 | MOL1 | C |
| ATOM | 582 | CD2 | LEU | A | 78 | 47.057 | −52.158 | −56.471 | 1.00 | 53.87 | MOL1 | C |
| ATOM | 583 | C | LEU | A | 78 | 43.266 | −49.795 | −55.273 | 1.00 | 50.05 | MOL1 | C |
| ATOM | 584 | O | LEU | A | 78 | 42.458 | −49.432 | −56.113 | 1.00 | 52.69 | MOL1 | O |
| ATOM | 585 | N | GLN | A | 79 | 43.913 | −48.960 | −54.478 | 1.00 | 51.14 | MOL1 | N |
| ATOM | 586 | CA | GLN | A | 79 | 43.686 | −47.533 | −54.505 | 1.00 | 54.98 | MOL1 | C |
| ATOM | 587 | CB | GLN | A | 79 | 43.013 | −47.138 | −53.195 | 1.00 | 59.11 | MOL1 | C |
| ATOM | 588 | CG | GLN | A | 79 | 41.566 | −47.551 | −53.132 | 1.00 | 56.17 | MOL1 | C |
| ATOM | 589 | CD | GLN | A | 79 | 40.705 | −46.616 | −53.944 | 1.00 | 65.00 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 590 | OE1 | GLN | A | 79 | 40.548 | −45.445 | −53.584 | 1.00 | 69.29 | MOL1 | O |
|---|---|---|---|---|---|---|---|---|---|---|---|---|
| ATOM | 591 | NE2 | GLN | A | 79 | 40.154 | −47.111 | −55.052 | 1.00 | 60.06 | MOL1 | N |
| ATOM | 592 | C | GLN | A | 79 | 44.998 | −46.782 | −54.696 | 1.00 | 55.91 | MOL1 | C |
| ATOM | 593 | O | GLN | A | 79 | 46.067 | −47.289 | −54.369 | 1.00 | 59.17 | MOL1 | O |
| ATOM | 594 | N | PRO | A | 80 | 44.932 | −45.553 | −55.216 | 1.00 | 54.38 | MOL1 | N |
| ATOM | 595 | CD | PRO | A | 80 | 43.722 | −44.744 | −55.426 | 1.00 | 55.89 | MOL1 | C |
| ATOM | 596 | CA | PRO | A | 80 | 46.132 | −44.753 | −55.445 | 1.00 | 56.22 | MOL1 | C |
| ATOM | 597 | CB | PRO | A | 80 | 45.579 | −43.344 | −55.609 | 1.00 | 56.08 | MOL1 | C |
| ATOM | 598 | CG | PRO | A | 80 | 44.255 | −43.577 | −56.221 | 1.00 | 57.32 | MOL1 | C |
| ATOM | 599 | C | PRO | A | 80 | 47.115 | −44.837 | −54.295 | 1.00 | 59.55 | MOL1 | C |
| ATOM | 600 | O | PRO | A | 80 | 48.287 | −45.128 | −54.486 | 1.00 | 63.58 | MOL1 | O |
| ATOM | 601 | N | GLU | A | 81 | 46.625 | −44.589 | −53.090 | 1.00 | 64.22 | MOL1 | N |
| ATOM | 602 | CA | GLU | A | 81 | 47.484 | −44.599 | −51.915 | 1.00 | 67.38 | MOL1 | C |
| ATOM | 603 | CB | GLU | A | 81 | 46.868 | −43.748 | −50.790 | 1.00 | 75.36 | MOL1 | C |
| ATOM | 604 | CG | GLU | A | 81 | 45.403 | −44.042 | −50.433 | 1.00 | 89.45 | MOL1 | C |
| ATOM | 605 | CD | GLU | A | 81 | 44.411 | −43.540 | −51.485 | 1.00 | 99.68 | MOL1 | C |
| ATOM | 606 | OE1 | GLU | A | 81 | 44.598 | −42.413 | −51.993 | 1.00 | 107.02 | MOL1 | O |
| ATOM | 607 | OE2 | GLU | A | 81 | 43.434 | −44.260 | −51.793 | 1.00 | 103.73 | MOL1 | O |
| ATOM | 608 | C | GLU | A | 81 | 47.838 | −45.972 | −51.373 | 1.00 | 63.47 | MOL1 | C |
| ATOM | 609 | O | GLU | A | 81 | 48.442 | −46.078 | −50.310 | 1.00 | 66.19 | MOL1 | O |
| ATOM | 610 | N | ASP | A | 82 | 47.478 | −47.025 | −52.093 | 1.00 | 55.40 | MOL1 | N |
| ATOM | 611 | CA | ASP | A | 82 | 47.787 | −48.360 | −51.612 | 1.00 | 52.01 | MOL1 | C |
| ATOM | 612 | CB | ASP | A | 82 | 46.642 | −49.312 | −51.938 | 1.00 | 56.83 | MOL1 | C |
| ATOM | 613 | CG | ASP | A | 82 | 45.415 | −49.054 | −51.078 | 1.00 | 66.32 | MOL1 | C |
| ATOM | 614 | OD1 | ASP | A | 82 | 44.359 | −49.654 | −51.361 | 1.00 | 72.61 | MOL1 | O |
| ATOM | 615 | OD2 | ASP | A | 82 | 45.509 | −48.256 | −50.113 | 1.00 | 68.72 | MOL1 | O |
| ATOM | 616 | C | ASP | A | 82 | 49.087 | −48.858 | −52.195 | 1.00 | 46.60 | MOL1 | C |
| ATOM | 617 | O | ASP | A | 82 | 49.567 | −49.941 | −51.874 | 1.00 | 43.30 | MOL1 | O |
| ATOM | 618 | N | PHE | A | 83 | 49.668 | −48.033 | −53.046 | 1.00 | 47.70 | MOL1 | N |
| ATOM | 619 | CA | PHE | A | 83 | 50.921 | −48.370 | −53.679 | 1.00 | 44.13 | MOL1 | C |
| ATOM | 620 | CB | PHE | A | 83 | 51.070 | −47.521 | −54.933 | 1.00 | 41.53 | MOL1 | C |
| ATOM | 621 | CG | PHE | A | 83 | 50.119 | −47.924 | −56.015 | 1.00 | 42.12 | MOL1 | C |
| ATOM | 622 | CD1 | PHE | A | 83 | 49.467 | −46.981 | −56.783 | 1.00 | 45.02 | MOL1 | C |
| ATOM | 623 | CD2 | PHE | A | 83 | 49.866 | −49.269 | −56.249 | 1.00 | 39.47 | MOL1 | C |
| ATOM | 624 | CE1 | PHE | A | 83 | 48.577 | −47.370 | −57.768 | 1.00 | 42.50 | MOL1 | C |
| ATOM | 625 | CE2 | PHE | A | 83 | 48.990 | −49.664 | −57.221 | 1.00 | 38.30 | MOL1 | C |
| ATOM | 626 | CZ | PHE | A | 83 | 48.341 | −48.713 | −57.985 | 1.00 | 45.95 | MOL1 | C |
| ATOM | 627 | C | PHE | A | 83 | 52.052 | −48.161 | −52.697 | 1.00 | 43.58 | MOL1 | C |
| ATOM | 628 | O | PHE | A | 83 | 52.493 | −47.032 | −52.449 | 1.00 | 45.73 | MOL1 | O |
| ATOM | 629 | N | ALA | A | 84 | 52.493 | −49.270 | −52.120 | 1.00 | 37.49 | MOL1 | N |
| ATOM | 630 | CA | ALA | A | 84 | 53.559 | −49.243 | −51.147 | 1.00 | 40.43 | MOL1 | C |
| ATOM | 631 | CB | ALA | A | 84 | 53.029 | −48.767 | −49.818 | 1.00 | 43.56 | MOL1 | C |
| ATOM | 632 | C | ALA | A | 84 | 54.132 | −50.634 | −51.006 | 1.00 | 42.01 | MOL1 | C |
| ATOM | 633 | O | ALA | A | 84 | 53.845 | −51.518 | −51.804 | 1.00 | 41.77 | MOL1 | O |
| ATOM | 634 | N | THR | A | 85 | 54.945 | −50.826 | −49.980 | 1.00 | 40.50 | MOL1 | N |
| ATOM | 635 | CA | THR | A | 85 | 55.553 | −52.116 | −49.747 | 1.00 | 39.92 | MOL1 | C |
| ATOM | 636 | CB | THR | A | 85 | 57.031 | −51.947 | −49.460 | 1.00 | 40.88 | MOL1 | C |
| ATOM | 637 | OG1 | THR | A | 85 | 57.604 | −51.091 | −50.459 | 1.00 | 42.78 | MOL1 | O |
| ATOM | 638 | CG2 | THR | A | 85 | 57.726 | −53.299 | −49.478 | 1.00 | 43.47 | MOL1 | C |
| ATOM | 639 | C | THR | A | 85 | 54.861 | −52.701 | −48.542 | 1.00 | 37.47 | MOL1 | C |
| ATOM | 640 | O | THR | A | 85 | 54.524 | −51.956 | −47.630 | 1.00 | 46.04 | MOL1 | O |
| ATOM | 641 | N | TYR | A | 86 | 54.645 | −54.015 | −48.533 | 1.00 | 28.79 | MOL1 | N |
| ATOM | 642 | CA | TYR | A | 86 | 53.965 | −54.650 | −47.410 | 1.00 | 31.98 | MOL1 | C |
| ATOM | 643 | CB | TYR | A | 86 | 52.646 | −55.275 | −47.867 | 1.00 | 26.49 | MOL1 | C |
| ATOM | 644 | CG | TYR | A | 86 | 51.683 | −54.268 | −48.411 | 1.00 | 31.80 | MOL1 | C |
| ATOM | 645 | CD1 | TYR | A | 86 | 51.686 | −53.929 | −49.751 | 1.00 | 35.58 | MOL1 | C |
| ATOM | 646 | CE1 | TYR | A | 86 | 50.866 | −52.925 | −50.235 | 1.00 | 41.53 | MOL1 | C |
| ATOM | 647 | CD2 | TYR | A | 86 | 50.826 | −53.581 | −47.563 | 1.00 | 39.59 | MOL1 | C |
| ATOM | 648 | CE2 | TYR | A | 86 | 50.004 | −52.575 | −48.034 | 1.00 | 44.60 | MOL1 | C |
| ATOM | 649 | CZ | TYR | A | 86 | 50.028 | −52.251 | −49.369 | 1.00 | 44.00 | MOL1 | C |
| ATOM | 650 | OH | TYR | A | 86 | 49.209 | −51.253 | −49.830 | 1.00 | 43.24 | MOL1 | O |
| ATOM | 651 | C | TYR | A | 86 | 54.802 | −55.709 | −46.734 | 1.00 | 34.26 | MOL1 | C |
| ATOM | 652 | O | TYR | A | 86 | 55.434 | −56.512 | −47.405 | 1.00 | 40.66 | MOL1 | O |
| ATOM | 653 | N | TYR | A | 87 | 54.803 | −55.717 | −45.405 | 1.00 | 33.32 | MOL1 | N |
| ATOM | 654 | CA | TYR | A | 87 | 55.568 | −56.712 | −44.658 | 1.00 | 38.87 | MOL1 | C |
| ATOM | 655 | CB | TYR | A | 87 | 56.624 | −56.051 | −43.773 | 1.00 | 36.89 | MOL1 | C |
| ATOM | 656 | CG | TYR | A | 87 | 57.685 | −55.249 | −44.478 | 1.00 | 42.15 | MOL1 | C |
| ATOM | 657 | CD1 | TYR | A | 87 | 58.720 | −55.857 | −45.146 | 1.00 | 40.66 | MOL1 | C |
| ATOM | 658 | CE1 | TYR | A | 87 | 59.692 | −55.105 | −45.755 | 1.00 | 45.97 | MOL1 | C |
| ATOM | 659 | CD2 | TYR | A | 87 | 57.656 | −53.869 | −44.443 | 1.00 | 50.79 | MOL1 | C |
| ATOM | 660 | CE2 | TYR | A | 87 | 58.614 | −53.116 | −45.043 | 1.00 | 44.67 | MOL1 | C |
| ATOM | 661 | CZ | TYR | A | 87 | 59.626 | −53.729 | −45.698 | 1.00 | 47.60 | MOL1 | C |
| ATOM | 662 | OH | TYR | A | 87 | 60.561 | −52.943 | −46.322 | 1.00 | 60.90 | MOL1 | O |
| ATOM | 663 | C | TYR | A | 87 | 54.697 | −57.563 | −43.729 | 1.00 | 41.64 | MOL1 | C |
| ATOM | 664 | O | TYR | A | 87 | 53.758 | −57.056 | −43.113 | 1.00 | 48.19 | MOL1 | O |
| ATOM | 665 | N | CYS | A | 88 | 55.008 | −58.852 | −43.622 | 1.00 | 36.06 | MOL1 | N |
| ATOM | 666 | CA | CYS | A | 88 | 54.294 | −59.709 | −42.699 | 1.00 | 35.87 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 667 | C | CYS | A | 88 | 55.242 | −59.871 | −41.530 | 1.00 | 35.09 | MOL1 | C |
|------|-----|-----|-----|---|----|--------|---------|---------|------|-------|------|---|
| ATOM | 668 | O | CYS | A | 88 | 56.423 | −59.588 | −41.652 | 1.00 | 35.96 | MOL1 | O |
| ATOM | 669 | CB | CYS | A | 88 | 53.976 | −61.072 | −43.305 | 1.00 | 46.96 | MOL1 | C |
| ATOM | 670 | SG | CYS | A | 88 | 55.305 | −61.989 | −44.165 | 1.00 | 71.08 | MOL1 | S |
| ATOM | 671 | N | GLN | A | 89 | 54.737 | −60.287 | −40.382 | 1.00 | 34.49 | MOL1 | N |
| ATOM | 672 | CA | GLN | A | 89 | 55.600 | −60.461 | −39.234 | 1.00 | 37.20 | MOL1 | C |
| ATOM | 673 | CB | GLN | A | 89 | 55.804 | −59.154 | −38.489 | 1.00 | 33.50 | MOL1 | C |
| ATOM | 674 | CG | GLN | A | 89 | 56.361 | −59.397 | −37.094 | 1.00 | 44.65 | MOL1 | C |
| ATOM | 675 | CD | GLN | A | 89 | 56.013 | −58.301 | −36.118 | 1.00 | 49.46 | MOL1 | C |
| ATOM | 676 | OE1 | GLN | A | 89 | 54.910 | −57.757 | −36.166 | 1.00 | 50.94 | MOL1 | O |
| ATOM | 677 | NE2 | GLN | A | 89 | 56.941 | −57.982 | −35.208 | 1.00 | 46.81 | MOL1 | N |
| ATOM | 678 | C | GLN | A | 89 | 54.978 | −61.454 | −38.291 | 1.00 | 44.45 | MOL1 | C |
| ATOM | 679 | O | GLN | A | 89 | 53.758 | −61.519 | −38.172 | 1.00 | 51.12 | MOL1 | O |
| ATOM | 680 | N | GLN | A | 90 | 55.820 | −62.229 | −37.619 | 1.00 | 47.34 | MOL1 | N |
| ATOM | 681 | CA | GLN | A | 90 | 55.348 | −63.226 | −36.672 | 1.00 | 50.10 | MOL1 | C |
| ATOM | 682 | CB | GLN | A | 90 | 55.862 | −64.608 | −37.060 | 1.00 | 55.58 | MOL1 | C |
| ATOM | 683 | CG | GLN | A | 90 | 57.377 | −64.774 | −37.019 | 1.00 | 61.93 | MOL1 | C |
| ATOM | 684 | CD | GLN | A | 90 | 57.891 | −65.004 | −35.615 | 1.00 | 71.03 | MOL1 | C |
| ATOM | 685 | OE1 | GLN | A | 90 | 57.237 | −65.669 | −34.812 | 1.00 | 74.70 | MOL1 | O |
| ATOM | 686 | NE2 | GLN | A | 90 | 59.075 | −64.472 | −35.313 | 1.00 | 76.62 | MOL1 | N |
| ATOM | 687 | C | GLN | A | 90 | 55.868 | −62.855 | −35.309 | 1.00 | 51.67 | MOL1 | C |
| ATOM | 688 | O | GLN | A | 90 | 56.885 | −62.179 | −35.202 | 1.00 | 58.41 | MOL1 | O |
| ATOM | 689 | N | THR | A | 91 | 55.168 | −63.280 | −34.265 | 1.00 | 51.85 | MOL1 | N |
| ATOM | 690 | CA | THR | A | 91 | 55.593 | −62.987 | −32.902 | 1.00 | 55.11 | MOL1 | C |
| ATOM | 691 | CB | THR | A | 91 | 54.778 | −61.855 | −32.274 | 1.00 | 46.22 | MOL1 | C |
| ATOM | 692 | OG1 | THR | A | 91 | 53.388 | −62.151 | −32.401 | 1.00 | 48.12 | MOL1 | O |
| ATOM | 693 | CG2 | THR | A | 91 | 55.077 | −60.541 | −32.946 | 1.00 | 44.09 | MOL1 | C |
| ATOM | 694 | C | THR | A | 91 | 55.435 | −64.220 | −32.027 | 1.00 | 64.53 | MOL1 | C |
| ATOM | 695 | O | THR | A | 91 | 55.304 | −64.120 | −30.808 | 1.00 | 67.98 | MOL1 | O |
| ATOM | 696 | N | TRP | A | 92 | 55.443 | −65.385 | −32.658 | 1.00 | 72.17 | MOL1 | N |
| ATOM | 697 | CA | TRP | A | 92 | 55.323 | −66.638 | −31.937 | 1.00 | 79.07 | MOL1 | C |
| ATOM | 698 | CB | TRP | A | 92 | 54.998 | −67.758 | −32.917 | 1.00 | 81.59 | MOL1 | C |
| ATOM | 699 | CG | TRP | A | 92 | 54.701 | −69.061 | −32.275 | 1.00 | 86.75 | MOL1 | C |
| ATOM | 700 | CD2 | TRP | A | 92 | 54.106 | −69.274 | −30.990 | 1.00 | 92.89 | MOL1 | C |
| ATOM | 701 | CE2 | TRP | A | 92 | 53.909 | −70.658 | −30.850 | 1.00 | 94.73 | MOL1 | C |
| ATOM | 702 | CE3 | TRP | A | 92 | 53.716 | −68.430 | −29.947 | 1.00 | 101.96 | MOL1 | C |
| ATOM | 703 | CD1 | TRP | A | 92 | 54.845 | −70.285 | −32.836 | 1.00 | 88.08 | MOL1 | C |
| ATOM | 704 | NE1 | TRP | A | 92 | 54.372 | −71.253 | −31.992 | 1.00 | 93.41 | MOL1 | N |
| ATOM | 705 | CZ2 | TRP | A | 92 | 53.337 | −71.222 | −29.712 | 1.00 | 100.68 | MOL1 | C |
| ATOM | 706 | CZ3 | TRP | A | 92 | 53.149 | −68.991 | −28.813 | 1.00 | 106.61 | MOL1 | C |
| ATOM | 707 | CH2 | TRP | A | 92 | 52.964 | −70.374 | −28.707 | 1.00 | 104.86 | MOL1 | C |
| ATOM | 708 | C | TRP | A | 92 | 56.654 | −66.939 | −31.253 | 1.00 | 83.90 | MOL1 | C |
| ATOM | 709 | O | TRP | A | 92 | 56.732 | −67.010 | −30.026 | 1.00 | 83.82 | MOL1 | O |
| ATOM | 710 | N | SER | A | 93 | 57.698 | −67.114 | −32.064 | 1.00 | 89.43 | MOL1 | N |
| ATOM | 711 | CA | SER | A | 93 | 59.036 | −67.419 | −31.562 | 1.00 | 93.50 | MOL1 | C |
| ATOM | 712 | CB | SER | A | 93 | 59.828 | −68.239 | −32.571 | 1.00 | 96.02 | MOL1 | C |
| ATOM | 713 | OG | SER | A | 93 | 61.175 | −68.365 | −32.142 | 1.00 | 102.98 | MOL1 | O |
| ATOM | 714 | C | SER | A | 93 | 59.807 | −66.157 | −31.260 | 1.00 | 95.51 | MOL1 | C |
| ATOM | 715 | O | SER | A | 93 | 59.839 | −65.233 | −32.079 | 1.00 | 95.35 | MOL1 | O |
| ATOM | 716 | N | ASP | A | 94 | 60.466 | −66.151 | −30.105 | 1.00 | 95.58 | MOL1 | N |
| ATOM | 717 | CA | ASP | A | 94 | 61.212 | −64.992 | −29.632 | 1.00 | 98.53 | MOL1 | C |
| ATOM | 718 | CB | ASP | A | 94 | 62.172 | −65.393 | −28.526 | 1.00 | 104.00 | MOL1 | C |
| ATOM | 719 | CG | ASP | A | 94 | 62.238 | −64.345 | −27.434 | 1.00 | 112.24 | MOL1 | C |
| ATOM | 720 | OD1 | ASP | A | 94 | 62.584 | −63.182 | −27.751 | 1.00 | 109.59 | MOL1 | O |
| ATOM | 721 | OD2 | ASP | A | 94 | 61.928 | −64.681 | −26.266 | 1.00 | 118.48 | MOL1 | O |
| ATOM | 722 | C | ASP | A | 94 | 61.936 | −64.090 | −30.638 | 1.00 | 97.05 | MOL1 | C |
| ATOM | 723 | O | ASP | A | 94 | 61.807 | −62.865 | −30.565 | 1.00 | 104.64 | MOL1 | O |
| ATOM | 724 | N | PRO | A | 95 | 62.742 | −64.653 | −31.552 | 1.00 | 87.92 | MOL1 | N |
| ATOM | 725 | CD | PRO | A | 95 | 63.460 | −65.934 | −31.551 | 1.00 | 81.97 | MOL1 | C |
| ATOM | 726 | CA | PRO | A | 95 | 63.374 | −63.703 | −32.477 | 1.00 | 79.51 | MOL1 | C |
| ATOM | 727 | CB | PRO | A | 95 | 64.457 | −64.533 | −33.148 | 1.00 | 69.47 | MOL1 | C |
| ATOM | 728 | CG | PRO | A | 95 | 64.798 | −65.520 | −32.099 | 1.00 | 80.78 | MOL1 | C |
| ATOM | 729 | C | PRO | A | 95 | 62.309 | −63.263 | −33.474 | 1.00 | 77.32 | MOL1 | C |
| ATOM | 730 | O | PRO | A | 95 | 62.249 | −63.778 | −34.587 | 1.00 | 82.32 | MOL1 | O |
| ATOM | 731 | N | TRP | A | 96 | 61.450 | −62.336 | −33.066 | 1.00 | 69.04 | MOL1 | N |
| ATOM | 732 | CA | TRP | A | 96 | 60.397 | −61.862 | −33.945 | 1.00 | 66.16 | MOL1 | C |
| ATOM | 733 | CB | TRP | A | 96 | 59.733 | −60.631 | −33.331 | 1.00 | 66.86 | MOL1 | C |
| ATOM | 734 | CG | TRP | A | 96 | 59.124 | −60.900 | −31.992 | 1.00 | 67.18 | MOL1 | C |
| ATOM | 735 | CD2 | TRP | A | 96 | 58.857 | −59.945 | −30.961 | 1.00 | 67.83 | MOL1 | C |
| ATOM | 736 | CE2 | TRP | A | 96 | 58.234 | −60.633 | −29.902 | 1.00 | 67.54 | MOL1 | C |
| ATOM | 737 | CE3 | TRP | A | 96 | 59.081 | −58.576 | −30.830 | 1.00 | 70.92 | MOL1 | C |
| ATOM | 738 | CD1 | TRP | A | 96 | 58.666 | −62.095 | −31.530 | 1.00 | 71.15 | MOL1 | C |
| ATOM | 739 | NE1 | TRP | A | 96 | 58.129 | −61.947 | −30.271 | 1.00 | 69.68 | MOL1 | N |
| ATOM | 740 | CZ2 | TRP | A | 96 | 57.835 | −60.000 | −28.736 | 1.00 | 68.19 | MOL1 | C |
| ATOM | 741 | CZ3 | TRP | A | 96 | 58.682 | −57.948 | −29.665 | 1.00 | 73.55 | MOL1 | C |
| ATOM | 742 | CH2 | TRP | A | 96 | 58.067 | −58.659 | −28.636 | 1.00 | 70.77 | MOL1 | C |
| ATOM | 743 | C | TRP | A | 96 | 60.997 | −61.542 | −35.317 | 1.00 | 64.17 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 744 | O | TRP | A | 96 | 61.995 | −60.836 | −35.418 | 1.00 | 64.70 | MOL1 | O |
|---|---|---|---|---|---|---|---|---|---|---|---|---|
| ATOM | 745 | N | THR | A | 97 | 60.387 | −62.058 | −36.374 | 1.00 | 59.27 | MOL1 | N |
| ATOM | 746 | CA | THR | A | 97 | 60.917 | −61.846 | −37.711 | 1.00 | 60.60 | MOL1 | C |
| ATOM | 747 | CB | THR | A | 97 | 61.405 | −63.167 | −38.259 | 1.00 | 60.68 | MOL1 | C |
| ATOM | 748 | OG1 | THR | A | 97 | 60.391 | −64.161 | −38.061 | 1.00 | 58.89 | MOL1 | O |
| ATOM | 749 | CG2 | THR | A | 97 | 62.645 | −63.598 | −37.526 | 1.00 | 61.36 | MOL1 | C |
| ATOM | 750 | C | THR | A | 97 | 59.937 | −61.239 | −38.705 | 1.00 | 61.06 | MOL1 | C |
| ATOM | 751 | O | THR | A | 97 | 58.726 | −61.358 | −38.544 | 1.00 | 69.11 | MOL1 | O |
| ATOM | 752 | N | PHE | A | 98 | 60.463 | −60.590 | −39.739 | 1.00 | 54.88 | MOL1 | N |
| ATOM | 753 | CA | PHE | A | 98 | 59.615 | −59.974 | −40.756 | 1.00 | 50.50 | MOL1 | C |
| ATOM | 754 | CB | PHE | A | 98 | 59.934 | −58.484 | −40.917 | 1.00 | 50.06 | MOL1 | C |
| ATOM | 755 | CG | PHE | A | 98 | 59.553 | −57.644 | −39.743 | 1.00 | 51.18 | MOL1 | C |
| ATOM | 756 | CD1 | PHE | A | 98 | 60.091 | −57.882 | −38.493 | 1.00 | 57.23 | MOL1 | C |
| ATOM | 757 | CD2 | PHE | A | 98 | 58.649 | −56.618 | −39.883 | 1.00 | 56.31 | MOL1 | C |
| ATOM | 758 | CE1 | PHE | A | 98 | 59.728 | −57.108 | −37.396 | 1.00 | 51.93 | MOL1 | C |
| ATOM | 759 | CE2 | PHE | A | 98 | 58.284 | −55.845 | −38.791 | 1.00 | 58.59 | MOL1 | C |
| ATOM | 760 | CZ | PHE | A | 98 | 58.827 | −56.096 | −37.549 | 1.00 | 52.32 | MOL1 | C |
| ATOM | 761 | C | PHE | A | 98 | 59.793 | −60.648 | −42.107 | 1.00 | 48.51 | MOL1 | C |
| ATOM | 762 | O | PHE | A | 98 | 60.632 | −61.517 | −42.279 | 1.00 | 52.64 | MOL1 | O |
| ATOM | 763 | N | GLY | A | 99 | 58.986 | −60.236 | −43.067 | 1.00 | 49.51 | MOL1 | N |
| ATOM | 764 | CA | GLY | A | 99 | 59.086 | −60.799 | −44.390 | 1.00 | 46.65 | MOL1 | C |
| ATOM | 765 | C | GLY | A | 99 | 60.040 | −59.922 | −45.160 | 1.00 | 49.43 | MOL1 | C |
| ATOM | 766 | O | GLY | A | 99 | 60.488 | −58.888 | −44.663 | 1.00 | 48.03 | MOL1 | O |
| ATOM | 767 | N | GLN | A | 100 | 60.366 | −60.340 | −46.371 | 1.00 | 50.20 | MOL1 | N |
| ATOM | 768 | CA | GLN | A | 100 | 61.262 | −59.578 | −47.211 | 1.00 | 49.98 | MOL1 | C |
| ATOM | 769 | CB | GLN | A | 100 | 61.723 | −60.441 | −48.363 | 1.00 | 57.87 | MOL1 | C |
| ATOM | 770 | CG | GLN | A | 100 | 60.998 | −61.778 | −48.411 | 1.00 | 68.47 | MOL1 | C |
| ATOM | 771 | CD | GLN | A | 100 | 59.849 | −61.780 | −49.397 | 1.00 | 70.21 | MOL1 | C |
| ATOM | 772 | OE1 | GLN | A | 100 | 59.070 | −62.737 | −49.461 | 1.00 | 66.70 | MOL1 | O |
| ATOM | 773 | NE2 | GLN | A | 100 | 59.745 | −60.709 | −50.183 | 1.00 | 65.68 | MOL1 | N |
| ATOM | 774 | C | GLN | A | 100 | 60.534 | −58.357 | −47.723 | 1.00 | 49.56 | MOL1 | C |
| ATOM | 775 | O | GLN | A | 100 | 61.161 | −57.399 | −48.161 | 1.00 | 54.53 | MOL1 | O |
| ATOM | 776 | N | GLY | A | 101 | 59.207 | −58.396 | −47.657 | 1.00 | 47.46 | MOL1 | N |
| ATOM | 777 | CA | GLY | A | 101 | 58.400 | −57.277 | −48.110 | 1.00 | 50.03 | MOL1 | C |
| ATOM | 778 | C | GLY | A | 101 | 58.022 | −57.342 | −49.576 | 1.00 | 50.81 | MOL1 | C |
| ATOM | 779 | O | GLY | A | 101 | 58.829 | −57.745 | −50.410 | 1.00 | 56.79 | MOL1 | O |
| ATOM | 780 | N | THR | A | 102 | 56.796 | −56.932 | −49.890 | 1.00 | 47.60 | MOL1 | N |
| ATOM | 781 | CA | THR | A | 102 | 56.305 | −56.952 | −51.258 | 1.00 | 40.57 | MOL1 | C |
| ATOM | 782 | CB | THR | A | 102 | 55.035 | −57.737 | −51.366 | 1.00 | 37.32 | MOL1 | C |
| ATOM | 783 | OG1 | THR | A | 102 | 55.265 | −59.080 | −50.931 | 1.00 | 38.63 | MOL1 | O |
| ATOM | 784 | CG2 | THR | A | 102 | 54.548 | −57.713 | −52.789 | 1.00 | 37.75 | MOL1 | C |
| ATOM | 785 | C | THR | A | 102 | 55.991 | −55.557 | −51.714 | 1.00 | 41.46 | MOL1 | C |
| ATOM | 786 | O | THR | A | 102 | 55.229 | −54.862 | −51.068 | 1.00 | 45.54 | MOL1 | O |
| ATOM | 787 | N | LYS | A | 103 | 56.569 | −55.138 | −52.827 | 1.00 | 45.04 | MOL1 | N |
| ATOM | 788 | CA | LYS | A | 103 | 56.305 | −53.795 | −53.304 | 1.00 | 48.50 | MOL1 | C |
| ATOM | 789 | CB | LYS | A | 103 | 57.573 | −53.127 | −53.850 | 1.00 | 49.21 | MOL1 | C |
| ATOM | 790 | CG | LYS | A | 103 | 57.312 | −51.723 | −54.383 | 1.00 | 57.11 | MOL1 | C |
| ATOM | 791 | CD | LYS | A | 103 | 58.550 | −51.076 | −54.977 | 1.00 | 63.39 | MOL1 | C |
| ATOM | 792 | CE | LYS | A | 103 | 59.560 | −50.704 | −53.914 | 1.00 | 69.51 | MOL1 | C |
| ATOM | 793 | NZ | LYS | A | 103 | 60.818 | −50.204 | −54.539 | 1.00 | 78.00 | MOL1 | N |
| ATOM | 794 | C | LYS | A | 103 | 55.256 | −53.843 | −54.383 | 1.00 | 49.26 | MOL1 | C |
| ATOM | 795 | O | LYS | A | 103 | 55.372 | −54.598 | −55.346 | 1.00 | 52.49 | MOL1 | O |
| ATOM | 796 | N | VAL | A | 104 | 54.219 | −53.038 | −54.205 | 1.00 | 49.35 | MOL1 | N |
| ATOM | 797 | CA | VAL | A | 104 | 53.135 | −52.957 | −55.168 | 1.00 | 42.36 | MOL1 | C |
| ATOM | 798 | CB | VAL | A | 104 | 51.783 | −52.894 | −54.469 | 1.00 | 33.97 | MOL1 | C |
| ATOM | 799 | CG1 | VAL | A | 104 | 50.715 | −52.688 | −55.481 | 1.00 | 32.23 | MOL1 | C |
| ATOM | 800 | CG2 | VAL | A | 104 | 51.540 | −54.173 | −53.674 | 1.00 | 28.43 | MOL1 | C |
| ATOM | 801 | C | VAL | A | 104 | 53.344 | −51.676 | −55.942 | 1.00 | 46.45 | MOL1 | C |
| ATOM | 802 | O | VAL | A | 104 | 53.462 | −50.605 | −55.346 | 1.00 | 46.72 | MOL1 | O |
| ATOM | 803 | N | GLU | A | 105 | 53.411 | −51.789 | −57.264 | 1.00 | 51.41 | MOL1 | N |
| ATOM | 804 | CA | GLU | A | 105 | 53.619 | −50.629 | −58.122 | 1.00 | 54.71 | MOL1 | C |
| ATOM | 805 | CB | GLU | A | 105 | 54.998 | −50.708 | −58.783 | 1.00 | 63.51 | MOL1 | C |
| ATOM | 806 | CG | GLU | A | 105 | 56.174 | −50.756 | −57.799 | 1.00 | 67.96 | MOL1 | C |
| ATOM | 807 | CD | GLU | A | 105 | 57.456 | −51.309 | −58.432 | 1.00 | 71.89 | MOL1 | C |
| ATOM | 808 | OE1 | GLU | A | 105 | 57.469 | −52.519 | −58.801 | 1.00 | 56.58 | MOL1 | O |
| ATOM | 809 | OE2 | GLU | A | 105 | 58.438 | −50.525 | −58.554 | 1.00 | 68.64 | MOL1 | O |
| ATOM | 810 | C | GLU | A | 105 | 52.521 | −50.551 | −59.176 | 1.00 | 52.25 | MOL1 | C |
| ATOM | 811 | O | GLU | A | 105 | 51.925 | −51.557 | −59.542 | 1.00 | 53.45 | MOL1 | O |
| ATOM | 812 | N | ILE | A | 106 | 52.263 | −49.353 | −59.672 | 1.00 | 50.55 | MOL1 | N |
| ATOM | 813 | CA | ILE | A | 106 | 51.212 | −49.166 | −60.646 | 1.00 | 52.76 | MOL1 | C |
| ATOM | 814 | CB | ILE | A | 106 | 50.803 | −47.677 | −60.680 | 1.00 | 62.26 | MOL1 | C |
| ATOM | 815 | CG2 | ILE | A | 106 | 52.016 | −46.794 | −60.970 | 1.00 | 61.54 | MOL1 | C |
| ATOM | 816 | CG1 | ILE | A | 106 | 49.673 | −47.476 | −61.688 | 1.00 | 73.48 | MOL1 | C |
| ATOM | 817 | CD1 | ILE | A | 106 | 48.388 | −48.201 | −61.320 | 1.00 | 75.44 | MOL1 | C |
| ATOM | 818 | C | ILE | A | 106 | 51.565 | −49.670 | −62.040 | 1.00 | 49.48 | MOL1 | C |
| ATOM | 819 | O | ILE | A | 106 | 52.576 | −49.281 | −62.616 | 1.00 | 52.58 | MOL1 | O |
| ATOM | 820 | N | LYS | A | 107 | 50.726 | −50.550 | −62.578 | 1.00 | 46.45 | MOL1 | N |

TABLE 1-continued

The atomic coordinates of IL17F in complex with 496 Fab
(H32; a = 189.4; b = 189.4; c = 490.9, α, β = 90°; γ = 120°)

| ATOM | 821 | CA | LYS | A | 107 | 50.959 | −51.104 | −63.909 | 1.00 | 43.56 | MOL1 | C |
|---|---|---|---|---|---|---|---|---|---|---|---|---|
| ATOM | 822 | CB | LYS | A | 107 | 50.135 | −52.362 | −64.130 | 1.00 | 41.97 | MOL1 | C |
| ATOM | 823 | CG | LYS | A | 107 | 50.252 | −52.892 | −65.538 | 1.00 | 53.11 | MOL1 | C |
| ATOM | 824 | CD | LYS | A | 107 | 49.597 | −54.256 | −65.679 | 1.00 | 69.11 | MOL1 | C |
| ATOM | 825 | CE | LYS | A | 107 | 50.142 | −55.255 | −64.660 | 1.00 | 75.38 | MOL1 | C |
| ATOM | 826 | NZ | LYS | A | 107 | 49.707 | −56.653 | −64.962 | 1.00 | 80.88 | MOL1 | N |
| ATOM | 827 | C | LYS | A | 107 | 50.609 | −50.118 | −64.987 | 1.00 | 36.97 | MOL1 | C |
| ATOM | 828 | O | LYS | A | 107 | 49.699 | −49.327 | −64.819 | 1.00 | 41.99 | MOL1 | O |
| ATOM | 829 | N | ARG | A | 108 | 51.347 | −50.141 | −66.087 | 1.00 | 38.31 | MOL1 | N |
| ATOM | 830 | CA | ARG | A | 108 | 51.041 | −49.252 | −67.199 | 1.00 | 44.40 | MOL1 | C |
| ATOM | 831 | CB | ARG | A | 108 | 51.575 | −47.840 | −66.976 | 1.00 | 30.99 | MOL1 | C |
| ATOM | 832 | CG | ARG | A | 108 | 53.067 | −47.713 | −66.891 | 1.00 | 31.05 | MOL1 | C |
| ATOM | 833 | CD | ARG | A | 108 | 53.482 | −46.405 | −67.515 | 1.00 | 18.10 | MOL1 | C |
| ATOM | 834 | NE | ARG | A | 108 | 53.424 | −46.544 | −68.961 | 1.00 | 27.26 | MOL1 | N |
| ATOM | 835 | CZ | ARG | A | 108 | 53.711 | −45.570 | −69.812 | 1.00 | 31.83 | MOL1 | C |
| ATOM | 836 | NH1 | ARG | A | 108 | 54.068 | −44.380 | −69.355 | 1.00 | 32.06 | MOL1 | N |
| ATOM | 837 | NH2 | ARG | A | 108 | 53.665 | −45.790 | −71.118 | 1.00 | 32.92 | MOL1 | N |
| ATOM | 838 | C | ARG | A | 108 | 51.502 | −49.757 | −68.555 | 1.00 | 50.59 | MOL1 | C |
| ATOM | 839 | O | ARG | A | 108 | 52.133 | −50.811 | −68.685 | 1.00 | 60.53 | MOL1 | O |
| ATOM | 840 | N | THR | A | 109 | 51.156 | −48.993 | −69.573 | 1.00 | 49.21 | MOL1 | N |
| ATOM | 841 | CA | THR | A | 109 | 51.473 | −49.344 | −70.926 | 1.00 | 43.13 | MOL1 | C |
| ATOM | 842 | CB | THR | A | 109 | 50.745 | −48.341 | −71.814 | 1.00 | 34.44 | MOL1 | C |
| ATOM | 843 | OG1 | THR | A | 109 | 50.114 | −49.046 | −72.886 | 1.00 | 53.46 | MOL1 | O |
| ATOM | 844 | CG2 | THR | A | 109 | 51.671 | −47.272 | −72.315 | 1.00 | 20.82 | MOL1 | C |
| ATOM | 845 | C | THR | A | 109 | 52.993 | −49.363 | −71.101 | 1.00 | 45.40 | MOL1 | C |
| ATOM | 846 | O | THR | A | 109 | 53.678 | −48.470 | −70.610 | 1.00 | 40.62 | MOL1 | O |
| ATOM | 847 | N | ASP | A | 110 | 53.519 | −50.406 | −71.754 | 1.00 | 45.48 | MOL1 | N |
| ATOM | 848 | CA | ASP | A | 110 | 54.965 | −50.524 | −71.980 | 1.00 | 42.11 | MOL1 | C |
| ATOM | 849 | CB | ASP | A | 110 | 55.299 | −51.763 | −72.815 | 1.00 | 44.93 | MOL1 | C |
| ATOM | 850 | CG | ASP | A | 110 | 55.170 | −53.058 | −72.035 | 1.00 | 55.76 | MOL1 | C |
| ATOM | 851 | OD1 | ASP | A | 110 | 54.900 | −53.007 | −70.809 | 1.00 | 53.90 | MOL1 | O |
| ATOM | 852 | OD2 | ASP | A | 110 | 55.347 | −54.132 | −72.663 | 1.00 | 53.88 | MOL1 | O |
| ATOM | 853 | C | ASP | A | 110 | 55.505 | −49.309 | −72.719 | 1.00 | 37.40 | MOL1 | C |
| ATOM | 854 | O | ASP | A | 110 | 54.789 | −48.670 | −73.481 | 1.00 | 35.95 | MOL1 | O |
| ATOM | 855 | N | ALA | A | 111 | 56.776 | −48.999 | −72.501 | 1.00 | 35.91 | MOL1 | N |
| ATOM | 856 | CA | ALA | A | 111 | 57.409 | −47.863 | −73.156 | 1.00 | 37.29 | MOL1 | C |
| ATOM | 857 | CB | ALA | A | 111 | 57.185 | −46.626 | −72.359 | 1.00 | 27.90 | MOL1 | C |
| ATOM | 858 | C | ALA | A | 111 | 58.897 | −48.102 | −73.294 | 1.00 | 43.95 | MOL1 | C |
| ATOM | 859 | O | ALA | A | 111 | 59.549 | −48.477 | −72.325 | 1.00 | 46.55 | MOL1 | O |
| ATOM | 860 | N | ALA | A | 112 | 59.434 | −47.872 | −74.491 | 1.00 | 45.93 | MOL1 | N |
| ATOM | 861 | CA | ALA | A | 112 | 60.852 | −48.060 | −74.740 | 1.00 | 41.01 | MOL1 | C |
| ATOM | 862 | CB | ALA | A | 112 | 61.090 | −48.142 | −76.198 | 1.00 | 50.24 | MOL1 | C |
| ATOM | 863 | C | ALA | A | 112 | 61.679 | −46.925 | −74.141 | 1.00 | 42.59 | MOL1 | C |
| ATOM | 864 | O | ALA | A | 112 | 61.250 | −45.769 | −74.093 | 1.00 | 39.12 | MOL1 | O |
| ATOM | 865 | N | PRO | A | 113 | 62.887 | −47.252 | −73.665 | 1.00 | 42.21 | MOL1 | N |
| ATOM | 866 | CD | PRO | A | 113 | 63.460 | −48.608 | −73.564 | 1.00 | 42.32 | MOL1 | C |
| ATOM | 867 | CA | PRO | A | 113 | 63.777 | −46.270 | −73.061 | 1.00 | 37.05 | MOL1 | C |
| ATOM | 868 | CB | PRO | A | 113 | 64.776 | −47.138 | −72.321 | 1.00 | 35.40 | MOL1 | C |
| ATOM | 869 | CG | PRO | A | 113 | 64.892 | −48.324 | −73.215 | 1.00 | 34.46 | MOL1 | C |
| ATOM | 870 | C | PRO | A | 113 | 64.416 | −45.373 | −74.089 | 1.00 | 41.43 | MOL1 | C |
| ATOM | 871 | O | PRO | A | 113 | 64.492 | −45.715 | −75.271 | 1.00 | 43.93 | MOL1 | O |
| ATOM | 872 | N | THR | A | 114 | 64.857 | −44.211 | −73.623 | 1.00 | 43.96 | MOL1 | N |
| ATOM | 873 | CA | THR | A | 114 | 65.505 | −43.217 | −74.465 | 1.00 | 45.40 | MOL1 | C |
| ATOM | 874 | CB | THR | A | 114 | 64.862 | −41.858 | −74.262 | 1.00 | 42.40 | MOL1 | C |
| ATOM | 875 | OG1 | THR | A | 114 | 63.582 | −42.033 | −73.645 | 1.00 | 50.43 | MOL1 | O |
| ATOM | 876 | CG2 | THR | A | 114 | 64.661 | −41.177 | −75.580 | 1.00 | 47.99 | MOL1 | C |
| ATOM | 877 | C | THR | A | 114 | 66.933 | −43.146 | −73.980 | 1.00 | 45.69 | MOL1 | C |
| ATOM | 878 | O | THR | A | 114 | 67.202 | −42.525 | −72.955 | 1.00 | 44.29 | MOL1 | O |
| ATOM | 879 | N | VAL | A | 115 | 67.844 | −43.772 | −74.721 | 1.00 | 49.35 | MOL1 | N |
| ATOM | 880 | CA | VAL | A | 115 | 69.248 | −43.815 | −74.327 | 1.00 | 50.65 | MOL1 | C |
| ATOM | 881 | CB | VAL | A | 115 | 69.926 | −45.069 | −74.873 | 1.00 | 51.06 | MOL1 | C |
| ATOM | 882 | CG1 | VAL | A | 115 | 71.027 | −45.497 | −73.935 | 1.00 | 52.20 | MOL1 | C |
| ATOM | 883 | CG2 | VAL | A | 115 | 68.902 | −46.183 | −75.043 | 1.00 | 54.78 | MOL1 | C |
| ATOM | 884 | C | VAL | A | 115 | 70.077 | −42.608 | −74.734 | 1.00 | 49.08 | MOL1 | C |
| ATOM | 885 | O | VAL | A | 115 | 69.758 | −41.904 | −75.690 | 1.00 | 49.93 | MOL1 | O |
| ATOM | 886 | N | SER | A | 116 | 71.154 | −42.390 | −73.992 | 1.00 | 48.80 | MOL1 | N |
| ATOM | 887 | CA | SER | A | 116 | 72.047 | −41.262 | −74.216 | 1.00 | 49.64 | MOL1 | C |
| ATOM | 888 | CB | SER | A | 116 | 71.497 | −40.025 | −73.494 | 1.00 | 52.26 | MOL1 | C |
| ATOM | 889 | OG | SER | A | 116 | 70.077 | −39.999 | −73.500 | 1.00 | 44.31 | MOL1 | O |
| ATOM | 890 | C | SER | A | 116 | 73.411 | −41.610 | −73.629 | 1.00 | 45.36 | MOL1 | C |
| ATOM | 891 | O | SER | A | 116 | 73.510 | −41.992 | −72.468 | 1.00 | 42.62 | MOL1 | O |
| ATOM | 892 | N | ILE | A | 117 | 74.467 | −41.471 | −74.413 | 1.00 | 43.99 | MOL1 | N |
| ATOM | 893 | CA | ILE | A | 117 | 75.783 | −41.802 | −73.897 | 1.00 | 42.40 | MOL1 | C |
| ATOM | 894 | CB | ILE | A | 117 | 76.410 | −42.915 | −74.736 | 1.00 | 34.43 | MOL1 | C |
| ATOM | 895 | CG2 | ILE | A | 117 | 76.462 | −42.512 | −76.169 | 1.00 | 27.33 | MOL1 | C |
| ATOM | 896 | CG1 | ILE | A | 117 | 77.796 | −43.242 | −74.217 | 1.00 | 37.61 | MOL1 | C |
| ATOM | 897 | CD1 | ILE | A | 117 | 78.356 | −44.492 | −74.811 | 1.00 | 37.38 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 898 | C | ILE | A | 117 | 76.676 | −40.568 | −73.854 | 1.00 | 44.59 | MOL1 | C |
|---|---|---|---|---|---|---|---|---|---|---|---|---|
| ATOM | 899 | O | ILE | A | 117 | 76.660 | −39.752 | −74.765 | 1.00 | 46.70 | MOL1 | O |
| ATOM | 900 | N | PHE | A | 118 | 77.448 | −40.434 | −72.783 | 1.00 | 45.25 | MOL1 | N |
| ATOM | 901 | CA | PHE | A | 118 | 78.300 | −39.276 | −72.607 | 1.00 | 45.88 | MOL1 | C |
| ATOM | 902 | CB | PHE | A | 118 | 77.759 | −38.445 | −71.452 | 1.00 | 48.35 | MOL1 | C |
| ATOM | 903 | CG | PHE | A | 118 | 76.312 | −38.114 | −71.585 | 1.00 | 56.32 | MOL1 | C |
| ATOM | 904 | CD1 | PHE | A | 118 | 75.353 | −39.105 | −71.499 | 1.00 | 69.53 | MOL1 | C |
| ATOM | 905 | CD2 | PHE | A | 118 | 75.906 | −36.830 | −71.862 | 1.00 | 59.44 | MOL1 | C |
| ATOM | 906 | CE1 | PHE | A | 118 | 74.010 | −38.823 | −71.695 | 1.00 | 69.87 | MOL1 | C |
| ATOM | 907 | CE2 | PHE | A | 118 | 74.572 | −36.541 | −72.060 | 1.00 | 64.76 | MOL1 | C |
| ATOM | 908 | CZ | PHE | A | 118 | 73.622 | −37.541 | −71.978 | 1.00 | 68.81 | MOL1 | C |
| ATOM | 909 | C | PHE | A | 118 | 79.769 | −39.596 | −72.366 | 1.00 | 50.89 | MOL1 | C |
| ATOM | 910 | O | PHE | A | 118 | 80.110 | −40.393 | −71.497 | 1.00 | 54.65 | MOL1 | O |
| ATOM | 911 | N | PRO | A | 119 | 80.661 | −38.962 | −73.142 | 1.00 | 50.77 | MOL1 | N |
| ATOM | 912 | CD | PRO | A | 119 | 80.315 | −38.188 | −74.337 | 1.00 | 52.45 | MOL1 | C |
| ATOM | 913 | CA | PRO | A | 119 | 82.109 | −39.134 | −73.064 | 1.00 | 46.97 | MOL1 | C |
| ATOM | 914 | CB | PRO | A | 119 | 82.614 | −38.430 | −74.310 | 1.00 | 47.01 | MOL1 | C |
| ATOM | 915 | CG | PRO | A | 119 | 81.470 | −38.517 | −75.244 | 1.00 | 50.48 | MOL1 | C |
| ATOM | 916 | C | PRO | A | 119 | 82.594 | −38.465 | −71.825 | 1.00 | 44.14 | MOL1 | C |
| ATOM | 917 | O | PRO | A | 119 | 81.990 | −37.524 | −71.360 | 1.00 | 45.15 | MOL1 | O |
| ATOM | 918 | N | PRO | A | 120 | 83.711 | −38.935 | −71.286 | 1.00 | 46.37 | MOL1 | N |
| ATOM | 919 | CD | PRO | A | 120 | 84.547 | −39.979 | −71.887 | 1.00 | 35.74 | MOL1 | C |
| ATOM | 920 | CA | PRO | A | 120 | 84.328 | −38.406 | −70.070 | 1.00 | 53.78 | MOL1 | C |
| ATOM | 921 | CB | PRO | A | 120 | 85.638 | −39.177 | −70.002 | 1.00 | 43.37 | MOL1 | C |
| ATOM | 922 | CG | PRO | A | 120 | 85.313 | −40.442 | −70.707 | 1.00 | 39.57 | MOL1 | C |
| ATOM | 923 | C | PRO | A | 120 | 84.537 | −36.883 | −70.112 | 1.00 | 60.86 | MOL1 | C |
| ATOM | 924 | O | PRO | A | 120 | 85.027 | −36.331 | −71.094 | 1.00 | 62.52 | MOL1 | O |
| ATOM | 925 | N | SER | A | 121 | 84.160 | −36.202 | −69.041 | 1.00 | 64.67 | MOL1 | N |
| ATOM | 926 | CA | SER | A | 121 | 84.322 | −34.765 | −69.001 | 1.00 | 66.66 | MOL1 | C |
| ATOM | 927 | CB | SER | A | 121 | 83.800 | −34.230 | −67.683 | 1.00 | 70.09 | MOL1 | C |
| ATOM | 928 | OG | SER | A | 121 | 84.417 | −34.910 | −66.611 | 1.00 | 64.61 | MOL1 | O |
| ATOM | 929 | C | SER | A | 121 | 85.793 | −34.443 | −69.125 | 1.00 | 71.01 | MOL1 | C |
| ATOM | 930 | O | SER | A | 121 | 86.617 | −35.034 | −68.435 | 1.00 | 71.34 | MOL1 | O |
| ATOM | 931 | N | SER | A | 122 | 86.130 | −33.507 | −70.005 | 1.00 | 76.31 | MOL1 | N |
| ATOM | 932 | CA | SER | A | 122 | 87.529 | −33.127 | −70.176 | 1.00 | 76.37 | MOL1 | C |
| ATOM | 933 | CB | SER | A | 122 | 87.671 | −31.970 | −71.165 | 1.00 | 72.40 | MOL1 | C |
| ATOM | 934 | OG | SER | A | 122 | 86.954 | −30.833 | −70.723 | 1.00 | 76.66 | MOL1 | O |
| ATOM | 935 | C | SER | A | 122 | 88.069 | −32.723 | −68.814 | 1.00 | 77.11 | MOL1 | C |
| ATOM | 936 | O | SER | A | 122 | 89.214 | −33.012 | −68.484 | 1.00 | 77.76 | MOL1 | O |
| ATOM | 937 | N | GLU | A | 123 | 87.234 | −32.063 | −68.019 | 1.00 | 78.60 | MOL1 | N |
| ATOM | 938 | CA | GLU | A | 123 | 87.647 | −31.656 | −66.684 | 1.00 | 81.77 | MOL1 | C |
| ATOM | 939 | CB | GLU | A | 123 | 86.547 | −30.857 | −65.968 | 1.00 | 83.15 | MOL1 | C |
| ATOM | 940 | CG | GLU | A | 123 | 85.145 | −31.113 | −66.475 | 1.00 | 90.86 | MOL1 | C |
| ATOM | 941 | CD | GLU | A | 123 | 84.764 | −30.199 | −67.631 | 1.00 | 96.41 | MOL1 | C |
| ATOM | 942 | OE1 | GLU | A | 123 | 84.556 | −28.990 | −67.387 | 1.00 | 101.06 | MOL1 | O |
| ATOM | 943 | OE2 | GLU | A | 123 | 84.676 | −30.682 | −68.782 | 1.00 | 99.78 | MOL1 | O |
| ATOM | 944 | C | GLU | A | 123 | 87.992 | −32.890 | −65.867 | 1.00 | 80.69 | MOL1 | C |
| ATOM | 945 | O | GLU | A | 123 | 88.842 | −32.835 | −64.982 | 1.00 | 83.59 | MOL1 | O |
| ATOM | 946 | N | GLN | A | 124 | 87.337 | −34.005 | −66.171 | 1.00 | 79.38 | MOL1 | N |
| ATOM | 947 | CA | GLN | A | 124 | 87.586 | −35.251 | −65.456 | 1.00 | 78.06 | MOL1 | C |
| ATOM | 948 | CB | GLN | A | 124 | 86.502 | −36.281 | −65.751 | 1.00 | 73.86 | MOL1 | C |
| ATOM | 949 | CG | GLN | A | 124 | 86.739 | −37.620 | −65.071 | 1.00 | 59.63 | MOL1 | C |
| ATOM | 950 | CD | GLN | A | 124 | 85.575 | −38.587 | −65.238 | 1.00 | 54.29 | MOL1 | C |
| ATOM | 951 | OE1 | GLN | A | 124 | 85.458 | −39.551 | −64.480 | 1.00 | 45.01 | MOL1 | O |
| ATOM | 952 | NE2 | GLN | A | 124 | 84.713 | −38.338 | −66.232 | 1.00 | 42.63 | MOL1 | N |
| ATOM | 953 | C | GLN | A | 124 | 88.904 | −35.853 | −65.857 | 1.00 | 79.64 | MOL1 | C |
| ATOM | 954 | O | GLN | A | 124 | 89.715 | −36.222 | −65.010 | 1.00 | 81.32 | MOL1 | O |
| ATOM | 955 | N | LEU | A | 125 | 89.105 | −35.971 | −67.162 | 1.00 | 81.92 | MOL1 | N |
| ATOM | 956 | CA | LEU | A | 125 | 90.333 | −36.553 | −67.675 | 1.00 | 84.75 | MOL1 | C |
| ATOM | 957 | CB | LEU | A | 125 | 90.366 | −36.466 | −69.199 | 1.00 | 77.26 | MOL1 | C |
| ATOM | 958 | CG | LEU | A | 125 | 89.469 | −37.507 | −69.872 | 1.00 | 69.34 | MOL1 | C |
| ATOM | 959 | CD1 | LEU | A | 125 | 89.519 | −37.371 | −71.373 | 1.00 | 68.70 | MOL1 | C |
| ATOM | 960 | CD2 | LEU | A | 125 | 89.937 | −38.881 | −69.476 | 1.00 | 67.26 | MOL1 | C |
| ATOM | 961 | C | LEU | A | 125 | 91.567 | −35.908 | −67.059 | 1.00 | 89.76 | MOL1 | C |
| ATOM | 962 | O | LEU | A | 125 | 92.572 | −36.579 | −66.826 | 1.00 | 91.29 | MOL1 | O |
| ATOM | 963 | N | THR | A | 126 | 91.486 | −34.614 | −66.775 | 1.00 | 92.21 | MOL1 | N |
| ATOM | 964 | CA | THR | A | 126 | 92.597 | −33.914 | −66.158 | 1.00 | 92.08 | MOL1 | C |
| ATOM | 965 | CB | THR | A | 126 | 92.426 | −32.407 | −66.302 | 1.00 | 90.10 | MOL1 | C |
| ATOM | 966 | OG1 | THR | A | 126 | 92.220 | −32.088 | −67.685 | 1.00 | 89.96 | MOL1 | O |
| ATOM | 967 | CG2 | THR | A | 126 | 93.660 | −31.685 | −65.795 | 1.00 | 91.12 | MOL1 | C |
| ATOM | 968 | C | THR | A | 126 | 92.631 | −34.286 | −64.679 | 1.00 | 94.73 | MOL1 | C |
| ATOM | 969 | O | THR | A | 126 | 92.619 | −33.422 | −63.806 | 1.00 | 99.63 | MOL1 | O |
| ATOM | 970 | N | SER | A | 127 | 92.656 | −35.589 | −64.414 | 1.00 | 95.33 | MOL1 | N |
| ATOM | 971 | CA | SER | A | 127 | 92.688 | −36.125 | −63.057 | 1.00 | 96.51 | MOL1 | C |
| ATOM | 972 | CB | SER | A | 127 | 91.344 | −35.912 | −62.351 | 1.00 | 94.61 | MOL1 | C |
| ATOM | 973 | OG | SER | A | 127 | 91.190 | −34.577 | −61.908 | 1.00 | 95.83 | MOL1 | O |
| ATOM | 974 | C | SER | A | 127 | 92.992 | −37.617 | −63.098 | 1.00 | 97.65 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 975 | O | SER | A | 127 | 92.757 | −38.336 | −62.125 | 1.00 | 97.78 | MOL1 | O |
|---|---|---|---|---|---|---|---|---|---|---|---|---|
| ATOM | 976 | N | GLY | A | 128 | 93.497 | −38.080 | −64.237 | 1.00 | 97.27 | MOL1 | N |
| ATOM | 977 | CA | GLY | A | 128 | 93.838 | −39.485 | −64.383 | 1.00 | 97.12 | MOL1 | C |
| ATOM | 978 | C | GLY | A | 128 | 92.659 | −40.439 | −64.311 | 1.00 | 94.12 | MOL1 | C |
| ATOM | 979 | O | GLY | A | 128 | 92.819 | −41.646 | −64.059 | 1.00 | 93.78 | MOL1 | O |
| ATOM | 980 | N | GLY | A | 129 | 91.468 | −39.902 | −64.533 | 1.00 | 87.00 | MOL1 | N |
| ATOM | 981 | CA | GLY | A | 129 | 90.285 | −40.734 | −64.495 | 1.00 | 78.41 | MOL1 | C |
| ATOM | 982 | C | GLY | A | 129 | 89.327 | −40.361 | −65.599 | 1.00 | 69.02 | MOL1 | C |
| ATOM | 983 | O | GLY | A | 129 | 89.384 | −39.249 | −66.119 | 1.00 | 70.34 | MOL1 | O |
| ATOM | 984 | N | ALA | A | 130 | 88.448 | −41.293 | −65.954 | 1.00 | 60.37 | MOL1 | N |
| ATOM | 985 | CA | ALA | A | 130 | 87.456 | −41.070 | −66.999 | 1.00 | 52.28 | MOL1 | C |
| ATOM | 986 | CB | ALA | A | 130 | 88.084 | −41.260 | −68.331 | 1.00 | 46.85 | MOL1 | C |
| ATOM | 987 | C | ALA | A | 130 | 86.258 | −42.007 | −66.853 | 1.00 | 48.05 | MOL1 | C |
| ATOM | 988 | O | ALA | A | 130 | 86.424 | −43.213 | −66.694 | 1.00 | 41.74 | MOL1 | O |
| ATOM | 989 | N | SER | A | 131 | 85.055 | −41.441 | −66.925 | 1.00 | 43.74 | MOL1 | N |
| ATOM | 990 | CA | SER | A | 131 | 83.834 | −42.207 | −66.780 | 1.00 | 40.24 | MOL1 | C |
| ATOM | 991 | CB | SER | A | 131 | 83.094 | −41.778 | −65.526 | 1.00 | 31.45 | MOL1 | C |
| ATOM | 992 | OG | SER | A | 131 | 83.790 | −42.166 | −64.358 | 1.00 | 41.51 | MOL1 | O |
| ATOM | 993 | C | SER | A | 131 | 82.922 | −41.984 | −67.950 | 1.00 | 43.06 | MOL1 | C |
| ATOM | 994 | O | SER | A | 131 | 82.745 | −40.851 | −68.375 | 1.00 | 52.63 | MOL1 | O |
| ATOM | 995 | N | VAL | A | 132 | 82.336 | −43.063 | −68.465 | 1.00 | 41.32 | MOL1 | N |
| ATOM | 996 | CA | VAL | A | 132 | 81.400 | −42.971 | −69.573 | 1.00 | 37.90 | MOL1 | C |
| ATOM | 997 | CB | VAL | A | 132 | 81.650 | −44.038 | −70.600 | 1.00 | 38.60 | MOL1 | C |
| ATOM | 998 | CG1 | VAL | A | 132 | 80.690 | −43.865 | −71.747 | 1.00 | 40.62 | MOL1 | C |
| ATOM | 999 | CG2 | VAL | A | 132 | 83.072 | −43.969 | −71.077 | 1.00 | 42.83 | MOL1 | C |
| ATOM | 1000 | C | VAL | A | 132 | 80.015 | −43.197 | −69.012 | 1.00 | 35.03 | MOL1 | C |
| ATOM | 1001 | O | VAL | A | 132 | 79.745 | −44.242 | −68.467 | 1.00 | 33.79 | MOL1 | O |
| ATOM | 1002 | N | VAL | A | 133 | 79.140 | −42.210 | −69.143 | 1.00 | 40.22 | MOL1 | N |
| ATOM | 1003 | CA | VAL | A | 133 | 77.797 | −42.328 | −68.610 | 1.00 | 39.25 | MOL1 | C |
| ATOM | 1004 | CB | VAL | A | 133 | 77.416 | −41.107 | −67.774 | 1.00 | 31.40 | MOL1 | C |
| ATOM | 1005 | CG1 | VAL | A | 133 | 76.000 | −41.233 | −67.297 | 1.00 | 26.08 | MOL1 | C |
| ATOM | 1006 | CG2 | VAL | A | 133 | 78.331 | −41.007 | −66.577 | 1.00 | 35.57 | MOL1 | C |
| ATOM | 1007 | C | VAL | A | 133 | 76.753 | −42.526 | −69.676 | 1.00 | 41.09 | MOL1 | C |
| ATOM | 1008 | O | VAL | A | 133 | 76.788 | −41.902 | −70.722 | 1.00 | 40.39 | MOL1 | O |
| ATOM | 1009 | N | CYS | A | 134 | 75.817 | −43.417 | −69.386 | 1.00 | 45.80 | MOL1 | N |
| ATOM | 1010 | CA | CYS | A | 134 | 74.738 | −43.733 | −70.295 | 1.00 | 43.25 | MOL1 | C |
| ATOM | 1011 | C | CYS | A | 134 | 73.434 | −43.691 | −69.513 | 1.00 | 44.02 | MOL1 | C |
| ATOM | 1012 | O | CYS | A | 134 | 73.291 | −44.369 | −68.500 | 1.00 | 46.19 | MOL1 | O |
| ATOM | 1013 | CB | CYS | A | 134 | 74.958 | −45.124 | −70.877 | 1.00 | 46.44 | MOL1 | C |
| ATOM | 1014 | SG | CYS | A | 134 | 73.902 | −45.560 | −72.287 | 1.00 | 48.44 | MOL1 | S |
| ATOM | 1015 | N | PHE | A | 135 | 72.498 | −42.868 | −69.979 | 1.00 | 43.05 | MOL1 | N |
| ATOM | 1016 | CA | PHE | A | 135 | 71.191 | −42.718 | −69.349 | 1.00 | 35.78 | MOL1 | C |
| ATOM | 1017 | CB | PHE | A | 135 | 70.779 | −41.247 | −69.295 | 1.00 | 23.02 | MOL1 | C |
| ATOM | 1018 | CG | PHE | A | 135 | 71.596 | −40.410 | −68.344 | 1.00 | 28.31 | MOL1 | C |
| ATOM | 1019 | CD1 | PHE | A | 135 | 72.291 | −39.297 | −68.797 | 1.00 | 23.76 | MOL1 | C |
| ATOM | 1020 | CD2 | PHE | A | 135 | 71.654 | −40.718 | −66.987 | 1.00 | 30.91 | MOL1 | C |
| ATOM | 1021 | CE1 | PHE | A | 135 | 73.026 | −38.503 | −67.912 | 1.00 | 23.81 | MOL1 | C |
| ATOM | 1022 | CE2 | PHE | A | 135 | 72.390 | −39.927 | −66.095 | 1.00 | 22.88 | MOL1 | C |
| ATOM | 1023 | CZ | PHE | A | 135 | 73.073 | −38.822 | −66.560 | 1.00 | 23.34 | MOL1 | C |
| ATOM | 1024 | C | PHE | A | 135 | 70.140 | −43.456 | −70.146 | 1.00 | 37.06 | MOL1 | C |
| ATOM | 1025 | O | PHE | A | 135 | 70.066 | −43.308 | −71.360 | 1.00 | 37.16 | MOL1 | O |
| ATOM | 1026 | N | LEU | A | 136 | 69.336 | −44.260 | −69.462 | 1.00 | 39.36 | MOL1 | N |
| ATOM | 1027 | CA | LEU | A | 136 | 68.239 | −44.977 | −70.100 | 1.00 | 42.77 | MOL1 | C |
| ATOM | 1028 | CB | LEU | A | 136 | 68.362 | −46.463 | −69.849 | 1.00 | 43.75 | MOL1 | C |
| ATOM | 1029 | CG | LEU | A | 136 | 69.589 | −47.133 | −70.444 | 1.00 | 45.83 | MOL1 | C |
| ATOM | 1030 | CD1 | LEU | A | 136 | 70.846 | −46.535 | −69.873 | 1.00 | 41.28 | MOL1 | C |
| ATOM | 1031 | CD2 | LEU | A | 136 | 69.511 | −48.610 | −70.142 | 1.00 | 45.54 | MOL1 | C |
| ATOM | 1032 | C | LEU | A | 136 | 67.016 | −44.426 | −69.377 | 1.00 | 47.65 | MOL1 | C |
| ATOM | 1033 | O | LEU | A | 136 | 66.652 | −44.907 | −68.307 | 1.00 | 52.16 | MOL1 | O |
| ATOM | 1034 | N | ASN | A | 137 | 66.387 | −43.410 | −69.962 | 1.00 | 49.66 | MOL1 | N |
| ATOM | 1035 | CA | ASN | A | 137 | 65.253 | −42.744 | −69.335 | 1.00 | 46.07 | MOL1 | C |
| ATOM | 1036 | CB | ASN | A | 137 | 65.383 | −41.248 | −69.493 | 1.00 | 45.12 | MOL1 | C |
| ATOM | 1037 | CG | ASN | A | 137 | 66.595 | −40.712 | −68.824 | 1.00 | 51.28 | MOL1 | C |
| ATOM | 1038 | OD1 | ASN | A | 137 | 66.810 | −40.958 | −67.644 | 1.00 | 50.62 | MOL1 | O |
| ATOM | 1039 | ND2 | ASN | A | 137 | 67.406 | −39.961 | −69.568 | 1.00 | 59.22 | MOL1 | N |
| ATOM | 1040 | C | ASN | A | 137 | 63.858 | −43.092 | −69.770 | 1.00 | 48.96 | MOL1 | C |
| ATOM | 1041 | O | ASN | A | 137 | 63.613 | −43.436 | −70.922 | 1.00 | 55.68 | MOL1 | O |
| ATOM | 1042 | N | ASN | A | 138 | 62.949 | −42.948 | −68.811 | 1.00 | 49.39 | MOL1 | N |
| ATOM | 1043 | CA | ASN | A | 138 | 61.517 | −43.167 | −68.967 | 1.00 | 45.92 | MOL1 | C |
| ATOM | 1044 | CB | ASN | A | 138 | 60.885 | −41.929 | −69.616 | 1.00 | 50.81 | MOL1 | C |
| ATOM | 1045 | CG | ASN | A | 138 | 61.317 | −40.624 | −68.940 | 1.00 | 59.24 | MOL1 | C |
| ATOM | 1046 | OD1 | ASN | A | 138 | 61.087 | −40.422 | −67.743 | 1.00 | 58.73 | MOL1 | O |
| ATOM | 1047 | ND2 | ASN | A | 138 | 61.952 | −39.735 | −69.711 | 1.00 | 65.58 | MOL1 | N |
| ATOM | 1048 | C | ASN | A | 138 | 61.101 | −44.406 | −69.721 | 1.00 | 38.79 | MOL1 | C |
| ATOM | 1049 | O | ASN | A | 138 | 60.709 | −44.329 | −70.884 | 1.00 | 47.05 | MOL1 | O |
| ATOM | 1050 | N | PHE | A | 139 | 61.163 | −45.550 | −69.064 | 1.00 | 29.02 | MOL1 | N |
| ATOM | 1051 | CA | PHE | A | 139 | 60.772 | −46.773 | −69.735 | 1.00 | 37.47 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 1052 | CB | PHE | A | 139 | 62.024 | −47.555 | −70.150 | 1.00 | 33.86 | MOL1 | C |
|------|------|-----|-----|---|-----|--------|---------|---------|------|-------|------|---|
| ATOM | 1053 | CG | PHE | A | 139 | 62.954 | −47.876 | −69.017 | 1.00 | 37.51 | MOL1 | C |
| ATOM | 1054 | CD1 | PHE | A | 139 | 62.819 | −49.061 | −68.301 | 1.00 | 32.17 | MOL1 | C |
| ATOM | 1055 | CD2 | PHE | A | 139 | 63.973 | −46.996 | −68.668 | 1.00 | 37.88 | MOL1 | C |
| ATOM | 1056 | CE1 | PHE | A | 139 | 63.678 | −49.355 | −67.267 | 1.00 | 32.92 | MOL1 | C |
| ATOM | 1057 | CE2 | PHE | A | 139 | 64.843 | −47.288 | −67.628 | 1.00 | 31.70 | MOL1 | C |
| ATOM | 1058 | CZ | PHE | A | 139 | 64.693 | −48.465 | −66.932 | 1.00 | 35.11 | MOL1 | C |
| ATOM | 1059 | C | PHE | A | 139 | 59.847 | −47.623 | −68.879 | 1.00 | 40.23 | MOL1 | C |
| ATOM | 1060 | O | PHE | A | 139 | 59.618 | −47.316 | −67.713 | 1.00 | 45.12 | MOL1 | O |
| ATOM | 1061 | N | TYR | A | 140 | 59.296 | −48.680 | −69.466 | 1.00 | 39.12 | MOL1 | N |
| ATOM | 1062 | CA | TYR | A | 140 | 58.406 | −49.571 | −68.740 | 1.00 | 34.87 | MOL1 | C |
| ATOM | 1063 | CB | TYR | A | 140 | 57.048 | −48.911 | −68.582 | 1.00 | 32.07 | MOL1 | C |
| ATOM | 1064 | CG | TYR | A | 140 | 56.178 | −49.612 | −67.580 | 1.00 | 32.18 | MOL1 | C |
| ATOM | 1065 | CD1 | TYR | A | 140 | 56.275 | −49.319 | −66.238 | 1.00 | 29.24 | MOL1 | C |
| ATOM | 1066 | CE1 | TYR | A | 140 | 55.558 | −50.017 | −65.312 | 1.00 | 32.32 | MOL1 | C |
| ATOM | 1067 | CD2 | TYR | A | 140 | 55.326 | −50.623 | −67.964 | 1.00 | 28.25 | MOL1 | C |
| ATOM | 1068 | CE2 | TYR | A | 140 | 54.609 | −51.325 | −67.037 | 1.00 | 26.33 | MOL1 | C |
| ATOM | 1069 | CZ | TYR | A | 140 | 54.732 | −51.022 | −65.719 | 1.00 | 25.07 | MOL1 | C |
| ATOM | 1070 | OH | TYR | A | 140 | 54.060 | −51.756 | −64.783 | 1.00 | 36.48 | MOL1 | O |
| ATOM | 1071 | C | TYR | A | 140 | 58.248 | −50.879 | −69.507 | 1.00 | 34.41 | MOL1 | C |
| ATOM | 1072 | O | TYR | A | 140 | 58.082 | −50.874 | −70.722 | 1.00 | 42.98 | MOL1 | O |
| ATOM | 1073 | N | PRO | A | 141 | 58.279 | −52.017 | −68.814 | 1.00 | 29.07 | MOL1 | N |
| ATOM | 1074 | CD | PRO | A | 141 | 57.905 | −53.293 | −69.443 | 1.00 | 29.25 | MOL1 | C |
| ATOM | 1075 | CA | PRO | A | 141 | 58.450 | −52.164 | −67.372 | 1.00 | 34.44 | MOL1 | C |
| ATOM | 1076 | CB | PRO | A | 141 | 58.049 | −53.616 | −67.119 | 1.00 | 38.89 | MOL1 | C |
| ATOM | 1077 | CG | PRO | A | 141 | 58.319 | −54.293 | −68.420 | 1.00 | 30.33 | MOL1 | C |
| ATOM | 1078 | C | PRO | A | 141 | 59.856 | −51.847 | −66.909 | 1.00 | 40.54 | MOL1 | C |
| ATOM | 1079 | O | PRO | A | 141 | 60.685 | −51.408 | −67.704 | 1.00 | 43.11 | MOL1 | O |
| ATOM | 1080 | N | LYS | A | 142 | 60.130 | −52.076 | −65.626 | 1.00 | 44.63 | MOL1 | N |
| ATOM | 1081 | CA | LYS | A | 142 | 61.445 | −51.758 | −65.077 | 1.00 | 48.29 | MOL1 | C |
| ATOM | 1082 | CB | LYS | A | 142 | 61.361 | −51.566 | −63.557 | 1.00 | 49.32 | MOL1 | C |
| ATOM | 1083 | CG | LYS | A | 142 | 60.855 | −52.783 | −62.805 | 1.00 | 65.69 | MOL1 | C |
| ATOM | 1084 | CD | LYS | A | 142 | 60.636 | −52.527 | −61.309 | 1.00 | 65.89 | MOL1 | C |
| ATOM | 1085 | CE | LYS | A | 142 | 60.122 | −53.799 | −60.621 | 1.00 | 70.08 | MOL1 | C |
| ATOM | 1086 | NZ | LYS | A | 142 | 59.673 | −53.597 | −59.215 | 1.00 | 70.23 | MOL1 | N |
| ATOM | 1087 | C | LYS | A | 142 | 62.532 | −52.758 | −65.417 | 1.00 | 48.98 | MOL1 | C |
| ATOM | 1088 | O | LYS | A | 142 | 63.711 | −52.414 | −65.400 | 1.00 | 49.13 | MOL1 | O |
| ATOM | 1089 | N | ASP | A | 143 | 62.146 | −53.991 | −65.722 | 1.00 | 49.38 | MOL1 | N |
| ATOM | 1090 | CA | ASP | A | 143 | 63.121 | −55.004 | −66.072 | 1.00 | 51.81 | MOL1 | C |
| ATOM | 1091 | CB | ASP | A | 143 | 62.405 | −56.349 | −66.242 | 1.00 | 59.75 | MOL1 | C |
| ATOM | 1092 | CG | ASP | A | 143 | 63.287 | −57.415 | −66.886 | 1.00 | 72.97 | MOL1 | C |
| ATOM | 1093 | OD1 | ASP | A | 143 | 63.166 | −57.631 | −68.120 | 1.00 | 77.86 | MOL1 | O |
| ATOM | 1094 | OD2 | ASP | A | 143 | 64.103 | −58.033 | −66.160 | 1.00 | 77.34 | MOL1 | O |
| ATOM | 1095 | C | ASP | A | 143 | 63.815 | −54.575 | −67.358 | 1.00 | 47.42 | MOL1 | C |
| ATOM | 1096 | O | ASP | A | 143 | 63.174 | −54.496 | −68.406 | 1.00 | 53.81 | MOL1 | O |
| ATOM | 1097 | N | ILE | A | 144 | 65.109 | −54.274 | −67.280 | 1.00 | 41.26 | MOL1 | N |
| ATOM | 1098 | CA | ILE | A | 144 | 65.866 | −53.860 | −68.458 | 1.00 | 38.16 | MOL1 | C |
| ATOM | 1099 | CB | ILE | A | 144 | 65.852 | −52.337 | −68.629 | 1.00 | 30.07 | MOL1 | C |
| ATOM | 1100 | CG2 | ILE | A | 144 | 66.828 | −51.680 | −67.685 | 1.00 | 20.04 | MOL1 | C |
| ATOM | 1101 | CG1 | ILE | A | 144 | 66.262 | −51.973 | −70.045 | 1.00 | 30.24 | MOL1 | C |
| ATOM | 1102 | CD1 | ILE | A | 144 | 66.502 | −50.492 | −70.220 | 1.00 | 31.80 | MOL1 | C |
| ATOM | 1103 | C | ILE | A | 144 | 67.289 | −54.332 | −68.292 | 1.00 | 46.52 | MOL1 | C |
| ATOM | 1104 | O | ILE | A | 144 | 67.712 | −54.630 | −67.178 | 1.00 | 60.07 | MOL1 | O |
| ATOM | 1105 | N | ASN | A | 145 | 68.040 | −54.386 | −69.383 | 1.00 | 49.45 | MOL1 | N |
| ATOM | 1106 | CA | ASN | A | 145 | 69.409 | −54.870 | −69.312 | 1.00 | 52.69 | MOL1 | C |
| ATOM | 1107 | CB | ASN | A | 145 | 69.427 | −56.322 | −69.798 | 1.00 | 60.84 | MOL1 | C |
| ATOM | 1108 | CG | ASN | A | 145 | 70.821 | −56.857 | −69.996 | 1.00 | 70.72 | MOL1 | C |
| ATOM | 1109 | OD1 | ASN | A | 145 | 71.513 | −57.186 | −69.028 | 1.00 | 81.80 | MOL1 | O |
| ATOM | 1110 | ND2 | ASN | A | 145 | 71.252 | −56.945 | −71.255 | 1.00 | 68.81 | MOL1 | N |
| ATOM | 1111 | C | ASN | A | 145 | 70.379 | −54.037 | −70.131 | 1.00 | 46.40 | MOL1 | C |
| ATOM | 1112 | O | ASN | A | 145 | 70.174 | −53.853 | −71.309 | 1.00 | 50.05 | MOL1 | O |
| ATOM | 1113 | N | VAL | A | 146 | 71.440 | −53.549 | −69.501 | 1.00 | 45.51 | MOL1 | N |
| ATOM | 1114 | CA | VAL | A | 146 | 72.448 | −52.755 | −70.183 | 1.00 | 40.80 | MOL1 | C |
| ATOM | 1115 | CB | VAL | A | 146 | 72.802 | −51.540 | −69.377 | 1.00 | 33.02 | MOL1 | C |
| ATOM | 1116 | CG1 | VAL | A | 146 | 73.935 | −50.820 | −70.011 | 1.00 | 39.18 | MOL1 | C |
| ATOM | 1117 | CG2 | VAL | A | 146 | 71.634 | −50.644 | −69.307 | 1.00 | 37.76 | MOL1 | C |
| ATOM | 1118 | C | VAL | A | 146 | 73.728 | −53.539 | −70.413 | 1.00 | 45.59 | MOL1 | C |
| ATOM | 1119 | O | VAL | A | 146 | 74.178 | −54.270 | −69.537 | 1.00 | 53.43 | MOL1 | O |
| ATOM | 1120 | N | LYS | A | 147 | 74.312 | −53.381 | −71.595 | 1.00 | 45.17 | MOL1 | N |
| ATOM | 1121 | CA | LYS | A | 147 | 75.546 | −54.062 | −71.934 | 1.00 | 41.57 | MOL1 | C |
| ATOM | 1122 | CB | LYS | A | 147 | 75.288 | −55.121 | −73.003 | 1.00 | 35.13 | MOL1 | C |
| ATOM | 1123 | CG | LYS | A | 147 | 76.499 | −55.994 | −73.323 | 1.00 | 48.78 | MOL1 | C |
| ATOM | 1124 | CD | LYS | A | 147 | 76.275 | −56.963 | −74.494 | 1.00 | 56.43 | MOL1 | C |
| ATOM | 1125 | CE | LYS | A | 147 | 75.326 | −58.104 | −74.130 | 1.00 | 63.35 | MOL1 | C |
| ATOM | 1126 | NZ | LYS | A | 147 | 74.942 | −58.897 | −75.338 | 1.00 | 68.95 | MOL1 | N |
| ATOM | 1127 | C | LYS | A | 147 | 76.536 | −53.032 | −72.447 | 1.00 | 42.36 | MOL1 | C |
| ATOM | 1128 | O | LYS | A | 147 | 76.182 | −52.211 | −73.278 | 1.00 | 49.48 | MOL1 | O |

TABLE 1-continued

The atomic coordinates of IL17F in complex with 496 Fab
(H32; a = 189.4; b = 189.4; c = 490.9, α, β = 90°; γ = 120°)

| ATOM | 1129 | N | TRP | A | 148 | 77.764 | −53.046 | −71.925 | 1.00 | 43.56 | MOL1 | N |
|---|---|---|---|---|---|---|---|---|---|---|---|---|
| ATOM | 1130 | CA | TRP | A | 148 | 78.794 | −52.119 | −72.386 | 1.00 | 36.05 | MOL1 | C |
| ATOM | 1131 | CB | TRP | A | 148 | 79.568 | −51.540 | −71.235 | 1.00 | 19.03 | MOL1 | C |
| ATOM | 1132 | CG | TRP | A | 148 | 78.816 | −50.550 | −70.479 | 1.00 | 23.02 | MOL1 | C |
| ATOM | 1133 | CD2 | TRP | A | 148 | 78.824 | −49.142 | −70.685 | 1.00 | 19.65 | MOL1 | C |
| ATOM | 1134 | CE2 | TRP | A | 148 | 77.996 | −48.575 | −69.713 | 1.00 | 17.44 | MOL1 | C |
| ATOM | 1135 | CE3 | TRP | A | 148 | 79.457 | −48.307 | −71.596 | 1.00 | 23.18 | MOL1 | C |
| ATOM | 1136 | CD1 | TRP | A | 148 | 78.002 | −50.779 | −69.421 | 1.00 | 26.45 | MOL1 | C |
| ATOM | 1137 | NE1 | TRP | A | 148 | 77.503 | −49.595 | −68.946 | 1.00 | 19.46 | MOL1 | N |
| ATOM | 1138 | CZ2 | TRP | A | 148 | 77.784 | −47.217 | −69.627 | 1.00 | 20.36 | MOL1 | C |
| ATOM | 1139 | CZ3 | TRP | A | 148 | 79.246 | −46.958 | −71.510 | 1.00 | 23.54 | MOL1 | C |
| ATOM | 1140 | CH2 | TRP | A | 148 | 78.418 | −46.424 | −70.536 | 1.00 | 28.60 | MOL1 | C |
| ATOM | 1141 | C | TRP | A | 148 | 79.769 | −52.794 | −73.326 | 1.00 | 33.56 | MOL1 | C |
| ATOM | 1142 | O | TRP | A | 148 | 80.045 | −53.971 | −73.202 | 1.00 | 37.20 | MOL1 | O |
| ATOM | 1143 | N | LYS | A | 149 | 80.295 | −52.042 | −74.274 | 1.00 | 36.11 | MOL1 | N |
| ATOM | 1144 | CA | LYS | A | 149 | 81.232 | −52.608 | −75.215 | 1.00 | 39.83 | MOL1 | C |
| ATOM | 1145 | CB | LYS | A | 149 | 80.489 | −53.080 | −76.462 | 1.00 | 26.76 | MOL1 | C |
| ATOM | 1146 | CG | LYS | A | 149 | 79.504 | −54.190 | −76.223 | 1.00 | 21.05 | MOL1 | C |
| ATOM | 1147 | CD | LYS | A | 149 | 79.086 | −54.833 | −77.556 | 1.00 | 31.10 | MOL1 | C |
| ATOM | 1148 | CE | LYS | A | 149 | 78.071 | −55.977 | −77.358 | 1.00 | 37.33 | MOL1 | C |
| ATOM | 1149 | NZ | LYS | A | 149 | 77.637 | −56.634 | −78.636 | 1.00 | 42.65 | MOL1 | N |
| ATOM | 1150 | C | LYS | A | 149 | 82.358 | −51.669 | −75.624 | 1.00 | 47.29 | MOL1 | C |
| ATOM | 1151 | O | LYS | A | 149 | 82.118 | −50.633 | −76.245 | 1.00 | 55.61 | MOL1 | O |
| ATOM | 1152 | N | ILE | A | 150 | 83.590 | −52.028 | −75.278 | 1.00 | 49.76 | MOL1 | N |
| ATOM | 1153 | CA | ILE | A | 150 | 84.721 | −51.210 | −75.683 | 1.00 | 52.87 | MOL1 | C |
| ATOM | 1154 | CB | ILE | A | 150 | 85.764 | −51.046 | −74.605 | 1.00 | 45.48 | MOL1 | C |
| ATOM | 1155 | CG2 | ILE | A | 150 | 86.757 | −50.004 | −75.057 | 1.00 | 38.52 | MOL1 | C |
| ATOM | 1156 | CG1 | ILE | A | 150 | 85.114 | −50.591 | −73.302 | 1.00 | 43.30 | MOL1 | C |
| ATOM | 1157 | CD1 | ILE | A | 150 | 86.118 | −50.230 | −72.233 | 1.00 | 45.01 | MOL1 | C |
| ATOM | 1158 | C | ILE | A | 150 | 85.389 | −51.861 | −76.873 | 1.00 | 56.06 | MOL1 | C |
| ATOM | 1159 | O | ILE | A | 150 | 85.836 | −52.997 | −76.810 | 1.00 | 61.44 | MOL1 | O |
| ATOM | 1160 | N | ASP | A | 151 | 85.444 | −51.132 | −77.971 | 1.00 | 59.45 | MOL1 | N |
| ATOM | 1161 | CA | ASP | A | 151 | 86.049 | −51.648 | −79.183 | 1.00 | 57.43 | MOL1 | C |
| ATOM | 1162 | CB | ASP | A | 151 | 87.559 | −51.826 | −79.013 | 1.00 | 55.63 | MOL1 | C |
| ATOM | 1163 | CG | ASP | A | 151 | 88.340 | −50.527 | −79.172 | 1.00 | 55.29 | MOL1 | C |
| ATOM | 1164 | OD1 | ASP | A | 151 | 87.733 | −49.459 | −79.419 | 1.00 | 54.09 | MOL1 | O |
| ATOM | 1165 | OD2 | ASP | A | 151 | 89.582 | −50.588 | −79.050 | 1.00 | 55.18 | MOL1 | O |
| ATOM | 1166 | C | ASP | A | 151 | 85.441 | −52.975 | −79.593 | 1.00 | 52.93 | MOL1 | C |
| ATOM | 1167 | O | ASP | A | 151 | 86.107 | −53.801 | −80.190 | 1.00 | 56.66 | MOL1 | O |
| ATOM | 1168 | N | GLY | A | 152 | 84.183 | −53.193 | −79.252 | 1.00 | 52.23 | MOL1 | N |
| ATOM | 1169 | CA | GLY | A | 152 | 83.534 | −54.413 | −79.674 | 1.00 | 56.75 | MOL1 | C |
| ATOM | 1170 | C | GLY | A | 152 | 83.393 | −55.515 | −78.664 | 1.00 | 59.09 | MOL1 | C |
| ATOM | 1171 | O | GLY | A | 152 | 82.607 | −56.431 | −78.866 | 1.00 | 67.69 | MOL1 | O |
| ATOM | 1172 | N | SER | A | 153 | 84.137 | −55.438 | −77.574 | 1.00 | 58.80 | MOL1 | N |
| ATOM | 1173 | CA | SER | A | 153 | 84.077 | −56.481 | −76.561 | 1.00 | 52.16 | MOL1 | C |
| ATOM | 1174 | CB | SER | A | 153 | 85.490 | −56.860 | −76.129 | 1.00 | 50.58 | MOL1 | C |
| ATOM | 1175 | OG | SER | A | 153 | 86.242 | −57.306 | −77.239 | 1.00 | 53.22 | MOL1 | O |
| ATOM | 1176 | C | SER | A | 153 | 83.280 | −56.051 | −75.353 | 1.00 | 46.06 | MOL1 | C |
| ATOM | 1177 | O | SER | A | 153 | 83.348 | −54.899 | −74.956 | 1.00 | 40.77 | MOL1 | O |
| ATOM | 1178 | N | GLU | A | 154 | 82.547 | −56.991 | −74.764 | 1.00 | 42.48 | MOL1 | N |
| ATOM | 1179 | CA | GLU | A | 154 | 81.719 | −56.722 | −73.596 | 1.00 | 37.93 | MOL1 | C |
| ATOM | 1180 | CB | GLU | A | 154 | 80.770 | −57.871 | −73.372 | 1.00 | 42.48 | MOL1 | C |
| ATOM | 1181 | CG | GLU | A | 154 | 79.710 | −57.630 | −72.329 | 1.00 | 56.00 | MOL1 | C |
| ATOM | 1182 | CD | GLU | A | 154 | 78.833 | −58.858 | −72.137 | 1.00 | 68.87 | MOL1 | C |
| ATOM | 1183 | OE1 | GLU | A | 154 | 78.314 | −59.374 | −73.160 | 1.00 | 73.99 | MOL1 | O |
| ATOM | 1184 | OE2 | GLU | A | 154 | 78.670 | −59.307 | −70.975 | 1.00 | 72.26 | MOL1 | O |
| ATOM | 1185 | C | GLU | A | 154 | 82.513 | −56.492 | −72.341 | 1.00 | 36.65 | MOL1 | C |
| ATOM | 1186 | O | GLU | A | 154 | 83.396 | −57.253 | −72.001 | 1.00 | 40.37 | MOL1 | O |
| ATOM | 1187 | N | ARG | A | 155 | 82.169 | −55.432 | −71.637 | 1.00 | 43.14 | MOL1 | N |
| ATOM | 1188 | CA | ARG | A | 155 | 82.845 | −55.045 | −70.407 | 1.00 | 51.06 | MOL1 | C |
| ATOM | 1189 | CB | ARG | A | 155 | 83.349 | −53.614 | −70.570 | 1.00 | 46.94 | MOL1 | C |
| ATOM | 1190 | CG | ARG | A | 155 | 84.389 | −53.150 | −69.581 | 1.00 | 57.47 | MOL1 | C |
| ATOM | 1191 | CD | ARG | A | 155 | 85.765 | −53.690 | −69.926 | 1.00 | 64.96 | MOL1 | C |
| ATOM | 1192 | NE | ARG | A | 155 | 86.819 | −52.963 | −69.222 | 1.00 | 71.72 | MOL1 | N |
| ATOM | 1193 | CZ | ARG | A | 155 | 86.825 | −52.725 | −67.913 | 1.00 | 69.39 | MOL1 | C |
| ATOM | 1194 | NH1 | ARG | A | 155 | 85.831 | −53.150 | −67.151 | 1.00 | 71.63 | MOL1 | N |
| ATOM | 1195 | NH2 | ARG | A | 155 | 87.837 | −52.072 | −67.365 | 1.00 | 66.54 | MOL1 | N |
| ATOM | 1196 | C | ARG | A | 155 | 81.840 | −55.110 | −69.253 | 1.00 | 53.67 | MOL1 | C |
| ATOM | 1197 | O | ARG | A | 155 | 80.711 | −54.638 | −69.390 | 1.00 | 55.24 | MOL1 | O |
| ATOM | 1198 | N | GLN | A | 156 | 82.231 | −55.696 | −68.124 | 1.00 | 55.04 | MOL1 | N |
| ATOM | 1199 | CA | GLN | A | 156 | 81.323 | −55.783 | −66.986 | 1.00 | 58.54 | MOL1 | C |
| ATOM | 1200 | CB | GLN | A | 156 | 81.004 | −57.229 | −66.615 | 1.00 | 61.59 | MOL1 | C |
| ATOM | 1201 | CG | GLN | A | 156 | 80.438 | −58.075 | −67.737 | 1.00 | 79.88 | MOL1 | C |
| ATOM | 1202 | CD | GLN | A | 156 | 79.966 | −59.440 | −67.262 | 1.00 | 87.41 | MOL1 | C |
| ATOM | 1203 | OE1 | GLN | A | 156 | 80.640 | −60.102 | −66.468 | 1.00 | 93.29 | MOL1 | O |
| ATOM | 1204 | NE2 | GLN | A | 156 | 78.805 | −59.873 | −67.755 | 1.00 | 89.51 | MOL1 | N |
| ATOM | 1205 | C | GLN | A | 156 | 81.928 | −55.130 | −65.778 | 1.00 | 59.64 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 1206 | O | GLN | A | 156 | 81.261 | −54.408 | −65.058 | 1.00 | 65.86 | MOL1 | O |
|---|---|---|---|---|---|---|---|---|---|---|---|---|
| ATOM | 1207 | N | ASN | A | 157 | 83.199 | −55.395 | −65.546 | 1.00 | 63.25 | MOL1 | N |
| ATOM | 1208 | CA | ASN | A | 157 | 83.864 | −54.823 | −64.394 | 1.00 | 71.10 | MOL1 | C |
| ATOM | 1209 | CB | ASN | A | 157 | 85.283 | −55.394 | −64.247 | 1.00 | 86.83 | MOL1 | C |
| ATOM | 1210 | CG | ASN | A | 157 | 85.302 | −56.760 | −63.568 | 1.00 | 98.45 | MOL1 | C |
| ATOM | 1211 | OD1 | ASN | A | 157 | 84.663 | −57.717 | −64.031 | 1.00 | 103.27 | MOL1 | O |
| ATOM | 1212 | ND2 | ASN | A | 157 | 86.042 | −56.857 | −62.463 | 1.00 | 102.54 | MOL1 | N |
| ATOM | 1213 | C | ASN | A | 157 | 83.936 | −53.316 | −64.490 | 1.00 | 65.06 | MOL1 | C |
| ATOM | 1214 | O | ASN | A | 157 | 84.121 | −52.756 | −65.555 | 1.00 | 58.63 | MOL1 | O |
| ATOM | 1215 | N | GLY | A | 158 | 83.781 | −52.661 | −63.355 | 1.00 | 66.40 | MOL1 | N |
| ATOM | 1216 | CA | GLY | A | 158 | 83.860 | −51.222 | −63.340 | 1.00 | 65.80 | MOL1 | C |
| ATOM | 1217 | C | GLY | A | 158 | 82.582 | −50.549 | −63.763 | 1.00 | 60.11 | MOL1 | C |
| ATOM | 1218 | O | GLY | A | 158 | 82.597 | −49.387 | −64.163 | 1.00 | 66.36 | MOL1 | O |
| ATOM | 1219 | N | VAL | A | 159 | 81.470 | −51.268 | −63.691 | 1.00 | 52.44 | MOL1 | N |
| ATOM | 1220 | CA | VAL | A | 159 | 80.195 | −50.670 | −64.060 | 1.00 | 41.97 | MOL1 | C |
| ATOM | 1221 | CB | VAL | A | 159 | 79.426 | −51.493 | −65.090 | 1.00 | 27.90 | MOL1 | C |
| ATOM | 1222 | CG1 | VAL | A | 159 | 78.090 | −50.867 | −65.301 | 1.00 | 28.67 | MOL1 | C |
| ATOM | 1223 | CG2 | VAL | A | 159 | 80.148 | −51.523 | −66.408 | 1.00 | 15.19 | MOL1 | C |
| ATOM | 1224 | C | VAL | A | 159 | 79.286 | −50.500 | −62.862 | 1.00 | 42.76 | MOL1 | C |
| ATOM | 1225 | O | VAL | A | 159 | 79.097 | −51.424 | −62.075 | 1.00 | 48.52 | MOL1 | O |
| ATOM | 1226 | N | LEU | A | 160 | 78.725 | −49.307 | −62.730 | 1.00 | 42.26 | MOL1 | N |
| ATOM | 1227 | CA | LEU | A | 160 | 77.820 | −48.994 | −61.632 | 1.00 | 45.51 | MOL1 | C |
| ATOM | 1228 | CB | LEU | A | 160 | 78.399 | −47.914 | −60.728 | 1.00 | 40.24 | MOL1 | C |
| ATOM | 1229 | CG | LEU | A | 160 | 79.395 | −48.483 | −59.731 | 1.00 | 46.31 | MOL1 | C |
| ATOM | 1230 | CD1 | LEU | A | 160 | 79.255 | −47.725 | −58.429 | 1.00 | 43.90 | MOL1 | C |
| ATOM | 1231 | CD2 | LEU | A | 160 | 79.122 | −49.969 | −59.517 | 1.00 | 38.91 | MOL1 | C |
| ATOM | 1232 | C | LEU | A | 160 | 76.470 | −48.517 | −62.121 | 1.00 | 46.77 | MOL1 | C |
| ATOM | 1233 | O | LEU | A | 160 | 76.371 | −47.542 | −62.854 | 1.00 | 45.73 | MOL1 | O |
| ATOM | 1234 | N | ASN | A | 161 | 75.421 | −49.198 | −61.684 | 1.00 | 48.44 | MOL1 | N |
| ATOM | 1235 | CA | ASN | A | 161 | 74.076 | −48.846 | −62.090 | 1.00 | 41.68 | MOL1 | C |
| ATOM | 1236 | CB | ASN | A | 161 | 73.372 | −50.060 | −62.683 | 1.00 | 31.00 | MOL1 | C |
| ATOM | 1237 | CG | ASN | A | 161 | 74.031 | −50.548 | −63.939 | 1.00 | 33.80 | MOL1 | C |
| ATOM | 1238 | OD1 | ASN | A | 161 | 74.470 | −49.752 | −64.760 | 1.00 | 44.82 | MOL1 | O |
| ATOM | 1239 | ND2 | ASN | A | 161 | 74.098 | −51.859 | −64.109 | 1.00 | 31.39 | MOL1 | N |
| ATOM | 1240 | C | ASN | A | 161 | 73.239 | −48.328 | −60.953 | 1.00 | 40.97 | MOL1 | C |
| ATOM | 1241 | O | ASN | A | 161 | 73.439 | −48.691 | −59.800 | 1.00 | 48.68 | MOL1 | O |
| ATOM | 1242 | N | SER | A | 162 | 72.284 | −47.483 | −61.299 | 1.00 | 42.52 | MOL1 | N |
| ATOM | 1243 | CA | SER | A | 162 | 71.360 | −46.920 | −60.335 | 1.00 | 47.61 | MOL1 | C |
| ATOM | 1244 | CB | SER | A | 162 | 71.866 | −45.590 | −59.816 | 1.00 | 44.97 | MOL1 | C |
| ATOM | 1245 | OG | SER | A | 162 | 70.996 | −45.115 | −58.808 | 1.00 | 56.75 | MOL1 | O |
| ATOM | 1246 | C | SER | A | 162 | 70.011 | −46.692 | −60.991 | 1.00 | 51.05 | MOL1 | C |
| ATOM | 1247 | O | SER | A | 162 | 69.925 | −45.990 | −61.995 | 1.00 | 52.94 | MOL1 | O |
| ATOM | 1248 | N | TRP | A | 163 | 68.958 | −47.279 | −60.426 | 1.00 | 53.80 | MOL1 | N |
| ATOM | 1249 | CA | TRP | A | 163 | 67.607 | −47.112 | −60.970 | 1.00 | 56.76 | MOL1 | C |
| ATOM | 1250 | CB | TRP | A | 163 | 66.916 | −48.468 | −61.105 | 1.00 | 56.83 | MOL1 | C |
| ATOM | 1251 | CG | TRP | A | 163 | 67.638 | −49.460 | −61.963 | 1.00 | 71.33 | MOL1 | C |
| ATOM | 1252 | CD2 | TRP | A | 163 | 68.714 | −50.316 | −61.561 | 1.00 | 75.62 | MOL1 | C |
| ATOM | 1253 | CE2 | TRP | A | 163 | 69.028 | −51.141 | −62.663 | 1.00 | 74.63 | MOL1 | C |
| ATOM | 1254 | CE3 | TRP | A | 163 | 69.438 | −50.468 | −60.375 | 1.00 | 82.34 | MOL1 | C |
| ATOM | 1255 | CD1 | TRP | A | 163 | 67.359 | −49.785 | −63.259 | 1.00 | 73.47 | MOL1 | C |
| ATOM | 1256 | NE1 | TRP | A | 163 | 68.188 | −50.798 | −63.687 | 1.00 | 71.93 | MOL1 | N |
| ATOM | 1257 | CZ2 | TRP | A | 163 | 70.031 | −52.104 | −62.614 | 1.00 | 85.23 | MOL1 | C |
| ATOM | 1258 | CZ3 | TRP | A | 163 | 70.439 | −51.430 | −60.326 | 1.00 | 90.96 | MOL1 | C |
| ATOM | 1259 | CH2 | TRP | A | 163 | 70.725 | −52.236 | −61.440 | 1.00 | 91.71 | MOL1 | C |
| ATOM | 1260 | C | TRP | A | 163 | 66.737 | −46.208 | −60.085 | 1.00 | 55.98 | MOL1 | C |
| ATOM | 1261 | O | TRP | A | 163 | 66.921 | −46.138 | −58.873 | 1.00 | 59.76 | MOL1 | O |
| ATOM | 1262 | N | THR | A | 164 | 65.780 | −45.518 | −60.689 | 1.00 | 55.09 | MOL1 | N |
| ATOM | 1263 | CA | THR | A | 164 | 64.887 | −44.652 | −59.925 | 1.00 | 54.84 | MOL1 | C |
| ATOM | 1264 | CB | THR | A | 164 | 64.590 | −43.356 | −60.667 | 1.00 | 52.35 | MOL1 | C |
| ATOM | 1265 | OG1 | THR | A | 164 | 63.390 | −43.517 | −61.435 | 1.00 | 50.16 | MOL1 | O |
| ATOM | 1266 | CG2 | THR | A | 164 | 65.724 | −43.016 | −61.605 | 1.00 | 46.71 | MOL1 | C |
| ATOM | 1267 | C | THR | A | 164 | 63.543 | −45.353 | −59.692 | 1.00 | 59.43 | MOL1 | C |
| ATOM | 1268 | O | THR | A | 164 | 63.308 | −46.466 | −60.169 | 1.00 | 58.45 | MOL1 | O |
| ATOM | 1269 | N | ASP | A | 165 | 62.653 | −44.688 | −58.970 | 1.00 | 62.09 | MOL1 | N |
| ATOM | 1270 | CA | ASP | A | 165 | 61.343 | −45.251 | −58.674 | 1.00 | 66.67 | MOL1 | C |
| ATOM | 1271 | CB | ASP | A | 165 | 60.917 | −44.820 | −57.280 | 1.00 | 80.07 | MOL1 | C |
| ATOM | 1272 | CG | ASP | A | 165 | 62.003 | −45.043 | −56.252 | 1.00 | 92.52 | MOL1 | C |
| ATOM | 1273 | OD1 | ASP | A | 165 | 62.051 | −46.153 | −55.671 | 1.00 | 95.82 | MOL1 | O |
| ATOM | 1274 | OD2 | ASP | A | 165 | 62.817 | −44.109 | −56.044 | 1.00 | 99.11 | MOL1 | O |
| ATOM | 1275 | C | ASP | A | 165 | 60.324 | −44.762 | −59.688 | 1.00 | 63.72 | MOL1 | C |
| ATOM | 1276 | O | ASP | A | 165 | 60.561 | −43.785 | −60.393 | 1.00 | 66.68 | MOL1 | O |
| ATOM | 1277 | N | GLN | A | 166 | 59.182 | −45.425 | −59.754 | 1.00 | 56.44 | MOL1 | N |
| ATOM | 1278 | CA | GLN | A | 166 | 58.178 | −45.033 | −60.713 | 1.00 | 58.67 | MOL1 | C |
| ATOM | 1279 | CB | GLN | A | 166 | 56.908 | −45.819 | −60.432 | 1.00 | 59.19 | MOL1 | C |
| ATOM | 1280 | CG | GLN | A | 166 | 56.084 | −46.112 | −61.663 | 1.00 | 58.86 | MOL1 | C |
| ATOM | 1281 | CD | GLN | A | 166 | 55.394 | −47.459 | −61.581 | 1.00 | 64.40 | MOL1 | C |
| ATOM | 1282 | OE1 | GLN | A | 166 | 55.010 | −47.911 | −60.499 | 1.00 | 64.45 | MOL1 | O |

TABLE 1-continued

The atomic coordinates of IL17F in complex with 496 Fab
(H32; a = 189.4; b = 189.4; c = 490.9, α, β = 90°; γ = 120°)

| ATOM | 1283 | NE2 | GLN | A | 166 | 55.223 | −48.104 | −62.726 | 1.00 | 66.99 | MOL1 | N |
|---|---|---|---|---|---|---|---|---|---|---|---|---|
| ATOM | 1284 | C | GLN | A | 166 | 57.950 | −43.520 | −60.653 | 1.00 | 62.82 | MOL1 | C |
| ATOM | 1285 | O | GLN | A | 166 | 57.456 | −42.996 | −59.658 | 1.00 | 68.37 | MOL1 | O |
| ATOM | 1286 | N | ASP | A | 167 | 58.342 | −42.816 | −61.714 | 1.00 | 65.41 | MOL1 | N |
| ATOM | 1287 | CA | ASP | A | 167 | 58.188 | −41.364 | −61.760 | 1.00 | 66.30 | MOL1 | C |
| ATOM | 1288 | CB | ASP | A | 167 | 58.740 | −40.756 | −63.042 | 1.00 | 70.81 | MOL1 | C |
| ATOM | 1289 | CG | ASP | A | 167 | 58.354 | −39.276 | −63.197 | 1.00 | 72.23 | MOL1 | C |
| ATOM | 1290 | OD1 | ASP | A | 167 | 58.940 | −38.401 | −62.506 | 1.00 | 73.65 | MOL1 | O |
| ATOM | 1291 | OD2 | ASP | A | 167 | 57.451 | −38.994 | −64.012 | 1.00 | 68.65 | MOL1 | O |
| ATOM | 1292 | C | ASP | A | 167 | 56.749 | −40.953 | −61.658 | 1.00 | 65.57 | MOL1 | C |
| ATOM | 1293 | O | ASP | A | 167 | 55.985 | −41.154 | −62.588 | 1.00 | 64.53 | MOL1 | O |
| ATOM | 1294 | N | SER | A | 168 | 56.411 | −40.346 | −60.523 | 1.00 | 73.23 | MOL1 | N |
| ATOM | 1295 | CA | SER | A | 168 | 55.066 | −39.872 | −60.208 | 1.00 | 74.94 | MOL1 | C |
| ATOM | 1296 | CB | SER | A | 168 | 55.128 | −38.780 | −59.149 | 1.00 | 71.48 | MOL1 | C |
| ATOM | 1297 | OG | SER | A | 168 | 55.701 | −37.605 | −59.694 | 1.00 | 75.17 | MOL1 | O |
| ATOM | 1298 | C | SER | A | 168 | 54.254 | −39.353 | −61.387 | 1.00 | 79.14 | MOL1 | C |
| ATOM | 1299 | O | SER | A | 168 | 53.053 | −39.603 | −61.455 | 1.00 | 84.23 | MOL1 | O |
| ATOM | 1300 | N | LYS | A | 169 | 54.880 | −38.629 | −62.311 | 1.00 | 80.12 | MOL1 | N |
| ATOM | 1301 | CA | LYS | A | 169 | 54.130 | −38.123 | −63.455 | 1.00 | 80.42 | MOL1 | C |
| ATOM | 1302 | CB | LYS | A | 169 | 54.921 | −37.044 | −64.185 | 1.00 | 84.94 | MOL1 | C |
| ATOM | 1303 | CG | LYS | A | 169 | 55.039 | −35.736 | −63.406 | 1.00 | 94.72 | MOL1 | C |
| ATOM | 1304 | CD | LYS | A | 169 | 53.685 | −35.073 | −63.163 | 1.00 | 98.23 | MOL1 | C |
| ATOM | 1305 | CE | LYS | A | 169 | 53.842 | −33.610 | −62.697 | 1.00 | 102.08 | MOL1 | C |
| ATOM | 1306 | NZ | LYS | A | 169 | 54.350 | −32.673 | −63.761 | 1.00 | 97.72 | MOL1 | N |
| ATOM | 1307 | C | LYS | A | 169 | 53.656 | −39.208 | −64.441 | 1.00 | 80.54 | MOL1 | C |
| ATOM | 1308 | O | LYS | A | 169 | 52.453 | −39.429 | −64.560 | 1.00 | 83.84 | MOL1 | O |
| ATOM | 1309 | N | ASP | A | 170 | 54.568 | −39.900 | −65.126 | 1.00 | 72.17 | MOL1 | N |
| ATOM | 1310 | CA | ASP | A | 170 | 54.145 | −40.923 | −66.077 | 1.00 | 61.39 | MOL1 | C |
| ATOM | 1311 | CB | ASP | A | 170 | 54.832 | −40.683 | −67.401 | 1.00 | 59.48 | MOL1 | C |
| ATOM | 1312 | CG | ASP | A | 170 | 56.303 | −40.674 | −67.257 | 1.00 | 59.53 | MOL1 | C |
| ATOM | 1313 | OD1 | ASP | A | 170 | 57.002 | −40.408 | −68.264 | 1.00 | 63.71 | MOL1 | O |
| ATOM | 1314 | OD2 | ASP | A | 170 | 56.740 | −40.942 | −66.114 | 1.00 | 48.77 | MOL1 | O |
| ATOM | 1315 | C | ASP | A | 170 | 54.357 | −42.372 | −65.631 | 1.00 | 56.39 | MOL1 | C |
| ATOM | 1316 | O | ASP | A | 170 | 54.340 | −43.301 | −66.436 | 1.00 | 56.20 | MOL1 | O |
| ATOM | 1317 | N | SER | A | 171 | 54.542 | −42.567 | −64.340 | 1.00 | 52.36 | MOL1 | N |
| ATOM | 1318 | CA | SER | A | 171 | 54.718 | −43.905 | −63.795 | 1.00 | 54.88 | MOL1 | C |
| ATOM | 1319 | CB | SER | A | 171 | 53.345 | −44.582 | −63.697 | 1.00 | 48.11 | MOL1 | C |
| ATOM | 1320 | OG | SER | A | 171 | 52.491 | −43.858 | −62.823 | 1.00 | 43.01 | MOL1 | O |
| ATOM | 1321 | C | SER | A | 171 | 55.730 | −44.828 | −64.510 | 1.00 | 55.50 | MOL1 | C |
| ATOM | 1322 | O | SER | A | 171 | 55.613 | −46.054 | −64.443 | 1.00 | 51.45 | MOL1 | O |
| ATOM | 1323 | N | THR | A | 172 | 56.728 | −44.230 | −65.163 | 1.00 | 55.06 | MOL1 | N |
| ATOM | 1324 | CA | THR | A | 172 | 57.784 | −44.968 | −65.872 | 1.00 | 55.45 | MOL1 | C |
| ATOM | 1325 | CB | THR | A | 172 | 58.251 | −44.191 | −67.076 | 1.00 | 55.67 | MOL1 | C |
| ATOM | 1326 | OG1 | THR | A | 172 | 58.701 | −42.897 | −66.648 | 1.00 | 59.46 | MOL1 | O |
| ATOM | 1327 | CG2 | THR | A | 172 | 57.131 | −44.038 | −68.061 | 1.00 | 58.93 | MOL1 | C |
| ATOM | 1328 | C | THR | A | 172 | 59.015 | −45.158 | −64.982 | 1.00 | 55.74 | MOL1 | C |
| ATOM | 1329 | O | THR | A | 172 | 58.996 | −44.796 | −63.817 | 1.00 | 63.90 | MOL1 | O |
| ATOM | 1330 | N | TYR | A | 173 | 60.085 | −45.727 | −65.526 | 1.00 | 52.56 | MOL1 | N |
| ATOM | 1331 | CA | TYR | A | 173 | 61.307 | −45.895 | −64.750 | 1.00 | 50.26 | MOL1 | C |
| ATOM | 1332 | CB | TYR | A | 173 | 61.607 | −47.367 | −64.509 | 1.00 | 43.79 | MOL1 | C |
| ATOM | 1333 | CG | TYR | A | 173 | 60.621 | −48.061 | −63.605 | 1.00 | 43.50 | MOL1 | C |
| ATOM | 1334 | CD1 | TYR | A | 173 | 59.493 | −48.681 | −64.113 | 1.00 | 44.80 | MOL1 | C |
| ATOM | 1335 | CE1 | TYR | A | 173 | 58.604 | −49.346 | −63.278 | 1.00 | 45.59 | MOL1 | C |
| ATOM | 1336 | CD2 | TYR | A | 173 | 60.831 | −48.117 | −62.239 | 1.00 | 44.97 | MOL1 | C |
| ATOM | 1337 | CE2 | TYR | A | 173 | 59.945 | −48.774 | −61.400 | 1.00 | 43.62 | MOL1 | C |
| ATOM | 1338 | CZ | TYR | A | 173 | 58.842 | −49.384 | −61.923 | 1.00 | 44.26 | MOL1 | C |
| ATOM | 1339 | OH | TYR | A | 173 | 57.978 | −50.036 | −61.082 | 1.00 | 51.59 | MOL1 | O |
| ATOM | 1340 | C | TYR | A | 173 | 62.475 | −45.251 | −65.486 | 1.00 | 55.17 | MOL1 | C |
| ATOM | 1341 | O | TYR | A | 173 | 62.322 | −44.788 | −66.618 | 1.00 | 62.28 | MOL1 | O |
| ATOM | 1342 | N | SER | A | 174 | 63.636 | −45.210 | −64.841 | 1.00 | 53.72 | MOL1 | N |
| ATOM | 1343 | CA | SER | A | 174 | 64.832 | −44.632 | −65.449 | 1.00 | 51.71 | MOL1 | C |
| ATOM | 1344 | CB | SER | A | 174 | 64.833 | −43.108 | −65.304 | 1.00 | 50.48 | MOL1 | C |
| ATOM | 1345 | OG | SER | A | 174 | 63.860 | −42.498 | −66.147 | 1.00 | 44.82 | MOL1 | O |
| ATOM | 1346 | C | SER | A | 174 | 66.065 | −45.223 | −64.793 | 1.00 | 52.24 | MOL1 | C |
| ATOM | 1347 | O | SER | A | 174 | 66.041 | −45.570 | −63.617 | 1.00 | 58.50 | MOL1 | O |
| ATOM | 1348 | N | MET | A | 175 | 67.143 | −45.338 | −65.553 | 1.00 | 49.18 | MOL1 | N |
| ATOM | 1349 | CA | MET | A | 175 | 68.363 | −45.922 | −65.031 | 1.00 | 47.47 | MOL1 | C |
| ATOM | 1350 | CB | MET | A | 175 | 68.417 | −47.380 | −65.443 | 1.00 | 40.24 | MOL1 | C |
| ATOM | 1351 | CG | MET | A | 175 | 69.757 | −48.007 | −65.277 | 1.00 | 42.37 | MOL1 | C |
| ATOM | 1352 | SD | MET | A | 175 | 69.821 | −49.506 | −66.218 | 1.00 | 45.65 | MOL1 | S |
| ATOM | 1353 | CE | MET | A | 175 | 70.994 | −50.394 | −65.304 | 1.00 | 40.57 | MOL1 | C |
| ATOM | 1354 | C | MET | A | 175 | 69.605 | −45.206 | −65.533 | 1.00 | 50.44 | MOL1 | C |
| ATOM | 1355 | O | MET | A | 175 | 69.617 | −44.676 | −66.647 | 1.00 | 55.74 | MOL1 | O |
| ATOM | 1356 | N | SER | A | 176 | 70.655 | −45.210 | −64.718 | 1.00 | 46.12 | MOL1 | N |
| ATOM | 1357 | CA | SER | A | 176 | 71.892 | −44.558 | −65.091 | 1.00 | 41.27 | MOL1 | C |
| ATOM | 1358 | CB | SER | A | 176 | 72.061 | −43.303 | −64.266 | 1.00 | 29.85 | MOL1 | C |
| ATOM | 1359 | OG | SER | A | 176 | 73.372 | −42.821 | −64.386 | 1.00 | 43.09 | MOL1 | O |

TABLE 1-continued

The atomic coordinates of IL17F in complex with 496 Fab
(H32; a = 189.4; b = 189.4; c = 490.9, α, β = 90°; γ = 120°)

| ATOM | 1360 | C | SER | A | 176 | 73.106 | −45.456 | −64.923 | 1.00 | 45.18 | MOL1 | C |
|---|---|---|---|---|---|---|---|---|---|---|---|---|
| ATOM | 1361 | O | SER | A | 176 | 73.592 | −45.658 | −63.812 | 1.00 | 54.11 | MOL1 | O |
| ATOM | 1362 | N | SER | A | 177 | 73.598 | −45.985 | −66.041 | 1.00 | 46.03 | MOL1 | N |
| ATOM | 1363 | CA | SER | A | 177 | 74.766 | −46.859 | −66.051 | 1.00 | 44.00 | MOL1 | C |
| ATOM | 1364 | CB | SER | A | 177 | 74.588 | −47.925 | −67.127 | 1.00 | 35.81 | MOL1 | C |
| ATOM | 1365 | OG | SER | A | 177 | 75.571 | −48.936 | −66.998 | 1.00 | 38.60 | MOL1 | O |
| ATOM | 1366 | C | SER | A | 177 | 76.042 | −46.049 | −66.314 | 1.00 | 43.36 | MOL1 | C |
| ATOM | 1367 | O | SER | A | 177 | 76.122 | −45.294 | −67.273 | 1.00 | 37.64 | MOL1 | O |
| ATOM | 1368 | N | THR | A | 178 | 77.040 | −46.225 | −65.458 | 1.00 | 49.84 | MOL1 | N |
| ATOM | 1369 | CA | THR | A | 178 | 78.297 | −45.497 | −65.574 | 1.00 | 52.81 | MOL1 | C |
| ATOM | 1370 | CB | THR | A | 178 | 78.464 | −44.563 | −64.380 | 1.00 | 52.72 | MOL1 | C |
| ATOM | 1371 | OG1 | THR | A | 178 | 77.268 | −43.784 | −64.208 | 1.00 | 53.19 | MOL1 | O |
| ATOM | 1372 | CG2 | THR | A | 178 | 79.661 | −43.672 | −64.585 | 1.00 | 49.15 | MOL1 | C |
| ATOM | 1373 | C | THR | A | 178 | 79.525 | −46.419 | −65.642 | 1.00 | 53.03 | MOL1 | C |
| ATOM | 1374 | O | THR | A | 178 | 79.827 | −47.156 | −64.706 | 1.00 | 50.94 | MOL1 | O |
| ATOM | 1375 | N | LEU | A | 179 | 80.235 | −46.368 | −66.758 | 1.00 | 52.76 | MOL1 | N |
| ATOM | 1376 | CA | LEU | A | 179 | 81.420 | −47.185 | −66.946 | 1.00 | 49.79 | MOL1 | C |
| ATOM | 1377 | CB | LEU | A | 179 | 81.573 | −47.529 | −68.423 | 1.00 | 36.69 | MOL1 | C |
| ATOM | 1378 | CG | LEU | A | 179 | 82.180 | −48.863 | −68.827 | 1.00 | 28.63 | MOL1 | C |
| ATOM | 1379 | CD1 | LEU | A | 179 | 82.723 | −48.732 | −70.234 | 1.00 | 9.54 | MOL1 | C |
| ATOM | 1380 | CD2 | LEU | A | 179 | 83.255 | −49.267 | −67.853 | 1.00 | 12.92 | MOL1 | C |
| ATOM | 1381 | C | LEU | A | 179 | 82.613 | −46.359 | −66.500 | 1.00 | 55.80 | MOL1 | C |
| ATOM | 1382 | O | LEU | A | 179 | 82.973 | −45.379 | −67.155 | 1.00 | 60.37 | MOL1 | O |
| ATOM | 1383 | N | THR | A | 180 | 83.220 | −46.732 | −65.380 | 1.00 | 59.90 | MOL1 | N |
| ATOM | 1384 | CA | THR | A | 180 | 84.376 | −45.994 | −64.909 | 1.00 | 61.75 | MOL1 | C |
| ATOM | 1385 | CB | THR | A | 180 | 84.280 | −45.653 | −63.441 | 1.00 | 63.39 | MOL1 | C |
| ATOM | 1386 | OG1 | THR | A | 180 | 83.254 | −44.670 | −63.262 | 1.00 | 70.29 | MOL1 | O |
| ATOM | 1387 | CG2 | THR | A | 180 | 85.597 | −45.084 | −62.955 | 1.00 | 62.81 | MOL1 | C |
| ATOM | 1388 | C | THR | A | 180 | 85.658 | −46.751 | −65.173 | 1.00 | 62.47 | MOL1 | C |
| ATOM | 1389 | O | THR | A | 180 | 85.851 | −47.886 | −64.737 | 1.00 | 54.28 | MOL1 | O |
| ATOM | 1390 | N | LEU | A | 181 | 86.526 | −46.084 | −65.920 | 1.00 | 65.09 | MOL1 | N |
| ATOM | 1391 | CA | LEU | A | 181 | 87.802 | −46.615 | −66.331 | 1.00 | 62.68 | MOL1 | C |
| ATOM | 1392 | CB | LEU | A | 181 | 87.846 | −46.659 | −67.856 | 1.00 | 47.31 | MOL1 | C |
| ATOM | 1393 | CG | LEU | A | 181 | 86.804 | −47.394 | −68.708 | 1.00 | 38.89 | MOL1 | C |
| ATOM | 1394 | CD1 | LEU | A | 181 | 86.855 | −46.908 | −70.141 | 1.00 | 32.49 | MOL1 | C |
| ATOM | 1395 | CD2 | LEU | A | 181 | 87.068 | −48.878 | −68.681 | 1.00 | 40.25 | MOL1 | C |
| ATOM | 1396 | C | LEU | A | 181 | 88.907 | −45.689 | −65.840 | 1.00 | 71.52 | MOL1 | C |
| ATOM | 1397 | O | LEU | A | 181 | 88.650 | −44.647 | −65.235 | 1.00 | 78.58 | MOL1 | O |
| ATOM | 1398 | N | THR | A | 182 | 90.142 | −46.078 | −66.124 | 1.00 | 74.68 | MOL1 | N |
| ATOM | 1399 | CA | THR | A | 182 | 91.306 | −45.298 | −65.758 | 1.00 | 74.62 | MOL1 | C |
| ATOM | 1400 | CB | THR | A | 182 | 92.413 | −46.237 | −65.283 | 1.00 | 62.12 | MOL1 | C |
| ATOM | 1401 | OG1 | THR | A | 182 | 93.526 | −45.466 | −64.827 | 1.00 | 74.80 | MOL1 | O |
| ATOM | 1402 | CG2 | THR | A | 182 | 92.834 | −47.157 | −66.395 | 1.00 | 52.68 | MOL1 | C |
| ATOM | 1403 | C | THR | A | 182 | 91.718 | −44.554 | −67.032 | 1.00 | 77.25 | MOL1 | C |
| ATOM | 1404 | O | THR | A | 182 | 91.715 | −45.133 | −68.108 | 1.00 | 74.29 | MOL1 | O |
| ATOM | 1405 | N | LYS | A | 183 | 92.060 | −43.274 | −66.924 | 1.00 | 83.74 | MOL1 | N |
| ATOM | 1406 | CA | LYS | A | 183 | 92.420 | −42.525 | −68.121 | 1.00 | 85.05 | MOL1 | C |
| ATOM | 1407 | CB | LYS | A | 183 | 93.107 | −41.200 | −67.783 | 1.00 | 84.93 | MOL1 | C |
| ATOM | 1408 | CG | LYS | A | 183 | 93.493 | −40.396 | −69.028 | 1.00 | 89.07 | MOL1 | C |
| ATOM | 1409 | CD | LYS | A | 183 | 94.113 | −39.041 | −68.690 | 1.00 | 95.34 | MOL1 | C |
| ATOM | 1410 | CE | LYS | A | 183 | 94.971 | −38.505 | −69.852 | 1.00 | 102.58 | MOL1 | C |
| ATOM | 1411 | NZ | LYS | A | 183 | 94.225 | −38.217 | −71.122 | 1.00 | 101.02 | MOL1 | N |
| ATOM | 1412 | C | LYS | A | 183 | 93.299 | −43.336 | −69.054 | 1.00 | 86.65 | MOL1 | C |
| ATOM | 1413 | O | LYS | A | 183 | 93.243 | −43.151 | −70.264 | 1.00 | 89.84 | MOL1 | O |
| ATOM | 1414 | N | ASP | A | 184 | 94.097 | −44.244 | −68.498 | 1.00 | 84.63 | MOL1 | N |
| ATOM | 1415 | CA | ASP | A | 184 | 94.968 | −45.074 | −69.320 | 1.00 | 78.83 | MOL1 | C |
| ATOM | 1416 | CB | ASP | A | 184 | 95.891 | −45.922 | −68.454 | 1.00 | 76.43 | MOL1 | C |
| ATOM | 1417 | CG | ASP | A | 184 | 97.093 | −45.160 | −67.978 | 1.00 | 74.31 | MOL1 | C |
| ATOM | 1418 | OD1 | ASP | A | 184 | 97.602 | −44.319 | −68.747 | 1.00 | 72.34 | MOL1 | O |
| ATOM | 1419 | OD2 | ASP | A | 184 | 97.537 | −45.412 | −66.845 | 1.00 | 77.64 | MOL1 | O |
| ATOM | 1420 | C | ASP | A | 184 | 94.164 | −45.986 | −70.222 | 1.00 | 74.98 | MOL1 | C |
| ATOM | 1421 | O | ASP | A | 184 | 94.232 | −45.882 | −71.442 | 1.00 | 74.18 | MOL1 | O |
| ATOM | 1422 | N | GLU | A | 185 | 93.410 | −46.886 | −69.602 | 1.00 | 72.44 | MOL1 | N |
| ATOM | 1423 | CA | GLU | A | 185 | 92.573 | −47.843 | −70.315 | 1.00 | 66.34 | MOL1 | C |
| ATOM | 1424 | CB | GLU | A | 185 | 91.754 | −48.663 | −69.314 | 1.00 | 63.30 | MOL1 | C |
| ATOM | 1425 | CG | GLU | A | 185 | 90.586 | −49.427 | −69.921 | 1.00 | 67.55 | MOL1 | C |
| ATOM | 1426 | CD | GLU | A | 185 | 90.754 | −50.947 | −69.877 | 1.00 | 72.80 | MOL1 | C |
| ATOM | 1427 | OE1 | GLU | A | 185 | 91.181 | −51.544 | −70.902 | 1.00 | 65.76 | MOL1 | O |
| ATOM | 1428 | OE2 | GLU | A | 185 | 90.456 | −51.536 | −68.810 | 1.00 | 70.09 | MOL1 | O |
| ATOM | 1429 | C | GLU | A | 185 | 91.632 | −47.153 | −71.280 | 1.00 | 60.58 | MOL1 | C |
| ATOM | 1430 | O | GLU | A | 185 | 91.301 | −47.688 | −72.326 | 1.00 | 59.86 | MOL1 | O |
| ATOM | 1431 | N | TYR | A | 186 | 91.198 | −45.956 | −70.929 | 1.00 | 57.50 | MOL1 | N |
| ATOM | 1432 | CA | TYR | A | 186 | 90.287 | −45.246 | −71.790 | 1.00 | 53.11 | MOL1 | C |
| ATOM | 1433 | CB | TYR | A | 186 | 89.787 | −43.998 | −71.107 | 1.00 | 44.58 | MOL1 | C |
| ATOM | 1434 | CG | TYR | A | 186 | 88.920 | −43.169 | −72.007 | 1.00 | 37.74 | MOL1 | C |
| ATOM | 1435 | CD1 | TYR | A | 186 | 89.158 | −41.819 | −72.167 | 1.00 | 31.73 | MOL1 | C |
| ATOM | 1436 | CE1 | TYR | A | 186 | 88.379 | −41.062 | −72.985 | 1.00 | 36.38 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 1437 | CD2 | TYR | A | 186 | 87.870 | −43.734 | −72.696 | 1.00 | 31.82 | MOL1 | C |
|---|---|---|---|---|---|---|---|---|---|---|---|---|
| ATOM | 1438 | CE2 | TYR | A | 186 | 87.080 | −42.980 | −73.522 | 1.00 | 32.78 | MOL1 | C |
| ATOM | 1439 | CZ | TYR | A | 186 | 87.336 | −41.641 | −73.664 | 1.00 | 35.16 | MOL1 | C |
| ATOM | 1440 | OH | TYR | A | 186 | 86.546 | −40.851 | −74.466 | 1.00 | 32.28 | MOL1 | O |
| ATOM | 1441 | C | TYR | A | 186 | 90.941 | −44.873 | −73.098 | 1.00 | 58.07 | MOL1 | C |
| ATOM | 1442 | O | TYR | A | 186 | 90.287 | −44.840 | −74.137 | 1.00 | 58.04 | MOL1 | O |
| ATOM | 1443 | N | GLU | A | 187 | 92.239 | −44.592 | −73.044 | 1.00 | 64.32 | MOL1 | N |
| ATOM | 1444 | CA | GLU | A | 187 | 92.986 | −44.205 | −74.235 | 1.00 | 63.73 | MOL1 | C |
| ATOM | 1445 | CB | GLU | A | 187 | 94.223 | −43.415 | −73.828 | 1.00 | 57.01 | MOL1 | C |
| ATOM | 1446 | CG | GLU | A | 187 | 93.924 | −42.217 | −72.923 | 1.00 | 62.09 | MOL1 | C |
| ATOM | 1447 | CD | GLU | A | 187 | 93.226 | −41.066 | −73.638 | 1.00 | 71.91 | MOL1 | C |
| ATOM | 1448 | OE1 | GLU | A | 187 | 93.049 | −39.993 | −73.018 | 1.00 | 72.14 | MOL1 | O |
| ATOM | 1449 | OE2 | GLU | A | 187 | 92.851 | −41.224 | −74.819 | 1.00 | 80.91 | MOL1 | O |
| ATOM | 1450 | C | GLU | A | 187 | 93.372 | −45.394 | −75.117 | 1.00 | 64.63 | MOL1 | C |
| ATOM | 1451 | O | GLU | A | 187 | 93.408 | −45.263 | −76.336 | 1.00 | 66.47 | MOL1 | O |
| ATOM | 1452 | N | ARG | A | 188 | 93.641 | −46.549 | −74.504 | 1.00 | 63.39 | MOL1 | N |
| ATOM | 1453 | CA | ARG | A | 188 | 94.005 | −47.768 | −75.234 | 1.00 | 58.30 | MOL1 | C |
| ATOM | 1454 | CB | ARG | A | 188 | 94.199 | −48.975 | −74.289 | 1.00 | 49.50 | MOL1 | C |
| ATOM | 1455 | CG | ARG | A | 188 | 95.198 | −48.838 | −73.133 | 1.00 | 57.70 | MOL1 | C |
| ATOM | 1456 | CD | ARG | A | 188 | 95.079 | −49.991 | −72.096 | 1.00 | 51.90 | MOL1 | C |
| ATOM | 1457 | NE | ARG | A | 188 | 94.958 | −51.299 | −72.754 | 1.00 | 76.56 | MOL1 | N |
| ATOM | 1458 | CZ | ARG | A | 188 | 94.852 | −52.466 | −72.116 | 1.00 | 81.12 | MOL1 | C |
| ATOM | 1459 | NH1 | ARG | A | 188 | 94.856 | −52.484 | −70.787 | 1.00 | 82.98 | MOL1 | N |
| ATOM | 1460 | NH2 | ARG | A | 188 | 94.739 | −53.612 | −72.800 | 1.00 | 68.90 | MOL1 | N |
| ATOM | 1461 | C | ARG | A | 188 | 92.938 | −48.176 | −76.254 | 1.00 | 59.20 | MOL1 | C |
| ATOM | 1462 | O | ARG | A | 188 | 93.225 | −48.956 | −77.152 | 1.00 | 65.46 | MOL1 | O |
| ATOM | 1463 | N | HIS | A | 189 | 91.712 | −47.673 | −76.112 | 1.00 | 56.80 | MOL1 | N |
| ATOM | 1464 | CA | HIS | A | 189 | 90.631 | −48.034 | −77.032 | 1.00 | 55.86 | MOL1 | C |
| ATOM | 1465 | CB | HIS | A | 189 | 89.620 | −48.900 | −76.317 | 1.00 | 42.17 | MOL1 | C |
| ATOM | 1466 | CG | HIS | A | 189 | 90.204 | −50.157 | −75.762 | 1.00 | 38.98 | MOL1 | C |
| ATOM | 1467 | CD2 | HIS | A | 189 | 90.437 | −51.360 | −76.337 | 1.00 | 30.28 | MOL1 | C |
| ATOM | 1468 | ND1 | HIS | A | 189 | 90.630 | −50.266 | −74.456 | 1.00 | 39.36 | MOL1 | N |
| ATOM | 1469 | CE1 | HIS | A | 189 | 91.097 | −51.484 | −74.245 | 1.00 | 35.00 | MOL1 | C |
| ATOM | 1470 | NE2 | HIS | A | 189 | 90.991 | −52.166 | −75.372 | 1.00 | 46.08 | MOL1 | N |
| ATOM | 1471 | C | HIS | A | 189 | 89.918 | −46.858 | −77.663 | 1.00 | 58.12 | MOL1 | C |
| ATOM | 1472 | O | HIS | A | 189 | 90.022 | −45.749 | −77.172 | 1.00 | 62.25 | MOL1 | O |
| ATOM | 1473 | N | ASN | A | 190 | 89.164 | −47.108 | −78.733 | 1.00 | 63.31 | MOL1 | N |
| ATOM | 1474 | CA | ASN | A | 190 | 88.482 | −46.036 | −79.459 | 1.00 | 71.60 | MOL1 | C |
| ATOM | 1475 | CB | ASN | A | 190 | 88.913 | −46.052 | −80.934 | 1.00 | 84.21 | MOL1 | C |
| ATOM | 1476 | CG | ASN | A | 190 | 90.226 | −46.810 | −81.158 | 1.00 | 102.56 | MOL1 | C |
| ATOM | 1477 | OD1 | ASN | A | 190 | 91.244 | −46.527 | −80.511 | 1.00 | 107.31 | MOL1 | O |
| ATOM | 1478 | ND2 | ASN | A | 190 | 90.207 | −47.779 | −82.082 | 1.00 | 104.96 | MOL1 | N |
| ATOM | 1479 | C | ASN | A | 190 | 86.964 | −46.031 | −79.416 | 1.00 | 67.58 | MOL1 | C |
| ATOM | 1480 | O | ASN | A | 190 | 86.351 | −44.999 | −79.160 | 1.00 | 72.39 | MOL1 | O |
| ATOM | 1481 | N | SER | A | 191 | 86.352 | −47.173 | −79.685 | 1.00 | 59.40 | MOL1 | N |
| ATOM | 1482 | CA | SER | A | 191 | 84.902 | −47.248 | −79.695 | 1.00 | 56.91 | MOL1 | C |
| ATOM | 1483 | CB | SER | A | 191 | 84.457 | −48.247 | −80.739 | 1.00 | 57.49 | MOL1 | C |
| ATOM | 1484 | OG | SER | A | 191 | 83.319 | −48.946 | −80.269 | 1.00 | 69.90 | MOL1 | O |
| ATOM | 1485 | C | SER | A | 191 | 84.239 | −47.610 | −78.375 | 1.00 | 54.40 | MOL1 | C |
| ATOM | 1486 | O | SER | A | 191 | 84.642 | −48.554 | −77.716 | 1.00 | 58.76 | MOL1 | O |
| ATOM | 1487 | N | TYR | A | 192 | 83.203 | −46.863 | −78.003 | 1.00 | 51.54 | MOL1 | N |
| ATOM | 1488 | CA | TYR | A | 192 | 82.451 | −47.120 | −76.773 | 1.00 | 43.81 | MOL1 | C |
| ATOM | 1489 | CB | TYR | A | 192 | 82.693 | −46.050 | −75.749 | 1.00 | 31.45 | MOL1 | C |
| ATOM | 1490 | CG | TYR | A | 192 | 84.071 | −46.101 | −75.234 | 1.00 | 33.88 | MOL1 | C |
| ATOM | 1491 | CD1 | TYR | A | 192 | 85.092 | −45.470 | −75.896 | 1.00 | 27.09 | MOL1 | C |
| ATOM | 1492 | CE1 | TYR | A | 192 | 86.359 | −45.561 | −75.446 | 1.00 | 30.45 | MOL1 | C |
| ATOM | 1493 | CD2 | TYR | A | 192 | 84.365 | −46.826 | −74.105 | 1.00 | 35.96 | MOL1 | C |
| ATOM | 1494 | CE2 | TYR | A | 192 | 85.638 | −46.925 | −73.650 | 1.00 | 36.01 | MOL1 | C |
| ATOM | 1495 | CZ | TYR | A | 192 | 86.626 | −46.291 | −74.322 | 1.00 | 31.98 | MOL1 | C |
| ATOM | 1496 | OH | TYR | A | 192 | 87.900 | −46.375 | −73.855 | 1.00 | 47.59 | MOL1 | O |
| ATOM | 1497 | C | TYR | A | 192 | 80.974 | −47.178 | −76.994 | 1.00 | 40.63 | MOL1 | C |
| ATOM | 1498 | O | TYR | A | 192 | 80.384 | −46.205 | −77.423 | 1.00 | 52.47 | MOL1 | O |
| ATOM | 1499 | N | THR | A | 193 | 80.357 | −48.308 | −76.706 | 1.00 | 37.69 | MOL1 | N |
| ATOM | 1500 | CA | THR | A | 193 | 78.928 | −48.374 | −76.892 | 1.00 | 38.83 | MOL1 | C |
| ATOM | 1501 | CB | THR | A | 193 | 78.503 | −49.230 | −78.093 | 1.00 | 37.54 | MOL1 | C |
| ATOM | 1502 | OG1 | THR | A | 193 | 78.013 | −50.486 | −77.614 | 1.00 | 45.73 | MOL1 | O |
| ATOM | 1503 | CG2 | THR | A | 193 | 79.662 | −49.433 | −79.084 | 1.00 | 33.88 | MOL1 | C |
| ATOM | 1504 | C | THR | A | 193 | 78.199 | −48.868 | −75.663 | 1.00 | 41.18 | MOL1 | C |
| ATOM | 1505 | O | THR | A | 193 | 78.737 | −49.561 | −74.816 | 1.00 | 38.28 | MOL1 | O |
| ATOM | 1506 | N | CYS | A | 194 | 76.941 | −48.476 | −75.598 | 1.00 | 47.42 | MOL1 | N |
| ATOM | 1507 | CA | CYS | A | 194 | 76.047 | −48.774 | −74.502 | 1.00 | 47.15 | MOL1 | C |
| ATOM | 1508 | C | CYS | A | 194 | 74.831 | −49.431 | −75.134 | 1.00 | 47.65 | MOL1 | C |
| ATOM | 1509 | O | CYS | A | 194 | 74.062 | −48.774 | −75.803 | 1.00 | 54.03 | MOL1 | O |
| ATOM | 1510 | CB | CYS | A | 194 | 75.684 | −47.442 | −73.858 | 1.00 | 39.68 | MOL1 | C |
| ATOM | 1511 | SG | CYS | A | 194 | 74.348 | −47.500 | −72.653 | 1.00 | 51.74 | MOL1 | S |
| ATOM | 1512 | N | GLU | A | 195 | 74.671 | −50.731 | −74.942 | 1.00 | 48.90 | MOL1 | N |
| ATOM | 1513 | CA | GLU | A | 195 | 73.563 | −51.470 | −75.536 | 1.00 | 49.80 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 1514 | CB | GLU | A | 195 | 74.036 | −52.807 | −76.101 | 1.00 | 53.85 | MOL1 | C |
|---|---|---|---|---|---|---|---|---|---|---|---|---|
| ATOM | 1515 | CG | GLU | A | 195 | 74.596 | −52.777 | −77.489 | 1.00 | 65.24 | MOL1 | C |
| ATOM | 1516 | CD | GLU | A | 195 | 75.010 | −54.161 | −77.957 | 1.00 | 74.76 | MOL1 | C |
| ATOM | 1517 | OE1 | GLU | A | 195 | 74.373 | −55.150 | −77.505 | 1.00 | 68.48 | MOL1 | O |
| ATOM | 1518 | OE2 | GLU | A | 195 | 75.960 | −54.249 | −78.784 | 1.00 | 78.03 | MOL1 | O |
| ATOM | 1519 | C | GLU | A | 195 | 72.477 | −51.790 | −74.549 | 1.00 | 49.53 | MOL1 | C |
| ATOM | 1520 | O | GLU | A | 195 | 72.682 | −52.576 | −73.630 | 1.00 | 54.30 | MOL1 | O |
| ATOM | 1521 | N | ALA | A | 196 | 71.299 | −51.231 | −74.779 | 1.00 | 48.84 | MOL1 | N |
| ATOM | 1522 | CA | ALA | A | 196 | 70.150 | −51.463 | −73.914 | 1.00 | 45.50 | MOL1 | C |
| ATOM | 1523 | CB | ALA | A | 196 | 69.484 | −50.169 | −73.632 | 1.00 | 36.22 | MOL1 | C |
| ATOM | 1524 | C | ALA | A | 196 | 69.127 | −52.425 | −74.496 | 1.00 | 42.90 | MOL1 | C |
| ATOM | 1525 | O | ALA | A | 196 | 68.513 | −52.128 | −75.505 | 1.00 | 44.36 | MOL1 | O |
| ATOM | 1526 | N | THR | A | 197 | 68.941 | −53.572 | −73.855 | 1.00 | 46.25 | MOL1 | N |
| ATOM | 1527 | CA | THR | A | 197 | 67.967 | −54.546 | −74.312 | 1.00 | 48.46 | MOL1 | C |
| ATOM | 1528 | CB | THR | A | 197 | 68.576 | −55.949 | −74.334 | 1.00 | 48.70 | MOL1 | C |
| ATOM | 1529 | OG1 | THR | A | 197 | 69.130 | −56.194 | −75.631 | 1.00 | 54.19 | MOL1 | O |
| ATOM | 1530 | CG2 | THR | A | 197 | 67.535 | −56.992 | −74.042 | 1.00 | 53.48 | MOL1 | C |
| ATOM | 1531 | C | THR | A | 197 | 66.702 | −54.494 | −73.439 | 1.00 | 49.26 | MOL1 | C |
| ATOM | 1532 | O | THR | A | 197 | 66.755 | −54.609 | −72.214 | 1.00 | 44.04 | MOL1 | O |
| ATOM | 1533 | N | HIS | A | 198 | 65.560 | −54.320 | −74.102 | 1.00 | 52.14 | MOL1 | N |
| ATOM | 1534 | CA | HIS | A | 198 | 64.278 | −54.182 | −73.429 | 1.00 | 48.51 | MOL1 | C |
| ATOM | 1535 | CB | HIS | A | 198 | 63.990 | −52.696 | −73.274 | 1.00 | 50.82 | MOL1 | C |
| ATOM | 1536 | CG | HIS | A | 198 | 62.824 | −52.388 | −72.395 | 1.00 | 51.96 | MOL1 | C |
| ATOM | 1537 | CD2 | HIS | A | 198 | 61.867 | −51.440 | −72.493 | 1.00 | 49.15 | MOL1 | C |
| ATOM | 1538 | ND1 | HIS | A | 198 | 62.600 | −53.040 | −71.201 | 1.00 | 54.81 | MOL1 | N |
| ATOM | 1539 | CE1 | HIS | A | 198 | 61.556 | −52.504 | −70.600 | 1.00 | 53.80 | MOL1 | C |
| ATOM | 1540 | NE2 | HIS | A | 198 | 61.094 | −51.530 | −71.363 | 1.00 | 55.59 | MOL1 | N |
| ATOM | 1541 | C | HIS | A | 198 | 63.084 | −54.851 | −74.106 | 1.00 | 47.86 | MOL1 | C |
| ATOM | 1542 | O | HIS | A | 198 | 62.980 | −54.892 | −75.323 | 1.00 | 51.50 | MOL1 | O |
| ATOM | 1543 | N | LYS | A | 199 | 62.177 | −55.352 | −73.279 | 1.00 | 50.89 | MOL1 | N |
| ATOM | 1544 | CA | LYS | A | 199 | 60.943 | −56.023 | −73.686 | 1.00 | 45.78 | MOL1 | C |
| ATOM | 1545 | CB | LYS | A | 199 | 59.970 | −56.037 | −72.489 | 1.00 | 44.61 | MOL1 | C |
| ATOM | 1546 | CG | LYS | A | 199 | 58.541 | −56.495 | −72.772 | 1.00 | 44.39 | MOL1 | C |
| ATOM | 1547 | CD | LYS | A | 199 | 57.756 | −56.707 | −71.466 | 1.00 | 47.28 | MOL1 | C |
| ATOM | 1548 | CE | LYS | A | 199 | 56.227 | −56.710 | −71.638 | 1.00 | 53.72 | MOL1 | C |
| ATOM | 1549 | NZ | LYS | A | 199 | 55.676 | −57.784 | −72.524 | 1.00 | 62.45 | MOL1 | N |
| ATOM | 1550 | C | LYS | A | 199 | 60.263 | −55.369 | −74.868 | 1.00 | 44.08 | MOL1 | C |
| ATOM | 1551 | O | LYS | A | 199 | 59.597 | −56.048 | −75.648 | 1.00 | 45.54 | MOL1 | O |
| ATOM | 1552 | N | THR | A | 200 | 60.429 | −54.054 | −75.000 | 1.00 | 38.03 | MOL1 | N |
| ATOM | 1553 | CA | THR | A | 200 | 59.778 | −53.323 | −76.077 | 1.00 | 39.11 | MOL1 | C |
| ATOM | 1554 | CB | THR | A | 200 | 59.803 | −51.790 | −75.832 | 1.00 | 35.10 | MOL1 | C |
| ATOM | 1555 | OG1 | THR | A | 200 | 61.140 | −51.292 | −75.896 | 1.00 | 43.36 | MOL1 | O |
| ATOM | 1556 | CG2 | THR | A | 200 | 59.243 | −51.468 | −74.483 | 1.00 | 40.65 | MOL1 | C |
| ATOM | 1557 | C | THR | A | 200 | 60.284 | −53.601 | −77.489 | 1.00 | 45.06 | MOL1 | C |
| ATOM | 1558 | O | THR | A | 200 | 59.611 | −53.251 | −78.461 | 1.00 | 46.28 | MOL1 | O |
| ATOM | 1559 | N | SER | A | 201 | 61.454 | −54.226 | −77.612 | 1.00 | 52.58 | MOL1 | N |
| ATOM | 1560 | CA | SER | A | 201 | 62.019 | −54.525 | −78.928 | 1.00 | 56.91 | MOL1 | C |
| ATOM | 1561 | CB | SER | A | 201 | 62.890 | −53.370 | −79.415 | 1.00 | 64.84 | MOL1 | C |
| ATOM | 1562 | OG | SER | A | 201 | 62.651 | −52.186 | −78.662 | 1.00 | 79.89 | MOL1 | O |
| ATOM | 1563 | C | SER | A | 201 | 62.858 | −55.786 | −78.927 | 1.00 | 58.33 | MOL1 | C |
| ATOM | 1564 | O | SER | A | 201 | 63.387 | −56.203 | −77.890 | 1.00 | 61.71 | MOL1 | O |
| ATOM | 1565 | N | THR | A | 202 | 62.979 | −56.377 | −80.111 | 1.00 | 55.24 | MOL1 | N |
| ATOM | 1566 | CA | THR | A | 202 | 63.742 | −57.598 | −80.313 | 1.00 | 54.05 | MOL1 | C |
| ATOM | 1567 | CB | THR | A | 202 | 63.183 | −58.385 | −81.491 | 1.00 | 45.01 | MOL1 | C |
| ATOM | 1568 | OG1 | THR | A | 202 | 63.108 | −57.522 | −82.631 | 1.00 | 44.48 | MOL1 | O |
| ATOM | 1569 | CG2 | THR | A | 202 | 61.810 | −58.921 | −81.171 | 1.00 | 37.84 | MOL1 | C |
| ATOM | 1570 | C | THR | A | 202 | 65.177 | −57.225 | −80.647 | 1.00 | 58.54 | MOL1 | C |
| ATOM | 1571 | O | THR | A | 202 | 66.090 | −58.049 | −80.582 | 1.00 | 64.29 | MOL1 | O |
| ATOM | 1572 | N | SER | A | 203 | 65.359 | −55.967 | −81.009 | 1.00 | 55.87 | MOL1 | N |
| ATOM | 1573 | CA | SER | A | 203 | 66.659 | −55.469 | −81.390 | 1.00 | 55.42 | MOL1 | C |
| ATOM | 1574 | CB | SER | A | 203 | 66.579 | −54.862 | −82.792 | 1.00 | 64.96 | MOL1 | C |
| ATOM | 1575 | OG | SER | A | 203 | 65.456 | −55.364 | −83.506 | 1.00 | 68.33 | MOL1 | O |
| ATOM | 1576 | C | SER | A | 203 | 67.032 | −54.401 | −80.405 | 1.00 | 51.49 | MOL1 | C |
| ATOM | 1577 | O | SER | A | 203 | 66.366 | −53.378 | −80.324 | 1.00 | 56.39 | MOL1 | O |
| ATOM | 1578 | N | PRO | A | 204 | 68.125 | −54.603 | −79.667 | 1.00 | 49.57 | MOL1 | N |
| ATOM | 1579 | CD | PRO | A | 204 | 69.104 | −55.652 | −79.978 | 1.00 | 45.62 | MOL1 | C |
| ATOM | 1580 | CA | PRO | A | 204 | 68.655 | −53.689 | −78.646 | 1.00 | 47.71 | MOL1 | C |
| ATOM | 1581 | CB | PRO | A | 204 | 69.883 | −54.423 | −78.143 | 1.00 | 36.27 | MOL1 | C |
| ATOM | 1582 | CG | PRO | A | 204 | 70.362 | −55.096 | −79.363 | 1.00 | 46.52 | MOL1 | C |
| ATOM | 1583 | C | PRO | A | 204 | 68.969 | −52.275 | −79.131 | 1.00 | 44.75 | MOL1 | C |
| ATOM | 1584 | O | PRO | A | 204 | 69.432 | −52.078 | −80.254 | 1.00 | 51.85 | MOL1 | O |
| ATOM | 1585 | N | ILE | A | 205 | 68.689 | −51.289 | −78.286 | 1.00 | 37.07 | MOL1 | N |
| ATOM | 1586 | CA | ILE | A | 205 | 68.956 | −49.906 | −78.636 | 1.00 | 35.88 | MOL1 | C |
| ATOM | 1587 | CB | ILE | A | 205 | 68.136 | −48.913 | −77.778 | 1.00 | 28.59 | MOL1 | C |
| ATOM | 1588 | CG2 | ILE | A | 205 | 68.284 | −47.508 | −78.298 | 1.00 | 13.39 | MOL1 | C |
| ATOM | 1589 | CG1 | ILE | A | 205 | 66.658 | −49.256 | −77.849 | 1.00 | 31.89 | MOL1 | C |
| ATOM | 1590 | CD1 | ILE | A | 205 | 65.760 | −48.190 | −77.275 | 1.00 | 39.23 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 1591 | C | ILE | A | 205 | 70.420 | −49.701 | −78.337 | 1.00 | 39.64 | MOL1 | C |
|---|---|---|---|---|---|---|---|---|---|---|---|---|
| ATOM | 1592 | O | ILE | A | 205 | 70.864 | −49.964 | −77.230 | 1.00 | 44.95 | MOL1 | O |
| ATOM | 1593 | N | VAL | A | 206 | 71.179 | −49.245 | −79.323 | 1.00 | 43.84 | MOL1 | N |
| ATOM | 1594 | CA | VAL | A | 206 | 72.603 | −49.033 | −79.113 | 1.00 | 46.15 | MOL1 | C |
| ATOM | 1595 | CB | VAL | A | 206 | 73.460 | −49.918 | −80.009 | 1.00 | 40.18 | MOL1 | C |
| ATOM | 1596 | CG1 | VAL | A | 206 | 72.920 | −51.328 | −80.020 | 1.00 | 42.45 | MOL1 | C |
| ATOM | 1597 | CG2 | VAL | A | 206 | 73.492 | −49.351 | −81.399 | 1.00 | 46.95 | MOL1 | C |
| ATOM | 1598 | C | VAL | A | 206 | 73.016 | −47.621 | −79.397 | 1.00 | 49.94 | MOL1 | C |
| ATOM | 1599 | O | VAL | A | 206 | 72.652 | −47.049 | −80.418 | 1.00 | 61.62 | MOL1 | O |
| ATOM | 1600 | N | LYS | A | 207 | 73.784 | −47.059 | −78.483 | 1.00 | 50.86 | MOL1 | N |
| ATOM | 1601 | CA | LYS | A | 207 | 74.274 | −45.707 | −78.639 | 1.00 | 58.81 | MOL1 | C |
| ATOM | 1602 | CB | LYS | A | 207 | 73.559 | −44.765 | −77.671 | 1.00 | 58.42 | MOL1 | C |
| ATOM | 1603 | CG | LYS | A | 207 | 72.054 | −44.611 | −77.924 | 1.00 | 64.34 | MOL1 | C |
| ATOM | 1604 | CD | LYS | A | 207 | 71.751 | −44.216 | −79.377 | 1.00 | 73.63 | MOL1 | C |
| ATOM | 1605 | CE | LYS | A | 207 | 70.355 | −43.607 | −79.559 | 1.00 | 74.77 | MOL1 | C |
| ATOM | 1606 | NZ | LYS | A | 207 | 70.253 | −42.210 | −79.017 | 1.00 | 80.67 | MOL1 | N |
| ATOM | 1607 | C | LYS | A | 207 | 75.760 | −45.757 | −78.342 | 1.00 | 62.66 | MOL1 | C |
| ATOM | 1608 | O | LYS | A | 207 | 76.181 | −46.435 | −77.409 | 1.00 | 66.08 | MOL1 | O |
| ATOM | 1609 | N | SER | A | 208 | 76.559 | −45.064 | −79.144 | 1.00 | 64.15 | MOL1 | N |
| ATOM | 1610 | CA | SER | A | 208 | 77.996 | −45.070 | −78.937 | 1.00 | 63.92 | MOL1 | C |
| ATOM | 1611 | CB | SER | A | 208 | 78.621 | −46.249 | −79.658 | 1.00 | 62.29 | MOL1 | C |
| ATOM | 1612 | OG | SER | A | 208 | 78.496 | −46.087 | −81.051 | 1.00 | 69.40 | MOL1 | O |
| ATOM | 1613 | C | SER | A | 208 | 78.660 | −43.803 | −79.414 | 1.00 | 66.06 | MOL1 | C |
| ATOM | 1614 | O | SER | A | 208 | 78.001 | −42.892 | −79.908 | 1.00 | 72.59 | MOL1 | O |
| ATOM | 1615 | N | PHE | A | 209 | 79.978 | −43.762 | −79.272 | 1.00 | 66.19 | MOL1 | N |
| ATOM | 1616 | CA | PHE | A | 209 | 80.750 | −42.605 | −79.676 | 1.00 | 71.93 | MOL1 | C |
| ATOM | 1617 | CB | PHE | A | 209 | 80.563 | −41.508 | −78.655 | 1.00 | 68.73 | MOL1 | C |
| ATOM | 1618 | CG | PHE | A | 209 | 81.399 | −41.692 | −77.441 | 1.00 | 62.75 | MOL1 | C |
| ATOM | 1619 | CD1 | PHE | A | 209 | 82.611 | −41.041 | −77.318 | 1.00 | 64.63 | MOL1 | C |
| ATOM | 1620 | CD2 | PHE | A | 209 | 81.001 | −42.548 | −76.443 | 1.00 | 64.44 | MOL1 | C |
| ATOM | 1621 | CE1 | PHE | A | 209 | 83.411 | −41.245 | −76.220 | 1.00 | 68.44 | MOL1 | C |
| ATOM | 1622 | CE2 | PHE | A | 209 | 81.797 | −42.759 | −75.339 | 1.00 | 71.39 | MOL1 | C |
| ATOM | 1623 | CZ | PHE | A | 209 | 83.006 | −42.107 | −75.227 | 1.00 | 71.78 | MOL1 | C |
| ATOM | 1624 | C | PHE | A | 209 | 82.222 | −42.972 | −79.725 | 1.00 | 75.88 | MOL1 | C |
| ATOM | 1625 | O | PHE | A | 209 | 82.674 | −43.788 | −78.937 | 1.00 | 79.10 | MOL1 | O |
| ATOM | 1626 | N | ASN | A | 210 | 82.970 | −42.364 | −80.639 | 1.00 | 80.19 | MOL1 | N |
| ATOM | 1627 | CA | ASN | A | 210 | 84.397 | −42.637 | −80.739 | 1.00 | 83.35 | MOL1 | C |
| ATOM | 1628 | CB | ASN | A | 210 | 84.787 | −42.975 | −82.168 | 1.00 | 74.44 | MOL1 | C |
| ATOM | 1629 | CG | ASN | A | 210 | 83.996 | −44.117 | −82.729 | 1.00 | 72.99 | MOL1 | C |
| ATOM | 1630 | OD1 | ASN | A | 210 | 84.357 | −44.680 | −83.759 | 1.00 | 75.22 | MOL1 | O |
| ATOM | 1631 | ND2 | ASN | A | 210 | 82.905 | −44.467 | −82.067 | 1.00 | 72.31 | MOL1 | N |
| ATOM | 1632 | C | ASN | A | 210 | 85.172 | −41.411 | −80.299 | 1.00 | 92.82 | MOL1 | C |
| ATOM | 1633 | O | ASN | A | 210 | 84.599 | −40.327 | −80.169 | 1.00 | 99.32 | MOL1 | O |
| ATOM | 1634 | N | ARG | A | 211 | 86.473 | −41.571 | −80.073 | 1.00 | 99.04 | MOL1 | N |
| ATOM | 1635 | CA | ARG | A | 211 | 87.287 | −40.439 | −79.659 | 1.00 | 107.02 | MOL1 | C |
| ATOM | 1636 | CB | ARG | A | 211 | 88.451 | −40.903 | −78.791 | 1.00 | 93.10 | MOL1 | C |
| ATOM | 1637 | CG | ARG | A | 211 | 88.073 | −41.235 | −77.356 | 1.00 | 79.51 | MOL1 | C |
| ATOM | 1638 | CD | ARG | A | 211 | 89.295 | −41.722 | −76.571 | 1.00 | 73.79 | MOL1 | C |
| ATOM | 1639 | NE | ARG | A | 211 | 90.006 | −42.738 | −77.341 | 1.00 | 71.41 | MOL1 | N |
| ATOM | 1640 | CZ | ARG | A | 211 | 91.270 | −42.640 | −77.738 | 1.00 | 70.17 | MOL1 | C |
| ATOM | 1641 | NH1 | ARG | A | 211 | 91.982 | −41.569 | −77.420 | 1.00 | 71.92 | MOL1 | N |
| ATOM | 1642 | NH2 | ARG | A | 211 | 91.805 | −43.587 | −78.506 | 1.00 | 68.06 | MOL1 | N |
| ATOM | 1643 | C | ARG | A | 211 | 87.804 | −39.593 | −80.827 | 1.00 | 121.27 | MOL1 | C |
| ATOM | 1644 | O | ARG | A | 211 | 88.444 | −40.099 | −81.766 | 1.00 | 119.32 | MOL1 | O |
| ATOM | 1645 | N | ASN | A | 212 | 87.487 | −38.298 | −80.752 | 1.00 | 135.01 | MOL1 | N |
| ATOM | 1646 | CA | ASN | A | 212 | 87.890 | −37.305 | −81.745 | 1.00 | 145.02 | MOL1 | C |
| ATOM | 1647 | CB | ASN | A | 212 | 86.663 | −36.718 | −82.458 | 1.00 | 137.80 | MOL1 | C |
| ATOM | 1648 | CG | ASN | A | 212 | 85.950 | −37.738 | −83.333 | 1.00 | 132.35 | MOL1 | C |
| ATOM | 1649 | OD1 | ASN | A | 212 | 86.566 | −38.393 | −84.177 | 1.00 | 126.73 | MOL1 | O |
| ATOM | 1650 | ND2 | ASN | A | 212 | 84.643 | −37.870 | −83.140 | 1.00 | 128.12 | MOL1 | N |
| ATOM | 1651 | C | ASN | A | 212 | 88.694 | −36.198 | −81.045 | 1.00 | 154.72 | MOL1 | C |
| ATOM | 1652 | O | ASN | A | 212 | 89.535 | −35.545 | −81.668 | 1.00 | 157.30 | MOL1 | O |
| ATOM | 1653 | N | GLU | A | 213 | 88.428 | −36.001 | −79.750 | 1.00 | 162.53 | MOL1 | N |
| ATOM | 1654 | CA | GLU | A | 213 | 89.138 | −35.014 | −78.920 | 1.00 | 168.79 | MOL1 | C |
| ATOM | 1655 | CB | GLU | A | 213 | 90.625 | −35.395 | −78.813 | 1.00 | 169.60 | MOL1 | C |
| ATOM | 1656 | CG | GLU | A | 213 | 90.907 | −36.740 | −78.141 | 1.00 | 170.51 | MOL1 | C |
| ATOM | 1657 | CD | GLU | A | 213 | 92.383 | −37.131 | −78.192 | 1.00 | 169.55 | MOL1 | C |
| ATOM | 1658 | OE1 | GLU | A | 213 | 92.749 | −38.162 | −77.588 | 1.00 | 168.02 | MOL1 | O |
| ATOM | 1659 | OE2 | GLU | A | 213 | 93.175 | −36.411 | −78.838 | 1.00 | 169.37 | MOL1 | O |
| ATOM | 1660 | C | GLU | A | 213 | 89.049 | −33.548 | −79.357 | 1.00 | 172.64 | MOL1 | C |
| ATOM | 1661 | O | GLU | A | 213 | 89.783 | −33.115 | −80.248 | 1.00 | 173.63 | MOL1 | O |
| ATOM | 1662 | N | CYS | A | 214 | 88.171 | −32.784 | −78.709 | 1.00 | 176.10 | MOL1 | N |
| ATOM | 1663 | CA | CYS | A | 214 | 87.997 | −31.359 | −79.010 | 1.00 | 179.13 | MOL1 | C |
| ATOM | 1664 | CB | CYS | A | 214 | 87.418 | −31.162 | −80.423 | 1.00 | 179.49 | MOL1 | C |
| ATOM | 1665 | SG | CYS | A | 214 | 88.420 | −30.127 | −81.553 | 1.00 | 180.10 | MOL1 | S |
| ATOM | 1666 | C | CYS | A | 214 | 87.067 | −30.702 | −77.984 | 1.00 | 180.20 | MOL1 | C |
| ATOM | 1667 | O | CYS | A | 214 | 86.648 | −31.400 | −77.034 | 1.00 | 181.04 | MOL1 | O |

TABLE 1-continued

The atomic coordinates of IL17F in complex with 496 Fab
(H32; a = 189.4; b = 189.4; c = 490.9, α, β = 90°; γ = 120°)

| ATOM | 1668 | OXT | CYS | A | 214 | 86.764 | −29.497 | −78.143 | 1.00 | 180.10 | MOL1 | O |
|---|---|---|---|---|---|---|---|---|---|---|---|---|
| ATOM | 1669 | CB | GLU | B | 1 | 46.708 | −39.422 | −29.729 | 1.00 | 92.80 | MOL1 | C |
| ATOM | 1670 | CG | GLU | B | 1 | 45.511 | −38.548 | −30.169 | 1.00 | 106.71 | MOL1 | C |
| ATOM | 1671 | CD | GLU | B | 1 | 45.054 | −37.536 | −29.111 | 1.00 | 113.96 | MOL1 | C |
| ATOM | 1672 | OE1 | GLU | B | 1 | 44.367 | −36.557 | −29.487 | 1.00 | 113.19 | MOL1 | O |
| ATOM | 1673 | OE2 | GLU | B | 1 | 45.363 | −37.722 | −27.908 | 1.00 | 118.07 | MOL1 | O |
| ATOM | 1674 | C | GLU | B | 1 | 49.136 | −39.618 | −29.188 | 1.00 | 76.62 | MOL1 | C |
| ATOM | 1675 | O | GLU | B | 1 | 49.286 | −39.476 | −27.979 | 1.00 | 79.69 | MOL1 | O |
| ATOM | 1676 | N | GLU | B | 1 | 48.419 | −38.707 | −31.390 | 1.00 | 83.29 | MOL1 | N |
| ATOM | 1677 | CA | GLU | B | 1 | 48.098 | −38.794 | −29.937 | 1.00 | 81.61 | MOL1 | C |
| ATOM | 1678 | N | VAL | B | 2 | 49.865 | −40.468 | −29.900 | 1.00 | 68.35 | MOL1 | N |
| ATOM | 1679 | CA | VAL | B | 2 | 50.857 | −41.313 | −29.248 | 1.00 | 63.27 | MOL1 | C |
| ATOM | 1680 | CB | VAL | B | 2 | 50.550 | −42.780 | −29.493 | 1.00 | 59.59 | MOL1 | C |
| ATOM | 1681 | CG1 | VAL | B | 2 | 51.267 | −43.634 | −28.481 | 1.00 | 51.24 | MOL1 | C |
| ATOM | 1682 | CG2 | VAL | B | 2 | 49.052 | −42.995 | −29.492 | 1.00 | 63.72 | MOL1 | C |
| ATOM | 1683 | C | VAL | B | 2 | 52.262 | −41.077 | −29.757 | 1.00 | 67.70 | MOL1 | C |
| ATOM | 1684 | O | VAL | B | 2 | 52.880 | −41.996 | −30.286 | 1.00 | 77.73 | MOL1 | O |
| ATOM | 1685 | N | GLN | B | 3 | 52.781 | −39.870 | −29.584 | 1.00 | 66.29 | MOL1 | N |
| ATOM | 1686 | CA | GLN | B | 3 | 54.125 | −39.534 | −30.060 | 1.00 | 62.99 | MOL1 | C |
| ATOM | 1687 | CB | GLN | B | 3 | 54.452 | −38.077 | −29.719 | 1.00 | 73.78 | MOL1 | C |
| ATOM | 1688 | CG | GLN | B | 3 | 53.589 | −37.034 | −30.427 | 1.00 | 91.77 | MOL1 | C |
| ATOM | 1689 | CD | GLN | B | 3 | 53.525 | −37.241 | −31.934 | 1.00 | 101.46 | MOL1 | C |
| ATOM | 1690 | OE1 | GLN | B | 3 | 52.813 | −38.126 | −32.421 | 1.00 | 106.00 | MOL1 | O |
| ATOM | 1691 | NE2 | GLN | B | 3 | 54.281 | −36.429 | −32.682 | 1.00 | 105.77 | MOL1 | N |
| ATOM | 1692 | C | GLN | B | 3 | 55.300 | −40.401 | −29.583 | 1.00 | 55.69 | MOL1 | C |
| ATOM | 1693 | O | GLN | B | 3 | 55.367 | −40.827 | −28.438 | 1.00 | 46.69 | MOL1 | O |
| ATOM | 1694 | N | LEU | B | 4 | 56.226 | −40.651 | −30.500 | 1.00 | 54.86 | MOL1 | N |
| ATOM | 1695 | CA | LEU | B | 4 | 57.460 | −41.395 | −30.236 | 1.00 | 51.40 | MOL1 | C |
| ATOM | 1696 | CB | LEU | B | 4 | 57.385 | −42.836 | −30.704 | 1.00 | 50.04 | MOL1 | C |
| ATOM | 1697 | CG | LEU | B | 4 | 56.609 | −43.772 | −29.813 | 1.00 | 53.16 | MOL1 | C |
| ATOM | 1698 | CD1 | LEU | B | 4 | 56.653 | −45.200 | −30.362 | 1.00 | 54.68 | MOL1 | C |
| ATOM | 1699 | CD2 | LEU | B | 4 | 57.235 | −43.682 | −28.448 | 1.00 | 57.66 | MOL1 | C |
| ATOM | 1700 | C | LEU | B | 4 | 58.491 | −40.688 | −31.090 | 1.00 | 52.50 | MOL1 | C |
| ATOM | 1701 | O | LEU | B | 4 | 58.267 | −40.482 | −32.290 | 1.00 | 55.22 | MOL1 | O |
| ATOM | 1702 | N | VAL | B | 5 | 59.603 | −40.279 | −30.491 | 1.00 | 51.49 | MOL1 | N |
| ATOM | 1703 | CA | VAL | B | 5 | 60.636 | −39.598 | −31.267 | 1.00 | 48.73 | MOL1 | C |
| ATOM | 1704 | CB | VAL | B | 5 | 60.564 | −38.054 | −31.130 | 1.00 | 38.29 | MOL1 | C |
| ATOM | 1705 | CG1 | VAL | B | 5 | 59.153 | −37.620 | −30.886 | 1.00 | 20.66 | MOL1 | C |
| ATOM | 1706 | CG2 | VAL | B | 5 | 61.470 | −37.580 | −30.024 | 1.00 | 46.70 | MOL1 | C |
| ATOM | 1707 | C | VAL | B | 5 | 62.033 | −40.067 | −30.891 | 1.00 | 51.85 | MOL1 | C |
| ATOM | 1708 | O | VAL | B | 5 | 62.441 | −40.045 | −29.724 | 1.00 | 53.70 | MOL1 | O |
| ATOM | 1709 | N | GLU | B | 6 | 62.759 | −40.517 | −31.904 | 1.00 | 54.55 | MOL1 | N |
| ATOM | 1710 | CA | GLU | B | 6 | 64.109 | −41.004 | −31.698 | 1.00 | 59.68 | MOL1 | C |
| ATOM | 1711 | CB | GLU | B | 6 | 64.419 | −42.179 | −32.638 | 1.00 | 58.72 | MOL1 | C |
| ATOM | 1712 | CG | GLU | B | 6 | 63.520 | −43.391 | −32.442 | 1.00 | 63.40 | MOL1 | C |
| ATOM | 1713 | CD | GLU | B | 6 | 62.481 | −43.540 | −33.538 | 1.00 | 68.99 | MOL1 | C |
| ATOM | 1714 | OE1 | GLU | B | 6 | 61.896 | −42.521 | −33.965 | 1.00 | 68.13 | MOL1 | O |
| ATOM | 1715 | OE2 | GLU | B | 6 | 62.239 | −44.684 | −33.969 | 1.00 | 72.32 | MOL1 | O |
| ATOM | 1716 | C | GLU | B | 6 | 65.102 | −39.877 | −31.926 | 1.00 | 62.51 | MOL1 | C |
| ATOM | 1717 | O | GLU | B | 6 | 64.779 | −38.840 | −32.519 | 1.00 | 62.23 | MOL1 | O |
| ATOM | 1718 | N | SER | B | 7 | 66.317 | −40.092 | −31.444 | 1.00 | 65.47 | MOL1 | N |
| ATOM | 1719 | CA | SER | B | 7 | 67.363 | −39.105 | −31.564 | 1.00 | 67.74 | MOL1 | C |
| ATOM | 1720 | CB | SER | B | 7 | 67.110 | −37.975 | −30.580 | 1.00 | 71.57 | MOL1 | C |
| ATOM | 1721 | OG | SER | B | 7 | 68.305 | −37.256 | −30.342 | 1.00 | 85.77 | MOL1 | O |
| ATOM | 1722 | C | SER | B | 7 | 68.714 | −39.718 | −31.272 | 1.00 | 69.29 | MOL1 | C |
| ATOM | 1723 | O | SER | B | 7 | 68.814 | −40.789 | −30.668 | 1.00 | 66.88 | MOL1 | O |
| ATOM | 1724 | N | GLY | B | 8 | 69.757 | −39.021 | −31.700 | 1.00 | 73.83 | MOL1 | N |
| ATOM | 1725 | CA | GLY | B | 8 | 71.101 | −39.503 | −31.462 | 1.00 | 79.51 | MOL1 | C |
| ATOM | 1726 | C | GLY | B | 8 | 71.689 | −40.148 | −32.690 | 1.00 | 81.37 | MOL1 | C |
| ATOM | 1727 | O | GLY | B | 8 | 72.599 | −40.967 | −32.594 | 1.00 | 80.82 | MOL1 | O |
| ATOM | 1728 | N | GLY | B | 9 | 71.167 | −39.775 | −33.851 | 1.00 | 84.19 | MOL1 | N |
| ATOM | 1729 | CA | GLY | B | 9 | 71.665 | −40.342 | −35.087 | 1.00 | 85.32 | MOL1 | C |
| ATOM | 1730 | C | GLY | B | 9 | 72.935 | −39.674 | −35.563 | 1.00 | 84.49 | MOL1 | C |
| ATOM | 1731 | O | GLY | B | 9 | 73.254 | −38.563 | −35.144 | 1.00 | 83.86 | MOL1 | O |
| ATOM | 1732 | N | GLY | B | 10 | 73.657 | −40.358 | −36.444 | 1.00 | 88.01 | MOL1 | N |
| ATOM | 1733 | CA | GLY | B | 10 | 74.897 | −39.823 | −36.982 | 1.00 | 91.06 | MOL1 | C |
| ATOM | 1734 | C | GLY | B | 10 | 75.817 | −40.917 | −37.498 | 1.00 | 90.60 | MOL1 | C |
| ATOM | 1735 | O | GLY | B | 10 | 75.444 | −42.097 | −37.503 | 1.00 | 89.39 | MOL1 | O |
| ATOM | 1736 | N | LEU | B | 11 | 77.016 | −40.535 | −37.940 | 1.00 | 87.59 | MOL1 | N |
| ATOM | 1737 | CA | LEU | B | 11 | 77.980 | −41.515 | −38.445 | 1.00 | 84.85 | MOL1 | C |
| ATOM | 1738 | CB | LEU | B | 11 | 78.654 | −41.035 | −39.732 | 1.00 | 83.78 | MOL1 | C |
| ATOM | 1739 | CG | LEU | B | 11 | 79.532 | −39.793 | −39.639 | 1.00 | 92.04 | MOL1 | C |
| ATOM | 1740 | CD1 | LEU | B | 11 | 80.000 | −39.404 | −41.038 | 1.00 | 89.62 | MOL1 | C |
| ATOM | 1741 | CD2 | LEU | B | 11 | 78.752 | −38.648 | −38.988 | 1.00 | 98.71 | MOL1 | C |
| ATOM | 1742 | C | LEU | B | 11 | 79.026 | −41.762 | −37.387 | 1.00 | 80.95 | MOL1 | C |
| ATOM | 1743 | O | LEU | B | 11 | 79.219 | −40.940 | −36.493 | 1.00 | 80.32 | MOL1 | O |
| ATOM | 1744 | N | VAL | B | 12 | 79.706 | −42.894 | −37.485 | 1.00 | 77.34 | MOL1 | N |

TABLE 1-continued

The atomic coordinates of IL17F in complex with 496 Fab
(H32; a = 189.4; b = 189.4; c = 490.9, α, β = 90°; γ = 120°)

| ATOM | 1745 | CA | VAL | B | 12 | 80.713 | −43.226 | −36.499 | 1.00 | 79.50 | MOL1 | C |
|---|---|---|---|---|---|---|---|---|---|---|---|---|
| ATOM | 1746 | CB | VAL | B | 12 | 80.055 | −43.626 | −35.169 | 1.00 | 78.17 | MOL1 | C |
| ATOM | 1747 | CG1 | VAL | B | 12 | 79.010 | −44.677 | −35.412 | 1.00 | 76.02 | MOL1 | C |
| ATOM | 1748 | CG2 | VAL | B | 12 | 81.099 | −44.151 | −34.203 | 1.00 | 82.85 | MOL1 | C |
| ATOM | 1749 | C | VAL | B | 12 | 81.602 | −44.362 | −36.964 | 1.00 | 81.68 | MOL1 | C |
| ATOM | 1750 | O | VAL | B | 12 | 81.129 | −45.441 | −37.276 | 1.00 | 85.47 | MOL1 | O |
| ATOM | 1751 | N | GLN | B | 13 | 82.902 | −44.103 | −37.004 | 1.00 | 87.73 | MOL1 | N |
| ATOM | 1752 | CA | GLN | B | 13 | 83.887 | −45.087 | −37.429 | 1.00 | 87.70 | MOL1 | C |
| ATOM | 1753 | CB | GLN | B | 13 | 85.299 | −44.564 | −37.106 | 1.00 | 93.25 | MOL1 | C |
| ATOM | 1754 | CG | GLN | B | 13 | 85.612 | −44.330 | −35.600 | 1.00 | 105.01 | MOL1 | C |
| ATOM | 1755 | CD | GLN | B | 13 | 84.752 | −43.241 | −34.923 | 1.00 | 108.62 | MOL1 | C |
| ATOM | 1756 | OE1 | GLN | B | 13 | 84.530 | −42.161 | −35.487 | 1.00 | 110.17 | MOL1 | O |
| ATOM | 1757 | NE2 | GLN | B | 13 | 84.289 | −43.521 | −33.698 | 1.00 | 100.71 | MOL1 | N |
| ATOM | 1758 | C | GLN | B | 13 | 83.650 | −46.441 | −36.767 | 1.00 | 81.85 | MOL1 | C |
| ATOM | 1759 | O | GLN | B | 13 | 83.176 | −46.522 | −35.644 | 1.00 | 83.04 | MOL1 | O |
| ATOM | 1760 | N | PRO | B | 14 | 83.955 | −47.527 | −37.473 | 1.00 | 78.83 | MOL1 | N |
| ATOM | 1761 | CD | PRO | B | 14 | 84.450 | −47.575 | −38.857 | 1.00 | 80.79 | MOL1 | C |
| ATOM | 1762 | CA | PRO | B | 14 | 83.772 | −48.872 | −36.929 | 1.00 | 81.36 | MOL1 | C |
| ATOM | 1763 | CB | PRO | B | 14 | 84.589 | −49.731 | −37.878 | 1.00 | 80.68 | MOL1 | C |
| ATOM | 1764 | CG | PRO | B | 14 | 84.344 | −49.058 | −39.191 | 1.00 | 84.61 | MOL1 | C |
| ATOM | 1765 | C | PRO | B | 14 | 84.300 | −48.942 | −35.511 | 1.00 | 84.32 | MOL1 | C |
| ATOM | 1766 | O | PRO | B | 14 | 85.114 | −48.116 | −35.112 | 1.00 | 85.63 | MOL1 | O |
| ATOM | 1767 | N | GLY | B | 15 | 83.842 | −49.927 | −34.750 | 1.00 | 89.73 | MOL1 | N |
| ATOM | 1768 | CA | GLY | B | 15 | 84.300 | −50.066 | −33.380 | 1.00 | 93.56 | MOL1 | C |
| ATOM | 1769 | C | GLY | B | 15 | 83.741 | −49.008 | −32.448 | 1.00 | 93.53 | MOL1 | C |
| ATOM | 1770 | O | GLY | B | 15 | 83.483 | −49.287 | −31.279 | 1.00 | 96.75 | MOL1 | O |
| ATOM | 1771 | N | GLY | B | 16 | 83.553 | −47.796 | −32.963 | 1.00 | 93.40 | MOL1 | N |
| ATOM | 1772 | CA | GLY | B | 16 | 83.020 | −46.708 | −32.156 | 1.00 | 93.36 | MOL1 | C |
| ATOM | 1773 | C | GLY | B | 16 | 81.716 | −47.030 | −31.443 | 1.00 | 92.55 | MOL1 | C |
| ATOM | 1774 | O | GLY | B | 16 | 81.203 | −48.151 | −31.535 | 1.00 | 92.88 | MOL1 | O |
| ATOM | 1775 | N | SER | B | 17 | 81.174 | −46.054 | −30.722 | 1.00 | 90.20 | MOL1 | N |
| ATOM | 1776 | CA | SER | B | 17 | 79.921 | −46.275 | −30.010 | 1.00 | 91.53 | MOL1 | C |
| ATOM | 1777 | CB | SER | B | 17 | 80.192 | −46.638 | −28.553 | 1.00 | 90.56 | MOL1 | C |
| ATOM | 1778 | OG | SER | B | 17 | 80.673 | −47.965 | −28.461 | 1.00 | 97.19 | MOL1 | O |
| ATOM | 1779 | C | SER | B | 17 | 78.934 | −45.114 | −30.066 | 1.00 | 91.20 | MOL1 | C |
| ATOM | 1780 | O | SER | B | 17 | 79.320 | −43.948 | −30.217 | 1.00 | 90.40 | MOL1 | O |
| ATOM | 1781 | N | LEU | B | 18 | 77.650 | −45.455 | −29.957 | 1.00 | 87.85 | MOL1 | N |
| ATOM | 1782 | CA | LEU | B | 18 | 76.585 | −44.466 | −29.973 | 1.00 | 81.60 | MOL1 | C |
| ATOM | 1783 | CB | LEU | B | 18 | 76.053 | −44.262 | −31.388 | 1.00 | 80.12 | MOL1 | C |
| ATOM | 1784 | CG | LEU | B | 18 | 76.209 | −42.801 | −31.815 | 1.00 | 81.32 | MOL1 | C |
| ATOM | 1785 | CD1 | LEU | B | 18 | 75.633 | −42.590 | −33.202 | 1.00 | 76.33 | MOL1 | C |
| ATOM | 1786 | CD2 | LEU | B | 18 | 75.517 | −41.904 | −30.788 | 1.00 | 85.69 | MOL1 | C |
| ATOM | 1787 | C | LEU | B | 18 | 75.449 | −44.875 | −29.051 | 1.00 | 80.39 | MOL1 | C |
| ATOM | 1788 | O | LEU | B | 18 | 75.233 | −46.064 | −28.795 | 1.00 | 77.79 | MOL1 | O |
| ATOM | 1789 | N | ARG | B | 19 | 74.740 | −43.870 | −28.541 | 1.00 | 80.56 | MOL1 | N |
| ATOM | 1790 | CA | ARG | B | 19 | 73.605 | −44.078 | −27.641 | 1.00 | 80.87 | MOL1 | C |
| ATOM | 1791 | CB | ARG | B | 19 | 73.897 | −43.494 | −26.254 | 1.00 | 85.72 | MOL1 | C |
| ATOM | 1792 | CG | ARG | B | 19 | 72.751 | −43.590 | −25.237 | 1.00 | 82.86 | MOL1 | C |
| ATOM | 1793 | CD | ARG | B | 19 | 72.952 | −42.531 | −24.160 | 1.00 | 87.91 | MOL1 | C |
| ATOM | 1794 | NE | ARG | B | 19 | 72.042 | −42.612 | −23.015 | 1.00 | 91.00 | MOL1 | N |
| ATOM | 1795 | CZ | ARG | B | 19 | 71.945 | −43.653 | −22.189 | 1.00 | 94.13 | MOL1 | C |
| ATOM | 1796 | NH1 | ARG | B | 19 | 72.693 | −44.741 | −22.376 | 1.00 | 84.28 | MOL1 | N |
| ATOM | 1797 | NH2 | ARG | B | 19 | 71.128 | −43.583 | −21.140 | 1.00 | 93.49 | MOL1 | N |
| ATOM | 1798 | C | ARG | B | 19 | 72.382 | −43.379 | −28.224 | 1.00 | 79.41 | MOL1 | C |
| ATOM | 1799 | O | ARG | B | 19 | 72.371 | −42.153 | −28.396 | 1.00 | 79.85 | MOL1 | O |
| ATOM | 1800 | N | LEU | B | 20 | 71.354 | −44.168 | −28.525 | 1.00 | 75.09 | MOL1 | N |
| ATOM | 1801 | CA | LEU | B | 20 | 70.123 | −43.640 | −29.088 | 1.00 | 66.85 | MOL1 | C |
| ATOM | 1802 | CB | LEU | B | 20 | 69.645 | −44.530 | −30.219 | 1.00 | 65.49 | MOL1 | C |
| ATOM | 1803 | CG | LEU | B | 20 | 70.528 | −44.532 | −31.456 | 1.00 | 62.82 | MOL1 | C |
| ATOM | 1804 | CD1 | LEU | B | 20 | 70.296 | −45.817 | −32.218 | 1.00 | 57.88 | MOL1 | C |
| ATOM | 1805 | CD2 | LEU | B | 20 | 70.231 | −43.293 | −32.299 | 1.00 | 58.37 | MOL1 | C |
| ATOM | 1806 | C | LEU | B | 20 | 69.042 | −43.537 | −28.035 | 1.00 | 67.03 | MOL1 | C |
| ATOM | 1807 | O | LEU | B | 20 | 68.948 | −44.373 | −27.120 | 1.00 | 61.60 | MOL1 | O |
| ATOM | 1808 | N | SER | B | 21 | 68.220 | −42.502 | −28.177 | 1.00 | 66.77 | MOL1 | N |
| ATOM | 1809 | CA | SER | B | 21 | 67.125 | −42.249 | −27.246 | 1.00 | 66.59 | MOL1 | C |
| ATOM | 1810 | CB | SER | B | 21 | 67.440 | −41.017 | −26.394 | 1.00 | 72.40 | MOL1 | C |
| ATOM | 1811 | OG | SER | B | 21 | 68.373 | −40.165 | −27.051 | 1.00 | 86.54 | MOL1 | O |
| ATOM | 1812 | C | SER | B | 21 | 65.795 | −42.063 | −27.962 | 1.00 | 59.32 | MOL1 | C |
| ATOM | 1813 | O | SER | B | 21 | 65.743 | −41.647 | −29.112 | 1.00 | 55.95 | MOL1 | O |
| ATOM | 1814 | N | CYS | B | 22 | 64.719 | −42.397 | −27.269 | 1.00 | 59.26 | MOL1 | N |
| ATOM | 1815 | CA | CYS | B | 22 | 63.376 | −42.272 | −27.823 | 1.00 | 63.35 | MOL1 | C |
| ATOM | 1816 | C | CYS | B | 22 | 62.480 | −41.702 | −26.749 | 1.00 | 58.51 | MOL1 | C |
| ATOM | 1817 | O | CYS | B | 22 | 62.360 | −42.256 | −25.661 | 1.00 | 55.11 | MOL1 | O |
| ATOM | 1818 | CB | CYS | B | 22 | 62.822 | −43.632 | −28.267 | 1.00 | 70.91 | MOL1 | C |
| ATOM | 1819 | SG | CYS | B | 22 | 61.092 | −43.638 | −28.868 | 1.00 | 69.75 | MOL1 | S |
| ATOM | 1820 | N | ALA | B | 23 | 61.858 | −40.581 | −27.064 | 1.00 | 55.49 | MOL1 | N |
| ATOM | 1821 | CA | ALA | B | 23 | 60.983 | −39.923 | −26.125 | 1.00 | 57.79 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 1822 | CB | ALA | B | 23 | 61.141 | −38.430 | −26.256 | 1.00 | 54.12 | MOL1 | C |
|---|---|---|---|---|---|---|---|---|---|---|---|---|
| ATOM | 1823 | C | ALA | B | 23 | 59.559 | −40.327 | −26.438 | 1.00 | 62.28 | MOL1 | C |
| ATOM | 1824 | O | ALA | B | 23 | 59.071 | −40.043 | −27.528 | 1.00 | 72.96 | MOL1 | O |
| ATOM | 1825 | N | ALA | B | 24 | 58.892 | −40.984 | −25.491 | 1.00 | 59.76 | MOL1 | N |
| ATOM | 1826 | CA | ALA | B | 24 | 57.515 | −41.429 | −25.692 | 1.00 | 55.65 | MOL1 | C |
| ATOM | 1827 | CB | ALA | B | 24 | 57.333 | −42.827 | −25.111 | 1.00 | 55.99 | MOL1 | C |
| ATOM | 1828 | C | ALA | B | 24 | 56.508 | −40.474 | −25.068 | 1.00 | 50.19 | MOL1 | C |
| ATOM | 1829 | O | ALA | B | 24 | 56.841 | −39.698 | −24.178 | 1.00 | 52.13 | MOL1 | O |
| ATOM | 1830 | N | SER | B | 25 | 55.271 | −40.545 | −25.529 | 1.00 | 45.27 | MOL1 | N |
| ATOM | 1831 | CA | SER | B | 25 | 54.232 | −39.683 | −25.010 | 1.00 | 48.65 | MOL1 | C |
| ATOM | 1832 | CB | SER | B | 25 | 54.467 | −38.251 | −25.461 | 1.00 | 48.57 | MOL1 | C |
| ATOM | 1833 | OG | SER | B | 25 | 53.339 | −37.781 | −26.179 | 1.00 | 54.52 | MOL1 | O |
| ATOM | 1834 | C | SER | B | 25 | 52.892 | −40.144 | −25.535 | 1.00 | 53.00 | MOL1 | C |
| ATOM | 1835 | O | SER | B | 25 | 52.822 | −40.851 | −26.536 | 1.00 | 61.24 | MOL1 | O |
| ATOM | 1836 | N | GLY | B | 26 | 51.822 | −39.726 | −24.872 | 1.00 | 54.62 | MOL1 | N |
| ATOM | 1837 | CA | GLY | B | 26 | 50.494 | −40.121 | −25.308 | 1.00 | 54.72 | MOL1 | C |
| ATOM | 1838 | C | GLY | B | 26 | 50.050 | −41.474 | −24.772 | 1.00 | 45.42 | MOL1 | C |
| ATOM | 1839 | O | GLY | B | 26 | 49.043 | −42.030 | −25.212 | 1.00 | 42.66 | MOL1 | O |
| ATOM | 1840 | N | PHE | B | 27 | 50.803 | −42.018 | −23.833 | 1.00 | 36.73 | MOL1 | N |
| ATOM | 1841 | CA | PHE | B | 27 | 50.425 | −43.293 | −23.273 | 1.00 | 45.67 | MOL1 | C |
| ATOM | 1842 | CB | PHE | B | 27 | 50.534 | −44.373 | −24.333 | 1.00 | 39.88 | MOL1 | C |
| ATOM | 1843 | CG | PHE | B | 27 | 51.939 | −44.750 | −24.695 | 1.00 | 46.62 | MOL1 | C |
| ATOM | 1844 | CD1 | PHE | B | 27 | 52.425 | −46.022 | −24.404 | 1.00 | 49.24 | MOL1 | C |
| ATOM | 1845 | CD2 | PHE | B | 27 | 52.750 | −43.875 | −25.393 | 1.00 | 49.02 | MOL1 | C |
| ATOM | 1846 | CE1 | PHE | B | 27 | 53.688 | −46.417 | −24.813 | 1.00 | 49.13 | MOL1 | C |
| ATOM | 1847 | CE2 | PHE | B | 27 | 54.016 | −44.266 | −25.803 | 1.00 | 53.94 | MOL1 | C |
| ATOM | 1848 | CZ | PHE | B | 27 | 54.483 | −45.542 | −25.514 | 1.00 | 52.90 | MOL1 | C |
| ATOM | 1849 | C | PHE | B | 27 | 51.206 | −43.700 | −22.027 | 1.00 | 52.80 | MOL1 | C |
| ATOM | 1850 | O | PHE | B | 27 | 52.308 | −43.208 | −21.763 | 1.00 | 56.14 | MOL1 | O |
| ATOM | 1851 | N | THR | B | 28 | 50.627 | −44.597 | −21.244 | 1.00 | 54.92 | MOL1 | N |
| ATOM | 1852 | CA | THR | B | 28 | 51.291 | −45.037 | −20.032 | 1.00 | 59.91 | MOL1 | C |
| ATOM | 1853 | CB | THR | B | 28 | 50.313 | −45.847 | −19.157 | 1.00 | 65.78 | MOL1 | C |
| ATOM | 1854 | OG1 | THR | B | 28 | 49.272 | −44.972 | −18.697 | 1.00 | 66.99 | MOL1 | O |
| ATOM | 1855 | CG2 | THR | B | 28 | 51.030 | −46.477 | −17.962 | 1.00 | 65.79 | MOL1 | C |
| ATOM | 1856 | C | THR | B | 28 | 52.523 | −45.861 | −20.388 | 1.00 | 57.46 | MOL1 | C |
| ATOM | 1857 | O | THR | B | 28 | 52.479 | −47.091 | −20.426 | 1.00 | 54.80 | MOL1 | O |
| ATOM | 1858 | N | PHE | B | 29 | 53.618 | −45.153 | −20.654 | 1.00 | 57.06 | MOL1 | N |
| ATOM | 1859 | CA | PHE | B | 29 | 54.895 | −45.759 | −21.036 | 1.00 | 60.02 | MOL1 | C |
| ATOM | 1860 | CB | PHE | B | 29 | 55.985 | −44.676 | −21.068 | 1.00 | 55.85 | MOL1 | C |
| ATOM | 1861 | CG | PHE | B | 29 | 57.351 | −45.190 | −21.448 | 1.00 | 57.00 | MOL1 | C |
| ATOM | 1862 | CD1 | PHE | B | 29 | 57.749 | −45.231 | −22.772 | 1.00 | 55.30 | MOL1 | C |
| ATOM | 1863 | CD2 | PHE | B | 29 | 58.224 | −45.676 | −20.477 | 1.00 | 59.98 | MOL1 | C |
| ATOM | 1864 | CE1 | PHE | B | 29 | 58.988 | −45.749 | −23.121 | 1.00 | 51.86 | MOL1 | C |
| ATOM | 1865 | CE2 | PHE | B | 29 | 59.465 | −46.197 | −20.822 | 1.00 | 50.05 | MOL1 | C |
| ATOM | 1866 | CZ | PHE | B | 29 | 59.843 | −46.233 | −22.145 | 1.00 | 50.50 | MOL1 | C |
| ATOM | 1867 | C | PHE | B | 29 | 55.321 | −46.885 | −20.090 | 1.00 | 63.14 | MOL1 | C |
| ATOM | 1868 | O | PHE | B | 29 | 55.647 | −48.003 | −20.518 | 1.00 | 57.84 | MOL1 | O |
| ATOM | 1869 | N | SER | B | 30 | 55.318 | −46.569 | −18.800 | 1.00 | 68.76 | MOL1 | N |
| ATOM | 1870 | CA | SER | B | 30 | 55.712 | −47.506 | −17.747 | 1.00 | 73.60 | MOL1 | C |
| ATOM | 1871 | CB | SER | B | 30 | 55.622 | −46.801 | −16.378 | 1.00 | 80.60 | MOL1 | C |
| ATOM | 1872 | OG | SER | B | 30 | 54.426 | −46.032 | −16.248 | 1.00 | 84.81 | MOL1 | O |
| ATOM | 1873 | C | SER | B | 30 | 54.877 | −48.782 | −17.722 | 1.00 | 70.64 | MOL1 | C |
| ATOM | 1874 | O | SER | B | 30 | 55.096 | −49.662 | −16.898 | 1.00 | 69.54 | MOL1 | O |
| ATOM | 1875 | N | ASP | B | 31 | 53.937 | −48.881 | −18.650 | 1.00 | 71.65 | MOL1 | N |
| ATOM | 1876 | CA | ASP | B | 31 | 53.034 | −50.013 | −18.714 | 1.00 | 70.16 | MOL1 | C |
| ATOM | 1877 | CB | ASP | B | 31 | 51.620 | −49.500 | −18.948 | 1.00 | 77.49 | MOL1 | C |
| ATOM | 1878 | CG | ASP | B | 31 | 50.622 | −50.126 | −18.027 | 1.00 | 88.93 | MOL1 | C |
| ATOM | 1879 | OD1 | ASP | B | 31 | 50.532 | −51.374 | −18.020 | 1.00 | 95.83 | MOL1 | O |
| ATOM | 1880 | OD2 | ASP | B | 31 | 49.929 | −49.367 | −17.310 | 1.00 | 96.84 | MOL1 | O |
| ATOM | 1881 | C | ASP | B | 31 | 53.346 | −51.035 | −19.784 | 1.00 | 65.89 | MOL1 | C |
| ATOM | 1882 | O | ASP | B | 31 | 53.055 | −52.207 | −19.615 | 1.00 | 67.11 | MOL1 | O |
| ATOM | 1883 | N | TYR | B | 32 | 53.927 | −50.599 | −20.891 | 1.00 | 64.43 | MOL1 | N |
| ATOM | 1884 | CA | TYR | B | 32 | 54.207 | −51.522 | −21.985 | 1.00 | 61.62 | MOL1 | C |
| ATOM | 1885 | CB | TYR | B | 32 | 53.581 | −50.999 | −23.266 | 1.00 | 55.41 | MOL1 | C |
| ATOM | 1886 | CG | TYR | B | 32 | 52.108 | −50.796 | −23.165 | 1.00 | 51.34 | MOL1 | C |
| ATOM | 1887 | CD1 | TYR | B | 32 | 51.230 | −51.709 | −23.716 | 1.00 | 49.66 | MOL1 | C |
| ATOM | 1888 | CE1 | TYR | B | 32 | 49.878 | −51.536 | −23.616 | 1.00 | 53.52 | MOL1 | C |
| ATOM | 1889 | CD2 | TYR | B | 32 | 51.592 | −49.700 | −22.506 | 1.00 | 51.65 | MOL1 | C |
| ATOM | 1890 | CE2 | TYR | B | 32 | 50.240 | −49.522 | −22.392 | 1.00 | 58.62 | MOL1 | C |
| ATOM | 1891 | CZ | TYR | B | 32 | 49.384 | −50.444 | −22.946 | 1.00 | 58.75 | MOL1 | C |
| ATOM | 1892 | OH | TYR | B | 32 | 48.026 | −50.297 | −22.785 | 1.00 | 70.25 | MOL1 | O |
| ATOM | 1893 | C | TYR | B | 32 | 55.665 | −51.785 | −22.266 | 1.00 | 61.33 | MOL1 | C |
| ATOM | 1894 | O | TYR | B | 32 | 56.533 | −51.008 | −21.877 | 1.00 | 64.82 | MOL1 | O |
| ATOM | 1895 | N | ASN | B | 33 | 55.928 | −52.888 | −22.959 | 1.00 | 60.89 | MOL1 | N |
| ATOM | 1896 | CA | ASN | B | 33 | 57.295 | −53.215 | −23.353 | 1.00 | 63.30 | MOL1 | C |
| ATOM | 1897 | CB | ASN | B | 33 | 57.429 | −54.661 | −23.868 | 1.00 | 64.44 | MOL1 | C |
| ATOM | 1898 | CG | ASN | B | 33 | 56.811 | −55.686 | −22.944 | 1.00 | 69.90 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 1899 | OD1 | ASN | B | 33 | 56.929 | −55.594 | −21.722 | 1.00 | 71.26 | MOL1 | O |
|---|---|---|---|---|---|---|---|---|---|---|---|---|
| ATOM | 1900 | ND2 | ASN | B | 33 | 56.159 | −56.692 | −23.534 | 1.00 | 73.88 | MOL1 | N |
| ATOM | 1901 | C | ASN | B | 33 | 57.651 | −52.276 | −24.519 | 1.00 | 62.16 | MOL1 | C |
| ATOM | 1902 | O | ASN | B | 33 | 56.778 | −51.737 | −25.189 | 1.00 | 64.71 | MOL1 | O |
| ATOM | 1903 | N | MET | B | 34 | 58.934 | −52.086 | −24.771 | 1.00 | 58.74 | MOL1 | N |
| ATOM | 1904 | CA | MET | B | 34 | 59.350 | −51.240 | −25.869 | 1.00 | 50.90 | MOL1 | C |
| ATOM | 1905 | CB | MET | B | 34 | 59.902 | −49.937 | −25.328 | 1.00 | 48.83 | MOL1 | C |
| ATOM | 1906 | CG | MET | B | 34 | 58.863 | −49.094 | −24.625 | 1.00 | 47.15 | MOL1 | C |
| ATOM | 1907 | SD | MET | B | 34 | 57.512 | −48.641 | −25.725 | 1.00 | 50.43 | MOL1 | S |
| ATOM | 1908 | CE | MET | B | 34 | 58.261 | −47.327 | −26.794 | 1.00 | 43.83 | MOL1 | C |
| ATOM | 1909 | C | MET | B | 34 | 60.414 | −51.986 | −26.658 | 1.00 | 52.46 | MOL1 | C |
| ATOM | 1910 | O | MET | B | 34 | 61.012 | −52.937 | −26.158 | 1.00 | 53.36 | MOL1 | O |
| ATOM | 1911 | N | ALA | B | 35 | 60.650 | −51.578 | −27.897 | 1.00 | 50.28 | MOL1 | N |
| ATOM | 1912 | CA | ALA | B | 35 | 61.648 | −52.266 | −28.700 | 1.00 | 45.02 | MOL1 | C |
| ATOM | 1913 | CB | ALA | B | 35 | 61.050 | −53.515 | −29.331 | 1.00 | 29.39 | MOL1 | C |
| ATOM | 1914 | C | ALA | B | 35 | 62.235 | −51.394 | −29.775 | 1.00 | 48.08 | MOL1 | C |
| ATOM | 1915 | O | ALA | B | 35 | 61.740 | −50.296 | −30.056 | 1.00 | 49.70 | MOL1 | O |
| ATOM | 1916 | N | TRP | B | 36 | 63.330 | −51.881 | −30.351 | 1.00 | 51.88 | MOL1 | N |
| ATOM | 1917 | CA | TRP | B | 36 | 63.975 | −51.177 | −31.443 | 1.00 | 51.95 | MOL1 | C |
| ATOM | 1918 | CB | TRP | B | 36 | 65.420 | −50.809 | −31.130 | 1.00 | 45.10 | MOL1 | C |
| ATOM | 1919 | CG | TRP | B | 36 | 65.565 | −49.798 | −30.057 | 1.00 | 43.87 | MOL1 | C |
| ATOM | 1920 | CD2 | TRP | B | 36 | 65.596 | −48.378 | −30.210 | 1.00 | 40.77 | MOL1 | C |
| ATOM | 1921 | CE2 | TRP | B | 36 | 65.788 | −47.822 | −28.923 | 1.00 | 45.65 | MOL1 | C |
| ATOM | 1922 | CE3 | TRP | B | 36 | 65.484 | −47.521 | −31.303 | 1.00 | 42.67 | MOL1 | C |
| ATOM | 1923 | CD1 | TRP | B | 36 | 65.730 | −50.043 | −28.729 | 1.00 | 54.15 | MOL1 | C |
| ATOM | 1924 | NE1 | TRP | B | 36 | 65.868 | −48.861 | −28.037 | 1.00 | 52.53 | MOL1 | N |
| ATOM | 1925 | CZ2 | TRP | B | 36 | 65.870 | −46.449 | −28.701 | 1.00 | 38.30 | MOL1 | C |
| ATOM | 1926 | CZ3 | TRP | B | 36 | 65.568 | −46.151 | −31.084 | 1.00 | 45.99 | MOL1 | C |
| ATOM | 1927 | CH2 | TRP | B | 36 | 65.759 | −45.631 | −29.789 | 1.00 | 42.88 | MOL1 | C |
| ATOM | 1928 | C | TRP | B | 36 | 63.934 | −52.117 | −32.623 | 1.00 | 49.95 | MOL1 | C |
| ATOM | 1929 | O | TRP | B | 36 | 64.092 | −53.334 | −32.475 | 1.00 | 45.55 | MOL1 | O |
| ATOM | 1930 | N | VAL | B | 37 | 63.687 | −51.540 | −33.788 | 1.00 | 46.39 | MOL1 | N |
| ATOM | 1931 | CA | VAL | B | 37 | 63.617 | −52.298 | −35.013 | 1.00 | 47.88 | MOL1 | C |
| ATOM | 1932 | CB | VAL | B | 37 | 62.169 | −52.400 | −35.492 | 1.00 | 41.67 | MOL1 | C |
| ATOM | 1933 | CG1 | VAL | B | 37 | 62.065 | −53.324 | −36.663 | 1.00 | 41.23 | MOL1 | C |
| ATOM | 1934 | CG2 | VAL | B | 37 | 61.320 | −52.898 | −34.384 | 1.00 | 41.38 | MOL1 | C |
| ATOM | 1935 | C | VAL | B | 37 | 64.427 | −51.461 | −35.975 | 1.00 | 52.48 | MOL1 | C |
| ATOM | 1936 | O | VAL | B | 37 | 64.256 | −50.241 | −36.035 | 1.00 | 55.74 | MOL1 | O |
| ATOM | 1937 | N | ARG | B | 38 | 65.316 | −52.105 | −36.718 | 1.00 | 52.27 | MOL1 | N |
| ATOM | 1938 | CA | ARG | B | 38 | 66.165 | −51.393 | −37.664 | 1.00 | 52.32 | MOL1 | C |
| ATOM | 1939 | CB | ARG | B | 38 | 67.613 | −51.778 | −37.423 | 1.00 | 59.42 | MOL1 | C |
| ATOM | 1940 | CG | ARG | B | 38 | 67.768 | −53.293 | −37.331 | 1.00 | 64.80 | MOL1 | C |
| ATOM | 1941 | CD | ARG | B | 38 | 69.102 | −53.780 | −37.846 | 1.00 | 65.87 | MOL1 | C |
| ATOM | 1942 | NE | ARG | B | 38 | 70.211 | −53.258 | −37.064 | 1.00 | 69.65 | MOL1 | N |
| ATOM | 1943 | CZ | ARG | B | 38 | 71.243 | −53.996 | −36.676 | 1.00 | 76.35 | MOL1 | C |
| ATOM | 1944 | NH1 | ARG | B | 38 | 71.299 | −55.286 | −36.997 | 1.00 | 78.10 | MOL1 | N |
| ATOM | 1945 | NH2 | ARG | B | 38 | 72.220 | −53.444 | −35.975 | 1.00 | 80.15 | MOL1 | N |
| ATOM | 1946 | C | ARG | B | 38 | 65.814 | −51.761 | −39.086 | 1.00 | 49.40 | MOL1 | C |
| ATOM | 1947 | O | ARG | B | 38 | 65.183 | −52.799 | −39.333 | 1.00 | 48.23 | MOL1 | O |
| ATOM | 1948 | N | GLN | B | 39 | 66.260 | −50.924 | −40.019 | 1.00 | 44.75 | MOL1 | N |
| ATOM | 1949 | CA | GLN | B | 39 | 66.027 | −51.157 | −41.438 | 1.00 | 43.64 | MOL1 | C |
| ATOM | 1950 | CB | GLN | B | 39 | 64.729 | −50.505 | −41.854 | 1.00 | 41.38 | MOL1 | C |
| ATOM | 1951 | CG | GLN | B | 39 | 64.449 | −50.506 | −43.329 | 1.00 | 34.67 | MOL1 | C |
| ATOM | 1952 | CD | GLN | B | 39 | 63.095 | −49.913 | −43.611 | 1.00 | 42.91 | MOL1 | C |
| ATOM | 1953 | OE1 | GLN | B | 39 | 62.779 | −48.805 | −43.156 | 1.00 | 43.88 | MOL1 | O |
| ATOM | 1954 | NE2 | GLN | B | 39 | 62.278 | −50.642 | −44.356 | 1.00 | 43.01 | MOL1 | N |
| ATOM | 1955 | C | GLN | B | 39 | 67.160 | −50.599 | −42.279 | 1.00 | 47.48 | MOL1 | C |
| ATOM | 1956 | O | GLN | B | 39 | 67.243 | −49.390 | −42.496 | 1.00 | 44.38 | MOL1 | O |
| ATOM | 1957 | N | ALA | B | 40 | 68.029 | −51.489 | −42.751 | 1.00 | 52.72 | MOL1 | N |
| ATOM | 1958 | CA | ALA | B | 40 | 69.166 | −51.097 | −43.577 | 1.00 | 57.93 | MOL1 | C |
| ATOM | 1959 | CB | ALA | B | 40 | 70.051 | −52.286 | −43.815 | 1.00 | 60.62 | MOL1 | C |
| ATOM | 1960 | C | ALA | B | 40 | 68.715 | −50.525 | −44.909 | 1.00 | 64.10 | MOL1 | C |
| ATOM | 1961 | O | ALA | B | 40 | 67.752 | −51.001 | −45.507 | 1.00 | 71.54 | MOL1 | O |
| ATOM | 1962 | N | PRO | B | 41 | 69.427 | −49.510 | −45.411 | 1.00 | 66.71 | MOL1 | N |
| ATOM | 1963 | CD | PRO | B | 41 | 70.733 | −49.035 | −44.936 | 1.00 | 66.97 | MOL1 | C |
| ATOM | 1964 | CA | PRO | B | 41 | 69.084 | −48.877 | −46.687 | 1.00 | 71.95 | MOL1 | C |
| ATOM | 1965 | CB | PRO | B | 41 | 70.376 | −48.181 | −47.081 | 1.00 | 65.76 | MOL1 | C |
| ATOM | 1966 | CG | PRO | B | 41 | 70.933 | −47.794 | −45.769 | 1.00 | 69.20 | MOL1 | C |
| ATOM | 1967 | C | PRO | B | 41 | 68.642 | −49.890 | −47.732 | 1.00 | 77.48 | MOL1 | C |
| ATOM | 1968 | O | PRO | B | 41 | 69.321 | −50.889 | −47.968 | 1.00 | 80.43 | MOL1 | O |
| ATOM | 1969 | N | GLY | B | 42 | 67.492 | −49.633 | −48.341 | 1.00 | 82.42 | MOL1 | N |
| ATOM | 1970 | CA | GLY | B | 42 | 66.977 | −50.529 | −49.357 | 1.00 | 82.41 | MOL1 | C |
| ATOM | 1971 | C | GLY | B | 42 | 66.426 | −51.829 | −48.809 | 1.00 | 79.86 | MOL1 | C |
| ATOM | 1972 | O | GLY | B | 42 | 65.435 | −52.347 | −49.323 | 1.00 | 81.14 | MOL1 | O |
| ATOM | 1973 | N | LYS | B | 43 | 67.053 | −52.351 | −47.760 | 1.00 | 75.67 | MOL1 | N |
| ATOM | 1974 | CA | LYS | B | 43 | 66.620 | −53.609 | −47.167 | 1.00 | 78.61 | MOL1 | C |
| ATOM | 1975 | CB | LYS | B | 43 | 67.745 | −54.174 | −46.297 | 1.00 | 87.21 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 1976 | CG | LYS | B | 43 | 69.005 | −54.545 | −47.080 | 1.00 | 100.19 | MOL1 | C |
|---|---|---|---|---|---|---|---|---|---|---|---|---|
| ATOM | 1977 | CD | LYS | B | 43 | 69.995 | −55.315 | −46.201 | 1.00 | 112.51 | MOL1 | C |
| ATOM | 1978 | CE | LYS | B | 43 | 69.365 | −56.593 | −45.627 | 1.00 | 117.15 | MOL1 | C |
| ATOM | 1979 | NZ | LYS | B | 43 | 70.287 | −57.328 | −44.705 | 1.00 | 117.37 | MOL1 | N |
| ATOM | 1980 | C | LYS | B | 43 | 65.306 | −53.582 | −46.367 | 1.00 | 73.40 | MOL1 | C |
| ATOM | 1981 | O | LYS | B | 43 | 64.650 | −52.543 | −46.241 | 1.00 | 68.85 | MOL1 | O |
| ATOM | 1982 | N | GLY | B | 44 | 64.939 | −54.747 | −45.835 | 1.00 | 67.59 | MOL1 | N |
| ATOM | 1983 | CA | GLY | B | 44 | 63.712 | −54.886 | −45.071 | 1.00 | 65.22 | MOL1 | C |
| ATOM | 1984 | C | GLY | B | 44 | 63.781 | −54.467 | −43.614 | 1.00 | 64.36 | MOL1 | C |
| ATOM | 1985 | O | GLY | B | 44 | 64.568 | −53.594 | −43.251 | 1.00 | 70.41 | MOL1 | O |
| ATOM | 1986 | N | LEU | B | 45 | 62.960 | −55.083 | −42.768 | 1.00 | 56.81 | MOL1 | N |
| ATOM | 1987 | CA | LEU | B | 45 | 62.943 | −54.720 | −41.357 | 1.00 | 51.84 | MOL1 | C |
| ATOM | 1988 | CB | LEU | B | 45 | 61.515 | −54.395 | −40.893 | 1.00 | 47.66 | MOL1 | C |
| ATOM | 1989 | CG | LEU | B | 45 | 60.686 | −53.353 | −41.671 | 1.00 | 49.11 | MOL1 | C |
| ATOM | 1990 | CD1 | LEU | B | 45 | 59.243 | −53.418 | −41.213 | 1.00 | 41.70 | MOL1 | C |
| ATOM | 1991 | CD2 | LEU | B | 45 | 61.229 | −51.951 | −41.487 | 1.00 | 34.18 | MOL1 | C |
| ATOM | 1992 | C | LEU | B | 45 | 63.511 | −55.831 | −40.505 | 1.00 | 55.33 | MOL1 | C |
| ATOM | 1993 | O | LEU | B | 45 | 63.154 | −57.000 | −40.665 | 1.00 | 59.00 | MOL1 | O |
| ATOM | 1994 | N | GLU | B | 46 | 64.400 | −55.452 | −39.593 | 1.00 | 57.69 | MOL1 | N |
| ATOM | 1995 | CA | GLU | B | 46 | 65.052 | −56.404 | −38.697 | 1.00 | 61.86 | MOL1 | C |
| ATOM | 1996 | CB | GLU | B | 46 | 66.557 | −56.435 | −38.971 | 1.00 | 75.49 | MOL1 | C |
| ATOM | 1997 | CG | GLU | B | 46 | 67.313 | −57.598 | −38.340 | 1.00 | 87.36 | MOL1 | C |
| ATOM | 1998 | CD | GLU | B | 46 | 68.743 | −57.703 | −38.864 | 1.00 | 92.97 | MOL1 | C |
| ATOM | 1999 | OE1 | GLU | B | 46 | 69.650 | −57.057 | −38.286 | 1.00 | 94.73 | MOL1 | O |
| ATOM | 2000 | OE2 | GLU | B | 46 | 68.951 | −58.423 | −39.869 | 1.00 | 93.69 | MOL1 | O |
| ATOM | 2001 | C | GLU | B | 46 | 64.819 | −55.955 | −37.277 | 1.00 | 58.22 | MOL1 | C |
| ATOM | 2002 | O | GLU | B | 46 | 64.976 | −54.773 | −36.965 | 1.00 | 53.10 | MOL1 | O |
| ATOM | 2003 | N | TRP | B | 47 | 64.443 | −56.895 | −36.419 | 1.00 | 57.07 | MOL1 | N |
| ATOM | 2004 | CA | TRP | B | 47 | 64.180 | −56.569 | −35.026 | 1.00 | 60.27 | MOL1 | C |
| ATOM | 2005 | CB | TRP | B | 47 | 63.291 | −57.625 | −34.381 | 1.00 | 57.30 | MOL1 | C |
| ATOM | 2006 | CG | TRP | B | 47 | 63.340 | −57.537 | −32.911 | 1.00 | 57.43 | MOL1 | C |
| ATOM | 2007 | CD2 | TRP | B | 47 | 63.840 | −58.524 | −32.010 | 1.00 | 64.30 | MOL1 | C |
| ATOM | 2008 | CE2 | TRP | B | 47 | 63.765 | −57.983 | −30.715 | 1.00 | 68.83 | MOL1 | C |
| ATOM | 2009 | CE3 | TRP | B | 47 | 64.348 | −59.813 | −32.172 | 1.00 | 69.52 | MOL1 | C |
| ATOM | 2010 | CD1 | TRP | B | 47 | 62.988 | −56.474 | −32.153 | 1.00 | 64.23 | MOL1 | C |
| ATOM | 2011 | NE1 | TRP | B | 47 | 63.238 | −56.727 | −30.828 | 1.00 | 68.28 | MOL1 | N |
| ATOM | 2012 | CZ2 | TRP | B | 47 | 64.180 | −58.683 | −29.592 | 1.00 | 69.21 | MOL1 | C |
| ATOM | 2013 | CZ3 | TRP | B | 47 | 64.758 | −60.507 | −31.057 | 1.00 | 69.35 | MOL1 | C |
| ATOM | 2014 | CH2 | TRP | B | 47 | 64.673 | −59.941 | −29.784 | 1.00 | 72.43 | MOL1 | C |
| ATOM | 2015 | C | TRP | B | 47 | 65.480 | −56.507 | −34.259 | 1.00 | 60.65 | MOL1 | C |
| ATOM | 2016 | O | TRP | B | 47 | 66.271 | −57.434 | −34.327 | 1.00 | 69.26 | MOL1 | O |
| ATOM | 2017 | N | VAL | B | 48 | 65.706 | −55.426 | −33.527 | 1.00 | 58.46 | MOL1 | N |
| ATOM | 2018 | CA | VAL | B | 48 | 66.940 | −55.305 | −32.764 | 1.00 | 55.72 | MOL1 | C |
| ATOM | 2019 | CB | VAL | B | 48 | 67.389 | −53.849 | −32.644 | 1.00 | 48.84 | MOL1 | C |
| ATOM | 2020 | CG1 | VAL | B | 48 | 68.417 | −53.724 | −31.552 | 1.00 | 42.05 | MOL1 | C |
| ATOM | 2021 | CG2 | VAL | B | 48 | 67.972 | −53.385 | −33.969 | 1.00 | 38.51 | MOL1 | C |
| ATOM | 2022 | C | VAL | B | 48 | 66.787 | −55.889 | −31.378 | 1.00 | 59.88 | MOL1 | C |
| ATOM | 2023 | O | VAL | B | 48 | 67.259 | −56.986 | −31.117 | 1.00 | 66.07 | MOL1 | O |
| ATOM | 2024 | N | ALA | B | 49 | 66.124 | −55.168 | −30.485 | 1.00 | 64.15 | MOL1 | N |
| ATOM | 2025 | CA | ALA | B | 49 | 65.933 | −55.677 | −29.136 | 1.00 | 68.80 | MOL1 | C |
| ATOM | 2026 | CB | ALA | B | 49 | 67.142 | −55.348 | −28.286 | 1.00 | 67.97 | MOL1 | C |
| ATOM | 2027 | C | ALA | B | 49 | 64.680 | −55.095 | −28.506 | 1.00 | 73.99 | MOL1 | C |
| ATOM | 2028 | O | ALA | B | 49 | 64.124 | −54.106 | −29.007 | 1.00 | 75.88 | MOL1 | O |
| ATOM | 2029 | N | THR | B | 50 | 64.234 | −55.727 | −27.420 | 1.00 | 73.72 | MOL1 | N |
| ATOM | 2030 | CA | THR | B | 50 | 63.061 | −55.266 | −26.675 | 1.00 | 70.84 | MOL1 | C |
| ATOM | 2031 | CB | THR | B | 50 | 61.765 | −56.065 | −27.022 | 1.00 | 70.46 | MOL1 | C |
| ATOM | 2032 | OG1 | THR | B | 50 | 61.053 | −56.353 | −25.812 | 1.00 | 66.20 | MOL1 | O |
| ATOM | 2033 | CG2 | THR | B | 50 | 62.084 | −57.352 | −27.765 | 1.00 | 63.45 | MOL1 | C |
| ATOM | 2034 | C | THR | B | 50 | 63.330 | −55.371 | −25.179 | 1.00 | 64.29 | MOL1 | C |
| ATOM | 2035 | O | THR | B | 50 | 64.051 | −56.257 | −24.739 | 1.00 | 66.34 | MOL1 | O |
| ATOM | 2036 | N | ILE | B | 51 | 62.750 | −54.450 | −24.418 | 1.00 | 59.03 | MOL1 | N |
| ATOM | 2037 | CA | ILE | B | 51 | 62.903 | −54.368 | −22.964 | 1.00 | 60.21 | MOL1 | C |
| ATOM | 2038 | CB | ILE | B | 51 | 63.628 | −53.059 | −22.574 | 1.00 | 63.37 | MOL1 | C |
| ATOM | 2039 | CG2 | ILE | B | 51 | 62.886 | −51.870 | −23.158 | 1.00 | 67.01 | MOL1 | C |
| ATOM | 2040 | CG1 | ILE | B | 51 | 63.689 | −52.880 | −21.056 | 1.00 | 60.34 | MOL1 | C |
| ATOM | 2041 | CD1 | ILE | B | 51 | 64.217 | −51.500 | −20.639 | 1.00 | 42.72 | MOL1 | C |
| ATOM | 2042 | C | ILE | B | 51 | 61.511 | −54.318 | −22.358 | 1.00 | 63.16 | MOL1 | C |
| ATOM | 2043 | O | ILE | B | 51 | 60.637 | −53.651 | −22.894 | 1.00 | 68.58 | MOL1 | O |
| ATOM | 2044 | N | THR | B | 52 | 61.309 | −54.984 | −21.229 | 1.00 | 64.43 | MOL1 | N |
| ATOM | 2045 | CA | THR | B | 52 | 59.999 | −55.014 | −20.588 | 1.00 | 66.52 | MOL1 | C |
| ATOM | 2046 | CB | THR | B | 52 | 59.940 | −56.170 | −19.640 | 1.00 | 63.07 | MOL1 | C |
| ATOM | 2047 | OG1 | THR | B | 52 | 60.431 | −57.338 | −20.311 | 1.00 | 58.32 | MOL1 | O |
| ATOM | 2048 | CG2 | THR | B | 52 | 58.517 | −56.403 | −19.208 | 1.00 | 71.39 | MOL1 | C |
| ATOM | 2049 | C | THR | B | 52 | 59.593 | −53.743 | −19.841 | 1.00 | 71.53 | MOL1 | C |
| ATOM | 2050 | O | THR | B | 52 | 60.427 | −52.898 | −19.546 | 1.00 | 74.19 | MOL1 | O |
| ATOM | 2051 | N | TYR | B | 53 | 58.308 | −53.613 | −19.526 | 1.00 | 77.80 | MOL1 | N |
| ATOM | 2052 | CA | TYR | B | 53 | 57.826 | −52.418 | −18.845 | 1.00 | 85.35 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 2053 | CB  | TYR | B | 53 | 56.298 | −52.455 | −18.698 | 1.00 | 88.65  | MOL1 | C |
|------|------|-----|-----|---|----|--------|---------|---------|------|--------|------|---|
| ATOM | 2054 | CG  | TYR | B | 53 | 55.755 | −53.391 | −17.635 | 1.00 | 96.94  | MOL1 | C |
| ATOM | 2055 | CD1 | TYR | B | 53 | 55.856 | −54.774 | −17.766 | 1.00 | 100.45 | MOL1 | C |
| ATOM | 2056 | CE1 | TYR | B | 53 | 55.303 | −55.628 | −16.816 | 1.00 | 103.92 | MOL1 | C |
| ATOM | 2057 | CD2 | TYR | B | 53 | 55.091 | −52.887 | −16.518 | 1.00 | 101.50 | MOL1 | C |
| ATOM | 2058 | CE2 | TYR | B | 53 | 54.537 | −53.728 | −15.567 | 1.00 | 105.53 | MOL1 | C |
| ATOM | 2059 | CZ  | TYR | B | 53 | 54.643 | −55.096 | −15.721 | 1.00 | 107.84 | MOL1 | C |
| ATOM | 2060 | OH  | TYR | B | 53 | 54.066 | −55.928 | −14.785 | 1.00 | 112.40 | MOL1 | O |
| ATOM | 2061 | C   | TYR | B | 53 | 58.476 | −52.148 | −17.492 | 1.00 | 89.73  | MOL1 | C |
| ATOM | 2062 | O   | TYR | B | 53 | 58.895 | −51.020 | −17.227 | 1.00 | 85.91  | MOL1 | O |
| ATOM | 2063 | N   | GLU | B | 54 | 58.555 | −53.174 | −16.644 | 1.00 | 95.57  | MOL1 | N |
| ATOM | 2064 | CA  | GLU | B | 54 | 59.158 | −53.054 | −15.315 | 1.00 | 96.04  | MOL1 | C |
| ATOM | 2065 | CB  | GLU | B | 54 | 59.150 | −54.406 | −14.616 | 1.00 | 96.47  | MOL1 | C |
| ATOM | 2066 | CG  | GLU | B | 54 | 59.909 | −55.466 | −15.386 | 1.00 | 102.64 | MOL1 | C |
| ATOM | 2067 | CD  | GLU | B | 54 | 59.069 | −56.704 | −15.648 | 1.00 | 109.60 | MOL1 | C |
| ATOM | 2068 | OE1 | GLU | B | 54 | 59.569 | −57.620 | −16.343 | 1.00 | 110.56 | MOL1 | O |
| ATOM | 2069 | OE2 | GLU | B | 54 | 57.913 | −56.763 | −15.160 | 1.00 | 106.82 | MOL1 | O |
| ATOM | 2070 | C   | GLU | B | 54 | 60.592 | −52.579 | −15.476 | 1.00 | 97.62  | MOL1 | C |
| ATOM | 2071 | O   | GLU | B | 54 | 61.138 | −51.884 | −14.620 | 1.00 | 96.02  | MOL1 | O |
| ATOM | 2072 | N   | GLY | B | 55 | 61.201 | −52.970 | −16.586 | 1.00 | 98.19  | MOL1 | N |
| ATOM | 2073 | CA  | GLY | B | 55 | 62.557 | −52.552 | −16.849 | 1.00 | 98.16  | MOL1 | C |
| ATOM | 2074 | C   | GLY | B | 55 | 63.572 | −53.608 | −16.510 | 1.00 | 99.02  | MOL1 | C |
| ATOM | 2075 | O   | GLY | B | 55 | 64.768 | −53.349 | −16.574 | 1.00 | 99.87  | MOL1 | O |
| ATOM | 2076 | N   | ARG | B | 56 | 63.117 | −54.801 | −16.151 | 1.00 | 102.67 | MOL1 | N |
| ATOM | 2077 | CA  | ARG | B | 56 | 64.071 | −55.846 | −15.815 | 1.00 | 109.99 | MOL1 | C |
| ATOM | 2078 | CB  | ARG | B | 56 | 64.027 | −56.143 | −14.310 | 1.00 | 120.09 | MOL1 | C |
| ATOM | 2079 | CG  | ARG | B | 56 | 65.396 | −56.531 | −13.704 | 1.00 | 131.53 | MOL1 | C |
| ATOM | 2080 | CD  | ARG | B | 56 | 66.519 | −55.506 | −14.023 | 1.00 | 138.72 | MOL1 | C |
| ATOM | 2081 | NE  | ARG | B | 56 | 66.268 | −54.159 | −13.493 | 1.00 | 142.56 | MOL1 | N |
| ATOM | 2082 | CZ  | ARG | B | 56 | 67.086 | −53.117 | −13.654 | 1.00 | 140.61 | MOL1 | C |
| ATOM | 2083 | NH1 | ARG | B | 56 | 68.219 | −53.255 | −14.331 | 1.00 | 139.77 | MOL1 | N |
| ATOM | 2084 | NH2 | ARG | B | 56 | 66.767 | −51.932 | −13.145 | 1.00 | 137.84 | MOL1 | N |
| ATOM | 2085 | C   | ARG | B | 56 | 63.876 | −57.122 | −16.625 | 1.00 | 107.40 | MOL1 | C |
| ATOM | 2086 | O   | ARG | B | 56 | 63.302 | −58.099 | −16.150 | 1.00 | 105.77 | MOL1 | O |
| ATOM | 2087 | N   | ASN | B | 57 | 64.370 | −57.075 | −17.859 | 1.00 | 106.30 | MOL1 | N |
| ATOM | 2088 | CA  | ASN | B | 57 | 64.330 | −58.175 | −18.819 | 1.00 | 103.13 | MOL1 | C |
| ATOM | 2089 | CB  | ASN | B | 57 | 63.020 | −58.954 | −18.735 | 1.00 | 109.31 | MOL1 | C |
| ATOM | 2090 | CG  | ASN | B | 57 | 63.171 | −60.237 | −17.943 | 1.00 | 116.48 | MOL1 | C |
| ATOM | 2091 | OD1 | ASN | B | 57 | 64.056 | −61.055 | −18.226 | 1.00 | 119.17 | MOL1 | O |
| ATOM | 2092 | ND2 | ASN | B | 57 | 62.312 | −60.424 | −16.946 | 1.00 | 119.65 | MOL1 | N |
| ATOM | 2093 | C   | ASN | B | 57 | 64.532 | −57.641 | −20.229 | 1.00 | 97.02  | MOL1 | C |
| ATOM | 2094 | O   | ASN | B | 57 | 63.639 | −57.047 | −20.824 | 1.00 | 94.31  | MOL1 | O |
| ATOM | 2095 | N   | THR | B | 58 | 65.735 | −57.858 | −20.742 | 1.00 | 91.48  | MOL1 | N |
| ATOM | 2096 | CA  | THR | B | 58 | 66.122 | −57.406 | −22.063 | 1.00 | 88.47  | MOL1 | C |
| ATOM | 2097 | CB  | THR | B | 58 | 67.462 | −56.667 | −21.981 | 1.00 | 89.89  | MOL1 | C |
| ATOM | 2098 | OG1 | THR | B | 58 | 68.491 | −57.583 | −21.580 | 1.00 | 90.62  | MOL1 | O |
| ATOM | 2099 | CG2 | THR | B | 58 | 67.375 | −55.537 | −20.956 | 1.00 | 86.04  | MOL1 | C |
| ATOM | 2100 | C   | THR | B | 58 | 66.273 | −58.637 | −22.939 | 1.00 | 87.58  | MOL1 | C |
| ATOM | 2101 | O   | THR | B | 58 | 66.523 | −59.723 | −22.418 | 1.00 | 86.67  | MOL1 | O |
| ATOM | 2102 | N   | TYR | B | 59 | 66.140 | −58.487 | −24.257 | 1.00 | 86.81  | MOL1 | N |
| ATOM | 2103 | CA  | TYR | B | 59 | 66.252 | −59.657 | −25.112 | 1.00 | 92.72  | MOL1 | C |
| ATOM | 2104 | CB  | TYR | B | 59 | 64.872 | −60.004 | −25.665 | 1.00 | 94.05  | MOL1 | C |
| ATOM | 2105 | CG  | TYR | B | 59 | 63.975 | −60.556 | −24.578 | 1.00 | 101.13 | MOL1 | C |
| ATOM | 2106 | CD1 | TYR | B | 59 | 63.472 | −59.727 | −23.579 | 1.00 | 103.97 | MOL1 | C |
| ATOM | 2107 | CE1 | TYR | B | 59 | 62.746 | −60.238 | −22.511 | 1.00 | 104.73 | MOL1 | C |
| ATOM | 2108 | CD2 | TYR | B | 59 | 63.715 | −61.923 | −24.485 | 1.00 | 103.68 | MOL1 | C |
| ATOM | 2109 | CE2 | TYR | B | 59 | 62.986 | −62.446 | −23.418 | 1.00 | 105.50 | MOL1 | C |
| ATOM | 2110 | CZ  | TYR | B | 59 | 62.508 | −61.595 | −22.433 | 1.00 | 106.12 | MOL1 | C |
| ATOM | 2111 | OH  | TYR | B | 59 | 61.816 | −62.095 | −21.352 | 1.00 | 105.21 | MOL1 | O |
| ATOM | 2112 | C   | TYR | B | 59 | 67.311 | −59.689 | −26.214 | 1.00 | 93.91  | MOL1 | C |
| ATOM | 2113 | O   | TYR | B | 59 | 68.066 | −60.661 | −26.304 | 1.00 | 101.59 | MOL1 | O |
| ATOM | 2114 | N   | TYR | B | 60 | 67.376 | −58.661 | −27.052 | 1.00 | 86.78  | MOL1 | N |
| ATOM | 2115 | CA  | TYR | B | 60 | 68.381 | −58.608 | −28.123 | 1.00 | 81.63  | MOL1 | C |
| ATOM | 2116 | CB  | TYR | B | 60 | 69.795 | −58.542 | −27.542 | 1.00 | 68.64  | MOL1 | C |
| ATOM | 2117 | CG  | TYR | B | 60 | 69.995 | −57.478 | −26.506 | 1.00 | 59.84  | MOL1 | C |
| ATOM | 2118 | CD1 | TYR | B | 60 | 69.653 | −57.705 | −25.181 | 1.00 | 59.97  | MOL1 | C |
| ATOM | 2119 | CE1 | TYR | B | 60 | 69.802 | −56.716 | −24.225 | 1.00 | 65.05  | MOL1 | C |
| ATOM | 2120 | CD2 | TYR | B | 60 | 70.496 | −56.235 | −26.852 | 1.00 | 57.42  | MOL1 | C |
| ATOM | 2121 | CE2 | TYR | B | 60 | 70.644 | −55.235 | −25.908 | 1.00 | 60.53  | MOL1 | C |
| ATOM | 2122 | CZ  | TYR | B | 60 | 70.294 | −55.477 | −24.595 | 1.00 | 65.79  | MOL1 | C |
| ATOM | 2123 | OH  | TYR | B | 60 | 70.397 | −54.476 | −23.654 | 1.00 | 66.07  | MOL1 | O |
| ATOM | 2124 | C   | TYR | B | 60 | 68.372 | −59.717 | −29.183 | 1.00 | 83.30  | MOL1 | C |
| ATOM | 2125 | O   | TYR | B | 60 | 67.950 | −60.850 | −28.948 | 1.00 | 83.74  | MOL1 | O |
| ATOM | 2126 | N   | ARG | B | 61 | 68.887 | −59.354 | −30.351 | 1.00 | 85.06  | MOL1 | N |
| ATOM | 2127 | CA  | ARG | B | 61 | 68.987 | −60.229 | −31.507 | 1.00 | 89.57  | MOL1 | C |
| ATOM | 2128 | CB  | ARG | B | 61 | 68.883 | −59.366 | −32.775 | 1.00 | 87.91  | MOL1 | C |
| ATOM | 2129 | CG  | ARG | B | 61 | 68.986 | −60.104 | −34.100 | 1.00 | 89.71  | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 2130 | CD | ARG | B | 61 | 68.604 | −59.191 | −35.265 | 1.00 | 91.21 | MOL1 | C |
|---|---|---|---|---|---|---|---|---|---|---|---|---|
| ATOM | 2131 | NE | ARG | B | 61 | 68.150 | −59.964 | −36.418 | 1.00 | 95.41 | MOL1 | N |
| ATOM | 2132 | CZ | ARG | B | 61 | 68.957 | −60.493 | −37.334 | 1.00 | 100.00 | MOL1 | C |
| ATOM | 2133 | NH1 | ARG | B | 61 | 70.271 | −60.318 | −37.239 | 1.00 | 101.90 | MOL1 | N |
| ATOM | 2134 | NH2 | ARG | B | 61 | 68.457 | −61.222 | −38.326 | 1.00 | 96.25 | MOL1 | N |
| ATOM | 2135 | C | ARG | B | 61 | 70.339 | −60.938 | −31.462 | 1.00 | 94.03 | MOL1 | C |
| ATOM | 2136 | O | ARG | B | 61 | 71.350 | −60.324 | −31.129 | 1.00 | 97.78 | MOL1 | O |
| ATOM | 2137 | N | ASP | B | 62 | 70.369 | −62.225 | −31.784 | 1.00 | 96.51 | MOL1 | N |
| ATOM | 2138 | CA | ASP | B | 62 | 71.633 | −62.952 | −31.779 | 1.00 | 97.02 | MOL1 | C |
| ATOM | 2139 | CB | ASP | B | 62 | 71.390 | −64.447 | −32.022 | 1.00 | 107.96 | MOL1 | C |
| ATOM | 2140 | CG | ASP | B | 62 | 71.171 | −65.232 | −30.728 | 1.00 | 114.45 | MOL1 | C |
| ATOM | 2141 | OD1 | ASP | B | 62 | 70.495 | −64.717 | −29.805 | 1.00 | 115.26 | MOL1 | O |
| ATOM | 2142 | OD2 | ASP | B | 62 | 71.672 | −66.376 | −30.644 | 1.00 | 115.30 | MOL1 | O |
| ATOM | 2143 | C | ASP | B | 62 | 72.497 | −62.382 | −32.888 | 1.00 | 92.57 | MOL1 | C |
| ATOM | 2144 | O | ASP | B | 62 | 72.675 | −63.016 | −33.921 | 1.00 | 96.14 | MOL1 | O |
| ATOM | 2145 | N | SER | B | 63 | 73.023 | −61.181 | −32.674 | 1.00 | 86.96 | MOL1 | N |
| ATOM | 2146 | CA | SER | B | 63 | 73.854 | −60.516 | −33.673 | 1.00 | 87.32 | MOL1 | C |
| ATOM | 2147 | CB | SER | B | 63 | 73.075 | −60.284 | −34.977 | 1.00 | 91.29 | MOL1 | C |
| ATOM | 2148 | OG | SER | B | 63 | 72.923 | −61.474 | −35.742 | 1.00 | 96.02 | MOL1 | O |
| ATOM | 2149 | C | SER | B | 63 | 74.340 | −59.177 | −33.161 | 1.00 | 85.60 | MOL1 | C |
| ATOM | 2150 | O | SER | B | 63 | 75.072 | −58.469 | −33.850 | 1.00 | 86.71 | MOL1 | O |
| ATOM | 2151 | N | VAL | B | 64 | 73.913 | −58.823 | −31.957 | 1.00 | 83.68 | MOL1 | N |
| ATOM | 2152 | CA | VAL | B | 64 | 74.314 | −57.565 | −31.355 | 1.00 | 88.45 | MOL1 | C |
| ATOM | 2153 | CB | VAL | B | 64 | 73.353 | −56.437 | −31.692 | 1.00 | 88.13 | MOL1 | C |
| ATOM | 2154 | CG1 | VAL | B | 64 | 73.352 | −56.179 | −33.179 | 1.00 | 94.20 | MOL1 | C |
| ATOM | 2155 | CG2 | VAL | B | 64 | 71.963 | −56.788 | −31.200 | 1.00 | 91.56 | MOL1 | C |
| ATOM | 2156 | C | VAL | B | 64 | 74.305 | −57.719 | −29.858 | 1.00 | 92.93 | MOL1 | C |
| ATOM | 2157 | O | VAL | B | 64 | 74.251 | −56.726 | −29.127 | 1.00 | 91.76 | MOL1 | O |
| ATOM | 2158 | N | LYS | B | 65 | 74.342 | −58.966 | −29.398 | 1.00 | 99.29 | MOL1 | N |
| ATOM | 2159 | CA | LYS | B | 65 | 74.343 | −59.222 | −27.962 | 1.00 | 104.57 | MOL1 | C |
| ATOM | 2160 | CB | LYS | B | 65 | 74.088 | −60.702 | −27.656 | 1.00 | 104.76 | MOL1 | C |
| ATOM | 2161 | CG | LYS | B | 65 | 73.871 | −60.958 | −26.173 | 1.00 | 110.85 | MOL1 | C |
| ATOM | 2162 | CD | LYS | B | 65 | 73.555 | −62.413 | −25.871 | 1.00 | 117.47 | MOL1 | C |
| ATOM | 2163 | CE | LYS | B | 65 | 73.388 | −62.625 | −24.367 | 1.00 | 119.04 | MOL1 | C |
| ATOM | 2164 | NZ | LYS | B | 65 | 73.094 | −64.045 | −24.021 | 1.00 | 118.64 | MOL1 | N |
| ATOM | 2165 | C | LYS | B | 65 | 75.684 | −58.793 | −27.376 | 1.00 | 104.37 | MOL1 | C |
| ATOM | 2166 | O | LYS | B | 65 | 76.731 | −58.921 | −28.021 | 1.00 | 103.03 | MOL1 | O |
| ATOM | 2167 | N | GLY | B | 66 | 75.646 | −58.274 | −26.154 | 1.00 | 102.25 | MOL1 | N |
| ATOM | 2168 | CA | GLY | B | 66 | 76.865 | −57.819 | −25.520 | 1.00 | 101.34 | MOL1 | C |
| ATOM | 2169 | C | GLY | B | 66 | 77.301 | −56.469 | −26.061 | 1.00 | 100.26 | MOL1 | C |
| ATOM | 2170 | O | GLY | B | 66 | 77.736 | −55.601 | −25.293 | 1.00 | 102.10 | MOL1 | O |
| ATOM | 2171 | N | ARG | B | 67 | 77.177 | −56.288 | −27.377 | 1.00 | 94.56 | MOL1 | N |
| ATOM | 2172 | CA | ARG | B | 67 | 77.562 | −55.039 | −28.037 | 1.00 | 91.19 | MOL1 | C |
| ATOM | 2173 | CB | ARG | B | 67 | 77.781 | −55.274 | −29.532 | 1.00 | 92.23 | MOL1 | C |
| ATOM | 2174 | CG | ARG | B | 67 | 78.604 | −56.509 | −29.831 | 1.00 | 96.75 | MOL1 | C |
| ATOM | 2175 | CD | ARG | B | 67 | 79.057 | −56.587 | −31.285 | 1.00 | 97.01 | MOL1 | C |
| ATOM | 2176 | NE | ARG | B | 67 | 77.961 | −56.587 | −32.252 | 1.00 | 92.98 | MOL1 | N |
| ATOM | 2177 | CZ | ARG | B | 67 | 77.561 | −55.515 | −32.927 | 1.00 | 90.72 | MOL1 | C |
| ATOM | 2178 | NH1 | ARG | B | 67 | 76.560 | −55.610 | −33.789 | 1.00 | 92.03 | MOL1 | N |
| ATOM | 2179 | NH2 | ARG | B | 67 | 78.165 | −54.348 | −32.746 | 1.00 | 87.27 | MOL1 | N |
| ATOM | 2180 | C | ARG | B | 67 | 76.520 | −53.937 | −27.842 | 1.00 | 89.64 | MOL1 | C |
| ATOM | 2181 | O | ARG | B | 67 | 76.863 | −52.764 | −27.696 | 1.00 | 82.64 | MOL1 | O |
| ATOM | 2182 | N | PHE | B | 68 | 75.245 | −54.315 | −27.853 | 1.00 | 90.14 | MOL1 | N |
| ATOM | 2183 | CA | PHE | B | 68 | 74.174 | −53.345 | −27.653 | 1.00 | 88.75 | MOL1 | C |
| ATOM | 2184 | CB | PHE | B | 68 | 73.011 | −53.548 | −28.633 | 1.00 | 93.55 | MOL1 | C |
| ATOM | 2185 | CG | PHE | B | 68 | 73.251 | −53.011 | −30.017 | 1.00 | 93.67 | MOL1 | C |
| ATOM | 2186 | CD1 | PHE | B | 68 | 74.102 | −51.950 | −30.237 | 1.00 | 92.74 | MOL1 | C |
| ATOM | 2187 | CD2 | PHE | B | 68 | 72.587 | −53.558 | −31.099 | 1.00 | 91.80 | MOL1 | C |
| ATOM | 2188 | CE1 | PHE | B | 68 | 74.280 | −51.455 | −31.512 | 1.00 | 92.25 | MOL1 | C |
| ATOM | 2189 | CE2 | PHE | B | 68 | 72.766 | −53.062 | −32.366 | 1.00 | 91.38 | MOL1 | C |
| ATOM | 2190 | CZ | PHE | B | 68 | 73.613 | −52.009 | −32.573 | 1.00 | 91.73 | MOL1 | C |
| ATOM | 2191 | C | PHE | B | 68 | 73.609 | −53.489 | −26.255 | 1.00 | 86.27 | MOL1 | C |
| ATOM | 2192 | O | PHE | B | 68 | 73.826 | −54.497 | −25.580 | 1.00 | 85.81 | MOL1 | O |
| ATOM | 2193 | N | THR | B | 69 | 72.862 | −52.475 | −25.839 | 1.00 | 82.42 | MOL1 | N |
| ATOM | 2194 | CA | THR | B | 69 | 72.224 | −52.481 | −24.534 | 1.00 | 85.27 | MOL1 | C |
| ATOM | 2195 | CB | THR | B | 69 | 73.225 | −52.072 | −23.422 | 1.00 | 89.83 | MOL1 | C |
| ATOM | 2196 | OG1 | THR | B | 69 | 74.120 | −53.164 | −23.171 | 1.00 | 91.62 | MOL1 | O |
| ATOM | 2197 | CG2 | THR | B | 69 | 72.494 | −51.712 | −22.127 | 1.00 | 88.90 | MOL1 | C |
| ATOM | 2198 | C | THR | B | 69 | 70.993 | −51.571 | −24.512 | 1.00 | 84.21 | MOL1 | C |
| ATOM | 2199 | O | THR | B | 69 | 71.096 | −50.352 | −24.666 | 1.00 | 84.76 | MOL1 | O |
| ATOM | 2200 | N | ILE | B | 70 | 69.822 | −52.180 | −24.333 | 1.00 | 81.35 | MOL1 | N |
| ATOM | 2201 | CA | ILE | B | 70 | 68.563 | −51.442 | −24.291 | 1.00 | 77.85 | MOL1 | C |
| ATOM | 2202 | CB | ILE | B | 70 | 67.428 | −52.236 | −24.926 | 1.00 | 77.51 | MOL1 | C |
| ATOM | 2203 | CG2 | ILE | B | 70 | 67.296 | −53.573 | −24.230 | 1.00 | 65.98 | MOL1 | C |
| ATOM | 2204 | CG1 | ILE | B | 70 | 66.131 | −51.420 | −24.857 | 1.00 | 78.19 | MOL1 | C |
| ATOM | 2205 | CD1 | ILE | B | 70 | 64.973 | −52.037 | −25.623 | 1.00 | 80.92 | MOL1 | C |
| ATOM | 2206 | C | ILE | B | 70 | 68.159 | −51.120 | −22.862 | 1.00 | 78.88 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 2207 | O | ILE | B | 70 | 68.299 | −51.946 | −21.964 | 1.00 | 78.72 | MOL1 | O |
|---|---|---|---|---|---|---|---|---|---|---|---|---|
| ATOM | 2208 | N | SER | B | 71 | 67.629 | −49.923 | −22.656 | 1.00 | 79.84 | MOL1 | N |
| ATOM | 2209 | CA | SER | B | 71 | 67.240 | −49.507 | −21.318 | 1.00 | 81.01 | MOL1 | C |
| ATOM | 2210 | CB | SER | B | 71 | 68.453 | −48.931 | −20.618 | 1.00 | 85.85 | MOL1 | C |
| ATOM | 2211 | OG | SER | B | 71 | 68.959 | −47.846 | −21.380 | 1.00 | 88.29 | MOL1 | O |
| ATOM | 2212 | C | SER | B | 71 | 66.149 | −48.450 | −21.343 | 1.00 | 81.45 | MOL1 | C |
| ATOM | 2213 | O | SER | B | 71 | 65.978 | −47.756 | −22.342 | 1.00 | 83.47 | MOL1 | O |
| ATOM | 2214 | N | ARG | B | 72 | 65.424 | −48.311 | −20.235 | 1.00 | 79.53 | MOL1 | N |
| ATOM | 2215 | CA | ARG | B | 72 | 64.360 | −47.312 | −20.156 | 1.00 | 75.39 | MOL1 | C |
| ATOM | 2216 | CB | ARG | B | 72 | 62.994 | −47.955 | −20.366 | 1.00 | 74.44 | MOL1 | C |
| ATOM | 2217 | CG | ARG | B | 72 | 62.578 | −48.879 | −19.254 | 1.00 | 72.98 | MOL1 | C |
| ATOM | 2218 | CD | ARG | B | 72 | 61.431 | −49.766 | −19.681 | 1.00 | 73.00 | MOL1 | C |
| ATOM | 2219 | NE | ARG | B | 72 | 60.224 | −49.014 | −20.004 | 1.00 | 74.85 | MOL1 | N |
| ATOM | 2220 | CZ | ARG | B | 72 | 59.201 | −49.538 | −20.670 | 1.00 | 79.77 | MOL1 | C |
| ATOM | 2221 | NH1 | ARG | B | 72 | 59.263 | −50.803 | −21.070 | 1.00 | 79.23 | MOL1 | N |
| ATOM | 2222 | NH2 | ARG | B | 72 | 58.128 | −48.807 | −20.944 | 1.00 | 76.87 | MOL1 | N |
| ATOM | 2223 | C | ARG | B | 72 | 64.368 | −46.587 | −18.826 | 1.00 | 73.41 | MOL1 | C |
| ATOM | 2224 | O | ARG | B | 72 | 65.080 | −46.979 | −17.904 | 1.00 | 73.02 | MOL1 | O |
| ATOM | 2225 | N | ASP | B | 73 | 63.554 | −45.539 | −18.740 | 1.00 | 74.36 | MOL1 | N |
| ATOM | 2226 | CA | ASP | B | 73 | 63.448 | −44.701 | −17.550 | 1.00 | 81.05 | MOL1 | C |
| ATOM | 2227 | CB | ASP | B | 73 | 63.675 | −43.243 | −17.955 | 1.00 | 83.64 | MOL1 | C |
| ATOM | 2228 | CG | ASP | B | 73 | 64.128 | −42.366 | −16.797 | 1.00 | 92.05 | MOL1 | C |
| ATOM | 2229 | OD1 | ASP | B | 73 | 64.058 | −41.122 | −16.932 | 1.00 | 94.63 | MOL1 | O |
| ATOM | 2230 | OD2 | ASP | B | 73 | 64.569 | −42.909 | −15.760 | 1.00 | 96.29 | MOL1 | O |
| ATOM | 2231 | C | ASP | B | 73 | 62.082 | −44.815 | −16.854 | 1.00 | 86.43 | MOL1 | C |
| ATOM | 2232 | O | ASP | B | 73 | 62.000 | −44.913 | −15.622 | 1.00 | 92.37 | MOL1 | O |
| ATOM | 2233 | N | ASN | B | 74 | 61.016 | −44.798 | −17.648 | 1.00 | 86.94 | MOL1 | N |
| ATOM | 2234 | CA | ASN | B | 74 | 59.648 | −44.868 | −17.138 | 1.00 | 85.28 | MOL1 | C |
| ATOM | 2235 | CB | ASN | B | 74 | 59.461 | −45.995 | −16.123 | 1.00 | 85.17 | MOL1 | C |
| ATOM | 2236 | CG | ASN | B | 74 | 59.699 | −47.366 | −16.723 | 1.00 | 88.63 | MOL1 | C |
| ATOM | 2237 | OD1 | ASN | B | 74 | 60.796 | −47.914 | −16.624 | 1.00 | 91.67 | MOL1 | O |
| ATOM | 2238 | ND2 | ASN | B | 74 | 58.676 | −47.925 | −17.357 | 1.00 | 89.10 | MOL1 | N |
| ATOM | 2239 | C | ASN | B | 74 | 59.337 | −43.538 | −16.493 | 1.00 | 87.31 | MOL1 | C |
| ATOM | 2240 | O | ASN | B | 74 | 58.180 | −43.192 | −16.275 | 1.00 | 89.89 | MOL1 | O |
| ATOM | 2241 | N | ALA | B | 75 | 60.389 | −42.806 | −16.164 | 1.00 | 90.07 | MOL1 | N |
| ATOM | 2242 | CA | ALA | B | 75 | 60.256 | −41.469 | −15.611 | 1.00 | 92.90 | MOL1 | C |
| ATOM | 2243 | CB | ALA | B | 75 | 61.235 | −41.264 | −14.466 | 1.00 | 92.92 | MOL1 | C |
| ATOM | 2244 | C | ALA | B | 75 | 60.701 | −40.707 | −16.850 | 1.00 | 96.53 | MOL1 | C |
| ATOM | 2245 | O | ALA | B | 75 | 61.474 | −41.246 | −17.651 | 1.00 | 95.38 | MOL1 | O |
| ATOM | 2246 | N | LYS | B | 76 | 60.212 | −39.489 | −17.051 | 1.00 | 98.10 | MOL1 | N |
| ATOM | 2247 | CA | LYS | B | 76 | 60.616 | −38.745 | −18.247 | 1.00 | 102.03 | MOL1 | C |
| ATOM | 2248 | CB | LYS | B | 76 | 62.130 | −38.474 | −18.242 | 1.00 | 108.64 | MOL1 | C |
| ATOM | 2249 | CG | LYS | B | 76 | 62.651 | −37.617 | −17.097 | 1.00 | 119.35 | MOL1 | C |
| ATOM | 2250 | CD | LYS | B | 76 | 64.154 | −37.329 | −17.254 | 1.00 | 121.07 | MOL1 | C |
| ATOM | 2251 | CE | LYS | B | 76 | 64.445 | −36.455 | −18.478 | 1.00 | 122.47 | MOL1 | C |
| ATOM | 2252 | NZ | LYS | B | 76 | 65.893 | −36.117 | −18.612 | 1.00 | 120.70 | MOL1 | N |
| ATOM | 2253 | C | LYS | B | 76 | 60.284 | −39.541 | −19.541 | 1.00 | 98.96 | MOL1 | C |
| ATOM | 2254 | O | LYS | B | 76 | 60.682 | −39.091 | −20.635 | 1.00 | 98.32 | MOL1 | O |
| ATOM | 2255 | N | ASN | B | 77 | 59.594 | −40.649 | −19.406 | 1.00 | 92.93 | MOL1 | N |
| ATOM | 2256 | CA | ASN | B | 77 | 59.181 | −41.484 | −20.541 | 1.00 | 83.37 | MOL1 | C |
| ATOM | 2257 | CB | ASN | B | 77 | 57.922 | −40.899 | −21.192 | 1.00 | 84.04 | MOL1 | C |
| ATOM | 2258 | CG | ASN | B | 77 | 56.797 | −40.662 | −20.205 | 1.00 | 82.21 | MOL1 | C |
| ATOM | 2259 | OD1 | ASN | B | 77 | 55.857 | −39.916 | −20.491 | 1.00 | 79.91 | MOL1 | O |
| ATOM | 2260 | ND2 | ASN | B | 77 | 56.878 | −41.301 | −19.046 | 1.00 | 85.38 | MOL1 | N |
| ATOM | 2261 | C | ASN | B | 77 | 60.242 | −41.606 | −21.629 | 1.00 | 78.60 | MOL1 | C |
| ATOM | 2262 | O | ASN | B | 77 | 60.103 | −40.983 | −22.682 | 1.00 | 81.00 | MOL1 | O |
| ATOM | 2263 | N | SER | B | 78 | 61.286 | −42.398 | −21.416 | 1.00 | 66.48 | MOL1 | N |
| ATOM | 2264 | CA | SER | B | 78 | 62.295 | −42.502 | −22.458 | 1.00 | 55.65 | MOL1 | C |
| ATOM | 2265 | CB | SER | B | 78 | 63.417 | −41.496 | −22.208 | 1.00 | 50.88 | MOL1 | C |
| ATOM | 2266 | OG | SER | B | 78 | 62.949 | −40.162 | −22.348 | 1.00 | 50.06 | MOL1 | O |
| ATOM | 2267 | C | SER | B | 78 | 62.876 | −43.880 | −22.645 | 1.00 | 55.66 | MOL1 | C |
| ATOM | 2268 | O | SER | B | 78 | 63.030 | −44.640 | −21.694 | 1.00 | 58.81 | MOL1 | O |
| ATOM | 2269 | N | LEU | B | 79 | 63.195 | −44.195 | −23.895 | 1.00 | 56.03 | MOL1 | N |
| ATOM | 2270 | CA | LEU | B | 79 | 63.763 | −45.484 | −24.252 | 1.00 | 55.87 | MOL1 | C |
| ATOM | 2271 | CB | LEU | B | 79 | 62.862 | −46.194 | −25.238 | 1.00 | 50.03 | MOL1 | C |
| ATOM | 2272 | CG | LEU | B | 79 | 63.500 | −47.475 | −25.721 | 1.00 | 55.46 | MOL1 | C |
| ATOM | 2273 | CD1 | LEU | B | 79 | 63.850 | −48.333 | −24.526 | 1.00 | 49.32 | MOL1 | C |
| ATOM | 2274 | CD2 | LEU | B | 79 | 62.548 | −48.181 | −26.668 | 1.00 | 63.53 | MOL1 | C |
| ATOM | 2275 | C | LEU | B | 79 | 65.125 | −45.234 | −24.877 | 1.00 | 61.11 | MOL1 | C |
| ATOM | 2276 | O | LEU | B | 79 | 65.275 | −44.350 | −25.717 | 1.00 | 64.98 | MOL1 | O |
| ATOM | 2277 | N | TYR | B | 80 | 66.113 | −46.024 | −24.472 | 1.00 | 65.65 | MOL1 | N |
| ATOM | 2278 | CA | TYR | B | 80 | 67.480 | −45.851 | −24.946 | 1.00 | 61.24 | MOL1 | C |
| ATOM | 2279 | CB | TYR | B | 80 | 68.356 | −45.415 | −23.779 | 1.00 | 61.18 | MOL1 | C |
| ATOM | 2280 | CG | TYR | B | 80 | 67.859 | −44.220 | −23.016 | 1.00 | 58.98 | MOL1 | C |
| ATOM | 2281 | CD1 | TYR | B | 80 | 67.927 | −42.957 | −23.570 | 1.00 | 62.20 | MOL1 | C |
| ATOM | 2282 | CE1 | TYR | B | 80 | 67.500 | −41.848 | −22.874 | 1.00 | 69.50 | MOL1 | C |
| ATOM | 2283 | CD2 | TYR | B | 80 | 67.342 | −44.352 | −21.733 | 1.00 | 56.61 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 2284 | CE2 | TYR | B | 80 | 66.909 | −43.245 | −21.026 | 1.00 | 63.76 | MOL1 | C |
|------|------|-----|-----|---|----|--------|---------|---------|------|-------|------|---|
| ATOM | 2285 | CZ | TYR | B | 80 | 66.992 | −41.991 | −21.607 | 1.00 | 66.48 | MOL1 | C |
| ATOM | 2286 | OH | TYR | B | 80 | 66.566 | −40.862 | −20.946 | 1.00 | 68.86 | MOL1 | O |
| ATOM | 2287 | C | TYR | B | 80 | 68.114 | −47.098 | −25.536 | 1.00 | 61.79 | MOL1 | C |
| ATOM | 2288 | O | TYR | B | 80 | 67.772 | −48.225 | −25.165 | 1.00 | 63.10 | MOL1 | O |
| ATOM | 2289 | N | LEU | B | 81 | 69.059 | −46.882 | −26.447 | 1.00 | 59.82 | MOL1 | N |
| ATOM | 2290 | CA | LEU | B | 81 | 69.812 | −47.982 | −27.036 | 1.00 | 61.74 | MOL1 | C |
| ATOM | 2291 | CB | LEU | B | 81 | 69.406 | −48.262 | −28.486 | 1.00 | 56.22 | MOL1 | C |
| ATOM | 2292 | CG | LEU | B | 81 | 70.141 | −49.486 | −29.055 | 1.00 | 46.81 | MOL1 | C |
| ATOM | 2293 | CD1 | LEU | B | 81 | 69.833 | −50.675 | −28.204 | 1.00 | 41.50 | MOL1 | C |
| ATOM | 2294 | CD2 | LEU | B | 81 | 69.740 | −49.759 | −30.483 | 1.00 | 47.33 | MOL1 | C |
| ATOM | 2295 | C | LEU | B | 81 | 71.288 | −47.608 | −26.990 | 1.00 | 65.52 | MOL1 | C |
| ATOM | 2296 | O | LEU | B | 81 | 71.699 | −46.578 | −27.524 | 1.00 | 64.49 | MOL1 | O |
| ATOM | 2297 | N | GLN | B | 82 | 72.077 | −48.443 | −26.325 | 1.00 | 70.88 | MOL1 | N |
| ATOM | 2298 | CA | GLN | B | 82 | 73.512 | −48.225 | −26.198 | 1.00 | 73.73 | MOL1 | C |
| ATOM | 2299 | CB | GLN | B | 82 | 73.973 | −48.589 | −24.790 | 1.00 | 76.90 | MOL1 | C |
| ATOM | 2300 | CG | GLN | B | 82 | 75.325 | −48.035 | −24.429 | 1.00 | 79.20 | MOL1 | C |
| ATOM | 2301 | CD | GLN | B | 82 | 75.358 | −46.529 | −24.538 | 1.00 | 83.44 | MOL1 | C |
| ATOM | 2302 | OE1 | GLN | B | 82 | 74.528 | −45.832 | −23.948 | 1.00 | 86.30 | MOL1 | O |
| ATOM | 2303 | NE2 | GLN | B | 82 | 76.319 | −46.015 | −25.294 | 1.00 | 84.32 | MOL1 | N |
| ATOM | 2304 | C | GLN | B | 82 | 74.216 | −49.120 | −27.206 | 1.00 | 77.08 | MOL1 | C |
| ATOM | 2305 | O | GLN | B | 82 | 74.270 | −50.352 | −27.046 | 1.00 | 77.12 | MOL1 | O |
| ATOM | 2306 | N | MET | B | 83 | 74.763 | −48.491 | −28.237 | 1.00 | 75.62 | MOL1 | N |
| ATOM | 2307 | CA | MET | B | 83 | 75.442 | −49.207 | −29.293 | 1.00 | 79.14 | MOL1 | C |
| ATOM | 2308 | CB | MET | B | 83 | 74.988 | −48.633 | −30.626 | 1.00 | 79.62 | MOL1 | C |
| ATOM | 2309 | CG | MET | B | 83 | 73.469 | −48.606 | −30.753 | 1.00 | 77.11 | MOL1 | C |
| ATOM | 2310 | SD | MET | B | 83 | 72.892 | −48.228 | −32.398 | 1.00 | 76.47 | MOL1 | S |
| ATOM | 2311 | CE | MET | B | 83 | 73.300 | −46.496 | −32.473 | 1.00 | 77.56 | MOL1 | C |
| ATOM | 2312 | C | MET | B | 83 | 76.956 | −49.133 | −29.165 | 1.00 | 84.61 | MOL1 | C |
| ATOM | 2313 | O | MET | B | 83 | 77.557 | −48.105 | −29.477 | 1.00 | 82.10 | MOL1 | O |
| ATOM | 2314 | N | ASN | B | 84 | 77.563 | −50.228 | −28.701 | 1.00 | 90.93 | MOL1 | N |
| ATOM | 2315 | CA | ASN | B | 84 | 79.016 | −50.311 | −28.526 | 1.00 | 94.51 | MOL1 | C |
| ATOM | 2316 | CB | ASN | B | 84 | 79.376 | −50.905 | −27.155 | 1.00 | 95.79 | MOL1 | C |
| ATOM | 2317 | CG | ASN | B | 84 | 78.835 | −50.094 | −25.989 | 1.00 | 96.64 | MOL1 | C |
| ATOM | 2318 | OD1 | ASN | B | 84 | 79.009 | −48.873 | −25.928 | 1.00 | 96.83 | MOL1 | O |
| ATOM | 2319 | ND2 | ASN | B | 84 | 78.190 | −50.779 | −25.042 | 1.00 | 94.23 | MOL1 | N |
| ATOM | 2320 | C | ASN | B | 84 | 79.627 | −51.206 | −29.603 | 1.00 | 96.78 | MOL1 | C |
| ATOM | 2321 | O | ASN | B | 84 | 78.947 | −52.075 | −30.152 | 1.00 | 98.20 | MOL1 | O |
| ATOM | 2322 | N | SER | B | 85 | 80.912 | −50.999 | −29.888 | 1.00 | 97.63 | MOL1 | N |
| ATOM | 2323 | CA | SER | B | 85 | 81.625 | −51.803 | −30.880 | 1.00 | 98.44 | MOL1 | C |
| ATOM | 2324 | CB | SER | B | 85 | 81.849 | −53.222 | −30.333 | 1.00 | 102.16 | MOL1 | C |
| ATOM | 2325 | OG | SER | B | 85 | 82.641 | −54.008 | −31.207 | 1.00 | 106.22 | MOL1 | O |
| ATOM | 2326 | C | SER | B | 85 | 80.842 | −51.855 | −32.186 | 1.00 | 95.62 | MOL1 | C |
| ATOM | 2327 | O | SER | B | 85 | 80.756 | −52.895 | −32.844 | 1.00 | 96.27 | MOL1 | O |
| ATOM | 2328 | N | LEU | B | 86 | 80.274 | −50.718 | −32.559 | 1.00 | 91.53 | MOL1 | N |
| ATOM | 2329 | CA | LEU | B | 86 | 79.482 | −50.633 | −33.774 | 1.00 | 91.52 | MOL1 | C |
| ATOM | 2330 | CB | LEU | B | 86 | 79.114 | −49.172 | −34.058 | 1.00 | 90.47 | MOL1 | C |
| ATOM | 2331 | CG | LEU | B | 86 | 77.932 | −48.622 | −33.253 | 1.00 | 87.14 | MOL1 | C |
| ATOM | 2332 | CD1 | LEU | B | 86 | 77.789 | −47.125 | −33.449 | 1.00 | 82.82 | MOL1 | C |
| ATOM | 2333 | CD2 | LEU | B | 86 | 76.673 | −49.345 | −33.693 | 1.00 | 84.80 | MOL1 | C |
| ATOM | 2334 | C | LEU | B | 86 | 80.153 | −51.231 | −34.997 | 1.00 | 89.27 | MOL1 | C |
| ATOM | 2335 | O | LEU | B | 86 | 81.104 | −50.667 | −35.517 | 1.00 | 86.74 | MOL1 | O |
| ATOM | 2336 | N | ARG | B | 87 | 79.656 | −52.379 | −35.446 | 1.00 | 91.09 | MOL1 | N |
| ATOM | 2337 | CA | ARG | B | 87 | 80.190 | −53.022 | −36.641 | 1.00 | 93.95 | MOL1 | C |
| ATOM | 2338 | CB | ARG | B | 87 | 79.627 | −54.444 | −36.801 | 1.00 | 100.00 | MOL1 | C |
| ATOM | 2339 | CG | ARG | B | 87 | 79.675 | −55.332 | −35.556 | 1.00 | 111.29 | MOL1 | C |
| ATOM | 2340 | CD | ARG | B | 87 | 81.094 | −55.636 | −35.096 | 1.00 | 124.71 | MOL1 | C |
| ATOM | 2341 | NE | ARG | B | 87 | 81.114 | −56.577 | −33.973 | 1.00 | 136.98 | MOL1 | N |
| ATOM | 2342 | CZ | ARG | B | 87 | 82.197 | −56.881 | −33.258 | 1.00 | 142.47 | MOL1 | C |
| ATOM | 2343 | NH1 | ARG | B | 87 | 83.366 | −56.317 | −33.542 | 1.00 | 145.24 | MOL1 | N |
| ATOM | 2344 | NH2 | ARG | B | 87 | 82.112 | −57.746 | −32.252 | 1.00 | 142.45 | MOL1 | N |
| ATOM | 2345 | C | ARG | B | 87 | 79.706 | −52.153 | −37.807 | 1.00 | 91.66 | MOL1 | C |
| ATOM | 2346 | O | ARG | B | 87 | 79.058 | −51.135 | −37.591 | 1.00 | 87.56 | MOL1 | O |
| ATOM | 2347 | N | ALA | B | 88 | 80.005 | −52.549 | −39.038 | 1.00 | 94.65 | MOL1 | N |
| ATOM | 2348 | CA | ALA | B | 88 | 79.567 | −51.769 | −40.193 | 1.00 | 95.57 | MOL1 | C |
| ATOM | 2349 | CB | ALA | B | 88 | 80.627 | −51.802 | −41.291 | 1.00 | 98.24 | MOL1 | C |
| ATOM | 2350 | C | ALA | B | 88 | 78.236 | −52.291 | −40.725 | 1.00 | 95.75 | MOL1 | C |
| ATOM | 2351 | O | ALA | B | 88 | 77.481 | −51.559 | −41.361 | 1.00 | 92.75 | MOL1 | O |
| ATOM | 2352 | N | GLU | B | 89 | 77.953 | −53.561 | −40.462 | 1.00 | 96.30 | MOL1 | N |
| ATOM | 2353 | CA | GLU | B | 89 | 76.707 | −54.154 | −40.905 | 1.00 | 97.62 | MOL1 | C |
| ATOM | 2354 | CB | GLU | B | 89 | 76.835 | −55.684 | −40.919 | 1.00 | 106.24 | MOL1 | C |
| ATOM | 2355 | CG | GLU | B | 89 | 77.211 | −56.320 | −39.581 | 1.00 | 120.92 | MOL1 | C |
| ATOM | 2356 | CD | GLU | B | 89 | 76.088 | −57.184 | −38.988 | 1.00 | 130.30 | MOL1 | C |
| ATOM | 2357 | OE1 | GLU | B | 89 | 76.312 | −57.809 | −37.924 | 1.00 | 131.94 | MOL1 | O |
| ATOM | 2358 | OE2 | GLU | B | 89 | 74.984 | −57.240 | −39.583 | 1.00 | 133.92 | MOL1 | O |
| ATOM | 2359 | C | GLU | B | 89 | 75.562 | −53.700 | −39.989 | 1.00 | 94.40 | MOL1 | C |
| ATOM | 2360 | O | GLU | B | 89 | 74.442 | −54.207 | −40.067 | 1.00 | 95.94 | MOL1 | O |

TABLE 1-continued

The atomic coordinates of IL17F in complex with 496 Fab
(H32; a = 189.4; b = 189.4; c = 490.9, α, β = 90°; γ = 120°)

| ATOM | 2361 | N | ASP | B | 90 | 75.848 | −52.724 | −39.131 | 1.00 | 89.39 | MOL1 | N |
|---|---|---|---|---|---|---|---|---|---|---|---|---|
| ATOM | 2362 | CA | ASP | B | 90 | 74.857 | −52.193 | −38.199 | 1.00 | 83.27 | MOL1 | C |
| ATOM | 2363 | CB | ASP | B | 90 | 75.499 | −51.873 | −36.842 | 1.00 | 85.32 | MOL1 | C |
| ATOM | 2364 | CG | ASP | B | 90 | 75.718 | −53.110 | −35.974 | 1.00 | 91.03 | MOL1 | C |
| ATOM | 2365 | OD1 | ASP | B | 90 | 75.267 | −54.217 | −36.357 | 1.00 | 89.00 | MOL1 | O |
| ATOM | 2366 | OD2 | ASP | B | 90 | 76.340 | −52.964 | −34.894 | 1.00 | 88.62 | MOL1 | O |
| ATOM | 2367 | C | ASP | B | 90 | 74.206 | −50.924 | −38.716 | 1.00 | 79.69 | MOL1 | C |
| ATOM | 2368 | O | ASP | B | 90 | 73.295 | −50.399 | −38.088 | 1.00 | 78.86 | MOL1 | O |
| ATOM | 2369 | N | THR | B | 91 | 74.686 | −50.420 | −39.848 | 1.00 | 78.76 | MOL1 | N |
| ATOM | 2370 | CA | THR | B | 91 | 74.142 | −49.194 | −40.433 | 1.00 | 73.34 | MOL1 | C |
| ATOM | 2371 | CB | THR | B | 91 | 74.872 | −48.823 | −41.706 | 1.00 | 68.24 | MOL1 | C |
| ATOM | 2372 | OG1 | THR | B | 91 | 76.279 | −48.980 | −41.516 | 1.00 | 69.85 | MOL1 | O |
| ATOM | 2373 | CG2 | THR | B | 91 | 74.572 | −47.409 | −42.073 | 1.00 | 62.10 | MOL1 | C |
| ATOM | 2374 | C | THR | B | 91 | 72.679 | −49.375 | −40.808 | 1.00 | 76.36 | MOL1 | C |
| ATOM | 2375 | O | THR | B | 91 | 72.315 | −50.390 | −41.410 | 1.00 | 81.79 | MOL1 | O |
| ATOM | 2376 | N | ALA | B | 92 | 71.846 | −48.395 | −40.465 | 1.00 | 70.36 | MOL1 | N |
| ATOM | 2377 | CA | ALA | B | 92 | 70.423 | −48.463 | −40.783 | 1.00 | 66.19 | MOL1 | C |
| ATOM | 2378 | CB | ALA | B | 92 | 69.854 | −49.814 | −40.373 | 1.00 | 64.76 | MOL1 | C |
| ATOM | 2379 | C | ALA | B | 92 | 69.651 | −47.370 | −40.081 | 1.00 | 64.77 | MOL1 | C |
| ATOM | 2380 | O | ALA | B | 92 | 70.229 | −46.506 | −39.420 | 1.00 | 67.65 | MOL1 | O |
| ATOM | 2381 | N | VAL | B | 93 | 68.334 | −47.393 | −40.250 | 1.00 | 60.04 | MOL1 | N |
| ATOM | 2382 | CA | VAL | B | 93 | 67.507 | −46.435 | −39.555 | 1.00 | 54.68 | MOL1 | C |
| ATOM | 2383 | CB | VAL | B | 93 | 66.386 | −45.886 | −40.390 | 1.00 | 52.41 | MOL1 | C |
| ATOM | 2384 | CG1 | VAL | B | 93 | 65.218 | −45.538 | −39.484 | 1.00 | 51.63 | MOL1 | C |
| ATOM | 2385 | CG2 | VAL | B | 93 | 66.852 | −44.630 | −41.082 | 1.00 | 54.11 | MOL1 | C |
| ATOM | 2386 | C | VAL | B | 93 | 66.917 | −47.182 | −38.382 | 1.00 | 55.09 | MOL1 | C |
| ATOM | 2387 | O | VAL | B | 93 | 66.327 | −48.256 | −38.529 | 1.00 | 53.60 | MOL1 | O |
| ATOM | 2388 | N | TYR | B | 94 | 67.112 | −46.622 | −37.202 | 1.00 | 52.57 | MOL1 | N |
| ATOM | 2389 | CA | TYR | B | 94 | 66.617 | −47.261 | −36.021 | 1.00 | 47.72 | MOL1 | C |
| ATOM | 2390 | CB | TYR | B | 94 | 67.615 | −47.108 | −34.885 | 1.00 | 48.04 | MOL1 | C |
| ATOM | 2391 | CG | TYR | B | 94 | 68.771 | −48.070 | −35.032 | 1.00 | 52.97 | MOL1 | C |
| ATOM | 2392 | CD1 | TYR | B | 94 | 69.714 | −47.909 | −36.045 | 1.00 | 58.49 | MOL1 | C |
| ATOM | 2393 | CE1 | TYR | B | 94 | 70.727 | −48.831 | −36.233 | 1.00 | 62.20 | MOL1 | C |
| ATOM | 2394 | CD2 | TYR | B | 94 | 68.880 | −49.182 | −34.209 | 1.00 | 50.31 | MOL1 | C |
| ATOM | 2395 | CE2 | TYR | B | 94 | 69.882 | −50.112 | −34.389 | 1.00 | 56.78 | MOL1 | C |
| ATOM | 2396 | CZ | TYR | B | 94 | 70.802 | −49.935 | −35.401 | 1.00 | 64.78 | MOL1 | C |
| ATOM | 2397 | OH | TYR | B | 94 | 71.788 | −50.876 | −35.585 | 1.00 | 67.91 | MOL1 | O |
| ATOM | 2398 | C | TYR | B | 94 | 65.277 | −46.716 | −35.648 | 1.00 | 47.66 | MOL1 | C |
| ATOM | 2399 | O | TYR | B | 94 | 65.106 | −45.509 | −35.519 | 1.00 | 47.18 | MOL1 | O |
| ATOM | 2400 | N | TYR | B | 95 | 64.330 | −47.642 | −35.499 | 1.00 | 47.28 | MOL1 | N |
| ATOM | 2401 | CA | TYR | B | 95 | 62.946 | −47.356 | −35.146 | 1.00 | 42.92 | MOL1 | C |
| ATOM | 2402 | CB | TYR | B | 95 | 62.009 | −48.074 | −36.112 | 1.00 | 41.96 | MOL1 | C |
| ATOM | 2403 | CG | TYR | B | 95 | 61.952 | −47.495 | −37.503 | 1.00 | 36.03 | MOL1 | C |
| ATOM | 2404 | CD1 | TYR | B | 95 | 62.216 | −48.286 | −38.610 | 1.00 | 31.42 | MOL1 | C |
| ATOM | 2405 | CE1 | TYR | B | 95 | 62.135 | −47.770 | −39.894 | 1.00 | 31.36 | MOL1 | C |
| ATOM | 2406 | CD2 | TYR | B | 95 | 61.605 | −46.169 | −37.714 | 1.00 | 32.69 | MOL1 | C |
| ATOM | 2407 | CE2 | TYR | B | 95 | 61.523 | −45.649 | −38.990 | 1.00 | 30.52 | MOL1 | C |
| ATOM | 2408 | CZ | TYR | B | 95 | 61.791 | −46.452 | −40.079 | 1.00 | 31.84 | MOL1 | C |
| ATOM | 2409 | OH | TYR | B | 95 | 61.740 | −45.936 | −41.358 | 1.00 | 37.32 | MOL1 | O |
| ATOM | 2410 | C | TYR | B | 95 | 62.565 | −47.757 | −33.716 | 1.00 | 44.74 | MOL1 | C |
| ATOM | 2411 | O | TYR | B | 95 | 62.956 | −48.813 | −33.208 | 1.00 | 43.15 | MOL1 | O |
| ATOM | 2412 | N | CYS | B | 96 | 61.769 | −46.898 | −33.096 | 1.00 | 42.45 | MOL1 | N |
| ATOM | 2413 | CA | CYS | B | 96 | 61.280 | −47.080 | −31.742 | 1.00 | 48.18 | MOL1 | C |
| ATOM | 2414 | C | CYS | B | 96 | 59.858 | −47.591 | −31.935 | 1.00 | 45.66 | MOL1 | C |
| ATOM | 2415 | O | CYS | B | 96 | 59.094 | −46.997 | −32.686 | 1.00 | 52.35 | MOL1 | O |
| ATOM | 2416 | CB | CYS | B | 96 | 61.289 | −45.712 | −31.041 | 1.00 | 56.99 | MOL1 | C |
| ATOM | 2417 | SG | CYS | B | 96 | 60.788 | −45.606 | −29.285 | 1.00 | 75.20 | MOL1 | S |
| ATOM | 2418 | N | ALA | B | 97 | 59.486 | −48.680 | −31.275 | 1.00 | 45.29 | MOL1 | N |
| ATOM | 2419 | CA | ALA | B | 97 | 58.133 | −49.219 | −31.462 | 1.00 | 48.97 | MOL1 | C |
| ATOM | 2420 | CB | ALA | B | 97 | 58.159 | −50.387 | −32.454 | 1.00 | 50.04 | MOL1 | C |
| ATOM | 2421 | C | ALA | B | 97 | 57.430 | −49.675 | −30.198 | 1.00 | 51.55 | MOL1 | C |
| ATOM | 2422 | O | ALA | B | 97 | 57.971 | −50.473 | −29.418 | 1.00 | 53.04 | MOL1 | O |
| ATOM | 2423 | N | SER | B | 98 | 56.201 | −49.201 | −30.011 | 1.00 | 48.82 | MOL1 | N |
| ATOM | 2424 | CA | SER | B | 98 | 55.446 | −49.593 | −28.830 | 1.00 | 49.76 | MOL1 | C |
| ATOM | 2425 | CB | SER | B | 98 | 54.932 | −48.364 | −28.088 | 1.00 | 52.60 | MOL1 | C |
| ATOM | 2426 | OG | SER | B | 98 | 53.682 | −47.961 | −28.593 | 1.00 | 57.72 | MOL1 | O |
| ATOM | 2427 | C | SER | B | 98 | 54.279 | −50.490 | −29.191 | 1.00 | 48.56 | MOL1 | C |
| ATOM | 2428 | O | SER | B | 98 | 53.865 | −50.547 | −30.337 | 1.00 | 56.57 | MOL1 | O |
| ATOM | 2429 | N | PRO | B | 99 | 53.742 | −51.225 | −28.215 | 1.00 | 48.25 | MOL1 | N |
| ATOM | 2430 | CD | PRO | B | 99 | 54.274 | −51.498 | −26.872 | 1.00 | 43.96 | MOL1 | C |
| ATOM | 2431 | CA | PRO | B | 99 | 52.610 | −52.100 | −28.520 | 1.00 | 49.92 | MOL1 | C |
| ATOM | 2432 | CB | PRO | B | 99 | 52.755 | −53.200 | −27.486 | 1.00 | 51.02 | MOL1 | C |
| ATOM | 2433 | CG | PRO | B | 99 | 53.243 | −52.431 | −26.296 | 1.00 | 49.83 | MOL1 | C |
| ATOM | 2434 | C | PRO | B | 99 | 51.284 | −51.323 | −28.417 | 1.00 | 49.50 | MOL1 | C |
| ATOM | 2435 | O | PRO | B | 99 | 51.265 | −50.148 | −28.028 | 1.00 | 42.62 | MOL1 | O |
| ATOM | 2436 | N | PRO | B | 100 | 50.164 | −51.973 | −28.766 | 1.00 | 49.50 | MOL1 | N |
| ATOM | 2437 | CD | PRO | B | 100 | 50.098 | −53.401 | −29.117 | 1.00 | 51.43 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 2438 | CA | PRO | B | 100 | 48.817 | −51.394 | −28.741 | 1.00 | 51.65 | MOL1 | C |
|---|---|---|---|---|---|---|---|---|---|---|---|---|
| ATOM | 2439 | CB | PRO | B | 100 | 47.961 | −52.496 | −29.362 | 1.00 | 47.03 | MOL1 | C |
| ATOM | 2440 | CG | PRO | B | 100 | 48.628 | −53.716 | −28.901 | 1.00 | 49.55 | MOL1 | C |
| ATOM | 2441 | C | PRO | B | 100 | 48.306 | −50.961 | −27.374 | 1.00 | 53.54 | MOL1 | C |
| ATOM | 2442 | O | PRO | B | 100 | 48.489 | −51.655 | −26.386 | 1.00 | 51.78 | MOL1 | O |
| ATOM | 2443 | N | GLN | B | 101 | 47.658 | −49.799 | −27.351 | 1.00 | 61.09 | MOL1 | N |
| ATOM | 2444 | CA | GLN | B | 101 | 47.094 | −49.205 | −26.147 | 1.00 | 61.80 | MOL1 | C |
| ATOM | 2445 | CB | GLN | B | 101 | 46.495 | −47.829 | −26.477 | 1.00 | 74.11 | MOL1 | C |
| ATOM | 2446 | CG | GLN | B | 101 | 47.203 | −47.058 | −27.621 | 1.00 | 89.30 | MOL1 | C |
| ATOM | 2447 | CD | GLN | B | 101 | 46.706 | −47.425 | −29.055 | 1.00 | 96.41 | MOL1 | C |
| ATOM | 2448 | OE1 | GLN | B | 101 | 46.819 | −48.574 | −29.511 | 1.00 | 84.58 | MOL1 | O |
| ATOM | 2449 | NE2 | GLN | B | 101 | 46.167 | −46.427 | −29.763 | 1.00 | 98.03 | MOL1 | N |
| ATOM | 2450 | C | GLN | B | 101 | 46.026 | −50.122 | −25.538 | 1.00 | 61.51 | MOL1 | C |
| ATOM | 2451 | O | GLN | B | 101 | 45.799 | −50.078 | −24.329 | 1.00 | 66.28 | MOL1 | O |
| ATOM | 2452 | N | TYR | B | 102 | 45.340 | −50.926 | −26.355 | 1.00 | 57.93 | MOL1 | N |
| ATOM | 2453 | CA | TYR | B | 102 | 44.368 | −51.870 | −25.795 | 1.00 | 58.68 | MOL1 | C |
| ATOM | 2454 | CB | TYR | B | 102 | 43.306 | −52.305 | −26.814 | 1.00 | 59.50 | MOL1 | C |
| ATOM | 2455 | CG | TYR | B | 102 | 43.723 | −52.267 | −28.270 | 1.00 | 67.62 | MOL1 | C |
| ATOM | 2456 | CD1 | TYR | B | 102 | 43.665 | −53.410 | −29.054 | 1.00 | 73.12 | MOL1 | C |
| ATOM | 2457 | CE1 | TYR | B | 102 | 44.086 | −53.404 | −30.379 | 1.00 | 70.43 | MOL1 | C |
| ATOM | 2458 | CD2 | TYR | B | 102 | 44.205 | −51.104 | −28.855 | 1.00 | 67.71 | MOL1 | C |
| ATOM | 2459 | CE2 | TYR | B | 102 | 44.629 | −51.089 | −30.179 | 1.00 | 70.68 | MOL1 | C |
| ATOM | 2460 | CZ | TYR | B | 102 | 44.574 | −52.244 | −30.930 | 1.00 | 68.95 | MOL1 | C |
| ATOM | 2461 | OH | TYR | B | 102 | 45.076 | −52.264 | −32.208 | 1.00 | 70.49 | MOL1 | O |
| ATOM | 2462 | C | TYR | B | 102 | 45.219 | −53.056 | −25.344 | 1.00 | 62.41 | MOL1 | C |
| ATOM | 2463 | O | TYR | B | 102 | 46.342 | −52.854 | −24.889 | 1.00 | 72.10 | MOL1 | O |
| ATOM | 2464 | N | TYR | B | 103 | 44.734 | −54.282 | −25.442 | 1.00 | 56.35 | MOL1 | N |
| ATOM | 2465 | CA | TYR | B | 103 | 45.562 | −55.419 | −25.004 | 1.00 | 55.06 | MOL1 | C |
| ATOM | 2466 | CB | TYR | B | 103 | 46.477 | −55.850 | −26.139 | 1.00 | 39.42 | MOL1 | C |
| ATOM | 2467 | CG | TYR | B | 103 | 45.779 | −56.647 | −27.189 | 1.00 | 40.53 | MOL1 | C |
| ATOM | 2468 | CD1 | TYR | B | 103 | 45.431 | −57.966 | −26.965 | 1.00 | 40.77 | MOL1 | C |
| ATOM | 2469 | CE1 | TYR | B | 103 | 44.739 | −58.689 | −27.913 | 1.00 | 39.01 | MOL1 | C |
| ATOM | 2470 | CD2 | TYR | B | 103 | 45.421 | −56.073 | −28.389 | 1.00 | 37.07 | MOL1 | C |
| ATOM | 2471 | CE2 | TYR | B | 103 | 44.725 | −56.785 | −29.340 | 1.00 | 37.65 | MOL1 | C |
| ATOM | 2472 | CZ | TYR | B | 103 | 44.385 | −58.092 | −29.098 | 1.00 | 40.30 | MOL1 | C |
| ATOM | 2473 | OH | TYR | B | 103 | 43.664 | −58.795 | −30.040 | 1.00 | 45.78 | MOL1 | O |
| ATOM | 2474 | C | TYR | B | 103 | 46.438 | −55.312 | −23.731 | 1.00 | 61.14 | MOL1 | C |
| ATOM | 2475 | O | TYR | B | 103 | 45.971 | −55.407 | −22.597 | 1.00 | 62.53 | MOL1 | O |
| ATOM | 2476 | N | GLU | B | 104 | 47.731 | −55.126 | −23.953 | 1.00 | 71.54 | MOL1 | N |
| ATOM | 2477 | CA | GLU | B | 104 | 48.736 | −55.073 | −22.892 | 1.00 | 75.42 | MOL1 | C |
| ATOM | 2478 | CB | GLU | B | 104 | 48.692 | −53.817 | −22.049 | 1.00 | 78.09 | MOL1 | C |
| ATOM | 2479 | CG | GLU | B | 104 | 50.036 | −53.557 | −21.290 | 1.00 | 87.24 | MOL1 | C |
| ATOM | 2480 | CD | GLU | B | 104 | 50.854 | −54.815 | −20.883 | 1.00 | 86.28 | MOL1 | C |
| ATOM | 2481 | OE1 | GLU | B | 104 | 51.228 | −55.640 | −21.750 | 1.00 | 77.83 | MOL1 | O |
| ATOM | 2482 | OE2 | GLU | B | 104 | 51.150 | −54.965 | −19.675 | 1.00 | 86.79 | MOL1 | O |
| ATOM | 2483 | C | GLU | B | 104 | 48.567 | −56.198 | −21.930 | 1.00 | 76.64 | MOL1 | C |
| ATOM | 2484 | O | GLU | B | 104 | 48.897 | −57.337 | −22.238 | 1.00 | 78.00 | MOL1 | O |
| ATOM | 2485 | N | GLY | B | 105 | 48.055 | −55.851 | −20.751 | 1.00 | 82.01 | MOL1 | N |
| ATOM | 2486 | CA | GLY | B | 105 | 47.872 | −56.824 | −19.687 | 1.00 | 92.10 | MOL1 | C |
| ATOM | 2487 | C | GLY | B | 105 | 49.226 | −57.315 | −19.172 | 1.00 | 95.69 | MOL1 | C |
| ATOM | 2488 | O | GLY | B | 105 | 49.336 | −57.738 | −18.017 | 1.00 | 97.30 | MOL1 | O |
| ATOM | 2489 | N | SER | B | 106 | 50.234 | −57.239 | −20.055 | 1.00 | 91.89 | MOL1 | N |
| ATOM | 2490 | CA | SER | B | 106 | 51.622 | −57.640 | −19.842 | 1.00 | 80.13 | MOL1 | C |
| ATOM | 2491 | CB | SER | B | 106 | 51.757 | −58.534 | −18.624 | 1.00 | 86.39 | MOL1 | C |
| ATOM | 2492 | OG | SER | B | 106 | 51.584 | −57.772 | −17.440 | 1.00 | 101.06 | MOL1 | O |
| ATOM | 2493 | C | SER | B | 106 | 52.076 | −58.392 | −21.075 | 1.00 | 76.46 | MOL1 | C |
| ATOM | 2494 | O | SER | B | 106 | 53.261 | −58.468 | −21.354 | 1.00 | 80.98 | MOL1 | O |
| ATOM | 2495 | N | ILE | B | 107 | 51.106 | −58.931 | −21.808 | 1.00 | 72.52 | MOL1 | N |
| ATOM | 2496 | CA | ILE | B | 107 | 51.317 | −59.712 | −23.026 | 1.00 | 69.30 | MOL1 | C |
| ATOM | 2497 | CB | ILE | B | 107 | 50.163 | −59.504 | −24.009 | 1.00 | 63.37 | MOL1 | C |
| ATOM | 2498 | CG2 | ILE | B | 107 | 50.364 | −60.364 | −25.232 | 1.00 | 69.72 | MOL1 | C |
| ATOM | 2499 | CG1 | ILE | B | 107 | 48.850 | −59.916 | −23.365 | 1.00 | 57.52 | MOL1 | C |
| ATOM | 2500 | CD1 | ILE | B | 107 | 47.709 | −59.969 | −24.330 | 1.00 | 59.21 | MOL1 | C |
| ATOM | 2501 | C | ILE | B | 107 | 52.626 | −59.449 | −23.762 | 1.00 | 75.37 | MOL1 | C |
| ATOM | 2502 | O | ILE | B | 107 | 52.846 | −58.365 | −24.315 | 1.00 | 80.43 | MOL1 | O |
| ATOM | 2503 | N | TYR | B | 108 | 53.491 | −60.459 | −23.799 | 1.00 | 76.32 | MOL1 | N |
| ATOM | 2504 | CA | TYR | B | 108 | 54.787 | −60.298 | −24.446 | 1.00 | 70.22 | MOL1 | C |
| ATOM | 2505 | CB | TYR | B | 108 | 55.791 | −61.316 | −23.879 | 1.00 | 72.00 | MOL1 | C |
| ATOM | 2506 | CG | TYR | B | 108 | 57.129 | −61.320 | −24.581 | 1.00 | 68.39 | MOL1 | C |
| ATOM | 2507 | CD1 | TYR | B | 108 | 57.881 | −60.166 | −24.681 | 1.00 | 67.40 | MOL1 | C |
| ATOM | 2508 | CE1 | TYR | B | 108 | 59.066 | −60.144 | −25.388 | 1.00 | 68.09 | MOL1 | C |
| ATOM | 2509 | CD2 | TYR | B | 108 | 57.606 | −62.465 | −25.201 | 1.00 | 70.66 | MOL1 | C |
| ATOM | 2510 | CE2 | TYR | B | 108 | 58.787 | −62.454 | −25.910 | 1.00 | 73.27 | MOL1 | C |
| ATOM | 2511 | CZ | TYR | B | 108 | 59.513 | −61.286 | −26.007 | 1.00 | 73.12 | MOL1 | C |
| ATOM | 2512 | OH | TYR | B | 108 | 60.659 | −61.241 | −26.779 | 1.00 | 78.13 | MOL1 | O |
| ATOM | 2513 | C | TYR | B | 108 | 54.763 | −60.376 | −25.966 | 1.00 | 63.70 | MOL1 | C |
| ATOM | 2514 | O | TYR | B | 108 | 55.273 | −59.478 | −26.626 | 1.00 | 63.97 | MOL1 | O |

TABLE 1-continued

The atomic coordinates of IL17F in complex with 496 Fab
(H32; a = 189.4; b = 189.4; c = 490.9, α, β = 90°; γ = 120°)

| ATOM | 2515 | N | ARG | B | 109 | 54.155 | −61.425 | −26.510 | 1.00 | 56.91 | MOL1 | N |
|---|---|---|---|---|---|---|---|---|---|---|---|---|
| ATOM | 2516 | CA | ARG | B | 109 | 54.105 | −61.642 | −27.958 | 1.00 | 58.47 | MOL1 | C |
| ATOM | 2517 | CB | ARG | B | 109 | 53.480 | −63.008 | −28.221 | 1.00 | 69.08 | MOL1 | C |
| ATOM | 2518 | CG | ARG | B | 109 | 53.583 | −63.920 | −27.003 | 1.00 | 81.72 | MOL1 | C |
| ATOM | 2519 | CD | ARG | B | 109 | 54.439 | −65.146 | −27.246 | 1.00 | 89.25 | MOL1 | C |
| ATOM | 2520 | NE | ARG | B | 109 | 54.686 | −65.846 | −25.985 | 1.00 | 103.95 | MOL1 | N |
| ATOM | 2521 | CZ | ARG | B | 109 | 55.168 | −67.084 | −25.885 | 1.00 | 107.07 | MOL1 | C |
| ATOM | 2522 | NH1 | ARG | B | 109 | 55.456 | −67.775 | −26.983 | 1.00 | 108.09 | MOL1 | N |
| ATOM | 2523 | NH2 | ARG | B | 109 | 55.362 | −67.629 | −24.683 | 1.00 | 102.84 | MOL1 | N |
| ATOM | 2524 | C | ARG | B | 109 | 53.410 | −60.554 | −28.790 | 1.00 | 52.75 | MOL1 | C |
| ATOM | 2525 | O | ARG | B | 109 | 53.235 | −60.691 | −30.002 | 1.00 | 47.41 | MOL1 | O |
| ATOM | 2526 | N | LEU | B | 110 | 53.047 | −59.465 | −28.126 | 1.00 | 50.30 | MOL1 | N |
| ATOM | 2527 | CA | LEU | B | 110 | 52.395 | −58.316 | −28.750 | 1.00 | 46.56 | MOL1 | C |
| ATOM | 2528 | CB | LEU | B | 110 | 52.212 | −57.227 | −27.706 | 1.00 | 47.54 | MOL1 | C |
| ATOM | 2529 | CG | LEU | B | 110 | 50.759 | −56.842 | −27.519 | 1.00 | 54.43 | MOL1 | C |
| ATOM | 2530 | CD1 | LEU | B | 110 | 49.916 | −58.104 | −27.459 | 1.00 | 59.21 | MOL1 | C |
| ATOM | 2531 | CD2 | LEU | B | 110 | 50.610 | −56.026 | −26.262 | 1.00 | 47.23 | MOL1 | C |
| ATOM | 2532 | C | LEU | B | 110 | 53.118 | −57.698 | −29.944 | 1.00 | 45.48 | MOL1 | C |
| ATOM | 2533 | O | LEU | B | 110 | 54.291 | −57.357 | −29.876 | 1.00 | 46.46 | MOL1 | O |
| ATOM | 2534 | N | TRP | B | 111 | 52.399 | −57.530 | −31.040 | 1.00 | 48.24 | MOL1 | N |
| ATOM | 2535 | CA | TRP | B | 111 | 52.964 | −56.916 | −32.237 | 1.00 | 48.84 | MOL1 | C |
| ATOM | 2536 | CB | TRP | B | 111 | 51.964 | −57.012 | −33.391 | 1.00 | 48.00 | MOL1 | C |
| ATOM | 2537 | CG | TRP | B | 111 | 50.647 | −56.428 | −33.029 | 1.00 | 46.57 | MOL1 | C |
| ATOM | 2538 | CD2 | TRP | B | 111 | 49.580 | −57.099 | −32.362 | 1.00 | 50.74 | MOL1 | C |
| ATOM | 2539 | CE2 | TRP | B | 111 | 48.584 | −56.150 | −32.102 | 1.00 | 52.04 | MOL1 | C |
| ATOM | 2540 | CE3 | TRP | B | 111 | 49.373 | −58.414 | −31.956 | 1.00 | 54.75 | MOL1 | C |
| ATOM | 2541 | CD1 | TRP | B | 111 | 50.262 | −55.132 | −33.152 | 1.00 | 51.34 | MOL1 | C |
| ATOM | 2542 | NE1 | TRP | B | 111 | 49.018 | −54.949 | −32.593 | 1.00 | 52.39 | MOL1 | N |
| ATOM | 2543 | CZ2 | TRP | B | 111 | 47.406 | −56.477 | −31.454 | 1.00 | 60.95 | MOL1 | C |
| ATOM | 2544 | CZ3 | TRP | B | 111 | 48.203 | −58.732 | −31.314 | 1.00 | 55.14 | MOL1 | C |
| ATOM | 2545 | CH2 | TRP | B | 111 | 47.237 | −57.776 | −31.069 | 1.00 | 56.14 | MOL1 | C |
| ATOM | 2546 | C | TRP | B | 111 | 53.129 | −55.463 | −31.863 | 1.00 | 50.24 | MOL1 | C |
| ATOM | 2547 | O | TRP | B | 111 | 53.102 | −55.116 | −30.673 | 1.00 | 55.63 | MOL1 | O |
| ATOM | 2548 | N | PHE | B | 112 | 53.309 | −54.598 | −32.851 | 1.00 | 46.77 | MOL1 | N |
| ATOM | 2549 | CA | PHE | B | 112 | 53.379 | −53.205 | −32.490 | 1.00 | 45.05 | MOL1 | C |
| ATOM | 2550 | CB | PHE | B | 112 | 54.753 | −52.826 | −31.905 | 1.00 | 54.59 | MOL1 | C |
| ATOM | 2551 | CG | PHE | B | 112 | 55.953 | −53.481 | −32.564 | 1.00 | 57.92 | MOL1 | C |
| ATOM | 2552 | CD1 | PHE | B | 112 | 56.749 | −54.370 | −31.842 | 1.00 | 62.59 | MOL1 | C |
| ATOM | 2553 | CD2 | PHE | B | 112 | 56.354 | −53.130 | −33.825 | 1.00 | 48.83 | MOL1 | C |
| ATOM | 2554 | CE1 | PHE | B | 112 | 57.913 | −54.882 | −32.363 | 1.00 | 51.33 | MOL1 | C |
| ATOM | 2555 | CE2 | PHE | B | 112 | 57.516 | −53.645 | −34.337 | 1.00 | 55.91 | MOL1 | C |
| ATOM | 2556 | CZ | PHE | B | 112 | 58.297 | −54.525 | −33.595 | 1.00 | 49.90 | MOL1 | C |
| ATOM | 2557 | C | PHE | B | 112 | 52.935 | −52.155 | −33.470 | 1.00 | 42.66 | MOL1 | C |
| ATOM | 2558 | O | PHE | B | 112 | 53.405 | −52.088 | −34.608 | 1.00 | 43.22 | MOL1 | O |
| ATOM | 2559 | N | ALA | B | 113 | 51.977 | −51.358 | −32.997 | 1.00 | 39.22 | MOL1 | N |
| ATOM | 2560 | CA | ALA | B | 113 | 51.449 | −50.220 | −33.736 | 1.00 | 40.32 | MOL1 | C |
| ATOM | 2561 | CB | ALA | B | 113 | 50.021 | −49.963 | −33.398 | 1.00 | 42.03 | MOL1 | C |
| ATOM | 2562 | C | ALA | B | 113 | 52.290 | −49.105 | −33.185 | 1.00 | 39.72 | MOL1 | C |
| ATOM | 2563 | O | ALA | B | 113 | 52.953 | −49.271 | −32.180 | 1.00 | 43.81 | MOL1 | O |
| ATOM | 2564 | N | HIS | B | 114 | 52.277 | −47.958 | −33.824 | 1.00 | 44.26 | MOL1 | N |
| ATOM | 2565 | CA | HIS | B | 114 | 53.095 | −46.866 | −33.327 | 1.00 | 47.45 | MOL1 | C |
| ATOM | 2566 | CB | HIS | B | 114 | 52.703 | −46.561 | −31.895 | 1.00 | 47.23 | MOL1 | C |
| ATOM | 2567 | CG | HIS | B | 114 | 51.233 | −46.414 | −31.723 | 1.00 | 51.11 | MOL1 | C |
| ATOM | 2568 | CD2 | HIS | B | 114 | 50.310 | −45.801 | −32.496 | 1.00 | 58.42 | MOL1 | C |
| ATOM | 2569 | ND1 | HIS | B | 114 | 50.543 | −47.002 | −30.688 | 1.00 | 54.21 | MOL1 | N |
| ATOM | 2570 | CE1 | HIS | B | 114 | 49.254 | −46.761 | −30.832 | 1.00 | 58.58 | MOL1 | C |
| ATOM | 2571 | NE2 | HIS | B | 114 | 49.086 | −46.035 | −31.922 | 1.00 | 67.53 | MOL1 | N |
| ATOM | 2572 | C | HIS | B | 114 | 54.597 | −47.136 | −33.424 | 1.00 | 46.61 | MOL1 | C |
| ATOM | 2573 | O | HIS | B | 114 | 55.181 | −47.914 | −32.653 | 1.00 | 39.62 | MOL1 | O |
| ATOM | 2574 | N | TRP | B | 115 | 55.190 | −46.471 | −34.410 | 1.00 | 46.04 | MOL1 | N |
| ATOM | 2575 | CA | TRP | B | 115 | 56.600 | −46.539 | −34.686 | 1.00 | 43.95 | MOL1 | C |
| ATOM | 2576 | CB | TRP | B | 115 | 56.829 | −47.107 | −36.088 | 1.00 | 43.82 | MOL1 | C |
| ATOM | 2577 | CG | TRP | B | 115 | 56.477 | −48.548 | −36.286 | 1.00 | 39.43 | MOL1 | C |
| ATOM | 2578 | CD2 | TRP | B | 115 | 57.369 | −49.604 | −36.671 | 1.00 | 41.48 | MOL1 | C |
| ATOM | 2579 | CE2 | TRP | B | 115 | 56.605 | −50.784 | −36.769 | 1.00 | 38.25 | MOL1 | C |
| ATOM | 2580 | CE3 | TRP | B | 115 | 58.737 | −49.665 | −36.941 | 1.00 | 37.30 | MOL1 | C |
| ATOM | 2581 | CD1 | TRP | B | 115 | 55.253 | −49.112 | −36.171 | 1.00 | 41.90 | MOL1 | C |
| ATOM | 2582 | NE1 | TRP | B | 115 | 55.313 | −50.459 | −36.460 | 1.00 | 37.95 | MOL1 | N |
| ATOM | 2583 | CZ2 | TRP | B | 115 | 57.162 | −52.007 | −37.122 | 1.00 | 29.39 | MOL1 | C |
| ATOM | 2584 | CZ3 | TRP | B | 115 | 59.283 | −50.880 | −37.291 | 1.00 | 37.81 | MOL1 | C |
| ATOM | 2585 | CH2 | TRP | B | 115 | 58.497 | −52.035 | −37.377 | 1.00 | 28.35 | MOL1 | C |
| ATOM | 2586 | C | TRP | B | 115 | 57.033 | −45.077 | −34.653 | 1.00 | 44.33 | MOL1 | C |
| ATOM | 2587 | O | TRP | B | 115 | 56.209 | −44.188 | −34.870 | 1.00 | 47.44 | MOL1 | O |
| ATOM | 2588 | N | GLY | B | 116 | 58.306 | −44.820 | −34.376 | 1.00 | 42.65 | MOL1 | N |
| ATOM | 2589 | CA | GLY | B | 116 | 58.788 | −43.451 | −34.384 | 1.00 | 44.00 | MOL1 | C |
| ATOM | 2590 | C | GLY | B | 116 | 59.147 | −43.119 | −35.819 | 1.00 | 47.25 | MOL1 | C |
| ATOM | 2591 | O | GLY | B | 116 | 58.853 | −43.902 | −36.710 | 1.00 | 48.39 | MOL1 | O |

TABLE 1-continued

The atomic coordinates of IL17F in complex with 496 Fab
(H32; a = 189.4; b = 189.4; c = 490.9, α, β = 90°; γ = 120°)

| ATOM | 2592 | N | GLN | B | 117 | 59.763 | −41.973 | −36.075 | 1.00 | 53.34 | MOL1 | N |
|------|------|-----|-----|---|-----|--------|---------|---------|------|-------|------|---|
| ATOM | 2593 | CA | GLN | B | 117 | 60.145 | −41.652 | −37.449 | 1.00 | 55.82 | MOL1 | C |
| ATOM | 2594 | CB | GLN | B | 117 | 60.268 | −40.147 | −37.671 | 1.00 | 63.13 | MOL1 | C |
| ATOM | 2595 | CG | GLN | B | 117 | 61.399 | −39.485 | −36.898 | 1.00 | 80.29 | MOL1 | C |
| ATOM | 2596 | CD | GLN | B | 117 | 61.066 | −39.298 | −35.429 | 1.00 | 90.29 | MOL1 | C |
| ATOM | 2597 | OE1 | GLN | B | 117 | 60.009 | −38.752 | −35.086 | 1.00 | 91.75 | MOL1 | O |
| ATOM | 2598 | NE2 | GLN | B | 117 | 61.968 | −39.739 | −34.551 | 1.00 | 90.06 | MOL1 | N |
| ATOM | 2599 | C | GLN | B | 117 | 61.490 | −42.306 | −37.710 | 1.00 | 52.56 | MOL1 | C |
| ATOM | 2600 | O | GLN | B | 117 | 61.863 | −42.539 | −38.852 | 1.00 | 53.79 | MOL1 | O |
| ATOM | 2601 | N | GLY | B | 118 | 62.212 | −42.596 | −36.632 | 1.00 | 52.43 | MOL1 | N |
| ATOM | 2602 | CA | GLY | B | 118 | 63.508 | −43.246 | −36.736 | 1.00 | 53.65 | MOL1 | C |
| ATOM | 2603 | C | GLY | B | 118 | 64.687 | −42.320 | −36.967 | 1.00 | 52.41 | MOL1 | C |
| ATOM | 2604 | O | GLY | B | 118 | 64.507 | −41.207 | −37.462 | 1.00 | 54.86 | MOL1 | O |
| ATOM | 2605 | N | THR | B | 119 | 65.884 | −42.769 | −36.579 | 1.00 | 49.15 | MOL1 | N |
| ATOM | 2606 | CA | THR | B | 119 | 67.110 | −41.997 | −36.793 | 1.00 | 49.60 | MOL1 | C |
| ATOM | 2607 | CB | THR | B | 119 | 67.827 | −41.574 | −35.514 | 1.00 | 49.83 | MOL1 | C |
| ATOM | 2608 | OG1 | THR | B | 119 | 67.548 | −42.508 | −34.471 | 1.00 | 53.93 | MOL1 | O |
| ATOM | 2609 | CG2 | THR | B | 119 | 67.453 | −40.166 | −35.136 | 1.00 | 53.96 | MOL1 | C |
| ATOM | 2610 | C | THR | B | 119 | 68.119 | −42.816 | −37.554 | 1.00 | 50.51 | MOL1 | C |
| ATOM | 2611 | O | THR | B | 119 | 68.283 | −44.019 | −37.318 | 1.00 | 47.34 | MOL1 | O |
| ATOM | 2612 | N | LEU | B | 120 | 68.825 | −42.131 | −38.442 | 1.00 | 48.83 | MOL1 | N |
| ATOM | 2613 | CA | LEU | B | 120 | 69.820 | −42.761 | −39.274 | 0.50 | 49.21 | MOL1 | C |
| ATOM | 2614 | CB | LEU | B | 120 | 70.031 | −41.891 | −40.498 | 1.00 | 48.65 | MOL1 | C |
| ATOM | 2615 | CG | LEU | B | 120 | 71.120 | −42.347 | −41.453 | 1.00 | 46.65 | MOL1 | C |
| ATOM | 2616 | CD1 | LEU | B | 120 | 71.069 | −43.865 | −41.702 | 1.00 | 30.50 | MOL1 | C |
| ATOM | 2617 | CD2 | LEU | B | 120 | 70.940 | −41.538 | −42.727 | 1.00 | 53.75 | MOL1 | C |
| ATOM | 2618 | C | LEU | B | 120 | 71.137 | −42.968 | −38.554 | 1.00 | 46.13 | MOL1 | C |
| ATOM | 2619 | O | LEU | B | 120 | 71.641 | −42.058 | −37.916 | 1.00 | 48.24 | MOL1 | O |
| ATOM | 2620 | N | VAL | B | 121 | 71.696 | −44.164 | −38.670 | 1.00 | 44.98 | MOL1 | N |
| ATOM | 2621 | CA | VAL | B | 121 | 72.966 | −44.463 | −38.034 | 1.00 | 51.17 | MOL1 | C |
| ATOM | 2622 | CB | VAL | B | 121 | 72.765 | −45.379 | −36.821 | 1.00 | 51.60 | MOL1 | C |
| ATOM | 2623 | CG1 | VAL | B | 121 | 74.104 | −45.701 | −36.172 | 1.00 | 40.79 | MOL1 | C |
| ATOM | 2624 | CG2 | VAL | B | 121 | 71.847 | −44.700 | −35.836 | 1.00 | 49.63 | MOL1 | C |
| ATOM | 2625 | C | VAL | B | 121 | 73.879 | −45.136 | −39.046 | 1.00 | 56.48 | MOL1 | C |
| ATOM | 2626 | O | VAL | B | 121 | 73.668 | −46.300 | −39.410 | 1.00 | 58.82 | MOL1 | O |
| ATOM | 2627 | N | THR | B | 122 | 74.890 | −44.396 | −39.503 | 1.00 | 59.17 | MOL1 | N |
| ATOM | 2628 | CA | THR | B | 122 | 75.838 | −44.905 | −40.497 | 1.00 | 61.81 | MOL1 | C |
| ATOM | 2629 | CB | THR | B | 122 | 75.924 | −43.949 | −41.736 | 1.00 | 52.31 | MOL1 | C |
| ATOM | 2630 | OG1 | THR | B | 122 | 75.576 | −42.622 | −41.342 | 1.00 | 46.25 | MOL1 | O |
| ATOM | 2631 | CG2 | THR | B | 122 | 74.970 | −44.378 | −42.848 | 1.00 | 52.37 | MOL1 | C |
| ATOM | 2632 | C | THR | B | 122 | 77.259 | −45.152 | −39.970 | 1.00 | 67.95 | MOL1 | C |
| ATOM | 2633 | O | THR | B | 122 | 78.011 | −44.216 | −39.694 | 1.00 | 72.78 | MOL1 | O |
| ATOM | 2634 | N | VAL | B | 123 | 77.617 | −46.423 | −39.836 | 1.00 | 71.58 | MOL1 | N |
| ATOM | 2635 | CA | VAL | B | 123 | 78.941 | −46.804 | −39.378 | 1.00 | 76.99 | MOL1 | C |
| ATOM | 2636 | CB | VAL | B | 123 | 78.872 | −48.098 | −38.544 | 1.00 | 75.96 | MOL1 | C |
| ATOM | 2637 | CG1 | VAL | B | 123 | 78.099 | −49.149 | −39.286 | 1.00 | 86.41 | MOL1 | C |
| ATOM | 2638 | CG2 | VAL | B | 123 | 80.254 | −48.607 | −38.261 | 1.00 | 84.18 | MOL1 | C |
| ATOM | 2639 | C | VAL | B | 123 | 79.872 | −46.995 | −40.592 | 1.00 | 81.61 | MOL1 | C |
| ATOM | 2640 | O | VAL | B | 123 | 79.843 | −48.030 | −41.269 | 1.00 | 81.81 | MOL1 | O |
| ATOM | 2641 | N | SER | B | 124 | 80.685 | −45.974 | −40.865 | 1.00 | 86.73 | MOL1 | N |
| ATOM | 2642 | CA | SER | B | 124 | 81.627 | −45.986 | −41.986 | 1.00 | 90.91 | MOL1 | C |
| ATOM | 2643 | CB | SER | B | 124 | 81.040 | −45.209 | −43.173 | 1.00 | 94.67 | MOL1 | C |
| ATOM | 2644 | OG | SER | B | 124 | 81.931 | −45.159 | −44.277 | 1.00 | 93.43 | MOL1 | O |
| ATOM | 2645 | C | SER | B | 124 | 82.956 | −45.355 | −41.572 | 1.00 | 92.08 | MOL1 | C |
| ATOM | 2646 | O | SER | B | 124 | 82.978 | −44.409 | −40.783 | 1.00 | 94.13 | MOL1 | O |
| ATOM | 2647 | N | SER | B | 125 | 84.058 | −45.877 | −42.110 | 1.00 | 90.43 | MOL1 | N |
| ATOM | 2648 | CA | SER | B | 125 | 85.388 | −45.366 | −41.794 | 1.00 | 83.28 | MOL1 | C |
| ATOM | 2649 | CB | SER | B | 125 | 86.423 | −46.486 | −41.903 | 1.00 | 79.81 | MOL1 | C |
| ATOM | 2650 | OG | SER | B | 125 | 86.211 | −47.259 | −43.068 | 1.00 | 85.28 | MOL1 | O |
| ATOM | 2651 | C | SER | B | 125 | 85.782 | −44.194 | −42.681 | 1.00 | 79.66 | MOL1 | C |
| ATOM | 2652 | O | SER | B | 125 | 86.730 | −43.481 | −42.384 | 1.00 | 78.73 | MOL1 | O |
| ATOM | 2653 | N | ALA | B | 126 | 85.044 | −43.990 | −43.763 | 1.00 | 79.96 | MOL1 | N |
| ATOM | 2654 | CA | ALA | B | 126 | 85.318 | −42.887 | −44.675 | 1.00 | 81.43 | MOL1 | C |
| ATOM | 2655 | CB | ALA | B | 126 | 84.326 | −42.895 | −45.809 | 1.00 | 86.30 | MOL1 | C |
| ATOM | 2656 | C | ALA | B | 126 | 85.265 | −41.548 | −43.954 | 1.00 | 81.14 | MOL1 | C |
| ATOM | 2657 | O | ALA | B | 126 | 84.682 | −41.431 | −42.875 | 1.00 | 82.37 | MOL1 | O |
| ATOM | 2658 | N | LYS | B | 127 | 85.859 | −40.535 | −44.573 | 1.00 | 81.98 | MOL1 | N |
| ATOM | 2659 | CA | LYS | B | 127 | 85.926 | −39.206 | −43.983 | 1.00 | 87.15 | MOL1 | C |
| ATOM | 2660 | CB | LYS | B | 127 | 87.391 | −38.794 | −43.795 | 1.00 | 99.20 | MOL1 | C |
| ATOM | 2661 | CG | LYS | B | 127 | 88.340 | −39.923 | −43.332 | 1.00 | 111.33 | MOL1 | C |
| ATOM | 2662 | CD | LYS | B | 127 | 88.734 | −40.877 | −44.484 | 1.00 | 116.04 | MOL1 | C |
| ATOM | 2663 | CE | LYS | B | 127 | 89.702 | −41.978 | −44.023 | 1.00 | 114.55 | MOL1 | C |
| ATOM | 2664 | NZ | LYS | B | 127 | 90.022 | −42.962 | −45.103 | 1.00 | 107.62 | MOL1 | N |
| ATOM | 2665 | C | LYS | B | 127 | 85.243 | −38.193 | −44.871 | 1.00 | 80.91 | MOL1 | C |
| ATOM | 2666 | O | LYS | B | 127 | 85.237 | −38.340 | −46.079 | 1.00 | 79.56 | MOL1 | O |
| ATOM | 2667 | N | THR | B | 128 | 84.683 | −37.155 | −44.267 | 1.00 | 79.13 | MOL1 | N |
| ATOM | 2668 | CA | THR | B | 128 | 83.999 | −36.115 | −45.026 | 1.00 | 80.44 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 2669 | CB | THR | B | 128 | 83.662 | −34.900 | −44.123 | 1.00 | 87.75 | MOL1 | C |
|---|---|---|---|---|---|---|---|---|---|---|---|---|
| ATOM | 2670 | OG1 | THR | B | 128 | 83.157 | −33.824 | −44.930 | 1.00 | 91.00 | MOL1 | O |
| ATOM | 2671 | CG2 | THR | B | 128 | 84.906 | −34.433 | −43.354 | 1.00 | 95.92 | MOL1 | C |
| ATOM | 2672 | C | THR | B | 128 | 84.809 | −35.622 | −46.228 | 1.00 | 73.65 | MOL1 | C |
| ATOM | 2673 | O | THR | B | 128 | 85.880 | −35.041 | −46.066 | 1.00 | 73.18 | MOL1 | O |
| ATOM | 2674 | N | THR | B | 129 | 84.277 | −35.852 | −47.428 | 1.00 | 67.55 | MOL1 | N |
| ATOM | 2675 | CA | THR | B | 129 | 84.915 | −35.451 | −48.687 | 1.00 | 63.55 | MOL1 | C |
| ATOM | 2676 | CB | THR | B | 129 | 85.295 | −36.655 | −49.546 | 1.00 | 55.93 | MOL1 | C |
| ATOM | 2677 | OG1 | THR | B | 129 | 86.154 | −37.538 | −48.824 | 1.00 | 47.85 | MOL1 | O |
| ATOM | 2678 | CG2 | THR | B | 129 | 85.970 | −36.184 | −50.808 | 1.00 | 52.38 | MOL1 | C |
| ATOM | 2679 | C | THR | B | 129 | 83.945 | −34.681 | −49.578 | 1.00 | 69.74 | MOL1 | C |
| ATOM | 2680 | O | THR | B | 129 | 82.822 | −35.132 | −49.801 | 1.00 | 72.74 | MOL1 | O |
| ATOM | 2681 | N | PRO | B | 130 | 84.365 | −33.534 | −50.135 | 1.00 | 71.79 | MOL1 | N |
| ATOM | 2682 | CD | PRO | B | 130 | 85.698 | −32.910 | −50.191 | 1.00 | 69.95 | MOL1 | C |
| ATOM | 2683 | CA | PRO | B | 130 | 83.422 | −32.813 | −50.994 | 1.00 | 74.26 | MOL1 | C |
| ATOM | 2684 | CB | PRO | B | 130 | 84.089 | −31.461 | −51.166 | 1.00 | 71.83 | MOL1 | C |
| ATOM | 2685 | CG | PRO | B | 130 | 85.521 | −31.858 | −51.298 | 1.00 | 71.38 | MOL1 | C |
| ATOM | 2686 | C | PRO | B | 130 | 83.356 | −33.576 | −52.310 | 1.00 | 75.56 | MOL1 | C |
| ATOM | 2687 | O | PRO | B | 130 | 84.231 | −34.384 | −52.599 | 1.00 | 70.43 | MOL1 | O |
| ATOM | 2688 | N | PRO | B | 131 | 82.327 | −33.319 | −53.130 | 1.00 | 79.47 | MOL1 | N |
| ATOM | 2689 | CD | PRO | B | 131 | 81.168 | −32.449 | −52.863 | 1.00 | 85.88 | MOL1 | C |
| ATOM | 2690 | CA | PRO | B | 131 | 82.155 | −33.989 | −54.414 | 1.00 | 77.67 | MOL1 | C |
| ATOM | 2691 | CB | PRO | B | 131 | 80.657 | −33.953 | −54.607 | 1.00 | 76.78 | MOL1 | C |
| ATOM | 2692 | CG | PRO | B | 131 | 80.355 | −32.572 | −54.162 | 1.00 | 79.89 | MOL1 | C |
| ATOM | 2693 | C | PRO | B | 131 | 82.866 | −33.286 | −55.549 | 1.00 | 77.13 | MOL1 | C |
| ATOM | 2694 | O | PRO | B | 131 | 83.061 | −32.072 | −55.528 | 1.00 | 78.86 | MOL1 | O |
| ATOM | 2695 | N | SER | B | 132 | 83.243 | −34.073 | −56.545 | 1.00 | 76.12 | MOL1 | N |
| ATOM | 2696 | CA | SER | B | 132 | 83.907 | −33.569 | −57.736 | 1.00 | 73.56 | MOL1 | C |
| ATOM | 2697 | CB | SER | B | 132 | 85.007 | −34.543 | −58.161 | 1.00 | 73.15 | MOL1 | C |
| ATOM | 2698 | OG | SER | B | 132 | 85.763 | −34.980 | −57.040 | 1.00 | 68.08 | MOL1 | O |
| ATOM | 2699 | C | SER | B | 132 | 82.787 | −33.547 | −58.767 | 1.00 | 69.58 | MOL1 | C |
| ATOM | 2700 | O | SER | B | 132 | 82.091 | −34.534 | −58.938 | 1.00 | 72.95 | MOL1 | O |
| ATOM | 2701 | N | VAL | B | 133 | 82.588 | −32.438 | −59.452 | 1.00 | 63.51 | MOL1 | N |
| ATOM | 2702 | CA | VAL | B | 133 | 81.497 | −32.403 | −60.407 | 1.00 | 60.40 | MOL1 | C |
| ATOM | 2703 | CB | VAL | B | 133 | 80.504 | −31.297 | −60.066 | 1.00 | 63.33 | MOL1 | C |
| ATOM | 2704 | CG1 | VAL | B | 133 | 79.595 | −31.022 | −61.262 | 1.00 | 55.60 | MOL1 | C |
| ATOM | 2705 | CG2 | VAL | B | 133 | 79.703 | −31.696 | −58.852 | 1.00 | 63.03 | MOL1 | C |
| ATOM | 2706 | C | VAL | B | 133 | 81.900 | −32.224 | −61.847 | 1.00 | 61.09 | MOL1 | C |
| ATOM | 2707 | O | VAL | B | 133 | 82.502 | −31.222 | −62.217 | 1.00 | 70.14 | MOL1 | O |
| ATOM | 2708 | N | TYR | B | 134 | 81.548 | −33.196 | −62.669 | 1.00 | 57.45 | MOL1 | N |
| ATOM | 2709 | CA | TYR | B | 134 | 81.873 | −33.138 | −64.084 | 1.00 | 56.17 | MOL1 | C |
| ATOM | 2710 | CB | TYR | B | 134 | 82.598 | −34.411 | −64.514 | 1.00 | 50.84 | MOL1 | C |
| ATOM | 2711 | CG | TYR | B | 134 | 83.717 | −34.851 | −63.598 | 1.00 | 47.52 | MOL1 | C |
| ATOM | 2712 | CD1 | TYR | B | 134 | 84.846 | −34.068 | −63.410 | 1.00 | 53.56 | MOL1 | C |
| ATOM | 2713 | CE1 | TYR | B | 134 | 85.896 | −34.481 | −62.580 | 1.00 | 48.90 | MOL1 | C |
| ATOM | 2714 | CD2 | TYR | B | 134 | 83.656 | −36.059 | −62.937 | 1.00 | 47.93 | MOL1 | C |
| ATOM | 2715 | CE2 | TYR | B | 134 | 84.693 | −36.477 | −62.114 | 1.00 | 53.51 | MOL1 | C |
| ATOM | 2716 | CZ | TYR | B | 134 | 85.812 | −35.685 | −61.939 | 1.00 | 50.11 | MOL1 | C |
| ATOM | 2717 | OH | TYR | B | 134 | 86.847 | −36.114 | −61.130 | 1.00 | 54.69 | MOL1 | O |
| ATOM | 2718 | C | TYR | B | 134 | 80.573 | −33.020 | −64.854 | 1.00 | 57.98 | MOL1 | C |
| ATOM | 2719 | O | TYR | B | 134 | 79.548 | −33.544 | −64.437 | 1.00 | 66.11 | MOL1 | O |
| ATOM | 2720 | N | PRO | B | 135 | 80.602 | −32.350 | −66.002 | 1.00 | 55.25 | MOL1 | N |
| ATOM | 2721 | CD | PRO | B | 135 | 81.773 | −31.604 | −66.474 | 1.00 | 55.20 | MOL1 | C |
| ATOM | 2722 | CA | PRO | B | 135 | 79.462 | −32.118 | −66.886 | 1.00 | 60.31 | MOL1 | C |
| ATOM | 2723 | CB | PRO | B | 135 | 79.797 | −30.778 | −67.489 | 1.00 | 62.52 | MOL1 | C |
| ATOM | 2724 | CG | PRO | B | 135 | 81.253 | −30.947 | −67.754 | 1.00 | 60.17 | MOL1 | C |
| ATOM | 2725 | C | PRO | B | 135 | 79.298 | −33.162 | −67.980 | 1.00 | 61.19 | MOL1 | C |
| ATOM | 2726 | O | PRO | B | 135 | 80.232 | −33.431 | −68.716 | 1.00 | 62.45 | MOL1 | O |
| ATOM | 2727 | N | LEU | B | 136 | 78.113 | −33.739 | −68.109 | 1.00 | 63.16 | MOL1 | N |
| ATOM | 2728 | CA | LEU | B | 136 | 77.899 | −34.718 | −69.164 | 1.00 | 64.19 | MOL1 | C |
| ATOM | 2729 | CB | LEU | B | 136 | 76.916 | −35.804 | −68.735 | 1.00 | 59.59 | MOL1 | C |
| ATOM | 2730 | CG | LEU | B | 136 | 77.425 | −37.016 | −67.963 | 1.00 | 54.68 | MOL1 | C |
| ATOM | 2731 | CD1 | LEU | B | 136 | 78.316 | −36.594 | −66.824 | 1.00 | 51.35 | MOL1 | C |
| ATOM | 2732 | CD2 | LEU | B | 136 | 76.233 | −37.783 | −67.448 | 1.00 | 50.74 | MOL1 | C |
| ATOM | 2733 | C | LEU | B | 136 | 77.348 | −34.011 | −70.387 | 1.00 | 67.26 | MOL1 | C |
| ATOM | 2734 | O | LEU | B | 136 | 76.183 | −33.621 | −70.421 | 1.00 | 67.76 | MOL1 | O |
| ATOM | 2735 | N | ALA | B | 137 | 78.196 | −33.841 | −71.391 | 1.00 | 71.61 | MOL1 | N |
| ATOM | 2736 | CA | ALA | B | 137 | 77.782 | −33.184 | −72.626 | 1.00 | 74.68 | MOL1 | C |
| ATOM | 2737 | CB | ALA | B | 137 | 78.735 | −32.051 | −72.966 | 1.00 | 78.07 | MOL1 | C |
| ATOM | 2738 | C | ALA | B | 137 | 77.775 | −34.205 | −73.744 | 1.00 | 76.08 | MOL1 | C |
| ATOM | 2739 | O | ALA | B | 137 | 78.578 | −35.130 | −73.745 | 1.00 | 79.25 | MOL1 | O |
| ATOM | 2740 | N | PRO | B | 138 | 76.874 | −34.046 | −74.718 | 1.00 | 77.50 | MOL1 | N |
| ATOM | 2741 | CD | PRO | B | 138 | 75.871 | −32.985 | −74.845 | 1.00 | 79.23 | MOL1 | C |
| ATOM | 2742 | CA | PRO | B | 138 | 76.783 | −34.981 | −75.841 | 1.00 | 82.58 | MOL1 | C |
| ATOM | 2743 | CB | PRO | B | 138 | 75.610 | −34.451 | −76.653 | 1.00 | 78.60 | MOL1 | C |
| ATOM | 2744 | CG | PRO | B | 138 | 75.611 | −33.004 | −76.329 | 1.00 | 85.88 | MOL1 | C |
| ATOM | 2745 | C | PRO | B | 138 | 78.048 | −35.128 | −76.659 | 1.00 | 89.70 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 2746 | O | PRO | B | 138 | 79.032 | −34.421 | −76.451 | 1.00 | 90.70 | MOL1 | O |
|---|---|---|---|---|---|---|---|---|---|---|---|---|
| ATOM | 2747 | N | GLY | B | 139 | 78.024 | −36.085 | −77.574 | 1.00 | 98.32 | MOL1 | N |
| ATOM | 2748 | CA | GLY | B | 139 | 79.177 | −36.318 | −78.413 | 1.00 | 113.85 | MOL1 | C |
| ATOM | 2749 | C | GLY | B | 139 | 78.962 | −35.612 | −79.730 | 1.00 | 124.92 | MOL1 | C |
| ATOM | 2750 | O | GLY | B | 139 | 77.951 | −34.928 | −79.916 | 1.00 | 126.20 | MOL1 | O |
| ATOM | 2751 | N | SER | B | 140 | 79.905 | −35.768 | −80.651 | 1.00 | 133.36 | MOL1 | N |
| ATOM | 2752 | CA | SER | B | 140 | 79.789 | −35.132 | −81.953 | 1.00 | 140.03 | MOL1 | C |
| ATOM | 2753 | CB | SER | B | 140 | 81.176 | −34.925 | −82.550 | 1.00 | 140.08 | MOL1 | C |
| ATOM | 2754 | OG | SER | B | 140 | 82.012 | −34.265 | −81.617 | 1.00 | 143.82 | MOL1 | O |
| ATOM | 2755 | C | SER | B | 140 | 78.940 | −35.998 | −82.879 | 1.00 | 145.00 | MOL1 | C |
| ATOM | 2756 | O | SER | B | 140 | 79.256 | −36.157 | −84.058 | 1.00 | 145.81 | MOL1 | O |
| ATOM | 2757 | N | ALA | B | 141 | 77.861 | −36.555 | −82.331 | 1.00 | 150.83 | MOL1 | N |
| ATOM | 2758 | CA | ALA | B | 141 | 76.948 | −37.411 | −83.087 | 1.00 | 154.88 | MOL1 | C |
| ATOM | 2759 | CB | ALA | B | 141 | 76.494 | −38.575 | −82.222 | 1.00 | 155.02 | MOL1 | C |
| ATOM | 2760 | C | ALA | B | 141 | 75.734 | −36.636 | −83.591 | 1.00 | 158.07 | MOL1 | C |
| ATOM | 2761 | O | ALA | B | 141 | 74.611 | −37.145 | −83.580 | 1.00 | 156.84 | MOL1 | O |
| ATOM | 2762 | N | ALA | B | 142 | 75.979 | −35.401 | −84.024 | 1.00 | 162.10 | MOL1 | N |
| ATOM | 2763 | CA | ALA | B | 142 | 74.948 | −34.514 | −84.556 | 1.00 | 163.53 | MOL1 | C |
| ATOM | 2764 | CB | ALA | B | 142 | 74.538 | −34.974 | −85.957 | 1.00 | 164.67 | MOL1 | C |
| ATOM | 2765 | C | ALA | B | 142 | 73.711 | −34.363 | −83.671 | 1.00 | 162.99 | MOL1 | C |
| ATOM | 2766 | O | ALA | B | 142 | 73.661 | −34.880 | −82.550 | 1.00 | 161.99 | MOL1 | O |
| ATOM | 2767 | N | GLN | B | 143 | 72.716 | −33.648 | −84.196 | 1.00 | 162.28 | MOL1 | N |
| ATOM | 2768 | CA | GLN | B | 143 | 71.471 | −33.386 | −83.480 | 1.00 | 160.11 | MOL1 | C |
| ATOM | 2769 | CB | GLN | B | 143 | 71.247 | −31.877 | −83.359 | 1.00 | 156.48 | MOL1 | C |
| ATOM | 2770 | CG | GLN | B | 143 | 69.969 | −31.516 | −82.638 | 1.00 | 150.39 | MOL1 | C |
| ATOM | 2771 | CD | GLN | B | 143 | 69.859 | −32.222 | −81.307 | 1.00 | 146.35 | MOL1 | C |
| ATOM | 2772 | OE1 | GLN | B | 143 | 70.743 | −32.106 | −80.459 | 1.00 | 141.00 | MOL1 | O |
| ATOM | 2773 | NE2 | GLN | B | 143 | 68.774 | −32.966 | −81.118 | 1.00 | 145.15 | MOL1 | N |
| ATOM | 2774 | C | GLN | B | 143 | 70.235 | −34.018 | −84.115 | 1.00 | 159.54 | MOL1 | C |
| ATOM | 2775 | O | GLN | B | 143 | 69.692 | −33.505 | −85.095 | 1.00 | 158.40 | MOL1 | O |
| ATOM | 2776 | N | THR | B | 144 | 69.796 | −35.135 | −83.546 | 1.00 | 159.59 | MOL1 | N |
| ATOM | 2777 | CA | THR | B | 144 | 68.609 | −35.826 | −84.032 | 1.00 | 157.12 | MOL1 | C |
| ATOM | 2778 | CB | THR | B | 144 | 68.856 | −37.357 | −84.186 | 1.00 | 155.18 | MOL1 | C |
| ATOM | 2779 | OG1 | THR | B | 144 | 69.976 | −37.584 | −85.055 | 1.00 | 147.12 | MOL1 | O |
| ATOM | 2780 | CG2 | THR | B | 144 | 67.622 | −38.043 | −84.775 | 1.00 | 151.91 | MOL1 | C |
| ATOM | 2781 | C | THR | B | 144 | 67.500 | −35.579 | −83.006 | 1.00 | 156.85 | MOL1 | C |
| ATOM | 2782 | O | THR | B | 144 | 67.773 | −35.375 | −81.817 | 1.00 | 157.41 | MOL1 | O |
| ATOM | 2783 | N | ASN | B | 145 | 66.255 | −35.579 | −83.474 | 1.00 | 153.16 | MOL1 | N |
| ATOM | 2784 | CA | ASN | B | 145 | 65.106 | −35.354 | −82.604 | 1.00 | 147.39 | MOL1 | C |
| ATOM | 2785 | CB | ASN | B | 145 | 65.129 | −36.354 | −81.432 | 1.00 | 151.09 | MOL1 | C |
| ATOM | 2786 | CG | ASN | B | 145 | 63.833 | −36.355 | −80.623 | 1.00 | 153.65 | MOL1 | C |
| ATOM | 2787 | OD1 | ASN | B | 145 | 62.736 | −36.473 | −81.178 | 1.00 | 155.14 | MOL1 | O |
| ATOM | 2788 | ND2 | ASN | B | 145 | 63.960 | −36.238 | −79.304 | 1.00 | 151.49 | MOL1 | N |
| ATOM | 2789 | C | ASN | B | 145 | 65.089 | −33.911 | −82.087 | 1.00 | 139.28 | MOL1 | C |
| ATOM | 2790 | O | ASN | B | 145 | 66.083 | −33.184 | −82.169 | 1.00 | 134.73 | MOL1 | O |
| ATOM | 2791 | N | SER | B | 146 | 63.942 | −33.513 | −81.556 | 1.00 | 130.39 | MOL1 | N |
| ATOM | 2792 | CA | SER | B | 146 | 63.742 | −32.174 | −81.039 | 1.00 | 121.32 | MOL1 | C |
| ATOM | 2793 | CB | SER | B | 146 | 62.252 | −31.872 | −81.046 | 1.00 | 121.39 | MOL1 | C |
| ATOM | 2794 | OG | SER | B | 146 | 61.539 | −32.977 | −80.523 | 1.00 | 119.93 | MOL1 | O |
| ATOM | 2795 | C | SER | B | 146 | 64.287 | −31.963 | −79.638 | 1.00 | 116.49 | MOL1 | C |
| ATOM | 2796 | O | SER | B | 146 | 64.423 | −30.829 | −79.190 | 1.00 | 117.95 | MOL1 | O |
| ATOM | 2797 | N | MET | B | 147 | 64.606 | −33.049 | −78.947 | 1.00 | 109.47 | MOL1 | N |
| ATOM | 2798 | CA | MET | B | 147 | 65.106 | −32.945 | −77.581 | 1.00 | 99.96 | MOL1 | C |
| ATOM | 2799 | CB | MET | B | 147 | 64.206 | −33.771 | −76.668 | 1.00 | 98.20 | MOL1 | C |
| ATOM | 2800 | CG | MET | B | 147 | 62.771 | −33.302 | −76.684 | 1.00 | 91.48 | MOL1 | C |
| ATOM | 2801 | SD | MET | B | 147 | 62.722 | −31.573 | −76.210 | 1.00 | 87.10 | MOL1 | S |
| ATOM | 2802 | CE | MET | B | 147 | 62.533 | −31.694 | −74.406 | 1.00 | 83.70 | MOL1 | C |
| ATOM | 2803 | C | MET | B | 147 | 66.559 | −33.372 | −77.387 | 1.00 | 93.01 | MOL1 | C |
| ATOM | 2804 | O | MET | B | 147 | 67.080 | −34.206 | −78.129 | 1.00 | 93.00 | MOL1 | O |
| ATOM | 2805 | N | VAL | B | 148 | 67.212 | −32.786 | −76.388 | 1.00 | 82.04 | MOL1 | N |
| ATOM | 2806 | CA | VAL | B | 148 | 68.590 | −33.132 | −76.080 | 1.00 | 80.26 | MOL1 | C |
| ATOM | 2807 | CB | VAL | B | 148 | 69.568 | −32.017 | −76.436 | 1.00 | 73.03 | MOL1 | C |
| ATOM | 2808 | CG1 | VAL | B | 148 | 69.355 | −31.586 | −77.857 | 1.00 | 79.27 | MOL1 | C |
| ATOM | 2809 | CG2 | VAL | B | 148 | 69.407 | −30.862 | −75.481 | 1.00 | 74.82 | MOL1 | C |
| ATOM | 2810 | C | VAL | B | 148 | 68.728 | −33.401 | −74.592 | 1.00 | 83.56 | MOL1 | C |
| ATOM | 2811 | O | VAL | B | 148 | 68.186 | −32.669 | −73.762 | 1.00 | 88.38 | MOL1 | O |
| ATOM | 2812 | N | THR | B | 149 | 69.455 | −34.457 | −74.247 | 1.00 | 79.56 | MOL1 | N |
| ATOM | 2813 | CA | THR | B | 149 | 69.642 | −34.792 | −72.845 | 1.00 | 65.55 | MOL1 | C |
| ATOM | 2814 | CB | THR | B | 149 | 69.385 | −36.266 | −72.587 | 1.00 | 57.01 | MOL1 | C |
| ATOM | 2815 | OG1 | THR | B | 149 | 68.077 | −36.610 | −73.051 | 1.00 | 50.89 | MOL1 | O |
| ATOM | 2816 | CG2 | THR | B | 149 | 69.479 | −36.550 | −71.110 | 1.00 | 53.41 | MOL1 | C |
| ATOM | 2817 | C | THR | B | 149 | 71.048 | −34.477 | −72.394 | 1.00 | 60.64 | MOL1 | C |
| ATOM | 2818 | O | THR | B | 149 | 72.009 | −34.912 | −73.003 | 1.00 | 63.37 | MOL1 | O |
| ATOM | 2819 | N | LEU | B | 150 | 71.156 | −33.698 | −71.331 | 1.00 | 57.09 | MOL1 | N |
| ATOM | 2820 | CA | LEU | B | 150 | 72.446 | −33.320 | −70.776 | 1.00 | 56.17 | MOL1 | C |
| ATOM | 2821 | CB | LEU | B | 150 | 72.576 | −31.801 | −70.667 | 1.00 | 51.09 | MOL1 | C |
| ATOM | 2822 | CG | LEU | B | 150 | 72.751 | −31.001 | −71.961 | 1.00 | 48.86 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 2823 | CD1 | LEU | B | 150 | 72.505 | −31.870 | −73.200 | 1.00 | 42.57 | MOL1 | C |
|------|------|-----|-----|---|-----|--------|---------|---------|------|-------|------|---|
| ATOM | 2824 | CD2 | LEU | B | 150 | 71.794 | −29.820 | −71.914 | 1.00 | 45.75 | MOL1 | C |
| ATOM | 2825 | C   | LEU | B | 150 | 72.550 | −33.936 | −69.402 | 1.00 | 56.81 | MOL1 | C |
| ATOM | 2826 | O   | LEU | B | 150 | 71.550 | −34.351 | −68.825 | 1.00 | 56.89 | MOL1 | O |
| ATOM | 2827 | N   | GLY | B | 151 | 73.758 | −33.992 | −68.867 | 1.00 | 57.09 | MOL1 | N |
| ATOM | 2828 | CA  | GLY | B | 151 | 73.912 | −34.609 | −67.569 | 1.00 | 61.99 | MOL1 | C |
| ATOM | 2829 | C   | GLY | B | 151 | 74.929 | −33.945 | −66.687 | 1.00 | 62.66 | MOL1 | C |
| ATOM | 2830 | O   | GLY | B | 151 | 75.595 | −32.999 | −67.085 | 1.00 | 67.22 | MOL1 | O |
| ATOM | 2831 | N   | CYS | B | 152 | 75.059 | −34.462 | −65.478 | 1.00 | 59.76 | MOL1 | N |
| ATOM | 2832 | CA  | CYS | B | 152 | 75.987 | −33.897 | −64.547 | 1.00 | 60.32 | MOL1 | C |
| ATOM | 2833 | C   | CYS | B | 152 | 76.411 | −34.971 | −63.561 | 1.00 | 59.67 | MOL1 | C |
| ATOM | 2834 | O   | CYS | B | 152 | 75.625 | −35.381 | −62.715 | 1.00 | 62.50 | MOL1 | O |
| ATOM | 2835 | CB  | CYS | B | 152 | 75.304 | −32.742 | −63.842 | 1.00 | 66.12 | MOL1 | C |
| ATOM | 2836 | SG  | CYS | B | 152 | 76.409 | −31.855 | −62.723 | 1.00 | 92.70 | MOL1 | S |
| ATOM | 2837 | N   | LEU | B | 153 | 77.655 | −35.432 | −63.677 | 1.00 | 55.92 | MOL1 | N |
| ATOM | 2838 | CA  | LEU | B | 153 | 78.167 | −36.475 | −62.794 | 1.00 | 51.19 | MOL1 | C |
| ATOM | 2839 | CB  | LEU | B | 153 | 79.177 | −37.346 | −63.533 | 1.00 | 46.56 | MOL1 | C |
| ATOM | 2840 | CG  | LEU | B | 153 | 79.817 | −38.482 | −62.739 | 1.00 | 45.38 | MOL1 | C |
| ATOM | 2841 | CD1 | LEU | B | 153 | 78.795 | −39.162 | −61.856 | 1.00 | 45.70 | MOL1 | C |
| ATOM | 2842 | CD2 | LEU | B | 153 | 80.412 | −39.469 | −63.708 | 1.00 | 40.29 | MOL1 | C |
| ATOM | 2843 | C   | LEU | B | 153 | 78.798 | −35.905 | −61.543 | 1.00 | 48.55 | MOL1 | C |
| ATOM | 2844 | O   | LEU | B | 153 | 79.663 | −35.045 | −61.612 | 1.00 | 53.93 | MOL1 | O |
| ATOM | 2845 | N   | VAL | B | 154 | 78.349 | −36.401 | −60.400 | 1.00 | 47.25 | MOL1 | N |
| ATOM | 2846 | CA  | VAL | B | 154 | 78.826 | −35.965 | −59.098 | 1.00 | 45.87 | MOL1 | C |
| ATOM | 2847 | CB  | VAL | B | 154 | 77.657 | −35.631 | −58.207 | 1.00 | 44.57 | MOL1 | C |
| ATOM | 2848 | CG1 | VAL | B | 154 | 78.155 | −35.068 | −56.905 | 1.00 | 47.69 | MOL1 | C |
| ATOM | 2849 | CG2 | VAL | B | 154 | 76.720 | −34.683 | −58.936 | 1.00 | 41.90 | MOL1 | C |
| ATOM | 2850 | C   | VAL | B | 154 | 79.578 | −37.129 | −58.480 | 1.00 | 50.77 | MOL1 | C |
| ATOM | 2851 | O   | VAL | B | 154 | 78.977 | −38.021 | −57.874 | 1.00 | 52.29 | MOL1 | O |
| ATOM | 2852 | N   | LYS | B | 155 | 80.898 | −37.103 | −58.611 | 1.00 | 51.62 | MOL1 | N |
| ATOM | 2853 | CA  | LYS | B | 155 | 81.726 | −38.187 | −58.128 | 1.00 | 47.10 | MOL1 | C |
| ATOM | 2854 | CB  | LYS | B | 155 | 82.759 | −38.509 | −59.200 | 1.00 | 45.20 | MOL1 | C |
| ATOM | 2855 | CG  | LYS | B | 155 | 82.964 | −39.984 | −59.438 | 1.00 | 48.09 | MOL1 | C |
| ATOM | 2856 | CD  | LYS | B | 155 | 83.884 | −40.241 | −60.616 | 1.00 | 49.66 | MOL1 | C |
| ATOM | 2857 | CE  | LYS | B | 155 | 83.733 | −41.672 | −61.098 | 1.00 | 53.64 | MOL1 | C |
| ATOM | 2858 | NZ  | LYS | B | 155 | 83.873 | −42.644 | −59.971 | 1.00 | 57.44 | MOL1 | N |
| ATOM | 2859 | C   | LYS | B | 155 | 82.416 | −38.002 | −56.791 | 1.00 | 48.90 | MOL1 | C |
| ATOM | 2860 | O   | LYS | B | 155 | 82.639 | −36.886 | −56.327 | 1.00 | 46.39 | MOL1 | O |
| ATOM | 2861 | N   | GLY | B | 156 | 82.741 | −39.140 | −56.189 | 1.00 | 55.33 | MOL1 | N |
| ATOM | 2862 | CA  | GLY | B | 156 | 83.435 | −39.204 | −54.912 | 1.00 | 65.86 | MOL1 | C |
| ATOM | 2863 | C   | GLY | B | 156 | 83.200 | −38.166 | −53.833 | 1.00 | 69.92 | MOL1 | C |
| ATOM | 2864 | O   | GLY | B | 156 | 84.041 | −37.293 | −53.618 | 1.00 | 77.50 | MOL1 | O |
| ATOM | 2865 | N   | TYR | B | 157 | 82.068 | −38.264 | −53.142 | 1.00 | 70.11 | MOL1 | N |
| ATOM | 2866 | CA  | TYR | B | 157 | 81.761 | −37.336 | −52.063 | 1.00 | 64.80 | MOL1 | C |
| ATOM | 2867 | CB  | TYR | B | 157 | 80.689 | −36.337 | −52.476 | 1.00 | 59.00 | MOL1 | C |
| ATOM | 2868 | CG  | TYR | B | 157 | 79.327 | −36.949 | −52.703 | 1.00 | 56.79 | MOL1 | C |
| ATOM | 2869 | CD1 | TYR | B | 157 | 78.771 | −37.001 | −53.974 | 1.00 | 54.06 | MOL1 | C |
| ATOM | 2870 | CE1 | TYR | B | 157 | 77.503 | −37.508 | −54.172 | 1.00 | 57.42 | MOL1 | C |
| ATOM | 2871 | CD2 | TYR | B | 157 | 78.574 | −37.433 | −51.636 | 1.00 | 53.29 | MOL1 | C |
| ATOM | 2872 | CE2 | TYR | B | 157 | 77.309 | −37.942 | −51.826 | 1.00 | 53.49 | MOL1 | C |
| ATOM | 2873 | CZ  | TYR | B | 157 | 76.775 | −37.974 | −53.093 | 1.00 | 54.99 | MOL1 | C |
| ATOM | 2874 | OH  | TYR | B | 157 | 75.499 | −38.445 | −53.273 | 1.00 | 54.48 | MOL1 | O |
| ATOM | 2875 | C   | TYR | B | 157 | 81.267 | −38.141 | −50.886 | 1.00 | 63.04 | MOL1 | C |
| ATOM | 2876 | O   | TYR | B | 157 | 80.821 | −39.272 | −51.039 | 1.00 | 59.06 | MOL1 | O |
| ATOM | 2877 | N   | PHE | B | 158 | 81.346 | −37.548 | −49.708 | 1.00 | 69.10 | MOL1 | N |
| ATOM | 2878 | CA  | PHE | B | 158 | 80.910 | −38.216 | −48.493 | 1.00 | 74.39 | MOL1 | C |
| ATOM | 2879 | CB  | PHE | B | 158 | 81.953 | −39.236 | −48.058 | 1.00 | 65.26 | MOL1 | C |
| ATOM | 2880 | CG  | PHE | B | 158 | 81.537 | −40.048 | −46.880 | 1.00 | 64.19 | MOL1 | C |
| ATOM | 2881 | CD1 | PHE | B | 158 | 81.138 | −41.366 | −47.036 | 1.00 | 72.15 | MOL1 | C |
| ATOM | 2882 | CD2 | PHE | B | 158 | 81.528 | −39.500 | −45.619 | 1.00 | 57.90 | MOL1 | C |
| ATOM | 2883 | CE1 | PHE | B | 158 | 80.736 | −42.127 | −45.947 | 1.00 | 68.39 | MOL1 | C |
| ATOM | 2884 | CE2 | PHE | B | 158 | 81.128 | −40.250 | −44.534 | 1.00 | 66.03 | MOL1 | C |
| ATOM | 2885 | CZ  | PHE | B | 158 | 80.732 | −41.566 | −44.698 | 1.00 | 64.34 | MOL1 | C |
| ATOM | 2886 | C   | PHE | B | 158 | 80.699 | −37.205 | −47.372 | 1.00 | 77.11 | MOL1 | C |
| ATOM | 2887 | O   | PHE | B | 158 | 81.484 | −36.273 | −47.214 | 1.00 | 76.37 | MOL1 | O |
| ATOM | 2888 | N   | PRO | B | 159 | 79.621 | −37.374 | −46.593 | 1.00 | 79.21 | MOL1 | N |
| ATOM | 2889 | CD  | PRO | B | 159 | 79.436 | −36.783 | −45.258 | 1.00 | 82.61 | MOL1 | C |
| ATOM | 2890 | CA  | PRO | B | 159 | 78.670 | −38.466 | −46.792 | 1.00 | 81.88 | MOL1 | C |
| ATOM | 2891 | CB  | PRO | B | 159 | 78.413 | −38.939 | −45.377 | 1.00 | 79.81 | MOL1 | C |
| ATOM | 2892 | CG  | PRO | B | 159 | 78.304 | −37.633 | −44.661 | 1.00 | 83.36 | MOL1 | C |
| ATOM | 2893 | C   | PRO | B | 159 | 77.401 | −37.925 | −47.440 | 1.00 | 83.67 | MOL1 | C |
| ATOM | 2894 | O   | PRO | B | 159 | 77.364 | −36.787 | −47.913 | 1.00 | 79.92 | MOL1 | O |
| ATOM | 2895 | N   | GLU | B | 160 | 76.361 | −38.748 | −47.469 | 1.00 | 84.54 | MOL1 | N |
| ATOM | 2896 | CA  | GLU | B | 160 | 75.104 | −38.307 | −48.032 | 1.00 | 83.10 | MOL1 | C |
| ATOM | 2897 | CB  | GLU | B | 160 | 74.082 | −39.444 | −47.971 | 1.00 | 85.56 | MOL1 | C |
| ATOM | 2898 | CG  | GLU | B | 160 | 74.270 | −40.523 | −49.046 | 1.00 | 82.66 | MOL1 | C |
| ATOM | 2899 | CD  | GLU | B | 160 | 73.359 | −40.326 | −50.260 | 1.00 | 85.85 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 2900 | OE1 | GLU | B | 160 | 73.429 | −39.260 | −50.926 | 1.00 | 75.99 | MOL1 | O |
|------|------|-----|-----|---|-----|--------|---------|---------|------|-------|------|---|
| ATOM | 2901 | OE2 | GLU | B | 160 | 72.565 | −41.251 | −50.541 | 1.00 | 87.30 | MOL1 | O |
| ATOM | 2902 | C   | GLU | B | 160 | 74.687 | −37.133 | −47.156 | 1.00 | 83.85 | MOL1 | C |
| ATOM | 2903 | O   | GLU | B | 160 | 75.079 | −37.043 | −46.002 | 1.00 | 91.45 | MOL1 | O |
| ATOM | 2904 | N   | PRO | B | 161 | 73.876 | −36.225 | −47.687 | 1.00 | 84.59 | MOL1 | N |
| ATOM | 2905 | CD  | PRO | B | 161 | 73.067 | −35.272 | −46.909 | 1.00 | 87.46 | MOL1 | C |
| ATOM | 2906 | CA  | PRO | B | 161 | 73.371 | −36.300 | −49.047 | 1.00 | 89.94 | MOL1 | C |
| ATOM | 2907 | CB  | PRO | B | 161 | 71.877 | −36.223 | −48.826 | 1.00 | 94.06 | MOL1 | C |
| ATOM | 2908 | CG  | PRO | B | 161 | 71.822 | −35.061 | −47.816 | 1.00 | 92.06 | MOL1 | C |
| ATOM | 2909 | C   | PRO | B | 161 | 73.854 | −35.095 | −49.828 | 1.00 | 89.06 | MOL1 | C |
| ATOM | 2910 | O   | PRO | B | 161 | 74.339 | −34.119 | −49.257 | 1.00 | 90.78 | MOL1 | O |
| ATOM | 2911 | N   | VAL | B | 162 | 73.706 | −35.170 | −51.140 | 1.00 | 84.16 | MOL1 | N |
| ATOM | 2912 | CA  | VAL | B | 162 | 74.078 | −34.072 | −51.996 | 1.00 | 81.00 | MOL1 | C |
| ATOM | 2913 | CB  | VAL | B | 162 | 75.002 | −34.526 | −53.121 | 1.00 | 79.53 | MOL1 | C |
| ATOM | 2914 | CG1 | VAL | B | 162 | 75.202 | −33.410 | −54.113 | 1.00 | 81.10 | MOL1 | C |
| ATOM | 2915 | CG2 | VAL | B | 162 | 76.316 | −34.922 | −52.553 | 1.00 | 79.59 | MOL1 | C |
| ATOM | 2916 | C   | VAL | B | 162 | 72.760 | −33.631 | −52.583 | 1.00 | 81.88 | MOL1 | C |
| ATOM | 2917 | O   | VAL | B | 162 | 71.836 | −34.439 | −52.701 | 1.00 | 83.89 | MOL1 | O |
| ATOM | 2918 | N   | THR | B | 163 | 72.657 | −32.356 | −52.935 | 1.00 | 79.62 | MOL1 | N |
| ATOM | 2919 | CA  | THR | B | 163 | 71.424 | −31.850 | −53.511 | 1.00 | 83.82 | MOL1 | C |
| ATOM | 2920 | CB  | THR | B | 163 | 70.814 | −30.706 | −52.668 | 1.00 | 88.23 | MOL1 | C |
| ATOM | 2921 | OG1 | THR | B | 163 | 71.513 | −29.485 | −52.941 | 1.00 | 92.89 | MOL1 | O |
| ATOM | 2922 | CG2 | THR | B | 163 | 70.906 | −31.022 | −51.178 | 1.00 | 90.95 | MOL1 | C |
| ATOM | 2923 | C   | THR | B | 163 | 71.715 | −31.297 | −54.890 | 1.00 | 82.59 | MOL1 | C |
| ATOM | 2924 | O   | THR | B | 163 | 72.513 | −30.376 | −55.037 | 1.00 | 83.05 | MOL1 | O |
| ATOM | 2925 | N   | VAL | B | 164 | 71.071 | −31.855 | −55.904 | 1.00 | 82.18 | MOL1 | N |
| ATOM | 2926 | CA  | VAL | B | 164 | 71.288 | −31.372 | −57.252 | 1.00 | 81.58 | MOL1 | C |
| ATOM | 2927 | CB  | VAL | B | 164 | 71.659 | −32.497 | −58.183 | 1.00 | 79.13 | MOL1 | C |
| ATOM | 2928 | CG1 | VAL | B | 164 | 71.828 | −31.964 | −59.589 | 1.00 | 80.19 | MOL1 | C |
| ATOM | 2929 | CG2 | VAL | B | 164 | 72.927 | −33.140 | −57.694 | 1.00 | 81.90 | MOL1 | C |
| ATOM | 2930 | C   | VAL | B | 164 | 70.059 | −30.683 | −57.793 | 1.00 | 85.73 | MOL1 | C |
| ATOM | 2931 | O   | VAL | B | 164 | 68.930 | −31.037 | −57.445 | 1.00 | 90.71 | MOL1 | O |
| ATOM | 2932 | N   | THR | B | 165 | 70.293 | −29.690 | −58.646 | 1.00 | 85.71 | MOL1 | N |
| ATOM | 2933 | CA  | THR | B | 165 | 69.223 | −28.911 | −59.254 | 1.00 | 86.99 | MOL1 | C |
| ATOM | 2934 | CB  | THR | B | 165 | 68.794 | −27.760 | −58.365 | 1.00 | 84.35 | MOL1 | C |
| ATOM | 2935 | OG1 | THR | B | 165 | 68.662 | −26.588 | −59.174 | 1.00 | 86.68 | MOL1 | O |
| ATOM | 2936 | CG2 | THR | B | 165 | 69.826 | −27.504 | −57.282 | 1.00 | 82.83 | MOL1 | C |
| ATOM | 2937 | C   | THR | B | 165 | 69.696 | −28.297 | −60.557 | 1.00 | 87.96 | MOL1 | C |
| ATOM | 2938 | O   | THR | B | 165 | 70.889 | −28.119 | −60.763 | 1.00 | 89.58 | MOL1 | O |
| ATOM | 2939 | N   | TRP | B | 166 | 68.764 | −27.957 | −61.436 | 1.00 | 89.74 | MOL1 | N |
| ATOM | 2940 | CA  | TRP | B | 166 | 69.156 | −27.363 | −62.703 | 1.00 | 95.35 | MOL1 | C |
| ATOM | 2941 | CB  | TRP | B | 166 | 68.700 | −28.246 | −63.870 | 1.00 | 95.27 | MOL1 | C |
| ATOM | 2942 | CG  | TRP | B | 166 | 69.333 | −29.610 | −63.827 | 1.00 | 92.11 | MOL1 | C |
| ATOM | 2943 | CD2 | TRP | B | 166 | 70.536 | −30.013 | −64.481 | 1.00 | 91.36 | MOL1 | C |
| ATOM | 2944 | CE2 | TRP | B | 166 | 70.811 | −31.331 | −64.076 | 1.00 | 90.40 | MOL1 | C |
| ATOM | 2945 | CE3 | TRP | B | 166 | 71.412 | −29.386 | −65.367 | 1.00 | 93.22 | MOL1 | C |
| ATOM | 2946 | CD1 | TRP | B | 166 | 68.934 | −30.675 | −63.077 | 1.00 | 91.33 | MOL1 | C |
| ATOM | 2947 | NE1 | TRP | B | 166 | 69.817 | −31.714 | −63.218 | 1.00 | 88.04 | MOL1 | N |
| ATOM | 2948 | CZ2 | TRP | B | 166 | 71.921 | −32.029 | −64.523 | 1.00 | 94.04 | MOL1 | C |
| ATOM | 2949 | CZ3 | TRP | B | 166 | 72.514 | −30.079 | −65.811 | 1.00 | 92.47 | MOL1 | C |
| ATOM | 2950 | CH2 | TRP | B | 166 | 72.760 | −31.385 | −65.390 | 1.00 | 95.29 | MOL1 | C |
| ATOM | 2951 | C   | TRP | B | 166 | 68.626 | −25.945 | −62.851 | 1.00 | 99.39 | MOL1 | C |
| ATOM | 2952 | O   | TRP | B | 166 | 67.432 | −25.692 | −62.691 | 1.00 | 105.82 | MOL1 | O |
| ATOM | 2953 | N   | ASN | B | 167 | 69.539 | −25.026 | −63.159 | 1.00 | 99.81 | MOL1 | N |
| ATOM | 2954 | CA  | ASN | B | 167 | 69.233 | −23.606 | −63.308 | 1.00 | 98.01 | MOL1 | C |
| ATOM | 2955 | CB  | ASN | B | 167 | 68.418 | −23.362 | −64.586 | 1.00 | 91.86 | MOL1 | C |
| ATOM | 2956 | CG  | ASN | B | 167 | 69.292 | −23.352 | −65.848 | 1.00 | 87.45 | MOL1 | C |
| ATOM | 2957 | OD1 | ASN | B | 167 | 70.279 | −22.622 | −65.929 | 1.00 | 83.06 | MOL1 | O |
| ATOM | 2958 | ND2 | ASN | B | 167 | 68.921 | −24.153 | −66.833 | 1.00 | 86.61 | MOL1 | N |
| ATOM | 2959 | C   | ASN | B | 167 | 68.531 | −23.075 | −62.051 | 1.00 | 97.63 | MOL1 | C |
| ATOM | 2960 | O   | ASN | B | 167 | 67.612 | −22.263 | −62.099 | 1.00 | 95.45 | MOL1 | O |
| ATOM | 2961 | N   | SER | B | 168 | 69.013 | −23.571 | −60.920 | 1.00 | 99.16 | MOL1 | N |
| ATOM | 2962 | CA  | SER | B | 168 | 68.530 | −23.209 | −59.605 | 1.00 | 103.13 | MOL1 | C |
| ATOM | 2963 | CB  | SER | B | 168 | 68.962 | −21.781 | −59.282 | 1.00 | 105.76 | MOL1 | C |
| ATOM | 2964 | OG  | SER | B | 168 | 70.379 | −21.701 | −59.186 | 1.00 | 104.13 | MOL1 | O |
| ATOM | 2965 | C   | SER | B | 168 | 67.034 | −23.389 | −59.391 | 1.00 | 105.80 | MOL1 | C |
| ATOM | 2966 | O   | SER | B | 168 | 66.469 | −22.866 | −58.430 | 1.00 | 112.60 | MOL1 | O |
| ATOM | 2967 | N   | GLY | B | 169 | 66.396 | −24.151 | −60.271 | 1.00 | 103.98 | MOL1 | N |
| ATOM | 2968 | CA  | GLY | B | 169 | 64.975 | −24.395 | −60.122 | 1.00 | 102.24 | MOL1 | C |
| ATOM | 2969 | C   | GLY | B | 169 | 64.203 | −24.118 | −61.390 | 1.00 | 101.31 | MOL1 | C |
| ATOM | 2970 | O   | GLY | B | 169 | 63.037 | −24.491 | −61.506 | 1.00 | 101.78 | MOL1 | O |
| ATOM | 2971 | N   | SER | B | 170 | 64.851 | −23.459 | −62.344 | 1.00 | 100.43 | MOL1 | N |
| ATOM | 2972 | CA  | SER | B | 170 | 64.206 | −23.136 | −63.610 | 1.00 | 103.82 | MOL1 | C |
| ATOM | 2973 | CB  | SER | B | 170 | 65.167 | −22.362 | −64.524 | 1.00 | 105.34 | MOL1 | C |
| ATOM | 2974 | OG  | SER | B | 170 | 65.513 | −21.096 | −63.976 | 1.00 | 106.93 | MOL1 | O |
| ATOM | 2975 | C   | SER | B | 170 | 63.739 | −24.410 | −64.312 | 1.00 | 103.24 | MOL1 | C |
| ATOM | 2976 | O   | SER | B | 170 | 62.668 | −24.447 | −64.916 | 1.00 | 104.85 | MOL1 | O |

TABLE 1-continued

The atomic coordinates of IL17F in complex with 496 Fab
(H32; a = 189.4; b = 189.4; c = 490.9, α, β = 90°; γ = 120°)

| ATOM | 2977 | N | LEU | B | 171 | 64.552 | −25.454 | −64.220 | 1.00 | 101.77 | MOL1 | N |
|---|---|---|---|---|---|---|---|---|---|---|---|---|
| ATOM | 2978 | CA | LEU | B | 171 | 64.245 | −26.737 | −64.838 | 1.00 | 97.44 | MOL1 | C |
| ATOM | 2979 | CB | LEU | B | 171 | 65.469 | −27.234 | −65.596 | 1.00 | 85.50 | MOL1 | C |
| ATOM | 2980 | CG | LEU | B | 171 | 65.734 | −26.597 | −66.954 | 1.00 | 75.09 | MOL1 | C |
| ATOM | 2981 | CD1 | LEU | B | 171 | 65.330 | −25.148 | −66.967 | 1.00 | 81.51 | MOL1 | C |
| ATOM | 2982 | CD2 | LEU | B | 171 | 67.183 | −26.741 | −67.257 | 1.00 | 74.81 | MOL1 | C |
| ATOM | 2983 | C | LEU | B | 171 | 63.859 | −27.751 | −63.774 | 1.00 | 100.19 | MOL1 | C |
| ATOM | 2984 | O | LEU | B | 171 | 64.701 | −28.165 | −62.975 | 1.00 | 99.25 | MOL1 | O |
| ATOM | 2985 | N | SER | B | 172 | 62.593 | −28.153 | −63.756 | 1.00 | 103.78 | MOL1 | N |
| ATOM | 2986 | CA | SER | B | 172 | 62.139 | −29.123 | −62.766 | 1.00 | 111.40 | MOL1 | C |
| ATOM | 2987 | CB | SER | B | 172 | 61.091 | −28.490 | −61.843 | 1.00 | 118.82 | MOL1 | C |
| ATOM | 2988 | OG | SER | B | 172 | 60.013 | −27.933 | −62.582 | 1.00 | 129.27 | MOL1 | O |
| ATOM | 2989 | C | SER | B | 172 | 61.560 | −30.351 | −63.450 | 1.00 | 110.58 | MOL1 | C |
| ATOM | 2990 | O | SER | B | 172 | 61.656 | −31.471 | −62.938 | 1.00 | 109.57 | MOL1 | O |
| ATOM | 2991 | N | SER | B | 173 | 60.966 | −30.128 | −64.615 | 1.00 | 109.96 | MOL1 | N |
| ATOM | 2992 | CA | SER | B | 173 | 60.360 | −31.200 | −65.385 | 1.00 | 110.01 | MOL1 | C |
| ATOM | 2993 | CB | SER | B | 173 | 59.115 | −30.675 | −66.105 | 1.00 | 115.15 | MOL1 | C |
| ATOM | 2994 | OG | SER | B | 173 | 59.278 | −29.312 | −66.472 | 1.00 | 120.73 | MOL1 | O |
| ATOM | 2995 | C | SER | B | 173 | 61.354 | −31.773 | −66.381 | 1.00 | 106.83 | MOL1 | C |
| ATOM | 2996 | O | SER | B | 173 | 62.180 | −31.047 | −66.939 | 1.00 | 106.61 | MOL1 | O |
| ATOM | 2997 | N | GLY | B | 174 | 61.272 | −33.082 | −66.594 | 1.00 | 103.41 | MOL1 | N |
| ATOM | 2998 | CA | GLY | B | 174 | 62.182 | −33.735 | −67.519 | 1.00 | 98.00 | MOL1 | C |
| ATOM | 2999 | C | GLY | B | 174 | 63.556 | −33.909 | −66.902 | 1.00 | 90.42 | MOL1 | C |
| ATOM | 3000 | O | GLY | B | 174 | 64.568 | −34.021 | −67.598 | 1.00 | 90.12 | MOL1 | O |
| ATOM | 3001 | N | VAL | B | 175 | 63.590 | −33.928 | −65.579 | 1.00 | 82.41 | MOL1 | N |
| ATOM | 3002 | CA | VAL | B | 175 | 64.839 | −34.086 | −64.867 | 1.00 | 75.83 | MOL1 | C |
| ATOM | 3003 | CB | VAL | B | 175 | 65.078 | −32.923 | −63.895 | 1.00 | 72.58 | MOL1 | C |
| ATOM | 3004 | CG1 | VAL | B | 175 | 65.923 | −33.385 | −62.725 | 1.00 | 68.11 | MOL1 | C |
| ATOM | 3005 | CG2 | VAL | B | 175 | 65.777 | −31.797 | −64.621 | 1.00 | 69.58 | MOL1 | C |
| ATOM | 3006 | C | VAL | B | 175 | 64.865 | −35.377 | −64.087 | 1.00 | 73.80 | MOL1 | C |
| ATOM | 3007 | O | VAL | B | 175 | 63.891 | −35.744 | −63.435 | 1.00 | 76.99 | MOL1 | O |
| ATOM | 3008 | N | HIS | B | 176 | 65.995 | −36.064 | −64.164 | 1.00 | 69.57 | MOL1 | N |
| ATOM | 3009 | CA | HIS | B | 176 | 66.170 | −37.313 | −63.459 | 1.00 | 63.67 | MOL1 | C |
| ATOM | 3010 | CB | HIS | B | 176 | 66.184 | −38.477 | −64.440 | 1.00 | 59.02 | MOL1 | C |
| ATOM | 3011 | CG | HIS | B | 176 | 64.846 | −38.786 | −65.024 | 1.00 | 54.57 | MOL1 | C |
| ATOM | 3012 | CD2 | HIS | B | 176 | 64.443 | −38.915 | −66.310 | 1.00 | 56.32 | MOL1 | C |
| ATOM | 3013 | ND1 | HIS | B | 176 | 63.741 | −39.040 | −64.245 | 1.00 | 47.59 | MOL1 | N |
| ATOM | 3014 | CE1 | HIS | B | 176 | 62.712 | −39.314 | −65.028 | 1.00 | 57.73 | MOL1 | C |
| ATOM | 3015 | NE2 | HIS | B | 176 | 63.111 | −39.245 | −66.286 | 1.00 | 55.09 | MOL1 | N |
| ATOM | 3016 | C | HIS | B | 176 | 67.473 | −37.301 | −62.687 | 1.00 | 60.01 | MOL1 | C |
| ATOM | 3017 | O | HIS | B | 176 | 68.550 | −37.359 | −63.277 | 1.00 | 63.17 | MOL1 | O |
| ATOM | 3018 | N | THR | B | 177 | 67.377 | −37.199 | −61.369 | 1.00 | 49.33 | MOL1 | N |
| ATOM | 3019 | CA | THR | B | 177 | 68.564 | −37.228 | −60.542 | 1.00 | 44.72 | MOL1 | C |
| ATOM | 3020 | CB | THR | B | 177 | 68.535 | −36.154 | −59.466 | 1.00 | 44.70 | MOL1 | C |
| ATOM | 3021 | OG1 | THR | B | 177 | 68.910 | −34.901 | −60.048 | 1.00 | 47.85 | MOL1 | O |
| ATOM | 3022 | CG2 | THR | B | 177 | 69.493 | −36.513 | −58.319 | 1.00 | 37.69 | MOL1 | C |
| ATOM | 3023 | C | THR | B | 177 | 68.557 | −38.587 | −59.883 | 1.00 | 44.14 | MOL1 | C |
| ATOM | 3024 | O | THR | B | 177 | 67.717 | −38.863 | −59.032 | 1.00 | 48.38 | MOL1 | O |
| ATOM | 3025 | N | PHE | B | 178 | 69.496 | −39.437 | −60.276 | 1.00 | 36.90 | MOL1 | N |
| ATOM | 3026 | CA | PHE | B | 178 | 69.556 | −40.784 | −59.757 | 1.00 | 35.45 | MOL1 | C |
| ATOM | 3027 | CB | PHE | B | 178 | 70.324 | −41.622 | −60.749 | 1.00 | 34.29 | MOL1 | C |
| ATOM | 3028 | CG | PHE | B | 178 | 69.831 | −41.470 | −62.154 | 1.00 | 34.63 | MOL1 | C |
| ATOM | 3029 | CD1 | PHE | B | 178 | 68.988 | −42.419 | −62.722 | 1.00 | 41.22 | MOL1 | C |
| ATOM | 3030 | CD2 | PHE | B | 178 | 70.168 | −40.363 | −62.898 | 1.00 | 31.17 | MOL1 | C |
| ATOM | 3031 | CE1 | PHE | B | 178 | 68.489 | −42.261 | −64.007 | 1.00 | 31.40 | MOL1 | C |
| ATOM | 3032 | CE2 | PHE | B | 178 | 69.671 | −40.200 | −64.187 | 1.00 | 36.21 | MOL1 | C |
| ATOM | 3033 | CZ | PHE | B | 178 | 68.834 | −41.147 | −64.735 | 1.00 | 34.22 | MOL1 | C |
| ATOM | 3034 | C | PHE | B | 178 | 70.133 | −40.938 | −58.361 | 1.00 | 38.82 | MOL1 | C |
| ATOM | 3035 | O | PHE | B | 178 | 70.817 | −40.066 | −57.844 | 1.00 | 41.93 | MOL1 | O |
| ATOM | 3036 | N | PRO | B | 179 | 69.823 | −42.053 | −57.717 | 1.00 | 39.92 | MOL1 | N |
| ATOM | 3037 | CD | PRO | B | 179 | 68.718 | −42.912 | −58.147 | 1.00 | 42.26 | MOL1 | C |
| ATOM | 3038 | CA | PRO | B | 179 | 70.266 | −42.412 | −56.374 | 1.00 | 47.21 | MOL1 | C |
| ATOM | 3039 | CB | PRO | B | 179 | 69.563 | −43.732 | −56.129 | 1.00 | 46.52 | MOL1 | C |
| ATOM | 3040 | CG | PRO | B | 179 | 68.292 | −43.536 | −56.842 | 1.00 | 52.05 | MOL1 | C |
| ATOM | 3041 | C | PRO | B | 179 | 71.763 | −42.577 | −56.319 | 1.00 | 55.33 | MOL1 | C |
| ATOM | 3042 | O | PRO | B | 179 | 72.362 | −43.179 | −57.207 | 1.00 | 63.13 | MOL1 | O |
| ATOM | 3043 | N | ALA | B | 180 | 72.374 | −42.053 | −55.270 | 1.00 | 61.91 | MOL1 | N |
| ATOM | 3044 | CA | ALA | B | 180 | 73.815 | −42.181 | −55.123 | 1.00 | 66.51 | MOL1 | C |
| ATOM | 3045 | CB | ALA | B | 180 | 74.289 | −41.361 | −53.931 | 1.00 | 67.83 | MOL1 | C |
| ATOM | 3046 | C | ALA | B | 180 | 74.169 | −43.653 | −54.925 | 1.00 | 65.38 | MOL1 | C |
| ATOM | 3047 | O | ALA | B | 180 | 73.400 | −44.417 | −54.350 | 1.00 | 64.94 | MOL1 | O |
| ATOM | 3048 | N | VAL | B | 181 | 75.335 | −44.050 | −55.410 | 1.00 | 64.96 | MOL1 | N |
| ATOM | 3049 | CA | VAL | B | 181 | 75.767 | −45.420 | −55.260 | 1.00 | 65.29 | MOL1 | C |
| ATOM | 3050 | CB | VAL | B | 181 | 75.769 | −46.121 | −56.625 | 1.00 | 61.30 | MOL1 | C |
| ATOM | 3051 | CG1 | VAL | B | 181 | 76.559 | −45.307 | −57.626 | 1.00 | 64.46 | MOL1 | C |
| ATOM | 3052 | CG2 | VAL | B | 181 | 76.329 | −47.508 | −56.486 | 1.00 | 64.55 | MOL1 | C |
| ATOM | 3053 | C | VAL | B | 181 | 77.149 | −45.427 | −54.610 | 1.00 | 66.47 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 3054 | O | VAL | B | 181 | 77.930 | −44.495 | −54.776 | 1.00 | 67.34 | MOL1 | O |
|---|---|---|---|---|---|---|---|---|---|---|---|---|
| ATOM | 3055 | N | LEU | B | 182 | 77.437 | −46.476 | −53.857 | 1.00 | 69.39 | MOL1 | N |
| ATOM | 3056 | CA | LEU | B | 182 | 78.691 | −46.592 | −53.137 | 1.00 | 78.26 | MOL1 | C |
| ATOM | 3057 | CB | LEU | B | 182 | 78.452 | −47.552 | −51.971 | 1.00 | 70.74 | MOL1 | C |
| ATOM | 3058 | CG | LEU | B | 182 | 79.035 | −47.244 | −50.592 | 1.00 | 65.11 | MOL1 | C |
| ATOM | 3059 | CD1 | LEU | B | 182 | 78.896 | −45.782 | −50.266 | 1.00 | 60.40 | MOL1 | C |
| ATOM | 3060 | CD2 | LEU | B | 182 | 78.320 | −48.081 | −49.560 | 1.00 | 60.68 | MOL1 | C |
| ATOM | 3061 | C | LEU | B | 182 | 79.862 | −47.069 | −54.004 | 1.00 | 87.33 | MOL1 | C |
| ATOM | 3062 | O | LEU | B | 182 | 79.929 | −48.242 | −54.360 | 1.00 | 91.59 | MOL1 | O |
| ATOM | 3063 | N | GLN | B | 183 | 80.782 | −46.166 | −54.347 | 1.00 | 95.95 | MOL1 | N |
| ATOM | 3064 | CA | GLN | B | 183 | 81.940 | −46.550 | −55.159 | 1.00 | 103.35 | MOL1 | C |
| ATOM | 3065 | CB | GLN | B | 183 | 82.149 | −45.585 | −56.339 | 1.00 | 105.01 | MOL1 | C |
| ATOM | 3066 | CG | GLN | B | 183 | 82.928 | −46.219 | −57.510 | 1.00 | 108.00 | MOL1 | C |
| ATOM | 3067 | CD | GLN | B | 183 | 83.172 | −45.267 | −58.686 | 1.00 | 107.81 | MOL1 | C |
| ATOM | 3068 | OE1 | GLN | B | 183 | 82.239 | −44.649 | −59.208 | 1.00 | 102.97 | MOL1 | O |
| ATOM | 3069 | NE2 | GLN | B | 183 | 84.433 | −45.161 | −59.114 | 1.00 | 106.13 | MOL1 | N |
| ATOM | 3070 | C | GLN | B | 183 | 83.192 | −46.588 | −54.282 | 1.00 | 107.21 | MOL1 | C |
| ATOM | 3071 | O | GLN | B | 183 | 83.994 | −45.644 | −54.255 | 1.00 | 107.06 | MOL1 | O |
| ATOM | 3072 | N | SER | B | 184 | 83.338 | −47.696 | −53.560 | 1.00 | 108.45 | MOL1 | N |
| ATOM | 3073 | CA | SER | B | 184 | 84.467 | −47.900 | −52.670 | 1.00 | 106.07 | MOL1 | C |
| ATOM | 3074 | CB | SER | B | 184 | 85.754 | −48.042 | −53.491 | 1.00 | 109.58 | MOL1 | C |
| ATOM | 3075 | OG | SER | B | 184 | 85.668 | −49.151 | −54.380 | 1.00 | 107.72 | MOL1 | O |
| ATOM | 3076 | C | SER | B | 184 | 84.577 | −46.756 | −51.664 | 1.00 | 102.55 | MOL1 | C |
| ATOM | 3077 | O | SER | B | 184 | 85.286 | −45.768 | −51.876 | 1.00 | 98.16 | MOL1 | O |
| ATOM | 3078 | N | ASP | B | 185 | 83.833 | −46.908 | −50.576 | 1.00 | 99.87 | MOL1 | N |
| ATOM | 3079 | CA | ASP | B | 185 | 83.800 | −45.945 | −49.489 | 1.00 | 99.99 | MOL1 | C |
| ATOM | 3080 | CB | ASP | B | 185 | 85.049 | −46.132 | −48.633 | 1.00 | 113.23 | MOL1 | C |
| ATOM | 3081 | CG | ASP | B | 185 | 85.294 | −47.599 | −48.287 | 1.00 | 121.20 | MOL1 | C |
| ATOM | 3082 | OD1 | ASP | B | 185 | 84.360 | −48.258 | −47.771 | 1.00 | 123.76 | MOL1 | O |
| ATOM | 3083 | OD2 | ASP | B | 185 | 86.417 | −48.092 | −48.537 | 1.00 | 125.07 | MOL1 | O |
| ATOM | 3084 | C | ASP | B | 185 | 83.642 | −44.500 | −49.939 | 1.00 | 93.27 | MOL1 | C |
| ATOM | 3085 | O | ASP | B | 185 | 84.261 | −43.592 | −49.402 | 1.00 | 91.74 | MOL1 | O |
| ATOM | 3086 | N | LEU | B | 186 | 82.783 | −44.297 | −50.926 | 1.00 | 89.70 | MOL1 | N |
| ATOM | 3087 | CA | LEU | B | 186 | 82.510 | −42.969 | −51.455 | 1.00 | 86.69 | MOL1 | C |
| ATOM | 3088 | CB | LEU | B | 186 | 83.707 | −42.465 | −52.251 | 1.00 | 88.84 | MOL1 | C |
| ATOM | 3089 | CG | LEU | B | 186 | 84.700 | −41.676 | −51.407 | 1.00 | 89.92 | MOL1 | C |
| ATOM | 3090 | CD1 | LEU | B | 186 | 86.042 | −41.580 | −52.110 | 1.00 | 95.15 | MOL1 | C |
| ATOM | 3091 | CD2 | LEU | B | 186 | 84.116 | −40.304 | −51.137 | 1.00 | 92.37 | MOL1 | C |
| ATOM | 3092 | C | LEU | B | 186 | 81.261 | −42.961 | −52.331 | 1.00 | 83.18 | MOL1 | C |
| ATOM | 3093 | O | LEU | B | 186 | 81.013 | −43.903 | −53.083 | 1.00 | 80.46 | MOL1 | O |
| ATOM | 3094 | N | TYR | B | 187 | 80.475 | −41.892 | −52.231 | 1.00 | 79.09 | MOL1 | N |
| ATOM | 3095 | CA | TYR | B | 187 | 79.246 | −41.781 | −53.008 | 1.00 | 71.05 | MOL1 | C |
| ATOM | 3096 | CB | TYR | B | 187 | 78.164 | −41.040 | −52.218 | 1.00 | 61.53 | MOL1 | C |
| ATOM | 3097 | CG | TYR | B | 187 | 77.685 | −41.764 | −50.982 | 1.00 | 57.01 | MOL1 | C |
| ATOM | 3098 | CD1 | TYR | B | 187 | 77.217 | −43.059 | −51.049 | 1.00 | 55.02 | MOL1 | C |
| ATOM | 3099 | CE1 | TYR | B | 187 | 76.772 | −43.715 | −49.925 | 1.00 | 55.39 | MOL1 | C |
| ATOM | 3100 | CD2 | TYR | B | 187 | 77.693 | −41.144 | −49.751 | 1.00 | 61.70 | MOL1 | C |
| ATOM | 3101 | CE2 | TYR | B | 187 | 77.248 | −41.797 | −48.616 | 1.00 | 66.45 | MOL1 | C |
| ATOM | 3102 | CZ | TYR | B | 187 | 76.790 | −43.084 | −48.709 | 1.00 | 63.73 | MOL1 | C |
| ATOM | 3103 | OH | TYR | B | 187 | 76.358 | −43.739 | −47.574 | 1.00 | 69.10 | MOL1 | O |
| ATOM | 3104 | C | TYR | B | 187 | 79.427 | −41.100 | −54.353 | 1.00 | 70.21 | MOL1 | C |
| ATOM | 3105 | O | TYR | B | 187 | 80.110 | −40.085 | −54.474 | 1.00 | 70.77 | MOL1 | O |
| ATOM | 3106 | N | THR | B | 188 | 78.791 | −41.680 | −55.362 | 1.00 | 69.39 | MOL1 | N |
| ATOM | 3107 | CA | THR | B | 188 | 78.835 | −41.170 | −56.723 | 1.00 | 67.27 | MOL1 | C |
| ATOM | 3108 | CB | THR | B | 188 | 79.666 | −42.073 | −57.625 | 1.00 | 69.30 | MOL1 | C |
| ATOM | 3109 | OG1 | THR | B | 188 | 81.015 | −42.117 | −57.148 | 1.00 | 79.26 | MOL1 | O |
| ATOM | 3110 | CG2 | THR | B | 188 | 79.631 | −41.560 | −59.049 | 1.00 | 66.69 | MOL1 | C |
| ATOM | 3111 | C | THR | B | 188 | 77.423 | −41.187 | −57.269 | 1.00 | 63.71 | MOL1 | C |
| ATOM | 3112 | O | THR | B | 188 | 76.751 | −42.216 | −57.202 | 1.00 | 65.03 | MOL1 | O |
| ATOM | 3113 | N | LEU | B | 189 | 76.966 | −40.062 | −57.806 | 1.00 | 54.59 | MOL1 | N |
| ATOM | 3114 | CA | LEU | B | 189 | 75.628 | −40.017 | −58.361 | 1.00 | 49.73 | MOL1 | C |
| ATOM | 3115 | CB | LEU | B | 189 | 74.648 | −39.449 | −57.338 | 1.00 | 42.85 | MOL1 | C |
| ATOM | 3116 | CG | LEU | B | 189 | 74.286 | −37.964 | −57.332 | 1.00 | 45.67 | MOL1 | C |
| ATOM | 3117 | CD1 | LEU | B | 189 | 73.527 | −37.544 | −58.587 | 1.00 | 38.70 | MOL1 | C |
| ATOM | 3118 | CD2 | LEU | B | 189 | 73.423 | −37.721 | −56.134 | 1.00 | 37.05 | MOL1 | C |
| ATOM | 3119 | C | LEU | B | 189 | 75.625 | −39.179 | −59.619 | 1.00 | 50.85 | MOL1 | C |
| ATOM | 3120 | O | LEU | B | 189 | 76.489 | −38.333 | −59.805 | 1.00 | 54.33 | MOL1 | O |
| ATOM | 3121 | N | SER | B | 190 | 74.649 | −39.424 | −60.482 | 1.00 | 52.64 | MOL1 | N |
| ATOM | 3122 | CA | SER | B | 190 | 74.530 | −38.697 | −61.735 | 1.00 | 54.20 | MOL1 | C |
| ATOM | 3123 | CB | SER | B | 190 | 74.757 | −39.646 | −62.900 | 1.00 | 57.86 | MOL1 | C |
| ATOM | 3124 | OG | SER | B | 190 | 73.943 | −40.796 | −62.755 | 1.00 | 67.10 | MOL1 | O |
| ATOM | 3125 | C | SER | B | 190 | 73.143 | −38.105 | −61.849 | 1.00 | 54.39 | MOL1 | C |
| ATOM | 3126 | O | SER | B | 190 | 72.240 | −38.492 | −61.119 | 1.00 | 54.55 | MOL1 | O |
| ATOM | 3127 | N | SER | B | 191 | 72.972 | −37.167 | −62.769 | 1.00 | 55.30 | MOL1 | N |
| ATOM | 3128 | CA | SER | B | 191 | 71.674 | −36.547 | −62.973 | 1.00 | 54.42 | MOL1 | C |
| ATOM | 3129 | CB | SER | B | 191 | 71.467 | −35.389 | −62.014 | 1.00 | 54.05 | MOL1 | C |
| ATOM | 3130 | OG | SER | B | 191 | 70.266 | −34.717 | −62.335 | 1.00 | 58.62 | MOL1 | O |

TABLE 1-continued

The atomic coordinates of IL17F in complex with 496 Fab
(H32; a = 189.4; b = 189.4; c = 490.9, α, β = 90°; γ = 120°)

| ATOM | 3131 | C | SER | B | 191 | 71.542 | −36.039 | −64.387 | 1.00 | 55.25 | MOL1 | C |
|---|---|---|---|---|---|---|---|---|---|---|---|---|
| ATOM | 3132 | O | SER | B | 191 | 72.363 | −35.252 | −64.845 | 1.00 | 55.60 | MOL1 | O |
| ATOM | 3133 | N | SER | B | 192 | 70.503 | −36.496 | −65.075 | 1.00 | 57.49 | MOL1 | N |
| ATOM | 3134 | CA | SER | B | 192 | 70.266 | −36.083 | −66.447 | 1.00 | 61.32 | MOL1 | C |
| ATOM | 3135 | CB | SER | B | 192 | 69.892 | −37.274 | −67.324 | 1.00 | 65.44 | MOL1 | C |
| ATOM | 3136 | OG | SER | B | 192 | 68.551 | −37.665 | −67.081 | 1.00 | 73.00 | MOL1 | O |
| ATOM | 3137 | C | SER | B | 192 | 69.132 | −35.086 | −66.492 | 1.00 | 59.32 | MOL1 | C |
| ATOM | 3138 | O | SER | B | 192 | 68.349 | −34.980 | −65.556 | 1.00 | 58.01 | MOL1 | O |
| ATOM | 3139 | N | VAL | B | 193 | 69.059 | −34.361 | −67.599 | 1.00 | 59.58 | MOL1 | N |
| ATOM | 3140 | CA | VAL | B | 193 | 68.026 | −33.364 | −67.820 | 1.00 | 59.14 | MOL1 | C |
| ATOM | 3141 | CB | VAL | B | 193 | 68.414 | −31.991 | −67.232 | 1.00 | 58.14 | MOL1 | C |
| ATOM | 3142 | CG1 | VAL | B | 193 | 69.794 | −31.566 | −67.710 | 1.00 | 50.78 | MOL1 | C |
| ATOM | 3143 | CG2 | VAL | B | 193 | 67.375 | −30.971 | −67.633 | 1.00 | 54.34 | MOL1 | C |
| ATOM | 3144 | C | VAL | B | 193 | 67.775 | −33.209 | −69.307 | 1.00 | 60.40 | MOL1 | C |
| ATOM | 3145 | O | VAL | B | 193 | 68.679 | −32.894 | −70.076 | 1.00 | 63.83 | MOL1 | O |
| ATOM | 3146 | N | THR | B | 194 | 66.545 | −33.448 | −69.725 | 1.00 | 59.61 | MOL1 | N |
| ATOM | 3147 | CA | THR | B | 194 | 66.239 | −33.325 | −71.133 | 1.00 | 67.96 | MOL1 | C |
| ATOM | 3148 | CB | THR | B | 194 | 65.172 | −34.333 | −71.551 | 1.00 | 68.81 | MOL1 | C |
| ATOM | 3149 | OG1 | THR | B | 194 | 65.509 | −35.610 | −70.996 | 1.00 | 77.62 | MOL1 | O |
| ATOM | 3150 | CG2 | THR | B | 194 | 65.114 | −34.466 | −73.079 | 1.00 | 63.49 | MOL1 | C |
| ATOM | 3151 | C | THR | B | 194 | 65.791 | −31.904 | −71.423 | 1.00 | 73.21 | MOL1 | C |
| ATOM | 3152 | O | THR | B | 194 | 65.368 | −31.179 | −70.527 | 1.00 | 76.10 | MOL1 | O |
| ATOM | 3153 | N | VAL | B | 195 | 65.883 | −31.506 | −72.684 | 1.00 | 76.41 | MOL1 | N |
| ATOM | 3154 | CA | VAL | B | 195 | 65.545 | −30.150 | −73.068 | 1.00 | 74.34 | MOL1 | C |
| ATOM | 3155 | CB | VAL | B | 195 | 66.631 | −29.206 | −72.555 | 1.00 | 66.37 | MOL1 | C |
| ATOM | 3156 | CG1 | VAL | B | 195 | 67.130 | −28.335 | −73.675 | 1.00 | 61.14 | MOL1 | C |
| ATOM | 3157 | CG2 | VAL | B | 195 | 66.110 | −28.397 | −71.401 | 1.00 | 63.66 | MOL1 | C |
| ATOM | 3158 | C | VAL | B | 195 | 65.457 | −30.016 | −74.585 | 1.00 | 81.67 | MOL1 | C |
| ATOM | 3159 | O | VAL | B | 195 | 66.125 | −30.733 | −75.325 | 1.00 | 83.13 | MOL1 | O |
| ATOM | 3160 | N | PRO | B | 196 | 64.634 | −29.081 | −75.066 | 1.00 | 88.47 | MOL1 | N |
| ATOM | 3161 | CD | PRO | B | 196 | 63.774 | −28.181 | −74.282 | 1.00 | 92.03 | MOL1 | C |
| ATOM | 3162 | CA | PRO | B | 196 | 64.462 | −28.854 | −76.506 | 1.00 | 91.83 | MOL1 | C |
| ATOM | 3163 | CB | PRO | B | 196 | 63.408 | −27.750 | −76.561 | 1.00 | 93.80 | MOL1 | C |
| ATOM | 3164 | CG | PRO | B | 196 | 62.659 | −27.902 | −75.253 | 1.00 | 94.40 | MOL1 | C |
| ATOM | 3165 | C | PRO | B | 196 | 65.763 | −28.429 | −77.180 | 1.00 | 94.22 | MOL1 | C |
| ATOM | 3166 | O | PRO | B | 196 | 66.427 | −27.493 | −76.734 | 1.00 | 92.88 | MOL1 | O |
| ATOM | 3167 | N | SER | B | 197 | 66.113 | −29.115 | −78.262 | 1.00 | 97.48 | MOL1 | N |
| ATOM | 3168 | CA | SER | B | 197 | 67.334 | −28.826 | −79.007 | 1.00 | 100.32 | MOL1 | C |
| ATOM | 3169 | CB | SER | B | 197 | 67.385 | −29.693 | −80.272 | 1.00 | 96.90 | MOL1 | C |
| ATOM | 3170 | OG | SER | B | 197 | 66.139 | −29.707 | −80.948 | 1.00 | 94.23 | MOL1 | O |
| ATOM | 3171 | C | SER | B | 197 | 67.478 | −27.356 | −79.377 | 1.00 | 104.09 | MOL1 | C |
| ATOM | 3172 | O | SER | B | 197 | 68.592 | −26.849 | −79.514 | 1.00 | 104.50 | MOL1 | O |
| ATOM | 3173 | N | SER | B | 198 | 66.347 | −26.674 | −79.533 | 1.00 | 109.43 | MOL1 | N |
| ATOM | 3174 | CA | SER | B | 198 | 66.355 | −25.263 | −79.897 | 1.00 | 110.51 | MOL1 | C |
| ATOM | 3175 | CB | SER | B | 198 | 64.976 | −24.833 | −80.411 | 1.00 | 108.99 | MOL1 | C |
| ATOM | 3176 | OG | SER | B | 198 | 63.989 | −24.930 | −79.401 | 1.00 | 111.15 | MOL1 | O |
| ATOM | 3177 | C | SER | B | 198 | 66.780 | −24.372 | −78.733 | 1.00 | 109.23 | MOL1 | C |
| ATOM | 3178 | O | SER | B | 198 | 67.292 | −23.275 | −78.952 | 1.00 | 110.24 | MOL1 | O |
| ATOM | 3179 | N | THR | B | 199 | 66.580 | −24.848 | −77.503 | 1.00 | 108.30 | MOL1 | N |
| ATOM | 3180 | CA | THR | B | 199 | 66.951 | −24.080 | −76.310 | 1.00 | 110.76 | MOL1 | C |
| ATOM | 3181 | CB | THR | B | 199 | 65.942 | −24.276 | −75.138 | 1.00 | 113.30 | MOL1 | C |
| ATOM | 3182 | OG1 | THR | B | 199 | 65.832 | −25.667 | −74.821 | 1.00 | 114.54 | MOL1 | O |
| ATOM | 3183 | CG2 | THR | B | 199 | 64.566 | −23.722 | −75.502 | 1.00 | 118.95 | MOL1 | C |
| ATOM | 3184 | C | THR | B | 199 | 68.343 | −24.413 | −75.769 | 1.00 | 108.82 | MOL1 | C |
| ATOM | 3185 | O | THR | B | 199 | 68.614 | −24.202 | −74.584 | 1.00 | 105.85 | MOL1 | O |
| ATOM | 3186 | N | TRP | B | 200 | 69.208 | −24.946 | −76.633 | 1.00 | 107.48 | MOL1 | N |
| ATOM | 3187 | CA | TRP | B | 200 | 70.586 | −25.292 | −76.269 | 1.00 | 103.53 | MOL1 | C |
| ATOM | 3188 | CB | TRP | B | 200 | 70.656 | −26.539 | −75.387 | 1.00 | 95.81 | MOL1 | C |
| ATOM | 3189 | CG | TRP | B | 200 | 72.013 | −26.735 | −74.724 | 1.00 | 90.49 | MOL1 | C |
| ATOM | 3190 | CD2 | TRP | B | 200 | 73.033 | −27.677 | −75.094 | 1.00 | 86.20 | MOL1 | C |
| ATOM | 3191 | CE2 | TRP | B | 200 | 74.106 | −27.515 | −74.183 | 1.00 | 82.66 | MOL1 | C |
| ATOM | 3192 | CE3 | TRP | B | 200 | 73.144 | −28.641 | −76.103 | 1.00 | 80.27 | MOL1 | C |
| ATOM | 3193 | CD1 | TRP | B | 200 | 72.503 | −26.059 | −73.638 | 1.00 | 91.69 | MOL1 | C |
| ATOM | 3194 | NE1 | TRP | B | 200 | 73.758 | −26.523 | −73.306 | 1.00 | 84.66 | MOL1 | N |
| ATOM | 3195 | CZ2 | TRP | B | 200 | 75.265 | −28.278 | −74.254 | 1.00 | 77.42 | MOL1 | C |
| ATOM | 3196 | CZ3 | TRP | B | 200 | 74.296 | −29.397 | −76.170 | 1.00 | 74.97 | MOL1 | C |
| ATOM | 3197 | CH2 | TRP | B | 200 | 75.341 | −29.213 | −75.252 | 1.00 | 78.91 | MOL1 | C |
| ATOM | 3198 | C | TRP | B | 200 | 71.377 | −25.572 | −77.531 | 1.00 | 106.26 | MOL1 | C |
| ATOM | 3199 | O | TRP | B | 200 | 70.889 | −26.238 | −78.443 | 1.00 | 105.91 | MOL1 | O |
| ATOM | 3200 | N | PRO | B | 201 | 72.622 | −25.080 | −77.597 | 1.00 | 109.15 | MOL1 | N |
| ATOM | 3201 | CD | PRO | B | 201 | 73.557 | −25.484 | −78.659 | 1.00 | 106.75 | MOL1 | C |
| ATOM | 3202 | CA | PRO | B | 201 | 73.313 | −24.290 | −76.566 | 1.00 | 110.89 | MOL1 | C |
| ATOM | 3203 | CB | PRO | B | 201 | 74.772 | −24.323 | −77.019 | 1.00 | 108.78 | MOL1 | C |
| ATOM | 3204 | CG | PRO | B | 201 | 74.846 | −25.553 | −77.912 | 1.00 | 108.54 | MOL1 | C |
| ATOM | 3205 | C | PRO | B | 201 | 72.801 | −22.855 | −76.450 | 1.00 | 114.98 | MOL1 | C |
| ATOM | 3206 | O | PRO | B | 201 | 73.366 | −22.051 | −75.706 | 1.00 | 115.76 | MOL1 | O |
| ATOM | 3207 | N | SER | B | 202 | 71.742 | −22.545 | −77.201 | 1.00 | 117.80 | MOL1 | N |

TABLE 1-continued

The atomic coordinates of IL17F in complex with 496 Fab
(H32; a = 189.4; b = 189.4; c = 490.9, α, β = 90°; γ = 120°)

| ATOM | 3208 | CA | SER | B | 202 | 71.126 | −21.219 | −77.212 | 1.00 | 119.64 | MOL1 | C |
|---|---|---|---|---|---|---|---|---|---|---|---|---|
| ATOM | 3209 | CB | SER | B | 202 | 69.705 | −21.322 | −77.764 | 1.00 | 117.95 | MOL1 | C |
| ATOM | 3210 | OG | SER | B | 202 | 69.691 | −22.078 | −78.964 | 1.00 | 117.45 | MOL1 | O |
| ATOM | 3211 | C | SER | B | 202 | 71.098 | −20.610 | −75.812 | 1.00 | 123.42 | MOL1 | C |
| ATOM | 3212 | O | SER | B | 202 | 71.941 | −19.774 | −75.476 | 1.00 | 126.01 | MOL1 | O |
| ATOM | 3213 | N | GLU | B | 203 | 70.126 | −21.013 | −74.997 | 1.00 | 125.06 | MOL1 | N |
| ATOM | 3214 | CA | GLU | B | 203 | 70.054 | −20.503 | −73.633 | 1.00 | 127.20 | MOL1 | C |
| ATOM | 3215 | CB | GLU | B | 203 | 68.661 | −20.722 | −73.028 | 1.00 | 132.57 | MOL1 | C |
| ATOM | 3216 | CG | GLU | B | 203 | 67.622 | −19.666 | −73.421 | 1.00 | 136.08 | MOL1 | C |
| ATOM | 3217 | CD | GLU | B | 203 | 66.306 | −19.821 | −72.662 | 1.00 | 139.23 | MOL1 | C |
| ATOM | 3218 | OE1 | GLU | B | 203 | 65.553 | −20.785 | −72.933 | 1.00 | 139.00 | MOL1 | O |
| ATOM | 3219 | OE2 | GLU | B | 203 | 66.028 | −18.977 | −71.783 | 1.00 | 141.09 | MOL1 | O |
| ATOM | 3220 | C | GLU | B | 203 | 71.115 | −21.241 | −72.820 | 1.00 | 126.53 | MOL1 | C |
| ATOM | 3221 | O | GLU | B | 203 | 71.971 | −21.915 | −73.389 | 1.00 | 125.59 | MOL1 | O |
| ATOM | 3222 | N | THR | B | 204 | 71.074 | −21.118 | −71.499 | 1.00 | 127.33 | MOL1 | N |
| ATOM | 3223 | CA | THR | B | 204 | 72.072 | −21.792 | −70.672 | 1.00 | 127.07 | MOL1 | C |
| ATOM | 3224 | CB | THR | B | 204 | 72.915 | −20.775 | −69.852 | 1.00 | 131.21 | MOL1 | C |
| ATOM | 3225 | OG1 | THR | B | 204 | 72.050 | −19.947 | −69.060 | 1.00 | 133.18 | MOL1 | O |
| ATOM | 3226 | CG2 | THR | B | 204 | 73.756 | −19.902 | −70.787 | 1.00 | 131.27 | MOL1 | C |
| ATOM | 3227 | C | THR | B | 204 | 71.500 | −22.841 | −69.718 | 1.00 | 124.11 | MOL1 | C |
| ATOM | 3228 | O | THR | B | 204 | 70.357 | −22.739 | −69.254 | 1.00 | 125.30 | MOL1 | O |
| ATOM | 3229 | N | VAL | B | 205 | 72.318 | −23.854 | −69.440 | 1.00 | 116.10 | MOL1 | N |
| ATOM | 3230 | CA | VAL | B | 205 | 71.960 | −24.957 | −68.553 | 1.00 | 105.02 | MOL1 | C |
| ATOM | 3231 | CB | VAL | B | 205 | 71.807 | −26.267 | −69.329 | 1.00 | 98.74 | MOL1 | C |
| ATOM | 3232 | CG1 | VAL | B | 205 | 70.477 | −26.318 | −70.020 | 1.00 | 96.87 | MOL1 | C |
| ATOM | 3233 | CG2 | VAL | B | 205 | 72.917 | −26.371 | −70.356 | 1.00 | 94.57 | MOL1 | C |
| ATOM | 3234 | C | VAL | B | 205 | 73.104 | −25.154 | −67.582 | 1.00 | 100.78 | MOL1 | C |
| ATOM | 3235 | O | VAL | B | 205 | 74.244 | −25.310 | −67.998 | 1.00 | 99.79 | MOL1 | O |
| ATOM | 3236 | N | THR | B | 206 | 72.808 | −25.153 | −66.292 | 1.00 | 97.98 | MOL1 | N |
| ATOM | 3237 | CA | THR | B | 206 | 73.856 | −25.337 | −65.302 | 1.00 | 95.66 | MOL1 | C |
| ATOM | 3238 | CB | THR | B | 206 | 74.294 | −23.992 | −64.699 | 1.00 | 93.03 | MOL1 | C |
| ATOM | 3239 | OG1 | THR | B | 206 | 74.887 | −23.186 | −65.725 | 1.00 | 91.37 | MOL1 | O |
| ATOM | 3240 | CG2 | THR | B | 206 | 75.300 | −24.209 | −63.579 | 1.00 | 90.05 | MOL1 | C |
| ATOM | 3241 | C | THR | B | 206 | 73.459 | −26.281 | −64.174 | 1.00 | 96.57 | MOL1 | C |
| ATOM | 3242 | O | THR | B | 206 | 72.320 | −26.311 | −63.715 | 1.00 | 99.11 | MOL1 | O |
| ATOM | 3243 | N | CYS | B | 207 | 74.432 | −27.059 | −63.739 | 1.00 | 94.81 | MOL1 | N |
| ATOM | 3244 | CA | CYS | B | 207 | 74.249 | −28.023 | −62.679 | 1.00 | 94.38 | MOL1 | C |
| ATOM | 3245 | C | CYS | B | 207 | 74.416 | −27.283 | −61.352 | 1.00 | 95.96 | MOL1 | C |
| ATOM | 3246 | O | CYS | B | 207 | 75.268 | −26.406 | −61.237 | 1.00 | 100.43 | MOL1 | O |
| ATOM | 3247 | CB | CYS | B | 207 | 75.324 | −29.091 | −62.840 | 1.00 | 92.91 | MOL1 | C |
| ATOM | 3248 | SG | CYS | B | 207 | 75.218 | −30.541 | −61.758 | 1.00 | 94.39 | MOL1 | S |
| ATOM | 3249 | N | ASN | B | 208 | 73.610 | −27.619 | −60.352 | 1.00 | 95.58 | MOL1 | N |
| ATOM | 3250 | CA | ASN | B | 208 | 73.728 | −26.957 | −59.054 | 1.00 | 93.33 | MOL1 | C |
| ATOM | 3251 | CB | ASN | B | 208 | 72.493 | −26.112 | −58.762 | 1.00 | 101.23 | MOL1 | C |
| ATOM | 3252 | CG | ASN | B | 208 | 72.342 | −24.967 | −59.729 | 1.00 | 106.59 | MOL1 | C |
| ATOM | 3253 | OD1 | ASN | B | 208 | 73.171 | −24.053 | −59.763 | 1.00 | 108.28 | MOL1 | O |
| ATOM | 3254 | ND2 | ASN | B | 208 | 71.284 | −25.010 | −60.533 | 1.00 | 110.86 | MOL1 | N |
| ATOM | 3255 | C | ASN | B | 208 | 73.920 | −27.963 | −57.946 | 1.00 | 89.80 | MOL1 | C |
| ATOM | 3256 | O | ASN | B | 208 | 72.980 | −28.305 | −57.224 | 1.00 | 93.52 | MOL1 | O |
| ATOM | 3257 | N | VAL | B | 209 | 75.152 | −28.430 | −57.804 | 1.00 | 82.22 | MOL1 | N |
| ATOM | 3258 | CA | VAL | B | 209 | 75.461 | −29.415 | −56.781 | 1.00 | 75.59 | MOL1 | C |
| ATOM | 3259 | CB | VAL | B | 209 | 76.679 | −30.275 | −57.181 | 1.00 | 69.13 | MOL1 | C |
| ATOM | 3260 | CG1 | VAL | B | 209 | 76.822 | −31.430 | −56.224 | 1.00 | 63.09 | MOL1 | C |
| ATOM | 3261 | CG2 | VAL | B | 209 | 76.521 | −30.788 | −58.604 | 1.00 | 61.88 | MOL1 | C |
| ATOM | 3262 | C | VAL | B | 209 | 75.735 | −28.747 | −55.442 | 1.00 | 76.74 | MOL1 | C |
| ATOM | 3263 | O | VAL | B | 209 | 76.397 | −27.715 | −55.377 | 1.00 | 77.01 | MOL1 | O |
| ATOM | 3264 | N | ALA | B | 210 | 75.220 | −29.340 | −54.371 | 1.00 | 78.60 | MOL1 | N |
| ATOM | 3265 | CA | ALA | B | 210 | 75.410 | −28.787 | −53.041 | 1.00 | 77.60 | MOL1 | C |
| ATOM | 3266 | CB | ALA | B | 210 | 74.193 | −27.986 | −52.641 | 1.00 | 80.72 | MOL1 | C |
| ATOM | 3267 | C | ALA | B | 210 | 75.682 | −29.877 | −52.020 | 1.00 | 80.42 | MOL1 | C |
| ATOM | 3268 | O | ALA | B | 210 | 74.932 | −30.850 | −51.914 | 1.00 | 83.39 | MOL1 | O |
| ATOM | 3269 | N | HIS | B | 211 | 76.757 | −29.695 | −51.262 | 1.00 | 83.26 | MOL1 | N |
| ATOM | 3270 | CA | HIS | B | 211 | 77.180 | −30.660 | −50.249 | 1.00 | 89.17 | MOL1 | C |
| ATOM | 3271 | CB | HIS | B | 211 | 78.591 | −31.157 | −50.612 | 1.00 | 80.09 | MOL1 | C |
| ATOM | 3272 | CG | HIS | B | 211 | 79.044 | −32.363 | −49.847 | 1.00 | 74.52 | MOL1 | C |
| ATOM | 3273 | CD2 | HIS | B | 211 | 80.257 | −32.694 | −49.343 | 1.00 | 73.27 | MOL1 | C |
| ATOM | 3274 | ND1 | HIS | B | 211 | 78.215 | −33.427 | −49.565 | 1.00 | 71.41 | MOL1 | N |
| ATOM | 3275 | CE1 | HIS | B | 211 | 78.897 | −34.357 | −48.918 | 1.00 | 67.19 | MOL1 | C |
| ATOM | 3276 | NE2 | HIS | B | 211 | 80.139 | −33.937 | −48.771 | 1.00 | 62.80 | MOL1 | N |
| ATOM | 3277 | C | HIS | B | 211 | 77.166 | −30.039 | −48.844 | 1.00 | 96.03 | MOL1 | C |
| ATOM | 3278 | O | HIS | B | 211 | 78.145 | −29.435 | −48.408 | 1.00 | 93.90 | MOL1 | O |
| ATOM | 3279 | N | PRO | B | 212 | 76.043 | −30.179 | −48.123 | 1.00 | 102.85 | MOL1 | N |
| ATOM | 3280 | CD | PRO | B | 212 | 74.773 | −30.777 | −48.572 | 1.00 | 105.49 | MOL1 | C |
| ATOM | 3281 | CA | PRO | B | 212 | 75.912 | −29.629 | −46.771 | 1.00 | 105.91 | MOL1 | C |
| ATOM | 3282 | CB | PRO | B | 212 | 74.529 | −30.117 | −46.338 | 1.00 | 107.78 | MOL1 | C |
| ATOM | 3283 | CG | PRO | B | 212 | 73.768 | −30.131 | −47.636 | 1.00 | 108.54 | MOL1 | C |
| ATOM | 3284 | C | PRO | B | 212 | 77.021 | −30.110 | −45.837 | 1.00 | 106.85 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 3285 | O | PRO | B | 212 | 77.750 | −29.304 | −45.265 | 1.00 | 109.43 | MOL1 | O |
|---|---|---|---|---|---|---|---|---|---|---|---|---|
| ATOM | 3286 | N | ALA | B | 213 | 77.143 | −31.426 | −45.691 | 1.00 | 106.07 | MOL1 | N |
| ATOM | 3287 | CA | ALA | B | 213 | 78.155 | −32.025 | −44.822 | 1.00 | 104.23 | MOL1 | C |
| ATOM | 3288 | CB | ALA | B | 213 | 78.274 | −33.511 | −45.109 | 1.00 | 104.88 | MOL1 | C |
| ATOM | 3289 | C | ALA | B | 213 | 79.522 | −31.376 | −44.961 | 1.00 | 102.80 | MOL1 | C |
| ATOM | 3290 | O | ALA | B | 213 | 80.322 | −31.401 | −44.029 | 1.00 | 105.87 | MOL1 | O |
| ATOM | 3291 | N | SER | B | 214 | 79.790 | −30.806 | −46.129 | 1.00 | 100.89 | MOL1 | N |
| ATOM | 3292 | CA | SER | B | 214 | 81.067 | −30.154 | −46.388 | 1.00 | 100.65 | MOL1 | C |
| ATOM | 3293 | CB | SER | B | 214 | 81.787 | −30.838 | −47.545 | 1.00 | 97.12 | MOL1 | C |
| ATOM | 3294 | OG | SER | B | 214 | 82.696 | −29.959 | −48.175 | 1.00 | 88.48 | MOL1 | O |
| ATOM | 3295 | C | SER | B | 214 | 80.876 | −28.689 | −46.719 | 1.00 | 104.48 | MOL1 | C |
| ATOM | 3296 | O | SER | B | 214 | 81.816 | −28.009 | −47.118 | 1.00 | 105.37 | MOL1 | O |
| ATOM | 3297 | N | SER | B | 215 | 79.650 | −28.208 | −46.558 | 1.00 | 109.71 | MOL1 | N |
| ATOM | 3298 | CA | SER | B | 215 | 79.318 | −26.810 | −46.837 | 1.00 | 113.22 | MOL1 | C |
| ATOM | 3299 | CB | SER | B | 215 | 79.953 | −25.881 | −45.789 | 1.00 | 113.27 | MOL1 | C |
| ATOM | 3300 | OG | SER | B | 215 | 81.366 | −25.857 | −45.892 | 1.00 | 110.37 | MOL1 | O |
| ATOM | 3301 | C | SER | B | 215 | 79.751 | −26.371 | −48.235 | 1.00 | 112.71 | MOL1 | C |
| ATOM | 3302 | O | SER | B | 215 | 79.950 | −25.181 | −48.487 | 1.00 | 110.22 | MOL1 | O |
| ATOM | 3303 | N | THR | B | 216 | 79.895 | −27.339 | −49.135 | 1.00 | 113.28 | MOL1 | N |
| ATOM | 3304 | CA | THR | B | 216 | 80.289 | −27.067 | −50.515 | 1.00 | 112.49 | MOL1 | C |
| ATOM | 3305 | CB | THR | B | 216 | 80.989 | −28.287 | −51.163 | 1.00 | 116.13 | MOL1 | C |
| ATOM | 3306 | OG1 | THR | B | 216 | 81.951 | −28.842 | −50.256 | 1.00 | 116.88 | MOL1 | O |
| ATOM | 3307 | CG2 | THR | B | 216 | 81.684 | −27.868 | −52.452 | 1.00 | 116.06 | MOL1 | C |
| ATOM | 3308 | C | THR | B | 216 | 79.026 | −26.791 | −51.320 | 1.00 | 109.89 | MOL1 | C |
| ATOM | 3309 | O | THR | B | 216 | 77.954 | −27.302 | −50.988 | 1.00 | 110.41 | MOL1 | O |
| ATOM | 3310 | N | LYS | B | 217 | 79.150 | −25.998 | −52.377 | 1.00 | 105.80 | MOL1 | N |
| ATOM | 3311 | CA | LYS | B | 217 | 78.004 | −25.675 | −53.212 | 1.00 | 109.45 | MOL1 | C |
| ATOM | 3312 | CB | LYS | B | 217 | 77.182 | −24.527 | −52.599 | 1.00 | 119.31 | MOL1 | C |
| ATOM | 3313 | CG | LYS | B | 217 | 76.444 | −24.889 | −51.289 | 1.00 | 129.29 | MOL1 | C |
| ATOM | 3314 | CD | LYS | B | 217 | 75.516 | −23.773 | −50.775 | 1.00 | 131.72 | MOL1 | C |
| ATOM | 3315 | CE | LYS | B | 217 | 74.728 | −24.222 | −49.533 | 1.00 | 133.19 | MOL1 | C |
| ATOM | 3316 | NZ | LYS | B | 217 | 73.777 | −23.188 | −49.007 | 1.00 | 131.75 | MOL1 | N |
| ATOM | 3317 | C | LYS | B | 217 | 78.509 | −25.271 | −54.576 | 1.00 | 107.36 | MOL1 | C |
| ATOM | 3318 | O | LYS | B | 217 | 78.557 | −24.085 | −54.899 | 1.00 | 110.84 | MOL1 | O |
| ATOM | 3319 | N | VAL | B | 218 | 78.882 | −26.265 | −55.375 | 1.00 | 103.91 | MOL1 | N |
| ATOM | 3320 | CA | VAL | B | 218 | 79.402 | −26.015 | −56.715 | 1.00 | 99.65 | MOL1 | C |
| ATOM | 3321 | CB | VAL | B | 218 | 80.450 | −27.042 | −57.108 | 1.00 | 97.19 | MOL1 | C |
| ATOM | 3322 | CG1 | VAL | B | 218 | 80.853 | −26.820 | −58.554 | 1.00 | 94.99 | MOL1 | C |
| ATOM | 3323 | CG2 | VAL | B | 218 | 81.647 | −26.933 | −56.186 | 1.00 | 100.48 | MOL1 | C |
| ATOM | 3324 | C | VAL | B | 218 | 78.379 | −25.983 | −57.839 | 1.00 | 98.84 | MOL1 | C |
| ATOM | 3325 | O | VAL | B | 218 | 77.386 | −26.710 | −57.833 | 1.00 | 99.53 | MOL1 | O |
| ATOM | 3326 | N | ASP | B | 219 | 78.637 | −25.123 | −58.812 | 1.00 | 98.56 | MOL1 | N |
| ATOM | 3327 | CA | ASP | B | 219 | 77.765 | −25.000 | −59.961 | 1.00 | 102.84 | MOL1 | C |
| ATOM | 3328 | CB | ASP | B | 219 | 77.104 | −23.613 | −59.998 | 1.00 | 112.70 | MOL1 | C |
| ATOM | 3329 | CG | ASP | B | 219 | 78.114 | −22.472 | −60.101 | 1.00 | 122.00 | MOL1 | C |
| ATOM | 3330 | OD1 | ASP | B | 219 | 79.026 | −22.396 | −59.245 | 1.00 | 127.83 | MOL1 | O |
| ATOM | 3331 | OD2 | ASP | B | 219 | 77.989 | −21.646 | −61.036 | 1.00 | 124.13 | MOL1 | O |
| ATOM | 3332 | C | ASP | B | 219 | 78.643 | −25.211 | −61.180 | 1.00 | 100.52 | MOL1 | C |
| ATOM | 3333 | O | ASP | B | 219 | 79.737 | −24.661 | −61.264 | 1.00 | 100.80 | MOL1 | O |
| ATOM | 3334 | N | LYS | B | 220 | 78.181 | −26.031 | −62.114 | 1.00 | 99.48 | MOL1 | N |
| ATOM | 3335 | CA | LYS | B | 220 | 78.959 | −26.285 | −63.318 | 1.00 | 102.77 | MOL1 | C |
| ATOM | 3336 | CB | LYS | B | 220 | 79.492 | −27.723 | −63.339 | 1.00 | 105.07 | MOL1 | C |
| ATOM | 3337 | CG | LYS | B | 220 | 80.752 | −27.941 | −64.205 | 1.00 | 101.06 | MOL1 | C |
| ATOM | 3338 | CD | LYS | B | 220 | 82.027 | −27.800 | −63.364 | 1.00 | 99.44 | MOL1 | C |
| ATOM | 3339 | CE | LYS | B | 220 | 83.278 | −28.285 | −64.093 | 1.00 | 96.80 | MOL1 | C |
| ATOM | 3340 | NZ | LYS | B | 220 | 84.404 | −28.566 | −63.141 | 1.00 | 91.69 | MOL1 | N |
| ATOM | 3341 | C | LYS | B | 220 | 78.084 | −26.056 | −64.536 | 1.00 | 103.79 | MOL1 | C |
| ATOM | 3342 | O | LYS | B | 220 | 77.029 | −26.668 | −64.682 | 1.00 | 105.73 | MOL1 | O |
| ATOM | 3343 | N | LYS | B | 221 | 78.530 | −25.161 | −65.406 | 1.00 | 104.74 | MOL1 | N |
| ATOM | 3344 | CA | LYS | B | 221 | 77.801 | −24.838 | −66.625 | 1.00 | 106.44 | MOL1 | C |
| ATOM | 3345 | CB | LYS | B | 221 | 78.335 | −23.527 | −67.230 | 1.00 | 115.48 | MOL1 | C |
| ATOM | 3346 | CG | LYS | B | 221 | 78.279 | −22.304 | −66.294 | 1.00 | 127.04 | MOL1 | C |
| ATOM | 3347 | CD | LYS | B | 221 | 79.219 | −21.154 | −66.729 | 1.00 | 131.38 | MOL1 | C |
| ATOM | 3348 | CE | LYS | B | 221 | 78.824 | −20.516 | −68.064 | 1.00 | 133.20 | MOL1 | C |
| ATOM | 3349 | NZ | LYS | B | 221 | 79.750 | −19.404 | −68.453 | 1.00 | 128.30 | MOL1 | N |
| ATOM | 3350 | C | LYS | B | 221 | 78.032 | −25.963 | −67.617 | 1.00 | 101.80 | MOL1 | C |
| ATOM | 3351 | O | LYS | B | 221 | 79.152 | −26.446 | −67.745 | 1.00 | 100.90 | MOL1 | O |
| ATOM | 3352 | N | ILE | B | 222 | 76.984 | −26.380 | −68.319 | 1.00 | 100.90 | MOL1 | N |
| ATOM | 3353 | CA | ILE | B | 222 | 77.120 | −27.442 | −69.315 | 1.00 | 96.97 | MOL1 | C |
| ATOM | 3354 | CB | ILE | B | 222 | 75.862 | −28.299 | −69.416 | 1.00 | 91.83 | MOL1 | C |
| ATOM | 3355 | CG2 | ILE | B | 222 | 76.044 | −29.337 | −70.493 | 1.00 | 89.24 | MOL1 | C |
| ATOM | 3356 | CG1 | ILE | B | 222 | 75.561 | −28.943 | −68.064 | 1.00 | 86.37 | MOL1 | C |
| ATOM | 3357 | CD1 | ILE | B | 222 | 76.703 | −29.721 | −67.504 | 1.00 | 85.83 | MOL1 | C |
| ATOM | 3358 | C | ILE | B | 222 | 77.394 | −26.851 | −70.689 | 1.00 | 98.76 | MOL1 | C |
| ATOM | 3359 | O | ILE | B | 222 | 76.498 | −26.307 | −71.341 | 1.00 | 100.71 | MOL1 | O |
| ATOM | 3360 | N | VAL | B | 223 | 78.641 | −26.972 | −71.122 | 1.00 | 99.19 | MOL1 | N |
| ATOM | 3361 | CA | VAL | B | 223 | 79.078 | −26.442 | −72.405 | 1.00 | 98.35 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 3362 | CB | VAL | B | 223 | 80.310 | −25.552 | −72.218 | 1.00 | 97.77 | MOL1 | C |
|---|---|---|---|---|---|---|---|---|---|---|---|---|
| ATOM | 3363 | CG1 | VAL | B | 223 | 81.118 | −26.030 | −71.006 | 1.00 | 94.96 | MOL1 | C |
| ATOM | 3364 | CG2 | VAL | B | 223 | 81.173 | −25.603 | −73.474 | 1.00 | 97.02 | MOL1 | C |
| ATOM | 3365 | C | VAL | B | 223 | 79.460 | −27.558 | −73.352 | 1.00 | 98.65 | MOL1 | C |
| ATOM | 3366 | O | VAL | B | 223 | 80.115 | −28.516 | −72.951 | 1.00 | 99.88 | MOL1 | O |
| ATOM | 3367 | N | PRO | B | 224 | 79.073 | −27.437 | −74.629 | 1.00 | 98.92 | MOL1 | N |
| ATOM | 3368 | CD | PRO | B | 224 | 78.286 | −26.316 | −75.161 | 1.00 | 94.90 | MOL1 | C |
| ATOM | 3369 | CA | PRO | B | 224 | 79.354 | −28.421 | −75.683 | 1.00 | 104.37 | MOL1 | C |
| ATOM | 3370 | CB | PRO | B | 224 | 78.488 | −27.942 | −76.842 | 1.00 | 96.75 | MOL1 | C |
| ATOM | 3371 | CG | PRO | B | 224 | 78.489 | −26.467 | −76.654 | 1.00 | 95.48 | MOL1 | C |
| ATOM | 3372 | C | PRO | B | 224 | 80.832 | −28.541 | −76.067 | 1.00 | 111.20 | MOL1 | C |
| ATOM | 3373 | O | PRO | B | 224 | 81.690 | −27.847 | −75.519 | 1.00 | 111.75 | MOL1 | O |
| ATOM | 3374 | N | ARG | B | 225 | 81.114 | −29.439 | −77.007 | 1.00 | 118.08 | MOL1 | N |
| ATOM | 3375 | CA | ARG | B | 225 | 82.473 | −29.677 | −77.486 | 1.00 | 124.84 | MOL1 | C |
| ATOM | 3376 | CB | ARG | B | 225 | 82.742 | −31.177 | −77.550 | 1.00 | 122.51 | MOL1 | C |
| ATOM | 3377 | CG | ARG | B | 225 | 82.489 | −31.912 | −76.239 | 1.00 | 119.75 | MOL1 | C |
| ATOM | 3378 | CD | ARG | B | 225 | 82.337 | −33.422 | −76.457 | 1.00 | 116.39 | MOL1 | C |
| ATOM | 3379 | NE | ARG | B | 225 | 82.076 | −34.124 | −75.205 | 1.00 | 111.70 | MOL1 | N |
| ATOM | 3380 | CZ | ARG | B | 225 | 83.001 | −34.393 | −74.287 | 1.00 | 112.50 | MOL1 | C |
| ATOM | 3381 | NH1 | ARG | B | 225 | 82.661 | −35.029 | −73.173 | 1.00 | 114.12 | MOL1 | N |
| ATOM | 3382 | NH2 | ARG | B | 225 | 84.267 | −34.045 | −74.490 | 1.00 | 109.27 | MOL1 | N |
| ATOM | 3383 | C | ARG | B | 225 | 82.613 | −29.069 | −78.878 | 1.00 | 133.06 | MOL1 | C |
| ATOM | 3384 | O | ARG | B | 225 | 81.621 | −28.913 | −79.594 | 1.00 | 135.73 | MOL1 | O |
| ATOM | 3385 | N | ASP | B | 226 | 83.840 | −28.738 | −79.269 | 1.00 | 140.52 | MOL1 | N |
| ATOM | 3386 | CA | ASP | B | 226 | 84.067 | −28.126 | −80.575 | 1.00 | 149.72 | MOL1 | C |
| ATOM | 3387 | CB | ASP | B | 226 | 85.360 | −27.296 | −80.554 | 1.00 | 145.64 | MOL1 | C |
| ATOM | 3388 | CG | ASP | B | 226 | 85.149 | −25.893 | −79.984 | 1.00 | 142.50 | MOL1 | C |
| ATOM | 3389 | OD1 | ASP | B | 226 | 86.143 | −25.150 | −79.854 | 1.00 | 139.30 | MOL1 | O |
| ATOM | 3390 | OD2 | ASP | B | 226 | 83.992 | −25.527 | −79.671 | 1.00 | 137.82 | MOL1 | O |
| ATOM | 3391 | C | ASP | B | 226 | 84.065 | −29.082 | −81.776 | 1.00 | 155.68 | MOL1 | C |
| ATOM | 3392 | O | ASP | B | 226 | 82.997 | −29.481 | −82.250 | 1.00 | 156.17 | MOL1 | O |
| ATOM | 3393 | N | CYS | B | 227 | 85.248 | −29.438 | −82.274 | 1.00 | 162.72 | MOL1 | N |
| ATOM | 3394 | CA | CYS | B | 227 | 85.352 | −30.325 | −83.435 | 1.00 | 168.19 | MOL1 | C |
| ATOM | 3395 | CB | CYS | B | 227 | 86.735 | −30.162 | −84.109 | 1.00 | 171.79 | MOL1 | C |
| ATOM | 3396 | SG | CYS | B | 227 | 88.179 | −31.014 | −83.367 | 1.00 | 175.58 | MOL1 | S |
| ATOM | 3397 | C | CYS | B | 227 | 85.079 | −31.797 | −83.104 | 1.00 | 169.02 | MOL1 | C |
| ATOM | 3398 | O | CYS | B | 227 | 84.756 | −32.089 | −81.930 | 1.00 | 168.83 | MOL1 | O |
| ATOM | 3399 | OXT | CYS | B | 227 | 85.171 | −32.640 | −84.026 | 1.00 | 169.12 | MOL1 | O |
| ATOM | 3400 | CB | GLU | F | 15 | 22.974 | −19.456 | −42.886 | 1.00 | 149.87 | MOL1 | C |
| ATOM | 3401 | CG | GLU | F | 15 | 22.375 | −19.287 | −41.505 | 1.00 | 144.07 | MOL1 | C |
| ATOM | 3402 | CD | GLU | F | 15 | 21.496 | −20.457 | −41.117 | 1.00 | 141.32 | MOL1 | C |
| ATOM | 3403 | OE1 | GLU | F | 15 | 22.037 | −21.457 | −40.599 | 1.00 | 139.31 | MOL1 | O |
| ATOM | 3404 | OE2 | GLU | F | 15 | 20.271 | −20.383 | −41.342 | 1.00 | 136.53 | MOL1 | O |
| ATOM | 3405 | C | GLU | F | 15 | 21.960 | −17.725 | −44.377 | 1.00 | 155.87 | MOL1 | C |
| ATOM | 3406 | O | GLU | F | 15 | 22.161 | −17.366 | −45.539 | 1.00 | 156.62 | MOL1 | O |
| ATOM | 3407 | N | GLU | F | 15 | 22.347 | −20.014 | −45.220 | 1.00 | 152.69 | MOL1 | N |
| ATOM | 3408 | CA | GLU | F | 15 | 21.974 | −19.212 | −44.018 | 1.00 | 153.60 | MOL1 | C |
| ATOM | 3409 | N | SER | F | 16 | 21.731 | −16.866 | −43.384 | 1.00 | 157.81 | MOL1 | N |
| ATOM | 3410 | CA | SER | F | 16 | 21.685 | −15.421 | −43.619 | 1.00 | 158.62 | MOL1 | C |
| ATOM | 3411 | CB | SER | F | 16 | 20.704 | −15.094 | −44.752 | 1.00 | 156.06 | MOL1 | C |
| ATOM | 3412 | OG | SER | F | 16 | 19.358 | −15.219 | −44.325 | 1.00 | 151.69 | MOL1 | O |
| ATOM | 3413 | C | SER | F | 16 | 21.286 | −14.614 | −42.382 | 1.00 | 161.17 | MOL1 | C |
| ATOM | 3414 | O | SER | F | 16 | 21.486 | −13.404 | −42.334 | 1.00 | 162.33 | MOL1 | O |
| ATOM | 3415 | N | CYS | F | 17 | 20.720 | −15.285 | −41.386 | 1.00 | 163.62 | MOL1 | N |
| ATOM | 3416 | CA | CYS | F | 17 | 20.282 | −14.628 | −40.154 | 1.00 | 164.31 | MOL1 | C |
| ATOM | 3417 | C | CYS | F | 17 | 21.380 | −13.767 | −39.528 | 1.00 | 165.32 | MOL1 | C |
| ATOM | 3418 | O | CYS | F | 17 | 22.566 | −13.976 | −39.785 | 1.00 | 164.46 | MOL1 | O |
| ATOM | 3419 | CB | CYS | F | 17 | 19.846 | −15.681 | −39.140 | 1.00 | 162.75 | MOL1 | C |
| ATOM | 3420 | SG | CYS | F | 17 | 19.205 | −17.206 | −39.897 | 1.00 | 160.53 | MOL1 | S |
| ATOM | 3421 | N | PRO | F | 18 | 20.987 | −12.782 | −38.698 | 1.00 | 166.83 | MOL1 | N |
| ATOM | 3422 | CD | PRO | F | 18 | 19.585 | −12.387 | −38.472 | 1.00 | 165.88 | MOL1 | C |
| ATOM | 3423 | CA | PRO | F | 18 | 21.903 | −11.865 | −38.006 | 1.00 | 167.58 | MOL1 | C |
| ATOM | 3424 | CB | PRO | F | 18 | 20.957 | −10.992 | −37.185 | 1.00 | 166.11 | MOL1 | C |
| ATOM | 3425 | CG | PRO | F | 18 | 19.725 | −10.947 | −38.036 | 1.00 | 166.04 | MOL1 | C |
| ATOM | 3426 | C | PRO | F | 18 | 22.880 | −12.636 | −37.122 | 1.00 | 169.16 | MOL1 | C |
| ATOM | 3427 | O | PRO | F | 18 | 22.543 | −13.037 | −36.008 | 1.00 | 167.54 | MOL1 | O |
| ATOM | 3428 | N | PRO | F | 19 | 24.111 | −12.837 | −37.611 | 1.00 | 172.45 | MOL1 | N |
| ATOM | 3429 | CD | PRO | F | 19 | 24.580 | −12.245 | −38.878 | 1.00 | 172.44 | MOL1 | C |
| ATOM | 3430 | CA | PRO | F | 19 | 25.202 | −13.555 | −36.940 | 1.00 | 175.08 | MOL1 | C |
| ATOM | 3431 | CB | PRO | F | 19 | 26.425 | −13.162 | −37.769 | 1.00 | 174.52 | MOL1 | C |
| ATOM | 3432 | CG | PRO | F | 19 | 25.850 | −13.024 | −39.149 | 1.00 | 173.92 | MOL1 | C |
| ATOM | 3433 | C | PRO | F | 19 | 25.402 | −13.286 | −35.441 | 1.00 | 176.12 | MOL1 | C |
| ATOM | 3434 | O | PRO | F | 19 | 24.737 | −12.436 | −34.841 | 1.00 | 174.47 | MOL1 | O |
| ATOM | 3435 | N | VAL | F | 20 | 26.322 | −14.041 | −34.848 | 1.00 | 177.57 | MOL1 | N |
| ATOM | 3436 | CA | VAL | F | 20 | 26.659 | −13.908 | −33.437 | 1.00 | 178.58 | MOL1 | C |
| ATOM | 3437 | CB | VAL | F | 20 | 26.466 | −15.253 | −32.686 | 1.00 | 178.29 | MOL1 | C |
| ATOM | 3438 | CG1 | VAL | F | 20 | 24.982 | −15.571 | −32.574 | 1.00 | 176.76 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 3439 | CG2 | VAL | F | 20 | 27.191 | −16.378 | −33.420 | 1.00 | 176.99 | MOL1 | C |
|---|---|---|---|---|---|---|---|---|---|---|---|---|
| ATOM | 3440 | C | VAL | F | 20 | 28.119 | −13.451 | −33.346 | 1.00 | 180.71 | MOL1 | C |
| ATOM | 3441 | O | VAL | F | 20 | 28.845 | −13.480 | −34.346 | 1.00 | 181.31 | MOL1 | O |
| ATOM | 3442 | N | PRO | F | 21 | 28.566 | −13.008 | −32.155 | 1.00 | 182.04 | MOL1 | N |
| ATOM | 3443 | CD | PRO | F | 21 | 27.795 | −12.900 | −30.899 | 1.00 | 182.08 | MOL1 | C |
| ATOM | 3444 | CA | PRO | F | 21 | 29.946 | −12.545 | −31.957 | 1.00 | 181.92 | MOL1 | C |
| ATOM | 3445 | CB | PRO | F | 21 | 30.098 | −12.597 | −30.440 | 1.00 | 181.19 | MOL1 | C |
| ATOM | 3446 | CG | PRO | F | 21 | 28.743 | −12.119 | −29.987 | 1.00 | 180.80 | MOL1 | C |
| ATOM | 3447 | C | PRO | F | 21 | 31.028 | −13.345 | −32.703 | 1.00 | 181.93 | MOL1 | C |
| ATOM | 3448 | O | PRO | F | 21 | 31.999 | −12.769 | −33.202 | 1.00 | 180.80 | MOL1 | O |
| ATOM | 3449 | N | GLY | F | 22 | 30.860 | −14.663 | −32.780 | 1.00 | 182.34 | MOL1 | N |
| ATOM | 3450 | CA | GLY | F | 22 | 31.831 | −15.486 | −33.484 | 1.00 | 181.41 | MOL1 | C |
| ATOM | 3451 | C | GLY | F | 22 | 32.213 | −16.792 | −32.806 | 1.00 | 180.52 | MOL1 | C |
| ATOM | 3452 | O | GLY | F | 22 | 32.647 | −16.800 | −31.651 | 1.00 | 181.38 | MOL1 | O |
| ATOM | 3453 | N | GLY | F | 23 | 32.055 | −17.900 | −33.530 | 1.00 | 178.22 | MOL1 | N |
| ATOM | 3454 | CA | GLY | F | 23 | 32.400 | −19.208 | −32.995 | 1.00 | 174.34 | MOL1 | C |
| ATOM | 3455 | C | GLY | F | 23 | 31.603 | −19.638 | −31.775 | 1.00 | 171.67 | MOL1 | C |
| ATOM | 3456 | O | GLY | F | 23 | 32.174 | −19.920 | −30.718 | 1.00 | 170.67 | MOL1 | O |
| ATOM | 3457 | N | SER | F | 24 | 30.281 | −19.692 | −31.920 | 1.00 | 168.80 | MOL1 | N |
| ATOM | 3458 | CA | SER | F | 24 | 29.402 | −20.095 | −30.825 | 1.00 | 164.63 | MOL1 | C |
| ATOM | 3459 | CB | SER | F | 24 | 29.323 | −18.982 | −29.772 | 1.00 | 165.56 | MOL1 | C |
| ATOM | 3460 | OG | SER | F | 24 | 28.530 | −19.374 | −28.662 | 1.00 | 164.93 | MOL1 | O |
| ATOM | 3461 | C | SER | F | 24 | 28.001 | −20.419 | −31.345 | 1.00 | 160.92 | MOL1 | C |
| ATOM | 3462 | O | SER | F | 24 | 27.533 | −19.812 | −32.314 | 1.00 | 160.03 | MOL1 | O |
| ATOM | 3463 | N | MET | F | 25 | 27.340 | −21.378 | −30.696 | 1.00 | 155.68 | MOL1 | N |
| ATOM | 3464 | CA | MET | F | 25 | 25.992 | −21.790 | −31.083 | 1.00 | 148.46 | MOL1 | C |
| ATOM | 3465 | CB | MET | F | 25 | 26.061 | −23.054 | −31.949 | 1.00 | 148.69 | MOL1 | C |
| ATOM | 3466 | CG | MET | F | 25 | 24.964 | −23.169 | −33.015 | 1.00 | 149.35 | MOL1 | C |
| ATOM | 3467 | SD | MET | F | 25 | 25.375 | −22.436 | −34.633 | 1.00 | 149.53 | MOL1 | S |
| ATOM | 3468 | CE | MET | F | 25 | 25.741 | −23.915 | −35.642 | 1.00 | 145.96 | MOL1 | C |
| ATOM | 3469 | C | MET | F | 25 | 25.141 | −22.048 | −29.829 | 1.00 | 143.51 | MOL1 | C |
| ATOM | 3470 | O | MET | F | 25 | 25.672 | −22.140 | −28.717 | 1.00 | 140.73 | MOL1 | O |
| ATOM | 3471 | N | LYS | F | 26 | 23.826 | −22.158 | −30.013 | 1.00 | 138.19 | MOL1 | N |
| ATOM | 3472 | CA | LYS | F | 26 | 22.907 | −22.392 | −28.897 | 1.00 | 134.01 | MOL1 | C |
| ATOM | 3473 | CB | LYS | F | 26 | 21.479 | −21.964 | −29.270 | 1.00 | 133.72 | MOL1 | C |
| ATOM | 3474 | CG | LYS | F | 26 | 21.216 | −20.465 | −29.159 | 1.00 | 133.94 | MOL1 | C |
| ATOM | 3475 | CD | LYS | F | 26 | 19.764 | −20.106 | −29.491 | 1.00 | 134.50 | MOL1 | C |
| ATOM | 3476 | CE | LYS | F | 26 | 18.769 | −20.636 | −28.457 | 1.00 | 134.34 | MOL1 | C |
| ATOM | 3477 | NZ | LYS | F | 26 | 18.842 | −19.931 | −27.142 | 1.00 | 135.55 | MOL1 | N |
| ATOM | 3478 | C | LYS | F | 26 | 22.879 | −23.833 | −28.398 | 1.00 | 129.94 | MOL1 | C |
| ATOM | 3479 | O | LYS | F | 26 | 22.459 | −24.746 | −29.111 | 1.00 | 130.92 | MOL1 | O |
| ATOM | 3480 | N | LEU | F | 27 | 23.316 | −24.026 | −27.158 | 1.00 | 123.18 | MOL1 | N |
| ATOM | 3481 | CA | LEU | F | 27 | 23.334 | −25.345 | −26.546 | 1.00 | 117.71 | MOL1 | C |
| ATOM | 3482 | CB | LEU | F | 27 | 24.752 | −25.718 | −26.127 | 1.00 | 108.77 | MOL1 | C |
| ATOM | 3483 | CG | LEU | F | 27 | 24.900 | −27.123 | −25.551 | 1.00 | 102.45 | MOL1 | C |
| ATOM | 3484 | CD1 | LEU | F | 27 | 24.569 | −28.130 | −26.638 | 1.00 | 99.22 | MOL1 | C |
| ATOM | 3485 | CD2 | LEU | F | 27 | 26.310 | −27.335 | −25.032 | 1.00 | 95.52 | MOL1 | C |
| ATOM | 3486 | C | LEU | F | 27 | 22.444 | −25.344 | −25.318 | 1.00 | 118.97 | MOL1 | C |
| ATOM | 3487 | O | LEU | F | 27 | 22.865 | −24.923 | −24.246 | 1.00 | 119.24 | MOL1 | O |
| ATOM | 3488 | N | ASP | F | 28 | 21.215 | −25.821 | −25.471 | 1.00 | 122.32 | MOL1 | N |
| ATOM | 3489 | CA | ASP | F | 28 | 20.278 | −25.862 | −24.358 | 1.00 | 125.99 | MOL1 | C |
| ATOM | 3490 | CB | ASP | F | 28 | 18.937 | −26.448 | −24.807 | 1.00 | 129.38 | MOL1 | C |
| ATOM | 3491 | CG | ASP | F | 28 | 18.465 | −25.880 | −26.135 | 1.00 | 135.42 | MOL1 | C |
| ATOM | 3492 | OD1 | ASP | F | 28 | 18.844 | −24.734 | −26.458 | 1.00 | 137.40 | MOL1 | O |
| ATOM | 3493 | OD2 | ASP | F | 28 | 17.707 | −26.573 | −26.852 | 1.00 | 136.01 | MOL1 | O |
| ATOM | 3494 | C | ASP | F | 28 | 20.820 | −26.689 | −23.201 | 1.00 | 128.20 | MOL1 | C |
| ATOM | 3495 | O | ASP | F | 28 | 21.489 | −27.702 | −23.401 | 1.00 | 127.44 | MOL1 | O |
| ATOM | 3496 | N | ILE | F | 29 | 20.532 | −26.238 | −21.985 | 1.00 | 132.62 | MOL1 | N |
| ATOM | 3497 | CA | ILE | F | 29 | 20.962 | −26.933 | −20.776 | 1.00 | 133.08 | MOL1 | C |
| ATOM | 3498 | CB | ILE | F | 29 | 20.752 | −26.077 | −19.507 | 1.00 | 132.47 | MOL1 | C |
| ATOM | 3499 | CG2 | ILE | F | 29 | 21.747 | −24.935 | −19.472 | 1.00 | 134.02 | MOL1 | C |
| ATOM | 3500 | CG1 | ILE | F | 29 | 19.305 | −25.575 | −19.461 | 1.00 | 131.56 | MOL1 | C |
| ATOM | 3501 | CD1 | ILE | F | 29 | 19.011 | −24.625 | −18.323 | 1.00 | 131.84 | MOL1 | C |
| ATOM | 3502 | C | ILE | F | 29 | 20.094 | −28.163 | −20.625 | 1.00 | 132.87 | MOL1 | C |
| ATOM | 3503 | O | ILE | F | 29 | 19.048 | −28.282 | −21.271 | 1.00 | 132.86 | MOL1 | O |
| ATOM | 3504 | N | GLY | F | 30 | 20.520 | −29.071 | −19.757 | 1.00 | 131.60 | MOL1 | N |
| ATOM | 3505 | CA | GLY | F | 30 | 19.751 | −30.278 | −19.537 | 1.00 | 129.89 | MOL1 | C |
| ATOM | 3506 | C | GLY | F | 30 | 20.037 | −31.345 | −20.571 | 1.00 | 126.50 | MOL1 | C |
| ATOM | 3507 | O | GLY | F | 30 | 19.802 | −31.158 | −21.767 | 1.00 | 128.12 | MOL1 | O |
| ATOM | 3508 | N | ILE | F | 31 | 20.543 | −32.475 | −20.098 | 1.00 | 121.94 | MOL1 | N |
| ATOM | 3509 | CA | ILE | F | 31 | 20.871 | −33.590 | −20.964 | 1.00 | 117.12 | MOL1 | C |
| ATOM | 3510 | CB | ILE | F | 31 | 22.120 | −34.327 | −20.471 | 1.00 | 115.73 | MOL1 | C |
| ATOM | 3511 | CG2 | ILE | F | 31 | 22.518 | −35.373 | −21.478 | 1.00 | 114.88 | MOL1 | C |
| ATOM | 3512 | CG1 | ILE | F | 31 | 23.265 | −33.339 | −20.237 | 1.00 | 116.43 | MOL1 | C |
| ATOM | 3513 | CD1 | ILE | F | 31 | 23.121 | −32.490 | −18.975 | 1.00 | 120.44 | MOL1 | C |
| ATOM | 3514 | C | ILE | F | 31 | 19.720 | −34.582 | −20.981 | 1.00 | 116.73 | MOL1 | C |
| ATOM | 3515 | O | ILE | F | 31 | 19.209 | −34.967 | −19.931 | 1.00 | 116.15 | MOL1 | O |

TABLE 1-continued

The atomic coordinates of IL17F in complex with 496 Fab
(H32; a = 189.4; b = 189.4; c = 490.9, α, β = 90°; γ = 120°)

| ATOM | 3516 | N | ILE | F | 32 | 19.317 | −34.994 | −22.176 | 1.00 | 118.68 | MOL1 | N |
|---|---|---|---|---|---|---|---|---|---|---|---|---|
| ATOM | 3517 | CA | ILE | F | 32 | 18.226 | −35.949 | −22.329 | 1.00 | 123.20 | MOL1 | C |
| ATOM | 3518 | CB | ILE | F | 32 | 17.780 | −36.044 | −23.805 | 1.00 | 123.36 | MOL1 | C |
| ATOM | 3519 | CG2 | ILE | F | 32 | 16.553 | −36.940 | −23.922 | 1.00 | 122.71 | MOL1 | C |
| ATOM | 3520 | CG1 | ILE | F | 32 | 17.480 | −34.644 | −24.349 | 1.00 | 122.75 | MOL1 | C |
| ATOM | 3521 | CD1 | ILE | F | 32 | 16.994 | −34.637 | −25.786 | 1.00 | 123.21 | MOL1 | C |
| ATOM | 3522 | C | ILE | F | 32 | 18.640 | −37.346 | −21.856 | 1.00 | 127.61 | MOL1 | C |
| ATOM | 3523 | O | ILE | F | 32 | 19.633 | −37.899 | −22.333 | 1.00 | 129.87 | MOL1 | O |
| ATOM | 3524 | N | ASN | F | 33 | 17.875 | −37.904 | −20.917 | 1.00 | 132.09 | MOL1 | N |
| ATOM | 3525 | CA | ASN | F | 33 | 18.128 | −39.239 | −20.362 | 1.00 | 136.09 | MOL1 | C |
| ATOM | 3526 | CB | ASN | F | 33 | 18.367 | −40.248 | −21.490 | 1.00 | 137.26 | MOL1 | C |
| ATOM | 3527 | CG | ASN | F | 33 | 17.174 | −40.378 | −22.422 | 1.00 | 141.15 | MOL1 | C |
| ATOM | 3528 | OD1 | ASN | F | 33 | 16.113 | −40.861 | −22.025 | 1.00 | 144.19 | MOL1 | O |
| ATOM | 3529 | ND2 | ASN | F | 33 | 17.340 | −39.940 | −23.667 | 1.00 | 141.99 | MOL1 | N |
| ATOM | 3530 | C | ASN | F | 33 | 19.297 | −39.289 | −19.379 | 1.00 | 139.95 | MOL1 | C |
| ATOM | 3531 | O | ASN | F | 33 | 19.952 | −40.319 | −19.241 | 1.00 | 140.54 | MOL1 | O |
| ATOM | 3532 | N | GLU | F | 34 | 19.550 | −38.177 | −18.694 | 1.00 | 145.31 | MOL1 | N |
| ATOM | 3533 | CA | GLU | F | 34 | 20.638 | −38.089 | −17.720 | 1.00 | 150.17 | MOL1 | C |
| ATOM | 3534 | CB | GLU | F | 34 | 20.604 | −36.710 | −17.049 | 1.00 | 152.50 | MOL1 | C |
| ATOM | 3535 | CG | GLU | F | 34 | 21.625 | −36.504 | −15.937 | 1.00 | 155.37 | MOL1 | C |
| ATOM | 3536 | CD | GLU | F | 34 | 21.432 | −35.184 | −15.207 | 1.00 | 155.48 | MOL1 | C |
| ATOM | 3537 | OE1 | GLU | F | 34 | 21.490 | −34.124 | −15.868 | 1.00 | 155.20 | MOL1 | O |
| ATOM | 3538 | OE2 | GLU | F | 34 | 21.224 | −35.208 | −13.972 | 1.00 | 153.96 | MOL1 | O |
| ATOM | 3539 | C | GLU | F | 34 | 20.514 | −39.185 | −16.659 | 1.00 | 153.84 | MOL1 | C |
| ATOM | 3540 | O | GLU | F | 34 | 21.434 | −39.414 | −15.871 | 1.00 | 152.98 | MOL1 | O |
| ATOM | 3541 | N | ASN | F | 35 | 19.368 | −39.863 | −16.660 | 1.00 | 159.41 | MOL1 | N |
| ATOM | 3542 | CA | ASN | F | 35 | 19.062 | −40.925 | −15.702 | 1.00 | 165.02 | MOL1 | C |
| ATOM | 3543 | CB | ASN | F | 35 | 17.544 | −41.041 | −15.518 | 1.00 | 167.52 | MOL1 | C |
| ATOM | 3544 | CG | ASN | F | 35 | 16.895 | −39.730 | −15.128 | 1.00 | 169.43 | MOL1 | C |
| ATOM | 3545 | OD1 | ASN | F | 35 | 17.154 | −39.189 | −14.052 | 1.00 | 171.02 | MOL1 | O |
| ATOM | 3546 | ND2 | ASN | F | 35 | 16.041 | −39.213 | −16.006 | 1.00 | 168.39 | MOL1 | N |
| ATOM | 3547 | C | ASN | F | 35 | 19.592 | −42.311 | −16.072 | 1.00 | 167.21 | MOL1 | C |
| ATOM | 3548 | O | ASN | F | 35 | 19.730 | −43.169 | −15.200 | 1.00 | 168.76 | MOL1 | O |
| ATOM | 3549 | N | GLN | F | 36 | 19.853 | −42.546 | −17.357 | 1.00 | 169.24 | MOL1 | N |
| ATOM | 3550 | CA | GLN | F | 36 | 20.358 | −43.848 | −17.798 | 1.00 | 170.44 | MOL1 | C |
| ATOM | 3551 | CB | GLN | F | 36 | 20.719 | −43.814 | −19.287 | 1.00 | 170.00 | MOL1 | C |
| ATOM | 3552 | CG | GLN | F | 36 | 19.540 | −44.006 | −20.228 | 1.00 | 166.49 | MOL1 | C |
| ATOM | 3553 | CD | GLN | F | 36 | 18.973 | −45.412 | −20.175 | 1.00 | 164.75 | MOL1 | C |
| ATOM | 3554 | OE1 | GLN | F | 36 | 18.015 | −45.732 | −20.878 | 1.00 | 163.00 | MOL1 | O |
| ATOM | 3555 | NE2 | GLN | F | 36 | 19.565 | −46.261 | −19.340 | 1.00 | 165.04 | MOL1 | N |
| ATOM | 3556 | C | GLN | F | 36 | 21.582 | −44.240 | −16.984 | 1.00 | 173.14 | MOL1 | C |
| ATOM | 3557 | O | GLN | F | 36 | 22.631 | −43.591 | −17.069 | 1.00 | 171.50 | MOL1 | O |
| ATOM | 3558 | N | ARG | F | 37 | 21.443 | −45.308 | −16.200 | 1.00 | 176.82 | MOL1 | N |
| ATOM | 3559 | CA | ARG | F | 37 | 22.527 | −45.780 | −15.342 | 1.00 | 179.91 | MOL1 | C |
| ATOM | 3560 | CB | ARG | F | 37 | 21.968 | −46.662 | −14.213 | 1.00 | 179.87 | MOL1 | C |
| ATOM | 3561 | CG | ARG | F | 37 | 20.898 | −45.987 | −13.352 | 1.00 | 177.94 | MOL1 | C |
| ATOM | 3562 | CD | ARG | F | 37 | 20.879 | −46.550 | −11.938 | 1.00 | 175.90 | MOL1 | C |
| ATOM | 3563 | NE | ARG | F | 37 | 22.089 | −46.191 | −11.204 | 1.00 | 175.74 | MOL1 | N |
| ATOM | 3564 | CZ | ARG | F | 37 | 22.415 | −44.947 | −10.859 | 1.00 | 175.03 | MOL1 | C |
| ATOM | 3565 | NH1 | ARG | F | 37 | 21.618 | −43.936 | −11.177 | 1.00 | 173.00 | MOL1 | N |
| ATOM | 3566 | NH2 | ARG | F | 37 | 23.541 | −44.714 | −10.199 | 1.00 | 174.73 | MOL1 | N |
| ATOM | 3567 | C | ARG | F | 37 | 23.633 | −46.533 | −16.079 | 1.00 | 180.73 | MOL1 | C |
| ATOM | 3568 | O | ARG | F | 37 | 23.379 | −47.259 | −17.047 | 1.00 | 178.26 | MOL1 | O |
| ATOM | 3569 | N | VAL | F | 38 | 24.861 | −46.337 | −15.597 | 1.00 | 182.74 | MOL1 | N |
| ATOM | 3570 | CA | VAL | F | 38 | 26.063 | −46.966 | −16.144 | 1.00 | 183.52 | MOL1 | C |
| ATOM | 3571 | CB | VAL | F | 38 | 27.300 | −46.666 | −15.240 | 1.00 | 183.75 | MOL1 | C |
| ATOM | 3572 | CG1 | VAL | F | 38 | 28.542 | −47.351 | −15.794 | 1.00 | 184.08 | MOL1 | C |
| ATOM | 3573 | CG2 | VAL | F | 38 | 27.521 | −45.161 | −15.132 | 1.00 | 181.36 | MOL1 | C |
| ATOM | 3574 | C | VAL | F | 38 | 25.878 | −48.481 | −16.224 | 1.00 | 183.05 | MOL1 | C |
| ATOM | 3575 | O | VAL | F | 38 | 26.288 | −49.208 | −15.313 | 1.00 | 182.81 | MOL1 | O |
| ATOM | 3576 | N | SER | F | 39 | 25.265 | −48.955 | −17.307 | 1.00 | 180.94 | MOL1 | N |
| ATOM | 3577 | CA | SER | F | 39 | 25.036 | −50.387 | −17.470 | 1.00 | 178.69 | MOL1 | C |
| ATOM | 3578 | CB | SER | F | 39 | 24.145 | −50.659 | −18.685 | 1.00 | 178.07 | MOL1 | C |
| ATOM | 3579 | OG | SER | F | 39 | 23.836 | −52.041 | −18.782 | 1.00 | 174.85 | MOL1 | O |
| ATOM | 3580 | C | SER | F | 39 | 26.357 | −51.134 | −17.619 | 1.00 | 177.48 | MOL1 | C |
| ATOM | 3581 | O | SER | F | 39 | 26.859 | −51.330 | −18.728 | 1.00 | 176.69 | MOL1 | O |
| ATOM | 3582 | N | MET | F | 40 | 26.912 | −51.548 | −16.483 | 1.00 | 175.26 | MOL1 | N |
| ATOM | 3583 | CA | MET | F | 40 | 28.174 | −52.271 | −16.457 | 1.00 | 170.51 | MOL1 | C |
| ATOM | 3584 | CB | MET | F | 40 | 29.294 | −51.325 | −16.004 | 1.00 | 173.33 | MOL1 | C |
| ATOM | 3585 | CG | MET | F | 40 | 30.706 | −51.782 | −16.345 | 1.00 | 175.64 | MOL1 | C |
| ATOM | 3586 | SD | MET | F | 40 | 31.936 | −50.475 | −16.064 | 1.00 | 176.59 | MOL1 | S |
| ATOM | 3587 | CE | MET | F | 40 | 31.861 | −49.599 | −17.635 | 1.00 | 173.87 | MOL1 | C |
| ATOM | 3588 | C | MET | F | 40 | 28.053 | −53.455 | −15.499 | 1.00 | 165.12 | MOL1 | C |
| ATOM | 3589 | O | MET | F | 40 | 28.501 | −53.381 | −14.354 | 1.00 | 163.85 | MOL1 | O |
| ATOM | 3590 | N | SER | F | 41 | 27.421 | −54.532 | −15.967 | 1.00 | 158.82 | MOL1 | N |
| ATOM | 3591 | CA | SER | F | 41 | 27.256 | −55.735 | −15.153 | 1.00 | 152.76 | MOL1 | C |
| ATOM | 3592 | CB | SER | F | 41 | 26.658 | −56.879 | −15.983 | 1.00 | 150.88 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 3593 | OG | SER | F | 41 | 25.380 | −56.542 | −16.494 | 1.00 | 146.30 | MOL1 | O |
|---|---|---|---|---|---|---|---|---|---|---|---|---|
| ATOM | 3594 | C | SER | F | 41 | 28.652 | −56.114 | −14.680 | 1.00 | 149.80 | MOL1 | C |
| ATOM | 3595 | O | SER | F | 41 | 29.417 | −56.745 | −15.407 | 1.00 | 149.13 | MOL1 | O |
| ATOM | 3596 | N | ARG | F | 42 | 28.977 | −55.714 | −13.458 | 1.00 | 145.39 | MOL1 | N |
| ATOM | 3597 | CA | ARG | F | 42 | 30.292 | −55.964 | −12.890 | 1.00 | 139.25 | MOL1 | C |
| ATOM | 3598 | CB | ARG | F | 42 | 30.286 | −55.570 | −11.410 | 1.00 | 141.33 | MOL1 | C |
| ATOM | 3599 | CG | ARG | F | 42 | 29.468 | −54.316 | −11.126 | 1.00 | 144.63 | MOL1 | C |
| ATOM | 3600 | CD | ARG | F | 42 | 29.711 | −53.788 | −9.723 | 1.00 | 150.26 | MOL1 | C |
| ATOM | 3601 | NE | ARG | F | 42 | 30.999 | −53.107 | −9.610 | 1.00 | 155.68 | MOL1 | N |
| ATOM | 3602 | CZ | ARG | F | 42 | 31.301 | −51.968 | −10.229 | 1.00 | 156.48 | MOL1 | C |
| ATOM | 3603 | NH1 | ARG | F | 42 | 30.404 | −51.376 | −11.009 | 1.00 | 157.71 | MOL1 | N |
| ATOM | 3604 | NH2 | ARG | F | 42 | 32.498 | −51.419 | −10.068 | 1.00 | 154.00 | MOL1 | N |
| ATOM | 3605 | C | ARG | F | 42 | 30.813 | −57.392 | −13.050 | 1.00 | 133.09 | MOL1 | C |
| ATOM | 3606 | O | ARG | F | 42 | 30.045 | −58.356 | −13.162 | 1.00 | 131.03 | MOL1 | O |
| ATOM | 3607 | N | ASN | F | 43 | 32.139 | −57.496 | −13.089 | 1.00 | 126.61 | MOL1 | N |
| ATOM | 3608 | CA | ASN | F | 43 | 32.849 | −58.769 | −13.192 | 1.00 | 119.43 | MOL1 | C |
| ATOM | 3609 | CB | ASN | F | 43 | 32.486 | −59.648 | −11.990 | 1.00 | 126.89 | MOL1 | C |
| ATOM | 3610 | CG | ASN | F | 43 | 32.751 | −58.959 | −10.661 | 1.00 | 132.70 | MOL1 | C |
| ATOM | 3611 | OD1 | ASN | F | 43 | 32.121 | −57.947 | −10.334 | 1.00 | 134.91 | MOL1 | O |
| ATOM | 3612 | ND2 | ASN | F | 43 | 33.690 | −59.503 | −9.887 | 1.00 | 135.04 | MOL1 | N |
| ATOM | 3613 | C | ASN | F | 43 | 32.713 | −59.604 | −14.468 | 1.00 | 109.71 | MOL1 | C |
| ATOM | 3614 | O | ASN | F | 43 | 33.448 | −60.582 | −14.636 | 1.00 | 105.52 | MOL1 | O |
| ATOM | 3615 | N | ILE | F | 44 | 31.794 | −59.256 | −15.365 | 1.00 | 98.14 | MOL1 | N |
| ATOM | 3616 | CA | ILE | F | 44 | 31.674 | −60.060 | −16.577 | 1.00 | 85.42 | MOL1 | C |
| ATOM | 3617 | CB | ILE | F | 44 | 30.413 | −59.714 | −17.403 | 1.00 | 80.25 | MOL1 | C |
| ATOM | 3618 | CG2 | ILE | F | 44 | 29.295 | −59.277 | −16.470 | 1.00 | 87.58 | MOL1 | C |
| ATOM | 3619 | CG1 | ILE | F | 44 | 30.710 | −58.630 | −18.427 | 1.00 | 69.53 | MOL1 | C |
| ATOM | 3620 | CD1 | ILE | F | 44 | 29.600 | −58.492 | −19.430 | 1.00 | 52.02 | MOL1 | C |
| ATOM | 3621 | C | ILE | F | 44 | 32.921 | −59.860 | −17.416 | 1.00 | 79.76 | MOL1 | C |
| ATOM | 3622 | O | ILE | F | 44 | 33.205 | −60.630 | −18.328 | 1.00 | 74.80 | MOL1 | O |
| ATOM | 3623 | N | GLU | F | 45 | 33.672 | −58.817 | −17.089 | 1.00 | 76.85 | MOL1 | N |
| ATOM | 3624 | CA | GLU | F | 45 | 34.911 | −58.545 | −17.784 | 1.00 | 75.75 | MOL1 | C |
| ATOM | 3625 | CB | GLU | F | 45 | 35.521 | −57.218 | −17.323 | 1.00 | 77.64 | MOL1 | C |
| ATOM | 3626 | CG | GLU | F | 45 | 35.481 | −56.970 | −15.822 | 1.00 | 79.53 | MOL1 | C |
| ATOM | 3627 | CD | GLU | F | 45 | 34.225 | −56.216 | −15.392 | 1.00 | 86.18 | MOL1 | C |
| ATOM | 3628 | OE1 | GLU | F | 45 | 34.088 | −55.899 | −14.186 | 1.00 | 83.20 | MOL1 | O |
| ATOM | 3629 | OE2 | GLU | F | 45 | 33.373 | −55.935 | −16.268 | 1.00 | 88.06 | MOL1 | O |
| ATOM | 3630 | C | GLU | F | 45 | 35.866 | −59.674 | −17.454 | 1.00 | 76.46 | MOL1 | C |
| ATOM | 3631 | O | GLU | F | 45 | 36.896 | −59.834 | −18.098 | 1.00 | 78.53 | MOL1 | O |
| ATOM | 3632 | N | SER | F | 46 | 35.515 | −60.467 | −16.448 | 1.00 | 78.34 | MOL1 | N |
| ATOM | 3633 | CA | SER | F | 46 | 36.370 | −61.572 | −16.038 | 1.00 | 78.87 | MOL1 | C |
| ATOM | 3634 | CB | SER | F | 46 | 36.734 | −61.432 | −14.561 | 1.00 | 85.43 | MOL1 | C |
| ATOM | 3635 | OG | SER | F | 46 | 37.743 | −62.365 | −14.209 | 1.00 | 97.78 | MOL1 | O |
| ATOM | 3636 | C | SER | F | 46 | 35.733 | −62.932 | −16.272 | 1.00 | 73.11 | MOL1 | C |
| ATOM | 3637 | O | SER | F | 46 | 36.406 | −63.957 | −16.206 | 1.00 | 72.67 | MOL1 | O |
| ATOM | 3638 | N | ARG | F | 47 | 34.433 | −62.931 | −16.537 | 1.00 | 69.60 | MOL1 | N |
| ATOM | 3639 | CA | ARG | F | 47 | 33.690 | −64.162 | −16.795 | 1.00 | 66.40 | MOL1 | C |
| ATOM | 3640 | CB | ARG | F | 47 | 32.225 | −64.007 | −16.371 | 1.00 | 71.81 | MOL1 | C |
| ATOM | 3641 | CG | ARG | F | 47 | 31.872 | −64.348 | −14.933 | 1.00 | 71.12 | MOL1 | C |
| ATOM | 3642 | CD | ARG | F | 47 | 30.491 | −63.785 | −14.607 | 1.00 | 70.56 | MOL1 | C |
| ATOM | 3643 | NE | ARG | F | 47 | 29.442 | −64.226 | −15.532 | 1.00 | 66.40 | MOL1 | N |
| ATOM | 3644 | CZ | ARG | F | 47 | 28.313 | −63.551 | −15.754 | 1.00 | 71.40 | MOL1 | C |
| ATOM | 3645 | NH1 | ARG | F | 47 | 28.080 | −62.397 | −15.128 | 1.00 | 69.35 | MOL1 | N |
| ATOM | 3646 | NH2 | ARG | F | 47 | 27.406 | −64.028 | −16.594 | 1.00 | 71.10 | MOL1 | N |
| ATOM | 3647 | C | ARG | F | 47 | 33.703 | −64.511 | −18.278 | 1.00 | 62.46 | MOL1 | C |
| ATOM | 3648 | O | ARG | F | 47 | 33.271 | −65.587 | −18.662 | 1.00 | 59.75 | MOL1 | O |
| ATOM | 3649 | N | SER | F | 48 | 34.174 | −63.594 | −19.114 | 1.00 | 62.70 | MOL1 | N |
| ATOM | 3650 | CA | SER | F | 48 | 34.206 | −63.839 | −20.555 | 1.00 | 60.28 | MOL1 | C |
| ATOM | 3651 | CB | SER | F | 48 | 34.254 | −62.517 | −21.324 | 1.00 | 63.61 | MOL1 | C |
| ATOM | 3652 | OG | SER | F | 48 | 34.348 | −62.744 | −22.724 | 1.00 | 61.71 | MOL1 | O |
| ATOM | 3653 | C | SER | F | 48 | 35.374 | −64.705 | −20.997 | 1.00 | 57.89 | MOL1 | C |
| ATOM | 3654 | O | SER | F | 48 | 36.443 | −64.684 | −20.393 | 1.00 | 60.33 | MOL1 | O |
| ATOM | 3655 | N | THR | F | 49 | 35.161 | −65.466 | −22.063 | 1.00 | 54.42 | MOL1 | N |
| ATOM | 3656 | CA | THR | F | 49 | 36.199 | −66.328 | −22.602 | 1.00 | 54.49 | MOL1 | C |
| ATOM | 3657 | CB | THR | F | 49 | 35.648 | −67.251 | −23.713 | 1.00 | 54.48 | MOL1 | C |
| ATOM | 3658 | OG1 | THR | F | 49 | 35.141 | −66.472 | −24.805 | 1.00 | 56.11 | MOL1 | O |
| ATOM | 3659 | CG2 | THR | F | 49 | 34.542 | −68.106 | −23.165 | 1.00 | 56.64 | MOL1 | C |
| ATOM | 3660 | C | THR | F | 49 | 37.314 | −65.462 | −23.177 | 1.00 | 56.33 | MOL1 | C |
| ATOM | 3661 | O | THR | F | 49 | 38.375 | −65.957 | −23.549 | 1.00 | 61.42 | MOL1 | O |
| ATOM | 3662 | N | SER | F | 50 | 37.055 | −64.162 | −23.246 | 1.00 | 54.40 | MOL1 | N |
| ATOM | 3663 | CA | SER | F | 50 | 38.005 | −63.187 | −23.757 | 1.00 | 47.36 | MOL1 | C |
| ATOM | 3664 | CB | SER | F | 50 | 37.578 | −62.740 | −25.154 | 1.00 | 46.06 | MOL1 | C |
| ATOM | 3665 | OG | SER | F | 50 | 36.163 | −62.674 | −25.266 | 1.00 | 42.87 | MOL1 | O |
| ATOM | 3666 | C | SER | F | 50 | 37.962 | −62.028 | −22.777 | 1.00 | 48.51 | MOL1 | C |
| ATOM | 3667 | O | SER | F | 50 | 37.405 | −60.978 | −23.056 | 1.00 | 49.58 | MOL1 | O |
| ATOM | 3668 | N | PRO | F | 51 | 38.544 | −62.229 | −21.594 | 1.00 | 50.16 | MOL1 | N |
| ATOM | 3669 | CD | PRO | F | 51 | 39.284 | −63.474 | −21.372 | 1.00 | 45.51 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 3670 | CA | PRO | F | 51 | 38.675 | −61.335 | −20.435 | 1.00 | 50.86 | MOL1 | C |
|------|------|-----|-----|---|----|--------|---------|---------|------|-------|------|---|
| ATOM | 3671 | CB | PRO | F | 51 | 39.525 | −62.151 | −19.476 | 1.00 | 50.48 | MOL1 | C |
| ATOM | 3672 | CG | PRO | F | 51 | 39.255 | −63.563 | −19.899 | 1.00 | 53.81 | MOL1 | C |
| ATOM | 3673 | C | PRO | F | 51 | 39.339 | −60.004 | −20.780 | 1.00 | 51.50 | MOL1 | C |
| ATOM | 3674 | O | PRO | F | 51 | 40.097 | −59.920 | −21.738 | 1.00 | 54.86 | MOL1 | O |
| ATOM | 3675 | N | TRP | F | 52 | 39.087 | −58.978 | −19.978 | 1.00 | 47.99 | MOL1 | N |
| ATOM | 3676 | CA | TRP | F | 52 | 39.646 | −57.673 | −20.254 | 1.00 | 46.10 | MOL1 | C |
| ATOM | 3677 | CB | TRP | F | 52 | 38.815 | −57.031 | −21.366 | 1.00 | 46.29 | MOL1 | C |
| ATOM | 3678 | CG | TRP | F | 52 | 37.361 | −56.685 | −21.016 | 1.00 | 45.96 | MOL1 | C |
| ATOM | 3679 | CD2 | TRP | F | 52 | 36.166 | −57.345 | −21.485 | 1.00 | 42.76 | MOL1 | C |
| ATOM | 3680 | CE2 | TRP | F | 52 | 35.061 | −56.624 | −20.980 | 1.00 | 39.10 | MOL1 | C |
| ATOM | 3681 | CE3 | TRP | F | 52 | 35.924 | −58.471 | −22.281 | 1.00 | 46.96 | MOL1 | C |
| ATOM | 3682 | CD1 | TRP | F | 52 | 36.930 | −55.626 | −20.264 | 1.00 | 42.72 | MOL1 | C |
| ATOM | 3683 | NE1 | TRP | F | 52 | 35.555 | −55.580 | −20.245 | 1.00 | 37.06 | MOL1 | N |
| ATOM | 3684 | CZ2 | TRP | F | 52 | 33.731 | −56.996 | −21.243 | 1.00 | 40.09 | MOL1 | C |
| ATOM | 3685 | CZ3 | TRP | F | 52 | 34.581 | −58.840 | −22.545 | 1.00 | 44.34 | MOL1 | C |
| ATOM | 3686 | CH2 | TRP | F | 52 | 33.514 | −58.103 | −22.024 | 1.00 | 34.21 | MOL1 | C |
| ATOM | 3687 | C | TRP | F | 52 | 39.664 | −56.789 | −19.018 | 1.00 | 51.45 | MOL1 | C |
| ATOM | 3688 | O | TRP | F | 52 | 38.757 | −56.873 | −18.198 | 1.00 | 59.40 | MOL1 | O |
| ATOM | 3689 | N | ASN | F | 53 | 40.686 | −55.949 | −18.865 | 1.00 | 55.05 | MOL1 | N |
| ATOM | 3690 | CA | ASN | F | 53 | 40.752 | −55.066 | −17.694 | 1.00 | 56.31 | MOL1 | C |
| ATOM | 3691 | CB | ASN | F | 53 | 42.187 | −54.834 | −17.234 | 1.00 | 68.05 | MOL1 | C |
| ATOM | 3692 | CG | ASN | F | 53 | 42.996 | −56.104 | −17.177 | 1.00 | 79.60 | MOL1 | C |
| ATOM | 3693 | OD1 | ASN | F | 53 | 44.233 | −56.063 | −17.167 | 1.00 | 89.95 | MOL1 | O |
| ATOM | 3694 | ND2 | ASN | F | 53 | 42.314 | −57.242 | −17.134 | 1.00 | 83.06 | MOL1 | N |
| ATOM | 3695 | C | ASN | F | 53 | 40.164 | −53.729 | −18.077 | 1.00 | 55.76 | MOL1 | C |
| ATOM | 3696 | O | ASN | F | 53 | 39.946 | −53.450 | −19.257 | 1.00 | 56.63 | MOL1 | O |
| ATOM | 3697 | N | TYR | F | 54 | 39.903 | −52.907 | −17.072 | 1.00 | 55.17 | MOL1 | N |
| ATOM | 3698 | CA | TYR | F | 54 | 39.351 | −51.581 | −17.291 | 1.00 | 59.25 | MOL1 | C |
| ATOM | 3699 | CB | TYR | F | 54 | 38.046 | −51.413 | −16.515 | 1.00 | 61.17 | MOL1 | C |
| ATOM | 3700 | CG | TYR | F | 54 | 36.839 | −52.002 | −17.210 | 1.00 | 65.10 | MOL1 | C |
| ATOM | 3701 | CD1 | TYR | F | 54 | 35.766 | −52.515 | −16.483 | 1.00 | 67.34 | MOL1 | C |
| ATOM | 3702 | CE1 | TYR | F | 54 | 34.649 | −53.049 | −17.125 | 1.00 | 68.18 | MOL1 | C |
| ATOM | 3703 | CD2 | TYR | F | 54 | 36.764 | −52.035 | −18.590 | 1.00 | 68.03 | MOL1 | C |
| ATOM | 3704 | CE2 | TYR | F | 54 | 35.654 | −52.564 | −19.239 | 1.00 | 72.89 | MOL1 | C |
| ATOM | 3705 | CZ | TYR | F | 54 | 34.601 | −53.071 | −18.507 | 1.00 | 68.10 | MOL1 | C |
| ATOM | 3706 | OH | TYR | F | 54 | 33.513 | −53.596 | −19.173 | 1.00 | 62.91 | MOL1 | O |
| ATOM | 3707 | C | TYR | F | 54 | 40.386 | −50.582 | −16.812 | 1.00 | 64.47 | MOL1 | C |
| ATOM | 3708 | O | TYR | F | 54 | 41.284 | −50.928 | −16.046 | 1.00 | 72.28 | MOL1 | O |
| ATOM | 3709 | N | THR | F | 55 | 40.268 | −49.346 | −17.269 | 1.00 | 67.47 | MOL1 | N |
| ATOM | 3710 | CA | THR | F | 55 | 41.212 | −48.304 | −16.897 | 1.00 | 70.95 | MOL1 | C |
| ATOM | 3711 | CB | THR | F | 55 | 42.319 | −48.181 | −17.946 | 1.00 | 76.93 | MOL1 | C |
| ATOM | 3712 | OG1 | THR | F | 55 | 42.509 | −49.447 | −18.591 | 1.00 | 81.50 | MOL1 | O |
| ATOM | 3713 | CG2 | THR | F | 55 | 43.618 | −47.754 | −17.291 | 1.00 | 85.52 | MOL1 | C |
| ATOM | 3714 | C | THR | F | 55 | 40.409 | −47.033 | −16.931 | 1.00 | 69.92 | MOL1 | C |
| ATOM | 3715 | O | THR | F | 55 | 39.929 | −46.649 | −17.996 | 1.00 | 73.31 | MOL1 | O |
| ATOM | 3716 | N | VAL | F | 56 | 40.256 | −46.370 | −15.794 | 1.00 | 67.42 | MOL1 | N |
| ATOM | 3717 | CA | VAL | F | 56 | 39.453 | −45.160 | −15.799 | 1.00 | 71.36 | MOL1 | C |
| ATOM | 3718 | CB | VAL | F | 56 | 38.452 | −45.142 | −14.632 | 1.00 | 73.26 | MOL1 | C |
| ATOM | 3719 | CG1 | VAL | F | 56 | 37.261 | −44.256 | −14.991 | 1.00 | 73.49 | MOL1 | C |
| ATOM | 3720 | CG2 | VAL | F | 56 | 38.005 | −46.558 | −14.303 | 1.00 | 76.29 | MOL1 | C |
| ATOM | 3721 | C | VAL | F | 56 | 40.269 | −43.888 | −15.750 | 1.00 | 71.95 | MOL1 | C |
| ATOM | 3722 | O | VAL | F | 56 | 41.329 | −43.832 | −15.135 | 1.00 | 78.43 | MOL1 | O |
| ATOM | 3723 | N | THR | F | 57 | 39.760 | −42.863 | −16.409 | 1.00 | 69.02 | MOL1 | N |
| ATOM | 3724 | CA | THR | F | 57 | 40.433 | −41.587 | −16.437 | 1.00 | 72.75 | MOL1 | C |
| ATOM | 3725 | CB | THR | F | 57 | 40.886 | −41.263 | −17.872 | 1.00 | 78.64 | MOL1 | C |
| ATOM | 3726 | OG1 | THR | F | 57 | 39.783 | −40.762 | −18.640 | 1.00 | 77.06 | MOL1 | O |
| ATOM | 3727 | CG2 | THR | F | 57 | 41.392 | −42.536 | −18.539 | 1.00 | 79.68 | MOL1 | C |
| ATOM | 3728 | C | THR | F | 57 | 39.395 | −40.585 | −15.977 | 1.00 | 72.29 | MOL1 | C |
| ATOM | 3729 | O | THR | F | 57 | 38.227 | −40.685 | −16.358 | 1.00 | 71.48 | MOL1 | O |
| ATOM | 3730 | N | TRP | F | 58 | 39.797 | −39.632 | −15.147 | 1.00 | 68.75 | MOL1 | N |
| ATOM | 3731 | CA | TRP | F | 58 | 38.842 | −38.646 | −14.685 | 1.00 | 67.42 | MOL1 | C |
| ATOM | 3732 | CB | TRP | F | 58 | 38.601 | −38.810 | −13.178 | 1.00 | 76.07 | MOL1 | C |
| ATOM | 3733 | CG | TRP | F | 58 | 37.579 | −37.852 | −12.651 | 1.00 | 87.01 | MOL1 | C |
| ATOM | 3734 | CD2 | TRP | F | 58 | 37.832 | −36.661 | −11.892 | 1.00 | 92.81 | MOL1 | C |
| ATOM | 3735 | CE2 | TRP | F | 58 | 36.597 | −35.995 | −11.735 | 1.00 | 94.18 | MOL1 | C |
| ATOM | 3736 | CE3 | TRP | F | 58 | 38.984 | −36.090 | −11.334 | 1.00 | 90.84 | MOL1 | C |
| ATOM | 3737 | CD1 | TRP | F | 58 | 36.236 | −37.866 | −12.903 | 1.00 | 86.10 | MOL1 | C |
| ATOM | 3738 | NE1 | TRP | F | 58 | 35.640 | −36.751 | −12.360 | 1.00 | 92.26 | MOL1 | N |
| ATOM | 3739 | CZ2 | TRP | F | 58 | 36.482 | −34.788 | −11.048 | 1.00 | 95.08 | MOL1 | C |
| ATOM | 3740 | CZ3 | TRP | F | 58 | 38.867 | −34.894 | −10.654 | 1.00 | 91.61 | MOL1 | C |
| ATOM | 3741 | CH2 | TRP | F | 58 | 37.626 | −34.254 | −10.517 | 1.00 | 95.27 | MOL1 | C |
| ATOM | 3742 | C | TRP | F | 58 | 39.304 | −37.233 | −15.006 | 1.00 | 62.54 | MOL1 | C |
| ATOM | 3743 | O | TRP | F | 58 | 40.418 | −36.851 | −14.682 | 1.00 | 66.07 | MOL1 | O |
| ATOM | 3744 | N | ASP | F | 59 | 38.447 | −36.468 | −15.666 | 1.00 | 62.09 | MOL1 | N |
| ATOM | 3745 | CA | ASP | F | 59 | 38.758 | −35.088 | −16.018 | 1.00 | 68.68 | MOL1 | C |
| ATOM | 3746 | CB | ASP | F | 59 | 38.986 | −34.921 | −17.517 | 1.00 | 71.70 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 3747 | CG | ASP | F | 59 | 39.302 | −33.480 | −17.896 | 1.00 | 73.25 | MOL1 | C |
|---|---|---|---|---|---|---|---|---|---|---|---|---|
| ATOM | 3748 | OD1 | ASP | F | 59 | 38.726 | −32.549 | −17.286 | 1.00 | 64.92 | MOL1 | O |
| ATOM | 3749 | OD2 | ASP | F | 59 | 40.125 | −33.281 | −18.815 | 1.00 | 80.05 | MOL1 | O |
| ATOM | 3750 | C | ASP | F | 59 | 37.580 | −34.221 | −15.648 | 1.00 | 74.69 | MOL1 | C |
| ATOM | 3751 | O | ASP | F | 59 | 36.504 | −34.332 | −16.247 | 1.00 | 74.80 | MOL1 | O |
| ATOM | 3752 | N | PRO | F | 60 | 37.768 | −33.335 | −14.664 | 1.00 | 78.98 | MOL1 | N |
| ATOM | 3753 | CD | PRO | F | 60 | 38.998 | −33.204 | −13.869 | 1.00 | 79.46 | MOL1 | C |
| ATOM | 3754 | CA | PRO | F | 60 | 36.738 | −32.415 | −14.178 | 1.00 | 80.65 | MOL1 | C |
| ATOM | 3755 | CB | PRO | F | 60 | 37.440 | −31.694 | −13.026 | 1.00 | 80.21 | MOL1 | C |
| ATOM | 3756 | CG | PRO | F | 60 | 38.886 | −31.799 | −13.381 | 1.00 | 80.21 | MOL1 | C |
| ATOM | 3757 | C | PRO | F | 60 | 36.164 | −31.457 | −15.233 | 1.00 | 81.09 | MOL1 | C |
| ATOM | 3758 | O | PRO | F | 60 | 35.046 | −30.951 | −15.067 | 1.00 | 83.18 | MOL1 | O |
| ATOM | 3759 | N | ASN | F | 61 | 36.912 | −31.217 | −16.309 | 1.00 | 76.42 | MOL1 | N |
| ATOM | 3760 | CA | ASN | F | 61 | 36.438 | −30.336 | −17.372 | 1.00 | 78.59 | MOL1 | C |
| ATOM | 3761 | CB | ASN | F | 61 | 37.543 | −29.386 | −17.828 | 1.00 | 90.58 | MOL1 | C |
| ATOM | 3762 | CG | ASN | F | 61 | 37.940 | −28.403 | −16.750 | 1.00 | 103.85 | MOL1 | C |
| ATOM | 3763 | OD1 | ASN | F | 61 | 37.083 | −27.799 | −16.097 | 1.00 | 106.74 | MOL1 | O |
| ATOM | 3764 | ND2 | ASN | F | 61 | 39.246 | −28.226 | −16.559 | 1.00 | 111.58 | MOL1 | N |
| ATOM | 3765 | C | ASN | F | 61 | 35.966 | −31.145 | −18.558 | 1.00 | 74.54 | MOL1 | C |
| ATOM | 3766 | O | ASN | F | 61 | 36.094 | −30.719 | −19.705 | 1.00 | 73.22 | MOL1 | O |
| ATOM | 3767 | N | ARG | F | 62 | 35.410 | −32.313 | −18.275 | 1.00 | 72.69 | MOL1 | N |
| ATOM | 3768 | CA | ARG | F | 62 | 34.933 | −33.189 | −19.328 | 1.00 | 72.28 | MOL1 | C |
| ATOM | 3769 | CB | ARG | F | 62 | 36.011 | −34.227 | −19.647 | 1.00 | 71.86 | MOL1 | C |
| ATOM | 3770 | CG | ARG | F | 62 | 35.657 | −35.181 | −20.775 | 1.00 | 73.66 | MOL1 | C |
| ATOM | 3771 | CD | ARG | F | 62 | 36.784 | −36.174 | −21.045 | 1.00 | 70.50 | MOL1 | C |
| ATOM | 3772 | NE | ARG | F | 62 | 37.021 | −37.058 | −19.909 | 1.00 | 63.47 | MOL1 | N |
| ATOM | 3773 | CZ | ARG | F | 62 | 37.876 | −38.076 | −19.922 | 1.00 | 62.97 | MOL1 | C |
| ATOM | 3774 | NH1 | ARG | F | 62 | 38.580 | −38.337 | −21.017 | 1.00 | 67.00 | MOL1 | N |
| ATOM | 3775 | NH2 | ARG | F | 62 | 38.017 | −38.843 | −18.849 | 1.00 | 58.63 | MOL1 | N |
| ATOM | 3776 | C | ARG | F | 62 | 33.653 | −33.897 | −18.917 | 1.00 | 72.52 | MOL1 | C |
| ATOM | 3777 | O | ARG | F | 62 | 33.569 | −34.453 | −17.820 | 1.00 | 74.93 | MOL1 | O |
| ATOM | 3778 | N | TYR | F | 63 | 32.648 | −33.868 | −19.785 | 1.00 | 68.99 | MOL1 | N |
| ATOM | 3779 | CA | TYR | F | 63 | 31.416 | −34.567 | −19.477 | 1.00 | 66.19 | MOL1 | C |
| ATOM | 3780 | CB | TYR | F | 63 | 30.227 | −33.630 | −19.378 | 1.00 | 74.78 | MOL1 | C |
| ATOM | 3781 | CG | TYR | F | 63 | 28.946 | −34.400 | −19.155 | 1.00 | 81.35 | MOL1 | C |
| ATOM | 3782 | CD1 | TYR | F | 63 | 27.948 | −34.430 | −20.117 | 1.00 | 83.49 | MOL1 | C |
| ATOM | 3783 | CE1 | TYR | F | 63 | 26.796 | −35.179 | −19.930 | 1.00 | 88.75 | MOL1 | C |
| ATOM | 3784 | CD2 | TYR | F | 63 | 28.759 | −35.137 | −17.994 | 1.00 | 87.18 | MOL1 | C |
| ATOM | 3785 | CE2 | TYR | F | 63 | 27.614 | −35.889 | −17.795 | 1.00 | 92.81 | MOL1 | C |
| ATOM | 3786 | CZ | TYR | F | 63 | 26.636 | −35.908 | −18.766 | 1.00 | 92.83 | MOL1 | C |
| ATOM | 3787 | OH | TYR | F | 63 | 25.506 | −36.673 | −18.569 | 1.00 | 96.03 | MOL1 | O |
| ATOM | 3788 | C | TYR | F | 63 | 31.130 | −35.575 | −20.552 | 1.00 | 63.85 | MOL1 | C |
| ATOM | 3789 | O | TYR | F | 63 | 31.003 | −35.223 | −21.725 | 1.00 | 67.96 | MOL1 | O |
| ATOM | 3790 | N | PRO | F | 64 | 31.055 | −36.853 | −20.171 | 1.00 | 58.19 | MOL1 | N |
| ATOM | 3791 | CD | PRO | F | 64 | 30.733 | −37.996 | −21.039 | 1.00 | 62.74 | MOL1 | C |
| ATOM | 3792 | CA | PRO | F | 64 | 31.237 | −37.303 | −18.798 | 1.00 | 57.91 | MOL1 | C |
| ATOM | 3793 | CB | PRO | F | 64 | 30.807 | −38.758 | −18.859 | 1.00 | 66.16 | MOL1 | C |
| ATOM | 3794 | CG | PRO | F | 64 | 31.243 | −39.160 | −20.219 | 1.00 | 63.83 | MOL1 | C |
| ATOM | 3795 | C | PRO | F | 64 | 32.668 | −37.167 | −18.319 | 1.00 | 60.20 | MOL1 | C |
| ATOM | 3796 | O | PRO | F | 64 | 33.603 | −37.219 | −19.107 | 1.00 | 55.01 | MOL1 | O |
| ATOM | 3797 | N | SER | F | 65 | 32.817 | −37.015 | −17.008 | 1.00 | 66.64 | MOL1 | N |
| ATOM | 3798 | CA | SER | F | 65 | 34.111 | −36.862 | −16.349 | 1.00 | 66.34 | MOL1 | C |
| ATOM | 3799 | CB | SER | F | 65 | 33.875 | −36.451 | −14.907 | 1.00 | 75.37 | MOL1 | C |
| ATOM | 3800 | OG | SER | F | 65 | 32.951 | −37.347 | −14.296 | 1.00 | 92.37 | MOL1 | O |
| ATOM | 3801 | C | SER | F | 65 | 34.950 | −38.137 | −16.375 | 1.00 | 63.39 | MOL1 | C |
| ATOM | 3802 | O | SER | F | 65 | 36.153 | −38.086 | −16.623 | 1.00 | 65.34 | MOL1 | O |
| ATOM | 3803 | N | GLU | F | 66 | 34.324 | −39.276 | −16.090 | 1.00 | 58.70 | MOL1 | N |
| ATOM | 3804 | CA | GLU | F | 66 | 35.033 | −40.551 | −16.106 | 1.00 | 60.70 | MOL1 | C |
| ATOM | 3805 | CB | GLU | F | 66 | 34.458 | −41.543 | −15.073 | 1.00 | 69.86 | MOL1 | C |
| ATOM | 3806 | CG | GLU | F | 66 | 34.838 | −41.313 | −13.593 | 1.00 | 97.36 | MOL1 | C |
| ATOM | 3807 | CD | GLU | F | 66 | 33.864 | −40.401 | −12.812 | 1.00 | 111.30 | MOL1 | C |
| ATOM | 3808 | OE1 | GLU | F | 66 | 34.168 | −40.083 | −11.635 | 1.00 | 113.19 | MOL1 | O |
| ATOM | 3809 | OE2 | GLU | F | 66 | 32.802 | −40.008 | −13.357 | 1.00 | 118.22 | MOL1 | O |
| ATOM | 3810 | C | GLU | F | 66 | 34.898 | −41.177 | −17.486 | 1.00 | 61.75 | MOL1 | C |
| ATOM | 3811 | O | GLU | F | 66 | 33.811 | −41.182 | −18.070 | 1.00 | 65.70 | MOL1 | O |
| ATOM | 3812 | N | VAL | F | 67 | 36.005 | −41.684 | −18.020 | 1.00 | 59.43 | MOL1 | N |
| ATOM | 3813 | CA | VAL | F | 67 | 35.980 | −42.357 | −19.313 | 1.00 | 54.35 | MOL1 | C |
| ATOM | 3814 | CB | VAL | F | 67 | 36.684 | −41.569 | −20.407 | 1.00 | 47.87 | MOL1 | C |
| ATOM | 3815 | CG1 | VAL | F | 67 | 36.666 | −42.369 | −21.679 | 1.00 | 45.44 | MOL1 | C |
| ATOM | 3816 | CG2 | VAL | F | 67 | 35.985 | −40.265 | −20.640 | 1.00 | 49.36 | MOL1 | C |
| ATOM | 3817 | C | VAL | F | 67 | 36.725 | −43.654 | −19.122 | 1.00 | 56.91 | MOL1 | C |
| ATOM | 3818 | O | VAL | F | 67 | 37.925 | −43.648 | −18.848 | 1.00 | 59.77 | MOL1 | O |
| ATOM | 3819 | N | VAL | F | 68 | 36.010 | −44.762 | −19.266 | 1.00 | 54.74 | MOL1 | N |
| ATOM | 3820 | CA | VAL | F | 68 | 36.603 | −46.067 | −19.074 | 1.00 | 53.09 | MOL1 | C |
| ATOM | 3821 | CB | VAL | F | 68 | 35.673 | −46.929 | −18.297 | 1.00 | 55.87 | MOL1 | C |
| ATOM | 3822 | CG1 | VAL | F | 68 | 36.351 | −48.230 | −17.923 | 1.00 | 58.77 | MOL1 | C |
| ATOM | 3823 | CG2 | VAL | F | 68 | 35.217 | −46.170 | −17.103 | 1.00 | 65.85 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 3824 | C | VAL | F | 68 | 36.941 | −46.794 | −20.358 | 1.00 | 54.55 | MOL1 | C |
|---|---|---|---|---|---|---|---|---|---|---|---|---|
| ATOM | 3825 | O | VAL | F | 68 | 36.078 | −46.982 | −21.232 | 1.00 | 52.08 | MOL1 | O |
| ATOM | 3826 | N | GLN | F | 69 | 38.199 | −47.227 | −20.438 | 1.00 | 51.16 | MOL1 | N |
| ATOM | 3827 | CA | GLN | F | 69 | 38.722 | −47.943 | −21.590 | 1.00 | 49.53 | MOL1 | C |
| ATOM | 3828 | CB | GLN | F | 69 | 39.974 | −47.243 | −22.097 | 1.00 | 50.63 | MOL1 | C |
| ATOM | 3829 | CG | GLN | F | 69 | 39.772 | −45.810 | −22.539 | 1.00 | 45.74 | MOL1 | C |
| ATOM | 3830 | CD | GLN | F | 69 | 39.337 | −45.726 | −23.977 | 1.00 | 48.55 | MOL1 | C |
| ATOM | 3831 | OE1 | GLN | F | 69 | 39.230 | −46.743 | −24.672 | 1.00 | 52.21 | MOL1 | O |
| ATOM | 3832 | NE2 | GLN | F | 69 | 39.092 | −44.512 | −24.441 | 1.00 | 40.51 | MOL1 | N |
| ATOM | 3833 | C | GLN | F | 69 | 39.081 | −49.352 | −21.170 | 1.00 | 50.82 | MOL1 | C |
| ATOM | 3834 | O | GLN | F | 69 | 39.650 | −49.548 | −20.096 | 1.00 | 51.37 | MOL1 | O |
| ATOM | 3835 | N | ALA | F | 70 | 38.758 | −50.321 | −22.024 | 1.00 | 52.64 | MOL1 | N |
| ATOM | 3836 | CA | ALA | F | 70 | 39.037 | −51.736 | −21.767 | 1.00 | 57.49 | MOL1 | C |
| ATOM | 3837 | CB | ALA | F | 70 | 37.879 | −52.577 | −22.266 | 1.00 | 55.06 | MOL1 | C |
| ATOM | 3838 | C | ALA | F | 70 | 40.321 | −52.181 | −22.460 | 1.00 | 57.95 | MOL1 | C |
| ATOM | 3839 | O | ALA | F | 70 | 40.815 | −51.489 | −23.341 | 1.00 | 66.12 | MOL1 | O |
| ATOM | 3840 | N | GLN | F | 71 | 40.850 | −53.339 | −22.077 | 1.00 | 55.45 | MOL1 | N |
| ATOM | 3841 | CA | GLN | F | 71 | 42.067 | −53.859 | −22.690 | 1.00 | 51.57 | MOL1 | C |
| ATOM | 3842 | CB | GLN | F | 71 | 43.286 | −53.410 | −21.893 | 1.00 | 57.65 | MOL1 | C |
| ATOM | 3843 | CG | GLN | F | 71 | 43.255 | −51.991 | −21.378 | 1.00 | 73.00 | MOL1 | C |
| ATOM | 3844 | CD | GLN | F | 71 | 44.614 | −51.574 | −20.838 | 1.00 | 89.88 | MOL1 | C |
| ATOM | 3845 | OE1 | GLN | F | 71 | 45.539 | −51.263 | −21.603 | 1.00 | 87.49 | MOL1 | O |
| ATOM | 3846 | NE2 | GLN | F | 71 | 44.751 | −51.590 | −19.512 | 1.00 | 98.59 | MOL1 | N |
| ATOM | 3847 | C | GLN | F | 71 | 42.030 | −55.376 | −22.649 | 1.00 | 45.36 | MOL1 | C |
| ATOM | 3848 | O | GLN | F | 71 | 42.037 | −55.923 | −21.563 | 1.00 | 49.02 | MOL1 | O |
| ATOM | 3849 | N | CYS | F | 72 | 42.007 | −56.067 | −23.787 | 1.00 | 40.81 | MOL1 | N |
| ATOM | 3850 | CA | CYS | F | 72 | 41.987 | −57.536 | −23.735 | 1.00 | 46.47 | MOL1 | C |
| ATOM | 3851 | C | CYS | F | 72 | 43.147 | −58.100 | −22.906 | 1.00 | 50.35 | MOL1 | C |
| ATOM | 3852 | O | CYS | F | 72 | 44.312 | −57.779 | −23.134 | 1.00 | 49.99 | MOL1 | O |
| ATOM | 3853 | CB | CYS | F | 72 | 42.036 | −58.167 | −25.130 | 1.00 | 49.20 | MOL1 | C |
| ATOM | 3854 | SG | CYS | F | 72 | 40.821 | −57.505 | −26.309 | 1.00 | 63.66 | MOL1 | S |
| ATOM | 3855 | N | ARG | F | 73 | 42.808 | −58.960 | −21.951 | 1.00 | 58.42 | MOL1 | N |
| ATOM | 3856 | CA | ARG | F | 73 | 43.772 | −59.571 | −21.043 | 1.00 | 60.73 | MOL1 | C |
| ATOM | 3857 | CB | ARG | F | 73 | 43.019 | −60.283 | −19.910 | 1.00 | 66.85 | MOL1 | C |
| ATOM | 3858 | CG | ARG | F | 73 | 43.140 | −59.651 | −18.519 | 1.00 | 75.53 | MOL1 | C |
| ATOM | 3859 | CD | ARG | F | 73 | 42.787 | −60.677 | −17.422 | 1.00 | 86.65 | MOL1 | C |
| ATOM | 3860 | NE | ARG | F | 73 | 43.657 | −61.858 | −17.489 | 1.00 | 99.91 | MOL1 | N |
| ATOM | 3861 | CZ | ARG | F | 73 | 43.302 | −63.086 | −17.111 | 1.00 | 102.54 | MOL1 | C |
| ATOM | 3862 | NH1 | ARG | F | 73 | 42.085 | −63.302 | −16.631 | 1.00 | 103.80 | MOL1 | N |
| ATOM | 3863 | NH2 | ARG | F | 73 | 44.153 | −64.103 | −17.235 | 1.00 | 99.72 | MOL1 | N |
| ATOM | 3864 | C | ARG | F | 73 | 44.750 | −60.554 | −21.685 | 1.00 | 61.26 | MOL1 | C |
| ATOM | 3865 | O | ARG | F | 73 | 45.881 | −60.682 | −21.226 | 1.00 | 62.79 | MOL1 | O |
| ATOM | 3866 | N | ASN | F | 74 | 44.325 | −61.251 | −22.732 | 1.00 | 60.98 | MOL1 | N |
| ATOM | 3867 | CA | ASN | F | 74 | 45.201 | −62.223 | −23.374 | 1.00 | 64.24 | MOL1 | C |
| ATOM | 3868 | CB | ASN | F | 74 | 44.846 | −63.619 | −22.878 | 1.00 | 75.85 | MOL1 | C |
| ATOM | 3869 | CG | ASN | F | 74 | 45.008 | −63.752 | −21.367 | 1.00 | 86.27 | MOL1 | C |
| ATOM | 3870 | OD1 | ASN | F | 74 | 44.398 | −64.618 | −20.733 | 1.00 | 96.59 | MOL1 | O |
| ATOM | 3871 | ND2 | ASN | F | 74 | 45.845 | −62.900 | −20.786 | 1.00 | 87.18 | MOL1 | N |
| ATOM | 3872 | C | ASN | F | 74 | 45.093 | −62.147 | −24.882 | 1.00 | 61.52 | MOL1 | C |
| ATOM | 3873 | O | ASN | F | 74 | 44.317 | −61.362 | −25.396 | 1.00 | 65.30 | MOL1 | O |
| ATOM | 3874 | N | LEU | F | 75 | 45.880 | −62.940 | −25.596 | 1.00 | 59.68 | MOL1 | N |
| ATOM | 3875 | CA | LEU | F | 75 | 45.820 | −62.906 | −27.049 | 1.00 | 57.37 | MOL1 | C |
| ATOM | 3876 | CB | LEU | F | 75 | 47.182 | −63.191 | −27.668 | 1.00 | 53.74 | MOL1 | C |
| ATOM | 3877 | CG | LEU | F | 75 | 48.268 | −62.124 | −27.616 | 1.00 | 53.32 | MOL1 | C |
| ATOM | 3878 | CD1 | LEU | F | 75 | 49.181 | −62.346 | −28.811 | 1.00 | 45.91 | MOL1 | C |
| ATOM | 3879 | CD2 | LEU | F | 75 | 47.671 | −60.728 | −27.665 | 1.00 | 48.65 | MOL1 | C |
| ATOM | 3880 | C | LEU | F | 75 | 44.831 | −63.920 | −27.570 | 1.00 | 62.93 | MOL1 | C |
| ATOM | 3881 | O | LEU | F | 75 | 44.110 | −63.657 | −28.525 | 1.00 | 64.55 | MOL1 | O |
| ATOM | 3882 | N | GLY | F | 76 | 44.816 | −65.096 | −26.956 | 1.00 | 71.53 | MOL1 | N |
| ATOM | 3883 | CA | GLY | F | 76 | 43.887 | −66.131 | −27.379 | 1.00 | 78.22 | MOL1 | C |
| ATOM | 3884 | C | GLY | F | 76 | 42.646 | −66.040 | −26.519 | 1.00 | 82.80 | MOL1 | C |
| ATOM | 3885 | O | GLY | F | 76 | 42.425 | −65.013 | −25.862 | 1.00 | 85.29 | MOL1 | O |
| ATOM | 3886 | N | CYS | F | 77 | 41.836 | −67.095 | −26.517 | 1.00 | 81.74 | MOL1 | N |
| ATOM | 3887 | CA | CYS | F | 77 | 40.624 | −67.120 | −25.707 | 1.00 | 84.88 | MOL1 | C |
| ATOM | 3888 | C | CYS | F | 77 | 40.850 | −68.125 | −24.597 | 1.00 | 85.30 | MOL1 | C |
| ATOM | 3889 | O | CYS | F | 77 | 41.829 | −68.859 | −24.622 | 1.00 | 90.02 | MOL1 | O |
| ATOM | 3890 | CB | CYS | F | 77 | 39.437 | −67.525 | −26.568 | 1.00 | 84.73 | MOL1 | C |
| ATOM | 3891 | SG | CYS | F | 77 | 39.328 | −66.515 | −28.080 | 1.00 | 95.89 | MOL1 | S |
| ATOM | 3892 | N | ILE | F | 78 | 39.944 | −68.165 | −23.634 | 1.00 | 87.14 | MOL1 | N |
| ATOM | 3893 | CA | ILE | F | 78 | 40.065 | −69.061 | −22.500 | 1.00 | 95.81 | MOL1 | C |
| ATOM | 3894 | CB | ILE | F | 78 | 39.979 | −68.213 | −21.219 | 1.00 | 94.33 | MOL1 | C |
| ATOM | 3895 | CG2 | ILE | F | 78 | 39.306 | −68.996 | −20.107 | 1.00 | 97.42 | MOL1 | C |
| ATOM | 3896 | CG1 | ILE | F | 78 | 41.372 | −67.662 | −20.891 | 1.00 | 94.21 | MOL1 | C |
| ATOM | 3897 | CD1 | ILE | F | 78 | 41.471 | −66.931 | −19.555 | 1.00 | 94.35 | MOL1 | C |
| ATOM | 3898 | C | ILE | F | 78 | 39.002 | −70.175 | −22.483 | 1.00 | 103.80 | MOL1 | C |
| ATOM | 3899 | O | ILE | F | 78 | 37.848 | −69.926 | −22.812 | 1.00 | 106.45 | MOL1 | O |
| ATOM | 3900 | N | ASN | F | 79 | 39.395 | −71.394 | −22.106 | 1.00 | 112.68 | MOL1 | N |

TABLE 1-continued

The atomic coordinates of IL17F in complex with 496 Fab
(H32; a = 189.4; b = 189.4; c = 490.9, α, β = 90°; γ = 120°)

| ATOM | 3901 | CA | ASN | F | 79 | 38.471 | −72.535 | −22.043 | 1.00 | 122.59 | MOL1 | C |
|---|---|---|---|---|---|---|---|---|---|---|---|---|
| ATOM | 3902 | CB | ASN | F | 79 | 39.182 | −73.837 | −22.434 | 1.00 | 129.08 | MOL1 | C |
| ATOM | 3903 | CG | ASN | F | 79 | 39.563 | −73.893 | −23.900 | 1.00 | 139.42 | MOL1 | C |
| ATOM | 3904 | OD1 | ASN | F | 79 | 38.707 | −73.800 | −24.788 | 1.00 | 144.42 | MOL1 | O |
| ATOM | 3905 | ND2 | ASN | F | 79 | 40.857 | −74.059 | −24.165 | 1.00 | 143.29 | MOL1 | N |
| ATOM | 3906 | C | ASN | F | 79 | 37.907 | −72.729 | −20.637 | 1.00 | 126.34 | MOL1 | C |
| ATOM | 3907 | O | ASN | F | 79 | 37.789 | −71.778 | −19.861 | 1.00 | 124.78 | MOL1 | O |
| ATOM | 3908 | N | ALA | F | 80 | 37.566 | −73.981 | −20.326 | 1.00 | 130.91 | MOL1 | N |
| ATOM | 3909 | CA | ALA | F | 80 | 37.036 | −74.346 | −19.014 | 1.00 | 133.29 | MOL1 | C |
| ATOM | 3910 | CB | ALA | F | 80 | 36.611 | −75.812 | −19.003 | 1.00 | 131.58 | MOL1 | C |
| ATOM | 3911 | C | ALA | F | 80 | 38.132 | −74.114 | −17.987 | 1.00 | 135.12 | MOL1 | C |
| ATOM | 3912 | O | ALA | F | 80 | 38.652 | −75.064 | −17.396 | 1.00 | 132.96 | MOL1 | O |
| ATOM | 3913 | N | GLN | F | 81 | 38.484 | −72.844 | −17.796 | 1.00 | 139.60 | MOL1 | N |
| ATOM | 3914 | CA | GLN | F | 81 | 39.526 | −72.455 | −16.852 | 1.00 | 142.21 | MOL1 | C |
| ATOM | 3915 | CB | GLN | F | 81 | 39.186 | −73.013 | −15.463 | 1.00 | 144.86 | MOL1 | C |
| ATOM | 3916 | CG | GLN | F | 81 | 40.143 | −72.625 | −14.348 | 1.00 | 147.70 | MOL1 | C |
| ATOM | 3917 | CD | GLN | F | 81 | 39.934 | −73.457 | −13.094 | 1.00 | 151.40 | MOL1 | C |
| ATOM | 3918 | OE1 | GLN | F | 81 | 40.540 | −73.195 | −12.054 | 1.00 | 154.30 | MOL1 | O |
| ATOM | 3919 | NE2 | GLN | F | 81 | 39.077 | −74.470 | −13.190 | 1.00 | 150.41 | MOL1 | N |
| ATOM | 3920 | C | GLN | F | 81 | 40.860 | −73.028 | −17.330 | 1.00 | 140.95 | MOL1 | C |
| ATOM | 3921 | O | GLN | F | 81 | 41.834 | −73.066 | −16.579 | 1.00 | 143.16 | MOL1 | O |
| ATOM | 3922 | N | GLY | F | 82 | 40.899 | −73.459 | −18.589 | 1.00 | 137.86 | MOL1 | N |
| ATOM | 3923 | CA | GLY | F | 82 | 42.101 | −74.066 | −19.130 | 1.00 | 132.06 | MOL1 | C |
| ATOM | 3924 | C | GLY | F | 82 | 43.000 | −73.207 | −19.990 | 1.00 | 126.42 | MOL1 | C |
| ATOM | 3925 | O | GLY | F | 82 | 43.433 | −73.635 | −21.055 | 1.00 | 124.30 | MOL1 | O |
| ATOM | 3926 | N | LYS | F | 83 | 43.282 | −71.997 | −19.527 | 1.00 | 123.62 | MOL1 | N |
| ATOM | 3927 | CA | LYS | F | 83 | 44.169 | −71.077 | −20.237 | 1.00 | 121.91 | MOL1 | C |
| ATOM | 3928 | CB | LYS | F | 83 | 45.638 | −71.440 | −19.938 | 1.00 | 128.60 | MOL1 | C |
| ATOM | 3929 | CG | LYS | F | 83 | 46.659 | −70.323 | −20.198 | 1.00 | 130.49 | MOL1 | C |
| ATOM | 3930 | CD | LYS | F | 83 | 48.091 | −70.760 | −19.873 | 1.00 | 133.53 | MOL1 | C |
| ATOM | 3931 | CE | LYS | F | 83 | 48.585 | −71.854 | −20.823 | 1.00 | 134.47 | MOL1 | C |
| ATOM | 3932 | NZ | LYS | F | 83 | 50.000 | −72.257 | −20.552 | 1.00 | 131.10 | MOL1 | N |
| ATOM | 3933 | C | LYS | F | 83 | 43.965 | −70.982 | −21.756 | 1.00 | 115.06 | MOL1 | C |
| ATOM | 3934 | O | LYS | F | 83 | 43.163 | −71.708 | −22.353 | 1.00 | 110.32 | MOL1 | O |
| ATOM | 3935 | N | GLU | F | 84 | 44.729 | −70.073 | −22.358 | 1.00 | 109.95 | MOL1 | N |
| ATOM | 3936 | CA | GLU | F | 84 | 44.687 | −69.776 | −23.786 | 1.00 | 102.67 | MOL1 | C |
| ATOM | 3937 | CB | GLU | F | 84 | 45.936 | −68.982 | −24.206 | 1.00 | 106.26 | MOL1 | C |
| ATOM | 3938 | CG | GLU | F | 84 | 45.882 | −67.490 | −23.901 | 1.00 | 110.45 | MOL1 | C |
| ATOM | 3939 | CD | GLU | F | 84 | 47.099 | −66.735 | −24.414 | 1.00 | 114.20 | MOL1 | C |
| ATOM | 3940 | OE1 | GLU | F | 84 | 47.116 | −65.489 | −24.292 | 1.00 | 116.18 | MOL1 | O |
| ATOM | 3941 | OE2 | GLU | F | 84 | 48.037 | −67.383 | −24.935 | 1.00 | 116.06 | MOL1 | O |
| ATOM | 3942 | C | GLU | F | 84 | 44.511 | −70.921 | −24.758 | 1.00 | 93.83 | MOL1 | C |
| ATOM | 3943 | O | GLU | F | 84 | 44.848 | −72.067 | −24.482 | 1.00 | 91.06 | MOL1 | O |
| ATOM | 3944 | N | ASP | F | 85 | 43.956 | −70.567 | −25.909 | 1.00 | 87.09 | MOL1 | N |
| ATOM | 3945 | CA | ASP | F | 85 | 43.753 | −71.489 | −27.007 | 1.00 | 84.02 | MOL1 | C |
| ATOM | 3946 | CB | ASP | F | 85 | 42.350 | −72.054 | −27.032 | 1.00 | 79.98 | MOL1 | C |
| ATOM | 3947 | CG | ASP | F | 85 | 42.134 | −72.933 | −28.234 | 1.00 | 81.68 | MOL1 | C |
| ATOM | 3948 | OD1 | ASP | F | 85 | 42.464 | −74.132 | −28.154 | 1.00 | 92.83 | MOL1 | O |
| ATOM | 3949 | OD2 | ASP | F | 85 | 41.674 | −72.420 | −29.272 | 1.00 | 73.58 | MOL1 | O |
| ATOM | 3950 | C | ASP | F | 85 | 43.964 | −70.688 | −28.283 | 1.00 | 80.46 | MOL1 | C |
| ATOM | 3951 | O | ASP | F | 85 | 43.022 | −70.425 | −29.023 | 1.00 | 83.23 | MOL1 | O |
| ATOM | 3952 | N | ILE | F | 86 | 45.210 | −70.305 | −28.528 | 1.00 | 73.01 | MOL1 | N |
| ATOM | 3953 | CA | ILE | F | 86 | 45.587 | −69.511 | −29.685 | 1.00 | 66.86 | MOL1 | C |
| ATOM | 3954 | CB | ILE | F | 86 | 47.086 | −69.616 | −29.916 | 1.00 | 62.51 | MOL1 | C |
| ATOM | 3955 | CG2 | ILE | F | 86 | 47.517 | −68.659 | −31.001 | 1.00 | 65.24 | MOL1 | C |
| ATOM | 3956 | CG1 | ILE | F | 86 | 47.819 | −69.275 | −28.627 | 1.00 | 63.85 | MOL1 | C |
| ATOM | 3957 | CD1 | ILE | F | 86 | 47.574 | −67.867 | −28.164 | 1.00 | 67.54 | MOL1 | C |
| ATOM | 3958 | C | ILE | F | 86 | 44.878 | −69.862 | −30.990 | 1.00 | 68.99 | MOL1 | C |
| ATOM | 3959 | O | ILE | F | 86 | 44.976 | −69.131 | −31.968 | 1.00 | 68.04 | MOL1 | O |
| ATOM | 3960 | N | SER | F | 87 | 44.180 | −70.986 | −31.019 | 1.00 | 71.82 | MOL1 | N |
| ATOM | 3961 | CA | SER | F | 87 | 43.469 | −71.387 | −32.221 | 1.00 | 74.84 | MOL1 | C |
| ATOM | 3962 | CB | SER | F | 87 | 42.552 | −72.576 | −31.903 | 1.00 | 82.77 | MOL1 | C |
| ATOM | 3963 | OG | SER | F | 87 | 41.886 | −73.074 | −33.056 | 1.00 | 95.03 | MOL1 | O |
| ATOM | 3964 | C | SER | F | 87 | 42.646 | −70.187 | −32.667 | 1.00 | 72.74 | MOL1 | C |
| ATOM | 3965 | O | SER | F | 87 | 42.545 | −69.884 | −33.857 | 1.00 | 76.14 | MOL1 | O |
| ATOM | 3966 | N | MET | F | 88 | 42.063 | −69.508 | −31.686 | 1.00 | 66.96 | MOL1 | N |
| ATOM | 3967 | CA | MET | F | 88 | 41.255 | −68.327 | −31.930 | 1.00 | 63.80 | MOL1 | C |
| ATOM | 3968 | CB | MET | F | 88 | 39.776 | −68.664 | −31.766 | 1.00 | 69.38 | MOL1 | C |
| ATOM | 3969 | CG | MET | F | 88 | 39.454 | −69.527 | −30.563 | 1.00 | 66.78 | MOL1 | C |
| ATOM | 3970 | SD | MET | F | 88 | 37.930 | −70.420 | −30.863 | 1.00 | 82.70 | MOL1 | S |
| ATOM | 3971 | CE | MET | F | 88 | 37.841 | −70.294 | −32.706 | 1.00 | 63.90 | MOL1 | C |
| ATOM | 3972 | C | MET | F | 88 | 41.698 | −67.259 | −30.946 | 1.00 | 59.78 | MOL1 | C |
| ATOM | 3973 | O | MET | F | 88 | 42.161 | −67.568 | −29.852 | 1.00 | 59.48 | MOL1 | O |
| ATOM | 3974 | N | ASN | F | 89 | 41.576 | −65.998 | −31.329 | 1.00 | 55.69 | MOL1 | N |
| ATOM | 3975 | CA | ASN | F | 89 | 42.027 | −64.939 | −30.444 | 1.00 | 53.75 | MOL1 | C |
| ATOM | 3976 | CB | ASN | F | 89 | 43.081 | −64.070 | −31.142 | 1.00 | 52.35 | MOL1 | C |
| ATOM | 3977 | CG | ASN | F | 89 | 43.344 | −64.504 | −32.578 | 1.00 | 64.68 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 3978 | OD1 | ASN | F | 89 | 42.488 | −64.364 | −33.479 | 1.00 | 58.98 | MOL1 | O |
|---|---|---|---|---|---|---|---|---|---|---|---|---|
| ATOM | 3979 | ND2 | ASN | F | 89 | 44.542 | −65.039 | −32.803 | 1.00 | 63.95 | MOL1 | N |
| ATOM | 3980 | C | ASN | F | 89 | 40.906 | −64.057 | −29.958 | 1.00 | 49.73 | MOL1 | C |
| ATOM | 3981 | O | ASN | F | 89 | 39.824 | −64.029 | −30.535 | 1.00 | 44.83 | MOL1 | O |
| ATOM | 3982 | N | SER | F | 90 | 41.187 | −63.339 | −28.882 | 1.00 | 47.88 | MOL1 | N |
| ATOM | 3983 | CA | SER | F | 90 | 40.236 | −62.421 | −28.309 | 1.00 | 46.14 | MOL1 | C |
| ATOM | 3984 | CB | SER | F | 90 | 40.332 | −62.444 | −26.788 | 1.00 | 50.49 | MOL1 | C |
| ATOM | 3985 | OG | SER | F | 90 | 41.550 | −61.893 | −26.350 | 1.00 | 54.17 | MOL1 | O |
| ATOM | 3986 | C | SER | F | 90 | 40.602 | −61.044 | −28.842 | 1.00 | 45.32 | MOL1 | C |
| ATOM | 3987 | O | SER | F | 90 | 41.759 | −60.661 | −28.846 | 1.00 | 44.68 | MOL1 | O |
| ATOM | 3988 | N | VAL | F | 91 | 39.606 | −60.299 | −29.296 | 1.00 | 49.75 | MOL1 | N |
| ATOM | 3989 | CA | VAL | F | 91 | 39.835 | −58.975 | −29.855 | 1.00 | 43.00 | MOL1 | C |
| ATOM | 3990 | CB | VAL | F | 91 | 39.562 | −58.996 | −31.353 | 1.00 | 44.58 | MOL1 | C |
| ATOM | 3991 | CG1 | VAL | F | 91 | 40.346 | −60.112 | −32.007 | 1.00 | 39.33 | MOL1 | C |
| ATOM | 3992 | CG2 | VAL | F | 91 | 38.088 | −59.190 | −31.590 | 1.00 | 43.86 | MOL1 | C |
| ATOM | 3993 | C | VAL | F | 91 | 38.951 | −57.901 | −29.225 | 1.00 | 40.23 | MOL1 | C |
| ATOM | 3994 | O | VAL | F | 91 | 37.839 | −58.165 | −28.784 | 1.00 | 41.96 | MOL1 | O |
| ATOM | 3995 | N | PRO | F | 92 | 39.438 | −56.664 | −29.196 | 1.00 | 38.69 | MOL1 | N |
| ATOM | 3996 | CD | PRO | F | 92 | 40.726 | −56.207 | −29.746 | 1.00 | 35.80 | MOL1 | C |
| ATOM | 3997 | CA | PRO | F | 92 | 38.702 | −55.543 | −28.622 | 1.00 | 36.62 | MOL1 | C |
| ATOM | 3998 | CB | PRO | F | 92 | 39.752 | −54.448 | −28.580 | 1.00 | 36.65 | MOL1 | C |
| ATOM | 3999 | CG | PRO | F | 92 | 40.517 | −54.706 | −29.835 | 1.00 | 30.67 | MOL1 | C |
| ATOM | 4000 | C | PRO | F | 92 | 37.536 | −55.119 | −29.479 | 1.00 | 40.66 | MOL1 | C |
| ATOM | 4001 | O | PRO | F | 92 | 37.569 | −55.269 | −30.707 | 1.00 | 34.89 | MOL1 | O |
| ATOM | 4002 | N | ILE | F | 93 | 36.510 | −54.586 | −28.817 | 1.00 | 47.41 | MOL1 | N |
| ATOM | 4003 | CA | ILE | F | 93 | 35.332 | −54.039 | −29.486 | 1.00 | 50.35 | MOL1 | C |
| ATOM | 4004 | CB | ILE | F | 93 | 34.036 | −54.655 | −28.992 | 1.00 | 45.89 | MOL1 | C |
| ATOM | 4005 | CG2 | ILE | F | 93 | 32.872 | −53.861 | −29.482 | 1.00 | 41.56 | MOL1 | C |
| ATOM | 4006 | CG1 | ILE | F | 93 | 33.907 | −56.042 | −29.582 | 1.00 | 52.55 | MOL1 | C |
| ATOM | 4007 | CD1 | ILE | F | 93 | 34.323 | −56.053 | −31.053 | 1.00 | 54.32 | MOL1 | C |
| ATOM | 4008 | C | ILE | F | 93 | 35.358 | −52.563 | −29.143 | 1.00 | 52.88 | MOL1 | C |
| ATOM | 4009 | O | ILE | F | 93 | 35.367 | −52.186 | −27.965 | 1.00 | 53.96 | MOL1 | O |
| ATOM | 4010 | N | GLN | F | 94 | 35.390 | −51.726 | −30.169 | 1.00 | 54.61 | MOL1 | N |
| ATOM | 4011 | CA | GLN | F | 94 | 35.480 | −50.299 | −29.932 | 1.00 | 61.83 | MOL1 | C |
| ATOM | 4012 | CB | GLN | F | 94 | 36.777 | −49.786 | −30.567 | 1.00 | 65.47 | MOL1 | C |
| ATOM | 4013 | CG | GLN | F | 94 | 37.895 | −50.835 | −30.493 | 1.00 | 73.25 | MOL1 | C |
| ATOM | 4014 | CD | GLN | F | 94 | 39.256 | −50.339 | −30.958 | 1.00 | 80.32 | MOL1 | C |
| ATOM | 4015 | OE1 | GLN | F | 94 | 39.385 | −49.742 | −32.025 | 1.00 | 85.68 | MOL1 | O |
| ATOM | 4016 | NE2 | GLN | F | 94 | 40.285 | −50.606 | −30.159 | 1.00 | 82.71 | MOL1 | N |
| ATOM | 4017 | C | GLN | F | 94 | 34.270 | −49.526 | −30.436 | 1.00 | 62.17 | MOL1 | C |
| ATOM | 4018 | O | GLN | F | 94 | 33.593 | −49.945 | −31.369 | 1.00 | 61.53 | MOL1 | O |
| ATOM | 4019 | N | GLN | F | 95 | 33.980 | −48.411 | −29.784 | 1.00 | 64.37 | MOL1 | N |
| ATOM | 4020 | CA | GLN | F | 95 | 32.865 | −47.585 | −30.193 | 1.00 | 69.61 | MOL1 | C |
| ATOM | 4021 | CB | GLN | F | 95 | 31.633 | −47.854 | −29.324 | 1.00 | 76.42 | MOL1 | C |
| ATOM | 4022 | CG | GLN | F | 95 | 30.368 | −47.159 | −29.829 | 1.00 | 90.85 | MOL1 | C |
| ATOM | 4023 | CD | GLN | F | 95 | 29.994 | −47.569 | −31.257 | 1.00 | 99.98 | MOL1 | C |
| ATOM | 4024 | OE1 | GLN | F | 95 | 30.834 | −47.553 | −32.165 | 1.00 | 101.86 | MOL1 | O |
| ATOM | 4025 | NE2 | GLN | F | 95 | 28.725 | −47.925 | −31.461 | 1.00 | 101.41 | MOL1 | N |
| ATOM | 4026 | C | GLN | F | 95 | 33.286 | −46.126 | −30.092 | 1.00 | 72.26 | MOL1 | C |
| ATOM | 4027 | O | GLN | F | 95 | 33.953 | −45.722 | −29.137 | 1.00 | 74.42 | MOL1 | O |
| ATOM | 4028 | N | GLU | F | 96 | 32.925 | −45.342 | −31.100 | 1.00 | 72.04 | MOL1 | N |
| ATOM | 4029 | CA | GLU | F | 96 | 33.260 | −43.926 | −31.106 | 1.00 | 73.98 | MOL1 | C |
| ATOM | 4030 | CB | GLU | F | 96 | 33.285 | −43.385 | −32.533 | 1.00 | 89.18 | MOL1 | C |
| ATOM | 4031 | CG | GLU | F | 96 | 33.479 | −44.450 | −33.609 | 1.00 | 111.90 | MOL1 | C |
| ATOM | 4032 | CD | GLU | F | 96 | 32.691 | −44.149 | −34.886 | 1.00 | 123.07 | MOL1 | C |
| ATOM | 4033 | OE1 | GLU | F | 96 | 32.906 | −43.070 | −35.490 | 1.00 | 128.72 | MOL1 | O |
| ATOM | 4034 | OE2 | GLU | F | 96 | 31.853 | −44.996 | −35.283 | 1.00 | 126.28 | MOL1 | O |
| ATOM | 4035 | C | GLU | F | 96 | 32.164 | −43.214 | −30.327 | 1.00 | 69.11 | MOL1 | C |
| ATOM | 4036 | O | GLU | F | 96 | 30.976 | −43.450 | −30.547 | 1.00 | 65.22 | MOL1 | O |
| ATOM | 4037 | N | THR | F | 97 | 32.553 | −42.346 | −29.409 | 1.00 | 66.72 | MOL1 | N |
| ATOM | 4038 | CA | THR | F | 97 | 31.563 | −41.626 | −28.639 | 1.00 | 65.32 | MOL1 | C |
| ATOM | 4039 | CB | THR | F | 97 | 31.453 | −42.179 | −27.217 | 1.00 | 70.87 | MOL1 | C |
| ATOM | 4040 | OG1 | THR | F | 97 | 30.424 | −41.476 | −26.502 | 1.00 | 77.01 | MOL1 | O |
| ATOM | 4041 | CG2 | THR | F | 97 | 32.777 | −42.012 | −26.490 | 1.00 | 74.82 | MOL1 | C |
| ATOM | 4042 | C | THR | F | 97 | 31.919 | −40.157 | −28.572 | 1.00 | 63.86 | MOL1 | C |
| ATOM | 4043 | O | THR | F | 97 | 33.015 | −39.749 | −28.959 | 1.00 | 62.62 | MOL1 | O |
| ATOM | 4044 | N | LEU | F | 98 | 30.972 | −39.367 | −28.083 | 1.00 | 62.38 | MOL1 | N |
| ATOM | 4045 | CA | LEU | F | 98 | 31.149 | −37.931 | −27.943 | 1.00 | 55.68 | MOL1 | C |
| ATOM | 4046 | CB | LEU | F | 98 | 29.928 | −37.211 | −28.489 | 1.00 | 46.64 | MOL1 | C |
| ATOM | 4047 | CG | LEU | F | 98 | 30.174 | −36.317 | −29.694 | 1.00 | 53.13 | MOL1 | C |
| ATOM | 4048 | CD1 | LEU | F | 98 | 31.477 | −36.689 | −30.361 | 1.00 | 50.09 | MOL1 | C |
| ATOM | 4049 | CD2 | LEU | F | 98 | 28.999 | −36.448 | −30.655 | 1.00 | 50.02 | MOL1 | C |
| ATOM | 4050 | C | LEU | F | 98 | 31.317 | −37.557 | −26.483 | 1.00 | 56.71 | MOL1 | C |
| ATOM | 4051 | O | LEU | F | 98 | 30.759 | −38.205 | −25.593 | 1.00 | 61.16 | MOL1 | O |
| ATOM | 4052 | N | VAL | F | 99 | 32.104 | −36.521 | −26.236 | 1.00 | 55.74 | MOL1 | N |
| ATOM | 4053 | CA | VAL | F | 99 | 32.297 | −36.019 | −24.879 | 1.00 | 59.04 | MOL1 | C |
| ATOM | 4054 | CB | VAL | F | 99 | 33.607 | −36.506 | −24.238 | 1.00 | 58.49 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 4055 | CG1 | VAL | F | 99 | 33.606 | −38.022 | −24.126 | 1.00 | 57.95 | MOL1 | C |
|---|---|---|---|---|---|---|---|---|---|---|---|---|
| ATOM | 4056 | CG2 | VAL | F | 99 | 34.780 | −36.021 | −25.046 | 1.00 | 61.88 | MOL1 | C |
| ATOM | 4057 | C | VAL | F | 99 | 32.349 | −34.513 | −25.011 | 1.00 | 59.25 | MOL1 | C |
| ATOM | 4058 | O | VAL | F | 99 | 32.518 | −33.992 | −26.107 | 1.00 | 61.46 | MOL1 | O |
| ATOM | 4059 | N | VAL | F | 100 | 32.190 | −33.800 | −23.911 | 1.00 | 60.54 | MOL1 | N |
| ATOM | 4060 | CA | VAL | F | 100 | 32.228 | −32.354 | −24.000 | 1.00 | 66.71 | MOL1 | C |
| ATOM | 4061 | CB | VAL | F | 100 | 30.931 | −31.750 | −23.498 | 1.00 | 65.97 | MOL1 | C |
| ATOM | 4062 | CG1 | VAL | F | 100 | 29.859 | −31.863 | −24.556 | 1.00 | 67.66 | MOL1 | C |
| ATOM | 4063 | CG2 | VAL | F | 100 | 30.506 | −32.480 | −22.247 | 1.00 | 64.33 | MOL1 | C |
| ATOM | 4064 | C | VAL | F | 100 | 33.362 | −31.793 | −23.178 | 1.00 | 73.23 | MOL1 | C |
| ATOM | 4065 | O | VAL | F | 100 | 33.632 | −32.274 | −22.070 | 1.00 | 74.60 | MOL1 | O |
| ATOM | 4066 | N | ARG | F | 101 | 34.032 | −30.783 | −23.727 | 1.00 | 76.93 | MOL1 | N |
| ATOM | 4067 | CA | ARG | F | 101 | 35.127 | −30.142 | −23.024 | 1.00 | 83.86 | MOL1 | C |
| ATOM | 4068 | CB | ARG | F | 101 | 36.377 | −30.089 | −23.896 | 1.00 | 85.11 | MOL1 | C |
| ATOM | 4069 | CG | ARG | F | 101 | 37.053 | −31.438 | −23.963 | 1.00 | 92.87 | MOL1 | C |
| ATOM | 4070 | CD | ARG | F | 101 | 38.536 | −31.369 | −24.259 | 1.00 | 97.30 | MOL1 | C |
| ATOM | 4071 | NE | ARG | F | 101 | 39.193 | −32.540 | −23.689 | 1.00 | 100.67 | MOL1 | N |
| ATOM | 4072 | CZ | ARG | F | 101 | 39.300 | −32.762 | −22.383 | 1.00 | 102.06 | MOL1 | C |
| ATOM | 4073 | NH1 | ARG | F | 101 | 38.803 | −31.884 | −21.521 | 1.00 | 100.04 | MOL1 | N |
| ATOM | 4074 | NH2 | ARG | F | 101 | 39.881 | −33.870 | −21.936 | 1.00 | 104.84 | MOL1 | N |
| ATOM | 4075 | C | ARG | F | 101 | 34.721 | −28.753 | −22.585 | 1.00 | 89.71 | MOL1 | C |
| ATOM | 4076 | O | ARG | F | 101 | 34.097 | −28.005 | −23.340 | 1.00 | 89.09 | MOL1 | O |
| ATOM | 4077 | N | ARG | F | 102 | 35.054 | −28.430 | −21.341 | 1.00 | 97.16 | MOL1 | N |
| ATOM | 4078 | CA | ARG | F | 102 | 34.730 | −27.135 | −20.767 | 1.00 | 107.35 | MOL1 | C |
| ATOM | 4079 | CB | ARG | F | 102 | 34.273 | −27.316 | −19.312 | 1.00 | 110.28 | MOL1 | C |
| ATOM | 4080 | CG | ARG | F | 102 | 33.813 | −26.036 | −18.622 | 1.00 | 116.90 | MOL1 | C |
| ATOM | 4081 | CD | ARG | F | 102 | 33.005 | −26.322 | −17.350 | 1.00 | 118.91 | MOL1 | C |
| ATOM | 4082 | NE | ARG | F | 102 | 33.782 | −26.977 | −16.298 | 1.00 | 119.03 | MOL1 | N |
| ATOM | 4083 | CZ | ARG | F | 102 | 33.271 | −27.386 | −15.140 | 1.00 | 119.45 | MOL1 | C |
| ATOM | 4084 | NH1 | ARG | F | 102 | 31.980 | −27.207 | −14.885 | 1.00 | 119.89 | MOL1 | N |
| ATOM | 4085 | NH2 | ARG | F | 102 | 34.046 | −27.974 | −14.237 | 1.00 | 117.70 | MOL1 | N |
| ATOM | 4086 | C | ARG | F | 102 | 35.983 | −26.276 | −20.837 | 1.00 | 113.63 | MOL1 | C |
| ATOM | 4087 | O | ARG | F | 102 | 36.818 | −26.307 | −19.931 | 1.00 | 116.27 | MOL1 | O |
| ATOM | 4088 | N | LYS | F | 103 | 36.121 | −25.518 | −21.922 | 1.00 | 120.15 | MOL1 | N |
| ATOM | 4089 | CA | LYS | F | 103 | 37.293 | −24.668 | −22.103 | 1.00 | 128.06 | MOL1 | C |
| ATOM | 4090 | CB | LYS | F | 103 | 37.552 | −24.419 | −23.600 | 1.00 | 129.18 | MOL1 | C |
| ATOM | 4091 | CG | LYS | F | 103 | 38.204 | −25.604 | −24.315 | 1.00 | 133.24 | MOL1 | C |
| ATOM | 4092 | CD | LYS | F | 103 | 38.661 | −25.262 | −25.732 | 1.00 | 137.99 | MOL1 | C |
| ATOM | 4093 | CE | LYS | F | 103 | 39.419 | −26.434 | −26.373 | 1.00 | 140.56 | MOL1 | C |
| ATOM | 4094 | NZ | LYS | F | 103 | 39.910 | −26.140 | −27.757 | 1.00 | 139.88 | MOL1 | N |
| ATOM | 4095 | C | LYS | F | 103 | 37.224 | −23.342 | −21.350 | 1.00 | 133.17 | MOL1 | C |
| ATOM | 4096 | O | LYS | F | 103 | 36.158 | −22.726 | −21.244 | 1.00 | 134.08 | MOL1 | O |
| ATOM | 4097 | N | HIS | F | 104 | 38.373 | −22.927 | −20.814 | 1.00 | 137.83 | MOL1 | N |
| ATOM | 4098 | CA | HIS | F | 104 | 38.500 | −21.675 | −20.074 | 1.00 | 144.47 | MOL1 | C |
| ATOM | 4099 | CB | HIS | F | 104 | 37.925 | −20.528 | −20.916 | 1.00 | 150.75 | MOL1 | C |
| ATOM | 4100 | CG | HIS | F | 104 | 38.359 | −20.554 | −22.353 | 1.00 | 158.24 | MOL1 | C |
| ATOM | 4101 | CD2 | HIS | F | 104 | 39.416 | −21.150 | −22.957 | 1.00 | 161.11 | MOL1 | C |
| ATOM | 4102 | ND1 | HIS | F | 104 | 37.660 | −19.911 | −23.354 | 1.00 | 160.78 | MOL1 | N |
| ATOM | 4103 | CE1 | HIS | F | 104 | 38.266 | −20.111 | −24.512 | 1.00 | 162.24 | MOL1 | C |
| ATOM | 4104 | NE2 | HIS | F | 104 | 39.334 | −20.860 | −24.299 | 1.00 | 162.96 | MOL1 | N |
| ATOM | 4105 | C | HIS | F | 104 | 37.800 | −21.739 | −18.707 | 1.00 | 147.30 | MOL1 | C |
| ATOM | 4106 | O | HIS | F | 104 | 37.140 | −22.730 | −18.378 | 1.00 | 145.39 | MOL1 | O |
| ATOM | 4107 | N | GLN | F | 105 | 37.956 | −20.683 | −17.909 | 1.00 | 150.81 | MOL1 | N |
| ATOM | 4108 | CA | GLN | F | 105 | 37.335 | −20.621 | −16.586 | 1.00 | 150.93 | MOL1 | C |
| ATOM | 4109 | CB | GLN | F | 105 | 38.403 | −20.763 | −15.478 | 1.00 | 153.40 | MOL1 | C |
| ATOM | 4110 | CG | GLN | F | 105 | 39.723 | −20.006 | −15.700 | 1.00 | 154.82 | MOL1 | C |
| ATOM | 4111 | CD | GLN | F | 105 | 39.681 | −18.548 | −15.257 | 1.00 | 155.99 | MOL1 | C |
| ATOM | 4112 | OE1 | GLN | F | 105 | 40.679 | −17.829 | −15.362 | 1.00 | 154.70 | MOL1 | O |
| ATOM | 4113 | NE2 | GLN | F | 105 | 38.531 | −18.108 | −14.755 | 1.00 | 155.92 | MOL1 | N |
| ATOM | 4114 | C | GLN | F | 105 | 36.496 | −19.357 | −16.366 | 1.00 | 149.14 | MOL1 | C |
| ATOM | 4115 | O | GLN | F | 105 | 36.445 | −18.464 | −17.221 | 1.00 | 145.42 | MOL1 | O |
| ATOM | 4116 | N | GLY | F | 106 | 35.819 | −19.305 | −15.223 | 1.00 | 147.74 | MOL1 | N |
| ATOM | 4117 | CA | GLY | F | 106 | 34.997 | −18.154 | −14.897 | 1.00 | 147.34 | MOL1 | C |
| ATOM | 4118 | C | GLY | F | 106 | 33.842 | −17.884 | −15.843 | 1.00 | 147.13 | MOL1 | C |
| ATOM | 4119 | O | GLY | F | 106 | 33.125 | −18.801 | −16.246 | 1.00 | 145.82 | MOL1 | O |
| ATOM | 4120 | N | CYS | F | 107 | 33.654 | −16.617 | −16.200 | 1.00 | 147.53 | MOL1 | N |
| ATOM | 4121 | CA | CYS | F | 107 | 32.558 | −16.255 | −17.086 | 1.00 | 148.41 | MOL1 | C |
| ATOM | 4122 | C | CYS | F | 107 | 32.903 | −16.477 | −18.554 | 1.00 | 145.11 | MOL1 | C |
| ATOM | 4123 | O | CYS | F | 107 | 32.017 | −16.507 | −19.409 | 1.00 | 142.60 | MOL1 | O |
| ATOM | 4124 | CB | CYS | F | 107 | 32.123 | −14.801 | −16.851 | 1.00 | 155.97 | MOL1 | C |
| ATOM | 4125 | SG | CYS | F | 107 | 31.605 | −14.369 | −15.144 | 1.00 | 165.92 | MOL1 | S |
| ATOM | 4126 | N | SER | F | 108 | 34.191 | −16.651 | −18.836 | 1.00 | 143.69 | MOL1 | N |
| ATOM | 4127 | CA | SER | F | 108 | 34.660 | −16.887 | −20.201 | 1.00 | 144.58 | MOL1 | C |
| ATOM | 4128 | CB | SER | F | 108 | 36.080 | −16.327 | −20.360 | 1.00 | 145.52 | MOL1 | C |
| ATOM | 4129 | OG | SER | F | 108 | 36.549 | −16.458 | −21.693 | 1.00 | 144.26 | MOL1 | O |
| ATOM | 4130 | C | SER | F | 108 | 34.646 | −18.389 | −20.532 | 1.00 | 143.38 | MOL1 | C |
| ATOM | 4131 | O | SER | F | 108 | 35.564 | −18.902 | −21.182 | 1.00 | 143.38 | MOL1 | O |

TABLE 1-continued

The atomic coordinates of IL17F in complex with 496 Fab
(H32; a = 189.4; b = 189.4; c = 490.9, α, β = 90°; γ = 120°)

| ATOM | 4132 | N | VAL | F | 109 | 33.591 | −19.078 | −20.090 | 1.00 | 139.43 | MOL1 | N |
| --- | --- | --- | --- | --- | --- | --- | --- | --- | --- | --- | --- | --- |
| ATOM | 4133 | CA | VAL | F | 109 | 33.429 | −20.521 | −20.303 | 1.00 | 131.17 | MOL1 | C |
| ATOM | 4134 | CB | VAL | F | 109 | 32.716 | −21.171 | −19.084 | 1.00 | 129.56 | MOL1 | C |
| ATOM | 4135 | CG1 | VAL | F | 109 | 31.765 | −22.265 | −19.543 | 1.00 | 127.20 | MOL1 | C |
| ATOM | 4136 | CG2 | VAL | F | 109 | 33.757 | −21.745 | −18.128 | 1.00 | 127.59 | MOL1 | C |
| ATOM | 4137 | C | VAL | F | 109 | 32.691 | −20.929 | −21.587 | 1.00 | 126.27 | MOL1 | C |
| ATOM | 4138 | O | VAL | F | 109 | 31.581 | −20.465 | −21.874 | 1.00 | 120.54 | MOL1 | O |
| ATOM | 4139 | N | SER | F | 110 | 33.334 | −21.813 | −22.344 | 1.00 | 121.64 | MOL1 | N |
| ATOM | 4140 | CA | SER | F | 110 | 32.800 | −22.328 | −23.595 | 1.00 | 117.57 | MOL1 | C |
| ATOM | 4141 | CB | SER | F | 110 | 33.668 | −21.847 | −24.759 | 1.00 | 118.18 | MOL1 | C |
| ATOM | 4142 | OG | SER | F | 110 | 35.003 | −22.314 | −24.627 | 1.00 | 114.40 | MOL1 | O |
| ATOM | 4143 | C | SER | F | 110 | 32.812 | −23.859 | −23.534 | 1.00 | 115.99 | MOL1 | C |
| ATOM | 4144 | O | SER | F | 110 | 33.538 | −24.449 | −22.724 | 1.00 | 113.41 | MOL1 | O |
| ATOM | 4145 | N | PHE | F | 111 | 32.013 | −24.493 | −24.393 | 1.00 | 111.00 | MOL1 | N |
| ATOM | 4146 | CA | PHE | F | 111 | 31.906 | −25.952 | −24.451 | 1.00 | 100.84 | MOL1 | C |
| ATOM | 4147 | CB | PHE | F | 111 | 30.495 | −26.371 | −24.048 | 1.00 | 102.04 | MOL1 | C |
| ATOM | 4148 | CG | PHE | F | 111 | 30.207 | −26.211 | −22.584 | 1.00 | 102.79 | MOL1 | C |
| ATOM | 4149 | CD1 | PHE | F | 111 | 28.910 | −26.274 | −22.112 | 1.00 | 102.51 | MOL1 | C |
| ATOM | 4150 | CD2 | PHE | F | 111 | 31.236 | −26.050 | −21.675 | 1.00 | 105.75 | MOL1 | C |
| ATOM | 4151 | CE1 | PHE | F | 111 | 28.643 | −26.185 | −20.763 | 1.00 | 104.73 | MOL1 | C |
| ATOM | 4152 | CE2 | PHE | F | 111 | 30.975 | −25.960 | −20.322 | 1.00 | 107.04 | MOL1 | C |
| ATOM | 4153 | CZ | PHE | F | 111 | 29.678 | −26.028 | −19.866 | 1.00 | 107.03 | MOL1 | C |
| ATOM | 4154 | C | PHE | F | 111 | 32.192 | −26.461 | −25.861 | 1.00 | 96.24 | MOL1 | C |
| ATOM | 4155 | O | PHE | F | 111 | 31.634 | −25.944 | −26.825 | 1.00 | 97.45 | MOL1 | O |
| ATOM | 4156 | N | GLN | F | 112 | 33.046 | −27.474 | −25.984 | 1.00 | 90.96 | MOL1 | N |
| ATOM | 4157 | CA | GLN | F | 112 | 33.377 | −28.027 | −27.302 | 1.00 | 88.10 | MOL1 | C |
| ATOM | 4158 | CB | GLN | F | 112 | 34.839 | −27.707 | −27.658 | 1.00 | 89.11 | MOL1 | C |
| ATOM | 4159 | CG | GLN | F | 112 | 35.134 | −27.663 | −29.163 | 1.00 | 92.05 | MOL1 | C |
| ATOM | 4160 | CD | GLN | F | 112 | 36.621 | −27.503 | −29.502 | 1.00 | 92.21 | MOL1 | C |
| ATOM | 4161 | OE1 | GLN | F | 112 | 36.976 | −27.271 | −30.659 | 1.00 | 96.55 | MOL1 | O |
| ATOM | 4162 | NE2 | GLN | F | 112 | 37.488 | −27.638 | −28.502 | 1.00 | 85.91 | MOL1 | N |
| ATOM | 4163 | C | GLN | F | 112 | 33.155 | −29.546 | −27.334 | 1.00 | 85.52 | MOL1 | C |
| ATOM | 4164 | O | GLN | F | 112 | 33.425 | −30.241 | −26.351 | 1.00 | 89.03 | MOL1 | O |
| ATOM | 4165 | N | LEU | F | 113 | 32.665 | −30.054 | −28.463 | 1.00 | 76.08 | MOL1 | N |
| ATOM | 4166 | CA | LEU | F | 113 | 32.401 | −31.481 | −28.616 | 1.00 | 74.73 | MOL1 | C |
| ATOM | 4167 | CB | LEU | F | 113 | 31.296 | −31.709 | −29.646 | 1.00 | 75.29 | MOL1 | C |
| ATOM | 4168 | CG | LEU | F | 113 | 29.823 | −31.586 | −29.268 | 1.00 | 72.94 | MOL1 | C |
| ATOM | 4169 | CD1 | LEU | F | 113 | 28.966 | −32.072 | −30.428 | 1.00 | 66.97 | MOL1 | C |
| ATOM | 4170 | CD2 | LEU | F | 113 | 29.547 | −32.422 | −28.041 | 1.00 | 74.24 | MOL1 | C |
| ATOM | 4171 | C | LEU | F | 113 | 33.609 | −32.289 | −29.063 | 1.00 | 76.76 | MOL1 | C |
| ATOM | 4172 | O | LEU | F | 113 | 34.010 | −32.193 | −30.214 | 1.00 | 82.45 | MOL1 | O |
| ATOM | 4173 | N | GLU | F | 114 | 34.174 | −33.102 | −28.174 | 1.00 | 78.11 | MOL1 | N |
| ATOM | 4174 | CA | GLU | F | 114 | 35.327 | −33.938 | −28.523 | 1.00 | 76.38 | MOL1 | C |
| ATOM | 4175 | CB | GLU | F | 114 | 36.298 | −34.020 | −27.346 | 1.00 | 83.54 | MOL1 | C |
| ATOM | 4176 | CG | GLU | F | 114 | 37.616 | −34.715 | −27.646 | 1.00 | 94.24 | MOL1 | C |
| ATOM | 4177 | CD | GLU | F | 114 | 38.585 | −34.679 | −26.460 | 1.00 | 102.03 | MOL1 | C |
| ATOM | 4178 | OE1 | GLU | F | 114 | 39.778 | −35.005 | −26.660 | 1.00 | 108.49 | MOL1 | O |
| ATOM | 4179 | OE2 | GLU | F | 114 | 38.159 | −34.334 | −25.331 | 1.00 | 97.17 | MOL1 | O |
| ATOM | 4180 | C | GLU | F | 114 | 34.834 | −35.336 | −28.891 | 1.00 | 73.99 | MOL1 | C |
| ATOM | 4181 | O | GLU | F | 114 | 33.780 | −35.776 | −28.422 | 1.00 | 77.13 | MOL1 | O |
| ATOM | 4182 | N | LYS | F | 115 | 35.600 | −36.028 | −29.728 | 1.00 | 67.97 | MOL1 | N |
| ATOM | 4183 | CA | LYS | F | 115 | 35.245 | −37.370 | −30.191 | 1.00 | 64.48 | MOL1 | C |
| ATOM | 4184 | CB | LYS | F | 115 | 35.253 | −37.370 | −31.715 | 1.00 | 58.29 | MOL1 | C |
| ATOM | 4185 | CG | LYS | F | 115 | 34.541 | −38.513 | −32.383 | 1.00 | 67.40 | MOL1 | C |
| ATOM | 4186 | CD | LYS | F | 115 | 34.404 | −38.195 | −33.871 | 1.00 | 76.87 | MOL1 | C |
| ATOM | 4187 | CE | LYS | F | 115 | 33.755 | −39.311 | −34.670 | 1.00 | 82.63 | MOL1 | C |
| ATOM | 4188 | NZ | LYS | F | 115 | 33.840 | −39.010 | −36.129 | 1.00 | 86.82 | MOL1 | N |
| ATOM | 4189 | C | LYS | F | 115 | 36.253 | −38.381 | −29.647 | 1.00 | 62.95 | MOL1 | C |
| ATOM | 4190 | O | LYS | F | 115 | 37.446 | −38.279 | −29.911 | 1.00 | 70.29 | MOL1 | O |
| ATOM | 4191 | N | VAL | F | 116 | 35.781 | −39.359 | −28.886 | 1.00 | 60.57 | MOL1 | N |
| ATOM | 4192 | CA | VAL | F | 116 | 36.677 | −40.346 | −28.291 | 1.00 | 60.31 | MOL1 | C |
| ATOM | 4193 | CB | VAL | F | 116 | 36.570 | −40.317 | −26.760 | 1.00 | 57.13 | MOL1 | C |
| ATOM | 4194 | CG1 | VAL | F | 116 | 37.397 | −41.430 | −26.164 | 1.00 | 56.19 | MOL1 | C |
| ATOM | 4195 | CG2 | VAL | F | 116 | 37.027 | −38.977 | −26.232 | 1.00 | 57.63 | MOL1 | C |
| ATOM | 4196 | C | VAL | F | 116 | 36.378 | −41.767 | −28.724 | 1.00 | 60.44 | MOL1 | C |
| ATOM | 4197 | O | VAL | F | 116 | 35.221 | −42.163 | −28.767 | 1.00 | 64.04 | MOL1 | O |
| ATOM | 4198 | N | LEU | F | 117 | 37.420 | −42.536 | −29.027 | 1.00 | 58.45 | MOL1 | N |
| ATOM | 4199 | CA | LEU | F | 117 | 37.247 | −43.922 | −29.437 | 1.00 | 55.47 | MOL1 | C |
| ATOM | 4200 | CB | LEU | F | 117 | 38.244 | −44.267 | −30.549 | 1.00 | 63.12 | MOL1 | C |
| ATOM | 4201 | CG | LEU | F | 117 | 38.288 | −45.628 | −31.284 | 1.00 | 67.28 | MOL1 | C |
| ATOM | 4202 | CD1 | LEU | F | 117 | 39.302 | −46.566 | −30.620 | 1.00 | 61.33 | MOL1 | C |
| ATOM | 4203 | CD2 | LEU | F | 117 | 36.883 | −46.240 | −31.360 | 1.00 | 69.08 | MOL1 | C |
| ATOM | 4204 | C | LEU | F | 117 | 37.515 | −44.764 | −28.210 | 1.00 | 53.29 | MOL1 | C |
| ATOM | 4205 | O | LEU | F | 117 | 38.617 | −44.725 | −27.660 | 1.00 | 51.96 | MOL1 | O |
| ATOM | 4206 | N | VAL | F | 118 | 36.515 | −45.523 | −27.776 | 1.00 | 49.31 | MOL1 | N |
| ATOM | 4207 | CA | VAL | F | 118 | 36.689 | −46.345 | −26.589 | 1.00 | 48.83 | MOL1 | C |
| ATOM | 4208 | CB | VAL | F | 118 | 35.680 | −45.968 | −25.488 | 1.00 | 46.37 | MOL1 | C |

TABLE 1-continued

The atomic coordinates of IL17F in complex with 496 Fab
(H32; a = 189.4; b = 189.4; c = 490.9, α, β = 90°; γ = 120°)

| ATOM | 4209 | CG1 | VAL | F | 118 | 34.759 | −44.865 | −25.976 | 1.00 | 45.08 | MOL1 | C |
|---|---|---|---|---|---|---|---|---|---|---|---|---|
| ATOM | 4210 | CG2 | VAL | F | 118 | 34.881 | −47.190 | −25.089 | 1.00 | 50.73 | MOL1 | C |
| ATOM | 4211 | C | VAL | F | 118 | 36.582 | −47.835 | −26.819 | 1.00 | 45.57 | MOL1 | C |
| ATOM | 4212 | O | VAL | F | 118 | 35.818 | −48.309 | −27.644 | 1.00 | 44.70 | MOL1 | O |
| ATOM | 4213 | N | THR | F | 119 | 37.374 | −48.572 | −26.068 | 1.00 | 48.59 | MOL1 | N |
| ATOM | 4214 | CA | THR | F | 119 | 37.362 | −50.014 | −26.154 | 1.00 | 52.88 | MOL1 | C |
| ATOM | 4215 | CB | THR | F | 119 | 38.759 | −50.590 | −25.885 | 1.00 | 59.66 | MOL1 | C |
| ATOM | 4216 | OG1 | THR | F | 119 | 39.762 | −49.777 | −26.527 | 1.00 | 56.23 | MOL1 | O |
| ATOM | 4217 | CG2 | THR | F | 119 | 38.832 | −52.001 | −26.410 | 1.00 | 59.86 | MOL1 | C |
| ATOM | 4218 | C | THR | F | 119 | 36.394 | −50.483 | −25.072 | 1.00 | 52.98 | MOL1 | C |
| ATOM | 4219 | O | THR | F | 119 | 36.707 | −50.477 | −23.874 | 1.00 | 58.84 | MOL1 | O |
| ATOM | 4220 | N | VAL | F | 120 | 35.207 | −50.875 | −25.500 | 1.00 | 48.92 | MOL1 | N |
| ATOM | 4221 | CA | VAL | F | 120 | 34.176 | −51.315 | −24.582 | 1.00 | 50.01 | MOL1 | C |
| ATOM | 4222 | CB | VAL | F | 120 | 32.853 | −51.393 | −25.294 | 1.00 | 51.62 | MOL1 | C |
| ATOM | 4223 | CG1 | VAL | F | 120 | 31.758 | −51.556 | −24.287 | 1.00 | 63.24 | MOL1 | C |
| ATOM | 4224 | CG2 | VAL | F | 120 | 32.640 | −50.145 | −26.107 | 1.00 | 59.91 | MOL1 | C |
| ATOM | 4225 | C | VAL | F | 120 | 34.444 | −52.670 | −23.950 | 1.00 | 50.12 | MOL1 | C |
| ATOM | 4226 | O | VAL | F | 120 | 34.011 | −52.946 | −22.827 | 1.00 | 52.69 | MOL1 | O |
| ATOM | 4227 | N | GLY | F | 121 | 35.146 | −53.523 | −24.681 | 1.00 | 51.02 | MOL1 | N |
| ATOM | 4228 | CA | GLY | F | 121 | 35.458 | −54.845 | −24.170 | 1.00 | 48.28 | MOL1 | C |
| ATOM | 4229 | C | GLY | F | 121 | 35.996 | −55.766 | −25.247 | 1.00 | 46.24 | MOL1 | C |
| ATOM | 4230 | O | GLY | F | 121 | 36.242 | −55.352 | −26.375 | 1.00 | 48.77 | MOL1 | O |
| ATOM | 4231 | N | CYS | F | 122 | 36.170 | −57.033 | −24.918 | 1.00 | 41.90 | MOL1 | N |
| ATOM | 4232 | CA | CYS | F | 122 | 36.701 | −57.955 | −25.898 | 1.00 | 42.96 | MOL1 | C |
| ATOM | 4233 | C | CYS | F | 122 | 35.763 | −59.099 | −26.193 | 1.00 | 38.05 | MOL1 | C |
| ATOM | 4234 | O | CYS | F | 122 | 34.935 | −59.456 | −25.377 | 1.00 | 42.43 | MOL1 | O |
| ATOM | 4235 | CB | CYS | F | 122 | 38.060 | −58.460 | −25.421 | 1.00 | 49.93 | MOL1 | C |
| ATOM | 4236 | SG | CYS | F | 122 | 39.197 | −57.060 | −25.173 | 1.00 | 57.69 | MOL1 | S |
| ATOM | 4237 | N | THR | F | 123 | 35.890 | −59.653 | −27.386 | 1.00 | 37.65 | MOL1 | N |
| ATOM | 4238 | CA | THR | F | 123 | 35.057 | −60.762 | −27.828 | 1.00 | 46.81 | MOL1 | C |
| ATOM | 4239 | CB | THR | F | 123 | 34.071 | −60.318 | −28.953 | 1.00 | 46.83 | MOL1 | C |
| ATOM | 4240 | OG1 | THR | F | 123 | 33.219 | −61.409 | −29.343 | 1.00 | 42.75 | MOL1 | O |
| ATOM | 4241 | CG2 | THR | F | 123 | 34.846 | −59.884 | −30.167 | 1.00 | 44.62 | MOL1 | C |
| ATOM | 4242 | C | THR | F | 123 | 35.998 | −61.802 | −28.416 | 1.00 | 49.43 | MOL1 | C |
| ATOM | 4243 | O | THR | F | 123 | 36.977 | −61.451 | −29.054 | 1.00 | 44.66 | MOL1 | O |
| ATOM | 4244 | N | CYS | F | 124 | 35.708 | −63.081 | −28.215 | 1.00 | 56.46 | MOL1 | N |
| ATOM | 4245 | CA | CYS | F | 124 | 36.570 | −64.114 | −28.772 | 1.00 | 62.94 | MOL1 | C |
| ATOM | 4246 | C | CYS | F | 124 | 36.189 | −64.448 | −30.209 | 1.00 | 63.67 | MOL1 | C |
| ATOM | 4247 | O | CYS | F | 124 | 35.094 | −64.939 | −30.473 | 1.00 | 65.06 | MOL1 | O |
| ATOM | 4248 | CB | CYS | F | 124 | 36.513 | −65.393 | −27.938 | 1.00 | 73.40 | MOL1 | C |
| ATOM | 4249 | SG | CYS | F | 124 | 37.416 | −66.770 | −28.722 | 1.00 | 83.45 | MOL1 | S |
| ATOM | 4250 | N | VAL | F | 125 | 37.103 | −64.194 | −31.139 | 1.00 | 64.45 | MOL1 | N |
| ATOM | 4251 | CA | VAL | F | 125 | 36.833 | −64.470 | −32.544 | 1.00 | 61.66 | MOL1 | C |
| ATOM | 4252 | CB | VAL | F | 125 | 36.962 | −63.201 | −33.401 | 1.00 | 63.16 | MOL1 | C |
| ATOM | 4253 | CG1 | VAL | F | 125 | 36.531 | −61.994 | −32.605 | 1.00 | 62.70 | MOL1 | C |
| ATOM | 4254 | CG2 | VAL | F | 125 | 38.389 | −63.041 | −33.878 | 1.00 | 68.18 | MOL1 | C |
| ATOM | 4255 | C | VAL | F | 125 | 37.775 | −65.508 | −33.130 | 1.00 | 60.75 | MOL1 | C |
| ATOM | 4256 | O | VAL | F | 125 | 38.869 | −65.755 | −32.609 | 1.00 | 58.76 | MOL1 | O |
| ATOM | 4257 | N | THR | F | 126 | 37.336 | −66.107 | −34.229 | 1.00 | 58.58 | MOL1 | N |
| ATOM | 4258 | CA | THR | F | 126 | 38.119 | −67.110 | −34.924 | 1.00 | 63.13 | MOL1 | C |
| ATOM | 4259 | CB | THR | F | 126 | 37.274 | −68.320 | −35.334 | 1.00 | 67.09 | MOL1 | C |
| ATOM | 4260 | OG1 | THR | F | 126 | 38.052 | −69.165 | −36.192 | 1.00 | 78.72 | MOL1 | O |
| ATOM | 4261 | CG2 | THR | F | 126 | 36.022 | −67.878 | −36.079 | 1.00 | 67.81 | MOL1 | C |
| ATOM | 4262 | C | THR | F | 126 | 38.666 | −66.472 | −36.181 | 1.00 | 62.28 | MOL1 | C |
| ATOM | 4263 | O | THR | F | 126 | 37.917 | −65.950 | −36.991 | 1.00 | 62.89 | MOL1 | O |
| ATOM | 4264 | N | PRO | F | 127 | 39.989 | −66.507 | −36.362 | 1.00 | 64.71 | MOL1 | N |
| ATOM | 4265 | CD | PRO | F | 127 | 40.989 | −67.318 | −35.652 | 1.00 | 69.31 | MOL1 | C |
| ATOM | 4266 | CA | PRO | F | 127 | 40.578 | −65.904 | −37.551 | 1.00 | 65.15 | MOL1 | C |
| ATOM | 4267 | CB | PRO | F | 127 | 42.042 | −66.317 | −37.461 | 1.00 | 64.98 | MOL1 | C |
| ATOM | 4268 | CG | PRO | F | 127 | 41.971 | −67.618 | −36.755 | 1.00 | 68.75 | MOL1 | C |
| ATOM | 4269 | C | PRO | F | 127 | 39.916 | −66.437 | −38.785 | 1.00 | 66.45 | MOL1 | C |
| ATOM | 4270 | O | PRO | F | 127 | 39.351 | −67.526 | −38.764 | 1.00 | 66.09 | MOL1 | O |
| ATOM | 4271 | N | VAL | F | 128 | 39.969 | −65.651 | −39.850 | 1.00 | 70.08 | MOL1 | N |
| ATOM | 4272 | CA | VAL | F | 128 | 39.386 | −66.046 | −41.115 | 1.00 | 80.54 | MOL1 | C |
| ATOM | 4273 | CB | VAL | F | 128 | 39.215 | −64.804 | −42.016 | 1.00 | 78.41 | MOL1 | C |
| ATOM | 4274 | CG1 | VAL | F | 128 | 40.414 | −63.935 | −41.878 | 1.00 | 82.53 | MOL1 | C |
| ATOM | 4275 | CG2 | VAL | F | 128 | 39.024 | −65.195 | −43.470 | 1.00 | 78.29 | MOL1 | C |
| ATOM | 4276 | C | VAL | F | 128 | 40.340 | −67.060 | −41.740 | 1.00 | 89.03 | MOL1 | C |
| ATOM | 4277 | O | VAL | F | 128 | 41.331 | −66.690 | −42.361 | 1.00 | 95.20 | MOL1 | O |
| ATOM | 4278 | N | ILE | F | 129 | 40.056 | −68.345 | −41.553 | 1.00 | 98.16 | MOL1 | N |
| ATOM | 4279 | CA | ILE | F | 129 | 40.912 | −69.395 | −42.102 | 1.00 | 107.61 | MOL1 | C |
| ATOM | 4280 | CB | ILE | F | 129 | 40.760 | −70.716 | −41.310 | 1.00 | 112.00 | MOL1 | C |
| ATOM | 4281 | CG2 | ILE | F | 129 | 41.726 | −71.764 | −41.847 | 1.00 | 107.86 | MOL1 | C |
| ATOM | 4282 | CG1 | ILE | F | 129 | 41.038 | −70.468 | −39.822 | 1.00 | 121.08 | MOL1 | C |
| ATOM | 4283 | CD1 | ILE | F | 129 | 40.925 | −71.714 | −38.933 | 1.00 | 126.52 | MOL1 | C |
| ATOM | 4284 | C | ILE | F | 129 | 40.580 | −69.666 | −43.567 | 1.00 | 112.94 | MOL1 | C |
| ATOM | 4285 | O | ILE | F | 129 | 41.411 | −70.172 | −44.314 | 1.00 | 113.20 | MOL1 | O |

TABLE 1-continued

The atomic coordinates of IL17F in complex with 496 Fab
(H32; a = 189.4; b = 189.4; c = 490.9, α, β = 90°; γ = 120°)

| ATOM | 4286 | N | HIS | F | 130 | 39.356 | −69.328 | −43.961 | 1.00 | 121.19 | MOL1 | N |
|---|---|---|---|---|---|---|---|---|---|---|---|---|
| ATOM | 4287 | CA | HIS | F | 130 | 38.863 | −69.516 | −45.329 | 1.00 | 127.35 | MOL1 | C |
| ATOM | 4288 | CB | HIS | F | 130 | 37.560 | −68.713 | −45.485 | 1.00 | 130.61 | MOL1 | C |
| ATOM | 4289 | CG | HIS | F | 130 | 36.861 | −68.454 | −44.181 | 1.00 | 134.06 | MOL1 | C |
| ATOM | 4290 | CD2 | HIS | F | 130 | 36.356 | −67.315 | −43.648 | 1.00 | 135.37 | MOL1 | C |
| ATOM | 4291 | ND1 | HIS | F | 130 | 36.673 | −69.435 | −43.229 | 1.00 | 135.79 | MOL1 | N |
| ATOM | 4292 | CE1 | HIS | F | 130 | 36.090 | −68.911 | −42.165 | 1.00 | 135.80 | MOL1 | C |
| ATOM | 4293 | NE2 | HIS | F | 130 | 35.888 | −67.625 | −42.392 | 1.00 | 135.87 | MOL1 | N |
| ATOM | 4294 | C | HIS | F | 130 | 39.913 | −69.107 | −46.383 | 1.00 | 128.31 | MOL1 | C |
| ATOM | 4295 | O | HIS | F | 130 | 39.855 | −68.006 | −46.948 | 1.00 | 121.52 | MOL1 | O |
| ATOM | 4296 | N | HIS | F | 131 | 40.850 | −70.030 | −46.629 | 1.00 | 133.20 | MOL1 | N |
| ATOM | 4297 | CA | HIS | F | 131 | 41.987 | −69.884 | −47.554 | 1.00 | 140.61 | MOL1 | C |
| ATOM | 4298 | CB | HIS | F | 131 | 41.730 | −70.652 | −48.864 | 1.00 | 144.36 | MOL1 | C |
| ATOM | 4299 | CG | HIS | F | 131 | 42.975 | −70.917 | −49.663 | 1.00 | 147.92 | MOL1 | C |
| ATOM | 4300 | CD2 | HIS | F | 131 | 43.462 | −72.061 | −50.203 | 1.00 | 148.07 | MOL1 | C |
| ATOM | 4301 | ND1 | HIS | F | 131 | 43.881 | −69.929 | −49.987 | 1.00 | 148.71 | MOL1 | N |
| ATOM | 4302 | CE1 | HIS | F | 131 | 44.871 | −70.451 | −50.689 | 1.00 | 148.41 | MOL1 | C |
| ATOM | 4303 | NE2 | HIS | F | 131 | 44.641 | −71.744 | −50.835 | 1.00 | 147.74 | MOL1 | N |
| ATOM | 4304 | C | HIS | F | 131 | 42.393 | −68.440 | −47.879 | 1.00 | 141.82 | MOL1 | C |
| ATOM | 4305 | O | HIS | F | 131 | 43.448 | −67.961 | −47.439 | 1.00 | 140.46 | MOL1 | O |
| ATOM | 4306 | N | VAL | F | 132 | 41.557 | −67.770 | −48.668 | 1.00 | 141.67 | MOL1 | N |
| ATOM | 4307 | CA | VAL | F | 132 | 41.771 | −66.384 | −49.077 | 1.00 | 139.40 | MOL1 | C |
| ATOM | 4308 | CB | VAL | F | 132 | 42.654 | −66.291 | −50.359 | 1.00 | 137.24 | MOL1 | C |
| ATOM | 4309 | CG1 | VAL | F | 132 | 42.877 | −64.827 | −50.736 | 1.00 | 135.57 | MOL1 | C |
| ATOM | 4310 | CG2 | VAL | F | 132 | 43.990 | −66.999 | −50.140 | 1.00 | 131.43 | MOL1 | C |
| ATOM | 4311 | C | VAL | F | 132 | 40.387 | −65.818 | −49.391 | 1.00 | 140.29 | MOL1 | C |
| ATOM | 4312 | O | VAL | F | 132 | 39.658 | −65.379 | −48.497 | 1.00 | 137.38 | MOL1 | O |
| ATOM | 4313 | N | GLN | F | 133 | 40.035 | −65.856 | −50.673 | 1.00 | 142.86 | MOL1 | N |
| ATOM | 4314 | CA | GLN | F | 133 | 38.746 | −65.377 | −51.162 | 1.00 | 143.14 | MOL1 | C |
| ATOM | 4315 | CB | GLN | F | 133 | 38.770 | −63.848 | −51.309 | 1.00 | 143.32 | MOL1 | C |
| ATOM | 4316 | CG | GLN | F | 133 | 37.404 | −63.157 | −51.215 | 1.00 | 142.55 | MOL1 | C |
| ATOM | 4317 | CD | GLN | F | 133 | 36.460 | −63.506 | −52.361 | 1.00 | 143.56 | MOL1 | C |
| ATOM | 4318 | OE1 | GLN | F | 133 | 36.766 | −63.274 | −53.536 | 1.00 | 141.91 | MOL1 | O |
| ATOM | 4319 | NE2 | GLN | F | 133 | 35.299 | −64.059 | −52.019 | 1.00 | 141.58 | MOL1 | N |
| ATOM | 4320 | C | GLN | F | 133 | 38.518 | −66.045 | −52.525 | 1.00 | 143.02 | MOL1 | C |
| ATOM | 4321 | O | GLN | F | 133 | 37.554 | −66.833 | −52.645 | 1.00 | 141.78 | MOL1 | O |
| ATOM | 4322 | OXT | GLN | F | 133 | 39.323 | −65.789 | −53.451 | 1.00 | 142.78 | MOL1 | O |
| ATOM | 4323 | CB | ALA | C | 1 | −4.305 | −58.626 | −73.057 | 1.00 | 101.99 | MOL2 | C |
| ATOM | 4324 | C | ALA | C | 1 | −3.330 | −57.854 | −70.875 | 1.00 | 96.91 | MOL2 | C |
| ATOM | 4325 | O | ALA | C | 1 | −3.606 | −57.740 | −69.680 | 1.00 | 100.25 | MOL2 | O |
| ATOM | 4326 | N | ALA | C | 1 | −4.184 | −56.198 | −72.502 | 1.00 | 100.33 | MOL2 | N |
| ATOM | 4327 | CA | ALA | C | 1 | −4.380 | −57.566 | −71.940 | 1.00 | 99.91 | MOL2 | C |
| ATOM | 4328 | N | ILE | C | 2 | −2.129 | −58.220 | −71.315 | 1.00 | 89.04 | MOL2 | N |
| ATOM | 4329 | CA | ILE | C | 2 | −1.038 | −58.535 | −70.405 | 1.00 | 80.58 | MOL2 | C |
| ATOM | 4330 | CB | ILE | C | 2 | 0.301 | −58.522 | −71.130 | 1.00 | 81.06 | MOL2 | C |
| ATOM | 4331 | CG2 | ILE | C | 2 | 1.248 | −59.482 | −70.461 | 1.00 | 83.33 | MOL2 | C |
| ATOM | 4332 | CG1 | ILE | C | 2 | 0.122 | −58.988 | −72.569 | 1.00 | 84.56 | MOL2 | C |
| ATOM | 4333 | CD1 | ILE | C | 2 | −0.287 | −60.430 | −72.679 | 1.00 | 91.18 | MOL2 | C |
| ATOM | 4334 | C | ILE | C | 2 | −0.999 | −57.491 | −69.307 | 1.00 | 77.29 | MOL2 | C |
| ATOM | 4335 | O | ILE | C | 2 | −0.803 | −56.316 | −69.581 | 1.00 | 73.54 | MOL2 | O |
| ATOM | 4336 | N | GLN | C | 3 | −1.181 | −57.929 | −68.066 | 1.00 | 76.96 | MOL2 | N |
| ATOM | 4337 | CA | GLN | C | 3 | −1.199 | −57.039 | −66.911 | 1.00 | 79.39 | MOL2 | C |
| ATOM | 4338 | CB | GLN | C | 3 | −2.445 | −57.357 | −66.071 | 1.00 | 86.34 | MOL2 | C |
| ATOM | 4339 | CG | GLN | C | 3 | −2.691 | −56.471 | −64.849 | 1.00 | 99.34 | MOL2 | C |
| ATOM | 4340 | CD | GLN | C | 3 | −3.626 | −55.296 | −65.133 | 1.00 | 110.28 | MOL2 | C |
| ATOM | 4341 | OE1 | GLN | C | 3 | −4.048 | −54.590 | −64.210 | 1.00 | 112.13 | MOL2 | O |
| ATOM | 4342 | NE2 | GLN | C | 3 | −3.953 | −55.083 | −66.411 | 1.00 | 111.21 | MOL2 | N |
| ATOM | 4343 | C | GLN | C | 3 | 0.067 | −57.203 | −66.063 | 1.00 | 78.09 | MOL2 | C |
| ATOM | 4344 | O | GLN | C | 3 | 0.296 | −58.261 | −65.481 | 1.00 | 79.09 | MOL2 | O |
| ATOM | 4345 | N | LEU | C | 4 | 0.882 | −56.155 | −65.991 | 1.00 | 75.88 | MOL2 | N |
| ATOM | 4346 | CA | LEU | C | 4 | 2.117 | −56.200 | −65.216 | 1.00 | 72.85 | MOL2 | C |
| ATOM | 4347 | CB | LEU | C | 4 | 3.166 | −55.282 | −65.836 | 1.00 | 74.18 | MOL2 | C |
| ATOM | 4348 | CG | LEU | C | 4 | 3.469 | −55.485 | −67.321 | 1.00 | 78.14 | MOL2 | C |
| ATOM | 4349 | CD1 | LEU | C | 4 | 4.755 | −54.744 | −67.666 | 1.00 | 82.52 | MOL2 | C |
| ATOM | 4350 | CD2 | LEU | C | 4 | 3.609 | −56.960 | −67.633 | 1.00 | 71.94 | MOL2 | C |
| ATOM | 4351 | C | LEU | C | 4 | 1.864 | −55.772 | −63.780 | 1.00 | 71.99 | MOL2 | C |
| ATOM | 4352 | O | LEU | C | 4 | 1.257 | −54.734 | −63.532 | 1.00 | 71.82 | MOL2 | O |
| ATOM | 4353 | N | THR | C | 5 | 2.358 | −56.563 | −62.835 | 1.00 | 71.36 | MOL2 | N |
| ATOM | 4354 | CA | THR | C | 5 | 2.151 | −56.267 | −61.429 | 1.00 | 71.70 | MOL2 | C |
| ATOM | 4355 | CB | THR | C | 5 | 1.342 | −57.383 | −60.759 | 1.00 | 79.04 | MOL2 | C |
| ATOM | 4356 | OG1 | THR | C | 5 | 0.251 | −57.766 | −61.612 | 1.00 | 80.97 | MOL2 | O |
| ATOM | 4357 | CG2 | THR | C | 5 | 0.810 | −56.912 | −59.406 | 1.00 | 77.86 | MOL2 | C |
| ATOM | 4358 | C | THR | C | 5 | 3.452 | −56.113 | −60.662 | 1.00 | 70.09 | MOL2 | C |
| ATOM | 4359 | O | THR | C | 5 | 4.030 | −57.097 | −60.187 | 1.00 | 70.80 | MOL2 | O |
| ATOM | 4360 | N | GLN | C | 6 | 3.912 | −54.876 | −60.536 | 1.00 | 67.35 | MOL2 | N |
| ATOM | 4361 | CA | GLN | C | 6 | 5.143 | −54.610 | −59.807 | 1.00 | 67.62 | MOL2 | C |
| ATOM | 4362 | CB | GLN | C | 6 | 5.601 | −53.173 | −60.032 | 1.00 | 65.55 | MOL2 | C |

TABLE 1-continued

The atomic coordinates of IL17F in complex with 496 Fab
(H32; a = 189.4; b = 189.4; c = 490.9, α, β = 90°; γ = 120°)

|  |  |  |  |  |  |  |  |  |  |  |  |  |
|---|---|---|---|---|---|---|---|---|---|---|---|---|
|  |  | OE1 | GLN | C | 6 | 7.145 | −50.820 | −60.667 | 1.00 | 62.41 | MOL2 | O |
| ATOM | 4366 | NE2 | GLN | C | 6 | 6.583 | −51.089 | −62.823 | 1.00 | 64.70 | MOL2 | N |
| ATOM | 4367 | C | GLN | C | 6 | 4.902 | −54.839 | −58.333 | 1.00 | 69.96 | MOL2 | C |
| ATOM | 4368 | O | GLN | C | 6 | 3.760 | −54.857 | −57.889 | 1.00 | 74.54 | MOL2 | O |
| ATOM | 4369 | N | SER | C | 7 | 5.980 | −54.999 | −57.573 | 1.00 | 71.78 | MOL2 | N |
| ATOM | 4370 | CA | SER | C | 7 | 5.879 | −55.249 | −56.137 | 1.00 | 72.15 | MOL2 | C |
| ATOM | 4371 | CB | SER | C | 7 | 5.253 | −56.625 | −55.895 | 1.00 | 80.15 | MOL2 | C |
| ATOM | 4372 | OG | SER | C | 7 | 5.884 | −57.629 | −56.687 | 1.00 | 87.70 | MOL2 | O |
| ATOM | 4373 | C | SER | C | 7 | 7.253 | −55.205 | −55.491 | 1.00 | 68.10 | MOL2 | C |
| ATOM | 4374 | O | SER | C | 7 | 8.187 | −55.837 | −55.963 | 1.00 | 72.62 | MOL2 | O |
| ATOM | 4375 | N | PRO | C | 8 | 7.395 | −54.462 | −54.393 | 1.00 | 65.56 | MOL2 | N |
| ATOM | 4376 | CD | PRO | C | 8 | 8.704 | −54.188 | −53.788 | 1.00 | 66.95 | MOL2 | C |
| ATOM | 4377 | CA | PRO | C | 8 | 6.363 | −53.673 | −53.728 | 1.00 | 69.73 | MOL2 | C |
| ATOM | 4378 | CB | PRO | C | 8 | 7.080 | −53.162 | −52.494 | 1.00 | 67.77 | MOL2 | C |
| ATOM | 4379 | CG | PRO | C | 8 | 8.434 | −52.910 | −53.015 | 1.00 | 63.16 | MOL2 | C |
| ATOM | 4380 | C | PRO | C | 8 | 5.917 | −52.528 | −54.606 | 1.00 | 71.09 | MOL2 | C |
| ATOM | 4381 | O | PRO | C | 8 | 6.499 | −52.286 | −55.653 | 1.00 | 76.45 | MOL2 | O |
| ATOM | 4382 | N | SER | C | 9 | 4.887 | −51.821 | −54.171 | 1.00 | 70.48 | MOL2 | N |
| ATOM | 4383 | CA | SER | C | 9 | 4.393 | −50.692 | −54.924 | 1.00 | 66.56 | MOL2 | C |
| ATOM | 4384 | CB | SER | C | 9 | 2.900 | −50.513 | −54.663 | 1.00 | 68.50 | MOL2 | C |
| ATOM | 4385 | OG | SER | C | 9 | 2.302 | −49.695 | −55.649 | 1.00 | 74.33 | MOL2 | O |
| ATOM | 4386 | C | SER | C | 9 | 5.187 | −49.507 | −54.396 | 1.00 | 65.19 | MOL2 | C |
| ATOM | 4387 | O | SER | C | 9 | 5.474 | −48.552 | −55.107 | 1.00 | 66.87 | MOL2 | O |
| ATOM | 4388 | N | SER | C | 10 | 5.548 | −49.584 | −53.127 | 1.00 | 63.71 | MOL2 | N |
| ATOM | 4389 | CA | SER | C | 10 | 6.332 | −48.532 | −52.511 | 1.00 | 63.51 | MOL2 | C |
| ATOM | 4390 | CB | SER | C | 10 | 5.446 | −47.646 | −51.635 | 1.00 | 65.35 | MOL2 | C |
| ATOM | 4391 | OG | SER | C | 10 | 6.177 | −46.533 | −51.147 | 1.00 | 70.90 | MOL2 | O |
| ATOM | 4392 | C | SER | C | 10 | 7.383 | −49.243 | −51.671 | 1.00 | 61.83 | MOL2 | C |
| ATOM | 4393 | O | SER | C | 10 | 7.347 | −50.469 | −51.541 | 1.00 | 66.16 | MOL2 | O |
| ATOM | 4394 | N | LEU | C | 11 | 8.326 | −48.495 | −51.113 | 1.00 | 52.84 | MOL2 | N |
| ATOM | 4395 | CA | LEU | C | 11 | 9.349 | −49.124 | −50.298 | 1.00 | 51.69 | MOL2 | C |
| ATOM | 4396 | CB | LEU | C | 11 | 10.048 | −50.220 | −51.099 | 1.00 | 39.27 | MOL2 | C |
| ATOM | 4397 | CG | LEU | C | 11 | 11.390 | −49.797 | −51.673 | 1.00 | 40.68 | MOL2 | C |
| ATOM | 4398 | CD1 | LEU | C | 11 | 12.440 | −49.932 | −50.588 | 1.00 | 43.91 | MOL2 | C |
| ATOM | 4399 | CD2 | LEU | C | 11 | 11.747 | −50.648 | −52.865 | 1.00 | 31.09 | MOL2 | C |
| ATOM | 4400 | C | LEU | C | 11 | 10.358 | −48.085 | −49.854 | 1.00 | 54.60 | MOL2 | C |
| ATOM | 4401 | O | LEU | C | 11 | 10.791 | −47.266 | −50.656 | 1.00 | 52.95 | MOL2 | O |
| ATOM | 4402 | N | SER | C | 12 | 10.726 | −48.112 | −48.576 | 1.00 | 62.06 | MOL2 | N |
| ATOM | 4403 | CA | SER | C | 12 | 11.705 | −47.153 | −48.056 | 1.00 | 67.26 | MOL2 | C |
| ATOM | 4404 | CB | SER | C | 12 | 11.246 | −46.553 | −46.718 | 1.00 | 73.13 | MOL2 | C |
| ATOM | 4405 | OG | SER | C | 12 | 11.103 | −47.546 | −45.707 | 1.00 | 91.16 | MOL2 | O |
| ATOM | 4406 | C | SER | C | 12 | 13.040 | −47.856 | −47.879 | 1.00 | 64.64 | MOL2 | C |
| ATOM | 4407 | O | SER | C | 12 | 13.093 | −49.007 | −47.428 | 1.00 | 73.92 | MOL2 | O |
| ATOM | 4408 | N | ALA | C | 13 | 14.112 | −47.160 | −48.239 | 1.00 | 52.40 | MOL2 | N |
| ATOM | 4409 | CA | ALA | C | 13 | 15.445 | −47.715 | −48.157 | 1.00 | 48.17 | MOL2 | C |
| ATOM | 4410 | CB | ALA | C | 13 | 15.804 | −48.349 | −49.452 | 1.00 | 46.27 | MOL2 | C |
| ATOM | 4411 | C | ALA | C | 13 | 16.430 | −46.623 | −47.855 | 1.00 | 53.29 | MOL2 | C |
| ATOM | 4412 | O | ALA | C | 13 | 16.083 | −45.442 | −47.903 | 1.00 | 51.42 | MOL2 | O |
| ATOM | 4413 | N | SER | C | 14 | 17.666 | −47.023 | −47.549 | 1.00 | 59.92 | MOL2 | N |
| ATOM | 4414 | CA | SER | C | 14 | 18.748 | −46.082 | −47.236 | 1.00 | 62.56 | MOL2 | C |
| ATOM | 4415 | CB | SER | C | 14 | 19.305 | −46.332 | −45.835 | 1.00 | 65.99 | MOL2 | C |
| ATOM | 4416 | OG | SER | C | 14 | 18.563 | −45.634 | −44.850 | 1.00 | 77.69 | MOL2 | O |
| ATOM | 4417 | C | SER | C | 14 | 19.879 | −46.222 | −48.229 | 1.00 | 60.39 | MOL2 | C |
| ATOM | 4418 | O | SER | C | 14 | 20.060 | −47.286 | −48.822 | 1.00 | 64.34 | MOL2 | O |
| ATOM | 4419 | N | VAL | C | 15 | 20.645 | −45.154 | −48.410 | 1.00 | 56.47 | MOL2 | N |
| ATOM | 4420 | CA | VAL | C | 15 | 21.752 | −45.215 | −49.346 | 1.00 | 55.09 | MOL2 | C |
| ATOM | 4421 | CB | VAL | C | 15 | 22.651 | −44.006 | −49.225 | 1.00 | 55.42 | MOL2 | C |
| ATOM | 4422 | CG1 | VAL | C | 15 | 23.957 | −44.274 | −49.958 | 1.00 | 52.75 | MOL2 | C |
| ATOM | 4423 | CG2 | VAL | C | 15 | 21.951 | −42.794 | −49.795 | 1.00 | 50.64 | MOL2 | C |
| ATOM | 4424 | C | VAL | C | 15 | 22.595 | −46.456 | −49.099 | 1.00 | 56.26 | MOL2 | C |
| ATOM | 4425 | O | VAL | C | 15 | 22.945 | −46.773 | −47.959 | 1.00 | 60.65 | MOL2 | O |
| ATOM | 4426 | N | GLY | C | 16 | 22.911 | −47.165 | −50.172 | 1.00 | 51.10 | MOL2 | N |
| ATOM | 4427 | CA | GLY | C | 16 | 23.709 | −48.361 | −50.034 | 1.00 | 52.45 | MOL2 | C |
| ATOM | 4428 | C | GLY | C | 16 | 22.879 | −49.619 | −50.137 | 1.00 | 54.77 | MOL2 | C |
| ATOM | 4429 | O | GLY | C | 16 | 23.300 | −50.604 | −50.759 | 1.00 | 58.98 | MOL2 | O |
| ATOM | 4430 | N | ASP | C | 17 | 21.696 | −49.598 | −49.537 | 1.00 | 52.74 | MOL2 | N |
| ATOM | 4431 | CA | ASP | C | 17 | 20.826 | −50.772 | −49.574 | 1.00 | 60.34 | MOL2 | C |
| ATOM | 4432 | CB | ASP | C | 17 | 19.399 | −50.404 | −49.122 | 1.00 | 67.58 | MOL2 | C |
| ATOM | 4433 | CG | ASP | C | 17 | 19.315 | −50.057 | −47.638 | 1.00 | 74.44 | MOL2 | C |
| ATOM | 4434 | OD1 | ASP | C | 17 | 18.195 | −49.783 | −47.153 | 1.00 | 76.43 | MOL2 | O |
| ATOM | 4435 | OD2 | ASP | C | 17 | 20.364 | −50.056 | −46.954 | 1.00 | 83.78 | MOL2 | O |
| ATOM | 4436 | C | ASP | C | 17 | 20.779 | −51.431 | −50.962 | 1.00 | 52.46 | MOL2 | C |
| ATOM | 4437 | O | ASP | C | 17 | 21.097 | −50.817 | −51.965 | 1.00 | 49.08 | MOL2 | O |
| ATOM | 4438 | N | ARG | C | 18 | 20.392 | −52.694 | −51.000 | 1.00 | 50.22 | MOL2 | N |
| ATOM | 4439 | CA | ARG | C | 18 | 20.294 | −53.411 | −52.251 | 1.00 | 56.08 | MOL2 | C |
| ATOM | 4363 | CG | GLN | C | 6 | 6.368 | −52.978 | −61.323 | 1.00 | 67.75 | MOL2 | C |
| ATOM | 4364 | CD | GLN | C | 6 | 6.728 | −51.530 | −61.577 | 1.00 | 66.51 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 4440 | CB | ARG | C | 18 | 21.000 | −54.765 | −52.127 | 1.00 | 66.53 | MOL2 | C |
|---|---|---|---|---|---|---|---|---|---|---|---|---|
| ATOM | 4441 | CG | ARG | C | 18 | 21.162 | −55.544 | −53.416 | 1.00 | 69.54 | MOL2 | C |
| ATOM | 4442 | CD | ARG | C | 18 | 22.473 | −56.333 | −53.410 | 1.00 | 76.41 | MOL2 | C |
| ATOM | 4443 | NE | ARG | C | 18 | 22.607 | −57.130 | −54.621 | 1.00 | 83.22 | MOL2 | N |
| ATOM | 4444 | CZ | ARG | C | 18 | 21.768 | −58.106 | −54.964 | 1.00 | 90.00 | MOL2 | C |
| ATOM | 4445 | NH1 | ARG | C | 18 | 20.736 | −58.411 | −54.178 | 1.00 | 91.48 | MOL2 | N |
| ATOM | 4446 | NH2 | ARG | C | 18 | 21.947 | −58.762 | −56.105 | 1.00 | 88.15 | MOL2 | N |
| ATOM | 4447 | C | ARG | C | 18 | 18.809 | −53.590 | −52.541 | 1.00 | 59.14 | MOL2 | C |
| ATOM | 4448 | O | ARG | C | 18 | 18.207 | −54.619 | −52.216 | 1.00 | 66.55 | MOL2 | O |
| ATOM | 4449 | N | VAL | C | 19 | 18.227 | −52.560 | −53.143 | 1.00 | 53.91 | MOL2 | N |
| ATOM | 4450 | CA | VAL | C | 19 | 16.814 | −52.531 | −53.500 | 1.00 | 48.82 | MOL2 | C |
| ATOM | 4451 | CB | VAL | C | 19 | 16.430 | −51.116 | −54.008 | 1.00 | 49.90 | MOL2 | C |
| ATOM | 4452 | CG1 | VAL | C | 19 | 14.942 | −50.897 | −53.896 | 1.00 | 55.27 | MOL2 | C |
| ATOM | 4453 | CG2 | VAL | C | 19 | 17.165 | −50.067 | −53.220 | 1.00 | 44.57 | MOL2 | C |
| ATOM | 4454 | C | VAL | C | 19 | 16.490 | −53.548 | −54.599 | 1.00 | 46.40 | MOL2 | C |
| ATOM | 4455 | O | VAL | C | 19 | 17.300 | −53.790 | −55.485 | 1.00 | 41.70 | MOL2 | O |
| ATOM | 4456 | N | THR | C | 20 | 15.303 | −54.138 | −54.548 | 1.00 | 48.52 | MOL2 | N |
| ATOM | 4457 | CA | THR | C | 20 | 14.909 | −55.111 | −55.560 | 1.00 | 52.40 | MOL2 | C |
| ATOM | 4458 | CB | THR | C | 20 | 15.237 | −56.558 | −55.100 | 1.00 | 56.67 | MOL2 | C |
| ATOM | 4459 | OG1 | THR | C | 20 | 16.636 | −56.668 | −54.828 | 1.00 | 62.88 | MOL2 | O |
| ATOM | 4460 | CG2 | THR | C | 20 | 14.882 | −57.565 | −56.176 | 1.00 | 59.26 | MOL2 | C |
| ATOM | 4461 | C | THR | C | 20 | 13.411 | −54.992 | −55.855 | 1.00 | 55.76 | MOL2 | C |
| ATOM | 4462 | O | THR | C | 20 | 12.566 | −55.195 | −54.969 | 1.00 | 60.73 | MOL2 | O |
| ATOM | 4463 | N | ILE | C | 21 | 13.102 | −54.667 | −57.109 | 1.00 | 49.17 | MOL2 | N |
| ATOM | 4464 | CA | ILE | C | 21 | 11.736 | −54.490 | −57.585 | 1.00 | 44.82 | MOL2 | C |
| ATOM | 4465 | CB | ILE | C | 21 | 11.641 | −53.267 | −58.516 | 1.00 | 42.78 | MOL2 | C |
| ATOM | 4466 | CG2 | ILE | C | 21 | 10.197 | −52.894 | −58.750 | 1.00 | 42.89 | MOL2 | C |
| ATOM | 4467 | CG1 | ILE | C | 21 | 12.416 | −52.086 | −57.923 | 1.00 | 40.47 | MOL2 | C |
| ATOM | 4468 | CD1 | ILE | C | 21 | 11.928 | −51.621 | −56.613 | 1.00 | 29.96 | MOL2 | C |
| ATOM | 4469 | C | ILE | C | 21 | 11.384 | −55.704 | −58.414 | 1.00 | 46.51 | MOL2 | C |
| ATOM | 4470 | O | ILE | C | 21 | 12.241 | −56.245 | −59.086 | 1.00 | 49.54 | MOL2 | O |
| ATOM | 4471 | N | THR | C | 22 | 10.128 | −56.121 | −58.389 | 1.00 | 52.70 | MOL2 | N |
| ATOM | 4472 | CA | THR | C | 22 | 9.705 | −57.276 | −59.164 | 1.00 | 56.36 | MOL2 | C |
| ATOM | 4473 | CB | THR | C | 22 | 9.221 | −58.386 | −58.250 | 1.00 | 57.04 | MOL2 | C |
| ATOM | 4474 | OG1 | THR | C | 22 | 10.014 | −58.400 | −57.054 | 1.00 | 57.35 | MOL2 | O |
| ATOM | 4475 | CG2 | THR | C | 22 | 9.335 | −59.722 | −58.962 | 1.00 | 61.74 | MOL2 | C |
| ATOM | 4476 | C | THR | C | 22 | 8.558 | −56.868 | −60.070 | 1.00 | 62.56 | MOL2 | C |
| ATOM | 4477 | O | THR | C | 22 | 7.879 | −55.877 | −59.806 | 1.00 | 67.37 | MOL2 | O |
| ATOM | 4478 | N | CYS | C | 23 | 8.324 | −57.632 | −61.129 | 1.00 | 64.49 | MOL2 | N |
| ATOM | 4479 | CA | CYS | C | 23 | 7.249 | −57.295 | −62.046 | 1.00 | 69.63 | MOL2 | C |
| ATOM | 4480 | C | CYS | C | 23 | 6.683 | −58.549 | −62.694 | 1.00 | 74.35 | MOL2 | C |
| ATOM | 4481 | O | CYS | C | 23 | 7.028 | −58.879 | −63.825 | 1.00 | 79.68 | MOL2 | O |
| ATOM | 4482 | CB | CYS | C | 23 | 7.790 | −56.321 | −63.097 | 1.00 | 66.66 | MOL2 | C |
| ATOM | 4483 | SG | CYS | C | 23 | 6.755 | −55.921 | −64.548 | 1.00 | 76.32 | MOL2 | S |
| ATOM | 4484 | N | ARG | C | 24 | 5.818 | −59.252 | −61.965 | 1.00 | 78.76 | MOL2 | N |
| ATOM | 4485 | CA | ARG | C | 24 | 5.189 | −60.471 | −62.476 | 1.00 | 84.17 | MOL2 | C |
| ATOM | 4486 | CB | ARG | C | 24 | 4.489 | −61.236 | −61.345 | 1.00 | 94.07 | MOL2 | C |
| ATOM | 4487 | CG | ARG | C | 24 | 5.418 | −62.065 | −60.462 | 1.00 | 108.22 | MOL2 | C |
| ATOM | 4488 | CD | ARG | C | 24 | 4.643 | −62.860 | −59.410 | 1.00 | 120.10 | MOL2 | C |
| ATOM | 4489 | NE | ARG | C | 24 | 3.463 | −63.534 | −59.964 | 1.00 | 130.87 | MOL2 | N |
| ATOM | 4490 | CZ | ARG | C | 24 | 2.741 | −64.452 | −59.318 | 1.00 | 135.36 | MOL2 | C |
| ATOM | 4491 | NH1 | ARG | C | 24 | 3.071 | −64.828 | −58.086 | 1.00 | 135.50 | MOL2 | N |
| ATOM | 4492 | NH2 | ARG | C | 24 | 1.673 | −64.987 | −59.900 | 1.00 | 136.70 | MOL2 | N |
| ATOM | 4493 | C | ARG | C | 24 | 4.162 | −60.075 | −63.520 | 1.00 | 82.37 | MOL2 | C |
| ATOM | 4494 | O | ARG | C | 24 | 3.525 | −59.035 | −63.382 | 1.00 | 84.85 | MOL2 | O |
| ATOM | 4495 | N | ALA | C | 25 | 3.984 | −60.894 | −64.554 | 1.00 | 80.09 | MOL2 | N |
| ATOM | 4496 | CA | ALA | C | 25 | 3.022 | −60.558 | −65.597 | 1.00 | 81.28 | MOL2 | C |
| ATOM | 4497 | CB | ALA | C | 25 | 3.750 | −60.042 | −66.804 | 1.00 | 74.63 | MOL2 | C |
| ATOM | 4498 | C | ALA | C | 25 | 2.054 | −61.652 | −66.029 | 1.00 | 85.27 | MOL2 | C |
| ATOM | 4499 | O | ALA | C | 25 | 2.420 | −62.815 | −66.178 | 1.00 | 84.26 | MOL2 | O |
| ATOM | 4500 | N | ASP | C | 26 | 0.809 | −61.232 | −66.234 | 1.00 | 93.13 | MOL2 | N |
| ATOM | 4501 | CA | ASP | C | 26 | −0.307 | −62.065 | −66.688 | 1.00 | 98.83 | MOL2 | C |
| ATOM | 4502 | CB | ASP | C | 26 | −1.270 | −61.153 | −67.466 | 1.00 | 106.45 | MOL2 | C |
| ATOM | 4503 | CG | ASP | C | 26 | −2.373 | −61.908 | −68.180 | 1.00 | 115.95 | MOL2 | C |
| ATOM | 4504 | OD1 | ASP | C | 26 | −2.074 | −62.825 | −68.981 | 1.00 | 117.86 | MOL2 | O |
| ATOM | 4505 | OD2 | ASP | C | 26 | −3.552 | −61.559 | −67.950 | 1.00 | 122.70 | MOL2 | O |
| ATOM | 4506 | C | ASP | C | 26 | 0.130 | −63.258 | −67.555 | 1.00 | 98.49 | MOL2 | C |
| ATOM | 4507 | O | ASP | C | 26 | 0.131 | −64.404 | −67.099 | 1.00 | 93.41 | MOL2 | O |
| ATOM | 4508 | N | GLU | C | 27 | 0.478 | −62.975 | −68.810 | 1.00 | 100.98 | MOL2 | N |
| ATOM | 4509 | CA | GLU | C | 27 | 0.932 | −63.998 | −69.754 | 1.00 | 102.53 | MOL2 | C |
| ATOM | 4510 | CB | GLU | C | 27 | 0.396 | −63.738 | −71.170 | 1.00 | 109.48 | MOL2 | C |
| ATOM | 4511 | CG | GLU | C | 27 | −1.094 | −63.983 | −71.392 | 1.00 | 119.13 | MOL2 | C |
| ATOM | 4512 | CD | GLU | C | 27 | −1.483 | −63.922 | −72.876 | 1.00 | 125.04 | MOL2 | C |
| ATOM | 4513 | OE1 | GLU | C | 27 | −2.697 | −63.949 | −73.180 | 1.00 | 127.79 | MOL2 | O |
| ATOM | 4514 | OE2 | GLU | C | 27 | −0.575 | −63.855 | −73.739 | 1.00 | 124.79 | MOL2 | O |
| ATOM | 4515 | C | GLU | C | 27 | 2.459 | −64.012 | −69.822 | 1.00 | 99.74 | MOL2 | C |
| ATOM | 4516 | O | GLU | C | 27 | 3.138 | −63.575 | −68.893 | 1.00 | 98.01 | MOL2 | O |

TABLE 1-continued

The atomic coordinates of IL17F in complex with 496 Fab
(H32; a = 189.4; b = 189.4; c = 490.9, α, β = 90°; γ = 120°)

| ATOM | 4517 | N   | SER | C | 28 | 2.989  | −64.510 | −70.935 | 1.00 | 98.17  | MOL2 | N |
|------|------|-----|-----|---|----|--------|---------|---------|------|--------|------|---|
| ATOM | 4518 | CA  | SER | C | 28 | 4.435  | −64.589 | −71.142 | 1.00 | 96.89  | MOL2 | C |
| ATOM | 4519 | CB  | SER | C | 28 | 4.820  | −65.977 | −71.685 | 1.00 | 101.41 | MOL2 | C |
| ATOM | 4520 | OG  | SER | C | 28 | 6.224  | −66.108 | −71.880 | 1.00 | 99.08  | MOL2 | O |
| ATOM | 4521 | C   | SER | C | 28 | 4.905  | −63.509 | −72.114 | 1.00 | 92.54  | MOL2 | C |
| ATOM | 4522 | O   | SER | C | 28 | 4.276  | −63.285 | −73.147 | 1.00 | 94.50  | MOL2 | O |
| ATOM | 4523 | N   | VAL | C | 29 | 6.017  | −62.853 | −71.787 | 1.00 | 85.57  | MOL2 | N |
| ATOM | 4524 | CA  | VAL | C | 29 | 6.566  | −61.793 | −72.633 | 1.00 | 78.41  | MOL2 | C |
| ATOM | 4525 | CB  | VAL | C | 29 | 6.654  | −60.478 | −71.864 | 1.00 | 74.78  | MOL2 | C |
| ATOM | 4526 | CG1 | VAL | C | 29 | 5.342  | −59.741 | −71.938 | 1.00 | 74.79  | MOL2 | C |
| ATOM | 4527 | CG2 | VAL | C | 29 | 6.994  | −60.764 | −70.423 | 1.00 | 74.97  | MOL2 | C |
| ATOM | 4528 | C   | VAL | C | 29 | 7.947  | −62.083 | −73.208 | 1.00 | 74.63  | MOL2 | C |
| ATOM | 4529 | O   | VAL | C | 29 | 8.374  | −61.415 | −74.144 | 1.00 | 74.56  | MOL2 | O |
| ATOM | 4530 | N   | THR | C | 30 | 8.638  | −63.066 | −72.640 | 1.00 | 69.19  | MOL2 | N |
| ATOM | 4531 | CA  | THR | C | 30 | 9.972  | −63.457 | −73.093 | 1.00 | 65.75  | MOL2 | C |
| ATOM | 4532 | CB  | THR | C | 30 | 9.957  | −64.420 | −74.307 | 1.00 | 66.75  | MOL2 | C |
| ATOM | 4533 | OG1 | THR | C | 30 | 9.099  | −63.893 | −75.332 | 1.00 | 50.46  | MOL2 | O |
| ATOM | 4534 | CG2 | THR | C | 30 | 9.543  | −65.835 | −73.885 | 1.00 | 73.47  | MOL2 | C |
| ATOM | 4535 | C   | THR | C | 30 | 10.876 | −62.338 | −73.525 | 1.00 | 64.89  | MOL2 | C |
| ATOM | 4536 | O   | THR | C | 30 | 10.728 | −61.798 | −74.614 | 1.00 | 71.06  | MOL2 | O |
| ATOM | 4537 | N   | THR | C | 31 | 11.831 | −62.005 | −72.681 | 1.00 | 59.01  | MOL2 | N |
| ATOM | 4538 | CA  | THR | C | 31 | 12.806 | −60.981 | −73.012 | 1.00 | 56.53  | MOL2 | C |
| ATOM | 4539 | CB  | THR | C | 31 | 13.746 | −61.468 | −74.127 | 1.00 | 53.95  | MOL2 | C |
| ATOM | 4540 | OG1 | THR | C | 31 | 13.024 | −61.599 | −75.354 | 1.00 | 46.97  | MOL2 | O |
| ATOM | 4541 | CG2 | THR | C | 31 | 14.329 | −62.811 | −73.768 | 1.00 | 62.15  | MOL2 | C |
| ATOM | 4542 | C   | THR | C | 31 | 12.302 | −59.604 | −73.407 | 1.00 | 55.57  | MOL2 | C |
| ATOM | 4543 | O   | THR | C | 31 | 13.057 | −58.634 | −73.336 | 1.00 | 60.99  | MOL2 | O |
| ATOM | 4544 | N   | LEU | C | 32 | 11.048 | −59.491 | −73.824 | 1.00 | 50.80  | MOL2 | N |
| ATOM | 4545 | CA  | LEU | C | 32 | 10.557 | −58.186 | −74.212 | 1.00 | 49.27  | MOL2 | C |
| ATOM | 4546 | CB  | LEU | C | 32 | 9.485  | −58.314 | −75.279 | 1.00 | 53.74  | MOL2 | C |
| ATOM | 4547 | CG  | LEU | C | 32 | 10.003 | −58.972 | −76.558 | 1.00 | 61.51  | MOL2 | C |
| ATOM | 4548 | CD1 | LEU | C | 32 | 9.155  | −58.525 | −77.738 | 1.00 | 67.47  | MOL2 | C |
| ATOM | 4549 | CD2 | LEU | C | 32 | 11.444 | −58.577 | −76.788 | 1.00 | 63.08  | MOL2 | C |
| ATOM | 4550 | C   | LEU | C | 32 | 10.040 | −57.369 | −73.044 | 1.00 | 49.73  | MOL2 | C |
| ATOM | 4551 | O   | LEU | C | 32 | 8.990  | −56.741 | −73.140 | 1.00 | 53.91  | MOL2 | O |
| ATOM | 4552 | N   | MET | C | 33 | 10.778 | −57.389 | −71.936 | 1.00 | 48.21  | MOL2 | N |
| ATOM | 4553 | CA  | MET | C | 33 | 10.417 | −56.605 | −70.753 | 1.00 | 50.67  | MOL2 | C |
| ATOM | 4554 | CB  | MET | C | 33 | 10.471 | −57.448 | −69.475 | 1.00 | 53.72  | MOL2 | C |
| ATOM | 4555 | CG  | MET | C | 33 | 10.063 | −56.693 | −68.203 | 1.00 | 63.35  | MOL2 | C |
| ATOM | 4556 | SD  | MET | C | 33 | 8.298  | −56.232 | −68.136 | 1.00 | 80.08  | MOL2 | S |
| ATOM | 4557 | CE  | MET | C | 33 | 7.649  | −57.505 | −67.077 | 1.00 | 69.12  | MOL2 | C |
| ATOM | 4558 | C   | MET | C | 33 | 11.442 | −55.471 | −70.682 | 1.00 | 47.74  | MOL2 | C |
| ATOM | 4559 | O   | MET | C | 33 | 12.608 | −55.670 | −71.009 | 1.00 | 47.46  | MOL2 | O |
| ATOM | 4560 | N   | HIS | C | 34 | 11.011 | −54.288 | −70.260 | 1.00 | 40.67  | MOL2 | N |
| ATOM | 4561 | CA  | HIS | C | 34 | 11.898 | −53.144 | −70.218 | 1.00 | 40.47  | MOL2 | C |
| ATOM | 4562 | CB  | HIS | C | 34 | 11.587 | −52.252 | −71.406 | 1.00 | 42.10  | MOL2 | C |
| ATOM | 4563 | CG  | HIS | C | 34 | 11.337 | −53.010 | −72.672 | 1.00 | 43.49  | MOL2 | C |
| ATOM | 4564 | CD2 | HIS | C | 34 | 10.320 | −52.950 | −73.561 | 1.00 | 46.48  | MOL2 | C |
| ATOM | 4565 | ND1 | HIS | C | 34 | 12.214 | −53.955 | −73.158 | 1.00 | 47.32  | MOL2 | N |
| ATOM | 4566 | CE1 | HIS | C | 34 | 11.751 | −54.440 | −74.295 | 1.00 | 48.54  | MOL2 | C |
| ATOM | 4567 | NE2 | HIS | C | 34 | 10.603 | −53.846 | −74.563 | 1.00 | 48.33  | MOL2 | N |
| ATOM | 4568 | C   | HIS | C | 34 | 11.686 | −52.378 | −68.943 | 1.00 | 42.71  | MOL2 | C |
| ATOM | 4569 | O   | HIS | C | 34 | 10.658 | −52.557 | −68.311 | 1.00 | 55.61  | MOL2 | O |
| ATOM | 4570 | N   | TRP | C | 35 | 12.638 | −51.525 | −68.563 | 1.00 | 36.83  | MOL2 | N |
| ATOM | 4571 | CA  | TRP | C | 35 | 12.502 | −50.747 | −67.333 | 1.00 | 39.88  | MOL2 | C |
| ATOM | 4572 | CB  | TRP | C | 35 | 13.483 | −51.223 | −66.255 | 1.00 | 40.79  | MOL2 | C |
| ATOM | 4573 | CG  | TRP | C | 35 | 13.136 | −52.538 | −65.657 | 1.00 | 43.11  | MOL2 | C |
| ATOM | 4574 | CD2 | TRP | C | 35 | 12.300 | −52.765 | −64.523 | 1.00 | 40.24  | MOL2 | C |
| ATOM | 4575 | CE2 | TRP | C | 35 | 12.155 | −54.154 | −64.383 | 1.00 | 42.15  | MOL2 | C |
| ATOM | 4576 | CE3 | TRP | C | 35 | 11.659 | −51.928 | −63.617 | 1.00 | 43.55  | MOL2 | C |
| ATOM | 4577 | CD1 | TRP | C | 35 | 13.463 | −53.769 | −66.141 | 1.00 | 46.19  | MOL2 | C |
| ATOM | 4578 | NE1 | TRP | C | 35 | 12.877 | −54.746 | −65.384 | 1.00 | 47.19  | MOL2 | N |
| ATOM | 4579 | CZ2 | TRP | C | 35 | 11.395 | −54.724 | −63.376 | 1.00 | 38.68  | MOL2 | C |
| ATOM | 4580 | CZ3 | TRP | C | 35 | 10.909 | −52.496 | −62.618 | 1.00 | 46.45  | MOL2 | C |
| ATOM | 4581 | CH2 | TRP | C | 35 | 10.782 | −53.881 | −62.505 | 1.00 | 42.43  | MOL2 | C |
| ATOM | 4582 | C   | TRP | C | 35 | 12.753 | −49.277 | −67.559 | 1.00 | 39.85  | MOL2 | C |
| ATOM | 4583 | O   | TRP | C | 35 | 13.663 | −48.920 | −68.283 | 1.00 | 42.09  | MOL2 | O |
| ATOM | 4584 | N   | TYR | C | 36 | 11.950 | −48.426 | −66.928 | 1.00 | 37.19  | MOL2 | N |
| ATOM | 4585 | CA  | TYR | C | 36 | 12.119 | −46.983 | −67.037 | 1.00 | 27.89  | MOL2 | C |
| ATOM | 4586 | CB  | TYR | C | 36 | 10.974 | −46.322 | −67.781 | 1.00 | 21.99  | MOL2 | C |
| ATOM | 4587 | CG  | TYR | C | 36 | 10.741 | −46.813 | −69.173 | 1.00 | 24.18  | MOL2 | C |
| ATOM | 4588 | CD1 | TYR | C | 36 | 11.354 | −46.196 | −70.255 | 1.00 | 24.27  | MOL2 | C |
| ATOM | 4589 | CE1 | TYR | C | 36 | 11.139 | −46.651 | −71.552 | 1.00 | 32.32  | MOL2 | C |
| ATOM | 4590 | CD2 | TYR | C | 36 | 9.903  | −47.901 | −69.412 | 1.00 | 23.69  | MOL2 | C |
| ATOM | 4591 | CE2 | TYR | C | 36 | 9.682  | −48.366 | −70.693 | 1.00 | 29.24  | MOL2 | C |
| ATOM | 4592 | CZ  | TYR | C | 36 | 10.303 | −47.739 | −71.763 | 1.00 | 38.05  | MOL2 | C |
| ATOM | 4593 | OH  | TYR | C | 36 | 10.100 | −48.207 | −73.047 | 1.00 | 47.12  | MOL2 | O |

TABLE 1-continued

The atomic coordinates of IL17F in complex with 496 Fab
(H32; a = 189.4; b = 189.4; c = 490.9, α, β = 90°; γ = 120°)

| ATOM | 4594 | C | TYR | C | 36 | 12.129 | −46.424 | −65.636 | 1.00 | 32.00 | MOL2 | C |
|---|---|---|---|---|---|---|---|---|---|---|---|---|
| ATOM | 4595 | O | TYR | C | 36 | 11.612 | −47.035 | −64.692 | 1.00 | 37.85 | MOL2 | O |
| ATOM | 4596 | N | GLN | C | 37 | 12.693 | −45.236 | −65.517 | 1.00 | 30.14 | MOL2 | N |
| ATOM | 4597 | CA | GLN | C | 37 | 12.802 | −44.566 | −64.242 | 1.00 | 33.69 | MOL2 | C |
| ATOM | 4598 | CB | GLN | C | 37 | 14.281 | −44.370 | −63.910 | 1.00 | 25.67 | MOL2 | C |
| ATOM | 4599 | CG | GLN | C | 37 | 14.536 | −43.723 | −62.571 | 1.00 | 29.66 | MOL2 | C |
| ATOM | 4600 | CD | GLN | C | 37 | 15.789 | −42.877 | −62.577 | 1.00 | 36.17 | MOL2 | C |
| ATOM | 4601 | OE1 | GLN | C | 37 | 16.014 | −42.092 | −63.498 | 1.00 | 42.76 | MOL2 | O |
| ATOM | 4602 | NE2 | GLN | C | 37 | 16.609 | −43.021 | −61.545 | 1.00 | 34.38 | MOL2 | N |
| ATOM | 4603 | C | GLN | C | 37 | 12.146 | −43.214 | −64.399 | 1.00 | 38.79 | MOL2 | C |
| ATOM | 4604 | O | GLN | C | 37 | 12.240 | −42.619 | −65.457 | 1.00 | 45.43 | MOL2 | O |
| ATOM | 4605 | N | GLN | C | 38 | 11.476 | −42.722 | −63.364 | 1.00 | 43.55 | MOL2 | N |
| ATOM | 4606 | CA | GLN | C | 38 | 10.872 | −41.403 | −63.458 | 1.00 | 43.76 | MOL2 | C |
| ATOM | 4607 | CB | GLN | C | 38 | 9.425 | −41.507 | −63.883 | 1.00 | 42.79 | MOL2 | C |
| ATOM | 4608 | CG | GLN | C | 38 | 8.736 | −40.175 | −63.802 | 1.00 | 46.09 | MOL2 | C |
| ATOM | 4609 | CD | GLN | C | 38 | 7.317 | −40.260 | −64.245 | 1.00 | 51.40 | MOL2 | C |
| ATOM | 4610 | OE1 | GLN | C | 38 | 7.016 | −40.096 | −65.424 | 1.00 | 49.67 | MOL2 | O |
| ATOM | 4611 | NE2 | GLN | C | 38 | 6.421 | −40.544 | −63.300 | 1.00 | 57.58 | MOL2 | N |
| ATOM | 4612 | C | GLN | C | 38 | 10.949 | −40.638 | −62.151 | 1.00 | 44.98 | MOL2 | C |
| ATOM | 4613 | O | GLN | C | 38 | 10.431 | −41.092 | −61.135 | 1.00 | 51.29 | MOL2 | O |
| ATOM | 4614 | N | LYS | C | 39 | 11.607 | −39.484 | −62.173 | 1.00 | 43.36 | MOL2 | N |
| ATOM | 4615 | CA | LYS | C | 39 | 11.731 | −38.667 | −60.976 | 1.00 | 46.56 | MOL2 | C |
| ATOM | 4616 | CB | LYS | C | 39 | 12.956 | −37.760 | −61.063 | 1.00 | 45.39 | MOL2 | C |
| ATOM | 4617 | CG | LYS | C | 39 | 14.272 | −38.457 | −61.390 | 1.00 | 52.65 | MOL2 | C |
| ATOM | 4618 | CD | LYS | C | 39 | 15.021 | −38.933 | −60.154 | 1.00 | 57.23 | MOL2 | C |
| ATOM | 4619 | CE | LYS | C | 39 | 16.433 | −39.450 | −60.494 | 1.00 | 62.86 | MOL2 | C |
| ATOM | 4620 | NZ | LYS | C | 39 | 17.409 | −38.418 | −61.000 | 1.00 | 63.36 | MOL2 | N |
| ATOM | 4621 | C | LYS | C | 39 | 10.479 | −37.811 | −60.953 | 1.00 | 56.54 | MOL2 | C |
| ATOM | 4622 | O | LYS | C | 39 | 9.767 | −37.725 | −61.948 | 1.00 | 60.11 | MOL2 | O |
| ATOM | 4623 | N | PRO | C | 40 | 10.193 | −37.159 | −59.822 | 1.00 | 64.58 | MOL2 | N |
| ATOM | 4624 | CD | PRO | C | 40 | 10.918 | −37.199 | −58.542 | 1.00 | 67.05 | MOL2 | C |
| ATOM | 4625 | CA | PRO | C | 40 | 8.999 | −36.314 | −59.725 | 1.00 | 65.12 | MOL2 | C |
| ATOM | 4626 | CB | PRO | C | 40 | 8.982 | −35.905 | −58.253 | 1.00 | 65.24 | MOL2 | C |
| ATOM | 4627 | CG | PRO | C | 40 | 9.807 | −36.975 | −57.570 | 1.00 | 71.18 | MOL2 | C |
| ATOM | 4628 | C | PRO | C | 40 | 9.117 | −35.100 | −60.637 | 1.00 | 66.71 | MOL2 | C |
| ATOM | 4629 | O | PRO | C | 40 | 10.122 | −34.373 | −60.581 | 1.00 | 63.72 | MOL2 | O |
| ATOM | 4630 | N | GLY | C | 41 | 8.107 | −34.893 | −61.482 | 1.00 | 65.67 | MOL2 | N |
| ATOM | 4631 | CA | GLY | C | 41 | 8.118 | −33.736 | −62.357 | 1.00 | 69.19 | MOL2 | C |
| ATOM | 4632 | C | GLY | C | 41 | 8.714 | −33.932 | −63.732 | 1.00 | 68.06 | MOL2 | C |
| ATOM | 4633 | O | GLY | C | 41 | 8.240 | −33.348 | −64.704 | 1.00 | 74.22 | MOL2 | O |
| ATOM | 4634 | N | LYS | C | 42 | 9.762 | −34.735 | −63.823 | 1.00 | 64.19 | MOL2 | N |
| ATOM | 4635 | CA | LYS | C | 42 | 10.391 | −34.989 | −65.105 | 1.00 | 61.08 | MOL2 | C |
| ATOM | 4636 | CB | LYS | C | 42 | 11.882 | −35.254 | −64.882 | 1.00 | 69.82 | MOL2 | C |
| ATOM | 4637 | CG | LYS | C | 42 | 12.633 | −34.071 | −64.233 | 1.00 | 79.68 | MOL2 | C |
| ATOM | 4638 | CD | LYS | C | 42 | 13.192 | −33.060 | −65.260 | 1.00 | 98.35 | MOL2 | C |
| ATOM | 4639 | CE | LYS | C | 42 | 14.349 | −33.664 | −66.104 | 1.00 | 110.67 | MOL2 | C |
| ATOM | 4640 | NZ | LYS | C | 42 | 14.865 | −32.795 | −67.225 | 1.00 | 109.90 | MOL2 | N |
| ATOM | 4641 | C | LYS | C | 42 | 9.688 | −36.164 | −65.814 | 1.00 | 56.57 | MOL2 | C |
| ATOM | 4642 | O | LYS | C | 42 | 8.760 | −36.766 | −65.262 | 1.00 | 54.63 | MOL2 | O |
| ATOM | 4643 | N | ALA | C | 43 | 10.112 | −36.483 | −67.033 | 1.00 | 51.70 | MOL2 | N |
| ATOM | 4644 | CA | ALA | C | 43 | 9.483 | −37.561 | −67.800 | 1.00 | 49.89 | MOL2 | C |
| ATOM | 4645 | CB | ALA | C | 43 | 9.429 | −37.170 | −69.249 | 1.00 | 52.86 | MOL2 | C |
| ATOM | 4646 | C | ALA | C | 43 | 10.219 | −38.879 | −67.655 | 1.00 | 46.72 | MOL2 | C |
| ATOM | 4647 | O | ALA | C | 43 | 11.384 | −38.896 | −67.281 | 1.00 | 47.15 | MOL2 | O |
| ATOM | 4648 | N | PRO | C | 44 | 9.558 | −40.001 | −67.978 | 1.00 | 44.39 | MOL2 | N |
| ATOM | 4649 | CD | PRO | C | 44 | 8.268 | −40.126 | −68.664 | 1.00 | 45.41 | MOL2 | C |
| ATOM | 4650 | CA | PRO | C | 44 | 10.202 | −41.314 | −67.862 | 1.00 | 44.83 | MOL2 | C |
| ATOM | 4651 | CB | PRO | C | 44 | 9.251 | −42.245 | −68.598 | 1.00 | 45.87 | MOL2 | C |
| ATOM | 4652 | CG | PRO | C | 44 | 7.938 | −41.584 | −68.419 | 1.00 | 52.20 | MOL2 | C |
| ATOM | 4653 | C | PRO | C | 44 | 11.546 | −41.275 | −68.537 | 1.00 | 45.42 | MOL2 | C |
| ATOM | 4654 | O | PRO | C | 44 | 11.802 | −40.387 | −69.348 | 1.00 | 52.33 | MOL2 | O |
| ATOM | 4655 | N | LYS | C | 45 | 12.405 | −42.226 | −68.192 | 1.00 | 45.13 | MOL2 | N |
| ATOM | 4656 | CA | LYS | C | 45 | 13.742 | −42.345 | −68.786 | 1.00 | 41.81 | MOL2 | C |
| ATOM | 4657 | CB | LYS | C | 45 | 14.806 | −41.625 | −67.964 | 1.00 | 39.22 | MOL2 | C |
| ATOM | 4658 | CG | LYS | C | 45 | 16.236 | −42.071 | −68.266 | 1.00 | 54.90 | MOL2 | C |
| ATOM | 4659 | CD | LYS | C | 45 | 17.180 | −41.630 | −67.110 | 1.00 | 72.09 | MOL2 | C |
| ATOM | 4660 | CE | LYS | C | 45 | 18.593 | −42.278 | −67.122 | 1.00 | 70.55 | MOL2 | C |
| ATOM | 4661 | NZ | LYS | C | 45 | 19.291 | −42.128 | −65.784 | 1.00 | 65.65 | MOL2 | N |
| ATOM | 4662 | C | LYS | C | 45 | 14.052 | −43.822 | −68.837 | 1.00 | 38.66 | MOL2 | C |
| ATOM | 4663 | O | LYS | C | 45 | 13.894 | −44.542 | −67.854 | 1.00 | 45.87 | MOL2 | O |
| ATOM | 4664 | N | LEU | C | 46 | 14.476 | −44.286 | −69.995 | 1.00 | 36.14 | MOL2 | N |
| ATOM | 4665 | CA | LEU | C | 46 | 14.766 | −45.698 | −70.150 | 1.00 | 34.95 | MOL2 | C |
| ATOM | 4666 | CB | LEU | C | 46 | 15.023 | −46.025 | −71.621 | 1.00 | 28.39 | MOL2 | C |
| ATOM | 4667 | CG | LEU | C | 46 | 15.497 | −47.425 | −71.985 | 1.00 | 23.94 | MOL2 | C |
| ATOM | 4668 | CD1 | LEU | C | 46 | 14.636 | −48.437 | −71.328 | 1.00 | 28.01 | MOL2 | C |
| ATOM | 4669 | CD2 | LEU | C | 46 | 15.437 | −47.614 | −73.474 | 1.00 | 23.58 | MOL2 | C |
| ATOM | 4670 | C | LEU | C | 46 | 15.960 | −46.108 | −69.322 | 1.00 | 39.09 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 4671 | O | LEU | C | 46 | 16.989 | −45.429 | −69.321 | 1.00 | 43.63 | MOL2 | O |
|------|------|------|------|---|----|--------|---------|---------|------|-------|------|---|
| ATOM | 4672 | N | LEU | C | 47 | 15.807 | −47.213 | −68.598 | 1.00 | 40.04 | MOL2 | N |
| ATOM | 4673 | CA | LEU | C | 47 | 16.880 | −47.746 | −67.773 | 1.00 | 36.49 | MOL2 | C |
| ATOM | 4674 | CB | LEU | C | 47 | 16.400 | −48.074 | −66.364 | 1.00 | 35.32 | MOL2 | C |
| ATOM | 4675 | CG | LEU | C | 47 | 16.526 | −46.945 | −65.348 | 1.00 | 45.46 | MOL2 | C |
| ATOM | 4676 | CD1 | LEU | C | 47 | 16.039 | −47.403 | −64.004 | 1.00 | 49.22 | MOL2 | C |
| ATOM | 4677 | CD2 | LEU | C | 47 | 17.964 | −46.526 | −65.240 | 1.00 | 52.10 | MOL2 | C |
| ATOM | 4678 | C | LEU | C | 47 | 17.418 | −49.009 | −68.390 | 1.00 | 37.87 | MOL2 | C |
| ATOM | 4679 | O | LEU | C | 47 | 18.606 | −49.117 | −68.623 | 1.00 | 44.63 | MOL2 | O |
| ATOM | 4680 | N | ILE | C | 48 | 16.537 | −49.958 | −68.679 | 1.00 | 36.23 | MOL2 | N |
| ATOM | 4681 | CA | ILE | C | 48 | 16.961 | −51.235 | −69.225 | 1.00 | 32.84 | MOL2 | C |
| ATOM | 4682 | CB | ILE | C | 48 | 17.074 | −52.258 | −68.070 | 1.00 | 34.34 | MOL2 | C |
| ATOM | 4683 | CG2 | ILE | C | 48 | 17.200 | −53.672 | −68.586 | 1.00 | 25.98 | MOL2 | C |
| ATOM | 4684 | CG1 | ILE | C | 48 | 18.268 | −51.897 | −67.194 | 1.00 | 36.96 | MOL2 | C |
| ATOM | 4685 | CD1 | ILE | C | 48 | 18.229 | −52.512 | −65.823 | 1.00 | 36.19 | MOL2 | C |
| ATOM | 4686 | C | ILE | C | 48 | 16.022 | −51.786 | −70.281 | 1.00 | 35.44 | MOL2 | C |
| ATOM | 4687 | O | ILE | C | 48 | 14.815 | −51.818 | −70.072 | 1.00 | 39.59 | MOL2 | O |
| ATOM | 4688 | N | TYR | C | 49 | 16.581 | −52.215 | −71.413 | 1.00 | 36.31 | MOL2 | N |
| ATOM | 4689 | CA | TYR | C | 49 | 15.797 | −52.813 | −72.493 | 1.00 | 37.52 | MOL2 | C |
| ATOM | 4690 | CB | TYR | C | 49 | 16.081 | −52.165 | −73.852 | 1.00 | 37.22 | MOL2 | C |
| ATOM | 4691 | CG | TYR | C | 49 | 17.514 | −52.236 | −74.361 | 1.00 | 38.82 | MOL2 | C |
| ATOM | 4692 | CD1 | TYR | C | 49 | 18.494 | −51.433 | −73.811 | 1.00 | 43.57 | MOL2 | C |
| ATOM | 4693 | CE1 | TYR | C | 49 | 19.759 | −51.371 | −74.352 | 1.00 | 36.43 | MOL2 | C |
| ATOM | 4694 | CD2 | TYR | C | 49 | 17.855 | −53.005 | −75.477 | 1.00 | 37.22 | MOL2 | C |
| ATOM | 4695 | CE2 | TYR | C | 49 | 19.127 | −52.949 | −76.032 | 1.00 | 24.31 | MOL2 | C |
| ATOM | 4696 | CZ | TYR | C | 49 | 20.066 | −52.122 | −75.456 | 1.00 | 35.68 | MOL2 | C |
| ATOM | 4697 | OH | TYR | C | 49 | 21.329 | −51.997 | −75.967 | 1.00 | 46.18 | MOL2 | O |
| ATOM | 4698 | C | TYR | C | 49 | 16.075 | −54.302 | −72.619 | 1.00 | 42.30 | MOL2 | C |
| ATOM | 4699 | O | TYR | C | 49 | 17.075 | −54.808 | −72.109 | 1.00 | 45.94 | MOL2 | O |
| ATOM | 4700 | N | LEU | C | 50 | 15.197 | −54.999 | −73.332 | 1.00 | 41.35 | MOL2 | N |
| ATOM | 4701 | CA | LEU | C | 50 | 15.333 | −56.434 | −73.504 | 1.00 | 37.64 | MOL2 | C |
| ATOM | 4702 | CB | LEU | C | 50 | 16.309 | −56.760 | −74.619 | 1.00 | 41.43 | MOL2 | C |
| ATOM | 4703 | CG | LEU | C | 50 | 15.801 | −56.897 | −76.060 | 1.00 | 49.42 | MOL2 | C |
| ATOM | 4704 | CD1 | LEU | C | 50 | 14.353 | −57.366 | −76.092 | 1.00 | 43.83 | MOL2 | C |
| ATOM | 4705 | CD2 | LEU | C | 50 | 15.953 | −55.576 | −76.752 | 1.00 | 49.87 | MOL2 | C |
| ATOM | 4706 | C | LEU | C | 50 | 15.803 | −57.131 | −72.232 | 1.00 | 38.81 | MOL2 | C |
| ATOM | 4707 | O | LEU | C | 50 | 16.858 | −57.741 | −72.204 | 1.00 | 39.05 | MOL2 | O |
| ATOM | 4708 | N | VAL | C | 51 | 15.011 | −57.008 | −71.179 | 1.00 | 39.86 | MOL2 | N |
| ATOM | 4709 | CA | VAL | C | 51 | 15.264 | −57.635 | −69.890 | 1.00 | 41.18 | MOL2 | C |
| ATOM | 4710 | CB | VAL | C | 51 | 15.333 | −59.142 | −69.983 | 1.00 | 40.58 | MOL2 | C |
| ATOM | 4711 | CG1 | VAL | C | 51 | 15.210 | −59.724 | −68.598 | 1.00 | 38.71 | MOL2 | C |
| ATOM | 4712 | CG2 | VAL | C | 51 | 14.249 | −59.650 | −70.861 | 1.00 | 40.41 | MOL2 | C |
| ATOM | 4713 | C | VAL | C | 51 | 16.455 | −57.249 | −69.062 | 1.00 | 44.87 | MOL2 | C |
| ATOM | 4714 | O | VAL | C | 51 | 16.310 | −57.004 | −67.863 | 1.00 | 52.89 | MOL2 | O |
| ATOM | 4715 | N | SER | C | 52 | 17.642 | −57.226 | −69.643 | 1.00 | 42.94 | MOL2 | N |
| ATOM | 4716 | CA | SER | C | 52 | 18.771 | −56.866 | −68.802 | 1.00 | 46.98 | MOL2 | C |
| ATOM | 4717 | CB | SER | C | 52 | 19.354 | −58.118 | −68.139 | 1.00 | 42.72 | MOL2 | C |
| ATOM | 4718 | OG | SER | C | 52 | 19.474 | −59.178 | −69.066 | 1.00 | 55.45 | MOL2 | O |
| ATOM | 4719 | C | SER | C | 52 | 19.877 | −56.021 | −69.407 | 1.00 | 44.33 | MOL2 | C |
| ATOM | 4720 | O | SER | C | 52 | 20.949 | −55.910 | −68.838 | 1.00 | 50.11 | MOL2 | O |
| ATOM | 4721 | N | ASN | C | 53 | 19.610 | −55.395 | −70.540 | 1.00 | 42.65 | MOL2 | N |
| ATOM | 4722 | CA | ASN | C | 53 | 20.604 | −54.541 | −71.167 | 1.00 | 41.62 | MOL2 | C |
| ATOM | 4723 | CB | ASN | C | 53 | 20.452 | −54.611 | −72.673 | 1.00 | 42.75 | MOL2 | C |
| ATOM | 4724 | CG | ASN | C | 53 | 20.612 | −55.998 | −73.197 | 1.00 | 47.39 | MOL2 | C |
| ATOM | 4725 | OD1 | ASN | C | 53 | 19.685 | −56.801 | −73.166 | 1.00 | 52.81 | MOL2 | O |
| ATOM | 4726 | ND2 | ASN | C | 53 | 21.808 | −56.304 | −73.673 | 1.00 | 56.43 | MOL2 | N |
| ATOM | 4727 | C | ASN | C | 53 | 20.395 | −53.103 | −70.717 | 1.00 | 44.00 | MOL2 | C |
| ATOM | 4728 | O | ASN | C | 53 | 19.272 | −52.606 | −70.749 | 1.00 | 48.58 | MOL2 | O |
| ATOM | 4729 | N | ARG | C | 54 | 21.450 | −52.407 | −70.315 | 1.00 | 42.36 | MOL2 | N |
| ATOM | 4730 | CA | ARG | C | 54 | 21.223 | −51.036 | −69.888 | 1.00 | 46.77 | MOL2 | C |
| ATOM | 4731 | CB | ARG | C | 54 | 21.966 | −50.745 | −68.565 | 1.00 | 54.04 | MOL2 | C |
| ATOM | 4732 | CG | ARG | C | 54 | 23.437 | −50.361 | −68.636 | 1.00 | 62.65 | MOL2 | C |
| ATOM | 4733 | CD | ARG | C | 54 | 23.970 | −50.206 | −67.220 | 1.00 | 53.90 | MOL2 | C |
| ATOM | 4734 | NE | ARG | C | 54 | 23.905 | −51.481 | −66.516 | 1.00 | 64.24 | MOL2 | N |
| ATOM | 4735 | CZ | ARG | C | 54 | 24.889 | −52.375 | −66.504 | 1.00 | 71.05 | MOL2 | C |
| ATOM | 4736 | NH1 | ARG | C | 54 | 26.019 | −52.120 | −67.153 | 1.00 | 76.78 | MOL2 | N |
| ATOM | 4737 | NH2 | ARG | C | 54 | 24.740 | −53.531 | −65.866 | 1.00 | 71.08 | MOL2 | N |
| ATOM | 4738 | C | ARG | C | 54 | 21.524 | −49.998 | −70.965 | 1.00 | 44.55 | MOL2 | C |
| ATOM | 4739 | O | ARG | C | 54 | 22.327 | −50.238 | −71.857 | 1.00 | 42.06 | MOL2 | O |
| ATOM | 4740 | N | GLU | C | 55 | 20.830 | −48.861 | −70.908 | 1.00 | 49.25 | MOL2 | N |
| ATOM | 4741 | CA | GLU | C | 55 | 21.039 | −47.799 | −71.892 | 1.00 | 52.24 | MOL2 | C |
| ATOM | 4742 | CB | GLU | C | 55 | 20.008 | −46.681 | −71.769 | 1.00 | 55.16 | MOL2 | C |
| ATOM | 4743 | CG | GLU | C | 55 | 18.911 | −46.718 | −72.816 | 1.00 | 64.00 | MOL2 | C |
| ATOM | 4744 | CD | GLU | C | 55 | 19.397 | −46.306 | −74.186 | 1.00 | 66.72 | MOL2 | C |
| ATOM | 4745 | OE1 | GLU | C | 55 | 20.377 | −46.908 | −74.668 | 1.00 | 73.90 | MOL2 | O |
| ATOM | 4746 | OE2 | GLU | C | 55 | 18.798 | −45.381 | −74.778 | 1.00 | 64.41 | MOL2 | O |
| ATOM | 4747 | C | GLU | C | 55 | 22.396 | −47.231 | −71.632 | 1.00 | 54.17 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 4748 | O | GLU | C | 55 | 22.987 | −47.496 | −70.586 | 1.00 | 52.51 | MOL2 | O |
|---|---|---|---|---|---|---|---|---|---|---|---|---|
| ATOM | 4749 | N | SER | C | 56 | 22.880 | −46.432 | −72.573 | 1.00 | 56.90 | MOL2 | N |
| ATOM | 4750 | CA | SER | C | 56 | 24.205 | −45.836 | −72.467 | 1.00 | 60.81 | MOL2 | C |
| ATOM | 4751 | CB | SER | C | 56 | 24.390 | −44.785 | −73.554 | 1.00 | 59.03 | MOL2 | C |
| ATOM | 4752 | OG | SER | C | 56 | 24.195 | −45.359 | −74.842 | 1.00 | 66.73 | MOL2 | O |
| ATOM | 4753 | C | SER | C | 56 | 24.523 | −45.225 | −71.106 | 1.00 | 65.30 | MOL2 | C |
| ATOM | 4754 | O | SER | C | 56 | 25.388 | −45.709 | −70.372 | 1.00 | 71.47 | MOL2 | O |
| ATOM | 4755 | N | GLY | C | 57 | 23.827 | −44.161 | −70.753 | 1.00 | 65.57 | MOL2 | N |
| ATOM | 4756 | CA | GLY | C | 57 | 24.110 | −43.535 | −69.473 | 1.00 | 62.49 | MOL2 | C |
| ATOM | 4757 | C | GLY | C | 57 | 23.886 | −44.364 | −68.219 | 1.00 | 55.75 | MOL2 | C |
| ATOM | 4758 | O | GLY | C | 57 | 24.646 | −44.243 | −67.272 | 1.00 | 57.46 | MOL2 | O |
| ATOM | 4759 | N | VAL | C | 58 | 22.852 | −45.201 | −68.214 | 1.00 | 51.16 | MOL2 | N |
| ATOM | 4760 | CA | VAL | C | 58 | 22.507 | −46.016 | −67.057 | 1.00 | 45.06 | MOL2 | C |
| ATOM | 4761 | CB | VAL | C | 58 | 21.632 | −47.208 | −67.461 | 1.00 | 43.86 | MOL2 | C |
| ATOM | 4762 | CG1 | VAL | C | 58 | 20.912 | −47.749 | −66.253 | 1.00 | 45.32 | MOL2 | C |
| ATOM | 4763 | CG2 | VAL | C | 58 | 20.642 | −46.801 | −68.498 | 1.00 | 39.41 | MOL2 | C |
| ATOM | 4764 | C | VAL | C | 58 | 23.735 | −46.551 | −66.334 | 1.00 | 48.33 | MOL2 | C |
| ATOM | 4765 | O | VAL | C | 58 | 24.558 | −47.247 | −66.931 | 1.00 | 45.45 | MOL2 | O |
| ATOM | 4766 | N | PRO | C | 59 | 23.867 | −46.231 | −65.032 | 1.00 | 48.70 | MOL2 | N |
| ATOM | 4767 | CD | PRO | C | 59 | 23.066 | −45.215 | −64.334 | 1.00 | 59.59 | MOL2 | C |
| ATOM | 4768 | CA | PRO | C | 59 | 24.972 | −46.646 | −64.181 | 1.00 | 45.60 | MOL2 | C |
| ATOM | 4769 | CB | PRO | C | 59 | 24.665 | −45.977 | −62.858 | 1.00 | 47.98 | MOL2 | C |
| ATOM | 4770 | CG | PRO | C | 59 | 24.041 | −44.724 | −63.272 | 1.00 | 56.22 | MOL2 | C |
| ATOM | 4771 | C | PRO | C | 59 | 25.117 | −48.125 | −64.043 | 1.00 | 51.02 | MOL2 | C |
| ATOM | 4772 | O | PRO | C | 59 | 24.229 | −48.900 | −64.364 | 1.00 | 53.55 | MOL2 | O |
| ATOM | 4773 | N | SER | C | 60 | 26.273 | −48.498 | −63.529 | 1.00 | 63.15 | MOL2 | N |
| ATOM | 4774 | CA | SER | C | 60 | 26.636 | −49.887 | −63.343 | 1.00 | 64.70 | MOL2 | C |
| ATOM | 4775 | CB | SER | C | 60 | 28.107 | −49.966 | −62.869 | 1.00 | 76.08 | MOL2 | C |
| ATOM | 4776 | OG | SER | C | 60 | 28.963 | −49.038 | −63.554 | 1.00 | 76.30 | MOL2 | O |
| ATOM | 4777 | C | SER | C | 60 | 25.705 | −50.637 | −62.374 | 1.00 | 60.32 | MOL2 | C |
| ATOM | 4778 | O | SER | C | 60 | 25.409 | −51.807 | −62.610 | 1.00 | 61.45 | MOL2 | O |
| ATOM | 4779 | N | ARG | C | 61 | 25.238 | −49.969 | −61.310 | 1.00 | 49.31 | MOL2 | N |
| ATOM | 4780 | CA | ARG | C | 61 | 24.365 | −50.590 | −60.305 | 1.00 | 43.23 | MOL2 | C |
| ATOM | 4781 | CB | ARG | C | 61 | 24.115 | −49.612 | −59.147 | 1.00 | 35.46 | MOL2 | C |
| ATOM | 4782 | CG | ARG | C | 61 | 24.043 | −48.138 | −59.542 | 1.00 | 42.58 | MOL2 | C |
| ATOM | 4783 | CD | ARG | C | 61 | 23.830 | −47.195 | −58.337 | 1.00 | 37.38 | MOL2 | C |
| ATOM | 4784 | NE | ARG | C | 61 | 23.442 | −45.821 | −58.702 | 1.00 | 36.31 | MOL2 | N |
| ATOM | 4785 | CZ | ARG | C | 61 | 24.218 | −44.943 | −59.338 | 1.00 | 43.03 | MOL2 | C |
| ATOM | 4786 | NH1 | ARG | C | 61 | 25.449 | −45.269 | −59.703 | 1.00 | 54.77 | MOL2 | N |
| ATOM | 4787 | NH2 | ARG | C | 61 | 23.772 | −43.724 | −59.606 | 1.00 | 45.96 | MOL2 | N |
| ATOM | 4788 | C | ARG | C | 61 | 23.027 | −51.186 | −60.763 | 1.00 | 44.64 | MOL2 | C |
| ATOM | 4789 | O | ARG | C | 61 | 22.603 | −52.226 | −60.266 | 1.00 | 49.46 | MOL2 | O |
| ATOM | 4790 | N | PHE | C | 62 | 22.362 | −50.552 | −61.715 | 1.00 | 42.85 | MOL2 | N |
| ATOM | 4791 | CA | PHE | C | 62 | 21.078 | −51.060 | −62.185 | 1.00 | 41.55 | MOL2 | C |
| ATOM | 4792 | CB | PHE | C | 62 | 20.400 | −50.000 | −63.034 | 1.00 | 32.24 | MOL2 | C |
| ATOM | 4793 | CG | PHE | C | 62 | 20.092 | −48.753 | −62.282 | 1.00 | 33.23 | MOL2 | C |
| ATOM | 4794 | CD1 | PHE | C | 62 | 18.952 | −48.661 | −61.510 | 1.00 | 30.43 | MOL2 | C |
| ATOM | 4795 | CD2 | PHE | C | 62 | 20.975 | −47.691 | −62.291 | 1.00 | 34.55 | MOL2 | C |
| ATOM | 4796 | CE1 | PHE | C | 62 | 18.697 | −47.539 | −60.760 | 1.00 | 31.63 | MOL2 | C |
| ATOM | 4797 | CE2 | PHE | C | 62 | 20.723 | −46.566 | −61.541 | 1.00 | 35.40 | MOL2 | C |
| ATOM | 4798 | CZ | PHE | C | 62 | 19.578 | −46.493 | −60.771 | 1.00 | 35.12 | MOL2 | C |
| ATOM | 4799 | C | PHE | C | 62 | 21.214 | −52.333 | −62.997 | 1.00 | 46.01 | MOL2 | C |
| ATOM | 4800 | O | PHE | C | 62 | 21.980 | −52.367 | −63.942 | 1.00 | 54.58 | MOL2 | O |
| ATOM | 4801 | N | SER | C | 63 | 20.464 | −53.376 | −62.652 | 1.00 | 48.82 | MOL2 | N |
| ATOM | 4802 | CA | SER | C | 63 | 20.531 | −54.624 | −63.407 | 1.00 | 47.97 | MOL2 | C |
| ATOM | 4803 | CB | SER | C | 63 | 21.560 | −55.551 | −62.776 | 1.00 | 55.17 | MOL2 | C |
| ATOM | 4804 | OG | SER | C | 63 | 21.678 | −55.300 | −61.382 | 1.00 | 63.54 | MOL2 | O |
| ATOM | 4805 | C | SER | C | 63 | 19.182 | −55.322 | −63.505 | 1.00 | 49.62 | MOL2 | C |
| ATOM | 4806 | O | SER | C | 63 | 18.454 | −55.438 | −62.520 | 1.00 | 51.38 | MOL2 | O |
| ATOM | 4807 | N | GLY | C | 64 | 18.848 | −55.781 | −64.704 | 1.00 | 52.59 | MOL2 | N |
| ATOM | 4808 | CA | GLY | C | 64 | 17.582 | −56.462 | −64.913 | 1.00 | 56.43 | MOL2 | C |
| ATOM | 4809 | C | GLY | C | 64 | 17.784 | −57.957 | −64.878 | 1.00 | 58.12 | MOL2 | C |
| ATOM | 4810 | O | GLY | C | 64 | 18.905 | −58.405 | −64.691 | 1.00 | 61.31 | MOL2 | O |
| ATOM | 4811 | N | SER | C | 65 | 16.712 | −58.727 | −65.044 | 1.00 | 61.30 | MOL2 | N |
| ATOM | 4812 | CA | SER | C | 65 | 16.789 | −60.191 | −65.035 | 1.00 | 63.04 | MOL2 | C |
| ATOM | 4813 | CB | SER | C | 65 | 17.555 | −60.696 | −63.808 | 1.00 | 60.37 | MOL2 | C |
| ATOM | 4814 | OG | SER | C | 65 | 17.103 | −60.090 | −62.615 | 1.00 | 64.71 | MOL2 | O |
| ATOM | 4815 | C | SER | C | 65 | 15.413 | −60.829 | −65.063 | 1.00 | 65.22 | MOL2 | C |
| ATOM | 4816 | O | SER | C | 65 | 14.523 | −60.420 | −64.321 | 1.00 | 69.55 | MOL2 | O |
| ATOM | 4817 | N | GLY | C | 66 | 15.230 | −61.834 | −65.914 | 1.00 | 65.22 | MOL2 | N |
| ATOM | 4818 | CA | GLY | C | 66 | 13.926 | −62.458 | −65.973 | 1.00 | 73.68 | MOL2 | C |
| ATOM | 4819 | C | GLY | C | 66 | 13.676 | −63.480 | −67.062 | 1.00 | 81.66 | MOL2 | C |
| ATOM | 4820 | O | GLY | C | 66 | 14.391 | −63.551 | −68.069 | 1.00 | 79.94 | MOL2 | O |
| ATOM | 4821 | N | SER | C | 67 | 12.627 | −64.272 | −66.844 | 1.00 | 89.51 | MOL2 | N |
| ATOM | 4822 | CA | SER | C | 67 | 12.224 | −65.331 | −67.764 | 1.00 | 93.54 | MOL2 | C |
| ATOM | 4823 | CB | SER | C | 67 | 11.482 | −66.435 | −67.005 | 1.00 | 93.70 | MOL2 | C |
| ATOM | 4824 | OG | SER | C | 67 | 10.333 | −65.914 | −66.356 | 1.00 | 92.11 | MOL2 | O |

TABLE 1-continued

The atomic coordinates of IL17F in complex with 496 Fab
(H32; a = 189.4; b = 189.4; c = 490.9, α, β = 90°; γ = 120°)

| ATOM | 4825 | C | SER | C | 67 | 11.321 | −64.782 | −68.845 | 1.00 | 94.61 | MOL2 | C |
|---|---|---|---|---|---|---|---|---|---|---|---|---|
| ATOM | 4826 | O | SER | C | 67 | 11.796 | −64.237 | −69.844 | 1.00 | 95.58 | MOL2 | O |
| ATOM | 4827 | N | GLY | C | 68 | 10.016 | −64.937 | −68.628 | 1.00 | 95.23 | MOL2 | N |
| ATOM | 4828 | CA | GLY | C | 68 | 9.020 | −64.463 | −69.574 | 1.00 | 96.12 | MOL2 | C |
| ATOM | 4829 | C | GLY | C | 68 | 7.683 | −64.269 | −68.886 | 1.00 | 96.00 | MOL2 | C |
| ATOM | 4830 | O | GLY | C | 68 | 6.660 | −64.056 | −69.537 | 1.00 | 96.37 | MOL2 | O |
| ATOM | 4831 | N | THR | C | 69 | 7.704 | −64.344 | −67.557 | 1.00 | 95.68 | MOL2 | N |
| ATOM | 4832 | CA | THR | C | 69 | 6.507 | −64.179 | −66.737 | 1.00 | 91.12 | MOL2 | C |
| ATOM | 4833 | CB | THR | C | 69 | 5.919 | −65.537 | −66.335 | 1.00 | 90.68 | MOL2 | C |
| ATOM | 4834 | OG1 | THR | C | 69 | 4.901 | −65.339 | −65.349 | 1.00 | 89.39 | MOL2 | O |
| ATOM | 4835 | CG2 | THR | C | 69 | 7.010 | −66.443 | −65.770 | 1.00 | 93.08 | MOL2 | C |
| ATOM | 4836 | C | THR | C | 69 | 6.844 | −63.395 | −65.472 | 1.00 | 88.46 | MOL2 | C |
| ATOM | 4837 | O | THR | C | 69 | 6.030 | −62.616 | −64.979 | 1.00 | 85.81 | MOL2 | O |
| ATOM | 4838 | N | ASP | C | 70 | 8.046 | −63.612 | −64.946 | 1.00 | 88.12 | MOL2 | N |
| ATOM | 4839 | CA | ASP | C | 70 | 8.500 | −62.905 | −63.752 | 1.00 | 85.65 | MOL2 | C |
| ATOM | 4840 | CB | ASP | C | 70 | 8.708 | −63.866 | −62.572 | 1.00 | 90.05 | MOL2 | C |
| ATOM | 4841 | CG | ASP | C | 70 | 7.424 | −64.558 | −62.132 | 1.00 | 95.17 | MOL2 | C |
| ATOM | 4842 | OD1 | ASP | C | 70 | 7.429 | −65.157 | −61.035 | 1.00 | 99.07 | MOL2 | O |
| ATOM | 4843 | OD2 | ASP | C | 70 | 6.419 | −64.519 | −62.873 | 1.00 | 96.71 | MOL2 | O |
| ATOM | 4844 | C | ASP | C | 70 | 9.819 | −62.199 | −64.056 | 1.00 | 79.36 | MOL2 | C |
| ATOM | 4845 | O | ASP | C | 70 | 10.718 | −62.769 | −64.676 | 1.00 | 81.13 | MOL2 | O |
| ATOM | 4846 | N | PHE | C | 71 | 9.923 | −60.947 | −63.632 | 1.00 | 68.65 | MOL2 | N |
| ATOM | 4847 | CA | PHE | C | 71 | 11.132 | −60.172 | −63.852 | 1.00 | 55.13 | MOL2 | C |
| ATOM | 4848 | CB | PHE | C | 71 | 10.950 | −59.221 | −65.005 | 1.00 | 47.53 | MOL2 | C |
| ATOM | 4849 | CG | PHE | C | 71 | 10.576 | −59.890 | −66.262 | 1.00 | 45.02 | MOL2 | C |
| ATOM | 4850 | CD1 | PHE | C | 71 | 11.465 | −59.963 | −67.307 | 1.00 | 46.41 | MOL2 | C |
| ATOM | 4851 | CD2 | PHE | C | 71 | 9.323 | −60.433 | −66.415 | 1.00 | 42.09 | MOL2 | C |
| ATOM | 4852 | CE1 | PHE | C | 71 | 11.103 | −60.562 | −68.485 | 1.00 | 44.29 | MOL2 | C |
| ATOM | 4853 | CE2 | PHE | C | 71 | 8.959 | −61.033 | −67.592 | 1.00 | 41.81 | MOL2 | C |
| ATOM | 4854 | CZ | PHE | C | 71 | 9.847 | −61.096 | −68.628 | 1.00 | 40.40 | MOL2 | C |
| ATOM | 4855 | C | PHE | C | 71 | 11.470 | −59.372 | −62.623 | 1.00 | 53.35 | MOL2 | C |
| ATOM | 4856 | O | PHE | C | 71 | 10.616 | −59.107 | −61.772 | 1.00 | 54.82 | MOL2 | O |
| ATOM | 4857 | N | THR | C | 72 | 12.719 | −58.957 | −62.544 | 1.00 | 47.38 | MOL2 | N |
| ATOM | 4858 | CA | THR | C | 72 | 13.162 | −58.212 | −61.395 | 1.00 | 51.19 | MOL2 | C |
| ATOM | 4859 | CB | THR | C | 72 | 13.820 | −59.138 | −60.369 | 1.00 | 57.83 | MOL2 | C |
| ATOM | 4860 | OG1 | THR | C | 72 | 12.830 | −59.643 | −59.463 | 1.00 | 69.70 | MOL2 | O |
| ATOM | 4861 | CG2 | THR | C | 72 | 14.903 | −58.385 | −59.603 | 1.00 | 59.36 | MOL2 | C |
| ATOM | 4862 | C | THR | C | 72 | 14.178 | −57.161 | −61.747 | 1.00 | 46.72 | MOL2 | C |
| ATOM | 4863 | O | THR | C | 72 | 15.110 | −57.419 | −62.489 | 1.00 | 49.28 | MOL2 | O |
| ATOM | 4864 | N | LEU | C | 73 | 13.990 | −55.966 | −61.211 | 1.00 | 46.28 | MOL2 | N |
| ATOM | 4865 | CA | LEU | C | 73 | 14.925 | −54.885 | −61.438 | 1.00 | 45.82 | MOL2 | C |
| ATOM | 4866 | CB | LEU | C | 73 | 14.196 | −53.578 | −61.712 | 1.00 | 45.60 | MOL2 | C |
| ATOM | 4867 | CG | LEU | C | 73 | 15.168 | −52.402 | −61.694 | 1.00 | 52.06 | MOL2 | C |
| ATOM | 4868 | CD1 | LEU | C | 73 | 16.429 | −52.775 | −62.453 | 1.00 | 54.73 | MOL2 | C |
| ATOM | 4869 | CD2 | LEU | C | 73 | 14.512 | −51.185 | −62.299 | 1.00 | 54.51 | MOL2 | C |
| ATOM | 4870 | C | LEU | C | 73 | 15.642 | −54.787 | −60.126 | 1.00 | 44.33 | MOL2 | C |
| ATOM | 4871 | O | LEU | C | 73 | 15.015 | −54.959 | −59.083 | 1.00 | 47.74 | MOL2 | O |
| ATOM | 4872 | N | THR | C | 74 | 16.942 | −54.521 | −60.150 | 1.00 | 42.16 | MOL2 | N |
| ATOM | 4873 | CA | THR | C | 74 | 17.665 | −54.436 | −58.890 | 1.00 | 46.63 | MOL2 | C |
| ATOM | 4874 | CB | THR | C | 74 | 18.187 | −55.818 | −58.459 | 1.00 | 50.79 | MOL2 | C |
| ATOM | 4875 | OG1 | THR | C | 74 | 19.400 | −55.649 | −57.714 | 1.00 | 53.78 | MOL2 | O |
| ATOM | 4876 | CG2 | THR | C | 74 | 18.412 | −56.723 | −59.683 | 1.00 | 50.86 | MOL2 | C |
| ATOM | 4877 | C | THR | C | 74 | 18.821 | −53.453 | −58.832 | 1.00 | 44.72 | MOL2 | C |
| ATOM | 4878 | O | THR | C | 74 | 19.681 | −53.425 | −59.707 | 1.00 | 45.79 | MOL2 | O |
| ATOM | 4879 | N | ILE | C | 75 | 18.831 | −52.648 | −57.779 | 1.00 | 42.15 | MOL2 | N |
| ATOM | 4880 | CA | ILE | C | 75 | 19.873 | −51.665 | −57.586 | 1.00 | 48.05 | MOL2 | C |
| ATOM | 4881 | CB | ILE | C | 75 | 19.282 | −50.316 | −57.156 | 1.00 | 47.25 | MOL2 | C |
| ATOM | 4882 | CG2 | ILE | C | 75 | 20.339 | −49.226 | −57.222 | 1.00 | 54.36 | MOL2 | C |
| ATOM | 4883 | CG1 | ILE | C | 75 | 18.145 | −49.932 | −58.091 | 1.00 | 41.76 | MOL2 | C |
| ATOM | 4884 | CD1 | ILE | C | 75 | 17.763 | −48.493 | −57.969 | 1.00 | 40.92 | MOL2 | C |
| ATOM | 4885 | C | ILE | C | 75 | 20.837 | −52.161 | −56.510 | 1.00 | 53.74 | MOL2 | C |
| ATOM | 4886 | O | ILE | C | 75 | 20.519 | −52.153 | −55.325 | 1.00 | 58.13 | MOL2 | O |
| ATOM | 4887 | N | SER | C | 76 | 22.017 | −52.589 | −56.947 | 1.00 | 56.34 | MOL2 | N |
| ATOM | 4888 | CA | SER | C | 76 | 23.071 | −53.111 | −56.085 | 1.00 | 55.62 | MOL2 | C |
| ATOM | 4889 | CB | SER | C | 76 | 24.334 | −53.347 | −56.900 | 1.00 | 61.50 | MOL2 | C |
| ATOM | 4890 | OG | SER | C | 76 | 24.075 | −54.209 | −57.995 | 1.00 | 81.73 | MOL2 | O |
| ATOM | 4891 | C | SER | C | 76 | 23.446 | −52.224 | −54.927 | 1.00 | 54.64 | MOL2 | C |
| ATOM | 4892 | O | SER | C | 76 | 23.716 | −52.699 | −53.830 | 1.00 | 61.45 | MOL2 | O |
| ATOM | 4893 | N | SER | C | 77 | 23.484 | −50.928 | −55.163 | 1.00 | 52.22 | MOL2 | N |
| ATOM | 4894 | CA | SER | C | 77 | 23.870 | −50.024 | −54.101 | 1.00 | 52.79 | MOL2 | C |
| ATOM | 4895 | CB | SER | C | 77 | 25.389 | −49.839 | −54.162 | 1.00 | 49.01 | MOL2 | C |
| ATOM | 4896 | OG | SER | C | 77 | 25.840 | −48.801 | −53.318 | 1.00 | 53.10 | MOL2 | O |
| ATOM | 4897 | C | SER | C | 77 | 23.138 | −48.689 | −54.235 | 1.00 | 54.66 | MOL2 | C |
| ATOM | 4898 | O | SER | C | 77 | 23.654 | −47.741 | −54.824 | 1.00 | 57.72 | MOL2 | O |
| ATOM | 4899 | N | LEU | C | 78 | 21.935 | −48.619 | −53.677 | 1.00 | 52.90 | MOL2 | N |
| ATOM | 4900 | CA | LEU | C | 78 | 21.130 | −47.412 | −53.756 | 1.00 | 50.36 | MOL2 | C |
| ATOM | 4901 | CB | LEU | C | 78 | 20.011 | −47.468 | −52.723 | 1.00 | 47.88 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 4902 | CG | LEU | C | 78 | 18.749 | −46.876 | −53.326 | 1.00 | 47.66 | MOL2 | C |
|---|---|---|---|---|---|---|---|---|---|---|---|---|
| ATOM | 4903 | CD1 | LEU | C | 78 | 18.558 | −47.499 | −54.675 | 1.00 | 48.44 | MOL2 | C |
| ATOM | 4904 | CD2 | LEU | C | 78 | 17.545 | −47.118 | −52.440 | 1.00 | 54.70 | MOL2 | C |
| ATOM | 4905 | C | LEU | C | 78 | 21.947 | −46.138 | −53.582 | 1.00 | 50.02 | MOL2 | C |
| ATOM | 4906 | O | LEU | C | 78 | 22.831 | −46.061 | −52.734 | 1.00 | 50.35 | MOL2 | O |
| ATOM | 4907 | N | GLN | C | 79 | 21.640 | −45.143 | −54.406 | 1.00 | 52.73 | MOL2 | N |
| ATOM | 4908 | CA | GLN | C | 79 | 22.334 | −43.857 | −54.393 | 1.00 | 54.06 | MOL2 | C |
| ATOM | 4909 | CB | GLN | C | 79 | 23.080 | −43.648 | −55.711 | 1.00 | 55.34 | MOL2 | C |
| ATOM | 4910 | CG | GLN | C | 79 | 24.229 | −44.593 | −55.899 | 1.00 | 54.70 | MOL2 | C |
| ATOM | 4911 | CD | GLN | C | 79 | 25.156 | −44.554 | −54.715 | 1.00 | 59.34 | MOL2 | C |
| ATOM | 4912 | OE1 | GLN | C | 79 | 25.829 | −43.547 | −54.475 | 1.00 | 60.93 | MOL2 | O |
| ATOM | 4913 | NE2 | GLN | C | 79 | 25.187 | −45.644 | −53.949 | 1.00 | 52.58 | MOL2 | N |
| ATOM | 4914 | C | GLN | C | 79 | 21.341 | −42.731 | −54.210 | 1.00 | 54.56 | MOL2 | C |
| ATOM | 4915 | O | GLN | C | 79 | 20.169 | −42.881 | −54.541 | 1.00 | 62.39 | MOL2 | O |
| ATOM | 4916 | N | PRO | C | 80 | 21.806 | −41.571 | −53.721 | 1.00 | 52.71 | MOL2 | N |
| ATOM | 4917 | CD | PRO | C | 80 | 23.220 | −41.182 | −53.617 | 1.00 | 49.20 | MOL2 | C |
| ATOM | 4918 | CA | PRO | C | 80 | 20.939 | −40.410 | −53.493 | 1.00 | 55.43 | MOL2 | C |
| ATOM | 4919 | CB | PRO | C | 80 | 21.930 | −39.266 | −53.320 | 1.00 | 49.94 | MOL2 | C |
| ATOM | 4920 | CG | PRO | C | 80 | 23.134 | −39.939 | −52.777 | 1.00 | 51.58 | MOL2 | C |
| ATOM | 4921 | C | PRO | C | 80 | 19.993 | −40.161 | −54.655 | 1.00 | 59.49 | MOL2 | C |
| ATOM | 4922 | O | PRO | C | 80 | 18.794 | −39.970 | −54.471 | 1.00 | 68.04 | MOL2 | O |
| ATOM | 4923 | N | GLU | C | 81 | 20.542 | −40.185 | −55.858 | 1.00 | 58.82 | MOL2 | N |
| ATOM | 4924 | CA | GLU | C | 81 | 19.765 | −39.927 | −57.051 | 1.00 | 65.03 | MOL2 | C |
| ATOM | 4925 | CB | GLU | C | 81 | 20.689 | −39.406 | −58.158 | 1.00 | 76.22 | MOL2 | C |
| ATOM | 4926 | CG | GLU | C | 81 | 22.051 | −40.110 | −58.272 | 1.00 | 88.01 | MOL2 | C |
| ATOM | 4927 | CD | GLU | C | 81 | 23.077 | −39.649 | −57.229 | 1.00 | 97.10 | MOL2 | C |
| ATOM | 4928 | OE1 | GLU | C | 81 | 24.225 | −40.147 | −57.275 | 1.00 | 101.10 | MOL2 | O |
| ATOM | 4929 | OE2 | GLU | C | 81 | 22.751 | −38.795 | −56.369 | 1.00 | 101.43 | MOL2 | O |
| ATOM | 4930 | C | GLU | C | 81 | 18.959 | −41.102 | −57.572 | 1.00 | 63.06 | MOL2 | C |
| ATOM | 4931 | O | GLU | C | 81 | 18.359 | −41.016 | −58.638 | 1.00 | 70.08 | MOL2 | O |
| ATOM | 4932 | N | ASP | C | 82 | 18.931 | −42.199 | −56.834 | 1.00 | 56.47 | MOL2 | N |
| ATOM | 4933 | CA | ASP | C | 82 | 18.178 | −43.356 | −57.291 | 1.00 | 56.08 | MOL2 | C |
| ATOM | 4934 | CB | ASP | C | 82 | 18.915 | −44.631 | −56.912 | 1.00 | 65.30 | MOL2 | C |
| ATOM | 4935 | CG | ASP | C | 82 | 20.182 | −44.808 | −57.704 | 1.00 | 75.06 | MOL2 | C |
| ATOM | 4936 | OD1 | ASP | C | 82 | 20.938 | −45.761 | −57.409 | 1.00 | 79.38 | MOL2 | O |
| ATOM | 4937 | OD2 | ASP | C | 82 | 20.407 | −43.989 | −58.628 | 1.00 | 78.88 | MOL2 | O |
| ATOM | 4938 | C | ASP | C | 82 | 16.778 | −43.366 | −56.716 | 1.00 | 50.07 | MOL2 | C |
| ATOM | 4939 | O | ASP | C | 82 | 15.960 | −44.244 | −57.018 | 1.00 | 43.69 | MOL2 | O |
| ATOM | 4940 | N | PHE | C | 83 | 16.512 | −42.377 | −55.880 | 1.00 | 46.85 | MOL2 | N |
| ATOM | 4941 | CA | PHE | C | 83 | 15.217 | −42.262 | −55.263 | 1.00 | 47.13 | MOL2 | C |
| ATOM | 4942 | CB | PHE | C | 83 | 15.316 | −41.358 | −54.038 | 1.00 | 41.56 | MOL2 | C |
| ATOM | 4943 | CG | PHE | C | 83 | 16.047 | −41.988 | −52.899 | 1.00 | 43.74 | MOL2 | C |
| ATOM | 4944 | CD1 | PHE | C | 83 | 17.214 | −41.435 | −52.409 | 1.00 | 47.35 | MOL2 | C |
| ATOM | 4945 | CD2 | PHE | C | 83 | 15.573 | −43.157 | −52.326 | 1.00 | 50.15 | MOL2 | C |
| ATOM | 4946 | CE1 | PHE | C | 83 | 17.899 | −42.038 | −51.367 | 1.00 | 47.11 | MOL2 | C |
| ATOM | 4947 | CE2 | PHE | C | 83 | 16.247 | −43.765 | −51.287 | 1.00 | 47.53 | MOL2 | C |
| ATOM | 4948 | CZ | PHE | C | 83 | 17.412 | −43.204 | −50.808 | 1.00 | 50.38 | MOL2 | C |
| ATOM | 4949 | C | PHE | C | 83 | 14.259 | −41.716 | −56.303 | 1.00 | 46.06 | MOL2 | C |
| ATOM | 4950 | O | PHE | C | 83 | 14.272 | −40.521 | −56.625 | 1.00 | 46.82 | MOL2 | O |
| ATOM | 4951 | N | ALA | C | 84 | 13.447 | −42.621 | −56.838 | 1.00 | 40.65 | MOL2 | N |
| ATOM | 4952 | CA | ALA | C | 84 | 12.472 | −42.291 | −57.854 | 1.00 | 41.88 | MOL2 | C |
| ATOM | 4953 | CB | ALA | C | 84 | 13.169 | −42.081 | −59.176 | 1.00 | 43.18 | MOL2 | C |
| ATOM | 4954 | C | ALA | C | 84 | 11.467 | −43.417 | −57.980 | 1.00 | 42.51 | MOL2 | C |
| ATOM | 4955 | O | ALA | C | 84 | 11.444 | −44.347 | −57.183 | 1.00 | 44.46 | MOL2 | O |
| ATOM | 4956 | N | THR | C | 85 | 10.638 | −43.340 | −58.997 | 1.00 | 40.74 | MOL2 | N |
| ATOM | 4957 | CA | THR | C | 85 | 9.659 | −44.371 | −59.185 | 1.00 | 45.97 | MOL2 | C |
| ATOM | 4958 | CB | THR | C | 85 | 8.312 | −43.744 | −59.441 | 1.00 | 52.46 | MOL2 | C |
| ATOM | 4959 | OG1 | THR | C | 85 | 8.011 | −42.858 | −58.352 | 1.00 | 55.95 | MOL2 | O |
| ATOM | 4960 | CG2 | THR | C | 85 | 7.236 | −44.817 | −59.564 | 1.00 | 57.54 | MOL2 | C |
| ATOM | 4961 | C | THR | C | 85 | 10.132 | −45.159 | −60.377 | 1.00 | 43.47 | MOL2 | C |
| ATOM | 4962 | O | THR | C | 85 | 10.725 | −44.579 | −61.274 | 1.00 | 46.85 | MOL2 | O |
| ATOM | 4963 | N | TYR | C | 86 | 9.896 | −46.470 | −60.386 | 1.00 | 38.56 | MOL2 | N |
| ATOM | 4964 | CA | TYR | C | 86 | 10.333 | −47.297 | −61.505 | 1.00 | 34.41 | MOL2 | C |
| ATOM | 4965 | CB | TYR | C | 86 | 11.420 | −48.263 | −61.050 | 1.00 | 29.81 | MOL2 | C |
| ATOM | 4966 | CG | TYR | C | 86 | 12.660 | −47.561 | −60.554 | 1.00 | 33.34 | MOL2 | C |
| ATOM | 4967 | CD1 | TYR | C | 86 | 12.753 | −47.089 | −59.249 | 1.00 | 30.80 | MOL2 | C |
| ATOM | 4968 | CE1 | TYR | C | 86 | 13.895 | −46.406 | −58.808 | 1.00 | 31.41 | MOL2 | C |
| ATOM | 4969 | CD2 | TYR | C | 86 | 13.734 | −47.331 | −61.407 | 1.00 | 38.84 | MOL2 | C |
| ATOM | 4970 | CE2 | TYR | C | 86 | 14.873 | −46.644 | −60.977 | 1.00 | 36.10 | MOL2 | C |
| ATOM | 4971 | CZ | TYR | C | 86 | 14.947 | −46.192 | −59.683 | 1.00 | 33.18 | MOL2 | C |
| ATOM | 4972 | OH | TYR | C | 86 | 16.087 | −45.553 | −59.275 | 1.00 | 29.32 | MOL2 | O |
| ATOM | 4973 | C | TYR | C | 86 | 9.192 | −48.057 | −62.136 | 1.00 | 37.41 | MOL2 | C |
| ATOM | 4974 | O | TYR | C | 86 | 8.342 | −48.594 | −61.433 | 1.00 | 42.90 | MOL2 | O |
| ATOM | 4975 | N | TYR | C | 87 | 9.166 | −48.097 | −63.464 | 1.00 | 35.15 | MOL2 | N |
| ATOM | 4976 | CA | TYR | C | 87 | 8.091 | −48.793 | −64.174 | 1.00 | 42.51 | MOL2 | C |
| ATOM | 4977 | CB | TYR | C | 87 | 7.300 | −47.825 | −65.078 | 1.00 | 42.87 | MOL2 | C |
| ATOM | 4978 | CG | TYR | C | 87 | 6.581 | −46.680 | −64.389 | 1.00 | 49.15 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 4979 | CD1 | TYR | C | 87 | 5.334 | −46.846 | −63.809 | 1.00 | 49.37 | MOL2 | C |
|---|---|---|---|---|---|---|---|---|---|---|---|---|
| ATOM | 4980 | CE1 | TYR | C | 87 | 4.699 | −45.785 | −63.161 | 1.00 | 55.42 | MOL2 | C |
| ATOM | 4981 | CD2 | TYR | C | 87 | 7.167 | −45.429 | −64.309 | 1.00 | 57.77 | MOL2 | C |
| ATOM | 4982 | CE2 | TYR | C | 87 | 6.543 | −44.370 | −63.667 | 1.00 | 58.59 | MOL2 | C |
| ATOM | 4983 | CZ | TYR | C | 87 | 5.318 | −44.548 | −63.093 | 1.00 | 55.31 | MOL2 | C |
| ATOM | 4984 | OH | TYR | C | 87 | 4.748 | −43.481 | −62.428 | 1.00 | 50.87 | MOL2 | O |
| ATOM | 4985 | C | TYR | C | 87 | 8.625 | −49.898 | −65.069 | 1.00 | 44.65 | MOL2 | C |
| ATOM | 4986 | O | TYR | C | 87 | 9.686 | −49.744 | −65.665 | 1.00 | 50.92 | MOL2 | O |
| ATOM | 4987 | N | CYS | C | 88 | 7.902 | −51.010 | −65.165 | 1.00 | 40.51 | MOL2 | N |
| ATOM | 4988 | CA | CYS | C | 88 | 8.321 | −52.063 | −66.074 | 1.00 | 44.56 | MOL2 | C |
| ATOM | 4989 | C | CYS | C | 88 | 7.382 | −51.954 | −67.247 | 1.00 | 44.14 | MOL2 | C |
| ATOM | 4990 | O | CYS | C | 88 | 6.341 | −51.336 | −67.127 | 1.00 | 50.52 | MOL2 | O |
| ATOM | 4991 | CB | CYS | C | 88 | 8.229 | −53.445 | −65.447 | 1.00 | 53.31 | MOL2 | C |
| ATOM | 4992 | SG | CYS | C | 88 | 6.697 | −53.880 | −64.577 | 1.00 | 73.27 | MOL2 | S |
| ATOM | 4993 | N | GLN | C | 89 | 7.744 | −52.514 | −68.391 | 1.00 | 42.16 | MOL2 | N |
| ATOM | 4994 | CA | GLN | C | 89 | 6.883 | −52.417 | −69.558 | 1.00 | 44.69 | MOL2 | C |
| ATOM | 4995 | CB | GLN | C | 89 | 7.140 | −51.123 | −70.337 | 1.00 | 43.41 | MOL2 | C |
| ATOM | 4996 | CG | GLN | C | 89 | 6.642 | −51.211 | −71.784 | 1.00 | 49.94 | MOL2 | C |
| ATOM | 4997 | CD | GLN | C | 89 | 7.269 | −50.188 | −72.718 | 1.00 | 50.73 | MOL2 | C |
| ATOM | 4998 | OE1 | GLN | C | 89 | 8.451 | −49.885 | −72.615 | 1.00 | 46.53 | MOL2 | O |
| ATOM | 4999 | NE2 | GLN | C | 89 | 6.480 | −49.675 | −73.656 | 1.00 | 52.51 | MOL2 | N |
| ATOM | 5000 | C | GLN | C | 89 | 7.137 | −53.582 | −70.473 | 1.00 | 48.95 | MOL2 | C |
| ATOM | 5001 | O | GLN | C | 89 | 8.263 | −54.033 | −70.605 | 1.00 | 51.54 | MOL2 | O |
| ATOM | 5002 | N | GLN | C | 90 | 6.083 | −54.053 | −71.121 | 1.00 | 53.29 | MOL2 | N |
| ATOM | 5003 | CA | GLN | C | 90 | 6.190 | −55.175 | −72.029 | 1.00 | 56.74 | MOL2 | C |
| ATOM | 5004 | CB | GLN | C | 90 | 5.246 | −56.286 | −71.568 | 1.00 | 59.25 | MOL2 | C |
| ATOM | 5005 | CG | GLN | C | 90 | 3.787 | −55.902 | −71.608 | 1.00 | 58.76 | MOL2 | C |
| ATOM | 5006 | CD | GLN | C | 90 | 3.185 | −56.140 | −72.969 | 1.00 | 68.50 | MOL2 | C |
| ATOM | 5007 | OE1 | GLN | C | 90 | 2.093 | −55.661 | −73.273 | 1.00 | 79.12 | MOL2 | O |
| ATOM | 5008 | NE2 | GLN | C | 90 | 3.892 | −56.895 | −73.803 | 1.00 | 67.31 | MOL2 | N |
| ATOM | 5009 | C | GLN | C | 90 | 5.798 | −54.677 | −73.407 | 1.00 | 60.06 | MOL2 | C |
| ATOM | 5010 | O | GLN | C | 90 | 5.064 | −53.696 | −73.520 | 1.00 | 60.76 | MOL2 | O |
| ATOM | 5011 | N | THR | C | 91 | 6.306 | −55.331 | −74.450 | 1.00 | 61.92 | MOL2 | N |
| ATOM | 5012 | CA | THR | C | 91 | 5.976 | −54.959 | −75.819 | 1.00 | 62.24 | MOL2 | C |
| ATOM | 5013 | CB | THR | C | 91 | 7.067 | −54.124 | −76.509 | 1.00 | 58.94 | MOL2 | C |
| ATOM | 5014 | OG1 | THR | C | 91 | 8.308 | −54.830 | −76.463 | 1.00 | 61.60 | MOL2 | O |
| ATOM | 5015 | CG2 | THR | C | 91 | 7.215 | −52.783 | −75.847 | 1.00 | 61.34 | MOL2 | C |
| ATOM | 5016 | C | THR | C | 91 | 5.777 | −56.201 | −76.648 | 1.00 | 66.54 | MOL2 | C |
| ATOM | 5017 | O | THR | C | 91 | 5.987 | −56.178 | −77.854 | 1.00 | 71.36 | MOL2 | O |
| ATOM | 5018 | N | TRP | C | 92 | 5.386 | −57.294 | −76.010 | 1.00 | 70.31 | MOL2 | N |
| ATOM | 5019 | CA | TRP | C | 92 | 5.149 | −58.508 | −76.762 | 1.00 | 80.64 | MOL2 | C |
| ATOM | 5020 | CB | TRP | C | 92 | 5.232 | −59.735 | −75.857 | 1.00 | 85.10 | MOL2 | C |
| ATOM | 5021 | CG | TRP | C | 92 | 5.571 | −60.982 | −76.607 | 1.00 | 97.56 | MOL2 | C |
| ATOM | 5022 | CD2 | TRP | C | 92 | 4.837 | −62.207 | −76.612 | 1.00 | 103.33 | MOL2 | C |
| ATOM | 5023 | CE2 | TRP | C | 92 | 5.527 | −63.108 | −77.457 | 1.00 | 108.01 | MOL2 | C |
| ATOM | 5024 | CE3 | TRP | C | 92 | 3.663 | −62.635 | −75.984 | 1.00 | 106.52 | MOL2 | C |
| ATOM | 5025 | CD1 | TRP | C | 92 | 6.650 | −61.180 | −77.428 | 1.00 | 104.29 | MOL2 | C |
| ATOM | 5026 | NE1 | TRP | C | 92 | 6.630 | −62.457 | −77.943 | 1.00 | 104.83 | MOL2 | N |
| ATOM | 5027 | CZ2 | TRP | C | 92 | 5.078 | −64.408 | −77.688 | 1.00 | 114.24 | MOL2 | C |
| ATOM | 5028 | CZ3 | TRP | C | 92 | 3.216 | −63.930 | −76.214 | 1.00 | 115.21 | MOL2 | C |
| ATOM | 5029 | CH2 | TRP | C | 92 | 3.923 | −64.801 | −77.059 | 1.00 | 118.29 | MOL2 | C |
| ATOM | 5030 | C | TRP | C | 92 | 3.766 | −58.397 | −77.405 | 1.00 | 87.15 | MOL2 | C |
| ATOM | 5031 | O | TRP | C | 92 | 3.638 | −58.507 | −78.626 | 1.00 | 89.95 | MOL2 | O |
| ATOM | 5032 | N | SER | C | 93 | 2.741 | −58.151 | −76.587 | 1.00 | 92.89 | MOL2 | N |
| ATOM | 5033 | CA | SER | C | 93 | 1.364 | −58.013 | −77.073 | 1.00 | 98.74 | MOL2 | C |
| ATOM | 5034 | CB | SER | C | 93 | 0.371 | −58.525 | −76.023 | 1.00 | 102.20 | MOL2 | C |
| ATOM | 5035 | OG | SER | C | 93 | 0.370 | −59.945 | −75.962 | 1.00 | 103.64 | MOL2 | O |
| ATOM | 5036 | C | SER | C | 93 | 1.025 | −56.568 | −77.427 | 1.00 | 100.18 | MOL2 | C |
| ATOM | 5037 | O | SER | C | 93 | 1.289 | −55.650 | −76.647 | 1.00 | 97.42 | MOL2 | O |
| ATOM | 5038 | N | ASP | C | 94 | 0.416 | −56.393 | −78.599 | 1.00 | 101.46 | MOL2 | N |
| ATOM | 5039 | CA | ASP | C | 94 | 0.042 | −55.086 | −79.131 | 1.00 | 104.82 | MOL2 | C |
| ATOM | 5040 | CB | ASP | C | 94 | −1.136 | −55.232 | −80.089 | 1.00 | 113.86 | MOL2 | C |
| ATOM | 5041 | CG | ASP | C | 94 | −1.477 | −53.923 | −80.778 | 1.00 | 123.75 | MOL2 | C |
| ATOM | 5042 | OD1 | ASP | C | 94 | −2.669 | −53.693 | −81.099 | 1.00 | 127.52 | MOL2 | O |
| ATOM | 5043 | OD2 | ASP | C | 94 | −0.535 | −53.126 | −81.001 | 1.00 | 124.10 | MOL2 | O |
| ATOM | 5044 | C | ASP | C | 94 | −0.282 | −53.949 | −78.153 | 1.00 | 101.57 | MOL2 | C |
| ATOM | 5045 | O | ASP | C | 94 | 0.285 | −52.857 | −78.251 | 1.00 | 108.20 | MOL2 | O |
| ATOM | 5046 | N | PRO | C | 95 | −1.225 | −54.164 | −77.224 | 1.00 | 93.00 | MOL2 | N |
| ATOM | 5047 | CD | PRO | C | 95 | −2.164 | −55.268 | −77.003 | 1.00 | 90.23 | MOL2 | C |
| ATOM | 5048 | CA | PRO | C | 95 | −1.500 | −53.046 | −76.312 | 1.00 | 85.27 | MOL2 | C |
| ATOM | 5049 | CB | PRO | C | 95 | −2.800 | −53.450 | −75.621 | 1.00 | 80.37 | MOL2 | C |
| ATOM | 5050 | CG | PRO | C | 95 | −3.372 | −54.514 | −76.521 | 1.00 | 91.74 | MOL2 | C |
| ATOM | 5051 | C | PRO | C | 95 | −0.361 | −52.954 | −75.318 | 1.00 | 80.12 | MOL2 | C |
| ATOM | 5052 | O | PRO | C | 95 | −0.492 | −53.406 | −74.186 | 1.00 | 84.08 | MOL2 | O |
| ATOM | 5053 | N | TRP | C | 96 | 0.763 | −52.394 | −75.742 | 1.00 | 69.19 | MOL2 | N |
| ATOM | 5054 | CA | TRP | C | 96 | 1.902 | −52.276 | −74.858 | 1.00 | 64.73 | MOL2 | C |
| ATOM | 5055 | CB | TRP | C | 96 | 2.939 | −51.339 | −75.472 | 1.00 | 67.03 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 5056 | CG | TRP | C | 96 | 3.479 | −51.811 | −76.799 | 1.00 | 65.50 | MOL2 | C |
|---|---|---|---|---|---|---|---|---|---|---|---|---|
| ATOM | 5057 | CD2 | TRP | C | 96 | 4.212 | −51.031 | −77.751 | 1.00 | 64.82 | MOL2 | C |
| ATOM | 5058 | CE2 | TRP | C | 96 | 4.535 | −51.883 | −78.830 | 1.00 | 64.27 | MOL2 | C |
| ATOM | 5059 | CE3 | TRP | C | 96 | 4.631 | −49.694 | −77.796 | 1.00 | 65.71 | MOL2 | C |
| ATOM | 5060 | CD1 | TRP | C | 96 | 3.393 | −53.074 | −77.324 | 1.00 | 62.32 | MOL2 | C |
| ATOM | 5061 | NE1 | TRP | C | 96 | 4.024 | −53.123 | −78.543 | 1.00 | 57.53 | MOL2 | N |
| ATOM | 5062 | CZ2 | TRP | C | 96 | 5.257 | −51.439 | −79.950 | 1.00 | 67.90 | MOL2 | C |
| ATOM | 5063 | CZ3 | TRP | C | 96 | 5.350 | −49.254 | −78.907 | 1.00 | 71.07 | MOL2 | C |
| ATOM | 5064 | CH2 | TRP | C | 96 | 5.654 | −50.127 | −79.971 | 1.00 | 69.11 | MOL2 | C |
| ATOM | 5065 | C | TRP | C | 96 | 1.448 | −51.751 | −73.499 | 1.00 | 62.33 | MOL2 | C |
| ATOM | 5066 | O | TRP | C | 96 | 0.760 | −50.736 | −73.411 | 1.00 | 61.48 | MOL2 | O |
| ATOM | 5067 | N | THR | C | 97 | 1.825 | −52.438 | −72.430 | 1.00 | 60.38 | MOL2 | N |
| ATOM | 5068 | CA | THR | C | 97 | 1.402 | −51.994 | −71.107 | 1.00 | 67.03 | MOL2 | C |
| ATOM | 5069 | CB | THR | C | 97 | 0.421 | −52.981 | −70.503 | 1.00 | 66.35 | MOL2 | C |
| ATOM | 5070 | OG1 | THR | C | 97 | 1.033 | −54.275 | −70.429 | 1.00 | 60.19 | MOL2 | O |
| ATOM | 5071 | CG2 | THR | C | 97 | −0.838 | −53.035 | −71.356 | 1.00 | 68.04 | MOL2 | C |
| ATOM | 5072 | C | THR | C | 97 | 2.517 | −51.743 | −70.093 | 1.00 | 67.76 | MOL2 | C |
| ATOM | 5073 | O | THR | C | 97 | 3.618 | −52.282 | −70.211 | 1.00 | 74.50 | MOL2 | O |
| ATOM | 5074 | N | PHE | C | 98 | 2.219 | −50.913 | −69.096 | 1.00 | 59.78 | MOL2 | N |
| ATOM | 5075 | CA | PHE | C | 98 | 3.187 | −50.571 | −68.068 | 1.00 | 57.99 | MOL2 | C |
| ATOM | 5076 | CB | PHE | C | 98 | 3.302 | −49.052 | −67.913 | 1.00 | 61.94 | MOL2 | C |
| ATOM | 5077 | CG | PHE | C | 98 | 4.001 | −48.362 | −69.039 | 1.00 | 61.57 | MOL2 | C |
| ATOM | 5078 | CD1 | PHE | C | 98 | 3.456 | −48.332 | −70.303 | 1.00 | 67.69 | MOL2 | C |
| ATOM | 5079 | CD2 | PHE | C | 98 | 5.194 | −47.711 | −68.823 | 1.00 | 66.48 | MOL2 | C |
| ATOM | 5080 | CE1 | PHE | C | 98 | 4.093 | −47.660 | −71.330 | 1.00 | 67.42 | MOL2 | C |
| ATOM | 5081 | CE2 | PHE | C | 98 | 5.833 | −47.039 | −69.846 | 1.00 | 68.13 | MOL2 | C |
| ATOM | 5082 | CZ | PHE | C | 98 | 5.282 | −47.014 | −71.097 | 1.00 | 66.10 | MOL2 | C |
| ATOM | 5083 | C | PHE | C | 98 | 2.795 | −51.131 | −66.706 | 1.00 | 59.07 | MOL2 | C |
| ATOM | 5084 | O | PHE | C | 98 | 1.687 | −51.611 | −66.501 | 1.00 | 62.87 | MOL2 | O |
| ATOM | 5085 | N | GLY | C | 99 | 3.724 | −51.036 | −65.765 | 1.00 | 59.70 | MOL2 | N |
| ATOM | 5086 | CA | GLY | C | 99 | 3.475 | −51.494 | −64.420 | 1.00 | 53.24 | MOL2 | C |
| ATOM | 5087 | C | GLY | C | 99 | 2.872 | −50.333 | −63.670 | 1.00 | 51.26 | MOL2 | C |
| ATOM | 5088 | O | GLY | C | 99 | 2.812 | −49.216 | −64.185 | 1.00 | 48.83 | MOL2 | O |
| ATOM | 5089 | N | GLN | C | 100 | 2.423 | −50.605 | −62.455 | 1.00 | 51.14 | MOL2 | N |
| ATOM | 5090 | CA | GLN | C | 100 | 1.798 | −49.603 | −61.623 | 1.00 | 55.18 | MOL2 | C |
| ATOM | 5091 | CB | GLN | C | 100 | 1.165 | −50.288 | −60.427 | 1.00 | 63.92 | MOL2 | C |
| ATOM | 5092 | CG | GLN | C | 100 | 2.172 | −51.079 | −59.621 | 1.00 | 74.70 | MOL2 | C |
| ATOM | 5093 | CD | GLN | C | 100 | 1.666 | −51.403 | −58.236 | 1.00 | 86.82 | MOL2 | C |
| ATOM | 5094 | OE1 | GLN | C | 100 | 2.423 | −51.875 | −57.376 | 1.00 | 92.54 | MOL2 | O |
| ATOM | 5095 | NE2 | GLN | C | 100 | 0.374 | −51.155 | −58.004 | 1.00 | 91.03 | MOL2 | N |
| ATOM | 5096 | C | GLN | C | 100 | 2.864 | −48.636 | −61.153 | 1.00 | 54.59 | MOL2 | C |
| ATOM | 5097 | O | GLN | C | 100 | 2.571 | −47.503 | −60.752 | 1.00 | 52.82 | MOL2 | O |
| ATOM | 5098 | N | GLY | C | 101 | 4.109 | −49.099 | −61.203 | 1.00 | 53.10 | MOL2 | N |
| ATOM | 5099 | CA | GLY | C | 101 | 5.221 | −48.274 | −60.761 | 1.00 | 53.78 | MOL2 | C |
| ATOM | 5100 | C | GLY | C | 101 | 5.540 | −48.436 | −59.280 | 1.00 | 52.00 | MOL2 | C |
| ATOM | 5101 | O | GLY | C | 101 | 4.632 | −48.520 | −58.442 | 1.00 | 50.84 | MOL2 | O |
| ATOM | 5102 | N | THR | C | 102 | 6.833 | −48.470 | −58.961 | 1.00 | 46.88 | MOL2 | N |
| ATOM | 5103 | CA | THR | C | 102 | 7.312 | −48.628 | −57.589 | 1.00 | 41.81 | MOL2 | C |
| ATOM | 5104 | CB | THR | C | 102 | 8.336 | −49.750 | −57.467 | 1.00 | 42.84 | MOL2 | C |
| ATOM | 5105 | OG1 | THR | C | 102 | 7.736 | −51.009 | −57.785 | 1.00 | 42.59 | MOL2 | O |
| ATOM | 5106 | CG2 | THR | C | 102 | 8.894 | −49.770 | −56.079 | 1.00 | 37.70 | MOL2 | C |
| ATOM | 5107 | C | THR | C | 102 | 8.042 | −47.382 | −57.151 | 1.00 | 39.95 | MOL2 | C |
| ATOM | 5108 | O | THR | C | 102 | 8.985 | −46.964 | −57.795 | 1.00 | 40.11 | MOL2 | O |
| ATOM | 5109 | N | LYS | C | 103 | 7.634 | −46.785 | −56.049 | 1.00 | 44.42 | MOL2 | N |
| ATOM | 5110 | CA | LYS | C | 103 | 8.325 | −45.588 | −55.613 | 1.00 | 49.42 | MOL2 | C |
| ATOM | 5111 | CB | LYS | C | 103 | 7.337 | −44.513 | −55.133 | 1.00 | 56.28 | MOL2 | C |
| ATOM | 5112 | CG | LYS | C | 103 | 7.986 | −43.208 | −54.646 | 1.00 | 57.48 | MOL2 | C |
| ATOM | 5113 | CD | LYS | C | 103 | 6.943 | −42.090 | −54.455 | 1.00 | 75.34 | MOL2 | C |
| ATOM | 5114 | CE | LYS | C | 103 | 6.175 | −41.808 | −55.767 | 1.00 | 93.46 | MOL2 | C |
| ATOM | 5115 | NZ | LYS | C | 103 | 5.148 | −40.707 | −55.711 | 1.00 | 98.17 | MOL2 | N |
| ATOM | 5116 | C | LYS | C | 103 | 9.280 | −45.947 | −54.505 | 1.00 | 50.29 | MOL2 | C |
| ATOM | 5117 | O | LYS | C | 103 | 8.903 | −46.585 | −53.518 | 1.00 | 55.19 | MOL2 | O |
| ATOM | 5118 | N | VAL | C | 104 | 10.529 | −45.546 | −54.688 | 1.00 | 46.27 | MOL2 | N |
| ATOM | 5119 | CA | VAL | C | 104 | 11.556 | −45.801 | −53.705 | 1.00 | 42.44 | MOL2 | C |
| ATOM | 5120 | CB | VAL | C | 104 | 12.848 | −46.242 | −54.366 | 1.00 | 41.07 | MOL2 | C |
| ATOM | 5121 | CG1 | VAL | C | 104 | 13.947 | −46.361 | −53.315 | 1.00 | 44.48 | MOL2 | C |
| ATOM | 5122 | CG2 | VAL | C | 104 | 12.621 | −47.571 | −55.066 | 1.00 | 35.63 | MOL2 | C |
| ATOM | 5123 | C | VAL | C | 104 | 11.803 | −44.522 | −52.957 | 1.00 | 40.72 | MOL2 | C |
| ATOM | 5124 | O | VAL | C | 104 | 12.099 | −43.505 | −53.569 | 1.00 | 38.61 | MOL2 | O |
| ATOM | 5125 | N | GLU | C | 105 | 11.671 | −44.576 | −51.633 | 1.00 | 47.49 | MOL2 | N |
| ATOM | 5126 | CA | GLU | C | 105 | 11.874 | −43.407 | −50.773 | 1.00 | 56.29 | MOL2 | C |
| ATOM | 5127 | CB | GLU | C | 105 | 10.555 | −43.003 | −50.112 | 1.00 | 60.05 | MOL2 | C |
| ATOM | 5128 | CG | GLU | C | 105 | 9.531 | −42.530 | −51.129 | 1.00 | 76.31 | MOL2 | C |
| ATOM | 5129 | CD | GLU | C | 105 | 8.137 | −42.380 | −50.563 | 1.00 | 83.54 | MOL2 | C |
| ATOM | 5130 | OE1 | GLU | C | 105 | 7.564 | −43.409 | −50.132 | 1.00 | 85.88 | MOL2 | O |
| ATOM | 5131 | OE2 | GLU | C | 105 | 7.617 | −41.236 | −50.559 | 1.00 | 87.48 | MOL2 | O |
| ATOM | 5132 | C | GLU | C | 105 | 12.924 | −43.665 | −49.710 | 1.00 | 56.45 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 5133 | O | GLU | C | 105 | 13.151 | −44.807 | −49.328 | 1.00 | 66.11 | MOL2 | O |
|---|---|---|---|---|---|---|---|---|---|---|---|---|
| ATOM | 5134 | N | ILE | C | 106 | 13.564 | −42.602 | −49.233 | 1.00 | 57.45 | MOL2 | N |
| ATOM | 5135 | CA | ILE | C | 106 | 14.614 | −42.710 | −48.210 | 1.00 | 63.29 | MOL2 | C |
| ATOM | 5136 | CB | ILE | C | 106 | 15.345 | −41.378 | −47.985 | 1.00 | 69.09 | MOL2 | C |
| ATOM | 5137 | CG2 | ILE | C | 106 | 16.817 | −41.562 | −48.252 | 1.00 | 73.60 | MOL2 | C |
| ATOM | 5138 | CG1 | ILE | C | 106 | 14.701 | −40.266 | −48.822 | 1.00 | 75.56 | MOL2 | C |
| ATOM | 5139 | CD1 | ILE | C | 106 | 15.339 | −38.880 | −48.647 | 1.00 | 72.29 | MOL2 | C |
| ATOM | 5140 | C | ILE | C | 106 | 14.116 | −43.108 | −46.830 | 1.00 | 62.98 | MOL2 | C |
| ATOM | 5141 | O | ILE | C | 106 | 13.289 | −42.409 | −46.257 | 1.00 | 68.92 | MOL2 | O |
| ATOM | 5142 | N | LYS | C | 107 | 14.649 | −44.200 | −46.283 | 1.00 | 58.93 | MOL2 | N |
| ATOM | 5143 | CA | LYS | C | 107 | 14.276 | −44.697 | −44.946 | 1.00 | 52.34 | MOL2 | C |
| ATOM | 5144 | CB | LYS | C | 107 | 14.875 | −46.086 | −44.728 | 1.00 | 53.80 | MOL2 | C |
| ATOM | 5145 | CG | LYS | C | 107 | 14.056 | −47.077 | −43.939 | 1.00 | 61.17 | MOL2 | C |
| ATOM | 5146 | CD | LYS | C | 107 | 13.947 | −46.753 | −42.471 | 1.00 | 67.82 | MOL2 | C |
| ATOM | 5147 | CE | LYS | C | 107 | 13.175 | −47.877 | −41.744 | 1.00 | 80.85 | MOL2 | C |
| ATOM | 5148 | NZ | LYS | C | 107 | 11.870 | −48.278 | −42.404 | 1.00 | 84.14 | MOL2 | N |
| ATOM | 5149 | C | LYS | C | 107 | 14.867 | −43.788 | −43.888 | 1.00 | 44.89 | MOL2 | C |
| ATOM | 5150 | O | LYS | C | 107 | 15.973 | −43.294 | −44.049 | 1.00 | 43.57 | MOL2 | O |
| ATOM | 5151 | N | ARG | C | 108 | 14.149 | −43.562 | −42.799 | 1.00 | 47.59 | MOL2 | N |
| ATOM | 5152 | CA | ARG | C | 108 | 14.698 | −42.731 | −41.719 | 1.00 | 53.58 | MOL2 | C |
| ATOM | 5153 | CB | ARG | C | 108 | 14.588 | −41.238 | −42.075 | 1.00 | 54.26 | MOL2 | C |
| ATOM | 5154 | CG | ARG | C | 108 | 13.184 | −40.659 | −42.059 | 1.00 | 55.57 | MOL2 | C |
| ATOM | 5155 | CD | ARG | C | 108 | 12.876 | −40.077 | −40.702 | 1.00 | 58.02 | MOL2 | C |
| ATOM | 5156 | NE | ARG | C | 108 | 13.231 | −38.665 | −40.573 | 1.00 | 56.78 | MOL2 | N |
| ATOM | 5157 | CZ | ARG | C | 108 | 13.332 | −38.031 | −39.407 | 1.00 | 54.67 | MOL2 | C |
| ATOM | 5158 | NH1 | ARG | C | 108 | 13.121 | −38.685 | −38.273 | 1.00 | 49.50 | MOL2 | N |
| ATOM | 5159 | NH2 | ARG | C | 108 | 13.613 | −36.737 | −39.370 | 1.00 | 53.79 | MOL2 | N |
| ATOM | 5160 | C | ARG | C | 108 | 14.098 | −43.020 | −40.322 | 1.00 | 53.05 | MOL2 | C |
| ATOM | 5161 | O | ARG | C | 108 | 13.123 | −43.785 | −40.174 | 1.00 | 50.99 | MOL2 | O |
| ATOM | 5162 | N | THR | C | 109 | 14.698 | −42.434 | −39.291 | 1.00 | 49.06 | MOL2 | N |
| ATOM | 5163 | CA | THR | C | 109 | 14.201 | −42.687 | −37.943 | 1.00 | 50.32 | MOL2 | C |
| ATOM | 5164 | CB | THR | C | 109 | 15.051 | −42.016 | −36.841 | 1.00 | 47.66 | MOL2 | C |
| ATOM | 5165 | OG1 | THR | C | 109 | 14.837 | −40.598 | −36.835 | 1.00 | 49.22 | MOL2 | O |
| ATOM | 5166 | CG2 | THR | C | 109 | 16.509 | −42.320 | −37.067 | 1.00 | 52.82 | MOL2 | C |
| ATOM | 5167 | C | THR | C | 109 | 12.789 | −42.197 | −37.830 | 1.00 | 50.20 | MOL2 | C |
| ATOM | 5168 | O | THR | C | 109 | 12.454 | −41.146 | −38.353 | 1.00 | 54.79 | MOL2 | O |
| ATOM | 5169 | N | ASP | C | 110 | 11.954 | −42.966 | −37.148 | 1.00 | 50.95 | MOL2 | N |
| ATOM | 5170 | CA | ASP | C | 110 | 10.557 | −42.593 | −36.982 | 1.00 | 53.05 | MOL2 | C |
| ATOM | 5171 | CB | ASP | C | 110 | 9.814 | −43.725 | −36.261 | 1.00 | 55.22 | MOL2 | C |
| ATOM | 5172 | CG | ASP | C | 110 | 9.661 | −44.982 | −37.140 | 1.00 | 65.59 | MOL2 | C |
| ATOM | 5173 | OD1 | ASP | C | 110 | 10.490 | −45.198 | −38.062 | 1.00 | 71.39 | MOL2 | O |
| ATOM | 5174 | OD2 | ASP | C | 110 | 8.716 | −45.765 | −36.905 | 1.00 | 64.73 | MOL2 | O |
| ATOM | 5175 | C | ASP | C | 110 | 10.424 | −41.265 | −36.238 | 1.00 | 51.10 | MOL2 | C |
| ATOM | 5176 | O | ASP | C | 110 | 11.309 | −40.875 | −35.477 | 1.00 | 50.89 | MOL2 | O |
| ATOM | 5177 | N | ALA | C | 111 | 9.340 | −40.544 | −36.494 | 1.00 | 50.53 | MOL2 | N |
| ATOM | 5178 | CA | ALA | C | 111 | 9.123 | −39.268 | −35.821 | 1.00 | 51.57 | MOL2 | C |
| ATOM | 5179 | CB | ALA | C | 111 | 9.864 | −38.157 | −36.528 | 1.00 | 52.34 | MOL2 | C |
| ATOM | 5180 | C | ALA | C | 111 | 7.638 | −38.961 | −35.759 | 1.00 | 53.06 | MOL2 | C |
| ATOM | 5181 | O | ALA | C | 111 | 6.908 | −39.124 | −36.739 | 1.00 | 47.58 | MOL2 | O |
| ATOM | 5182 | N | ALA | C | 112 | 7.203 | −38.529 | −34.581 | 1.00 | 53.40 | MOL2 | N |
| ATOM | 5183 | CA | ALA | C | 112 | 5.814 | −38.210 | −34.349 | 1.00 | 50.17 | MOL2 | C |
| ATOM | 5184 | CB | ALA | C | 112 | 5.564 | −38.185 | −32.880 | 1.00 | 55.55 | MOL2 | C |
| ATOM | 5185 | C | ALA | C | 112 | 5.410 | −36.880 | −34.975 | 1.00 | 53.70 | MOL2 | C |
| ATOM | 5186 | O | ALA | C | 112 | 6.202 | −35.931 | −35.052 | 1.00 | 54.34 | MOL2 | O |
| ATOM | 5187 | N | PRO | C | 113 | 4.156 | −36.798 | −35.432 | 1.00 | 53.05 | MOL2 | N |
| ATOM | 5188 | CD | PRO | C | 113 | 3.166 | −37.881 | −35.344 | 1.00 | 52.40 | MOL2 | C |
| ATOM | 5189 | CA | PRO | C | 113 | 3.559 | −35.626 | −36.066 | 1.00 | 55.03 | MOL2 | C |
| ATOM | 5190 | CB | PRO | C | 113 | 2.263 | −36.176 | −36.623 | 1.00 | 55.06 | MOL2 | C |
| ATOM | 5191 | CG | PRO | C | 113 | 1.873 | −37.135 | −35.581 | 1.00 | 51.19 | MOL2 | C |
| ATOM | 5192 | C | PRO | C | 113 | 3.284 | −34.525 | −35.074 | 1.00 | 59.02 | MOL2 | C |
| ATOM | 5193 | O | PRO | C | 113 | 3.070 | −34.785 | −33.892 | 1.00 | 64.39 | MOL2 | O |
| ATOM | 5194 | N | THR | C | 114 | 3.290 | −33.293 | −35.561 | 1.00 | 62.28 | MOL2 | N |
| ATOM | 5195 | CA | THR | C | 114 | 3.000 | −32.149 | −34.719 | 1.00 | 66.52 | MOL2 | C |
| ATOM | 5196 | CB | THR | C | 114 | 4.086 | −31.088 | −34.827 | 1.00 | 72.58 | MOL2 | C |
| ATOM | 5197 | OG1 | THR | C | 114 | 5.212 | −31.486 | −34.037 | 1.00 | 83.95 | MOL2 | O |
| ATOM | 5198 | CG2 | THR | C | 114 | 3.572 | −29.752 | −34.345 | 1.00 | 74.22 | MOL2 | C |
| ATOM | 5199 | C | THR | C | 114 | 1.698 | −31.605 | −35.247 | 1.00 | 68.36 | MOL2 | C |
| ATOM | 5200 | O | THR | C | 114 | 1.666 | −30.956 | −36.293 | 1.00 | 72.84 | MOL2 | O |
| ATOM | 5201 | N | VAL | C | 115 | 0.619 | −31.890 | −34.527 | 1.00 | 69.64 | MOL2 | N |
| ATOM | 5202 | CA | VAL | C | 115 | −0.711 | −31.454 | −34.942 | 1.00 | 71.67 | MOL2 | C |
| ATOM | 5203 | CB | VAL | C | 115 | −1.792 | −32.401 | −34.392 | 1.00 | 68.29 | MOL2 | C |
| ATOM | 5204 | CG1 | VAL | C | 115 | −3.165 | −31.978 | −34.883 | 1.00 | 65.89 | MOL2 | C |
| ATOM | 5205 | CG2 | VAL | C | 115 | −1.494 | −33.812 | −34.824 | 1.00 | 68.29 | MOL2 | C |
| ATOM | 5206 | C | VAL | C | 115 | −1.083 | −30.021 | −34.558 | 1.00 | 76.27 | MOL2 | C |
| ATOM | 5207 | O | VAL | C | 115 | −0.536 | −29.433 | −33.611 | 1.00 | 80.19 | MOL2 | O |
| ATOM | 5208 | N | SER | C | 116 | −2.026 | −29.468 | −35.311 | 1.00 | 74.82 | MOL2 | N |
| ATOM | 5209 | CA | SER | C | 116 | −2.495 | −28.117 | −35.086 | 1.00 | 72.32 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 5210 | CB | SER | C | 116 | −1.538 | −27.122 | −35.757 | 1.00 | 75.16 | MOL2 | C |
|---|---|---|---|---|---|---|---|---|---|---|---|---|
| ATOM | 5211 | OG | SER | C | 116 | −0.198 | −27.312 | −35.319 | 1.00 | 74.38 | MOL2 | O |
| ATOM | 5212 | C | SER | C | 116 | −3.883 | −28.024 | −35.700 | 1.00 | 71.04 | MOL2 | C |
| ATOM | 5213 | O | SER | C | 116 | −4.092 | −28.417 | −36.850 | 1.00 | 67.49 | MOL2 | O |
| ATOM | 5214 | N | ILE | C | 117 | −4.847 | −27.532 | −34.936 | 1.00 | 72.51 | MOL2 | N |
| ATOM | 5215 | CA | ILE | C | 117 | −6.183 | −27.413 | −35.496 | 1.00 | 76.85 | MOL2 | C |
| ATOM | 5216 | CB | ILE | C | 117 | −7.188 | −28.294 | −34.712 | 1.00 | 74.89 | MOL2 | C |
| ATOM | 5217 | CG2 | ILE | C | 117 | −7.482 | −27.688 | −33.360 | 1.00 | 75.13 | MOL2 | C |
| ATOM | 5218 | CG1 | ILE | C | 117 | −8.458 | −28.482 | −35.540 | 1.00 | 73.77 | MOL2 | C |
| ATOM | 5219 | CD1 | ILE | C | 117 | −9.384 | −29.550 | −35.002 | 1.00 | 70.72 | MOL2 | C |
| ATOM | 5220 | C | ILE | C | 117 | −6.619 | −25.939 | −35.571 | 1.00 | 79.10 | MOL2 | C |
| ATOM | 5221 | O | ILE | C | 117 | −6.304 | −25.124 | −34.689 | 1.00 | 75.27 | MOL2 | O |
| ATOM | 5222 | N | PHE | C | 118 | −7.312 | −25.594 | −36.654 | 1.00 | 79.06 | MOL2 | N |
| ATOM | 5223 | CA | PHE | C | 118 | −7.734 | −24.226 | −36.841 | 1.00 | 82.93 | MOL2 | C |
| ATOM | 5224 | CB | PHE | C | 118 | −6.868 | −23.600 | −37.922 | 1.00 | 88.66 | MOL2 | C |
| ATOM | 5225 | CG | PHE | C | 118 | −5.412 | −23.779 | −37.668 | 1.00 | 92.35 | MOL2 | C |
| ATOM | 5226 | CD1 | PHE | C | 118 | −4.698 | −24.765 | −38.319 | 1.00 | 100.70 | MOL2 | C |
| ATOM | 5227 | CD2 | PHE | C | 118 | −4.770 | −23.010 | −36.718 | 1.00 | 94.88 | MOL2 | C |
| ATOM | 5228 | CE1 | PHE | C | 118 | −3.358 | −24.982 | −38.022 | 1.00 | 108.64 | MOL2 | C |
| ATOM | 5229 | CE2 | PHE | C | 118 | −3.436 | −23.220 | −36.414 | 1.00 | 102.11 | MOL2 | C |
| ATOM | 5230 | CZ | PHE | C | 118 | −2.727 | −24.206 | −37.065 | 1.00 | 106.08 | MOL2 | C |
| ATOM | 5231 | C | PHE | C | 118 | −9.215 | −24.045 | −37.125 | 1.00 | 84.79 | MOL2 | C |
| ATOM | 5232 | O | PHE | C | 118 | −9.797 | −24.722 | −37.981 | 1.00 | 84.33 | MOL2 | O |
| ATOM | 5233 | N | PRO | C | 119 | −9.845 | −23.123 | −36.378 | 1.00 | 84.75 | MOL2 | N |
| ATOM | 5234 | CD | PRO | C | 119 | −9.142 | −22.344 | −35.345 | 1.00 | 86.66 | MOL2 | C |
| ATOM | 5235 | CA | PRO | C | 119 | −11.260 | −22.746 | −36.435 | 1.00 | 82.20 | MOL2 | C |
| ATOM | 5236 | CB | PRO | C | 119 | −11.425 | −21.842 | −35.219 | 1.00 | 89.30 | MOL2 | C |
| ATOM | 5237 | CG | PRO | C | 119 | −10.216 | −22.175 | −34.332 | 1.00 | 89.26 | MOL2 | C |
| ATOM | 5238 | C | PRO | C | 119 | −11.509 | −21.989 | −37.719 | 1.00 | 81.90 | MOL2 | C |
| ATOM | 5239 | O | PRO | C | 119 | −10.617 | −21.295 | −38.211 | 1.00 | 85.94 | MOL2 | O |
| ATOM | 5240 | N | PRO | C | 120 | −12.728 | −22.088 | −38.266 | 1.00 | 79.18 | MOL2 | N |
| ATOM | 5241 | CD | PRO | C | 120 | −13.891 | −22.740 | −37.654 | 1.00 | 74.33 | MOL2 | C |
| ATOM | 5242 | CA | PRO | C | 120 | −13.109 | −21.414 | −39.514 | 1.00 | 83.28 | MOL2 | C |
| ATOM | 5243 | CB | PRO | C | 120 | −14.613 | −21.666 | −39.598 | 1.00 | 78.99 | MOL2 | C |
| ATOM | 5244 | CG | PRO | C | 120 | −14.785 | −22.936 | −38.853 | 1.00 | 79.17 | MOL2 | C |
| ATOM | 5245 | C | PRO | C | 120 | −12.781 | −19.918 | −39.496 | 1.00 | 88.69 | MOL2 | C |
| ATOM | 5246 | O | PRO | C | 120 | −13.058 | −19.227 | −38.512 | 1.00 | 88.57 | MOL2 | O |
| ATOM | 5247 | N | SER | C | 121 | −12.181 | −19.420 | −40.577 | 1.00 | 93.69 | MOL2 | N |
| ATOM | 5248 | CA | SER | C | 121 | −11.840 | −18.002 | −40.654 | 1.00 | 98.12 | MOL2 | C |
| ATOM | 5249 | CB | SER | C | 121 | −11.149 | −17.666 | −41.986 | 1.00 | 103.21 | MOL2 | C |
| ATOM | 5250 | OG | SER | C | 121 | −9.860 | −18.249 | −42.094 | 1.00 | 106.70 | MOL2 | O |
| ATOM | 5251 | C | SER | C | 121 | −13.130 | −17.196 | −40.549 | 1.00 | 99.93 | MOL2 | C |
| ATOM | 5252 | O | SER | C | 121 | −14.105 | −17.485 | −41.254 | 1.00 | 98.91 | MOL2 | O |
| ATOM | 5253 | N | SER | C | 122 | −13.144 | −16.195 | −39.669 | 1.00 | 100.00 | MOL2 | N |
| ATOM | 5254 | CA | SER | C | 122 | −14.333 | −15.355 | −39.516 | 1.00 | 98.46 | MOL2 | C |
| ATOM | 5255 | CB | SER | C | 122 | −14.039 | −14.168 | −38.593 | 1.00 | 96.67 | MOL2 | C |
| ATOM | 5256 | OG | SER | C | 122 | −13.835 | −14.597 | −37.260 | 1.00 | 95.18 | MOL2 | O |
| ATOM | 5257 | C | SER | C | 122 | −14.733 | −14.850 | −40.901 | 1.00 | 97.46 | MOL2 | C |
| ATOM | 5258 | O | SER | C | 122 | −15.912 | −14.780 | −41.250 | 1.00 | 95.78 | MOL2 | O |
| ATOM | 5259 | N | GLU | C | 123 | −13.719 | −14.515 | −41.685 | 1.00 | 95.17 | MOL2 | N |
| ATOM | 5260 | CA | GLU | C | 123 | −13.897 | −14.021 | −43.031 | 1.00 | 96.49 | MOL2 | C |
| ATOM | 5261 | CB | GLU | C | 123 | −12.513 | −13.741 | −43.626 | 1.00 | 101.06 | MOL2 | C |
| ATOM | 5262 | CG | GLU | C | 123 | −11.598 | −12.872 | −42.722 | 1.00 | 105.38 | MOL2 | C |
| ATOM | 5263 | CD | GLU | C | 123 | −11.419 | −13.419 | −41.291 | 1.00 | 107.61 | MOL2 | C |
| ATOM | 5264 | OE1 | GLU | C | 123 | −11.022 | −14.594 | −41.134 | 1.00 | 111.76 | MOL2 | O |
| ATOM | 5265 | OE2 | GLU | C | 123 | −11.670 | −12.673 | −40.316 | 1.00 | 103.87 | MOL2 | O |
| ATOM | 5266 | C | GLU | C | 123 | −14.656 | −15.072 | −43.845 | 1.00 | 97.39 | MOL2 | C |
| ATOM | 5267 | O | GLU | C | 123 | −15.453 | −14.742 | −44.728 | 1.00 | 97.52 | MOL2 | O |
| ATOM | 5268 | N | GLN | C | 124 | −14.414 | −16.340 | −43.525 | 1.00 | 97.89 | MOL2 | N |
| ATOM | 5269 | CA | GLN | C | 124 | −15.059 | −17.460 | −44.212 | 1.00 | 101.57 | MOL2 | C |
| ATOM | 5270 | CB | GLN | C | 124 | −14.358 | −18.771 | −43.837 | 1.00 | 105.91 | MOL2 | C |
| ATOM | 5271 | CG | GLN | C | 124 | −15.008 | −20.006 | −44.441 | 1.00 | 107.01 | MOL2 | C |
| ATOM | 5272 | CD | GLN | C | 124 | −14.364 | −21.295 | −43.978 | 1.00 | 103.71 | MOL2 | C |
| ATOM | 5273 | OE1 | GLN | C | 124 | −14.499 | −22.331 | −44.631 | 1.00 | 101.30 | MOL2 | O |
| ATOM | 5274 | NE2 | GLN | C | 124 | −13.673 | −21.244 | −42.841 | 1.00 | 99.29 | MOL2 | N |
| ATOM | 5275 | C | GLN | C | 124 | −16.529 | −17.559 | −43.823 | 1.00 | 99.96 | MOL2 | C |
| ATOM | 5276 | O | GLN | C | 124 | −17.417 | −17.669 | −44.677 | 1.00 | 94.72 | MOL2 | O |
| ATOM | 5277 | N | LEU | C | 125 | −16.750 | −17.544 | −42.514 | 1.00 | 100.90 | MOL2 | N |
| ATOM | 5278 | CA | LEU | C | 125 | −18.077 | −17.616 | −41.919 | 1.00 | 105.80 | MOL2 | C |
| ATOM | 5279 | CB | LEU | C | 125 | −18.006 | −17.163 | −40.460 | 1.00 | 107.11 | MOL2 | C |
| ATOM | 5280 | CG | LEU | C | 125 | −17.051 | −17.885 | −39.509 | 1.00 | 112.14 | MOL2 | C |
| ATOM | 5281 | CD1 | LEU | C | 125 | −16.864 | −17.060 | −38.238 | 1.00 | 111.82 | MOL2 | C |
| ATOM | 5282 | CD2 | LEU | C | 125 | −17.602 | −19.270 | −39.189 | 1.00 | 113.18 | MOL2 | C |
| ATOM | 5283 | C | LEU | C | 125 | −19.037 | −16.693 | −42.655 | 1.00 | 109.20 | MOL2 | C |
| ATOM | 5284 | O | LEU | C | 125 | −20.187 | −17.050 | −42.942 | 1.00 | 109.87 | MOL2 | O |
| ATOM | 5285 | N | THR | C | 126 | −18.553 | −15.488 | −42.939 | 1.00 | 110.02 | MOL2 | N |
| ATOM | 5286 | CA | THR | C | 126 | −19.352 | −14.487 | −43.627 | 1.00 | 110.15 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 5287 | CB | THR | C | 126 | −18.690 | −13.090 | −43.555 | 1.00 | 111.30 | MOL2 | C |
|------|------|------|-----|---|-----|---------|---------|---------|------|--------|------|---|
| ATOM | 5288 | OG1 | THR | C | 126 | −17.549 | −13.055 | −44.421 | 1.00 | 116.23 | MOL2 | O |
| ATOM | 5289 | CG2 | THR | C | 126 | −18.240 | −12.781 | −42.125 | 1.00 | 110.60 | MOL2 | C |
| ATOM | 5290 | C | THR | C | 126 | −19.519 | −14.880 | −45.089 | 1.00 | 111.30 | MOL2 | C |
| ATOM | 5291 | O | THR | C | 126 | −19.216 | −14.096 | −45.991 | 1.00 | 113.98 | MOL2 | O |
| ATOM | 5292 | N | SER | C | 127 | −19.993 | −16.101 | −45.316 | 1.00 | 110.58 | MOL2 | N |
| ATOM | 5293 | CA | SER | C | 127 | −20.208 | −16.602 | −46.668 | 1.00 | 111.26 | MOL2 | C |
| ATOM | 5294 | CB | SER | C | 127 | −18.870 | −16.820 | −47.385 | 1.00 | 115.20 | MOL2 | C |
| ATOM | 5295 | OG | SER | C | 127 | −19.073 | −17.129 | −48.757 | 1.00 | 114.55 | MOL2 | O |
| ATOM | 5296 | C | SER | C | 127 | −20.980 | −17.910 | −46.610 | 1.00 | 110.60 | MOL2 | C |
| ATOM | 5297 | O | SER | C | 127 | −21.007 | −18.672 | −47.580 | 1.00 | 110.21 | MOL2 | O |
| ATOM | 5298 | N | GLY | C | 128 | −21.600 | −18.166 | −45.461 | 1.00 | 109.69 | MOL2 | N |
| ATOM | 5299 | CA | GLY | C | 128 | −22.384 | −19.379 | −45.292 | 1.00 | 110.41 | MOL2 | C |
| ATOM | 5300 | C | GLY | C | 128 | −21.583 | −20.668 | −45.338 | 1.00 | 108.79 | MOL2 | C |
| ATOM | 5301 | O | GLY | C | 128 | −22.125 | −21.751 | −45.585 | 1.00 | 107.03 | MOL2 | O |
| ATOM | 5302 | N | GLY | C | 129 | −20.283 | −20.556 | −45.098 | 1.00 | 106.35 | MOL2 | N |
| ATOM | 5303 | CA | GLY | C | 129 | −19.442 | −21.734 | −45.117 | 1.00 | 104.12 | MOL2 | C |
| ATOM | 5304 | C | GLY | C | 129 | −18.409 | −21.660 | −44.017 | 1.00 | 102.84 | MOL2 | C |
| ATOM | 5305 | O | GLY | C | 129 | −18.098 | −20.564 | −43.523 | 1.00 | 96.92 | MOL2 | O |
| ATOM | 5306 | N | ALA | C | 130 | −17.885 | −22.827 | −43.634 | 1.00 | 102.40 | MOL2 | N |
| ATOM | 5307 | CA | ALA | C | 130 | −16.870 | −22.927 | −42.582 | 1.00 | 98.21 | MOL2 | C |
| ATOM | 5308 | CB | ALA | C | 130 | −17.524 | −22.848 | −41.193 | 1.00 | 102.42 | MOL2 | C |
| ATOM | 5309 | C | ALA | C | 130 | −16.077 | −24.222 | −42.702 | 1.00 | 93.42 | MOL2 | C |
| ATOM | 5310 | O | ALA | C | 130 | −16.649 | −25.302 | −42.884 | 1.00 | 89.92 | MOL2 | O |
| ATOM | 5311 | N | SER | C | 131 | −14.756 | −24.108 | −42.607 | 1.00 | 89.44 | MOL2 | N |
| ATOM | 5312 | CA | SER | C | 131 | −13.896 | −25.279 | −42.684 | 1.00 | 84.50 | MOL2 | C |
| ATOM | 5313 | CB | SER | C | 131 | −13.157 | −25.330 | −44.023 | 1.00 | 88.74 | MOL2 | C |
| ATOM | 5314 | OG | SER | C | 131 | −14.002 | −25.863 | −45.031 | 1.00 | 96.57 | MOL2 | O |
| ATOM | 5315 | C | SER | C | 131 | −12.903 | −25.319 | −41.542 | 1.00 | 78.50 | MOL2 | C |
| ATOM | 5316 | O | SER | C | 131 | −12.319 | −24.293 | −41.170 | 1.00 | 74.59 | MOL2 | O |
| ATOM | 5317 | N | VAL | C | 132 | −12.745 | −26.502 | −40.955 | 1.00 | 74.38 | MOL2 | N |
| ATOM | 5318 | CA | VAL | C | 132 | −11.783 | −26.644 | −39.878 | 1.00 | 74.12 | MOL2 | C |
| ATOM | 5319 | CB | VAL | C | 132 | −12.332 | −27.379 | −38.674 | 1.00 | 76.94 | MOL2 | C |
| ATOM | 5320 | CG1 | VAL | C | 132 | −11.266 | −27.399 | −37.588 | 1.00 | 73.30 | MOL2 | C |
| ATOM | 5321 | CG2 | VAL | C | 132 | −13.578 | −26.684 | −38.170 | 1.00 | 80.37 | MOL2 | C |
| ATOM | 5322 | C | VAL | C | 132 | −10.586 | −27.400 | −40.411 | 1.00 | 72.25 | MOL2 | C |
| ATOM | 5323 | O | VAL | C | 132 | −10.688 | −28.531 | −40.890 | 1.00 | 66.86 | MOL2 | O |
| ATOM | 5324 | N | VAL | C | 133 | −9.441 | −26.746 | −40.331 | 1.00 | 72.51 | MOL2 | N |
| ATOM | 5325 | CA | VAL | C | 133 | −8.217 | −27.310 | −40.840 | 1.00 | 71.90 | MOL2 | C |
| ATOM | 5326 | CB | VAL | C | 133 | −7.479 | −26.261 | −41.712 | 1.00 | 70.60 | MOL2 | C |
| ATOM | 5327 | CG1 | VAL | C | 133 | −6.087 | −26.743 | −42.083 | 1.00 | 64.45 | MOL2 | C |
| ATOM | 5328 | CG2 | VAL | C | 133 | −8.301 | −25.984 | −42.958 | 1.00 | 64.26 | MOL2 | C |
| ATOM | 5329 | C | VAL | C | 133 | −7.318 | −27.824 | −39.726 | 1.00 | 75.65 | MOL2 | C |
| ATOM | 5330 | O | VAL | C | 133 | −7.151 | −27.189 | −38.675 | 1.00 | 71.43 | MOL2 | O |
| ATOM | 5331 | N | CYS | C | 134 | −6.751 | −28.998 | −39.984 | 1.00 | 78.14 | MOL2 | N |
| ATOM | 5332 | CA | CYS | C | 134 | −5.856 | −29.671 | −39.058 | 1.00 | 75.48 | MOL2 | C |
| ATOM | 5333 | C | CYS | C | 134 | −4.587 | −30.106 | −39.816 | 1.00 | 70.11 | MOL2 | C |
| ATOM | 5334 | O | CYS | C | 134 | −4.651 | −30.847 | −40.799 | 1.00 | 61.50 | MOL2 | O |
| ATOM | 5335 | CB | CYS | C | 134 | −6.592 | −30.873 | −38.461 | 1.00 | 79.82 | MOL2 | C |
| ATOM | 5336 | SG | CYS | C | 134 | −5.788 | −31.675 | −37.042 | 1.00 | 94.89 | MOL2 | S |
| ATOM | 5337 | N | PHE | C | 135 | −3.439 | −29.612 | −39.365 | 1.00 | 70.18 | MOL2 | N |
| ATOM | 5338 | CA | PHE | C | 135 | −2.160 | −29.933 | −39.986 | 1.00 | 69.90 | MOL2 | C |
| ATOM | 5339 | CB | PHE | C | 135 | −1.278 | −28.679 | −40.115 | 1.00 | 76.29 | MOL2 | C |
| ATOM | 5340 | CG | PHE | C | 135 | −1.846 | −27.613 | −41.011 | 1.00 | 82.52 | MOL2 | C |
| ATOM | 5341 | CD1 | PHE | C | 135 | −1.694 | −26.270 | −40.685 | 1.00 | 81.78 | MOL2 | C |
| ATOM | 5342 | CD2 | PHE | C | 135 | −2.512 | −27.947 | −42.185 | 1.00 | 83.39 | MOL2 | C |
| ATOM | 5343 | CE1 | PHE | C | 135 | −2.194 | −25.281 | −41.509 | 1.00 | 85.51 | MOL2 | C |
| ATOM | 5344 | CE2 | PHE | C | 135 | −3.014 | −26.962 | −43.016 | 1.00 | 86.16 | MOL2 | C |
| ATOM | 5345 | CZ | PHE | C | 135 | −2.855 | −25.626 | −42.677 | 1.00 | 90.03 | MOL2 | C |
| ATOM | 5346 | C | PHE | C | 135 | −1.415 | −30.948 | −39.139 | 1.00 | 66.86 | MOL2 | C |
| ATOM | 5347 | O | PHE | C | 135 | −1.311 | −30.804 | −37.919 | 1.00 | 64.94 | MOL2 | O |
| ATOM | 5348 | N | LEU | C | 136 | −0.906 | −31.979 | −39.798 | 1.00 | 64.71 | MOL2 | N |
| ATOM | 5349 | CA | LEU | C | 136 | −0.118 | −33.015 | −39.139 | 1.00 | 63.06 | MOL2 | C |
| ATOM | 5350 | CB | LEU | C | 136 | −0.717 | −34.401 | −39.409 | 1.00 | 61.67 | MOL2 | C |
| ATOM | 5351 | CG | LEU | C | 136 | −2.218 | −34.640 | −39.217 | 1.00 | 55.96 | MOL2 | C |
| ATOM | 5352 | CD1 | LEU | C | 136 | −2.673 | −34.038 | −37.926 | 1.00 | 51.18 | MOL2 | C |
| ATOM | 5353 | CD2 | LEU | C | 136 | −2.974 | −34.029 | −40.358 | 1.00 | 61.97 | MOL2 | C |
| ATOM | 5354 | C | LEU | C | 136 | 1.230 | −32.879 | −39.840 | 1.00 | 61.45 | MOL2 | C |
| ATOM | 5355 | O | LEU | C | 136 | 1.433 | −33.449 | −40.913 | 1.00 | 65.67 | MOL2 | O |
| ATOM | 5356 | N | ASN | C | 137 | 2.149 | −32.126 | −39.249 | 1.00 | 58.41 | MOL2 | N |
| ATOM | 5357 | CA | ASN | C | 137 | 3.420 | −31.896 | −39.916 | 1.00 | 64.32 | MOL2 | C |
| ATOM | 5358 | CB | ASN | C | 137 | 3.778 | −30.404 | −39.885 | 1.00 | 70.81 | MOL2 | C |
| ATOM | 5359 | CG | ASN | C | 137 | 2.629 | −29.516 | −40.307 | 1.00 | 75.64 | MOL2 | C |
| ATOM | 5360 | OD1 | ASN | C | 137 | 2.040 | −29.702 | −41.373 | 1.00 | 79.28 | MOL2 | O |
| ATOM | 5361 | ND2 | ASN | C | 137 | 2.306 | −28.536 | −39.470 | 1.00 | 77.18 | MOL2 | N |
| ATOM | 5362 | C | ASN | C | 137 | 4.632 | −32.663 | −39.451 | 1.00 | 64.01 | MOL2 | C |
| ATOM | 5363 | O | ASN | C | 137 | 4.753 | −33.048 | −38.291 | 1.00 | 67.80 | MOL2 | O |

TABLE 1-continued

The atomic coordinates of IL17F in complex with 496 Fab
(H32; a = 189.4; b = 189.4; c = 490.9, α, β = 90°; γ = 120°)

| ATOM | 5364 | N | ASN | C | 138 | 5.531 | −32.865 | −40.402 | 1.00 | 64.58 | MOL2 | N |
|---|---|---|---|---|---|---|---|---|---|---|---|---|
| ATOM | 5365 | CA | ASN | C | 138 | 6.800 | −33.516 | −40.160 | 1.00 | 68.57 | MOL2 | C |
| ATOM | 5366 | CB | ASN | C | 138 | 7.705 | −32.506 | −39.472 | 1.00 | 66.72 | MOL2 | C |
| ATOM | 5367 | CG | ASN | C | 138 | 7.733 | −31.195 | −40.202 | 1.00 | 69.15 | MOL2 | C |
| ATOM | 5368 | OD1 | ASN | C | 138 | 8.169 | −31.129 | −41.349 | 1.00 | 71.75 | MOL2 | O |
| ATOM | 5369 | ND2 | ASN | C | 138 | 7.248 | −30.142 | −39.556 | 1.00 | 77.70 | MOL2 | N |
| ATOM | 5370 | C | ASN | C | 138 | 6.767 | −34.817 | −39.367 | 1.00 | 69.69 | MOL2 | C |
| ATOM | 5371 | O | ASN | C | 138 | 7.131 | −34.840 | −38.185 | 1.00 | 74.89 | MOL2 | O |
| ATOM | 5372 | N | PHE | C | 139 | 6.352 | −35.901 | −40.013 | 1.00 | 63.17 | MOL2 | N |
| ATOM | 5373 | CA | PHE | C | 139 | 6.311 | −37.180 | −39.330 | 1.00 | 60.21 | MOL2 | C |
| ATOM | 5374 | CB | PHE | C | 139 | 4.882 | −37.496 | −38.912 | 1.00 | 58.82 | MOL2 | C |
| ATOM | 5375 | CG | PHE | C | 139 | 3.937 | −37.691 | −40.050 | 1.00 | 55.93 | MOL2 | C |
| ATOM | 5376 | CD1 | PHE | C | 139 | 3.626 | −38.967 | −40.498 | 1.00 | 55.11 | MOL2 | C |
| ATOM | 5377 | CD2 | PHE | C | 139 | 3.298 | −36.607 | −40.626 | 1.00 | 55.63 | MOL2 | C |
| ATOM | 5378 | CE1 | PHE | C | 139 | 2.681 | −39.158 | −41.498 | 1.00 | 56.66 | MOL2 | C |
| ATOM | 5379 | CE2 | PHE | C | 139 | 2.350 | −36.794 | −41.631 | 1.00 | 58.47 | MOL2 | C |
| ATOM | 5380 | CZ | PHE | C | 139 | 2.041 | −38.070 | −42.064 | 1.00 | 52.74 | MOL2 | C |
| ATOM | 5381 | C | PHE | C | 139 | 6.892 | −38.298 | −40.180 | 1.00 | 60.49 | MOL2 | C |
| ATOM | 5382 | O | PHE | C | 139 | 7.191 | −38.093 | −41.352 | 1.00 | 65.37 | MOL2 | O |
| ATOM | 5383 | N | TYR | C | 140 | 7.057 | −39.476 | −39.584 | 1.00 | 56.93 | MOL2 | N |
| ATOM | 5384 | CA | TYR | C | 140 | 7.640 | −40.617 | −40.280 | 1.00 | 50.75 | MOL2 | C |
| ATOM | 5385 | CB | TYR | C | 140 | 9.164 | −40.461 | −40.370 | 1.00 | 53.03 | MOL2 | C |
| ATOM | 5386 | CG | TYR | C | 140 | 9.813 | −41.442 | −41.314 | 1.00 | 56.37 | MOL2 | C |
| ATOM | 5387 | CD1 | TYR | C | 140 | 9.818 | −41.211 | −42.676 | 1.00 | 59.38 | MOL2 | C |
| ATOM | 5388 | CE1 | TYR | C | 140 | 10.285 | −42.155 | −43.565 | 1.00 | 59.29 | MOL2 | C |
| ATOM | 5389 | CD2 | TYR | C | 140 | 10.313 | −42.650 | −40.861 | 1.00 | 59.76 | MOL2 | C |
| ATOM | 5390 | CE2 | TYR | C | 140 | 10.784 | −43.603 | −41.749 | 1.00 | 59.78 | MOL2 | C |
| ATOM | 5391 | CZ | TYR | C | 140 | 10.757 | −43.348 | −43.101 | 1.00 | 56.94 | MOL2 | C |
| ATOM | 5392 | OH | TYR | C | 140 | 11.148 | −44.301 | −44.004 | 1.00 | 60.05 | MOL2 | O |
| ATOM | 5393 | C | TYR | C | 140 | 7.349 | −41.865 | −39.484 | 1.00 | 50.85 | MOL2 | C |
| ATOM | 5394 | O | TYR | C | 140 | 7.496 | −41.871 | −38.262 | 1.00 | 54.51 | MOL2 | O |
| ATOM | 5395 | N | PRO | C | 141 | 6.947 | −42.948 | −40.157 | 1.00 | 46.94 | MOL2 | N |
| ATOM | 5396 | CD | PRO | C | 141 | 6.842 | −44.281 | −39.555 | 1.00 | 46.87 | MOL2 | C |
| ATOM | 5397 | CA | PRO | C | 141 | 6.760 | −43.037 | −41.598 | 1.00 | 50.29 | MOL2 | C |
| ATOM | 5398 | CB | PRO | C | 141 | 6.637 | −44.532 | −41.838 | 1.00 | 54.32 | MOL2 | C |
| ATOM | 5399 | CG | PRO | C | 141 | 6.046 | −45.016 | −40.589 | 1.00 | 49.13 | MOL2 | C |
| ATOM | 5400 | C | PRO | C | 141 | 5.537 | −42.285 | −42.067 | 1.00 | 57.77 | MOL2 | C |
| ATOM | 5401 | O | PRO | C | 141 | 4.907 | −41.569 | −41.284 | 1.00 | 58.00 | MOL2 | O |
| ATOM | 5402 | N | LYS | C | 142 | 5.207 | −42.469 | −43.345 | 1.00 | 61.24 | MOL2 | N |
| ATOM | 5403 | CA | LYS | C | 142 | 4.086 | −41.794 | −43.973 | 1.00 | 61.92 | MOL2 | C |
| ATOM | 5404 | CB | LYS | C | 142 | 4.259 | −41.804 | −45.488 | 1.00 | 68.52 | MOL2 | C |
| ATOM | 5405 | CG | LYS | C | 142 | 4.625 | −43.160 | −46.075 | 1.00 | 86.64 | MOL2 | C |
| ATOM | 5406 | CD | LYS | C | 142 | 4.708 | −43.117 | −47.608 | 1.00 | 91.64 | MOL2 | C |
| ATOM | 5407 | CE | LYS | C | 142 | 5.222 | −44.440 | −48.198 | 1.00 | 98.10 | MOL2 | C |
| ATOM | 5408 | NZ | LYS | C | 142 | 4.341 | −45.622 | −47.914 | 1.00 | 102.50 | MOL2 | N |
| ATOM | 5409 | C | LYS | C | 142 | 2.718 | −42.331 | −43.623 | 1.00 | 60.19 | MOL2 | C |
| ATOM | 5410 | O | LYS | C | 142 | 1.750 | −41.586 | −43.648 | 1.00 | 65.75 | MOL2 | O |
| ATOM | 5411 | N | ASP | C | 143 | 2.614 | −43.612 | −43.302 | 1.00 | 60.86 | MOL2 | N |
| ATOM | 5412 | CA | ASP | C | 143 | 1.302 | −44.156 | −42.968 | 1.00 | 66.49 | MOL2 | C |
| ATOM | 5413 | CB | ASP | C | 143 | 1.365 | −45.675 | −42.862 | 1.00 | 80.74 | MOL2 | C |
| ATOM | 5414 | CG | ASP | C | 143 | 1.948 | −46.312 | −44.118 | 1.00 | 98.49 | MOL2 | C |
| ATOM | 5415 | OD1 | ASP | C | 143 | 1.239 | −46.356 | −45.150 | 1.00 | 102.89 | MOL2 | O |
| ATOM | 5416 | OD2 | ASP | C | 143 | 3.125 | −46.752 | −44.080 | 1.00 | 107.17 | MOL2 | O |
| ATOM | 5417 | C | ASP | C | 143 | 0.824 | −43.535 | −41.674 | 1.00 | 64.02 | MOL2 | C |
| ATOM | 5418 | O | ASP | C | 143 | 1.454 | −43.666 | −40.626 | 1.00 | 70.52 | MOL2 | O |
| ATOM | 5419 | N | ILE | C | 144 | −0.281 | −42.810 | −41.767 | 1.00 | 62.33 | MOL2 | N |
| ATOM | 5420 | CA | ILE | C | 144 | −0.862 | −42.140 | −40.607 | 1.00 | 61.79 | MOL2 | C |
| ATOM | 5421 | CB | ILE | C | 144 | −0.432 | −40.688 | −40.487 | 1.00 | 52.91 | MOL2 | C |
| ATOM | 5422 | CG2 | ILE | C | 144 | −1.199 | −39.859 | −41.480 | 1.00 | 41.58 | MOL2 | C |
| ATOM | 5423 | CG1 | ILE | C | 144 | −0.771 | −40.168 | −39.093 | 1.00 | 48.15 | MOL2 | C |
| ATOM | 5424 | CD1 | ILE | C | 144 | −0.151 | −38.833 | −38.788 | 1.00 | 47.62 | MOL2 | C |
| ATOM | 5425 | C | ILE | C | 144 | −2.356 | −42.117 | −40.798 | 1.00 | 65.02 | MOL2 | C |
| ATOM | 5426 | O | ILE | C | 144 | −2.839 | −42.255 | −41.918 | 1.00 | 64.19 | MOL2 | O |
| ATOM | 5427 | N | ASN | C | 145 | −3.093 | −41.926 | −39.714 | 1.00 | 68.11 | MOL2 | N |
| ATOM | 5428 | CA | ASN | C | 145 | −4.532 | −41.906 | −39.837 | 1.00 | 76.59 | MOL2 | C |
| ATOM | 5429 | CB | ASN | C | 145 | −5.093 | −43.281 | −39.473 | 1.00 | 86.33 | MOL2 | C |
| ATOM | 5430 | CG | ASN | C | 145 | −6.573 | −43.397 | −39.768 | 1.00 | 100.33 | MOL2 | C |
| ATOM | 5431 | OD1 | ASN | C | 145 | −7.015 | −43.141 | −40.894 | 1.00 | 108.69 | MOL2 | O |
| ATOM | 5432 | ND2 | ASN | C | 145 | −7.353 | −43.782 | −38.757 | 1.00 | 104.92 | MOL2 | N |
| ATOM | 5433 | C | ASN | C | 145 | −5.179 | −40.806 | −38.999 | 1.00 | 79.08 | MOL2 | C |
| ATOM | 5434 | O | ASN | C | 145 | −4.922 | −40.676 | −37.794 | 1.00 | 81.54 | MOL2 | O |
| ATOM | 5435 | N | VAL | C | 146 | −6.023 | −40.013 | −39.657 | 1.00 | 78.50 | MOL2 | N |
| ATOM | 5436 | CA | VAL | C | 146 | −6.703 | −38.898 | −39.012 | 1.00 | 77.82 | MOL2 | C |
| ATOM | 5437 | CB | VAL | C | 146 | −6.609 | −37.632 | −39.884 | 1.00 | 75.85 | MOL2 | C |
| ATOM | 5438 | CG1 | VAL | C | 146 | −7.477 | −37.790 | −41.121 | 1.00 | 77.98 | MOL2 | C |
| ATOM | 5439 | CG2 | VAL | C | 146 | −7.012 | −36.422 | −39.085 | 1.00 | 76.44 | MOL2 | C |
| ATOM | 5440 | C | VAL | C | 146 | −8.170 | −39.222 | −38.757 | 1.00 | 79.53 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 5441 | O | VAL | C | 146 | −8.844 | −39.818 | −39.601 | 1.00 | 79.89 | MOL2 | O |
|---|---|---|---|---|---|---|---|---|---|---|---|---|
| ATOM | 5442 | N | LYS | C | 147 | −8.651 | −38.821 | −37.583 | 1.00 | 83.36 | MOL2 | N |
| ATOM | 5443 | CA | LYS | C | 147 | −10.031 | −39.056 | −37.166 | 1.00 | 84.28 | MOL2 | C |
| ATOM | 5444 | CB | LYS | C | 147 | −10.034 | −40.026 | −35.978 | 1.00 | 90.58 | MOL2 | C |
| ATOM | 5445 | CG | LYS | C | 147 | −11.297 | −40.862 | −35.799 | 1.00 | 100.75 | MOL2 | C |
| ATOM | 5446 | CD | LYS | C | 147 | −11.402 | −41.970 | −36.854 | 1.00 | 106.03 | MOL2 | C |
| ATOM | 5447 | CE | LYS | C | 147 | −12.371 | −43.079 | −36.418 | 1.00 | 106.05 | MOL2 | C |
| ATOM | 5448 | NZ | LYS | C | 147 | −11.915 | −43.811 | −35.193 | 1.00 | 99.23 | MOL2 | N |
| ATOM | 5449 | C | LYS | C | 147 | −10.648 | −37.718 | −36.730 | 1.00 | 83.61 | MOL2 | C |
| ATOM | 5450 | O | LYS | C | 147 | −10.072 | −37.000 | −35.896 | 1.00 | 79.83 | MOL2 | O |
| ATOM | 5451 | N | TRP | C | 148 | −11.806 | −37.385 | −37.299 | 1.00 | 82.15 | MOL2 | N |
| ATOM | 5452 | CA | TRP | C | 148 | −12.518 | −36.148 | −36.961 | 1.00 | 82.38 | MOL2 | C |
| ATOM | 5453 | CB | TRP | C | 148 | −13.112 | −35.510 | −38.223 | 1.00 | 79.87 | MOL2 | C |
| ATOM | 5454 | CG | TRP | C | 148 | −12.131 | −34.739 | −39.039 | 1.00 | 78.56 | MOL2 | C |
| ATOM | 5455 | CD2 | TRP | C | 148 | −11.536 | −33.488 | −38.691 | 1.00 | 74.63 | MOL2 | C |
| ATOM | 5456 | CE2 | TRP | C | 148 | −10.660 | −33.138 | −39.733 | 1.00 | 75.12 | MOL2 | C |
| ATOM | 5457 | CE3 | TRP | C | 148 | −11.660 | −32.629 | −37.597 | 1.00 | 75.81 | MOL2 | C |
| ATOM | 5458 | CD1 | TRP | C | 148 | −11.607 | −35.090 | −40.252 | 1.00 | 75.00 | MOL2 | C |
| ATOM | 5459 | NE1 | TRP | C | 148 | −10.722 | −34.132 | −40.675 | 1.00 | 71.58 | MOL2 | N |
| ATOM | 5460 | CZ2 | TRP | C | 148 | −9.910 | −31.965 | −39.711 | 1.00 | 78.98 | MOL2 | C |
| ATOM | 5461 | CZ3 | TRP | C | 148 | −10.918 | −31.469 | −37.576 | 1.00 | 77.16 | MOL2 | C |
| ATOM | 5462 | CH2 | TRP | C | 148 | −10.052 | −31.146 | −38.626 | 1.00 | 80.07 | MOL2 | C |
| ATOM | 5463 | C | TRP | C | 148 | −13.662 | −36.422 | −35.978 | 1.00 | 86.86 | MOL2 | C |
| ATOM | 5464 | O | TRP | C | 148 | −14.372 | −37.429 | −36.105 | 1.00 | 86.90 | MOL2 | O |
| ATOM | 5465 | N | LYS | C | 149 | −13.851 | −35.532 | −35.005 | 1.00 | 88.93 | MOL2 | N |
| ATOM | 5466 | CA | LYS | C | 149 | −14.933 | −35.708 | −34.040 | 1.00 | 89.42 | MOL2 | C |
| ATOM | 5467 | CB | LYS | C | 149 | −14.421 | −36.397 | −32.765 | 1.00 | 91.44 | MOL2 | C |
| ATOM | 5468 | CG | LYS | C | 149 | −14.301 | −37.924 | −32.862 | 1.00 | 92.37 | MOL2 | C |
| ATOM | 5469 | CD | LYS | C | 149 | −13.833 | −38.516 | −31.527 | 1.00 | 97.01 | MOL2 | C |
| ATOM | 5470 | CE | LYS | C | 149 | −13.685 | −40.035 | −31.572 | 1.00 | 94.56 | MOL2 | C |
| ATOM | 5471 | NZ | LYS | C | 149 | −13.188 | −40.560 | −30.266 | 1.00 | 92.95 | MOL2 | N |
| ATOM | 5472 | C | LYS | C | 149 | −15.657 | −34.408 | −33.676 | 1.00 | 91.10 | MOL2 | C |
| ATOM | 5473 | O | LYS | C | 149 | −15.070 | −33.467 | −33.120 | 1.00 | 88.06 | MOL2 | O |
| ATOM | 5474 | N | ILE | C | 150 | −16.944 | −34.378 | −34.018 | 1.00 | 93.01 | MOL2 | N |
| ATOM | 5475 | CA | ILE | C | 150 | −17.832 | −33.246 | −33.742 | 1.00 | 92.66 | MOL2 | C |
| ATOM | 5476 | CB | ILE | C | 150 | −18.829 | −33.022 | −34.928 | 1.00 | 88.95 | MOL2 | C |
| ATOM | 5477 | CG2 | ILE | C | 150 | −18.145 | −32.293 | −36.070 | 1.00 | 82.58 | MOL2 | C |
| ATOM | 5478 | CG1 | ILE | C | 150 | −19.378 | −34.372 | −35.410 | 1.00 | 85.89 | MOL2 | C |
| ATOM | 5479 | CD1 | ILE | C | 150 | −20.283 | −34.287 | −36.620 | 1.00 | 82.92 | MOL2 | C |
| ATOM | 5480 | C | ILE | C | 150 | −18.627 | −33.578 | −32.471 | 1.00 | 93.45 | MOL2 | C |
| ATOM | 5481 | O | ILE | C | 150 | −19.451 | −34.498 | −32.470 | 1.00 | 92.06 | MOL2 | O |
| ATOM | 5482 | N | ASP | C | 151 | −18.378 | −32.836 | −31.395 | 1.00 | 95.21 | MOL2 | N |
| ATOM | 5483 | CA | ASP | C | 151 | −19.063 | −33.075 | −30.128 | 1.00 | 103.28 | MOL2 | C |
| ATOM | 5484 | CB | ASP | C | 151 | −20.524 | −32.594 | −30.198 | 1.00 | 115.41 | MOL2 | C |
| ATOM | 5485 | CG | ASP | C | 151 | −20.695 | −31.151 | −29.712 | 1.00 | 123.70 | MOL2 | C |
| ATOM | 5486 | OD1 | ASP | C | 151 | −20.264 | −30.842 | −28.575 | 1.00 | 125.67 | MOL2 | O |
| ATOM | 5487 | OD2 | ASP | C | 151 | −21.266 | −30.331 | −30.463 | 1.00 | 127.57 | MOL2 | O |
| ATOM | 5488 | C | ASP | C | 151 | −19.004 | −34.541 | −29.673 | 1.00 | 102.98 | MOL2 | C |
| ATOM | 5489 | O | ASP | C | 151 | −19.953 | −35.064 | −29.070 | 1.00 | 103.40 | MOL2 | O |
| ATOM | 5490 | N | GLY | C | 152 | −17.886 | −35.203 | −29.968 | 1.00 | 99.06 | MOL2 | N |
| ATOM | 5491 | CA | GLY | C | 152 | −17.721 | −36.583 | −29.544 | 1.00 | 96.11 | MOL2 | C |
| ATOM | 5492 | C | GLY | C | 152 | −17.970 | −37.689 | −30.553 | 1.00 | 94.54 | MOL2 | C |
| ATOM | 5493 | O | GLY | C | 152 | −17.555 | −38.829 | −30.333 | 1.00 | 95.10 | MOL2 | O |
| ATOM | 5494 | N | SER | C | 153 | −18.648 | −37.382 | −31.651 | 1.00 | 93.68 | MOL2 | N |
| ATOM | 5495 | CA | SER | C | 153 | −18.911 | −38.406 | −32.651 | 1.00 | 97.25 | MOL2 | C |
| ATOM | 5496 | CB | SER | C | 153 | −20.401 | −38.398 | −33.043 | 1.00 | 102.40 | MOL2 | C |
| ATOM | 5497 | OG | SER | C | 153 | −20.879 | −37.091 | −33.319 | 1.00 | 104.42 | MOL2 | O |
| ATOM | 5498 | C | SER | C | 153 | −18.011 | −38.290 | −33.891 | 1.00 | 98.07 | MOL2 | C |
| ATOM | 5499 | O | SER | C | 153 | −17.672 | −37.193 | −34.351 | 1.00 | 94.93 | MOL2 | O |
| ATOM | 5500 | N | GLU | C | 154 | −17.621 | −39.448 | −34.412 | 1.00 | 99.80 | MOL2 | N |
| ATOM | 5501 | CA | GLU | C | 154 | −16.760 | −39.555 | −35.586 | 1.00 | 101.67 | MOL2 | C |
| ATOM | 5502 | CB | GLU | C | 154 | −16.365 | −41.028 | −35.789 | 1.00 | 112.22 | MOL2 | C |
| ATOM | 5503 | CG | GLU | C | 154 | −17.573 | −41.987 | −35.942 | 1.00 | 122.85 | MOL2 | C |
| ATOM | 5504 | CD | GLU | C | 154 | −17.182 | −43.460 | −36.123 | 1.00 | 128.93 | MOL2 | C |
| ATOM | 5505 | OE1 | GLU | C | 154 | −18.094 | −44.311 | −36.263 | 1.00 | 128.05 | MOL2 | O |
| ATOM | 5506 | OE2 | GLU | C | 154 | −15.969 | −43.768 | −36.125 | 1.00 | 132.10 | MOL2 | O |
| ATOM | 5507 | C | GLU | C | 154 | −17.422 | −39.049 | −36.867 | 1.00 | 100.46 | MOL2 | C |
| ATOM | 5508 | O | GLU | C | 154 | −18.530 | −39.473 | −37.212 | 1.00 | 95.86 | MOL2 | O |
| ATOM | 5509 | N | ARG | C | 155 | −16.752 | −38.147 | −37.576 | 1.00 | 101.89 | MOL2 | N |
| ATOM | 5510 | CA | ARG | C | 155 | −17.303 | −37.664 | −38.834 | 1.00 | 104.81 | MOL2 | C |
| ATOM | 5511 | CB | ARG | C | 155 | −17.558 | −36.153 | −38.794 | 1.00 | 115.43 | MOL2 | C |
| ATOM | 5512 | CG | ARG | C | 155 | −18.542 | −35.687 | −39.879 | 1.00 | 124.32 | MOL2 | C |
| ATOM | 5513 | CD | ARG | C | 155 | −19.678 | −36.706 | −40.048 | 1.00 | 130.47 | MOL2 | C |
| ATOM | 5514 | NE | ARG | C | 155 | −20.698 | −36.285 | −41.007 | 1.00 | 133.53 | MOL2 | N |
| ATOM | 5515 | CZ | ARG | C | 155 | −21.548 | −37.114 | −41.609 | 1.00 | 135.26 | MOL2 | C |
| ATOM | 5516 | NH1 | ARG | C | 155 | −21.503 | −38.421 | −41.360 | 1.00 | 135.19 | MOL2 | N |
| ATOM | 5517 | NH2 | ARG | C | 155 | −22.452 | −36.636 | −42.454 | 1.00 | 132.94 | MOL2 | N |

TABLE 1-continued

The atomic coordinates of IL17F in complex with 496 Fab
(H32; a = 189.4; b = 189.4; c = 490.9, α, β = 90°; γ = 120°)

| ATOM | 5518 | C | ARG | C | 155 | −16.334 | −38.018 | −39.953 | 1.00 | 102.03 | MOL2 | C |
|---|---|---|---|---|---|---|---|---|---|---|---|---|
| ATOM | 5519 | O | ARG | C | 155 | −15.115 | −37.886 | −39.796 | 1.00 | 100.80 | MOL2 | O |
| ATOM | 5520 | N | GLN | C | 156 | −16.872 | −38.496 | −41.073 | 1.00 | 99.85 | MOL2 | N |
| ATOM | 5521 | CA | GLN | C | 156 | −16.021 | −38.870 | −42.194 | 1.00 | 102.60 | MOL2 | C |
| ATOM | 5522 | CB | GLN | C | 156 | −16.088 | −40.395 | −42.429 | 1.00 | 106.25 | MOL2 | C |
| ATOM | 5523 | CG | GLN | C | 156 | −17.039 | −40.858 | −43.537 | 1.00 | 113.94 | MOL2 | C |
| ATOM | 5524 | CD | GLN | C | 156 | −16.388 | −40.889 | −44.922 | 1.00 | 117.43 | MOL2 | C |
| ATOM | 5525 | OE1 | GLN | C | 156 | −17.072 | −41.043 | −45.941 | 1.00 | 117.35 | MOL2 | O |
| ATOM | 5526 | NE2 | GLN | C | 156 | −15.063 | −40.756 | −44.960 | 1.00 | 120.20 | MOL2 | N |
| ATOM | 5527 | C | GLN | C | 156 | −16.382 | −38.098 | −43.471 | 1.00 | 101.69 | MOL2 | C |
| ATOM | 5528 | O | GLN | C | 156 | −15.495 | −37.649 | −44.211 | 1.00 | 102.59 | MOL2 | O |
| ATOM | 5529 | N | ASN | C | 157 | −17.673 | −37.919 | −43.730 | 1.00 | 98.72 | MOL2 | N |
| ATOM | 5530 | CA | ASN | C | 157 | −18.057 | −37.207 | −44.936 | 1.00 | 98.32 | MOL2 | C |
| ATOM | 5531 | CB | ASN | C | 157 | −19.551 | −37.377 | −45.217 | 1.00 | 105.31 | MOL2 | C |
| ATOM | 5532 | CG | ASN | C | 157 | −19.926 | −38.823 | −45.526 | 1.00 | 113.27 | MOL2 | C |
| ATOM | 5533 | OD1 | ASN | C | 157 | −19.856 | −39.694 | −44.655 | 1.00 | 119.33 | MOL2 | O |
| ATOM | 5534 | ND2 | ASN | C | 157 | −20.320 | −39.085 | −46.771 | 1.00 | 116.14 | MOL2 | N |
| ATOM | 5535 | C | ASN | C | 157 | −17.679 | −35.737 | −44.852 | 1.00 | 96.79 | MOL2 | C |
| ATOM | 5536 | O | ASN | C | 157 | −17.705 | −35.126 | −43.775 | 1.00 | 93.05 | MOL2 | O |
| ATOM | 5537 | N | GLY | C | 158 | −17.300 | −35.184 | −46.001 | 1.00 | 95.37 | MOL2 | N |
| ATOM | 5538 | CA | GLY | C | 158 | −16.906 | −33.789 | −46.060 | 1.00 | 93.14 | MOL2 | C |
| ATOM | 5539 | C | GLY | C | 158 | −15.480 | −33.578 | −45.592 | 1.00 | 91.67 | MOL2 | C |
| ATOM | 5540 | O | GLY | C | 158 | −15.116 | −32.478 | −45.165 | 1.00 | 95.46 | MOL2 | O |
| ATOM | 5541 | N | VAL | C | 159 | −14.669 | −34.629 | −45.669 | 1.00 | 85.73 | MOL2 | N |
| ATOM | 5542 | CA | VAL | C | 159 | −13.281 | −34.540 | −45.245 | 1.00 | 82.29 | MOL2 | C |
| ATOM | 5543 | CB | VAL | C | 159 | −12.945 | −35.652 | −44.238 | 1.00 | 83.40 | MOL2 | C |
| ATOM | 5544 | CG1 | VAL | C | 159 | −11.493 | −35.546 | −43.819 | 1.00 | 88.32 | MOL2 | C |
| ATOM | 5545 | CG2 | VAL | C | 159 | −13.848 | −35.545 | −43.025 | 1.00 | 82.27 | MOL2 | C |
| ATOM | 5546 | C | VAL | C | 159 | −12.352 | −34.678 | −46.436 | 1.00 | 79.59 | MOL2 | C |
| ATOM | 5547 | O | VAL | C | 159 | −12.479 | −35.624 | −47.209 | 1.00 | 81.26 | MOL2 | O |
| ATOM | 5548 | N | LEU | C | 160 | −11.428 | −33.734 | −46.588 | 1.00 | 77.19 | MOL2 | N |
| ATOM | 5549 | CA | LEU | C | 160 | −10.471 | −33.789 | −47.688 | 1.00 | 78.45 | MOL2 | C |
| ATOM | 5550 | CB | LEU | C | 160 | −10.703 | −32.652 | −48.678 | 1.00 | 81.34 | MOL2 | C |
| ATOM | 5551 | CG | LEU | C | 160 | −11.919 | −32.873 | −49.574 | 1.00 | 85.85 | MOL2 | C |
| ATOM | 5552 | CD1 | LEU | C | 160 | −11.724 | −32.078 | −50.861 | 1.00 | 88.04 | MOL2 | C |
| ATOM | 5553 | CD2 | LEU | C | 160 | −12.084 | −34.361 | −49.888 | 1.00 | 80.45 | MOL2 | C |
| ATOM | 5554 | C | LEU | C | 160 | −9.037 | −33.752 | −47.190 | 1.00 | 79.38 | MOL2 | C |
| ATOM | 5555 | O | LEU | C | 160 | −8.625 | −32.838 | −46.459 | 1.00 | 79.90 | MOL2 | O |
| ATOM | 5556 | N | ASN | C | 161 | −8.266 | −34.748 | −47.606 | 1.00 | 75.54 | MOL2 | N |
| ATOM | 5557 | CA | ASN | C | 161 | −6.894 | −34.827 | −47.167 | 1.00 | 73.49 | MOL2 | C |
| ATOM | 5558 | CB | ASN | C | 161 | −6.724 | −36.137 | −46.418 | 1.00 | 77.61 | MOL2 | C |
| ATOM | 5559 | CG | ASN | C | 161 | −7.811 | −36.337 | −45.382 | 1.00 | 77.08 | MOL2 | C |
| ATOM | 5560 | OD1 | ASN | C | 161 | −8.011 | −35.489 | −44.510 | 1.00 | 74.15 | MOL2 | O |
| ATOM | 5561 | ND2 | ASN | C | 161 | −8.528 | −37.452 | −45.478 | 1.00 | 76.33 | MOL2 | N |
| ATOM | 5562 | C | ASN | C | 161 | −5.895 | −34.680 | −48.305 | 1.00 | 70.79 | MOL2 | C |
| ATOM | 5563 | O | ASN | C | 161 | −6.196 | −34.991 | −49.460 | 1.00 | 70.84 | MOL2 | O |
| ATOM | 5564 | N | SER | C | 162 | −4.714 | −34.179 | −47.960 | 1.00 | 66.45 | MOL2 | N |
| ATOM | 5565 | CA | SER | C | 162 | −3.646 | −33.957 | −48.917 | 1.00 | 69.71 | MOL2 | C |
| ATOM | 5566 | CB | SER | C | 162 | −3.715 | −32.526 | −49.440 | 1.00 | 74.54 | MOL2 | C |
| ATOM | 5567 | OG | SER | C | 162 | −2.530 | −32.176 | −50.132 | 1.00 | 82.17 | MOL2 | O |
| ATOM | 5568 | C | SER | C | 162 | −2.307 | −34.175 | −48.239 | 1.00 | 71.75 | MOL2 | C |
| ATOM | 5569 | O | SER | C | 162 | −2.013 | −33.536 | −47.228 | 1.00 | 75.21 | MOL2 | O |
| ATOM | 5570 | N | TRP | C | 163 | −1.489 | −35.060 | −48.801 | 1.00 | 70.73 | MOL2 | N |
| ATOM | 5571 | CA | TRP | C | 163 | −0.181 | −35.358 | −48.226 | 1.00 | 68.71 | MOL2 | C |
| ATOM | 5572 | CB | TRP | C | 163 | −0.054 | −36.864 | −48.056 | 1.00 | 74.55 | MOL2 | C |
| ATOM | 5573 | CG | TRP | C | 163 | −1.266 | −37.475 | −47.441 | 1.00 | 79.91 | MOL2 | C |
| ATOM | 5574 | CD2 | TRP | C | 163 | −2.469 | −37.843 | −48.118 | 1.00 | 81.33 | MOL2 | C |
| ATOM | 5575 | CE2 | TRP | C | 163 | −3.340 | −38.391 | −47.152 | 1.00 | 83.58 | MOL2 | C |
| ATOM | 5576 | CE3 | TRP | C | 163 | −2.896 | −37.765 | −49.447 | 1.00 | 86.25 | MOL2 | C |
| ATOM | 5577 | CD1 | TRP | C | 163 | −1.448 | −37.799 | −46.127 | 1.00 | 80.97 | MOL2 | C |
| ATOM | 5578 | NE1 | TRP | C | 163 | −2.690 | −38.353 | −45.946 | 1.00 | 80.59 | MOL2 | N |
| ATOM | 5579 | CZ2 | TRP | C | 163 | −4.615 | −38.862 | −47.472 | 1.00 | 87.30 | MOL2 | C |
| ATOM | 5580 | CZ3 | TRP | C | 163 | −4.167 | −38.236 | −49.768 | 1.00 | 92.21 | MOL2 | C |
| ATOM | 5581 | CH2 | TRP | C | 163 | −5.010 | −38.777 | −48.783 | 1.00 | 90.22 | MOL2 | C |
| ATOM | 5582 | C | TRP | C | 163 | 0.951 | −34.840 | −49.107 | 1.00 | 61.85 | MOL2 | C |
| ATOM | 5583 | O | TRP | C | 163 | 0.816 | −34.778 | −50.319 | 1.00 | 65.33 | MOL2 | O |
| ATOM | 5584 | N | THR | C | 164 | 2.070 | −34.470 | −48.506 | 1.00 | 55.65 | MOL2 | N |
| ATOM | 5585 | CA | THR | C | 164 | 3.194 | −33.992 | −49.292 | 1.00 | 56.35 | MOL2 | C |
| ATOM | 5586 | CB | THR | C | 164 | 3.838 | −32.807 | −48.622 | 1.00 | 53.31 | MOL2 | C |
| ATOM | 5587 | OG1 | THR | C | 164 | 4.522 | −33.230 | −47.432 | 1.00 | 41.23 | MOL2 | O |
| ATOM | 5588 | CG2 | THR | C | 164 | 2.774 | −31.816 | −48.260 | 1.00 | 56.03 | MOL2 | C |
| ATOM | 5589 | C | THR | C | 164 | 4.245 | −35.088 | −49.476 | 1.00 | 65.48 | MOL2 | C |
| ATOM | 5590 | O | THR | C | 164 | 4.087 | −36.206 | −48.977 | 1.00 | 69.34 | MOL2 | O |
| ATOM | 5591 | N | ASP | C | 165 | 5.319 | −34.779 | −50.193 | 1.00 | 69.90 | MOL2 | N |
| ATOM | 5592 | CA | ASP | C | 165 | 6.356 | −35.772 | −50.406 | 1.00 | 74.84 | MOL2 | C |
| ATOM | 5593 | CB | ASP | C | 165 | 6.834 | −35.720 | −51.848 | 1.00 | 89.04 | MOL2 | C |
| ATOM | 5594 | CG | ASP | C | 165 | 5.751 | −36.151 | −52.825 | 1.00 | 103.78 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 5595 | OD1 | ASP | C | 165 | 5.047 | −37.148 | −52.521 | 1.00 | 102.42 | MOL2 | O |
|---|---|---|---|---|---|---|---|---|---|---|---|---|
| ATOM | 5596 | OD2 | ASP | C | 165 | 5.609 | −35.502 | −53.892 | 1.00 | 113.76 | MOL2 | O |
| ATOM | 5597 | C | ASP | C | 165 | 7.514 | −35.596 | −49.444 | 1.00 | 71.07 | MOL2 | C |
| ATOM | 5598 | O | ASP | C | 165 | 7.635 | −34.570 | −48.790 | 1.00 | 69.30 | MOL2 | O |
| ATOM | 5599 | N | GLN | C | 166 | 8.352 | −36.617 | −49.340 | 1.00 | 67.93 | MOL2 | N |
| ATOM | 5600 | CA | GLN | C | 166 | 9.495 | −36.563 | −48.443 | 1.00 | 70.95 | MOL2 | C |
| ATOM | 5601 | CB | GLN | C | 166 | 10.494 | −37.653 | −48.845 | 1.00 | 75.14 | MOL2 | C |
| ATOM | 5602 | CG | GLN | C | 166 | 11.259 | −38.271 | −47.694 | 1.00 | 69.86 | MOL2 | C |
| ATOM | 5603 | CD | GLN | C | 166 | 11.247 | −39.774 | −47.778 | 1.00 | 73.46 | MOL2 | C |
| ATOM | 5604 | OE1 | GLN | C | 166 | 10.985 | −40.451 | −46.791 | 1.00 | 74.44 | MOL2 | O |
| ATOM | 5605 | NE2 | GLN | C | 166 | 11.523 | −40.311 | −48.966 | 1.00 | 71.21 | MOL2 | N |
| ATOM | 5606 | C | GLN | C | 166 | 10.177 | −35.183 | −48.472 | 1.00 | 69.79 | MOL2 | C |
| ATOM | 5607 | O | GLN | C | 166 | 10.872 | −34.842 | −49.426 | 1.00 | 73.54 | MOL2 | O |
| ATOM | 5608 | N | ASP | C | 167 | 9.980 | −34.395 | −47.423 | 1.00 | 65.97 | MOL2 | N |
| ATOM | 5609 | CA | ASP | C | 167 | 10.571 | −33.069 | −47.341 | 1.00 | 70.13 | MOL2 | C |
| ATOM | 5610 | CB | ASP | C | 167 | 10.181 | −32.413 | −46.005 | 1.00 | 77.64 | MOL2 | C |
| ATOM | 5611 | CG | ASP | C | 167 | 10.426 | −30.896 | −45.981 | 1.00 | 83.32 | MOL2 | C |
| ATOM | 5612 | OD1 | ASP | C | 167 | 9.714 | −30.161 | −46.709 | 1.00 | 84.29 | MOL2 | O |
| ATOM | 5613 | OD2 | ASP | C | 167 | 11.324 | −30.442 | −45.228 | 1.00 | 76.26 | MOL2 | O |
| ATOM | 5614 | C | ASP | C | 167 | 12.088 | −33.127 | −47.465 | 1.00 | 72.07 | MOL2 | C |
| ATOM | 5615 | O | ASP | C | 167 | 12.775 | −33.505 | −46.527 | 1.00 | 70.94 | MOL2 | O |
| ATOM | 5616 | N | SER | C | 168 | 12.592 | −32.741 | −48.631 | 1.00 | 79.29 | MOL2 | N |
| ATOM | 5617 | CA | SER | C | 168 | 14.025 | −32.704 | −48.936 | 1.00 | 88.10 | MOL2 | C |
| ATOM | 5618 | CB | SER | C | 168 | 14.262 | −31.612 | −49.976 | 1.00 | 93.34 | MOL2 | C |
| ATOM | 5619 | OG | SER | C | 168 | 13.535 | −30.441 | −49.622 | 1.00 | 98.24 | MOL2 | O |
| ATOM | 5620 | C | SER | C | 168 | 14.979 | −32.486 | −47.749 | 1.00 | 89.30 | MOL2 | C |
| ATOM | 5621 | O | SER | C | 168 | 16.055 | −33.097 | −47.683 | 1.00 | 91.01 | MOL2 | O |
| ATOM | 5622 | N | LYS | C | 169 | 14.587 | −31.611 | −46.825 | 1.00 | 88.09 | MOL2 | N |
| ATOM | 5623 | CA | LYS | C | 169 | 15.400 | −31.303 | −45.649 | 1.00 | 92.44 | MOL2 | C |
| ATOM | 5624 | CB | LYS | C | 169 | 14.773 | −30.140 | −44.879 | 1.00 | 100.12 | MOL2 | C |
| ATOM | 5625 | CG | LYS | C | 169 | 14.461 | −28.908 | −45.715 | 1.00 | 116.06 | MOL2 | C |
| ATOM | 5626 | CD | LYS | C | 169 | 13.644 | −27.890 | −44.907 | 1.00 | 126.27 | MOL2 | C |
| ATOM | 5627 | CE | LYS | C | 169 | 13.220 | −26.682 | −45.747 | 1.00 | 128.00 | MOL2 | C |
| ATOM | 5628 | NZ | LYS | C | 169 | 12.237 | −25.821 | −45.023 | 1.00 | 129.09 | MOL2 | N |
| ATOM | 5629 | C | LYS | C | 169 | 15.571 | −32.482 | −44.677 | 1.00 | 90.77 | MOL2 | C |
| ATOM | 5630 | O | LYS | C | 169 | 16.654 | −33.078 | −44.572 | 1.00 | 93.81 | MOL2 | O |
| ATOM | 5631 | N | ASP | C | 170 | 14.484 | −32.803 | −43.977 | 1.00 | 82.39 | MOL2 | N |
| ATOM | 5632 | CA | ASP | C | 170 | 14.441 | −33.866 | −42.969 | 1.00 | 71.05 | MOL2 | C |
| ATOM | 5633 | CB | ASP | C | 170 | 13.663 | −33.344 | −41.763 | 1.00 | 69.29 | MOL2 | C |
| ATOM | 5634 | CG | ASP | C | 170 | 12.240 | −32.947 | −42.127 | 1.00 | 68.19 | MOL2 | C |
| ATOM | 5635 | OD1 | ASP | C | 170 | 11.489 | −32.485 | −41.239 | 1.00 | 60.97 | MOL2 | O |
| ATOM | 5636 | OD2 | ASP | C | 170 | 11.873 | −33.106 | −43.313 | 1.00 | 63.76 | MOL2 | O |
| ATOM | 5637 | C | ASP | C | 170 | 13.815 | −35.200 | −43.429 | 1.00 | 65.02 | MOL2 | C |
| ATOM | 5638 | O | ASP | C | 170 | 13.528 | −36.080 | −42.619 | 1.00 | 60.81 | MOL2 | O |
| ATOM | 5639 | N | SER | C | 171 | 13.578 | −35.333 | −44.722 | 1.00 | 59.46 | MOL2 | N |
| ATOM | 5640 | CA | SER | C | 171 | 13.022 | −36.553 | −45.270 | 1.00 | 54.15 | MOL2 | C |
| ATOM | 5641 | CB | SER | C | 171 | 14.138 | −37.597 | −45.292 | 1.00 | 51.78 | MOL2 | C |
| ATOM | 5642 | OG | SER | C | 171 | 15.347 | −36.995 | −45.758 | 1.00 | 42.36 | MOL2 | O |
| ATOM | 5643 | C | SER | C | 171 | 11.754 | −37.064 | −44.563 | 1.00 | 51.92 | MOL2 | C |
| ATOM | 5644 | O | SER | C | 171 | 11.426 | −38.243 | −44.642 | 1.00 | 54.05 | MOL2 | O |
| ATOM | 5645 | N | THR | C | 172 | 11.031 | −36.157 | −43.901 | 1.00 | 51.32 | MOL2 | N |
| ATOM | 5646 | CA | THR | C | 172 | 9.772 | −36.480 | −43.197 | 1.00 | 54.67 | MOL2 | C |
| ATOM | 5647 | CB | THR | C | 172 | 9.515 | −35.542 | −42.014 | 1.00 | 59.05 | MOL2 | C |
| ATOM | 5648 | OG1 | THR | C | 172 | 9.148 | −34.247 | −42.520 | 1.00 | 59.61 | MOL2 | O |
| ATOM | 5649 | CG2 | THR | C | 172 | 10.749 | −35.422 | −41.132 | 1.00 | 62.03 | MOL2 | C |
| ATOM | 5650 | C | THR | C | 172 | 8.553 | −36.284 | −44.103 | 1.00 | 52.87 | MOL2 | C |
| ATOM | 5651 | O | THR | C | 172 | 8.685 | −35.951 | −45.270 | 1.00 | 63.57 | MOL2 | O |
| ATOM | 5652 | N | TYR | C | 173 | 7.358 | −36.465 | −43.557 | 1.00 | 48.76 | MOL2 | N |
| ATOM | 5653 | CA | TYR | C | 173 | 6.135 | −36.276 | −44.331 | 1.00 | 49.61 | MOL2 | C |
| ATOM | 5654 | CB | TYR | C | 173 | 5.379 | −37.598 | −44.470 | 1.00 | 47.69 | MOL2 | C |
| ATOM | 5655 | CG | TYR | C | 173 | 6.084 | −38.569 | −45.370 | 1.00 | 58.69 | MOL2 | C |
| ATOM | 5656 | CD1 | TYR | C | 173 | 7.430 | −38.840 | −45.194 | 1.00 | 65.87 | MOL2 | C |
| ATOM | 5657 | CE1 | TYR | C | 173 | 8.131 | −39.643 | −46.075 | 1.00 | 67.64 | MOL2 | C |
| ATOM | 5658 | CD2 | TYR | C | 173 | 5.444 | −39.145 | −46.450 | 1.00 | 64.37 | MOL2 | C |
| ATOM | 5659 | CE2 | TYR | C | 173 | 6.140 | −39.959 | −47.341 | 1.00 | 69.47 | MOL2 | C |
| ATOM | 5660 | CZ | TYR | C | 173 | 7.488 | −40.194 | −47.145 | 1.00 | 67.62 | MOL2 | C |
| ATOM | 5661 | OH | TYR | C | 173 | 8.222 | −40.938 | −48.034 | 1.00 | 72.08 | MOL2 | O |
| ATOM | 5662 | C | TYR | C | 173 | 5.251 | −35.249 | −43.636 | 1.00 | 54.70 | MOL2 | C |
| ATOM | 5663 | O | TYR | C | 173 | 5.546 | −34.820 | −42.520 | 1.00 | 58.65 | MOL2 | O |
| ATOM | 5664 | N | SER | C | 174 | 4.175 | −34.841 | −44.301 | 1.00 | 55.44 | MOL2 | N |
| ATOM | 5665 | CA | SER | C | 174 | 3.233 | −33.882 | −43.725 | 1.00 | 51.27 | MOL2 | C |
| ATOM | 5666 | CB | SER | C | 174 | 3.734 | −32.449 | −43.893 | 1.00 | 51.27 | MOL2 | C |
| ATOM | 5667 | OG | SER | C | 174 | 4.931 | −32.233 | −43.160 | 1.00 | 52.62 | MOL2 | O |
| ATOM | 5668 | C | SER | C | 174 | 1.885 | −34.051 | −44.395 | 1.00 | 50.66 | MOL2 | C |
| ATOM | 5669 | O | SER | C | 174 | 1.804 | −34.427 | −45.569 | 1.00 | 49.82 | MOL2 | O |
| ATOM | 5670 | N | MET | C | 175 | 0.825 | −33.791 | −43.643 | 1.00 | 53.28 | MOL2 | N |
| ATOM | 5671 | CA | MET | C | 175 | −0.531 | −33.941 | −44.169 | 1.00 | 61.42 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 5672 | CB | MET | C | 175 | −1.126 | −35.277 | −43.738 | 1.00 | 56.48 | MOL2 | C |
|---|---|---|---|---|---|---|---|---|---|---|---|---|
| ATOM | 5673 | CG | MET | C | 175 | −2.586 | −35.392 | −44.081 | 1.00 | 50.77 | MOL2 | C |
| ATOM | 5674 | SD | MET | C | 175 | −3.360 | −36.575 | −43.020 | 1.00 | 66.93 | MOL2 | S |
| ATOM | 5675 | CE | MET | C | 175 | −4.501 | −37.411 | −44.143 | 1.00 | 53.52 | MOL2 | C |
| ATOM | 5676 | C | MET | C | 175 | −1.470 | −32.833 | −43.708 | 1.00 | 64.71 | MOL2 | C |
| ATOM | 5677 | O | MET | C | 175 | −1.327 | −32.312 | −42.599 | 1.00 | 69.75 | MOL2 | O |
| ATOM | 5678 | N | SER | C | 176 | −2.442 | −32.491 | −44.549 | 1.00 | 62.56 | MOL2 | N |
| ATOM | 5679 | CA | SER | C | 176 | −3.388 | −31.440 | −44.203 | 1.00 | 68.23 | MOL2 | C |
| ATOM | 5680 | CB | SER | C | 176 | −3.102 | −30.187 | −45.050 | 1.00 | 72.17 | MOL2 | C |
| ATOM | 5681 | OG | SER | C | 176 | −3.896 | −29.081 | −44.649 | 1.00 | 75.40 | MOL2 | O |
| ATOM | 5682 | C | SER | C | 176 | −4.847 | −31.879 | −44.375 | 1.00 | 70.83 | MOL2 | C |
| ATOM | 5683 | O | SER | C | 176 | −5.383 | −31.908 | −45.492 | 1.00 | 72.93 | MOL2 | O |
| ATOM | 5684 | N | SER | C | 177 | −5.490 | −32.223 | −43.262 | 1.00 | 71.42 | MOL2 | N |
| ATOM | 5685 | CA | SER | C | 177 | −6.890 | −32.635 | −43.312 | 1.00 | 70.80 | MOL2 | C |
| ATOM | 5686 | CB | SER | C | 177 | −7.183 | −33.735 | −42.296 | 1.00 | 66.64 | MOL2 | C |
| ATOM | 5687 | OG | SER | C | 177 | −8.517 | −34.185 | −42.443 | 1.00 | 57.08 | MOL2 | O |
| ATOM | 5688 | C | SER | C | 177 | −7.799 | −31.438 | −43.037 | 1.00 | 73.96 | MOL2 | C |
| ATOM | 5689 | O | SER | C | 177 | −7.594 | −30.681 | −42.081 | 1.00 | 70.44 | MOL2 | O |
| ATOM | 5690 | N | THR | C | 178 | −8.805 | −31.267 | −43.888 | 1.00 | 79.89 | MOL2 | N |
| ATOM | 5691 | CA | THR | C | 178 | −9.736 | −30.153 | −43.736 | 1.00 | 83.31 | MOL2 | C |
| ATOM | 5692 | CB | THR | C | 178 | −9.576 | −29.107 | −44.884 | 1.00 | 89.72 | MOL2 | C |
| ATOM | 5693 | OG1 | THR | C | 178 | −8.203 | −28.704 | −44.989 | 1.00 | 98.13 | MOL2 | O |
| ATOM | 5694 | CG2 | THR | C | 178 | −10.426 | −27.878 | −44.606 | 1.00 | 86.77 | MOL2 | C |
| ATOM | 5695 | C | THR | C | 178 | −11.193 | −30.620 | −43.694 | 1.00 | 81.67 | MOL2 | C |
| ATOM | 5696 | O | THR | C | 178 | −11.696 | −31.244 | −44.642 | 1.00 | 75.38 | MOL2 | O |
| ATOM | 5697 | N | LEU | C | 179 | −11.861 | −30.327 | −42.578 | 1.00 | 82.75 | MOL2 | N |
| ATOM | 5698 | CA | LEU | C | 179 | −13.267 | −30.688 | −42.426 | 1.00 | 83.11 | MOL2 | C |
| ATOM | 5699 | CB | LEU | C | 179 | −13.638 | −30.983 | −40.974 | 1.00 | 79.30 | MOL2 | C |
| ATOM | 5700 | CG | LEU | C | 179 | −14.785 | −32.000 | −40.909 | 1.00 | 73.97 | MOL2 | C |
| ATOM | 5701 | CD1 | LEU | C | 179 | −15.327 | −32.017 | −39.512 | 1.00 | 73.79 | MOL2 | C |
| ATOM | 5702 | CD2 | LEU | C | 179 | −15.884 | −31.665 | −41.912 | 1.00 | 61.79 | MOL2 | C |
| ATOM | 5703 | C | LEU | C | 179 | −14.095 | −29.511 | −42.904 | 1.00 | 84.35 | MOL2 | C |
| ATOM | 5704 | O | LEU | C | 179 | −14.118 | −28.453 | −42.267 | 1.00 | 81.74 | MOL2 | O |
| ATOM | 5705 | N | THR | C | 180 | −14.773 | −29.707 | −44.028 | 1.00 | 83.44 | MOL2 | N |
| ATOM | 5706 | CA | THR | C | 180 | −15.598 | −28.673 | −44.613 | 1.00 | 85.77 | MOL2 | C |
| ATOM | 5707 | CB | THR | C | 180 | −15.359 | −28.592 | −46.158 | 1.00 | 88.62 | MOL2 | C |
| ATOM | 5708 | OG1 | THR | C | 180 | −16.342 | −27.747 | −46.763 | 1.00 | 86.12 | MOL2 | O |
| ATOM | 5709 | CG2 | THR | C | 180 | −15.426 | −29.975 | −46.799 | 1.00 | 92.07 | MOL2 | C |
| ATOM | 5710 | C | THR | C | 180 | −17.069 | −28.931 | −44.315 | 1.00 | 89.54 | MOL2 | C |
| ATOM | 5711 | O | THR | C | 180 | −17.636 | −29.952 | −44.713 | 1.00 | 87.13 | MOL2 | O |
| ATOM | 5712 | N | LEU | C | 181 | −17.675 | −28.001 | −43.586 | 1.00 | 95.28 | MOL2 | N |
| ATOM | 5713 | CA | LEU | C | 181 | −19.087 | −28.100 | −43.247 | 1.00 | 100.55 | MOL2 | C |
| ATOM | 5714 | CB | LEU | C | 181 | −19.253 | −28.373 | −41.744 | 1.00 | 101.03 | MOL2 | C |
| ATOM | 5715 | CG | LEU | C | 181 | −18.023 | −28.175 | −40.848 | 1.00 | 101.25 | MOL2 | C |
| ATOM | 5716 | CD1 | LEU | C | 181 | −17.724 | −26.683 | −40.687 | 1.00 | 98.19 | MOL2 | C |
| ATOM | 5717 | CD2 | LEU | C | 181 | −18.277 | −28.825 | −39.491 | 1.00 | 97.16 | MOL2 | C |
| ATOM | 5718 | C | LEU | C | 181 | −19.816 | −26.819 | −43.671 | 1.00 | 104.10 | MOL2 | C |
| ATOM | 5719 | O | LEU | C | 181 | −19.203 | −25.888 | −44.214 | 1.00 | 102.19 | MOL2 | O |
| ATOM | 5720 | N | THR | C | 182 | −21.129 | −26.786 | −43.463 | 1.00 | 108.71 | MOL2 | N |
| ATOM | 5721 | CA | THR | C | 182 | −21.913 | −25.604 | −43.813 | 1.00 | 111.41 | MOL2 | C |
| ATOM | 5722 | CB | THR | C | 182 | −23.308 | −25.961 | −44.372 | 1.00 | 113.22 | MOL2 | C |
| ATOM | 5723 | OG1 | THR | C | 182 | −24.150 | −26.433 | −43.309 | 1.00 | 114.49 | MOL2 | O |
| ATOM | 5724 | CG2 | THR | C | 182 | −23.183 | −27.028 | −45.453 | 1.00 | 111.82 | MOL2 | C |
| ATOM | 5725 | C | THR | C | 182 | −22.103 | −24.784 | −42.546 | 1.00 | 112.00 | MOL2 | C |
| ATOM | 5726 | O | THR | C | 182 | −22.343 | −25.336 | −41.471 | 1.00 | 111.30 | MOL2 | O |
| ATOM | 5727 | N | LYS | C | 183 | −21.985 | −23.469 | −42.672 | 1.00 | 113.84 | MOL2 | N |
| ATOM | 5728 | CA | LYS | C | 183 | −22.141 | −22.578 | −41.528 | 1.00 | 116.17 | MOL2 | C |
| ATOM | 5729 | CB | LYS | C | 183 | −22.474 | −21.164 | −42.017 | 1.00 | 122.32 | MOL2 | C |
| ATOM | 5730 | CG | LYS | C | 183 | −22.940 | −20.217 | −40.928 | 1.00 | 127.78 | MOL2 | C |
| ATOM | 5731 | CD | LYS | C | 183 | −22.291 | −18.853 | −41.076 | 1.00 | 133.45 | MOL2 | C |
| ATOM | 5732 | CE | LYS | C | 183 | −20.832 | −18.885 | −40.633 | 1.00 | 134.43 | MOL2 | C |
| ATOM | 5733 | NZ | LYS | C | 183 | −19.983 | −19.798 | −41.448 | 1.00 | 135.94 | MOL2 | N |
| ATOM | 5734 | C | LYS | C | 183 | −23.223 | −23.058 | −40.560 | 1.00 | 114.83 | MOL2 | C |
| ATOM | 5735 | O | LYS | C | 183 | −23.110 | −22.879 | −39.343 | 1.00 | 114.09 | MOL2 | O |
| ATOM | 5736 | N | ASP | C | 184 | −24.266 | −23.673 | −41.110 | 1.00 | 112.78 | MOL2 | N |
| ATOM | 5737 | CA | ASP | C | 184 | −25.374 | −24.171 | −40.302 | 1.00 | 111.31 | MOL2 | C |
| ATOM | 5738 | CB | ASP | C | 184 | −26.502 | −24.691 | −41.212 | 1.00 | 122.40 | MOL2 | C |
| ATOM | 5739 | CG | ASP | C | 184 | −26.976 | −23.645 | −42.228 | 1.00 | 129.47 | MOL2 | C |
| ATOM | 5740 | OD1 | ASP | C | 184 | −27.293 | −22.503 | −41.819 | 1.00 | 130.84 | MOL2 | O |
| ATOM | 5741 | OD2 | ASP | C | 184 | −27.038 | −23.972 | −43.437 | 1.00 | 131.20 | MOL2 | O |
| ATOM | 5742 | C | ASP | C | 184 | −24.913 | −25.278 | −39.357 | 1.00 | 105.04 | MOL2 | C |
| ATOM | 5743 | O | ASP | C | 184 | −24.942 | −25.108 | −38.133 | 1.00 | 99.16 | MOL2 | O |
| ATOM | 5744 | N | GLU | C | 185 | −24.494 | −26.402 | −39.942 | 1.00 | 100.32 | MOL2 | N |
| ATOM | 5745 | CA | GLU | C | 185 | −24.010 | −27.568 | −39.197 | 1.00 | 97.52 | MOL2 | C |
| ATOM | 5746 | CB | GLU | C | 185 | −23.495 | −28.630 | −40.172 | 1.00 | 103.77 | MOL2 | C |
| ATOM | 5747 | CG | GLU | C | 185 | −24.525 | −29.640 | −40.672 | 1.00 | 114.29 | MOL2 | C |
| ATOM | 5748 | CD | GLU | C | 185 | −24.581 | −30.906 | −39.817 | 1.00 | 120.06 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 5749 | OE1 | GLU | C | 185 | −25.092 | −31.938 | −40.314 | 1.00 | 119.67 | MOL2 | O |
|---|---|---|---|---|---|---|---|---|---|---|---|---|
| ATOM | 5750 | OE2 | GLU | C | 185 | −24.122 | −30.871 | −38.651 | 1.00 | 121.57 | MOL2 | O |
| ATOM | 5751 | C | GLU | C | 185 | −22.890 | −27.214 | −38.215 | 1.00 | 93.65 | MOL2 | C |
| ATOM | 5752 | O | GLU | C | 185 | −22.768 | −27.818 | −37.143 | 1.00 | 89.39 | MOL2 | O |
| ATOM | 5753 | N | TYR | C | 186 | −22.061 | −26.243 | −38.585 | 1.00 | 91.15 | MOL2 | N |
| ATOM | 5754 | CA | TYR | C | 186 | −20.969 | −25.846 | −37.712 | 1.00 | 90.99 | MOL2 | C |
| ATOM | 5755 | CB | TYR | C | 186 | −20.048 | −24.823 | −38.383 | 1.00 | 93.51 | MOL2 | C |
| ATOM | 5756 | CG | TYR | C | 186 | −19.012 | −24.246 | −37.436 | 1.00 | 93.52 | MOL2 | C |
| ATOM | 5757 | CD1 | TYR | C | 186 | −19.361 | −23.297 | −36.486 | 1.00 | 97.80 | MOL2 | C |
| ATOM | 5758 | CE1 | TYR | C | 186 | −18.435 | −22.797 | −35.590 | 1.00 | 98.27 | MOL2 | C |
| ATOM | 5759 | CD2 | TYR | C | 186 | −17.698 | −24.677 | −37.463 | 1.00 | 94.43 | MOL2 | C |
| ATOM | 5760 | CE2 | TYR | C | 186 | −16.765 | −24.179 | −36.568 | 1.00 | 96.25 | MOL2 | C |
| ATOM | 5761 | CZ | TYR | C | 186 | −17.142 | −23.240 | −35.637 | 1.00 | 94.84 | MOL2 | C |
| ATOM | 5762 | OH | TYR | C | 186 | −16.227 | −22.728 | −34.755 | 1.00 | 96.28 | MOL2 | O |
| ATOM | 5763 | C | TYR | C | 186 | −21.510 | −25.261 | −36.424 | 1.00 | 93.77 | MOL2 | C |
| ATOM | 5764 | O | TYR | C | 186 | −20.935 | −25.479 | −35.358 | 1.00 | 96.72 | MOL2 | O |
| ATOM | 5765 | N | GLU | C | 187 | −22.612 | −24.518 | −36.525 | 1.00 | 95.78 | MOL2 | N |
| ATOM | 5766 | CA | GLU | C | 187 | −23.236 | −23.877 | −35.364 | 1.00 | 97.26 | MOL2 | C |
| ATOM | 5767 | CB | GLU | C | 187 | −24.255 | −22.825 | −35.831 | 1.00 | 104.73 | MOL2 | C |
| ATOM | 5768 | CG | GLU | C | 187 | −23.687 | −21.655 | −36.637 | 1.00 | 111.79 | MOL2 | C |
| ATOM | 5769 | CD | GLU | C | 187 | −22.778 | −20.739 | −35.820 | 1.00 | 118.04 | MOL2 | C |
| ATOM | 5770 | OE1 | GLU | C | 187 | −22.470 | −19.630 | −36.312 | 1.00 | 117.06 | MOL2 | O |
| ATOM | 5771 | OE2 | GLU | C | 187 | −22.365 | −21.120 | −34.699 | 1.00 | 121.68 | MOL2 | O |
| ATOM | 5772 | C | GLU | C | 187 | −23.935 | −24.864 | −34.424 | 1.00 | 95.32 | MOL2 | C |
| ATOM | 5773 | O | GLU | C | 187 | −23.872 | −24.713 | −33.198 | 1.00 | 85.41 | MOL2 | O |
| ATOM | 5774 | N | ARG | C | 188 | −24.597 | −25.864 | −35.016 | 1.00 | 97.41 | MOL2 | N |
| ATOM | 5775 | CA | ARG | C | 188 | −25.340 | −26.887 | −34.277 | 1.00 | 98.56 | MOL2 | C |
| ATOM | 5776 | CB | ARG | C | 188 | −25.955 | −27.891 | −35.255 | 1.00 | 97.07 | MOL2 | C |
| ATOM | 5777 | CG | ARG | C | 188 | −26.790 | −27.227 | −36.328 | 1.00 | 104.21 | MOL2 | C |
| ATOM | 5778 | CD | ARG | C | 188 | −27.252 | −28.208 | −37.392 | 1.00 | 112.70 | MOL2 | C |
| ATOM | 5779 | NE | ARG | C | 188 | −27.661 | −27.498 | −38.604 | 1.00 | 122.18 | MOL2 | N |
| ATOM | 5780 | CZ | ARG | C | 188 | −27.990 | −28.087 | −39.751 | 1.00 | 124.20 | MOL2 | C |
| ATOM | 5781 | NH1 | ARG | C | 188 | −27.962 | −29.409 | −39.848 | 1.00 | 126.54 | MOL2 | N |
| ATOM | 5782 | NH2 | ARG | C | 188 | −28.329 | −27.352 | −40.807 | 1.00 | 121.65 | MOL2 | N |
| ATOM | 5783 | C | ARG | C | 188 | −24.512 | −27.634 | −33.229 | 1.00 | 100.68 | MOL2 | C |
| ATOM | 5784 | O | ARG | C | 188 | −25.077 | −28.256 | −32.324 | 1.00 | 101.42 | MOL2 | O |
| ATOM | 5785 | N | HIS | C | 189 | −23.185 | −27.571 | −33.343 | 1.00 | 100.30 | MOL2 | N |
| ATOM | 5786 | CA | HIS | C | 189 | −22.310 | −28.256 | −32.390 | 1.00 | 97.49 | MOL2 | C |
| ATOM | 5787 | CB | HIS | C | 189 | −21.672 | −29.472 | −33.055 | 1.00 | 101.41 | MOL2 | C |
| ATOM | 5788 | CG | HIS | C | 189 | −22.663 | −30.382 | −33.710 | 1.00 | 105.48 | MOL2 | C |
| ATOM | 5789 | CD2 | HIS | C | 189 | −23.194 | −31.561 | −33.308 | 1.00 | 106.26 | MOL2 | C |
| ATOM | 5790 | ND1 | HIS | C | 189 | −23.243 | −30.096 | −34.929 | 1.00 | 108.49 | MOL2 | N |
| ATOM | 5791 | CE1 | HIS | C | 189 | −24.086 | −31.061 | −35.251 | 1.00 | 109.87 | MOL2 | C |
| ATOM | 5792 | NE2 | HIS | C | 189 | −24.075 | −31.962 | −34.285 | 1.00 | 111.52 | MOL2 | N |
| ATOM | 5793 | C | HIS | C | 189 | −21.234 | −27.343 | −31.802 | 1.00 | 96.73 | MOL2 | C |
| ATOM | 5794 | O | HIS | C | 189 | −20.976 | −26.254 | −32.321 | 1.00 | 94.15 | MOL2 | O |
| ATOM | 5795 | N | ASN | C | 190 | −20.593 | −27.793 | −30.727 | 1.00 | 99.11 | MOL2 | N |
| ATOM | 5796 | CA | ASN | C | 190 | −19.589 | −26.967 | −30.058 | 1.00 | 106.33 | MOL2 | C |
| ATOM | 5797 | CB | ASN | C | 190 | −20.060 | −26.674 | −28.619 | 1.00 | 118.99 | MOL2 | C |
| ATOM | 5798 | CG | ASN | C | 190 | −19.356 | −25.466 | −27.991 | 1.00 | 128.44 | MOL2 | C |
| ATOM | 5799 | OD1 | ASN | C | 190 | −18.126 | −25.435 | −27.877 | 1.00 | 132.56 | MOL2 | O |
| ATOM | 5800 | ND2 | ASN | C | 190 | −20.142 | −24.470 | −27.573 | 1.00 | 130.77 | MOL2 | N |
| ATOM | 5801 | C | ASN | C | 190 | −18.143 | −27.488 | −30.031 | 1.00 | 104.71 | MOL2 | C |
| ATOM | 5802 | O | ASN | C | 190 | −17.205 | −26.711 | −30.257 | 1.00 | 102.41 | MOL2 | O |
| ATOM | 5803 | N | SER | C | 191 | −17.948 | −28.779 | −29.747 | 1.00 | 102.86 | MOL2 | N |
| ATOM | 5804 | CA | SER | C | 191 | −16.588 | −29.330 | −29.688 | 1.00 | 98.88 | MOL2 | C |
| ATOM | 5805 | CB | SER | C | 191 | −16.441 | −30.332 | −28.521 | 1.00 | 100.66 | MOL2 | C |
| ATOM | 5806 | OG | SER | C | 191 | −17.297 | −31.457 | −28.638 | 1.00 | 102.00 | MOL2 | O |
| ATOM | 5807 | C | SER | C | 191 | −16.111 | −29.967 | −30.993 | 1.00 | 96.99 | MOL2 | C |
| ATOM | 5808 | O | SER | C | 191 | −16.820 | −30.764 | −31.620 | 1.00 | 92.58 | MOL2 | O |
| ATOM | 5809 | N | TYR | C | 192 | −14.898 | −29.588 | −31.394 | 1.00 | 96.21 | MOL2 | N |
| ATOM | 5810 | CA | TYR | C | 192 | −14.286 | −30.090 | −32.621 | 1.00 | 94.20 | MOL2 | C |
| ATOM | 5811 | CB | TYR | C | 192 | −14.210 | −28.977 | −33.670 | 1.00 | 98.25 | MOL2 | C |
| ATOM | 5812 | CG | TYR | C | 192 | −15.552 | −28.622 | −34.269 | 1.00 | 102.09 | MOL2 | C |
| ATOM | 5813 | CD1 | TYR | C | 192 | −15.948 | −27.297 | −34.397 | 1.00 | 101.80 | MOL2 | C |
| ATOM | 5814 | CE1 | TYR | C | 192 | −17.182 | −26.971 | −34.932 | 1.00 | 105.33 | MOL2 | C |
| ATOM | 5815 | CD2 | TYR | C | 192 | −16.431 | −29.619 | −34.698 | 1.00 | 100.60 | MOL2 | C |
| ATOM | 5816 | CE2 | TYR | C | 192 | −17.665 | −29.300 | −35.237 | 1.00 | 101.03 | MOL2 | C |
| ATOM | 5817 | CZ | TYR | C | 192 | −18.037 | −27.975 | −35.352 | 1.00 | 104.61 | MOL2 | C |
| ATOM | 5818 | OH | TYR | C | 192 | −19.262 | −27.644 | −35.894 | 1.00 | 103.77 | MOL2 | O |
| ATOM | 5819 | C | TYR | C | 192 | −12.898 | −30.635 | −32.334 | 1.00 | 92.21 | MOL2 | C |
| ATOM | 5820 | O | TYR | C | 192 | −12.010 | −29.911 | −31.862 | 1.00 | 91.97 | MOL2 | O |
| ATOM | 5821 | N | THR | C | 193 | −12.714 | −31.916 | −32.633 | 1.00 | 87.96 | MOL2 | N |
| ATOM | 5822 | CA | THR | C | 193 | −11.443 | −32.574 | −32.386 | 1.00 | 86.37 | MOL2 | C |
| ATOM | 5823 | CB | THR | C | 193 | −11.602 | −33.679 | −31.349 | 1.00 | 89.98 | MOL2 | C |
| ATOM | 5824 | OG1 | THR | C | 193 | −12.186 | −34.830 | −31.977 | 1.00 | 90.57 | MOL2 | O |
| ATOM | 5825 | CG2 | THR | C | 193 | −12.516 | −33.220 | −30.222 | 1.00 | 95.21 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 5826 | C | THR | C | 193 | −10.875 | −33.237 | −33.628 | 1.00 | 85.96 | MOL2 | C |
|---|---|---|---|---|---|---|---|---|---|---|---|---|
| ATOM | 5827 | O | THR | C | 193 | −11.608 | −33.720 | −34.496 | 1.00 | 80.74 | MOL2 | O |
| ATOM | 5828 | N | CYS | C | 194 | −9.552 | −33.281 | −33.680 | 1.00 | 88.35 | MOL2 | N |
| ATOM | 5829 | CA | CYS | C | 194 | −8.835 | −33.903 | −34.778 | 1.00 | 86.66 | MOL2 | C |
| ATOM | 5830 | C | CYS | C | 194 | −7.866 | −34.866 | −34.096 | 1.00 | 85.37 | MOL2 | C |
| ATOM | 5831 | O | CYS | C | 194 | −6.920 | −34.446 | −33.421 | 1.00 | 84.98 | MOL2 | O |
| ATOM | 5832 | CB | CYS | C | 194 | −8.123 | −32.815 | −35.571 | 1.00 | 89.98 | MOL2 | C |
| ATOM | 5833 | SG | CYS | C | 194 | −6.893 | −33.362 | −36.776 | 1.00 | 89.61 | MOL2 | S |
| ATOM | 5834 | N | GLU | C | 195 | −8.138 | −36.161 | −34.230 | 1.00 | 84.20 | MOL2 | N |
| ATOM | 5835 | CA | GLU | C | 195 | −7.300 | −37.172 | −33.590 | 1.00 | 84.87 | MOL2 | C |
| ATOM | 5836 | CB | GLU | C | 195 | −8.159 | −38.157 | −32.783 | 1.00 | 94.33 | MOL2 | C |
| ATOM | 5837 | CG | GLU | C | 195 | −9.060 | −37.488 | −31.737 | 1.00 | 104.52 | MOL2 | C |
| ATOM | 5838 | CD | GLU | C | 195 | −9.777 | −38.477 | −30.816 | 1.00 | 110.31 | MOL2 | C |
| ATOM | 5839 | OE1 | GLU | C | 195 | −10.283 | −39.511 | −31.312 | 1.00 | 115.56 | MOL2 | O |
| ATOM | 5840 | OE2 | GLU | C | 195 | −9.848 | −38.209 | −29.594 | 1.00 | 111.25 | MOL2 | O |
| ATOM | 5841 | C | GLU | C | 195 | −6.425 | −37.930 | −34.576 | 1.00 | 82.75 | MOL2 | C |
| ATOM | 5842 | O | GLU | C | 195 | −6.911 | −38.637 | −35.471 | 1.00 | 77.51 | MOL2 | O |
| ATOM | 5843 | N | ALA | C | 196 | −5.117 | −37.782 | −34.397 | 1.00 | 81.78 | MOL2 | N |
| ATOM | 5844 | CA | ALA | C | 196 | −4.157 | −38.437 | −35.278 | 1.00 | 78.73 | MOL2 | C |
| ATOM | 5845 | CB | ALA | C | 196 | −3.095 | −37.436 | −35.740 | 1.00 | 79.10 | MOL2 | C |
| ATOM | 5846 | C | ALA | C | 196 | −3.488 | −39.645 | −34.634 | 1.00 | 76.27 | MOL2 | C |
| ATOM | 5847 | O | ALA | C | 196 | −2.815 | −39.527 | −33.599 | 1.00 | 78.76 | MOL2 | O |
| ATOM | 5848 | N | THR | C | 197 | −3.687 | −40.806 | −35.258 | 1.00 | 69.31 | MOL2 | N |
| ATOM | 5849 | CA | THR | C | 197 | −3.105 | −42.066 | −34.793 | 1.00 | 65.11 | MOL2 | C |
| ATOM | 5850 | CB | THR | C | 197 | −4.145 | −43.221 | −34.890 | 1.00 | 64.89 | MOL2 | C |
| ATOM | 5851 | OG1 | THR | C | 197 | −4.013 | −44.073 | −33.746 | 1.00 | 72.06 | MOL2 | O |
| ATOM | 5852 | CG2 | THR | C | 197 | −3.940 | −44.053 | −36.150 | 1.00 | 56.49 | MOL2 | C |
| ATOM | 5853 | C | THR | C | 197 | −1.853 | −42.402 | −35.634 | 1.00 | 64.02 | MOL2 | C |
| ATOM | 5854 | O | THR | C | 197 | −1.904 | −42.476 | −36.866 | 1.00 | 54.75 | MOL2 | O |
| ATOM | 5855 | N | HIS | C | 198 | −0.729 | −42.616 | −34.955 | 1.00 | 66.83 | MOL2 | N |
| ATOM | 5856 | CA | HIS | C | 198 | 0.538 | −42.882 | −35.633 | 1.00 | 64.57 | MOL2 | C |
| ATOM | 5857 | CB | HIS | C | 198 | 1.261 | −41.535 | −35.811 | 1.00 | 62.18 | MOL2 | C |
| ATOM | 5858 | CG | HIS | C | 198 | 2.485 | −41.593 | −36.668 | 1.00 | 63.38 | MOL2 | C |
| ATOM | 5859 | CD2 | HIS | C | 198 | 3.764 | −41.223 | −36.417 | 1.00 | 60.84 | MOL2 | C |
| ATOM | 5860 | ND1 | HIS | C | 198 | 2.460 | −42.024 | −37.978 | 1.00 | 62.33 | MOL2 | N |
| ATOM | 5861 | CE1 | HIS | C | 198 | 3.671 | −41.916 | −38.495 | 1.00 | 63.38 | MOL2 | C |
| ATOM | 5862 | NE2 | HIS | C | 198 | 4.480 | −41.432 | −37.570 | 1.00 | 60.65 | MOL2 | N |
| ATOM | 5863 | C | HIS | C | 198 | 1.449 | −43.895 | −34.909 | 1.00 | 63.67 | MOL2 | C |
| ATOM | 5864 | O | HIS | C | 198 | 1.548 | −43.913 | −33.682 | 1.00 | 70.98 | MOL2 | O |
| ATOM | 5865 | N | LYS | C | 199 | 2.110 | −44.729 | −35.699 | 1.00 | 61.78 | MOL2 | N |
| ATOM | 5866 | CA | LYS | C | 199 | 3.030 | −45.756 | −35.219 | 1.00 | 56.62 | MOL2 | C |
| ATOM | 5867 | CB | LYS | C | 199 | 3.878 | −46.232 | −36.402 | 1.00 | 61.39 | MOL2 | C |
| ATOM | 5868 | CG | LYS | C | 199 | 5.123 | −47.018 | −36.059 | 1.00 | 58.85 | MOL2 | C |
| ATOM | 5869 | CD | LYS | C | 199 | 5.719 | −47.591 | −37.335 | 1.00 | 58.87 | MOL2 | C |
| ATOM | 5870 | CE | LYS | C | 199 | 7.112 | −48.137 | −37.114 | 1.00 | 61.59 | MOL2 | C |
| ATOM | 5871 | NZ | LYS | C | 199 | 7.774 | −48.382 | −38.423 | 1.00 | 69.57 | MOL2 | N |
| ATOM | 5872 | C | LYS | C | 199 | 3.925 | −45.310 | −34.068 | 1.00 | 53.02 | MOL2 | C |
| ATOM | 5873 | O | LYS | C | 199 | 4.378 | −46.128 | −33.270 | 1.00 | 55.72 | MOL2 | O |
| ATOM | 5874 | N | THR | C | 200 | 4.173 | −44.012 | −33.980 | 1.00 | 47.42 | MOL2 | N |
| ATOM | 5875 | CA | THR | C | 200 | 5.010 | −43.455 | −32.925 | 1.00 | 55.51 | MOL2 | C |
| ATOM | 5876 | CB | THR | C | 200 | 5.255 | −41.963 | −33.182 | 1.00 | 57.59 | MOL2 | C |
| ATOM | 5877 | OG1 | THR | C | 200 | 4.061 | −41.375 | −33.715 | 1.00 | 62.14 | MOL2 | O |
| ATOM | 5878 | CG2 | THR | C | 200 | 6.391 | −41.767 | −34.147 | 1.00 | 57.64 | MOL2 | C |
| ATOM | 5879 | C | THR | C | 200 | 4.451 | −43.598 | −31.496 | 1.00 | 58.33 | MOL2 | C |
| ATOM | 5880 | O | THR | C | 200 | 5.201 | −43.513 | −30.513 | 1.00 | 56.11 | MOL2 | O |
| ATOM | 5881 | N | SER | C | 201 | 3.142 | −43.789 | −31.376 | 1.00 | 58.57 | MOL2 | N |
| ATOM | 5882 | CA | SER | C | 201 | 2.535 | −43.917 | −30.062 | 1.00 | 65.13 | MOL2 | C |
| ATOM | 5883 | CB | SER | C | 201 | 2.133 | −42.551 | −29.498 | 1.00 | 75.06 | MOL2 | C |
| ATOM | 5884 | OG | SER | C | 201 | 1.660 | −42.651 | −28.155 | 1.00 | 76.72 | MOL2 | O |
| ATOM | 5885 | C | SER | C | 201 | 1.316 | −44.797 | −30.084 | 1.00 | 68.79 | MOL2 | C |
| ATOM | 5886 | O | SER | C | 201 | 0.698 | −45.002 | −31.124 | 1.00 | 71.76 | MOL2 | O |
| ATOM | 5887 | N | THR | C | 202 | 0.981 | −45.301 | −28.902 | 1.00 | 71.34 | MOL2 | N |
| ATOM | 5888 | CA | THR | C | 202 | −0.160 | −46.179 | −28.683 | 1.00 | 66.29 | MOL2 | C |
| ATOM | 5889 | CB | THR | C | 202 | 0.122 | −47.043 | −27.496 | 1.00 | 61.94 | MOL2 | C |
| ATOM | 5890 | OG1 | THR | C | 202 | 0.569 | −46.207 | −26.414 | 1.00 | 61.91 | MOL2 | O |
| ATOM | 5891 | CG2 | THR | C | 202 | 1.203 | −48.029 | −27.834 | 1.00 | 62.11 | MOL2 | C |
| ATOM | 5892 | C | THR | C | 202 | −1.391 | −45.338 | −28.380 | 1.00 | 71.53 | MOL2 | C |
| ATOM | 5893 | O | THR | C | 202 | −2.532 | −45.799 | −28.497 | 1.00 | 68.75 | MOL2 | O |
| ATOM | 5894 | N | SER | C | 203 | −1.132 | −44.095 | −27.985 | 1.00 | 74.60 | MOL2 | N |
| ATOM | 5895 | CA | SER | C | 203 | −2.175 | −43.149 | −27.637 | 1.00 | 75.06 | MOL2 | C |
| ATOM | 5896 | CB | SER | C | 203 | −1.944 | −42.627 | −26.207 | 1.00 | 78.78 | MOL2 | C |
| ATOM | 5897 | OG | SER | C | 203 | −0.582 | −42.302 | −25.977 | 1.00 | 74.75 | MOL2 | O |
| ATOM | 5898 | C | SER | C | 203 | −2.184 | −41.999 | −28.628 | 1.00 | 73.19 | MOL2 | C |
| ATOM | 5899 | O | SER | C | 203 | −1.217 | −41.237 | −28.701 | 1.00 | 72.48 | MOL2 | O |
| ATOM | 5900 | N | PRO | C | 204 | −3.283 | −41.869 | −29.405 | 1.00 | 74.35 | MOL2 | N |
| ATOM | 5901 | CD | PRO | C | 204 | −4.374 | −42.866 | −29.369 | 1.00 | 74.62 | MOL2 | C |
| ATOM | 5902 | CA | PRO | C | 204 | −3.554 | −40.854 | −30.436 | 1.00 | 70.15 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 5903 | CB  | PRO | C | 204 | -5.025  | -41.084 | -30.763 | 1.00 | 67.10  | MOL2 | C |
|------|------|-----|-----|---|-----|---------|---------|---------|------|--------|------|---|
| ATOM | 5904 | CG  | PRO | C | 204 | -5.146  | -42.573 | -30.652 | 1.00 | 69.63  | MOL2 | C |
| ATOM | 5905 | C   | PRO | C | 204 | -3.308  | -39.427 | -29.989 | 1.00 | 69.69  | MOL2 | C |
| ATOM | 5906 | O   | PRO | C | 204 | -3.640  | -39.063 | -28.858 | 1.00 | 72.58  | MOL2 | O |
| ATOM | 5907 | N   | ILE | C | 205 | -2.713  | -38.628 | -30.874 | 1.00 | 70.09  | MOL2 | N |
| ATOM | 5908 | CA  | ILE | C | 205 | -2.458  | -37.225 | -30.570 | 1.00 | 71.17  | MOL2 | C |
| ATOM | 5909 | CB  | ILE | C | 205 | -1.315  | -36.633 | -31.448 | 1.00 | 67.23  | MOL2 | C |
| ATOM | 5910 | CG2 | ILE | C | 205 | -1.212  | -35.133 | -31.230 | 1.00 | 64.64  | MOL2 | C |
| ATOM | 5911 | CG1 | ILE | C | 205 | 0.022   | -37.289 | -31.075 | 1.00 | 71.12  | MOL2 | C |
| ATOM | 5912 | CD1 | ILE | C | 205 | 1.259   | -36.419 | -31.340 | 1.00 | 70.56  | MOL2 | C |
| ATOM | 5913 | C   | ILE | C | 205 | -3.782  | -36.535 | -30.873 | 1.00 | 73.78  | MOL2 | C |
| ATOM | 5914 | O   | ILE | C | 205 | -4.331  | -36.671 | -31.977 | 1.00 | 67.96  | MOL2 | O |
| ATOM | 5915 | N   | VAL | C | 206 | -4.317  | -35.829 | -29.879 | 1.00 | 76.89  | MOL2 | N |
| ATOM | 5916 | CA  | VAL | C | 206 | -5.593  | -35.160 | -30.060 | 1.00 | 81.99  | MOL2 | C |
| ATOM | 5917 | CB  | VAL | C | 206 | -6.659  | -35.771 | -29.128 | 1.00 | 76.92  | MOL2 | C |
| ATOM | 5918 | CG1 | VAL | C | 206 | -8.023  | -35.259 | -29.506 | 1.00 | 83.47  | MOL2 | C |
| ATOM | 5919 | CG2 | VAL | C | 206 | -6.638  | -37.266 | -29.228 | 1.00 | 74.77  | MOL2 | C |
| ATOM | 5920 | C   | VAL | C | 206 | -5.521  | -33.652 | -29.817 | 1.00 | 87.24  | MOL2 | C |
| ATOM | 5921 | O   | VAL | C | 206 | -4.991  | -33.194 | -28.790 | 1.00 | 88.17  | MOL2 | O |
| ATOM | 5922 | N   | LYS | C | 207 | -6.041  | -32.888 | -30.777 | 1.00 | 86.74  | MOL2 | N |
| ATOM | 5923 | CA  | LYS | C | 207 | -6.074  | -31.437 | -30.668 | 1.00 | 89.73  | MOL2 | C |
| ATOM | 5924 | CB  | LYS | C | 207 | -5.084  | -30.790 | -31.640 | 1.00 | 92.01  | MOL2 | C |
| ATOM | 5925 | CG  | LYS | C | 207 | -3.610  | -31.037 | -31.305 | 1.00 | 90.07  | MOL2 | C |
| ATOM | 5926 | CD  | LYS | C | 207 | -3.231  | -30.490 | -29.936 | 1.00 | 94.48  | MOL2 | C |
| ATOM | 5927 | CE  | LYS | C | 207 | -1.722  | -30.567 | -29.694 | 1.00 | 97.81  | MOL2 | C |
| ATOM | 5928 | NZ  | LYS | C | 207 | -1.303  | -30.034 | -28.355 | 1.00 | 99.93  | MOL2 | N |
| ATOM | 5929 | C   | LYS | C | 207 | -7.502  | -31.021 | -30.990 | 1.00 | 93.06  | MOL2 | C |
| ATOM | 5930 | O   | LYS | C | 207 | -8.111  | -31.550 | -31.929 | 1.00 | 90.15  | MOL2 | O |
| ATOM | 5931 | N   | SER | C | 208 | -8.042  | -30.098 | -30.191 | 1.00 | 95.64  | MOL2 | N |
| ATOM | 5932 | CA  | SER | C | 208 | -9.418  | -29.633 | -30.376 | 1.00 | 96.16  | MOL2 | C |
| ATOM | 5933 | CB  | SER | C | 208 | -10.400 | -30.478 | -29.550 | 1.00 | 92.40  | MOL2 | C |
| ATOM | 5934 | OG  | SER | C | 208 | -10.301 | -31.851 | -29.858 | 1.00 | 86.23  | MOL2 | O |
| ATOM | 5935 | C   | SER | C | 208 | -9.592  | -28.186 | -29.964 | 1.00 | 98.80  | MOL2 | C |
| ATOM | 5936 | O   | SER | C | 208 | -8.657  | -27.538 | -29.490 | 1.00 | 96.21  | MOL2 | O |
| ATOM | 5937 | N   | PHE | C | 209 | -10.818 | -27.703 | -30.126 | 1.00 | 104.94 | MOL2 | N |
| ATOM | 5938 | CA  | PHE | C | 209 | -11.165 | -26.331 | -29.788 | 1.00 | 112.91 | MOL2 | C |
| ATOM | 5939 | CB  | PHE | C | 209 | -10.646 | -25.379 | -30.867 | 1.00 | 119.37 | MOL2 | C |
| ATOM | 5940 | CG  | PHE | C | 209 | -11.603 | -25.205 | -32.013 | 1.00 | 125.03 | MOL2 | C |
| ATOM | 5941 | CD1 | PHE | C | 209 | -12.188 | -23.975 | -32.261 | 1.00 | 127.55 | MOL2 | C |
| ATOM | 5942 | CD2 | PHE | C | 209 | -11.974 | -26.289 | -32.796 | 1.00 | 127.39 | MOL2 | C |
| ATOM | 5943 | CE1 | PHE | C | 209 | -13.128 | -23.832 | -33.264 | 1.00 | 132.81 | MOL2 | C |
| ATOM | 5944 | CE2 | PHE | C | 209 | -12.913 | -26.151 | -33.798 | 1.00 | 131.06 | MOL2 | C |
| ATOM | 5945 | CZ  | PHE | C | 209 | -13.492 | -24.924 | -34.033 | 1.00 | 134.21 | MOL2 | C |
| ATOM | 5946 | C   | PHE | C | 209 | -12.692 | -26.208 | -29.732 | 1.00 | 116.65 | MOL2 | C |
| ATOM | 5947 | O   | PHE | C | 209 | -13.413 | -26.882 | -30.486 | 1.00 | 114.04 | MOL2 | O |
| ATOM | 5948 | N   | ASN | C | 210 | -13.179 | -25.343 | -28.843 | 1.00 | 119.28 | MOL2 | N |
| ATOM | 5949 | CA  | ASN | C | 210 | -14.613 | -25.107 | -28.715 | 1.00 | 122.10 | MOL2 | C |
| ATOM | 5950 | CB  | ASN | C | 210 | -15.063 | -25.285 | -27.266 | 1.00 | 122.85 | MOL2 | C |
| ATOM | 5951 | CG  | ASN | C | 210 | -15.326 | -26.733 | -26.920 | 1.00 | 124.32 | MOL2 | C |
| ATOM | 5952 | OD1 | ASN | C | 210 | -16.123 | -27.399 | -27.580 | 1.00 | 120.86 | MOL2 | O |
| ATOM | 5953 | ND2 | ASN | C | 210 | -14.659 | -27.229 | -25.884 | 1.00 | 126.41 | MOL2 | N |
| ATOM | 5954 | C   | ASN | C | 210 | -14.945 | -23.697 | -29.188 | 1.00 | 125.34 | MOL2 | C |
| ATOM | 5955 | O   | ASN | C | 210 | -14.053 | -22.852 | -29.316 | 1.00 | 124.68 | MOL2 | O |
| ATOM | 5956 | N   | ARG | C | 211 | -16.228 | -23.448 | -29.445 | 1.00 | 130.51 | MOL2 | N |
| ATOM | 5957 | CA  | ARG | C | 211 | -16.687 | -22.137 | -29.905 | 1.00 | 135.75 | MOL2 | C |
| ATOM | 5958 | CB  | ARG | C | 211 | -18.032 | -22.273 | -30.626 | 1.00 | 135.55 | MOL2 | C |
| ATOM | 5959 | CG  | ARG | C | 211 | -18.058 | -23.334 | -31.715 | 1.00 | 138.83 | MOL2 | C |
| ATOM | 5960 | CD  | ARG | C | 211 | -19.445 | -23.492 | -32.338 | 1.00 | 143.96 | MOL2 | C |
| ATOM | 5961 | NE  | ARG | C | 211 | -20.477 | -23.824 | -31.355 | 1.00 | 150.84 | MOL2 | N |
| ATOM | 5962 | CZ  | ARG | C | 211 | -21.122 | -22.932 | -30.603 | 1.00 | 156.30 | MOL2 | C |
| ATOM | 5963 | NH1 | ARG | C | 211 | -20.850 | -21.638 | -30.717 | 1.00 | 159.23 | MOL2 | N |
| ATOM | 5964 | NH2 | ARG | C | 211 | -22.037 | -23.334 | -29.727 | 1.00 | 157.52 | MOL2 | N |
| ATOM | 5965 | C   | ARG | C | 211 | -16.825 | -21.130 | -28.756 | 1.00 | 141.28 | MOL2 | C |
| ATOM | 5966 | O   | ARG | C | 211 | -17.563 | -21.351 | -27.787 | 1.00 | 138.31 | MOL2 | O |
| ATOM | 5967 | N   | ASN | C | 212 | -16.102 | -20.022 | -28.893 | 1.00 | 149.64 | MOL2 | N |
| ATOM | 5968 | CA  | ASN | C | 212 | -16.077 | -18.930 | -27.925 | 1.00 | 157.26 | MOL2 | C |
| ATOM | 5969 | CB  | ASN | C | 212 | -14.645 | -18.774 | -27.385 | 1.00 | 158.65 | MOL2 | C |
| ATOM | 5970 | CG  | ASN | C | 212 | -13.580 | -18.869 | -28.491 | 1.00 | 160.07 | MOL2 | C |
| ATOM | 5971 | OD1 | ASN | C | 212 | -13.470 | -17.989 | -29.352 | 1.00 | 159.67 | MOL2 | O |
| ATOM | 5972 | ND2 | ASN | C | 212 | -12.799 | -19.947 | -28.468 | 1.00 | 157.43 | MOL2 | N |
| ATOM | 5973 | C   | ASN | C | 212 | -16.525 | -17.643 | -28.633 | 1.00 | 162.36 | MOL2 | C |
| ATOM | 5974 | O   | ASN | C | 212 | -17.142 | -16.760 | -28.027 | 1.00 | 162.64 | MOL2 | O |
| ATOM | 5975 | N   | GLU | C | 213 | -16.193 | -17.561 | -29.923 | 1.00 | 168.08 | MOL2 | N |
| ATOM | 5976 | CA  | GLU | C | 213 | -16.534 | -16.432 | -30.794 | 1.00 | 172.24 | MOL2 | C |
| ATOM | 5977 | CB  | GLU | C | 213 | -18.060 | -16.334 | -30.957 | 1.00 | 174.81 | MOL2 | C |
| ATOM | 5978 | CG  | GLU | C | 213 | -18.588 | -16.676 | -32.363 | 1.00 | 178.79 | MOL2 | C |
| ATOM | 5979 | CD  | GLU | C | 213 | -18.485 | -18.160 | -32.725 | 1.00 | 180.90 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 5980 | OE1 | GLU | C | 213 | −19.059 | −18.999 | −31.995 | 1.00 | 182.92 | MOL2 | O |
|---|---|---|---|---|---|---|---|---|---|---|---|---|
| ATOM | 5981 | OE2 | GLU | C | 213 | −17.840 | −18.486 | −33.748 | 1.00 | 179.09 | MOL2 | O |
| ATOM | 5982 | C | GLU | C | 213 | −15.981 | −15.067 | −30.379 | 1.00 | 173.25 | MOL2 | C |
| ATOM | 5983 | O | GLU | C | 213 | −16.527 | −14.402 | −29.499 | 1.00 | 173.91 | MOL2 | O |
| ATOM | 5984 | N | CYS | C | 214 | −14.900 | −14.653 | −31.034 | 1.00 | 174.34 | MOL2 | N |
| ATOM | 5985 | CA | CYS | C | 214 | −14.271 | −13.364 | −30.765 | 1.00 | 176.87 | MOL2 | C |
| ATOM | 5986 | CB | CYS | C | 214 | −13.684 | −13.328 | −29.352 | 1.00 | 177.45 | MOL2 | C |
| ATOM | 5987 | SG | CYS | C | 214 | −14.578 | −12.272 | −28.158 | 1.00 | 178.63 | MOL2 | S |
| ATOM | 5988 | C | CYS | C | 214 | −13.166 | −13.089 | −31.782 | 1.00 | 177.57 | MOL2 | C |
| ATOM | 5989 | O | CYS | C | 214 | −12.996 | −13.915 | −32.703 | 1.00 | 177.03 | MOL2 | O |
| ATOM | 5990 | OXT | CYS | C | 214 | −12.485 | −12.051 | −31.648 | 1.00 | 178.26 | MOL2 | O |
| ATOM | 5991 | CB | GLU | D | 1 | 22.314 | −35.760 | −79.347 | 1.00 | 84.87 | MOL2 | C |
| ATOM | 5992 | CG | GLU | D | 1 | 22.427 | −36.327 | −80.787 | 1.00 | 101.66 | MOL2 | C |
| ATOM | 5993 | CD | GLU | D | 1 | 23.307 | −35.500 | −81.745 | 1.00 | 109.46 | MOL2 | C |
| ATOM | 5994 | OE1 | GLU | D | 1 | 23.251 | −35.754 | −82.981 | 1.00 | 102.99 | MOL2 | O |
| ATOM | 5995 | OE2 | GLU | D | 1 | 24.058 | −34.614 | −81.266 | 1.00 | 111.21 | MOL2 | O |
| ATOM | 5996 | C | GLU | D | 1 | 19.956 | −35.196 | −79.880 | 1.00 | 69.87 | MOL2 | C |
| ATOM | 5997 | O | GLU | D | 1 | 19.881 | −35.083 | −81.098 | 1.00 | 75.70 | MOL2 | O |
| ATOM | 5998 | N | GLU | D | 1 | 20.944 | −34.490 | −77.692 | 1.00 | 75.00 | MOL2 | N |
| ATOM | 5999 | CA | GLU | D | 1 | 21.198 | −34.723 | −79.145 | 1.00 | 73.87 | MOL2 | C |
| ATOM | 6000 | N | VAL | D | 2 | 18.974 | −35.724 | −79.162 | 1.00 | 63.06 | MOL2 | N |
| ATOM | 6001 | CA | VAL | D | 2 | 17.762 | −36.194 | −79.827 | 1.00 | 55.58 | MOL2 | C |
| ATOM | 6002 | CB | VAL | D | 2 | 17.566 | −37.689 | −79.628 | 1.00 | 47.21 | MOL2 | C |
| ATOM | 6003 | CG1 | VAL | D | 2 | 16.454 | −38.199 | −80.509 | 1.00 | 20.53 | MOL2 | C |
| ATOM | 6004 | CG2 | VAL | D | 2 | 18.854 | −38.402 | −79.914 | 1.00 | 52.31 | MOL2 | C |
| ATOM | 6005 | C | VAL | D | 2 | 16.514 | −35.503 | −79.331 | 1.00 | 60.47 | MOL2 | C |
| ATOM | 6006 | O | VAL | D | 2 | 15.623 | −36.155 | −78.805 | 1.00 | 66.99 | MOL2 | O |
| ATOM | 6007 | N | GLN | D | 3 | 16.439 | −34.192 | −79.527 | 1.00 | 62.47 | MOL2 | N |
| ATOM | 6008 | CA | GLN | D | 3 | 15.305 | −33.390 | −79.078 | 1.00 | 60.74 | MOL2 | C |
| ATOM | 6009 | CB | GLN | D | 3 | 15.532 | −31.937 | −79.505 | 1.00 | 68.39 | MOL2 | C |
| ATOM | 6010 | CG | GLN | D | 3 | 16.934 | −31.419 | −79.214 | 1.00 | 90.44 | MOL2 | C |
| ATOM | 6011 | CD | GLN | D | 3 | 17.198 | −30.040 | −79.819 | 1.00 | 104.39 | MOL2 | C |
| ATOM | 6012 | OE1 | GLN | D | 3 | 18.353 | −29.614 | −79.949 | 1.00 | 112.27 | MOL2 | O |
| ATOM | 6013 | NE2 | GLN | D | 3 | 16.126 | −29.334 | −80.186 | 1.00 | 106.58 | MOL2 | N |
| ATOM | 6014 | C | GLN | D | 3 | 13.911 | −33.840 | −79.546 | 1.00 | 52.32 | MOL2 | C |
| ATOM | 6015 | O | GLN | D | 3 | 13.716 | −34.239 | −80.690 | 1.00 | 46.30 | MOL2 | O |
| ATOM | 6016 | N | LEU | D | 4 | 12.951 | −33.776 | −78.630 | 1.00 | 47.94 | MOL2 | N |
| ATOM | 6017 | CA | LEU | D | 4 | 11.550 | −34.087 | −78.905 | 1.00 | 45.55 | MOL2 | C |
| ATOM | 6018 | CB | LEU | D | 4 | 11.184 | −35.486 | −78.423 | 1.00 | 36.42 | MOL2 | C |
| ATOM | 6019 | CG | LEU | D | 4 | 11.126 | −36.543 | −79.515 | 1.00 | 40.93 | MOL2 | C |
| ATOM | 6020 | CD1 | LEU | D | 4 | 12.450 | −36.560 | −80.210 | 1.00 | 48.51 | MOL2 | C |
| ATOM | 6021 | CD2 | LEU | D | 4 | 10.802 | −37.918 | −78.947 | 1.00 | 37.15 | MOL2 | C |
| ATOM | 6022 | C | LEU | D | 4 | 10.784 | −33.048 | −78.095 | 1.00 | 51.22 | MOL2 | C |
| ATOM | 6023 | O | LEU | D | 4 | 11.038 | −32.902 | −76.885 | 1.00 | 57.44 | MOL2 | O |
| ATOM | 6024 | N | VAL | D | 5 | 9.893 | −32.291 | −78.742 | 1.00 | 48.35 | MOL2 | N |
| ATOM | 6025 | CA | VAL | D | 5 | 9.128 | −31.282 | −78.008 | 1.00 | 48.38 | MOL2 | C |
| ATOM | 6026 | CB | VAL | D | 5 | 9.726 | −29.864 | −78.176 | 1.00 | 39.25 | MOL2 | C |
| ATOM | 6027 | CG1 | VAL | D | 5 | 11.212 | −29.956 | −78.478 | 1.00 | 29.62 | MOL2 | C |
| ATOM | 6028 | CG2 | VAL | D | 5 | 8.995 | −29.114 | −79.250 | 1.00 | 51.89 | MOL2 | C |
| ATOM | 6029 | C | VAL | D | 5 | 7.652 | −31.267 | −78.381 | 1.00 | 52.00 | MOL2 | C |
| ATOM | 6030 | O | VAL | D | 5 | 7.280 | −31.145 | −79.555 | 1.00 | 54.17 | MOL2 | O |
| ATOM | 6031 | N | GLU | D | 6 | 6.812 | −31.418 | −77.363 | 1.00 | 56.64 | MOL2 | N |
| ATOM | 6032 | CA | GLU | D | 6 | 5.379 | −31.428 | −77.570 | 1.00 | 62.34 | MOL2 | C |
| ATOM | 6033 | CB | GLU | D | 6 | 4.720 | −32.458 | −76.657 | 1.00 | 65.34 | MOL2 | C |
| ATOM | 6034 | CG | GLU | D | 6 | 5.275 | −33.857 | −76.832 | 1.00 | 74.88 | MOL2 | C |
| ATOM | 6035 | CD | GLU | D | 6 | 6.236 | −34.247 | −75.728 | 1.00 | 79.38 | MOL2 | C |
| ATOM | 6036 | OE1 | GLU | D | 6 | 7.023 | −33.380 | −75.290 | 1.00 | 75.80 | MOL2 | O |
| ATOM | 6037 | OE2 | GLU | D | 6 | 6.203 | −35.426 | −75.307 | 1.00 | 82.65 | MOL2 | O |
| ATOM | 6038 | C | GLU | D | 6 | 4.803 | −30.044 | −77.319 | 1.00 | 66.15 | MOL2 | C |
| ATOM | 6039 | O | GLU | D | 6 | 5.439 | −29.187 | −76.681 | 1.00 | 61.42 | MOL2 | O |
| ATOM | 6040 | N | SER | D | 7 | 3.602 | −29.826 | −77.844 | 1.00 | 69.22 | MOL2 | N |
| ATOM | 6041 | CA | SER | D | 7 | 2.930 | −28.549 | −77.691 | 1.00 | 70.93 | MOL2 | C |
| ATOM | 6042 | CB | SER | D | 7 | 3.601 | −27.486 | −78.574 | 1.00 | 74.24 | MOL2 | C |
| ATOM | 6043 | OG | SER | D | 7 | 4.164 | −28.060 | −79.748 | 1.00 | 77.33 | MOL2 | O |
| ATOM | 6044 | C | SER | D | 7 | 1.463 | −28.680 | −78.031 | 1.00 | 70.64 | MOL2 | C |
| ATOM | 6045 | O | SER | D | 7 | 1.029 | −29.683 | −78.622 | 1.00 | 63.72 | MOL2 | O |
| ATOM | 6046 | N | GLY | D | 8 | 0.702 | −27.665 | −77.634 | 1.00 | 73.56 | MOL2 | N |
| ATOM | 6047 | CA | GLY | D | 8 | −0.722 | −27.665 | −77.901 | 1.00 | 81.67 | MOL2 | C |
| ATOM | 6048 | C | GLY | D | 8 | −1.499 | −28.062 | −76.673 | 1.00 | 83.23 | MOL2 | C |
| ATOM | 6049 | O | GLY | D | 8 | −2.624 | −28.547 | −76.769 | 1.00 | 83.26 | MOL2 | O |
| ATOM | 6050 | N | GLY | D | 9 | −0.890 | −27.852 | −75.513 | 1.00 | 88.14 | MOL2 | N |
| ATOM | 6051 | CA | GLY | D | 9 | −1.547 | −28.206 | −74.269 | 1.00 | 94.12 | MOL2 | C |
| ATOM | 6052 | C | GLY | D | 9 | −2.523 | −27.148 | −73.805 | 1.00 | 94.96 | MOL2 | C |
| ATOM | 6053 | O | GLY | D | 9 | −2.441 | −25.995 | −74.236 | 1.00 | 96.58 | MOL2 | O |
| ATOM | 6054 | N | GLY | D | 10 | −3.443 | −27.544 | −72.926 | 1.00 | 95.77 | MOL2 | N |
| ATOM | 6055 | CA | GLY | D | 10 | −4.438 | −26.621 | −72.407 | 1.00 | 93.74 | MOL2 | C |
| ATOM | 6056 | C | GLY | D | 10 | −5.672 | −27.331 | −71.882 | 1.00 | 90.23 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 6057 | O | GLY | D | 10 | −5.716 | −28.563 | −71.821 | 1.00 | 87.47 | MOL2 | O |
|---|---|---|---|---|---|---|---|---|---|---|---|---|
| ATOM | 6058 | N | LEU | D | 11 | −6.681 | −26.549 | −71.513 | 1.00 | 87.23 | MOL2 | N |
| ATOM | 6059 | CA | LEU | D | 11 | −7.929 | −27.083 | −70.975 | 1.00 | 85.72 | MOL2 | C |
| ATOM | 6060 | CB | LEU | D | 11 | −8.429 | −26.209 | −69.828 | 1.00 | 86.17 | MOL2 | C |
| ATOM | 6061 | CG | LEU | D | 11 | −7.397 | −25.409 | −69.026 | 1.00 | 92.46 | MOL2 | C |
| ATOM | 6062 | CD1 | LEU | D | 11 | −6.610 | −24.445 | −69.933 | 1.00 | 92.06 | MOL2 | C |
| ATOM | 6063 | CD2 | LEU | D | 11 | −8.134 | −24.642 | −67.938 | 1.00 | 92.18 | MOL2 | C |
| ATOM | 6064 | C | LEU | D | 11 | −8.973 | −27.054 | −72.057 | 1.00 | 81.57 | MOL2 | C |
| ATOM | 6065 | O | LEU | D | 11 | −8.858 | −26.296 | −73.007 | 1.00 | 81.09 | MOL2 | O |
| ATOM | 6066 | N | VAL | D | 12 | −10.007 | −27.860 | −71.911 | 1.00 | 81.34 | MOL2 | N |
| ATOM | 6067 | CA | VAL | D | 12 | −11.050 | −27.851 | −72.911 | 1.00 | 90.17 | MOL2 | C |
| ATOM | 6068 | CB | VAL | D | 12 | −10.484 | −28.360 | −74.253 | 1.00 | 85.76 | MOL2 | C |
| ATOM | 6069 | CG1 | VAL | D | 12 | −9.519 | −29.480 | −73.995 | 1.00 | 88.33 | MOL2 | C |
| ATOM | 6070 | CG2 | VAL | D | 12 | −11.607 | −28.814 | −75.170 | 1.00 | 93.86 | MOL2 | C |
| ATOM | 6071 | C | VAL | D | 12 | −12.283 | −28.644 | −72.464 | 1.00 | 96.91 | MOL2 | C |
| ATOM | 6072 | O | VAL | D | 12 | −12.196 | −29.827 | −72.130 | 1.00 | 100.56 | MOL2 | O |
| ATOM | 6073 | N | GLN | D | 13 | −13.428 | −27.961 | −72.442 | 1.00 | 100.84 | MOL2 | N |
| ATOM | 6074 | CA | GLN | D | 13 | −14.702 | −28.555 | −72.036 | 1.00 | 99.10 | MOL2 | C |
| ATOM | 6075 | CB | GLN | D | 13 | −15.880 | −27.642 | −72.450 | 1.00 | 105.56 | MOL2 | C |
| ATOM | 6076 | CG | GLN | D | 13 | −15.513 | −26.216 | −72.931 | 1.00 | 107.21 | MOL2 | C |
| ATOM | 6077 | CD | GLN | D | 13 | −15.442 | −25.179 | −71.807 | 1.00 | 109.35 | MOL2 | C |
| ATOM | 6078 | OE1 | GLN | D | 13 | −16.437 | −24.911 | −71.125 | 1.00 | 104.19 | MOL2 | O |
| ATOM | 6079 | NE2 | GLN | D | 13 | −14.263 | −24.587 | −71.619 | 1.00 | 106.68 | MOL2 | N |
| ATOM | 6080 | C | GLN | D | 13 | −14.898 | −29.935 | −72.665 | 1.00 | 93.48 | MOL2 | C |
| ATOM | 6081 | O | GLN | D | 13 | −14.483 | −30.186 | −73.802 | 1.00 | 85.32 | MOL2 | O |
| ATOM | 6082 | N | PRO | D | 14 | −15.529 | −30.853 | −71.922 | 1.00 | 92.73 | MOL2 | N |
| ATOM | 6083 | CD | PRO | D | 14 | −15.928 | −30.745 | −70.506 | 1.00 | 91.49 | MOL2 | C |
| ATOM | 6084 | CA | PRO | D | 14 | −15.766 | −32.200 | −72.448 | 1.00 | 93.50 | MOL2 | C |
| ATOM | 6085 | CB | PRO | D | 14 | −16.742 | −32.789 | −71.442 | 1.00 | 93.16 | MOL2 | C |
| ATOM | 6086 | CG | PRO | D | 14 | −16.228 | −32.190 | −70.136 | 1.00 | 96.15 | MOL2 | C |
| ATOM | 6087 | C | PRO | D | 14 | −16.328 | −32.121 | −73.861 | 1.00 | 95.56 | MOL2 | C |
| ATOM | 6088 | O | PRO | D | 14 | −16.834 | −31.077 | −74.278 | 1.00 | 95.24 | MOL2 | O |
| ATOM | 6089 | N | GLY | D | 15 | −16.226 | −33.218 | −74.602 | 1.00 | 99.20 | MOL2 | N |
| ATOM | 6090 | CA | GLY | D | 15 | −16.714 | −33.222 | −75.969 | 1.00 | 100.83 | MOL2 | C |
| ATOM | 6091 | C | GLY | D | 15 | −15.810 | −32.426 | −76.900 | 1.00 | 101.96 | MOL2 | C |
| ATOM | 6092 | O | GLY | D | 15 | −15.628 | −32.814 | −78.058 | 1.00 | 105.17 | MOL2 | O |
| ATOM | 6093 | N | GLY | D | 16 | −15.244 | −31.322 | −76.399 | 1.00 | 97.91 | MOL2 | N |
| ATOM | 6094 | CA | GLY | D | 16 | −14.362 | −30.485 | −77.200 | 1.00 | 92.60 | MOL2 | C |
| ATOM | 6095 | C | GLY | D | 16 | −13.253 | −31.244 | −77.912 | 1.00 | 93.12 | MOL2 | C |
| ATOM | 6096 | O | GLY | D | 16 | −13.158 | −32.474 | −77.809 | 1.00 | 94.06 | MOL2 | O |
| ATOM | 6097 | N | SER | D | 17 | −12.405 | −30.519 | −78.640 | 1.00 | 90.56 | MOL2 | N |
| ATOM | 6098 | CA | SER | D | 17 | −11.305 | −31.152 | −79.368 | 1.00 | 88.06 | MOL2 | C |
| ATOM | 6099 | CB | SER | D | 17 | −11.666 | −31.329 | −80.849 | 1.00 | 84.28 | MOL2 | C |
| ATOM | 6100 | OG | SER | D | 17 | −11.944 | −32.684 | −81.155 | 1.00 | 71.92 | MOL2 | O |
| ATOM | 6101 | C | SER | D | 17 | −9.988 | −30.395 | −79.279 | 1.00 | 86.85 | MOL2 | C |
| ATOM | 6102 | O | SER | D | 17 | −9.972 | −29.168 | −79.144 | 1.00 | 82.24 | MOL2 | O |
| ATOM | 6103 | N | LEU | D | 18 | −8.889 | −31.149 | −79.358 | 1.00 | 87.92 | MOL2 | N |
| ATOM | 6104 | CA | LEU | D | 18 | −7.537 | −30.591 | −79.318 | 1.00 | 83.54 | MOL2 | C |
| ATOM | 6105 | CB | LEU | D | 18 | −6.970 | −30.620 | −77.901 | 1.00 | 78.94 | MOL2 | C |
| ATOM | 6106 | CG | LEU | D | 18 | −6.472 | −29.234 | −77.506 | 1.00 | 78.53 | MOL2 | C |
| ATOM | 6107 | CD1 | LEU | D | 18 | −5.626 | −29.308 | −76.241 | 1.00 | 74.08 | MOL2 | C |
| ATOM | 6108 | CD2 | LEU | D | 18 | −5.683 | −28.658 | −78.673 | 1.00 | 78.57 | MOL2 | C |
| ATOM | 6109 | C | LEU | D | 18 | −6.594 | −31.357 | −80.237 | 1.00 | 81.40 | MOL2 | C |
| ATOM | 6110 | O | LEU | D | 18 | −6.772 | −32.557 | −80.473 | 1.00 | 80.75 | MOL2 | O |
| ATOM | 6111 | N | ARG | D | 19 | −5.597 | −30.648 | −80.757 | 1.00 | 79.15 | MOL2 | N |
| ATOM | 6112 | CA | ARG | D | 19 | −4.599 | −31.241 | −81.644 | 1.00 | 78.03 | MOL2 | C |
| ATOM | 6113 | CB | ARG | D | 19 | −4.678 | −30.634 | −83.039 | 1.00 | 78.17 | MOL2 | C |
| ATOM | 6114 | CG | ARG | D | 19 | −3.535 | −31.018 | −83.949 | 1.00 | 65.90 | MOL2 | C |
| ATOM | 6115 | CD | ARG | D | 19 | −3.131 | −29.824 | −84.786 | 1.00 | 69.08 | MOL2 | C |
| ATOM | 6116 | NE | ARG | D | 19 | −2.427 | −30.199 | −86.005 | 1.00 | 74.67 | MOL2 | N |
| ATOM | 6117 | CZ | ARG | D | 19 | −2.777 | −31.215 | −86.793 | 1.00 | 75.43 | MOL2 | C |
| ATOM | 6118 | NH1 | ARG | D | 19 | −3.823 | −31.978 | −86.487 | 1.00 | 65.68 | MOL2 | N |
| ATOM | 6119 | NH2 | ARG | D | 19 | −2.093 | −31.453 | −87.909 | 1.00 | 79.00 | MOL2 | N |
| ATOM | 6120 | C | ARG | D | 19 | −3.215 | −30.986 | −81.073 | 1.00 | 78.02 | MOL2 | C |
| ATOM | 6121 | O | ARG | D | 19 | −2.788 | −29.831 | −80.907 | 1.00 | 72.90 | MOL2 | O |
| ATOM | 6122 | N | LEU | D | 20 | −2.526 | −32.085 | −80.777 | 1.00 | 77.70 | MOL2 | N |
| ATOM | 6123 | CA | LEU | D | 20 | −1.187 | −32.051 | −80.211 | 1.00 | 75.48 | MOL2 | C |
| ATOM | 6124 | CB | LEU | D | 20 | −1.058 | −33.127 | −79.137 | 1.00 | 77.70 | MOL2 | C |
| ATOM | 6125 | CG | LEU | D | 20 | −1.804 | −32.904 | −77.828 | 1.00 | 78.75 | MOL2 | C |
| ATOM | 6126 | CD1 | LEU | D | 20 | −1.722 | −34.166 | −76.990 | 1.00 | 76.76 | MOL2 | C |
| ATOM | 6127 | CD2 | LEU | D | 20 | −1.205 | −31.702 | −77.100 | 1.00 | 77.37 | MOL2 | C |
| ATOM | 6128 | C | LEU | D | 20 | −0.113 | −32.289 | −81.265 | 1.00 | 75.06 | MOL2 | C |
| ATOM | 6129 | O | LEU | D | 20 | −0.276 | −33.122 | −82.174 | 1.00 | 66.09 | MOL2 | O |
| ATOM | 6130 | N | SER | D | 21 | 0.992 | −31.564 | −81.127 | 1.00 | 73.95 | MOL2 | N |
| ATOM | 6131 | CA | SER | D | 21 | 2.104 | −31.715 | −82.049 | 1.00 | 72.69 | MOL2 | C |
| ATOM | 6132 | CB | SER | D | 21 | 2.227 | −30.478 | −82.927 | 1.00 | 70.61 | MOL2 | C |
| ATOM | 6133 | OG | SER | D | 21 | 2.423 | −29.334 | −82.123 | 1.00 | 79.90 | MOL2 | O |

TABLE 1-continued

The atomic coordinates of IL17F in complex with 496 Fab
(H32; a = 189.4; b = 189.4; c = 490.9, α, β = 90°; γ = 120°)

| ATOM | 6134 | C | SER | D | 21 | 3.412 | −31.955 | −81.288 | 1.00 | 71.91 | MOL2 | C |
|---|---|---|---|---|---|---|---|---|---|---|---|---|
| ATOM | 6135 | O | SER | D | 21 | 3.579 | −31.529 | −80.139 | 1.00 | 71.22 | MOL2 | O |
| ATOM | 6136 | N | CYS | D | 22 | 4.326 | −32.659 | −81.945 | 1.00 | 70.37 | MOL2 | N |
| ATOM | 6137 | CA | CYS | D | 22 | 5.631 | −32.983 | −81.386 | 1.00 | 65.79 | MOL2 | C |
| ATOM | 6138 | C | CYS | D | 22 | 6.688 | −32.757 | −82.450 | 1.00 | 57.43 | MOL2 | C |
| ATOM | 6139 | O | CYS | D | 22 | 6.630 | −33.341 | −83.527 | 1.00 | 54.04 | MOL2 | O |
| ATOM | 6140 | CB | CYS | D | 22 | 5.663 | −34.443 | −80.951 | 1.00 | 73.70 | MOL2 | C |
| ATOM | 6141 | SG | CYS | D | 22 | 7.282 | −35.006 | −80.333 | 1.00 | 84.99 | MOL2 | S |
| ATOM | 6142 | N | ALA | D | 23 | 7.648 | −31.899 | −82.155 | 1.00 | 52.00 | MOL2 | N |
| ATOM | 6143 | CA | ALA | D | 23 | 8.698 | −31.629 | −83.117 | 1.00 | 54.76 | MOL2 | C |
| ATOM | 6144 | CB | ALA | D | 23 | 9.031 | −30.160 | −83.132 | 1.00 | 64.70 | MOL2 | C |
| ATOM | 6145 | C | ALA | D | 23 | 9.923 | −32.435 | −82.747 | 1.00 | 58.66 | MOL2 | C |
| ATOM | 6146 | O | ALA | D | 23 | 10.476 | −32.278 | −81.658 | 1.00 | 64.59 | MOL2 | O |
| ATOM | 6147 | N | ALA | D | 24 | 10.353 | −33.296 | −83.660 | 1.00 | 56.45 | MOL2 | N |
| ATOM | 6148 | CA | ALA | D | 24 | 11.507 | −34.144 | −83.422 | 1.00 | 50.35 | MOL2 | C |
| ATOM | 6149 | CB | ALA | D | 24 | 11.214 | −35.531 | −83.917 | 1.00 | 53.80 | MOL2 | C |
| ATOM | 6150 | C | ALA | D | 24 | 12.754 | −33.625 | −84.097 | 1.00 | 47.82 | MOL2 | C |
| ATOM | 6151 | O | ALA | D | 24 | 12.690 | −32.843 | −85.034 | 1.00 | 56.17 | MOL2 | O |
| ATOM | 6152 | N | SER | D | 25 | 13.902 | −34.072 | −83.626 | 1.00 | 45.00 | MOL2 | N |
| ATOM | 6153 | CA | SER | D | 25 | 15.161 | −33.661 | −84.227 | 1.00 | 44.92 | MOL2 | C |
| ATOM | 6154 | CB | SER | D | 25 | 15.457 | −32.185 | −83.964 | 1.00 | 35.52 | MOL2 | C |
| ATOM | 6155 | OG | SER | D | 25 | 16.204 | −32.031 | −82.768 | 1.00 | 42.35 | MOL2 | O |
| ATOM | 6156 | C | SER | D | 25 | 16.267 | −34.505 | −83.636 | 1.00 | 47.14 | MOL2 | C |
| ATOM | 6157 | O | SER | D | 25 | 16.072 | −35.179 | −82.627 | 1.00 | 56.46 | MOL2 | O |
| ATOM | 6158 | N | GLY | D | 26 | 17.433 | −34.464 | −84.259 | 1.00 | 43.68 | MOL2 | N |
| ATOM | 6159 | CA | GLY | D | 26 | 18.537 | −35.247 | −83.757 | 1.00 | 46.50 | MOL2 | C |
| ATOM | 6160 | C | GLY | D | 26 | 18.520 | −36.681 | −84.252 | 1.00 | 43.78 | MOL2 | C |
| ATOM | 6161 | O | GLY | D | 26 | 19.283 | −37.508 | −83.763 | 1.00 | 45.34 | MOL2 | O |
| ATOM | 6162 | N | PHE | D | 27 | 17.650 | −36.992 | −85.205 | 1.00 | 38.63 | MOL2 | N |
| ATOM | 6163 | CA | PHE | D | 27 | 17.612 | −38.343 | −85.746 | 1.00 | 39.22 | MOL2 | C |
| ATOM | 6164 | CB | PHE | D | 27 | 17.191 | −39.314 | −84.669 | 1.00 | 24.50 | MOL2 | C |
| ATOM | 6165 | CG | PHE | D | 27 | 15.738 | −39.268 | −84.334 | 1.00 | 28.38 | MOL2 | C |
| ATOM | 6166 | CD1 | PHE | D | 27 | 14.876 | −40.235 | −84.822 | 1.00 | 27.26 | MOL2 | C |
| ATOM | 6167 | CD2 | PHE | D | 27 | 15.239 | −38.304 | −83.474 | 1.00 | 36.41 | MOL2 | C |
| ATOM | 6168 | CE1 | PHE | D | 27 | 13.552 | −40.243 | −84.451 | 1.00 | 30.72 | MOL2 | C |
| ATOM | 6169 | CE2 | PHE | D | 27 | 13.900 | −38.304 | −83.094 | 1.00 | 31.86 | MOL2 | C |
| ATOM | 6170 | CZ | PHE | D | 27 | 13.060 | −39.271 | −83.579 | 1.00 | 32.53 | MOL2 | C |
| ATOM | 6171 | C | PHE | D | 27 | 16.738 | −38.508 | −86.983 | 1.00 | 46.31 | MOL2 | C |
| ATOM | 6172 | O | PHE | D | 27 | 15.866 | −37.676 | −87.273 | 1.00 | 52.97 | MOL2 | O |
| ATOM | 6173 | N | THR | D | 28 | 16.964 | −39.574 | −87.740 | 1.00 | 46.42 | MOL2 | N |
| ATOM | 6174 | CA | THR | D | 28 | 16.165 | −39.706 | −88.940 | 1.00 | 53.33 | MOL2 | C |
| ATOM | 6175 | CB | THR | D | 28 | 16.824 | −40.642 | −89.998 | 1.00 | 52.12 | MOL2 | C |
| ATOM | 6176 | OG1 | THR | D | 28 | 16.286 | −41.959 | −89.886 | 1.00 | 62.36 | MOL2 | O |
| ATOM | 6177 | CG2 | THR | D | 28 | 18.345 | −40.660 | −89.824 | 1.00 | 46.59 | MOL2 | C |
| ATOM | 6178 | C | THR | D | 28 | 14.748 | −40.133 | −88.596 | 1.00 | 51.79 | MOL2 | C |
| ATOM | 6179 | O | THR | D | 28 | 14.407 | −41.313 | −88.553 | 1.00 | 48.04 | MOL2 | O |
| ATOM | 6180 | N | PHE | D | 29 | 13.929 | −39.117 | −88.348 | 1.00 | 53.46 | MOL2 | N |
| ATOM | 6181 | CA | PHE | D | 29 | 12.531 | −39.278 | −87.979 | 1.00 | 54.72 | MOL2 | C |
| ATOM | 6182 | CB | PHE | D | 29 | 11.881 | −37.895 | −87.926 | 1.00 | 62.47 | MOL2 | C |
| ATOM | 6183 | CG | PHE | D | 29 | 10.451 | −37.898 | −87.455 | 1.00 | 66.59 | MOL2 | C |
| ATOM | 6184 | CD1 | PHE | D | 29 | 9.420 | −38.253 | −88.310 | 1.00 | 68.36 | MOL2 | C |
| ATOM | 6185 | CD2 | PHE | D | 29 | 10.143 | −37.514 | −86.164 | 1.00 | 66.24 | MOL2 | C |
| ATOM | 6186 | CE1 | PHE | D | 29 | 8.118 | −38.219 | −87.890 | 1.00 | 68.35 | MOL2 | C |
| ATOM | 6187 | CE2 | PHE | D | 29 | 8.849 | −37.480 | −85.738 | 1.00 | 68.10 | MOL2 | C |
| ATOM | 6188 | CZ | PHE | D | 29 | 7.830 | −37.832 | −86.603 | 1.00 | 73.32 | MOL2 | C |
| ATOM | 6189 | C | PHE | D | 29 | 11.759 | −40.183 | −88.928 | 1.00 | 54.82 | MOL2 | C |
| ATOM | 6190 | O | PHE | D | 29 | 11.075 | −41.110 | −88.506 | 1.00 | 48.52 | MOL2 | O |
| ATOM | 6191 | N | SER | D | 30 | 11.876 | −39.900 | −90.218 | 1.00 | 60.43 | MOL2 | N |
| ATOM | 6192 | CA | SER | D | 30 | 11.183 | −40.659 | −91.253 | 1.00 | 60.64 | MOL2 | C |
| ATOM | 6193 | CB | SER | D | 30 | 11.528 | −40.087 | −92.625 | 1.00 | 60.73 | MOL2 | C |
| ATOM | 6194 | OG | SER | D | 30 | 12.897 | −40.295 | −92.920 | 1.00 | 59.38 | MOL2 | O |
| ATOM | 6195 | C | SER | D | 30 | 11.539 | −42.135 | −91.243 | 1.00 | 60.18 | MOL2 | C |
| ATOM | 6196 | O | SER | D | 30 | 11.050 | −42.898 | −92.070 | 1.00 | 56.89 | MOL2 | O |
| ATOM | 6197 | N | ASP | D | 31 | 12.391 | −42.539 | −90.311 | 1.00 | 60.72 | MOL2 | N |
| ATOM | 6198 | CA | ASP | D | 31 | 12.809 | −43.926 | −90.263 | 1.00 | 59.43 | MOL2 | C |
| ATOM | 6199 | CB | ASP | D | 31 | 14.328 | −44.025 | −90.173 | 1.00 | 61.21 | MOL2 | C |
| ATOM | 6200 | CG | ASP | D | 31 | 14.944 | −44.592 | −91.432 | 1.00 | 68.54 | MOL2 | C |
| ATOM | 6201 | OD1 | ASP | D | 31 | 14.563 | −45.722 | −91.815 | 1.00 | 78.88 | MOL2 | O |
| ATOM | 6202 | OD2 | ASP | D | 31 | 15.801 | −43.916 | −92.040 | 1.00 | 68.22 | MOL2 | O |
| ATOM | 6203 | C | ASP | D | 31 | 12.209 | −44.732 | −89.151 | 1.00 | 57.94 | MOL2 | C |
| ATOM | 6204 | O | ASP | D | 31 | 12.081 | −45.941 | −89.272 | 1.00 | 59.54 | MOL2 | O |
| ATOM | 6205 | N | TYR | D | 32 | 11.822 | −44.070 | −88.074 | 1.00 | 57.77 | MOL2 | N |
| ATOM | 6206 | CA | TYR | D | 32 | 11.280 | −44.769 | −86.925 | 1.00 | 57.85 | MOL2 | C |
| ATOM | 6207 | CB | TYR | D | 32 | 12.081 | −44.358 | −85.689 | 1.00 | 55.56 | MOL2 | C |
| ATOM | 6208 | CG | TYR | D | 32 | 13.524 | −44.813 | −85.736 | 1.00 | 57.47 | MOL2 | C |
| ATOM | 6209 | CD1 | TYR | D | 32 | 14.485 | −44.106 | −86.443 | 1.00 | 58.58 | MOL2 | C |
| ATOM | 6210 | CE1 | TYR | D | 32 | 15.775 | −44.593 | −86.560 | 1.00 | 62.62 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 6211 | CD2 | TYR | D | 32 | 13.901 | −46.006 | −85.139 | 1.00 | 55.62 | MOL2 | C |
|---|---|---|---|---|---|---|---|---|---|---|---|---|
| ATOM | 6212 | CE2 | TYR | D | 32 | 15.166 | −46.490 | −85.246 | 1.00 | 51.87 | MOL2 | C |
| ATOM | 6213 | CZ | TYR | D | 32 | 16.103 | −45.799 | −85.961 | 1.00 | 63.39 | MOL2 | C |
| ATOM | 6214 | OH | TYR | D | 32 | 17.347 | −46.371 | −86.130 | 1.00 | 70.01 | MOL2 | O |
| ATOM | 6215 | C | TYR | D | 32 | 9.796 | −44.556 | −86.663 | 1.00 | 60.28 | MOL2 | C |
| ATOM | 6216 | O | TYR | D | 32 | 9.220 | −43.567 | −87.096 | 1.00 | 66.37 | MOL2 | O |
| ATOM | 6217 | N | ASN | D | 33 | 9.176 | −45.493 | −85.953 | 1.00 | 60.37 | MOL2 | N |
| ATOM | 6218 | CA | ASN | D | 33 | 7.769 | −45.367 | −85.596 | 1.00 | 56.47 | MOL2 | C |
| ATOM | 6219 | CB | ASN | D | 33 | 7.224 | −46.708 | −85.112 | 1.00 | 56.79 | MOL2 | C |
| ATOM | 6220 | CG | ASN | D | 33 | 7.470 | −47.815 | −86.109 | 1.00 | 66.86 | MOL2 | C |
| ATOM | 6221 | OD1 | ASN | D | 33 | 8.551 | −47.901 | −86.684 | 1.00 | 78.81 | MOL2 | O |
| ATOM | 6222 | ND2 | ASN | D | 33 | 6.476 | −48.671 | −86.321 | 1.00 | 68.08 | MOL2 | N |
| ATOM | 6223 | C | ASN | D | 33 | 7.728 | −44.362 | −84.459 | 1.00 | 53.80 | MOL2 | C |
| ATOM | 6224 | O | ASN | D | 33 | 8.735 | −44.112 | −83.810 | 1.00 | 58.25 | MOL2 | O |
| ATOM | 6225 | N | MET | D | 34 | 6.574 | −43.772 | −84.212 | 1.00 | 50.73 | MOL2 | N |
| ATOM | 6226 | CA | MET | D | 34 | 6.474 | −42.811 | −83.127 | 1.00 | 50.71 | MOL2 | C |
| ATOM | 6227 | CB | MET | D | 34 | 6.370 | −41.407 | −83.686 | 1.00 | 53.02 | MOL2 | C |
| ATOM | 6228 | CG | MET | D | 34 | 7.641 | −40.933 | −84.344 | 1.00 | 52.86 | MOL2 | C |
| ATOM | 6229 | SD | MET | D | 34 | 8.901 | −40.768 | −83.107 | 1.00 | 49.81 | MOL2 | S |
| ATOM | 6230 | CE | MET | D | 34 | 8.706 | −39.069 | −82.552 | 1.00 | 51.28 | MOL2 | C |
| ATOM | 6231 | C | MET | D | 34 | 5.248 | −43.134 | −82.321 | 1.00 | 47.40 | MOL2 | C |
| ATOM | 6232 | O | MET | D | 34 | 4.383 | −43.860 | −82.792 | 1.00 | 49.62 | MOL2 | O |
| ATOM | 6233 | N | ALA | D | 35 | 5.168 | −42.618 | −81.104 | 1.00 | 42.59 | MOL2 | N |
| ATOM | 6234 | CA | ALA | D | 35 | 3.997 | −42.901 | −80.289 | 1.00 | 44.94 | MOL2 | C |
| ATOM | 6235 | CB | ALA | D | 35 | 4.106 | −44.285 | −79.657 | 1.00 | 32.32 | MOL2 | C |
| ATOM | 6236 | C | ALA | D | 35 | 3.711 | −41.866 | −79.214 | 1.00 | 46.03 | MOL2 | C |
| ATOM | 6237 | O | ALA | D | 35 | 4.533 | −40.981 | −78.906 | 1.00 | 40.89 | MOL2 | O |
| ATOM | 6238 | N | TRP | D | 36 | 2.506 | −41.967 | −78.669 | 1.00 | 44.59 | MOL2 | N |
| ATOM | 6239 | CA | TRP | D | 36 | 2.094 | −41.069 | −77.618 | 1.00 | 44.38 | MOL2 | C |
| ATOM | 6240 | CB | TRP | D | 36 | 0.825 | −40.306 | −78.000 | 1.00 | 38.84 | MOL2 | C |
| ATOM | 6241 | CG | TRP | D | 36 | 1.033 | −39.334 | −79.074 | 1.00 | 28.40 | MOL2 | C |
| ATOM | 6242 | CD2 | TRP | D | 36 | 1.448 | −37.980 | −78.919 | 1.00 | 26.98 | MOL2 | C |
| ATOM | 6243 | CE2 | TRP | D | 36 | 1.624 | −37.449 | −80.209 | 1.00 | 29.52 | MOL2 | C |
| ATOM | 6244 | CE3 | TRP | D | 36 | 1.697 | −37.163 | −77.811 | 1.00 | 33.21 | MOL2 | C |
| ATOM | 6245 | CD1 | TRP | D | 36 | 0.965 | −39.571 | −80.414 | 1.00 | 31.07 | MOL2 | C |
| ATOM | 6246 | NE1 | TRP | D | 36 | 1.323 | −38.444 | −81.106 | 1.00 | 29.81 | MOL2 | N |
| ATOM | 6247 | CZ2 | TRP | D | 36 | 2.042 | −36.129 | −80.426 | 1.00 | 24.35 | MOL2 | C |
| ATOM | 6248 | CZ3 | TRP | D | 36 | 2.114 | −35.854 | −78.024 | 1.00 | 30.24 | MOL2 | C |
| ATOM | 6249 | CH2 | TRP | D | 36 | 2.281 | −35.353 | −79.327 | 1.00 | 27.49 | MOL2 | C |
| ATOM | 6250 | C | TRP | D | 36 | 1.832 | −41.944 | −76.421 | 1.00 | 44.63 | MOL2 | C |
| ATOM | 6251 | O | TRP | D | 36 | 1.315 | −43.052 | −76.551 | 1.00 | 45.46 | MOL2 | O |
| ATOM | 6252 | N | VAL | D | 37 | 2.211 | −41.438 | −75.262 | 1.00 | 41.30 | MOL2 | N |
| ATOM | 6253 | CA | VAL | D | 37 | 2.038 | −42.148 | −74.025 | 1.00 | 49.84 | MOL2 | C |
| ATOM | 6254 | CB | VAL | D | 37 | 3.395 | −42.719 | −73.560 | 1.00 | 56.87 | MOL2 | C |
| ATOM | 6255 | CG1 | VAL | D | 37 | 3.386 | −42.972 | −72.067 | 1.00 | 63.23 | MOL2 | C |
| ATOM | 6256 | CG2 | VAL | D | 37 | 3.690 | −44.006 | −74.304 | 1.00 | 60.97 | MOL2 | C |
| ATOM | 6257 | C | VAL | D | 37 | 1.560 | −41.086 | −73.064 | 1.00 | 55.18 | MOL2 | C |
| ATOM | 6258 | O | VAL | D | 37 | 2.156 | −40.003 | −72.996 | 1.00 | 54.18 | MOL2 | O |
| ATOM | 6259 | N | ARG | D | 38 | 0.473 | −41.358 | −72.343 | 1.00 | 58.77 | MOL2 | N |
| ATOM | 6260 | CA | ARG | D | 38 | −0.004 | −40.359 | −71.391 | 1.00 | 60.58 | MOL2 | C |
| ATOM | 6261 | CB | ARG | D | 38 | −1.442 | −39.886 | −71.682 | 1.00 | 69.17 | MOL2 | C |
| ATOM | 6262 | CG | ARG | D | 38 | −2.578 | −40.905 | −71.597 | 1.00 | 75.27 | MOL2 | C |
| ATOM | 6263 | CD | ARG | D | 38 | −3.921 | −40.148 | −71.651 | 1.00 | 85.53 | MOL2 | C |
| ATOM | 6264 | NE | ARG | D | 38 | −5.021 | −40.914 | −72.235 | 1.00 | 88.71 | MOL2 | N |
| ATOM | 6265 | CZ | ARG | D | 38 | −5.593 | −41.964 | −71.655 | 1.00 | 95.44 | MOL2 | C |
| ATOM | 6266 | NH1 | ARG | D | 38 | −5.178 | −42.378 | −70.465 | 1.00 | 96.28 | MOL2 | N |
| ATOM | 6267 | NH2 | ARG | D | 38 | −6.567 | −42.615 | −72.275 | 1.00 | 98.30 | MOL2 | N |
| ATOM | 6268 | C | ARG | D | 38 | 0.103 | −40.826 | −69.967 | 1.00 | 56.56 | MOL2 | C |
| ATOM | 6269 | O | ARG | D | 38 | 0.255 | −42.023 | −69.698 | 1.00 | 51.91 | MOL2 | O |
| ATOM | 6270 | N | GLN | D | 39 | 0.028 | −39.860 | −69.056 | 1.00 | 53.51 | MOL2 | N |
| ATOM | 6271 | CA | GLN | D | 39 | 0.139 | −40.141 | −67.634 | 1.00 | 55.30 | MOL2 | C |
| ATOM | 6272 | CB | GLN | D | 39 | 1.582 | −39.968 | −67.220 | 1.00 | 55.50 | MOL2 | C |
| ATOM | 6273 | CG | GLN | D | 39 | 1.860 | −40.157 | −65.765 | 1.00 | 53.77 | MOL2 | C |
| ATOM | 6274 | CD | GLN | D | 39 | 3.308 | −39.849 | −65.454 | 1.00 | 63.42 | MOL2 | C |
| ATOM | 6275 | OE1 | GLN | D | 39 | 3.801 | −38.728 | −65.701 | 1.00 | 55.69 | MOL2 | O |
| ATOM | 6276 | NE2 | GLN | D | 39 | 4.010 | −40.844 | −64.922 | 1.00 | 67.76 | MOL2 | N |
| ATOM | 6277 | C | GLN | D | 39 | −0.744 | −39.226 | −66.796 | 1.00 | 60.85 | MOL2 | C |
| ATOM | 6278 | O | GLN | D | 39 | −0.403 | −38.061 | −66.559 | 1.00 | 58.46 | MOL2 | O |
| ATOM | 6279 | N | ALA | D | 40 | −1.870 | −39.771 | −66.338 | 1.00 | 64.05 | MOL2 | N |
| ATOM | 6280 | CA | ALA | D | 40 | −2.830 | −39.028 | −65.537 | 1.00 | 65.19 | MOL2 | C |
| ATOM | 6281 | CB | ALA | D | 40 | −4.008 | −39.906 | −65.248 | 1.00 | 71.21 | MOL2 | C |
| ATOM | 6282 | C | ALA | D | 40 | −2.197 | −38.578 | −64.242 | 1.00 | 68.48 | MOL2 | C |
| ATOM | 6283 | O | ALA | D | 40 | −1.424 | −39.311 | −63.649 | 1.00 | 74.09 | MOL2 | O |
| ATOM | 6284 | N | PRO | D | 41 | −2.531 | −37.373 | −63.768 | 1.00 | 73.48 | MOL2 | N |
| ATOM | 6285 | CD | PRO | D | 41 | −3.523 | −36.419 | −64.275 | 1.00 | 78.11 | MOL2 | C |
| ATOM | 6286 | CA | PRO | D | 41 | −1.946 | −36.885 | −62.517 | 1.00 | 79.78 | MOL2 | C |
| ATOM | 6287 | CB | PRO | D | 41 | −2.818 | −35.687 | −62.171 | 1.00 | 76.98 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 6288 | CG | PRO | D | 41 | −3.152 | −35.159 | −63.505 | 1.00 | 81.73 | MOL2 | C |
|---|---|---|---|---|---|---|---|---|---|---|---|---|
| ATOM | 6289 | C | PRO | D | 41 | −1.926 | −37.940 | −61.411 | 1.00 | 83.13 | MOL2 | C |
| ATOM | 6290 | O | PRO | D | 41 | −2.927 | −38.617 | −61.135 | 1.00 | 85.49 | MOL2 | O |
| ATOM | 6291 | N | GLY | D | 42 | −0.762 | −38.082 | −60.793 | 1.00 | 80.93 | MOL2 | N |
| ATOM | 6292 | CA | GLY | D | 42 | −0.614 | −39.051 | −59.738 | 1.00 | 79.13 | MOL2 | C |
| ATOM | 6293 | C | GLY | D | 42 | −0.533 | −40.467 | −60.263 | 1.00 | 80.48 | MOL2 | C |
| ATOM | 6294 | O | GLY | D | 42 | 0.230 | −41.265 | −59.733 | 1.00 | 89.17 | MOL2 | O |
| ATOM | 6295 | N | LYS | D | 43 | −1.297 | −40.791 | −61.302 | 1.00 | 76.33 | MOL2 | N |
| ATOM | 6296 | CA | LYS | D | 43 | −1.289 | −42.147 | −61.845 | 1.00 | 76.92 | MOL2 | C |
| ATOM | 6297 | CB | LYS | D | 43 | −2.559 | −42.375 | −62.669 | 1.00 | 87.60 | MOL2 | C |
| ATOM | 6298 | CG | LYS | D | 43 | −3.852 | −42.332 | −61.841 | 1.00 | 100.68 | MOL2 | C |
| ATOM | 6299 | CD | LYS | D | 43 | −3.882 | −43.434 | −60.770 | 1.00 | 111.98 | MOL2 | C |
| ATOM | 6300 | CE | LYS | D | 43 | −5.192 | −43.448 | −59.964 | 1.00 | 116.94 | MOL2 | C |
| ATOM | 6301 | NZ | LYS | D | 43 | −6.398 | −43.856 | −60.758 | 1.00 | 120.34 | MOL2 | N |
| ATOM | 6302 | C | LYS | D | 43 | −0.046 | −42.572 | −62.650 | 1.00 | 71.83 | MOL2 | C |
| ATOM | 6303 | O | LYS | D | 43 | 0.917 | −41.806 | −62.805 | 1.00 | 65.21 | MOL2 | O |
| ATOM | 6304 | N | GLY | D | 44 | −0.083 | −43.809 | −63.147 | 1.00 | 67.68 | MOL2 | N |
| ATOM | 6305 | CA | GLY | D | 44 | 1.027 | −44.366 | −63.905 | 1.00 | 68.58 | MOL2 | C |
| ATOM | 6306 | C | GLY | D | 44 | 1.138 | −43.967 | −65.367 | 1.00 | 69.48 | MOL2 | C |
| ATOM | 6307 | O | GLY | D | 44 | 0.738 | −42.867 | −65.756 | 1.00 | 74.59 | MOL2 | O |
| ATOM | 6308 | N | LEU | D | 45 | 1.688 | −44.858 | −66.187 | 1.00 | 64.01 | MOL2 | N |
| ATOM | 6309 | CA | LEU | D | 45 | 1.852 | −44.557 | −67.603 | 1.00 | 60.60 | MOL2 | C |
| ATOM | 6310 | CB | LEU | D | 45 | 3.320 | −44.748 | −68.025 | 1.00 | 54.13 | MOL2 | C |
| ATOM | 6311 | CG | LEU | D | 45 | 4.370 | −43.830 | −67.366 | 1.00 | 53.54 | MOL2 | C |
| ATOM | 6312 | CD1 | LEU | D | 45 | 5.787 | −44.216 | −67.791 | 1.00 | 44.54 | MOL2 | C |
| ATOM | 6313 | CD2 | LEU | D | 45 | 4.097 | −42.397 | −67.738 | 1.00 | 41.93 | MOL2 | C |
| ATOM | 6314 | C | LEU | D | 45 | 0.938 | −45.426 | −68.453 | 1.00 | 64.12 | MOL2 | C |
| ATOM | 6315 | O | LEU | D | 45 | 0.864 | −46.641 | −68.263 | 1.00 | 69.15 | MOL2 | O |
| ATOM | 6316 | N | GLU | D | 46 | 0.235 | −44.786 | −69.382 | 1.00 | 64.42 | MOL2 | N |
| ATOM | 6317 | CA | GLU | D | 46 | −0.688 | −45.471 | −70.275 | 1.00 | 64.76 | MOL2 | C |
| ATOM | 6318 | CB | GLU | D | 46 | −2.119 | −44.975 | −70.049 | 1.00 | 71.52 | MOL2 | C |
| ATOM | 6319 | CG | GLU | D | 46 | −2.683 | −45.278 | −68.676 | 1.00 | 89.62 | MOL2 | C |
| ATOM | 6320 | CD | GLU | D | 46 | −3.848 | −44.373 | −68.310 | 1.00 | 100.48 | MOL2 | C |
| ATOM | 6321 | OE1 | GLU | D | 46 | −4.866 | −44.380 | −69.042 | 1.00 | 101.04 | MOL2 | O |
| ATOM | 6322 | OE2 | GLU | D | 46 | −3.739 | −43.654 | −67.284 | 1.00 | 108.36 | MOL2 | O |
| ATOM | 6323 | C | GLU | D | 46 | −0.286 | −45.152 | −71.694 | 1.00 | 62.81 | MOL2 | C |
| ATOM | 6324 | O | GLU | D | 46 | −0.028 | −43.995 | −72.031 | 1.00 | 55.53 | MOL2 | O |
| ATOM | 6325 | N | TRP | D | 47 | −0.226 | −46.173 | −72.535 | 1.00 | 65.54 | MOL2 | N |
| ATOM | 6326 | CA | TRP | D | 47 | 0.124 | −45.927 | −73.917 | 1.00 | 65.61 | MOL2 | C |
| ATOM | 6327 | CB | TRP | D | 47 | 0.730 | −47.159 | −74.551 | 1.00 | 62.17 | MOL2 | C |
| ATOM | 6328 | CG | TRP | D | 47 | 0.787 | −47.004 | −76.002 | 1.00 | 65.07 | MOL2 | C |
| ATOM | 6329 | CD2 | TRP | D | 47 | 0.012 | −47.719 | −76.961 | 1.00 | 70.61 | MOL2 | C |
| ATOM | 6330 | CE2 | TRP | D | 47 | 0.336 | −47.205 | −78.225 | 1.00 | 72.82 | MOL2 | C |
| ATOM | 6331 | CE3 | TRP | D | 47 | −0.929 | −48.747 | −76.873 | 1.00 | 74.31 | MOL2 | C |
| ATOM | 6332 | CD1 | TRP | D | 47 | 1.533 | −46.109 | −76.698 | 1.00 | 67.74 | MOL2 | C |
| ATOM | 6333 | NE1 | TRP | D | 47 | 1.270 | −46.220 | −78.040 | 1.00 | 73.44 | MOL2 | N |
| ATOM | 6334 | CZ2 | TRP | D | 47 | −0.247 | −47.683 | −79.390 | 1.00 | 79.25 | MOL2 | C |
| ATOM | 6335 | CZ3 | TRP | D | 47 | −1.504 | −49.220 | −78.031 | 1.00 | 75.33 | MOL2 | C |
| ATOM | 6336 | CH2 | TRP | D | 47 | −1.163 | −48.689 | −79.272 | 1.00 | 78.23 | MOL2 | C |
| ATOM | 6337 | C | TRP | D | 47 | −1.112 | −45.509 | −74.709 | 1.00 | 67.66 | MOL2 | C |
| ATOM | 6338 | O | TRP | D | 47 | −2.158 | −46.149 | −74.642 | 1.00 | 72.85 | MOL2 | O |
| ATOM | 6339 | N | VAL | D | 48 | −0.988 | −44.424 | −75.457 | 1.00 | 65.33 | MOL2 | N |
| ATOM | 6340 | CA | VAL | D | 48 | −2.090 | −43.923 | −76.259 | 1.00 | 58.35 | MOL2 | C |
| ATOM | 6341 | CB | VAL | D | 48 | −1.967 | −42.418 | −76.437 | 1.00 | 54.66 | MOL2 | C |
| ATOM | 6342 | CG1 | VAL | D | 48 | −2.995 | −41.931 | −77.412 | 1.00 | 49.86 | MOL2 | C |
| ATOM | 6343 | CG2 | VAL | D | 48 | −2.119 | −41.729 | −75.091 | 1.00 | 57.15 | MOL2 | C |
| ATOM | 6344 | C | VAL | D | 48 | −2.122 | −44.572 | −77.637 | 1.00 | 61.39 | MOL2 | C |
| ATOM | 6345 | O | VAL | D | 48 | −2.918 | −45.473 | −77.888 | 1.00 | 64.06 | MOL2 | O |
| ATOM | 6346 | N | ALA | D | 49 | −1.254 | −44.118 | −78.531 | 1.00 | 63.57 | MOL2 | N |
| ATOM | 6347 | CA | ALA | D | 49 | −1.217 | −44.668 | −79.878 | 1.00 | 67.27 | MOL2 | C |
| ATOM | 6348 | CB | ALA | D | 49 | −2.186 | −43.930 | −80.753 | 1.00 | 67.63 | MOL2 | C |
| ATOM | 6349 | C | ALA | D | 49 | 0.168 | −44.580 | −80.485 | 1.00 | 71.79 | MOL2 | C |
| ATOM | 6350 | O | ALA | D | 49 | 1.030 | −43.847 | −79.995 | 1.00 | 73.85 | MOL2 | O |
| ATOM | 6351 | N | THR | D | 50 | 0.369 | −45.339 | −81.558 | 1.00 | 72.05 | MOL2 | N |
| ATOM | 6352 | CA | THR | D | 50 | 1.636 | −45.349 | −82.277 | 1.00 | 70.38 | MOL2 | C |
| ATOM | 6353 | CB | THR | D | 50 | 2.541 | −46.560 | −81.866 | 1.00 | 70.10 | MOL2 | C |
| ATOM | 6354 | OG1 | THR | D | 50 | 3.552 | −46.738 | −82.861 | 1.00 | 83.42 | MOL2 | O |
| ATOM | 6355 | CG2 | THR | D | 50 | 1.760 | −47.853 | −81.757 | 1.00 | 64.64 | MOL2 | C |
| ATOM | 6356 | C | THR | D | 50 | 1.370 | −45.390 | −83.786 | 1.00 | 66.34 | MOL2 | C |
| ATOM | 6357 | O | THR | D | 50 | 0.409 | −46.007 | −84.228 | 1.00 | 72.25 | MOL2 | O |
| ATOM | 6358 | N | ILE | D | 51 | 2.211 | −44.715 | −84.561 | 1.00 | 60.82 | MOL2 | N |
| ATOM | 6359 | CA | ILE | D | 51 | 2.089 | −44.659 | −86.018 | 1.00 | 59.66 | MOL2 | C |
| ATOM | 6360 | CB | ILE | D | 51 | 1.791 | −43.226 | −86.488 | 1.00 | 59.51 | MOL2 | C |
| ATOM | 6361 | CG2 | ILE | D | 51 | 2.830 | −42.257 | −85.943 | 1.00 | 45.70 | MOL2 | C |
| ATOM | 6362 | CG1 | ILE | D | 51 | 1.813 | −43.161 | −88.009 | 1.00 | 57.26 | MOL2 | C |
| ATOM | 6363 | CD1 | ILE | D | 51 | 1.666 | −41.750 | −88.529 | 1.00 | 60.49 | MOL2 | C |
| ATOM | 6364 | C | ILE | D | 51 | 3.424 | −45.079 | −86.605 | 1.00 | 63.20 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 6365 | O   | ILE | D | 51 | 4.465  | −44.721 | −86.055 | 1.00 | 72.07  | MOL2 | O |
|------|------|-----|-----|---|----|--------|---------|---------|------|--------|------|---|
| ATOM | 6366 | N   | THR | D | 52 | 3.429  | −45.809 | −87.717 | 1.00 | 58.77  | MOL2 | N |
| ATOM | 6367 | CA  | THR | D | 52 | 4.711  | −46.242 | −88.267 | 1.00 | 64.58  | MOL2 | C |
| ATOM | 6368 | CB  | THR | D | 52 | 4.577  | −47.476 | −89.140 | 1.00 | 67.42  | MOL2 | C |
| ATOM | 6369 | OG1 | THR | D | 52 | 4.114  | −47.086 | −90.435 | 1.00 | 79.19  | MOL2 | O |
| ATOM | 6370 | CG2 | THR | D | 52 | 3.609  | −48.463 | −88.516 | 1.00 | 68.84  | MOL2 | C |
| ATOM | 6371 | C   | THR | D | 52 | 5.469  | −45.195 | −89.067 | 1.00 | 67.67  | MOL2 | C |
| ATOM | 6372 | O   | THR | D | 52 | 4.945  | −44.136 | −89.384 | 1.00 | 73.88  | MOL2 | O |
| ATOM | 6373 | N   | TYR | D | 53 | 6.715  | −45.508 | −89.396 | 1.00 | 73.17  | MOL2 | N |
| ATOM | 6374 | CA  | TYR | D | 53 | 7.584  | −44.595 | −90.133 | 1.00 | 81.30  | MOL2 | C |
| ATOM | 6375 | CB  | TYR | D | 53 | 8.954  | −45.247 | −90.337 | 1.00 | 81.09  | MOL2 | C |
| ATOM | 6376 | CG  | TYR | D | 53 | 8.931  | −46.494 | −91.195 | 1.00 | 75.76  | MOL2 | C |
| ATOM | 6377 | CD1 | TYR | D | 53 | 9.213  | −46.436 | −92.557 | 1.00 | 69.59  | MOL2 | C |
| ATOM | 6378 | CE1 | TYR | D | 53 | 9.211  | −47.572 | −93.332 | 1.00 | 68.27  | MOL2 | C |
| ATOM | 6379 | CD2 | TYR | D | 53 | 8.639  | −47.732 | −90.639 | 1.00 | 75.59  | MOL2 | C |
| ATOM | 6380 | CE2 | TYR | D | 53 | 8.632  | −48.874 | −91.408 | 1.00 | 74.16  | MOL2 | C |
| ATOM | 6381 | CZ  | TYR | D | 53 | 8.921  | −48.790 | −92.751 | 1.00 | 73.12  | MOL2 | C |
| ATOM | 6382 | OH  | TYR | D | 53 | 8.936  | −49.940 | −93.502 | 1.00 | 77.65  | MOL2 | O |
| ATOM | 6383 | C   | TYR | D | 53 | 7.041  | −44.130 | −91.478 | 1.00 | 86.35  | MOL2 | C |
| ATOM | 6384 | O   | TYR | D | 53 | 7.011  | −42.931 | −91.763 | 1.00 | 85.84  | MOL2 | O |
| ATOM | 6385 | N   | GLU | D | 54 | 6.636  | −45.090 | −92.305 | 1.00 | 92.68  | MOL2 | N |
| ATOM | 6386 | CA  | GLU | D | 54 | 6.086  | −44.825 | −93.633 | 1.00 | 95.67  | MOL2 | C |
| ATOM | 6387 | CB  | GLU | D | 54 | 5.591  | −46.135 | −94.237 | 1.00 | 98.17  | MOL2 | C |
| ATOM | 6388 | CG  | GLU | D | 54 | 4.537  | −46.831 | −93.382 | 1.00 | 103.97 | MOL2 | C |
| ATOM | 6389 | CD  | GLU | D | 54 | 4.883  | −48.285 | −93.112 | 1.00 | 112.26 | MOL2 | C |
| ATOM | 6390 | OE1 | GLU | D | 54 | 4.140  | −48.960 | −92.361 | 1.00 | 114.82 | MOL2 | O |
| ATOM | 6391 | OE2 | GLU | D | 54 | 5.904  | −48.756 | −93.658 | 1.00 | 115.58 | MOL2 | O |
| ATOM | 6392 | C   | GLU | D | 54 | 4.917  | −43.858 | −93.508 | 1.00 | 95.71  | MOL2 | C |
| ATOM | 6393 | O   | GLU | D | 54 | 4.665  | −43.033 | −94.389 | 1.00 | 92.35  | MOL2 | O |
| ATOM | 6394 | N   | GLY | D | 55 | 4.199  | −43.987 | −92.399 | 1.00 | 96.32  | MOL2 | N |
| ATOM | 6395 | CA  | GLY | D | 55 | 3.066  | −43.129 | −92.141 | 1.00 | 95.86  | MOL2 | C |
| ATOM | 6396 | C   | GLY | D | 55 | 1.754  | −43.803 | −92.463 | 1.00 | 99.83  | MOL2 | C |
| ATOM | 6397 | O   | GLY | D | 55 | 0.706  | −43.162 | −92.397 | 1.00 | 100.50 | MOL2 | O |
| ATOM | 6398 | N   | ARG | D | 56 | 1.789  | −45.086 | −92.810 | 1.00 | 101.58 | MOL2 | N |
| ATOM | 6399 | CA  | ARG | D | 56 | 0.547  | −45.768 | −93.141 | 1.00 | 107.62 | MOL2 | C |
| ATOM | 6400 | CB  | ARG | D | 56 | 0.512  | −46.141 | −94.626 | 1.00 | 120.65 | MOL2 | C |
| ATOM | 6401 | CG  | ARG | D | 56 | −0.912 | −46.353 | −95.176 | 1.00 | 134.36 | MOL2 | C |
| ATOM | 6402 | CD  | ARG | D | 56 | −1.736 | −45.047 | −95.179 | 1.00 | 140.80 | MOL2 | C |
| ATOM | 6403 | NE  | ARG | D | 56 | −3.118 | −45.228 | −95.637 | 1.00 | 145.28 | MOL2 | N |
| ATOM | 6404 | CZ  | ARG | D | 56 | −4.144 | −45.563 | −94.854 | 1.00 | 146.77 | MOL2 | C |
| ATOM | 6405 | NH1 | ARG | D | 56 | −3.964 | −45.757 | −93.549 | 1.00 | 145.89 | MOL2 | N |
| ATOM | 6406 | NH2 | ARG | D | 56 | −5.357 | −45.707 | −95.380 | 1.00 | 144.12 | MOL2 | N |
| ATOM | 6407 | C   | ARG | D | 56 | 0.300  | −47.002 | −92.303 | 1.00 | 103.95 | MOL2 | C |
| ATOM | 6408 | O   | ARG | D | 56 | 0.527  | −48.126 | −92.748 | 1.00 | 104.42 | MOL2 | O |
| ATOM | 6409 | N   | ASN | D | 57 | −0.179 | −46.763 | −91.088 | 1.00 | 101.45 | MOL2 | N |
| ATOM | 6410 | CA  | ASN | D | 57 | −0.503 | −47.800 | −90.117 | 1.00 | 98.58  | MOL2 | C |
| ATOM | 6411 | CB  | ASN | D | 57 | 0.499  | −48.949 | −90.176 | 1.00 | 100.68 | MOL2 | C |
| ATOM | 6412 | CG  | ASN | D | 57 | −0.112 | −50.208 | −90.740 | 1.00 | 103.67 | MOL2 | C |
| ATOM | 6413 | OD1 | ASN | D | 57 | −1.112 | −50.707 | −90.217 | 1.00 | 103.03 | MOL2 | O |
| ATOM | 6414 | ND2 | ASN | D | 57 | 0.477  | −50.729 | −91.816 | 1.00 | 102.70 | MOL2 | N |
| ATOM | 6415 | C   | ASN | D | 57 | −0.518 | −47.216 | −88.718 | 1.00 | 94.68  | MOL2 | C |
| ATOM | 6416 | O   | ASN | D | 57 | 0.530  | −46.956 | −88.128 | 1.00 | 94.60  | MOL2 | O |
| ATOM | 6417 | N   | THR | D | 58 | −1.718 | −46.993 | −88.199 | 1.00 | 90.14  | MOL2 | N |
| ATOM | 6418 | CA  | THR | D | 58 | −1.873 | −46.442 | −86.861 | 1.00 | 90.16  | MOL2 | C |
| ATOM | 6419 | CB  | THR | D | 58 | −2.844 | −45.271 | −86.835 | 1.00 | 89.77  | MOL2 | C |
| ATOM | 6420 | OG1 | THR | D | 58 | −4.171 | −45.757 | −87.075 | 1.00 | 86.89  | MOL2 | O |
| ATOM | 6421 | CG2 | THR | D | 58 | −2.465 | −44.246 | −87.890 | 1.00 | 89.64  | MOL2 | C |
| ATOM | 6422 | C   | THR | D | 58 | −2.457 | −47.535 | −85.992 | 1.00 | 91.44  | MOL2 | C |
| ATOM | 6423 | O   | THR | D | 58 | −3.041 | −48.484 | −86.517 | 1.00 | 92.68  | MOL2 | O |
| ATOM | 6424 | N   | TYR | D | 59 | −2.319 | −47.419 | −84.671 | 1.00 | 91.79  | MOL2 | N |
| ATOM | 6425 | CA  | TYR | D | 59 | −2.869 | −48.461 | −83.822 | 1.00 | 92.64  | MOL2 | C |
| ATOM | 6426 | CB  | TYR | D | 59 | −1.749 | −49.320 | −83.269 | 1.00 | 91.25  | MOL2 | C |
| ATOM | 6427 | CG  | TYR | D | 59 | −1.160 | −50.188 | −84.359 | 1.00 | 94.38  | MOL2 | C |
| ATOM | 6428 | CD1 | TYR | D | 59 | −0.217 | −49.680 | −85.243 | 1.00 | 95.77  | MOL2 | C |
| ATOM | 6429 | CE1 | TYR | D | 59 | 0.300  | −50.450 | −86.269 | 1.00 | 96.30  | MOL2 | C |
| ATOM | 6430 | CD2 | TYR | D | 59 | −1.576 | −51.501 | −84.532 | 1.00 | 93.99  | MOL2 | C |
| ATOM | 6431 | CE2 | TYR | D | 59 | −1.065 | −52.281 | −85.557 | 1.00 | 99.36  | MOL2 | C |
| ATOM | 6432 | CZ  | TYR | D | 59 | −0.123 | −51.749 | −86.424 | 1.00 | 99.00  | MOL2 | C |
| ATOM | 6433 | OH  | TYR | D | 59 | 0.409  | −52.514 | −87.443 | 1.00 | 99.74  | MOL2 | O |
| ATOM | 6434 | C   | TYR | D | 59 | −3.867 | −48.102 | −82.735 | 1.00 | 93.37  | MOL2 | C |
| ATOM | 6435 | O   | TYR | D | 59 | −4.913 | −48.750 | −82.641 | 1.00 | 96.61  | MOL2 | O |
| ATOM | 6436 | N   | TYR | D | 60 | −3.576 | −47.099 | −81.915 | 1.00 | 90.48  | MOL2 | N |
| ATOM | 6437 | CA  | TYR | D | 60 | −4.528 | −46.683 | −80.866 | 1.00 | 89.79  | MOL2 | C |
| ATOM | 6438 | CB  | TYR | D | 60 | −5.837 | −46.165 | −81.493 | 1.00 | 77.88  | MOL2 | C |
| ATOM | 6439 | CG  | TYR | D | 60 | −5.663 | −45.067 | −82.515 | 1.00 | 68.52  | MOL2 | C |
| ATOM | 6440 | CD1 | TYR | D | 60 | −5.633 | −45.354 | −83.868 | 1.00 | 64.19  | MOL2 | C |
| ATOM | 6441 | CE1 | TYR | D | 60 | −5.407 | −44.366 | −84.798 | 1.00 | 63.93  | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 6442 | CD2 | TYR | D | 60 | −5.469 | −43.749 | −82.120 | 1.00 | 66.79 | MOL2 | C |
|------|------|-----|-----|---|----|--------|---------|---------|------|-------|------|---|
| ATOM | 6443 | CE2 | TYR | D | 60 | −5.239 | −42.752 | −83.046 | 1.00 | 60.35 | MOL2 | C |
| ATOM | 6444 | CZ | TYR | D | 60 | −5.206 | −43.068 | −84.380 | 1.00 | 62.83 | MOL2 | C |
| ATOM | 6445 | OH | TYR | D | 60 | −4.941 | −42.088 | −85.304 | 1.00 | 62.53 | MOL2 | O |
| ATOM | 6446 | C | TYR | D | 60 | −4.910 | −47.703 | −79.776 | 1.00 | 91.68 | MOL2 | C |
| ATOM | 6447 | O | TYR | D | 60 | −4.931 | −48.921 | −79.983 | 1.00 | 94.46 | MOL2 | O |
| ATOM | 6448 | N | ARG | D | 61 | −5.247 | −47.164 | −78.614 | 1.00 | 90.81 | MOL2 | N |
| ATOM | 6449 | CA | ARG | D | 61 | −5.641 | −47.944 | −77.457 | 1.00 | 94.73 | MOL2 | C |
| ATOM | 6450 | CB | ARG | D | 61 | −5.288 | −47.146 | −76.213 | 1.00 | 95.67 | MOL2 | C |
| ATOM | 6451 | CG | ARG | D | 61 | −5.768 | −47.721 | −74.905 | 1.00 | 100.42 | MOL2 | C |
| ATOM | 6452 | CD | ARG | D | 61 | −5.581 | −46.685 | −73.814 | 1.00 | 100.21 | MOL2 | C |
| ATOM | 6453 | NE | ARG | D | 61 | −5.327 | −47.288 | −72.515 | 1.00 | 98.24 | MOL2 | N |
| ATOM | 6454 | CZ | ARG | D | 61 | −5.114 | −46.582 | −71.415 | 1.00 | 101.13 | MOL2 | C |
| ATOM | 6455 | NH1 | ARG | D | 61 | −5.131 | −45.257 | −71.476 | 1.00 | 102.89 | MOL2 | N |
| ATOM | 6456 | NH2 | ARG | D | 61 | −4.876 | −47.194 | −70.263 | 1.00 | 101.10 | MOL2 | N |
| ATOM | 6457 | C | ARG | D | 61 | −7.144 | −48.157 | −77.501 | 1.00 | 101.27 | MOL2 | C |
| ATOM | 6458 | O | ARG | D | 61 | −7.882 | −47.234 | −77.842 | 1.00 | 106.90 | MOL2 | O |
| ATOM | 6459 | N | ASP | D | 62 | −7.614 | −49.354 | −77.162 | 1.00 | 104.77 | MOL2 | N |
| ATOM | 6460 | CA | ASP | D | 62 | −9.060 | −49.592 | −77.167 | 1.00 | 102.92 | MOL2 | C |
| ATOM | 6461 | CB | ASP | D | 62 | −9.385 | −51.071 | −76.934 | 1.00 | 108.77 | MOL2 | C |
| ATOM | 6462 | CG | ASP | D | 62 | −9.107 | −51.927 | −78.159 | 1.00 | 118.71 | MOL2 | C |
| ATOM | 6463 | OD1 | ASP | D | 62 | −9.686 | −51.635 | −79.231 | 1.00 | 121.33 | MOL2 | O |
| ATOM | 6464 | OD2 | ASP | D | 62 | −8.312 | −52.888 | −78.054 | 1.00 | 122.02 | MOL2 | O |
| ATOM | 6465 | C | ASP | D | 62 | −9.693 | −48.752 | −76.074 | 1.00 | 97.24 | MOL2 | C |
| ATOM | 6466 | O | ASP | D | 62 | −10.092 | −49.275 | −75.042 | 1.00 | 98.94 | MOL2 | O |
| ATOM | 6467 | N | SER | D | 63 | −9.770 | −47.447 | −76.308 | 1.00 | 92.08 | MOL2 | N |
| ATOM | 6468 | CA | SER | D | 63 | −10.346 | −46.514 | −75.345 | 1.00 | 90.99 | MOL2 | C |
| ATOM | 6469 | CB | SER | D | 63 | −9.567 | −46.522 | −74.033 | 1.00 | 93.68 | MOL2 | C |
| ATOM | 6470 | OG | SER | D | 63 | −9.989 | −45.447 | −73.210 | 1.00 | 93.02 | MOL2 | O |
| ATOM | 6471 | C | SER | D | 63 | −10.358 | −45.096 | −75.880 | 1.00 | 90.23 | MOL2 | C |
| ATOM | 6472 | O | SER | D | 63 | −10.830 | −44.174 | −75.211 | 1.00 | 87.81 | MOL2 | O |
| ATOM | 6473 | N | VAL | D | 64 | −9.798 | −44.919 | −77.071 | 1.00 | 89.75 | MOL2 | N |
| ATOM | 6474 | CA | VAL | D | 64 | −9.780 | −43.613 | −77.718 | 1.00 | 88.97 | MOL2 | C |
| ATOM | 6475 | CB | VAL | D | 64 | −8.539 | −42.757 | −77.355 | 1.00 | 79.69 | MOL2 | C |
| ATOM | 6476 | CG1 | VAL | D | 64 | −8.510 | −42.484 | −75.875 | 1.00 | 78.62 | MOL2 | C |
| ATOM | 6477 | CG2 | VAL | D | 64 | −7.283 | −43.444 | −77.803 | 1.00 | 80.89 | MOL2 | C |
| ATOM | 6478 | C | VAL | D | 64 | −9.799 | −43.810 | −79.216 | 1.00 | 92.31 | MOL2 | C |
| ATOM | 6479 | O | VAL | D | 64 | −9.427 | −42.912 | −79.970 | 1.00 | 93.73 | MOL2 | O |
| ATOM | 6480 | N | LYS | D | 65 | −10.231 | −44.991 | −79.646 | 1.00 | 95.44 | MOL2 | N |
| ATOM | 6481 | CA | LYS | D | 65 | −10.302 | −45.274 | −81.068 | 1.00 | 104.70 | MOL2 | C |
| ATOM | 6482 | CB | LYS | D | 65 | −10.561 | −46.767 | −81.295 | 1.00 | 110.03 | MOL2 | C |
| ATOM | 6483 | CG | LYS | D | 65 | −10.427 | −47.214 | −82.750 | 1.00 | 120.86 | MOL2 | C |
| ATOM | 6484 | CD | LYS | D | 65 | −10.767 | −48.697 | −82.898 | 1.00 | 131.56 | MOL2 | C |
| ATOM | 6485 | CE | LYS | D | 65 | −10.699 | −49.167 | −84.351 | 1.00 | 134.98 | MOL2 | C |
| ATOM | 6486 | NZ | LYS | D | 65 | −11.066 | −50.612 | −84.486 | 1.00 | 134.04 | MOL2 | N |
| ATOM | 6487 | C | LYS | D | 65 | −11.423 | −44.420 | −81.677 | 1.00 | 107.60 | MOL2 | C |
| ATOM | 6488 | O | LYS | D | 65 | −12.437 | −44.143 | −81.025 | 1.00 | 106.75 | MOL2 | O |
| ATOM | 6489 | N | GLY | D | 66 | −11.227 | −43.987 | −82.920 | 1.00 | 108.89 | MOL2 | N |
| ATOM | 6490 | CA | GLY | D | 66 | −12.226 | −43.163 | −83.579 | 1.00 | 108.07 | MOL2 | C |
| ATOM | 6491 | C | GLY | D | 66 | −12.202 | −41.732 | −83.069 | 1.00 | 108.09 | MOL2 | C |
| ATOM | 6492 | O | GLY | D | 66 | −12.325 | −40.778 | −83.853 | 1.00 | 111.82 | MOL2 | O |
| ATOM | 6493 | N | ARG | D | 67 | −12.031 | −41.583 | −81.756 | 1.00 | 100.42 | MOL2 | N |
| ATOM | 6494 | CA | ARG | D | 67 | −11.997 | −40.271 | −81.119 | 1.00 | 96.02 | MOL2 | C |
| ATOM | 6495 | CB | ARG | D | 67 | −12.311 | −40.427 | −79.633 | 1.00 | 92.86 | MOL2 | C |
| ATOM | 6496 | CG | ARG | D | 67 | −12.980 | −39.325 | −79.320 | 1.00 | 93.72 | MOL2 | C |
| ATOM | 6497 | CD | ARG | D | 67 | −13.668 | −41.794 | −77.965 | 1.00 | 97.60 | MOL2 | C |
| ATOM | 6498 | NE | ARG | D | 67 | −12.752 | −41.696 | −76.830 | 1.00 | 100.96 | MOL2 | N |
| ATOM | 6499 | CZ | ARG | D | 67 | −12.272 | −40.556 | −76.340 | 1.00 | 102.31 | MOL2 | C |
| ATOM | 6500 | NH1 | ARG | D | 67 | −11.443 | −40.583 | −75.301 | 1.00 | 95.79 | MOL2 | N |
| ATOM | 6501 | NH2 | ARG | D | 67 | −12.624 | −39.392 | −76.879 | 1.00 | 99.79 | MOL2 | N |
| ATOM | 6502 | C | ARG | D | 67 | −10.643 | −39.592 | −81.313 | 1.00 | 97.11 | MOL2 | C |
| ATOM | 6503 | O | ARG | D | 67 | −10.574 | −38.372 | −81.491 | 1.00 | 96.74 | MOL2 | O |
| ATOM | 6504 | N | PHE | D | 68 | −9.573 | −40.387 | −81.280 | 1.00 | 95.76 | MOL2 | N |
| ATOM | 6505 | CA | PHE | D | 68 | −8.216 | −39.876 | −81.464 | 1.00 | 92.42 | MOL2 | C |
| ATOM | 6506 | CB | PHE | D | 68 | −7.263 | −40.475 | −80.427 | 1.00 | 91.66 | MOL2 | C |
| ATOM | 6507 | CG | PHE | D | 68 | −7.269 | −39.756 | −79.106 | 1.00 | 93.60 | MOL2 | C |
| ATOM | 6508 | CD1 | PHE | D | 68 | −7.987 | −38.589 | −78.939 | 1.00 | 91.22 | MOL2 | C |
| ATOM | 6509 | CD2 | PHE | D | 68 | −6.535 | −40.239 | −78.035 | 1.00 | 94.01 | MOL2 | C |
| ATOM | 6510 | CE1 | PHE | D | 68 | −7.970 | −37.924 | −77.735 | 1.00 | 88.23 | MOL2 | C |
| ATOM | 6511 | CE2 | PHE | D | 68 | −6.517 | −39.571 | −76.828 | 1.00 | 90.67 | MOL2 | C |
| ATOM | 6512 | CZ | PHE | D | 68 | −7.234 | −38.413 | −76.681 | 1.00 | 87.13 | MOL2 | C |
| ATOM | 6513 | C | PHE | D | 68 | −7.707 | −40.204 | −82.857 | 1.00 | 90.96 | MOL2 | C |
| ATOM | 6514 | O | PHE | D | 68 | −8.232 | −41.104 | −83.523 | 1.00 | 87.76 | MOL2 | O |
| ATOM | 6515 | N | THR | D | 69 | −6.675 | −39.473 | −83.279 | 1.00 | 90.57 | MOL2 | N |
| ATOM | 6516 | CA | THR | D | 69 | −6.069 | −39.647 | −84.595 | 1.00 | 91.01 | MOL2 | C |
| ATOM | 6517 | CB | THR | D | 69 | −6.830 | −38.814 | −85.658 | 1.00 | 102.06 | MOL2 | C |
| ATOM | 6518 | OG1 | THR | D | 69 | −8.195 | −39.262 | −85.735 | 1.00 | 110.64 | MOL2 | O |

TABLE 1-continued

The atomic coordinates of IL17F in complex with 496 Fab
(H32; a = 189.4; b = 189.4; c = 490.9, α, β = 90°; γ = 120°)

| ATOM | 6519 | CG2 | THR | D | 69 | −6.166 | −38.948 | −87.030 | 1.00 | 104.69 | MOL2 | C |
|---|---|---|---|---|---|---|---|---|---|---|---|---|
| ATOM | 6520 | C | THR | D | 69 | −4.598 | −39.222 | −84.595 | 1.00 | 82.97 | MOL2 | C |
| ATOM | 6521 | O | THR | D | 69 | −4.284 | −38.044 | −84.439 | 1.00 | 75.27 | MOL2 | O |
| ATOM | 6522 | N | ILE | D | 70 | −3.705 | −40.191 | −84.779 | 1.00 | 80.23 | MOL2 | N |
| ATOM | 6523 | CA | ILE | D | 70 | −2.264 | −39.944 | −84.799 | 1.00 | 77.34 | MOL2 | C |
| ATOM | 6524 | CB | ILE | D | 70 | −1.502 | −41.109 | −84.119 | 1.00 | 79.22 | MOL2 | C |
| ATOM | 6525 | CG2 | ILE | D | 70 | −1.609 | −42.366 | −84.980 | 1.00 | 75.94 | MOL2 | C |
| ATOM | 6526 | CG1 | ILE | D | 70 | −0.040 | −40.718 | −83.864 | 1.00 | 78.09 | MOL2 | C |
| ATOM | 6527 | CD1 | ILE | D | 70 | 0.751 | −41.757 | −83.079 | 1.00 | 70.08 | MOL2 | C |
| ATOM | 6528 | C | ILE | D | 70 | −1.770 | −39.790 | −86.236 | 1.00 | 75.49 | MOL2 | C |
| ATOM | 6529 | O | ILE | D | 70 | −2.178 | −40.531 | −87.129 | 1.00 | 74.46 | MOL2 | O |
| ATOM | 6530 | N | SER | D | 71 | −0.875 | −38.836 | −86.455 | 1.00 | 74.47 | MOL2 | N |
| ATOM | 6531 | CA | SER | D | 71 | −0.372 | −38.586 | −87.799 | 1.00 | 76.63 | MOL2 | C |
| ATOM | 6532 | CB | SER | D | 71 | −1.278 | −37.584 | −88.484 | 1.00 | 82.72 | MOL2 | C |
| ATOM | 6533 | OG | SER | D | 71 | −1.178 | −36.331 | −87.812 | 1.00 | 80.06 | MOL2 | O |
| ATOM | 6534 | C | SER | D | 71 | 1.019 | −37.984 | −87.776 | 1.00 | 77.66 | MOL2 | C |
| ATOM | 6535 | O | SER | D | 71 | 1.397 | −37.343 | −86.793 | 1.00 | 76.58 | MOL2 | O |
| ATOM | 6536 | N | ARG | D | 72 | 1.758 | −38.153 | −88.875 | 1.00 | 74.37 | MOL2 | N |
| ATOM | 6537 | CA | ARG | D | 72 | 3.104 | −37.591 | −88.979 | 1.00 | 75.79 | MOL2 | C |
| ATOM | 6538 | CB | ARG | D | 72 | 4.164 | −38.665 | −88.730 | 1.00 | 70.15 | MOL2 | C |
| ATOM | 6539 | CG | ARG | D | 72 | 4.143 | −39.800 | −89.717 | 1.00 | 72.34 | MOL2 | C |
| ATOM | 6540 | CD | ARG | D | 72 | 4.925 | −40.991 | −89.201 | 1.00 | 69.56 | MOL2 | C |
| ATOM | 6541 | NE | ARG | D | 72 | 6.348 | −40.709 | −89.071 | 1.00 | 73.65 | MOL2 | N |
| ATOM | 6542 | CZ | ARG | D | 72 | 7.192 | −41.476 | −88.388 | 1.00 | 77.79 | MOL2 | C |
| ATOM | 6543 | NH1 | ARG | D | 72 | 6.746 | −42.565 | −87.774 | 1.00 | 77.00 | MOL2 | N |
| ATOM | 6544 | NH2 | ARG | D | 72 | 8.479 | −41.157 | −88.316 | 1.00 | 77.02 | MOL2 | N |
| ATOM | 6545 | C | ARG | D | 72 | 3.351 | −36.924 | −90.327 | 1.00 | 79.00 | MOL2 | C |
| ATOM | 6546 | O | ARG | D | 72 | 2.566 | −37.088 | −91.267 | 1.00 | 80.72 | MOL2 | O |
| ATOM | 6547 | N | ASP | D | 73 | 4.455 | −36.183 | −90.410 | 1.00 | 82.17 | MOL2 | N |
| ATOM | 6548 | CA | ASP | D | 73 | 4.832 | −35.450 | −91.615 | 1.00 | 87.06 | MOL2 | C |
| ATOM | 6549 | CB | ASP | D | 73 | 5.075 | −33.983 | −91.238 | 1.00 | 91.76 | MOL2 | C |
| ATOM | 6550 | CG | ASP | D | 73 | 4.737 | −33.015 | −92.363 | 1.00 | 99.70 | MOL2 | C |
| ATOM | 6551 | OD1 | ASP | D | 73 | 4.754 | −31.786 | −92.108 | 1.00 | 100.05 | MOL2 | O |
| ATOM | 6552 | OD2 | ASP | D | 73 | 4.457 | −33.476 | −93.495 | 1.00 | 101.53 | MOL2 | O |
| ATOM | 6553 | C | ASP | D | 73 | 6.084 | −36.020 | −92.290 | 1.00 | 87.31 | MOL2 | C |
| ATOM | 6554 | O | ASP | D | 73 | 6.133 | −36.178 | −93.509 | 1.00 | 93.87 | MOL2 | O |
| ATOM | 6555 | N | ASN | D | 74 | 7.094 | −36.328 | −91.487 | 1.00 | 84.23 | MOL2 | N |
| ATOM | 6556 | CA | ASN | D | 74 | 8.351 | −36.850 | −91.999 | 1.00 | 79.42 | MOL2 | C |
| ATOM | 6557 | CB | ASN | D | 74 | 8.115 | −37.996 | −92.963 | 1.00 | 72.75 | MOL2 | C |
| ATOM | 6558 | CG | ASN | D | 74 | 7.733 | −39.255 | −92.251 | 1.00 | 73.16 | MOL2 | C |
| ATOM | 6559 | OD1 | ASN | D | 74 | 7.630 | −40.318 | −92.853 | 1.00 | 80.95 | MOL2 | O |
| ATOM | 6560 | ND2 | ASN | D | 74 | 7.519 | −39.146 | −90.948 | 1.00 | 68.82 | MOL2 | N |
| ATOM | 6561 | C | ASN | D | 74 | 9.090 | −35.723 | −92.677 | 1.00 | 81.64 | MOL2 | C |
| ATOM | 6562 | O | ASN | D | 74 | 10.296 | −35.799 | −92.909 | 1.00 | 87.26 | MOL2 | O |
| ATOM | 6563 | N | ALA | D | 75 | 8.345 | −34.681 | −93.015 | 1.00 | 77.76 | MOL2 | N |
| ATOM | 6564 | CA | ALA | D | 75 | 8.923 | −33.491 | −93.592 | 1.00 | 76.86 | MOL2 | C |
| ATOM | 6565 | CB | ALA | D | 75 | 8.081 | −33.000 | −94.724 | 1.00 | 71.80 | MOL2 | C |
| ATOM | 6566 | C | ALA | D | 75 | 8.761 | −32.611 | −92.364 | 1.00 | 84.05 | MOL2 | C |
| ATOM | 6567 | O | ALA | D | 75 | 7.855 | −32.850 | −91.554 | 1.00 | 81.14 | MOL2 | O |
| ATOM | 6568 | N | LYS | D | 76 | 9.635 | −31.626 | −92.195 | 1.00 | 90.91 | MOL2 | N |
| ATOM | 6569 | CA | LYS | D | 76 | 9.582 | −30.745 | −91.021 | 1.00 | 98.36 | MOL2 | C |
| ATOM | 6570 | CB | LYS | D | 76 | 8.387 | −29.779 | −91.114 | 1.00 | 103.87 | MOL2 | C |
| ATOM | 6571 | CG | LYS | D | 76 | 8.652 | −28.418 | −90.455 | 1.00 | 109.13 | MOL2 | C |
| ATOM | 6572 | CD | LYS | D | 76 | 7.739 | −27.316 | −91.012 | 1.00 | 115.11 | MOL2 | C |
| ATOM | 6573 | CE | LYS | D | 76 | 8.117 | −25.936 | −90.450 | 1.00 | 116.96 | MOL2 | C |
| ATOM | 6574 | NZ | LYS | D | 76 | 7.366 | −24.796 | −91.063 | 1.00 | 109.06 | MOL2 | N |
| ATOM | 6575 | C | LYS | D | 76 | 9.555 | −31.533 | −89.690 | 1.00 | 96.32 | MOL2 | C |
| ATOM | 6576 | O | LYS | D | 76 | 9.290 | −30.967 | −88.622 | 1.00 | 97.98 | MOL2 | O |
| ATOM | 6577 | N | ASN | D | 77 | 9.832 | −32.837 | −89.780 | 1.00 | 90.60 | MOL2 | N |
| ATOM | 6578 | CA | ASN | D | 77 | 9.923 | −33.741 | −88.630 | 1.00 | 80.86 | MOL2 | C |
| ATOM | 6579 | CB | ASN | D | 77 | 11.292 | −33.577 | −87.936 | 1.00 | 86.75 | MOL2 | C |
| ATOM | 6580 | CG | ASN | D | 77 | 12.456 | −33.342 | −88.912 | 1.00 | 87.19 | MOL2 | C |
| ATOM | 6581 | OD1 | ASN | D | 77 | 13.420 | −32.625 | −88.588 | 1.00 | 78.03 | MOL2 | O |
| ATOM | 6582 | ND2 | ASN | D | 77 | 12.386 | −33.959 | −90.091 | 1.00 | 87.81 | MOL2 | N |
| ATOM | 6583 | C | ASN | D | 77 | 8.868 | −33.504 | −87.565 | 1.00 | 73.53 | MOL2 | C |
| ATOM | 6584 | O | ASN | D | 77 | 9.196 | −32.963 | −86.514 | 1.00 | 76.79 | MOL2 | O |
| ATOM | 6585 | N | SER | D | 78 | 7.623 | −33.897 | −87.786 | 1.00 | 63.94 | MOL2 | N |
| ATOM | 6586 | CA | SER | D | 78 | 6.628 | −33.653 | −86.743 | 1.00 | 56.85 | MOL2 | C |
| ATOM | 6587 | CB | SER | D | 78 | 5.863 | −32.354 | −87.005 | 1.00 | 59.67 | MOL2 | C |
| ATOM | 6588 | OG | SER | D | 78 | 6.551 | −31.227 | −86.488 | 1.00 | 63.76 | MOL2 | O |
| ATOM | 6589 | C | SER | D | 78 | 5.644 | −34.772 | −86.520 | 1.00 | 50.99 | MOL2 | C |
| ATOM | 6590 | O | SER | D | 78 | 5.284 | −35.496 | −87.443 | 1.00 | 48.98 | MOL2 | O |
| ATOM | 6591 | N | LEU | D | 79 | 5.209 | −34.885 | −85.272 | 1.00 | 46.07 | MOL2 | N |
| ATOM | 6592 | CA | LEU | D | 79 | 4.279 | −35.912 | −84.849 | 1.00 | 50.82 | MOL2 | C |
| ATOM | 6593 | CB | LEU | D | 79 | 4.934 | −36.741 | −83.755 | 1.00 | 43.72 | MOL2 | C |
| ATOM | 6594 | CG | LEU | D | 79 | 4.076 | −37.885 | −83.244 | 1.00 | 46.89 | MOL2 | C |
| ATOM | 6595 | CD1 | LEU | D | 79 | 3.956 | −38.948 | −84.311 | 1.00 | 36.23 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 6596 | CD2 | LEU | D | 79 | 4.702 | −38.440 | −81.987 | 1.00 | 54.82 | MOL2 | C |
|---|---|---|---|---|---|---|---|---|---|---|---|---|
| ATOM | 6597 | C | LEU | D | 79 | 3.042 | −35.221 | −84.297 | 1.00 | 57.32 | MOL2 | C |
| ATOM | 6598 | O | LEU | D | 79 | 3.165 | −34.319 | −83.467 | 1.00 | 63.41 | MOL2 | O |
| ATOM | 6599 | N | TYR | D | 80 | 1.855 | −35.652 | −84.725 | 1.00 | 59.14 | MOL2 | N |
| ATOM | 6600 | CA | TYR | D | 80 | 0.620 | −35.016 | −84.274 | 1.00 | 58.02 | MOL2 | C |
| ATOM | 6601 | CB | TYR | D | 80 | −0.059 | −34.341 | −85.453 | 1.00 | 60.14 | MOL2 | C |
| ATOM | 6602 | CG | TYR | D | 80 | 0.807 | −33.393 | −86.229 | 1.00 | 54.99 | MOL2 | C |
| ATOM | 6603 | CD1 | TYR | D | 80 | 1.178 | −32.170 | −85.683 | 1.00 | 52.64 | MOL2 | C |
| ATOM | 6604 | CE1 | TYR | D | 80 | 1.939 | −31.278 | −86.402 | 1.00 | 59.89 | MOL2 | C |
| ATOM | 6605 | CD2 | TYR | D | 80 | 1.228 | −33.706 | −87.523 | 1.00 | 47.37 | MOL2 | C |
| ATOM | 6606 | CE2 | TYR | D | 80 | 1.992 | −32.821 | −88.252 | 1.00 | 52.27 | MOL2 | C |
| ATOM | 6607 | CZ | TYR | D | 80 | 2.344 | −31.603 | −87.686 | 1.00 | 59.50 | MOL2 | C |
| ATOM | 6608 | OH | TYR | D | 80 | 3.098 | −30.691 | −88.391 | 1.00 | 64.84 | MOL2 | O |
| ATOM | 6609 | C | TYR | D | 80 | −0.396 | −35.957 | −83.665 | 1.00 | 59.54 | MOL2 | C |
| ATOM | 6610 | O | TYR | D | 80 | −0.469 | −37.137 | −84.037 | 1.00 | 58.51 | MOL2 | O |
| ATOM | 6611 | N | LEU | D | 81 | −1.195 | −35.416 | −82.744 | 1.00 | 60.10 | MOL2 | N |
| ATOM | 6612 | CA | LEU | D | 81 | −2.271 | −36.185 | −82.126 | 1.00 | 67.71 | MOL2 | C |
| ATOM | 6613 | CB | LEU | D | 81 | −1.956 | −36.545 | −80.669 | 1.00 | 62.82 | MOL2 | C |
| ATOM | 6614 | CG | LEU | D | 81 | −2.938 | −37.601 | −80.125 | 1.00 | 61.33 | MOL2 | C |
| ATOM | 6615 | CD1 | LEU | D | 81 | −2.759 | −38.913 | −80.868 | 1.00 | 45.84 | MOL2 | C |
| ATOM | 6616 | CD2 | LEU | D | 81 | −2.724 | −37.810 | −78.642 | 1.00 | 65.24 | MOL2 | C |
| ATOM | 6617 | C | LEU | D | 81 | −3.561 | −35.360 | −82.184 | 1.00 | 71.66 | MOL2 | C |
| ATOM | 6618 | O | LEU | D | 81 | −3.623 | −34.248 | −81.641 | 1.00 | 62.04 | MOL2 | O |
| ATOM | 6619 | N | GLN | D | 82 | −4.575 | −35.905 | −82.865 | 1.00 | 78.53 | MOL2 | N |
| ATOM | 6620 | CA | GLN | D | 82 | −5.869 | −35.236 | −82.999 | 1.00 | 82.97 | MOL2 | C |
| ATOM | 6621 | CB | GLN | D | 82 | −6.431 | −35.399 | −84.418 | 1.00 | 88.33 | MOL2 | C |
| ATOM | 6622 | CG | GLN | D | 82 | −7.588 | −34.445 | −84.723 | 1.00 | 84.59 | MOL2 | C |
| ATOM | 6623 | CD | GLN | D | 82 | −7.160 | −32.983 | −84.694 | 1.00 | 82.81 | MOL2 | C |
| ATOM | 6624 | OE1 | GLN | D | 82 | −6.554 | −32.483 | −85.643 | 1.00 | 87.05 | MOL2 | O |
| ATOM | 6625 | NE2 | GLN | D | 82 | −7.464 | −32.298 | −83.599 | 1.00 | 72.36 | MOL2 | N |
| ATOM | 6626 | C | GLN | D | 82 | −6.849 | −35.823 | −81.992 | 1.00 | 81.23 | MOL2 | C |
| ATOM | 6627 | O | GLN | D | 82 | −7.336 | −36.948 | −82.150 | 1.00 | 75.67 | MOL2 | O |
| ATOM | 6628 | N | MET | D | 83 | −7.130 | −35.040 | −80.959 | 1.00 | 82.00 | MOL2 | N |
| ATOM | 6629 | CA | MET | D | 83 | −8.024 | −35.448 | −79.890 | 1.00 | 86.17 | MOL2 | C |
| ATOM | 6630 | CB | MET | D | 83 | −7.446 | −34.980 | −78.541 | 1.00 | 88.02 | MOL2 | C |
| ATOM | 6631 | CG | MET | D | 83 | −6.007 | −35.464 | −78.206 | 1.00 | 80.98 | MOL2 | C |
| ATOM | 6632 | SD | MET | D | 83 | −5.522 | −35.280 | −76.425 | 1.00 | 79.63 | MOL2 | S |
| ATOM | 6633 | CE | MET | D | 83 | −4.961 | −33.553 | −76.357 | 1.00 | 52.91 | MOL2 | C |
| ATOM | 6634 | C | MET | D | 83 | −9.443 | −34.886 | −80.061 | 1.00 | 91.51 | MOL2 | C |
| ATOM | 6635 | O | MET | D | 83 | −9.687 | −33.714 | −79.761 | 1.00 | 87.76 | MOL2 | O |
| ATOM | 6636 | N | ASN | D | 84 | −10.370 | −35.726 | −80.532 | 1.00 | 96.49 | MOL2 | N |
| ATOM | 6637 | CA | ASN | D | 84 | −11.769 | −35.331 | −80.739 | 1.00 | 99.14 | MOL2 | C |
| ATOM | 6638 | CB | ASN | D | 84 | −12.297 | −35.848 | −82.084 | 1.00 | 95.82 | MOL2 | C |
| ATOM | 6639 | CG | ASN | D | 84 | −11.383 | −35.533 | −83.243 | 1.00 | 93.42 | MOL2 | C |
| ATOM | 6640 | OD1 | ASN | D | 84 | −10.973 | −34.386 | −83.436 | 1.00 | 86.04 | MOL2 | O |
| ATOM | 6641 | ND2 | ASN | D | 84 | −11.072 | −36.554 | −84.040 | 1.00 | 94.89 | MOL2 | N |
| ATOM | 6642 | C | ASN | D | 84 | −12.653 | −35.927 | −79.649 | 1.00 | 103.46 | MOL2 | C |
| ATOM | 6643 | O | ASN | D | 84 | −12.306 | −36.954 | −79.062 | 1.00 | 107.51 | MOL2 | O |
| ATOM | 6644 | N | SER | D | 85 | −13.804 | −35.305 | −79.398 | 1.00 | 105.03 | MOL2 | N |
| ATOM | 6645 | CA | SER | D | 85 | −14.740 | −35.813 | −78.392 | 1.00 | 107.26 | MOL2 | C |
| ATOM | 6646 | CB | SER | D | 85 | −15.378 | −37.132 | −78.866 | 1.00 | 111.39 | MOL2 | C |
| ATOM | 6647 | OG | SER | D | 85 | −16.139 | −36.967 | −80.052 | 1.00 | 116.59 | MOL2 | O |
| ATOM | 6648 | C | SER | D | 85 | −14.032 | −36.065 | −77.067 | 1.00 | 104.93 | MOL2 | C |
| ATOM | 6649 | O | SER | D | 85 | −14.312 | −37.052 | −76.378 | 1.00 | 105.14 | MOL2 | O |
| ATOM | 6650 | N | LEU | D | 86 | −13.113 | −35.174 | −76.720 | 1.00 | 99.33 | MOL2 | N |
| ATOM | 6651 | CA | LEU | D | 86 | −12.354 | −35.304 | −75.486 | 1.00 | 98.56 | MOL2 | C |
| ATOM | 6652 | CB | LEU | D | 86 | −11.593 | −34.007 | −75.189 | 1.00 | 98.51 | MOL2 | C |
| ATOM | 6653 | CG | LEU | D | 86 | −10.273 | −33.733 | −75.920 | 1.00 | 99.69 | MOL2 | C |
| ATOM | 6654 | CD1 | LEU | D | 86 | −9.790 | −32.325 | −75.618 | 1.00 | 96.54 | MOL2 | C |
| ATOM | 6655 | CD2 | LEU | D | 86 | −9.231 | −34.743 | −75.481 | 1.00 | 98.93 | MOL2 | C |
| ATOM | 6656 | C | LEU | D | 86 | −13.202 | −35.643 | −74.272 | 1.00 | 98.72 | MOL2 | C |
| ATOM | 6657 | O | LEU | D | 86 | −13.931 | −34.790 | −73.778 | 1.00 | 98.95 | MOL2 | O |
| ATOM | 6658 | N | ARG | D | 87 | −13.111 | −36.883 | −73.794 | 1.00 | 101.21 | MOL2 | N |
| ATOM | 6659 | CA | ARG | D | 87 | −13.843 | −37.291 | −72.594 | 1.00 | 101.51 | MOL2 | C |
| ATOM | 6660 | CB | ARG | D | 87 | −13.814 | −38.819 | −72.419 | 1.00 | 105.31 | MOL2 | C |
| ATOM | 6661 | CG | ARG | D | 87 | −14.538 | −39.626 | −73.504 | 1.00 | 113.87 | MOL2 | C |
| ATOM | 6662 | CD | ARG | D | 87 | −16.036 | −39.755 | −73.237 | 1.00 | 125.62 | MOL2 | C |
| ATOM | 6663 | NE | ARG | D | 87 | −16.714 | −40.567 | −74.249 | 1.00 | 134.03 | MOL2 | N |
| ATOM | 6664 | CZ | ARG | D | 87 | −18.010 | −40.878 | −74.227 | 1.00 | 137.45 | MOL2 | C |
| ATOM | 6665 | NH1 | ARG | D | 87 | −18.788 | −40.449 | −73.240 | 1.00 | 138.83 | MOL2 | N |
| ATOM | 6666 | NH2 | ARG | D | 87 | −18.530 | −41.622 | −75.196 | 1.00 | 137.42 | MOL2 | N |
| ATOM | 6667 | C | ARG | D | 87 | −13.105 | −36.621 | −71.428 | 1.00 | 98.36 | MOL2 | C |
| ATOM | 6668 | O | ARG | D | 87 | −12.152 | −35.875 | −71.640 | 1.00 | 94.50 | MOL2 | O |
| ATOM | 6669 | N | ALA | D | 88 | −13.533 | −36.885 | −70.202 | 1.00 | 98.54 | MOL2 | N |
| ATOM | 6670 | CA | ALA | D | 88 | −12.891 | −36.278 | −69.044 | 1.00 | 100.19 | MOL2 | C |
| ATOM | 6671 | CB | ALA | D | 88 | −13.930 | −36.014 | −67.968 | 1.00 | 103.20 | MOL2 | C |
| ATOM | 6672 | C | ALA | D | 88 | −11.786 | −37.181 | −68.500 | 1.00 | 101.21 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 6673 | O | ALA | D | 88 | −10.823 | −36.717 | −67.872 | 1.00 | 95.02 | MOL2 | O |
|---|---|---|---|---|---|---|---|---|---|---|---|---|
| ATOM | 6674 | N | GLU | D | 89 | −11.938 | −38.478 | −68.746 | 1.00 | 100.97 | MOL2 | N |
| ATOM | 6675 | CA | GLU | D | 89 | −10.964 | −39.454 | −68.290 | 1.00 | 101.58 | MOL2 | C |
| ATOM | 6676 | CB | GLU | D | 89 | −11.575 | −40.863 | −68.315 | 1.00 | 104.95 | MOL2 | C |
| ATOM | 6677 | CG | GLU | D | 89 | −11.812 | −41.452 | −69.702 | 1.00 | 111.56 | MOL2 | C |
| ATOM | 6678 | CD | GLU | D | 89 | −12.453 | −42.838 | −69.654 | 1.00 | 117.47 | MOL2 | C |
| ATOM | 6679 | OE1 | GLU | D | 89 | −12.602 | −43.472 | −70.724 | 1.00 | 117.62 | MOL2 | O |
| ATOM | 6680 | OE2 | GLU | D | 89 | −12.813 | −43.294 | −68.545 | 1.00 | 120.03 | MOL2 | O |
| ATOM | 6681 | C | GLU | D | 89 | −9.718 | −39.404 | −69.172 | 1.00 | 100.85 | MOL2 | C |
| ATOM | 6682 | O | GLU | D | 89 | −8.835 | −40.258 | −69.063 | 1.00 | 104.28 | MOL2 | O |
| ATOM | 6683 | N | ASP | D | 90 | −9.648 | −38.398 | −70.042 | 1.00 | 96.71 | MOL2 | N |
| ATOM | 6684 | CA | ASP | D | 90 | −8.510 | −38.248 | −70.941 | 1.00 | 88.61 | MOL2 | C |
| ATOM | 6685 | CB | ASP | D | 90 | −8.964 | −37.840 | −72.340 | 1.00 | 88.20 | MOL2 | C |
| ATOM | 6686 | CG | ASP | D | 90 | −9.630 | −38.978 | −73.087 | 1.00 | 94.26 | MOL2 | C |
| ATOM | 6687 | OD1 | ASP | D | 90 | −9.246 | −40.146 | −72.846 | 1.00 | 97.45 | MOL2 | O |
| ATOM | 6688 | OD2 | ASP | D | 90 | −10.522 | −38.707 | −73.923 | 1.00 | 88.46 | MOL2 | O |
| ATOM | 6689 | C | ASP | D | 90 | −7.506 | −37.237 | −70.443 | 1.00 | 84.13 | MOL2 | C |
| ATOM | 6690 | O | ASP | D | 90 | −6.471 | −37.051 | −71.072 | 1.00 | 82.84 | MOL2 | O |
| ATOM | 6691 | N | THR | D | 91 | −7.806 | −36.577 | −69.323 | 1.00 | 80.97 | MOL2 | N |
| ATOM | 6692 | CA | THR | D | 91 | −6.872 | −35.588 | −68.770 | 1.00 | 78.78 | MOL2 | C |
| ATOM | 6693 | CB | THR | D | 91 | −7.379 | −34.903 | −67.480 | 1.00 | 76.06 | MOL2 | C |
| ATOM | 6694 | OG1 | THR | D | 91 | −8.269 | −33.836 | −67.810 | 1.00 | 74.74 | MOL2 | O |
| ATOM | 6695 | CG2 | THR | D | 91 | −6.198 | −34.323 | −66.690 | 1.00 | 67.86 | MOL2 | C |
| ATOM | 6696 | C | THR | D | 91 | −5.568 | −36.264 | −68.400 | 1.00 | 80.42 | MOL2 | C |
| ATOM | 6697 | O | THR | D | 91 | −5.576 | −37.339 | −67.798 | 1.00 | 85.81 | MOL2 | O |
| ATOM | 6698 | N | ALA | D | 92 | −4.453 | −35.624 | −68.740 | 1.00 | 77.33 | MOL2 | N |
| ATOM | 6699 | CA | ALA | D | 92 | −3.137 | −36.179 | −68.450 | 1.00 | 73.83 | MOL2 | C |
| ATOM | 6700 | CB | ALA | D | 92 | −3.067 | −37.628 | −68.946 | 1.00 | 69.79 | MOL2 | C |
| ATOM | 6701 | C | ALA | D | 92 | −2.025 | −35.377 | −69.111 | 1.00 | 72.09 | MOL2 | C |
| ATOM | 6702 | O | ALA | D | 92 | −2.260 | −34.351 | −69.749 | 1.00 | 72.25 | MOL2 | O |
| ATOM | 6703 | N | VAL | D | 93 | −0.797 | −35.849 | −68.935 | 1.00 | 70.26 | MOL2 | N |
| ATOM | 6704 | CA | VAL | D | 93 | 0.334 | −35.221 | −69.585 | 1.00 | 65.02 | MOL2 | C |
| ATOM | 6705 | CB | VAL | D | 93 | 1.548 | −35.120 | −68.688 | 1.00 | 61.28 | MOL2 | C |
| ATOM | 6706 | CG1 | VAL | D | 93 | 2.746 | −34.691 | −69.522 | 1.00 | 46.91 | MOL2 | C |
| ATOM | 6707 | CG2 | VAL | D | 93 | 1.272 | −34.123 | −67.562 | 1.00 | 60.55 | MOL2 | C |
| ATOM | 6708 | C | VAL | D | 93 | 0.645 | −36.152 | −70.744 | 1.00 | 67.42 | MOL2 | C |
| ATOM | 6709 | O | VAL | D | 93 | 0.847 | −37.366 | −70.559 | 1.00 | 64.71 | MOL2 | O |
| ATOM | 6710 | N | TYR | D | 94 | 0.643 | −35.584 | −71.944 | 1.00 | 65.44 | MOL2 | N |
| ATOM | 6711 | CA | TYR | D | 94 | 0.886 | −36.368 | −73.127 | 1.00 | 61.43 | MOL2 | C |
| ATOM | 6712 | CB | TYR | D | 94 | −0.046 | −35.902 | −74.241 | 1.00 | 63.00 | MOL2 | C |
| ATOM | 6713 | CG | TYR | D | 94 | −1.454 | −36.380 | −73.983 | 1.00 | 61.43 | MOL2 | C |
| ATOM | 6714 | CD1 | TYR | D | 94 | −2.186 | −35.883 | −72.907 | 1.00 | 58.91 | MOL2 | C |
| ATOM | 6715 | CE1 | TYR | D | 94 | −3.426 | −36.398 | −72.586 | 1.00 | 65.56 | MOL2 | C |
| ATOM | 6716 | CD2 | TYR | D | 94 | −2.008 | −37.405 | −74.742 | 1.00 | 62.03 | MOL2 | C |
| ATOM | 6717 | CE2 | TYR | D | 94 | −3.248 | −37.929 | −74.433 | 1.00 | 71.17 | MOL2 | C |
| ATOM | 6718 | CZ | TYR | D | 94 | −3.954 | −37.425 | −73.350 | 1.00 | 74.81 | MOL2 | C |
| ATOM | 6719 | OH | TYR | D | 94 | −5.178 | −37.977 | −73.017 | 1.00 | 83.02 | MOL2 | O |
| ATOM | 6720 | C | TYR | D | 94 | 2.337 | −36.321 | −73.525 | 1.00 | 59.37 | MOL2 | C |
| ATOM | 6721 | O | TYR | D | 94 | 2.927 | −35.244 | −73.661 | 1.00 | 56.47 | MOL2 | O |
| ATOM | 6722 | N | TYR | D | 95 | 2.900 | −37.521 | −73.672 | 1.00 | 53.66 | MOL2 | N |
| ATOM | 6723 | CA | TYR | D | 95 | 4.294 | −37.713 | −74.021 | 1.00 | 47.62 | MOL2 | C |
| ATOM | 6724 | CB | TYR | D | 95 | 4.941 | −38.698 | −73.068 | 1.00 | 35.07 | MOL2 | C |
| ATOM | 6725 | CG | TYR | D | 95 | 5.205 | −38.152 | −71.705 | 1.00 | 29.66 | MOL2 | C |
| ATOM | 6726 | CD1 | TYR | D | 95 | 4.568 | −38.696 | −70.588 | 1.00 | 29.99 | MOL2 | C |
| ATOM | 6727 | CE1 | TYR | D | 95 | 4.810 | −38.205 | −69.309 | 1.00 | 27.04 | MOL2 | C |
| ATOM | 6728 | CD2 | TYR | D | 95 | 6.093 | −37.099 | −71.519 | 1.00 | 20.23 | MOL2 | C |
| ATOM | 6729 | CE2 | TYR | D | 95 | 6.340 | −36.601 | −70.251 | 1.00 | 29.21 | MOL2 | C |
| ATOM | 6730 | CZ | TYR | D | 95 | 5.696 | −37.161 | −69.147 | 1.00 | 31.88 | MOL2 | C |
| ATOM | 6731 | OH | TYR | D | 95 | 5.936 | −36.691 | −67.878 | 1.00 | 39.95 | MOL2 | O |
| ATOM | 6732 | C | TYR | D | 95 | 4.530 | −38.223 | −75.423 | 1.00 | 51.77 | MOL2 | C |
| ATOM | 6733 | O | TYR | D | 95 | 3.817 | −39.092 | −75.924 | 1.00 | 57.51 | MOL2 | O |
| ATOM | 6734 | N | CYS | D | 96 | 5.578 | −37.693 | −76.029 | 1.00 | 50.26 | MOL2 | N |
| ATOM | 6735 | CA | CYS | D | 96 | 5.999 | −38.064 | −77.363 | 1.00 | 51.95 | MOL2 | C |
| ATOM | 6736 | C | CYS | D | 96 | 7.170 | −39.032 | −77.135 | 1.00 | 50.54 | MOL2 | C |
| ATOM | 6737 | O | CYS | D | 96 | 8.108 | −38.704 | −76.403 | 1.00 | 49.17 | MOL2 | O |
| ATOM | 6738 | CB | CYS | D | 96 | 6.470 | −36.799 | −78.065 | 1.00 | 59.27 | MOL2 | C |
| ATOM | 6739 | SG | CYS | D | 96 | 6.930 | −36.942 | −79.815 | 1.00 | 80.95 | MOL2 | S |
| ATOM | 6740 | N | ALA | D | 97 | 7.133 | −40.213 | −77.747 | 1.00 | 45.76 | MOL2 | N |
| ATOM | 6741 | CA | ALA | D | 97 | 8.209 | −41.179 | −77.532 | 1.00 | 41.80 | MOL2 | C |
| ATOM | 6742 | CB | ALA | D | 97 | 7.745 | −42.221 | −76.546 | 1.00 | 46.21 | MOL2 | C |
| ATOM | 6743 | C | ALA | D | 97 | 8.737 | −41.873 | −78.784 | 1.00 | 45.59 | MOL2 | C |
| ATOM | 6744 | O | ALA | D | 97 | 7.963 | −42.456 | −79.565 | 1.00 | 46.25 | MOL2 | O |
| ATOM | 6745 | N | SER | D | 98 | 10.063 | −41.849 | −78.946 | 1.00 | 42.44 | MOL2 | N |
| ATOM | 6746 | CA | SER | D | 98 | 10.723 | −42.464 | −80.103 | 1.00 | 40.03 | MOL2 | C |
| ATOM | 6747 | CB | SER | D | 98 | 11.696 | −41.479 | −80.693 | 1.00 | 42.55 | MOL2 | C |
| ATOM | 6748 | OG | SER | D | 98 | 12.374 | −40.862 | −79.623 | 1.00 | 54.54 | MOL2 | O |
| ATOM | 6749 | C | SER | D | 98 | 11.489 | −43.703 | −79.737 | 1.00 | 36.36 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 6750 | O | SER | D | 98 | 11.851 | −43.895 | −78.594 | 1.00 | 42.91 | MOL2 | O |
|---|---|---|---|---|---|---|---|---|---|---|---|---|
| ATOM | 6751 | N | PRO | D | 99 | 11.761 | −44.566 | −80.709 | 1.00 | 37.36 | MOL2 | N |
| ATOM | 6752 | CD | PRO | D | 99 | 11.268 | −44.578 | −82.092 | 1.00 | 34.42 | MOL2 | C |
| ATOM | 6753 | CA | PRO | D | 99 | 12.510 | −45.782 | −80.401 | 1.00 | 42.07 | MOL2 | C |
| ATOM | 6754 | CB | PRO | D | 99 | 12.008 | −46.751 | −81.457 | 1.00 | 39.85 | MOL2 | C |
| ATOM | 6755 | CG | PRO | D | 99 | 11.850 | −45.873 | −82.636 | 1.00 | 38.08 | MOL2 | C |
| ATOM | 6756 | C | PRO | D | 99 | 14.019 | −45.483 | −80.490 | 1.00 | 47.47 | MOL2 | C |
| ATOM | 6757 | O | PRO | D | 99 | 14.419 | −44.382 | −80.884 | 1.00 | 49.75 | MOL2 | O |
| ATOM | 6758 | N | PRO | D | 100 | 14.867 | −46.455 | −80.122 | 1.00 | 47.56 | MOL2 | N |
| ATOM | 6759 | CD | PRO | D | 100 | 14.434 | −47.833 | −79.853 | 1.00 | 50.64 | MOL2 | C |
| ATOM | 6760 | CA | PRO | D | 100 | 16.332 | −46.377 | −80.119 | 1.00 | 48.54 | MOL2 | C |
| ATOM | 6761 | CB | PRO | D | 100 | 16.726 | −47.700 | −79.508 | 1.00 | 49.03 | MOL2 | C |
| ATOM | 6762 | CG | PRO | D | 100 | 15.697 | −48.606 | −80.077 | 1.00 | 52.38 | MOL2 | C |
| ATOM | 6763 | C | PRO | D | 100 | 16.981 | −46.170 | −81.482 | 1.00 | 50.59 | MOL2 | C |
| ATOM | 6764 | O | PRO | D | 100 | 16.611 | −46.807 | −82.455 | 1.00 | 50.59 | MOL2 | O |
| ATOM | 6765 | N | GLN | D | 101 | 17.964 | −45.278 | −81.522 | 1.00 | 56.02 | MOL2 | N |
| ATOM | 6766 | CA | GLN | D | 101 | 18.681 | −44.943 | −82.736 | 1.00 | 52.49 | MOL2 | C |
| ATOM | 6767 | CB | GLN | D | 101 | 19.703 | −43.823 | −82.468 | 1.00 | 66.20 | MOL2 | C |
| ATOM | 6768 | CG | GLN | D | 101 | 19.377 | −42.834 | −81.318 | 1.00 | 81.01 | MOL2 | C |
| ATOM | 6769 | CD | GLN | D | 101 | 19.949 | −43.253 | −79.927 | 1.00 | 90.03 | MOL2 | C |
| ATOM | 6770 | OE1 | GLN | D | 101 | 19.424 | −44.154 | −79.252 | 1.00 | 80.73 | MOL2 | O |
| ATOM | 6771 | NE2 | GLN | D | 101 | 21.027 | −42.585 | −79.509 | 1.00 | 89.51 | MOL2 | N |
| ATOM | 6772 | C | GLN | D | 101 | 19.382 | −46.181 | −83.304 | 1.00 | 53.84 | MOL2 | C |
| ATOM | 6773 | O | GLN | D | 101 | 19.583 | −46.257 | −84.512 | 1.00 | 56.95 | MOL2 | O |
| ATOM | 6774 | N | TYR | D | 102 | 19.798 | −47.138 | −82.467 | 1.00 | 56.67 | MOL2 | N |
| ATOM | 6775 | CA | TYR | D | 102 | 20.401 | −48.368 | −83.025 | 1.00 | 59.06 | MOL2 | C |
| ATOM | 6776 | CB | TYR | D | 102 | 21.317 | −49.135 | −82.038 | 1.00 | 53.29 | MOL2 | C |
| ATOM | 6777 | CG | TYR | D | 102 | 20.971 | −49.019 | −80.563 | 1.00 | 60.79 | MOL2 | C |
| ATOM | 6778 | CD1 | TYR | D | 102 | 20.040 | −49.865 | −79.978 | 1.00 | 58.44 | MOL2 | C |
| ATOM | 6779 | CE1 | TYR | D | 102 | 19.629 | −49.684 | −78.670 | 1.00 | 55.09 | MOL2 | C |
| ATOM | 6780 | CD2 | TYR | D | 102 | 21.500 | −47.992 | −79.781 | 1.00 | 57.34 | MOL2 | C |
| ATOM | 6781 | CE2 | TYR | D | 102 | 21.092 | −47.803 | −78.474 | 1.00 | 56.52 | MOL2 | C |
| ATOM | 6782 | CZ | TYR | D | 102 | 20.147 | −48.645 | −77.927 | 1.00 | 57.97 | MOL2 | C |
| ATOM | 6783 | OH | TYR | D | 102 | 19.644 | −48.394 | −76.666 | 1.00 | 64.12 | MOL2 | O |
| ATOM | 6784 | C | TYR | D | 102 | 19.201 | −49.217 | −83.438 | 1.00 | 64.63 | MOL2 | C |
| ATOM | 6785 | O | TYR | D | 102 | 18.190 | −48.662 | −83.878 | 1.00 | 76.43 | MOL2 | O |
| ATOM | 6786 | N | TYR | D | 103 | 19.267 | −50.534 | −83.321 | 1.00 | 56.82 | MOL2 | N |
| ATOM | 6787 | CA | TYR | D | 103 | 18.111 | −51.346 | −83.732 | 1.00 | 58.69 | MOL2 | C |
| ATOM | 6788 | CB | TYR | D | 103 | 17.122 | −51.458 | −82.573 | 1.00 | 43.86 | MOL2 | C |
| ATOM | 6789 | CG | TYR | D | 103 | 17.538 | −52.461 | −81.545 | 1.00 | 43.71 | MOL2 | C |
| ATOM | 6790 | CD1 | TYR | D | 103 | 17.591 | −53.806 | −81.845 | 1.00 | 44.13 | MOL2 | C |
| ATOM | 6791 | CE1 | TYR | D | 103 | 18.071 | −54.717 | −80.938 | 1.00 | 40.31 | MOL2 | C |
| ATOM | 6792 | CD2 | TYR | D | 103 | 17.967 | −52.057 | −80.304 | 1.00 | 49.09 | MOL2 | C |
| ATOM | 6793 | CE2 | TYR | D | 103 | 18.451 | −52.956 | −79.390 | 1.00 | 51.91 | MOL2 | C |
| ATOM | 6794 | CZ | TYR | D | 103 | 18.503 | −54.282 | −79.716 | 1.00 | 47.11 | MOL2 | C |
| ATOM | 6795 | OH | TYR | D | 103 | 19.030 | −55.161 | −78.812 | 1.00 | 55.04 | MOL2 | O |
| ATOM | 6796 | C | TYR | D | 103 | 17.309 | −50.967 | −85.011 | 1.00 | 65.35 | MOL2 | C |
| ATOM | 6797 | O | TYR | D | 103 | 17.717 | −51.222 | −86.151 | 1.00 | 63.13 | MOL2 | O |
| ATOM | 6798 | N | GLU | D | 104 | 16.151 | −50.358 | −84.795 | 1.00 | 74.03 | MOL2 | N |
| ATOM | 6799 | CA | GLU | D | 104 | 15.235 | −49.998 | −85.869 | 1.00 | 78.43 | MOL2 | C |
| ATOM | 6800 | CB | GLU | D | 104 | 15.699 | −48.817 | −86.692 | 1.00 | 80.98 | MOL2 | C |
| ATOM | 6801 | CG | GLU | D | 104 | 14.640 | −48.463 | −87.754 | 1.00 | 85.46 | MOL2 | C |
| ATOM | 6802 | CD | GLU | D | 104 | 13.205 | −48.758 | −87.276 | 1.00 | 83.54 | MOL2 | C |
| ATOM | 6803 | OE1 | GLU | D | 104 | 12.792 | −48.195 | −86.246 | 1.00 | 88.99 | MOL2 | O |
| ATOM | 6804 | OE2 | GLU | D | 104 | 12.479 | −49.545 | −87.919 | 1.00 | 62.12 | MOL2 | O |
| ATOM | 6805 | C | GLU | D | 104 | 15.016 | −51.128 | −86.831 | 1.00 | 79.96 | MOL2 | C |
| ATOM | 6806 | O | GLU | D | 104 | 14.310 | −52.078 | −86.520 | 1.00 | 80.54 | MOL2 | O |
| ATOM | 6807 | N | GLY | D | 105 | 15.634 | −51.006 | −88.005 | 1.00 | 85.01 | MOL2 | N |
| ATOM | 6808 | CA | GLY | D | 105 | 15.476 | −52.001 | −89.050 | 1.00 | 93.60 | MOL2 | C |
| ATOM | 6809 | C | GLY | D | 105 | 14.037 | −52.024 | −89.569 | 1.00 | 97.58 | MOL2 | C |
| ATOM | 6810 | O | GLY | D | 105 | 13.798 | −52.401 | −90.722 | 1.00 | 102.45 | MOL2 | O |
| ATOM | 6811 | N | SER | D | 106 | 13.100 | −51.610 | −88.705 | 1.00 | 92.53 | MOL2 | N |
| ATOM | 6812 | CA | SER | D | 106 | 11.654 | −51.559 | −88.954 | 1.00 | 79.31 | MOL2 | C |
| ATOM | 6813 | CB | SER | D | 106 | 11.248 | −52.469 | −90.112 | 1.00 | 78.55 | MOL2 | C |
| ATOM | 6814 | OG | SER | D | 106 | 11.367 | −53.835 | −89.753 | 1.00 | 70.96 | MOL2 | O |
| ATOM | 6815 | C | SER | D | 106 | 10.973 | −52.057 | −87.682 | 1.00 | 75.84 | MOL2 | C |
| ATOM | 6816 | O | SER | D | 106 | 9.836 | −51.701 | −87.409 | 1.00 | 76.84 | MOL2 | O |
| ATOM | 6817 | N | ILE | D | 107 | 11.696 | −52.889 | −86.928 | 1.00 | 70.17 | MOL2 | N |
| ATOM | 6818 | CA | ILE | D | 107 | 11.257 | −53.508 | −85.675 | 1.00 | 67.60 | MOL2 | C |
| ATOM | 6819 | CB | ILE | D | 107 | 12.397 | −53.559 | −84.655 | 1.00 | 65.73 | MOL2 | C |
| ATOM | 6820 | CG2 | ILE | D | 107 | 11.908 | −54.227 | −83.395 | 1.00 | 68.97 | MOL2 | C |
| ATOM | 6821 | CG1 | ILE | D | 107 | 13.584 | −54.342 | −85.207 | 1.00 | 64.47 | MOL2 | C |
| ATOM | 6822 | CD1 | ILE | D | 107 | 13.335 | −55.820 | −85.356 | 1.00 | 70.08 | MOL2 | C |
| ATOM | 6823 | C | ILE | D | 107 | 10.086 | −52.832 | −84.975 | 1.00 | 73.93 | MOL2 | C |
| ATOM | 6824 | O | ILE | D | 107 | 10.231 | −51.739 | −84.425 | 1.00 | 76.91 | MOL2 | O |
| ATOM | 6825 | N | TYR | D | 108 | 8.940 | −53.506 | −84.942 | 1.00 | 75.99 | MOL2 | N |
| ATOM | 6826 | CA | TYR | D | 108 | 7.739 | −52.937 | −84.329 | 1.00 | 73.60 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 6827 | CB  | TYR | D | 108 | 6.497  | −53.680 | −84.859 | 1.00 | 78.84  | MOL2 | C |
|------|------|-----|-----|---|-----|--------|---------|---------|------|--------|------|---|
| ATOM | 6828 | CG  | TYR | D | 108 | 5.187  | −53.283 | −84.201 | 1.00 | 84.09  | MOL2 | C |
| ATOM | 6829 | CD1 | TYR | D | 108 | 4.714  | −51.975 | −84.259 | 1.00 | 81.93  | MOL2 | C |
| ATOM | 6830 | CE1 | TYR | D | 108 | 3.547  | −51.600 | −83.595 | 1.00 | 80.60  | MOL2 | C |
| ATOM | 6831 | CD2 | TYR | D | 108 | 4.451  | −54.211 | −83.470 | 1.00 | 88.09  | MOL2 | C |
| ATOM | 6832 | CE2 | TYR | D | 108 | 3.288  | −53.846 | −82.806 | 1.00 | 87.51  | MOL2 | C |
| ATOM | 6833 | CZ  | TYR | D | 108 | 2.844  | −52.541 | −82.865 | 1.00 | 84.81  | MOL2 | C |
| ATOM | 6834 | OH  | TYR | D | 108 | 1.725  | −52.183 | −82.144 | 1.00 | 82.26  | MOL2 | O |
| ATOM | 6835 | C   | TYR | D | 108 | 7.736  | −52.936 | −82.800 | 1.00 | 69.77  | MOL2 | C |
| ATOM | 6836 | O   | TYR | D | 108 | 7.526  | −51.887 | −82.172 | 1.00 | 66.35  | MOL2 | O |
| ATOM | 6837 | N   | ARG | D | 109 | 7.976  | −54.113 | −82.222 | 1.00 | 63.80  | MOL2 | N |
| ATOM | 6838 | CA  | ARG | D | 109 | 7.986  | −54.324 | −80.771 | 1.00 | 59.44  | MOL2 | C |
| ATOM | 6839 | CB  | ARG | D | 109 | 8.273  | −55.796 | −80.497 | 1.00 | 66.44  | MOL2 | C |
| ATOM | 6840 | CG  | ARG | D | 109 | 7.355  | −56.764 | −81.229 | 1.00 | 76.80  | MOL2 | C |
| ATOM | 6841 | CD  | ARG | D | 109 | 5.919  | −56.612 | −80.765 | 1.00 | 85.59  | MOL2 | C |
| ATOM | 6842 | NE  | ARG | D | 109 | 5.202  | −57.885 | −80.769 | 1.00 | 96.62  | MOL2 | N |
| ATOM | 6843 | CZ  | ARG | D | 109 | 4.776  | −58.508 | −81.864 | 1.00 | 104.01 | MOL2 | C |
| ATOM | 6844 | NH1 | ARG | D | 109 | 4.988  | −57.976 | −83.062 | 1.00 | 107.13 | MOL2 | N |
| ATOM | 6845 | NH2 | ARG | D | 109 | 4.136  | −59.668 | −81.759 | 1.00 | 107.22 | MOL2 | N |
| ATOM | 6846 | C   | ARG | D | 109 | 8.958  | −53.469 | −79.946 | 1.00 | 53.98  | MOL2 | C |
| ATOM | 6847 | O   | ARG | D | 109 | 9.020  | −53.580 | −78.729 | 1.00 | 51.15  | MOL2 | O |
| ATOM | 6848 | N   | LEU | D | 110 | 9.706  | −52.611 | −80.619 | 1.00 | 56.29  | MOL2 | N |
| ATOM | 6849 | CA  | LEU | D | 110 | 10.696 | −51.731 | −79.996 | 1.00 | 49.13  | MOL2 | C |
| ATOM | 6850 | CB  | LEU | D | 110 | 11.282 | −50.813 | −81.063 | 1.00 | 48.52  | MOL2 | C |
| ATOM | 6851 | CG  | LEU | D | 110 | 12.788 | −50.737 | −81.240 | 1.00 | 47.52  | MOL2 | C |
| ATOM | 6852 | CD1 | LEU | D | 110 | 13.380 | −52.115 | −81.438 | 1.00 | 50.99  | MOL2 | C |
| ATOM | 6853 | CD2 | LEU | D | 110 | 13.061 | −49.876 | −82.436 | 1.00 | 40.58  | MOL2 | C |
| ATOM | 6854 | C   | LEU | D | 110 | 10.200 | −50.874 | −78.840 | 1.00 | 47.05  | MOL2 | C |
| ATOM | 6855 | O   | LEU | D | 110 | 9.189  | −50.191 | −78.940 | 1.00 | 50.30  | MOL2 | O |
| ATOM | 6856 | N   | TRP | D | 111 | 10.940 | −50.900 | −77.741 | 1.00 | 49.64  | MOL2 | N |
| ATOM | 6857 | CA  | TRP | D | 111 | 10.608 | −50.104 | −76.558 | 1.00 | 45.27  | MOL2 | C |
| ATOM | 6858 | CB  | TRP | D | 111 | 11.531 | −50.467 | −75.405 | 1.00 | 39.40  | MOL2 | C |
| ATOM | 6859 | CG  | TRP | D | 111 | 12.966 | −50.319 | −75.783 | 1.00 | 41.28  | MOL2 | C |
| ATOM | 6860 | CD2 | TRP | D | 111 | 13.743 | −51.256 | −76.511 | 1.00 | 42.25  | MOL2 | C |
| ATOM | 6861 | CE2 | TRP | D | 111 | 15.020 | −50.694 | −76.697 | 1.00 | 43.24  | MOL2 | C |
| ATOM | 6862 | CE3 | TRP | D | 111 | 13.483 | −52.521 | −77.030 | 1.00 | 47.78  | MOL2 | C |
| ATOM | 6863 | CD1 | TRP | D | 111 | 13.778 | −49.246 | −75.557 | 1.00 | 49.49  | MOL2 | C |
| ATOM | 6864 | NE1 | TRP | D | 111 | 15.024 | −49.463 | −76.102 | 1.00 | 45.39  | MOL2 | N |
| ATOM | 6865 | CZ2 | TRP | D | 111 | 16.021 | −51.353 | −77.377 | 1.00 | 48.26  | MOL2 | C |
| ATOM | 6866 | CZ3 | TRP | D | 111 | 14.476 | −53.170 | −77.704 | 1.00 | 50.24  | MOL2 | C |
| ATOM | 6867 | CH2 | TRP | D | 111 | 15.730 | −52.591 | −77.874 | 1.00 | 49.52  | MOL2 | C |
| ATOM | 6868 | C   | TRP | D | 111 | 10.913 | −48.692 | −76.965 | 1.00 | 42.86  | MOL2 | C |
| ATOM | 6869 | O   | TRP | D | 111 | 11.050 | −48.401 | −78.157 | 1.00 | 46.45  | MOL2 | O |
| ATOM | 6870 | N   | PHE | D | 112 | 11.029 | −47.799 | −75.995 | 1.00 | 39.79  | MOL2 | N |
| ATOM | 6871 | CA  | PHE | D | 112 | 11.379 | −46.446 | −76.367 | 1.00 | 42.21  | MOL2 | C |
| ATOM | 6872 | CB  | PHE | D | 112 | 10.157 | −45.626 | −76.846 | 1.00 | 53.83  | MOL2 | C |
| ATOM | 6873 | CG  | PHE | D | 112 | 8.855  | −45.936 | −76.150 | 1.00 | 52.89  | MOL2 | C |
| ATOM | 6874 | CD1 | PHE | D | 112 | 7.745  | −46.333 | −76.900 | 1.00 | 51.25  | MOL2 | C |
| ATOM | 6875 | CD2 | PHE | D | 112 | 8.733  | −45.838 | −74.782 | 1.00 | 49.56  | MOL2 | C |
| ATOM | 6876 | CE1 | PHE | D | 112 | 6.548  | −46.632 | −76.306 | 1.00 | 48.12  | MOL2 | C |
| ATOM | 6877 | CE2 | PHE | D | 112 | 7.532  | −46.137 | −74.182 | 1.00 | 55.71  | MOL2 | C |
| ATOM | 6878 | CZ  | PHE | D | 112 | 6.435  | −46.537 | −74.952 | 1.00 | 54.08  | MOL2 | C |
| ATOM | 6879 | C   | PHE | D | 112 | 12.162 | −45.598 | −75.414 | 1.00 | 39.35  | MOL2 | C |
| ATOM | 6880 | O   | PHE | D | 112 | 11.717 | −45.330 | −74.294 | 1.00 | 33.59  | MOL2 | O |
| ATOM | 6881 | N   | ALA | D | 113 | 13.342 | −45.193 | −75.901 | 1.00 | 37.45  | MOL2 | N |
| ATOM | 6882 | CA  | ALA | D | 113 | 14.262 | −44.290 | −75.208 | 1.00 | 36.05  | MOL2 | C |
| ATOM | 6883 | CB  | ALA | D | 113 | 15.657 | −44.522 | −75.627 | 1.00 | 23.09  | MOL2 | C |
| ATOM | 6884 | C   | ALA | D | 113 | 13.822 | −42.978 | −75.768 | 1.00 | 39.33  | MOL2 | C |
| ATOM | 6885 | O   | ALA | D | 113 | 13.131 | −42.946 | −76.769 | 1.00 | 47.39  | MOL2 | O |
| ATOM | 6886 | N   | HIS | D | 114 | 14.208 | −41.884 | −75.150 | 1.00 | 46.27  | MOL2 | N |
| ATOM | 6887 | CA  | HIS | D | 114 | 13.787 | −40.590 | −75.673 | 1.00 | 48.63  | MOL2 | C |
| ATOM | 6888 | CB  | HIS | D | 114 | 14.269 | −40.458 | −77.111 | 1.00 | 50.91  | MOL2 | C |
| ATOM | 6889 | CG  | HIS | D | 114 | 15.692 | −40.869 | −77.294 | 1.00 | 56.10  | MOL2 | C |
| ATOM | 6890 | CD2 | HIS | D | 114 | 16.829 | −40.421 | −76.712 | 1.00 | 60.79  | MOL2 | C |
| ATOM | 6891 | ND1 | HIS | D | 114 | 16.068 | −41.875 | −78.158 | 1.00 | 57.90  | MOL2 | N |
| ATOM | 6892 | CE1 | HIS | D | 114 | 17.379 | −42.029 | −78.102 | 1.00 | 64.05  | MOL2 | C |
| ATOM | 6893 | NE2 | HIS | D | 114 | 17.865 | −41.159 | −77.232 | 1.00 | 69.07  | MOL2 | N |
| ATOM | 6894 | C   | HIS | D | 114 | 12.267 | −40.337 | −75.583 | 1.00 | 45.81  | MOL2 | C |
| ATOM | 6895 | O   | HIS | D | 114 | 11.447 | −40.878 | −76.346 | 1.00 | 35.80  | MOL2 | O |
| ATOM | 6896 | N   | TRP | D | 115 | 11.933 | −39.494 | −74.612 | 1.00 | 46.75  | MOL2 | N |
| ATOM | 6897 | CA  | TRP | D | 115 | 10.586 | −39.062 | −74.316 | 1.00 | 44.18  | MOL2 | C |
| ATOM | 6898 | CB  | TRP | D | 115 | 10.226 | −39.439 | −72.876 | 1.00 | 48.59  | MOL2 | C |
| ATOM | 6899 | CG  | TRP | D | 115 | 10.103 | −40.894 | −72.609 | 1.00 | 47.04  | MOL2 | C |
| ATOM | 6900 | CD2 | TRP | D | 115 | 8.908  | −41.589 | −72.242 | 1.00 | 47.75  | MOL2 | C |
| ATOM | 6901 | CE2 | TRP | D | 115 | 9.228  | −42.958 | −72.174 | 1.00 | 47.16  | MOL2 | C |
| ATOM | 6902 | CE3 | TRP | D | 115 | 7.598  | −41.185 | −71.972 | 1.00 | 41.48  | MOL2 | C |
| ATOM | 6903 | CD1 | TRP | D | 115 | 11.070 | −41.832 | −72.732 | 1.00 | 45.40  | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 6904 | NE1 | TRP | D | 115 | 10.555 | −43.081 | −72.478 | 1.00 | 48.57 | MOL2 | N |
|---|---|---|---|---|---|---|---|---|---|---|---|---|
| ATOM | 6905 | CZ2 | TRP | D | 115 | 8.287 | −43.929 | −71.851 | 1.00 | 46.86 | MOL2 | C |
| ATOM | 6906 | CZ3 | TRP | D | 115 | 6.663 | −42.148 | −71.653 | 1.00 | 47.51 | MOL2 | C |
| ATOM | 6907 | CH2 | TRP | D | 115 | 7.011 | −43.507 | −71.596 | 1.00 | 50.61 | MOL2 | C |
| ATOM | 6908 | C | TRP | D | 115 | 10.659 | −37.539 | −74.411 | 1.00 | 43.89 | MOL2 | C |
| ATOM | 6909 | O | TRP | D | 115 | 11.731 | −36.944 | −74.245 | 1.00 | 36.86 | MOL2 | O |
| ATOM | 6910 | N | GLY | D | 116 | 9.532 | −36.902 | −74.682 | 1.00 | 47.55 | MOL2 | N |
| ATOM | 6911 | CA | GLY | D | 116 | 9.535 | −35.453 | −74.728 | 1.00 | 52.44 | MOL2 | C |
| ATOM | 6912 | C | GLY | D | 116 | 9.308 | −34.980 | −73.306 | 1.00 | 52.89 | MOL2 | C |
| ATOM | 6913 | O | GLY | D | 116 | 9.311 | −35.776 | −72.382 | 1.00 | 54.01 | MOL2 | O |
| ATOM | 6914 | N | GLN | D | 117 | 9.120 | −33.690 | −73.109 | 1.00 | 54.85 | MOL2 | N |
| ATOM | 6915 | CA | GLN | D | 117 | 8.871 | −33.202 | −71.768 | 1.00 | 57.81 | MOL2 | C |
| ATOM | 6916 | CB | GLN | D | 117 | 9.264 | −31.729 | −71.701 | 1.00 | 65.05 | MOL2 | C |
| ATOM | 6917 | CG | GLN | D | 117 | 9.732 | −31.160 | −73.051 | 1.00 | 77.65 | MOL2 | C |
| ATOM | 6918 | CD | GLN | D | 117 | 8.725 | −30.196 | −73.683 | 1.00 | 84.05 | MOL2 | C |
| ATOM | 6919 | OE1 | GLN | D | 117 | 8.417 | −29.144 | −73.120 | 1.00 | 85.67 | MOL2 | O |
| ATOM | 6920 | NE2 | GLN | D | 117 | 8.214 | −30.554 | −74.858 | 1.00 | 87.61 | MOL2 | N |
| ATOM | 6921 | C | GLN | D | 117 | 7.375 | −33.402 | −71.489 | 1.00 | 58.38 | MOL2 | C |
| ATOM | 6922 | O | GLN | D | 117 | 6.953 | −33.530 | −70.339 | 1.00 | 59.78 | MOL2 | O |
| ATOM | 6923 | N | GLY | D | 118 | 6.589 | −33.441 | −72.566 | 1.00 | 58.82 | MOL2 | N |
| ATOM | 6924 | CA | GLY | D | 118 | 5.151 | −33.637 | −72.471 | 1.00 | 54.19 | MOL2 | C |
| ATOM | 6925 | C | GLY | D | 118 | 4.357 | −32.363 | −72.263 | 1.00 | 55.02 | MOL2 | C |
| ATOM | 6926 | O | GLY | D | 118 | 4.900 | −31.358 | −71.793 | 1.00 | 51.92 | MOL2 | O |
| ATOM | 6927 | N | THR | D | 119 | 3.074 | −32.396 | −72.633 | 1.00 | 56.36 | MOL2 | N |
| ATOM | 6928 | CA | THR | D | 119 | 2.177 | −31.244 | −72.439 | 1.00 | 54.88 | MOL2 | C |
| ATOM | 6929 | CB | THR | D | 119 | 1.655 | −30.628 | −73.744 | 1.00 | 52.27 | MOL2 | C |
| ATOM | 6930 | OG1 | THR | D | 119 | 1.567 | −31.644 | −74.751 | 1.00 | 44.54 | MOL2 | O |
| ATOM | 6931 | CG2 | THR | D | 119 | 2.522 | −29.450 | −74.171 | 1.00 | 50.75 | MOL2 | C |
| ATOM | 6932 | C | THR | D | 119 | 0.945 | −31.655 | −71.666 | 1.00 | 54.33 | MOL2 | C |
| ATOM | 6933 | O | THR | D | 119 | 0.402 | −32.747 | −71.867 | 1.00 | 55.03 | MOL2 | O |
| ATOM | 6934 | N | LEU | D | 120 | 0.488 | −30.757 | −70.803 | 1.00 | 54.06 | MOL2 | N |
| ATOM | 6935 | CA | LEU | D | 120 | −0.682 | −31.039 | −69.995 | 0.50 | 59.28 | MOL2 | C |
| ATOM | 6936 | CB | LEU | D | 120 | −0.639 | −30.219 | −68.709 | 1.00 | 65.21 | MOL2 | C |
| ATOM | 6937 | CG | LEU | D | 120 | −1.719 | −30.637 | −67.710 | 1.00 | 72.15 | MOL2 | C |
| ATOM | 6938 | CD1 | LEU | D | 120 | −2.020 | −32.134 | −67.835 | 1.00 | 72.95 | MOL2 | C |
| ATOM | 6939 | CD2 | LEU | D | 120 | −1.248 | −30.282 | −66.310 | 1.00 | 75.68 | MOL2 | C |
| ATOM | 6940 | C | LEU | D | 120 | −1.981 | −30.776 | −70.740 | 1.00 | 58.18 | MOL2 | C |
| ATOM | 6941 | O | LEU | D | 120 | −2.146 | −29.750 | −71.393 | 1.00 | 58.09 | MOL2 | O |
| ATOM | 6942 | N | VAL | D | 121 | −2.905 | −31.717 | −70.623 | 1.00 | 58.63 | MOL2 | N |
| ATOM | 6943 | CA | VAL | D | 121 | −4.189 | −31.625 | −71.291 | 1.00 | 65.61 | MOL2 | C |
| ATOM | 6944 | CB | VAL | D | 121 | −4.259 | −32.665 | −72.409 | 1.00 | 66.65 | MOL2 | C |
| ATOM | 6945 | CG1 | VAL | D | 121 | −5.471 | −32.437 | −73.273 | 1.00 | 72.47 | MOL2 | C |
| ATOM | 6946 | CG2 | VAL | D | 121 | −2.998 | −32.605 | −73.221 | 1.00 | 71.38 | MOL2 | C |
| ATOM | 6947 | C | VAL | D | 121 | −5.290 | −31.912 | −70.278 | 1.00 | 72.09 | MOL2 | C |
| ATOM | 6948 | O | VAL | D | 121 | −5.499 | −33.070 | −69.900 | 1.00 | 75.73 | MOL2 | O |
| ATOM | 6949 | N | THR | D | 122 | −5.994 | −30.864 | −69.845 | 1.00 | 76.78 | MOL2 | N |
| ATOM | 6950 | CA | THR | D | 122 | −7.074 | −31.009 | −68.860 | 1.00 | 77.46 | MOL2 | C |
| ATOM | 6951 | CB | THR | D | 122 | −6.846 | −30.073 | −67.652 | 1.00 | 72.23 | MOL2 | C |
| ATOM | 6952 | OG1 | THR | D | 122 | −6.042 | −28.956 | −68.051 | 1.00 | 62.85 | MOL2 | O |
| ATOM | 6953 | CG2 | THR | D | 122 | −6.144 | −30.819 | −66.532 | 1.00 | 81.85 | MOL2 | C |
| ATOM | 6954 | C | THR | D | 122 | −8.500 | −30.790 | −69.382 | 1.00 | 79.79 | MOL2 | C |
| ATOM | 6955 | O | THR | D | 122 | −8.916 | −29.669 | −69.675 | 1.00 | 82.67 | MOL2 | O |
| ATOM | 6956 | N | VAL | D | 123 | −9.241 | −31.882 | −69.491 | 1.00 | 81.95 | MOL2 | N |
| ATOM | 6957 | CA | VAL | D | 123 | −10.623 | −31.848 | −69.947 | 1.00 | 87.80 | MOL2 | C |
| ATOM | 6958 | CB | VAL | D | 123 | −10.998 | −33.178 | −70.658 | 1.00 | 87.08 | MOL2 | C |
| ATOM | 6959 | CG1 | VAL | D | 123 | −10.485 | −34.360 | −69.862 | 1.00 | 90.66 | MOL2 | C |
| ATOM | 6960 | CG2 | VAL | D | 123 | −12.494 | −33.294 | −70.794 | 1.00 | 87.68 | MOL2 | C |
| ATOM | 6961 | C | VAL | D | 123 | −11.567 | −31.638 | −68.753 | 1.00 | 92.45 | MOL2 | C |
| ATOM | 6962 | O | VAL | D | 123 | −11.915 | −32.595 | −68.053 | 1.00 | 92.78 | MOL2 | O |
| ATOM | 6963 | N | SER | D | 124 | −11.970 | −30.389 | −68.521 | 1.00 | 96.50 | MOL2 | N |
| ATOM | 6964 | CA | SER | D | 124 | −12.876 | −30.053 | −67.419 | 1.00 | 101.35 | MOL2 | C |
| ATOM | 6965 | CB | SER | D | 124 | −12.083 | −29.484 | −66.233 | 1.00 | 104.48 | MOL2 | C |
| ATOM | 6966 | OG | SER | D | 124 | −12.917 | −29.260 | −65.104 | 1.00 | 108.20 | MOL2 | O |
| ATOM | 6967 | C | SER | D | 124 | −13.926 | −29.030 | −67.871 | 1.00 | 101.90 | MOL2 | C |
| ATOM | 6968 | O | SER | D | 124 | −13.644 | −28.163 | −68.701 | 1.00 | 102.22 | MOL2 | O |
| ATOM | 6969 | N | SER | D | 125 | −15.131 | −29.133 | −67.316 | 1.00 | 100.56 | MOL2 | N |
| ATOM | 6970 | CA | SER | D | 125 | −16.221 | −28.225 | −67.660 | 1.00 | 95.36 | MOL2 | C |
| ATOM | 6971 | CB | SER | D | 125 | −17.568 | −28.925 | −67.473 | 1.00 | 98.73 | MOL2 | C |
| ATOM | 6972 | OG | SER | D | 125 | −17.762 | −29.293 | −66.116 | 1.00 | 104.20 | MOL2 | O |
| ATOM | 6973 | C | SER | D | 125 | −16.194 | −26.959 | −66.814 | 1.00 | 89.46 | MOL2 | C |
| ATOM | 6974 | O | SER | D | 125 | −16.840 | −25.974 | −67.148 | 1.00 | 86.33 | MOL2 | O |
| ATOM | 6975 | N | ALA | D | 126 | −15.450 | −26.993 | −65.717 | 1.00 | 87.90 | MOL2 | N |
| ATOM | 6976 | CA | ALA | D | 126 | −15.351 | −25.842 | −64.828 | 1.00 | 89.29 | MOL2 | C |
| ATOM | 6977 | CB | ALA | D | 126 | −14.423 | −26.151 | −63.674 | 1.00 | 94.78 | MOL2 | C |
| ATOM | 6978 | C | ALA | D | 126 | −14.855 | −24.614 | −65.566 | 1.00 | 89.69 | MOL2 | C |
| ATOM | 6979 | O | ALA | D | 126 | −14.252 | −24.718 | −66.632 | 1.00 | 92.07 | MOL2 | O |
| ATOM | 6980 | N | LYS | D | 127 | −15.100 | −23.451 | −64.975 | 1.00 | 90.14 | MOL2 | N |

TABLE 1-continued

The atomic coordinates of IL17F in complex with 496 Fab
(H32; a = 189.4; b = 189.4; c = 490.9, α, β = 90°; γ = 120°)

| ATOM | 6981 | CA | LYS | D | 127 | −14.708 | −22.176 | −65.564 | 1.00 | 92.16 | MOL2 | C |
|---|---|---|---|---|---|---|---|---|---|---|---|---|
| ATOM | 6982 | CB | LYS | D | 127 | −15.944 | −21.289 | −65.763 | 1.00 | 104.26 | MOL2 | C |
| ATOM | 6983 | CG | LYS | D | 127 | −15.652 | −19.877 | −66.292 | 1.00 | 114.56 | MOL2 | C |
| ATOM | 6984 | CD | LYS | D | 127 | −15.048 | −19.903 | −67.702 | 1.00 | 119.37 | MOL2 | C |
| ATOM | 6985 | CE | LYS | D | 127 | −14.849 | −18.500 | −68.257 | 1.00 | 116.80 | MOL2 | C |
| ATOM | 6986 | NZ | LYS | D | 127 | −14.183 | −18.545 | −69.584 | 1.00 | 117.75 | MOL2 | N |
| ATOM | 6987 | C | LYS | D | 127 | −13.724 | −21.440 | −64.679 | 1.00 | 86.37 | MOL2 | C |
| ATOM | 6988 | O | LYS | D | 127 | −13.770 | −21.548 | −63.462 | 1.00 | 81.01 | MOL2 | O |
| ATOM | 6989 | N | THR | D | 128 | −12.850 | −20.668 | −65.306 | 1.00 | 86.45 | MOL2 | N |
| ATOM | 6990 | CA | THR | D | 128 | −11.845 | −19.898 | −64.587 | 1.00 | 88.78 | MOL2 | C |
| ATOM | 6991 | CB | THR | D | 128 | −11.136 | −18.903 | −65.555 | 1.00 | 94.01 | MOL2 | C |
| ATOM | 6992 | OG1 | THR | D | 128 | −12.100 | −17.997 | −66.106 | 1.00 | 102.80 | MOL2 | O |
| ATOM | 6993 | CG2 | THR | D | 128 | −10.464 | −19.658 | −66.712 | 1.00 | 92.70 | MOL2 | C |
| ATOM | 6994 | C | THR | D | 128 | −12.436 | −19.125 | −63.403 | 1.00 | 82.79 | MOL2 | C |
| ATOM | 6995 | O | THR | D | 128 | −13.214 | −18.206 | −63.594 | 1.00 | 86.68 | MOL2 | O |
| ATOM | 6996 | N | THR | D | 129 | −12.063 | −19.506 | −62.185 | 1.00 | 80.34 | MOL2 | N |
| ATOM | 6997 | CA | THR | D | 129 | −12.541 | −18.847 | −60.958 | 1.00 | 81.32 | MOL2 | C |
| ATOM | 6998 | CB | THR | D | 129 | −13.413 | −19.789 | −60.086 | 1.00 | 76.32 | MOL2 | C |
| ATOM | 6999 | OG1 | THR | D | 129 | −14.608 | −20.155 | −60.783 | 1.00 | 72.46 | MOL2 | O |
| ATOM | 7000 | CG2 | THR | D | 129 | −13.753 | −19.111 | −58.767 | 1.00 | 66.69 | MOL2 | C |
| ATOM | 7001 | C | THR | D | 129 | −11.366 | −18.439 | −60.059 | 1.00 | 88.41 | MOL2 | C |
| ATOM | 7002 | O | THR | D | 129 | −10.451 | −19.233 | −59.823 | 1.00 | 95.15 | MOL2 | O |
| ATOM | 7003 | N | PRO | D | 130 | −11.372 | −17.208 | −59.529 | 1.00 | 89.99 | MOL2 | N |
| ATOM | 7004 | CD | PRO | D | 130 | −12.421 | −16.177 | −59.487 | 1.00 | 94.23 | MOL2 | C |
| ATOM | 7005 | CA | PRO | D | 130 | −10.248 | −16.835 | −58.665 | 1.00 | 91.27 | MOL2 | C |
| ATOM | 7006 | CB | PRO | D | 130 | −10.413 | −15.335 | −58.519 | 1.00 | 89.62 | MOL2 | C |
| ATOM | 7007 | CG | PRO | D | 130 | −11.896 | −15.225 | −58.394 | 1.00 | 96.63 | MOL2 | C |
| ATOM | 7008 | C | PRO | D | 130 | −10.455 | −17.558 | −57.339 | 1.00 | 93.88 | MOL2 | C |
| ATOM | 7009 | O | PRO | D | 130 | −11.553 | −18.047 | −57.051 | 1.00 | 88.45 | MOL2 | O |
| ATOM | 7010 | N | PRO | D | 131 | −9.413 | −17.600 | −56.498 | 1.00 | 98.43 | MOL2 | N |
| ATOM | 7011 | CD | PRO | D | 131 | −8.148 | −16.857 | −56.658 | 1.00 | 102.54 | MOL2 | C |
| ATOM | 7012 | CA | PRO | D | 131 | −9.435 | −18.260 | −55.195 | 1.00 | 98.47 | MOL2 | C |
| ATOM | 7013 | CB | PRO | D | 131 | −7.975 | −18.575 | −54.977 | 1.00 | 102.75 | MOL2 | C |
| ATOM | 7014 | CG | PRO | D | 131 | −7.361 | −17.243 | −55.378 | 1.00 | 102.15 | MOL2 | C |
| ATOM | 7015 | C | PRO | D | 131 | −9.944 | −17.357 | −54.087 | 1.00 | 97.59 | MOL2 | C |
| ATOM | 7016 | O | PRO | D | 131 | −9.760 | −16.137 | −54.131 | 1.00 | 97.03 | MOL2 | O |
| ATOM | 7017 | N | SER | D | 132 | −10.564 | −17.980 | −53.088 | 1.00 | 95.89 | MOL2 | N |
| ATOM | 7018 | CA | SER | D | 132 | −11.072 | −17.293 | −51.898 | 1.00 | 93.25 | MOL2 | C |
| ATOM | 7019 | CB | SER | D | 132 | −12.403 | −17.915 | −51.454 | 1.00 | 93.74 | MOL2 | C |
| ATOM | 7020 | OG | SER | D | 132 | −13.239 | −18.221 | −52.562 | 1.00 | 91.87 | MOL2 | O |
| ATOM | 7021 | C | SER | D | 132 | −9.993 | −17.599 | −50.852 | 1.00 | 91.14 | MOL2 | C |
| ATOM | 7022 | O | SER | D | 132 | −9.657 | −18.769 | −50.643 | 1.00 | 93.07 | MOL2 | O |
| ATOM | 7023 | N | VAL | D | 133 | −9.451 | −16.578 | −50.196 | 1.00 | 84.88 | MOL2 | N |
| ATOM | 7024 | CA | VAL | D | 133 | −8.382 | −16.810 | −49.231 | 1.00 | 82.43 | MOL2 | C |
| ATOM | 7025 | CB | VAL | D | 133 | −7.166 | −15.975 | −49.561 | 1.00 | 84.02 | MOL2 | C |
| ATOM | 7026 | CG1 | VAL | D | 133 | −6.151 | −16.108 | −48.442 | 1.00 | 88.68 | MOL2 | C |
| ATOM | 7027 | CG2 | VAL | D | 133 | −6.592 | −16.402 | −50.898 | 1.00 | 87.42 | MOL2 | C |
| ATOM | 7028 | C | VAL | D | 133 | −8.687 | −16.523 | −47.780 | 1.00 | 81.22 | MOL2 | C |
| ATOM | 7029 | O | VAL | D | 133 | −8.857 | −15.376 | −47.402 | 1.00 | 83.29 | MOL2 | O |
| ATOM | 7030 | N | TYR | D | 134 | −8.725 | −17.557 | −46.951 | 1.00 | 84.52 | MOL2 | N |
| ATOM | 7031 | CA | TYR | D | 134 | −8.992 | −17.351 | −45.531 | 1.00 | 86.30 | MOL2 | C |
| ATOM | 7032 | CB | TYR | D | 134 | −10.159 | −18.220 | −45.022 | 1.00 | 85.81 | MOL2 | C |
| ATOM | 7033 | CG | TYR | D | 134 | −11.338 | −18.401 | −45.964 | 1.00 | 90.17 | MOL2 | C |
| ATOM | 7034 | CD1 | TYR | D | 134 | −11.781 | −17.377 | −46.794 | 1.00 | 92.10 | MOL2 | C |
| ATOM | 7035 | CE1 | TYR | D | 134 | −12.865 | −17.568 | −47.653 | 1.00 | 94.29 | MOL2 | C |
| ATOM | 7036 | CD2 | TYR | D | 134 | −12.011 | −19.615 | −46.015 | 1.00 | 94.78 | MOL2 | C |
| ATOM | 7037 | CE2 | TYR | D | 134 | −13.089 | −19.815 | −46.865 | 1.00 | 96.04 | MOL2 | C |
| ATOM | 7038 | CZ | TYR | D | 134 | −13.513 | −18.796 | −47.680 | 1.00 | 96.73 | MOL2 | C |
| ATOM | 7039 | OH | TYR | D | 134 | −14.584 | −19.032 | −48.518 | 1.00 | 95.03 | MOL2 | O |
| ATOM | 7040 | C | TYR | D | 134 | −7.734 | −17.696 | −44.739 | 1.00 | 89.37 | MOL2 | C |
| ATOM | 7041 | O | TYR | D | 134 | −6.965 | −18.587 | −45.117 | 1.00 | 93.82 | MOL2 | O |
| ATOM | 7042 | N | PRO | D | 135 | −7.509 | −16.986 | −43.625 | 1.00 | 89.74 | MOL2 | N |
| ATOM | 7043 | CD | PRO | D | 135 | −8.262 | −15.768 | −43.276 | 1.00 | 91.40 | MOL2 | C |
| ATOM | 7044 | CA | PRO | D | 135 | −6.360 | −17.156 | −42.725 | 1.00 | 89.81 | MOL2 | C |
| ATOM | 7045 | CB | PRO | D | 135 | −6.175 | −15.754 | −42.159 | 1.00 | 92.08 | MOL2 | C |
| ATOM | 7046 | CG | PRO | D | 135 | −7.592 | −15.324 | −41.973 | 1.00 | 93.53 | MOL2 | C |
| ATOM | 7047 | C | PRO | D | 135 | −6.570 | −18.181 | −41.610 | 1.00 | 87.93 | MOL2 | C |
| ATOM | 7048 | O | PRO | D | 135 | −7.551 | −18.111 | −40.879 | 1.00 | 88.59 | MOL2 | O |
| ATOM | 7049 | N | LEU | D | 136 | −5.645 | −19.125 | −41.471 | 1.00 | 88.40 | MOL2 | N |
| ATOM | 7050 | CA | LEU | D | 136 | −5.754 | −20.126 | −40.415 | 1.00 | 87.79 | MOL2 | C |
| ATOM | 7051 | CB | LEU | D | 136 | −5.094 | −21.449 | −40.823 | 1.00 | 88.32 | MOL2 | C |
| ATOM | 7052 | CG | LEU | D | 136 | −5.763 | −22.371 | −41.841 | 1.00 | 87.50 | MOL2 | C |
| ATOM | 7053 | CD1 | LEU | D | 136 | −7.157 | −22.734 | −41.345 | 1.00 | 88.15 | MOL2 | C |
| ATOM | 7054 | CD2 | LEU | D | 136 | −5.832 | −21.693 | −43.191 | 1.00 | 84.04 | MOL2 | C |
| ATOM | 7055 | C | LEU | D | 136 | −5.045 | −19.603 | −39.181 | 1.00 | 90.22 | MOL2 | C |
| ATOM | 7056 | O | LEU | D | 136 | −3.813 | −19.621 | −39.116 | 1.00 | 93.68 | MOL2 | O |
| ATOM | 7057 | N | ALA | D | 137 | −5.819 | −19.135 | −38.207 | 1.00 | 91.57 | MOL2 | N |

TABLE 1-continued

The atomic coordinates of IL17F in complex with 496 Fab
(H32; a = 189.4; b = 189.4; c = 490.9, α, β = 90°; γ = 120°)

| ATOM | 7058 | CA | ALA | D | 137 | −5.253 | −18.616 | −36.962 | 1.00 | 91.47 | MOL2 | C |
|---|---|---|---|---|---|---|---|---|---|---|---|---|
| ATOM | 7059 | CB | ALA | D | 137 | −5.798 | −17.226 | −36.677 | 1.00 | 95.97 | MOL2 | C |
| ATOM | 7060 | C | ALA | D | 137 | −5.573 | −19.558 | −35.800 | 1.00 | 89.69 | MOL2 | C |
| ATOM | 7061 | O | ALA | D | 137 | −6.616 | −20.224 | −35.785 | 1.00 | 81.02 | MOL2 | O |
| ATOM | 7062 | N | PRO | D | 138 | −4.680 | −19.604 | −34.798 | 1.00 | 91.96 | MOL2 | N |
| ATOM | 7063 | CD | PRO | D | 138 | −3.585 | −18.637 | −34.624 | 1.00 | 92.07 | MOL2 | C |
| ATOM | 7064 | CA | PRO | D | 138 | −4.805 | −20.449 | −33.605 | 1.00 | 96.61 | MOL2 | C |
| ATOM | 7065 | CB | PRO | D | 138 | −3.639 | −19.992 | −32.720 | 1.00 | 90.39 | MOL2 | C |
| ATOM | 7066 | CG | PRO | D | 138 | −2.680 | −19.366 | −33.673 | 1.00 | 91.23 | MOL2 | C |
| ATOM | 7067 | C | PRO | D | 138 | −6.122 | −20.247 | −32.888 | 1.00 | 101.66 | MOL2 | C |
| ATOM | 7068 | O | PRO | D | 138 | −6.863 | −19.318 | −33.185 | 1.00 | 105.65 | MOL2 | O |
| ATOM | 7069 | N | GLY | D | 139 | −6.402 | −21.125 | −31.936 | 1.00 | 107.92 | MOL2 | N |
| ATOM | 7070 | CA | GLY | D | 139 | −7.608 | −20.995 | −31.147 | 1.00 | 118.65 | MOL2 | C |
| ATOM | 7071 | C | GLY | D | 139 | −7.190 | −20.365 | −29.832 | 1.00 | 127.42 | MOL2 | C |
| ATOM | 7072 | O | GLY | D | 139 | −6.011 | −20.041 | −29.646 | 1.00 | 127.52 | MOL2 | O |
| ATOM | 7073 | N | SER | D | 140 | −8.141 | −20.185 | −28.920 | 1.00 | 135.65 | MOL2 | N |
| ATOM | 7074 | CA | SER | D | 140 | −7.851 | −19.596 | −27.615 | 1.00 | 143.05 | MOL2 | C |
| ATOM | 7075 | CB | SER | D | 140 | −9.124 | −18.992 | −27.011 | 1.00 | 139.74 | MOL2 | C |
| ATOM | 7076 | OG | SER | D | 140 | −10.098 | −19.993 | −26.759 | 1.00 | 131.79 | MOL2 | O |
| ATOM | 7077 | C | SER | D | 140 | −7.310 | −20.665 | −26.667 | 1.00 | 150.39 | MOL2 | C |
| ATOM | 7078 | O | SER | D | 140 | −7.655 | −20.675 | −25.485 | 1.00 | 152.05 | MOL2 | O |
| ATOM | 7079 | N | ALA | D | 141 | −6.474 | −21.564 | −27.190 | 1.00 | 156.60 | MOL2 | N |
| ATOM | 7080 | CA | ALA | D | 141 | −5.892 | −22.647 | −26.394 | 1.00 | 160.16 | MOL2 | C |
| ATOM | 7081 | CB | ALA | D | 141 | −5.860 | −23.938 | −27.212 | 1.00 | 159.05 | MOL2 | C |
| ATOM | 7082 | C | ALA | D | 141 | −4.487 | −22.313 | −25.884 | 1.00 | 163.47 | MOL2 | C |
| ATOM | 7083 | O | ALA | D | 141 | −3.603 | −23.176 | −25.851 | 1.00 | 162.83 | MOL2 | O |
| ATOM | 7084 | N | ALA | D | 142 | −4.299 | −21.053 | −25.490 | 1.00 | 166.92 | MOL2 | N |
| ATOM | 7085 | CA | ALA | D | 142 | −3.030 | −20.551 | −24.958 | 1.00 | 169.09 | MOL2 | C |
| ATOM | 7086 | CB | ALA | D | 142 | −2.801 | −21.105 | −23.550 | 1.00 | 169.18 | MOL2 | C |
| ATOM | 7087 | C | ALA | D | 142 | −1.805 | −20.829 | −25.834 | 1.00 | 170.10 | MOL2 | C |
| ATOM | 7088 | O | ALA | D | 142 | −1.919 | −21.350 | −26.947 | 1.00 | 170.73 | MOL2 | O |
| ATOM | 7089 | N | GLN | D | 143 | −0.633 | −20.472 | −25.313 | 1.00 | 169.73 | MOL2 | N |
| ATOM | 7090 | CA | GLN | D | 143 | 0.630 | −20.657 | −26.025 | 1.00 | 169.60 | MOL2 | C |
| ATOM | 7091 | CB | GLN | D | 143 | 1.345 | −19.304 | −26.175 | 1.00 | 171.11 | MOL2 | C |
| ATOM | 7092 | CG | GLN | D | 143 | 2.808 | −19.384 | −26.651 | 1.00 | 174.47 | MOL2 | C |
| ATOM | 7093 | CD | GLN | D | 143 | 2.960 | −19.853 | −28.099 | 1.00 | 176.58 | MOL2 | C |
| ATOM | 7094 | OE1 | GLN | D | 143 | 2.457 | −19.213 | −29.029 | 1.00 | 176.14 | MOL2 | O |
| ATOM | 7095 | NE2 | GLN | D | 143 | 3.666 | −20.969 | −28.294 | 1.00 | 175.36 | MOL2 | N |
| ATOM | 7096 | C | GLN | D | 143 | 1.576 | −21.666 | −25.362 | 1.00 | 168.61 | MOL2 | C |
| ATOM | 7097 | O | GLN | D | 143 | 2.253 | −21.353 | −24.374 | 1.00 | 168.76 | MOL2 | O |
| ATOM | 7098 | N | THR | D | 144 | 1.617 | −22.875 | −25.917 | 1.00 | 165.57 | MOL2 | N |
| ATOM | 7099 | CA | THR | D | 144 | 2.493 | −23.927 | −25.417 | 1.00 | 162.67 | MOL2 | C |
| ATOM | 7100 | CB | THR | D | 144 | 1.749 | −25.280 | −25.304 | 1.00 | 163.46 | MOL2 | C |
| ATOM | 7101 | OG1 | THR | D | 144 | 0.558 | −25.108 | −24.525 | 1.00 | 164.15 | MOL2 | O |
| ATOM | 7102 | CG2 | THR | D | 144 | 2.638 | −26.330 | −24.633 | 1.00 | 161.04 | MOL2 | C |
| ATOM | 7103 | C | THR | D | 144 | 3.641 | −24.067 | −26.420 | 1.00 | 160.35 | MOL2 | C |
| ATOM | 7104 | O | THR | D | 144 | 3.468 | −23.802 | −27.612 | 1.00 | 159.06 | MOL2 | O |
| ATOM | 7105 | N | ASN | D | 145 | 4.806 | −24.477 | −25.926 | 1.00 | 157.50 | MOL2 | N |
| ATOM | 7106 | CA | ASN | D | 145 | 6.007 | −24.656 | −26.744 | 1.00 | 151.64 | MOL2 | C |
| ATOM | 7107 | CB | ASN | D | 145 | 5.756 | −25.672 | −27.878 | 1.00 | 155.26 | MOL2 | C |
| ATOM | 7108 | CG | ASN | D | 145 | 7.047 | −26.346 | −28.370 | 1.00 | 156.04 | MOL2 | C |
| ATOM | 7109 | OD1 | ASN | D | 145 | 7.834 | −26.869 | −27.575 | 1.00 | 156.83 | MOL2 | O |
| ATOM | 7110 | ND2 | ASN | D | 145 | 7.254 | −26.345 | −29.683 | 1.00 | 155.28 | MOL2 | N |
| ATOM | 7111 | C | ASN | D | 145 | 6.497 | −23.322 | −27.312 | 1.00 | 144.30 | MOL2 | C |
| ATOM | 7112 | O | ASN | D | 145 | 5.791 | −22.309 | −27.274 | 1.00 | 139.79 | MOL2 | O |
| ATOM | 7113 | N | SER | D | 146 | 7.721 | −23.336 | −27.827 | 1.00 | 138.02 | MOL2 | N |
| ATOM | 7114 | CA | SER | D | 146 | 8.340 | −22.143 | −28.379 | 1.00 | 132.73 | MOL2 | C |
| ATOM | 7115 | CB | SER | D | 146 | 9.865 | −22.288 | −28.356 | 1.00 | 131.99 | MOL2 | C |
| ATOM | 7116 | OG | SER | D | 146 | 10.355 | −22.370 | −27.030 | 1.00 | 132.70 | MOL2 | O |
| ATOM | 7117 | C | SER | D | 146 | 7.899 | −21.800 | −29.794 | 1.00 | 129.36 | MOL2 | C |
| ATOM | 7118 | O | SER | D | 146 | 8.140 | −20.688 | −30.258 | 1.00 | 133.00 | MOL2 | O |
| ATOM | 7119 | N | MET | D | 147 | 7.249 | −22.733 | −30.481 | 1.00 | 122.87 | MOL2 | N |
| ATOM | 7120 | CA | MET | D | 147 | 6.831 | −22.467 | −31.851 | 1.00 | 116.75 | MOL2 | C |
| ATOM | 7121 | CB | MET | D | 147 | 7.433 | −23.516 | −32.789 | 1.00 | 120.71 | MOL2 | C |
| ATOM | 7122 | CG | MET | D | 147 | 8.942 | −23.699 | −32.641 | 1.00 | 125.86 | MOL2 | C |
| ATOM | 7123 | SD | MET | D | 147 | 9.939 | −22.254 | −33.097 | 1.00 | 130.92 | MOL2 | S |
| ATOM | 7124 | CE | MET | D | 147 | 10.431 | −22.679 | −34.789 | 1.00 | 132.60 | MOL2 | C |
| ATOM | 7125 | C | MET | D | 147 | 5.326 | −22.418 | −32.046 | 1.00 | 112.57 | MOL2 | C |
| ATOM | 7126 | O | MET | D | 147 | 4.564 | −23.045 | −31.306 | 1.00 | 111.57 | MOL2 | O |
| ATOM | 7127 | N | VAL | D | 148 | 4.905 | −21.661 | −33.053 | 1.00 | 108.32 | MOL2 | N |
| ATOM | 7128 | CA | VAL | D | 148 | 3.490 | −21.535 | −33.365 | 1.00 | 106.32 | MOL2 | C |
| ATOM | 7129 | CB | VAL | D | 148 | 2.960 | −20.149 | −33.012 | 1.00 | 110.34 | MOL2 | C |
| ATOM | 7130 | CG1 | VAL | D | 148 | 1.446 | −20.208 | −32.891 | 1.00 | 111.40 | MOL2 | C |
| ATOM | 7131 | CG2 | VAL | D | 148 | 3.602 | −19.657 | −31.723 | 1.00 | 111.14 | MOL2 | C |
| ATOM | 7132 | C | VAL | D | 148 | 3.269 | −21.774 | −34.848 | 1.00 | 103.55 | MOL2 | C |
| ATOM | 7133 | O | VAL | D | 148 | 4.022 | −21.280 | −35.692 | 1.00 | 104.24 | MOL2 | O |
| ATOM | 7134 | N | THR | D | 149 | 2.231 | −22.536 | −35.164 | 1.00 | 98.66 | MOL2 | N |

TABLE 1-continued

The atomic coordinates of IL17F in complex with 496 Fab
(H32; a = 189.4; b = 189.4; c = 490.9, α, β = 90°; γ = 120°)

| ATOM | 7135 | CA | THR | D | 149 | 1.935 | −22.851 | −36.549 | 1.00 | 96.52 | MOL2 | C |
|------|------|-----|-----|---|-----|--------|---------|---------|------|--------|------|---|
| ATOM | 7136 | CB | THR | D | 149 | 1.669 | −24.363 | −36.713 | 1.00 | 98.96 | MOL2 | C |
| ATOM | 7137 | OG1 | THR | D | 149 | 2.910 | −25.080 | −36.671 | 1.00 | 93.78 | MOL2 | O |
| ATOM | 7138 | CG2 | THR | D | 149 | 0.951 | −24.638 | −38.020 | 1.00 | 100.27 | MOL2 | C |
| ATOM | 7139 | C | THR | D | 149 | 0.724 | −22.082 | −37.049 | 1.00 | 93.42 | MOL2 | C |
| ATOM | 7140 | O | THR | D | 149 | −0.354 | −22.158 | −36.454 | 1.00 | 91.24 | MOL2 | O |
| ATOM | 7141 | N | LEU | D | 150 | 0.907 | −21.333 | −38.132 | 1.00 | 89.17 | MOL2 | N |
| ATOM | 7142 | CA | LEU | D | 150 | −0.193 | −20.578 | −38.715 | 1.00 | 86.07 | MOL2 | C |
| ATOM | 7143 | CB | LEU | D | 150 | 0.136 | −19.087 | −38.777 | 1.00 | 90.77 | MOL2 | C |
| ATOM | 7144 | CG | LEU | D | 150 | −0.033 | −18.397 | −37.427 | 1.00 | 88.03 | MOL2 | C |
| ATOM | 7145 | CD1 | LEU | D | 150 | −1.311 | −18.924 | −36.788 | 1.00 | 82.95 | MOL2 | C |
| ATOM | 7146 | CD2 | LEU | D | 150 | 1.159 | −18.679 | −36.532 | 1.00 | 90.89 | MOL2 | C |
| ATOM | 7147 | C | LEU | D | 150 | −0.477 | −21.120 | −40.101 | 1.00 | 83.75 | MOL2 | C |
| ATOM | 7148 | O | LEU | D | 150 | 0.377 | −21.775 | −40.705 | 1.00 | 81.69 | MOL2 | O |
| ATOM | 7149 | N | GLY | D | 151 | −1.677 | −20.853 | −40.605 | 1.00 | 79.74 | MOL2 | N |
| ATOM | 7150 | CA | GLY | D | 151 | −2.031 | −21.370 | −41.908 | 1.00 | 82.13 | MOL2 | C |
| ATOM | 7151 | C | GLY | D | 151 | −2.755 | −20.401 | −42.809 | 1.00 | 83.28 | MOL2 | C |
| ATOM | 7152 | O | GLY | D | 151 | −3.049 | −19.271 | −42.433 | 1.00 | 84.80 | MOL2 | O |
| ATOM | 7153 | N | CYS | D | 152 | −3.050 | −20.861 | −44.014 | 1.00 | 83.96 | MOL2 | N |
| ATOM | 7154 | CA | CYS | D | 152 | −3.731 | −20.038 | −44.984 | 1.00 | 84.35 | MOL2 | C |
| ATOM | 7155 | C | CYS | D | 152 | −4.481 | −20.952 | −45.943 | 1.00 | 82.11 | MOL2 | C |
| ATOM | 7156 | O | CYS | D | 152 | −3.868 | −21.646 | −46.759 | 1.00 | 86.66 | MOL2 | O |
| ATOM | 7157 | CB | CYS | D | 152 | −2.708 | −19.191 | −45.731 | 1.00 | 94.24 | MOL2 | C |
| ATOM | 7158 | SG | CYS | D | 152 | −3.447 | −18.069 | −46.950 | 1.00 | 115.85 | MOL2 | S |
| ATOM | 7159 | N | LEU | D | 153 | −5.806 | −20.974 | −45.828 | 1.00 | 73.20 | MOL2 | N |
| ATOM | 7160 | CA | LEU | D | 153 | −6.622 | −21.816 | −46.694 | 1.00 | 70.35 | MOL2 | C |
| ATOM | 7161 | CB | LEU | D | 153 | −7.883 | −22.280 | −45.950 | 1.00 | 64.70 | MOL2 | C |
| ATOM | 7162 | CG | LEU | D | 153 | −8.887 | −23.091 | −46.786 | 1.00 | 68.18 | MOL2 | C |
| ATOM | 7163 | CD1 | LEU | D | 153 | −8.173 | −24.268 | −47.414 | 1.00 | 73.13 | MOL2 | C |
| ATOM | 7164 | CD2 | LEU | D | 153 | −10.045 | −23.583 | −45.929 | 1.00 | 64.94 | MOL2 | C |
| ATOM | 7165 | C | LEU | D | 153 | −7.005 | −21.088 | −47.992 | 1.00 | 71.66 | MOL2 | C |
| ATOM | 7166 | O | LEU | D | 153 | −7.522 | −19.980 | −47.967 | 1.00 | 76.30 | MOL2 | O |
| ATOM | 7167 | N | VAL | D | 154 | −6.734 | −21.716 | −49.127 | 1.00 | 69.81 | MOL2 | N |
| ATOM | 7168 | CA | VAL | D | 154 | −7.047 | −21.137 | −50.421 | 1.00 | 65.94 | MOL2 | C |
| ATOM | 7169 | CB | VAL | D | 154 | −5.778 | −21.102 | −51.301 | 1.00 | 68.33 | MOL2 | C |
| ATOM | 7170 | CG1 | VAL | D | 154 | −6.106 | −20.627 | −52.707 | 1.00 | 68.34 | MOL2 | C |
| ATOM | 7171 | CG2 | VAL | D | 154 | −4.747 | −20.179 | −50.651 | 1.00 | 67.27 | MOL2 | C |
| ATOM | 7172 | C | VAL | D | 154 | −8.140 | −21.999 | −51.033 | 1.00 | 67.13 | MOL2 | C |
| ATOM | 7173 | O | VAL | D | 154 | −7.877 | −23.061 | −51.616 | 1.00 | 68.63 | MOL2 | O |
| ATOM | 7174 | N | LYS | D | 155 | −9.378 | −21.536 | −50.892 | 1.00 | 66.86 | MOL2 | N |
| ATOM | 7175 | CA | LYS | D | 155 | −10.525 | −22.293 | −51.390 | 1.00 | 74.83 | MOL2 | C |
| ATOM | 7176 | CB | LYS | D | 155 | −11.660 | −22.258 | −50.354 | 1.00 | 78.06 | MOL2 | C |
| ATOM | 7177 | CG | LYS | D | 155 | −12.702 | −23.379 | −50.523 | 1.00 | 82.35 | MOL2 | C |
| ATOM | 7178 | CD | LYS | D | 155 | −13.491 | −23.616 | −49.227 | 1.00 | 82.38 | MOL2 | C |
| ATOM | 7179 | CE | LYS | D | 155 | −14.386 | −24.856 | −49.318 | 1.00 | 81.12 | MOL2 | C |
| ATOM | 7180 | NZ | LYS | D | 155 | −15.380 | −24.801 | −50.442 | 1.00 | 79.53 | MOL2 | N |
| ATOM | 7181 | C | LYS | D | 155 | −11.096 | −21.928 | −52.761 | 1.00 | 77.15 | MOL2 | C |
| ATOM | 7182 | O | LYS | D | 155 | −10.905 | −20.813 | −53.270 | 1.00 | 76.18 | MOL2 | O |
| ATOM | 7183 | N | GLY | D | 156 | −11.800 | −22.905 | −53.339 | 1.00 | 78.12 | MOL2 | N |
| ATOM | 7184 | CA | GLY | D | 156 | −12.443 | −22.766 | −54.638 | 1.00 | 81.40 | MOL2 | C |
| ATOM | 7185 | C | GLY | D | 156 | −11.833 | −21.890 | −55.726 | 1.00 | 83.33 | MOL2 | C |
| ATOM | 7186 | O | GLY | D | 156 | −12.312 | −20.784 | −55.986 | 1.00 | 87.51 | MOL2 | O |
| ATOM | 7187 | N | TYR | D | 157 | −10.783 | −22.377 | −56.375 | 1.00 | 81.41 | MOL2 | N |
| ATOM | 7188 | CA | TYR | D | 157 | −10.164 | −21.622 | −57.450 | 1.00 | 79.33 | MOL2 | C |
| ATOM | 7189 | CB | TYR | D | 157 | −8.839 | −21.031 | −57.000 | 1.00 | 80.57 | MOL2 | C |
| ATOM | 7190 | CG | TYR | D | 157 | −7.844 | −22.078 | −56.617 | 1.00 | 91.76 | MOL2 | C |
| ATOM | 7191 | CD1 | TYR | D | 157 | −7.775 | −22.559 | −55.320 | 1.00 | 97.13 | MOL2 | C |
| ATOM | 7192 | CE1 | TYR | D | 157 | −6.878 | −23.548 | −54.980 | 1.00 | 100.61 | MOL2 | C |
| ATOM | 7193 | CD2 | TYR | D | 157 | −6.991 | −22.615 | −57.562 | 1.00 | 96.42 | MOL2 | C |
| ATOM | 7194 | CE2 | TYR | D | 157 | −6.096 | −23.601 | −57.235 | 1.00 | 99.83 | MOL2 | C |
| ATOM | 7195 | CZ | TYR | D | 157 | −6.040 | −24.063 | −55.948 | 1.00 | 100.07 | MOL2 | C |
| ATOM | 7196 | OH | TYR | D | 157 | −5.125 | −25.035 | −55.638 | 1.00 | 102.18 | MOL2 | O |
| ATOM | 7197 | C | TYR | D | 157 | −9.954 | −22.585 | −58.606 | 1.00 | 79.39 | MOL2 | C |
| ATOM | 7198 | O | TYR | D | 157 | −9.916 | −23.804 | −58.404 | 1.00 | 77.77 | MOL2 | O |
| ATOM | 7199 | N | PHE | D | 158 | −9.821 | −22.032 | −59.810 | 1.00 | 80.14 | MOL2 | N |
| ATOM | 7200 | CA | PHE | D | 158 | −9.658 | −22.829 | −61.022 | 1.00 | 82.87 | MOL2 | C |
| ATOM | 7201 | CB | PHE | D | 158 | −11.019 | −23.382 | −61.454 | 1.00 | 78.27 | MOL2 | C |
| ATOM | 7202 | CG | PHE | D | 158 | −10.950 | −24.358 | −62.583 | 1.00 | 77.77 | MOL2 | C |
| ATOM | 7203 | CD1 | PHE | D | 158 | −11.146 | −25.710 | −62.356 | 1.00 | 82.81 | MOL2 | C |
| ATOM | 7204 | CD2 | PHE | D | 158 | −10.703 | −23.928 | −63.872 | 1.00 | 74.35 | MOL2 | C |
| ATOM | 7205 | CE1 | PHE | D | 158 | −11.098 | −26.618 | −63.400 | 1.00 | 85.17 | MOL2 | C |
| ATOM | 7206 | CE2 | PHE | D | 158 | −10.652 | −24.823 | −64.919 | 1.00 | 77.99 | MOL2 | C |
| ATOM | 7207 | CZ | PHE | D | 158 | −10.851 | −26.172 | −64.685 | 1.00 | 81.90 | MOL2 | C |
| ATOM | 7208 | C | PHE | D | 158 | −9.104 | −21.956 | −62.133 | 1.00 | 85.00 | MOL2 | C |
| ATOM | 7209 | O | PHE | D | 158 | −9.521 | −20.828 | −62.307 | 1.00 | 88.25 | MOL2 | O |
| ATOM | 7210 | N | PRO | D | 159 | −8.150 | −22.472 | −62.897 | 1.00 | 89.94 | MOL2 | N |
| ATOM | 7211 | CD | PRO | D | 159 | −7.851 | −21.969 | −64.249 | 1.00 | 92.24 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 7212 | CA | PRO | D | 159 | −7.627 | −23.822 | −62.700 | 1.00 | 93.46 | MOL2 | C |
|---|---|---|---|---|---|---|---|---|---|---|---|---|
| ATOM | 7213 | CB | PRO | D | 159 | −7.566 | −24.358 | −64.115 | 1.00 | 99.28 | MOL2 | C |
| ATOM | 7214 | CG | PRO | D | 159 | −7.094 | −23.128 | −64.881 | 1.00 | 102.81 | MOL2 | C |
| ATOM | 7215 | C | PRO | D | 159 | −6.246 | −23.737 | −62.051 | 1.00 | 93.51 | MOL2 | C |
| ATOM | 7216 | O | PRO | D | 159 | −5.829 | −22.671 | −61.582 | 1.00 | 87.00 | MOL2 | O |
| ATOM | 7217 | N | GLU | D | 160 | −5.551 | −24.866 | −62.018 | 1.00 | 94.34 | MOL2 | N |
| ATOM | 7218 | CA | GLU | D | 160 | −4.214 | −24.906 | −61.465 | 1.00 | 94.97 | MOL2 | C |
| ATOM | 7219 | CB | GLU | D | 160 | −3.640 | −26.307 | −61.643 | 1.00 | 102.82 | MOL2 | C |
| ATOM | 7220 | CG | GLU | D | 160 | −4.451 | −27.404 | −60.983 | 1.00 | 104.68 | MOL2 | C |
| ATOM | 7221 | CD | GLU | D | 160 | −4.126 | −27.551 | −59.516 | 1.00 | 107.82 | MOL2 | C |
| ATOM | 7222 | OE1 | GLU | D | 160 | −4.149 | −26.529 | −58.792 | 1.00 | 106.91 | MOL2 | O |
| ATOM | 7223 | OE2 | GLU | D | 160 | −3.843 | −28.693 | −59.094 | 1.00 | 109.05 | MOL2 | O |
| ATOM | 7224 | C | GLU | D | 160 | −3.441 | −23.926 | −62.330 | 1.00 | 94.31 | MOL2 | C |
| ATOM | 7225 | O | GLU | D | 160 | −3.754 | −23.751 | −63.500 | 1.00 | 97.38 | MOL2 | O |
| ATOM | 7226 | N | PRO | D | 161 | −2.402 | −23.303 | −61.785 | 1.00 | 93.91 | MOL2 | N |
| ATOM | 7227 | CD | PRO | D | 161 | −1.293 | −22.753 | −62.584 | 1.00 | 99.05 | MOL2 | C |
| ATOM | 7228 | CA | PRO | D | 161 | −1.973 | −23.515 | −60.413 | 1.00 | 96.35 | MOL2 | C |
| ATOM | 7229 | CB | PRO | D | 161 | −0.544 | −23.974 | −60.601 | 1.00 | 105.77 | MOL2 | C |
| ATOM | 7230 | CG | PRO | D | 161 | −0.067 | −22.959 | −61.658 | 1.00 | 104.99 | MOL2 | C |
| ATOM | 7231 | C | PRO | D | 161 | −2.016 | −22.201 | −59.663 | 1.00 | 93.78 | MOL2 | C |
| ATOM | 7232 | O | PRO | D | 161 | −2.131 | −21.139 | −60.265 | 1.00 | 91.29 | MOL2 | O |
| ATOM | 7233 | N | VAL | D | 162 | −1.916 | −22.287 | −58.344 | 1.00 | 91.79 | MOL2 | N |
| ATOM | 7234 | CA | VAL | D | 162 | −1.883 | −21.109 | −57.493 | 1.00 | 87.39 | MOL2 | C |
| ATOM | 7235 | CB | VAL | D | 162 | −2.845 | −21.211 | −56.278 | 1.00 | 90.09 | MOL2 | C |
| ATOM | 7236 | CG1 | VAL | D | 162 | −2.479 | −20.146 | −55.241 | 1.00 | 87.38 | MOL2 | C |
| ATOM | 7237 | CG2 | VAL | D | 162 | −4.283 | −21.031 | −56.715 | 1.00 | 87.82 | MOL2 | C |
| ATOM | 7238 | C | VAL | D | 162 | −0.481 | −21.118 | −56.938 | 1.00 | 85.24 | MOL2 | C |
| ATOM | 7239 | O | VAL | D | 162 | 0.134 | −22.181 | −56.827 | 1.00 | 89.31 | MOL2 | O |
| ATOM | 7240 | N | THR | D | 163 | 0.030 | −19.950 | −56.588 | 1.00 | 80.88 | MOL2 | N |
| ATOM | 7241 | CA | THR | D | 163 | 1.361 | −19.885 | −56.014 | 1.00 | 85.73 | MOL2 | C |
| ATOM | 7242 | CB | THR | D | 163 | 2.342 | −19.078 | −56.916 | 1.00 | 88.94 | MOL2 | C |
| ATOM | 7243 | OG1 | THR | D | 163 | 2.954 | −18.025 | −56.154 | 1.00 | 87.05 | MOL2 | O |
| ATOM | 7244 | CG2 | THR | D | 163 | 1.609 | −18.498 | −58.123 | 1.00 | 90.22 | MOL2 | C |
| ATOM | 7245 | C | THR | D | 163 | 1.272 | −19.231 | −54.650 | 1.00 | 83.87 | MOL2 | C |
| ATOM | 7246 | O | THR | D | 163 | 0.841 | −18.092 | −54.543 | 1.00 | 82.71 | MOL2 | O |
| ATOM | 7247 | N | VAL | D | 164 | 1.655 | −19.956 | −53.603 | 1.00 | 85.61 | MOL2 | N |
| ATOM | 7248 | CA | VAL | D | 164 | 1.619 | −19.373 | −52.270 | 1.00 | 85.22 | MOL2 | C |
| ATOM | 7249 | CB | VAL | D | 164 | 0.825 | −20.216 | −51.277 | 1.00 | 81.96 | MOL2 | C |
| ATOM | 7250 | CG1 | VAL | D | 164 | 0.810 | −19.517 | −49.918 | 1.00 | 72.46 | MOL2 | C |
| ATOM | 7251 | CG2 | VAL | D | 164 | −0.592 | −20.415 | −51.792 | 1.00 | 77.75 | MOL2 | C |
| ATOM | 7252 | C | VAL | D | 164 | 3.009 | −19.142 | −51.712 | 1.00 | 89.12 | MOL2 | C |
| ATOM | 7253 | O | VAL | D | 164 | 3.959 | −19.864 | −52.029 | 1.00 | 92.47 | MOL2 | O |
| ATOM | 7254 | N | THR | D | 165 | 3.113 | −18.113 | −50.882 | 1.00 | 91.76 | MOL2 | N |
| ATOM | 7255 | CA | THR | D | 165 | 4.377 | −17.723 | −50.275 | 1.00 | 99.22 | MOL2 | C |
| ATOM | 7256 | CB | THR | D | 165 | 5.179 | −16.788 | −51.205 | 1.00 | 106.57 | MOL2 | C |
| ATOM | 7257 | OG1 | THR | D | 165 | 5.686 | −15.683 | −50.439 | 1.00 | 108.68 | MOL2 | O |
| ATOM | 7258 | CG2 | THR | D | 165 | 4.292 | −16.259 | −52.343 | 1.00 | 106.51 | MOL2 | C |
| ATOM | 7259 | C | THR | D | 165 | 4.115 | −16.958 | −48.989 | 1.00 | 97.95 | MOL2 | C |
| ATOM | 7260 | O | THR | D | 165 | 3.040 | −16.400 | −48.812 | 1.00 | 95.05 | MOL2 | O |
| ATOM | 7261 | N | TRP | D | 166 | 5.094 | −16.929 | −48.091 | 1.00 | 100.90 | MOL2 | N |
| ATOM | 7262 | CA | TRP | D | 166 | 4.923 | −16.198 | −46.842 | 1.00 | 105.67 | MOL2 | C |
| ATOM | 7263 | CB | TRP | D | 166 | 5.028 | −17.136 | −45.626 | 1.00 | 109.45 | MOL2 | C |
| ATOM | 7264 | CG | TRP | D | 166 | 3.847 | −18.088 | −45.503 | 1.00 | 114.29 | MOL2 | C |
| ATOM | 7265 | CD2 | TRP | D | 166 | 2.735 | −17.973 | −44.605 | 1.00 | 116.27 | MOL2 | C |
| ATOM | 7266 | CE2 | TRP | D | 166 | 1.847 | −19.031 | −44.899 | 1.00 | 117.82 | MOL2 | C |
| ATOM | 7267 | CE3 | TRP | D | 166 | 2.401 | −17.076 | −43.586 | 1.00 | 119.27 | MOL2 | C |
| ATOM | 7268 | CD1 | TRP | D | 166 | 3.594 | −19.188 | −46.277 | 1.00 | 117.59 | MOL2 | C |
| ATOM | 7269 | NE1 | TRP | D | 166 | 2.395 | −19.759 | −45.921 | 1.00 | 115.70 | MOL2 | N |
| ATOM | 7270 | CZ2 | TRP | D | 166 | 0.648 | −19.214 | −44.213 | 1.00 | 120.98 | MOL2 | C |
| ATOM | 7271 | CZ3 | TRP | D | 166 | 1.207 | −17.259 | −42.905 | 1.00 | 122.60 | MOL2 | C |
| ATOM | 7272 | CH2 | TRP | D | 166 | 0.345 | −18.319 | −43.223 | 1.00 | 123.26 | MOL2 | C |
| ATOM | 7273 | C | TRP | D | 166 | 5.910 | −15.038 | −46.728 | 1.00 | 109.48 | MOL2 | C |
| ATOM | 7274 | O | TRP | D | 166 | 7.126 | −15.207 | −46.875 | 1.00 | 109.46 | MOL2 | O |
| ATOM | 7275 | N | ASN | D | 167 | 5.353 | −13.856 | −46.466 | 1.00 | 113.38 | MOL2 | N |
| ATOM | 7276 | CA | ASN | D | 167 | 6.104 | −12.608 | −46.352 | 1.00 | 114.54 | MOL2 | C |
| ATOM | 7277 | CB | ASN | D | 167 | 6.947 | −12.600 | −45.078 | 1.00 | 118.94 | MOL2 | C |
| ATOM | 7278 | CG | ASN | D | 167 | 6.109 | −12.324 | −43.834 | 1.00 | 124.05 | MOL2 | C |
| ATOM | 7279 | OD1 | ASN | D | 167 | 4.937 | −12.710 | −43.760 | 1.00 | 122.77 | MOL2 | O |
| ATOM | 7280 | ND2 | ASN | D | 167 | 6.711 | −11.663 | −42.847 | 1.00 | 127.26 | MOL2 | N |
| ATOM | 7281 | C | ASN | D | 167 | 6.952 | −12.374 | −47.594 | 1.00 | 114.51 | MOL2 | C |
| ATOM | 7282 | O | ASN | D | 167 | 8.093 | −11.908 | −47.529 | 1.00 | 112.51 | MOL2 | O |
| ATOM | 7283 | N | SER | D | 168 | 6.349 | −12.713 | −48.729 | 1.00 | 114.88 | MOL2 | N |
| ATOM | 7284 | CA | SER | D | 168 | 6.948 | −12.559 | −50.046 | 1.00 | 117.71 | MOL2 | C |
| ATOM | 7285 | CB | SER | D | 168 | 7.043 | −11.068 | −50.384 | 1.00 | 120.77 | MOL2 | C |
| ATOM | 7286 | OG | SER | D | 168 | 5.760 | −10.461 | −50.326 | 1.00 | 120.73 | MOL2 | O |
| ATOM | 7287 | C | SER | D | 168 | 8.308 | −13.240 | −50.236 | 1.00 | 118.45 | MOL2 | C |
| ATOM | 7288 | O | SER | D | 168 | 9.033 | −12.940 | −51.190 | 1.00 | 119.88 | MOL2 | O |

TABLE 1-continued

The atomic coordinates of IL17F in complex with 496 Fab
(H32; a = 189.4; b = 189.4; c = 490.9, α, β = 90°; γ = 120°)

| ATOM | 7289 | N   | GLY | D | 169 | 8.647  | −14.167 | −49.345 | 1.00 | 116.49 | MOL2 | N |
|------|------|-----|-----|---|-----|--------|---------|---------|------|--------|------|---|
| ATOM | 7290 | CA  | GLY | D | 169 | 9.916  | −14.863 | −49.470 | 1.00 | 115.34 | MOL2 | C |
| ATOM | 7291 | C   | GLY | D | 169 | 10.733 | −14.831 | −48.196 | 1.00 | 116.67 | MOL2 | C |
| ATOM | 7292 | O   | GLY | D | 169 | 11.731 | −15.547 | −48.068 | 1.00 | 116.08 | MOL2 | O |
| ATOM | 7293 | N   | SER | D | 170 | 10.305 | −13.991 | −47.257 | 1.00 | 117.66 | MOL2 | N |
| ATOM | 7294 | CA  | SER | D | 170 | 10.968 | −13.838 | −45.962 | 1.00 | 118.92 | MOL2 | C |
| ATOM | 7295 | CB  | SER | D | 170 | 10.208 | −12.789 | −45.123 | 1.00 | 118.48 | MOL2 | C |
| ATOM | 7296 | OG  | SER | D | 170 | 10.823 | −12.535 | −43.870 | 1.00 | 117.76 | MOL2 | O |
| ATOM | 7297 | C   | SER | D | 170 | 11.005 | −15.193 | −45.236 | 1.00 | 118.99 | MOL2 | C |
| ATOM | 7298 | O   | SER | D | 170 | 12.025 | −15.567 | −44.638 | 1.00 | 120.02 | MOL2 | O |
| ATOM | 7299 | N   | LEU | D | 171 | 9.890  | −15.922 | −45.299 | 1.00 | 114.98 | MOL2 | N |
| ATOM | 7300 | CA  | LEU | D | 171 | 9.788  | −17.233 | −44.664 | 1.00 | 111.28 | MOL2 | C |
| ATOM | 7301 | CB  | LEU | D | 171 | 8.481  | −17.377 | −43.885 | 1.00 | 106.75 | MOL2 | C |
| ATOM | 7302 | CG  | LEU | D | 171 | 8.112  | −16.341 | −42.832 | 1.00 | 104.87 | MOL2 | C |
| ATOM | 7303 | CD1 | LEU | D | 171 | 9.349  | −15.874 | −42.057 | 1.00 | 102.21 | MOL2 | C |
| ATOM | 7304 | CD2 | LEU | D | 171 | 7.458  | −15.196 | −43.537 | 1.00 | 104.02 | MOL2 | C |
| ATOM | 7305 | C   | LEU | D | 171 | 9.815  | −18.323 | −45.712 | 1.00 | 112.63 | MOL2 | C |
| ATOM | 7306 | O   | LEU | D | 171 | 8.872  | −18.450 | −46.488 | 1.00 | 113.84 | MOL2 | O |
| ATOM | 7307 | N   | SER | D | 172 | 10.885 | −19.114 | −45.734 | 1.00 | 116.51 | MOL2 | N |
| ATOM | 7308 | CA  | SER | D | 172 | 10.991 | −20.211 | −46.699 | 1.00 | 120.66 | MOL2 | C |
| ATOM | 7309 | CB  | SER | D | 172 | 12.198 | −20.009 | −47.633 | 1.00 | 122.80 | MOL2 | C |
| ATOM | 7310 | OG  | SER | D | 172 | 13.427 | −19.984 | −46.924 | 1.00 | 128.10 | MOL2 | O |
| ATOM | 7311 | C   | SER | D | 172 | 11.115 | −21.546 | −45.966 | 1.00 | 120.50 | MOL2 | C |
| ATOM | 7312 | O   | SER | D | 172 | 10.645 | −22.582 | −46.451 | 1.00 | 117.91 | MOL2 | O |
| ATOM | 7313 | N   | SER | D | 173 | 11.737 | −21.494 | −44.787 | 1.00 | 120.00 | MOL2 | N |
| ATOM | 7314 | CA  | SER | D | 173 | 11.958 | −22.666 | −43.943 | 1.00 | 117.46 | MOL2 | C |
| ATOM | 7315 | CB  | SER | D | 173 | 13.241 | −22.490 | −43.119 | 1.00 | 119.76 | MOL2 | C |
| ATOM | 7316 | OG  | SER | D | 173 | 13.086 | −21.472 | −42.140 | 1.00 | 120.60 | MOL2 | O |
| ATOM | 7317 | C   | SER | D | 173 | 10.791 | −22.871 | −42.988 | 1.00 | 113.90 | MOL2 | C |
| ATOM | 7318 | O   | SER | D | 173 | 10.213 | −21.907 | −42.487 | 1.00 | 111.94 | MOL2 | O |
| ATOM | 7319 | N   | GLY | D | 174 | 10.460 | −24.129 | −42.724 | 1.00 | 111.91 | MOL2 | N |
| ATOM | 7320 | CA  | GLY | D | 174 | 9.361  | −24.417 | −41.819 | 1.00 | 109.17 | MOL2 | C |
| ATOM | 7321 | C   | GLY | D | 174 | 8.008  | −24.127 | −42.447 | 1.00 | 105.52 | MOL2 | C |
| ATOM | 7322 | O   | GLY | D | 174 | 7.022  | −23.867 | −41.753 | 1.00 | 99.48  | MOL2 | O |
| ATOM | 7323 | N   | VAL | D | 175 | 7.961  | −24.171 | −43.773 | 1.00 | 103.61 | MOL2 | N |
| ATOM | 7324 | CA  | VAL | D | 175 | 6.718  | −23.913 | −44.481 | 1.00 | 99.51  | MOL2 | C |
| ATOM | 7325 | CB  | VAL | D | 175 | 6.875  | −22.731 | −45.459 | 1.00 | 105.14 | MOL2 | C |
| ATOM | 7326 | CG1 | VAL | D | 175 | 5.512  | −22.351 | −46.038 | 1.00 | 105.60 | MOL2 | C |
| ATOM | 7327 | CG2 | VAL | D | 175 | 7.528  | −21.549 | −44.742 | 1.00 | 101.57 | MOL2 | C |
| ATOM | 7328 | C   | VAL | D | 175 | 6.264  | −25.151 | −45.245 | 1.00 | 94.61  | MOL2 | C |
| ATOM | 7329 | O   | VAL | D | 175 | 7.066  | −25.840 | −45.888 | 1.00 | 96.65  | MOL2 | O |
| ATOM | 7330 | N   | HIS | D | 176 | 4.971  | −25.434 | −45.156 | 1.00 | 87.43  | MOL2 | N |
| ATOM | 7331 | CA  | HIS | D | 176 | 4.397  | −26.587 | −45.834 | 1.00 | 86.07  | MOL2 | C |
| ATOM | 7332 | CB  | HIS | D | 176 | 3.950  | −27.660 | −44.827 | 1.00 | 86.41  | MOL2 | C |
| ATOM | 7333 | CG  | HIS | D | 176 | 5.073  | −28.275 | −44.049 | 1.00 | 88.28  | MOL2 | C |
| ATOM | 7334 | CD2 | HIS | D | 176 | 5.081  | −28.931 | −42.864 | 1.00 | 88.64  | MOL2 | C |
| ATOM | 7335 | ND1 | HIS | D | 176 | 6.380  | −28.259 | −44.487 | 1.00 | 88.23  | MOL2 | N |
| ATOM | 7336 | CE1 | HIS | D | 176 | 7.146  | −28.875 | −43.604 | 1.00 | 88.02  | MOL2 | C |
| ATOM | 7337 | NE2 | HIS | D | 176 | 6.382  | −29.292 | −42.610 | 1.00 | 89.74  | MOL2 | N |
| ATOM | 7338 | C   | HIS | D | 176 | 3.190  | −26.170 | −46.646 | 1.00 | 81.52  | MOL2 | C |
| ATOM | 7339 | O   | HIS | D | 176 | 2.136  | −25.899 | −46.086 | 1.00 | 80.11  | MOL2 | O |
| ATOM | 7340 | N   | THR | D | 177 | 3.340  | −26.116 | −47.962 | 1.00 | 76.57  | MOL2 | N |
| ATOM | 7341 | CA  | THR | D | 177 | 2.224  | −25.754 | −48.816 | 1.00 | 72.97  | MOL2 | C |
| ATOM | 7342 | CB  | THR | D | 177 | 2.662  | −24.744 | −49.877 | 1.00 | 80.82  | MOL2 | C |
| ATOM | 7343 | OG1 | THR | D | 177 | 3.372  | −23.671 | −49.242 | 1.00 | 85.30  | MOL2 | O |
| ATOM | 7344 | CG2 | THR | D | 177 | 1.450  | −24.183 | −50.599 | 1.00 | 83.37  | MOL2 | C |
| ATOM | 7345 | C   | THR | D | 177 | 1.772  | −27.051 | −49.467 | 1.00 | 67.91  | MOL2 | C |
| ATOM | 7346 | O   | THR | D | 177 | 2.470  | −27.619 | −50.313 | 1.00 | 70.89  | MOL2 | O |
| ATOM | 7347 | N   | PHE | D | 178 | 0.601  | −27.513 | −49.056 | 1.00 | 60.03  | MOL2 | N |
| ATOM | 7348 | CA  | PHE | D | 178 | 0.041  | −28.771 | −49.527 | 1.00 | 61.67  | MOL2 | C |
| ATOM | 7349 | CB  | PHE | D | 178 | −1.032 | −29.216 | −48.529 | 1.00 | 68.29  | MOL2 | C |
| ATOM | 7350 | CG  | PHE | D | 178 | −0.528 | −29.307 | −47.100 | 1.00 | 73.75  | MOL2 | C |
| ATOM | 7351 | CD1 | PHE | D | 178 | −0.041 | −30.499 | −46.590 | 1.00 | 72.53  | MOL2 | C |
| ATOM | 7352 | CD2 | PHE | D | 178 | −0.482 | −28.183 | −46.293 | 1.00 | 75.98  | MOL2 | C |
| ATOM | 7353 | CE1 | PHE | D | 178 | 0.481  | −30.564 | −45.314 | 1.00 | 71.77  | MOL2 | C |
| ATOM | 7354 | CE2 | PHE | D | 178 | 0.041  | −28.247 | −45.013 | 1.00 | 76.50  | MOL2 | C |
| ATOM | 7355 | CZ  | PHE | D | 178 | 0.523  | −29.436 | −44.527 | 1.00 | 73.58  | MOL2 | C |
| ATOM | 7356 | C   | PHE | D | 178 | −0.531 | −28.770 | −50.931 | 1.00 | 60.36  | MOL2 | C |
| ATOM | 7357 | O   | PHE | D | 178 | −0.891 | −27.736 | −51.465 | 1.00 | 62.95  | MOL2 | O |
| ATOM | 7358 | N   | PRO | D | 179 | −0.579 | −29.944 | −51.561 | 1.00 | 63.42  | MOL2 | N |
| ATOM | 7359 | CD  | PRO | D | 179 | 0.313  | −31.052 | −51.192 | 1.00 | 71.38  | MOL2 | C |
| ATOM | 7360 | CA  | PRO | D | 179 | −1.104 | −30.153 | −52.908 | 1.00 | 68.95  | MOL2 | C |
| ATOM | 7361 | CB  | PRO | D | 179 | −0.856 | −31.636 | −53.137 | 1.00 | 70.55  | MOL2 | C |
| ATOM | 7362 | CG  | PRO | D | 179 | 0.475  | −31.800 | −52.516 | 1.00 | 74.91  | MOL2 | C |
| ATOM | 7363 | C   | PRO | D | 179 | −2.577 | −29.813 | −52.968 | 1.00 | 70.15  | MOL2 | C |
| ATOM | 7364 | O   | PRO | D | 179 | −3.340 | −30.171 | −52.072 | 1.00 | 70.16  | MOL2 | O |
| ATOM | 7365 | N   | ALA | D | 180 | −2.980 | −29.115 | −54.018 | 1.00 | 72.73  | MOL2 | N |

TABLE 1-continued

The atomic coordinates of IL17F in complex with 496 Fab
(H32; a = 189.4; b = 189.4; c = 490.9, α, β = 90°; γ = 120°)

| ATOM | 7366 | CA | ALA | D | 180 | −4.382 | −28.767 | −54.157 | 1.00 | 74.70 | MOL2 | C |
|---|---|---|---|---|---|---|---|---|---|---|---|---|
| ATOM | 7367 | CB | ALA | D | 180 | −4.580 | −27.830 | −55.315 | 1.00 | 76.02 | MOL2 | C |
| ATOM | 7368 | C | ALA | D | 180 | −5.172 | −30.038 | −54.388 | 1.00 | 78.51 | MOL2 | C |
| ATOM | 7369 | O | ALA | D | 180 | −4.664 | −31.013 | −54.952 | 1.00 | 80.95 | MOL2 | O |
| ATOM | 7370 | N | VAL | D | 181 | −6.415 | −30.040 | −53.935 | 1.00 | 83.08 | MOL2 | N |
| ATOM | 7371 | CA | VAL | D | 181 | −7.260 | −31.205 | −54.138 | 1.00 | 86.75 | MOL2 | C |
| ATOM | 7372 | CB | VAL | D | 181 | −7.495 | −31.978 | −52.812 | 1.00 | 89.63 | MOL2 | C |
| ATOM | 7373 | CG1 | VAL | D | 181 | −8.201 | −31.098 | −51.794 | 1.00 | 92.37 | MOL2 | C |
| ATOM | 7374 | CG2 | VAL | D | 181 | −8.286 | −33.244 | −53.096 | 1.00 | 91.56 | MOL2 | C |
| ATOM | 7375 | C | VAL | D | 181 | −8.579 | −30.763 | −54.771 | 1.00 | 85.95 | MOL2 | C |
| ATOM | 7376 | O | VAL | D | 181 | −9.027 | −29.629 | −54.586 | 1.00 | 82.58 | MOL2 | O |
| ATOM | 7377 | N | LEU | D | 182 | −9.188 | −31.652 | −55.542 | 1.00 | 89.33 | MOL2 | N |
| ATOM | 7378 | CA | LEU | D | 182 | −10.438 | −31.319 | −56.213 | 1.00 | 99.47 | MOL2 | C |
| ATOM | 7379 | CB | LEU | D | 182 | −10.663 | −32.212 | −57.438 | 1.00 | 103.48 | MOL2 | C |
| ATOM | 7380 | CG | LEU | D | 182 | −9.979 | −31.802 | −58.741 | 1.00 | 104.61 | MOL2 | C |
| ATOM | 7381 | CD1 | LEU | D | 182 | −10.465 | −30.434 | −59.175 | 1.00 | 101.89 | MOL2 | C |
| ATOM | 7382 | CD2 | LEU | D | 182 | −8.479 | −31.803 | −58.533 | 1.00 | 111.01 | MOL2 | C |
| ATOM | 7383 | C | LEU | D | 182 | −11.675 | −31.397 | −55.337 | 1.00 | 105.64 | MOL2 | C |
| ATOM | 7384 | O | LEU | D | 182 | −12.117 | −32.487 | −54.957 | 1.00 | 106.49 | MOL2 | O |
| ATOM | 7385 | N | GLN | D | 183 | −12.244 | −30.234 | −55.038 | 1.00 | 111.66 | MOL2 | N |
| ATOM | 7386 | CA | GLN | D | 183 | −13.452 | −30.167 | −54.228 | 1.00 | 117.55 | MOL2 | C |
| ATOM | 7387 | CB | GLN | D | 183 | −13.296 | −29.107 | −53.134 | 1.00 | 121.80 | MOL2 | C |
| ATOM | 7388 | CG | GLN | D | 183 | −14.429 | −29.097 | −52.125 | 1.00 | 127.48 | MOL2 | C |
| ATOM | 7389 | CD | GLN | D | 183 | −14.151 | −28.176 | −50.956 | 1.00 | 134.62 | MOL2 | C |
| ATOM | 7390 | OE1 | GLN | D | 183 | −13.935 | −26.976 | −51.136 | 1.00 | 137.26 | MOL2 | O |
| ATOM | 7391 | NE2 | GLN | D | 183 | −14.154 | −28.735 | −49.745 | 1.00 | 136.36 | MOL2 | N |
| ATOM | 7392 | C | GLN | D | 183 | −14.642 | −29.828 | −55.132 | 1.00 | 117.41 | MOL2 | C |
| ATOM | 7393 | O | GLN | D | 183 | −15.074 | −28.674 | −55.206 | 1.00 | 115.92 | MOL2 | O |
| ATOM | 7394 | N | SER | D | 184 | −15.153 | −30.848 | −55.821 | 1.00 | 117.21 | MOL2 | N |
| ATOM | 7395 | CA | SER | D | 184 | −16.284 | −30.695 | −56.735 | 1.00 | 116.49 | MOL2 | C |
| ATOM | 7396 | CB | SER | D | 184 | −17.567 | −30.374 | −55.952 | 1.00 | 118.76 | MOL2 | C |
| ATOM | 7397 | OG | SER | D | 184 | −18.715 | −30.434 | −56.785 | 1.00 | 117.15 | MOL2 | O |
| ATOM | 7398 | C | SER | D | 184 | −16.001 | −29.599 | −57.766 | 1.00 | 114.43 | MOL2 | C |
| ATOM | 7399 | O | SER | D | 184 | −16.331 | −28.423 | −57.566 | 1.00 | 113.94 | MOL2 | O |
| ATOM | 7400 | N | ASP | D | 185 | −15.373 | −30.003 | −58.866 | 1.00 | 109.97 | MOL2 | N |
| ATOM | 7401 | CA | ASP | D | 185 | −15.027 | −29.092 | −59.953 | 1.00 | 106.35 | MOL2 | C |
| ATOM | 7402 | CB | ASP | D | 185 | −16.276 | −28.756 | −60.778 | 1.00 | 109.89 | MOL2 | C |
| ATOM | 7403 | CG | ASP | D | 185 | −16.703 | −29.900 | −61.688 | 1.00 | 114.04 | MOL2 | C |
| ATOM | 7404 | OD1 | ASP | D | 185 | −16.865 | −31.031 | −61.181 | 1.00 | 116.14 | MOL2 | O |
| ATOM | 7405 | OD2 | ASP | D | 185 | −16.879 | −29.666 | −62.908 | 1.00 | 111.22 | MOL2 | O |
| ATOM | 7406 | C | ASP | D | 185 | −14.362 | −27.800 | −59.491 | 1.00 | 101.63 | MOL2 | C |
| ATOM | 7407 | O | ASP | D | 185 | −14.626 | −26.734 | −60.036 | 1.00 | 101.10 | MOL2 | O |
| ATOM | 7408 | N | LEU | D | 186 | −13.497 | −27.894 | −58.489 | 1.00 | 97.57 | MOL2 | N |
| ATOM | 7409 | CA | LEU | D | 186 | −12.804 | −26.719 | −57.982 | 1.00 | 94.35 | MOL2 | C |
| ATOM | 7410 | CB | LEU | D | 186 | −13.771 | −25.834 | −57.206 | 1.00 | 97.44 | MOL2 | C |
| ATOM | 7411 | CG | LEU | D | 186 | −13.994 | −24.493 | −57.894 | 1.00 | 98.32 | MOL2 | C |
| ATOM | 7412 | CD1 | LEU | D | 186 | −14.678 | −23.525 | −56.955 | 1.00 | 101.00 | MOL2 | C |
| ATOM | 7413 | CD2 | LEU | D | 186 | −12.656 | −23.944 | −58.309 | 1.00 | 96.21 | MOL2 | C |
| ATOM | 7414 | C | LEU | D | 186 | −11.629 | −27.089 | −57.093 | 1.00 | 91.57 | MOL2 | C |
| ATOM | 7415 | O | LEU | D | 186 | −11.710 | −28.030 | −56.298 | 1.00 | 87.44 | MOL2 | O |
| ATOM | 7416 | N | TYR | D | 187 | −10.545 | −26.329 | −57.220 | 1.00 | 88.85 | MOL2 | N |
| ATOM | 7417 | CA | TYR | D | 187 | −9.332 | −26.589 | −56.452 | 1.00 | 89.15 | MOL2 | C |
| ATOM | 7418 | CB | TYR | D | 187 | −8.094 | −26.188 | −57.270 | 1.00 | 90.53 | MOL2 | C |
| ATOM | 7419 | CG | TYR | D | 187 | −7.915 | −26.965 | −58.560 | 1.00 | 97.55 | MOL2 | C |
| ATOM | 7420 | CD1 | TYR | D | 187 | −7.866 | −28.353 | −58.568 | 1.00 | 98.39 | MOL2 | C |
| ATOM | 7421 | CE1 | TYR | D | 187 | −7.693 | −29.055 | −59.747 | 1.00 | 100.52 | MOL2 | C |
| ATOM | 7422 | CD2 | TYR | D | 187 | −7.786 | −26.308 | −59.772 | 1.00 | 103.60 | MOL2 | C |
| ATOM | 7423 | CE2 | TYR | D | 187 | −7.615 | −27.007 | −60.957 | 1.00 | 106.54 | MOL2 | C |
| ATOM | 7424 | CZ | TYR | D | 187 | −7.569 | −28.378 | −60.936 | 1.00 | 105.62 | MOL2 | C |
| ATOM | 7425 | OH | TYR | D | 187 | −7.388 | −29.067 | −62.112 | 1.00 | 112.90 | MOL2 | O |
| ATOM | 7426 | C | TYR | D | 187 | −9.278 | −25.893 | −55.098 | 1.00 | 84.84 | MOL2 | C |
| ATOM | 7427 | O | TYR | D | 187 | −9.577 | −24.710 | −54.989 | 1.00 | 81.67 | MOL2 | O |
| ATOM | 7428 | N | THR | D | 188 | −8.889 | −26.645 | −54.072 | 1.00 | 83.80 | MOL2 | N |
| ATOM | 7429 | CA | THR | D | 188 | −8.757 | −26.120 | −52.716 | 1.00 | 82.80 | MOL2 | C |
| ATOM | 7430 | CB | THR | D | 188 | −9.873 | −26.626 | −51.790 | 1.00 | 86.64 | MOL2 | C |
| ATOM | 7431 | OG1 | THR | D | 188 | −11.155 | −26.274 | −52.327 | 1.00 | 92.13 | MOL2 | O |
| ATOM | 7432 | CG2 | THR | D | 188 | −9.715 | −26.012 | −50.412 | 1.00 | 85.38 | MOL2 | C |
| ATOM | 7433 | C | THR | D | 188 | −7.432 | −26.618 | −52.149 | 1.00 | 80.21 | MOL2 | C |
| ATOM | 7434 | O | THR | D | 188 | −7.135 | −27.816 | −52.213 | 1.00 | 77.53 | MOL2 | O |
| ATOM | 7435 | N | LEU | D | 189 | −6.638 | −25.703 | −51.601 | 1.00 | 75.75 | MOL2 | N |
| ATOM | 7436 | CA | LEU | D | 189 | −5.344 | −26.068 | −51.036 | 1.00 | 71.42 | MOL2 | C |
| ATOM | 7437 | CB | LEU | D | 189 | −4.214 | −25.786 | −52.035 | 1.00 | 67.24 | MOL2 | C |
| ATOM | 7438 | CG | LEU | D | 189 | −3.627 | −24.369 | −52.109 | 1.00 | 63.69 | MOL2 | C |
| ATOM | 7439 | CD1 | LEU | D | 189 | −2.736 | −24.067 | −50.915 | 1.00 | 55.23 | MOL2 | C |
| ATOM | 7440 | CD2 | LEU | D | 189 | −2.802 | −24.260 | −53.371 | 1.00 | 68.68 | MOL2 | C |
| ATOM | 7441 | C | LEU | D | 189 | −5.093 | −25.264 | −49.780 | 1.00 | 69.79 | MOL2 | C |
| ATOM | 7442 | O | LEU | D | 189 | −5.613 | −24.168 | −49.625 | 1.00 | 69.82 | MOL2 | O |

TABLE 1-continued

The atomic coordinates of IL17F in complex with 496 Fab
(H32; a = 189.4; b = 189.4; c = 490.9, α, β = 90°; γ = 120°)

| ATOM | 7443 | N | SER | D | 190 | −4.268 | −25.810 | −48.899 | 1.00 | 70.07 | MOL2 | N |
|---|---|---|---|---|---|---|---|---|---|---|---|---|
| ATOM | 7444 | CA | SER | D | 190 | −3.926 | −25.157 | −47.643 | 1.00 | 66.76 | MOL2 | C |
| ATOM | 7445 | CB | SER | D | 190 | −4.446 | −26.000 | −46.478 | 1.00 | 67.94 | MOL2 | C |
| ATOM | 7446 | OG | SER | D | 190 | −4.713 | −27.343 | −46.889 | 1.00 | 68.93 | MOL2 | O |
| ATOM | 7447 | C | SER | D | 190 | −2.418 | −25.006 | −47.541 | 1.00 | 65.99 | MOL2 | C |
| ATOM | 7448 | O | SER | D | 190 | −1.666 | −25.640 | −48.285 | 1.00 | 71.65 | MOL2 | O |
| ATOM | 7449 | N | SER | D | 191 | −1.966 | −24.168 | −46.625 | 1.00 | 61.24 | MOL2 | N |
| ATOM | 7450 | CA | SER | D | 191 | −0.535 | −23.979 | −46.463 | 1.00 | 67.78 | MOL2 | C |
| ATOM | 7451 | CB | SER | D | 191 | −0.012 | −22.949 | −47.461 | 1.00 | 64.40 | MOL2 | C |
| ATOM | 7452 | OG | SER | D | 191 | 1.351 | −22.654 | −47.200 | 1.00 | 64.07 | MOL2 | O |
| ATOM | 7453 | C | SER | D | 191 | −0.201 | −23.527 | −45.055 | 1.00 | 71.33 | MOL2 | C |
| ATOM | 7454 | O | SER | D | 191 | −0.644 | −22.475 | −44.614 | 1.00 | 72.50 | MOL2 | O |
| ATOM | 7455 | N | SER | D | 192 | 0.592 | −24.329 | −44.357 | 1.00 | 74.03 | MOL2 | N |
| ATOM | 7456 | CA | SER | D | 192 | 0.984 | −24.018 | −43.003 | 1.00 | 76.14 | MOL2 | C |
| ATOM | 7457 | CB | SER | D | 192 | 0.948 | −25.274 | −42.154 | 1.00 | 78.39 | MOL2 | C |
| ATOM | 7458 | OG | SER | D | 192 | 1.638 | −25.057 | −40.940 | 1.00 | 88.40 | MOL2 | O |
| ATOM | 7459 | C | SER | D | 192 | 2.378 | −23.420 | −42.940 | 1.00 | 81.28 | MOL2 | C |
| ATOM | 7460 | O | SER | D | 192 | 3.200 | −23.601 | −43.848 | 1.00 | 81.58 | MOL2 | O |
| ATOM | 7461 | N | VAL | D | 193 | 2.631 | −22.716 | −41.842 | 1.00 | 84.79 | MOL2 | N |
| ATOM | 7462 | CA | VAL | D | 193 | 3.910 | −22.069 | −41.591 | 1.00 | 87.41 | MOL2 | C |
| ATOM | 7463 | CB | VAL | D | 193 | 3.912 | −20.611 | −42.080 | 1.00 | 88.21 | MOL2 | C |
| ATOM | 7464 | CG1 | VAL | D | 193 | 2.707 | −19.880 | −41.523 | 1.00 | 87.93 | MOL2 | C |
| ATOM | 7465 | CG2 | VAL | D | 193 | 5.186 | −19.919 | −41.616 | 1.00 | 89.40 | MOL2 | C |
| ATOM | 7466 | C | VAL | D | 193 | 4.176 | −22.046 | −40.088 | 1.00 | 87.14 | MOL2 | C |
| ATOM | 7467 | O | VAL | D | 193 | 3.368 | −21.529 | −39.310 | 1.00 | 76.15 | MOL2 | O |
| ATOM | 7468 | N | THR | D | 194 | 5.305 | −22.617 | −39.685 | 1.00 | 90.79 | MOL2 | N |
| ATOM | 7469 | CA | THR | D | 194 | 5.677 | −22.636 | −38.281 | 1.00 | 94.76 | MOL2 | C |
| ATOM | 7470 | CB | THR | D | 194 | 6.478 | −23.898 | −37.926 | 1.00 | 102.47 | MOL2 | C |
| ATOM | 7471 | OG1 | THR | D | 194 | 5.656 | −25.054 | −38.129 | 1.00 | 113.20 | MOL2 | O |
| ATOM | 7472 | CG2 | THR | D | 194 | 6.933 | −23.850 | −36.469 | 1.00 | 104.71 | MOL2 | C |
| ATOM | 7473 | C | THR | D | 194 | 6.540 | −21.416 | −38.016 | 1.00 | 93.94 | MOL2 | C |
| ATOM | 7474 | O | THR | D | 194 | 7.185 | −20.889 | −38.929 | 1.00 | 91.41 | MOL2 | O |
| ATOM | 7475 | N | VAL | D | 195 | 6.560 | −20.977 | −36.763 | 1.00 | 94.99 | MOL2 | N |
| ATOM | 7476 | CA | VAL | D | 195 | 7.321 | −19.793 | −36.391 | 1.00 | 96.41 | MOL2 | C |
| ATOM | 7477 | CB | VAL | D | 195 | 6.609 | −18.518 | −36.904 | 1.00 | 99.17 | MOL2 | C |
| ATOM | 7478 | CG1 | VAL | D | 195 | 5.292 | −18.323 | −36.148 | 1.00 | 93.52 | MOL2 | C |
| ATOM | 7479 | CG2 | VAL | D | 195 | 7.510 | −17.300 | −36.744 | 1.00 | 102.91 | MOL2 | C |
| ATOM | 7480 | C | VAL | D | 195 | 7.448 | −19.672 | −34.879 | 1.00 | 97.60 | MOL2 | C |
| ATOM | 7481 | O | VAL | D | 195 | 6.560 | −20.091 | −34.129 | 1.00 | 91.61 | MOL2 | O |
| ATOM | 7482 | N | PRO | D | 196 | 8.561 | −19.088 | −34.410 | 1.00 | 101.67 | MOL2 | N |
| ATOM | 7483 | CD | PRO | D | 196 | 9.788 | −18.768 | −35.166 | 1.00 | 103.43 | MOL2 | C |
| ATOM | 7484 | CA | PRO | D | 196 | 8.774 | −18.918 | −32.970 | 1.00 | 105.47 | MOL2 | C |
| ATOM | 7485 | CB | PRO | D | 196 | 10.160 | −18.277 | −32.900 | 1.00 | 106.21 | MOL2 | C |
| ATOM | 7486 | CG | PRO | D | 196 | 10.857 | −18.870 | −34.100 | 1.00 | 107.54 | MOL2 | C |
| ATOM | 7487 | C | PRO | D | 196 | 7.687 | −18.046 | −32.331 | 1.00 | 107.87 | MOL2 | C |
| ATOM | 7488 | O | PRO | D | 196 | 7.369 | −16.965 | −32.831 | 1.00 | 107.05 | MOL2 | O |
| ATOM | 7489 | N | SER | D | 197 | 7.119 | −18.533 | −31.230 | 1.00 | 111.25 | MOL2 | N |
| ATOM | 7490 | CA | SER | D | 197 | 6.068 | −17.822 | −30.501 | 1.00 | 114.37 | MOL2 | C |
| ATOM | 7491 | CB | SER | D | 197 | 5.747 | −18.555 | −29.201 | 1.00 | 114.73 | MOL2 | C |
| ATOM | 7492 | OG | SER | D | 197 | 4.997 | −17.719 | −28.336 | 1.00 | 117.18 | MOL2 | O |
| ATOM | 7493 | C | SER | D | 197 | 6.426 | −16.376 | −30.160 | 1.00 | 115.72 | MOL2 | C |
| ATOM | 7494 | O | SER | D | 197 | 5.548 | −15.517 | −30.029 | 1.00 | 112.73 | MOL2 | O |
| ATOM | 7495 | N | SER | D | 198 | 7.718 | −16.117 | −30.001 | 1.00 | 118.69 | MOL2 | N |
| ATOM | 7496 | CA | SER | D | 198 | 8.196 | −14.782 | −29.668 | 1.00 | 119.63 | MOL2 | C |
| ATOM | 7497 | CB | SER | D | 198 | 9.660 | −14.843 | −29.212 | 1.00 | 121.19 | MOL2 | C |
| ATOM | 7498 | OG | SER | D | 198 | 9.826 | −15.760 | −28.143 | 1.00 | 123.39 | MOL2 | O |
| ATOM | 7499 | C | SER | D | 198 | 8.076 | −13.823 | −30.848 | 1.00 | 119.24 | MOL2 | C |
| ATOM | 7500 | O | SER | D | 198 | 7.943 | −12.619 | −30.650 | 1.00 | 120.42 | MOL2 | O |
| ATOM | 7501 | N | THR | D | 199 | 8.123 | −14.355 | −32.070 | 1.00 | 119.47 | MOL2 | N |
| ATOM | 7502 | CA | THR | D | 199 | 8.033 | −13.521 | −33.269 | 1.00 | 119.49 | MOL2 | C |
| ATOM | 7503 | CB | THR | D | 199 | 9.011 | −14.010 | −34.391 | 1.00 | 122.39 | MOL2 | C |
| ATOM | 7504 | OG1 | THR | D | 199 | 8.584 | −15.281 | −34.899 | 1.00 | 120.61 | MOL2 | O |
| ATOM | 7505 | CG2 | THR | D | 199 | 10.443 | −14.133 | −33.842 | 1.00 | 121.02 | MOL2 | C |
| ATOM | 7506 | C | THR | D | 199 | 6.614 | −13.423 | −33.840 | 1.00 | 117.74 | MOL2 | C |
| ATOM | 7507 | O | THR | D | 199 | 6.429 | −13.194 | −35.036 | 1.00 | 118.98 | MOL2 | O |
| ATOM | 7508 | N | TRP | D | 200 | 5.620 | −13.593 | −32.971 | 1.00 | 115.27 | MOL2 | N |
| ATOM | 7509 | CA | TRP | D | 200 | 4.214 | −13.498 | −33.358 | 1.00 | 115.29 | MOL2 | C |
| ATOM | 7510 | CB | TRP | D | 200 | 3.794 | −14.690 | −34.209 | 1.00 | 112.54 | MOL2 | C |
| ATOM | 7511 | CG | TRP | D | 200 | 2.404 | −14.547 | −34.760 | 1.00 | 112.93 | MOL2 | C |
| ATOM | 7512 | CD2 | TRP | D | 200 | 1.199 | −15.076 | −34.195 | 1.00 | 111.49 | MOL2 | C |
| ATOM | 7513 | CE2 | TRP | D | 200 | 0.133 | −14.685 | −35.039 | 1.00 | 111.78 | MOL2 | C |
| ATOM | 7514 | CE3 | TRP | D | 200 | 0.916 | −15.840 | −33.058 | 1.00 | 108.68 | MOL2 | C |
| ATOM | 7515 | CD1 | TRP | D | 200 | 2.031 | −13.872 | −35.893 | 1.00 | 113.78 | MOL2 | C |
| ATOM | 7516 | NE1 | TRP | D | 200 | 0.667 | −13.953 | −36.067 | 1.00 | 111.33 | MOL2 | N |
| ATOM | 7517 | CZ2 | TRP | D | 200 | −1.192 | −15.036 | −34.780 | 1.00 | 111.08 | MOL2 | C |
| ATOM | 7518 | CZ3 | TRP | D | 200 | −0.402 | −16.188 | −32.803 | 1.00 | 110.71 | MOL2 | C |
| ATOM | 7519 | CH2 | TRP | D | 200 | −1.438 | −15.787 | −33.661 | 1.00 | 110.41 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 7520 | C | TRP | D | 200 | 3.348 | −13.462 | −32.101 | 1.00 | 118.97 | MOL2 | C |
|---|---|---|---|---|---|---|---|---|---|---|---|---|
| ATOM | 7521 | O | TRP | D | 200 | 3.570 | −14.241 | −31.171 | 1.00 | 119.87 | MOL2 | O |
| ATOM | 7522 | N | PRO | D | 201 | 2.337 | −12.570 | −32.061 | 1.00 | 121.33 | MOL2 | N |
| ATOM | 7523 | CD | PRO | D | 201 | 1.373 | −12.527 | −30.948 | 1.00 | 120.64 | MOL2 | C |
| ATOM | 7524 | CA | PRO | D | 201 | 1.952 | −11.607 | −33.103 | 1.00 | 120.57 | MOL2 | C |
| ATOM | 7525 | CB | PRO | D | 201 | 0.572 | −11.119 | −32.643 | 1.00 | 120.36 | MOL2 | C |
| ATOM | 7526 | CG | PRO | D | 201 | 0.101 | −12.181 | −31.666 | 1.00 | 119.61 | MOL2 | C |
| ATOM | 7527 | C | PRO | D | 201 | 2.925 | −10.440 | −33.249 | 1.00 | 120.32 | MOL2 | C |
| ATOM | 7528 | O | PRO | D | 201 | 2.673 | −9.522 | −34.031 | 1.00 | 118.99 | MOL2 | O |
| ATOM | 7529 | N | SER | D | 202 | 4.017 | −10.478 | −32.482 | 1.00 | 121.83 | MOL2 | N |
| ATOM | 7530 | CA | SER | D | 202 | 5.046 | −9.433 | −32.501 | 1.00 | 123.93 | MOL2 | C |
| ATOM | 7531 | CB | SER | D | 202 | 6.362 | −9.976 | −31.927 | 1.00 | 120.25 | MOL2 | C |
| ATOM | 7532 | OG | SER | D | 202 | 7.385 | −8.992 | −31.938 | 1.00 | 112.87 | MOL2 | O |
| ATOM | 7533 | C | SER | D | 202 | 5.283 | −8.901 | −33.913 | 1.00 | 127.62 | MOL2 | C |
| ATOM | 7534 | O | SER | D | 202 | 4.783 | −7.829 | −34.275 | 1.00 | 129.11 | MOL2 | O |
| ATOM | 7535 | N | GLU | D | 203 | 6.057 | −9.640 | −34.704 | 1.00 | 128.68 | MOL2 | N |
| ATOM | 7536 | CA | GLU | D | 203 | 6.317 | −9.244 | −36.083 | 1.00 | 129.64 | MOL2 | C |
| ATOM | 7537 | CB | GLU | D | 203 | 7.517 | −10.005 | −36.649 | 1.00 | 129.05 | MOL2 | C |
| ATOM | 7538 | CG | GLU | D | 203 | 8.854 | −9.554 | −36.090 | 1.00 | 132.77 | MOL2 | C |
| ATOM | 7539 | CD | GLU | D | 203 | 10.022 | −10.330 | −36.671 | 1.00 | 134.26 | MOL2 | C |
| ATOM | 7540 | OE1 | GLU | D | 203 | 10.046 | −10.528 | −37.906 | 1.00 | 133.87 | MOL2 | O |
| ATOM | 7541 | OE2 | GLU | D | 203 | 10.917 | −10.732 | −35.895 | 1.00 | 134.13 | MOL2 | O |
| ATOM | 7542 | C | GLU | D | 203 | 5.067 | −9.578 | −36.886 | 1.00 | 131.08 | MOL2 | C |
| ATOM | 7543 | O | GLU | D | 203 | 4.026 | −9.920 | −36.316 | 1.00 | 130.66 | MOL2 | O |
| ATOM | 7544 | N | THR | D | 204 | 5.156 | −9.488 | −38.207 | 1.00 | 132.69 | MOL2 | N |
| ATOM | 7545 | CA | THR | D | 204 | 3.995 | −9.792 | −39.035 | 1.00 | 132.69 | MOL2 | C |
| ATOM | 7546 | CB | THR | D | 204 | 3.553 | −8.550 | −39.863 | 1.00 | 134.41 | MOL2 | C |
| ATOM | 7547 | OG1 | THR | D | 204 | 3.013 | −7.557 | −38.978 | 1.00 | 133.83 | MOL2 | O |
| ATOM | 7548 | CG2 | THR | D | 204 | 2.495 | −8.931 | −40.899 | 1.00 | 132.04 | MOL2 | C |
| ATOM | 7549 | C | THR | D | 204 | 4.204 | −10.988 | −39.964 | 1.00 | 130.56 | MOL2 | C |
| ATOM | 7550 | O | THR | D | 204 | 5.324 | −11.295 | −40.391 | 1.00 | 130.19 | MOL2 | O |
| ATOM | 7551 | N | VAL | D | 205 | 3.104 | −11.668 | −40.252 | 1.00 | 126.51 | MOL2 | N |
| ATOM | 7552 | CA | VAL | D | 205 | 3.125 | −12.827 | −41.118 | 1.00 | 121.52 | MOL2 | C |
| ATOM | 7553 | CB | VAL | D | 205 | 3.030 | −14.114 | −40.276 | 1.00 | 124.28 | MOL2 | C |
| ATOM | 7554 | CG1 | VAL | D | 205 | 4.268 | −14.228 | −39.378 | 1.00 | 121.43 | MOL2 | C |
| ATOM | 7555 | CG2 | VAL | D | 205 | 1.757 | −14.090 | −39.427 | 1.00 | 122.84 | MOL2 | C |
| ATOM | 7556 | C | VAL | D | 205 | 1.945 | −12.713 | −42.073 | 1.00 | 117.56 | MOL2 | C |
| ATOM | 7557 | O | VAL | D | 205 | 0.802 | −12.528 | −41.649 | 1.00 | 115.24 | MOL2 | O |
| ATOM | 7558 | N | THR | D | 206 | 2.219 | −12.802 | −43.367 | 1.00 | 112.79 | MOL2 | N |
| ATOM | 7559 | CA | THR | D | 206 | 1.141 | −12.691 | −44.325 | 1.00 | 111.02 | MOL2 | C |
| ATOM | 7560 | CB | THR | D | 206 | 1.084 | −11.265 | −44.917 | 1.00 | 114.63 | MOL2 | C |
| ATOM | 7561 | OG1 | THR | D | 206 | 0.963 | −10.313 | −43.849 | 1.00 | 109.86 | MOL2 | O |
| ATOM | 7562 | CG2 | THR | D | 206 | −0.111 | −11.114 | −45.849 | 1.00 | 113.16 | MOL2 | C |
| ATOM | 7563 | C | THR | D | 206 | 1.221 | −13.726 | −45.435 | 1.00 | 109.15 | MOL2 | C |
| ATOM | 7564 | O | THR | D | 206 | 2.305 | −14.134 | −45.863 | 1.00 | 108.58 | MOL2 | O |
| ATOM | 7565 | N | CYS | D | 207 | 0.043 | −14.156 | −45.867 | 1.00 | 104.94 | MOL2 | N |
| ATOM | 7566 | CA | CYS | D | 207 | −0.124 | −15.136 | −46.924 | 1.00 | 103.36 | MOL2 | C |
| ATOM | 7567 | C | CYS | D | 207 | 0.015 | −14.415 | −48.274 | 1.00 | 99.64 | MOL2 | C |
| ATOM | 7568 | O | CYS | D | 207 | −0.456 | −13.294 | −48.429 | 1.00 | 97.98 | MOL2 | O |
| ATOM | 7569 | CB | CYS | D | 207 | −1.517 | −15.744 | −46.782 | 1.00 | 105.15 | MOL2 | C |
| ATOM | 7570 | SG | CYS | D | 207 | −1.843 | −17.186 | −47.834 | 1.00 | 123.02 | MOL2 | S |
| ATOM | 7571 | N | ASN | D | 208 | 0.659 | −15.044 | −49.248 | 1.00 | 97.46 | MOL2 | N |
| ATOM | 7572 | CA | ASN | D | 208 | 0.831 | −14.404 | −50.544 | 1.00 | 97.44 | MOL2 | C |
| ATOM | 7573 | CB | ASN | D | 208 | 2.301 | −14.067 | −50.755 | 1.00 | 105.34 | MOL2 | C |
| ATOM | 7574 | CG | ASN | D | 208 | 2.936 | −13.463 | −49.517 | 1.00 | 111.70 | MOL2 | C |
| ATOM | 7575 | OD1 | ASN | D | 208 | 2.369 | −12.562 | −48.890 | 1.00 | 114.09 | MOL2 | O |
| ATOM | 7576 | ND2 | ASN | D | 208 | 4.120 | −13.956 | −49.157 | 1.00 | 111.26 | MOL2 | N |
| ATOM | 7577 | C | ASN | D | 208 | 0.317 | −15.293 | −51.665 | 1.00 | 96.87 | MOL2 | C |
| ATOM | 7578 | O | ASN | D | 208 | 1.089 | −15.943 | −52.381 | 1.00 | 99.33 | MOL2 | O |
| ATOM | 7579 | N | VAL | D | 209 | −1.004 | −15.290 | −51.803 | 1.00 | 90.22 | MOL2 | N |
| ATOM | 7580 | CA | VAL | D | 209 | −1.737 | −16.073 | −52.789 | 1.00 | 86.47 | MOL2 | C |
| ATOM | 7581 | CB | VAL | D | 209 | −3.190 | −16.114 | −52.361 | 1.00 | 79.39 | MOL2 | C |
| ATOM | 7582 | CG1 | VAL | D | 209 | −3.849 | −17.395 | −52.824 | 1.00 | 82.38 | MOL2 | C |
| ATOM | 7583 | CG2 | VAL | D | 209 | −3.257 | −15.935 | −50.859 | 1.00 | 73.42 | MOL2 | C |
| ATOM | 7584 | C | VAL | D | 209 | −1.682 | −15.443 | −54.179 | 1.00 | 88.23 | MOL2 | C |
| ATOM | 7585 | O | VAL | D | 209 | −1.900 | −14.252 | −54.306 | 1.00 | 88.62 | MOL2 | O |
| ATOM | 7586 | N | ALA | D | 210 | −1.411 | −16.227 | −55.219 | 1.00 | 90.91 | MOL2 | N |
| ATOM | 7587 | CA | ALA | D | 210 | −1.374 | −15.670 | −56.567 | 1.00 | 93.72 | MOL2 | C |
| ATOM | 7588 | CB | ALA | D | 210 | 0.059 | −15.320 | −56.958 | 1.00 | 96.40 | MOL2 | C |
| ATOM | 7589 | C | ALA | D | 210 | −1.993 | −16.637 | −57.575 | 1.00 | 99.43 | MOL2 | C |
| ATOM | 7590 | O | ALA | D | 210 | −1.615 | −17.815 | −57.642 | 1.00 | 106.33 | MOL2 | O |
| ATOM | 7591 | N | HIS | D | 211 | −2.943 | −16.125 | −58.391 | 1.00 | 98.35 | MOL2 | N |
| ATOM | 7592 | CA | HIS | D | 211 | −3.667 | −16.907 | −59.359 | 1.00 | 98.05 | MOL2 | C |
| ATOM | 7593 | CB | HIS | D | 211 | −5.168 | −16.816 | −59.043 | 1.00 | 87.59 | MOL2 | C |
| ATOM | 7594 | CG | HIS | D | 211 | −6.012 | −17.859 | −59.714 | 1.00 | 88.25 | MOL2 | C |
| ATOM | 7595 | CD2 | HIS | D | 211 | −7.155 | −18.469 | −59.315 | 1.00 | 87.50 | MOL2 | C |
| ATOM | 7596 | ND1 | HIS | D | 211 | −5.730 | −18.364 | −60.965 | 1.00 | 91.95 | MOL2 | N |

TABLE 1-continued

The atomic coordinates of IL17F in complex with 496 Fab
(H32; a = 189.4; b = 189.4; c = 490.9, α, β = 90°; γ = 120°)

| ATOM | 7597 | CE1 | HIS | D | 211 | −6.660 | −19.242 | −61.305 | 1.00 | 89.03 | MOL2 | C |
|---|---|---|---|---|---|---|---|---|---|---|---|---|
| ATOM | 7598 | NE2 | HIS | D | 211 | −7.537 | −19.324 | −60.321 | 1.00 | 83.10 | MOL2 | N |
| ATOM | 7599 | C | HIS | D | 211 | −3.403 | −16.370 | −60.779 | 1.00 | 104.17 | MOL2 | C |
| ATOM | 7600 | O | HIS | D | 211 | −4.120 | −15.495 | −61.253 | 1.00 | 104.17 | MOL2 | O |
| ATOM | 7601 | N | PRO | D | 212 | −2.364 | −16.876 | −61.468 | 1.00 | 111.35 | MOL2 | N |
| ATOM | 7602 | CD | PRO | D | 212 | −1.230 | −17.666 | −60.952 | 1.00 | 117.49 | MOL2 | C |
| ATOM | 7603 | CA | PRO | D | 212 | −2.080 | −16.395 | −62.825 | 1.00 | 115.33 | MOL2 | C |
| ATOM | 7604 | CB | PRO | D | 212 | −0.877 | −17.242 | −63.242 | 1.00 | 120.03 | MOL2 | C |
| ATOM | 7605 | CG | PRO | D | 212 | −0.114 | −17.342 | −61.952 | 1.00 | 120.33 | MOL2 | C |
| ATOM | 7606 | C | PRO | D | 212 | −3.267 | −16.532 | −63.777 | 1.00 | 114.41 | MOL2 | C |
| ATOM | 7607 | O | PRO | D | 212 | −3.687 | −15.553 | −64.393 | 1.00 | 113.77 | MOL2 | O |
| ATOM | 7608 | N | ALA | D | 213 | −3.809 | −17.741 | −63.885 | 1.00 | 113.04 | MOL2 | N |
| ATOM | 7609 | CA | ALA | D | 213 | −4.946 | −18.001 | −64.764 | 1.00 | 115.76 | MOL2 | C |
| ATOM | 7610 | CB | ALA | D | 213 | −5.530 | −19.385 | −64.440 | 1.00 | 115.79 | MOL2 | C |
| ATOM | 7611 | C | ALA | D | 213 | −6.041 | −16.919 | −64.664 | 1.00 | 115.30 | MOL2 | C |
| ATOM | 7612 | O | ALA | D | 213 | −6.790 | −16.675 | −65.622 | 1.00 | 117.39 | MOL2 | O |
| ATOM | 7613 | N | SER | D | 214 | −6.125 | −16.272 | −63.506 | 1.00 | 110.64 | MOL2 | N |
| ATOM | 7614 | CA | SER | D | 214 | −7.123 | −15.234 | −63.275 | 1.00 | 109.17 | MOL2 | C |
| ATOM | 7615 | CB | SER | D | 214 | −8.030 | −15.629 | −62.104 | 1.00 | 108.82 | MOL2 | C |
| ATOM | 7616 | OG | SER | D | 214 | −8.768 | −14.523 | −61.618 | 1.00 | 103.35 | MOL2 | O |
| ATOM | 7617 | C | SER | D | 214 | −6.451 | −13.906 | −62.976 | 1.00 | 111.11 | MOL2 | C |
| ATOM | 7618 | O | SER | D | 214 | −7.110 | −12.935 | −62.605 | 1.00 | 110.06 | MOL2 | O |
| ATOM | 7619 | N | SER | D | 215 | −5.133 | −13.875 | −63.137 | 1.00 | 114.63 | MOL2 | N |
| ATOM | 7620 | CA | SER | D | 215 | −4.337 | −12.673 | −62.888 | 1.00 | 118.87 | MOL2 | C |
| ATOM | 7621 | CB | SER | D | 215 | −4.591 | −11.626 | −63.989 | 1.00 | 120.23 | MOL2 | C |
| ATOM | 7622 | OG | SER | D | 215 | −3.463 | −10.778 | −64.168 | 1.00 | 116.07 | MOL2 | O |
| ATOM | 7623 | C | SER | D | 215 | −4.609 | −12.067 | −61.501 | 1.00 | 119.10 | MOL2 | C |
| ATOM | 7624 | O | SER | D | 215 | −4.390 | −10.872 | −61.277 | 1.00 | 119.46 | MOL2 | O |
| ATOM | 7625 | N | THR | D | 216 | −5.091 | −12.892 | −60.574 | 1.00 | 118.68 | MOL2 | N |
| ATOM | 7626 | CA | THR | D | 216 | −5.354 | −12.426 | −59.216 | 1.00 | 116.60 | MOL2 | C |
| ATOM | 7627 | CB | THR | D | 216 | −6.481 | −13.216 | −58.532 | 1.00 | 116.16 | MOL2 | C |
| ATOM | 7628 | OG1 | THR | D | 216 | −7.666 | −13.150 | −59.335 | 1.00 | 114.80 | MOL2 | O |
| ATOM | 7629 | CG2 | THR | D | 216 | −6.767 | −12.635 | −57.145 | 1.00 | 110.81 | MOL2 | C |
| ATOM | 7630 | C | THR | D | 216 | −4.081 | −12.600 | −58.397 | 1.00 | 117.22 | MOL2 | C |
| ATOM | 7631 | O | THR | D | 216 | −3.238 | −13.450 | −58.708 | 1.00 | 119.85 | MOL2 | O |
| ATOM | 7632 | N | LYS | D | 217 | −3.943 | −11.792 | −57.354 | 1.00 | 114.88 | MOL2 | N |
| ATOM | 7633 | CA | LYS | D | 217 | −2.765 | −11.846 | −56.497 | 1.00 | 115.84 | MOL2 | C |
| ATOM | 7634 | CB | LYS | D | 217 | −1.620 | −11.055 | −57.141 | 1.00 | 118.61 | MOL2 | C |
| ATOM | 7635 | CG | LYS | D | 217 | −2.046 | −9.699 | −57.675 | 1.00 | 123.65 | MOL2 | C |
| ATOM | 7636 | CD | LYS | D | 217 | −1.064 | −9.156 | −58.700 | 1.00 | 124.05 | MOL2 | C |
| ATOM | 7637 | CE | LYS | D | 217 | −1.624 | −7.903 | −59.354 | 1.00 | 124.41 | MOL2 | C |
| ATOM | 7638 | NZ | LYS | D | 217 | −3.007 | −8.134 | −59.873 | 1.00 | 119.34 | MOL2 | N |
| ATOM | 7639 | C | LYS | D | 217 | −3.108 | −11.271 | −55.128 | 1.00 | 113.12 | MOL2 | C |
| ATOM | 7640 | O | LYS | D | 217 | −2.713 | −10.152 | −54.795 | 1.00 | 108.06 | MOL2 | O |
| ATOM | 7641 | N | VAL | D | 218 | −3.840 | −12.056 | −54.337 | 1.00 | 112.90 | MOL2 | N |
| ATOM | 7642 | CA | VAL | D | 218 | −4.269 | −11.637 | −53.004 | 1.00 | 110.59 | MOL2 | C |
| ATOM | 7643 | CB | VAL | D | 218 | −5.656 | −12.250 | −52.645 | 1.00 | 107.90 | MOL2 | C |
| ATOM | 7644 | CG1 | VAL | D | 218 | −6.068 | −11.833 | −51.233 | 1.00 | 100.83 | MOL2 | C |
| ATOM | 7645 | CG2 | VAL | D | 218 | −6.700 | −11.803 | −53.664 | 1.00 | 103.53 | MOL2 | C |
| ATOM | 7646 | C | VAL | D | 218 | −3.293 | −11.935 | −51.863 | 1.00 | 112.13 | MOL2 | C |
| ATOM | 7647 | O | VAL | D | 218 | −2.633 | −12.984 | −51.833 | 1.00 | 113.22 | MOL2 | O |
| ATOM | 7648 | N | ASP | D | 219 | −3.212 | −10.983 | −50.934 | 1.00 | 112.43 | MOL2 | N |
| ATOM | 7649 | CA | ASP | D | 219 | −2.355 | −11.072 | −49.749 | 1.00 | 115.90 | MOL2 | C |
| ATOM | 7650 | CB | ASP | D | 219 | −1.429 | −9.846 | −49.618 | 1.00 | 124.25 | MOL2 | C |
| ATOM | 7651 | CG | ASP | D | 219 | −0.305 | −9.822 | −50.643 | 1.00 | 134.23 | MOL2 | C |
| ATOM | 7652 | OD1 | ASP | D | 219 | 0.555 | −10.733 | −50.624 | 1.00 | 137.14 | MOL2 | O |
| ATOM | 7653 | OD2 | ASP | D | 219 | −0.275 | −8.874 | −51.461 | 1.00 | 140.38 | MOL2 | O |
| ATOM | 7654 | C | ASP | D | 219 | −3.289 | −11.031 | −48.555 | 1.00 | 113.75 | MOL2 | C |
| ATOM | 7655 | O | ASP | D | 219 | −4.150 | −10.161 | −48.493 | 1.00 | 112.98 | MOL2 | O |
| ATOM | 7656 | N | LYS | D | 220 | −3.125 | −11.948 | −47.608 | 1.00 | 114.33 | MOL2 | N |
| ATOM | 7657 | CA | LYS | D | 220 | −3.967 | −11.942 | −46.415 | 1.00 | 112.98 | MOL2 | C |
| ATOM | 7658 | CB | LYS | D | 220 | −4.909 | −13.149 | −46.405 | 1.00 | 113.88 | MOL2 | C |
| ATOM | 7659 | CG | LYS | D | 220 | −6.128 | −13.003 | −45.484 | 1.00 | 119.26 | MOL2 | C |
| ATOM | 7660 | CD | LYS | D | 220 | −7.269 | −12.211 | −46.153 | 1.00 | 124.16 | MOL2 | C |
| ATOM | 7661 | CE | LYS | D | 220 | −8.589 | −12.281 | −45.354 | 1.00 | 122.46 | MOL2 | C |
| ATOM | 7662 | NZ | LYS | D | 220 | −9.769 | −11.697 | −46.077 | 1.00 | 114.42 | MOL2 | N |
| ATOM | 7663 | C | LYS | D | 220 | −3.064 | −11.980 | −45.186 | 1.00 | 113.40 | MOL2 | C |
| ATOM | 7664 | O | LYS | D | 220 | −2.262 | −12.901 | −45.016 | 1.00 | 115.05 | MOL2 | O |
| ATOM | 7665 | N | LYS | D | 221 | −3.175 | −10.962 | −44.342 | 1.00 | 114.57 | MOL2 | N |
| ATOM | 7666 | CA | LYS | D | 221 | −2.372 | −10.896 | −43.128 | 1.00 | 116.68 | MOL2 | C |
| ATOM | 7667 | CB | LYS | D | 221 | −2.352 | −9.463 | −42.571 | 1.00 | 123.35 | MOL2 | C |
| ATOM | 7668 | CG | LYS | D | 221 | −1.714 | −9.334 | −41.178 | 1.00 | 128.89 | MOL2 | C |
| ATOM | 7669 | CD | LYS | D | 221 | −1.555 | −7.875 | −40.736 | 1.00 | 130.70 | MOL2 | C |
| ATOM | 7670 | CE | LYS | D | 221 | −0.842 | −7.770 | −39.386 | 1.00 | 131.81 | MOL2 | C |
| ATOM | 7671 | NZ | LYS | D | 221 | −0.531 | −6.361 | −39.001 | 1.00 | 131.94 | MOL2 | N |
| ATOM | 7672 | C | LYS | D | 221 | −2.980 | −11.836 | −42.095 | 1.00 | 114.90 | MOL2 | C |
| ATOM | 7673 | O | LYS | D | 221 | −4.204 | −11.909 | −41.964 | 1.00 | 111.76 | MOL2 | O |

TABLE 1-continued

The atomic coordinates of IL17F in complex with 496 Fab
(H32; a = 189.4; b = 189.4; c = 490.9, α, β = 90°; γ = 120°)

| ATOM | 7674 | N | ILE | D | 222 | −2.124 | −12.559 | −41.376 | 1.00 | 115.97 | MOL2 | N |
|---|---|---|---|---|---|---|---|---|---|---|---|---|
| ATOM | 7675 | CA | ILE | D | 222 | −2.582 | −13.491 | −40.345 | 1.00 | 118.06 | MOL2 | C |
| ATOM | 7676 | CB | ILE | D | 222 | −1.621 | −14.705 | −40.190 | 1.00 | 121.25 | MOL2 | C |
| ATOM | 7677 | CG2 | ILE | D | 222 | −1.821 | −15.356 | −38.823 | 1.00 | 122.94 | MOL2 | C |
| ATOM | 7678 | CG1 | ILE | D | 222 | −1.895 | −15.743 | −41.281 | 1.00 | 121.04 | MOL2 | C |
| ATOM | 7679 | CD1 | ILE | D | 222 | −3.209 | −16.481 | −41.092 | 1.00 | 118.43 | MOL2 | C |
| ATOM | 7680 | C | ILE | D | 222 | −2.680 | −12.790 | −38.998 | 1.00 | 116.34 | MOL2 | C |
| ATOM | 7681 | O | ILE | D | 222 | −1.666 | −12.516 | −38.352 | 1.00 | 114.18 | MOL2 | O |
| ATOM | 7682 | N | VAL | D | 223 | −3.908 | −12.505 | −38.578 | 1.00 | 117.55 | MOL2 | N |
| ATOM | 7683 | CA | VAL | D | 223 | −4.140 | −11.830 | −37.310 | 1.00 | 120.95 | MOL2 | C |
| ATOM | 7684 | CB | VAL | D | 223 | −4.933 | −10.521 | −37.512 | 1.00 | 128.80 | MOL2 | C |
| ATOM | 7685 | CG1 | VAL | D | 223 | −4.119 | −9.537 | −38.358 | 1.00 | 130.83 | MOL2 | C |
| ATOM | 7686 | CG2 | VAL | D | 223 | −6.279 | −10.830 | −38.173 | 1.00 | 132.56 | MOL2 | C |
| ATOM | 7687 | C | VAL | D | 223 | −4.918 | −12.716 | −36.349 | 1.00 | 118.69 | MOL2 | C |
| ATOM | 7688 | O | VAL | D | 223 | −5.879 | −13.385 | −36.741 | 1.00 | 115.68 | MOL2 | O |
| ATOM | 7689 | N | PRO | D | 224 | −4.515 | −12.709 | −35.068 | 1.00 | 118.99 | MOL2 | N |
| ATOM | 7690 | CD | PRO | D | 224 | −3.433 | −11.836 | −34.576 | 1.00 | 119.65 | MOL2 | C |
| ATOM | 7691 | CA | PRO | D | 224 | −5.100 | −13.475 | −33.963 | 1.00 | 121.19 | MOL2 | C |
| ATOM | 7692 | CB | PRO | D | 224 | −4.166 | −13.156 | −32.792 | 1.00 | 120.92 | MOL2 | C |
| ATOM | 7693 | CG | PRO | D | 224 | −3.721 | −11.767 | −33.091 | 1.00 | 119.21 | MOL2 | C |
| ATOM | 7694 | C | PRO | D | 224 | −6.550 | −13.137 | −33.636 | 1.00 | 124.07 | MOL2 | C |
| ATOM | 7695 | O | PRO | D | 224 | −7.150 | −12.242 | −34.239 | 1.00 | 122.61 | MOL2 | O |
| ATOM | 7696 | N | ARG | D | 225 | −7.095 | −13.875 | −32.671 | 1.00 | 130.19 | MOL2 | N |
| ATOM | 7697 | CA | ARG | D | 225 | −8.465 | −13.698 | −32.196 | 1.00 | 139.13 | MOL2 | C |
| ATOM | 7698 | CB | ARG | D | 225 | −9.151 | −15.061 | −32.026 | 1.00 | 137.87 | MOL2 | C |
| ATOM | 7699 | CG | ARG | D | 225 | −9.317 | −15.887 | −33.291 | 1.00 | 134.46 | MOL2 | C |
| ATOM | 7700 | CD | ARG | D | 225 | −10.057 | −17.175 | −32.961 | 1.00 | 134.51 | MOL2 | C |
| ATOM | 7701 | NE | ARG | D | 225 | −10.826 | −17.679 | −34.095 | 1.00 | 138.46 | MOL2 | N |
| ATOM | 7702 | CZ | ARG | D | 225 | −11.841 | −18.534 | −33.989 | 1.00 | 139.86 | MOL2 | C |
| ATOM | 7703 | NH1 | ARG | D | 225 | −12.488 | −18.939 | −35.077 | 1.00 | 136.69 | MOL2 | N |
| ATOM | 7704 | NH2 | ARG | D | 225 | −12.215 | −18.981 | −32.793 | 1.00 | 142.11 | MOL2 | N |
| ATOM | 7705 | C | ARG | D | 225 | −8.404 | −13.006 | −30.828 | 1.00 | 145.80 | MOL2 | C |
| ATOM | 7706 | O | ARG | D | 225 | −7.409 | −13.143 | −30.107 | 1.00 | 146.28 | MOL2 | O |
| ATOM | 7707 | N | ASP | D | 226 | −9.469 | −12.290 | −30.466 | 1.00 | 152.47 | MOL2 | N |
| ATOM | 7708 | CA | ASP | D | 226 | −9.529 | −11.571 | −29.188 | 1.00 | 158.98 | MOL2 | C |
| ATOM | 7709 | CB | ASP | D | 226 | −10.587 | −10.454 | −29.262 | 1.00 | 161.05 | MOL2 | C |
| ATOM | 7710 | CG | ASP | D | 226 | −10.243 | −9.372 | −30.288 | 1.00 | 161.69 | MOL2 | C |
| ATOM | 7711 | OD1 | ASP | D | 226 | −9.174 | −8.733 | −30.159 | 1.00 | 160.52 | MOL2 | O |
| ATOM | 7712 | OD2 | ASP | D | 226 | −11.050 | −9.157 | −31.220 | 1.00 | 160.76 | MOL2 | O |
| ATOM | 7713 | C | ASP | D | 226 | −9.814 | −12.459 | −27.963 | 1.00 | 161.54 | MOL2 | C |
| ATOM | 7714 | O | ASP | D | 226 | −8.927 | −13.160 | −27.469 | 1.00 | 159.48 | MOL2 | O |
| ATOM | 7715 | N | CYS | D | 227 | −11.055 | −12.410 | −27.475 | 1.00 | 166.54 | MOL2 | N |
| ATOM | 7716 | CA | CYS | D | 227 | −11.473 | −13.187 | −26.301 | 1.00 | 171.26 | MOL2 | C |
| ATOM | 7717 | CB | CYS | D | 227 | −12.784 | −12.616 | −25.715 | 1.00 | 173.22 | MOL2 | C |
| ATOM | 7718 | SG | CYS | D | 227 | −14.355 | −13.267 | −26.401 | 1.00 | 176.60 | MOL2 | S |
| ATOM | 7719 | C | CYS | D | 227 | −11.657 | −14.679 | −26.608 | 1.00 | 172.68 | MOL2 | C |
| ATOM | 7720 | O | CYS | D | 227 | −11.457 | −15.078 | −27.777 | 1.00 | 172.11 | MOL2 | O |
| ATOM | 7721 | OXT | CYS | D | 227 | −11.994 | −15.439 | −25.669 | 1.00 | 173.46 | MOL2 | O |
| ATOM | 7722 | CB | GLU | E | 15 | 51.662 | −25.120 | −64.599 | 1.00 | 165.76 | MOL2 | C |
| ATOM | 7723 | CG | GLU | E | 15 | 50.846 | −24.875 | −63.330 | 1.00 | 164.41 | MOL2 | C |
| ATOM | 7724 | CD | GLU | E | 15 | 51.155 | −25.879 | −62.227 | 1.00 | 162.45 | MOL2 | C |
| ATOM | 7725 | OE1 | GLU | E | 15 | 52.286 | −25.854 | −61.695 | 1.00 | 160.73 | MOL2 | O |
| ATOM | 7726 | OE2 | GLU | E | 15 | 50.268 | −26.697 | −61.897 | 1.00 | 158.74 | MOL2 | O |
| ATOM | 7727 | C | GLU | E | 15 | 51.943 | −22.740 | −65.385 | 1.00 | 163.50 | MOL2 | C |
| ATOM | 7728 | O | GLU | E | 15 | 51.249 | −21.928 | −64.759 | 1.00 | 160.46 | MOL2 | O |
| ATOM | 7729 | N | GLU | E | 15 | 52.006 | −24.644 | −67.006 | 1.00 | 163.87 | MOL2 | N |
| ATOM | 7730 | CA | GLU | E | 15 | 51.393 | −24.131 | −65.743 | 1.00 | 164.49 | MOL2 | C |
| ATOM | 7731 | N | SER | E | 16 | 53.188 | −22.472 | −65.782 | 1.00 | 162.49 | MOL2 | N |
| ATOM | 7732 | CA | SER | E | 16 | 53.814 | −21.180 | −65.514 | 1.00 | 160.48 | MOL2 | C |
| ATOM | 7733 | CB | SER | E | 16 | 54.848 | −21.321 | −64.390 | 1.00 | 155.37 | MOL2 | C |
| ATOM | 7734 | OG | SER | E | 16 | 55.761 | −22.369 | −64.652 | 1.00 | 146.87 | MOL2 | O |
| ATOM | 7735 | C | SER | E | 16 | 54.465 | −20.572 | −66.762 | 1.00 | 162.64 | MOL2 | C |
| ATOM | 7736 | O | SER | E | 16 | 54.681 | −19.361 | −66.835 | 1.00 | 162.08 | MOL2 | O |
| ATOM | 7737 | N | CYS | E | 17 | 54.764 | −21.418 | −67.743 | 1.00 | 165.84 | MOL2 | N |
| ATOM | 7738 | CA | CYS | E | 17 | 55.385 | −20.984 | −68.994 | 1.00 | 169.05 | MOL2 | C |
| ATOM | 7739 | CB | CYS | E | 17 | 55.466 | −22.178 | −69.959 | 1.00 | 170.47 | MOL2 | C |
| ATOM | 7740 | SG | CYS | E | 17 | 54.361 | −23.581 | −69.559 | 1.00 | 170.59 | MOL2 | S |
| ATOM | 7741 | C | CYS | E | 17 | 54.644 | −19.813 | −69.659 | 1.00 | 169.88 | MOL2 | C |
| ATOM | 7742 | O | CYS | E | 17 | 53.450 | −19.617 | −69.426 | 1.00 | 168.81 | MOL2 | O |
| ATOM | 7743 | N | PRO | E | 18 | 55.356 | −19.011 | −70.480 | 1.00 | 171.24 | MOL2 | N |
| ATOM | 7744 | CD | PRO | E | 18 | 56.821 | −19.037 | −70.640 | 1.00 | 172.22 | MOL2 | C |
| ATOM | 7745 | CA | PRO | E | 18 | 54.787 | −17.857 | −71.191 | 1.00 | 171.55 | MOL2 | C |
| ATOM | 7746 | CB | PRO | E | 18 | 55.972 | −17.326 | −71.991 | 1.00 | 170.97 | MOL2 | C |
| ATOM | 7747 | CG | PRO | E | 18 | 57.121 | −17.617 | −71.089 | 1.00 | 172.24 | MOL2 | C |
| ATOM | 7748 | C | PRO | E | 18 | 53.626 | −18.273 | −72.086 | 1.00 | 172.56 | MOL2 | C |
| ATOM | 7749 | O | PRO | E | 18 | 53.825 | −18.782 | −73.193 | 1.00 | 172.11 | MOL2 | O |
| ATOM | 7750 | N | PRO | E | 19 | 52.393 | −18.047 | −71.612 | 1.00 | 174.22 | MOL2 | N |

TABLE 1-continued

The atomic coordinates of IL17F in complex with 496 Fab
(H32; a = 189.4; b = 189.4; c = 490.9, α, β = 90°; γ = 120°)

| ATOM | 7751 | CD | PRO | E | 19 | 52.130 | −17.333 | −70.347 | 1.00 | 174.01 | MOL2 | C |
|---|---|---|---|---|---|---|---|---|---|---|---|---|
| ATOM | 7752 | CA | PRO | E | 19 | 51.134 | −18.369 | −72.290 | 1.00 | 176.12 | MOL2 | C |
| ATOM | 7753 | CB | PRO | E | 19 | 50.105 | −17.576 | −71.482 | 1.00 | 175.32 | MOL2 | C |
| ATOM | 7754 | CG | PRO | E | 19 | 50.666 | −17.640 | −70.096 | 1.00 | 173.61 | MOL2 | C |
| ATOM | 7755 | C | PRO | E | 19 | 51.048 | −18.080 | −73.795 | 1.00 | 177.67 | MOL2 | C |
| ATOM | 7756 | O | PRO | E | 19 | 51.959 | −17.505 | −74.403 | 1.00 | 176.41 | MOL2 | O |
| ATOM | 7757 | N | VAL | E | 20 | 49.928 | −18.506 | −74.377 | 1.00 | 178.75 | MOL2 | N |
| ATOM | 7758 | CA | VAL | E | 20 | 49.634 | −18.333 | −75.795 | 1.00 | 178.94 | MOL2 | C |
| ATOM | 7759 | CB | VAL | E | 20 | 49.264 | −19.683 | −76.448 | 1.00 | 177.15 | MOL2 | C |
| ATOM | 7760 | CG1 | VAL | E | 20 | 50.459 | −20.621 | −76.422 | 1.00 | 175.05 | MOL2 | C |
| ATOM | 7761 | CG2 | VAL | E | 20 | 48.081 | −20.303 | −75.712 | 1.00 | 174.69 | MOL2 | C |
| ATOM | 7762 | C | VAL | E | 20 | 48.434 | −17.392 | −75.915 | 1.00 | 180.62 | MOL2 | C |
| ATOM | 7763 | O | VAL | E | 20 | 47.744 | −17.133 | −74.926 | 1.00 | 179.57 | MOL2 | O |
| ATOM | 7764 | N | PRO | E | 21 | 48.164 | −16.877 | −77.129 | 1.00 | 182.24 | MOL2 | N |
| ATOM | 7765 | CD | PRO | E | 21 | 48.847 | −17.196 | −78.399 | 1.00 | 182.86 | MOL2 | C |
| ATOM | 7766 | CA | PRO | E | 21 | 47.038 | −15.963 | −77.362 | 1.00 | 182.34 | MOL2 | C |
| ATOM | 7767 | CB | PRO | E | 21 | 46.858 | −16.030 | −78.878 | 1.00 | 182.71 | MOL2 | C |
| ATOM | 7768 | CG | PRO | E | 21 | 48.270 | −16.164 | −79.359 | 1.00 | 182.86 | MOL2 | C |
| ATOM | 7769 | C | PRO | E | 21 | 45.758 | −16.336 | −76.602 | 1.00 | 181.69 | MOL2 | C |
| ATOM | 7770 | O | PRO | E | 21 | 45.037 | −15.459 | −76.114 | 1.00 | 181.15 | MOL2 | O |
| ATOM | 7771 | N | GLY | E | 22 | 45.476 | −17.634 | −76.507 | 1.00 | 180.67 | MOL2 | N |
| ATOM | 7772 | CA | GLY | E | 22 | 44.287 | −18.075 | −75.797 | 1.00 | 179.02 | MOL2 | C |
| ATOM | 7773 | C | GLY | E | 22 | 43.492 | −19.189 | −76.460 | 1.00 | 176.89 | MOL2 | C |
| ATOM | 7774 | O | GLY | E | 22 | 43.083 | −19.075 | −77.618 | 1.00 | 176.38 | MOL2 | O |
| ATOM | 7775 | N | GLY | E | 23 | 43.271 | −20.269 | −75.715 | 1.00 | 174.14 | MOL2 | N |
| ATOM | 7776 | CA | GLY | E | 23 | 42.512 | −21.395 | −76.231 | 1.00 | 169.82 | MOL2 | C |
| ATOM | 7777 | C | GLY | E | 23 | 43.125 | −22.093 | −77.431 | 1.00 | 166.75 | MOL2 | C |
| ATOM | 7778 | O | GLY | E | 23 | 42.496 | −22.190 | −78.484 | 1.00 | 167.74 | MOL2 | O |
| ATOM | 7779 | N | SER | E | 24 | 44.352 | −22.580 | −77.276 | 1.00 | 162.62 | MOL2 | N |
| ATOM | 7780 | CA | SER | E | 24 | 45.051 | −23.287 | −78.349 | 1.00 | 157.52 | MOL2 | C |
| ATOM | 7781 | CB | SER | E | 24 | 45.517 | −22.311 | −79.438 | 1.00 | 156.73 | MOL2 | C |
| ATOM | 7782 | OG | SER | E | 24 | 44.455 | −21.948 | −80.306 | 1.00 | 153.24 | MOL2 | O |
| ATOM | 7783 | C | SER | E | 24 | 46.252 | −24.052 | −77.802 | 1.00 | 154.76 | MOL2 | C |
| ATOM | 7784 | O | SER | E | 24 | 46.885 | −23.619 | −76.839 | 1.00 | 156.52 | MOL2 | O |
| ATOM | 7785 | N | MET | E | 25 | 46.555 | −25.189 | −78.425 | 1.00 | 149.50 | MOL2 | N |
| ATOM | 7786 | CA | MET | E | 25 | 47.674 | −26.038 | −78.017 | 1.00 | 143.87 | MOL2 | C |
| ATOM | 7787 | CB | MET | E | 25 | 47.157 | −27.224 | −77.198 | 1.00 | 144.07 | MOL2 | C |
| ATOM | 7788 | CG | MET | E | 25 | 46.428 | −26.844 | −75.912 | 1.00 | 147.06 | MOL2 | C |
| ATOM | 7789 | SD | MET | E | 25 | 47.499 | −26.726 | −74.455 | 1.00 | 149.22 | MOL2 | S |
| ATOM | 7790 | CE | MET | E | 25 | 46.918 | −28.149 | −73.463 | 1.00 | 146.97 | MOL2 | C |
| ATOM | 7791 | C | MET | E | 25 | 48.413 | −26.562 | −79.248 | 1.00 | 140.29 | MOL2 | C |
| ATOM | 7792 | O | MET | E | 25 | 47.906 | −26.485 | −80.367 | 1.00 | 138.37 | MOL2 | O |
| ATOM | 7793 | N | LYS | E | 26 | 49.607 | −27.106 | −79.037 | 1.00 | 137.30 | MOL2 | N |
| ATOM | 7794 | CA | LYS | E | 26 | 50.398 | −27.635 | −80.142 | 1.00 | 134.87 | MOL2 | C |
| ATOM | 7795 | CB | LYS | E | 26 | 51.885 | −27.670 | −79.765 | 1.00 | 139.86 | MOL2 | C |
| ATOM | 7796 | CG | LYS | E | 26 | 52.739 | −26.527 | −80.345 | 1.00 | 144.54 | MOL2 | C |
| ATOM | 7797 | CD | LYS | E | 26 | 52.323 | −25.143 | −79.831 | 1.00 | 148.51 | MOL2 | C |
| ATOM | 7798 | CE | LYS | E | 26 | 51.285 | −24.461 | −80.732 | 1.00 | 150.28 | MOL2 | C |
| ATOM | 7799 | NZ | LYS | E | 26 | 51.826 | −24.051 | −82.065 | 1.00 | 147.62 | MOL2 | N |
| ATOM | 7800 | C | LYS | E | 26 | 49.954 | −29.022 | −80.606 | 1.00 | 129.54 | MOL2 | C |
| ATOM | 7801 | O | LYS | E | 26 | 50.030 | −29.998 | −79.861 | 1.00 | 126.97 | MOL2 | O |
| ATOM | 7802 | N | LEU | E | 27 | 49.483 | −29.097 | −81.846 | 1.00 | 124.85 | MOL2 | N |
| ATOM | 7803 | CA | LEU | E | 27 | 49.060 | −30.365 | −82.423 | 1.00 | 120.35 | MOL2 | C |
| ATOM | 7804 | CB | LEU | E | 27 | 47.589 | −30.328 | −82.829 | 1.00 | 116.49 | MOL2 | C |
| ATOM | 7805 | CG | LEU | E | 27 | 47.133 | −31.589 | −83.575 | 1.00 | 112.14 | MOL2 | C |
| ATOM | 7806 | CD1 | LEU | E | 27 | 47.115 | −32.755 | −82.613 | 1.00 | 110.03 | MOL2 | C |
| ATOM | 7807 | CD2 | LEU | E | 27 | 45.759 | −31.385 | −84.188 | 1.00 | 106.67 | MOL2 | C |
| ATOM | 7808 | C | LEU | E | 27 | 49.906 | −30.661 | −83.652 | 1.00 | 121.58 | MOL2 | C |
| ATOM | 7809 | O | LEU | E | 27 | 49.665 | −30.120 | −84.729 | 1.00 | 120.63 | MOL2 | O |
| ATOM | 7810 | N | ASP | E | 28 | 50.902 | −31.521 | −83.483 | 1.00 | 124.70 | MOL2 | N |
| ATOM | 7811 | CA | ASP | E | 28 | 51.780 | −31.887 | −84.584 | 1.00 | 128.71 | MOL2 | C |
| ATOM | 7812 | CB | ASP | E | 28 | 52.836 | −32.900 | −84.130 | 1.00 | 133.78 | MOL2 | C |
| ATOM | 7813 | CG | ASP | E | 28 | 53.636 | −32.421 | −82.934 | 1.00 | 140.19 | MOL2 | C |
| ATOM | 7814 | OD1 | ASP | E | 28 | 54.226 | −31.320 | −83.006 | 1.00 | 144.46 | MOL2 | O |
| ATOM | 7815 | OD2 | ASP | E | 28 | 53.681 | −33.154 | −81.920 | 1.00 | 141.62 | MOL2 | O |
| ATOM | 7816 | C | ASP | E | 28 | 50.985 | −32.497 | −85.726 | 1.00 | 130.05 | MOL2 | C |
| ATOM | 7817 | O | ASP | E | 28 | 50.007 | −33.216 | −85.516 | 1.00 | 128.49 | MOL2 | O |
| ATOM | 7818 | N | ILE | E | 29 | 51.417 | −32.202 | −86.942 | 1.00 | 133.66 | MOL2 | N |
| ATOM | 7819 | CA | ILE | E | 29 | 50.776 | −32.729 | −88.133 | 1.00 | 135.62 | MOL2 | C |
| ATOM | 7820 | CB | ILE | E | 29 | 51.201 | −31.912 | −89.369 | 1.00 | 138.97 | MOL2 | C |
| ATOM | 7821 | CG2 | ILE | E | 29 | 50.452 | −30.583 | −89.395 | 1.00 | 136.61 | MOL2 | C |
| ATOM | 7822 | CG1 | ILE | E | 29 | 52.719 | −31.683 | −89.338 | 1.00 | 139.95 | MOL2 | C |
| ATOM | 7823 | CD1 | ILE | E | 29 | 53.226 | −30.690 | −90.368 | 1.00 | 139.38 | MOL2 | C |
| ATOM | 7824 | C | ILE | E | 29 | 51.207 | −34.186 | −88.286 | 1.00 | 134.73 | MOL2 | C |
| ATOM | 7825 | O | ILE | E | 29 | 52.165 | −34.626 | −87.644 | 1.00 | 136.22 | MOL2 | O |
| ATOM | 7826 | N | GLY | E | 30 | 50.499 | −34.934 | −89.124 | 1.00 | 131.08 | MOL2 | N |
| ATOM | 7827 | CA | GLY | E | 30 | 50.846 | −36.329 | −89.314 | 1.00 | 127.61 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 7828 | C | GLY | E | 30 | 50.227 | −37.232 | −88.261 | 1.00 | 124.18 | MOL2 | C |
|---|---|---|---|---|---|---|---|---|---|---|---|---|
| ATOM | 7829 | O | GLY | E | 30 | 50.530 | −37.129 | −87.066 | 1.00 | 121.16 | MOL2 | O |
| ATOM | 7830 | N | ILE | E | 31 | 49.349 | −38.123 | −88.710 | 1.00 | 120.51 | MOL2 | N |
| ATOM | 7831 | CA | ILE | E | 31 | 48.679 | −39.055 | −87.816 | 1.00 | 112.52 | MOL2 | C |
| ATOM | 7832 | CB | ILE | E | 31 | 47.232 | −39.338 | −88.257 | 1.00 | 108.57 | MOL2 | C |
| ATOM | 7833 | CG2 | ILE | E | 31 | 46.681 | −40.502 | −87.476 | 1.00 | 106.81 | MOL2 | C |
| ATOM | 7834 | CG1 | ILE | E | 31 | 46.355 | −38.106 | −88.042 | 1.00 | 109.85 | MOL2 | C |
| ATOM | 7835 | CD1 | ILE | E | 31 | 46.629 | −36.976 | −89.010 | 1.00 | 115.80 | MOL2 | C |
| ATOM | 7836 | C | ILE | E | 31 | 49.420 | −40.376 | −87.778 | 1.00 | 110.19 | MOL2 | C |
| ATOM | 7837 | O | ILE | E | 31 | 49.772 | −40.932 | −88.815 | 1.00 | 113.42 | MOL2 | O |
| ATOM | 7838 | N | ILE | E | 32 | 49.654 | −40.873 | −86.574 | 1.00 | 108.04 | MOL2 | N |
| ATOM | 7839 | CA | ILE | E | 32 | 50.344 | −42.140 | −86.374 | 1.00 | 107.81 | MOL2 | C |
| ATOM | 7840 | CB | ILE | E | 32 | 50.661 | −42.340 | −84.890 | 1.00 | 98.99 | MOL2 | C |
| ATOM | 7841 | CG2 | ILE | E | 32 | 50.986 | −43.783 | −84.619 | 1.00 | 96.09 | MOL2 | C |
| ATOM | 7842 | CG1 | ILE | E | 32 | 51.796 | −41.407 | −84.480 | 1.00 | 95.71 | MOL2 | C |
| ATOM | 7843 | CD1 | ILE | E | 32 | 52.151 | −41.478 | −83.021 | 1.00 | 98.06 | MOL2 | C |
| ATOM | 7844 | C | ILE | E | 32 | 49.505 | −43.326 | −86.851 | 1.00 | 112.29 | MOL2 | C |
| ATOM | 7845 | O | ILE | E | 32 | 48.386 | −43.512 | −86.391 | 1.00 | 115.51 | MOL2 | O |
| ATOM | 7846 | N | ASN | E | 33 | 50.052 | −44.121 | −87.766 | 1.00 | 117.06 | MOL2 | N |
| ATOM | 7847 | CA | ASN | E | 33 | 49.363 | −45.295 | −88.304 | 1.00 | 122.38 | MOL2 | C |
| ATOM | 7848 | CB | ASN | E | 33 | 48.759 | −46.133 | −87.177 | 1.00 | 118.52 | MOL2 | C |
| ATOM | 7849 | CG | ASN | E | 33 | 49.795 | −46.927 | −86.418 | 1.00 | 119.07 | MOL2 | C |
| ATOM | 7850 | OD1 | ASN | E | 33 | 50.413 | −47.841 | −86.961 | 1.00 | 119.36 | MOL2 | O |
| ATOM | 7851 | ND2 | ASN | E | 33 | 49.993 | −46.584 | −85.150 | 1.00 | 121.47 | MOL2 | N |
| ATOM | 7852 | C | ASN | E | 33 | 48.262 | −44.968 | −89.299 | 1.00 | 128.50 | MOL2 | C |
| ATOM | 7853 | O | ASN | E | 33 | 47.304 | −45.727 | −89.428 | 1.00 | 132.14 | MOL2 | O |
| ATOM | 7854 | N | GLU | E | 34 | 48.402 | −43.855 | −90.013 | 1.00 | 134.94 | MOL2 | N |
| ATOM | 7855 | CA | GLU | E | 34 | 47.396 | −43.438 | −90.991 | 1.00 | 141.44 | MOL2 | C |
| ATOM | 7856 | CB | GLU | E | 34 | 47.833 | −42.128 | −91.670 | 1.00 | 139.56 | MOL2 | C |
| ATOM | 7857 | CG | GLU | E | 34 | 46.690 | −41.309 | −92.283 | 1.00 | 136.65 | MOL2 | C |
| ATOM | 7858 | CD | GLU | E | 34 | 47.143 | −39.952 | −92.820 | 1.00 | 134.53 | MOL2 | C |
| ATOM | 7859 | OE1 | GLU | E | 34 | 47.775 | −39.183 | −92.060 | 1.00 | 129.99 | MOL2 | O |
| ATOM | 7860 | OE2 | GLU | E | 34 | 46.858 | −39.652 | −94.003 | 1.00 | 133.64 | MOL2 | O |
| ATOM | 7861 | C | GLU | E | 34 | 47.168 | −44.525 | −92.042 | 1.00 | 146.34 | MOL2 | C |
| ATOM | 7862 | O | GLU | E | 34 | 46.245 | −44.440 | −92.852 | 1.00 | 146.31 | MOL2 | O |
| ATOM | 7863 | N | ASN | E | 35 | 48.008 | −45.554 | −92.003 | 1.00 | 153.14 | MOL2 | N |
| ATOM | 7864 | CA | ASN | E | 35 | 47.939 | −46.663 | −92.947 | 1.00 | 159.76 | MOL2 | C |
| ATOM | 7865 | CB | ASN | E | 35 | 49.347 | −47.222 | −93.180 | 1.00 | 164.22 | MOL2 | C |
| ATOM | 7866 | CG | ASN | E | 35 | 50.070 | −47.551 | −91.880 | 1.00 | 167.00 | MOL2 | C |
| ATOM | 7867 | OD1 | ASN | E | 35 | 50.435 | −46.656 | −91.116 | 1.00 | 168.89 | MOL2 | O |
| ATOM | 7868 | ND2 | ASN | E | 35 | 50.275 | −48.841 | −91.623 | 1.00 | 167.83 | MOL2 | N |
| ATOM | 7869 | C | ASN | E | 35 | 47.005 | −47.811 | −92.551 | 1.00 | 160.59 | MOL2 | C |
| ATOM | 7870 | O | ASN | E | 35 | 46.604 | −48.605 | −93.404 | 1.00 | 163.30 | MOL2 | O |
| ATOM | 7871 | N | GLN | E | 36 | 46.666 | −47.916 | −91.271 | 1.00 | 159.41 | MOL2 | N |
| ATOM | 7872 | CA | GLN | E | 36 | 45.784 | −48.993 | −90.842 | 1.00 | 159.83 | MOL2 | C |
| ATOM | 7873 | CB | GLN | E | 36 | 45.512 | −48.899 | −89.339 | 1.00 | 152.95 | MOL2 | C |
| ATOM | 7874 | CG | GLN | E | 36 | 46.776 | −49.016 | −88.494 | 1.00 | 141.32 | MOL2 | C |
| ATOM | 7875 | CD | GLN | E | 36 | 46.548 | −49.745 | −87.184 | 1.00 | 132.84 | MOL2 | C |
| ATOM | 7876 | OE1 | GLN | E | 36 | 46.144 | −50.905 | −87.172 | 1.00 | 127.00 | MOL2 | O |
| ATOM | 7877 | NE2 | GLN | E | 36 | 46.814 | −49.070 | −86.075 | 1.00 | 129.59 | MOL2 | N |
| ATOM | 7878 | C | GLN | E | 36 | 44.485 | −48.951 | −91.642 | 1.00 | 165.05 | MOL2 | C |
| ATOM | 7879 | O | GLN | E | 36 | 43.716 | −47.989 | −91.557 | 1.00 | 165.30 | MOL2 | O |
| ATOM | 7880 | N | ARG | E | 37 | 44.259 | −50.004 | −92.428 | 1.00 | 169.69 | MOL2 | N |
| ATOM | 7881 | CA | ARG | E | 37 | 43.080 | −50.105 | −93.287 | 1.00 | 173.53 | MOL2 | C |
| ATOM | 7882 | CB | ARG | E | 37 | 43.319 | −51.146 | −94.398 | 1.00 | 172.93 | MOL2 | C |
| ATOM | 7883 | CG | ARG | E | 37 | 42.164 | −51.309 | −95.410 | 1.00 | 171.95 | MOL2 | C |
| ATOM | 7884 | CD | ARG | E | 37 | 42.470 | −52.411 | −96.442 | 1.00 | 169.85 | MOL2 | C |
| ATOM | 7885 | NE | ARG | E | 37 | 41.321 | −52.815 | −97.266 | 1.00 | 167.65 | MOL2 | N |
| ATOM | 7886 | CZ | ARG | E | 37 | 40.895 | −52.178 | −98.357 | 1.00 | 165.79 | MOL2 | C |
| ATOM | 7887 | NH1 | ARG | E | 37 | 41.516 | −51.086 | −98.778 | 1.00 | 166.96 | MOL2 | N |
| ATOM | 7888 | NH2 | ARG | E | 37 | 39.852 | −52.643 | −99.041 | 1.00 | 159.83 | MOL2 | N |
| ATOM | 7889 | C | ARG | E | 37 | 41.790 | −50.436 | −92.542 | 1.00 | 175.83 | MOL2 | C |
| ATOM | 7890 | O | ARG | E | 37 | 41.790 | −51.190 | −91.566 | 1.00 | 174.15 | MOL2 | O |
| ATOM | 7891 | N | VAL | E | 38 | 40.695 | −49.856 | −93.031 | 1.00 | 179.53 | MOL2 | N |
| ATOM | 7892 | CA | VAL | E | 38 | 39.364 | −50.045 | −92.462 | 1.00 | 181.52 | MOL2 | C |
| ATOM | 7893 | CB | VAL | E | 38 | 38.281 | −49.336 | −93.332 | 1.00 | 182.97 | MOL2 | C |
| ATOM | 7894 | CG1 | VAL | E | 38 | 36.956 | −49.274 | −92.577 | 1.00 | 183.06 | MOL2 | C |
| ATOM | 7895 | CG2 | VAL | E | 38 | 38.751 | −47.934 | −93.725 | 1.00 | 182.19 | MOL2 | C |
| ATOM | 7896 | C | VAL | E | 38 | 39.023 | −51.533 | −92.366 | 1.00 | 180.77 | MOL2 | C |
| ATOM | 7897 | O | VAL | E | 38 | 38.405 | −52.099 | −93.270 | 1.00 | 180.76 | MOL2 | O |
| ATOM | 7898 | N | SER | E | 39 | 39.432 | −52.164 | −91.268 | 1.00 | 178.92 | MOL2 | N |
| ATOM | 7899 | CA | SER | E | 39 | 39.163 | −53.582 | −91.066 | 1.00 | 177.53 | MOL2 | C |
| ATOM | 7900 | CB | SER | E | 39 | 39.867 | −54.092 | −89.809 | 1.00 | 178.45 | MOL2 | C |
| ATOM | 7901 | OG | SER | E | 39 | 39.526 | −55.447 | −89.561 | 1.00 | 177.85 | MOL2 | O |
| ATOM | 7902 | C | SER | E | 39 | 37.667 | −53.835 | −90.937 | 1.00 | 176.25 | MOL2 | C |
| ATOM | 7903 | O | SER | E | 39 | 37.117 | −53.823 | −89.834 | 1.00 | 175.39 | MOL2 | O |
| ATOM | 7904 | N | MET | E | 40 | 37.020 | −54.070 | −92.074 | 1.00 | 174.10 | MOL2 | N |

TABLE 1-continued

The atomic coordinates of IL17F in complex with 496 Fab
(H32; a = 189.4; b = 189.4; c = 490.9, α, β = 90°; γ = 120°)

| ATOM | 7905 | CA | MET | E | 40 | 35.584 | −54.322 | −92.117 | 1.00 | 168.67 | MOL2 | C |
|---|---|---|---|---|---|---|---|---|---|---|---|---|
| ATOM | 7906 | CB | MET | E | 40 | 34.868 | −53.068 | −92.635 | 1.00 | 167.61 | MOL2 | C |
| ATOM | 7907 | CG | MET | E | 40 | 33.356 | −53.067 | −92.501 | 1.00 | 164.71 | MOL2 | C |
| ATOM | 7908 | SD | MET | E | 40 | 32.661 | −51.506 | −93.099 | 1.00 | 158.86 | MOL2 | S |
| ATOM | 7909 | CE | MET | E | 40 | 33.038 | −50.424 | −91.726 | 1.00 | 156.43 | MOL2 | C |
| ATOM | 7910 | C | MET | E | 40 | 35.309 | −55.508 | −93.044 | 1.00 | 164.36 | MOL2 | C |
| ATOM | 7911 | O | MET | E | 40 | 34.901 | −55.318 | −94.193 | 1.00 | 163.95 | MOL2 | O |
| ATOM | 7912 | N | SER | E | 41 | 35.556 | −56.722 | −92.554 | 1.00 | 156.89 | MOL2 | N |
| ATOM | 7913 | CA | SER | E | 41 | 35.316 | −57.914 | −93.356 | 1.00 | 150.06 | MOL2 | C |
| ATOM | 7914 | CB | SER | E | 41 | 35.521 | −59.183 | −92.528 | 1.00 | 150.16 | MOL2 | C |
| ATOM | 7915 | OG | SER | E | 41 | 35.292 | −60.342 | −93.315 | 1.00 | 149.67 | MOL2 | O |
| ATOM | 7916 | C | SER | E | 41 | 33.875 | −57.821 | −93.826 | 1.00 | 146.92 | MOL2 | C |
| ATOM | 7917 | O | SER | E | 41 | 32.944 | −58.146 | −93.092 | 1.00 | 147.48 | MOL2 | O |
| ATOM | 7918 | N | ARG | E | 42 | 33.699 | −57.359 | −95.057 | 1.00 | 142.70 | MOL2 | N |
| ATOM | 7919 | CA | ARG | E | 42 | 32.371 | −57.178 | −95.620 | 1.00 | 136.00 | MOL2 | C |
| ATOM | 7920 | CB | ARG | E | 42 | 32.482 | −56.781 | −97.096 | 1.00 | 134.72 | MOL2 | C |
| ATOM | 7921 | CG | ARG | E | 42 | 33.169 | −55.432 | −97.297 | 1.00 | 136.79 | MOL2 | C |
| ATOM | 7922 | CD | ARG | E | 42 | 33.201 | −55.032 | −98.763 | 1.00 | 143.02 | MOL2 | C |
| ATOM | 7923 | NE | ARG | E | 42 | 33.765 | −53.698 | −98.969 | 1.00 | 146.55 | MOL2 | N |
| ATOM | 7924 | CZ | ARG | E | 42 | 33.867 | −53.103 | −100.157 | 1.00 | 148.75 | MOL2 | C |
| ATOM | 7925 | NH1 | ARG | E | 42 | 33.442 | −53.721 | −101.253 | 1.00 | 148.61 | MOL2 | N |
| ATOM | 7926 | NH2 | ARG | E | 42 | 34.393 | −51.887 | −100.251 | 1.00 | 147.55 | MOL2 | N |
| ATOM | 7927 | C | ARG | E | 42 | 31.409 | −58.351 | −95.450 | 1.00 | 130.16 | MOL2 | C |
| ATOM | 7928 | O | ARG | E | 42 | 31.809 | −59.513 | −95.312 | 1.00 | 126.81 | MOL2 | O |
| ATOM | 7929 | N | ASN | E | 43 | 30.128 | −57.995 | −95.431 | 1.00 | 124.14 | MOL2 | N |
| ATOM | 7930 | CA | ASN | E | 43 | 29.007 | −58.916 | −95.297 | 1.00 | 115.62 | MOL2 | C |
| ATOM | 7931 | CB | ASN | E | 43 | 28.922 | −59.817 | −96.534 | 1.00 | 119.35 | MOL2 | C |
| ATOM | 7932 | CG | ASN | E | 43 | 28.530 | −59.042 | −97.791 | 1.00 | 122.58 | MOL2 | C |
| ATOM | 7933 | OD1 | ASN | E | 43 | 29.253 | −58.141 | −98.232 | 1.00 | 121.38 | MOL2 | O |
| ATOM | 7934 | ND2 | ASN | E | 43 | 27.379 | −59.388 | −98.363 | 1.00 | 121.45 | MOL2 | N |
| ATOM | 7935 | C | ASN | E | 43 | 28.878 | −59.759 | −94.029 | 1.00 | 106.29 | MOL2 | C |
| ATOM | 7936 | O | ASN | E | 43 | 27.872 | −60.455 | −93.867 | 1.00 | 105.11 | MOL2 | O |
| ATOM | 7937 | N | ILE | E | 44 | 29.851 | −59.705 | −93.120 | 1.00 | 92.85 | MOL2 | N |
| ATOM | 7938 | CA | ILE | E | 44 | 29.698 | −60.503 | −91.909 | 1.00 | 80.61 | MOL2 | C |
| ATOM | 7939 | CB | ILE | E | 44 | 30.965 | −60.545 | −91.049 | 1.00 | 73.95 | MOL2 | C |
| ATOM | 7940 | CG2 | ILE | E | 44 | 32.186 | −60.582 | −91.942 | 1.00 | 83.11 | MOL2 | C |
| ATOM | 7941 | CG1 | ILE | E | 44 | 31.001 | −59.360 | −90.100 | 1.00 | 61.18 | MOL2 | C |
| ATOM | 7942 | CD1 | ILE | E | 44 | 32.077 | −59.492 | −89.073 | 1.00 | 44.22 | MOL2 | C |
| ATOM | 7943 | C | ILE | E | 44 | 28.576 | −59.893 | −91.099 | 1.00 | 75.70 | MOL2 | C |
| ATOM | 7944 | O | ILE | E | 44 | 28.028 | −60.518 | −90.203 | 1.00 | 72.48 | MOL2 | O |
| ATOM | 7945 | N | GLU | E | 45 | 28.233 | −58.658 | −91.431 | 1.00 | 73.35 | MOL2 | N |
| ATOM | 7946 | CA | GLU | E | 45 | 27.153 | −57.979 | −90.750 | 1.00 | 72.10 | MOL2 | C |
| ATOM | 7947 | CB | GLU | E | 45 | 27.115 | −56.515 | −91.191 | 1.00 | 71.82 | MOL2 | C |
| ATOM | 7948 | CG | GLU | E | 45 | 27.688 | −56.282 | −92.573 | 1.00 | 72.25 | MOL2 | C |
| ATOM | 7949 | CD | GLU | E | 45 | 26.624 | −56.339 | −93.639 | 1.00 | 78.46 | MOL2 | C |
| ATOM | 7950 | OE1 | GLU | E | 45 | 25.671 | −57.128 | −93.465 | 1.00 | 84.47 | MOL2 | O |
| ATOM | 7951 | OE2 | GLU | E | 45 | 26.738 | −55.607 | −94.650 | 1.00 | 80.02 | MOL2 | O |
| ATOM | 7952 | C | GLU | E | 45 | 25.858 | −58.706 | −91.088 | 1.00 | 72.10 | MOL2 | C |
| ATOM | 7953 | O | GLU | E | 45 | 24.812 | −58.465 | −90.485 | 1.00 | 76.04 | MOL2 | O |
| ATOM | 7954 | N | SER | E | 46 | 25.938 | −59.624 | −92.042 | 1.00 | 70.43 | MOL2 | N |
| ATOM | 7955 | CA | SER | E | 46 | 24.763 | −60.368 | −92.441 | 1.00 | 70.92 | MOL2 | C |
| ATOM | 7956 | CB | SER | E | 46 | 24.453 | −60.116 | −93.901 | 1.00 | 70.73 | MOL2 | C |
| ATOM | 7957 | OG | SER | E | 46 | 23.185 | −60.661 | −94.198 | 1.00 | 83.10 | MOL2 | O |
| ATOM | 7958 | C | SER | E | 46 | 24.912 | −61.859 | −92.215 | 1.00 | 70.22 | MOL2 | C |
| ATOM | 7959 | O | SER | E | 46 | 23.942 | −62.609 | −92.324 | 1.00 | 73.24 | MOL2 | O |
| ATOM | 7960 | N | ARG | E | 47 | 26.129 | −62.288 | −91.908 | 1.00 | 67.88 | MOL2 | N |
| ATOM | 7961 | CA | ARG | E | 47 | 26.399 | −63.700 | −91.651 | 1.00 | 65.71 | MOL2 | C |
| ATOM | 7962 | CB | ARG | E | 47 | 27.822 | −64.065 | −92.117 | 1.00 | 67.97 | MOL2 | C |
| ATOM | 7963 | CG | ARG | E | 47 | 28.027 | −64.302 | −93.629 | 1.00 | 66.34 | MOL2 | C |
| ATOM | 7964 | CD | ARG | E | 47 | 29.511 | −64.178 | −94.016 | 1.00 | 61.33 | MOL2 | C |
| ATOM | 7965 | NE | ARG | E | 47 | 30.383 | −64.894 | −93.081 | 1.00 | 71.70 | MOL2 | N |
| ATOM | 7966 | CZ | ARG | E | 47 | 31.634 | −64.538 | −92.769 | 1.00 | 75.39 | MOL2 | C |
| ATOM | 7967 | NH1 | ARG | E | 47 | 32.195 | −63.462 | −93.314 | 1.00 | 70.80 | MOL2 | N |
| ATOM | 7968 | NH2 | ARG | E | 47 | 32.326 | −65.254 | −91.888 | 1.00 | 77.23 | MOL2 | N |
| ATOM | 7969 | C | ARG | E | 47 | 26.257 | −63.997 | −90.148 | 1.00 | 65.68 | MOL2 | C |
| ATOM | 7970 | O | ARG | E | 47 | 26.263 | −65.151 | −89.736 | 1.00 | 68.35 | MOL2 | O |
| ATOM | 7971 | N | SER | E | 48 | 26.129 | −62.957 | −89.331 | 1.00 | 60.86 | MOL2 | N |
| ATOM | 7972 | CA | SER | E | 48 | 26.007 | −63.144 | −87.891 | 1.00 | 57.17 | MOL2 | C |
| ATOM | 7973 | CB | SER | E | 48 | 26.350 | −61.844 | −87.162 | 1.00 | 56.06 | MOL2 | C |
| ATOM | 7974 | OG | SER | E | 48 | 26.119 | −61.967 | −85.767 | 1.00 | 56.81 | MOL2 | O |
| ATOM | 7975 | C | SER | E | 48 | 24.615 | −63.601 | −87.468 | 1.00 | 58.73 | MOL2 | C |
| ATOM | 7976 | O | SER | E | 48 | 23.625 | −63.316 | −88.141 | 1.00 | 57.30 | MOL2 | O |
| ATOM | 7977 | N | THR | E | 49 | 24.544 | −64.320 | −86.351 | 1.00 | 58.32 | MOL2 | N |
| ATOM | 7978 | CA | THR | E | 49 | 23.261 | −64.780 | −85.845 | 1.00 | 55.76 | MOL2 | C |
| ATOM | 7979 | CB | THR | E | 49 | 23.404 | −65.832 | −84.720 | 1.00 | 60.87 | MOL2 | C |
| ATOM | 7980 | OG1 | THR | E | 49 | 24.360 | −65.388 | −83.753 | 1.00 | 66.62 | MOL2 | O |
| ATOM | 7981 | CG2 | THR | E | 49 | 23.839 | −67.162 | −85.286 | 1.00 | 63.93 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 7982 | C | THR | E | 49 | 22.517 | −63.577 | −85.300 | 1.00 | 53.59 | MOL2 | C |
|---|---|---|---|---|---|---|---|---|---|---|---|---|
| ATOM | 7983 | O | THR | E | 49 | 21.354 | −63.666 | −84.952 | 1.00 | 58.38 | MOL2 | O |
| ATOM | 7984 | N | SER | E | 50 | 23.212 | −62.451 | −85.223 | 1.00 | 54.20 | MOL2 | N |
| ATOM | 7985 | CA | SER | E | 50 | 22.642 | −61.199 | −84.745 | 1.00 | 51.98 | MOL2 | C |
| ATOM | 7986 | CB | SER | E | 50 | 23.176 | −60.870 | −83.343 | 1.00 | 60.19 | MOL2 | C |
| ATOM | 7987 | OG | SER | E | 50 | 24.595 | −60.942 | −83.265 | 1.00 | 60.82 | MOL2 | O |
| ATOM | 7988 | C | SER | E | 50 | 23.083 | −60.142 | −85.745 | 1.00 | 49.67 | MOL2 | C |
| ATOM | 7989 | O | SER | E | 50 | 23.962 | −59.337 | −85.464 | 1.00 | 51.17 | MOL2 | O |
| ATOM | 7990 | N | PRO | E | 51 | 22.484 | −60.159 | −86.943 | 1.00 | 47.99 | MOL2 | N |
| ATOM | 7991 | CD | PRO | E | 51 | 21.442 | −61.162 | −87.202 | 1.00 | 45.73 | MOL2 | C |
| ATOM | 7992 | CA | PRO | E | 51 | 22.679 | −59.294 | −88.118 | 1.00 | 43.36 | MOL2 | C |
| ATOM | 7993 | CB | PRO | E | 51 | 21.665 | −59.830 | −89.109 | 1.00 | 47.50 | MOL2 | C |
| ATOM | 7994 | CG | PRO | E | 51 | 21.491 | −61.266 | −88.687 | 1.00 | 51.77 | MOL2 | C |
| ATOM | 7995 | C | PRO | E | 51 | 22.459 | −57.819 | −87.834 | 1.00 | 43.28 | MOL2 | C |
| ATOM | 7996 | O | PRO | E | 51 | 21.758 | −57.451 | −86.902 | 1.00 | 50.95 | MOL2 | O |
| ATOM | 7997 | N | TRP | E | 52 | 23.028 | −56.967 | −88.660 | 1.00 | 41.57 | MOL2 | N |
| ATOM | 7998 | CA | TRP | E | 52 | 22.905 | −55.546 | −88.411 | 1.00 | 50.00 | MOL2 | C |
| ATOM | 7999 | CB | TRP | E | 52 | 23.895 | −55.159 | −87.320 | 1.00 | 47.15 | MOL2 | C |
| ATOM | 8000 | CG | TRP | E | 52 | 25.353 | −55.231 | −87.744 | 1.00 | 45.30 | MOL2 | C |
| ATOM | 8001 | CD2 | TRP | E | 52 | 26.308 | −56.259 | −87.418 | 1.00 | 42.68 | MOL2 | C |
| ATOM | 8002 | CE2 | TRP | E | 52 | 27.551 | −55.853 | −87.930 | 1.00 | 41.16 | MOL2 | C |
| ATOM | 8003 | CE3 | TRP | E | 52 | 26.230 | −57.475 | −86.740 | 1.00 | 44.00 | MOL2 | C |
| ATOM | 8004 | CD1 | TRP | E | 52 | 26.043 | −54.285 | −88.436 | 1.00 | 46.32 | MOL2 | C |
| ATOM | 8005 | NE1 | TRP | E | 52 | 27.365 | −54.646 | −88.548 | 1.00 | 47.01 | MOL2 | N |
| ATOM | 8006 | CZ2 | TRP | E | 52 | 28.704 | −56.614 | −87.782 | 1.00 | 33.73 | MOL2 | C |
| ATOM | 8007 | CZ3 | TRP | E | 52 | 27.383 | −58.230 | −86.596 | 1.00 | 44.70 | MOL2 | C |
| ATOM | 8008 | CH2 | TRP | E | 52 | 28.601 | −57.794 | −87.114 | 1.00 | 37.12 | MOL2 | C |
| ATOM | 8009 | C | TRP | E | 52 | 23.189 | −54.735 | −89.665 | 1.00 | 58.16 | MOL2 | C |
| ATOM | 8010 | O | TRP | E | 52 | 24.000 | −55.148 | −90.501 | 1.00 | 62.69 | MOL2 | O |
| ATOM | 8011 | N | ASN | E | 53 | 22.536 | −53.579 | −89.788 | 1.00 | 59.20 | MOL2 | N |
| ATOM | 8012 | CA | ASN | E | 53 | 22.713 | −52.713 | −90.946 | 1.00 | 60.83 | MOL2 | C |
| ATOM | 8013 | CB | ASN | E | 53 | 21.368 | −52.103 | −91.331 | 1.00 | 70.19 | MOL2 | C |
| ATOM | 8014 | CG | ASN | E | 53 | 20.325 | −53.167 | −91.687 | 1.00 | 83.70 | MOL2 | C |
| ATOM | 8015 | OD1 | ASN | E | 53 | 19.115 | −52.957 | −91.522 | 1.00 | 91.13 | MOL2 | O |
| ATOM | 8016 | ND2 | ASN | E | 53 | 20.792 | −54.313 | −92.188 | 1.00 | 82.23 | MOL2 | N |
| ATOM | 8017 | C | ASN | E | 53 | 23.725 | −51.629 | −90.615 | 1.00 | 61.28 | MOL2 | C |
| ATOM | 8018 | O | ASN | E | 53 | 24.013 | −51.374 | −89.444 | 1.00 | 64.11 | MOL2 | O |
| ATOM | 8019 | N | TYR | E | 54 | 24.280 | −51.016 | −91.654 | 1.00 | 58.86 | MOL2 | N |
| ATOM | 8020 | CA | TYR | E | 54 | 25.268 | −49.960 | −91.501 | 1.00 | 61.22 | MOL2 | C |
| ATOM | 8021 | CB | TYR | E | 54 | 26.493 | −50.254 | −92.369 | 1.00 | 67.26 | MOL2 | C |
| ATOM | 8022 | CG | TYR | E | 54 | 27.529 | −51.169 | −91.755 | 1.00 | 84.17 | MOL2 | C |
| ATOM | 8023 | CD1 | TYR | E | 54 | 28.531 | −51.732 | −92.538 | 1.00 | 94.87 | MOL2 | C |
| ATOM | 8024 | CE1 | TYR | E | 54 | 29.520 | −52.546 | −91.971 | 1.00 | 101.40 | MOL2 | C |
| ATOM | 8025 | CD2 | TYR | E | 54 | 27.539 | −51.441 | −90.389 | 1.00 | 91.15 | MOL2 | C |
| ATOM | 8026 | CE2 | TYR | E | 54 | 28.525 | −52.252 | −89.814 | 1.00 | 92.49 | MOL2 | C |
| ATOM | 8027 | CZ | TYR | E | 54 | 29.509 | −52.799 | −90.610 | 1.00 | 96.52 | MOL2 | C |
| ATOM | 8028 | OH | TYR | E | 54 | 30.487 | −53.596 | −90.056 | 1.00 | 102.91 | MOL2 | O |
| ATOM | 8029 | C | TYR | E | 54 | 24.622 | −48.680 | −91.993 | 1.00 | 63.34 | MOL2 | C |
| ATOM | 8030 | O | TYR | E | 54 | 23.662 | −48.721 | −92.755 | 1.00 | 66.67 | MOL2 | O |
| ATOM | 8031 | N | THR | E | 55 | 25.140 | −47.542 | −91.560 | 1.00 | 64.79 | MOL2 | N |
| ATOM | 8032 | CA | THR | E | 55 | 24.613 | −46.264 | −92.004 | 1.00 | 61.47 | MOL2 | C |
| ATOM | 8033 | CB | THR | E | 55 | 23.485 | −45.757 | −91.107 | 1.00 | 61.61 | MOL2 | C |
| ATOM | 8034 | OG1 | THR | E | 55 | 23.001 | −46.822 | −90.274 | 1.00 | 63.86 | MOL2 | O |
| ATOM | 8035 | CG2 | THR | E | 55 | 22.352 | −45.240 | −91.970 | 1.00 | 64.48 | MOL2 | C |
| ATOM | 8036 | C | THR | E | 55 | 25.792 | −45.324 | −91.926 | 1.00 | 63.76 | MOL2 | C |
| ATOM | 8037 | O | THR | E | 55 | 26.353 | −45.105 | −90.851 | 1.00 | 70.50 | MOL2 | O |
| ATOM | 8038 | N | VAL | E | 56 | 26.177 | −44.774 | −93.068 | 1.00 | 61.24 | MOL2 | N |
| ATOM | 8039 | CA | VAL | E | 56 | 27.331 | −43.899 | −93.110 | 1.00 | 63.31 | MOL2 | C |
| ATOM | 8040 | CB | VAL | E | 56 | 28.201 | −44.233 | −94.312 | 1.00 | 62.79 | MOL2 | C |
| ATOM | 8041 | CG1 | VAL | E | 56 | 29.659 | −44.194 | −93.907 | 1.00 | 70.35 | MOL2 | C |
| ATOM | 8042 | CG2 | VAL | E | 56 | 27.818 | −45.592 | −94.866 | 1.00 | 59.65 | MOL2 | C |
| ATOM | 8043 | C | VAL | E | 56 | 27.000 | −42.427 | −93.164 | 1.00 | 63.17 | MOL2 | C |
| ATOM | 8044 | O | VAL | E | 56 | 26.024 | −42.020 | −93.786 | 1.00 | 72.43 | MOL2 | O |
| ATOM | 8045 | N | THR | E | 57 | 27.833 | −41.629 | −92.521 | 1.00 | 58.69 | MOL2 | N |
| ATOM | 8046 | CA | THR | E | 57 | 27.626 | −40.201 | −92.499 | 1.00 | 63.82 | MOL2 | C |
| ATOM | 8047 | CB | THR | E | 57 | 27.309 | −39.733 | −91.056 | 1.00 | 67.38 | MOL2 | C |
| ATOM | 8048 | OG1 | THR | E | 57 | 28.520 | −39.593 | −90.290 | 1.00 | 63.97 | MOL2 | O |
| ATOM | 8049 | CG2 | THR | E | 57 | 26.404 | −40.776 | −90.374 | 1.00 | 65.24 | MOL2 | C |
| ATOM | 8050 | C | THR | E | 57 | 28.934 | −39.622 | −92.990 | 1.00 | 62.36 | MOL2 | C |
| ATOM | 8051 | O | THR | E | 57 | 29.990 | −40.123 | −92.640 | 1.00 | 58.52 | MOL2 | O |
| ATOM | 8052 | N | TRP | E | 58 | 28.871 | −38.589 | −93.819 | 1.00 | 62.62 | MOL2 | N |
| ATOM | 8053 | CA | TRP | E | 58 | 30.092 | −37.987 | −94.332 | 1.00 | 58.98 | MOL2 | C |
| ATOM | 8054 | CB | TRP | E | 58 | 30.190 | −38.250 | −95.846 | 1.00 | 59.77 | MOL2 | C |
| ATOM | 8055 | CG | TRP | E | 58 | 31.457 | −37.738 | −96.444 | 1.00 | 64.58 | MOL2 | C |
| ATOM | 8056 | CD2 | TRP | E | 58 | 31.589 | −36.681 | −97.400 | 1.00 | 65.84 | MOL2 | C |
| ATOM | 8057 | CE2 | TRP | E | 58 | 32.965 | −36.450 | −97.576 | 1.00 | 63.71 | MOL2 | C |
| ATOM | 8058 | CE3 | TRP | E | 58 | 30.676 | −35.903 | −98.120 | 1.00 | 68.04 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 8059 | CD1 | TRP | E | 58 | 32.727 | −38.103 | −96.104 | 1.00 | 62.50 | MOL2 | C |
|---|---|---|---|---|---|---|---|---|---|---|---|---|
| ATOM | 8060 | NE1 | TRP | E | 58 | 33.637 | −37.335 | −96.775 | 1.00 | 61.01 | MOL2 | N |
| ATOM | 8061 | CZ2 | TRP | E | 58 | 33.452 | −35.472 | −98.437 | 1.00 | 61.12 | MOL2 | C |
| ATOM | 8062 | CZ3 | TRP | E | 58 | 31.160 | −34.935 | −98.974 | 1.00 | 64.62 | MOL2 | C |
| ATOM | 8063 | CH2 | TRP | E | 58 | 32.537 | −34.727 | −99.124 | 1.00 | 63.57 | MOL2 | C |
| ATOM | 8064 | C | TRP | E | 58 | 30.141 | −36.490 | −94.028 | 1.00 | 56.58 | MOL2 | C |
| ATOM | 8065 | O | TRP | E | 58 | 29.213 | −35.754 | −94.348 | 1.00 | 63.01 | MOL2 | O |
| ATOM | 8066 | N | ASP | E | 59 | 31.219 | −36.043 | −93.401 | 1.00 | 50.44 | MOL2 | N |
| ATOM | 8067 | CA | ASP | E | 59 | 31.363 | −34.635 | −93.050 | 1.00 | 52.34 | MOL2 | C |
| ATOM | 8068 | CB | ASP | E | 59 | 31.127 | −34.435 | −91.550 | 1.00 | 57.20 | MOL2 | C |
| ATOM | 8069 | CG | ASP | E | 59 | 31.466 | −33.029 | −91.076 | 1.00 | 63.00 | MOL2 | C |
| ATOM | 8070 | OD1 | ASP | E | 59 | 32.027 | −32.228 | −91.853 | 1.00 | 61.86 | MOL2 | O |
| ATOM | 8071 | OD2 | ASP | E | 59 | 31.176 | −32.728 | −89.900 | 1.00 | 72.14 | MOL2 | O |
| ATOM | 8072 | C | ASP | E | 59 | 32.759 | −34.199 | −93.409 | 1.00 | 50.93 | MOL2 | C |
| ATOM | 8073 | O | ASP | E | 59 | 33.728 | −34.595 | −92.785 | 1.00 | 54.75 | MOL2 | O |
| ATOM | 8074 | N | PRO | E | 60 | 32.884 | −33.389 | −94.444 | 1.00 | 51.08 | MOL2 | N |
| ATOM | 8075 | CD | PRO | E | 60 | 32.016 | −33.418 | −95.623 | 1.00 | 50.12 | MOL2 | C |
| ATOM | 8076 | CA | PRO | E | 60 | 34.220 | −32.950 | −94.817 | 1.00 | 52.23 | MOL2 | C |
| ATOM | 8077 | CB | PRO | E | 60 | 33.999 | −32.221 | −96.147 | 1.00 | 48.88 | MOL2 | C |
| ATOM | 8078 | CG | PRO | E | 60 | 32.514 | −32.248 | −96.376 | 1.00 | 44.79 | MOL2 | C |
| ATOM | 8079 | C | PRO | E | 60 | 35.031 | −32.157 | −93.798 | 1.00 | 54.56 | MOL2 | C |
| ATOM | 8080 | O | PRO | E | 60 | 36.230 | −32.015 | −93.962 | 1.00 | 58.78 | MOL2 | O |
| ATOM | 8081 | N | ASN | E | 61 | 34.412 | −31.648 | −92.746 | 1.00 | 57.99 | MOL2 | N |
| ATOM | 8082 | CA | ASN | E | 61 | 35.189 | −30.925 | −91.753 | 1.00 | 65.15 | MOL2 | C |
| ATOM | 8083 | CB | ASN | E | 61 | 34.534 | −29.600 | −91.392 | 1.00 | 76.68 | MOL2 | C |
| ATOM | 8084 | CG | ASN | E | 61 | 34.849 | −28.515 | −92.392 | 1.00 | 85.10 | MOL2 | C |
| ATOM | 8085 | OD1 | ASN | E | 61 | 35.999 | −28.375 | −92.829 | 1.00 | 84.88 | MOL2 | O |
| ATOM | 8086 | ND2 | ASN | E | 61 | 33.836 | −27.727 | −92.754 | 1.00 | 90.97 | MOL2 | N |
| ATOM | 8087 | C | ASN | E | 61 | 35.329 | −31.788 | −90.529 | 1.00 | 65.74 | MOL2 | C |
| ATOM | 8088 | O | ASN | E | 61 | 35.362 | −31.298 | −89.398 | 1.00 | 73.49 | MOL2 | O |
| ATOM | 8089 | N | ARG | E | 62 | 35.423 | −33.088 | −90.778 | 1.00 | 64.01 | MOL2 | N |
| ATOM | 8090 | CA | ARG | E | 62 | 35.541 | −34.092 | −89.724 | 1.00 | 61.06 | MOL2 | C |
| ATOM | 8091 | CB | ARG | E | 62 | 34.194 | −34.787 | −89.500 | 1.00 | 50.21 | MOL2 | C |
| ATOM | 8092 | CG | ARG | E | 62 | 34.311 | −36.035 | −88.668 | 1.00 | 42.12 | MOL2 | C |
| ATOM | 8093 | CD | ARG | E | 62 | 32.982 | −36.696 | −88.378 | 1.00 | 38.17 | MOL2 | C |
| ATOM | 8094 | NE | ARG | E | 62 | 32.435 | −37.392 | −89.534 | 1.00 | 33.78 | MOL2 | N |
| ATOM | 8095 | CZ | ARG | E | 62 | 31.304 | −38.096 | −89.503 | 1.00 | 39.49 | MOL2 | C |
| ATOM | 8096 | NH1 | ARG | E | 62 | 30.614 | −38.194 | −88.381 | 1.00 | 40.48 | MOL2 | N |
| ATOM | 8097 | NH2 | ARG | E | 62 | 30.849 | −38.700 | −90.587 | 1.00 | 40.15 | MOL2 | N |
| ATOM | 8098 | C | ARG | E | 62 | 36.548 | −35.172 | −90.073 | 1.00 | 60.67 | MOL2 | C |
| ATOM | 8099 | O | ARG | E | 62 | 36.480 | −35.764 | −91.150 | 1.00 | 58.25 | MOL2 | O |
| ATOM | 8100 | N | TYR | E | 63 | 37.485 | −35.441 | −89.174 | 1.00 | 59.80 | MOL2 | N |
| ATOM | 8101 | CA | TYR | E | 63 | 38.432 | −36.512 | −89.439 | 1.00 | 60.11 | MOL2 | C |
| ATOM | 8102 | CB | TYR | E | 63 | 39.871 | −36.025 | −89.508 | 1.00 | 72.93 | MOL2 | C |
| ATOM | 8103 | CG | TYR | E | 63 | 40.835 | −37.175 | −89.726 | 1.00 | 74.02 | MOL2 | C |
| ATOM | 8104 | CD1 | TYR | E | 63 | 42.055 | −37.229 | −89.071 | 1.00 | 76.81 | MOL2 | C |
| ATOM | 8105 | CE1 | TYR | E | 63 | 42.919 | −38.290 | −89.260 | 1.00 | 81.34 | MOL2 | C |
| ATOM | 8106 | CD2 | TYR | E | 63 | 40.510 | −38.210 | −90.577 | 1.00 | 77.48 | MOL2 | C |
| ATOM | 8107 | CE2 | TYR | E | 63 | 41.364 | −39.269 | −90.775 | 1.00 | 84.68 | MOL2 | C |
| ATOM | 8108 | CZ | TYR | E | 63 | 42.570 | −39.310 | −90.116 | 1.00 | 82.69 | MOL2 | C |
| ATOM | 8109 | OH | TYR | E | 63 | 43.422 | −40.375 | −90.330 | 1.00 | 82.64 | MOL2 | O |
| ATOM | 8110 | C | TYR | E | 63 | 38.356 | −37.546 | −88.346 | 1.00 | 55.62 | MOL2 | C |
| ATOM | 8111 | O | TYR | E | 63 | 38.590 | −37.246 | −87.172 | 1.00 | 57.14 | MOL2 | O |
| ATOM | 8112 | N | PRO | E | 64 | 37.989 | −38.775 | −88.710 | 1.00 | 49.22 | MOL2 | N |
| ATOM | 8113 | CD | PRO | E | 64 | 37.768 | −39.882 | −87.772 | 1.00 | 51.20 | MOL2 | C |
| ATOM | 8114 | CA | PRO | E | 64 | 37.652 | −39.199 | −90.067 | 1.00 | 52.71 | MOL2 | C |
| ATOM | 8115 | CB | PRO | E | 64 | 37.484 | −40.694 | −89.914 | 1.00 | 52.36 | MOL2 | C |
| ATOM | 8116 | CG | PRO | E | 64 | 36.860 | −40.793 | −88.578 | 1.00 | 49.85 | MOL2 | C |
| ATOM | 8117 | C | PRO | E | 64 | 36.375 | −38.570 | −90.606 | 1.00 | 58.88 | MOL2 | C |
| ATOM | 8118 | O | PRO | E | 64 | 35.459 | −38.254 | −89.856 | 1.00 | 64.95 | MOL2 | O |
| ATOM | 8119 | N | SER | E | 65 | 36.309 | −38.428 | −91.921 | 1.00 | 58.49 | MOL2 | N |
| ATOM | 8120 | CA | SER | E | 65 | 35.155 | −37.842 | −92.568 | 1.00 | 58.30 | MOL2 | C |
| ATOM | 8121 | CB | SER | E | 65 | 35.487 | −37.534 | −94.021 | 1.00 | 58.38 | MOL2 | C |
| ATOM | 8122 | OG | SER | E | 65 | 35.377 | −38.696 | −94.813 | 1.00 | 50.72 | MOL2 | O |
| ATOM | 8123 | C | SER | E | 65 | 33.939 | −38.758 | −92.517 | 1.00 | 58.26 | MOL2 | C |
| ATOM | 8124 | O | SER | E | 65 | 32.811 | −38.297 | −92.299 | 1.00 | 65.58 | MOL2 | O |
| ATOM | 8125 | N | GLU | E | 66 | 34.156 | −40.047 | −92.739 | 1.00 | 49.77 | MOL2 | N |
| ATOM | 8126 | CA | GLU | E | 66 | 33.054 | −40.996 | −92.716 | 1.00 | 51.35 | MOL2 | C |
| ATOM | 8127 | CB | GLU | E | 66 | 33.248 | −42.107 | −93.761 | 1.00 | 53.88 | MOL2 | C |
| ATOM | 8128 | CG | GLU | E | 66 | 34.518 | −41.987 | −94.597 | 1.00 | 82.21 | MOL2 | C |
| ATOM | 8129 | CD | GLU | E | 66 | 35.815 | −42.096 | −93.773 | 1.00 | 93.90 | MOL2 | C |
| ATOM | 8130 | OE1 | GLU | E | 66 | 36.344 | −43.224 | −93.624 | 1.00 | 101.45 | MOL2 | O |
| ATOM | 8131 | OE2 | GLU | E | 66 | 36.306 | −41.054 | −93.271 | 1.00 | 97.26 | MOL2 | O |
| ATOM | 8132 | C | GLU | E | 66 | 32.971 | −41.626 | −91.347 | 1.00 | 49.22 | MOL2 | C |
| ATOM | 8133 | O | GLU | E | 66 | 33.986 | −41.945 | −90.748 | 1.00 | 53.58 | MOL2 | O |
| ATOM | 8134 | N | VAL | E | 67 | 31.763 | −41.766 | −90.825 | 1.00 | 48.38 | MOL2 | N |
| ATOM | 8135 | CA | VAL | E | 67 | 31.592 | −42.432 | −89.552 | 1.00 | 44.38 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 8136 | CB | VAL | E | 67 | 31.315 | −41.495 | −88.419 | 1.00 | 41.29 | MOL2 | C |
| --- | --- | --- | --- | --- | --- | --- | --- | --- | --- | --- | --- | --- |
| ATOM | 8137 | CG1 | VAL | E | 67 | 31.101 | −42.303 | −87.156 | 1.00 | 34.89 | MOL2 | C |
| ATOM | 8138 | CG2 | VAL | E | 67 | 32.487 | −40.566 | −88.243 | 1.00 | 44.80 | MOL2 | C |
| ATOM | 8139 | C | VAL | E | 67 | 30.424 | −43.350 | −89.718 | 1.00 | 46.42 | MOL2 | C |
| ATOM | 8140 | O | VAL | E | 67 | 29.305 | −42.915 | −89.974 | 1.00 | 52.39 | MOL2 | O |
| ATOM | 8141 | N | VAL | E | 68 | 30.692 | −44.637 | −89.598 | 1.00 | 46.79 | MOL2 | N |
| ATOM | 8142 | CA | VAL | E | 68 | 29.639 | −45.615 | −89.767 | 1.00 | 48.74 | MOL2 | C |
| ATOM | 8143 | CB | VAL | E | 68 | 30.083 | −46.733 | −90.699 | 1.00 | 44.80 | MOL2 | C |
| ATOM | 8144 | CG1 | VAL | E | 68 | 31.587 | −46.827 | −90.679 | 1.00 | 51.42 | MOL2 | C |
| ATOM | 8145 | CG2 | VAL | E | 68 | 29.438 | −48.049 | −90.273 | 1.00 | 38.95 | MOL2 | C |
| ATOM | 8146 | C | VAL | E | 68 | 29.115 | −46.204 | −88.463 | 1.00 | 51.62 | MOL2 | C |
| ATOM | 8147 | O | VAL | E | 68 | 29.884 | −46.640 | −87.593 | 1.00 | 51.97 | MOL2 | O |
| ATOM | 8148 | N | GLN | E | 69 | 27.785 | −46.196 | −88.360 | 1.00 | 48.19 | MOL2 | N |
| ATOM | 8149 | CA | GLN | E | 69 | 27.055 | −46.676 | −87.200 | 1.00 | 44.45 | MOL2 | C |
| ATOM | 8150 | CB | GLN | E | 69 | 26.099 | −45.604 | −86.732 | 1.00 | 39.76 | MOL2 | C |
| ATOM | 8151 | CG | GLN | E | 69 | 26.752 | −44.362 | −86.241 | 1.00 | 44.61 | MOL2 | C |
| ATOM | 8152 | CD | GLN | E | 69 | 27.284 | −44.556 | −84.865 | 1.00 | 52.58 | MOL2 | C |
| ATOM | 8153 | OE1 | GLN | E | 69 | 26.876 | −45.488 | −84.159 | 1.00 | 60.19 | MOL2 | O |
| ATOM | 8154 | NE2 | GLN | E | 69 | 28.186 | −43.674 | −84.451 | 1.00 | 52.03 | MOL2 | N |
| ATOM | 8155 | C | GLN | E | 69 | 26.247 | −47.885 | −87.602 | 1.00 | 48.34 | MOL2 | C |
| ATOM | 8156 | O | GLN | E | 69 | 25.657 | −47.909 | −88.674 | 1.00 | 49.92 | MOL2 | O |
| ATOM | 8157 | N | ALA | E | 70 | 26.201 | −48.886 | −86.738 | 1.00 | 49.90 | MOL2 | N |
| ATOM | 8158 | CA | ALA | E | 70 | 25.438 | −50.081 | −87.053 | 1.00 | 52.19 | MOL2 | C |
| ATOM | 8159 | CB | ALA | E | 70 | 26.241 | −51.297 | −86.697 | 1.00 | 56.24 | MOL2 | C |
| ATOM | 8160 | C | ALA | E | 70 | 24.123 | −50.083 | −86.293 | 1.00 | 54.52 | MOL2 | C |
| ATOM | 8161 | O | ALA | E | 70 | 23.935 | −49.283 | −85.389 | 1.00 | 64.93 | MOL2 | O |
| ATOM | 8162 | N | GLN | E | 71 | 23.205 | −50.967 | −86.668 | 1.00 | 51.19 | MOL2 | N |
| ATOM | 8163 | CA | GLN | E | 71 | 21.927 | −51.077 | −85.971 | 1.00 | 48.31 | MOL2 | C |
| ATOM | 8164 | CB | GLN | E | 71 | 20.872 | −50.148 | −86.568 | 1.00 | 54.09 | MOL2 | C |
| ATOM | 8165 | CG | GLN | E | 71 | 21.257 | −49.407 | −87.821 | 1.00 | 72.60 | MOL2 | C |
| ATOM | 8166 | CD | GLN | E | 71 | 20.024 | −48.832 | −88.507 | 1.00 | 89.45 | MOL2 | C |
| ATOM | 8167 | OE1 | GLN | E | 71 | 19.225 | −48.123 | −87.880 | 1.00 | 92.14 | MOL2 | O |
| ATOM | 8168 | NE2 | GLN | E | 71 | 19.856 | −49.143 | −89.798 | 1.00 | 91.96 | MOL2 | N |
| ATOM | 8169 | C | GLN | E | 71 | 21.441 | −52.513 | −86.053 | 1.00 | 41.89 | MOL2 | C |
| ATOM | 8170 | O | GLN | E | 71 | 21.283 | −53.038 | −87.138 | 1.00 | 39.47 | MOL2 | O |
| ATOM | 8171 | N | CYS | E | 72 | 21.202 | −53.158 | −84.917 | 1.00 | 40.31 | MOL2 | N |
| ATOM | 8172 | CA | CYS | E | 72 | 20.753 | −54.550 | −84.954 | 1.00 | 44.02 | MOL2 | C |
| ATOM | 8173 | C | CYS | E | 72 | 19.472 | −54.722 | −85.763 | 1.00 | 48.09 | MOL2 | C |
| ATOM | 8174 | O | CYS | E | 72 | 18.469 | −54.048 | −85.531 | 1.00 | 46.70 | MOL2 | O |
| ATOM | 8175 | CB | CYS | E | 72 | 20.566 | −55.108 | −83.540 | 1.00 | 43.82 | MOL2 | C |
| ATOM | 8176 | SG | CYS | E | 72 | 22.020 | −54.777 | −82.503 | 1.00 | 50.10 | MOL2 | S |
| ATOM | 8177 | N | ARG | E | 73 | 19.517 | −55.645 | −86.719 | 1.00 | 55.21 | MOL2 | N |
| ATOM | 8178 | CA | ARG | E | 73 | 18.382 | −55.909 | −87.592 | 1.00 | 58.95 | MOL2 | C |
| ATOM | 8179 | CB | ARG | E | 73 | 18.808 | −56.797 | −88.756 | 1.00 | 62.39 | MOL2 | C |
| ATOM | 8180 | CG | ARG | E | 73 | 19.601 | −56.092 | −89.847 | 1.00 | 77.27 | MOL2 | C |
| ATOM | 8181 | CD | ARG | E | 73 | 19.235 | −56.699 | −91.191 | 1.00 | 91.12 | MOL2 | C |
| ATOM | 8182 | NE | ARG | E | 73 | 18.715 | −58.048 | −90.981 | 1.00 | 107.33 | MOL2 | N |
| ATOM | 8183 | CZ | ARG | E | 73 | 18.205 | −58.827 | −91.928 | 1.00 | 113.35 | MOL2 | C |
| ATOM | 8184 | NH1 | ARG | E | 73 | 18.141 | −58.395 | −93.185 | 1.00 | 113.41 | MOL2 | N |
| ATOM | 8185 | NH2 | ARG | E | 73 | 17.748 | −60.037 | −91.606 | 1.00 | 114.87 | MOL2 | N |
| ATOM | 8186 | C | ARG | E | 73 | 17.146 | −56.522 | −86.945 | 1.00 | 61.16 | MOL2 | C |
| ATOM | 8187 | O | ARG | E | 73 | 16.032 | −56.280 | −87.408 | 1.00 | 63.88 | MOL2 | O |
| ATOM | 8188 | N | ASN | E | 74 | 17.331 | −57.309 | −85.887 | 1.00 | 60.75 | MOL2 | N |
| ATOM | 8189 | CA | ASN | E | 74 | 16.211 | −57.957 | −85.204 | 1.00 | 58.58 | MOL2 | C |
| ATOM | 8190 | CB | ASN | E | 74 | 16.179 | −59.432 | −85.573 | 1.00 | 63.88 | MOL2 | C |
| ATOM | 8191 | CG | ASN | E | 74 | 15.723 | −59.657 | −86.987 | 1.00 | 73.21 | MOL2 | C |
| ATOM | 8192 | OD1 | ASN | E | 74 | 16.306 | −60.453 | −87.730 | 1.00 | 77.35 | MOL2 | O |
| ATOM | 8193 | ND2 | ASN | E | 74 | 14.656 | −58.960 | −87.373 | 1.00 | 82.26 | MOL2 | N |
| ATOM | 8194 | C | ASN | E | 74 | 16.307 | −57.836 | −83.696 | 1.00 | 55.64 | MOL2 | C |
| ATOM | 8195 | O | ASN | E | 74 | 17.282 | −57.316 | −83.175 | 1.00 | 54.84 | MOL2 | O |
| ATOM | 8196 | N | LEU | E | 75 | 15.292 | −58.320 | −82.992 | 1.00 | 55.82 | MOL2 | N |
| ATOM | 8197 | CA | LEU | E | 75 | 15.304 | −58.273 | −81.534 | 1.00 | 57.06 | MOL2 | C |
| ATOM | 8198 | CB | LEU | E | 75 | 13.893 | −58.148 | −80.958 | 1.00 | 52.04 | MOL2 | C |
| ATOM | 8199 | CG | LEU | E | 75 | 13.217 | −56.784 | −80.985 | 1.00 | 51.80 | MOL2 | C |
| ATOM | 8200 | CD1 | LEU | E | 75 | 12.080 | −56.788 | −79.997 | 1.00 | 49.65 | MOL2 | C |
| ATOM | 8201 | CD2 | LEU | E | 75 | 14.206 | −55.703 | −80.609 | 1.00 | 55.31 | MOL2 | C |
| ATOM | 8202 | C | LEU | E | 75 | 15.921 | −59.545 | −80.997 | 1.00 | 63.81 | MOL2 | C |
| ATOM | 8203 | O | LEU | E | 75 | 16.712 | −59.510 | −80.055 | 1.00 | 68.47 | MOL2 | O |
| ATOM | 8204 | N | GLY | E | 76 | 15.536 | −60.676 | −81.584 | 1.00 | 66.68 | MOL2 | N |
| ATOM | 8205 | CA | GLY | E | 76 | 16.087 | −61.949 | −81.158 | 1.00 | 71.12 | MOL2 | C |
| ATOM | 8206 | C | GLY | E | 76 | 17.291 | −62.285 | −82.022 | 1.00 | 76.93 | MOL2 | C |
| ATOM | 8207 | O | GLY | E | 76 | 17.827 | −61.409 | −82.705 | 1.00 | 79.58 | MOL2 | O |
| ATOM | 8208 | N | CYS | E | 77 | 17.736 | −63.539 | −81.996 | 1.00 | 78.39 | MOL2 | N |
| ATOM | 8209 | CA | CYS | E | 77 | 18.875 | −63.957 | −82.816 | 1.00 | 78.17 | MOL2 | C |
| ATOM | 8210 | C | CYS | E | 77 | 18.320 | −64.899 | −83.858 | 1.00 | 76.71 | MOL2 | C |
| ATOM | 8211 | O | CYS | E | 77 | 17.166 | −65.294 | −83.764 | 1.00 | 81.20 | MOL2 | O |
| ATOM | 8212 | CB | CYS | E | 77 | 19.917 | −64.690 | −81.977 | 1.00 | 78.22 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 8213 | SG  | CYS | E | 77 | 20.364 | −63.798 | −80.459 | 1.00 | 89.73  | MOL2 | S |
|------|------|-----|-----|---|----|--------|---------|---------|------|--------|------|---|
| ATOM | 8214 | N   | ILE | E | 78 | 19.112 | −65.263 | −84.857 | 1.00 | 76.75  | MOL2 | N |
| ATOM | 8215 | CA  | ILE | E | 78 | 18.595 | −66.174 | −85.862 | 1.00 | 80.49  | MOL2 | C |
| ATOM | 8216 | CB  | ILE | E | 78 | 18.601 | −65.556 | −87.258 | 1.00 | 75.11  | MOL2 | C |
| ATOM | 8217 | CG2 | ILE | E | 78 | 17.856 | −64.245 | −87.222 | 1.00 | 64.70  | MOL2 | C |
| ATOM | 8218 | CG1 | ILE | E | 78 | 20.034 | −65.386 | −87.764 | 1.00 | 85.80  | MOL2 | C |
| ATOM | 8219 | CD1 | ILE | E | 78 | 20.612 | −66.611 | −88.489 | 1.00 | 90.17  | MOL2 | C |
| ATOM | 8220 | C   | ILE | E | 78 | 19.332 | −67.492 | −85.885 | 1.00 | 89.07  | MOL2 | C |
| ATOM | 8221 | O   | ILE | E | 78 | 20.520 | −67.550 | −85.586 | 1.00 | 92.56  | MOL2 | O |
| ATOM | 8222 | N   | ASN | E | 79 | 18.617 | −68.562 | −86.221 | 1.00 | 98.50  | MOL2 | N |
| ATOM | 8223 | CA  | ASN | E | 79 | 19.241 | −69.877 | −86.256 | 1.00 | 110.09 | MOL2 | C |
| ATOM | 8224 | CB  | ASN | E | 79 | 18.358 | −70.928 | −85.585 | 1.00 | 107.86 | MOL2 | C |
| ATOM | 8225 | CG  | ASN | E | 79 | 17.128 | −71.233 | −86.377 | 1.00 | 108.80 | MOL2 | C |
| ATOM | 8226 | OD1 | ASN | E | 79 | 16.256 | −70.385 | −86.534 | 1.00 | 110.53 | MOL2 | O |
| ATOM | 8227 | ND2 | ASN | E | 79 | 17.047 | −72.452 | −86.897 | 1.00 | 113.64 | MOL2 | N |
| ATOM | 8228 | C   | ASN | E | 79 | 19.592 | −70.311 | −87.671 | 1.00 | 118.27 | MOL2 | C |
| ATOM | 8229 | O   | ASN | E | 79 | 19.956 | −69.475 | −88.501 | 1.00 | 121.27 | MOL2 | O |
| ATOM | 8230 | N   | ALA | E | 80 | 19.514 | −71.615 | −87.935 | 1.00 | 125.19 | MOL2 | N |
| ATOM | 8231 | CA  | ALA | E | 80 | 19.834 | −72.158 | −89.256 | 1.00 | 130.61 | MOL2 | C |
| ATOM | 8232 | CB  | ALA | E | 80 | 19.715 | −73.673 | −89.235 | 1.00 | 128.53 | MOL2 | C |
| ATOM | 8233 | C   | ALA | E | 80 | 18.878 | −71.571 | −90.291 | 1.00 | 134.25 | MOL2 | C |
| ATOM | 8234 | O   | ALA | E | 80 | 18.054 | −72.287 | −90.865 | 1.00 | 133.17 | MOL2 | O |
| ATOM | 8235 | N   | GLN | E | 81 | 19.009 | −70.265 | −90.521 | 1.00 | 137.89 | MOL2 | N |
| ATOM | 8236 | CA  | GLN | E | 81 | 18.156 | −69.523 | −91.445 | 1.00 | 139.14 | MOL2 | C |
| ATOM | 8237 | CB  | GLN | E | 81 | 18.337 | −70.014 | −92.887 | 1.00 | 144.30 | MOL2 | C |
| ATOM | 8238 | CG  | GLN | E | 81 | 19.145 | −69.054 | −93.762 | 1.00 | 149.40 | MOL2 | C |
| ATOM | 8239 | CD  | GLN | E | 81 | 19.094 | −69.405 | −95.243 | 1.00 | 152.30 | MOL2 | C |
| ATOM | 8240 | OE1 | GLN | E | 81 | 19.635 | −70.427 | −95.671 | 1.00 | 153.27 | MOL2 | O |
| ATOM | 8241 | NE2 | GLN | E | 81 | 18.436 | −68.556 | −96.031 | 1.00 | 150.03 | MOL2 | N |
| ATOM | 8242 | C   | GLN | E | 81 | 16.698 | −69.655 | −91.021 | 1.00 | 135.84 | MOL2 | C |
| ATOM | 8243 | O   | GLN | E | 81 | 15.786 | −69.412 | −91.808 | 1.00 | 135.95 | MOL2 | O |
| ATOM | 8244 | N   | GLY | E | 82 | 16.489 | −70.022 | −89.760 | 1.00 | 131.45 | MOL2 | N |
| ATOM | 8245 | CA  | GLY | E | 82 | 15.140 | −70.198 | −89.255 | 1.00 | 126.03 | MOL2 | C |
| ATOM | 8246 | C   | GLY | E | 82 | 14.604 | −69.061 | −88.410 | 1.00 | 119.59 | MOL2 | C |
| ATOM | 8247 | O   | GLY | E | 82 | 14.038 | −69.284 | −87.342 | 1.00 | 117.87 | MOL2 | O |
| ATOM | 8248 | N   | LYS | E | 83 | 14.769 | −67.842 | −88.903 | 1.00 | 114.72 | MOL2 | N |
| ATOM | 8249 | CA  | LYS | E | 83 | 14.314 | −66.643 | −88.210 | 1.00 | 114.48 | MOL2 | C |
| ATOM | 8250 | CB  | LYS | E | 83 | 12.882 | −66.288 | −88.642 | 1.00 | 119.53 | MOL2 | C |
| ATOM | 8251 | CG  | LYS | E | 83 | 12.830 | −65.305 | −89.833 | 1.00 | 123.26 | MOL2 | C |
| ATOM | 8252 | CD  | LYS | E | 83 | 13.557 | −63.989 | −89.496 | 1.00 | 122.89 | MOL2 | C |
| ATOM | 8253 | CE  | LYS | E | 83 | 13.596 | −62.996 | −90.660 | 1.00 | 121.89 | MOL2 | C |
| ATOM | 8254 | NZ  | LYS | E | 83 | 14.360 | −61.750 | −90.315 | 1.00 | 114.22 | MOL2 | N |
| ATOM | 8255 | C   | LYS | E | 83 | 14.442 | −66.610 | −86.677 | 1.00 | 108.72 | MOL2 | C |
| ATOM | 8256 | O   | LYS | E | 83 | 14.914 | −67.556 | −86.047 | 1.00 | 105.13 | MOL2 | O |
| ATOM | 8257 | N   | GLU | E | 84 | 14.023 | −65.482 | −86.105 | 1.00 | 102.09 | MOL2 | N |
| ATOM | 8258 | CA  | GLU | E | 84 | 14.101 | −65.198 | −84.678 | 1.00 | 91.74  | MOL2 | C |
| ATOM | 8259 | CB  | GLU | E | 84 | 13.147 | −64.053 | −84.329 | 1.00 | 87.64  | MOL2 | C |
| ATOM | 8260 | CG  | GLU | E | 84 | 13.637 | −62.700 | −84.802 | 1.00 | 86.66  | MOL2 | C |
| ATOM | 8261 | CD  | GLU | E | 84 | 12.865 | −61.559 | −84.198 | 1.00 | 87.09  | MOL2 | C |
| ATOM | 8262 | OE1 | GLU | E | 84 | 13.296 | −60.396 | −84.357 | 1.00 | 88.12  | MOL2 | O |
| ATOM | 8263 | OE2 | GLU | E | 84 | 11.823 | −61.824 | −83.565 | 1.00 | 92.87  | MOL2 | O |
| ATOM | 8264 | C   | GLU | E | 84 | 13.908 | −66.315 | −83.676 | 1.00 | 87.00  | MOL2 | C |
| ATOM | 8265 | O   | GLU | E | 84 | 13.220 | −67.293 | −83.926 | 1.00 | 89.11  | MOL2 | O |
| ATOM | 8266 | N   | ASP | E | 85 | 14.546 | −66.139 | −82.528 | 1.00 | 82.08  | MOL2 | N |
| ATOM | 8267 | CA  | ASP | E | 85 | 14.463 | −67.066 | −81.416 | 1.00 | 77.74  | MOL2 | C |
| ATOM | 8268 | CB  | ASP | E | 85 | 15.656 | −68.012 | −81.403 | 1.00 | 75.72  | MOL2 | C |
| ATOM | 8269 | CG  | ASP | E | 85 | 15.702 | −68.864 | −80.144 | 1.00 | 80.58  | MOL2 | C |
| ATOM | 8270 | OD1 | ASP | E | 85 | 16.701 | −69.580 | −79.925 | 1.00 | 85.99  | MOL2 | O |
| ATOM | 8271 | OD2 | ASP | E | 85 | 14.729 | −68.821 | −79.365 | 1.00 | 83.71  | MOL2 | O |
| ATOM | 8272 | C   | ASP | E | 85 | 14.509 | −66.192 | −80.174 | 1.00 | 78.30  | MOL2 | C |
| ATOM | 8273 | O   | ASP | E | 85 | 15.496 | −66.208 | −79.440 | 1.00 | 80.45  | MOL2 | O |
| ATOM | 8274 | N   | ILE | E | 86 | 13.443 | −65.427 | −79.951 | 1.00 | 75.25  | MOL2 | N |
| ATOM | 8275 | CA  | ILE | E | 86 | 13.344 | −64.510 | −78.819 | 1.00 | 71.69  | MOL2 | C |
| ATOM | 8276 | CB  | ILE | E | 86 | 11.875 | −64.045 | −78.634 | 1.00 | 71.23  | MOL2 | C |
| ATOM | 8277 | CG2 | ILE | E | 86 | 11.667 | −63.457 | −77.263 | 1.00 | 77.83  | MOL2 | C |
| ATOM | 8278 | CG1 | ILE | E | 86 | 11.527 | −62.988 | −79.674 | 1.00 | 69.23  | MOL2 | C |
| ATOM | 8279 | CD1 | ILE | E | 86 | 11.462 | −63.523 | −81.068 | 1.00 | 79.34  | MOL2 | C |
| ATOM | 8280 | C   | ILE | E | 86 | 13.881 | −65.028 | −77.481 | 1.00 | 71.67  | MOL2 | C |
| ATOM | 8281 | O   | ILE | E | 86 | 14.058 | −64.248 | −76.543 | 1.00 | 67.22  | MOL2 | O |
| ATOM | 8282 | N   | SER | E | 87 | 14.145 | −66.330 | −77.376 | 1.00 | 72.81  | MOL2 | N |
| ATOM | 8283 | CA  | SER | E | 87 | 14.654 | −66.859 | −76.116 | 1.00 | 72.24  | MOL2 | C |
| ATOM | 8284 | CB  | SER | E | 87 | 14.984 | −68.359 | −76.223 | 1.00 | 72.21  | MOL2 | C |
| ATOM | 8285 | OG  | SER | E | 87 | 15.928 | −68.635 | −77.239 | 1.00 | 78.01  | MOL2 | O |
| ATOM | 8286 | C   | SER | E | 87 | 15.886 | −66.044 | −75.729 | 1.00 | 71.37  | MOL2 | C |
| ATOM | 8287 | O   | SER | E | 87 | 16.111 | −65.770 | −74.544 | 1.00 | 70.16  | MOL2 | O |
| ATOM | 8288 | N   | MET | E | 88 | 16.646 | −65.633 | −76.746 | 1.00 | 68.20  | MOL2 | N |
| ATOM | 8289 | CA  | MET | E | 88 | 17.861 | −64.833 | −76.588 | 1.00 | 68.21  | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 8290 | CB | MET | E | 88 | 19.088 | −65.642 | −77.008 | 1.00 | 77.59 | MOL2 | C |
|---|---|---|---|---|---|---|---|---|---|---|---|---|
| ATOM | 8291 | CG | MET | E | 88 | 19.161 | −67.040 | −76.439 | 1.00 | 86.89 | MOL2 | C |
| ATOM | 8292 | SD | MET | E | 88 | 20.421 | −68.022 | −77.268 | 1.00 | 102.29 | MOL2 | S |
| ATOM | 8293 | CE | MET | E | 88 | 19.438 | −68.906 | −78.523 | 1.00 | 93.64 | MOL2 | C |
| ATOM | 8294 | C | MET | E | 88 | 17.738 | −63.650 | −77.539 | 1.00 | 62.85 | MOL2 | C |
| ATOM | 8295 | O | MET | E | 88 | 17.182 | −63.792 | −78.619 | 1.00 | 65.48 | MOL2 | O |
| ATOM | 8296 | N | ASN | E | 89 | 18.272 | −62.496 | −77.166 | 1.00 | 55.62 | MOL2 | N |
| ATOM | 8297 | CA | ASN | E | 89 | 18.178 | −61.335 | −78.040 | 1.00 | 50.85 | MOL2 | C |
| ATOM | 8298 | CB | ASN | E | 89 | 17.564 | −60.161 | −77.288 | 1.00 | 49.55 | MOL2 | C |
| ATOM | 8299 | CG | ASN | E | 89 | 16.982 | −60.568 | −75.947 | 1.00 | 57.40 | MOL2 | C |
| ATOM | 8300 | OD1 | ASN | E | 89 | 17.692 | −60.692 | −74.938 | 1.00 | 53.95 | MOL2 | O |
| ATOM | 8301 | ND2 | ASN | E | 89 | 15.676 | −60.787 | −75.932 | 1.00 | 61.21 | MOL2 | N |
| ATOM | 8302 | C | ASN | E | 89 | 19.536 | −60.915 | −78.556 | 1.00 | 50.59 | MOL2 | C |
| ATOM | 8303 | O | ASN | E | 89 | 20.570 | −61.272 | −77.981 | 1.00 | 48.04 | MOL2 | O |
| ATOM | 8304 | N | SER | E | 90 | 19.519 | −60.154 | −79.648 | 1.00 | 48.61 | MOL2 | N |
| ATOM | 8305 | CA | SER | E | 90 | 20.740 | −59.633 | −80.244 | 1.00 | 47.70 | MOL2 | C |
| ATOM | 8306 | CB | SER | E | 90 | 20.662 | −59.693 | −81.773 | 1.00 | 46.19 | MOL2 | C |
| ATOM | 8307 | OG | SER | E | 90 | 19.531 | −59.018 | −82.267 | 1.00 | 50.16 | MOL2 | O |
| ATOM | 8308 | C | SER | E | 90 | 20.874 | −58.195 | −79.752 | 1.00 | 44.95 | MOL2 | C |
| ATOM | 8309 | O | SER | E | 90 | 19.905 | −57.450 | −79.738 | 1.00 | 44.20 | MOL2 | O |
| ATOM | 8310 | N | VAL | E | 91 | 22.072 | −57.813 | −79.330 | 1.00 | 44.28 | MOL2 | N |
| ATOM | 8311 | CA | VAL | E | 91 | 22.288 | −56.475 | −78.808 | 1.00 | 43.66 | MOL2 | C |
| ATOM | 8312 | CB | VAL | E | 91 | 22.482 | −56.538 | −77.309 | 1.00 | 41.57 | MOL2 | C |
| ATOM | 8313 | CG1 | VAL | E | 91 | 21.187 | −56.883 | −76.658 | 1.00 | 44.38 | MOL2 | C |
| ATOM | 8314 | CG2 | VAL | E | 91 | 23.499 | −57.607 | −76.977 | 1.00 | 39.58 | MOL2 | C |
| ATOM | 8315 | C | VAL | E | 91 | 23.487 | −55.773 | −79.427 | 1.00 | 44.74 | MOL2 | C |
| ATOM | 8316 | O | VAL | E | 91 | 24.452 | −56.403 | −79.835 | 1.00 | 43.70 | MOL2 | O |
| ATOM | 8317 | N | PRO | E | 92 | 23.440 | −54.443 | −79.496 | 1.00 | 42.31 | MOL2 | N |
| ATOM | 8318 | CD | PRO | E | 92 | 22.345 | −53.554 | −79.093 | 1.00 | 42.44 | MOL2 | C |
| ATOM | 8319 | CA | PRO | E | 92 | 24.530 | −53.673 | −80.072 | 1.00 | 40.29 | MOL2 | C |
| ATOM | 8320 | CB | PRO | E | 92 | 23.917 | −52.298 | −80.247 | 1.00 | 40.11 | MOL2 | C |
| ATOM | 8321 | CG | PRO | E | 92 | 23.028 | −52.208 | −79.090 | 1.00 | 41.06 | MOL2 | C |
| ATOM | 8322 | C | PRO | E | 92 | 25.748 | −53.621 | −79.191 | 1.00 | 43.13 | MOL2 | C |
| ATOM | 8323 | O | PRO | E | 92 | 25.655 | −53.723 | −77.974 | 1.00 | 42.59 | MOL2 | O |
| ATOM | 8324 | N | ILE | E | 93 | 26.892 | −53.453 | −79.837 | 1.00 | 48.16 | MOL2 | N |
| ATOM | 8325 | CA | ILE | E | 93 | 28.187 | −53.343 | −79.180 | 1.00 | 49.81 | MOL2 | C |
| ATOM | 8326 | CB | ILE | E | 93 | 29.195 | −54.299 | −79.803 | 1.00 | 46.92 | MOL2 | C |
| ATOM | 8327 | CG2 | ILE | E | 93 | 30.533 | −54.107 | −79.178 | 1.00 | 44.02 | MOL2 | C |
| ATOM | 8328 | CG1 | ILE | E | 93 | 28.729 | −55.730 | −79.601 | 1.00 | 51.27 | MOL2 | C |
| ATOM | 8329 | CD1 | ILE | E | 93 | 28.373 | −56.023 | −78.157 | 1.00 | 53.71 | MOL2 | C |
| ATOM | 8330 | C | ILE | E | 93 | 28.624 | −51.935 | −79.503 | 1.00 | 52.28 | MOL2 | C |
| ATOM | 8331 | O | ILE | E | 93 | 28.746 | −51.587 | −80.679 | 1.00 | 57.40 | MOL2 | O |
| ATOM | 8332 | N | GLN | E | 94 | 28.865 | −51.123 | −78.485 | 1.00 | 49.84 | MOL2 | N |
| ATOM | 8333 | CA | GLN | E | 94 | 29.246 | −49.742 | −78.732 | 1.00 | 56.54 | MOL2 | C |
| ATOM | 8334 | CB | GLN | E | 94 | 28.224 | −48.823 | −78.052 | 1.00 | 59.34 | MOL2 | C |
| ATOM | 8335 | CG | GLN | E | 94 | 26.780 | −49.139 | −78.458 | 1.00 | 70.43 | MOL2 | C |
| ATOM | 8336 | CD | GLN | E | 94 | 25.730 | −48.440 | −77.604 | 1.00 | 75.73 | MOL2 | C |
| ATOM | 8337 | OE1 | GLN | E | 94 | 25.596 | −47.216 | −77.637 | 1.00 | 77.91 | MOL2 | O |
| ATOM | 8338 | NE2 | GLN | E | 94 | 24.974 | −49.223 | −76.836 | 1.00 | 79.77 | MOL2 | N |
| ATOM | 8339 | C | GLN | E | 94 | 30.660 | −49.417 | −78.269 | 1.00 | 59.38 | MOL2 | C |
| ATOM | 8340 | O | GLN | E | 94 | 31.153 | −49.996 | −77.309 | 1.00 | 65.31 | MOL2 | O |
| ATOM | 8341 | N | GLN | E | 95 | 31.302 | −48.484 | −78.962 | 1.00 | 61.31 | MOL2 | N |
| ATOM | 8342 | CA | GLN | E | 95 | 32.663 | −48.063 | −78.653 | 1.00 | 62.87 | MOL2 | C |
| ATOM | 8343 | CB | GLN | E | 95 | 33.612 | −48.677 | −79.690 | 1.00 | 67.12 | MOL2 | C |
| ATOM | 8344 | CG | GLN | E | 95 | 34.979 | −48.016 | −79.837 | 1.00 | 74.36 | MOL2 | C |
| ATOM | 8345 | CD | GLN | E | 95 | 35.848 | −48.154 | −78.597 | 1.00 | 85.35 | MOL2 | C |
| ATOM | 8346 | OE1 | GLN | E | 95 | 37.015 | −47.749 | −78.601 | 1.00 | 89.40 | MOL2 | O |
| ATOM | 8347 | NE2 | GLN | E | 95 | 35.287 | −48.723 | −77.526 | 1.00 | 86.40 | MOL2 | N |
| ATOM | 8348 | C | GLN | E | 95 | 32.753 | −46.541 | −78.705 | 1.00 | 64.12 | MOL2 | C |
| ATOM | 8349 | O | GLN | E | 95 | 32.292 | −45.928 | −79.663 | 1.00 | 65.85 | MOL2 | O |
| ATOM | 8350 | N | GLU | E | 96 | 33.327 | −45.927 | −77.676 | 1.00 | 65.29 | MOL2 | N |
| ATOM | 8351 | CA | GLU | E | 96 | 33.480 | −44.477 | −77.663 | 1.00 | 68.39 | MOL2 | C |
| ATOM | 8352 | CB | GLU | E | 96 | 33.680 | −43.969 | −76.235 | 1.00 | 81.52 | MOL2 | C |
| ATOM | 8353 | CG | GLU | E | 96 | 34.980 | −44.494 | −75.605 | 1.00 | 107.35 | MOL2 | C |
| ATOM | 8354 | CD | GLU | E | 96 | 35.366 | −43.816 | −74.290 | 1.00 | 119.77 | MOL2 | C |
| ATOM | 8355 | OE1 | GLU | E | 96 | 34.585 | −43.908 | −73.313 | 1.00 | 126.29 | MOL2 | O |
| ATOM | 8356 | OE2 | GLU | E | 96 | 36.460 | −43.199 | −74.236 | 1.00 | 121.87 | MOL2 | O |
| ATOM | 8357 | C | GLU | E | 96 | 34.734 | −44.177 | −78.478 | 1.00 | 63.33 | MOL2 | C |
| ATOM | 8358 | O | GLU | E | 96 | 35.786 | −44.764 | −78.248 | 1.00 | 58.01 | MOL2 | O |
| ATOM | 8359 | N | THR | E | 97 | 34.622 | −43.272 | −79.438 | 1.00 | 63.40 | MOL2 | N |
| ATOM | 8360 | CA | THR | E | 97 | 35.767 | −42.914 | −80.261 | 1.00 | 63.98 | MOL2 | C |
| ATOM | 8361 | CB | THR | E | 97 | 35.613 | −43.480 | −81.692 | 1.00 | 66.25 | MOL2 | C |
| ATOM | 8362 | OG1 | THR | E | 97 | 36.594 | −42.892 | −82.568 | 1.00 | 69.23 | MOL2 | O |
| ATOM | 8363 | CG2 | THR | E | 97 | 34.221 | −43.211 | −82.208 | 1.00 | 58.80 | MOL2 | C |
| ATOM | 8364 | C | THR | E | 97 | 35.963 | −41.400 | −80.332 | 1.00 | 62.45 | MOL2 | C |
| ATOM | 8365 | O | THR | E | 97 | 35.090 | −40.618 | −79.952 | 1.00 | 60.21 | MOL2 | O |
| ATOM | 8366 | N | LEU | E | 98 | 37.125 | −41.002 | −80.825 | 1.00 | 58.41 | MOL2 | N |

TABLE 1-continued

The atomic coordinates of IL17F in complex with 496 Fab
(H32; a = 189.4; b = 189.4; c = 490.9, α, β = 90°; γ = 120°)

| ATOM | 8367 | CA | LEU | E | 98 | 37.469 | −39.607 | −80.950 | 1.00 | 51.78 | MOL2 | C |
|---|---|---|---|---|---|---|---|---|---|---|---|---|
| ATOM | 8368 | CB | LEU | E | 98 | 38.867 | −39.411 | −80.421 | 1.00 | 47.88 | MOL2 | C |
| ATOM | 8369 | CG | LEU | E | 98 | 39.022 | −38.238 | −79.499 | 1.00 | 44.52 | MOL2 | C |
| ATOM | 8370 | CD1 | LEU | E | 98 | 38.088 | −38.411 | −78.326 | 1.00 | 37.36 | MOL2 | C |
| ATOM | 8371 | CD2 | LEU | E | 98 | 40.465 | −38.175 | −79.066 | 1.00 | 45.64 | MOL2 | C |
| ATOM | 8372 | C | LEU | E | 98 | 37.454 | −39.220 | −82.414 | 1.00 | 52.01 | MOL2 | C |
| ATOM | 8373 | O | LEU | E | 98 | 37.773 | −40.036 | −83.277 | 1.00 | 57.53 | MOL2 | O |
| ATOM | 8374 | N | VAL | E | 99 | 37.084 | −37.979 | −82.693 | 1.00 | 47.39 | MOL2 | N |
| ATOM | 8375 | CA | VAL | E | 99 | 37.076 | −37.466 | −84.059 | 1.00 | 43.63 | MOL2 | C |
| ATOM | 8376 | CB | VAL | E | 99 | 35.686 | −37.468 | −84.676 | 1.00 | 36.40 | MOL2 | C |
| ATOM | 8377 | CG1 | VAL | E | 99 | 35.425 | −38.771 | −85.360 | 1.00 | 36.46 | MOL2 | C |
| ATOM | 8378 | CG2 | VAL | E | 99 | 34.664 | −37.258 | −83.598 | 1.00 | 40.01 | MOL2 | C |
| ATOM | 8379 | C | VAL | E | 99 | 37.539 | −36.038 | −83.951 | 1.00 | 47.78 | MOL2 | C |
| ATOM | 8380 | O | VAL | E | 99 | 37.568 | −35.476 | −82.856 | 1.00 | 54.67 | MOL2 | O |
| ATOM | 8381 | N | VAL | E | 100 | 37.910 | −35.440 | −85.071 | 1.00 | 49.89 | MOL2 | N |
| ATOM | 8382 | CA | VAL | E | 100 | 38.379 | −34.072 | −85.021 | 1.00 | 53.73 | MOL2 | C |
| ATOM | 8383 | CB | VAL | E | 100 | 39.815 | −33.971 | −85.542 | 1.00 | 46.88 | MOL2 | C |
| ATOM | 8384 | CG1 | VAL | E | 100 | 40.419 | −32.651 | −85.129 | 1.00 | 48.36 | MOL2 | C |
| ATOM | 8385 | CG2 | VAL | E | 100 | 40.646 | −35.096 | −84.997 | 1.00 | 44.54 | MOL2 | C |
| ATOM | 8386 | C | VAL | E | 100 | 37.489 | −33.181 | −85.859 | 1.00 | 61.88 | MOL2 | C |
| ATOM | 8387 | O | VAL | E | 100 | 37.089 | −33.566 | −86.954 | 1.00 | 61.99 | MOL2 | O |
| ATOM | 8388 | N | ARG | E | 101 | 37.175 | −31.999 | −85.331 | 1.00 | 70.51 | MOL2 | N |
| ATOM | 8389 | CA | ARG | E | 101 | 36.339 | −31.027 | −86.023 | 1.00 | 76.01 | MOL2 | C |
| ATOM | 8390 | CB | ARG | E | 101 | 35.261 | −30.471 | −85.077 | 1.00 | 78.41 | MOL2 | C |
| ATOM | 8391 | CG | ARG | E | 101 | 33.868 | −31.075 | −85.255 | 1.00 | 82.62 | MOL2 | C |
| ATOM | 8392 | CD | ARG | E | 101 | 33.364 | −30.846 | −86.677 | 1.00 | 87.29 | MOL2 | C |
| ATOM | 8393 | NE | ARG | E | 101 | 32.050 | −31.429 | −86.929 | 1.00 | 89.15 | MOL2 | N |
| ATOM | 8394 | CZ | ARG | E | 101 | 31.724 | −32.691 | −86.666 | 1.00 | 97.26 | MOL2 | C |
| ATOM | 8395 | NH1 | ARG | E | 101 | 32.615 | −33.513 | −86.129 | 1.00 | 101.19 | MOL2 | N |
| ATOM | 8396 | NH2 | ARG | E | 101 | 30.510 | −33.144 | −86.957 | 1.00 | 101.44 | MOL2 | N |
| ATOM | 8397 | C | ARG | E | 101 | 37.212 | −29.889 | −86.523 | 1.00 | 79.13 | MOL2 | C |
| ATOM | 8398 | O | ARG | E | 101 | 38.080 | −29.396 | −85.798 | 1.00 | 80.39 | MOL2 | O |
| ATOM | 8399 | N | ARG | E | 102 | 36.991 | −29.487 | −87.769 | 1.00 | 82.53 | MOL2 | N |
| ATOM | 8400 | CA | ARG | E | 102 | 37.746 | −28.394 | −88.348 | 1.00 | 94.21 | MOL2 | C |
| ATOM | 8401 | CB | ARG | E | 102 | 38.169 | −28.751 | −89.784 | 1.00 | 89.08 | MOL2 | C |
| ATOM | 8402 | CG | ARG | E | 102 | 39.107 | −27.719 | −90.411 | 1.00 | 94.33 | MOL2 | C |
| ATOM | 8403 | CD | ARG | E | 102 | 39.931 | −28.228 | −91.597 | 1.00 | 90.53 | MOL2 | C |
| ATOM | 8404 | NE | ARG | E | 102 | 39.124 | −28.737 | −92.707 | 1.00 | 96.73 | MOL2 | N |
| ATOM | 8405 | CZ | ARG | E | 102 | 39.600 | −28.956 | −93.932 | 1.00 | 96.62 | MOL2 | C |
| ATOM | 8406 | NH1 | ARG | E | 102 | 40.873 | −28.696 | −94.198 | 1.00 | 96.35 | MOL2 | N |
| ATOM | 8407 | NH2 | ARG | E | 102 | 38.818 | −29.460 | −94.884 | 1.00 | 92.42 | MOL2 | N |
| ATOM | 8408 | C | ARG | E | 102 | 36.859 | −27.143 | −88.312 | 1.00 | 102.33 | MOL2 | C |
| ATOM | 8409 | O | ARG | E | 102 | 36.078 | −26.904 | −89.227 | 1.00 | 109.01 | MOL2 | O |
| ATOM | 8410 | N | LYS | E | 103 | 36.975 | −26.358 | −87.241 | 1.00 | 107.68 | MOL2 | N |
| ATOM | 8411 | CA | LYS | E | 103 | 36.172 | −25.150 | −87.074 | 1.00 | 116.53 | MOL2 | C |
| ATOM | 8412 | CB | LYS | E | 103 | 36.121 | −24.745 | −85.596 | 1.00 | 120.05 | MOL2 | C |
| ATOM | 8413 | CG | LYS | E | 103 | 35.175 | −25.552 | −84.711 | 1.00 | 122.89 | MOL2 | C |
| ATOM | 8414 | CD | LYS | E | 103 | 35.071 | −24.912 | −83.321 | 1.00 | 126.56 | MOL2 | C |
| ATOM | 8415 | CE | LYS | E | 103 | 34.599 | −23.449 | −83.411 | 1.00 | 130.65 | MOL2 | C |
| ATOM | 8416 | NZ | LYS | E | 103 | 34.624 | −22.698 | −82.111 | 1.00 | 128.86 | MOL2 | N |
| ATOM | 8417 | C | LYS | E | 103 | 36.664 | −23.956 | −87.891 | 1.00 | 122.22 | MOL2 | C |
| ATOM | 8418 | O | LYS | E | 103 | 37.867 | −23.740 | −88.025 | 1.00 | 124.36 | MOL2 | O |
| ATOM | 8419 | N | HIS | E | 104 | 35.714 | −23.187 | −88.424 | 1.00 | 128.02 | MOL2 | N |
| ATOM | 8420 | CA | HIS | E | 104 | 35.993 | −21.995 | −89.223 | 1.00 | 133.44 | MOL2 | C |
| ATOM | 8421 | CB | HIS | E | 104 | 36.836 | −21.029 | −88.407 | 1.00 | 135.13 | MOL2 | C |
| ATOM | 8422 | CG | HIS | E | 104 | 36.226 | −20.694 | −87.086 | 1.00 | 141.12 | MOL2 | C |
| ATOM | 8423 | CD2 | HIS | E | 104 | 34.936 | −20.701 | −86.677 | 1.00 | 143.94 | MOL2 | C |
| ATOM | 8424 | ND1 | HIS | E | 104 | 36.974 | −20.320 | −85.990 | 1.00 | 145.74 | MOL2 | N |
| ATOM | 8425 | CE1 | HIS | E | 104 | 36.170 | −20.115 | −84.962 | 1.00 | 148.35 | MOL2 | C |
| ATOM | 8426 | NE2 | HIS | E | 104 | 34.928 | −20.339 | −85.352 | 1.00 | 148.24 | MOL2 | N |
| ATOM | 8427 | C | HIS | E | 104 | 36.659 | −22.305 | −90.558 | 1.00 | 137.66 | MOL2 | C |
| ATOM | 8428 | O | HIS | E | 104 | 36.969 | −23.461 | −90.851 | 1.00 | 137.91 | MOL2 | O |
| ATOM | 8429 | N | GLN | E | 105 | 36.865 | −21.272 | −91.373 | 1.00 | 141.84 | MOL2 | N |
| ATOM | 8430 | CA | GLN | E | 105 | 37.472 | −21.447 | −92.694 | 1.00 | 144.01 | MOL2 | C |
| ATOM | 8431 | CB | GLN | E | 105 | 36.443 | −21.151 | −93.800 | 1.00 | 143.87 | MOL2 | C |
| ATOM | 8432 | CG | GLN | E | 105 | 35.011 | −21.615 | −93.506 | 1.00 | 145.95 | MOL2 | C |
| ATOM | 8433 | CD | GLN | E | 105 | 34.162 | −20.553 | −92.795 | 1.00 | 146.60 | MOL2 | C |
| ATOM | 8434 | OE1 | GLN | E | 105 | 34.565 | −19.995 | −91.772 | 1.00 | 146.19 | MOL2 | O |
| ATOM | 8435 | NE2 | GLN | E | 105 | 32.977 | −20.281 | −93.339 | 1.00 | 145.01 | MOL2 | N |
| ATOM | 8436 | C | GLN | E | 105 | 38.702 | −20.561 | −92.912 | 1.00 | 144.82 | MOL2 | C |
| ATOM | 8437 | O | GLN | E | 105 | 39.045 | −19.725 | −92.070 | 1.00 | 146.22 | MOL2 | O |
| ATOM | 8438 | N | GLY | E | 106 | 39.364 | −20.758 | −94.049 | 1.00 | 143.26 | MOL2 | N |
| ATOM | 8439 | CA | GLY | E | 106 | 40.534 | −19.965 | −94.379 | 1.00 | 140.46 | MOL2 | C |
| ATOM | 8440 | C | GLY | E | 106 | 41.700 | −20.064 | −93.416 | 1.00 | 139.38 | MOL2 | C |
| ATOM | 8441 | O | GLY | E | 106 | 42.065 | −21.153 | −92.982 | 1.00 | 136.71 | MOL2 | O |
| ATOM | 8442 | N | CYS | E | 107 | 42.282 | −18.914 | −93.084 | 1.00 | 140.88 | MOL2 | N |
| ATOM | 8443 | CA | CYS | E | 107 | 43.436 | −18.846 | −92.187 | 1.00 | 141.09 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 8444 | CB | CYS | E | 107 | 44.184 | −17.524 | −92.394 | 1.00 | 144.81 | MOL2 | C |
|---|---|---|---|---|---|---|---|---|---|---|---|---|
| ATOM | 8445 | SG | CYS | E | 107 | 44.506 | −17.088 | −94.132 | 1.00 | 150.21 | MOL2 | S |
| ATOM | 8446 | C | CYS | E | 107 | 43.042 | −18.969 | −90.724 | 1.00 | 138.31 | MOL2 | C |
| ATOM | 8447 | O | CYS | E | 107 | 43.869 | −19.298 | −89.874 | 1.00 | 134.91 | MOL2 | O |
| ATOM | 8448 | N | SER | E | 108 | 41.775 | −18.693 | −90.439 | 1.00 | 137.79 | MOL2 | N |
| ATOM | 8449 | CA | SER | E | 108 | 41.250 | −18.761 | −89.080 | 1.00 | 137.28 | MOL2 | C |
| ATOM | 8450 | CB | SER | E | 108 | 40.115 | −17.748 | −88.935 | 1.00 | 136.25 | MOL2 | C |
| ATOM | 8451 | OG | SER | E | 108 | 39.337 | −17.709 | −90.122 | 1.00 | 133.03 | MOL2 | O |
| ATOM | 8452 | C | SER | E | 108 | 40.755 | −20.164 | −88.720 | 1.00 | 135.53 | MOL2 | C |
| ATOM | 8453 | O | SER | E | 108 | 39.730 | −20.316 | −88.052 | 1.00 | 135.14 | MOL2 | O |
| ATOM | 8454 | N | VAL | E | 109 | 41.498 | −21.183 | −89.150 | 1.00 | 133.48 | MOL2 | N |
| ATOM | 8455 | CA | VAL | E | 109 | 41.126 | −22.575 | −88.886 | 1.00 | 127.95 | MOL2 | C |
| ATOM | 8456 | CB | VAL | E | 109 | 41.530 | −23.517 | −90.053 | 1.00 | 126.09 | MOL2 | C |
| ATOM | 8457 | CG1 | VAL | E | 109 | 43.048 | −23.621 | −90.153 | 1.00 | 123.85 | MOL2 | C |
| ATOM | 8458 | CG2 | VAL | E | 109 | 40.930 | −24.892 | −89.832 | 1.00 | 122.13 | MOL2 | C |
| ATOM | 8459 | C | VAL | E | 109 | 41.701 | −23.170 | −87.600 | 1.00 | 125.62 | MOL2 | C |
| ATOM | 8460 | O | VAL | E | 109 | 42.902 | −23.074 | −87.318 | 1.00 | 125.31 | MOL2 | O |
| ATOM | 8461 | N | SER | E | 110 | 40.817 | −23.792 | −86.828 | 1.00 | 121.03 | MOL2 | N |
| ATOM | 8462 | CA | SER | E | 110 | 41.188 | −24.438 | −85.576 | 1.00 | 116.37 | MOL2 | C |
| ATOM | 8463 | CB | SER | E | 110 | 40.598 | −23.681 | −84.380 | 1.00 | 118.52 | MOL2 | C |
| ATOM | 8464 | OG | SER | E | 110 | 39.182 | −23.629 | −84.436 | 1.00 | 117.06 | MOL2 | O |
| ATOM | 8465 | C | SER | E | 110 | 40.655 | −25.869 | −85.605 | 1.00 | 111.82 | MOL2 | C |
| ATOM | 8466 | O | SER | E | 110 | 39.785 | −26.195 | −86.416 | 1.00 | 111.72 | MOL2 | O |
| ATOM | 8467 | N | PHE | E | 111 | 41.179 | −26.717 | −84.724 | 1.00 | 103.94 | MOL2 | N |
| ATOM | 8468 | CA | PHE | E | 111 | 40.768 | −28.117 | −84.647 | 1.00 | 94.38 | MOL2 | C |
| ATOM | 8469 | CB | PHE | E | 111 | 41.935 | −29.025 | −84.994 | 1.00 | 95.39 | MOL2 | C |
| ATOM | 8470 | CG | PHE | E | 111 | 42.360 | −28.947 | −86.413 | 1.00 | 96.16 | MOL2 | C |
| ATOM | 8471 | CD1 | PHE | E | 111 | 43.616 | −29.383 | −86.790 | 1.00 | 98.09 | MOL2 | C |
| ATOM | 8472 | CD2 | PHE | E | 111 | 41.498 | −28.469 | −87.380 | 1.00 | 98.78 | MOL2 | C |
| ATOM | 8473 | CE1 | PHE | E | 111 | 44.008 | −29.345 | −88.109 | 1.00 | 102.22 | MOL2 | C |
| ATOM | 8474 | CE2 | PHE | E | 111 | 41.880 | −28.426 | −88.705 | 1.00 | 102.39 | MOL2 | C |
| ATOM | 8475 | CZ | PHE | E | 111 | 43.138 | −28.865 | −89.072 | 1.00 | 103.46 | MOL2 | C |
| ATOM | 8476 | C | PHE | E | 111 | 40.325 | −28.459 | −83.246 | 1.00 | 89.06 | MOL2 | C |
| ATOM | 8477 | O | PHE | E | 111 | 41.009 | −28.124 | −82.288 | 1.00 | 92.32 | MOL2 | O |
| ATOM | 8478 | N | GLN | E | 112 | 39.205 | −29.156 | −83.125 | 1.00 | 83.17 | MOL2 | N |
| ATOM | 8479 | CA | GLN | E | 112 | 38.696 | −29.532 | −81.813 | 1.00 | 84.29 | MOL2 | C |
| ATOM | 8480 | CB | GLN | E | 112 | 37.455 | −28.693 | −81.507 | 1.00 | 86.73 | MOL2 | C |
| ATOM | 8481 | CG | GLN | E | 112 | 36.813 | −28.977 | −80.171 | 1.00 | 90.55 | MOL2 | C |
| ATOM | 8482 | CD | GLN | E | 112 | 35.873 | −27.876 | −79.748 | 1.00 | 91.46 | MOL2 | C |
| ATOM | 8483 | OE1 | GLN | E | 112 | 35.122 | −27.334 | −80.563 | 1.00 | 88.26 | MOL2 | O |
| ATOM | 8484 | NE2 | GLN | E | 112 | 35.901 | −27.541 | −78.462 | 1.00 | 97.18 | MOL2 | N |
| ATOM | 8485 | C | GLN | E | 112 | 38.376 | −31.031 | −81.738 | 1.00 | 82.43 | MOL2 | C |
| ATOM | 8486 | O | GLN | E | 112 | 37.858 | −31.602 | −82.695 | 1.00 | 77.70 | MOL2 | O |
| ATOM | 8487 | N | LEU | E | 113 | 38.685 | −31.662 | −80.602 | 1.00 | 80.30 | MOL2 | N |
| ATOM | 8488 | CA | LEU | E | 113 | 38.437 | −33.100 | −80.425 | 1.00 | 74.22 | MOL2 | C |
| ATOM | 8489 | CB | LEU | E | 113 | 39.433 | −33.709 | −79.433 | 1.00 | 66.96 | MOL2 | C |
| ATOM | 8490 | CG | LEU | E | 113 | 40.872 | −33.756 | −79.932 | 1.00 | 65.93 | MOL2 | C |
| ATOM | 8491 | CD1 | LEU | E | 113 | 41.740 | −34.570 | −79.004 | 1.00 | 55.44 | MOL2 | C |
| ATOM | 8492 | CD2 | LEU | E | 113 | 40.868 | −34.357 | −81.321 | 1.00 | 66.02 | MOL2 | C |
| ATOM | 8493 | C | LEU | E | 113 | 37.043 | −33.448 | −79.954 | 1.00 | 72.97 | MOL2 | C |
| ATOM | 8494 | O | LEU | E | 113 | 36.702 | −33.198 | −78.803 | 1.00 | 80.24 | MOL2 | O |
| ATOM | 8495 | N | GLU | E | 114 | 36.238 | −34.032 | −80.836 | 1.00 | 72.95 | MOL2 | N |
| ATOM | 8496 | CA | GLU | E | 114 | 34.880 | −34.440 | −80.471 | 1.00 | 70.69 | MOL2 | C |
| ATOM | 8497 | CB | GLU | E | 114 | 33.897 | −34.241 | −81.613 | 1.00 | 72.79 | MOL2 | C |
| ATOM | 8498 | CG | GLU | E | 114 | 32.513 | −34.748 | −81.275 | 1.00 | 83.81 | MOL2 | C |
| ATOM | 8499 | CD | GLU | E | 114 | 31.487 | −34.412 | −82.342 | 1.00 | 94.74 | MOL2 | C |
| ATOM | 8500 | OE1 | GLU | E | 114 | 30.303 | −34.771 | −82.148 | 1.00 | 100.33 | MOL2 | O |
| ATOM | 8501 | OE2 | GLU | E | 114 | 31.859 | −33.793 | −83.369 | 1.00 | 93.70 | MOL2 | O |
| ATOM | 8502 | C | GLU | E | 114 | 34.872 | −35.904 | −80.088 | 1.00 | 66.76 | MOL2 | C |
| ATOM | 8503 | O | GLU | E | 114 | 35.710 | −36.679 | −80.542 | 1.00 | 69.93 | MOL2 | O |
| ATOM | 8504 | N | LYS | E | 115 | 33.911 | −36.282 | −79.260 | 1.00 | 61.81 | MOL2 | N |
| ATOM | 8505 | CA | LYS | E | 115 | 33.806 | −37.653 | −78.787 | 1.00 | 60.98 | MOL2 | C |
| ATOM | 8506 | CB | LYS | E | 115 | 33.812 | −37.650 | −77.262 | 1.00 | 58.52 | MOL2 | C |
| ATOM | 8507 | CG | LYS | E | 115 | 34.286 | −38.916 | −76.620 | 1.00 | 61.92 | MOL2 | C |
| ATOM | 8508 | CD | LYS | E | 115 | 34.557 | −38.667 | −75.152 | 1.00 | 67.44 | MOL2 | C |
| ATOM | 8509 | CE | LYS | E | 115 | 35.260 | −39.837 | −74.498 | 1.00 | 75.96 | MOL2 | C |
| ATOM | 8510 | NZ | LYS | E | 115 | 35.543 | −39.532 | −73.069 | 1.00 | 84.28 | MOL2 | N |
| ATOM | 8511 | C | LYS | E | 115 | 32.515 | −38.261 | −79.306 | 1.00 | 59.27 | MOL2 | C |
| ATOM | 8512 | O | LYS | E | 115 | 31.439 | −37.736 | −79.061 | 1.00 | 66.71 | MOL2 | O |
| ATOM | 8513 | N | VAL | E | 116 | 32.605 | −39.359 | −80.041 | 1.00 | 56.90 | MOL2 | N |
| ATOM | 8514 | CA | VAL | E | 116 | 31.392 | −39.972 | −80.556 | 1.00 | 53.33 | MOL2 | C |
| ATOM | 8515 | CB | VAL | E | 116 | 31.273 | −39.843 | −82.094 | 1.00 | 51.59 | MOL2 | C |
| ATOM | 8516 | CG1 | VAL | E | 116 | 32.630 | −39.693 | −82.723 | 1.00 | 53.36 | MOL2 | C |
| ATOM | 8517 | CG2 | VAL | E | 116 | 30.569 | −41.056 | −82.652 | 1.00 | 52.36 | MOL2 | C |
| ATOM | 8518 | C | VAL | E | 116 | 31.274 | −41.422 | −80.164 | 1.00 | 52.05 | MOL2 | C |
| ATOM | 8519 | O | VAL | E | 116 | 32.259 | −42.155 | −80.144 | 1.00 | 49.32 | MOL2 | O |
| ATOM | 8520 | N | LEU | E | 117 | 30.050 | −41.819 | −79.837 | 1.00 | 55.22 | MOL2 | N |

TABLE 1-continued

The atomic coordinates of IL17F in complex with 496 Fab
(H32; a = 189.4; b = 189.4; c = 490.9, α, β = 90°; γ = 120°)

| ATOM | 8521 | CA | LEU | E | 117 | 29.759 | −43.183 | −79.410 | 1.00 | 54.66 | MOL2 | C |
|---|---|---|---|---|---|---|---|---|---|---|---|---|
| ATOM | 8522 | CB | LEU | E | 117 | 28.731 | −43.149 | −78.263 | 1.00 | 55.56 | MOL2 | C |
| ATOM | 8523 | CG | LEU | E | 117 | 28.243 | −44.328 | −77.403 | 1.00 | 52.46 | MOL2 | C |
| ATOM | 8524 | CD1 | LEU | E | 117 | 26.836 | −44.720 | −77.799 | 1.00 | 48.83 | MOL2 | C |
| ATOM | 8525 | CD2 | LEU | E | 117 | 29.198 | −45.482 | −77.503 | 1.00 | 61.71 | MOL2 | C |
| ATOM | 8526 | C | LEU | E | 117 | 29.211 | −43.905 | −80.620 | 1.00 | 51.02 | MOL2 | C |
| ATOM | 8527 | O | LEU | E | 117 | 28.190 | −43.497 | −81.183 | 1.00 | 51.27 | MOL2 | O |
| ATOM | 8528 | N | VAL | E | 118 | 29.901 | −44.959 | −81.042 | 1.00 | 43.55 | MOL2 | N |
| ATOM | 8529 | CA | VAL | E | 118 | 29.430 | −45.695 | −82.201 | 1.00 | 43.29 | MOL2 | C |
| ATOM | 8530 | CB | VAL | E | 118 | 30.409 | −45.609 | −83.389 | 1.00 | 34.40 | MOL2 | C |
| ATOM | 8531 | CG1 | VAL | E | 118 | 31.719 | −45.019 | −82.944 | 1.00 | 33.59 | MOL2 | C |
| ATOM | 8532 | CG2 | VAL | E | 118 | 30.587 | −46.987 | −83.997 | 1.00 | 28.61 | MOL2 | C |
| ATOM | 8533 | C | VAL | E | 118 | 29.075 | −47.154 | −81.976 | 1.00 | 41.49 | MOL2 | C |
| ATOM | 8534 | O | VAL | E | 118 | 29.663 | −47.859 | −81.164 | 1.00 | 43.98 | MOL2 | O |
| ATOM | 8535 | N | THR | E | 119 | 28.069 | −47.593 | −82.703 | 1.00 | 38.79 | MOL2 | N |
| ATOM | 8536 | CA | THR | E | 119 | 27.639 | −48.950 | −82.596 | 1.00 | 43.76 | MOL2 | C |
| ATOM | 8537 | CB | THR | E | 119 | 26.170 | −49.081 | −82.858 | 1.00 | 47.34 | MOL2 | C |
| ATOM | 8538 | OG1 | THR | E | 119 | 25.448 | −48.479 | −81.780 | 1.00 | 54.24 | MOL2 | O |
| ATOM | 8539 | CG2 | THR | E | 119 | 25.796 | −50.541 | −82.985 | 1.00 | 48.29 | MOL2 | C |
| ATOM | 8540 | C | THR | E | 119 | 28.386 | −49.696 | −83.658 | 1.00 | 50.94 | MOL2 | C |
| ATOM | 8541 | O | THR | E | 119 | 28.091 | −49.579 | −84.847 | 1.00 | 56.95 | MOL2 | O |
| ATOM | 8542 | N | VAL | E | 120 | 29.368 | −50.466 | −83.219 | 1.00 | 53.83 | MOL2 | N |
| ATOM | 8543 | CA | VAL | E | 120 | 30.201 | −51.243 | −84.116 | 1.00 | 49.09 | MOL2 | C |
| ATOM | 8544 | CB | VAL | E | 120 | 31.428 | −51.728 | −83.387 | 1.00 | 49.53 | MOL2 | C |
| ATOM | 8545 | CG1 | VAL | E | 120 | 32.415 | −52.247 | −84.370 | 1.00 | 58.28 | MOL2 | C |
| ATOM | 8546 | CG2 | VAL | E | 120 | 32.014 | −50.597 | −82.566 | 1.00 | 52.75 | MOL2 | C |
| ATOM | 8547 | C | VAL | E | 120 | 29.490 | −52.453 | −84.701 | 1.00 | 46.16 | MOL2 | C |
| ATOM | 8548 | O | VAL | E | 120 | 29.819 | −52.906 | −85.796 | 1.00 | 49.10 | MOL2 | O |
| ATOM | 8549 | N | GLY | E | 121 | 28.518 | −52.979 | −83.970 | 1.00 | 44.37 | MOL2 | N |
| ATOM | 8550 | CA | GLY | E | 121 | 27.789 | −54.136 | −84.457 | 1.00 | 46.49 | MOL2 | C |
| ATOM | 8551 | C | GLY | E | 121 | 26.955 | −54.812 | −83.382 | 1.00 | 48.38 | MOL2 | C |
| ATOM | 8552 | O | GLY | E | 121 | 26.834 | −54.312 | −82.263 | 1.00 | 53.22 | MOL2 | O |
| ATOM | 8553 | N | CYS | E | 122 | 26.396 | −55.967 | −83.709 | 1.00 | 40.67 | MOL2 | N |
| ATOM | 8554 | CA | CYS | E | 122 | 25.561 | −56.680 | −82.765 | 1.00 | 42.06 | MOL2 | C |
| ATOM | 8555 | C | CYS | E | 122 | 26.093 | −58.047 | −82.405 | 1.00 | 43.02 | MOL2 | C |
| ATOM | 8556 | O | CYS | E | 122 | 26.796 | −58.667 | −83.175 | 1.00 | 45.04 | MOL2 | O |
| ATOM | 8557 | CB | CYS | E | 122 | 24.168 | −56.806 | −83.356 | 1.00 | 44.10 | MOL2 | C |
| ATOM | 8558 | SG | CYS | E | 122 | 23.574 | −55.152 | −83.768 | 1.00 | 48.47 | MOL2 | S |
| ATOM | 8559 | N | THR | E | 123 | 25.757 | −58.507 | −81.211 | 1.00 | 46.59 | MOL2 | N |
| ATOM | 8560 | CA | THR | E | 123 | 26.184 | −59.811 | −80.753 | 1.00 | 44.87 | MOL2 | C |
| ATOM | 8561 | CB | THR | E | 123 | 27.307 | −59.719 | −79.694 | 1.00 | 41.29 | MOL2 | C |
| ATOM | 8562 | OG1 | THR | E | 123 | 27.780 | −61.036 | −79.403 | 1.00 | 47.66 | MOL2 | O |
| ATOM | 8563 | CG2 | THR | E | 123 | 26.798 | −59.090 | −78.402 | 1.00 | 33.38 | MOL2 | C |
| ATOM | 8564 | C | THR | E | 123 | 24.958 | −60.436 | −80.130 | 1.00 | 47.20 | MOL2 | C |
| ATOM | 8565 | O | THR | E | 123 | 24.136 | −59.735 | −79.543 | 1.00 | 38.36 | MOL2 | O |
| ATOM | 8566 | N | CYS | E | 124 | 24.829 | −61.748 | −80.270 | 1.00 | 53.73 | MOL2 | N |
| ATOM | 8567 | CA | CYS | E | 124 | 23.684 | −62.450 | −79.712 | 1.00 | 62.27 | MOL2 | C |
| ATOM | 8568 | C | CYS | E | 124 | 23.901 | −62.856 | −78.256 | 1.00 | 61.78 | MOL2 | C |
| ATOM | 8569 | O | CYS | E | 124 | 24.773 | −63.671 | −77.959 | 1.00 | 60.46 | MOL2 | O |
| ATOM | 8570 | CB | CYS | E | 124 | 23.379 | −63.689 | −80.548 | 1.00 | 70.88 | MOL2 | C |
| ATOM | 8571 | SG | CYS | E | 124 | 22.062 | −64.702 | −79.822 | 1.00 | 84.89 | MOL2 | S |
| ATOM | 8572 | N | VAL | E | 125 | 23.105 | −62.292 | −77.350 | 1.00 | 62.42 | MOL2 | N |
| ATOM | 8573 | CA | VAL | E | 125 | 23.237 | −62.611 | −75.934 | 1.00 | 62.51 | MOL2 | C |
| ATOM | 8574 | CB | VAL | E | 125 | 23.522 | −61.368 | −75.104 | 1.00 | 61.79 | MOL2 | C |
| ATOM | 8575 | CG1 | VAL | E | 125 | 24.824 | −60.773 | −75.542 | 1.00 | 69.24 | MOL2 | C |
| ATOM | 8576 | CG2 | VAL | E | 125 | 22.394 | −60.367 | −75.253 | 1.00 | 62.28 | MOL2 | C |
| ATOM | 8577 | C | VAL | E | 125 | 22.011 | −63.278 | −75.342 | 1.00 | 62.04 | MOL2 | C |
| ATOM | 8578 | O | VAL | E | 125 | 20.911 | −63.189 | −75.887 | 1.00 | 60.12 | MOL2 | O |
| ATOM | 8579 | N | THR | E | 126 | 22.224 | −63.952 | −74.219 | 1.00 | 60.85 | MOL2 | N |
| ATOM | 8580 | CA | THR | E | 126 | 21.167 | −64.641 | −73.509 | 1.00 | 63.22 | MOL2 | C |
| ATOM | 8581 | CB | THR | E | 126 | 21.598 | −66.086 | −73.111 | 1.00 | 66.38 | MOL2 | C |
| ATOM | 8582 | OG1 | THR | E | 126 | 20.792 | −66.548 | −72.021 | 1.00 | 70.91 | MOL2 | O |
| ATOM | 8583 | CG2 | THR | E | 126 | 23.061 | −66.131 | −72.710 | 1.00 | 66.04 | MOL2 | C |
| ATOM | 8584 | C | THR | E | 126 | 20.868 | −63.820 | −72.270 | 1.00 | 61.55 | MOL2 | C |
| ATOM | 8585 | O | THR | E | 126 | 21.759 | −63.546 | −71.472 | 1.00 | 60.05 | MOL2 | O |
| ATOM | 8586 | N | PRO | E | 127 | 19.603 | −63.407 | −72.100 | 1.00 | 63.20 | MOL2 | N |
| ATOM | 8587 | CD | PRO | E | 127 | 18.407 | −63.909 | −72.793 | 1.00 | 63.34 | MOL2 | C |
| ATOM | 8588 | CA | PRO | E | 127 | 19.227 | −62.604 | −70.936 | 1.00 | 65.60 | MOL2 | C |
| ATOM | 8589 | CB | PRO | E | 127 | 17.716 | −62.508 | −71.059 | 1.00 | 64.20 | MOL2 | C |
| ATOM | 8590 | CG | PRO | E | 127 | 17.365 | −63.811 | −71.718 | 1.00 | 67.87 | MOL2 | C |
| ATOM | 8591 | C | PRO | E | 127 | 19.658 | −63.289 | −69.666 | 1.00 | 69.28 | MOL2 | C |
| ATOM | 8592 | O | PRO | E | 127 | 19.838 | −64.505 | −69.650 | 1.00 | 69.92 | MOL2 | O |
| ATOM | 8593 | N | VAL | E | 128 | 19.853 | −62.499 | −68.618 | 1.00 | 73.88 | MOL2 | N |
| ATOM | 8594 | CA | VAL | E | 128 | 20.257 | −63.017 | −67.315 | 1.00 | 81.61 | MOL2 | C |
| ATOM | 8595 | CB | VAL | E | 128 | 20.750 | −61.857 | −66.399 | 1.00 | 74.28 | MOL2 | C |
| ATOM | 8596 | CG1 | VAL | E | 128 | 21.333 | −62.389 | −65.117 | 1.00 | 69.48 | MOL2 | C |
| ATOM | 8597 | CG2 | VAL | E | 128 | 21.774 | −61.034 | −67.125 | 1.00 | 75.99 | MOL2 | C |

TABLE 1-continued

The atomic coordinates of IL17F in complex with 496 Fab
(H32; a = 189.4; b = 189.4; c = 490.9, α, β = 90°; γ = 120°)

| ATOM | 8598 | C | VAL | E | 128 | 19.015 | −63.665 | −66.693 | 1.00 | 90.59 | MOL2 | C |
|---|---|---|---|---|---|---|---|---|---|---|---|---|
| ATOM | 8599 | O | VAL | E | 128 | 18.207 | −62.983 | −66.067 | 1.00 | 93.36 | MOL2 | O |
| ATOM | 8600 | N | ILE | E | 129 | 18.844 | −64.970 | −66.877 | 1.00 | 100.93 | MOL2 | N |
| ATOM | 8601 | CA | ILE | E | 129 | 17.677 | −65.654 | −66.319 | 1.00 | 111.73 | MOL2 | C |
| ATOM | 8602 | CB | ILE | E | 129 | 17.392 | −66.995 | −67.036 | 1.00 | 115.39 | MOL2 | C |
| ATOM | 8603 | CG2 | ILE | E | 129 | 16.052 | −67.555 | −66.569 | 1.00 | 115.30 | MOL2 | C |
| ATOM | 8604 | CG1 | ILE | E | 129 | 17.365 | −66.795 | −68.554 | 1.00 | 119.20 | MOL2 | C |
| ATOM | 8605 | CD1 | ILE | E | 129 | 17.191 | −68.094 | −69.346 | 1.00 | 119.72 | MOL2 | C |
| ATOM | 8606 | C | ILE | E | 129 | 17.936 | −65.952 | −64.851 | 1.00 | 118.58 | MOL2 | C |
| ATOM | 8607 | O | ILE | E | 129 | 17.010 | −66.180 | −64.066 | 1.00 | 119.20 | MOL2 | O |
| ATOM | 8608 | N | HIS | E | 130 | 19.218 | −65.943 | −64.505 | 1.00 | 127.54 | MOL2 | N |
| ATOM | 8609 | CA | HIS | E | 130 | 19.681 | −66.209 | −63.152 | 1.00 | 134.90 | MOL2 | C |
| ATOM | 8610 | CB | HIS | E | 130 | 21.217 | −66.270 | −63.153 | 1.00 | 140.06 | MOL2 | C |
| ATOM | 8611 | CG | HIS | E | 130 | 21.805 | −66.572 | −64.503 | 1.00 | 142.96 | MOL2 | C |
| ATOM | 8612 | CD2 | HIS | E | 130 | 22.751 | −65.927 | −65.228 | 1.00 | 143.29 | MOL2 | C |
| ATOM | 8613 | ND1 | HIS | E | 130 | 21.389 | −67.634 | −65.280 | 1.00 | 142.37 | MOL2 | N |
| ATOM | 8614 | CE1 | HIS | E | 130 | 22.048 | −67.627 | −66.425 | 1.00 | 141.96 | MOL2 | C |
| ATOM | 8615 | NE2 | HIS | E | 130 | 22.881 | −66.601 | −66.419 | 1.00 | 143.30 | MOL2 | N |
| ATOM | 8616 | C | HIS | E | 130 | 19.170 | −65.099 | −62.234 | 1.00 | 135.23 | MOL2 | C |
| ATOM | 8617 | O | HIS | E | 130 | 19.423 | −63.919 | −62.469 | 1.00 | 131.96 | MOL2 | O |
| ATOM | 8618 | N | HIS | E | 131 | 18.443 | −65.490 | −61.192 | 1.00 | 139.05 | MOL2 | N |
| ATOM | 8619 | CA | HIS | E | 131 | 17.866 | −64.539 | −60.244 | 1.00 | 143.24 | MOL2 | C |
| ATOM | 8620 | CB | HIS | E | 131 | 17.216 | −65.302 | −59.078 | 1.00 | 145.79 | MOL2 | C |
| ATOM | 8621 | CG | HIS | E | 131 | 15.724 | −65.174 | −59.030 | 1.00 | 149.44 | MOL2 | C |
| ATOM | 8622 | CD2 | HIS | E | 131 | 14.901 | −64.673 | −58.076 | 1.00 | 151.04 | MOL2 | C |
| ATOM | 8623 | ND1 | HIS | E | 131 | 14.906 | −65.581 | −60.063 | 1.00 | 149.84 | MOL2 | N |
| ATOM | 8624 | CE1 | HIS | E | 131 | 13.646 | −65.336 | −59.749 | 1.00 | 150.96 | MOL2 | C |
| ATOM | 8625 | NE2 | HIS | E | 131 | 13.615 | −64.785 | −58.548 | 1.00 | 152.08 | MOL2 | N |
| ATOM | 8626 | C | HIS | E | 131 | 18.797 | −63.445 | −59.688 | 1.00 | 141.97 | MOL2 | C |
| ATOM | 8627 | O | HIS | E | 131 | 19.808 | −63.071 | −60.302 | 1.00 | 136.76 | MOL2 | O |
| ATOM | 8628 | N | VAL | E | 132 | 18.426 | −62.935 | −58.516 | 1.00 | 141.68 | MOL2 | N |
| ATOM | 8629 | CA | VAL | E | 132 | 19.171 | −61.878 | −57.839 | 1.00 | 142.44 | MOL2 | C |
| ATOM | 8630 | CB | VAL | E | 132 | 18.212 | −60.982 | −57.024 | 1.00 | 140.65 | MOL2 | C |
| ATOM | 8631 | CG1 | VAL | E | 132 | 18.942 | −59.736 | −56.533 | 1.00 | 136.17 | MOL2 | C |
| ATOM | 8632 | CG2 | VAL | E | 132 | 16.999 | −60.624 | −57.869 | 1.00 | 138.71 | MOL2 | C |
| ATOM | 8633 | C | VAL | E | 132 | 20.238 | −62.424 | −56.886 | 1.00 | 143.76 | MOL2 | C |
| ATOM | 8634 | O | VAL | E | 132 | 19.918 | −63.128 | −55.924 | 1.00 | 141.93 | MOL2 | O |
| ATOM | 8635 | N | GLN | E | 133 | 21.502 | −62.093 | −57.152 | 1.00 | 145.86 | MOL2 | N |
| ATOM | 8636 | CA | GLN | E | 133 | 22.609 | −62.542 | −56.303 | 1.00 | 148.52 | MOL2 | C |
| ATOM | 8637 | CB | GLN | E | 133 | 23.952 | −62.350 | −57.032 | 1.00 | 144.77 | MOL2 | C |
| ATOM | 8638 | CG | GLN | E | 133 | 25.105 | −63.232 | −56.523 | 1.00 | 141.17 | MOL2 | C |
| ATOM | 8639 | CD | GLN | E | 133 | 25.532 | −62.927 | −55.086 | 1.00 | 139.96 | MOL2 | C |
| ATOM | 8640 | OE1 | GLN | E | 133 | 25.939 | −61.802 | −54.766 | 1.00 | 136.60 | MOL2 | O |
| ATOM | 8641 | NE2 | GLN | E | 133 | 25.447 | −63.934 | −54.217 | 1.00 | 133.66 | MOL2 | N |
| ATOM | 8642 | C | GLN | E | 133 | 22.597 | −61.738 | −54.987 | 1.00 | 151.27 | MOL2 | C |
| ATOM | 8643 | O | GLN | E | 133 | 23.612 | −61.068 | −54.674 | 1.00 | 152.40 | MOL2 | O |
| ATOM | 8644 | OXT | GLN | E | 133 | 21.560 | −61.783 | −54.281 | 1.00 | 153.34 | MOL2 | O |
| ATOM | 8645 | CB | ALA | G | 1 | 6.918 | −80.524 | −18.660 | 1.00 | 91.84 | MOL3 | C |
| ATOM | 8646 | C | ALA | G | 1 | 7.127 | −79.369 | −16.435 | 1.00 | 91.18 | MOL3 | C |
| ATOM | 8647 | O | ALA | G | 1 | 6.816 | −79.460 | −15.244 | 1.00 | 95.13 | MOL3 | O |
| ATOM | 8648 | N | ALA | G | 1 | 5.398 | −78.657 | −18.062 | 1.00 | 92.12 | MOL3 | N |
| ATOM | 8649 | CA | ALA | G | 1 | 6.157 | −79.816 | −17.524 | 1.00 | 93.07 | MOL3 | C |
| ATOM | 8650 | N | ILE | G | 2 | 8.294 | −78.876 | −16.837 | 1.00 | 84.94 | MOL3 | N |
| ATOM | 8651 | CA | ILE | G | 2 | 9.285 | −78.450 | −15.863 | 1.00 | 79.05 | MOL3 | C |
| ATOM | 8652 | CB | ILE | G | 2 | 10.438 | −77.677 | −16.498 | 1.00 | 76.63 | MOL3 | C |
| ATOM | 8653 | CG2 | ILE | G | 2 | 11.472 | −77.343 | −15.430 | 1.00 | 72.92 | MOL3 | C |
| ATOM | 8654 | CG1 | ILE | G | 2 | 11.081 | −78.519 | −17.602 | 1.00 | 77.29 | MOL3 | C |
| ATOM | 8655 | CD1 | ILE | G | 2 | 12.396 | −77.976 | −18.127 | 1.00 | 73.60 | MOL3 | C |
| ATOM | 8656 | C | ILE | G | 2 | 8.649 | −77.579 | −14.815 | 1.00 | 77.42 | MOL3 | C |
| ATOM | 8657 | O | ILE | G | 2 | 8.068 | −76.549 | −15.135 | 1.00 | 75.41 | MOL3 | O |
| ATOM | 8658 | N | GLN | G | 3 | 8.745 | −78.008 | −13.562 | 1.00 | 78.74 | MOL3 | N |
| ATOM | 8659 | CA | GLN | G | 3 | 8.166 | −77.244 | −12.469 | 1.00 | 84.91 | MOL3 | C |
| ATOM | 8660 | CB | GLN | G | 3 | 7.195 | −78.100 | −11.649 | 1.00 | 95.45 | MOL3 | C |
| ATOM | 8661 | CG | GLN | G | 3 | 5.769 | −78.049 | −12.184 | 1.00 | 107.19 | MOL3 | C |
| ATOM | 8662 | CD | GLN | G | 3 | 4.794 | −78.847 | −11.350 | 1.00 | 114.04 | MOL3 | C |
| ATOM | 8663 | OE1 | GLN | G | 3 | 4.835 | −80.079 | −11.331 | 1.00 | 119.23 | MOL3 | O |
| ATOM | 8664 | NE2 | GLN | G | 3 | 3.907 | −78.147 | −10.647 | 1.00 | 117.58 | MOL3 | N |
| ATOM | 8665 | C | GLN | G | 3 | 9.218 | −76.624 | −11.573 | 1.00 | 81.14 | MOL3 | C |
| ATOM | 8666 | O | GLN | G | 3 | 10.046 | −77.302 | −10.971 | 1.00 | 81.04 | MOL3 | O |
| ATOM | 8667 | N | LEU | G | 4 | 9.174 | −75.306 | −11.499 | 1.00 | 78.11 | MOL3 | N |
| ATOM | 8668 | CA | LEU | G | 4 | 10.122 | −74.565 | −10.698 | 1.00 | 77.58 | MOL3 | C |
| ATOM | 8669 | CB | LEU | G | 4 | 10.384 | −73.206 | −11.354 | 1.00 | 85.28 | MOL3 | C |
| ATOM | 8670 | CG | LEU | G | 4 | 11.170 | −73.309 | −12.667 | 1.00 | 86.95 | MOL3 | C |
| ATOM | 8671 | CD1 | LEU | G | 4 | 10.859 | −72.141 | −13.580 | 1.00 | 87.02 | MOL3 | C |
| ATOM | 8672 | CD2 | LEU | G | 4 | 12.650 | −73.373 | −12.342 | 1.00 | 89.44 | MOL3 | C |
| ATOM | 8673 | C | LEU | G | 4 | 9.612 | −74.405 | −9.278 | 1.00 | 73.04 | MOL3 | C |
| ATOM | 8674 | O | LEU | G | 4 | 8.464 | −74.046 | −9.047 | 1.00 | 72.43 | MOL3 | O |

TABLE 1-continued

The atomic coordinates of IL17F in complex with 496 Fab
(H32; a = 189.4; b = 189.4; c = 490.9, α, β = 90°; γ = 120°)

| ATOM | 8675 | N | THR | G | 5 | 10.492 | −74.653 | −8.323 | 1.00 | 69.68 | MOL3 | N |
|---|---|---|---|---|---|---|---|---|---|---|---|---|
| ATOM | 8676 | CA | THR | G | 5 | 10.120 | −74.580 | −6.928 | 1.00 | 68.17 | MOL3 | C |
| ATOM | 8677 | CB | THR | G | 5 | 10.227 | −75.975 | −6.317 | 1.00 | 74.80 | MOL3 | C |
| ATOM | 8678 | OG1 | THR | G | 5 | 9.836 | −76.945 | −7.302 | 1.00 | 70.27 | MOL3 | O |
| ATOM | 8679 | CG2 | THR | G | 5 | 9.334 | −76.094 | −5.091 | 1.00 | 75.75 | MOL3 | C |
| ATOM | 8680 | C | THR | G | 5 | 10.975 | −73.611 | −6.115 | 1.00 | 63.96 | MOL3 | C |
| ATOM | 8681 | O | THR | G | 5 | 11.994 | −73.984 | −5.547 | 1.00 | 61.45 | MOL3 | O |
| ATOM | 8682 | N | GLN | G | 6 | 10.554 | −72.362 | −6.056 | 1.00 | 63.21 | MOL3 | N |
| ATOM | 8683 | CA | GLN | G | 6 | 11.283 | −71.367 | −5.296 | 1.00 | 67.36 | MOL3 | C |
| ATOM | 8684 | CB | GLN | G | 6 | 10.688 | −69.991 | −5.509 | 1.00 | 71.70 | MOL3 | C |
| ATOM | 8685 | CG | GLN | G | 6 | 10.886 | −69.442 | −6.880 | 1.00 | 70.50 | MOL3 | C |
| ATOM | 8686 | CD | GLN | G | 6 | 10.194 | −68.131 | −7.015 | 1.00 | 72.30 | MOL3 | C |
| ATOM | 8687 | OE1 | GLN | G | 6 | 10.414 | −67.219 | −6.218 | 1.00 | 65.58 | MOL3 | O |
| ATOM | 8688 | NE2 | GLN | G | 6 | 9.335 | −68.021 | −8.015 | 1.00 | 78.17 | MOL3 | N |
| ATOM | 8689 | C | GLN | G | 6 | 11.207 | −71.698 | −3.827 | 1.00 | 68.24 | MOL3 | C |
| ATOM | 8690 | O | GLN | G | 6 | 10.354 | −72.465 | −3.416 | 1.00 | 72.35 | MOL3 | O |
| ATOM | 8691 | N | SER | G | 7 | 12.079 | −71.081 | −3.036 | 1.00 | 70.04 | MOL3 | N |
| ATOM | 8692 | CA | SER | G | 7 | 12.131 | −71.326 | −1.602 | 1.00 | 67.82 | MOL3 | C |
| ATOM | 8693 | CB | SER | G | 7 | 12.558 | −72.763 | −1.365 | 1.00 | 76.29 | MOL3 | C |
| ATOM | 8694 | OG | SER | G | 7 | 13.694 | −73.063 | −2.167 | 1.00 | 77.00 | MOL3 | O |
| ATOM | 8695 | C | SER | G | 7 | 13.146 | −70.412 | −0.953 | 1.00 | 65.88 | MOL3 | C |
| ATOM | 8696 | O | SER | G | 7 | 14.267 | −70.284 | −1.432 | 1.00 | 70.74 | MOL3 | O |
| ATOM | 8697 | N | PRO | G | 8 | 12.771 | −69.757 | 0.145 | 1.00 | 64.24 | MOL3 | N |
| ATOM | 8698 | CD | PRO | G | 8 | 13.676 | −68.911 | 0.941 | 1.00 | 64.90 | MOL3 | C |
| ATOM | 8699 | CA | PRO | G | 8 | 11.457 | −69.843 | 0.775 | 1.00 | 68.98 | MOL3 | C |
| ATOM | 8700 | CB | PRO | G | 8 | 11.643 | −69.027 | 2.054 | 1.00 | 69.10 | MOL3 | C |
| ATOM | 8701 | CG | PRO | G | 8 | 12.716 | −68.038 | 1.681 | 1.00 | 61.90 | MOL3 | C |
| ATOM | 8702 | C | PRO | G | 8 | 10.374 | −69.260 | −0.117 | 1.00 | 71.03 | MOL3 | C |
| ATOM | 8703 | O | PRO | G | 8 | 10.672 | −68.720 | −1.175 | 1.00 | 77.14 | MOL3 | O |
| ATOM | 8704 | N | SER | G | 9 | 9.121 | −69.378 | 0.310 | 1.00 | 70.20 | MOL3 | N |
| ATOM | 8705 | CA | SER | G | 9 | 8.011 | −68.826 | −0.450 | 1.00 | 67.43 | MOL3 | C |
| ATOM | 8706 | CB | SER | G | 9 | 6.728 | −69.630 | −0.215 | 1.00 | 68.38 | MOL3 | C |
| ATOM | 8707 | OG | SER | G | 9 | 6.810 | −70.906 | −0.830 | 1.00 | 72.35 | MOL3 | O |
| ATOM | 8708 | C | SER | G | 9 | 7.845 | −67.417 | 0.066 | 1.00 | 62.26 | MOL3 | C |
| ATOM | 8709 | O | SER | G | 9 | 7.467 | −66.508 | −0.664 | 1.00 | 67.60 | MOL3 | O |
| ATOM | 8710 | N | SER | G | 10 | 8.137 | −67.246 | 1.342 | 1.00 | 54.62 | MOL3 | N |
| ATOM | 8711 | CA | SER | G | 10 | 8.053 | −65.941 | 1.957 | 1.00 | 57.69 | MOL3 | C |
| ATOM | 8712 | CB | SER | G | 10 | 6.832 | −65.821 | 2.860 | 1.00 | 62.57 | MOL3 | C |
| ATOM | 8713 | OG | SER | G | 10 | 6.836 | −64.555 | 3.507 | 1.00 | 66.90 | MOL3 | O |
| ATOM | 8714 | C | SER | G | 10 | 9.309 | −65.799 | 2.780 | 1.00 | 57.88 | MOL3 | C |
| ATOM | 8715 | O | SER | G | 10 | 10.072 | −66.754 | 2.905 | 1.00 | 55.54 | MOL3 | O |
| ATOM | 8716 | N | LEU | G | 11 | 9.512 | −64.625 | 3.365 | 1.00 | 56.79 | MOL3 | N |
| ATOM | 8717 | CA | LEU | G | 11 | 10.727 | −64.386 | 4.125 | 1.00 | 58.29 | MOL3 | C |
| ATOM | 8718 | CB | LEU | G | 11 | 11.905 | −64.647 | 3.192 | 1.00 | 54.73 | MOL3 | C |
| ATOM | 8719 | CG | LEU | G | 11 | 13.362 | −64.319 | 3.495 | 1.00 | 60.88 | MOL3 | C |
| ATOM | 8720 | CD1 | LEU | G | 11 | 14.124 | −64.570 | 2.206 | 1.00 | 58.03 | MOL3 | C |
| ATOM | 8721 | CD2 | LEU | G | 11 | 13.567 | −62.880 | 3.951 | 1.00 | 57.82 | MOL3 | C |
| ATOM | 8722 | C | LEU | G | 11 | 10.771 | −62.942 | 4.610 | 1.00 | 62.20 | MOL3 | C |
| ATOM | 8723 | O | LEU | G | 11 | 10.544 | −62.014 | 3.829 | 1.00 | 62.91 | MOL3 | O |
| ATOM | 8724 | N | SER | G | 12 | 11.068 | −62.736 | 5.886 | 1.00 | 62.61 | MOL3 | N |
| ATOM | 8725 | CA | SER | G | 12 | 11.144 | −61.373 | 6.367 | 1.00 | 67.16 | MOL3 | C |
| ATOM | 8726 | CB | SER | G | 12 | 10.332 | −61.206 | 7.641 | 1.00 | 73.51 | MOL3 | C |
| ATOM | 8727 | OG | SER | G | 12 | 9.834 | −59.880 | 7.724 | 1.00 | 82.94 | MOL3 | O |
| ATOM | 8728 | C | SER | G | 12 | 12.602 | −61.041 | 6.612 | 1.00 | 68.56 | MOL3 | C |
| ATOM | 8729 | O | SER | G | 12 | 13.360 | −61.877 | 7.096 | 1.00 | 73.77 | MOL3 | O |
| ATOM | 8730 | N | ALA | G | 13 | 13.001 | −59.830 | 6.242 | 1.00 | 67.01 | MOL3 | N |
| ATOM | 8731 | CA | ALA | G | 13 | 14.378 | −59.401 | 6.429 | 1.00 | 65.17 | MOL3 | C |
| ATOM | 8732 | CB | ALA | G | 13 | 15.219 | −59.770 | 5.229 | 1.00 | 62.47 | MOL3 | C |
| ATOM | 8733 | C | ALA | G | 13 | 14.404 | −57.906 | 6.653 | 1.00 | 67.37 | MOL3 | C |
| ATOM | 8734 | O | ALA | G | 13 | 13.370 | −57.240 | 6.537 | 1.00 | 66.94 | MOL3 | O |
| ATOM | 8735 | N | SER | G | 14 | 15.581 | −57.386 | 7.000 | 1.00 | 70.46 | MOL3 | N |
| ATOM | 8736 | CA | SER | G | 14 | 15.736 | −55.954 | 7.247 | 1.00 | 70.22 | MOL3 | C |
| ATOM | 8737 | CB | SER | G | 14 | 16.066 | −55.692 | 8.730 | 1.00 | 72.47 | MOL3 | C |
| ATOM | 8738 | OG | SER | G | 14 | 16.879 | −56.718 | 9.296 | 1.00 | 81.85 | MOL3 | O |
| ATOM | 8739 | C | SER | G | 14 | 16.779 | −55.330 | 6.315 | 1.00 | 64.57 | MOL3 | C |
| ATOM | 8740 | O | SER | G | 14 | 17.643 | −56.023 | 5.764 | 1.00 | 56.15 | MOL3 | O |
| ATOM | 8741 | N | VAL | G | 15 | 16.649 | −54.025 | 6.106 | 1.00 | 61.18 | MOL3 | N |
| ATOM | 8742 | CA | VAL | G | 15 | 17.553 | −53.280 | 5.248 | 1.00 | 61.26 | MOL3 | C |
| ATOM | 8743 | CB | VAL | G | 15 | 17.486 | −51.785 | 5.572 | 1.00 | 62.15 | MOL3 | C |
| ATOM | 8744 | CG1 | VAL | G | 15 | 16.808 | −51.037 | 4.467 | 1.00 | 62.23 | MOL3 | C |
| ATOM | 8745 | CG2 | VAL | G | 15 | 16.734 | −51.584 | 6.889 | 1.00 | 68.77 | MOL3 | C |
| ATOM | 8746 | C | VAL | G | 15 | 18.982 | −53.735 | 5.494 | 1.00 | 65.74 | MOL3 | C |
| ATOM | 8747 | O | VAL | G | 15 | 19.430 | −53.803 | 6.643 | 1.00 | 66.93 | MOL3 | O |
| ATOM | 8748 | N | GLY | G | 16 | 19.700 | −54.048 | 4.423 | 1.00 | 66.48 | MOL3 | N |
| ATOM | 8749 | CA | GLY | G | 16 | 21.077 | −54.468 | 4.578 | 1.00 | 63.83 | MOL3 | C |
| ATOM | 8750 | C | GLY | G | 16 | 21.273 | −55.964 | 4.519 | 1.00 | 62.52 | MOL3 | C |
| ATOM | 8751 | O | GLY | G | 16 | 22.256 | −56.437 | 3.950 | 1.00 | 69.68 | MOL3 | O |

TABLE 1-continued

The atomic coordinates of IL17F in complex with 496 Fab
(H32; a = 189.4; b = 189.4; c = 490.9, α, β = 90°; γ = 120°)

| ATOM | 8752 | N | ASP | G | 17 | 20.348 | −56.716 | 5.096 | 1.00 | 57.89 | MOL3 | N |
|---|---|---|---|---|---|---|---|---|---|---|---|---|
| ATOM | 8753 | CA | ASP | G | 17 | 20.473 | −58.169 | 5.087 | 1.00 | 64.37 | MOL3 | C |
| ATOM | 8754 | CB | ASP | G | 17 | 19.154 | −58.817 | 5.558 | 1.00 | 78.26 | MOL3 | C |
| ATOM | 8755 | CG | ASP | G | 17 | 18.807 | −58.490 | 7.027 | 1.00 | 85.13 | MOL3 | C |
| ATOM | 8756 | OD1 | ASP | G | 17 | 17.831 | −59.081 | 7.553 | 1.00 | 81.20 | MOL3 | O |
| ATOM | 8757 | OD2 | ASP | G | 17 | 19.499 | −57.649 | 7.650 | 1.00 | 88.96 | MOL3 | O |
| ATOM | 8758 | C | ASP | G | 17 | 20.876 | −58.723 | 3.706 | 1.00 | 58.61 | MOL3 | C |
| ATOM | 8759 | O | ASP | G | 17 | 20.709 | −58.066 | 2.687 | 1.00 | 57.95 | MOL3 | O |
| ATOM | 8760 | N | ARG | G | 18 | 21.437 | −59.924 | 3.684 | 1.00 | 56.36 | MOL3 | N |
| ATOM | 8761 | CA | ARG | G | 18 | 21.837 | −60.546 | 2.431 | 1.00 | 60.67 | MOL3 | C |
| ATOM | 8762 | CB | ARG | G | 18 | 23.250 | −61.136 | 2.540 | 1.00 | 63.66 | MOL3 | C |
| ATOM | 8763 | CG | ARG | G | 18 | 23.639 | −62.143 | 1.444 | 1.00 | 62.43 | MOL3 | C |
| ATOM | 8764 | CD | ARG | G | 18 | 25.081 | −61.935 | 0.971 | 1.00 | 69.18 | MOL3 | C |
| ATOM | 8765 | NE | ARG | G | 18 | 25.821 | −63.190 | 0.872 | 1.00 | 82.75 | MOL3 | N |
| ATOM | 8766 | CZ | ARG | G | 18 | 25.481 | −64.218 | 0.093 | 1.00 | 93.44 | MOL3 | C |
| ATOM | 8767 | NH1 | ARG | G | 18 | 24.402 | −64.152 | −0.674 | 1.00 | 100.10 | MOL3 | N |
| ATOM | 8768 | NH2 | ARG | G | 18 | 26.218 | −65.325 | 0.089 | 1.00 | 99.11 | MOL3 | N |
| ATOM | 8769 | C | ARG | G | 18 | 20.833 | −61.642 | 2.119 | 1.00 | 64.02 | MOL3 | C |
| ATOM | 8770 | O | ARG | G | 18 | 21.063 | −62.815 | 2.420 | 1.00 | 68.60 | MOL3 | O |
| ATOM | 8771 | N | VAL | G | 19 | 19.715 | −61.248 | 1.517 | 1.00 | 62.61 | MOL3 | N |
| ATOM | 8772 | CA | VAL | G | 19 | 18.658 | −62.187 | 1.170 | 1.00 | 58.01 | MOL3 | C |
| ATOM | 8773 | CB | VAL | G | 19 | 17.400 | −61.444 | 0.737 | 1.00 | 61.47 | MOL3 | C |
| ATOM | 8774 | CG1 | VAL | G | 19 | 16.274 | −62.444 | 0.537 | 1.00 | 62.19 | MOL3 | C |
| ATOM | 8775 | CG2 | VAL | G | 19 | 17.040 | −60.364 | 1.775 | 1.00 | 52.69 | MOL3 | C |
| ATOM | 8776 | C | VAL | G | 19 | 19.069 | −63.145 | 0.057 | 1.00 | 55.13 | MOL3 | C |
| ATOM | 8777 | O | VAL | G | 19 | 19.856 | −62.795 | −0.815 | 1.00 | 58.93 | MOL3 | O |
| ATOM | 8778 | N | THR | G | 20 | 18.532 | −64.355 | 0.086 | 1.00 | 51.84 | MOL3 | N |
| ATOM | 8779 | CA | THR | G | 20 | 18.872 | −65.341 | −0.924 | 1.00 | 54.45 | MOL3 | C |
| ATOM | 8780 | CB | THR | G | 20 | 20.012 | −66.222 | −0.441 | 1.00 | 55.50 | MOL3 | C |
| ATOM | 8781 | OG1 | THR | G | 20 | 21.151 | −65.402 | −0.164 | 1.00 | 55.70 | MOL3 | O |
| ATOM | 8782 | CG2 | THR | G | 20 | 20.348 | −67.288 | −1.488 | 1.00 | 51.26 | MOL3 | C |
| ATOM | 8783 | C | THR | G | 20 | 17.689 | −66.237 | −1.258 | 1.00 | 57.97 | MOL3 | C |
| ATOM | 8784 | O | THR | G | 20 | 17.187 | −66.967 | −0.398 | 1.00 | 65.17 | MOL3 | O |
| ATOM | 8785 | N | ILE | G | 21 | 17.248 | −66.183 | −2.510 | 1.00 | 54.89 | MOL3 | N |
| ATOM | 8786 | CA | ILE | G | 21 | 16.118 | −66.990 | −2.963 | 1.00 | 53.86 | MOL3 | C |
| ATOM | 8787 | CB | ILE | G | 21 | 15.148 | −66.196 | −3.876 | 1.00 | 49.43 | MOL3 | C |
| ATOM | 8788 | CG2 | ILE | G | 21 | 13.760 | −66.820 | −3.803 | 1.00 | 49.67 | MOL3 | C |
| ATOM | 8789 | CG1 | ILE | G | 21 | 15.096 | −64.724 | −3.466 | 1.00 | 36.38 | MOL3 | C |
| ATOM | 8790 | CD1 | ILE | G | 21 | 14.613 | −64.517 | −2.105 | 1.00 | 25.30 | MOL3 | C |
| ATOM | 8791 | C | ILE | G | 21 | 16.655 | −68.138 | −3.795 | 1.00 | 54.41 | MOL3 | C |
| ATOM | 8792 | O | ILE | G | 21 | 17.677 | −67.997 | −4.453 | 1.00 | 59.19 | MOL3 | O |
| ATOM | 8793 | N | THR | G | 22 | 15.965 | −69.267 | −3.786 | 1.00 | 51.44 | MOL3 | N |
| ATOM | 8794 | CA | THR | G | 22 | 16.423 | −70.396 | −4.565 | 1.00 | 53.57 | MOL3 | C |
| ATOM | 8795 | CB | THR | G | 22 | 16.757 | −71.541 | −3.683 | 1.00 | 50.35 | MOL3 | C |
| ATOM | 8796 | OG1 | THR | G | 22 | 17.501 | −71.057 | −2.564 | 1.00 | 57.43 | MOL3 | O |
| ATOM | 8797 | CG2 | THR | G | 22 | 17.575 | −72.545 | −4.442 | 1.00 | 54.90 | MOL3 | C |
| ATOM | 8798 | C | THR | G | 22 | 15.323 | −70.821 | −5.492 | 1.00 | 61.94 | MOL3 | C |
| ATOM | 8799 | O | THR | G | 22 | 14.166 | −70.484 | −5.261 | 1.00 | 71.19 | MOL3 | O |
| ATOM | 8800 | N | CYS | G | 23 | 15.667 | −71.576 | −6.529 | 1.00 | 63.01 | MOL3 | N |
| ATOM | 8801 | CA | CYS | G | 23 | 14.667 | −72.003 | −7.487 | 1.00 | 69.22 | MOL3 | C |
| ATOM | 8802 | C | CYS | G | 23 | 15.061 | −73.319 | −8.108 | 1.00 | 73.52 | MOL3 | C |
| ATOM | 8803 | O | CYS | G | 23 | 15.566 | −73.342 | −9.219 | 1.00 | 76.20 | MOL3 | O |
| ATOM | 8804 | CB | CYS | G | 23 | 14.532 | −70.935 | −8.570 | 1.00 | 72.22 | MOL3 | C |
| ATOM | 8805 | SG | CYS | G | 23 | 13.397 | −71.266 | −9.964 | 1.00 | 89.83 | MOL3 | S |
| ATOM | 8806 | N | ARG | G | 24 | 14.840 | −74.415 | −7.390 | 1.00 | 81.91 | MOL3 | N |
| ATOM | 8807 | CA | ARG | G | 24 | 15.165 | −75.740 | −7.914 | 1.00 | 84.07 | MOL3 | C |
| ATOM | 8808 | CB | ARG | G | 24 | 15.182 | −76.773 | −6.790 | 1.00 | 90.97 | MOL3 | C |
| ATOM | 8809 | CG | ARG | G | 24 | 16.189 | −76.490 | −5.693 | 1.00 | 101.39 | MOL3 | C |
| ATOM | 8810 | CD | ARG | G | 24 | 16.499 | −77.754 | −4.906 | 1.00 | 113.69 | MOL3 | C |
| ATOM | 8811 | NE | ARG | G | 24 | 17.186 | −78.751 | −5.731 | 1.00 | 124.74 | MOL3 | N |
| ATOM | 8812 | CZ | ARG | G | 24 | 16.599 | −79.545 | −6.627 | 1.00 | 128.78 | MOL3 | C |
| ATOM | 8813 | NH1 | ARG | G | 24 | 15.288 | −79.483 | −6.833 | 1.00 | 129.96 | MOL3 | N |
| ATOM | 8814 | NH2 | ARG | G | 24 | 17.331 | −80.405 | −7.329 | 1.00 | 129.99 | MOL3 | N |
| ATOM | 8815 | C | ARG | G | 24 | 14.122 | −76.122 | −8.969 | 1.00 | 79.77 | MOL3 | C |
| ATOM | 8816 | O | ARG | G | 24 | 12.957 | −75.732 | −8.873 | 1.00 | 75.21 | MOL3 | O |
| ATOM | 8817 | N | ALA | G | 25 | 14.531 | −76.883 | −9.976 | 1.00 | 76.22 | MOL3 | N |
| ATOM | 8818 | CA | ALA | G | 25 | 13.595 | −77.248 | −11.023 | 1.00 | 79.16 | MOL3 | C |
| ATOM | 8819 | CB | ALA | G | 25 | 13.835 | −76.383 | −12.226 | 1.00 | 78.01 | MOL3 | C |
| ATOM | 8820 | C | ALA | G | 25 | 13.581 | −78.715 | −11.440 | 1.00 | 84.40 | MOL3 | C |
| ATOM | 8821 | O | ALA | G | 25 | 14.625 | −79.356 | −11.562 | 1.00 | 83.67 | MOL3 | O |
| ATOM | 8822 | N | ASP | G | 26 | 12.367 | −79.214 | −11.678 | 1.00 | 89.59 | MOL3 | N |
| ATOM | 8823 | CA | ASP | G | 26 | 12.110 | −80.591 | −12.088 | 1.00 | 93.62 | MOL3 | C |
| ATOM | 8824 | CB | ASP | G | 26 | 10.775 | −80.669 | −12.843 | 1.00 | 101.41 | MOL3 | C |
| ATOM | 8825 | CG | ASP | G | 26 | 10.495 | −82.060 | −13.411 | 1.00 | 111.44 | MOL3 | C |
| ATOM | 8826 | OD1 | ASP | G | 26 | 9.615 | −82.184 | −14.292 | 1.00 | 113.51 | MOL3 | O |
| ATOM | 8827 | OD2 | ASP | G | 26 | 11.147 | −83.034 | −12.975 | 1.00 | 119.43 | MOL3 | O |
| ATOM | 8828 | C | ASP | G | 26 | 13.216 | −81.194 | −12.947 | 1.00 | 93.33 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 8829 | O | ASP | G | 26 | 13.965 | −82.052 | −12.486 | 1.00 | 92.24 | MOL3 | O |
|---|---|---|---|---|---|---|---|---|---|---|---|---|
| ATOM | 8830 | N | GLU | G | 27 | 13.308 | −80.746 | −14.193 | 1.00 | 95.09 | MOL3 | N |
| ATOM | 8831 | CA | GLU | G | 27 | 14.305 | −81.246 | −15.131 | 1.00 | 100.09 | MOL3 | C |
| ATOM | 8832 | CB | GLU | G | 27 | 13.644 | −81.419 | −16.503 | 1.00 | 101.62 | MOL3 | C |
| ATOM | 8833 | CG | GLU | G | 27 | 14.321 | −82.407 | −17.439 | 1.00 | 110.10 | MOL3 | C |
| ATOM | 8834 | CD | GLU | G | 27 | 13.460 | −82.729 | −18.653 | 1.00 | 113.57 | MOL3 | C |
| ATOM | 8835 | OE1 | GLU | G | 27 | 13.874 | −83.559 | −19.493 | 1.00 | 117.99 | MOL3 | O |
| ATOM | 8836 | OE2 | GLU | G | 27 | 12.362 | −82.149 | −18.768 | 1.00 | 112.12 | MOL3 | O |
| ATOM | 8837 | C | GLU | G | 27 | 15.491 | −80.272 | −15.204 | 1.00 | 102.38 | MOL3 | C |
| ATOM | 8838 | O | GLU | G | 27 | 15.726 | −79.506 | −14.261 | 1.00 | 102.53 | MOL3 | O |
| ATOM | 8839 | N | SER | G | 28 | 16.241 | −80.307 | −16.309 | 1.00 | 102.36 | MOL3 | N |
| ATOM | 8840 | CA | SER | G | 28 | 17.393 | −79.415 | −16.486 | 1.00 | 98.93 | MOL3 | C |
| ATOM | 8841 | CB | SER | G | 28 | 18.624 | −80.183 | −16.975 | 1.00 | 102.05 | MOL3 | C |
| ATOM | 8842 | OG | SER | G | 28 | 19.726 | −79.304 | −17.163 | 1.00 | 94.87 | MOL3 | O |
| ATOM | 8843 | C | SER | G | 28 | 17.085 | −78.312 | −17.482 | 1.00 | 94.49 | MOL3 | C |
| ATOM | 8844 | O | SER | G | 28 | 16.481 | −78.562 | −18.524 | 1.00 | 96.23 | MOL3 | O |
| ATOM | 8845 | N | VAL | G | 29 | 17.508 | −77.094 | −17.167 | 1.00 | 88.27 | MOL3 | N |
| ATOM | 8846 | CA | VAL | G | 29 | 17.258 | −75.968 | −18.055 | 1.00 | 83.41 | MOL3 | C |
| ATOM | 8847 | CB | VAL | G | 29 | 16.364 | −74.915 | −17.382 | 1.00 | 80.02 | MOL3 | C |
| ATOM | 8848 | CG1 | VAL | G | 29 | 14.928 | −75.363 | −17.436 | 1.00 | 81.55 | MOL3 | C |
| ATOM | 8849 | CG2 | VAL | G | 29 | 16.790 | −74.709 | −15.943 | 1.00 | 71.21 | MOL3 | C |
| ATOM | 8850 | C | VAL | G | 29 | 18.514 | −75.275 | −18.574 | 1.00 | 84.10 | MOL3 | C |
| ATOM | 8851 | O | VAL | G | 29 | 18.437 | −74.486 | −19.508 | 1.00 | 87.75 | MOL3 | O |
| ATOM | 8852 | N | THR | G | 30 | 19.663 | −75.565 | −17.968 | 1.00 | 81.73 | MOL3 | N |
| ATOM | 8853 | CA | THR | G | 30 | 20.943 | −74.976 | −18.374 | 1.00 | 76.67 | MOL3 | C |
| ATOM | 8854 | CB | THR | G | 30 | 21.601 | −75.705 | −19.555 | 1.00 | 83.22 | MOL3 | C |
| ATOM | 8855 | OG1 | THR | G | 30 | 20.730 | −75.655 | −20.701 | 1.00 | 75.07 | MOL3 | O |
| ATOM | 8856 | CG2 | THR | G | 30 | 21.946 | −77.140 | −19.177 | 1.00 | 94.30 | MOL3 | C |
| ATOM | 8857 | C | THR | G | 30 | 20.896 | −73.540 | −18.824 | 1.00 | 74.85 | MOL3 | C |
| ATOM | 8858 | O | THR | G | 30 | 20.438 | −73.240 | −19.933 | 1.00 | 77.39 | MOL3 | O |
| ATOM | 8859 | N | THR | G | 31 | 21.405 | −72.656 | −17.981 | 1.00 | 68.57 | MOL3 | N |
| ATOM | 8860 | CA | THR | G | 31 | 21.475 | −71.231 | −18.307 | 1.00 | 60.87 | MOL3 | C |
| ATOM | 8861 | CB | THR | G | 31 | 22.583 | −70.972 | −19.361 | 1.00 | 54.59 | MOL3 | C |
| ATOM | 8862 | OG1 | THR | G | 31 | 22.166 | −71.434 | −20.654 | 1.00 | 39.54 | MOL3 | O |
| ATOM | 8863 | CG2 | THR | G | 31 | 23.847 | −71.704 | −18.963 | 1.00 | 51.28 | MOL3 | C |
| ATOM | 8864 | C | THR | G | 31 | 20.186 | −70.510 | −18.754 | 1.00 | 57.16 | MOL3 | C |
| ATOM | 8865 | O | THR | G | 31 | 20.115 | −69.275 | −18.671 | 1.00 | 52.70 | MOL3 | O |
| ATOM | 8866 | N | LEU | G | 32 | 19.174 | −71.249 | −19.215 | 1.00 | 44.36 | MOL3 | N |
| ATOM | 8867 | CA | LEU | G | 32 | 17.950 | −70.589 | −19.617 | 1.00 | 41.23 | MOL3 | C |
| ATOM | 8868 | CB | LEU | G | 32 | 17.260 | −71.357 | −20.743 | 1.00 | 35.40 | MOL3 | C |
| ATOM | 8869 | CG | LEU | G | 32 | 17.627 | −70.692 | −22.077 | 1.00 | 37.32 | MOL3 | C |
| ATOM | 8870 | CD1 | LEU | G | 32 | 19.134 | −70.555 | −22.091 | 1.00 | 36.21 | MOL3 | C |
| ATOM | 8871 | CD2 | LEU | G | 32 | 17.120 | −71.459 | −23.306 | 1.00 | 25.34 | MOL3 | C |
| ATOM | 8872 | C | LEU | G | 32 | 16.990 | −70.320 | −18.463 | 1.00 | 42.25 | MOL3 | C |
| ATOM | 8873 | O | LEU | G | 32 | 15.784 | −70.530 | −18.573 | 1.00 | 47.72 | MOL3 | O |
| ATOM | 8874 | N | MET | G | 33 | 17.542 | −69.830 | −17.359 | 1.00 | 39.62 | MOL3 | N |
| ATOM | 8875 | CA | MET | G | 33 | 16.760 | −69.493 | −16.189 | 1.00 | 43.39 | MOL3 | C |
| ATOM | 8876 | CB | MET | G | 33 | 17.405 | −70.114 | −14.953 | 1.00 | 44.25 | MOL3 | C |
| ATOM | 8877 | CG | MET | G | 33 | 16.639 | −69.918 | −13.643 | 1.00 | 63.10 | MOL3 | C |
| ATOM | 8878 | SD | MET | G | 33 | 14.963 | −70.591 | −13.654 | 1.00 | 80.75 | MOL3 | S |
| ATOM | 8879 | CE | MET | G | 33 | 15.180 | −72.028 | −14.730 | 1.00 | 76.36 | MOL3 | C |
| ATOM | 8880 | C | MET | G | 33 | 16.792 | −67.967 | −16.116 | 1.00 | 48.11 | MOL3 | C |
| ATOM | 8881 | O | MET | G | 33 | 17.819 | −67.360 | −16.400 | 1.00 | 55.26 | MOL3 | O |
| ATOM | 8882 | N | HIS | G | 34 | 15.674 | −67.346 | −15.748 | 1.00 | 46.45 | MOL3 | N |
| ATOM | 8883 | CA | HIS | G | 34 | 15.601 | −65.896 | −15.665 | 1.00 | 43.17 | MOL3 | C |
| ATOM | 8884 | CB | HIS | G | 34 | 14.799 | −65.393 | −16.850 | 1.00 | 40.62 | MOL3 | C |
| ATOM | 8885 | CG | HIS | G | 34 | 15.128 | −66.084 | −18.132 | 1.00 | 37.95 | MOL3 | C |
| ATOM | 8886 | CD2 | HIS | G | 34 | 14.343 | −66.733 | −19.023 | 1.00 | 45.85 | MOL3 | C |
| ATOM | 8887 | ND1 | HIS | G | 34 | 16.404 | −66.127 | −18.646 | 1.00 | 43.97 | MOL3 | N |
| ATOM | 8888 | CE1 | HIS | G | 34 | 16.391 | −66.768 | −19.802 | 1.00 | 43.56 | MOL3 | C |
| ATOM | 8889 | NE2 | HIS | G | 34 | 15.152 | −67.146 | −20.055 | 1.00 | 44.43 | MOL3 | N |
| ATOM | 8890 | C | HIS | G | 34 | 14.922 | −65.461 | −14.363 | 1.00 | 45.87 | MOL3 | C |
| ATOM | 8891 | O | HIS | G | 34 | 14.261 | −66.267 | −13.724 | 1.00 | 51.04 | MOL3 | O |
| ATOM | 8892 | N | TRP | G | 35 | 15.080 | −64.198 | −13.967 | 1.00 | 45.08 | MOL3 | N |
| ATOM | 8893 | CA | TRP | G | 35 | 14.441 | −63.712 | −12.745 | 1.00 | 45.19 | MOL3 | C |
| ATOM | 8894 | CB | TRP | G | 35 | 15.456 | −63.497 | −11.619 | 1.00 | 48.06 | MOL3 | C |
| ATOM | 8895 | CG | TRP | G | 35 | 16.068 | −64.764 | −11.109 | 1.00 | 56.84 | MOL3 | C |
| ATOM | 8896 | CD2 | TRP | G | 35 | 15.642 | −65.535 | −9.977 | 1.00 | 60.98 | MOL3 | C |
| ATOM | 8897 | CE2 | TRP | G | 35 | 16.460 | −66.675 | −9.918 | 1.00 | 62.91 | MOL3 | C |
| ATOM | 8898 | CE3 | TRP | G | 35 | 14.646 | −65.374 | −9.013 | 1.00 | 62.34 | MOL3 | C |
| ATOM | 8899 | CD1 | TRP | G | 35 | 17.098 | −65.450 | −11.666 | 1.00 | 61.49 | MOL3 | C |
| ATOM | 8900 | NE1 | TRP | G | 35 | 17.343 | −66.599 | −10.961 | 1.00 | 64.24 | MOL3 | N |
| ATOM | 8901 | CZ2 | TRP | G | 35 | 16.314 | −67.650 | −8.935 | 1.00 | 61.50 | MOL3 | C |
| ATOM | 8902 | CZ3 | TRP | G | 35 | 14.505 | −66.342 | −8.041 | 1.00 | 65.72 | MOL3 | C |
| ATOM | 8903 | CH2 | TRP | G | 35 | 15.335 | −67.467 | −8.009 | 1.00 | 60.76 | MOL3 | C |
| ATOM | 8904 | C | TRP | G | 35 | 13.697 | −62.421 | −12.989 | 1.00 | 46.63 | MOL3 | C |
| ATOM | 8905 | O | TRP | G | 35 | 14.182 | −61.542 | −13.701 | 1.00 | 55.62 | MOL3 | O |

TABLE 1-continued

The atomic coordinates of IL17F in complex with 496 Fab
(H32; a = 189.4; b = 189.4; c = 490.9, α, β = 90°; γ = 120°)

| ATOM | 8906 | N | TYR | G | 36 | 12.517 | −62.318 | −12.388 | 1.00 | 39.63 | MOL3 | N |
|---|---|---|---|---|---|---|---|---|---|---|---|---|
| ATOM | 8907 | CA | TYR | G | 36 | 11.669 | −61.145 | −12.521 | 1.00 | 40.41 | MOL3 | C |
| ATOM | 8908 | CB | TYR | G | 36 | 10.385 | −61.506 | −13.229 | 1.00 | 31.06 | MOL3 | C |
| ATOM | 8909 | CG | TYR | G | 36 | 10.585 | −61.970 | −14.621 | 1.00 | 30.83 | MOL3 | C |
| ATOM | 8910 | CD1 | TYR | G | 36 | 10.547 | −61.073 | −15.664 | 1.00 | 32.67 | MOL3 | C |
| ATOM | 8911 | CE1 | TYR | G | 36 | 10.677 | −61.501 | −16.959 | 1.00 | 40.12 | MOL3 | C |
| ATOM | 8912 | CD2 | TYR | G | 36 | 10.772 | −63.315 | −14.905 | 1.00 | 28.80 | MOL3 | C |
| ATOM | 8913 | CE2 | TYR | G | 36 | 10.906 | −63.755 | −16.191 | 1.00 | 25.97 | MOL3 | C |
| ATOM | 8914 | CZ | TYR | G | 36 | 10.855 | −62.843 | −17.217 | 1.00 | 36.74 | MOL3 | C |
| ATOM | 8915 | OH | TYR | G | 36 | 10.967 | −63.246 | −18.526 | 1.00 | 47.56 | MOL3 | O |
| ATOM | 8916 | C | TYR | G | 36 | 11.307 | −60.652 | −11.141 | 1.00 | 41.90 | MOL3 | C |
| ATOM | 8917 | O | TYR | G | 36 | 11.337 | −61.415 | −10.187 | 1.00 | 42.96 | MOL3 | O |
| ATOM | 8918 | N | GLN | G | 37 | 10.939 | −59.382 | −11.044 | 1.00 | 39.72 | MOL3 | N |
| ATOM | 8919 | CA | GLN | G | 37 | 10.559 | −58.806 | −9.775 | 1.00 | 38.19 | MOL3 | C |
| ATOM | 8920 | CB | GLN | G | 37 | 11.556 | −57.735 | −9.379 | 1.00 | 35.77 | MOL3 | C |
| ATOM | 8921 | CG | GLN | G | 37 | 11.420 | −57.270 | −7.963 | 1.00 | 39.74 | MOL3 | C |
| ATOM | 8922 | CD | GLN | G | 37 | 11.640 | −55.792 | −7.837 | 1.00 | 44.01 | MOL3 | C |
| ATOM | 8923 | OE1 | GLN | G | 37 | 12.251 | −55.330 | −6.872 | 1.00 | 49.05 | MOL3 | O |
| ATOM | 8924 | NE2 | GLN | G | 37 | 11.127 | −55.027 | −8.807 | 1.00 | 35.77 | MOL3 | N |
| ATOM | 8925 | C | GLN | G | 37 | 9.194 | −58.179 | −9.974 | 1.00 | 43.08 | MOL3 | C |
| ATOM | 8926 | O | GLN | G | 37 | 8.907 | −57.649 | −11.042 | 1.00 | 49.64 | MOL3 | O |
| ATOM | 8927 | N | GLN | G | 38 | 8.343 | −58.235 | −8.956 | 1.00 | 42.91 | MOL3 | N |
| ATOM | 8928 | CA | GLN | G | 38 | 7.011 | −57.652 | −9.071 | 1.00 | 40.05 | MOL3 | C |
| ATOM | 8929 | CB | GLN | G | 38 | 5.996 | −58.730 | −9.415 | 1.00 | 32.88 | MOL3 | C |
| ATOM | 8930 | CG | GLN | G | 38 | 4.633 | −58.160 | −9.709 | 1.00 | 40.34 | MOL3 | C |
| ATOM | 8931 | CD | GLN | G | 38 | 3.682 | −59.179 | −10.278 | 1.00 | 38.95 | MOL3 | C |
| ATOM | 8932 | OE1 | GLN | G | 38 | 2.708 | −58.839 | −10.942 | 1.00 | 37.89 | MOL3 | O |
| ATOM | 8933 | NE2 | GLN | G | 38 | 3.954 | −60.437 | −10.011 | 1.00 | 48.71 | MOL3 | N |
| ATOM | 8934 | C | GLN | G | 38 | 6.568 | −56.985 | −7.784 | 1.00 | 40.19 | MOL3 | C |
| ATOM | 8935 | O | GLN | G | 38 | 6.453 | −57.637 | −6.760 | 1.00 | 42.15 | MOL3 | O |
| ATOM | 8936 | N | LYS | G | 39 | 6.316 | −55.687 | −7.820 | 1.00 | 42.89 | MOL3 | N |
| ATOM | 8937 | CA | LYS | G | 39 | 5.873 | −55.016 | −6.608 | 1.00 | 42.63 | MOL3 | C |
| ATOM | 8938 | CB | LYS | G | 39 | 6.290 | −53.544 | −6.623 | 1.00 | 42.81 | MOL3 | C |
| ATOM | 8939 | CG | LYS | G | 39 | 7.790 | −53.298 | −6.780 | 1.00 | 48.90 | MOL3 | C |
| ATOM | 8940 | CD | LYS | G | 39 | 8.493 | −53.118 | −5.449 | 1.00 | 57.46 | MOL3 | C |
| ATOM | 8941 | CE | LYS | G | 39 | 9.485 | −51.945 | −5.486 | 1.00 | 65.19 | MOL3 | C |
| ATOM | 8942 | NZ | LYS | G | 39 | 10.555 | −52.099 | −6.529 | 1.00 | 76.82 | MOL3 | N |
| ATOM | 8943 | C | LYS | G | 39 | 4.364 | −55.152 | −6.635 | 1.00 | 42.94 | MOL3 | C |
| ATOM | 8944 | O | LYS | G | 39 | 3.811 | −55.538 | −7.645 | 1.00 | 44.17 | MOL3 | O |
| ATOM | 8945 | N | PRO | G | 40 | 3.677 | −54.848 | −5.524 | 1.00 | 50.24 | MOL3 | N |
| ATOM | 8946 | CD | PRO | G | 40 | 4.209 | −54.444 | −4.213 | 1.00 | 57.50 | MOL3 | C |
| ATOM | 8947 | CA | PRO | G | 40 | 2.216 | −54.955 | −5.472 | 1.00 | 48.69 | MOL3 | C |
| ATOM | 8948 | CB | PRO | G | 40 | 1.885 | −54.630 | −4.022 | 1.00 | 46.58 | MOL3 | C |
| ATOM | 8949 | CG | PRO | G | 40 | 3.138 | −54.939 | −3.284 | 1.00 | 56.38 | MOL3 | C |
| ATOM | 8950 | C | PRO | G | 40 | 1.549 | −53.956 | −6.391 | 1.00 | 51.16 | MOL3 | C |
| ATOM | 8951 | O | PRO | G | 40 | 1.821 | −52.762 | −6.307 | 1.00 | 51.34 | MOL3 | O |
| ATOM | 8952 | N | GLY | G | 41 | 0.678 | −54.445 | −7.266 | 1.00 | 54.84 | MOL3 | N |
| ATOM | 8953 | CA | GLY | G | 41 | −0.040 | −53.557 | −8.159 | 1.00 | 59.57 | MOL3 | C |
| ATOM | 8954 | C | GLY | G | 41 | 0.581 | −53.345 | −9.516 | 1.00 | 61.10 | MOL3 | C |
| ATOM | 8955 | O | GLY | G | 41 | −0.127 | −53.227 | −10.519 | 1.00 | 66.90 | MOL3 | O |
| ATOM | 8956 | N | LYS | G | 42 | 1.903 | −53.281 | −9.552 | 1.00 | 57.43 | MOL3 | N |
| ATOM | 8957 | CA | LYS | G | 42 | 2.614 | −53.087 | −10.800 | 1.00 | 60.62 | MOL3 | C |
| ATOM | 8958 | CB | LYS | G | 42 | 3.954 | −52.407 | −10.501 | 1.00 | 67.78 | MOL3 | C |
| ATOM | 8959 | CG | LYS | G | 42 | 3.805 | −51.137 | −9.658 | 1.00 | 79.31 | MOL3 | C |
| ATOM | 8960 | CD | LYS | G | 42 | 2.668 | −50.248 | −10.189 | 1.00 | 90.76 | MOL3 | C |
| ATOM | 8961 | CE | LYS | G | 42 | 2.420 | −49.007 | −9.321 | 1.00 | 96.21 | MOL3 | C |
| ATOM | 8962 | NZ | LYS | G | 42 | 3.581 | −48.062 | −9.275 | 1.00 | 99.49 | MOL3 | N |
| ATOM | 8963 | C | LYS | G | 42 | 2.813 | −54.442 | −11.513 | 1.00 | 58.76 | MOL3 | C |
| ATOM | 8964 | O | LYS | G | 42 | 2.462 | −55.490 | −10.968 | 1.00 | 56.71 | MOL3 | O |
| ATOM | 8965 | N | ALA | G | 43 | 3.357 | −54.430 | −12.728 | 1.00 | 54.02 | MOL3 | N |
| ATOM | 8966 | CA | ALA | G | 43 | 3.566 | −55.671 | −13.455 | 1.00 | 42.73 | MOL3 | C |
| ATOM | 8967 | CB | ALA | G | 43 | 3.259 | −55.471 | −14.894 | 1.00 | 43.30 | MOL3 | C |
| ATOM | 8968 | C | ALA | G | 43 | 4.986 | −56.164 | −13.305 | 1.00 | 44.91 | MOL3 | C |
| ATOM | 8969 | O | ALA | G | 43 | 5.878 | −55.417 | −12.918 | 1.00 | 48.07 | MOL3 | O |
| ATOM | 8970 | N | PRO | G | 44 | 5.216 | −57.447 | −13.603 | 1.00 | 45.65 | MOL3 | N |
| ATOM | 8971 | CD | PRO | G | 44 | 4.228 | −58.435 | −14.084 | 1.00 | 44.36 | MOL3 | C |
| ATOM | 8972 | CA | PRO | G | 44 | 6.552 | −58.037 | −13.504 | 1.00 | 42.93 | MOL3 | C |
| ATOM | 8973 | CB | PRO | G | 44 | 6.403 | −59.338 | −14.293 | 1.00 | 42.13 | MOL3 | C |
| ATOM | 8974 | CG | PRO | G | 44 | 4.989 | −59.738 | −14.004 | 1.00 | 38.67 | MOL3 | C |
| ATOM | 8975 | C | PRO | G | 44 | 7.587 | −57.112 | −14.130 | 1.00 | 42.72 | MOL3 | C |
| ATOM | 8976 | O | PRO | G | 44 | 7.255 | −56.267 | −14.953 | 1.00 | 53.64 | MOL3 | O |
| ATOM | 8977 | N | LYS | G | 45 | 8.840 | −57.280 | −13.750 | 1.00 | 41.95 | MOL3 | N |
| ATOM | 8978 | CA | LYS | G | 45 | 9.925 | −56.471 | −14.287 | 1.00 | 39.52 | MOL3 | C |
| ATOM | 8979 | CB | LYS | G | 45 | 10.189 | −55.278 | −13.359 | 1.00 | 42.39 | MOL3 | C |
| ATOM | 8980 | CG | LYS | G | 45 | 11.621 | −54.772 | −13.365 | 1.00 | 66.59 | MOL3 | C |
| ATOM | 8981 | CD | LYS | G | 45 | 12.081 | −54.429 | −14.790 | 1.00 | 87.61 | MOL3 | C |
| ATOM | 8982 | CE | LYS | G | 45 | 13.540 | −53.949 | −14.837 | 1.00 | 89.77 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 8983 | NZ | LYS | G | 45 | 13.975 | −53.701 | −16.246 | 1.00 | 86.88 | MOL3 | N |
|---|---|---|---|---|---|---|---|---|---|---|---|---|
| ATOM | 8984 | C | LYS | G | 45 | 11.133 | −57.390 | −14.357 | 1.00 | 34.88 | MOL3 | C |
| ATOM | 8985 | O | LYS | G | 45 | 11.492 | −58.022 | −13.376 | 1.00 | 34.54 | MOL3 | O |
| ATOM | 8986 | N | LEU | G | 46 | 11.751 | −57.487 | −15.521 | 1.00 | 31.84 | MOL3 | N |
| ATOM | 8987 | CA | LEU | G | 46 | 12.904 | −58.361 | −15.652 | 1.00 | 30.83 | MOL3 | C |
| ATOM | 8988 | CB | LEU | G | 46 | 13.305 | −58.450 | −17.114 | 1.00 | 26.43 | MOL3 | C |
| ATOM | 8989 | CG | LEU | G | 46 | 14.584 | −59.179 | −17.456 | 1.00 | 23.79 | MOL3 | C |
| ATOM | 8990 | CD1 | LEU | G | 46 | 14.722 | −60.416 | −16.599 | 1.00 | 28.71 | MOL3 | C |
| ATOM | 8991 | CD2 | LEU | G | 46 | 14.546 | −59.528 | −18.922 | 1.00 | 19.57 | MOL3 | C |
| ATOM | 8992 | C | LEU | G | 46 | 14.079 | −57.907 | −14.796 | 1.00 | 31.59 | MOL3 | C |
| ATOM | 8993 | O | LEU | G | 46 | 14.435 | −56.729 | −14.776 | 1.00 | 33.27 | MOL3 | O |
| ATOM | 8994 | N | LEU | G | 47 | 14.662 | −58.860 | −14.078 | 1.00 | 30.77 | MOL3 | N |
| ATOM | 8995 | CA | LEU | G | 47 | 15.796 | −58.612 | −13.201 | 1.00 | 32.12 | MOL3 | C |
| ATOM | 8996 | CB | LEU | G | 47 | 15.580 | −59.279 | −11.851 | 1.00 | 31.97 | MOL3 | C |
| ATOM | 8997 | CG | LEU | G | 47 | 15.187 | −58.328 | −10.735 | 1.00 | 41.78 | MOL3 | C |
| ATOM | 8998 | CD1 | LEU | G | 47 | 16.168 | −58.404 | −9.585 | 1.00 | 39.67 | MOL3 | C |
| ATOM | 8999 | CD2 | LEU | G | 47 | 15.156 | −56.934 | −11.312 | 1.00 | 46.47 | MOL3 | C |
| ATOM | 9000 | C | LEU | G | 47 | 17.060 | −59.180 | −13.780 | 1.00 | 33.13 | MOL3 | C |
| ATOM | 9001 | O | LEU | G | 47 | 18.051 | −58.482 | −13.944 | 1.00 | 39.23 | MOL3 | O |
| ATOM | 9002 | N | ILE | G | 48 | 17.015 | −60.464 | −14.103 | 1.00 | 31.38 | MOL3 | N |
| ATOM | 9003 | CA | ILE | G | 48 | 18.190 | −61.137 | −14.610 | 1.00 | 32.41 | MOL3 | C |
| ATOM | 9004 | CB | ILE | G | 48 | 18.884 | −61.860 | −13.460 | 1.00 | 31.26 | MOL3 | C |
| ATOM | 9005 | CG2 | ILE | G | 48 | 20.001 | −62.712 | −13.982 | 1.00 | 31.43 | MOL3 | C |
| ATOM | 9006 | CG1 | ILE | G | 48 | 19.368 | −60.831 | −12.436 | 1.00 | 35.51 | MOL3 | C |
| ATOM | 9007 | CD1 | ILE | G | 48 | 19.885 | −61.416 | −11.154 | 1.00 | 36.86 | MOL3 | C |
| ATOM | 9008 | C | ILE | G | 48 | 17.858 | −62.137 | −15.681 | 1.00 | 34.00 | MOL3 | C |
| ATOM | 9009 | O | ILE | G | 48 | 16.918 | −62.895 | −15.535 | 1.00 | 38.04 | MOL3 | O |
| ATOM | 9010 | N | TYR | G | 49 | 18.625 | −62.132 | −16.761 | 1.00 | 38.94 | MOL3 | N |
| ATOM | 9011 | CA | TYR | G | 49 | 18.401 | −63.084 | −17.845 | 1.00 | 45.76 | MOL3 | C |
| ATOM | 9012 | CB | TYR | G | 49 | 18.189 | −62.371 | −19.195 | 1.00 | 49.55 | MOL3 | C |
| ATOM | 9013 | CG | TYR | G | 49 | 19.338 | −61.497 | −19.673 | 1.00 | 49.70 | MOL3 | C |
| ATOM | 9014 | CD1 | TYR | G | 49 | 19.602 | −60.275 | −19.073 | 1.00 | 49.20 | MOL3 | C |
| ATOM | 9015 | CE1 | TYR | G | 49 | 20.610 | −59.448 | −19.544 | 1.00 | 50.05 | MOL3 | C |
| ATOM | 9016 | CD2 | TYR | G | 49 | 20.125 | −61.873 | −20.758 | 1.00 | 44.58 | MOL3 | C |
| ATOM | 9017 | CE2 | TYR | G | 49 | 21.134 | −61.050 | −21.239 | 1.00 | 42.55 | MOL3 | C |
| ATOM | 9018 | CZ | TYR | G | 49 | 21.370 | −59.838 | −20.627 | 1.00 | 49.78 | MOL3 | C |
| ATOM | 9019 | OH | TYR | G | 49 | 22.354 | −58.994 | −21.089 | 1.00 | 50.96 | MOL3 | O |
| ATOM | 9020 | C | TYR | G | 49 | 19.581 | −64.043 | −17.947 | 1.00 | 48.45 | MOL3 | C |
| ATOM | 9021 | O | TYR | G | 49 | 20.657 | −63.789 | −17.382 | 1.00 | 47.87 | MOL3 | O |
| ATOM | 9022 | N | LEU | G | 50 | 19.374 | −65.138 | −18.676 | 1.00 | 44.95 | MOL3 | N |
| ATOM | 9023 | CA | LEU | G | 50 | 20.395 | −66.154 | −18.837 | 1.00 | 42.62 | MOL3 | C |
| ATOM | 9024 | CB | LEU | G | 50 | 21.295 | −65.799 | −20.014 | 1.00 | 43.27 | MOL3 | C |
| ATOM | 9025 | CG | LEU | G | 50 | 20.880 | −66.606 | −21.246 | 1.00 | 43.57 | MOL3 | C |
| ATOM | 9026 | CD1 | LEU | G | 50 | 19.410 | −66.884 | −21.160 | 1.00 | 40.55 | MOL3 | C |
| ATOM | 9027 | CD2 | LEU | G | 50 | 21.226 | −65.874 | −22.524 | 1.00 | 39.39 | MOL3 | C |
| ATOM | 9028 | C | LEU | G | 50 | 21.209 | −66.363 | −17.562 | 1.00 | 45.78 | MOL3 | C |
| ATOM | 9029 | O | LEU | G | 50 | 22.406 | −66.100 | −17.515 | 1.00 | 48.05 | MOL3 | O |
| ATOM | 9030 | N | VAL | G | 51 | 20.521 | −66.812 | −16.520 | 1.00 | 46.34 | MOL3 | N |
| ATOM | 9031 | CA | VAL | G | 51 | 21.125 | −67.119 | −15.230 | 1.00 | 48.58 | MOL3 | C |
| ATOM | 9032 | CB | VAL | G | 51 | 22.234 | −68.170 | −15.363 | 1.00 | 49.60 | MOL3 | C |
| ATOM | 9033 | CG1 | VAL | G | 51 | 22.955 | −68.321 | −14.026 | 1.00 | 44.74 | MOL3 | C |
| ATOM | 9034 | CG2 | VAL | G | 51 | 21.658 | −69.485 | −15.813 | 1.00 | 48.42 | MOL3 | C |
| ATOM | 9035 | C | VAL | G | 51 | 21.741 | −66.035 | −14.376 | 1.00 | 51.00 | MOL3 | C |
| ATOM | 9036 | O | VAL | G | 51 | 21.434 | −65.920 | −13.178 | 1.00 | 50.83 | MOL3 | O |
| ATOM | 9037 | N | SER | G | 52 | 22.631 | −65.251 | −14.964 | 1.00 | 49.31 | MOL3 | N |
| ATOM | 9038 | CA | SER | G | 52 | 23.310 | −64.269 | −14.145 | 1.00 | 55.39 | MOL3 | C |
| ATOM | 9039 | CB | SER | G | 52 | 24.646 | −64.865 | −13.711 | 1.00 | 57.96 | MOL3 | C |
| ATOM | 9040 | OG | SER | G | 52 | 25.195 | −64.106 | −12.655 | 1.00 | 72.85 | MOL3 | O |
| ATOM | 9041 | C | SER | G | 52 | 23.538 | −62.877 | −14.717 | 1.00 | 50.82 | MOL3 | C |
| ATOM | 9042 | O | SER | G | 52 | 24.233 | −62.065 | −14.113 | 1.00 | 48.84 | MOL3 | O |
| ATOM | 9043 | N | ASN | G | 53 | 22.951 | −62.587 | −15.866 | 1.00 | 47.12 | MOL3 | N |
| ATOM | 9044 | CA | ASN | G | 53 | 23.139 | −61.279 | −16.450 | 1.00 | 44.83 | MOL3 | C |
| ATOM | 9045 | CB | ASN | G | 53 | 23.211 | −61.412 | −17.967 | 1.00 | 47.38 | MOL3 | C |
| ATOM | 9046 | CG | ASN | G | 53 | 24.324 | −62.346 | −18.419 | 1.00 | 53.95 | MOL3 | C |
| ATOM | 9047 | OD1 | ASN | G | 53 | 24.100 | −63.542 | −18.610 | 1.00 | 59.31 | MOL3 | O |
| ATOM | 9048 | ND2 | ASN | G | 53 | 25.535 | −61.804 | −18.582 | 1.00 | 50.66 | MOL3 | N |
| ATOM | 9049 | C | ASN | G | 53 | 22.016 | −60.324 | −16.042 | 1.00 | 45.87 | MOL3 | C |
| ATOM | 9050 | O | ASN | G | 53 | 20.834 | −60.680 | −16.116 | 1.00 | 44.59 | MOL3 | O |
| ATOM | 9051 | N | ARG | G | 54 | 22.384 | −59.116 | −15.607 | 1.00 | 40.72 | MOL3 | N |
| ATOM | 9052 | CA | ARG | G | 54 | 21.401 | −58.116 | −15.194 | 1.00 | 42.15 | MOL3 | C |
| ATOM | 9053 | CB | ARG | G | 54 | 21.982 | −57.171 | −14.143 | 1.00 | 41.21 | MOL3 | C |
| ATOM | 9054 | CG | ARG | G | 54 | 22.235 | −57.764 | −12.792 | 1.00 | 52.19 | MOL3 | C |
| ATOM | 9055 | CD | ARG | G | 54 | 23.690 | −58.127 | −12.653 | 1.00 | 68.42 | MOL3 | C |
| ATOM | 9056 | NE | ARG | G | 54 | 24.412 | −57.203 | −11.791 | 1.00 | 74.48 | MOL3 | N |
| ATOM | 9057 | CZ | ARG | G | 54 | 24.268 | −55.883 | −11.820 | 1.00 | 84.27 | MOL3 | C |
| ATOM | 9058 | NH1 | ARG | G | 54 | 23.421 | −55.307 | −12.663 | 1.00 | 85.29 | MOL3 | N |
| ATOM | 9059 | NH2 | ARG | G | 54 | 24.995 | −55.133 | −11.011 | 1.00 | 91.76 | MOL3 | N |

TABLE 1-continued

The atomic coordinates of IL17F in complex with 496 Fab
(H32; a = 189.4; b = 189.4; c = 490.9, α, β = 90°; γ = 120°)

| ATOM | 9060 | C | ARG | G | 54 | 20.898 | −57.234 | −16.326 | 1.00 | 47.47 | MOL3 | C |
|---|---|---|---|---|---|---|---|---|---|---|---|---|
| ATOM | 9061 | O | ARG | G | 54 | 21.649 | −56.906 | −17.246 | 1.00 | 53.93 | MOL3 | O |
| ATOM | 9062 | N | GLU | G | 55 | 19.633 | −56.828 | −16.244 | 1.00 | 50.13 | MOL3 | N |
| ATOM | 9063 | CA | GLU | G | 55 | 19.054 | −55.935 | −17.239 | 1.00 | 55.45 | MOL3 | C |
| ATOM | 9064 | CB | GLU | G | 55 | 17.545 | −55.810 | −17.019 | 1.00 | 58.42 | MOL3 | C |
| ATOM | 9065 | CG | GLU | G | 55 | 16.674 | −56.365 | −18.141 | 1.00 | 62.39 | MOL3 | C |
| ATOM | 9066 | CD | GLU | G | 55 | 16.850 | −55.610 | −19.449 | 1.00 | 68.28 | MOL3 | C |
| ATOM | 9067 | OE1 | GLU | G | 55 | 15.834 | −55.391 | −20.141 | 1.00 | 64.08 | MOL3 | O |
| ATOM | 9068 | OE2 | GLU | G | 55 | 18.001 | −55.240 | −19.792 | 1.00 | 73.31 | MOL3 | O |
| ATOM | 9069 | C | GLU | G | 55 | 19.731 | −54.588 | −17.012 | 1.00 | 58.68 | MOL3 | C |
| ATOM | 9070 | O | GLU | G | 55 | 20.348 | −54.371 | −15.968 | 1.00 | 60.53 | MOL3 | O |
| ATOM | 9071 | N | SER | G | 56 | 19.617 | −53.686 | −17.976 | 1.00 | 59.87 | MOL3 | N |
| ATOM | 9072 | CA | SER | G | 56 | 20.242 | −52.377 | −17.870 | 1.00 | 62.94 | MOL3 | C |
| ATOM | 9073 | CB | SER | G | 56 | 19.701 | −51.480 | −18.975 | 1.00 | 65.70 | MOL3 | C |
| ATOM | 9074 | OG | SER | G | 56 | 19.658 | −52.200 | −20.201 | 1.00 | 79.30 | MOL3 | O |
| ATOM | 9075 | C | SER | G | 56 | 20.061 | −51.700 | −16.505 | 1.00 | 63.43 | MOL3 | C |
| ATOM | 9076 | O | SER | G | 56 | 21.020 | −51.523 | −15.749 | 1.00 | 68.59 | MOL3 | O |
| ATOM | 9077 | N | GLY | G | 57 | 18.832 | −51.334 | −16.180 | 1.00 | 57.93 | MOL3 | N |
| ATOM | 9078 | CA | GLY | G | 57 | 18.589 | −50.655 | −14.922 | 1.00 | 53.96 | MOL3 | C |
| ATOM | 9079 | C | GLY | G | 57 | 18.896 | −51.412 | −13.648 | 1.00 | 52.63 | MOL3 | C |
| ATOM | 9080 | O | GLY | G | 57 | 19.326 | −50.819 | −12.667 | 1.00 | 55.85 | MOL3 | O |
| ATOM | 9081 | N | VAL | G | 58 | 18.680 | −52.720 | −13.648 | 1.00 | 52.62 | MOL3 | N |
| ATOM | 9082 | CA | VAL | G | 58 | 18.915 | −53.521 | −12.451 | 1.00 | 49.03 | MOL3 | C |
| ATOM | 9083 | CB | VAL | G | 58 | 18.962 | −55.017 | −12.758 | 1.00 | 47.64 | MOL3 | C |
| ATOM | 9084 | CG1 | VAL | G | 58 | 18.743 | −55.793 | −11.486 | 1.00 | 47.52 | MOL3 | C |
| ATOM | 9085 | CG2 | VAL | G | 58 | 17.929 | −55.379 | −13.787 | 1.00 | 47.12 | MOL3 | C |
| ATOM | 9086 | C | VAL | G | 58 | 20.201 | −53.172 | −11.711 | 1.00 | 52.13 | MOL3 | C |
| ATOM | 9087 | O | VAL | G | 58 | 21.308 | −53.207 | −12.281 | 1.00 | 51.96 | MOL3 | O |
| ATOM | 9088 | N | PRO | G | 59 | 20.061 | −52.826 | −10.421 | 1.00 | 48.32 | MOL3 | N |
| ATOM | 9089 | CD | PRO | G | 59 | 18.752 | −52.511 | −9.826 | 1.00 | 51.53 | MOL3 | C |
| ATOM | 9090 | CA | PRO | G | 59 | 21.125 | −52.453 | −9.500 | 1.00 | 47.77 | MOL3 | C |
| ATOM | 9091 | CB | PRO | G | 59 | 20.388 | −52.257 | −8.192 | 1.00 | 41.55 | MOL3 | C |
| ATOM | 9092 | CG | PRO | G | 59 | 19.141 | −51.633 | −8.640 | 1.00 | 49.21 | MOL3 | C |
| ATOM | 9093 | C | PRO | G | 59 | 22.244 | −53.451 | −9.383 | 1.00 | 51.58 | MOL3 | C |
| ATOM | 9094 | O | PRO | G | 59 | 22.138 | −54.607 | −9.778 | 1.00 | 54.15 | MOL3 | O |
| ATOM | 9095 | N | SER | G | 60 | 23.323 | −52.964 | −8.805 | 1.00 | 62.14 | MOL3 | N |
| ATOM | 9096 | CA | SER | G | 60 | 24.530 | −53.725 | −8.621 | 1.00 | 68.95 | MOL3 | C |
| ATOM | 9097 | CB | SER | G | 60 | 25.622 | −52.755 | −8.125 | 1.00 | 81.46 | MOL3 | C |
| ATOM | 9098 | OG | SER | G | 60 | 25.507 | −51.455 | −8.744 | 1.00 | 80.56 | MOL3 | O |
| ATOM | 9099 | C | SER | G | 60 | 24.339 | −54.919 | −7.672 | 1.00 | 68.86 | MOL3 | C |
| ATOM | 9100 | O | SER | G | 60 | 24.908 | −55.988 | −7.908 | 1.00 | 69.31 | MOL3 | O |
| ATOM | 9101 | N | ARG | G | 61 | 23.518 | −54.749 | −6.629 | 1.00 | 65.79 | MOL3 | N |
| ATOM | 9102 | CA | ARG | G | 61 | 23.286 | −55.816 | −5.634 | 1.00 | 62.21 | MOL3 | C |
| ATOM | 9103 | CB | ARG | G | 61 | 22.516 | −55.260 | −4.424 | 1.00 | 60.42 | MOL3 | C |
| ATOM | 9104 | CG | ARG | G | 61 | 21.300 | −54.400 | −4.754 | 1.00 | 60.78 | MOL3 | C |
| ATOM | 9105 | CD | ARG | G | 61 | 20.636 | −53.836 | −3.486 | 1.00 | 53.34 | MOL3 | C |
| ATOM | 9106 | NE | ARG | G | 61 | 19.376 | −53.161 | −3.783 | 1.00 | 45.70 | MOL3 | N |
| ATOM | 9107 | CZ | ARG | G | 61 | 19.286 | −51.988 | −4.395 | 1.00 | 47.19 | MOL3 | C |
| ATOM | 9108 | NH1 | ARG | G | 61 | 20.387 | −51.361 | −4.762 | 1.00 | 57.68 | MOL3 | N |
| ATOM | 9109 | NH2 | ARG | G | 61 | 18.101 | −51.451 | −4.664 | 1.00 | 47.81 | MOL3 | N |
| ATOM | 9110 | C | ARG | G | 61 | 22.630 | −57.132 | −6.094 | 1.00 | 60.08 | MOL3 | C |
| ATOM | 9111 | O | ARG | G | 61 | 22.955 | −58.206 | −5.586 | 1.00 | 60.15 | MOL3 | O |
| ATOM | 9112 | N | PHE | G | 62 | 21.721 | −57.068 | −7.052 | 1.00 | 53.77 | MOL3 | N |
| ATOM | 9113 | CA | PHE | G | 62 | 21.077 | −58.280 | −7.517 | 1.00 | 53.49 | MOL3 | C |
| ATOM | 9114 | CB | PHE | G | 62 | 19.879 | −57.901 | −8.377 | 1.00 | 52.45 | MOL3 | C |
| ATOM | 9115 | CG | PHE | G | 62 | 18.787 | −57.226 | −7.622 | 1.00 | 44.28 | MOL3 | C |
| ATOM | 9116 | CD1 | PHE | G | 62 | 17.984 | −57.944 | −6.759 | 1.00 | 49.58 | MOL3 | C |
| ATOM | 9117 | CD2 | PHE | G | 62 | 18.563 | −55.879 | −7.768 | 1.00 | 45.93 | MOL3 | C |
| ATOM | 9118 | CE1 | PHE | G | 62 | 16.973 | −57.328 | −6.054 | 1.00 | 52.92 | MOL3 | C |
| ATOM | 9119 | CE2 | PHE | G | 62 | 17.552 | −55.252 | −7.065 | 1.00 | 53.51 | MOL3 | C |
| ATOM | 9120 | CZ | PHE | G | 62 | 16.756 | −55.980 | −6.206 | 1.00 | 54.67 | MOL3 | C |
| ATOM | 9121 | C | PHE | G | 62 | 22.042 | −59.161 | −8.313 | 1.00 | 54.06 | MOL3 | C |
| ATOM | 9122 | O | PHE | G | 62 | 22.699 | −58.676 | −9.230 | 1.00 | 57.70 | MOL3 | O |
| ATOM | 9123 | N | SER | G | 63 | 22.122 | −60.448 | −7.979 | 1.00 | 52.56 | MOL3 | N |
| ATOM | 9124 | CA | SER | G | 63 | 23.018 | −61.363 | −8.693 | 1.00 | 54.21 | MOL3 | C |
| ATOM | 9125 | CB | SER | G | 63 | 24.372 | −61.412 | −7.989 | 1.00 | 55.60 | MOL3 | C |
| ATOM | 9126 | OG | SER | G | 63 | 24.221 | −61.114 | −6.612 | 1.00 | 52.29 | MOL3 | O |
| ATOM | 9127 | C | SER | G | 63 | 22.465 | −62.775 | −8.827 | 1.00 | 53.10 | MOL3 | C |
| ATOM | 9128 | O | SER | G | 63 | 22.010 | −63.364 | −7.862 | 1.00 | 55.14 | MOL3 | O |
| ATOM | 9129 | N | GLY | G | 64 | 22.515 | −63.321 | −10.033 | 1.00 | 57.59 | MOL3 | N |
| ATOM | 9130 | CA | GLY | G | 64 | 22.005 | −64.663 | −10.256 | 1.00 | 62.03 | MOL3 | C |
| ATOM | 9131 | C | GLY | G | 64 | 23.120 | −65.678 | −10.150 | 1.00 | 65.50 | MOL3 | C |
| ATOM | 9132 | O | GLY | G | 64 | 24.254 | −65.299 | −9.872 | 1.00 | 66.87 | MOL3 | O |
| ATOM | 9133 | N | SER | G | 65 | 22.811 | −66.957 | −10.364 | 1.00 | 68.23 | MOL3 | N |
| ATOM | 9134 | CA | SER | G | 65 | 23.821 | −68.018 | −10.285 | 1.00 | 67.23 | MOL3 | C |
| ATOM | 9135 | CB | SER | G | 65 | 24.641 | −67.882 | −8.993 | 1.00 | 68.42 | MOL3 | C |
| ATOM | 9136 | OG | SER | G | 65 | 23.874 | −68.137 | −7.828 | 1.00 | 62.79 | MOL3 | O |

TABLE 1-continued

The atomic coordinates of IL17F in complex with 496 Fab
(H32; a = 189.4; b = 189.4; c = 490.9, α, β = 90°; γ = 120°)

| ATOM | 9137 | C | SER | G | 65 | 23.197 | −69.406 | −10.335 | 1.00 | 67.16 | MOL3 | C |
|---|---|---|---|---|---|---|---|---|---|---|---|---|
| ATOM | 9138 | O | SER | G | 65 | 22.237 | −69.679 | −9.618 | 1.00 | 72.98 | MOL3 | O |
| ATOM | 9139 | N | GLY | G | 66 | 23.734 | −70.290 | −11.166 | 1.00 | 62.84 | MOL3 | N |
| ATOM | 9140 | CA | GLY | G | 66 | 23.155 | −71.615 | −11.226 | 1.00 | 68.73 | MOL3 | C |
| ATOM | 9141 | C | GLY | G | 66 | 23.649 | −72.558 | −12.302 | 1.00 | 76.81 | MOL3 | C |
| ATOM | 9142 | O | GLY | G | 66 | 24.269 | −72.153 | −13.290 | 1.00 | 73.43 | MOL3 | O |
| ATOM | 9143 | N | SER | G | 67 | 23.354 | −73.840 | −12.095 | 1.00 | 85.49 | MOL3 | N |
| ATOM | 9144 | CA | SER | G | 67 | 23.755 | −74.893 | −13.021 | 1.00 | 90.60 | MOL3 | C |
| ATOM | 9145 | CB | SER | G | 67 | 23.982 | −76.214 | −12.270 | 1.00 | 90.93 | MOL3 | C |
| ATOM | 9146 | OG | SER | G | 67 | 22.826 | −76.617 | −11.559 | 1.00 | 90.02 | MOL3 | O |
| ATOM | 9147 | C | SER | G | 67 | 22.714 | −75.089 | −14.110 | 1.00 | 91.68 | MOL3 | C |
| ATOM | 9148 | O | SER | G | 67 | 22.721 | −74.380 | −15.122 | 1.00 | 94.33 | MOL3 | O |
| ATOM | 9149 | N | GLY | G | 68 | 21.825 | −76.054 | −13.893 | 1.00 | 90.54 | MOL3 | N |
| ATOM | 9150 | CA | GLY | G | 68 | 20.782 | −76.346 | −14.858 | 1.00 | 89.44 | MOL3 | C |
| ATOM | 9151 | C | GLY | G | 68 | 19.638 | −77.073 | −14.187 | 1.00 | 88.47 | MOL3 | C |
| ATOM | 9152 | O | GLY | G | 68 | 18.751 | −77.608 | −14.849 | 1.00 | 84.62 | MOL3 | O |
| ATOM | 9153 | N | THR | G | 69 | 19.674 | −77.087 | −12.857 | 1.00 | 90.20 | MOL3 | N |
| ATOM | 9154 | CA | THR | G | 69 | 18.653 | −77.739 | −12.051 | 1.00 | 92.56 | MOL3 | C |
| ATOM | 9155 | CB | THR | G | 69 | 19.085 | −79.139 | −11.627 | 1.00 | 98.74 | MOL3 | C |
| ATOM | 9156 | OG1 | THR | G | 69 | 18.174 | −79.633 | −10.638 | 1.00 | 108.30 | MOL3 | O |
| ATOM | 9157 | CG2 | THR | G | 69 | 20.491 | −79.108 | −11.042 | 1.00 | 103.92 | MOL3 | C |
| ATOM | 9158 | C | THR | G | 69 | 18.380 | −76.929 | −10.794 | 1.00 | 88.90 | MOL3 | C |
| ATOM | 9159 | O | THR | G | 69 | 17.254 | −76.887 | −10.304 | 1.00 | 91.65 | MOL3 | O |
| ATOM | 9160 | N | ASP | G | 70 | 19.421 | −76.300 | −10.264 | 1.00 | 85.97 | MOL3 | N |
| ATOM | 9161 | CA | ASP | G | 70 | 19.279 | −75.469 | −9.072 | 1.00 | 88.69 | MOL3 | C |
| ATOM | 9162 | CB | ASP | G | 70 | 20.038 | −76.059 | −7.870 | 1.00 | 96.68 | MOL3 | C |
| ATOM | 9163 | CG | ASP | G | 70 | 20.738 | −77.366 | −8.196 | 1.00 | 105.12 | MOL3 | C |
| ATOM | 9164 | OD1 | ASP | G | 70 | 21.579 | −77.390 | −9.121 | 1.00 | 108.66 | MOL3 | O |
| ATOM | 9165 | OD2 | ASP | G | 70 | 20.451 | −78.374 | −7.519 | 1.00 | 111.25 | MOL3 | O |
| ATOM | 9166 | C | ASP | G | 70 | 19.821 | −74.078 | −9.369 | 1.00 | 83.52 | MOL3 | C |
| ATOM | 9167 | O | ASP | G | 70 | 20.894 | −73.928 | −9.954 | 1.00 | 85.96 | MOL3 | O |
| ATOM | 9168 | N | PHE | G | 71 | 19.078 | −73.057 | −8.970 | 1.00 | 73.77 | MOL3 | N |
| ATOM | 9169 | CA | PHE | G | 71 | 19.514 | −71.692 | −9.198 | 1.00 | 62.74 | MOL3 | C |
| ATOM | 9170 | CB | PHE | G | 71 | 18.786 | −71.103 | −10.387 | 1.00 | 58.07 | MOL3 | C |
| ATOM | 9171 | CG | PHE | G | 71 | 18.984 | −71.871 | −11.644 | 1.00 | 60.46 | MOL3 | C |
| ATOM | 9172 | CD1 | PHE | G | 71 | 20.165 | −71.771 | −12.349 | 1.00 | 64.47 | MOL3 | C |
| ATOM | 9173 | CD2 | PHE | G | 71 | 17.995 | −72.702 | −12.121 | 1.00 | 63.44 | MOL3 | C |
| ATOM | 9174 | CE1 | PHE | G | 71 | 20.357 | −72.483 | −13.508 | 1.00 | 61.95 | MOL3 | C |
| ATOM | 9175 | CE2 | PHE | G | 71 | 18.178 | −73.417 | −13.278 | 1.00 | 62.01 | MOL3 | C |
| ATOM | 9176 | CZ | PHE | G | 71 | 19.362 | −73.306 | −13.972 | 1.00 | 65.54 | MOL3 | C |
| ATOM | 9177 | C | PHE | G | 71 | 19.216 | −70.865 | −7.979 | 1.00 | 60.82 | MOL3 | C |
| ATOM | 9178 | O | PHE | G | 71 | 18.389 | −71.237 | −7.146 | 1.00 | 68.29 | MOL3 | O |
| ATOM | 9179 | N | THR | G | 72 | 19.889 | −69.738 | −7.858 | 1.00 | 54.02 | MOL3 | N |
| ATOM | 9180 | CA | THR | G | 72 | 19.628 | −68.893 | −6.718 | 1.00 | 56.28 | MOL3 | C |
| ATOM | 9181 | CB | THR | G | 72 | 20.530 | −69.243 | −5.510 | 1.00 | 58.97 | MOL3 | C |
| ATOM | 9182 | OG1 | THR | G | 72 | 21.429 | −68.154 | −5.267 | 1.00 | 63.51 | MOL3 | O |
| ATOM | 9183 | CG2 | THR | G | 72 | 21.314 | −70.536 | −5.757 | 1.00 | 52.40 | MOL3 | C |
| ATOM | 9184 | C | THR | G | 72 | 19.808 | −67.429 | −7.064 | 1.00 | 54.68 | MOL3 | C |
| ATOM | 9185 | O | THR | G | 72 | 20.738 | −67.047 | −7.762 | 1.00 | 57.65 | MOL3 | O |
| ATOM | 9186 | N | LEU | G | 73 | 18.877 | −66.614 | −6.602 | 1.00 | 51.57 | MOL3 | N |
| ATOM | 9187 | CA | LEU | G | 73 | 18.949 | −65.197 | −6.844 | 1.00 | 50.13 | MOL3 | C |
| ATOM | 9188 | CB | LEU | G | 73 | 17.587 | −64.671 | −7.285 | 1.00 | 49.88 | MOL3 | C |
| ATOM | 9189 | CG | LEU | G | 73 | 17.396 | −63.169 | −7.104 | 1.00 | 57.46 | MOL3 | C |
| ATOM | 9190 | CD1 | LEU | G | 73 | 18.479 | −62.395 | −7.836 | 1.00 | 59.43 | MOL3 | C |
| ATOM | 9191 | CD2 | LEU | G | 73 | 16.024 | −62.795 | −7.606 | 1.00 | 57.80 | MOL3 | C |
| ATOM | 9192 | C | LEU | G | 73 | 19.357 | −64.646 | −5.497 | 1.00 | 50.52 | MOL3 | C |
| ATOM | 9193 | O | LEU | G | 73 | 18.968 | −65.185 | −4.466 | 1.00 | 56.98 | MOL3 | O |
| ATOM | 9194 | N | THR | G | 74 | 20.161 | −63.595 | −5.482 | 1.00 | 50.75 | MOL3 | N |
| ATOM | 9195 | CA | THR | G | 74 | 20.589 | −63.057 | −4.206 | 1.00 | 52.46 | MOL3 | C |
| ATOM | 9196 | CB | THR | G | 74 | 21.825 | −63.841 | −3.655 | 1.00 | 56.91 | MOL3 | C |
| ATOM | 9197 | OG1 | THR | G | 74 | 22.632 | −62.961 | −2.860 | 1.00 | 58.92 | MOL3 | O |
| ATOM | 9198 | CG2 | THR | G | 74 | 22.646 | −64.466 | −4.793 | 1.00 | 49.58 | MOL3 | C |
| ATOM | 9199 | C | THR | G | 74 | 20.861 | −61.562 | −4.162 | 1.00 | 51.48 | MOL3 | C |
| ATOM | 9200 | O | THR | G | 74 | 21.551 | −60.997 | −5.011 | 1.00 | 51.31 | MOL3 | O |
| ATOM | 9201 | N | ILE | G | 75 | 20.299 | −60.933 | −3.142 | 1.00 | 50.98 | MOL3 | N |
| ATOM | 9202 | CA | ILE | G | 75 | 20.440 | −59.509 | −2.938 | 1.00 | 61.03 | MOL3 | C |
| ATOM | 9203 | CB | ILE | G | 75 | 19.086 | −58.888 | −2.513 | 1.00 | 65.72 | MOL3 | C |
| ATOM | 9204 | CG2 | ILE | G | 75 | 19.144 | −57.369 | −2.596 | 1.00 | 66.90 | MOL3 | C |
| ATOM | 9205 | CG1 | ILE | G | 75 | 17.976 | −59.392 | −3.438 | 1.00 | 68.75 | MOL3 | C |
| ATOM | 9206 | CD1 | ILE | G | 75 | 16.610 | −58.811 | −3.133 | 1.00 | 68.20 | MOL3 | C |
| ATOM | 9207 | C | ILE | G | 75 | 21.487 | −59.256 | −1.853 | 1.00 | 65.69 | MOL3 | C |
| ATOM | 9208 | O | ILE | G | 75 | 21.226 | −59.446 | −0.664 | 1.00 | 65.40 | MOL3 | O |
| ATOM | 9209 | N | SER | G | 76 | 22.669 | −58.823 | −2.286 | 1.00 | 67.38 | MOL3 | N |
| ATOM | 9210 | CA | SER | G | 76 | 23.792 | −58.532 | −1.404 | 1.00 | 67.37 | MOL3 | C |
| ATOM | 9211 | CB | SER | G | 76 | 24.922 | −57.899 | −2.208 | 1.00 | 72.25 | MOL3 | C |
| ATOM | 9212 | OG | SER | G | 76 | 25.279 | −58.731 | −3.291 | 1.00 | 86.18 | MOL3 | O |
| ATOM | 9213 | C | SER | G | 76 | 23.458 | −57.609 | −0.243 | 1.00 | 65.06 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 9214 | O | SER | G | 76 | 23.943 | −57.801 | 0.872 | 1.00 | 71.05 | MOL3 | O |
|---|---|---|---|---|---|---|---|---|---|---|---|---|
| ATOM | 9215 | N | SER | G | 77 | 22.649 | −56.595 | −0.495 | 1.00 | 56.07 | MOL3 | N |
| ATOM | 9216 | CA | SER | G | 77 | 22.315 | −55.678 | 0.571 | 1.00 | 57.30 | MOL3 | C |
| ATOM | 9217 | CB | SER | G | 77 | 23.299 | −54.518 | 0.600 | 1.00 | 57.18 | MOL3 | C |
| ATOM | 9218 | OG | SER | G | 77 | 22.852 | −53.526 | 1.511 | 1.00 | 64.33 | MOL3 | O |
| ATOM | 9219 | C | SER | G | 77 | 20.923 | −55.136 | 0.397 | 1.00 | 60.30 | MOL3 | C |
| ATOM | 9220 | O | SER | G | 77 | 20.737 | −54.091 | −0.222 | 1.00 | 66.45 | MOL3 | O |
| ATOM | 9221 | N | LEU | G | 78 | 19.944 | −55.828 | 0.972 | 1.00 | 61.04 | MOL3 | N |
| ATOM | 9222 | CA | LEU | G | 78 | 18.545 | −55.420 | 0.843 | 1.00 | 57.10 | MOL3 | C |
| ATOM | 9223 | CB | LEU | G | 78 | 17.638 | −56.148 | 1.837 | 1.00 | 59.14 | MOL3 | C |
| ATOM | 9224 | CG | LEU | G | 78 | 16.232 | −56.405 | 1.272 | 1.00 | 59.20 | MOL3 | C |
| ATOM | 9225 | CD1 | LEU | G | 78 | 16.362 | −57.395 | 0.137 | 1.00 | 62.71 | MOL3 | C |
| ATOM | 9226 | CD2 | LEU | G | 78 | 15.294 | −56.975 | 2.317 | 1.00 | 62.35 | MOL3 | C |
| ATOM | 9227 | C | LEU | G | 78 | 18.344 | −53.939 | 1.011 | 1.00 | 54.97 | MOL3 | C |
| ATOM | 9228 | O | LEU | G | 78 | 18.943 | −53.308 | 1.876 | 1.00 | 55.56 | MOL3 | O |
| ATOM | 9229 | N | GLN | G | 79 | 17.486 | −53.394 | 0.163 | 1.00 | 56.22 | MOL3 | N |
| ATOM | 9230 | CA | GLN | G | 79 | 17.183 | −51.979 | 0.188 | 1.00 | 59.47 | MOL3 | C |
| ATOM | 9231 | CB | GLN | G | 79 | 17.692 | −51.311 | −1.086 | 1.00 | 62.26 | MOL3 | C |
| ATOM | 9232 | CG | GLN | G | 79 | 19.195 | −51.202 | −1.148 | 1.00 | 65.36 | MOL3 | C |
| ATOM | 9233 | CD | GLN | G | 79 | 19.748 | −50.412 | 0.018 | 1.00 | 73.04 | MOL3 | C |
| ATOM | 9234 | OE1 | GLN | G | 79 | 19.414 | −49.235 | 0.204 | 1.00 | 75.65 | MOL3 | O |
| ATOM | 9235 | NE2 | GLN | G | 79 | 20.597 | −51.055 | 0.818 | 1.00 | 72.21 | MOL3 | N |
| ATOM | 9236 | C | GLN | G | 79 | 15.687 | −51.779 | 0.323 | 1.00 | 59.35 | MOL3 | C |
| ATOM | 9237 | O | GLN | G | 79 | 14.897 | −52.654 | −0.017 | 1.00 | 58.67 | MOL3 | O |
| ATOM | 9238 | N | PRO | G | 80 | 15.279 | −50.609 | 0.819 | 1.00 | 61.07 | MOL3 | N |
| ATOM | 9239 | CD | PRO | G | 80 | 16.110 | −49.428 | 1.105 | 1.00 | 57.69 | MOL3 | C |
| ATOM | 9240 | CA | PRO | G | 80 | 13.857 | −50.309 | 0.995 | 1.00 | 64.17 | MOL3 | C |
| ATOM | 9241 | CB | PRO | G | 80 | 13.852 | −48.796 | 1.192 | 1.00 | 64.30 | MOL3 | C |
| ATOM | 9242 | CG | PRO | G | 80 | 15.157 | −48.552 | 1.880 | 1.00 | 62.04 | MOL3 | C |
| ATOM | 9243 | C | PRO | G | 80 | 13.013 | −50.740 | −0.202 | 1.00 | 66.97 | MOL3 | C |
| ATOM | 9244 | O | PRO | G | 80 | 12.004 | −51.416 | −0.054 | 1.00 | 72.11 | MOL3 | O |
| ATOM | 9245 | N | GLU | G | 81 | 13.447 | −50.358 | −1.391 | 1.00 | 68.09 | MOL3 | N |
| ATOM | 9246 | CA | GLU | G | 81 | 12.722 | −50.671 | −2.608 | 1.00 | 71.02 | MOL3 | C |
| ATOM | 9247 | CB | GLU | G | 81 | 13.141 | −49.691 | −3.716 | 1.00 | 86.99 | MOL3 | C |
| ATOM | 9248 | CG | GLU | G | 81 | 14.665 | −49.488 | −3.906 | 1.00 | 98.03 | MOL3 | C |
| ATOM | 9249 | CD | GLU | G | 81 | 15.341 | −48.753 | −2.738 | 1.00 | 105.74 | MOL3 | C |
| ATOM | 9250 | OE1 | GLU | G | 81 | 14.685 | −47.901 | −2.091 | 1.00 | 107.20 | MOL3 | O |
| ATOM | 9251 | OE2 | GLU | G | 81 | 16.538 | −49.012 | −2.480 | 1.00 | 106.18 | MOL3 | O |
| ATOM | 9252 | C | GLU | G | 81 | 12.868 | −52.094 | −3.108 | 1.00 | 64.50 | MOL3 | C |
| ATOM | 9253 | O | GLU | G | 81 | 12.366 | −52.429 | −4.174 | 1.00 | 65.83 | MOL3 | O |
| ATOM | 9254 | N | ASP | G | 82 | 13.557 | −52.936 | −2.358 | 1.00 | 58.56 | MOL3 | N |
| ATOM | 9255 | CA | ASP | G | 82 | 13.730 | −54.309 | −2.812 | 1.00 | 60.36 | MOL3 | C |
| ATOM | 9256 | CB | ASP | G | 82 | 15.109 | −54.839 | −2.426 | 1.00 | 67.23 | MOL3 | C |
| ATOM | 9257 | CG | ASP | G | 82 | 16.218 | −54.123 | −3.140 | 1.00 | 71.60 | MOL3 | C |
| ATOM | 9258 | OD1 | ASP | G | 82 | 16.071 | −53.888 | −4.361 | 1.00 | 75.55 | MOL3 | O |
| ATOM | 9259 | OD2 | ASP | G | 82 | 17.232 | −53.804 | −2.485 | 1.00 | 72.12 | MOL3 | O |
| ATOM | 9260 | C | ASP | G | 82 | 12.657 | −55.227 | −2.252 | 1.00 | 56.97 | MOL3 | C |
| ATOM | 9261 | O | ASP | G | 82 | 12.586 | −56.418 | −2.579 | 1.00 | 49.48 | MOL3 | O |
| ATOM | 9262 | N | PHE | G | 83 | 11.811 | −54.666 | −1.399 | 1.00 | 57.41 | MOL3 | N |
| ATOM | 9263 | CA | PHE | G | 83 | 10.740 | −55.455 | −0.810 | 1.00 | 54.23 | MOL3 | C |
| ATOM | 9264 | CB | PHE | G | 83 | 10.170 | −54.762 | 0.431 | 1.00 | 54.67 | MOL3 | C |
| ATOM | 9265 | CG | PHE | G | 83 | 11.083 | −54.818 | 1.615 | 1.00 | 55.87 | MOL3 | C |
| ATOM | 9266 | CD1 | PHE | G | 83 | 11.510 | −53.658 | 2.235 | 1.00 | 56.89 | MOL3 | C |
| ATOM | 9267 | CD2 | PHE | G | 83 | 11.538 | −56.039 | 2.091 | 1.00 | 59.94 | MOL3 | C |
| ATOM | 9268 | CE1 | PHE | G | 83 | 12.379 | −53.715 | 3.308 | 1.00 | 63.08 | MOL3 | C |
| ATOM | 9269 | CE2 | PHE | G | 83 | 12.404 | −56.108 | 3.162 | 1.00 | 60.38 | MOL3 | C |
| ATOM | 9270 | CZ | PHE | G | 83 | 12.828 | −54.943 | 3.773 | 1.00 | 63.94 | MOL3 | C |
| ATOM | 9271 | C | PHE | G | 83 | 9.648 | −55.680 | −1.832 | 1.00 | 49.88 | MOL3 | C |
| ATOM | 9272 | O | PHE | G | 83 | 8.812 | −54.800 | −2.093 | 1.00 | 52.08 | MOL3 | O |
| ATOM | 9273 | N | ALA | G | 84 | 9.675 | −56.865 | −2.422 | 1.00 | 39.92 | MOL3 | N |
| ATOM | 9274 | CA | ALA | G | 84 | 8.693 | −57.237 | −3.427 | 1.00 | 42.71 | MOL3 | C |
| ATOM | 9275 | CB | ALA | G | 84 | 9.042 | −56.613 | −4.764 | 1.00 | 47.88 | MOL3 | C |
| ATOM | 9276 | C | ALA | G | 84 | 8.670 | −58.743 | −3.563 | 1.00 | 41.30 | MOL3 | C |
| ATOM | 9277 | O | ALA | G | 84 | 9.245 | −59.460 | −2.761 | 1.00 | 47.67 | MOL3 | O |
| ATOM | 9278 | N | THR | G | 85 | 8.006 | −59.231 | −4.588 | 1.00 | 34.38 | MOL3 | N |
| ATOM | 9279 | CA | THR | G | 85 | 7.945 | −60.661 | −4.786 | 1.00 | 36.94 | MOL3 | C |
| ATOM | 9280 | CB | THR | G | 85 | 6.519 | −61.109 | −5.157 | 1.00 | 43.40 | MOL3 | C |
| ATOM | 9281 | OG1 | THR | G | 85 | 5.602 | −60.720 | −4.119 | 1.00 | 40.46 | MOL3 | O |
| ATOM | 9282 | CG2 | THR | G | 85 | 6.478 | −62.621 | −5.370 | 1.00 | 42.50 | MOL3 | C |
| ATOM | 9283 | C | THR | G | 85 | 8.871 | −60.963 | −5.935 | 1.00 | 36.36 | MOL3 | C |
| ATOM | 9284 | O | THR | G | 85 | 8.993 | −60.147 | −6.839 | 1.00 | 46.03 | MOL3 | O |
| ATOM | 9285 | N | TYR | G | 86 | 9.513 | −62.126 | −5.914 | 1.00 | 31.26 | MOL3 | N |
| ATOM | 9286 | CA | TYR | G | 86 | 10.442 | −62.491 | −6.973 | 1.00 | 31.58 | MOL3 | C |
| ATOM | 9287 | CB | TYR | G | 86 | 11.853 | −62.590 | −6.409 | 1.00 | 26.22 | MOL3 | C |
| ATOM | 9288 | CG | TYR | G | 86 | 12.354 | −61.261 | −5.918 | 1.00 | 34.59 | MOL3 | C |
| ATOM | 9289 | CD1 | TYR | G | 86 | 12.060 | −60.816 | −4.637 | 1.00 | 35.54 | MOL3 | C |
| ATOM | 9290 | CE1 | TYR | G | 86 | 12.448 | −59.562 | −4.205 | 1.00 | 30.13 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 9291 | CD2 | TYR | G | 86 | 13.057 | −60.411 | −6.755 | 1.00 | 35.99 | MOL3 | C |
|---|---|---|---|---|---|---|---|---|---|---|---|---|
| ATOM | 9292 | CE2 | TYR | G | 86 | 13.445 | −59.151 | −6.322 | 1.00 | 42.17 | MOL3 | C |
| ATOM | 9293 | CZ | TYR | G | 86 | 13.130 | −58.738 | −5.047 | 1.00 | 33.44 | MOL3 | C |
| ATOM | 9294 | OH | TYR | G | 86 | 13.452 | −57.478 | −4.634 | 1.00 | 36.13 | MOL3 | O |
| ATOM | 9295 | C | TYR | G | 86 | 10.086 | −63.787 | −7.646 | 1.00 | 32.93 | MOL3 | C |
| ATOM | 9296 | O | TYR | G | 86 | 9.800 | −64.754 | −6.978 | 1.00 | 42.80 | MOL3 | O |
| ATOM | 9297 | N | TYR | G | 87 | 10.112 | −63.816 | −8.970 | 1.00 | 34.25 | MOL3 | N |
| ATOM | 9298 | CA | TYR | G | 87 | 9.785 | −65.035 | −9.693 | 1.00 | 38.30 | MOL3 | C |
| ATOM | 9299 | CB | TYR | G | 87 | 8.571 | −64.824 | −10.591 | 1.00 | 41.15 | MOL3 | C |
| ATOM | 9300 | CG | TYR | G | 87 | 7.252 | −64.592 | −9.903 | 1.00 | 44.49 | MOL3 | C |
| ATOM | 9301 | CD1 | TYR | G | 87 | 6.368 | −65.628 | −9.694 | 1.00 | 50.72 | MOL3 | C |
| ATOM | 9302 | CE1 | TYR | G | 87 | 5.127 | −65.399 | −9.142 | 1.00 | 56.99 | MOL3 | C |
| ATOM | 9303 | CD2 | TYR | G | 87 | 6.862 | −63.323 | −9.530 | 1.00 | 48.02 | MOL3 | C |
| ATOM | 9304 | CE2 | TYR | G | 87 | 5.630 | −63.087 | −8.977 | 1.00 | 53.20 | MOL3 | C |
| ATOM | 9305 | CZ | TYR | G | 87 | 4.763 | −64.123 | −8.784 | 1.00 | 52.52 | MOL3 | C |
| ATOM | 9306 | OH | TYR | G | 87 | 3.528 | −63.879 | −8.226 | 1.00 | 54.41 | MOL3 | O |
| ATOM | 9307 | C | TYR | G | 87 | 10.922 | −65.495 | −10.590 | 1.00 | 41.02 | MOL3 | C |
| ATOM | 9308 | O | TYR | G | 87 | 11.599 | −64.674 | −11.201 | 1.00 | 46.26 | MOL3 | O |
| ATOM | 9309 | N | CYS | G | 88 | 11.125 | −66.804 | −10.674 | 1.00 | 38.26 | MOL3 | N |
| ATOM | 9310 | CA | CYS | G | 88 | 12.130 | −67.341 | −11.563 | 1.00 | 42.99 | MOL3 | C |
| ATOM | 9311 | C | CYS | G | 88 | 11.368 | −67.897 | −12.756 | 1.00 | 41.84 | MOL3 | C |
| ATOM | 9312 | O | CYS | G | 88 | 10.178 | −68.150 | −12.654 | 1.00 | 46.96 | MOL3 | O |
| ATOM | 9313 | CB | CYS | G | 88 | 12.954 | −68.416 | −10.864 | 1.00 | 57.83 | MOL3 | C |
| ATOM | 9314 | SG | CYS | G | 88 | 12.076 | −69.701 | −9.911 | 1.00 | 83.37 | MOL3 | S |
| ATOM | 9315 | N | GLN | G | 89 | 12.018 | −68.046 | −13.902 | 1.00 | 38.75 | MOL3 | N |
| ATOM | 9316 | CA | GLN | G | 89 | 11.324 | −68.564 | −15.075 | 1.00 | 43.83 | MOL3 | C |
| ATOM | 9317 | CB | GLN | G | 89 | 10.688 | −67.432 | −15.895 | 1.00 | 40.77 | MOL3 | C |
| ATOM | 9318 | CG | GLN | G | 89 | 10.243 | −67.872 | −17.308 | 1.00 | 44.08 | MOL3 | C |
| ATOM | 9319 | CD | GLN | G | 89 | 10.165 | −66.711 | −18.290 | 1.00 | 44.65 | MOL3 | C |
| ATOM | 9320 | OE1 | GLN | G | 89 | 10.778 | −65.681 | −18.072 | 1.00 | 46.53 | MOL3 | O |
| ATOM | 9321 | NE2 | GLN | G | 89 | 9.428 | −66.882 | −19.382 | 1.00 | 45.67 | MOL3 | N |
| ATOM | 9322 | C | GLN | G | 89 | 12.290 | −69.318 | −15.958 | 1.00 | 50.40 | MOL3 | C |
| ATOM | 9323 | O | GLN | G | 89 | 13.459 | −68.950 | −16.054 | 1.00 | 54.43 | MOL3 | O |
| ATOM | 9324 | N | GLN | G | 90 | 11.798 | −70.366 | −16.611 | 1.00 | 51.12 | MOL3 | N |
| ATOM | 9325 | CA | GLN | G | 90 | 12.631 | −71.169 | −17.491 | 1.00 | 53.88 | MOL3 | C |
| ATOM | 9326 | CB | GLN | G | 90 | 12.610 | −72.645 | −17.053 | 1.00 | 54.93 | MOL3 | C |
| ATOM | 9327 | CG | GLN | G | 90 | 11.279 | −73.372 | −17.270 | 1.00 | 60.36 | MOL3 | C |
| ATOM | 9328 | CD | GLN | G | 90 | 11.121 | −73.903 | −18.687 | 1.00 | 65.13 | MOL3 | C |
| ATOM | 9329 | OE1 | GLN | G | 90 | 10.036 | −74.322 | −19.105 | 1.00 | 65.50 | MOL3 | O |
| ATOM | 9330 | NE2 | GLN | G | 90 | 12.213 | −73.893 | −19.432 | 1.00 | 71.24 | MOL3 | N |
| ATOM | 9331 | C | GLN | G | 90 | 12.056 | −71.028 | −18.878 | 1.00 | 53.56 | MOL3 | C |
| ATOM | 9332 | O | GLN | G | 90 | 10.868 | −70.755 | −19.021 | 1.00 | 50.35 | MOL3 | O |
| ATOM | 9333 | N | THR | G | 91 | 12.900 | −71.198 | −19.891 | 1.00 | 55.41 | MOL3 | N |
| ATOM | 9334 | CA | THR | G | 91 | 12.456 | −71.106 | −21.270 | 1.00 | 60.76 | MOL3 | C |
| ATOM | 9335 | CB | THR | G | 91 | 12.789 | −69.732 | −21.901 | 1.00 | 61.23 | MOL3 | C |
| ATOM | 9336 | OG1 | THR | G | 91 | 14.137 | −69.370 | −21.587 | 1.00 | 66.23 | MOL3 | O |
| ATOM | 9337 | CG2 | THR | G | 91 | 11.847 | −68.662 | −21.390 | 1.00 | 59.04 | MOL3 | C |
| ATOM | 9338 | C | THR | G | 91 | 13.098 | −72.201 | −22.101 | 1.00 | 66.38 | MOL3 | C |
| ATOM | 9339 | O | THR | G | 91 | 13.228 | −72.070 | −23.311 | 1.00 | 68.83 | MOL3 | O |
| ATOM | 9340 | N | TRP | G | 92 | 13.508 | −73.282 | −21.450 | 1.00 | 72.90 | MOL3 | N |
| ATOM | 9341 | CA | TRP | G | 92 | 14.101 | −74.391 | −22.179 | 1.00 | 82.64 | MOL3 | C |
| ATOM | 9342 | CB | TRP | G | 92 | 14.903 | −75.317 | −21.249 | 1.00 | 92.36 | MOL3 | C |
| ATOM | 9343 | CG | TRP | G | 92 | 16.135 | −75.882 | −21.919 | 1.00 | 107.39 | MOL3 | C |
| ATOM | 9344 | CD2 | TRP | G | 92 | 16.173 | −76.874 | −22.951 | 1.00 | 113.90 | MOL3 | C |
| ATOM | 9345 | CE2 | TRP | G | 92 | 17.515 | −76.985 | −23.378 | 1.00 | 116.36 | MOL3 | C |
| ATOM | 9346 | CE3 | TRP | G | 92 | 15.203 | −77.673 | −23.561 | 1.00 | 120.18 | MOL3 | C |
| ATOM | 9347 | CD1 | TRP | G | 92 | 17.424 | −75.455 | −21.762 | 1.00 | 112.31 | MOL3 | C |
| ATOM | 9348 | NE1 | TRP | G | 92 | 18.259 | −76.108 | −22.634 | 1.00 | 112.14 | MOL3 | N |
| ATOM | 9349 | CZ2 | TRP | G | 92 | 17.909 | −77.862 | −24.386 | 1.00 | 121.41 | MOL3 | C |
| ATOM | 9350 | CZ3 | TRP | G | 92 | 15.595 | −78.546 | −24.566 | 1.00 | 125.94 | MOL3 | C |
| ATOM | 9351 | CH2 | TRP | G | 92 | 16.937 | −78.632 | −24.968 | 1.00 | 126.33 | MOL3 | C |
| ATOM | 9352 | C | TRP | G | 92 | 12.985 | −75.188 | −22.852 | 1.00 | 85.04 | MOL3 | C |
| ATOM | 9353 | O | TRP | G | 92 | 12.970 | −75.333 | −24.070 | 1.00 | 86.92 | MOL3 | O |
| ATOM | 9354 | N | SER | G | 93 | 12.040 | −75.685 | −22.056 | 1.00 | 90.80 | MOL3 | N |
| ATOM | 9355 | CA | SER | G | 93 | 10.924 | −76.486 | −22.572 | 1.00 | 98.46 | MOL3 | C |
| ATOM | 9356 | CB | SER | G | 93 | 10.498 | −77.523 | −21.522 | 1.00 | 106.12 | MOL3 | C |
| ATOM | 9357 | OG | SER | G | 93 | 9.909 | −78.668 | −22.123 | 1.00 | 113.34 | MOL3 | O |
| ATOM | 9358 | C | SER | G | 93 | 9.737 | −75.602 | −22.944 | 1.00 | 98.41 | MOL3 | C |
| ATOM | 9359 | O | SER | G | 93 | 9.324 | −74.751 | −22.153 | 1.00 | 97.41 | MOL3 | O |
| ATOM | 9360 | N | ASP | G | 94 | 9.178 | −75.839 | −24.132 | 1.00 | 97.22 | MOL3 | N |
| ATOM | 9361 | CA | ASP | G | 94 | 8.076 | −75.042 | −24.657 | 1.00 | 99.78 | MOL3 | C |
| ATOM | 9362 | CB | ASP | G | 94 | 7.395 | −75.780 | −25.799 | 1.00 | 105.41 | MOL3 | C |
| ATOM | 9363 | CG | ASP | G | 94 | 7.862 | −75.274 | −27.155 | 1.00 | 113.87 | MOL3 | C |
| ATOM | 9364 | OD1 | ASP | G | 94 | 7.655 | −74.072 | −27.437 | 1.00 | 113.60 | MOL3 | O |
| ATOM | 9365 | OD2 | ASP | G | 94 | 8.445 | −76.063 | −27.932 | 1.00 | 120.61 | MOL3 | O |
| ATOM | 9366 | C | ASP | G | 94 | 7.035 | −74.443 | −23.713 | 1.00 | 100.01 | MOL3 | C |
| ATOM | 9367 | O | ASP | G | 94 | 6.713 | −73.254 | −23.829 | 1.00 | 106.52 | MOL3 | O |

TABLE 1-continued

The atomic coordinates of IL17F in complex with 496 Fab
(H32; a = 189.4; b = 189.4; c = 490.9, α, β = 90°; γ = 120°)

| ATOM | 9368 | N | PRO | G | 95 | 6.466 | −75.235 | −22.792 | 1.00 | 93.31 | MOL3 | N |
|---|---|---|---|---|---|---|---|---|---|---|---|---|
| ATOM | 9369 | CD | PRO | G | 95 | 6.356 | −76.694 | −22.678 | 1.00 | 89.29 | MOL3 | C |
| ATOM | 9370 | CA | PRO | G | 95 | 5.489 | −74.561 | −21.924 | 1.00 | 84.85 | MOL3 | C |
| ATOM | 9371 | CB | PRO | G | 95 | 4.767 | −75.711 | −21.238 | 1.00 | 77.59 | MOL3 | C |
| ATOM | 9372 | CG | PRO | G | 95 | 4.938 | −76.839 | −22.198 | 1.00 | 91.35 | MOL3 | C |
| ATOM | 9373 | C | PRO | G | 95 | 6.294 | −73.750 | −20.920 | 1.00 | 81.43 | MOL3 | C |
| ATOM | 9374 | O | PRO | G | 95 | 6.496 | −74.203 | −19.798 | 1.00 | 84.19 | MOL3 | O |
| ATOM | 9375 | N | TRP | G | 96 | 6.777 | −72.575 | −21.322 | 1.00 | 72.95 | MOL3 | N |
| ATOM | 9376 | CA | TRP | G | 96 | 7.571 | −71.760 | −20.413 | 1.00 | 66.65 | MOL3 | C |
| ATOM | 9377 | CB | TRP | G | 96 | 7.819 | −70.377 | −21.008 | 1.00 | 66.86 | MOL3 | C |
| ATOM | 9378 | CG | TRP | G | 96 | 8.524 | −70.410 | −22.314 | 1.00 | 67.77 | MOL3 | C |
| ATOM | 9379 | CD2 | TRP | G | 96 | 8.432 | −69.441 | −23.362 | 1.00 | 73.87 | MOL3 | C |
| ATOM | 9380 | CE2 | TRP | G | 96 | 9.248 | −69.889 | −24.420 | 1.00 | 72.77 | MOL3 | C |
| ATOM | 9381 | CE3 | TRP | G | 96 | 7.738 | −68.237 | −23.510 | 1.00 | 75.04 | MOL3 | C |
| ATOM | 9382 | CD1 | TRP | G | 96 | 9.373 | −71.373 | −22.758 | 1.00 | 70.29 | MOL3 | C |
| ATOM | 9383 | NE1 | TRP | G | 96 | 9.813 | −71.073 | −24.028 | 1.00 | 71.16 | MOL3 | N |
| ATOM | 9384 | CZ2 | TRP | G | 96 | 9.385 | −69.179 | −25.608 | 1.00 | 73.12 | MOL3 | C |
| ATOM | 9385 | CZ3 | TRP | G | 96 | 7.878 | −67.534 | −24.694 | 1.00 | 76.94 | MOL3 | C |
| ATOM | 9386 | CH2 | TRP | G | 96 | 8.693 | −68.006 | −25.725 | 1.00 | 74.23 | MOL3 | C |
| ATOM | 9387 | C | TRP | G | 96 | 6.847 | −71.650 | −19.073 | 1.00 | 65.18 | MOL3 | C |
| ATOM | 9388 | O | TRP | G | 96 | 5.660 | −71.319 | −19.019 | 1.00 | 66.34 | MOL3 | O |
| ATOM | 9389 | N | THR | G | 97 | 7.561 | −71.925 | −17.988 | 1.00 | 61.09 | MOL3 | N |
| ATOM | 9390 | CA | THR | G | 97 | 6.955 | −71.899 | −16.659 | 1.00 | 65.03 | MOL3 | C |
| ATOM | 9391 | CB | THR | G | 97 | 7.001 | −73.293 | −16.032 | 1.00 | 67.22 | MOL3 | C |
| ATOM | 9392 | OG1 | THR | G | 97 | 8.353 | −73.768 | −16.020 | 1.00 | 63.22 | MOL3 | O |
| ATOM | 9393 | CG2 | THR | G | 97 | 6.153 | −74.254 | −16.833 | 1.00 | 74.80 | MOL3 | C |
| ATOM | 9394 | C | THR | G | 97 | 7.585 | −70.938 | −15.664 | 1.00 | 62.36 | MOL3 | C |
| ATOM | 9395 | O | THR | G | 97 | 8.752 | −70.581 | −15.794 | 1.00 | 70.37 | MOL3 | O |
| ATOM | 9396 | N | PHE | G | 98 | 6.815 | −70.532 | −14.660 | 1.00 | 52.65 | MOL3 | N |
| ATOM | 9397 | CA | PHE | G | 98 | 7.334 | −69.622 | −13.656 | 1.00 | 54.09 | MOL3 | C |
| ATOM | 9398 | CB | PHE | G | 98 | 6.497 | −68.342 | −13.605 | 1.00 | 56.03 | MOL3 | C |
| ATOM | 9399 | CG | PHE | G | 98 | 6.612 | −67.493 | −14.836 | 1.00 | 54.73 | MOL3 | C |
| ATOM | 9400 | CD1 | PHE | G | 98 | 6.221 | −67.979 | −16.072 | 1.00 | 58.99 | MOL3 | C |
| ATOM | 9401 | CD2 | PHE | G | 98 | 7.127 | −66.224 | −14.764 | 1.00 | 49.70 | MOL3 | C |
| ATOM | 9402 | CE1 | PHE | G | 98 | 6.347 | −67.209 | −17.217 | 1.00 | 52.80 | MOL3 | C |
| ATOM | 9403 | CE2 | PHE | G | 98 | 7.252 | −65.456 | −15.905 | 1.00 | 57.24 | MOL3 | C |
| ATOM | 9404 | CZ | PHE | G | 98 | 6.860 | −65.952 | −17.133 | 1.00 | 52.09 | MOL3 | C |
| ATOM | 9405 | C | PHE | G | 98 | 7.343 | −70.273 | −12.285 | 1.00 | 56.18 | MOL3 | C |
| ATOM | 9406 | O | PHE | G | 98 | 6.818 | −71.362 | −12.095 | 1.00 | 60.20 | MOL3 | O |
| ATOM | 9407 | N | GLY | G | 99 | 7.958 | −69.599 | −11.326 | 1.00 | 59.27 | MOL3 | N |
| ATOM | 9408 | CA | GLY | G | 99 | 8.003 | −70.117 | −9.977 | 1.00 | 54.28 | MOL3 | C |
| ATOM | 9409 | C | GLY | G | 99 | 6.782 | −69.592 | −9.243 | 1.00 | 58.17 | MOL3 | C |
| ATOM | 9410 | O | GLY | G | 99 | 6.030 | −68.750 | −9.758 | 1.00 | 51.24 | MOL3 | O |
| ATOM | 9411 | N | GLN | G | 100 | 6.578 | −70.100 | −8.035 | 1.00 | 60.52 | MOL3 | N |
| ATOM | 9412 | CA | GLN | G | 100 | 5.449 | −69.696 | −7.211 | 1.00 | 58.73 | MOL3 | C |
| ATOM | 9413 | CB | GLN | G | 100 | 5.346 | −70.563 | −5.959 | 1.00 | 66.97 | MOL3 | C |
| ATOM | 9414 | CG | GLN | G | 100 | 6.680 | −71.019 | −5.412 | 1.00 | 69.67 | MOL3 | C |
| ATOM | 9415 | CD | GLN | G | 100 | 7.207 | −72.178 | −6.222 | 1.00 | 80.37 | MOL3 | C |
| ATOM | 9416 | OE1 | GLN | G | 100 | 8.397 | −72.470 | −6.213 | 1.00 | 83.56 | MOL3 | O |
| ATOM | 9417 | NE2 | GLN | G | 100 | 6.307 | −72.857 | −6.932 | 1.00 | 80.26 | MOL3 | N |
| ATOM | 9418 | C | GLN | G | 100 | 5.641 | −68.280 | −6.763 | 1.00 | 56.38 | MOL3 | C |
| ATOM | 9419 | O | GLN | G | 100 | 4.683 | −67.620 | −6.381 | 1.00 | 60.88 | MOL3 | O |
| ATOM | 9420 | N | GLY | G | 101 | 6.889 | −67.829 | −6.783 | 1.00 | 53.37 | MOL3 | N |
| ATOM | 9421 | CA | GLY | G | 101 | 7.196 | −66.480 | −6.349 | 1.00 | 53.27 | MOL3 | C |
| ATOM | 9422 | C | GLY | G | 101 | 7.527 | −66.401 | −4.866 | 1.00 | 52.19 | MOL3 | C |
| ATOM | 9423 | O | GLY | G | 101 | 6.896 | −67.059 | −4.040 | 1.00 | 54.76 | MOL3 | O |
| ATOM | 9424 | N | THR | G | 102 | 8.517 | −65.581 | −4.533 | 1.00 | 51.37 | MOL3 | N |
| ATOM | 9425 | CA | THR | G | 102 | 8.963 | −65.395 | −3.155 | 1.00 | 48.52 | MOL3 | C |
| ATOM | 9426 | CB | THR | G | 102 | 10.475 | −65.654 | −3.026 | 1.00 | 47.16 | MOL3 | C |
| ATOM | 9427 | OG1 | THR | G | 102 | 10.760 | −67.011 | −3.386 | 1.00 | 45.24 | MOL3 | O |
| ATOM | 9428 | CG2 | THR | G | 102 | 10.947 | −65.366 | −1.613 | 1.00 | 28.54 | MOL3 | C |
| ATOM | 9429 | C | THR | G | 102 | 8.708 | −63.965 | −2.715 | 1.00 | 49.06 | MOL3 | C |
| ATOM | 9430 | O | THR | G | 102 | 9.189 | −63.026 | −3.341 | 1.00 | 50.78 | MOL3 | O |
| ATOM | 9431 | N | LYS | G | 103 | 7.959 | −63.794 | −1.638 | 1.00 | 47.88 | MOL3 | N |
| ATOM | 9432 | CA | LYS | G | 103 | 7.681 | −62.456 | −1.168 | 1.00 | 53.43 | MOL3 | C |
| ATOM | 9433 | CB | LYS | G | 103 | 6.246 | −62.359 | −0.628 | 1.00 | 53.18 | MOL3 | C |
| ATOM | 9434 | CG | LYS | G | 103 | 5.942 | −60.998 | −0.003 | 1.00 | 63.25 | MOL3 | C |
| ATOM | 9435 | CD | LYS | G | 103 | 4.625 | −60.396 | −0.499 | 1.00 | 78.01 | MOL3 | C |
| ATOM | 9436 | CE | LYS | G | 103 | 3.422 | −60.787 | 0.370 | 1.00 | 85.65 | MOL3 | C |
| ATOM | 9437 | NZ | LYS | G | 103 | 2.142 | −60.134 | −0.074 | 1.00 | 86.23 | MOL3 | N |
| ATOM | 9438 | C | LYS | G | 103 | 8.667 | −62.078 | −0.079 | 1.00 | 52.90 | MOL3 | C |
| ATOM | 9439 | O | LYS | G | 103 | 8.808 | −62.803 | 0.898 | 1.00 | 55.67 | MOL3 | O |
| ATOM | 9440 | N | VAL | G | 104 | 9.362 | −60.958 | −0.257 | 1.00 | 48.13 | MOL3 | N |
| ATOM | 9441 | CA | VAL | G | 104 | 10.302 | −60.488 | 0.749 | 1.00 | 46.61 | MOL3 | C |
| ATOM | 9442 | CB | VAL | G | 104 | 11.600 | −59.944 | 0.151 | 1.00 | 44.34 | MOL3 | C |
| ATOM | 9443 | CG1 | VAL | G | 104 | 12.285 | −59.072 | 1.173 | 1.00 | 47.16 | MOL3 | C |
| ATOM | 9444 | CG2 | VAL | G | 104 | 12.527 | −61.087 | −0.236 | 1.00 | 34.69 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 9445 | C | VAL | G | 104 | 9.620 | −59.361 | 1.478 | 1.00 | 51.75 | MOL3 | C |
|---|---|---|---|---|---|---|---|---|---|---|---|---|
| ATOM | 9446 | O | VAL | G | 104 | 9.178 | −58.398 | 0.850 | 1.00 | 56.13 | MOL3 | O |
| ATOM | 9447 | N | GLU | G | 105 | 9.550 | −59.485 | 2.802 | 1.00 | 56.30 | MOL3 | N |
| ATOM | 9448 | CA | GLU | G | 105 | 8.883 | −58.508 | 3.657 | 1.00 | 62.68 | MOL3 | C |
| ATOM | 9449 | CB | GLU | G | 105 | 7.687 | −59.188 | 4.331 | 1.00 | 68.61 | MOL3 | C |
| ATOM | 9450 | CG | GLU | G | 105 | 6.761 | −59.913 | 3.345 | 1.00 | 81.12 | MOL3 | C |
| ATOM | 9451 | CD | GLU | G | 105 | 5.877 | −60.980 | 4.000 | 1.00 | 89.16 | MOL3 | C |
| ATOM | 9452 | OE1 | GLU | G | 105 | 6.429 | −61.894 | 4.665 | 1.00 | 87.13 | MOL3 | O |
| ATOM | 9453 | OE2 | GLU | G | 105 | 4.631 | −60.906 | 3.836 | 1.00 | 90.53 | MOL3 | O |
| ATOM | 9454 | C | GLU | G | 105 | 9.846 | −57.972 | 4.708 | 1.00 | 61.84 | MOL3 | C |
| ATOM | 9455 | O | GLU | G | 105 | 10.789 | −58.659 | 5.087 | 1.00 | 60.52 | MOL3 | O |
| ATOM | 9456 | N | ILE | G | 106 | 9.595 | −56.756 | 5.185 | 1.00 | 63.70 | MOL3 | N |
| ATOM | 9457 | CA | ILE | G | 106 | 10.457 | −56.123 | 6.180 | 1.00 | 66.29 | MOL3 | C |
| ATOM | 9458 | CB | ILE | G | 106 | 10.163 | −54.609 | 6.272 | 1.00 | 75.24 | MOL3 | C |
| ATOM | 9459 | CG2 | ILE | G | 106 | 8.792 | −54.358 | 6.907 | 1.00 | 73.40 | MOL3 | C |
| ATOM | 9460 | CG1 | ILE | G | 106 | 11.240 | −53.929 | 7.109 | 1.00 | 83.07 | MOL3 | C |
| ATOM | 9461 | CD1 | ILE | G | 106 | 10.937 | −52.475 | 7.395 | 1.00 | 94.36 | MOL3 | C |
| ATOM | 9462 | C | ILE | G | 106 | 10.298 | −56.724 | 7.570 | 1.00 | 63.00 | MOL3 | C |
| ATOM | 9463 | O | ILE | G | 106 | 9.198 | −56.736 | 8.115 | 1.00 | 62.22 | MOL3 | O |
| ATOM | 9464 | N | LYS | G | 107 | 11.397 | −57.215 | 8.148 | 1.00 | 61.89 | MOL3 | N |
| ATOM | 9465 | CA | LYS | G | 107 | 11.348 | −57.803 | 9.490 | 1.00 | 58.32 | MOL3 | C |
| ATOM | 9466 | CB | LYS | G | 107 | 12.560 | −58.703 | 9.756 | 1.00 | 64.24 | MOL3 | C |
| ATOM | 9467 | CG | LYS | G | 107 | 12.556 | −59.302 | 11.164 | 1.00 | 76.68 | MOL3 | C |
| ATOM | 9468 | CD | LYS | G | 107 | 12.882 | −60.809 | 11.191 | 1.00 | 84.55 | MOL3 | C |
| ATOM | 9469 | CE | LYS | G | 107 | 12.665 | −61.387 | 12.607 | 1.00 | 92.40 | MOL3 | C |
| ATOM | 9470 | NZ | LYS | G | 107 | 13.074 | −62.821 | 12.794 | 1.00 | 93.06 | MOL3 | N |
| ATOM | 9471 | C | LYS | G | 107 | 11.290 | −56.737 | 10.561 | 1.00 | 50.25 | MOL3 | C |
| ATOM | 9472 | O | LYS | G | 107 | 11.867 | −55.674 | 10.412 | 1.00 | 53.80 | MOL3 | O |
| ATOM | 9473 | N | ARG | G | 108 | 10.576 | −57.008 | 11.639 | 1.00 | 50.03 | MOL3 | N |
| ATOM | 9474 | CA | ARG | G | 108 | 10.494 | −56.038 | 12.717 | 1.00 | 55.61 | MOL3 | C |
| ATOM | 9475 | CB | ARG | G | 108 | 9.475 | −54.948 | 12.375 | 1.00 | 57.58 | MOL3 | C |
| ATOM | 9476 | CG | ARG | G | 108 | 8.027 | −55.399 | 12.345 | 1.00 | 61.93 | MOL3 | C |
| ATOM | 9477 | CD | ARG | G | 108 | 7.352 | −55.151 | 13.680 | 1.00 | 64.48 | MOL3 | C |
| ATOM | 9478 | NE | ARG | G | 108 | 6.746 | −53.827 | 13.804 | 1.00 | 67.68 | MOL3 | N |
| ATOM | 9479 | CZ | ARG | G | 108 | 6.291 | −53.321 | 14.950 | 1.00 | 72.94 | MOL3 | C |
| ATOM | 9480 | NH1 | ARG | G | 108 | 6.386 | −54.027 | 16.072 | 1.00 | 69.80 | MOL3 | N |
| ATOM | 9481 | NH2 | ARG | G | 108 | 5.721 | −52.119 | 14.980 | 1.00 | 70.24 | MOL3 | N |
| ATOM | 9482 | C | ARG | G | 108 | 10.175 | −56.658 | 14.080 | 1.00 | 60.90 | MOL3 | C |
| ATOM | 9483 | O | ARG | G | 108 | 9.930 | −57.867 | 14.210 | 1.00 | 65.41 | MOL3 | O |
| ATOM | 9484 | N | THR | G | 109 | 10.211 | −55.817 | 15.105 | 1.00 | 62.58 | MOL3 | N |
| ATOM | 9485 | CA | THR | G | 109 | 9.940 | −56.237 | 16.471 | 1.00 | 60.47 | MOL3 | C |
| ATOM | 9486 | CB | THR | G | 109 | 10.003 | −55.043 | 17.404 | 1.00 | 60.71 | MOL3 | C |
| ATOM | 9487 | OG1 | THR | G | 109 | 9.235 | −55.311 | 18.580 | 1.00 | 73.35 | MOL3 | O |
| ATOM | 9488 | CG2 | THR | G | 109 | 9.408 | −53.842 | 16.721 | 1.00 | 66.48 | MOL3 | C |
| ATOM | 9489 | C | THR | G | 109 | 8.543 | −56.816 | 16.562 | 1.00 | 59.71 | MOL3 | C |
| ATOM | 9490 | O | THR | G | 109 | 7.607 | −56.240 | 16.026 | 1.00 | 58.88 | MOL3 | O |
| ATOM | 9491 | N | ASP | G | 110 | 8.393 | −57.943 | 17.251 | 1.00 | 61.73 | MOL3 | N |
| ATOM | 9492 | CA | ASP | G | 110 | 7.075 | −58.564 | 17.399 | 1.00 | 60.21 | MOL3 | C |
| ATOM | 9493 | CB | ASP | G | 110 | 7.203 | −59.886 | 18.156 | 1.00 | 65.63 | MOL3 | C |
| ATOM | 9494 | CG | ASP | G | 110 | 8.011 | −60.914 | 17.387 | 1.00 | 75.02 | MOL3 | C |
| ATOM | 9495 | OD1 | ASP | G | 110 | 9.028 | −60.522 | 16.767 | 1.00 | 80.50 | MOL3 | O |
| ATOM | 9496 | OD2 | ASP | G | 110 | 7.637 | −62.109 | 17.407 | 1.00 | 75.96 | MOL3 | O |
| ATOM | 9497 | C | ASP | G | 110 | 6.102 | −57.638 | 18.127 | 1.00 | 54.74 | MOL3 | C |
| ATOM | 9498 | O | ASP | G | 110 | 6.510 | −56.783 | 18.921 | 1.00 | 47.51 | MOL3 | O |
| ATOM | 9499 | N | ALA | G | 111 | 4.815 | −57.788 | 17.832 | 1.00 | 49.84 | MOL3 | N |
| ATOM | 9500 | CA | ALA | G | 111 | 3.798 | −56.966 | 18.481 | 1.00 | 53.97 | MOL3 | C |
| ATOM | 9501 | CB | ALA | G | 111 | 3.636 | −55.640 | 17.783 | 1.00 | 51.21 | MOL3 | C |
| ATOM | 9502 | C | ALA | G | 111 | 2.473 | −57.699 | 18.512 | 1.00 | 58.54 | MOL3 | C |
| ATOM | 9503 | O | ALA | G | 111 | 2.041 | −58.288 | 17.517 | 1.00 | 53.64 | MOL3 | O |
| ATOM | 9504 | N | ALA | G | 112 | 1.833 | −57.663 | 19.676 | 1.00 | 62.23 | MOL3 | N |
| ATOM | 9505 | CA | ALA | G | 112 | 0.564 | −58.345 | 19.866 | 1.00 | 57.12 | MOL3 | C |
| ATOM | 9506 | CB | ALA | G | 112 | 0.285 | −58.531 | 21.339 | 1.00 | 60.78 | MOL3 | C |
| ATOM | 9507 | C | ALA | G | 112 | −0.572 | −57.595 | 19.226 | 1.00 | 56.03 | MOL3 | C |
| ATOM | 9508 | O | ALA | G | 112 | −0.569 | −56.362 | 19.147 | 1.00 | 61.24 | MOL3 | O |
| ATOM | 9509 | N | PRO | G | 113 | −1.573 | −58.338 | 18.761 | 1.00 | 51.66 | MOL3 | N |
| ATOM | 9510 | CD | PRO | G | 113 | −1.613 | −59.802 | 18.801 | 1.00 | 51.71 | MOL3 | C |
| ATOM | 9511 | CA | PRO | G | 113 | −2.769 | −57.824 | 18.108 | 1.00 | 52.64 | MOL3 | C |
| ATOM | 9512 | CB | PRO | G | 113 | −3.399 | −59.073 | 17.523 | 1.00 | 52.21 | MOL3 | C |
| ATOM | 9513 | CG | PRO | G | 113 | −3.086 | −60.069 | 18.534 | 1.00 | 52.02 | MOL3 | C |
| ATOM | 9514 | C | PRO | G | 113 | −3.695 | −57.165 | 19.087 | 1.00 | 55.64 | MOL3 | C |
| ATOM | 9515 | O | PRO | G | 113 | −3.695 | −57.483 | 20.272 | 1.00 | 58.00 | MOL3 | O |
| ATOM | 9516 | N | THR | G | 114 | −4.496 | −56.250 | 18.570 | 1.00 | 60.16 | MOL3 | N |
| ATOM | 9517 | CA | THR | G | 114 | −5.474 | −55.537 | 19.368 | 1.00 | 64.05 | MOL3 | C |
| ATOM | 9518 | CB | THR | G | 114 | −5.299 | −54.054 | 19.174 | 1.00 | 62.25 | MOL3 | C |
| ATOM | 9519 | OG1 | THR | G | 114 | −3.938 | −53.718 | 19.479 | 1.00 | 69.10 | MOL3 | O |
| ATOM | 9520 | CG2 | THR | G | 114 | −6.260 | −53.285 | 20.055 | 1.00 | 54.79 | MOL3 | C |
| ATOM | 9521 | C | THR | G | 114 | −6.823 | −55.980 | 18.833 | 1.00 | 66.27 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 9522 | O | THR | G | 114 | −7.265 | −55.517 | 17.785 | 1.00 | 68.25 | MOL3 | O |
|---|---|---|---|---|---|---|---|---|---|---|---|---|
| ATOM | 9523 | N | VAL | G | 115 | −7.474 | −56.888 | 19.550 | 1.00 | 66.96 | MOL3 | N |
| ATOM | 9524 | CA | VAL | G | 115 | −8.755 | −57.412 | 19.098 | 1.00 | 65.05 | MOL3 | C |
| ATOM | 9525 | CB | VAL | G | 115 | −8.996 | −58.818 | 19.640 | 1.00 | 60.15 | MOL3 | C |
| ATOM | 9526 | CG1 | VAL | G | 115 | −10.030 | −59.531 | 18.791 | 1.00 | 52.83 | MOL3 | C |
| ATOM | 9527 | CG2 | VAL | G | 115 | −7.697 | −59.579 | 19.652 | 1.00 | 64.42 | MOL3 | C |
| ATOM | 9528 | C | VAL | G | 115 | −9.960 | −56.563 | 19.450 | 1.00 | 67.57 | MOL3 | C |
| ATOM | 9529 | O | VAL | G | 115 | −9.931 | −55.750 | 20.378 | 1.00 | 69.52 | MOL3 | O |
| ATOM | 9530 | N | SER | G | 116 | −11.028 | −56.776 | 18.690 | 1.00 | 69.63 | MOL3 | N |
| ATOM | 9531 | CA | SER | G | 116 | −12.285 | −56.062 | 18.870 | 1.00 | 70.90 | MOL3 | C |
| ATOM | 9532 | CB | SER | G | 116 | −12.180 | −54.701 | 18.203 | 1.00 | 75.40 | MOL3 | C |
| ATOM | 9533 | OG | SER | G | 116 | −11.305 | −54.796 | 17.089 | 1.00 | 82.22 | MOL3 | O |
| ATOM | 9534 | C | SER | G | 116 | −13.398 | −56.885 | 18.231 | 1.00 | 67.95 | MOL3 | C |
| ATOM | 9535 | O | SER | G | 116 | −13.283 | −57.307 | 17.083 | 1.00 | 63.09 | MOL3 | O |
| ATOM | 9536 | N | ILE | G | 117 | −14.466 | −57.129 | 18.981 | 1.00 | 67.87 | MOL3 | N |
| ATOM | 9537 | CA | ILE | G | 117 | −15.580 | −57.916 | 18.461 | 1.00 | 69.73 | MOL3 | C |
| ATOM | 9538 | CB | ILE | G | 117 | −15.907 | −59.111 | 19.385 | 1.00 | 70.07 | MOL3 | C |
| ATOM | 9539 | CG2 | ILE | G | 117 | −16.750 | −58.648 | 20.557 | 1.00 | 69.94 | MOL3 | C |
| ATOM | 9540 | CG1 | ILE | G | 117 | −16.697 | −60.170 | 18.619 | 1.00 | 70.23 | MOL3 | C |
| ATOM | 9541 | CD1 | ILE | G | 117 | −16.683 | −61.525 | 19.300 | 1.00 | 70.26 | MOL3 | C |
| ATOM | 9542 | C | ILE | G | 117 | −16.833 | −57.054 | 18.311 | 1.00 | 71.08 | MOL3 | C |
| ATOM | 9543 | O | ILE | G | 117 | −17.148 | −56.227 | 19.174 | 1.00 | 69.98 | MOL3 | O |
| ATOM | 9544 | N | PHE | G | 118 | −17.549 | −57.259 | 17.211 | 1.00 | 70.99 | MOL3 | N |
| ATOM | 9545 | CA | PHE | G | 118 | −18.750 | −56.487 | 16.922 | 1.00 | 69.44 | MOL3 | C |
| ATOM | 9546 | CB | PHE | G | 118 | −18.530 | −55.614 | 15.681 | 1.00 | 62.42 | MOL3 | C |
| ATOM | 9547 | CG | PHE | G | 118 | −17.466 | −54.575 | 15.846 | 1.00 | 54.81 | MOL3 | C |
| ATOM | 9548 | CD1 | PHE | G | 118 | −16.128 | −54.925 | 15.839 | 1.00 | 55.60 | MOL3 | C |
| ATOM | 9549 | CD2 | PHE | G | 118 | −17.805 | −53.242 | 16.011 | 1.00 | 51.96 | MOL3 | C |
| ATOM | 9550 | CE1 | PHE | G | 118 | −15.142 | −53.959 | 15.992 | 1.00 | 54.63 | MOL3 | C |
| ATOM | 9551 | CE2 | PHE | G | 118 | −16.834 | −52.270 | 16.164 | 1.00 | 49.00 | MOL3 | C |
| ATOM | 9552 | CZ | PHE | G | 118 | −15.495 | −52.632 | 16.154 | 1.00 | 52.65 | MOL3 | C |
| ATOM | 9553 | C | PHE | G | 118 | −19.996 | −57.332 | 16.686 | 1.00 | 72.36 | MOL3 | C |
| ATOM | 9554 | O | PHE | G | 118 | −20.001 | −58.243 | 15.850 | 1.00 | 71.00 | MOL3 | O |
| ATOM | 9555 | N | PRO | G | 119 | −21.083 | −57.014 | 17.407 | 1.00 | 75.07 | MOL3 | N |
| ATOM | 9556 | CD | PRO | G | 119 | −21.103 | −55.985 | 18.455 | 1.00 | 76.76 | MOL3 | C |
| ATOM | 9557 | CA | PRO | G | 119 | −22.382 | −57.694 | 17.332 | 1.00 | 73.75 | MOL3 | C |
| ATOM | 9558 | CB | PRO | G | 119 | −23.150 | −57.126 | 18.519 | 1.00 | 75.13 | MOL3 | C |
| ATOM | 9559 | CG | PRO | G | 119 | −22.062 | −56.590 | 19.432 | 1.00 | 80.98 | MOL3 | C |
| ATOM | 9560 | C | PRO | G | 119 | −23.027 | −57.282 | 16.036 | 1.00 | 70.57 | MOL3 | C |
| ATOM | 9561 | O | PRO | G | 119 | −22.787 | −56.185 | 15.554 | 1.00 | 73.68 | MOL3 | O |
| ATOM | 9562 | N | PRO | G | 120 | −23.857 | −58.150 | 15.457 | 1.00 | 69.35 | MOL3 | N |
| ATOM | 9563 | CD | PRO | G | 120 | −24.086 | −59.537 | 15.888 | 1.00 | 74.69 | MOL3 | C |
| ATOM | 9564 | CA | PRO | G | 120 | −24.552 | −57.875 | 14.199 | 1.00 | 69.18 | MOL3 | C |
| ATOM | 9565 | CB | PRO | G | 120 | −25.495 | −59.055 | 14.060 | 1.00 | 67.07 | MOL3 | C |
| ATOM | 9566 | CG | PRO | G | 120 | −24.688 | −60.165 | 14.633 | 1.00 | 76.37 | MOL3 | C |
| ATOM | 9567 | C | PRO | G | 120 | −25.294 | −56.559 | 14.209 | 1.00 | 73.59 | MOL3 | C |
| ATOM | 9568 | O | PRO | G | 120 | −25.978 | −56.215 | 15.171 | 1.00 | 77.28 | MOL3 | O |
| ATOM | 9569 | N | SER | G | 121 | −25.145 | −55.815 | 13.127 | 1.00 | 80.20 | MOL3 | N |
| ATOM | 9570 | CA | SER | G | 121 | −25.808 | −54.532 | 13.000 | 1.00 | 86.41 | MOL3 | C |
| ATOM | 9571 | CB | SER | G | 121 | −25.455 | −53.930 | 11.640 | 1.00 | 85.97 | MOL3 | C |
| ATOM | 9572 | OG | SER | G | 121 | −26.166 | −52.727 | 11.424 | 1.00 | 92.58 | MOL3 | O |
| ATOM | 9573 | C | SER | G | 121 | −27.322 | −54.730 | 13.110 | 1.00 | 88.90 | MOL3 | C |
| ATOM | 9574 | O | SER | G | 121 | −27.882 | −55.582 | 12.422 | 1.00 | 90.54 | MOL3 | O |
| ATOM | 9575 | N | SER | G | 122 | −27.979 | −53.963 | 13.977 | 1.00 | 88.80 | MOL3 | N |
| ATOM | 9576 | CA | SER | G | 122 | −29.427 | −54.064 | 14.126 | 1.00 | 88.92 | MOL3 | C |
| ATOM | 9577 | CB | SER | G | 122 | −29.949 | −52.912 | 14.982 | 1.00 | 87.53 | MOL3 | C |
| ATOM | 9578 | OG | SER | G | 122 | −29.744 | −51.671 | 14.324 | 1.00 | 81.66 | MOL3 | O |
| ATOM | 9579 | C | SER | G | 122 | −30.018 | −53.959 | 12.721 | 1.00 | 91.86 | MOL3 | C |
| ATOM | 9580 | O | SER | G | 122 | −30.960 | −54.682 | 12.368 | 1.00 | 95.70 | MOL3 | O |
| ATOM | 9581 | N | GLU | G | 123 | −29.448 | −53.049 | 11.929 | 1.00 | 88.58 | MOL3 | N |
| ATOM | 9582 | CA | GLU | G | 123 | −29.878 | −52.829 | 10.552 | 1.00 | 90.03 | MOL3 | C |
| ATOM | 9583 | CB | GLU | G | 123 | −28.981 | −51.806 | 9.859 | 1.00 | 93.16 | MOL3 | C |
| ATOM | 9584 | CG | GLU | G | 123 | −29.097 | −50.381 | 10.358 | 1.00 | 104.12 | MOL3 | C |
| ATOM | 9585 | CD | GLU | G | 123 | −28.124 | −49.442 | 9.649 | 1.00 | 107.92 | MOL3 | C |
| ATOM | 9586 | OE1 | GLU | G | 123 | −28.038 | −49.505 | 8.399 | 1.00 | 107.64 | MOL3 | O |
| ATOM | 9587 | OE2 | GLU | G | 123 | −27.451 | −48.641 | 10.339 | 1.00 | 106.83 | MOL3 | O |
| ATOM | 9588 | C | GLU | G | 123 | −29.784 | −54.122 | 9.766 | 1.00 | 89.02 | MOL3 | C |
| ATOM | 9589 | O | GLU | G | 123 | −30.599 | −54.395 | 8.887 | 1.00 | 90.23 | MOL3 | O |
| ATOM | 9590 | N | GLN | G | 124 | −28.772 | −54.919 | 10.074 | 1.00 | 87.71 | MOL3 | N |
| ATOM | 9591 | CA | GLN | G | 124 | −28.590 | −56.166 | 9.359 | 1.00 | 85.87 | MOL3 | C |
| ATOM | 9592 | CB | GLN | G | 124 | −27.158 | −56.700 | 9.549 | 1.00 | 83.04 | MOL3 | C |
| ATOM | 9593 | CG | GLN | G | 124 | −26.679 | −57.575 | 8.380 | 1.00 | 72.78 | MOL3 | C |
| ATOM | 9594 | CD | GLN | G | 124 | −25.579 | −58.571 | 8.745 | 1.00 | 67.34 | MOL3 | C |
| ATOM | 9595 | OE1 | GLN | G | 124 | −25.236 | −59.432 | 7.941 | 1.00 | 64.50 | MOL3 | O |
| ATOM | 9596 | NE2 | GLN | G | 124 | −25.029 | −58.458 | 9.952 | 1.00 | 62.37 | MOL3 | N |
| ATOM | 9597 | C | GLN | G | 124 | −29.624 | −57.200 | 9.804 | 1.00 | 88.09 | MOL3 | C |
| ATOM | 9598 | O | GLN | G | 124 | −30.260 | −57.840 | 8.969 | 1.00 | 88.19 | MOL3 | O |

TABLE 1-continued

The atomic coordinates of IL17F in complex with 496 Fab
(H32; a = 189.4; b = 189.4; c = 490.9, α, β = 90°; γ = 120°)

| ATOM | 9599 | N | LEU | G | 125 | −29.800 | −57.345 | 11.116 | 1.00 | 88.35 | MOL3 | N |
|---|---|---|---|---|---|---|---|---|---|---|---|---|
| ATOM | 9600 | CA | LEU | G | 125 | −30.749 | −58.302 | 11.664 | 1.00 | 88.57 | MOL3 | C |
| ATOM | 9601 | CB | LEU | G | 125 | −30.919 | −58.060 | 13.154 | 1.00 | 81.47 | MOL3 | C |
| ATOM | 9602 | CG | LEU | G | 125 | −29.566 | −58.007 | 13.846 | 1.00 | 80.53 | MOL3 | C |
| ATOM | 9603 | CD1 | LEU | G | 125 | −29.715 | −58.053 | 15.361 | 1.00 | 81.15 | MOL3 | C |
| ATOM | 9604 | CD2 | LEU | G | 125 | −28.758 | −59.180 | 13.353 | 1.00 | 82.76 | MOL3 | C |
| ATOM | 9605 | C | LEU | G | 125 | −32.089 | −58.185 | 10.964 | 1.00 | 94.05 | MOL3 | C |
| ATOM | 9606 | O | LEU | G | 125 | −32.764 | −59.186 | 10.721 | 1.00 | 99.06 | MOL3 | O |
| ATOM | 9607 | N | THR | G | 126 | −32.470 | −56.957 | 10.635 | 1.00 | 94.75 | MOL3 | N |
| ATOM | 9608 | CA | THR | G | 126 | −33.729 | −56.724 | 9.955 | 1.00 | 98.01 | MOL3 | C |
| ATOM | 9609 | CB | THR | G | 126 | −34.145 | −55.249 | 10.056 | 1.00 | 99.91 | MOL3 | C |
| ATOM | 9610 | OG1 | THR | G | 126 | −33.243 | −54.445 | 9.290 | 1.00 | 106.32 | MOL3 | O |
| ATOM | 9611 | CG2 | THR | G | 126 | −34.118 | −54.792 | 11.511 | 1.00 | 96.26 | MOL3 | C |
| ATOM | 9612 | C | THR | G | 126 | −33.588 | −57.123 | 8.488 | 1.00 | 98.92 | MOL3 | C |
| ATOM | 9613 | O | THR | G | 126 | −33.844 | −56.334 | 7.581 | 1.00 | 100.22 | MOL3 | O |
| ATOM | 9614 | N | SER | G | 127 | −33.166 | −58.360 | 8.268 | 1.00 | 100.96 | MOL3 | N |
| ATOM | 9615 | CA | SER | G | 127 | −33.001 | −58.884 | 6.925 | 1.00 | 102.45 | MOL3 | C |
| ATOM | 9616 | CB | SER | G | 127 | −31.882 | −58.136 | 6.206 | 1.00 | 101.05 | MOL3 | C |
| ATOM | 9617 | OG | SER | G | 127 | −32.089 | −58.172 | 4.807 | 1.00 | 101.36 | MOL3 | O |
| ATOM | 9618 | C | SER | G | 127 | −32.701 | −60.385 | 6.991 | 1.00 | 105.77 | MOL3 | C |
| ATOM | 9619 | O | SER | G | 127 | −32.175 | −60.974 | 6.044 | 1.00 | 106.86 | MOL3 | O |
| ATOM | 9620 | N | GLY | G | 128 | −33.046 | −60.994 | 8.126 | 1.00 | 107.93 | MOL3 | N |
| ATOM | 9621 | CA | GLY | G | 128 | −32.845 | −62.422 | 8.321 | 1.00 | 105.90 | MOL3 | C |
| ATOM | 9622 | C | GLY | G | 128 | −31.399 | −62.877 | 8.319 | 1.00 | 104.35 | MOL3 | C |
| ATOM | 9623 | O | GLY | G | 128 | −31.117 | −64.069 | 8.144 | 1.00 | 106.10 | MOL3 | O |
| ATOM | 9624 | N | GLY | G | 129 | −30.482 | −61.933 | 8.515 | 1.00 | 98.25 | MOL3 | N |
| ATOM | 9625 | CA | GLY | G | 129 | −29.072 | −62.272 | 8.531 | 1.00 | 92.35 | MOL3 | C |
| ATOM | 9626 | C | GLY | G | 129 | −28.356 | −61.561 | 9.655 | 1.00 | 88.02 | MOL3 | C |
| ATOM | 9627 | O | GLY | G | 129 | −28.850 | −60.549 | 10.158 | 1.00 | 84.86 | MOL3 | O |
| ATOM | 9628 | N | ALA | G | 130 | −27.201 | −62.092 | 10.051 | 1.00 | 83.24 | MOL3 | N |
| ATOM | 9629 | CA | ALA | G | 130 | −26.406 | −61.500 | 11.124 | 1.00 | 78.99 | MOL3 | C |
| ATOM | 9630 | CB | ALA | G | 130 | −26.986 | −61.877 | 12.471 | 1.00 | 81.34 | MOL3 | C |
| ATOM | 9631 | C | ALA | G | 130 | −24.957 | −61.949 | 11.037 | 1.00 | 75.59 | MOL3 | C |
| ATOM | 9632 | O | ALA | G | 130 | −24.675 | −63.136 | 10.889 | 1.00 | 77.64 | MOL3 | O |
| ATOM | 9633 | N | SER | G | 131 | −24.043 | −60.988 | 11.134 | 1.00 | 72.17 | MOL3 | N |
| ATOM | 9634 | CA | SER | G | 131 | −22.609 | −61.264 | 11.054 | 1.00 | 70.55 | MOL3 | C |
| ATOM | 9635 | CB | SER | G | 131 | −22.006 | −60.599 | 9.805 | 1.00 | 72.57 | MOL3 | C |
| ATOM | 9636 | OG | SER | G | 131 | −22.620 | −61.021 | 8.601 | 1.00 | 74.24 | MOL3 | O |
| ATOM | 9637 | C | SER | G | 131 | −21.864 | −60.719 | 12.266 | 1.00 | 67.32 | MOL3 | C |
| ATOM | 9638 | O | SER | G | 131 | −22.089 | −59.584 | 12.682 | 1.00 | 68.97 | MOL3 | O |
| ATOM | 9639 | N | VAL | G | 132 | −20.967 | −61.514 | 12.827 | 1.00 | 61.90 | MOL3 | N |
| ATOM | 9640 | CA | VAL | G | 132 | −20.195 | −61.036 | 13.952 | 1.00 | 64.01 | MOL3 | C |
| ATOM | 9641 | CB | VAL | G | 132 | −20.099 | −62.062 | 15.040 | 1.00 | 70.94 | MOL3 | C |
| ATOM | 9642 | CG1 | VAL | G | 132 | −19.661 | −61.380 | 16.337 | 1.00 | 74.41 | MOL3 | C |
| ATOM | 9643 | CG2 | VAL | G | 132 | −21.425 | −62.771 | 15.180 | 1.00 | 77.72 | MOL3 | C |
| ATOM | 9644 | C | VAL | G | 132 | −18.803 | −60.775 | 13.435 | 1.00 | 63.54 | MOL3 | C |
| ATOM | 9645 | O | VAL | G | 132 | −18.135 | −61.678 | 12.939 | 1.00 | 64.96 | MOL3 | O |
| ATOM | 9646 | N | VAL | G | 133 | −18.364 | −59.533 | 13.557 | 1.00 | 62.84 | MOL3 | N |
| ATOM | 9647 | CA | VAL | G | 133 | −17.059 | −59.143 | 13.068 | 1.00 | 61.23 | MOL3 | C |
| ATOM | 9648 | CB | VAL | G | 133 | −17.155 | −57.818 | 12.311 | 1.00 | 62.34 | MOL3 | C |
| ATOM | 9649 | CG1 | VAL | G | 133 | −15.788 | −57.429 | 11.772 | 1.00 | 62.81 | MOL3 | C |
| ATOM | 9650 | CG2 | VAL | G | 133 | −18.183 | −57.937 | 11.193 | 1.00 | 60.96 | MOL3 | C |
| ATOM | 9651 | C | VAL | G | 133 | −16.029 | −58.990 | 14.168 | 1.00 | 61.49 | MOL3 | C |
| ATOM | 9652 | O | VAL | G | 133 | −16.300 | −58.410 | 15.218 | 1.00 | 61.66 | MOL3 | O |
| ATOM | 9653 | N | CYS | G | 134 | −14.836 | −59.503 | 13.905 | 1.00 | 61.34 | MOL3 | N |
| ATOM | 9654 | CA | CYS | G | 134 | −13.753 | −59.426 | 14.857 | 1.00 | 63.20 | MOL3 | C |
| ATOM | 9655 | C | CYS | G | 134 | −12.486 | −58.942 | 14.146 | 1.00 | 61.23 | MOL3 | C |
| ATOM | 9656 | O | CYS | G | 134 | −12.020 | −59.574 | 13.194 | 1.00 | 55.75 | MOL3 | O |
| ATOM | 9657 | CB | CYS | G | 134 | −13.536 | −60.800 | 15.477 | 1.00 | 66.10 | MOL3 | C |
| ATOM | 9658 | SG | CYS | G | 134 | −12.545 | −60.717 | 16.988 | 1.00 | 79.72 | MOL3 | S |
| ATOM | 9659 | N | PHE | G | 135 | −11.949 | −57.811 | 14.606 | 1.00 | 60.15 | MOL3 | N |
| ATOM | 9660 | CA | PHE | G | 135 | −10.740 | −57.226 | 14.030 | 1.00 | 58.08 | MOL3 | C |
| ATOM | 9661 | CB | PHE | G | 135 | −10.891 | −55.709 | 13.881 | 1.00 | 52.88 | MOL3 | C |
| ATOM | 9662 | CG | PHE | G | 135 | −11.871 | −55.295 | 12.824 | 1.00 | 59.57 | MOL3 | C |
| ATOM | 9663 | CD1 | PHE | G | 135 | −12.689 | −54.190 | 13.014 | 1.00 | 59.21 | MOL3 | C |
| ATOM | 9664 | CD2 | PHE | G | 135 | −11.975 | −56.001 | 11.635 | 1.00 | 60.35 | MOL3 | C |
| ATOM | 9665 | CE1 | PHE | G | 135 | −13.596 | −53.796 | 12.036 | 1.00 | 57.13 | MOL3 | C |
| ATOM | 9666 | CE2 | PHE | G | 135 | −12.880 | −55.610 | 10.653 | 1.00 | 58.75 | MOL3 | C |
| ATOM | 9667 | CZ | PHE | G | 135 | −13.689 | −54.507 | 10.857 | 1.00 | 56.82 | MOL3 | C |
| ATOM | 9668 | C | PHE | G | 135 | −9.526 | −57.504 | 14.902 | 1.00 | 59.96 | MOL3 | C |
| ATOM | 9669 | O | PHE | G | 135 | −9.570 | −57.320 | 16.122 | 1.00 | 62.07 | MOL3 | O |
| ATOM | 9670 | N | LEU | G | 136 | −8.451 | −57.968 | 14.273 | 1.00 | 58.93 | MOL3 | N |
| ATOM | 9671 | CA | LEU | G | 136 | −7.194 | −58.232 | 14.973 | 1.00 | 58.93 | MOL3 | C |
| ATOM | 9672 | CB | LEU | G | 136 | −6.729 | −59.685 | 14.772 | 1.00 | 57.75 | MOL3 | C |
| ATOM | 9673 | CG | LEU | G | 136 | −7.605 | −60.857 | 15.231 | 1.00 | 54.84 | MOL3 | C |
| ATOM | 9674 | CD1 | LEU | G | 136 | −8.895 | −60.870 | 14.426 | 1.00 | 58.56 | MOL3 | C |
| ATOM | 9675 | CD2 | LEU | G | 136 | −6.863 | −62.172 | 15.036 | 1.00 | 49.67 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 9676 | C | LEU | G | 136 | −6.231 | −57.277 | 14.274 | 1.00 | 59.50 | MOL3 | C |
|------|------|------|-----|---|-----|--------|---------|--------|------|--------|------|---|
| ATOM | 9677 | O | LEU | G | 136 | −5.652 | −57.607 | 13.240 | 1.00 | 62.27 | MOL3 | O |
| ATOM | 9678 | N | ASN | G | 137 | −6.059 | −56.089 | 14.835 | 1.00 | 56.71 | MOL3 | N |
| ATOM | 9679 | CA | ASN | G | 137 | −5.215 | −55.095 | 14.200 | 1.00 | 55.72 | MOL3 | C |
| ATOM | 9680 | CB | ASN | G | 137 | −5.887 | −53.716 | 14.259 | 1.00 | 59.86 | MOL3 | C |
| ATOM | 9681 | CG | ASN | G | 137 | −7.166 | −53.642 | 13.447 | 1.00 | 61.03 | MOL3 | C |
| ATOM | 9682 | OD1 | ASN | G | 137 | −7.364 | −54.407 | 12.506 | 1.00 | 64.04 | MOL3 | O |
| ATOM | 9683 | ND2 | ASN | G | 137 | −8.033 | −52.698 | 13.797 | 1.00 | 62.22 | MOL3 | N |
| ATOM | 9684 | C | ASN | G | 137 | −3.795 | −54.929 | 14.690 | 1.00 | 57.23 | MOL3 | C |
| ATOM | 9685 | O | ASN | G | 137 | −3.467 | −55.182 | 15.845 | 1.00 | 59.63 | MOL3 | O |
| ATOM | 9686 | N | ASN | G | 138 | −2.966 | −54.463 | 13.767 | 1.00 | 62.41 | MOL3 | N |
| ATOM | 9687 | CA | ASN | G | 138 | −1.561 | −54.162 | 13.996 | 1.00 | 64.31 | MOL3 | C |
| ATOM | 9688 | CB | ASN | G | 138 | −1.441 | −52.794 | 14.650 | 1.00 | 68.13 | MOL3 | C |
| ATOM | 9689 | CG | ASN | G | 138 | −2.342 | −51.783 | 14.014 | 1.00 | 72.04 | MOL3 | C |
| ATOM | 9690 | OD1 | ASN | G | 138 | −2.252 | −51.524 | 12.811 | 1.00 | 72.39 | MOL3 | O |
| ATOM | 9691 | ND2 | ASN | G | 138 | −3.236 | −51.207 | 14.813 | 1.00 | 80.31 | MOL3 | N |
| ATOM | 9692 | C | ASN | G | 138 | −0.773 | −55.158 | 14.813 | 1.00 | 59.99 | MOL3 | C |
| ATOM | 9693 | O | ASN | G | 138 | −0.503 | −54.926 | 15.988 | 1.00 | 64.26 | MOL3 | O |
| ATOM | 9694 | N | PHE | G | 139 | −0.383 | −56.258 | 14.192 | 1.00 | 53.94 | MOL3 | N |
| ATOM | 9695 | CA | PHE | G | 139 | 0.403 | −57.244 | 14.909 | 1.00 | 59.73 | MOL3 | C |
| ATOM | 9696 | CB | PHE | G | 139 | −0.486 | −58.416 | 15.366 | 1.00 | 60.06 | MOL3 | C |
| ATOM | 9697 | CG | PHE | G | 139 | −1.159 | −59.163 | 14.248 | 1.00 | 54.71 | MOL3 | C |
| ATOM | 9698 | CD1 | PHE | G | 139 | −0.525 | −60.218 | 13.623 | 1.00 | 50.69 | MOL3 | C |
| ATOM | 9699 | CD2 | PHE | G | 139 | −2.436 | −58.814 | 13.835 | 1.00 | 57.51 | MOL3 | C |
| ATOM | 9700 | CE1 | PHE | G | 139 | −1.155 | −60.914 | 12.607 | 1.00 | 55.12 | MOL3 | C |
| ATOM | 9701 | CE2 | PHE | G | 139 | −3.070 | −59.507 | 12.819 | 1.00 | 56.29 | MOL3 | C |
| ATOM | 9702 | CZ | PHE | G | 139 | −2.428 | −60.557 | 12.206 | 1.00 | 52.91 | MOL3 | C |
| ATOM | 9703 | C | PHE | G | 139 | 1.582 | −57.733 | 14.076 | 1.00 | 60.66 | MOL3 | C |
| ATOM | 9704 | O | PHE | G | 139 | 1.694 | −57.394 | 12.900 | 1.00 | 68.95 | MOL3 | O |
| ATOM | 9705 | N | TYR | G | 140 | 2.473 | −58.502 | 14.697 | 1.00 | 56.57 | MOL3 | N |
| ATOM | 9706 | CA | TYR | G | 140 | 3.643 | −59.036 | 14.017 | 1.00 | 51.98 | MOL3 | C |
| ATOM | 9707 | CB | TYR | G | 140 | 4.698 | −57.956 | 13.795 | 1.00 | 59.30 | MOL3 | C |
| ATOM | 9708 | CG | TYR | G | 140 | 5.811 | −58.435 | 12.897 | 1.00 | 62.50 | MOL3 | C |
| ATOM | 9709 | CD1 | TYR | G | 140 | 5.587 | −58.621 | 11.547 | 1.00 | 66.09 | MOL3 | C |
| ATOM | 9710 | CE1 | TYR | G | 140 | 6.548 | −59.154 | 10.722 | 1.00 | 67.77 | MOL3 | C |
| ATOM | 9711 | CD2 | TYR | G | 140 | 7.049 | −58.789 | 13.404 | 1.00 | 65.14 | MOL3 | C |
| ATOM | 9712 | CE2 | TYR | G | 140 | 8.026 | −59.325 | 12.575 | 1.00 | 69.26 | MOL3 | C |
| ATOM | 9713 | CZ | TYR | G | 140 | 7.758 | −59.506 | 11.235 | 1.00 | 65.47 | MOL3 | C |
| ATOM | 9714 | OH | TYR | G | 140 | 8.673 | −60.074 | 10.392 | 1.00 | 65.00 | MOL3 | O |
| ATOM | 9715 | C | TYR | G | 140 | 4.264 | −60.132 | 14.855 | 1.00 | 53.24 | MOL3 | C |
| ATOM | 9716 | O | TYR | G | 140 | 4.395 | −59.993 | 16.074 | 1.00 | 56.49 | MOL3 | O |
| ATOM | 9717 | N | PRO | G | 141 | 4.680 | −61.230 | 14.216 | 1.00 | 51.56 | MOL3 | N |
| ATOM | 9718 | CD | PRO | G | 141 | 5.455 | −62.287 | 14.880 | 1.00 | 50.59 | MOL3 | C |
| ATOM | 9719 | CA | PRO | G | 141 | 4.595 | −61.482 | 12.777 | 1.00 | 57.08 | MOL3 | C |
| ATOM | 9720 | CB | PRO | G | 141 | 5.491 | −62.701 | 12.585 | 1.00 | 59.79 | MOL3 | C |
| ATOM | 9721 | CG | PRO | G | 141 | 5.371 | −63.406 | 13.887 | 1.00 | 57.48 | MOL3 | C |
| ATOM | 9722 | C | PRO | G | 141 | 3.178 | −61.709 | 12.277 | 1.00 | 60.51 | MOL3 | C |
| ATOM | 9723 | O | PRO | G | 141 | 2.216 | −61.594 | 13.041 | 1.00 | 55.20 | MOL3 | O |
| ATOM | 9724 | N | LYS | G | 142 | 3.071 | −62.034 | 10.989 | 1.00 | 64.09 | MOL3 | N |
| ATOM | 9725 | CA | LYS | G | 142 | 1.786 | −62.239 | 10.325 | 1.00 | 68.66 | MOL3 | C |
| ATOM | 9726 | CB | LYS | G | 142 | 1.971 | −62.222 | 8.803 | 1.00 | 71.39 | MOL3 | C |
| ATOM | 9727 | CG | LYS | G | 142 | 3.050 | −63.186 | 8.328 | 1.00 | 77.11 | MOL3 | C |
| ATOM | 9728 | CD | LYS | G | 142 | 3.074 | −63.350 | 6.822 | 1.00 | 74.18 | MOL3 | C |
| ATOM | 9729 | CE | LYS | G | 142 | 4.323 | −64.109 | 6.405 | 1.00 | 78.10 | MOL3 | C |
| ATOM | 9730 | NZ | LYS | G | 142 | 4.537 | −65.339 | 7.227 | 1.00 | 78.29 | MOL3 | N |
| ATOM | 9731 | C | LYS | G | 142 | 1.083 | −63.524 | 10.709 | 1.00 | 68.55 | MOL3 | C |
| ATOM | 9732 | O | LYS | G | 142 | −0.146 | −63.600 | 10.676 | 1.00 | 67.33 | MOL3 | O |
| ATOM | 9733 | N | ASP | G | 143 | 1.855 | −64.546 | 11.050 | 1.00 | 72.24 | MOL3 | N |
| ATOM | 9734 | CA | ASP | G | 143 | 1.252 | −65.825 | 11.417 | 1.00 | 78.88 | MOL3 | C |
| ATOM | 9735 | CB | ASP | G | 143 | 2.325 | −66.898 | 11.693 | 1.00 | 95.87 | MOL3 | C |
| ATOM | 9736 | CG | ASP | G | 143 | 3.157 | −67.246 | 10.454 | 1.00 | 111.13 | MOL3 | C |
| ATOM | 9737 | OD1 | ASP | G | 143 | 2.596 | −67.846 | 9.505 | 1.00 | 117.55 | MOL3 | O |
| ATOM | 9738 | OD2 | ASP | G | 143 | 4.372 | −66.919 | 10.429 | 1.00 | 115.57 | MOL3 | O |
| ATOM | 9739 | C | ASP | G | 143 | 0.413 | −65.639 | 12.664 | 1.00 | 72.28 | MOL3 | C |
| ATOM | 9740 | O | ASP | G | 143 | 0.928 | −65.311 | 13.726 | 1.00 | 74.20 | MOL3 | O |
| ATOM | 9741 | N | ILE | G | 144 | −0.891 | −65.817 | 12.532 | 1.00 | 68.45 | MOL3 | N |
| ATOM | 9742 | CA | ILE | G | 144 | −1.772 | −65.703 | 13.685 | 1.00 | 66.27 | MOL3 | C |
| ATOM | 9743 | CB | ILE | G | 144 | −2.317 | −64.286 | 13.903 | 1.00 | 65.85 | MOL3 | C |
| ATOM | 9744 | CG2 | ILE | G | 144 | −3.636 | −64.111 | 13.172 | 1.00 | 62.97 | MOL3 | C |
| ATOM | 9745 | CG1 | ILE | G | 144 | −2.594 | −64.078 | 15.390 | 1.00 | 66.78 | MOL3 | C |
| ATOM | 9746 | CD1 | ILE | G | 144 | −3.305 | −62.784 | 15.706 | 1.00 | 70.79 | MOL3 | C |
| ATOM | 9747 | C | ILE | G | 144 | −2.945 | −66.624 | 13.450 | 1.00 | 66.44 | MOL3 | C |
| ATOM | 9748 | O | ILE | G | 144 | −3.213 | −67.026 | 12.325 | 1.00 | 69.05 | MOL3 | O |
| ATOM | 9749 | N | ASN | G | 145 | −3.654 | −66.969 | 14.509 | 1.00 | 70.48 | MOL3 | N |
| ATOM | 9750 | CA | ASN | G | 145 | −4.778 | −67.865 | 14.340 | 1.00 | 75.42 | MOL3 | C |
| ATOM | 9751 | CB | ASN | G | 145 | −4.360 | −69.294 | 14.683 | 1.00 | 84.58 | MOL3 | C |
| ATOM | 9752 | CG | ASN | G | 145 | −5.480 | −70.279 | 14.481 | 1.00 | 95.33 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 9753 | OD1 | ASN | G | 145 | −6.085 | −70.332 | 13.405 | 1.00 | 104.55 | MOL3 | O |
|---|---|---|---|---|---|---|---|---|---|---|---|---|
| ATOM | 9754 | ND2 | ASN | G | 145 | −5.773 | −71.068 | 15.514 | 1.00 | 99.08 | MOL3 | N |
| ATOM | 9755 | C | ASN | G | 145 | −5.990 | −67.456 | 15.163 | 1.00 | 75.42 | MOL3 | C |
| ATOM | 9756 | O | ASN | G | 145 | −5.891 | −67.205 | 16.368 | 1.00 | 77.45 | MOL3 | O |
| ATOM | 9757 | N | VAL | G | 146 | −7.137 | −67.386 | 14.495 | 1.00 | 73.39 | MOL3 | N |
| ATOM | 9758 | CA | VAL | G | 146 | −8.383 | −67.004 | 15.150 | 1.00 | 75.23 | MOL3 | C |
| ATOM | 9759 | CB | VAL | G | 146 | −9.191 | −65.996 | 14.326 | 1.00 | 75.12 | MOL3 | C |
| ATOM | 9760 | CG1 | VAL | G | 146 | −9.664 | −66.641 | 13.031 | 1.00 | 79.48 | MOL3 | C |
| ATOM | 9761 | CG2 | VAL | G | 146 | −10.395 | −65.538 | 15.122 | 1.00 | 77.82 | MOL3 | C |
| ATOM | 9762 | C | VAL | G | 146 | −9.294 | −68.202 | 15.365 | 1.00 | 80.03 | MOL3 | C |
| ATOM | 9763 | O | VAL | G | 146 | −9.412 | −69.075 | 14.496 | 1.00 | 83.39 | MOL3 | O |
| ATOM | 9764 | N | LYS | G | 147 | −9.943 | −68.232 | 16.525 | 1.00 | 81.58 | MOL3 | N |
| ATOM | 9765 | CA | LYS | G | 147 | −10.869 | −69.307 | 16.862 | 1.00 | 81.06 | MOL3 | C |
| ATOM | 9766 | CB | LYS | G | 147 | −10.309 | −70.171 | 18.001 | 1.00 | 88.49 | MOL3 | C |
| ATOM | 9767 | CG | LYS | G | 147 | −11.250 | −71.290 | 18.466 | 1.00 | 95.72 | MOL3 | C |
| ATOM | 9768 | CD | LYS | G | 147 | −10.867 | −71.867 | 19.848 | 1.00 | 103.44 | MOL3 | C |
| ATOM | 9769 | CE | LYS | G | 147 | −9.612 | −72.749 | 19.802 | 1.00 | 109.76 | MOL3 | C |
| ATOM | 9770 | NZ | LYS | G | 147 | −9.194 | −73.266 | 21.148 | 1.00 | 107.54 | MOL3 | N |
| ATOM | 9771 | C | LYS | G | 147 | −12.182 | −68.671 | 17.303 | 1.00 | 79.53 | MOL3 | C |
| ATOM | 9772 | O | LYS | G | 147 | −12.181 | −67.742 | 18.122 | 1.00 | 73.12 | MOL3 | O |
| ATOM | 9773 | N | TRP | G | 148 | −13.292 | −69.150 | 16.739 | 1.00 | 79.00 | MOL3 | N |
| ATOM | 9774 | CA | TRP | G | 148 | −14.620 | −68.642 | 17.104 | 1.00 | 79.95 | MOL3 | C |
| ATOM | 9775 | CB | TRP | G | 148 | −15.516 | −68.452 | 15.884 | 1.00 | 83.56 | MOL3 | C |
| ATOM | 9776 | CG | TRP | G | 148 | −15.232 | −67.229 | 15.076 | 1.00 | 90.17 | MOL3 | C |
| ATOM | 9777 | CD2 | TRP | G | 148 | −15.864 | −65.950 | 15.205 | 1.00 | 90.02 | MOL3 | C |
| ATOM | 9778 | CE2 | TRP | G | 148 | −15.314 | −65.112 | 14.220 | 1.00 | 88.30 | MOL3 | C |
| ATOM | 9779 | CE3 | TRP | G | 148 | −16.839 | −65.436 | 16.057 | 1.00 | 91.12 | MOL3 | C |
| ATOM | 9780 | CD1 | TRP | G | 148 | −14.344 | −67.113 | 14.048 | 1.00 | 90.30 | MOL3 | C |
| ATOM | 9781 | NE1 | TRP | G | 148 | −14.389 | −65.845 | 13.526 | 1.00 | 90.45 | MOL3 | N |
| ATOM | 9782 | CZ2 | TRP | G | 148 | −15.708 | −63.790 | 14.063 | 1.00 | 87.46 | MOL3 | C |
| ATOM | 9783 | CZ3 | TRP | G | 148 | −17.226 | −64.125 | 15.898 | 1.00 | 91.84 | MOL3 | C |
| ATOM | 9784 | CH2 | TRP | G | 148 | −16.662 | −63.317 | 14.910 | 1.00 | 88.91 | MOL3 | C |
| ATOM | 9785 | C | TRP | G | 148 | −15.322 | −69.612 | 18.045 | 1.00 | 82.25 | MOL3 | C |
| ATOM | 9786 | O | TRP | G | 148 | −15.204 | −70.833 | 17.895 | 1.00 | 84.18 | MOL3 | O |
| ATOM | 9787 | N | LYS | G | 149 | −16.065 | −69.069 | 19.007 | 1.00 | 83.17 | MOL3 | N |
| ATOM | 9788 | CA | LYS | G | 149 | −16.788 | −69.896 | 19.980 | 1.00 | 82.26 | MOL3 | C |
| ATOM | 9789 | CB | LYS | G | 149 | −16.024 | −69.975 | 21.315 | 1.00 | 79.77 | MOL3 | C |
| ATOM | 9790 | CG | LYS | G | 149 | −14.836 | −70.934 | 21.359 | 1.00 | 78.20 | MOL3 | C |
| ATOM | 9791 | CD | LYS | G | 149 | −14.230 | −70.986 | 22.760 | 1.00 | 75.18 | MOL3 | C |
| ATOM | 9792 | CE | LYS | G | 149 | −13.063 | −71.955 | 22.824 | 1.00 | 79.05 | MOL3 | C |
| ATOM | 9793 | NZ | LYS | G | 149 | −12.535 | −72.081 | 24.209 | 1.00 | 84.73 | MOL3 | N |
| ATOM | 9794 | C | LYS | G | 149 | −18.205 | −69.405 | 20.281 | 1.00 | 83.68 | MOL3 | C |
| ATOM | 9795 | O | LYS | G | 149 | −18.392 | −68.315 | 20.830 | 1.00 | 80.33 | MOL3 | O |
| ATOM | 9796 | N | ILE | G | 150 | −19.196 | −70.220 | 19.921 | 1.00 | 86.68 | MOL3 | N |
| ATOM | 9797 | CA | ILE | G | 150 | −20.598 | −69.904 | 20.189 | 1.00 | 87.86 | MOL3 | C |
| ATOM | 9798 | CB | ILE | G | 150 | −21.532 | −70.330 | 19.037 | 1.00 | 86.02 | MOL3 | C |
| ATOM | 9799 | CG2 | ILE | G | 150 | −22.933 | −69.878 | 19.337 | 1.00 | 87.62 | MOL3 | C |
| ATOM | 9800 | CG1 | ILE | G | 150 | −21.097 | −69.705 | 17.715 | 1.00 | 86.63 | MOL3 | C |
| ATOM | 9801 | CD1 | ILE | G | 150 | −22.057 | −69.992 | 16.563 | 1.00 | 81.81 | MOL3 | C |
| ATOM | 9802 | C | ILE | G | 150 | −21.015 | −70.694 | 21.434 | 1.00 | 90.38 | MOL3 | C |
| ATOM | 9803 | O | ILE | G | 150 | −21.044 | −71.933 | 21.424 | 1.00 | 90.62 | MOL3 | O |
| ATOM | 9804 | N | ASP | G | 151 | −21.339 | −69.977 | 22.503 | 1.00 | 92.97 | MOL3 | N |
| ATOM | 9805 | CA | ASP | G | 151 | −21.737 | −70.612 | 23.754 | 1.00 | 97.87 | MOL3 | C |
| ATOM | 9806 | CB | ASP | G | 151 | −23.142 | −71.224 | 23.629 | 1.00 | 105.42 | MOL3 | C |
| ATOM | 9807 | CG | ASP | G | 151 | −24.238 | −70.283 | 24.127 | 1.00 | 109.22 | MOL3 | C |
| ATOM | 9808 | OD1 | ASP | G | 151 | −24.107 | −69.782 | 25.267 | 1.00 | 112.65 | MOL3 | O |
| ATOM | 9809 | OD2 | ASP | G | 151 | −25.227 | −70.050 | 23.393 | 1.00 | 106.71 | MOL3 | O |
| ATOM | 9810 | C | ASP | G | 151 | −20.741 | −71.668 | 24.234 | 1.00 | 97.93 | MOL3 | C |
| ATOM | 9811 | O | ASP | G | 151 | −21.128 | −72.669 | 24.839 | 1.00 | 99.58 | MOL3 | O |
| ATOM | 9812 | N | GLY | G | 152 | −19.459 | −71.442 | 23.959 | 1.00 | 96.41 | MOL3 | N |
| ATOM | 9813 | CA | GLY | G | 152 | −18.439 | −72.374 | 24.408 | 1.00 | 95.92 | MOL3 | C |
| ATOM | 9814 | C | GLY | G | 152 | −17.883 | −73.377 | 23.412 | 1.00 | 96.33 | MOL3 | C |
| ATOM | 9815 | O | GLY | G | 152 | −16.823 | −73.962 | 23.662 | 1.00 | 98.05 | MOL3 | O |
| ATOM | 9816 | N | SER | G | 153 | −18.577 | −73.598 | 22.297 | 1.00 | 95.12 | MOL3 | N |
| ATOM | 9817 | CA | SER | G | 153 | −18.091 | −74.548 | 21.297 | 1.00 | 96.65 | MOL3 | C |
| ATOM | 9818 | CB | SER | G | 153 | −19.213 | −75.502 | 20.858 | 1.00 | 100.75 | MOL3 | C |
| ATOM | 9819 | OG | SER | G | 153 | −19.102 | −76.754 | 21.525 | 1.00 | 103.57 | MOL3 | O |
| ATOM | 9820 | C | SER | G | 153 | −17.466 | −73.878 | 20.074 | 1.00 | 94.68 | MOL3 | C |
| ATOM | 9821 | O | SER | G | 153 | −17.938 | −72.850 | 19.591 | 1.00 | 92.19 | MOL3 | O |
| ATOM | 9822 | N | GLU | G | 154 | −16.393 | −74.481 | 19.584 | 1.00 | 94.33 | MOL3 | N |
| ATOM | 9823 | CA | GLU | G | 154 | −15.666 | −73.973 | 18.431 | 1.00 | 94.79 | MOL3 | C |
| ATOM | 9824 | CB | GLU | G | 154 | −14.354 | −74.758 | 18.301 | 1.00 | 102.83 | MOL3 | C |
| ATOM | 9825 | CG | GLU | G | 154 | −13.459 | −74.392 | 17.127 | 1.00 | 110.04 | MOL3 | C |
| ATOM | 9826 | CD | GLU | G | 154 | −12.185 | −75.219 | 17.110 | 1.00 | 114.65 | MOL3 | C |
| ATOM | 9827 | OE1 | GLU | G | 154 | −12.284 | −76.463 | 17.013 | 1.00 | 115.83 | MOL3 | O |
| ATOM | 9828 | OE2 | GLU | G | 154 | −11.087 | −74.627 | 17.199 | 1.00 | 118.09 | MOL3 | O |
| ATOM | 9829 | C | GLU | G | 154 | −16.479 | −74.061 | 17.135 | 1.00 | 94.30 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 9830 | O | GLU | G | 154 | −17.040 | −75.112 | 16.806 | 1.00 | 95.73 | MOL3 | O |
|---|---|---|---|---|---|---|---|---|---|---|---|---|
| ATOM | 9831 | N | ARG | G | 155 | −16.549 | −72.947 | 16.410 | 1.00 | 92.64 | MOL3 | N |
| ATOM | 9832 | CA | ARG | G | 155 | −17.266 | −72.905 | 15.139 | 1.00 | 93.70 | MOL3 | C |
| ATOM | 9833 | CB | ARG | G | 155 | −18.348 | −71.823 | 15.160 | 1.00 | 100.45 | MOL3 | C |
| ATOM | 9834 | CG | ARG | G | 155 | −19.171 | −71.729 | 13.872 | 1.00 | 109.67 | MOL3 | C |
| ATOM | 9835 | CD | ARG | G | 155 | −19.914 | −73.029 | 13.582 | 1.00 | 123.25 | MOL3 | C |
| ATOM | 9836 | NE | ARG | G | 155 | −20.850 | −72.903 | 12.463 | 1.00 | 134.78 | MOL3 | N |
| ATOM | 9837 | CZ | ARG | G | 155 | −21.639 | −73.884 | 12.024 | 1.00 | 138.84 | MOL3 | C |
| ATOM | 9838 | NH1 | ARG | G | 155 | −21.613 | −75.078 | 12.608 | 1.00 | 138.39 | MOL3 | N |
| ATOM | 9839 | NH2 | ARG | G | 155 | −22.459 | −73.672 | 11.000 | 1.00 | 139.22 | MOL3 | N |
| ATOM | 9840 | C | ARG | G | 155 | −16.260 | −72.600 | 14.041 | 1.00 | 91.55 | MOL3 | C |
| ATOM | 9841 | O | ARG | G | 155 | −15.385 | −71.748 | 14.215 | 1.00 | 92.19 | MOL3 | O |
| ATOM | 9842 | N | GLN | G | 156 | −16.376 | −73.288 | 12.912 | 1.00 | 87.81 | MOL3 | N |
| ATOM | 9843 | CA | GLN | G | 156 | −15.440 | −73.056 | 11.830 | 1.00 | 90.55 | MOL3 | C |
| ATOM | 9844 | CB | GLN | G | 156 | −14.591 | −74.308 | 11.624 | 1.00 | 95.83 | MOL3 | C |
| ATOM | 9845 | CG | GLN | G | 156 | −14.291 | −75.037 | 12.923 | 1.00 | 100.09 | MOL3 | C |
| ATOM | 9846 | CD | GLN | G | 156 | −13.026 | −75.863 | 12.854 | 1.00 | 102.50 | MOL3 | C |
| ATOM | 9847 | OE1 | GLN | G | 156 | −12.863 | −76.711 | 11.973 | 1.00 | 103.44 | MOL3 | O |
| ATOM | 9848 | NE2 | GLN | G | 156 | −12.119 | −75.619 | 13.791 | 1.00 | 102.22 | MOL3 | N |
| ATOM | 9849 | C | GLN | G | 156 | −16.169 | −72.689 | 10.551 | 1.00 | 91.14 | MOL3 | C |
| ATOM | 9850 | O | GLN | G | 156 | −15.755 | −71.786 | 9.824 | 1.00 | 93.38 | MOL3 | O |
| ATOM | 9851 | N | ASN | G | 157 | −17.264 | −73.389 | 10.290 | 1.00 | 92.22 | MOL3 | N |
| ATOM | 9852 | CA | ASN | G | 157 | −18.072 | −73.167 | 9.098 | 1.00 | 93.67 | MOL3 | C |
| ATOM | 9853 | CB | ASN | G | 157 | −19.184 | −74.217 | 9.050 | 1.00 | 103.01 | MOL3 | C |
| ATOM | 9854 | CG | ASN | G | 157 | −19.000 | −75.313 | 10.104 | 1.00 | 113.70 | MOL3 | C |
| ATOM | 9855 | OD1 | ASN | G | 157 | −18.963 | −75.041 | 11.310 | 1.00 | 116.52 | MOL3 | O |
| ATOM | 9856 | ND2 | ASN | G | 157 | −18.879 | −76.558 | 9.650 | 1.00 | 120.16 | MOL3 | N |
| ATOM | 9857 | C | ASN | G | 157 | −18.690 | −71.775 | 9.124 | 1.00 | 91.09 | MOL3 | C |
| ATOM | 9858 | O | ASN | G | 157 | −19.125 | −71.302 | 10.172 | 1.00 | 90.64 | MOL3 | O |
| ATOM | 9859 | N | GLY | G | 158 | −18.733 | −71.119 | 7.971 | 1.00 | 88.90 | MOL3 | N |
| ATOM | 9860 | CA | GLY | G | 158 | −19.320 | −69.794 | 7.915 | 1.00 | 85.15 | MOL3 | C |
| ATOM | 9861 | C | GLY | G | 158 | −18.383 | −68.697 | 8.376 | 1.00 | 83.29 | MOL3 | C |
| ATOM | 9862 | O | GLY | G | 158 | −18.819 | −67.627 | 8.795 | 1.00 | 84.35 | MOL3 | O |
| ATOM | 9863 | N | VAL | G | 159 | −17.086 | −68.955 | 8.312 | 1.00 | 80.65 | MOL3 | N |
| ATOM | 9864 | CA | VAL | G | 159 | −16.131 | −67.943 | 8.715 | 1.00 | 77.65 | MOL3 | C |
| ATOM | 9865 | CB | VAL | G | 159 | −15.233 | −68.440 | 9.841 | 1.00 | 79.21 | MOL3 | C |
| ATOM | 9866 | CG1 | VAL | G | 159 | −14.099 | −67.454 | 10.057 | 1.00 | 82.28 | MOL3 | C |
| ATOM | 9867 | CG2 | VAL | G | 159 | −16.051 | −68.590 | 11.113 | 1.00 | 76.09 | MOL3 | C |
| ATOM | 9868 | C | VAL | G | 159 | −15.270 | −67.503 | 7.542 | 1.00 | 76.70 | MOL3 | C |
| ATOM | 9869 | O | VAL | G | 159 | −14.730 | −68.332 | 6.805 | 1.00 | 78.83 | MOL3 | O |
| ATOM | 9870 | N | LEU | G | 160 | −15.166 | −66.191 | 7.361 | 1.00 | 72.58 | MOL3 | N |
| ATOM | 9871 | CA | LEU | G | 160 | −14.370 | −65.636 | 6.278 | 1.00 | 69.53 | MOL3 | C |
| ATOM | 9872 | CB | LEU | G | 160 | −15.273 | −64.953 | 5.251 | 1.00 | 65.42 | MOL3 | C |
| ATOM | 9873 | CG | LEU | G | 160 | −15.965 | −65.936 | 4.300 | 1.00 | 67.82 | MOL3 | C |
| ATOM | 9874 | CD1 | LEU | G | 160 | −16.960 | −65.220 | 3.396 | 1.00 | 68.08 | MOL3 | C |
| ATOM | 9875 | CD2 | LEU | G | 160 | −14.904 | −66.629 | 3.458 | 1.00 | 73.53 | MOL3 | C |
| ATOM | 9876 | C | LEU | G | 160 | −13.318 | −64.669 | 6.795 | 1.00 | 70.51 | MOL3 | C |
| ATOM | 9877 | O | LEU | G | 160 | −13.617 | −63.708 | 7.510 | 1.00 | 77.01 | MOL3 | O |
| ATOM | 9878 | N | ASN | G | 161 | −12.073 | −64.930 | 6.430 | 1.00 | 66.58 | MOL3 | N |
| ATOM | 9879 | CA | ASN | G | 161 | −11.001 | −64.076 | 6.881 | 1.00 | 67.48 | MOL3 | C |
| ATOM | 9880 | CB | ASN | G | 161 | −10.018 | −64.905 | 7.679 | 1.00 | 70.89 | MOL3 | C |
| ATOM | 9881 | CG | ASN | G | 161 | −10.684 | −65.600 | 8.832 | 1.00 | 75.10 | MOL3 | C |
| ATOM | 9882 | OD1 | ASN | G | 161 | −11.721 | −65.146 | 9.317 | 1.00 | 77.22 | MOL3 | O |
| ATOM | 9883 | ND2 | ASN | G | 161 | −10.097 | −66.699 | 9.291 | 1.00 | 78.58 | MOL3 | N |
| ATOM | 9884 | C | ASN | G | 161 | −10.300 | −63.327 | 5.764 | 1.00 | 67.68 | MOL3 | C |
| ATOM | 9885 | O | ASN | G | 161 | −10.274 | −63.770 | 4.618 | 1.00 | 68.83 | MOL3 | O |
| ATOM | 9886 | N | SER | G | 162 | −9.748 | −62.173 | 6.113 | 1.00 | 65.86 | MOL3 | N |
| ATOM | 9887 | CA | SER | G | 162 | −9.045 | −61.348 | 5.156 | 1.00 | 65.92 | MOL3 | C |
| ATOM | 9888 | CB | SER | G | 162 | −9.997 | −60.323 | 4.550 | 1.00 | 65.97 | MOL3 | C |
| ATOM | 9889 | OG | SER | G | 162 | −9.422 | −59.716 | 3.404 | 1.00 | 78.43 | MOL3 | O |
| ATOM | 9890 | C | SER | G | 162 | −7.907 | −60.648 | 5.878 | 1.00 | 67.24 | MOL3 | C |
| ATOM | 9891 | O | SER | G | 162 | −8.121 | −60.003 | 6.909 | 1.00 | 70.91 | MOL3 | O |
| ATOM | 9892 | N | TRP | G | 163 | −6.698 | −60.789 | 5.338 | 1.00 | 66.24 | MOL3 | N |
| ATOM | 9893 | CA | TRP | G | 163 | −5.502 | −60.181 | 5.920 | 1.00 | 64.80 | MOL3 | C |
| ATOM | 9894 | CB | TRP | G | 163 | −4.408 | −61.248 | 6.071 | 1.00 | 68.16 | MOL3 | C |
| ATOM | 9895 | CG | TRP | G | 163 | −4.822 | −62.514 | 6.795 | 1.00 | 76.12 | MOL3 | C |
| ATOM | 9896 | CD2 | TRP | G | 163 | −5.513 | −63.643 | 6.235 | 1.00 | 80.83 | MOL3 | C |
| ATOM | 9897 | CE2 | TRP | G | 163 | −5.652 | −64.603 | 7.264 | 1.00 | 83.42 | MOL3 | C |
| ATOM | 9898 | CE3 | TRP | G | 163 | −6.025 | −63.937 | 4.966 | 1.00 | 82.68 | MOL3 | C |
| ATOM | 9899 | CD1 | TRP | G | 163 | −4.582 | −62.830 | 8.104 | 1.00 | 80.00 | MOL3 | C |
| ATOM | 9900 | NE1 | TRP | G | 163 | −5.076 | −64.084 | 8.394 | 1.00 | 80.39 | MOL3 | N |
| ATOM | 9901 | CZ2 | TRP | G | 163 | −6.281 | −65.834 | 7.060 | 1.00 | 85.36 | MOL3 | C |
| ATOM | 9902 | CZ3 | TRP | G | 163 | −6.648 | −65.160 | 4.766 | 1.00 | 84.45 | MOL3 | C |
| ATOM | 9903 | CH2 | TRP | G | 163 | −6.770 | −66.092 | 5.807 | 1.00 | 87.80 | MOL3 | C |
| ATOM | 9904 | C | TRP | G | 163 | −4.982 | −59.033 | 5.036 | 1.00 | 60.39 | MOL3 | C |
| ATOM | 9905 | O | TRP | G | 163 | −5.153 | −59.050 | 3.818 | 1.00 | 60.85 | MOL3 | O |
| ATOM | 9906 | N | THR | G | 164 | −4.342 | −58.045 | 5.650 | 1.00 | 56.00 | MOL3 | N |

TABLE 1-continued

The atomic coordinates of IL17F in complex with 496 Fab
(H32; a = 189.4; b = 189.4; c = 490.9, α, β = 90°; γ = 120°)

| ATOM | 9907 | CA  | THR | G | 164 | -3.800 | -56.913 | 4.909  | 1.00 | 56.33  | MOL3 | C |
|------|------|-----|-----|---|-----|--------|---------|--------|------|--------|------|---|
| ATOM | 9908 | CB  | THR | G | 164 | -4.027 | -55.612 | 5.673  | 1.00 | 54.45  | MOL3 | C |
| ATOM | 9909 | OG1 | THR | G | 164 | -3.045 | -55.487 | 6.712  | 1.00 | 41.34  | MOL3 | O |
| ATOM | 9910 | CG2 | THR | G | 164 | -5.413 | -55.610 | 6.283  | 1.00 | 48.18  | MOL3 | C |
| ATOM | 9911 | C   | THR | G | 164 | -2.292 | -57.082 | 4.717  | 1.00 | 59.82  | MOL3 | C |
| ATOM | 9912 | O   | THR | G | 164 | -1.705 | -58.035 | 5.205  | 1.00 | 56.32  | MOL3 | O |
| ATOM | 9913 | N   | ASP | G | 165 | -1.658 | -56.166 | 3.999  | 1.00 | 68.37  | MOL3 | N |
| ATOM | 9914 | CA  | ASP | G | 165 | -0.215 | -56.272 | 3.819  | 1.00 | 72.80  | MOL3 | C |
| ATOM | 9915 | CB  | ASP | G | 165 | 0.195  | -55.934 | 2.387  | 1.00 | 88.52  | MOL3 | C |
| ATOM | 9916 | CG  | ASP | G | 165 | 0.372  | -57.179 | 1.528  | 1.00 | 101.27 | MOL3 | C |
| ATOM | 9917 | OD1 | ASP | G | 165 | 1.022  | -58.140 | 2.009  | 1.00 | 108.00 | MOL3 | O |
| ATOM | 9918 | OD2 | ASP | G | 165 | -0.128 | -57.195 | 0.378  | 1.00 | 107.68 | MOL3 | O |
| ATOM | 9919 | C   | ASP | G | 165 | 0.513  | -55.375 | 4.803  | 1.00 | 68.97  | MOL3 | C |
| ATOM | 9920 | O   | ASP | G | 165 | -0.095 | -54.527 | 5.447  | 1.00 | 69.68  | MOL3 | O |
| ATOM | 9921 | N   | GLN | G | 166 | 1.817  | -55.566 | 4.930  | 1.00 | 64.10  | MOL3 | N |
| ATOM | 9922 | CA  | GLN | G | 166 | 2.572  | -54.768 | 5.880  | 1.00 | 66.76  | MOL3 | C |
| ATOM | 9923 | CB  | GLN | G | 166 | 4.072  | -54.971 | 5.684  | 1.00 | 70.21  | MOL3 | C |
| ATOM | 9924 | CG  | GLN | G | 166 | 4.544  | -56.407 | 5.851  | 1.00 | 69.53  | MOL3 | C |
| ATOM | 9925 | CD  | GLN | G | 166 | 5.937  | -56.477 | 6.448  | 1.00 | 69.81  | MOL3 | C |
| ATOM | 9926 | OE1 | GLN | G | 166 | 6.139  | -56.096 | 7.598  | 1.00 | 68.78  | MOL3 | O |
| ATOM | 9927 | NE2 | GLN | G | 166 | 6.903  | -56.949 | 5.669  | 1.00 | 66.64  | MOL3 | N |
| ATOM | 9928 | C   | GLN | G | 166 | 2.234  | -53.286 | 5.792  | 1.00 | 68.28  | MOL3 | C |
| ATOM | 9929 | O   | GLN | G | 166 | 2.546  | -52.622 | 4.806  | 1.00 | 76.25  | MOL3 | O |
| ATOM | 9930 | N   | ASP | G | 167 | 1.588  | -52.780 | 6.837  | 1.00 | 67.95  | MOL3 | N |
| ATOM | 9931 | CA  | ASP | G | 167 | 1.176  | -51.380 | 6.925  | 1.00 | 72.67  | MOL3 | C |
| ATOM | 9932 | CB  | ASP | G | 167 | 0.516  | -51.125 | 8.284  | 1.00 | 75.03  | MOL3 | C |
| ATOM | 9933 | CG  | ASP | G | 167 | 0.059  | -49.683 | 8.463  | 1.00 | 79.58  | MOL3 | C |
| ATOM | 9934 | OD1 | ASP | G | 167 | -0.983 | -49.295 | 7.876  | 1.00 | 80.64  | MOL3 | O |
| ATOM | 9935 | OD2 | ASP | G | 167 | 0.747  | -48.939 | 9.198  | 1.00 | 79.05  | MOL3 | O |
| ATOM | 9936 | C   | ASP | G | 167 | 2.353  | -50.438 | 6.779  | 1.00 | 74.31  | MOL3 | C |
| ATOM | 9937 | O   | ASP | G | 167 | 3.114  | -50.286 | 7.716  | 1.00 | 76.93  | MOL3 | O |
| ATOM | 9938 | N   | SER | G | 168 | 2.481  | -49.800 | 5.616  | 1.00 | 79.70  | MOL3 | N |
| ATOM | 9939 | CA  | SER | G | 168 | 3.563  | -48.851 | 5.322  | 1.00 | 82.79  | MOL3 | C |
| ATOM | 9940 | CB  | SER | G | 168 | 3.085  | -47.838 | 4.290  | 1.00 | 86.90  | MOL3 | C |
| ATOM | 9941 | OG  | SER | G | 168 | 2.048  | -47.042 | 4.840  | 1.00 | 93.16  | MOL3 | O |
| ATOM | 9942 | C   | SER | G | 168 | 4.104  | -48.080 | 6.530  | 1.00 | 83.03  | MOL3 | C |
| ATOM | 9943 | O   | SER | G | 168 | 5.310  | -47.868 | 6.651  | 1.00 | 86.44  | MOL3 | O |
| ATOM | 9944 | N   | LYS | G | 169 | 3.209  | -47.646 | 7.409  | 1.00 | 81.18  | MOL3 | N |
| ATOM | 9945 | CA  | LYS | G | 169 | 3.594  | -46.903 | 8.606  | 1.00 | 86.39  | MOL3 | C |
| ATOM | 9946 | CB  | LYS | G | 169 | 2.340  | -46.462 | 9.375  | 1.00 | 92.95  | MOL3 | C |
| ATOM | 9947 | CG  | LYS | G | 169 | 1.747  | -45.123 | 8.946  | 1.00 | 106.84 | MOL3 | C |
| ATOM | 9948 | CD  | LYS | G | 169 | 2.542  | -43.944 | 9.520  | 1.00 | 112.36 | MOL3 | C |
| ATOM | 9949 | CE  | LYS | G | 169 | 2.008  | -42.599 | 9.026  | 1.00 | 113.28 | MOL3 | C |
| ATOM | 9950 | NZ  | LYS | G | 169 | 2.110  | -42.459 | 7.540  | 1.00 | 112.32 | MOL3 | N |
| ATOM | 9951 | C   | LYS | G | 169 | 4.492  | -47.692 | 9.565  | 1.00 | 86.36  | MOL3 | C |
| ATOM | 9952 | O   | LYS | G | 169 | 5.699  | -47.446 | 9.655  | 1.00 | 88.48  | MOL3 | O |
| ATOM | 9953 | N   | ASP | G | 170 | 3.888  | -48.642 | 10.281 | 1.00 | 82.00  | MOL3 | N |
| ATOM | 9954 | CA  | ASP | G | 170 | 4.612  | -49.451 | 11.264 | 1.00 | 70.61  | MOL3 | C |
| ATOM | 9955 | CB  | ASP | G | 170 | 3.832  | -49.494 | 12.566 | 1.00 | 71.34  | MOL3 | C |
| ATOM | 9956 | CG  | ASP | G | 170 | 2.594  | -50.323 | 12.450 | 1.00 | 74.59  | MOL3 | C |
| ATOM | 9957 | OD1 | ASP | G | 170 | 1.832  | -50.374 | 13.439 | 1.00 | 79.81  | MOL3 | O |
| ATOM | 9958 | OD2 | ASP | G | 170 | 2.393  | -50.924 | 11.365 | 1.00 | 65.94  | MOL3 | O |
| ATOM | 9959 | C   | ASP | G | 170 | 4.950  | -50.886 | 10.860 | 1.00 | 62.81  | MOL3 | C |
| ATOM | 9960 | O   | ASP | G | 170 | 5.218  | -51.724 | 11.707 | 1.00 | 56.54  | MOL3 | O |
| ATOM | 9961 | N   | SER | G | 171 | 4.929  | -51.174 | 9.571  | 1.00 | 62.07  | MOL3 | N |
| ATOM | 9962 | CA  | SER | G | 171 | 5.273  | -52.508 | 9.086  | 1.00 | 58.38  | MOL3 | C |
| ATOM | 9963 | CB  | SER | G | 171 | 6.782  | -52.725 | 9.214  | 1.00 | 50.52  | MOL3 | C |
| ATOM | 9964 | OG  | SER | G | 171 | 7.489  | -51.576 | 8.807  | 1.00 | 49.85  | MOL3 | O |
| ATOM | 9965 | C   | SER | G | 171 | 4.561  | -53.681 | 9.774  | 1.00 | 57.67  | MOL3 | C |
| ATOM | 9966 | O   | SER | G | 171 | 5.067  | -54.800 | 9.736  | 1.00 | 58.28  | MOL3 | O |
| ATOM | 9967 | N   | THR | G | 172 | 3.406  | -53.446 | 10.397 | 1.00 | 54.13  | MOL3 | N |
| ATOM | 9968 | CA  | THR | G | 172 | 2.664  | -54.527 | 11.063 | 1.00 | 53.93  | MOL3 | C |
| ATOM | 9969 | CB  | THR | G | 172 | 1.859  | -54.026 | 12.256 | 1.00 | 58.95  | MOL3 | C |
| ATOM | 9970 | OG1 | THR | G | 172 | 0.843  | -53.126 | 11.793 | 1.00 | 57.39  | MOL3 | O |
| ATOM | 9971 | CG2 | THR | G | 172 | 2.758  | -53.332 | 13.257 | 1.00 | 69.20  | MOL3 | C |
| ATOM | 9972 | C   | THR | G | 172 | 1.639  | -55.170 | 10.144 | 1.00 | 53.31  | MOL3 | C |
| ATOM | 9973 | O   | THR | G | 172 | 1.560  | -54.837 | 8.973  | 1.00 | 66.87  | MOL3 | O |
| ATOM | 9974 | N   | TYR | G | 173 | 0.836  | -56.080 | 10.685 | 1.00 | 48.31  | MOL3 | N |
| ATOM | 9975 | CA  | TYR | G | 173 | -0.211 | -56.742 | 9.911  | 1.00 | 47.98  | MOL3 | C |
| ATOM | 9976 | CB  | TYR | G | 173 | 0.036  | -58.239 | 9.835  | 1.00 | 43.77  | MOL3 | C |
| ATOM | 9977 | CG  | TYR | G | 173 | 1.259  | -58.612 | 9.060  | 1.00 | 44.45  | MOL3 | C |
| ATOM | 9978 | CD1 | TYR | G | 173 | 2.425  | -58.940 | 9.697  | 1.00 | 48.66  | MOL3 | C |
| ATOM | 9979 | CE1 | TYR | G | 173 | 3.559  | -59.283 | 8.982  | 1.00 | 61.26  | MOL3 | C |
| ATOM | 9980 | CD2 | TYR | G | 173 | 1.246  | -58.630 | 7.681  | 1.00 | 52.61  | MOL3 | C |
| ATOM | 9981 | CE2 | TYR | G | 173 | 2.374  | -58.967 | 6.948  | 1.00 | 59.87  | MOL3 | C |
| ATOM | 9982 | CZ  | TYR | G | 173 | 3.533  | -59.295 | 7.605  | 1.00 | 62.30  | MOL3 | C |
| ATOM | 9983 | OH  | TYR | G | 173 | 4.672  | -59.634 | 6.897  | 1.00 | 63.25  | MOL3 | O |

TABLE 1-continued

The atomic coordinates of IL17F in complex with 496 Fab
(H32; a = 189.4; b = 189.4; c = 490.9, α, β = 90°; γ = 120°)

| ATOM | 9984 | C | TYR | G | 173 | −1.567 | −56.517 | 10.557 | 1.00 | 50.67 | MOL3 | C |
|---|---|---|---|---|---|---|---|---|---|---|---|---|
| ATOM | 9985 | O | TYR | G | 173 | −1.649 | −55.969 | 11.650 | 1.00 | 58.20 | MOL3 | O |
| ATOM | 9986 | N | SER | G | 174 | −2.628 | −56.948 | 9.883 | 1.00 | 48.70 | MOL3 | N |
| ATOM | 9987 | CA | SER | G | 174 | −3.988 | −56.805 | 10.400 | 1.00 | 50.67 | MOL3 | C |
| ATOM | 9988 | CB | SER | G | 174 | −4.544 | −55.400 | 10.147 | 1.00 | 50.56 | MOL3 | C |
| ATOM | 9989 | OG | SER | G | 174 | −4.494 | −54.599 | 11.311 | 1.00 | 52.36 | MOL3 | O |
| ATOM | 9990 | C | SER | G | 174 | −4.886 | −57.806 | 9.710 | 1.00 | 51.11 | MOL3 | C |
| ATOM | 9991 | O | SER | G | 174 | −4.674 | −58.138 | 8.550 | 1.00 | 52.00 | MOL3 | O |
| ATOM | 9992 | N | MET | G | 175 | −5.898 | −58.280 | 10.423 | 1.00 | 53.77 | MOL3 | N |
| ATOM | 9993 | CA | MET | G | 175 | −6.830 | −59.247 | 9.864 | 1.00 | 51.80 | MOL3 | C |
| ATOM | 9994 | CB | MET | G | 175 | −6.387 | −60.659 | 10.206 | 1.00 | 55.64 | MOL3 | C |
| ATOM | 9995 | CG | MET | G | 175 | −7.512 | −61.550 | 10.678 | 1.00 | 61.16 | MOL3 | C |
| ATOM | 9996 | SD | MET | G | 175 | −6.922 | −63.203 | 11.089 | 1.00 | 65.42 | MOL3 | S |
| ATOM | 9997 | CE | MET | G | 175 | −8.312 | −64.181 | 10.519 | 1.00 | 62.23 | MOL3 | C |
| ATOM | 9998 | C | MET | G | 175 | −8.251 | −59.038 | 10.348 | 1.00 | 53.07 | MOL3 | C |
| ATOM | 9999 | O | MET | G | 175 | −8.491 | −58.573 | 11.470 | 1.00 | 51.37 | MOL3 | O |
| ATOM | 10000 | N | SER | G | 176 | −9.193 | −59.406 | 9.492 | 1.00 | 52.08 | MOL3 | N |
| ATOM | 10001 | CA | SER | G | 176 | −10.600 | −59.251 | 9.805 | 1.00 | 56.47 | MOL3 | C |
| ATOM | 10002 | CB | SER | G | 176 | −11.217 | −58.188 | 8.907 | 1.00 | 52.46 | MOL3 | C |
| ATOM | 10003 | OG | SER | G | 176 | −12.607 | −58.410 | 8.761 | 1.00 | 55.22 | MOL3 | O |
| ATOM | 10004 | C | SER | G | 176 | −11.398 | −60.530 | 9.647 | 1.00 | 62.89 | MOL3 | C |
| ATOM | 10005 | O | SER | G | 176 | −11.744 | −60.919 | 8.525 | 1.00 | 63.70 | MOL3 | O |
| ATOM | 10006 | N | SER | G | 177 | −11.711 | −61.173 | 10.771 | 1.00 | 67.40 | MOL3 | N |
| ATOM | 10007 | CA | SER | G | 177 | −12.504 | −62.403 | 10.746 | 1.00 | 65.51 | MOL3 | C |
| ATOM | 10008 | CB | SER | G | 177 | −12.038 | −63.372 | 11.830 | 1.00 | 67.97 | MOL3 | C |
| ATOM | 10009 | OG | SER | G | 177 | −12.620 | −64.648 | 11.628 | 1.00 | 69.26 | MOL3 | O |
| ATOM | 10010 | C | SER | G | 177 | −13.980 | −62.078 | 10.953 | 1.00 | 62.13 | MOL3 | C |
| ATOM | 10011 | O | SER | G | 177 | −14.354 | −61.357 | 11.877 | 1.00 | 57.16 | MOL3 | O |
| ATOM | 10012 | N | THR | G | 178 | −14.814 | −62.633 | 10.088 | 1.00 | 64.74 | MOL3 | N |
| ATOM | 10013 | CA | THR | G | 178 | −16.249 | −62.391 | 10.129 | 1.00 | 71.96 | MOL3 | C |
| ATOM | 10014 | CB | THR | G | 178 | −16.683 | −61.613 | 8.857 | 1.00 | 75.70 | MOL3 | C |
| ATOM | 10015 | OG1 | THR | G | 178 | −16.030 | −60.336 | 8.829 | 1.00 | 76.12 | MOL3 | O |
| ATOM | 10016 | CG2 | THR | G | 178 | −18.195 | −61.443 | 8.811 | 1.00 | 73.86 | MOL3 | C |
| ATOM | 10017 | C | THR | G | 178 | −17.072 | −63.683 | 10.213 | 1.00 | 72.48 | MOL3 | C |
| ATOM | 10018 | O | THR | G | 178 | −17.084 | −64.490 | 9.281 | 1.00 | 73.46 | MOL3 | O |
| ATOM | 10019 | N | LEU | G | 179 | −17.765 | −63.877 | 11.327 | 1.00 | 72.44 | MOL3 | N |
| ATOM | 10020 | CA | LEU | G | 179 | −18.606 | −65.056 | 11.494 | 1.00 | 73.90 | MOL3 | C |
| ATOM | 10021 | CB | LEU | G | 179 | −18.697 | −65.433 | 12.974 | 1.00 | 68.50 | MOL3 | C |
| ATOM | 10022 | CG | LEU | G | 179 | −19.314 | −66.790 | 13.310 | 1.00 | 58.82 | MOL3 | C |
| ATOM | 10023 | CD1 | LEU | G | 179 | −19.602 | −66.819 | 14.790 | 1.00 | 47.08 | MOL3 | C |
| ATOM | 10024 | CD2 | LEU | G | 179 | −20.581 | −67.025 | 12.506 | 1.00 | 45.68 | MOL3 | C |
| ATOM | 10025 | C | LEU | G | 179 | −20.002 | −64.718 | 10.968 | 1.00 | 76.98 | MOL3 | C |
| ATOM | 10026 | O | LEU | G | 179 | −20.728 | −63.922 | 11.567 | 1.00 | 76.00 | MOL3 | O |
| ATOM | 10027 | N | THR | G | 180 | −20.380 | −65.319 | 9.849 | 1.00 | 80.86 | MOL3 | N |
| ATOM | 10028 | CA | THR | G | 180 | −21.694 | −65.052 | 9.286 | 1.00 | 86.01 | MOL3 | C |
| ATOM | 10029 | CB | THR | G | 180 | −21.614 | −64.782 | 7.772 | 1.00 | 90.77 | MOL3 | C |
| ATOM | 10030 | OG1 | THR | G | 180 | −20.824 | −63.605 | 7.537 | 1.00 | 95.99 | MOL3 | O |
| ATOM | 10031 | CG2 | THR | G | 180 | −23.006 | −64.576 | 7.199 | 1.00 | 89.94 | MOL3 | C |
| ATOM | 10032 | C | THR | G | 180 | −22.652 | −66.205 | 9.554 | 1.00 | 88.98 | MOL3 | C |
| ATOM | 10033 | O | THR | G | 180 | −22.431 | −67.346 | 9.140 | 1.00 | 90.30 | MOL3 | O |
| ATOM | 10034 | N | LEU | G | 181 | −23.722 | −65.874 | 10.266 | 1.00 | 93.59 | MOL3 | N |
| ATOM | 10035 | CA | LEU | G | 181 | −24.768 | −66.813 | 10.663 | 1.00 | 96.51 | MOL3 | C |
| ATOM | 10036 | CB | LEU | G | 181 | −24.936 | −66.802 | 12.181 | 1.00 | 91.11 | MOL3 | C |
| ATOM | 10037 | CG | LEU | G | 181 | −23.812 | −67.221 | 13.108 | 1.00 | 90.42 | MOL3 | C |
| ATOM | 10038 | CD1 | LEU | G | 181 | −24.134 | −66.766 | 14.525 | 1.00 | 86.50 | MOL3 | C |
| ATOM | 10039 | CD2 | LEU | G | 181 | −23.645 | −68.735 | 13.029 | 1.00 | 96.53 | MOL3 | C |
| ATOM | 10040 | C | LEU | G | 181 | −26.103 | −66.368 | 10.095 | 1.00 | 100.13 | MOL3 | C |
| ATOM | 10041 | O | LEU | G | 181 | −26.216 | −65.306 | 9.477 | 1.00 | 98.69 | MOL3 | O |
| ATOM | 10042 | N | THR | G | 182 | −27.125 | −67.181 | 10.340 | 1.00 | 105.38 | MOL3 | N |
| ATOM | 10043 | CA | THR | G | 182 | −28.477 | −66.844 | 9.914 | 1.00 | 107.74 | MOL3 | C |
| ATOM | 10044 | CB | THR | G | 182 | −29.257 | −68.074 | 9.395 | 1.00 | 110.79 | MOL3 | C |
| ATOM | 10045 | OG1 | THR | G | 182 | −30.540 | −67.644 | 8.915 | 1.00 | 109.92 | MOL3 | O |
| ATOM | 10046 | CG2 | THR | G | 182 | −29.438 | −69.123 | 10.507 | 1.00 | 108.26 | MOL3 | C |
| ATOM | 10047 | C | THR | G | 182 | −29.171 | −66.309 | 11.163 | 1.00 | 107.32 | MOL3 | C |
| ATOM | 10048 | O | THR | G | 182 | −28.976 | −66.841 | 12.259 | 1.00 | 109.13 | MOL3 | O |
| ATOM | 10049 | N | LYS | G | 183 | −29.967 | −65.258 | 11.001 | 1.00 | 104.23 | MOL3 | N |
| ATOM | 10050 | CA | LYS | G | 183 | −30.668 | −64.653 | 12.129 | 1.00 | 104.07 | MOL3 | C |
| ATOM | 10051 | CB | LYS | G | 183 | −31.821 | −63.787 | 11.612 | 1.00 | 102.44 | MOL3 | C |
| ATOM | 10052 | CG | LYS | G | 183 | −32.242 | −62.680 | 12.572 | 1.00 | 105.36 | MOL3 | C |
| ATOM | 10053 | CD | LYS | G | 183 | −33.511 | −61.955 | 12.110 | 1.00 | 109.07 | MOL3 | C |
| ATOM | 10054 | CE | LYS | G | 183 | −34.050 | −61.024 | 13.207 | 1.00 | 110.44 | MOL3 | C |
| ATOM | 10055 | NZ | LYS | G | 183 | −35.418 | −60.484 | 12.935 | 1.00 | 107.50 | MOL3 | N |
| ATOM | 10056 | C | LYS | G | 183 | −31.194 | −65.718 | 13.102 | 1.00 | 105.08 | MOL3 | C |
| ATOM | 10057 | O | LYS | G | 183 | −31.237 | −65.505 | 14.319 | 1.00 | 102.43 | MOL3 | O |
| ATOM | 10058 | N | ASP | G | 184 | −31.580 | −66.870 | 12.559 | 1.00 | 105.91 | MOL3 | N |
| ATOM | 10059 | CA | ASP | G | 184 | −32.094 | −67.967 | 13.373 | 1.00 | 107.91 | MOL3 | C |
| ATOM | 10060 | CB | ASP | G | 184 | −32.557 | −69.140 | 12.498 | 1.00 | 117.94 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 10061 | CG | ASP | G | 184 | −33.616 | −68.747 | 11.486 | 1.00 | 126.79 | MOL3 | C |
|---|---|---|---|---|---|---|---|---|---|---|---|---|
| ATOM | 10062 | OD1 | ASP | G | 184 | −34.290 | −67.708 | 11.690 | 1.00 | 127.71 | MOL3 | O |
| ATOM | 10063 | OD2 | ASP | G | 184 | −33.777 | −69.497 | 10.491 | 1.00 | 128.78 | MOL3 | O |
| ATOM | 10064 | C | ASP | G | 184 | −31.043 | −68.494 | 14.341 | 1.00 | 104.94 | MOL3 | C |
| ATOM | 10065 | O | ASP | G | 184 | −31.191 | −68.358 | 15.558 | 1.00 | 104.52 | MOL3 | O |
| ATOM | 10066 | N | GLU | G | 185 | −29.991 | −69.102 | 13.789 | 1.00 | 101.31 | MOL3 | N |
| ATOM | 10067 | CA | GLU | G | 185 | −28.907 | −69.688 | 14.584 | 1.00 | 98.96 | MOL3 | C |
| ATOM | 10068 | CB | GLU | G | 185 | −27.840 | −70.296 | 13.650 | 1.00 | 108.09 | MOL3 | C |
| ATOM | 10069 | CG | GLU | G | 185 | −26.705 | −71.111 | 14.332 | 1.00 | 117.38 | MOL3 | C |
| ATOM | 10070 | CD | GLU | G | 185 | −27.117 | −72.518 | 14.798 | 1.00 | 123.07 | MOL3 | C |
| ATOM | 10071 | OE1 | GLU | G | 185 | −26.212 | −73.311 | 15.148 | 1.00 | 124.88 | MOL3 | O |
| ATOM | 10072 | OE2 | GLU | G | 185 | −28.328 | −72.835 | 14.823 | 1.00 | 125.11 | MOL3 | O |
| ATOM | 10073 | C | GLU | G | 185 | −28.282 | −68.661 | 15.536 | 1.00 | 93.54 | MOL3 | C |
| ATOM | 10074 | O | GLU | G | 185 | −27.782 | −69.011 | 16.610 | 1.00 | 89.75 | MOL3 | O |
| ATOM | 10075 | N | TYR | G | 186 | −28.325 | −67.394 | 15.141 | 1.00 | 88.78 | MOL3 | N |
| ATOM | 10076 | CA | TYR | G | 186 | −27.785 | −66.304 | 15.944 | 1.00 | 86.97 | MOL3 | C |
| ATOM | 10077 | CB | TYR | G | 186 | −27.950 | −64.989 | 15.161 | 1.00 | 82.46 | MOL3 | C |
| ATOM | 10078 | CG | TYR | G | 186 | −27.565 | −63.729 | 15.910 | 1.00 | 77.50 | MOL3 | C |
| ATOM | 10079 | CD1 | TYR | G | 186 | −28.173 | −62.518 | 15.618 | 1.00 | 73.38 | MOL3 | C |
| ATOM | 10080 | CE1 | TYR | G | 186 | −27.861 | −61.371 | 16.324 | 1.00 | 70.40 | MOL3 | C |
| ATOM | 10081 | CD2 | TYR | G | 186 | −26.623 | −63.754 | 16.925 | 1.00 | 75.60 | MOL3 | C |
| ATOM | 10082 | CE2 | TYR | G | 186 | −26.306 | −62.613 | 17.634 | 1.00 | 73.45 | MOL3 | C |
| ATOM | 10083 | CZ | TYR | G | 186 | −26.930 | −61.427 | 17.334 | 1.00 | 73.00 | MOL3 | C |
| ATOM | 10084 | OH | TYR | G | 186 | −26.645 | −60.304 | 18.078 | 1.00 | 75.84 | MOL3 | O |
| ATOM | 10085 | C | TYR | G | 186 | −28.556 | −66.233 | 17.262 | 1.00 | 88.23 | MOL3 | C |
| ATOM | 10086 | O | TYR | G | 186 | −27.981 | −66.039 | 18.333 | 1.00 | 88.50 | MOL3 | O |
| ATOM | 10087 | N | GLU | G | 187 | −29.868 | −66.402 | 17.157 | 1.00 | 91.02 | MOL3 | N |
| ATOM | 10088 | CA | GLU | G | 187 | −30.778 | −66.351 | 18.297 | 1.00 | 94.93 | MOL3 | C |
| ATOM | 10089 | CB | GLU | G | 187 | −32.207 | −66.253 | 17.766 | 1.00 | 102.44 | MOL3 | C |
| ATOM | 10090 | CG | GLU | G | 187 | −32.416 | −65.167 | 16.721 | 1.00 | 105.29 | MOL3 | C |
| ATOM | 10091 | CD | GLU | G | 187 | −32.148 | −63.778 | 17.267 | 1.00 | 110.80 | MOL3 | C |
| ATOM | 10092 | OE1 | GLU | G | 187 | −32.541 | −62.790 | 16.608 | 1.00 | 112.95 | MOL3 | O |
| ATOM | 10093 | OE2 | GLU | G | 187 | −31.541 | −63.671 | 18.355 | 1.00 | 110.62 | MOL3 | O |
| ATOM | 10094 | C | GLU | G | 187 | −30.676 | −67.550 | 19.252 | 1.00 | 94.53 | MOL3 | C |
| ATOM | 10095 | O | GLU | G | 187 | −30.734 | −67.401 | 20.477 | 1.00 | 88.00 | MOL3 | O |
| ATOM | 10096 | N | ARG | G | 188 | −30.537 | −68.736 | 18.668 | 1.00 | 96.61 | MOL3 | N |
| ATOM | 10097 | CA | ARG | G | 188 | −30.443 | −69.985 | 19.415 | 1.00 | 101.16 | MOL3 | C |
| ATOM | 10098 | CB | ARG | G | 188 | −30.269 | −71.148 | 18.419 | 1.00 | 104.44 | MOL3 | C |
| ATOM | 10099 | CG | ARG | G | 188 | −31.359 | −71.174 | 17.348 | 1.00 | 110.74 | MOL3 | C |
| ATOM | 10100 | CD | ARG | G | 188 | −30.994 | −72.003 | 16.116 | 1.00 | 120.65 | MOL3 | C |
| ATOM | 10101 | NE | ARG | G | 188 | −31.985 | −71.825 | 15.047 | 1.00 | 132.41 | MOL3 | N |
| ATOM | 10102 | CZ | ARG | G | 188 | −31.869 | −72.307 | 13.808 | 1.00 | 138.16 | MOL3 | C |
| ATOM | 10103 | NH1 | ARG | G | 188 | −30.797 | −73.009 | 13.458 | 1.00 | 140.93 | MOL3 | N |
| ATOM | 10104 | NH2 | ARG | G | 188 | −32.829 | −72.085 | 12.913 | 1.00 | 137.85 | MOL3 | N |
| ATOM | 10105 | C | ARG | G | 188 | −29.336 | −70.007 | 20.486 | 1.00 | 103.12 | MOL3 | C |
| ATOM | 10106 | O | ARG | G | 188 | −29.368 | −70.847 | 21.394 | 1.00 | 107.79 | MOL3 | O |
| ATOM | 10107 | N | HIS | G | 189 | −28.369 | −69.094 | 20.403 | 1.00 | 99.75 | MOL3 | N |
| ATOM | 10108 | CA | HIS | G | 189 | −27.293 | −69.071 | 21.393 | 1.00 | 98.72 | MOL3 | C |
| ATOM | 10109 | CB | HIS | G | 189 | −26.008 | −69.609 | 20.773 | 1.00 | 106.66 | MOL3 | C |
| ATOM | 10110 | CG | HIS | G | 189 | −26.170 | −70.941 | 20.109 | 1.00 | 115.83 | MOL3 | C |
| ATOM | 10111 | CD2 | HIS | G | 189 | −25.758 | −72.179 | 20.475 | 1.00 | 120.97 | MOL3 | C |
| ATOM | 10112 | ND1 | HIS | G | 189 | −26.831 | −71.099 | 18.909 | 1.00 | 119.62 | MOL3 | N |
| ATOM | 10113 | CE1 | HIS | G | 189 | −26.818 | −72.375 | 18.564 | 1.00 | 122.11 | MOL3 | C |
| ATOM | 10114 | NE2 | HIS | G | 189 | −26.173 | −73.051 | 19.497 | 1.00 | 124.75 | MOL3 | N |
| ATOM | 10115 | C | HIS | G | 189 | −27.065 | −67.677 | 21.966 | 1.00 | 97.69 | MOL3 | C |
| ATOM | 10116 | O | HIS | G | 189 | −27.562 | −66.694 | 21.418 | 1.00 | 96.04 | MOL3 | O |
| ATOM | 10117 | N | ASN | G | 190 | −26.317 | −67.581 | 23.064 | 1.00 | 97.69 | MOL3 | N |
| ATOM | 10118 | CA | ASN | G | 190 | −26.090 | −66.271 | 23.673 | 1.00 | 101.88 | MOL3 | C |
| ATOM | 10119 | CB | ASN | G | 190 | −26.754 | −66.199 | 25.066 | 1.00 | 111.52 | MOL3 | C |
| ATOM | 10120 | CG | ASN | G | 190 | −26.257 | −67.279 | 26.033 | 1.00 | 118.94 | MOL3 | C |
| ATOM | 10121 | OD1 | ASN | G | 190 | −25.113 | −67.242 | 26.503 | 1.00 | 121.56 | MOL3 | O |
| ATOM | 10122 | ND2 | ASN | G | 190 | −27.129 | −68.240 | 26.342 | 1.00 | 118.18 | MOL3 | N |
| ATOM | 10123 | C | ASN | G | 190 | −24.658 | −65.739 | 23.755 | 1.00 | 101.17 | MOL3 | C |
| ATOM | 10124 | O | ASN | G | 190 | −24.443 | −64.544 | 23.542 | 1.00 | 98.80 | MOL3 | O |
| ATOM | 10125 | N | SER | G | 191 | −23.682 | −66.600 | 24.051 | 1.00 | 101.74 | MOL3 | N |
| ATOM | 10126 | CA | SER | G | 191 | −22.289 | −66.148 | 24.155 | 1.00 | 99.25 | MOL3 | C |
| ATOM | 10127 | CB | SER | G | 191 | −21.549 | −66.894 | 25.280 | 1.00 | 103.81 | MOL3 | C |
| ATOM | 10128 | OG | SER | G | 191 | −21.036 | −68.143 | 24.845 | 1.00 | 107.17 | MOL3 | O |
| ATOM | 10129 | C | SER | G | 191 | −21.504 | −66.288 | 22.849 | 1.00 | 95.81 | MOL3 | C |
| ATOM | 10130 | O | SER | G | 191 | −21.521 | −67.340 | 22.197 | 1.00 | 92.47 | MOL3 | O |
| ATOM | 10131 | N | TYR | G | 192 | −20.810 | −65.207 | 22.495 | 1.00 | 93.09 | MOL3 | N |
| ATOM | 10132 | CA | TYR | G | 192 | −20.004 | −65.120 | 21.277 | 1.00 | 87.50 | MOL3 | C |
| ATOM | 10133 | CB | TYR | G | 192 | −20.645 | −64.109 | 20.328 | 1.00 | 85.26 | MOL3 | C |
| ATOM | 10134 | CG | TYR | G | 192 | −21.857 | −64.646 | 19.624 | 1.00 | 84.55 | MOL3 | C |
| ATOM | 10135 | CD1 | TYR | G | 192 | −23.026 | −63.913 | 19.552 | 1.00 | 83.90 | MOL3 | C |
| ATOM | 10136 | CE1 | TYR | G | 192 | −24.122 | −64.393 | 18.861 | 1.00 | 83.21 | MOL3 | C |
| ATOM | 10137 | CD2 | TYR | G | 192 | −21.816 | −65.877 | 18.991 | 1.00 | 86.20 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 10138 | CE2 | TYR | G | 192 | −22.903 | −66.362 | 18.297 | 1.00 | 85.84 | MOL3 | C |
|---|---|---|---|---|---|---|---|---|---|---|---|---|
| ATOM | 10139 | CZ | TYR | G | 192 | −24.055 | −65.618 | 18.229 | 1.00 | 84.00 | MOL3 | C |
| ATOM | 10140 | OH | TYR | G | 192 | −25.121 | −66.094 | 17.493 | 1.00 | 77.64 | MOL3 | O |
| ATOM | 10141 | C | TYR | G | 192 | −18.575 | −64.676 | 21.568 | 1.00 | 82.36 | MOL3 | C |
| ATOM | 10142 | O | TYR | G | 192 | −18.354 | −63.550 | 22.011 | 1.00 | 74.42 | MOL3 | O |
| ATOM | 10143 | N | THR | G | 193 | −17.604 | −65.547 | 21.319 | 1.00 | 81.47 | MOL3 | N |
| ATOM | 10144 | CA | THR | G | 193 | −16.225 | −65.165 | 21.564 | 1.00 | 82.88 | MOL3 | C |
| ATOM | 10145 | CB | THR | G | 193 | −15.598 | −65.942 | 22.746 | 1.00 | 84.76 | MOL3 | C |
| ATOM | 10146 | OG1 | THR | G | 193 | −15.403 | −67.308 | 22.367 | 1.00 | 92.41 | MOL3 | O |
| ATOM | 10147 | CG2 | THR | G | 193 | −16.501 | −65.899 | 23.964 | 1.00 | 86.43 | MOL3 | C |
| ATOM | 10148 | C | THR | G | 193 | −15.337 | −65.351 | 20.335 | 1.00 | 83.61 | MOL3 | C |
| ATOM | 10149 | O | THR | G | 193 | −15.567 | −66.204 | 19.463 | 1.00 | 76.78 | MOL3 | O |
| ATOM | 10150 | N | CYS | G | 194 | −14.309 | −64.518 | 20.298 | 1.00 | 86.39 | MOL3 | N |
| ATOM | 10151 | CA | CYS | G | 194 | −13.326 | −64.489 | 19.236 | 1.00 | 84.64 | MOL3 | C |
| ATOM | 10152 | C | CYS | G | 194 | −11.977 | −64.646 | 19.959 | 1.00 | 83.31 | MOL3 | C |
| ATOM | 10153 | O | CYS | G | 194 | −11.527 | −63.745 | 20.670 | 1.00 | 79.54 | MOL3 | O |
| ATOM | 10154 | CB | CYS | G | 194 | −13.474 | −63.143 | 18.519 | 1.00 | 82.79 | MOL3 | C |
| ATOM | 10155 | SG | CYS | G | 194 | −12.135 | −62.657 | 17.402 | 1.00 | 90.85 | MOL3 | S |
| ATOM | 10156 | N | GLU | G | 195 | −11.357 | −65.812 | 19.793 | 1.00 | 83.79 | MOL3 | N |
| ATOM | 10157 | CA | GLU | G | 195 | −10.098 | −66.126 | 20.461 | 1.00 | 85.48 | MOL3 | C |
| ATOM | 10158 | CB | GLU | G | 195 | −10.225 | −67.519 | 21.088 | 1.00 | 96.62 | MOL3 | C |
| ATOM | 10159 | CG | GLU | G | 195 | −9.171 | −67.893 | 22.116 | 1.00 | 106.95 | MOL3 | C |
| ATOM | 10160 | CD | GLU | G | 195 | −9.346 | −69.322 | 22.613 | 1.00 | 112.29 | MOL3 | C |
| ATOM | 10161 | OE1 | GLU | G | 195 | −9.191 | −70.258 | 21.796 | 1.00 | 111.34 | MOL3 | O |
| ATOM | 10162 | OE2 | GLU | G | 195 | −9.646 | −69.508 | 23.816 | 1.00 | 117.09 | MOL3 | O |
| ATOM | 10163 | C | GLU | G | 195 | −8.906 | −66.075 | 19.503 | 1.00 | 82.05 | MOL3 | C |
| ATOM | 10164 | O | GLU | G | 195 | −8.790 | −66.886 | 18.579 | 1.00 | 76.55 | MOL3 | O |
| ATOM | 10165 | N | ALA | G | 196 | −8.013 | −65.124 | 19.743 | 1.00 | 79.13 | MOL3 | N |
| ATOM | 10166 | CA | ALA | G | 196 | −6.848 | −64.961 | 18.894 | 1.00 | 76.76 | MOL3 | C |
| ATOM | 10167 | CB | ALA | G | 196 | −6.714 | −63.504 | 18.491 | 1.00 | 82.89 | MOL3 | C |
| ATOM | 10168 | C | ALA | G | 196 | −5.567 | −65.437 | 19.558 | 1.00 | 74.35 | MOL3 | C |
| ATOM | 10169 | O | ALA | G | 196 | −5.144 | −64.892 | 20.584 | 1.00 | 72.00 | MOL3 | O |
| ATOM | 10170 | N | THR | G | 197 | −4.948 | −66.451 | 18.965 | 1.00 | 70.32 | MOL3 | N |
| ATOM | 10171 | CA | THR | G | 197 | −3.704 | −66.970 | 19.498 | 1.00 | 71.07 | MOL3 | C |
| ATOM | 10172 | CB | THR | G | 197 | −3.787 | −68.487 | 19.597 | 1.00 | 77.77 | MOL3 | C |
| ATOM | 10173 | OG1 | THR | G | 197 | −2.517 | −69.003 | 20.010 | 1.00 | 89.33 | MOL3 | O |
| ATOM | 10174 | CG2 | THR | G | 197 | −4.228 | −69.084 | 18.266 | 1.00 | 82.46 | MOL3 | C |
| ATOM | 10175 | C | THR | G | 197 | −2.499 | −66.494 | 18.657 | 1.00 | 65.77 | MOL3 | C |
| ATOM | 10176 | O | THR | G | 197 | −2.459 | −66.648 | 17.432 | 1.00 | 61.20 | MOL3 | O |
| ATOM | 10177 | N | HIS | G | 198 | −1.517 | −65.910 | 19.341 | 1.00 | 63.27 | MOL3 | N |
| ATOM | 10178 | CA | HIS | G | 198 | −0.356 | −65.341 | 18.679 | 1.00 | 61.38 | MOL3 | C |
| ATOM | 10179 | CB | HIS | G | 198 | −0.638 | −63.860 | 18.447 | 1.00 | 60.91 | MOL3 | C |
| ATOM | 10180 | CG | HIS | G | 198 | 0.358 | −63.187 | 17.567 | 1.00 | 69.52 | MOL3 | C |
| ATOM | 10181 | CD2 | HIS | G | 198 | 1.128 | −62.092 | 17.767 | 1.00 | 69.32 | MOL3 | C |
| ATOM | 10182 | ND1 | HIS | G | 198 | 0.648 | −63.636 | 16.296 | 1.00 | 71.63 | MOL3 | N |
| ATOM | 10183 | CE1 | HIS | G | 198 | 1.556 | −62.846 | 15.751 | 1.00 | 77.19 | MOL3 | C |
| ATOM | 10184 | NE2 | HIS | G | 198 | 1.864 | −61.901 | 16.623 | 1.00 | 76.10 | MOL3 | N |
| ATOM | 10185 | C | HIS | G | 198 | 0.986 | −65.508 | 19.409 | 1.00 | 58.64 | MOL3 | C |
| ATOM | 10186 | O | HIS | G | 198 | 1.064 | −65.443 | 20.627 | 1.00 | 55.62 | MOL3 | O |
| ATOM | 10187 | N | LYS | G | 199 | 2.041 | −65.712 | 18.630 | 1.00 | 61.35 | MOL3 | N |
| ATOM | 10188 | CA | LYS | G | 199 | 3.400 | −65.882 | 19.136 | 1.00 | 60.15 | MOL3 | C |
| ATOM | 10189 | CB | LYS | G | 199 | 4.402 | −65.647 | 17.992 | 1.00 | 62.47 | MOL3 | C |
| ATOM | 10190 | CG | LYS | G | 199 | 5.857 | −65.529 | 18.439 | 1.00 | 65.67 | MOL3 | C |
| ATOM | 10191 | CD | LYS | G | 199 | 6.779 | −65.126 | 17.299 | 1.00 | 64.96 | MOL3 | C |
| ATOM | 10192 | CE | LYS | G | 199 | 6.775 | −66.158 | 16.187 | 1.00 | 69.07 | MOL3 | C |
| ATOM | 10193 | NZ | LYS | G | 199 | 7.322 | −67.468 | 16.637 | 1.00 | 72.23 | MOL3 | N |
| ATOM | 10194 | C | LYS | G | 199 | 3.757 | −64.969 | 20.312 | 1.00 | 59.42 | MOL3 | C |
| ATOM | 10195 | O | LYS | G | 199 | 4.593 | −65.326 | 21.144 | 1.00 | 60.57 | MOL3 | O |
| ATOM | 10196 | N | THR | G | 200 | 3.129 | −63.798 | 20.374 | 1.00 | 57.91 | MOL3 | N |
| ATOM | 10197 | CA | THR | G | 200 | 3.394 | −62.822 | 21.431 | 1.00 | 63.29 | MOL3 | C |
| ATOM | 10198 | CB | THR | G | 200 | 2.626 | −61.515 | 21.200 | 1.00 | 67.33 | MOL3 | C |
| ATOM | 10199 | OG1 | THR | G | 200 | 1.234 | −61.807 | 20.997 | 1.00 | 73.03 | MOL3 | O |
| ATOM | 10200 | CG2 | THR | G | 200 | 3.189 | −60.775 | 20.011 | 1.00 | 73.14 | MOL3 | C |
| ATOM | 10201 | C | THR | G | 200 | 3.037 | −63.276 | 22.839 | 1.00 | 68.06 | MOL3 | C |
| ATOM | 10202 | O | THR | G | 200 | 3.555 | −62.727 | 23.821 | 1.00 | 64.89 | MOL3 | O |
| ATOM | 10203 | N | SER | G | 201 | 2.132 | −64.250 | 22.941 | 1.00 | 73.50 | MOL3 | N |
| ATOM | 10204 | CA | SER | G | 201 | 1.714 | −64.753 | 24.247 | 1.00 | 74.67 | MOL3 | C |
| ATOM | 10205 | CB | SER | G | 201 | 0.534 | −63.945 | 24.789 | 1.00 | 82.63 | MOL3 | C |
| ATOM | 10206 | OG | SER | G | 201 | 0.280 | −64.276 | 26.147 | 1.00 | 89.89 | MOL3 | O |
| ATOM | 10207 | C | SER | G | 201 | 1.344 | −66.227 | 24.253 | 1.00 | 71.10 | MOL3 | C |
| ATOM | 10208 | O | SER | G | 201 | 0.992 | −66.807 | 23.227 | 1.00 | 69.80 | MOL3 | O |
| ATOM | 10209 | N | THR | G | 202 | 1.434 | −66.811 | 25.443 | 1.00 | 69.54 | MOL3 | N |
| ATOM | 10210 | CA | THR | G | 202 | 1.135 | −68.216 | 25.684 | 1.00 | 65.82 | MOL3 | C |
| ATOM | 10211 | CB | THR | G | 202 | 1.889 | −68.733 | 26.934 | 1.00 | 64.23 | MOL3 | C |
| ATOM | 10212 | OG1 | THR | G | 202 | 1.654 | −67.841 | 28.034 | 1.00 | 63.14 | MOL3 | O |
| ATOM | 10213 | CG2 | THR | G | 202 | 3.383 | −68.831 | 26.668 | 1.00 | 57.12 | MOL3 | C |
| ATOM | 10214 | C | THR | G | 202 | −0.352 | −68.370 | 25.950 | 1.00 | 65.86 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 10215 | O | THR | G | 202 | −0.910 | −69.460 | 25.864 | 1.00 | 66.45 | MOL3 | O |
|---|---|---|---|---|---|---|---|---|---|---|---|---|
| ATOM | 10216 | N | SER | G | 203 | −0.988 | −67.260 | 26.284 | 1.00 | 67.90 | MOL3 | N |
| ATOM | 10217 | CA | SER | G | 203 | −2.400 | −67.276 | 26.589 | 1.00 | 74.26 | MOL3 | C |
| ATOM | 10218 | CB | SER | G | 203 | −2.615 | −66.792 | 28.022 | 1.00 | 86.52 | MOL3 | C |
| ATOM | 10219 | OG | SER | G | 203 | −1.850 | −67.582 | 28.928 | 1.00 | 98.19 | MOL3 | O |
| ATOM | 10220 | C | SER | G | 203 | −3.117 | −66.390 | 25.602 | 1.00 | 73.09 | MOL3 | C |
| ATOM | 10221 | O | SER | G | 203 | −2.874 | −65.180 | 25.550 | 1.00 | 75.09 | MOL3 | O |
| ATOM | 10222 | N | PRO | G | 204 | −4.018 | −66.989 | 24.804 | 1.00 | 70.86 | MOL3 | N |
| ATOM | 10223 | CD | PRO | G | 204 | −4.427 | −68.387 | 25.007 | 1.00 | 67.00 | MOL3 | C |
| ATOM | 10224 | CA | PRO | G | 204 | −4.842 | −66.366 | 23.760 | 1.00 | 67.61 | MOL3 | C |
| ATOM | 10225 | CB | PRO | G | 204 | −5.745 | −67.511 | 23.299 | 1.00 | 64.27 | MOL3 | C |
| ATOM | 10226 | CG | PRO | G | 204 | −5.844 | −68.363 | 24.497 | 1.00 | 68.63 | MOL3 | C |
| ATOM | 10227 | C | PRO | G | 204 | −5.634 | −65.139 | 24.186 | 1.00 | 65.42 | MOL3 | C |
| ATOM | 10228 | O | PRO | G | 204 | −6.176 | −65.091 | 25.294 | 1.00 | 65.92 | MOL3 | O |
| ATOM | 10229 | N | ILE | G | 205 | −5.679 | −64.142 | 23.301 | 1.00 | 63.63 | MOL3 | N |
| ATOM | 10230 | CA | ILE | G | 205 | −6.429 | −62.921 | 23.571 | 1.00 | 61.97 | MOL3 | C |
| ATOM | 10231 | CB | ILE | G | 205 | −6.025 | −61.735 | 22.666 | 1.00 | 58.63 | MOL3 | C |
| ATOM | 10232 | CG2 | ILE | G | 205 | −6.863 | −60.528 | 23.044 | 1.00 | 52.45 | MOL3 | C |
| ATOM | 10233 | CG1 | ILE | G | 205 | −4.531 | −61.395 | 22.814 | 1.00 | 61.60 | MOL3 | C |
| ATOM | 10234 | CD1 | ILE | G | 205 | −4.220 | −60.163 | 23.701 | 1.00 | 58.09 | MOL3 | C |
| ATOM | 10235 | C | ILE | G | 205 | −7.862 | −63.266 | 23.235 | 1.00 | 64.06 | MOL3 | C |
| ATOM | 10236 | O | ILE | G | 205 | −8.161 | −63.712 | 22.125 | 1.00 | 58.68 | MOL3 | O |
| ATOM | 10237 | N | VAL | G | 206 | −8.750 | −63.068 | 24.198 | 1.00 | 71.48 | MOL3 | N |
| ATOM | 10238 | CA | VAL | G | 206 | −10.148 | −63.387 | 23.985 | 1.00 | 78.37 | MOL3 | C |
| ATOM | 10239 | CB | VAL | G | 206 | −10.588 | −64.517 | 24.915 | 1.00 | 81.01 | MOL3 | C |
| ATOM | 10240 | CG1 | VAL | G | 206 | −12.056 | −64.852 | 24.669 | 1.00 | 84.85 | MOL3 | C |
| ATOM | 10241 | CG2 | VAL | G | 206 | −9.697 | −65.731 | 24.690 | 1.00 | 86.24 | MOL3 | C |
| ATOM | 10242 | C | VAL | G | 206 | −11.068 | −62.201 | 24.202 | 1.00 | 79.75 | MOL3 | C |
| ATOM | 10243 | O | VAL | G | 206 | −10.978 | −61.504 | 25.218 | 1.00 | 82.00 | MOL3 | O |
| ATOM | 10244 | N | LYS | G | 207 | −11.944 | −61.974 | 23.229 | 1.00 | 80.26 | MOL3 | N |
| ATOM | 10245 | CA | LYS | G | 207 | −12.915 | −60.896 | 23.298 | 1.00 | 84.36 | MOL3 | C |
| ATOM | 10246 | CB | LYS | G | 207 | −12.578 | −59.794 | 22.295 | 1.00 | 86.52 | MOL3 | C |
| ATOM | 10247 | CG | LYS | G | 207 | −11.353 | −58.973 | 22.673 | 1.00 | 98.47 | MOL3 | C |
| ATOM | 10248 | CD | LYS | G | 207 | −11.526 | −58.294 | 24.037 | 1.00 | 111.91 | MOL3 | C |
| ATOM | 10249 | CE | LYS | G | 207 | −10.304 | −57.448 | 24.421 | 1.00 | 116.09 | MOL3 | C |
| ATOM | 10250 | NZ | LYS | G | 207 | −10.490 | −56.698 | 25.704 | 1.00 | 120.25 | MOL3 | N |
| ATOM | 10251 | C | LYS | G | 207 | −14.268 | −61.506 | 22.972 | 1.00 | 88.09 | MOL3 | C |
| ATOM | 10252 | O | LYS | G | 207 | −14.384 | −62.316 | 22.048 | 1.00 | 87.63 | MOL3 | O |
| ATOM | 10253 | N | SER | G | 208 | −15.287 | −61.130 | 23.739 | 1.00 | 91.76 | MOL3 | N |
| ATOM | 10254 | CA | SER | G | 208 | −16.626 | −61.667 | 23.528 | 1.00 | 91.34 | MOL3 | C |
| ATOM | 10255 | CB | SER | G | 208 | −16.802 | −62.950 | 24.336 | 1.00 | 93.27 | MOL3 | C |
| ATOM | 10256 | OG | SER | G | 208 | −16.601 | −62.715 | 25.722 | 1.00 | 92.76 | MOL3 | O |
| ATOM | 10257 | C | SER | G | 208 | −17.720 | −60.687 | 23.920 | 1.00 | 91.18 | MOL3 | C |
| ATOM | 10258 | O | SER | G | 208 | −17.450 | −59.577 | 24.381 | 1.00 | 87.72 | MOL3 | O |
| ATOM | 10259 | N | PHE | G | 209 | −18.961 | −61.119 | 23.732 | 1.00 | 92.63 | MOL3 | N |
| ATOM | 10260 | CA | PHE | G | 209 | −20.115 | −60.304 | 24.073 | 1.00 | 97.21 | MOL3 | C |
| ATOM | 10261 | CB | PHE | G | 209 | −20.281 | −59.167 | 23.057 | 1.00 | 95.06 | MOL3 | C |
| ATOM | 10262 | CG | PHE | G | 209 | −20.996 | −59.572 | 21.793 | 1.00 | 93.57 | MOL3 | C |
| ATOM | 10263 | CD1 | PHE | G | 209 | −22.350 | −59.352 | 21.647 | 1.00 | 90.72 | MOL3 | C |
| ATOM | 10264 | CD2 | PHE | G | 209 | −20.315 | −60.185 | 20.758 | 1.00 | 95.77 | MOL3 | C |
| ATOM | 10265 | CE1 | PHE | G | 209 | −23.009 | −59.734 | 20.496 | 1.00 | 92.12 | MOL3 | C |
| ATOM | 10266 | CE2 | PHE | G | 209 | −20.973 | −60.569 | 19.604 | 1.00 | 92.90 | MOL3 | C |
| ATOM | 10267 | CZ | PHE | G | 209 | −22.321 | −60.343 | 19.475 | 1.00 | 91.92 | MOL3 | C |
| ATOM | 10268 | C | PHE | G | 209 | −21.353 | −61.195 | 24.088 | 1.00 | 103.82 | MOL3 | C |
| ATOM | 10269 | O | PHE | G | 209 | −21.449 | −62.160 | 23.314 | 1.00 | 102.26 | MOL3 | O |
| ATOM | 10270 | N | ASN | G | 210 | −22.290 | −60.873 | 24.978 | 1.00 | 110.23 | MOL3 | N |
| ATOM | 10271 | CA | ASN | G | 210 | −23.531 | −61.633 | 25.117 | 1.00 | 117.84 | MOL3 | C |
| ATOM | 10272 | CB | ASN | G | 210 | −23.762 | −61.980 | 26.594 | 1.00 | 123.10 | MOL3 | C |
| ATOM | 10273 | CG | ASN | G | 210 | −22.563 | −62.675 | 27.228 | 1.00 | 129.22 | MOL3 | C |
| ATOM | 10274 | OD1 | ASN | G | 210 | −22.209 | −63.796 | 26.852 | 1.00 | 133.16 | MOL3 | O |
| ATOM | 10275 | ND2 | ASN | G | 210 | −21.927 | −62.007 | 28.190 | 1.00 | 129.15 | MOL3 | N |
| ATOM | 10276 | C | ASN | G | 210 | −24.693 | −60.789 | 24.602 | 1.00 | 120.46 | MOL3 | C |
| ATOM | 10277 | O | ASN | G | 210 | −24.560 | −59.571 | 24.462 | 1.00 | 119.58 | MOL3 | O |
| ATOM | 10278 | N | ARG | G | 211 | −25.829 | −61.423 | 24.320 | 1.00 | 124.75 | MOL3 | N |
| ATOM | 10279 | CA | ARG | G | 211 | −26.979 | −60.670 | 23.839 | 1.00 | 130.59 | MOL3 | C |
| ATOM | 10280 | CB | ARG | G | 211 | −27.890 | −61.539 | 22.977 | 1.00 | 131.16 | MOL3 | C |
| ATOM | 10281 | CG | ARG | G | 211 | −27.566 | −61.483 | 21.503 | 1.00 | 130.04 | MOL3 | C |
| ATOM | 10282 | CD | ARG | G | 211 | −27.004 | −62.801 | 21.041 | 1.00 | 133.22 | MOL3 | C |
| ATOM | 10283 | NE | ARG | G | 211 | −27.930 | −63.897 | 21.313 | 1.00 | 137.59 | MOL3 | N |
| ATOM | 10284 | CZ | ARG | G | 211 | −29.186 | −63.941 | 20.877 | 1.00 | 138.83 | MOL3 | C |
| ATOM | 10285 | NH1 | ARG | G | 211 | −29.673 | −62.944 | 20.148 | 1.00 | 138.40 | MOL3 | N |
| ATOM | 10286 | NH2 | ARG | G | 211 | −29.955 | −64.985 | 21.163 | 1.00 | 137.56 | MOL3 | N |
| ATOM | 10287 | C | ARG | G | 211 | −27.795 | −60.035 | 24.958 | 1.00 | 137.45 | MOL3 | C |
| ATOM | 10288 | O | ARG | G | 211 | −28.240 | −60.705 | 25.901 | 1.00 | 135.00 | MOL3 | O |
| ATOM | 10289 | N | ASN | G | 212 | −27.967 | −58.721 | 24.837 | 1.00 | 146.87 | MOL3 | N |
| ATOM | 10290 | CA | ASN | G | 212 | −28.733 | −57.921 | 25.787 | 1.00 | 155.81 | MOL3 | C |
| ATOM | 10291 | CB | ASN | G | 212 | −27.832 | −56.886 | 26.487 | 1.00 | 155.75 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 10292 | CG  | ASN | G | 212 | −26.473 | −56.724 | 25.813  | 1.00 | 156.88 | MOL3 | C |
|------|-------|-----|-----|---|-----|---------|---------|---------|------|--------|------|---|
| ATOM | 10293 | OD1 | ASN | G | 212 | −26.382 | −56.437 | 24.615  | 1.00 | 158.35 | MOL3 | O |
| ATOM | 10294 | ND2 | ASN | G | 212 | −25.408 | −56.898 | 26.589  | 1.00 | 155.49 | MOL3 | N |
| ATOM | 10295 | C   | ASN | G | 212 | −29.864 | −57.214 | 25.031  | 1.00 | 161.50 | MOL3 | C |
| ATOM | 10296 | O   | ASN | G | 212 | −30.919 | −56.922 | 25.600  | 1.00 | 162.29 | MOL3 | O |
| ATOM | 10297 | N   | GLU | G | 213 | −29.621 | −56.951 | 23.745  | 1.00 | 167.90 | MOL3 | N |
| ATOM | 10298 | CA  | GLU | G | 213 | −30.572 | −56.302 | 22.833  | 1.00 | 173.47 | MOL3 | C |
| ATOM | 10299 | CB  | GLU | G | 213 | −31.773 | −57.228 | 22.588  | 1.00 | 173.00 | MOL3 | C |
| ATOM | 10300 | CG  | GLU | G | 213 | −32.233 | −57.300 | 21.128  | 1.00 | 170.59 | MOL3 | C |
| ATOM | 10301 | CD  | GLU | G | 213 | −31.234 | −58.015 | 20.224  | 1.00 | 169.54 | MOL3 | C |
| ATOM | 10302 | OE1 | GLU | G | 213 | −31.531 | −58.181 | 19.020  | 1.00 | 167.25 | MOL3 | O |
| ATOM | 10303 | OE2 | GLU | G | 213 | −30.155 | −58.412 | 20.714  | 1.00 | 169.23 | MOL3 | O |
| ATOM | 10304 | C   | GLU | G | 213 | −31.069 | −54.906 | 23.246  | 1.00 | 176.92 | MOL3 | C |
| ATOM | 10305 | O   | GLU | G | 213 | −31.944 | −54.770 | 24.108  | 1.00 | 177.92 | MOL3 | O |
| ATOM | 10306 | N   | CYS | G | 214 | −30.508 | −53.875 | 22.612  | 1.00 | 179.94 | MOL3 | N |
| ATOM | 10307 | CA  | CYS | G | 214 | −30.882 | −52.482 | 22.879  | 1.00 | 182.62 | MOL3 | C |
| ATOM | 10308 | CB  | CYS | G | 214 | −30.427 | −52.051 | 24.283  | 1.00 | 184.29 | MOL3 | C |
| ATOM | 10309 | SG  | CYS | G | 214 | −31.491 | −50.813 | 25.116  | 1.00 | 183.85 | MOL3 | S |
| ATOM | 10310 | C   | CYS | G | 214 | −30.238 | −51.559 | 21.840  | 1.00 | 183.45 | MOL3 | C |
| ATOM | 10311 | O   | CYS | G | 214 | −29.526 | −52.080 | 20.951  | 1.00 | 184.03 | MOL3 | O |
| ATOM | 10312 | OXT | CYS | G | 214 | −30.454 | −50.329 | 21.926  | 1.00 | 183.24 | MOL3 | O |
| ATOM | 10313 | CB  | GLU | H | 1   | 12.319  | −45.817 | −24.866 | 1.00 | 80.69  | MOL3 | C |
| ATOM | 10314 | CG  | GLU | H | 1   | 12.972  | −44.504 | −24.427 | 1.00 | 96.38  | MOL3 | C |
| ATOM | 10315 | CD  | GLU | H | 1   | 14.460  | −44.643 | −24.132 | 1.00 | 103.23 | MOL3 | C |
| ATOM | 10316 | OE1 | GLU | H | 1   | 15.209  | −45.116 | −25.019 | 1.00 | 106.26 | MOL3 | O |
| ATOM | 10317 | OE2 | GLU | H | 1   | 14.875  | −44.275 | −23.007 | 1.00 | 104.29 | MOL3 | O |
| ATOM | 10318 | C   | GLU | H | 1   | 10.202  | −47.001 | −25.487 | 1.00 | 70.52  | MOL3 | C |
| ATOM | 10319 | O   | GLU | H | 1   | 10.107  | −46.972 | −26.716 | 1.00 | 78.90  | MOL3 | O |
| ATOM | 10320 | N   | GLU | H | 1   | 10.426  | −45.808 | −23.286 | 1.00 | 67.19  | MOL3 | N |
| ATOM | 10321 | CA  | GLU | H | 1   | 10.796  | −45.818 | −24.727 | 1.00 | 71.31  | MOL3 | C |
| ATOM | 10322 | N   | VAL | H | 2   | 9.781   | −48.028 | −24.758 | 1.00 | 63.85  | MOL3 | N |
| ATOM | 10323 | CA  | VAL | H | 2   | 9.219   | −49.211 | −25.381 | 1.00 | 56.70  | MOL3 | C |
| ATOM | 10324 | CB  | VAL | H | 2   | 10.013  | −50.434 | −25.007 | 1.00 | 49.62  | MOL3 | C |
| ATOM | 10325 | CG1 | VAL | H | 2   | 9.649   | −51.582 | −25.928 | 1.00 | 34.77  | MOL3 | C |
| ATOM | 10326 | CG2 | VAL | H | 2   | 11.493  | −50.104 | −25.018 | 1.00 | 51.72  | MOL3 | C |
| ATOM | 10327 | C   | VAL | H | 2   | 7.806   | −49.477 | −24.927 | 1.00 | 61.99  | MOL3 | C |
| ATOM | 10328 | O   | VAL | H | 2   | 7.545   | −50.540 | −24.386 | 1.00 | 73.31  | MOL3 | O |
| ATOM | 10329 | N   | GLN | H | 3   | 6.889   | −48.543 | −25.158 | 1.00 | 61.09  | MOL3 | N |
| ATOM | 10330 | CA  | GLN | H | 3   | 5.497   | −48.718 | −24.730 | 1.00 | 57.29  | MOL3 | C |
| ATOM | 10331 | CB  | GLN | H | 3   | 4.665   | −47.496 | −25.096 | 1.00 | 67.65  | MOL3 | C |
| ATOM | 10332 | CG  | GLN | H | 3   | 5.258   | −46.184 | −24.650 | 1.00 | 91.59  | MOL3 | C |
| ATOM | 10333 | CD  | GLN | H | 3   | 5.242   | −45.147 | −25.770 | 1.00 | 104.67 | MOL3 | C |
| ATOM | 10334 | OE1 | GLN | H | 3   | 4.181   | −44.834 | −26.333 | 1.00 | 109.12 | MOL3 | O |
| ATOM | 10335 | NE2 | GLN | H | 3   | 6.421   | −44.612 | −26.103 | 1.00 | 104.81 | MOL3 | N |
| ATOM | 10336 | C   | GLN | H | 3   | 4.758   | −49.954 | −25.240 | 1.00 | 47.41  | MOL3 | C |
| ATOM | 10337 | O   | GLN | H | 3   | 4.892   | −50.377 | −26.385 | 1.00 | 47.05  | MOL3 | O |
| ATOM | 10338 | N   | LEU | H | 4   | 3.950   | −50.502 | −24.353 | 1.00 | 41.92  | MOL3 | N |
| ATOM | 10339 | CA  | LEU | H | 4   | 3.135   | −51.674 | −24.608 | 1.00 | 43.25  | MOL3 | C |
| ATOM | 10340 | CB  | LEU | H | 4   | 3.844   | −52.888 | −24.022 | 1.00 | 40.95  | MOL3 | C |
| ATOM | 10341 | CG  | LEU | H | 4   | 3.979   | −54.166 | −24.842 | 1.00 | 45.87  | MOL3 | C |
| ATOM | 10342 | CD1 | LEU | H | 4   | 4.318   | −53.862 | −26.299 | 1.00 | 43.17  | MOL3 | C |
| ATOM | 10343 | CD2 | LEU | H | 4   | 5.065   | −55.009 | −24.198 | 1.00 | 42.82  | MOL3 | C |
| ATOM | 10344 | C   | LEU | H | 4   | 1.834   | −51.381 | −23.847 | 1.00 | 44.33  | MOL3 | C |
| ATOM | 10345 | O   | LEU | H | 4   | 1.867   | −51.103 | −22.635 | 1.00 | 45.49  | MOL3 | O |
| ATOM | 10346 | N   | VAL | H | 5   | 0.700   | −51.414 | −24.541 | 1.00 | 40.36  | MOL3 | N |
| ATOM | 10347 | CA  | VAL | H | 5   | −0.565  | −51.117 | −23.886 | 1.00 | 43.21  | MOL3 | C |
| ATOM | 10348 | CB  | VAL | H | 5   | −1.029  | −49.715 | −24.222 | 1.00 | 35.32  | MOL3 | C |
| ATOM | 10349 | CG1 | VAL | H | 5   | −2.317  | −49.418 | −23.491 | 1.00 | 30.52  | MOL3 | C |
| ATOM | 10350 | CG2 | VAL | H | 5   | 0.037   | −48.732 | −23.841 | 1.00 | 28.24  | MOL3 | C |
| ATOM | 10351 | C   | VAL | H | 5   | −1.695  | −52.065 | −24.235 | 1.00 | 49.10  | MOL3 | C |
| ATOM | 10352 | O   | VAL | H | 5   | −2.084  | −52.181 | −25.396 | 1.00 | 51.42  | MOL3 | O |
| ATOM | 10353 | N   | GLU | H | 6   | −2.232  | −52.723 | −23.212 | 1.00 | 53.46  | MOL3 | N |
| ATOM | 10354 | CA  | GLU | H | 6   | −3.316  | −53.678 | −23.381 | 1.00 | 55.93  | MOL3 | C |
| ATOM | 10355 | CB  | GLU | H | 6   | −3.160  | −54.803 | −22.358 | 1.00 | 53.21  | MOL3 | C |
| ATOM | 10356 | CG  | GLU | H | 6   | −2.063  | −54.533 | −21.321 | 1.00 | 56.79  | MOL3 | C |
| ATOM | 10357 | CD  | GLU | H | 6   | −0.982  | −55.607 | −21.310 | 1.00 | 64.46  | MOL3 | C |
| ATOM | 10358 | OE1 | GLU | H | 6   | −0.073  | −55.560 | −20.452 | 1.00 | 62.83  | MOL3 | O |
| ATOM | 10359 | OE2 | GLU | H | 6   | −1.041  | −56.508 | −22.169 | 1.00 | 72.08  | MOL3 | O |
| ATOM | 10360 | C   | GLU | H | 6   | −4.662  | −52.995 | −23.211 | 1.00 | 57.62  | MOL3 | C |
| ATOM | 10361 | O   | GLU | H | 6   | −4.752  | −51.909 | −22.632 | 1.00 | 57.43  | MOL3 | O |
| ATOM | 10362 | N   | SER | H | 7   | −5.707  | −53.633 | −23.723 | 1.00 | 59.33  | MOL3 | N |
| ATOM | 10363 | CA  | SER | H | 7   | −7.051  | −53.084 | −23.625 | 1.00 | 62.56  | MOL3 | C |
| ATOM | 10364 | CB  | SER | H | 7   | −7.209  | −51.891 | −24.564 | 1.00 | 66.75  | MOL3 | C |
| ATOM | 10365 | OG  | SER | H | 7   | −6.737  | −52.205 | −25.866 | 1.00 | 77.01  | MOL3 | O |
| ATOM | 10366 | C   | SER | H | 7   | −8.072  | −54.140 | −23.967 | 1.00 | 62.44  | MOL3 | C |
| ATOM | 10367 | O   | SER | H | 7   | −7.735  | −55.183 | −24.524 | 1.00 | 61.19  | MOL3 | O |
| ATOM | 10368 | N   | GLY | H | 8   | −9.321  | −53.865 | −23.619 | 1.00 | 67.04  | MOL3 | N |

TABLE 1-continued

The atomic coordinates of IL17F in complex with 496 Fab
(H32; a = 189.4; b = 189.4; c = 490.9, α, β = 90°; γ = 120°)

| ATOM | 10369 | CA | GLY | H | 8 | −10.386 | −54.809 | −23.895 | 1.00 | 76.02 | MOL3 | C |
|---|---|---|---|---|---|---|---|---|---|---|---|---|
| ATOM | 10370 | C | GLY | H | 8 | −10.749 | −55.612 | −22.665 | 1.00 | 81.10 | MOL3 | C |
| ATOM | 10371 | O | GLY | H | 8 | −11.307 | −56.702 | −22.754 | 1.00 | 79.02 | MOL3 | O |
| ATOM | 10372 | N | GLY | H | 9 | −10.429 | −55.070 | −21.499 | 1.00 | 88.12 | MOL3 | N |
| ATOM | 10373 | CA | GLY | H | 9 | −10.737 | −55.776 | −20.273 | 1.00 | 90.21 | MOL3 | C |
| ATOM | 10374 | C | GLY | H | 9 | −12.179 | −55.589 | −19.862 | 1.00 | 91.24 | MOL3 | C |
| ATOM | 10375 | O | GLY | H | 9 | −12.856 | −54.671 | −20.339 | 1.00 | 94.44 | MOL3 | O |
| ATOM | 10376 | N | GLY | H | 10 | −12.647 | −56.465 | −18.976 | 1.00 | 91.00 | MOL3 | N |
| ATOM | 10377 | CA | GLY | H | 10 | −14.016 | −56.389 | −18.485 | 1.00 | 88.13 | MOL3 | C |
| ATOM | 10378 | C | GLY | H | 10 | −14.495 | −57.727 | −17.962 | 1.00 | 82.14 | MOL3 | C |
| ATOM | 10379 | O | GLY | H | 10 | −13.719 | −58.681 | −17.906 | 1.00 | 79.67 | MOL3 | O |
| ATOM | 10380 | N | LEU | H | 11 | −15.759 | −57.810 | −17.562 | 1.00 | 77.90 | MOL3 | N |
| ATOM | 10381 | CA | LEU | H | 11 | −16.270 | −59.082 | −17.077 | 1.00 | 74.98 | MOL3 | C |
| ATOM | 10382 | CB | LEU | H | 11 | −17.031 | −58.934 | −15.764 | 1.00 | 71.57 | MOL3 | C |
| ATOM | 10383 | CG | LEU | H | 11 | −18.320 | −58.134 | −15.791 | 1.00 | 77.35 | MOL3 | C |
| ATOM | 10384 | CD1 | LEU | H | 11 | −18.985 | −58.225 | −14.436 | 1.00 | 82.67 | MOL3 | C |
| ATOM | 10385 | CD2 | LEU | H | 11 | −18.023 | −56.693 | −16.147 | 1.00 | 85.15 | MOL3 | C |
| ATOM | 10386 | C | LEU | H | 11 | −17.163 | −59.671 | −18.139 | 1.00 | 74.43 | MOL3 | C |
| ATOM | 10387 | O | LEU | H | 11 | −17.611 | −58.973 | −19.045 | 1.00 | 72.67 | MOL3 | O |
| ATOM | 10388 | N | VAL | H | 12 | −17.405 | −60.968 | −18.043 | 1.00 | 77.54 | MOL3 | N |
| ATOM | 10389 | CA | VAL | H | 12 | −18.235 | −61.637 | −19.026 | 1.00 | 84.43 | MOL3 | C |
| ATOM | 10390 | CB | VAL | H | 12 | −17.499 | −61.779 | −20.365 | 1.00 | 86.47 | MOL3 | C |
| ATOM | 10391 | CG1 | VAL | H | 12 | −16.214 | −62.564 | −20.172 | 1.00 | 85.38 | MOL3 | C |
| ATOM | 10392 | CG2 | VAL | H | 12 | −18.397 | −62.472 | −21.373 | 1.00 | 95.20 | MOL3 | C |
| ATOM | 10393 | C | VAL | H | 12 | −18.656 | −63.020 | −18.561 | 1.00 | 87.93 | MOL3 | C |
| ATOM | 10394 | O | VAL | H | 12 | −17.820 | −63.846 | −18.206 | 1.00 | 92.06 | MOL3 | O |
| ATOM | 10395 | N | GLN | H | 13 | −19.963 | −63.264 | −18.570 | 1.00 | 93.30 | MOL3 | N |
| ATOM | 10396 | CA | GLN | H | 13 | −20.525 | −64.547 | −18.144 | 1.00 | 93.98 | MOL3 | C |
| ATOM | 10397 | CB | GLN | H | 13 | −22.020 | −64.630 | −18.507 | 1.00 | 101.62 | MOL3 | C |
| ATOM | 10398 | CG | GLN | H | 13 | −22.372 | −64.091 | −19.903 | 1.00 | 114.56 | MOL3 | C |
| ATOM | 10399 | CD | GLN | H | 13 | −22.366 | −62.559 | −19.985 | 1.00 | 122.12 | MOL3 | C |
| ATOM | 10400 | OE1 | GLN | H | 13 | −23.149 | −61.885 | −19.306 | 1.00 | 124.57 | MOL3 | O |
| ATOM | 10401 | NE2 | GLN | H | 13 | −21.484 | −62.009 | −20.823 | 1.00 | 120.27 | MOL3 | N |
| ATOM | 10402 | C | GLN | H | 13 | −19.771 | −65.715 | −18.767 | 1.00 | 86.99 | MOL3 | C |
| ATOM | 10403 | O | GLN | H | 13 | −19.267 | −65.613 | −19.887 | 1.00 | 82.90 | MOL3 | O |
| ATOM | 10404 | N | PRO | H | 14 | −19.676 | −66.839 | −18.040 | 1.00 | 80.78 | MOL3 | N |
| ATOM | 10405 | CD | PRO | H | 14 | −20.285 | −67.128 | −16.734 | 1.00 | 79.55 | MOL3 | C |
| ATOM | 10406 | CA | PRO | H | 14 | −18.973 | −68.015 | −18.546 | 1.00 | 80.09 | MOL3 | C |
| ATOM | 10407 | CB | PRO | H | 14 | −19.374 | −69.102 | −17.563 | 1.00 | 75.48 | MOL3 | C |
| ATOM | 10408 | CG | PRO | H | 14 | −19.520 | −68.359 | −16.300 | 1.00 | 73.51 | MOL3 | C |
| ATOM | 10409 | C | PRO | H | 14 | −19.422 | −68.318 | −19.965 | 1.00 | 85.55 | MOL3 | C |
| ATOM | 10410 | O | PRO | H | 14 | −20.480 | −67.866 | −20.394 | 1.00 | 90.37 | MOL3 | O |
| ATOM | 10411 | N | GLY | H | 15 | −18.618 | −69.080 | −20.695 | 1.00 | 89.51 | MOL3 | N |
| ATOM | 10412 | CA | GLY | H | 15 | −18.963 | −69.397 | −22.068 | 1.00 | 91.81 | MOL3 | C |
| ATOM | 10413 | C | GLY | H | 15 | −18.782 | −68.213 | −23.009 | 1.00 | 94.38 | MOL3 | C |
| ATOM | 10414 | O | GLY | H | 15 | −18.402 | −68.390 | −24.168 | 1.00 | 96.38 | MOL3 | O |
| ATOM | 10415 | N | GLY | H | 16 | −19.052 | −67.005 | −22.515 | 1.00 | 95.37 | MOL3 | N |
| ATOM | 10416 | CA | GLY | H | 16 | −18.916 | −65.807 | −23.329 | 1.00 | 93.58 | MOL3 | C |
| ATOM | 10417 | C | GLY | H | 16 | −17.553 | −65.651 | −23.983 | 1.00 | 91.42 | MOL3 | C |
| ATOM | 10418 | O | GLY | H | 16 | −16.675 | −66.494 | −23.818 | 1.00 | 89.53 | MOL3 | O |
| ATOM | 10419 | N | SER | H | 17 | −17.368 | −64.569 | −24.729 | 1.00 | 90.50 | MOL3 | N |
| ATOM | 10420 | CA | SER | H | 17 | −16.096 | −64.345 | −25.399 | 1.00 | 88.77 | MOL3 | C |
| ATOM | 10421 | CB | SER | H | 17 | −16.183 | −64.769 | −26.872 | 1.00 | 93.79 | MOL3 | C |
| ATOM | 10422 | OG | SER | H | 17 | −16.939 | −63.845 | −27.646 | 1.00 | 101.08 | MOL3 | O |
| ATOM | 10423 | C | SER | H | 17 | −15.603 | −62.904 | −25.315 | 1.00 | 86.43 | MOL3 | C |
| ATOM | 10424 | O | SER | H | 17 | −16.389 | −61.956 | −25.176 | 1.00 | 85.00 | MOL3 | O |
| ATOM | 10425 | N | LEU | H | 18 | −14.284 | −62.761 | −25.408 | 1.00 | 80.10 | MOL3 | N |
| ATOM | 10426 | CA | LEU | H | 18 | −13.633 | −61.465 | −25.353 | 1.00 | 75.09 | MOL3 | C |
| ATOM | 10427 | CB | LEU | H | 18 | −13.170 | −61.178 | −23.933 | 1.00 | 68.07 | MOL3 | C |
| ATOM | 10428 | CG | LEU | H | 18 | −13.953 | −60.096 | −23.210 | 1.00 | 62.48 | MOL3 | C |
| ATOM | 10429 | CD1 | LEU | H | 18 | −13.285 | −59.884 | −21.891 | 1.00 | 62.03 | MOL3 | C |
| ATOM | 10430 | CD2 | LEU | H | 18 | −13.989 | −58.799 | −24.016 | 1.00 | 59.71 | MOL3 | C |
| ATOM | 10431 | C | LEU | H | 18 | −12.427 | −61.428 | −26.273 | 1.00 | 73.76 | MOL3 | C |
| ATOM | 10432 | O | LEU | H | 18 | −11.813 | −62.463 | −26.530 | 1.00 | 71.85 | MOL3 | O |
| ATOM | 10433 | N | ARG | H | 19 | −12.098 | −60.234 | −26.762 | 1.00 | 71.25 | MOL3 | N |
| ATOM | 10434 | CA | ARG | H | 19 | −10.945 | −60.046 | −27.633 | 1.00 | 70.80 | MOL3 | C |
| ATOM | 10435 | CB | ARG | H | 19 | −11.393 | −59.676 | −29.046 | 1.00 | 76.31 | MOL3 | C |
| ATOM | 10436 | CG | ARG | H | 19 | −10.262 | −59.469 | −30.054 | 1.00 | 81.86 | MOL3 | C |
| ATOM | 10437 | CD | ARG | H | 19 | −10.782 | −59.612 | −31.486 | 1.00 | 87.72 | MOL3 | C |
| ATOM | 10438 | NE | ARG | H | 19 | −9.862 | −59.094 | −32.497 | 1.00 | 89.33 | MOL3 | N |
| ATOM | 10439 | CZ | ARG | H | 19 | −9.536 | −57.810 | −32.623 | 1.00 | 94.54 | MOL3 | C |
| ATOM | 10440 | NH1 | ARG | H | 19 | −10.051 | −56.903 | −31.800 | 1.00 | 93.84 | MOL3 | N |
| ATOM | 10441 | NH2 | ARG | H | 19 | −8.706 | −57.428 | −33.584 | 1.00 | 97.79 | MOL3 | N |
| ATOM | 10442 | C | ARG | H | 19 | −10.071 | −58.947 | −27.051 | 1.00 | 69.54 | MOL3 | C |
| ATOM | 10443 | O | ARG | H | 19 | −10.500 | −57.795 | −26.937 | 1.00 | 70.47 | MOL3 | O |
| ATOM | 10444 | N | LEU | H | 20 | −8.847 | −59.324 | −26.682 | 1.00 | 63.89 | MOL3 | N |
| ATOM | 10445 | CA | LEU | H | 20 | −7.877 | −58.417 | −26.090 | 1.00 | 56.44 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 10446 | CB | LEU | H | 20 | −7.129 | −59.149 | −24.985 | 1.00 | 53.18 | MOL3 | C |
|---|---|---|---|---|---|---|---|---|---|---|---|---|
| ATOM | 10447 | CG | LEU | H | 20 | −7.988 | −59.770 | −23.877 | 1.00 | 53.71 | MOL3 | C |
| ATOM | 10448 | CD1 | LEU | H | 20 | −7.117 | −60.610 | −22.954 | 1.00 | 49.56 | MOL3 | C |
| ATOM | 10449 | CD2 | LEU | H | 20 | −8.680 | −58.672 | −23.084 | 1.00 | 52.72 | MOL3 | C |
| ATOM | 10450 | C | LEU | H | 20 | −6.891 | −57.895 | −27.127 | 1.00 | 55.93 | MOL3 | C |
| ATOM | 10451 | O | LEU | H | 20 | −6.503 | −58.621 | −28.043 | 1.00 | 55.63 | MOL3 | O |
| ATOM | 10452 | N | SER | H | 21 | −6.486 | −56.638 | −26.971 | 1.00 | 53.32 | MOL3 | N |
| ATOM | 10453 | CA | SER | H | 21 | −5.549 | −56.011 | −27.892 | 1.00 | 55.06 | MOL3 | C |
| ATOM | 10454 | CB | SER | H | 21 | −6.246 | −54.909 | −28.674 | 1.00 | 58.91 | MOL3 | C |
| ATOM | 10455 | OG | SER | H | 21 | −7.620 | −55.205 | −28.830 | 1.00 | 74.44 | MOL3 | O |
| ATOM | 10456 | C | SER | H | 21 | −4.388 | −55.399 | −27.131 | 1.00 | 55.70 | MOL3 | C |
| ATOM | 10457 | O | SER | H | 21 | −4.523 | −55.019 | −25.971 | 1.00 | 57.26 | MOL3 | O |
| ATOM | 10458 | N | CYS | H | 22 | −3.248 | −55.300 | −27.802 | 1.00 | 56.67 | MOL3 | N |
| ATOM | 10459 | CA | CYS | H | 22 | −2.046 | −54.727 | −27.220 | 1.00 | 56.43 | MOL3 | C |
| ATOM | 10460 | C | CYS | H | 22 | −1.400 | −53.853 | −28.269 | 1.00 | 50.74 | MOL3 | C |
| ATOM | 10461 | O | CYS | H | 22 | −1.092 | −54.322 | −29.352 | 1.00 | 52.24 | MOL3 | O |
| ATOM | 10462 | CB | CYS | H | 22 | −1.077 | −55.840 | −26.817 | 1.00 | 63.13 | MOL3 | C |
| ATOM | 10463 | SG | CYS | H | 22 | 0.529 | −55.285 | −26.142 | 1.00 | 72.78 | MOL3 | S |
| ATOM | 10464 | N | ALA | H | 23 | −1.210 | −52.581 | −27.961 | 1.00 | 48.24 | MOL3 | N |
| ATOM | 10465 | CA | ALA | H | 23 | −0.590 | −51.687 | −28.912 | 1.00 | 51.21 | MOL3 | C |
| ATOM | 10466 | CB | ALA | H | 23 | −1.292 | −50.353 | −28.892 | 1.00 | 57.28 | MOL3 | C |
| ATOM | 10467 | C | ALA | H | 23 | 0.869 | −51.532 | −28.519 | 1.00 | 52.95 | MOL3 | C |
| ATOM | 10468 | O | ALA | H | 23 | 1.175 | −51.127 | −27.402 | 1.00 | 56.88 | MOL3 | O |
| ATOM | 10469 | N | ALA | H | 24 | 1.771 | −51.865 | −29.431 | 1.00 | 50.57 | MOL3 | N |
| ATOM | 10470 | CA | ALA | H | 24 | 3.187 | −51.762 | −29.132 | 1.00 | 51.81 | MOL3 | C |
| ATOM | 10471 | CB | ALA | H | 24 | 3.903 | −53.016 | −29.587 | 1.00 | 62.83 | MOL3 | C |
| ATOM | 10472 | C | ALA | H | 24 | 3.811 | −50.547 | −29.783 | 1.00 | 49.99 | MOL3 | C |
| ATOM | 10473 | O | ALA | H | 24 | 3.286 | −50.016 | −30.759 | 1.00 | 53.01 | MOL3 | O |
| ATOM | 10474 | N | SER | H | 25 | 4.949 | −50.123 | −29.249 | 1.00 | 45.42 | MOL3 | N |
| ATOM | 10475 | CA | SER | H | 25 | 5.651 | −48.962 | −29.775 | 1.00 | 48.13 | MOL3 | C |
| ATOM | 10476 | CB | SER | H | 25 | 4.977 | −47.677 | −29.318 | 1.00 | 46.68 | MOL3 | C |
| ATOM | 10477 | OG | SER | H | 25 | 5.893 | −46.919 | −28.544 | 1.00 | 47.00 | MOL3 | O |
| ATOM | 10478 | C | SER | H | 25 | 7.057 | −48.935 | −29.230 | 1.00 | 47.04 | MOL3 | C |
| ATOM | 10479 | O | SER | H | 25 | 7.347 | −49.595 | −28.252 | 1.00 | 52.69 | MOL3 | O |
| ATOM | 10480 | N | GLY | H | 26 | 7.919 | −48.140 | −29.842 | 1.00 | 49.40 | MOL3 | N |
| ATOM | 10481 | CA | GLY | H | 26 | 9.279 | −48.038 | −29.359 | 1.00 | 47.23 | MOL3 | C |
| ATOM | 10482 | C | GLY | H | 26 | 10.185 | −49.149 | −29.838 | 1.00 | 46.49 | MOL3 | C |
| ATOM | 10483 | O | GLY | H | 26 | 11.295 | −49.289 | −29.328 | 1.00 | 46.28 | MOL3 | O |
| ATOM | 10484 | N | PHE | H | 27 | 9.727 | −49.944 | −30.802 | 1.00 | 43.77 | MOL3 | N |
| ATOM | 10485 | CA | PHE | H | 27 | 10.566 | −51.014 | −31.318 | 1.00 | 51.46 | MOL3 | C |
| ATOM | 10486 | CB | PHE | H | 27 | 10.827 | −52.049 | −30.222 | 1.00 | 48.70 | MOL3 | C |
| ATOM | 10487 | CG | PHE | H | 27 | 9.601 | −52.772 | −29.752 | 1.00 | 49.82 | MOL3 | C |
| ATOM | 10488 | CD1 | PHE | H | 27 | 9.280 | −54.017 | −30.247 | 1.00 | 48.99 | MOL3 | C |
| ATOM | 10489 | CD2 | PHE | H | 27 | 8.782 | −52.216 | −28.793 | 1.00 | 57.82 | MOL3 | C |
| ATOM | 10490 | CE1 | PHE | H | 27 | 8.168 | −54.692 | −29.790 | 1.00 | 47.68 | MOL3 | C |
| ATOM | 10491 | CE2 | PHE | H | 27 | 7.667 | −52.888 | −28.334 | 1.00 | 55.96 | MOL3 | C |
| ATOM | 10492 | CZ | PHE | H | 27 | 7.363 | −54.127 | −28.836 | 1.00 | 51.20 | MOL3 | C |
| ATOM | 10493 | C | PHE | H | 27 | 10.027 | −51.696 | −32.566 | 1.00 | 56.33 | MOL3 | C |
| ATOM | 10494 | O | PHE | H | 27 | 8.831 | −51.653 | −32.848 | 1.00 | 57.40 | MOL3 | O |
| ATOM | 10495 | N | THR | H | 28 | 10.921 | −52.318 | −33.326 | 1.00 | 59.29 | MOL3 | N |
| ATOM | 10496 | CA | THR | H | 28 | 10.506 | −53.000 | −34.536 | 1.00 | 59.20 | MOL3 | C |
| ATOM | 10497 | CB | THR | H | 28 | 11.727 | −53.364 | −35.386 | 1.00 | 62.43 | MOL3 | C |
| ATOM | 10498 | OG1 | THR | H | 28 | 12.903 | −53.377 | −34.559 | 1.00 | 75.00 | MOL3 | O |
| ATOM | 10499 | CG2 | THR | H | 28 | 11.912 | −52.336 | −36.478 | 1.00 | 62.63 | MOL3 | C |
| ATOM | 10500 | C | THR | H | 28 | 9.666 | −54.231 | −34.202 | 1.00 | 53.56 | MOL3 | C |
| ATOM | 10501 | O | THR | H | 28 | 10.155 | −55.353 | −34.154 | 1.00 | 51.45 | MOL3 | O |
| ATOM | 10502 | N | PHE | H | 29 | 8.389 | −53.973 | −33.954 | 1.00 | 50.42 | MOL3 | N |
| ATOM | 10503 | CA | PHE | H | 29 | 7.392 | −54.982 | −33.621 | 1.00 | 52.34 | MOL3 | C |
| ATOM | 10504 | CB | PHE | H | 29 | 6.010 | −54.327 | −33.673 | 1.00 | 49.86 | MOL3 | C |
| ATOM | 10505 | CG | PHE | H | 29 | 4.895 | −55.191 | −33.169 | 1.00 | 46.09 | MOL3 | C |
| ATOM | 10506 | CD1 | PHE | H | 29 | 4.605 | −55.248 | −31.817 | 1.00 | 41.19 | MOL3 | C |
| ATOM | 10507 | CD2 | PHE | H | 29 | 4.123 | −55.937 | −34.054 | 1.00 | 47.78 | MOL3 | C |
| ATOM | 10508 | CE1 | PHE | H | 29 | 3.565 | −56.032 | −31.352 | 1.00 | 45.08 | MOL3 | C |
| ATOM | 10509 | CE2 | PHE | H | 29 | 3.079 | −56.725 | −33.597 | 1.00 | 44.39 | MOL3 | C |
| ATOM | 10510 | CZ | PHE | H | 29 | 2.801 | −56.770 | −32.241 | 1.00 | 47.36 | MOL3 | C |
| ATOM | 10511 | C | PHE | H | 29 | 7.413 | −56.189 | −34.565 | 1.00 | 57.28 | MOL3 | C |
| ATOM | 10512 | O | PHE | H | 29 | 7.488 | −57.338 | −34.119 | 1.00 | 58.37 | MOL3 | O |
| ATOM | 10513 | N | SER | H | 30 | 7.335 | −55.921 | −35.867 | 1.00 | 58.55 | MOL3 | N |
| ATOM | 10514 | CA | SER | H | 30 | 7.323 | −56.967 | −36.882 | 1.00 | 58.10 | MOL3 | C |
| ATOM | 10515 | CB | SER | H | 30 | 7.137 | −56.339 | −38.262 | 1.00 | 60.76 | MOL3 | C |
| ATOM | 10516 | OG | SER | H | 30 | 6.942 | −54.932 | −38.165 | 1.00 | 73.31 | MOL3 | O |
| ATOM | 10517 | C | SER | H | 30 | 8.578 | −57.832 | −36.872 | 1.00 | 60.85 | MOL3 | C |
| ATOM | 10518 | O | SER | H | 30 | 8.715 | −58.739 | −37.697 | 1.00 | 59.99 | MOL3 | O |
| ATOM | 10519 | N | ASP | H | 31 | 9.484 | −57.557 | −35.932 | 1.00 | 64.35 | MOL3 | N |
| ATOM | 10520 | CA | ASP | H | 31 | 10.736 | −58.305 | −35.805 | 1.00 | 64.12 | MOL3 | C |
| ATOM | 10521 | CB | ASP | H | 31 | 11.916 | −57.376 | −35.534 | 1.00 | 66.03 | MOL3 | C |
| ATOM | 10522 | CG | ASP | H | 31 | 12.343 | −56.599 | −36.745 | 1.00 | 76.69 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 10523 | OD1 | ASP | H | 31 | 13.473 | −56.066 | −36.714 | 1.00 | 82.61 | MOL3 | O |
|---|---|---|---|---|---|---|---|---|---|---|---|---|
| ATOM | 10524 | OD2 | ASP | H | 31 | 11.562 | −56.510 | −37.719 | 1.00 | 83.16 | MOL3 | O |
| ATOM | 10525 | C | ASP | H | 31 | 10.754 | −59.337 | −34.699 | 1.00 | 61.93 | MOL3 | C |
| ATOM | 10526 | O | ASP | H | 31 | 11.432 | −60.345 | −34.820 | 1.00 | 70.22 | MOL3 | O |
| ATOM | 10527 | N | TYR | H | 32 | 10.025 | −59.084 | −33.620 | 1.00 | 58.60 | MOL3 | N |
| ATOM | 10528 | CA | TYR | H | 32 | 10.033 | −59.983 | −32.474 | 1.00 | 57.91 | MOL3 | C |
| ATOM | 10529 | CB | TYR | H | 32 | 10.303 | −59.176 | −31.209 | 1.00 | 58.87 | MOL3 | C |
| ATOM | 10530 | CG | TYR | H | 32 | 11.612 | −58.433 | −31.201 | 1.00 | 56.33 | MOL3 | C |
| ATOM | 10531 | CD1 | TYR | H | 32 | 11.845 | −57.382 | −32.060 | 1.00 | 58.83 | MOL3 | C |
| ATOM | 10532 | CE1 | TYR | H | 32 | 13.049 | −56.727 | −32.049 | 1.00 | 71.93 | MOL3 | C |
| ATOM | 10533 | CD2 | TYR | H | 32 | 12.616 | −58.801 | −30.334 | 1.00 | 59.34 | MOL3 | C |
| ATOM | 10534 | CE2 | TYR | H | 32 | 13.810 | −58.163 | −30.313 | 1.00 | 66.80 | MOL3 | C |
| ATOM | 10535 | CZ | TYR | H | 32 | 14.035 | −57.130 | −31.166 | 1.00 | 74.47 | MOL3 | C |
| ATOM | 10536 | OH | TYR | H | 32 | 15.270 | −56.521 | −31.141 | 1.00 | 84.60 | MOL3 | O |
| ATOM | 10537 | C | TYR | H | 32 | 8.774 | −60.790 | −32.245 | 1.00 | 55.77 | MOL3 | C |
| ATOM | 10538 | O | TYR | H | 32 | 7.702 | −60.418 | −32.703 | 1.00 | 58.85 | MOL3 | O |
| ATOM | 10539 | N | ASN | H | 33 | 8.906 | −61.889 | −31.514 | 1.00 | 52.56 | MOL3 | N |
| ATOM | 10540 | CA | ASN | H | 33 | 7.741 | −62.695 | −31.206 | 1.00 | 56.62 | MOL3 | C |
| ATOM | 10541 | CB | ASN | H | 33 | 8.143 | −64.085 | −30.714 | 1.00 | 61.20 | MOL3 | C |
| ATOM | 10542 | CG | ASN | H | 33 | 9.292 | −64.670 | −31.492 | 1.00 | 66.30 | MOL3 | C |
| ATOM | 10543 | OD1 | ASN | H | 33 | 9.240 | −64.795 | −32.724 | 1.00 | 68.76 | MOL3 | O |
| ATOM | 10544 | ND2 | ASN | H | 33 | 10.346 | −65.043 | −30.773 | 1.00 | 70.28 | MOL3 | N |
| ATOM | 10545 | C | ASN | H | 33 | 7.027 | −61.952 | −30.081 | 1.00 | 56.59 | MOL3 | C |
| ATOM | 10546 | O | ASN | H | 33 | 7.626 | −61.124 | −29.403 | 1.00 | 59.09 | MOL3 | O |
| ATOM | 10547 | N | MET | H | 34 | 5.753 | −62.249 | −29.881 | 1.00 | 53.23 | MOL3 | N |
| ATOM | 10548 | CA | MET | H | 34 | 4.987 | −61.606 | −28.834 | 1.00 | 48.63 | MOL3 | C |
| ATOM | 10549 | CB | MET | H | 34 | 3.983 | −60.650 | −29.467 | 1.00 | 43.44 | MOL3 | C |
| ATOM | 10550 | CG | MET | H | 34 | 4.614 | −59.421 | −30.057 | 1.00 | 40.62 | MOL3 | C |
| ATOM | 10551 | SD | MET | H | 34 | 5.626 | −58.584 | −28.818 | 1.00 | 51.97 | MOL3 | S |
| ATOM | 10552 | CE | MET | H | 34 | 4.381 | −57.816 | −27.805 | 1.00 | 46.46 | MOL3 | C |
| ATOM | 10553 | C | MET | H | 34 | 4.267 | −62.676 | −28.020 | 1.00 | 51.21 | MOL3 | C |
| ATOM | 10554 | O | MET | H | 34 | 4.102 | −63.797 | −28.488 | 1.00 | 53.62 | MOL3 | O |
| ATOM | 10555 | N | ALA | H | 35 | 3.841 | −62.346 | −26.806 | 1.00 | 51.15 | MOL3 | N |
| ATOM | 10556 | CA | ALA | H | 35 | 3.145 | −63.323 | −25.982 | 1.00 | 47.47 | MOL3 | C |
| ATOM | 10557 | CB | ALA | H | 35 | 4.152 | −64.228 | −25.287 | 1.00 | 41.63 | MOL3 | C |
| ATOM | 10558 | C | ALA | H | 35 | 2.226 | −62.704 | −24.944 | 1.00 | 47.83 | MOL3 | C |
| ATOM | 10559 | O | ALA | H | 35 | 2.284 | −61.508 | −24.654 | 1.00 | 49.61 | MOL3 | O |
| ATOM | 10560 | N | TRP | H | 36 | 1.361 | −63.545 | −24.395 | 1.00 | 47.61 | MOL3 | N |
| ATOM | 10561 | CA | TRP | H | 36 | 0.443 | −63.127 | −23.356 | 1.00 | 45.28 | MOL3 | C |
| ATOM | 10562 | CB | TRP | H | 36 | −1.001 | −63.401 | −23.743 | 1.00 | 38.09 | MOL3 | C |
| ATOM | 10563 | CG | TRP | H | 36 | −1.506 | −62.574 | −24.843 | 1.00 | 35.79 | MOL3 | C |
| ATOM | 10564 | CD2 | TRP | H | 36 | −2.105 | −61.286 | −24.731 | 1.00 | 39.24 | MOL3 | C |
| ATOM | 10565 | CE2 | TRP | H | 36 | −2.485 | −60.884 | −26.030 | 1.00 | 43.04 | MOL3 | C |
| ATOM | 10566 | CE3 | TRP | H | 36 | −2.361 | −60.431 | −23.661 | 1.00 | 34.67 | MOL3 | C |
| ATOM | 10567 | CD1 | TRP | H | 36 | −1.537 | −62.897 | −26.166 | 1.00 | 44.70 | MOL3 | C |
| ATOM | 10568 | NE1 | TRP | H | 36 | −2.131 | −61.889 | −26.892 | 1.00 | 43.27 | MOL3 | N |
| ATOM | 10569 | CZ2 | TRP | H | 36 | −3.104 | −59.666 | −26.283 | 1.00 | 33.90 | MOL3 | C |
| ATOM | 10570 | CZ3 | TRP | H | 36 | −2.975 | −59.228 | −23.917 | 1.00 | 38.12 | MOL3 | C |
| ATOM | 10571 | CH2 | TRP | H | 36 | −3.340 | −58.854 | −25.217 | 1.00 | 30.70 | MOL3 | C |
| ATOM | 10572 | C | TRP | H | 36 | 0.780 | −63.956 | −22.137 | 1.00 | 45.18 | MOL3 | C |
| ATOM | 10573 | O | TRP | H | 36 | 1.065 | −65.147 | −22.241 | 1.00 | 48.92 | MOL3 | O |
| ATOM | 10574 | N | VAL | H | 37 | 0.758 | −63.321 | −20.983 | 1.00 | 39.79 | MOL3 | N |
| ATOM | 10575 | CA | VAL | H | 37 | 1.052 | −64.005 | −19.747 | 1.00 | 40.84 | MOL3 | C |
| ATOM | 10576 | CB | VAL | H | 37 | 2.428 | −63.617 | −19.209 | 1.00 | 37.48 | MOL3 | C |
| ATOM | 10577 | CG1 | VAL | H | 37 | 2.698 | −64.337 | −17.922 | 1.00 | 31.38 | MOL3 | C |
| ATOM | 10578 | CG2 | VAL | H | 37 | 3.479 | −63.954 | −20.221 | 1.00 | 31.44 | MOL3 | C |
| ATOM | 10579 | C | VAL | H | 37 | −0.014 | −63.499 | −18.814 | 1.00 | 49.24 | MOL3 | C |
| ATOM | 10580 | O | VAL | H | 37 | −0.270 | −62.293 | −18.745 | 1.00 | 54.99 | MOL3 | O |
| ATOM | 10581 | N | ARG | H | 38 | −0.643 | −64.415 | −18.097 | 1.00 | 49.75 | MOL3 | N |
| ATOM | 10582 | CA | ARG | H | 38 | −1.713 | −64.038 | −17.196 | 1.00 | 52.55 | MOL3 | C |
| ATOM | 10583 | CB | ARG | H | 38 | −2.929 | −64.875 | −17.509 | 1.00 | 56.84 | MOL3 | C |
| ATOM | 10584 | CG | ARG | H | 38 | −2.602 | −66.341 | −17.420 | 1.00 | 62.25 | MOL3 | C |
| ATOM | 10585 | CD | ARG | H | 38 | −3.791 | −67.152 | −16.954 | 1.00 | 69.06 | MOL3 | C |
| ATOM | 10586 | NE | ARG | H | 38 | −4.874 | −67.146 | −17.923 | 1.00 | 61.89 | MOL3 | N |
| ATOM | 10587 | CZ | ARG | H | 38 | −5.525 | −68.241 | −18.271 | 1.00 | 64.52 | MOL3 | C |
| ATOM | 10588 | NH1 | ARG | H | 38 | −5.191 | −69.404 | −17.722 | 1.00 | 62.42 | MOL3 | N |
| ATOM | 10589 | NH2 | ARG | H | 38 | −6.493 | −68.177 | −19.168 | 1.00 | 67.54 | MOL3 | N |
| ATOM | 10590 | C | ARG | H | 38 | −1.335 | −64.261 | −15.750 | 1.00 | 51.86 | MOL3 | C |
| ATOM | 10591 | O | ARG | H | 38 | −0.419 | −65.013 | −15.450 | 1.00 | 48.15 | MOL3 | O |
| ATOM | 10592 | N | GLN | H | 39 | −2.070 | −63.621 | −14.851 | 1.00 | 55.25 | MOL3 | N |
| ATOM | 10593 | CA | GLN | H | 39 | −1.810 | −63.759 | −13.429 | 1.00 | 54.03 | MOL3 | C |
| ATOM | 10594 | CB | GLN | H | 39 | −0.761 | −62.737 | −13.012 | 1.00 | 52.59 | MOL3 | C |
| ATOM | 10595 | CG | GLN | H | 39 | −0.508 | −62.653 | −11.540 | 1.00 | 49.71 | MOL3 | C |
| ATOM | 10596 | CD | GLN | H | 39 | 0.474 | −61.563 | −11.214 | 1.00 | 49.39 | MOL3 | C |
| ATOM | 10597 | OE1 | GLN | H | 39 | 0.339 | −60.433 | −11.681 | 1.00 | 48.74 | MOL3 | O |
| ATOM | 10598 | NE2 | GLN | H | 39 | 1.467 | −61.888 | −10.405 | 1.00 | 45.99 | MOL3 | N |
| ATOM | 10599 | C | GLN | H | 39 | −3.106 | −63.582 | −12.637 | 1.00 | 57.67 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 10600 | O | GLN | H | 39 | −3.627 | −62.470 | −12.479 | 1.00 | 61.21 | MOL3 | O |
|---|---|---|---|---|---|---|---|---|---|---|---|---|
| ATOM | 10601 | N | ALA | H | 40 | −3.626 | −64.706 | −12.156 | 1.00 | 55.62 | MOL3 | N |
| ATOM | 10602 | CA | ALA | H | 40 | −4.855 | −64.734 | −11.385 | 1.00 | 55.64 | MOL3 | C |
| ATOM | 10603 | CB | ALA | H | 40 | −5.244 | −66.144 | −11.145 | 1.00 | 53.44 | MOL3 | C |
| ATOM | 10604 | C | ALA | H | 40 | −4.697 | −64.011 | −10.060 | 1.00 | 63.02 | MOL3 | C |
| ATOM | 10605 | O | ALA | H | 40 | −3.658 | −64.095 | −9.421 | 1.00 | 70.41 | MOL3 | O |
| ATOM | 10606 | N | PRO | H | 41 | −5.745 | −63.313 | −9.612 | 1.00 | 67.97 | MOL3 | N |
| ATOM | 10607 | CD | PRO | H | 41 | −7.127 | −63.480 | −10.088 | 1.00 | 68.50 | MOL3 | C |
| ATOM | 10608 | CA | PRO | H | 41 | −5.713 | −62.567 | −8.349 | 1.00 | 71.98 | MOL3 | C |
| ATOM | 10609 | CB | PRO | H | 41 | −7.189 | −62.398 | −8.019 | 1.00 | 74.44 | MOL3 | C |
| ATOM | 10610 | CG | PRO | H | 41 | −7.839 | −62.379 | −9.373 | 1.00 | 70.53 | MOL3 | C |
| ATOM | 10611 | C | PRO | H | 41 | −4.972 | −63.321 | −7.252 | 1.00 | 74.99 | MOL3 | C |
| ATOM | 10612 | O | PRO | H | 41 | −5.248 | −64.488 | −6.987 | 1.00 | 76.25 | MOL3 | O |
| ATOM | 10613 | N | GLY | H | 42 | −4.021 | −62.653 | −6.620 | 1.00 | 78.76 | MOL3 | N |
| ATOM | 10614 | CA | GLY | H | 42 | −3.267 | −63.297 | −5.563 | 1.00 | 82.26 | MOL3 | C |
| ATOM | 10615 | C | GLY | H | 42 | −2.257 | −64.326 | −6.044 | 1.00 | 81.56 | MOL3 | C |
| ATOM | 10616 | O | GLY | H | 42 | −1.160 | −64.421 | −5.488 | 1.00 | 85.89 | MOL3 | O |
| ATOM | 10617 | N | LYS | H | 43 | −2.599 | −65.090 | −7.075 | 1.00 | 74.50 | MOL3 | N |
| ATOM | 10618 | CA | LYS | H | 43 | −1.675 | −66.100 | −7.555 | 1.00 | 74.34 | MOL3 | C |
| ATOM | 10619 | CB | LYS | H | 43 | −2.447 | −67.170 | −8.314 | 1.00 | 81.90 | MOL3 | C |
| ATOM | 10620 | CG | LYS | H | 43 | −3.471 | −67.877 | −7.436 | 1.00 | 93.04 | MOL3 | C |
| ATOM | 10621 | CD | LYS | H | 43 | −3.947 | −69.194 | −8.050 | 1.00 | 104.70 | MOL3 | C |
| ATOM | 10622 | CE | LYS | H | 43 | −2.781 | −70.168 | −8.263 | 1.00 | 110.69 | MOL3 | C |
| ATOM | 10623 | NZ | LYS | H | 43 | −3.221 | −71.520 | −8.733 | 1.00 | 110.14 | MOL3 | N |
| ATOM | 10624 | C | LYS | H | 43 | −0.457 | −65.617 | −8.368 | 1.00 | 73.13 | MOL3 | C |
| ATOM | 10625 | O | LYS | H | 43 | −0.224 | −64.414 | −8.533 | 1.00 | 71.85 | MOL3 | O |
| ATOM | 10626 | N | GLY | H | 44 | 0.326 | −66.578 | −8.853 | 1.00 | 69.00 | MOL3 | N |
| ATOM | 10627 | CA | GLY | H | 44 | 1.528 | −66.272 | −9.606 | 1.00 | 62.52 | MOL3 | C |
| ATOM | 10628 | C | GLY | H | 44 | 1.356 | −65.945 | −11.075 | 1.00 | 64.11 | MOL3 | C |
| ATOM | 10629 | O | GLY | H | 44 | 0.316 | −65.431 | −11.504 | 1.00 | 68.38 | MOL3 | O |
| ATOM | 10630 | N | LEU | H | 45 | 2.383 | −66.257 | −11.858 | 1.00 | 58.47 | MOL3 | N |
| ATOM | 10631 | CA | LEU | H | 45 | 2.376 | −65.958 | −13.285 | 1.00 | 54.84 | MOL3 | C |
| ATOM | 10632 | CB | LEU | H | 45 | 3.660 | −65.206 | −13.657 | 1.00 | 51.82 | MOL3 | C |
| ATOM | 10633 | CG | LEU | H | 45 | 3.926 | −63.899 | −12.905 | 1.00 | 48.64 | MOL3 | C |
| ATOM | 10634 | CD1 | LEU | H | 45 | 5.399 | −63.508 | −12.993 | 1.00 | 43.07 | MOL3 | C |
| ATOM | 10635 | CD2 | LEU | H | 45 | 3.016 | −62.828 | −13.473 | 1.00 | 42.51 | MOL3 | C |
| ATOM | 10636 | C | LEU | H | 45 | 2.258 | −67.213 | −14.132 | 1.00 | 54.17 | MOL3 | C |
| ATOM | 10637 | O | LEU | H | 45 | 2.986 | −68.183 | −13.944 | 1.00 | 50.26 | MOL3 | O |
| ATOM | 10638 | N | GLU | H | 46 | 1.339 | −67.180 | −15.084 | 1.00 | 58.43 | MOL3 | N |
| ATOM | 10639 | CA | GLU | H | 46 | 1.123 | −68.311 | −15.965 | 1.00 | 60.38 | MOL3 | C |
| ATOM | 10640 | CB | GLU | H | 46 | −0.250 | −68.919 | −15.686 | 1.00 | 71.49 | MOL3 | C |
| ATOM | 10641 | CG | GLU | H | 46 | −0.426 | −70.361 | −16.110 | 1.00 | 83.80 | MOL3 | C |
| ATOM | 10642 | CD | GLU | H | 46 | −1.757 | −70.929 | −15.654 | 1.00 | 91.71 | MOL3 | C |
| ATOM | 10643 | OE1 | GLU | H | 46 | −2.779 | −70.679 | −16.336 | 1.00 | 91.50 | MOL3 | O |
| ATOM | 10644 | OE2 | GLU | H | 46 | −1.775 | −71.611 | −14.602 | 1.00 | 92.19 | MOL3 | O |
| ATOM | 10645 | C | GLU | H | 46 | 1.200 | −67.805 | −17.395 | 1.00 | 60.49 | MOL3 | C |
| ATOM | 10646 | O | GLU | H | 46 | 0.626 | −66.760 | −17.740 | 1.00 | 61.39 | MOL3 | O |
| ATOM | 10647 | N | TRP | H | 47 | 1.926 | −68.537 | −18.227 | 1.00 | 57.40 | MOL3 | N |
| ATOM | 10648 | CA | TRP | H | 47 | 2.071 | −68.147 | −19.617 | 1.00 | 57.25 | MOL3 | C |
| ATOM | 10649 | CB | TRP | H | 47 | 3.319 | −68.772 | −20.211 | 1.00 | 51.55 | MOL3 | C |
| ATOM | 10650 | CG | TRP | H | 47 | 3.294 | −68.709 | −21.680 | 1.00 | 58.49 | MOL3 | C |
| ATOM | 10651 | CD2 | TRP | H | 47 | 3.195 | −69.816 | −22.571 | 1.00 | 65.35 | MOL3 | C |
| ATOM | 10652 | CE2 | TRP | H | 47 | 3.104 | −69.298 | −23.875 | 1.00 | 68.55 | MOL3 | C |
| ATOM | 10653 | CE3 | TRP | H | 47 | 3.171 | −71.200 | −22.394 | 1.00 | 68.81 | MOL3 | C |
| ATOM | 10654 | CD1 | TRP | H | 47 | 3.268 | −67.586 | −22.455 | 1.00 | 62.40 | MOL3 | C |
| ATOM | 10655 | NE1 | TRP | H | 47 | 3.152 | −67.930 | −23.782 | 1.00 | 67.20 | MOL3 | N |
| ATOM | 10656 | CZ2 | TRP | H | 47 | 2.987 | −70.117 | −24.991 | 1.00 | 70.75 | MOL3 | C |
| ATOM | 10657 | CZ3 | TRP | H | 47 | 3.057 | −72.007 | −23.503 | 1.00 | 70.26 | MOL3 | C |
| ATOM | 10658 | CH2 | TRP | H | 47 | 2.965 | −71.466 | −24.783 | 1.00 | 69.71 | MOL3 | C |
| ATOM | 10659 | C | TRP | H | 47 | 0.870 | −68.584 | −20.432 | 1.00 | 56.11 | MOL3 | C |
| ATOM | 10660 | O | TRP | H | 47 | 0.484 | −69.739 | −20.377 | 1.00 | 62.69 | MOL3 | O |
| ATOM | 10661 | N | VAL | H | 48 | 0.272 | −67.673 | −21.188 | 1.00 | 55.01 | MOL3 | N |
| ATOM | 10662 | CA | VAL | H | 48 | −0.879 | −68.039 | −22.005 | 1.00 | 53.56 | MOL3 | C |
| ATOM | 10663 | CB | VAL | H | 48 | −1.857 | −66.856 | −22.151 | 1.00 | 51.33 | MOL3 | C |
| ATOM | 10664 | CG1 | VAL | H | 48 | −2.811 | −67.067 | −23.312 | 1.00 | 44.69 | MOL3 | C |
| ATOM | 10665 | CG2 | VAL | H | 48 | −2.653 | −66.732 | −20.880 | 1.00 | 56.05 | MOL3 | C |
| ATOM | 10666 | C | VAL | H | 48 | −0.444 | −68.539 | −23.376 | 1.00 | 54.95 | MOL3 | C |
| ATOM | 10667 | O | VAL | H | 48 | −0.430 | −69.739 | −23.625 | 1.00 | 53.09 | MOL3 | O |
| ATOM | 10668 | N | ALA | H | 49 | −0.068 | −67.631 | −24.265 | 1.00 | 58.16 | MOL3 | N |
| ATOM | 10669 | CA | ALA | H | 49 | 0.362 | −68.046 | −25.590 | 1.00 | 62.56 | MOL3 | C |
| ATOM | 10670 | CB | ALA | H | 49 | −0.830 | −68.144 | −26.509 | 1.00 | 61.76 | MOL3 | C |
| ATOM | 10671 | C | ALA | H | 49 | 1.374 | −67.081 | −26.176 | 1.00 | 66.37 | MOL3 | C |
| ATOM | 10672 | O | ALA | H | 49 | 1.571 | −65.980 | −25.660 | 1.00 | 69.42 | MOL3 | O |
| ATOM | 10673 | N | THR | H | 50 | 2.025 | −67.514 | −27.249 | 1.00 | 65.01 | MOL3 | N |
| ATOM | 10674 | CA | THR | H | 50 | 2.987 | −66.675 | −27.948 | 1.00 | 65.55 | MOL3 | C |
| ATOM | 10675 | CB | THR | H | 50 | 4.472 | −66.949 | −27.505 | 1.00 | 66.68 | MOL3 | C |
| ATOM | 10676 | OG1 | THR | H | 50 | 5.249 | −67.338 | −28.641 | 1.00 | 71.68 | MOL3 | O |

TABLE 1-continued

The atomic coordinates of IL17F in complex with 496 Fab
(H32; a = 189.4; b = 189.4; c = 490.9, α, β = 90°; γ = 120°)

| ATOM | 10677 | CG2 | THR | H | 50 | 4.559 | −68.028 | −26.459 | 1.00 | 56.41 | MOL3 | C |
|------|-------|-----|-----|---|----|-------|---------|---------|------|-------|------|---|
| ATOM | 10678 | C | THR | H | 50 | 2.843 | −66.898 | −29.457 | 1.00 | 62.54 | MOL3 | C |
| ATOM | 10679 | O | THR | H | 50 | 2.513 | −67.993 | −29.897 | 1.00 | 66.24 | MOL3 | O |
| ATOM | 10680 | N | ILE | H | 51 | 3.061 | −65.848 | −30.239 | 1.00 | 57.78 | MOL3 | N |
| ATOM | 10681 | CA | ILE | H | 51 | 2.970 | −65.925 | −31.688 | 1.00 | 58.59 | MOL3 | C |
| ATOM | 10682 | CB | ILE | H | 51 | 1.789 | −65.127 | −32.221 | 1.00 | 61.74 | MOL3 | C |
| ATOM | 10683 | CG2 | ILE | H | 51 | 1.719 | −63.778 | −31.532 | 1.00 | 65.58 | MOL3 | C |
| ATOM | 10684 | CG1 | ILE | H | 51 | 1.924 | −64.965 | −33.736 | 1.00 | 63.13 | MOL3 | C |
| ATOM | 10685 | CD1 | ILE | H | 51 | 0.898 | −64.033 | −34.342 | 1.00 | 60.29 | MOL3 | C |
| ATOM | 10686 | C | ILE | H | 51 | 4.247 | −65.335 | −32.244 | 1.00 | 61.40 | MOL3 | C |
| ATOM | 10687 | O | ILE | H | 51 | 4.776 | −64.383 | −31.686 | 1.00 | 63.89 | MOL3 | O |
| ATOM | 10688 | N | THR | H | 52 | 4.743 | −65.884 | −33.347 | 1.00 | 65.83 | MOL3 | N |
| ATOM | 10689 | CA | THR | H | 52 | 6.002 | −65.409 | −33.917 | 1.00 | 69.29 | MOL3 | C |
| ATOM | 10690 | CB | THR | H | 52 | 6.639 | −66.493 | −34.770 | 1.00 | 68.24 | MOL3 | C |
| ATOM | 10691 | OG1 | THR | H | 52 | 5.882 | −66.647 | −35.975 | 1.00 | 78.52 | MOL3 | O |
| ATOM | 10692 | CG2 | THR | H | 52 | 6.650 | −67.819 | −34.006 | 1.00 | 60.36 | MOL3 | C |
| ATOM | 10693 | C | THR | H | 52 | 5.919 | −64.120 | −34.725 | 1.00 | 71.78 | MOL3 | C |
| ATOM | 10694 | O | THR | H | 52 | 4.839 | −63.665 | −35.092 | 1.00 | 71.56 | MOL3 | O |
| ATOM | 10695 | N | TYR | H | 53 | 7.078 | −63.538 | −35.004 | 1.00 | 76.82 | MOL3 | N |
| ATOM | 10696 | CA | TYR | H | 53 | 7.134 | −62.279 | −35.728 | 1.00 | 83.93 | MOL3 | C |
| ATOM | 10697 | CB | TYR | H | 53 | 8.586 | −61.813 | −35.844 | 1.00 | 81.83 | MOL3 | C |
| ATOM | 10698 | CG | TYR | H | 53 | 9.427 | −62.665 | −36.751 | 1.00 | 82.92 | MOL3 | C |
| ATOM | 10699 | CD1 | TYR | H | 53 | 9.616 | −62.317 | −38.080 | 1.00 | 81.60 | MOL3 | C |
| ATOM | 10700 | CE1 | TYR | H | 53 | 10.367 | −63.106 | −38.924 | 1.00 | 85.19 | MOL3 | C |
| ATOM | 10701 | CD2 | TYR | H | 53 | 10.013 | −63.831 | −36.287 | 1.00 | 86.43 | MOL3 | C |
| ATOM | 10702 | CE2 | TYR | H | 53 | 10.767 | −64.630 | −37.126 | 1.00 | 89.89 | MOL3 | C |
| ATOM | 10703 | CZ | TYR | H | 53 | 10.942 | −64.263 | −38.445 | 1.00 | 87.12 | MOL3 | C |
| ATOM | 10704 | OH | TYR | H | 53 | 11.703 | −65.053 | −39.280 | 1.00 | 88.25 | MOL3 | O |
| ATOM | 10705 | C | TYR | H | 53 | 6.476 | −62.296 | −37.105 | 1.00 | 89.59 | MOL3 | C |
| ATOM | 10706 | O | TYR | H | 53 | 5.673 | −61.411 | −37.414 | 1.00 | 90.27 | MOL3 | O |
| ATOM | 10707 | N | GLU | H | 54 | 6.807 | −63.291 | −37.930 | 1.00 | 95.40 | MOL3 | N |
| ATOM | 10708 | CA | GLU | H | 54 | 6.237 | −63.378 | −39.276 | 1.00 | 97.31 | MOL3 | C |
| ATOM | 10709 | CB | GLU | H | 54 | 6.765 | −64.602 | −40.025 | 1.00 | 98.84 | MOL3 | C |
| ATOM | 10710 | CG | GLU | H | 54 | 5.928 | −65.850 | −39.812 | 1.00 | 108.31 | MOL3 | C |
| ATOM | 10711 | CD | GLU | H | 54 | 6.561 | −66.823 | −38.845 | 1.00 | 112.31 | MOL3 | C |
| ATOM | 10712 | OE1 | GLU | H | 54 | 5.872 | −67.781 | −38.434 | 1.00 | 111.19 | MOL3 | O |
| ATOM | 10713 | OE2 | GLU | H | 54 | 7.751 | −66.635 | −38.506 | 1.00 | 114.93 | MOL3 | O |
| ATOM | 10714 | C | GLU | H | 54 | 4.722 | −63.464 | −39.168 | 1.00 | 97.26 | MOL3 | C |
| ATOM | 10715 | O | GLU | H | 54 | 3.994 | −63.033 | −40.061 | 1.00 | 94.50 | MOL3 | O |
| ATOM | 10716 | N | GLY | H | 55 | 4.256 | −64.024 | −38.059 | 1.00 | 96.91 | MOL3 | N |
| ATOM | 10717 | CA | GLY | H | 55 | 2.832 | −64.135 | −37.846 | 1.00 | 99.34 | MOL3 | C |
| ATOM | 10718 | C | GLY | H | 55 | 2.269 | −65.493 | −38.188 | 1.00 | 102.51 | MOL3 | C |
| ATOM | 10719 | O | GLY | H | 55 | 1.053 | −65.678 | −38.161 | 1.00 | 104.24 | MOL3 | O |
| ATOM | 10720 | N | ARG | H | 56 | 3.130 | −66.452 | −38.510 | 1.00 | 105.17 | MOL3 | N |
| ATOM | 10721 | CA | ARG | H | 56 | 2.632 | −67.782 | −38.849 | 1.00 | 110.29 | MOL3 | C |
| ATOM | 10722 | CB | ARG | H | 56 | 2.876 | −68.087 | −40.341 | 1.00 | 117.75 | MOL3 | C |
| ATOM | 10723 | CG | ARG | H | 56 | 1.864 | −69.075 | −40.980 | 1.00 | 124.33 | MOL3 | C |
| ATOM | 10724 | CD | ARG | H | 56 | 0.399 | −68.588 | −40.858 | 1.00 | 128.22 | MOL3 | C |
| ATOM | 10725 | NE | ARG | H | 56 | −0.565 | −69.460 | −41.539 | 1.00 | 127.99 | MOL3 | N |
| ATOM | 10726 | CZ | ARG | H | 56 | −1.888 | −69.376 | −41.404 | 1.00 | 127.35 | MOL3 | C |
| ATOM | 10727 | NH1 | ARG | H | 56 | −2.421 | −68.456 | −40.608 | 1.00 | 124.80 | MOL3 | N |
| ATOM | 10728 | NH2 | ARG | H | 56 | −2.682 | −70.212 | −42.067 | 1.00 | 122.83 | MOL3 | N |
| ATOM | 10729 | C | ARG | H | 56 | 3.244 | −68.873 | −37.971 | 1.00 | 107.22 | MOL3 | C |
| ATOM | 10730 | O | ARG | H | 56 | 4.154 | −69.588 | −38.386 | 1.00 | 107.49 | MOL3 | O |
| ATOM | 10731 | N | ASN | H | 57 | 2.722 | −68.984 | −36.753 | 1.00 | 104.15 | MOL3 | N |
| ATOM | 10732 | CA | ASN | H | 57 | 3.172 | −69.969 | −35.776 | 1.00 | 101.40 | MOL3 | C |
| ATOM | 10733 | CB | ASN | H | 57 | 4.701 | −70.090 | −35.799 | 1.00 | 104.71 | MOL3 | C |
| ATOM | 10734 | CG | ASN | H | 57 | 5.173 | −71.513 | −36.054 | 1.00 | 106.01 | MOL3 | C |
| ATOM | 10735 | OD1 | ASN | H | 57 | 4.768 | −72.146 | −37.029 | 1.00 | 104.49 | MOL3 | O |
| ATOM | 10736 | ND2 | ASN | H | 57 | 6.038 | −72.020 | −35.178 | 1.00 | 104.68 | MOL3 | N |
| ATOM | 10737 | C | ASN | H | 57 | 2.714 | −69.536 | −34.386 | 1.00 | 95.59 | MOL3 | C |
| ATOM | 10738 | O | ASN | H | 57 | 3.310 | −68.656 | −33.777 | 1.00 | 92.89 | MOL3 | O |
| ATOM | 10739 | N | THR | H | 58 | 1.649 | −70.156 | −33.898 | 1.00 | 89.66 | MOL3 | N |
| ATOM | 10740 | CA | THR | H | 58 | 1.117 | −69.833 | −32.590 | 1.00 | 87.41 | MOL3 | C |
| ATOM | 10741 | CB | THR | H | 58 | −0.370 | −69.535 | −32.690 | 1.00 | 88.89 | MOL3 | C |
| ATOM | 10742 | OG1 | THR | H | 58 | −1.049 | −70.677 | −33.219 | 1.00 | 93.56 | MOL3 | O |
| ATOM | 10743 | CG2 | THR | H | 58 | −0.603 | −68.357 | −33.616 | 1.00 | 89.97 | MOL3 | C |
| ATOM | 10744 | C | THR | H | 58 | 1.364 | −71.033 | −31.697 | 1.00 | 86.81 | MOL3 | C |
| ATOM | 10745 | O | THR | H | 58 | 1.544 | −72.135 | −32.205 | 1.00 | 87.41 | MOL3 | O |
| ATOM | 10746 | N | TYR | H | 59 | 1.375 | −70.837 | −30.377 | 1.00 | 87.09 | MOL3 | N |
| ATOM | 10747 | CA | TYR | H | 59 | 1.656 | −71.949 | −29.477 | 1.00 | 87.89 | MOL3 | C |
| ATOM | 10748 | CB | TYR | H | 59 | 3.011 | −71.724 | −28.815 | 1.00 | 86.52 | MOL3 | C |
| ATOM | 10749 | CG | TYR | H | 59 | 4.159 | −71.914 | −29.785 | 1.00 | 92.68 | MOL3 | C |
| ATOM | 10750 | CD1 | TYR | H | 59 | 4.409 | −70.987 | −30.789 | 1.00 | 93.63 | MOL3 | C |
| ATOM | 10751 | CE1 | TYR | H | 59 | 5.423 | −71.186 | −31.715 | 1.00 | 97.03 | MOL3 | C |
| ATOM | 10752 | CD2 | TYR | H | 59 | 4.962 | −73.050 | −29.730 | 1.00 | 95.37 | MOL3 | C |
| ATOM | 10753 | CE2 | TYR | H | 59 | 5.980 | −73.258 | −30.651 | 1.00 | 96.17 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 10754 | CZ | TYR | H | 59 | 6.205 | −72.324 | −31.643 | 1.00 | 98.10 | MOL3 | C |
|---|---|---|---|---|---|---|---|---|---|---|---|---|
| ATOM | 10755 | OH | TYR | H | 59 | 7.201 | −72.536 | −32.575 | 1.00 | 100.34 | MOL3 | O |
| ATOM | 10756 | C | TYR | H | 59 | 0.620 | −72.348 | −28.434 | 1.00 | 88.98 | MOL3 | C |
| ATOM | 10757 | O | TYR | H | 59 | 0.255 | −73.522 | −28.352 | 1.00 | 97.11 | MOL3 | O |
| ATOM | 10758 | N | TYR | H | 60 | 0.159 | −71.411 | −27.619 | 1.00 | 84.78 | MOL3 | N |
| ATOM | 10759 | CA | TYR | H | 60 | −0.870 | −71.736 | −26.621 | 1.00 | 83.82 | MOL3 | C |
| ATOM | 10760 | CB | TYR | H | 60 | −2.136 | −72.260 | −27.327 | 1.00 | 72.84 | MOL3 | C |
| ATOM | 10761 | CG | TYR | H | 60 | −2.630 | −71.361 | −28.436 | 1.00 | 65.27 | MOL3 | C |
| ATOM | 10762 | CD1 | TYR | H | 60 | −2.171 | −71.509 | −29.735 | 1.00 | 61.04 | MOL3 | C |
| ATOM | 10763 | CE1 | TYR | H | 60 | −2.547 | −70.630 | −30.726 | 1.00 | 61.15 | MOL3 | C |
| ATOM | 10764 | CD2 | TYR | H | 60 | −3.490 | −70.307 | −28.164 | 1.00 | 64.94 | MOL3 | C |
| ATOM | 10765 | CE2 | TYR | H | 60 | −3.870 | −69.418 | −29.149 | 1.00 | 63.80 | MOL3 | C |
| ATOM | 10766 | CZ | TYR | H | 60 | −3.392 | −69.582 | −30.427 | 1.00 | 65.02 | MOL3 | C |
| ATOM | 10767 | OH | TYR | H | 60 | −3.741 | −68.673 | −31.397 | 1.00 | 65.42 | MOL3 | O |
| ATOM | 10768 | C | TYR | H | 60 | −0.499 | −72.730 | −25.513 | 1.00 | 83.92 | MOL3 | C |
| ATOM | 10769 | O | TYR | H | 60 | 0.293 | −73.649 | −25.708 | 1.00 | 83.62 | MOL3 | O |
| ATOM | 10770 | N | ARG | H | 61 | −1.107 | −72.546 | −24.348 | 1.00 | 87.10 | MOL3 | N |
| ATOM | 10771 | CA | ARG | H | 61 | −0.863 | −73.432 | −23.227 | 1.00 | 90.67 | MOL3 | C |
| ATOM | 10772 | CB | ARG | H | 61 | −0.879 | −72.648 | −21.910 | 1.00 | 89.04 | MOL3 | C |
| ATOM | 10773 | CG | ARG | H | 61 | −1.978 | −73.017 | −20.925 | 1.00 | 88.73 | MOL3 | C |
| ATOM | 10774 | CD | ARG | H | 61 | −1.397 | −73.411 | −19.565 | 1.00 | 91.73 | MOL3 | C |
| ATOM | 10775 | NE | ARG | H | 61 | −0.283 | −72.553 | −19.170 | 1.00 | 93.52 | MOL3 | N |
| ATOM | 10776 | CZ | ARG | H | 61 | 0.477 | −72.744 | −18.093 | 1.00 | 96.29 | MOL3 | C |
| ATOM | 10777 | NH1 | ARG | H | 61 | 0.252 | −73.767 | −17.278 | 1.00 | 97.97 | MOL3 | N |
| ATOM | 10778 | NH2 | ARG | H | 61 | 1.486 | −71.918 | −17.844 | 1.00 | 100.59 | MOL3 | N |
| ATOM | 10779 | C | ARG | H | 61 | −1.919 | −74.527 | −23.227 | 1.00 | 97.16 | MOL3 | C |
| ATOM | 10780 | O | ARG | H | 61 | −3.079 | −74.294 | −23.582 | 1.00 | 102.79 | MOL3 | O |
| ATOM | 10781 | N | ASP | H | 62 | −1.502 | −75.736 | −22.867 | 1.00 | 100.75 | MOL3 | N |
| ATOM | 10782 | CA | ASP | H | 62 | −2.410 | −76.881 | −22.803 | 1.00 | 103.41 | MOL3 | C |
| ATOM | 10783 | CB | ASP | H | 62 | −1.659 | −78.133 | −22.330 | 1.00 | 108.69 | MOL3 | C |
| ATOM | 10784 | CG | ASP | H | 62 | −1.031 | −78.913 | −23.464 | 1.00 | 115.91 | MOL3 | C |
| ATOM | 10785 | OD1 | ASP | H | 62 | −0.409 | −79.959 | −23.175 | 1.00 | 117.07 | MOL3 | O |
| ATOM | 10786 | OD2 | ASP | H | 62 | −1.162 | −78.488 | −24.634 | 1.00 | 120.19 | MOL3 | O |
| ATOM | 10787 | C | ASP | H | 62 | −3.499 | −76.590 | −21.783 | 1.00 | 100.29 | MOL3 | C |
| ATOM | 10788 | O | ASP | H | 62 | −3.495 | −77.191 | −20.711 | 1.00 | 102.03 | MOL3 | O |
| ATOM | 10789 | N | SER | H | 63 | −4.423 | −75.687 | −22.095 | 1.00 | 93.82 | MOL3 | N |
| ATOM | 10790 | CA | SER | H | 63 | −5.476 | −75.357 | −21.147 | 1.00 | 90.28 | MOL3 | C |
| ATOM | 10791 | CB | SER | H | 63 | −4.859 | −74.879 | −19.835 | 1.00 | 87.21 | MOL3 | C |
| ATOM | 10792 | OG | SER | H | 63 | −5.861 | −74.488 | −18.921 | 1.00 | 92.41 | MOL3 | O |
| ATOM | 10793 | C | SER | H | 63 | −6.394 | −74.284 | −21.701 | 1.00 | 91.17 | MOL3 | C |
| ATOM | 10794 | O | SER | H | 63 | −7.370 | −73.886 | −21.059 | 1.00 | 91.75 | MOL3 | O |
| ATOM | 10795 | N | VAL | H | 64 | −6.069 | −73.811 | −22.896 | 1.00 | 91.49 | MOL3 | N |
| ATOM | 10796 | CA | VAL | H | 64 | −6.865 | −72.787 | −23.553 | 1.00 | 94.39 | MOL3 | C |
| ATOM | 10797 | CB | VAL | H | 64 | −6.385 | −71.370 | −23.201 | 1.00 | 93.70 | MOL3 | C |
| ATOM | 10798 | CG1 | VAL | H | 64 | −6.499 | −71.140 | −21.711 | 1.00 | 96.30 | MOL3 | C |
| ATOM | 10799 | CG2 | VAL | H | 64 | −4.954 | −71.175 | −23.674 | 1.00 | 94.32 | MOL3 | C |
| ATOM | 10800 | C | VAL | H | 64 | −6.748 | −72.961 | −25.053 | 1.00 | 96.79 | MOL3 | C |
| ATOM | 10801 | O | VAL | H | 64 | −7.037 | −72.035 | −25.816 | 1.00 | 96.76 | MOL3 | O |
| ATOM | 10802 | N | LYS | H | 65 | −6.308 | −74.145 | −25.473 | 1.00 | 95.31 | MOL3 | N |
| ATOM | 10803 | CA | LYS | H | 65 | −6.168 | −74.411 | −26.892 | 1.00 | 94.68 | MOL3 | C |
| ATOM | 10804 | CB | LYS | H | 65 | −5.389 | −75.703 | −27.120 | 1.00 | 97.79 | MOL3 | C |
| ATOM | 10805 | CG | LYS | H | 65 | −3.917 | −75.620 | −26.727 | 1.00 | 105.41 | MOL3 | C |
| ATOM | 10806 | CD | LYS | H | 65 | −3.130 | −76.823 | −27.248 | 1.00 | 111.88 | MOL3 | C |
| ATOM | 10807 | CE | LYS | H | 65 | −3.241 | −76.949 | −28.776 | 1.00 | 117.99 | MOL3 | C |
| ATOM | 10808 | NZ | LYS | H | 65 | −2.605 | −78.188 | −29.340 | 1.00 | 117.99 | MOL3 | N |
| ATOM | 10809 | C | LYS | H | 65 | −7.548 | −74.499 | −27.519 | 1.00 | 93.17 | MOL3 | C |
| ATOM | 10810 | O | LYS | H | 65 | −8.502 | −74.954 | −26.891 | 1.00 | 90.62 | MOL3 | O |
| ATOM | 10811 | N | GLY | H | 66 | −7.654 | −74.041 | −28.758 | 1.00 | 94.38 | MOL3 | N |
| ATOM | 10812 | CA | GLY | H | 66 | −8.934 | −74.064 | −29.441 | 1.00 | 97.52 | MOL3 | C |
| ATOM | 10813 | C | GLY | H | 66 | −9.857 | −72.956 | −28.961 | 1.00 | 98.00 | MOL3 | C |
| ATOM | 10814 | O | GLY | H | 66 | −10.562 | −72.320 | −29.757 | 1.00 | 100.20 | MOL3 | O |
| ATOM | 10815 | N | ARG | H | 67 | −9.843 | −72.716 | −27.652 | 1.00 | 91.62 | MOL3 | N |
| ATOM | 10816 | CA | ARG | H | 67 | −10.680 | −71.694 | −27.043 | 1.00 | 83.37 | MOL3 | C |
| ATOM | 10817 | CB | ARG | H | 67 | −10.836 | −72.011 | −25.561 | 1.00 | 73.95 | MOL3 | C |
| ATOM | 10818 | CG | ARG | H | 67 | −10.741 | −73.499 | −25.317 | 1.00 | 73.72 | MOL3 | C |
| ATOM | 10819 | CD | ARG | H | 67 | −11.347 | −73.936 | −24.004 | 1.00 | 80.67 | MOL3 | C |
| ATOM | 10820 | NE | ARG | H | 67 | −10.576 | −73.505 | −22.843 | 1.00 | 82.41 | MOL3 | N |
| ATOM | 10821 | CZ | ARG | H | 67 | −10.706 | −72.323 | −22.254 | 1.00 | 76.67 | MOL3 | C |
| ATOM | 10822 | NH1 | ARG | H | 67 | −9.953 | −72.026 | −21.200 | 1.00 | 69.65 | MOL3 | N |
| ATOM | 10823 | NH2 | ARG | H | 67 | −11.596 | −71.449 | −22.715 | 1.00 | 72.65 | MOL3 | N |
| ATOM | 10824 | C | ARG | H | 67 | −10.089 | −70.305 | −27.247 | 1.00 | 83.65 | MOL3 | C |
| ATOM | 10825 | O | ARG | H | 67 | −10.817 | −69.342 | −27.477 | 1.00 | 86.32 | MOL3 | O |
| ATOM | 10826 | N | PHE | H | 68 | −8.764 | −70.212 | −27.171 | 1.00 | 81.89 | MOL3 | N |
| ATOM | 10827 | CA | PHE | H | 68 | −8.058 | −68.948 | −27.352 | 1.00 | 81.08 | MOL3 | C |
| ATOM | 10828 | CB | PHE | H | 68 | −6.939 | −68.819 | −26.321 | 1.00 | 72.92 | MOL3 | C |
| ATOM | 10829 | CG | PHE | H | 68 | −7.395 | −68.365 | −24.971 | 1.00 | 71.33 | MOL3 | C |
| ATOM | 10830 | CD1 | PHE | H | 68 | −8.714 | −68.485 | −24.589 | 1.00 | 73.75 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 10831 | CD2 | PHE | H | 68 | −6.487 | −67.856 | −24.061 | 1.00 | 72.40 | MOL3 | C |
|---|---|---|---|---|---|---|---|---|---|---|---|---|
| ATOM | 10832 | CE1 | PHE | H | 68 | −9.123 | −68.109 | −23.320 | 1.00 | 69.11 | MOL3 | C |
| ATOM | 10833 | CE2 | PHE | H | 68 | −6.887 | −67.480 | −22.795 | 1.00 | 70.70 | MOL3 | C |
| ATOM | 10834 | CZ | PHE | H | 68 | −8.210 | −67.609 | −22.425 | 1.00 | 69.29 | MOL3 | C |
| ATOM | 10835 | C | PHE | H | 68 | −7.436 | −68.881 | −28.743 | 1.00 | 84.69 | MOL3 | C |
| ATOM | 10836 | O | PHE | H | 68 | −7.245 | −69.911 | −29.399 | 1.00 | 84.19 | MOL3 | O |
| ATOM | 10837 | N | THR | H | 69 | −7.117 | −67.665 | −29.184 | 1.00 | 85.37 | MOL3 | N |
| ATOM | 10838 | CA | THR | H | 69 | −6.479 | −67.449 | −30.480 | 1.00 | 81.81 | MOL3 | C |
| ATOM | 10839 | CB | THR | H | 69 | −7.502 | −67.428 | −31.627 | 1.00 | 85.13 | MOL3 | C |
| ATOM | 10840 | OG1 | THR | H | 69 | −7.912 | −68.771 | −31.927 | 1.00 | 89.96 | MOL3 | O |
| ATOM | 10841 | CG2 | THR | H | 69 | −6.892 | −66.806 | −32.868 | 1.00 | 86.41 | MOL3 | C |
| ATOM | 10842 | C | THR | H | 69 | −5.675 | −66.154 | −30.484 | 1.00 | 78.76 | MOL3 | C |
| ATOM | 10843 | O | THR | H | 69 | −6.221 | −65.056 | −30.378 | 1.00 | 81.27 | MOL3 | O |
| ATOM | 10844 | N | ILE | H | 70 | −4.364 | −66.309 | −30.612 | 1.00 | 72.91 | MOL3 | N |
| ATOM | 10845 | CA | ILE | H | 70 | −3.426 | −65.196 | −30.602 | 1.00 | 70.91 | MOL3 | C |
| ATOM | 10846 | CB | ILE | H | 70 | −2.139 | −65.656 | −29.849 | 1.00 | 65.12 | MOL3 | C |
| ATOM | 10847 | CG2 | ILE | H | 70 | −1.458 | −66.745 | −30.625 | 1.00 | 66.98 | MOL3 | C |
| ATOM | 10848 | CG1 | ILE | H | 70 | −1.180 | −64.495 | −29.604 | 1.00 | 60.99 | MOL3 | C |
| ATOM | 10849 | CD1 | ILE | H | 70 | 0.021 | −64.911 | −28.791 | 1.00 | 42.86 | MOL3 | C |
| ATOM | 10850 | C | ILE | H | 70 | −3.125 | −64.740 | −32.035 | 1.00 | 71.17 | MOL3 | C |
| ATOM | 10851 | O | ILE | H | 70 | −2.949 | −65.561 | −32.926 | 1.00 | 72.08 | MOL3 | O |
| ATOM | 10852 | N | SER | H | 71 | −3.070 | −63.431 | −32.260 | 1.00 | 74.25 | MOL3 | N |
| ATOM | 10853 | CA | SER | H | 71 | −2.810 | −62.913 | −33.600 | 1.00 | 77.76 | MOL3 | C |
| ATOM | 10854 | CB | SER | H | 71 | −4.120 | −62.832 | −34.368 | 1.00 | 84.72 | MOL3 | C |
| ATOM | 10855 | OG | SER | H | 71 | −5.076 | −62.078 | −33.634 | 1.00 | 92.41 | MOL3 | O |
| ATOM | 10856 | C | SER | H | 71 | −2.167 | −61.537 | −33.575 | 1.00 | 78.41 | MOL3 | C |
| ATOM | 10857 | O | SER | H | 71 | −2.275 | −60.818 | −32.583 | 1.00 | 80.38 | MOL3 | O |
| ATOM | 10858 | N | ARG | H | 72 | −1.517 | −61.162 | −34.673 | 1.00 | 76.70 | MOL3 | N |
| ATOM | 10859 | CA | ARG | H | 72 | −0.866 | −59.857 | −34.754 | 1.00 | 77.38 | MOL3 | C |
| ATOM | 10860 | CB | ARG | H | 72 | 0.632 | −60.005 | −34.480 | 1.00 | 75.59 | MOL3 | C |
| ATOM | 10861 | CG | ARG | H | 72 | 1.340 | −60.977 | −35.391 | 1.00 | 72.05 | MOL3 | C |
| ATOM | 10862 | CD | ARG | H | 72 | 2.717 | −61.268 | −34.866 | 1.00 | 71.05 | MOL3 | C |
| ATOM | 10863 | NE | ARG | H | 72 | 3.498 | −60.050 | −34.695 | 1.00 | 74.56 | MOL3 | N |
| ATOM | 10864 | CZ | ARG | H | 72 | 4.619 | −59.986 | −33.984 | 1.00 | 78.18 | MOL3 | C |
| ATOM | 10865 | NH1 | ARG | H | 72 | 5.084 | −61.071 | −33.378 | 1.00 | 76.57 | MOL3 | N |
| ATOM | 10866 | NH2 | ARG | H | 72 | 5.280 | −58.841 | −33.881 | 1.00 | 79.10 | MOL3 | N |
| ATOM | 10867 | C | ARG | H | 72 | −1.073 | −59.198 | −36.108 | 1.00 | 78.26 | MOL3 | C |
| ATOM | 10868 | O | ARG | H | 72 | −1.565 | −59.838 | −37.040 | 1.00 | 80.43 | MOL3 | O |
| ATOM | 10869 | N | ASP | H | 73 | −0.701 | −57.922 | −36.215 | 1.00 | 79.15 | MOL3 | N |
| ATOM | 10870 | CA | ASP | H | 73 | −0.842 | −57.204 | −37.478 | 1.00 | 83.39 | MOL3 | C |
| ATOM | 10871 | CB | ASP | H | 73 | −1.724 | −55.968 | −37.318 | 1.00 | 87.45 | MOL3 | C |
| ATOM | 10872 | CG | ASP | H | 73 | −2.487 | −55.623 | −38.597 | 1.00 | 95.41 | MOL3 | C |
| ATOM | 10873 | OD1 | ASP | H | 73 | −1.859 | −55.575 | −39.682 | 1.00 | 100.81 | MOL3 | O |
| ATOM | 10874 | OD2 | ASP | H | 73 | −3.718 | −55.399 | −38.520 | 1.00 | 97.72 | MOL3 | O |
| ATOM | 10875 | C | ASP | H | 73 | 0.498 | −56.785 | −38.083 | 1.00 | 84.03 | MOL3 | C |
| ATOM | 10876 | O | ASP | H | 73 | 0.688 | −56.864 | −39.295 | 1.00 | 89.76 | MOL3 | O |
| ATOM | 10877 | N | ASN | H | 74 | 1.425 | −56.354 | −37.240 | 1.00 | 83.32 | MOL3 | N |
| ATOM | 10878 | CA | ASN | H | 74 | 2.731 | −55.913 | −37.701 | 1.00 | 83.34 | MOL3 | C |
| ATOM | 10879 | CB | ASN | H | 74 | 3.367 | −56.961 | −38.605 | 1.00 | 84.66 | MOL3 | C |
| ATOM | 10880 | CG | ASN | H | 74 | 3.817 | −58.182 | −37.827 | 1.00 | 89.27 | MOL3 | C |
| ATOM | 10881 | OD1 | ASN | H | 74 | 4.520 | −59.046 | −38.351 | 1.00 | 93.50 | MOL3 | O |
| ATOM | 10882 | ND2 | ASN | H | 74 | 3.411 | −58.257 | −36.562 | 1.00 | 85.97 | MOL3 | N |
| ATOM | 10883 | C | ASN | H | 74 | 2.581 | −54.581 | −38.400 | 1.00 | 83.52 | MOL3 | C |
| ATOM | 10884 | O | ASN | H | 74 | 3.550 | −53.856 | −38.603 | 1.00 | 89.31 | MOL3 | O |
| ATOM | 10885 | N | ALA | H | 75 | 1.348 | −54.272 | −38.776 | 1.00 | 84.62 | MOL3 | N |
| ATOM | 10886 | CA | ALA | H | 75 | 1.014 | −52.986 | −39.371 | 1.00 | 85.59 | MOL3 | C |
| ATOM | 10887 | CB | ALA | H | 75 | 0.045 | −53.148 | −40.524 | 1.00 | 81.20 | MOL3 | C |
| ATOM | 10888 | C | ALA | H | 75 | 0.299 | −52.415 | −38.165 | 1.00 | 89.52 | MOL3 | C |
| ATOM | 10889 | O | ALA | H | 75 | −0.260 | −53.180 | −37.374 | 1.00 | 92.00 | MOL3 | O |
| ATOM | 10890 | N | LYS | H | 76 | 0.328 | −51.101 | −37.989 | 1.00 | 91.06 | MOL3 | N |
| ATOM | 10891 | CA | LYS | H | 76 | −0.327 | −50.490 | −36.828 | 1.00 | 93.31 | MOL3 | C |
| ATOM | 10892 | CB | LYS | H | 76 | −1.851 | −50.634 | −36.941 | 1.00 | 90.27 | MOL3 | C |
| ATOM | 10893 | CG | LYS | H | 76 | −2.399 | −51.881 | −36.289 | 1.00 | 82.81 | MOL3 | C |
| ATOM | 10894 | CD | LYS | H | 76 | −3.886 | −52.035 | −36.517 | 1.00 | 82.37 | MOL3 | C |
| ATOM | 10895 | CE | LYS | H | 76 | −4.199 | −52.498 | −37.922 | 1.00 | 76.83 | MOL3 | C |
| ATOM | 10896 | NZ | LYS | H | 76 | −5.476 | −53.263 | −37.927 | 1.00 | 76.47 | MOL3 | N |
| ATOM | 10897 | C | LYS | H | 76 | 0.158 | −51.097 | −35.490 | 1.00 | 92.31 | MOL3 | C |
| ATOM | 10898 | O | LYS | H | 76 | −0.420 | −50.837 | −34.432 | 1.00 | 94.15 | MOL3 | O |
| ATOM | 10899 | N | ASN | H | 77 | 1.212 | −51.912 | −35.550 | 1.00 | 87.30 | MOL3 | N |
| ATOM | 10900 | CA | ASN | H | 77 | 1.806 | −52.529 | −34.363 | 1.00 | 78.14 | MOL3 | C |
| ATOM | 10901 | CB | ASN | H | 77 | 2.726 | −51.536 | −33.656 | 1.00 | 83.99 | MOL3 | C |
| ATOM | 10902 | CG | ASN | H | 77 | 3.860 | −51.068 | −34.518 | 1.00 | 82.72 | MOL3 | C |
| ATOM | 10903 | OD1 | ASN | H | 77 | 4.629 | −50.196 | −34.108 | 1.00 | 80.57 | MOL3 | O |
| ATOM | 10904 | ND2 | ASN | H | 77 | 3.986 | −51.642 | −35.714 | 1.00 | 84.30 | MOL3 | N |
| ATOM | 10905 | C | ASN | H | 77 | 0.819 | −53.012 | −33.314 | 1.00 | 70.11 | MOL3 | C |
| ATOM | 10906 | O | ASN | H | 77 | 0.691 | −52.382 | −32.267 | 1.00 | 66.82 | MOL3 | O |
| ATOM | 10907 | N | SER | H | 78 | 0.143 | −54.124 | −33.550 | 1.00 | 60.84 | MOL3 | N |

TABLE 1-continued

The atomic coordinates of IL17F in complex with 496 Fab
(H32; a = 189.4; b = 189.4; c = 490.9, α, β = 90°; γ = 120°)

| ATOM | 10908 | CA | SER | H | 78 | −0.807 | −54.606 | −32.554 | 1.00 | 57.37 | MOL3 | C |
|---|---|---|---|---|---|---|---|---|---|---|---|---|
| ATOM | 10909 | CB | SER | H | 78 | −2.229 | −54.175 | −32.905 | 1.00 | 56.83 | MOL3 | C |
| ATOM | 10910 | OG | SER | H | 78 | −2.395 | −52.781 | −32.769 | 1.00 | 66.79 | MOL3 | O |
| ATOM | 10911 | C | SER | H | 78 | −0.829 | −56.101 | −32.328 | 1.00 | 53.26 | MOL3 | C |
| ATOM | 10912 | O | SER | H | 78 | −0.669 | −56.886 | −33.244 | 1.00 | 52.52 | MOL3 | O |
| ATOM | 10913 | N | LEU | H | 79 | −1.060 | −56.483 | −31.083 | 1.00 | 56.04 | MOL3 | N |
| ATOM | 10914 | CA | LEU | H | 79 | −1.139 | −57.886 | −30.703 | 1.00 | 58.73 | MOL3 | C |
| ATOM | 10915 | CB | LEU | H | 79 | −0.110 | −58.233 | −29.627 | 1.00 | 63.94 | MOL3 | C |
| ATOM | 10916 | CG | LEU | H | 79 | −0.303 | −59.632 | −29.027 | 1.00 | 67.03 | MOL3 | C |
| ATOM | 10917 | CD1 | LEU | H | 79 | −0.069 | −60.710 | −30.095 | 1.00 | 61.98 | MOL3 | C |
| ATOM | 10918 | CD2 | LEU | H | 79 | 0.653 | −59.813 | −27.860 | 1.00 | 69.74 | MOL3 | C |
| ATOM | 10919 | C | LEU | H | 79 | −2.525 | −58.127 | −30.140 | 1.00 | 59.16 | MOL3 | C |
| ATOM | 10920 | O | LEU | H | 79 | −3.005 | −57.355 | −29.310 | 1.00 | 60.85 | MOL3 | O |
| ATOM | 10921 | N | TYR | H | 80 | −3.160 | −59.207 | −30.581 | 1.00 | 59.60 | MOL3 | N |
| ATOM | 10922 | CA | TYR | H | 80 | −4.511 | −59.533 | −30.129 | 1.00 | 58.99 | MOL3 | C |
| ATOM | 10923 | CB | TYR | H | 80 | −5.503 | −59.465 | −31.293 | 1.00 | 55.82 | MOL3 | C |
| ATOM | 10924 | CG | TYR | H | 80 | −5.399 | −58.235 | −32.150 | 1.00 | 59.36 | MOL3 | C |
| ATOM | 10925 | CD1 | TYR | H | 80 | −5.652 | −56.974 | −31.629 | 1.00 | 64.60 | MOL3 | C |
| ATOM | 10926 | CE1 | TYR | H | 80 | −5.537 | −55.843 | −32.416 | 1.00 | 65.64 | MOL3 | C |
| ATOM | 10927 | CD2 | TYR | H | 80 | −5.030 | −58.329 | −33.481 | 1.00 | 61.01 | MOL3 | C |
| ATOM | 10928 | CE2 | TYR | H | 80 | −4.910 | −57.204 | −34.271 | 1.00 | 59.14 | MOL3 | C |
| ATOM | 10929 | CZ | TYR | H | 80 | −5.165 | −55.971 | −33.735 | 1.00 | 60.95 | MOL3 | C |
| ATOM | 10930 | OH | TYR | H | 80 | −5.060 | −54.859 | −34.522 | 1.00 | 67.08 | MOL3 | O |
| ATOM | 10931 | C | TYR | H | 80 | −4.644 | −60.919 | −29.513 | 1.00 | 60.27 | MOL3 | C |
| ATOM | 10932 | O | TYR | H | 80 | −3.871 | −61.833 | −29.806 | 1.00 | 60.76 | MOL3 | O |
| ATOM | 10933 | N | LEU | H | 81 | −5.644 | −61.063 | −28.655 | 1.00 | 58.53 | MOL3 | N |
| ATOM | 10934 | CA | LEU | H | 81 | −5.931 | −62.346 | −28.044 | 1.00 | 59.99 | MOL3 | C |
| ATOM | 10935 | CB | LEU | H | 81 | −5.462 | −62.403 | −26.595 | 1.00 | 50.64 | MOL3 | C |
| ATOM | 10936 | CG | LEU | H | 81 | −5.792 | −63.749 | −25.952 | 1.00 | 44.10 | MOL3 | C |
| ATOM | 10937 | CD1 | LEU | H | 81 | −4.999 | −64.816 | −26.630 | 1.00 | 40.53 | MOL3 | C |
| ATOM | 10938 | CD2 | LEU | H | 81 | −5.475 | −63.740 | −24.477 | 1.00 | 47.90 | MOL3 | C |
| ATOM | 10939 | C | LEU | H | 81 | −7.438 | −62.530 | −28.110 | 1.00 | 65.84 | MOL3 | C |
| ATOM | 10940 | O | LEU | H | 81 | −8.195 | −61.711 | −27.584 | 1.00 | 68.73 | MOL3 | O |
| ATOM | 10941 | N | GLN | H | 82 | −7.866 | −63.592 | −28.785 | 1.00 | 71.66 | MOL3 | N |
| ATOM | 10942 | CA | GLN | H | 82 | −9.286 | −63.898 | −28.925 | 1.00 | 76.01 | MOL3 | C |
| ATOM | 10943 | CB | GLN | H | 82 | −9.612 | −64.394 | −30.326 | 1.00 | 77.87 | MOL3 | C |
| ATOM | 10944 | CG | GLN | H | 82 | −11.094 | −64.592 | −30.554 | 1.00 | 79.24 | MOL3 | C |
| ATOM | 10945 | CD | GLN | H | 82 | −11.871 | −63.287 | −30.477 | 1.00 | 82.83 | MOL3 | C |
| ATOM | 10946 | OE1 | GLN | H | 82 | −11.562 | −62.321 | −31.183 | 1.00 | 79.11 | MOL3 | O |
| ATOM | 10947 | NE2 | GLN | H | 82 | −12.891 | −63.255 | −29.623 | 1.00 | 82.97 | MOL3 | N |
| ATOM | 10948 | C | GLN | H | 82 | −9.655 | −64.982 | −27.940 | 1.00 | 78.00 | MOL3 | C |
| ATOM | 10949 | O | GLN | H | 82 | −9.270 | −66.141 | −28.104 | 1.00 | 75.52 | MOL3 | O |
| ATOM | 10950 | N | MET | H | 83 | −10.409 | −64.603 | −26.919 | 1.00 | 81.38 | MOL3 | N |
| ATOM | 10951 | CA | MET | H | 83 | −10.813 | −65.556 | −25.904 | 1.00 | 83.45 | MOL3 | C |
| ATOM | 10952 | CB | MET | H | 83 | −10.563 | −64.971 | −24.517 | 1.00 | 83.00 | MOL3 | C |
| ATOM | 10953 | CG | MET | H | 83 | −9.147 | −64.454 | −24.314 | 1.00 | 73.51 | MOL3 | C |
| ATOM | 10954 | SD | MET | H | 83 | −8.778 | −64.189 | −22.577 | 1.00 | 72.08 | MOL3 | S |
| ATOM | 10955 | CE | MET | H | 83 | −9.688 | −62.657 | −22.254 | 1.00 | 75.89 | MOL3 | C |
| ATOM | 10956 | C | MET | H | 83 | −12.271 | −65.983 | −26.062 | 1.00 | 86.73 | MOL3 | C |
| ATOM | 10957 | O | MET | H | 83 | −13.200 | −65.215 | −25.790 | 1.00 | 89.34 | MOL3 | O |
| ATOM | 10958 | N | ASN | H | 84 | −12.450 | −67.219 | −26.522 | 1.00 | 87.09 | MOL3 | N |
| ATOM | 10959 | CA | ASN | H | 84 | −13.773 | −67.799 | −26.738 | 1.00 | 88.83 | MOL3 | C |
| ATOM | 10960 | CB | ASN | H | 84 | −13.856 | −68.522 | −28.095 | 1.00 | 87.32 | MOL3 | C |
| ATOM | 10961 | CG | ASN | H | 84 | −13.628 | −67.600 | −29.289 | 1.00 | 90.12 | MOL3 | C |
| ATOM | 10962 | OD1 | ASN | H | 84 | −14.228 | −66.531 | −29.390 | 1.00 | 90.38 | MOL3 | O |
| ATOM | 10963 | ND2 | ASN | H | 84 | −12.770 | −68.030 | −30.215 | 1.00 | 89.58 | MOL3 | N |
| ATOM | 10964 | C | ASN | H | 84 | −14.050 | −68.823 | −25.645 | 1.00 | 90.92 | MOL3 | C |
| ATOM | 10965 | O | ASN | H | 84 | −13.127 | −69.347 | −25.022 | 1.00 | 91.60 | MOL3 | O |
| ATOM | 10966 | N | SER | H | 85 | −15.325 | −69.116 | −25.422 | 1.00 | 92.60 | MOL3 | N |
| ATOM | 10967 | CA | SER | H | 85 | −15.709 | −70.103 | −24.419 | 1.00 | 92.77 | MOL3 | C |
| ATOM | 10968 | CB | SER | H | 85 | −15.327 | −71.503 | −24.898 | 1.00 | 93.17 | MOL3 | C |
| ATOM | 10969 | OG | SER | H | 85 | −15.907 | −71.784 | −26.162 | 1.00 | 95.37 | MOL3 | O |
| ATOM | 10970 | C | SER | H | 85 | −15.022 | −69.832 | −23.094 | 1.00 | 91.07 | MOL3 | C |
| ATOM | 10971 | O | SER | H | 85 | −14.607 | −70.755 | −22.399 | 1.00 | 92.03 | MOL3 | O |
| ATOM | 10972 | N | LEU | H | 86 | −14.907 | −68.562 | −22.745 | 1.00 | 89.75 | MOL3 | N |
| ATOM | 10973 | CA | LEU | H | 86 | −14.245 | −68.194 | −21.512 | 1.00 | 89.08 | MOL3 | C |
| ATOM | 10974 | CB | LEU | H | 86 | −14.381 | −66.691 | −21.274 | 1.00 | 85.61 | MOL3 | C |
| ATOM | 10975 | CG | LEU | H | 86 | −13.384 | −65.865 | −22.086 | 1.00 | 78.91 | MOL3 | C |
| ATOM | 10976 | CD1 | LEU | H | 86 | −13.579 | −64.384 | −21.829 | 1.00 | 79.31 | MOL3 | C |
| ATOM | 10977 | CD2 | LEU | H | 86 | −11.980 | −66.292 | −21.703 | 1.00 | 74.10 | MOL3 | C |
| ATOM | 10978 | C | LEU | H | 86 | −14.725 | −68.960 | −20.295 | 1.00 | 89.90 | MOL3 | C |
| ATOM | 10979 | O | LEU | H | 86 | −15.843 | −68.768 | −19.834 | 1.00 | 93.13 | MOL3 | O |
| ATOM | 10980 | N | ARG | H | 87 | −13.880 | −69.847 | −19.783 | 1.00 | 92.08 | MOL3 | N |
| ATOM | 10981 | CA | ARG | H | 87 | −14.232 | −70.594 | −18.584 | 1.00 | 96.78 | MOL3 | C |
| ATOM | 10982 | CB | ARG | H | 87 | −13.291 | −71.787 | −18.383 | 1.00 | 102.37 | MOL3 | C |
| ATOM | 10983 | CG | ARG | H | 87 | −13.471 | −72.934 | −19.379 | 1.00 | 112.26 | MOL3 | C |
| ATOM | 10984 | CD | ARG | H | 87 | −12.508 | −74.078 | −19.059 | 1.00 | 120.23 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 10985 | NE | ARG | H | 87 | −12.595 | −75.188 | −20.006 | 1.00 | 131.15 | MOL3 | N |
|---|---|---|---|---|---|---|---|---|---|---|---|---|
| ATOM | 10986 | CZ | ARG | H | 87 | −11.737 | −76.205 | −20.039 | 1.00 | 136.65 | MOL3 | C |
| ATOM | 10987 | NH1 | ARG | H | 87 | −10.728 | −76.251 | −19.178 | 1.00 | 139.89 | MOL3 | N |
| ATOM | 10988 | NH2 | ARG | H | 87 | −11.882 | −77.173 | −20.934 | 1.00 | 139.76 | MOL3 | N |
| ATOM | 10989 | C | ARG | H | 87 | −14.098 | −69.607 | −17.419 | 1.00 | 96.43 | MOL3 | C |
| ATOM | 10990 | O | ARG | H | 87 | −13.832 | −68.430 | −17.635 | 1.00 | 96.71 | MOL3 | O |
| ATOM | 10991 | N | ALA | H | 88 | −14.280 | −70.071 | −16.190 | 1.00 | 96.62 | MOL3 | N |
| ATOM | 10992 | CA | ALA | H | 88 | −14.184 | −69.183 | −15.038 | 1.00 | 95.02 | MOL3 | C |
| ATOM | 10993 | CB | ALA | H | 88 | −15.168 | −69.617 | −13.963 | 1.00 | 100.74 | MOL3 | C |
| ATOM | 10994 | C | ALA | H | 88 | −12.777 | −69.156 | −14.472 | 1.00 | 92.76 | MOL3 | C |
| ATOM | 10995 | O | ALA | H | 88 | −12.364 | −68.189 | −13.845 | 1.00 | 90.60 | MOL3 | O |
| ATOM | 10996 | N | GLU | H | 89 | −12.045 | −70.234 | −14.693 | 1.00 | 92.27 | MOL3 | N |
| ATOM | 10997 | CA | GLU | H | 89 | −10.687 | −70.326 | −14.202 | 1.00 | 93.53 | MOL3 | C |
| ATOM | 10998 | CB | GLU | H | 89 | −10.242 | −71.793 | −14.182 | 1.00 | 101.54 | MOL3 | C |
| ATOM | 10999 | CG | GLU | H | 89 | −10.041 | −72.426 | −15.559 | 1.00 | 113.37 | MOL3 | C |
| ATOM | 11000 | CD | GLU | H | 89 | −10.782 | −73.752 | −15.724 | 1.00 | 120.39 | MOL3 | C |
| ATOM | 11001 | OE1 | GLU | H | 89 | −10.482 | −74.489 | −16.694 | 1.00 | 121.99 | MOL3 | O |
| ATOM | 11002 | OE2 | GLU | H | 89 | −11.670 | −74.050 | −14.890 | 1.00 | 122.54 | MOL3 | O |
| ATOM | 11003 | C | GLU | H | 89 | −9.758 | −69.493 | −15.083 | 1.00 | 89.20 | MOL3 | C |
| ATOM | 11004 | O | GLU | H | 89 | −8.536 | −69.547 | −14.944 | 1.00 | 89.55 | MOL3 | O |
| ATOM | 11005 | N | ASP | H | 90 | −10.335 | −68.715 | −15.990 | 1.00 | 82.95 | MOL3 | N |
| ATOM | 11006 | CA | ASP | H | 90 | −9.517 | −67.888 | −16.867 | 1.00 | 80.12 | MOL3 | C |
| ATOM | 11007 | CB | ASP | H | 90 | −10.044 | −67.903 | −18.306 | 1.00 | 80.37 | MOL3 | C |
| ATOM | 11008 | CG | ASP | H | 90 | −9.933 | −69.272 | −18.969 | 1.00 | 82.38 | MOL3 | C |
| ATOM | 11009 | OD1 | ASP | H | 90 | −8.988 | −70.036 | −18.662 | 1.00 | 79.57 | MOL3 | O |
| ATOM | 11010 | OD2 | ASP | H | 90 | −10.794 | −69.575 | −19.823 | 1.00 | 83.84 | MOL3 | O |
| ATOM | 11011 | C | ASP | H | 90 | −9.427 | −66.451 | −16.384 | 1.00 | 78.47 | MOL3 | C |
| ATOM | 11012 | O | ASP | H | 90 | −8.768 | −65.624 | −17.011 | 1.00 | 78.94 | MOL3 | O |
| ATOM | 11013 | N | THR | H | 91 | −10.088 | −66.159 | −15.268 | 1.00 | 76.99 | MOL3 | N |
| ATOM | 11014 | CA | THR | H | 91 | −10.083 | −64.820 | −14.685 | 1.00 | 72.56 | MOL3 | C |
| ATOM | 11015 | CB | THR | H | 91 | −10.919 | −64.779 | −13.414 | 1.00 | 68.77 | MOL3 | C |
| ATOM | 11016 | OG1 | THR | H | 91 | −12.197 | −65.366 | −13.658 | 1.00 | 66.56 | MOL3 | O |
| ATOM | 11017 | CG2 | THR | H | 91 | −11.113 | −63.356 | −12.973 | 1.00 | 78.03 | MOL3 | C |
| ATOM | 11018 | C | THR | H | 91 | −8.665 | −64.444 | −14.295 | 1.00 | 71.90 | MOL3 | C |
| ATOM | 11019 | O | THR | H | 91 | −7.977 | −65.248 | −13.670 | 1.00 | 74.87 | MOL3 | O |
| ATOM | 11020 | N | ALA | H | 92 | −8.236 | −63.233 | −14.649 | 1.00 | 70.95 | MOL3 | N |
| ATOM | 11021 | CA | ALA | H | 92 | −6.886 | −62.769 | −14.318 | 1.00 | 71.24 | MOL3 | C |
| ATOM | 11022 | CB | ALA | H | 92 | −5.853 | −63.826 | −14.695 | 1.00 | 70.68 | MOL3 | C |
| ATOM | 11023 | C | ALA | H | 92 | −6.533 | −61.467 | −15.011 | 1.00 | 69.69 | MOL3 | C |
| ATOM | 11024 | O | ALA | H | 92 | −7.360 | −60.858 | −15.701 | 1.00 | 71.59 | MOL3 | O |
| ATOM | 11025 | N | VAL | H | 93 | −5.292 | −61.043 | −14.808 | 1.00 | 64.42 | MOL3 | N |
| ATOM | 11026 | CA | VAL | H | 93 | −4.786 | −59.838 | −15.432 | 1.00 | 61.96 | MOL3 | C |
| ATOM | 11027 | CB | VAL | H | 93 | −3.846 | −59.099 | −14.520 | 1.00 | 57.64 | MOL3 | C |
| ATOM | 11028 | CG1 | VAL | H | 93 | −3.438 | −57.804 | −15.164 | 1.00 | 59.76 | MOL3 | C |
| ATOM | 11029 | CG2 | VAL | H | 93 | −4.508 | −58.870 | −13.192 | 1.00 | 66.11 | MOL3 | C |
| ATOM | 11030 | C | VAL | H | 93 | −3.978 | −60.333 | −16.613 | 1.00 | 63.36 | MOL3 | C |
| ATOM | 11031 | O | VAL | H | 93 | −3.042 | −61.113 | −16.443 | 1.00 | 64.35 | MOL3 | O |
| ATOM | 11032 | N | TYR | H | 94 | −4.343 | −59.898 | −17.810 | 1.00 | 60.17 | MOL3 | N |
| ATOM | 11033 | CA | TYR | H | 94 | −3.636 | −60.336 | −18.988 | 1.00 | 56.31 | MOL3 | C |
| ATOM | 11034 | CB | TYR | H | 94 | −4.621 | −60.527 | −20.151 | 1.00 | 60.66 | MOL3 | C |
| ATOM | 11035 | CG | TYR | H | 94 | −5.413 | −61.812 | −20.006 | 1.00 | 62.05 | MOL3 | C |
| ATOM | 11036 | CD1 | TYR | H | 94 | −6.233 | −62.017 | −18.902 | 1.00 | 62.04 | MOL3 | C |
| ATOM | 11037 | CE1 | TYR | H | 94 | −6.836 | −63.237 | −18.674 | 1.00 | 64.76 | MOL3 | C |
| ATOM | 11038 | CD2 | TYR | H | 94 | −5.235 | −62.871 | −20.896 | 1.00 | 59.57 | MOL3 | C |
| ATOM | 11039 | CE2 | TYR | H | 94 | −5.836 | −64.100 | −20.674 | 1.00 | 60.07 | MOL3 | C |
| ATOM | 11040 | CZ | TYR | H | 94 | −6.628 | −64.275 | −19.554 | 1.00 | 64.86 | MOL3 | C |
| ATOM | 11041 | OH | TYR | H | 94 | −7.164 | −65.503 | −19.265 | 1.00 | 66.73 | MOL3 | O |
| ATOM | 11042 | C | TYR | H | 94 | −2.543 | −59.355 | −19.334 | 1.00 | 56.03 | MOL3 | C |
| ATOM | 11043 | O | TYR | H | 94 | −2.800 | −58.162 | −19.488 | 1.00 | 58.70 | MOL3 | O |
| ATOM | 11044 | N | TYR | H | 95 | −1.321 | −59.881 | −19.431 | 1.00 | 51.55 | MOL3 | N |
| ATOM | 11045 | CA | TYR | H | 95 | −0.137 | −59.101 | −19.744 | 1.00 | 42.22 | MOL3 | C |
| ATOM | 11046 | CB | TYR | H | 95 | 0.966 | −59.419 | −18.755 | 1.00 | 38.82 | MOL3 | C |
| ATOM | 11047 | CG | TYR | H | 95 | 0.683 | −58.970 | −17.355 | 1.00 | 39.30 | MOL3 | C |
| ATOM | 11048 | CD1 | TYR | H | 95 | 0.518 | −59.893 | −16.326 | 1.00 | 37.89 | MOL3 | C |
| ATOM | 11049 | CE1 | TYR | H | 95 | 0.306 | −59.476 | −15.026 | 1.00 | 34.23 | MOL3 | C |
| ATOM | 11050 | CD2 | TYR | H | 95 | 0.621 | −57.619 | −17.047 | 1.00 | 34.46 | MOL3 | C |
| ATOM | 11051 | CE2 | TYR | H | 95 | 0.412 | −57.199 | −15.761 | 1.00 | 36.30 | MOL3 | C |
| ATOM | 11052 | CZ | TYR | H | 95 | 0.256 | −58.127 | −14.750 | 1.00 | 34.68 | MOL3 | C |
| ATOM | 11053 | OH | TYR | H | 95 | 0.062 | −57.687 | −13.461 | 1.00 | 39.66 | MOL3 | O |
| ATOM | 11054 | C | TYR | H | 95 | 0.387 | −59.354 | −21.141 | 1.00 | 44.72 | MOL3 | C |
| ATOM | 11055 | O | TYR | H | 95 | 0.356 | −60.478 | −21.658 | 1.00 | 46.91 | MOL3 | O |
| ATOM | 11056 | N | CYS | H | 96 | 0.893 | −58.288 | −21.734 | 1.00 | 43.61 | MOL3 | N |
| ATOM | 11057 | CA | CYS | H | 96 | 1.454 | −58.327 | −23.064 | 1.00 | 45.33 | MOL3 | C |
| ATOM | 11058 | C | CYS | H | 96 | 2.967 | −58.281 | −22.830 | 1.00 | 43.95 | MOL3 | C |
| ATOM | 11059 | O | CYS | H | 96 | 3.444 | −57.446 | −22.060 | 1.00 | 48.14 | MOL3 | O |
| ATOM | 11060 | CB | CYS | H | 96 | 0.949 | −57.104 | −23.794 | 1.00 | 43.81 | MOL3 | C |
| ATOM | 11061 | SG | CYS | H | 96 | 1.413 | −57.008 | −25.520 | 1.00 | 63.60 | MOL3 | S |

TABLE 1-continued

The atomic coordinates of IL17F in complex with 496 Fab
(H32; a = 189.4; b = 189.4; c = 490.9, α, β = 90°; γ = 120°)

| ATOM | 11062 | N | ALA | H | 97 | 3.731 | −59.172 | −23.455 | 1.00 | 39.34 | MOL3 | N |
|---|---|---|---|---|---|---|---|---|---|---|---|---|
| ATOM | 11063 | CA | ALA | H | 97 | 5.169 | −59.161 | −23.208 | 1.00 | 39.98 | MOL3 | C |
| ATOM | 11064 | CB | ALA | H | 97 | 5.505 | −60.193 | −22.169 | 1.00 | 41.47 | MOL3 | C |
| ATOM | 11065 | C | ALA | H | 97 | 6.040 | −59.369 | −24.428 | 1.00 | 43.99 | MOL3 | C |
| ATOM | 11066 | O | ALA | H | 97 | 5.839 | −60.323 | −25.185 | 1.00 | 49.59 | MOL3 | O |
| ATOM | 11067 | N | SER | H | 98 | 7.029 | −58.490 | −24.599 | 1.00 | 45.50 | MOL3 | N |
| ATOM | 11068 | CA | SER | H | 98 | 7.949 | −58.582 | −25.739 | 1.00 | 48.71 | MOL3 | C |
| ATOM | 11069 | CB | SER | H | 98 | 8.040 | −57.237 | −26.455 | 1.00 | 47.09 | MOL3 | C |
| ATOM | 11070 | OG | SER | H | 98 | 8.883 | −56.349 | −25.738 | 1.00 | 52.41 | MOL3 | O |
| ATOM | 11071 | C | SER | H | 98 | 9.363 | −59.014 | −25.327 | 1.00 | 48.46 | MOL3 | C |
| ATOM | 11072 | O | SER | H | 98 | 9.743 | −58.927 | −24.163 | 1.00 | 52.57 | MOL3 | O |
| ATOM | 11073 | N | PRO | H | 99 | 10.160 | −59.496 | −26.284 | 1.00 | 46.43 | MOL3 | N |
| ATOM | 11074 | CD | PRO | H | 99 | 9.820 | −59.832 | −27.673 | 1.00 | 45.79 | MOL3 | C |
| ATOM | 11075 | CA | PRO | H | 99 | 11.522 | −59.923 | −25.968 | 1.00 | 47.57 | MOL3 | C |
| ATOM | 11076 | CB | PRO | H | 99 | 11.836 | −60.899 | −27.084 | 1.00 | 47.27 | MOL3 | C |
| ATOM | 11077 | CG | PRO | H | 99 | 11.155 | −60.268 | −28.228 | 1.00 | 45.69 | MOL3 | C |
| ATOM | 11078 | C | PRO | H | 99 | 12.439 | −58.718 | −26.008 | 1.00 | 48.22 | MOL3 | C |
| ATOM | 11079 | O | PRO | H | 99 | 12.025 | −57.635 | −26.412 | 1.00 | 46.92 | MOL3 | O |
| ATOM | 11080 | N | PRO | H | 100 | 13.703 | −58.899 | −25.609 | 1.00 | 48.79 | MOL3 | N |
| ATOM | 11081 | CD | PRO | H | 100 | 14.264 | −60.173 | −25.141 | 1.00 | 50.49 | MOL3 | C |
| ATOM | 11082 | CA | PRO | H | 100 | 14.723 | −57.852 | −25.579 | 1.00 | 47.39 | MOL3 | C |
| ATOM | 11083 | CB | PRO | H | 100 | 15.859 | −58.518 | −24.825 | 1.00 | 46.63 | MOL3 | C |
| ATOM | 11084 | CG | PRO | H | 100 | 15.738 | −59.919 | −25.254 | 1.00 | 49.38 | MOL3 | C |
| ATOM | 11085 | C | PRO | H | 100 | 15.133 | −57.318 | −26.954 | 1.00 | 48.05 | MOL3 | C |
| ATOM | 11086 | O | PRO | H | 100 | 15.271 | −58.067 | −27.914 | 1.00 | 46.59 | MOL3 | O |
| ATOM | 11087 | N | GLN | H | 101 | 15.311 | −56.000 | −27.015 | 1.00 | 52.43 | MOL3 | N |
| ATOM | 11088 | CA | GLN | H | 101 | 15.673 | −55.276 | −28.222 | 1.00 | 47.42 | MOL3 | C |
| ATOM | 11089 | CB | GLN | H | 101 | 15.685 | −53.763 | −27.932 | 1.00 | 50.83 | MOL3 | C |
| ATOM | 11090 | CG | GLN | H | 101 | 14.380 | −53.185 | −27.330 | 1.00 | 56.39 | MOL3 | C |
| ATOM | 11091 | CD | GLN | H | 101 | 14.554 | −52.571 | −25.905 | 1.00 | 67.61 | MOL3 | C |
| ATOM | 11092 | OE1 | GLN | H | 101 | 14.920 | −53.261 | −24.932 | 1.00 | 59.74 | MOL3 | O |
| ATOM | 11093 | NE2 | GLN | H | 101 | 14.282 | −51.268 | −25.790 | 1.00 | 69.40 | MOL3 | N |
| ATOM | 11094 | C | GLN | H | 101 | 17.025 | −55.755 | −28.760 | 1.00 | 50.03 | MOL3 | C |
| ATOM | 11095 | O | GLN | H | 101 | 17.267 | −55.677 | −29.967 | 1.00 | 48.86 | MOL3 | O |
| ATOM | 11096 | N | TYR | H | 102 | 17.923 | −56.221 | −27.887 | 1.00 | 50.25 | MOL3 | N |
| ATOM | 11097 | CA | TYR | H | 102 | 19.182 | −56.772 | −28.394 | 1.00 | 55.53 | MOL3 | C |
| ATOM | 11098 | CB | TYR | H | 102 | 20.284 | −56.770 | −27.336 | 1.00 | 46.94 | MOL3 | C |
| ATOM | 11099 | CG | TYR | H | 102 | 19.803 | −56.769 | −25.913 | 1.00 | 55.59 | MOL3 | C |
| ATOM | 11100 | CD1 | TYR | H | 102 | 19.351 | −57.930 | −25.316 | 1.00 | 69.84 | MOL3 | C |
| ATOM | 11101 | CE1 | TYR | H | 102 | 18.923 | −57.950 | −23.989 | 1.00 | 67.91 | MOL3 | C |
| ATOM | 11102 | CD2 | TYR | H | 102 | 19.816 | −55.617 | −25.154 | 1.00 | 53.29 | MOL3 | C |
| ATOM | 11103 | CE2 | TYR | H | 102 | 19.390 | −55.623 | −23.830 | 1.00 | 62.04 | MOL3 | C |
| ATOM | 11104 | CZ | TYR | H | 102 | 18.944 | −56.796 | −23.256 | 1.00 | 63.06 | MOL3 | C |
| ATOM | 11105 | OH | TYR | H | 102 | 18.500 | −56.827 | −21.958 | 1.00 | 65.21 | MOL3 | O |
| ATOM | 11106 | C | TYR | H | 102 | 18.831 | −58.200 | −28.834 | 1.00 | 60.02 | MOL3 | C |
| ATOM | 11107 | O | TYR | H | 102 | 17.725 | −58.442 | −29.325 | 1.00 | 64.79 | MOL3 | O |
| ATOM | 11108 | N | TYR | H | 103 | 19.729 | −59.156 | −28.691 | 1.00 | 57.42 | MOL3 | N |
| ATOM | 11109 | CA | TYR | H | 103 | 19.374 | −60.518 | −29.114 | 1.00 | 60.46 | MOL3 | C |
| ATOM | 11110 | CB | TYR | H | 103 | 18.664 | −61.242 | −27.961 | 1.00 | 45.82 | MOL3 | C |
| ATOM | 11111 | CG | TYR | H | 103 | 19.618 | −61.651 | −26.880 | 1.00 | 39.77 | MOL3 | C |
| ATOM | 11112 | CD1 | TYR | H | 103 | 20.638 | −62.551 | −27.146 | 1.00 | 36.24 | MOL3 | C |
| ATOM | 11113 | CE1 | TYR | H | 103 | 21.625 | −62.806 | −26.220 | 1.00 | 34.88 | MOL3 | C |
| ATOM | 11114 | CD2 | TYR | H | 103 | 19.599 | −61.029 | −25.642 | 1.00 | 33.49 | MOL3 | C |
| ATOM | 11115 | CE2 | TYR | H | 103 | 20.582 | −61.275 | −24.704 | 1.00 | 34.89 | MOL3 | C |
| ATOM | 11116 | CZ | TYR | H | 103 | 21.597 | −62.163 | −25.002 | 1.00 | 37.47 | MOL3 | C |
| ATOM | 11117 | OH | TYR | H | 103 | 22.610 | −62.383 | −24.096 | 1.00 | 40.59 | MOL3 | O |
| ATOM | 11118 | C | TYR | H | 103 | 18.557 | −60.772 | −30.413 | 1.00 | 62.77 | MOL3 | C |
| ATOM | 11119 | O | TYR | H | 103 | 19.063 | −60.708 | −31.538 | 1.00 | 64.32 | MOL3 | O |
| ATOM | 11120 | N | GLU | H | 104 | 17.281 | −61.067 | −30.219 | 1.00 | 68.52 | MOL3 | N |
| ATOM | 11121 | CA | GLU | H | 104 | 16.352 | −61.445 | −31.280 | 1.00 | 73.65 | MOL3 | C |
| ATOM | 11122 | CB | GLU | H | 104 | 15.765 | −60.284 | −32.065 | 1.00 | 75.49 | MOL3 | C |
| ATOM | 11123 | CG | GLU | H | 104 | 14.287 | −60.576 | −32.462 | 1.00 | 79.39 | MOL3 | C |
| ATOM | 11124 | CD | GLU | H | 104 | 14.026 | −61.971 | −33.098 | 1.00 | 81.53 | MOL3 | C |
| ATOM | 11125 | OE1 | GLU | H | 104 | 14.326 | −62.152 | −34.298 | 1.00 | 83.61 | MOL3 | O |
| ATOM | 11126 | OE2 | GLU | H | 104 | 13.504 | −62.885 | −32.412 | 1.00 | 71.90 | MOL3 | O |
| ATOM | 11127 | C | GLU | H | 104 | 16.970 | −62.390 | −32.255 | 1.00 | 77.87 | MOL3 | C |
| ATOM | 11128 | O | GLU | H | 104 | 17.094 | −63.566 | −31.945 | 1.00 | 82.18 | MOL3 | O |
| ATOM | 11129 | N | GLY | H | 105 | 17.356 | −61.883 | −33.426 | 1.00 | 83.29 | MOL3 | N |
| ATOM | 11130 | CA | GLY | H | 105 | 17.925 | −62.738 | −34.461 | 1.00 | 91.56 | MOL3 | C |
| ATOM | 11131 | C | GLY | H | 105 | 16.860 | −63.698 | −35.008 | 1.00 | 94.92 | MOL3 | C |
| ATOM | 11132 | O | GLY | H | 105 | 16.944 | −64.140 | −36.159 | 1.00 | 98.10 | MOL3 | O |
| ATOM | 11133 | N | SER | H | 106 | 15.865 | −63.993 | −34.157 | 1.00 | 91.38 | MOL3 | N |
| ATOM | 11134 | CA | SER | H | 106 | 14.724 | −64.883 | −34.406 | 1.00 | 79.67 | MOL3 | C |
| ATOM | 11135 | CB | SER | H | 106 | 14.992 | −65.830 | −35.568 | 1.00 | 82.97 | MOL3 | C |
| ATOM | 11136 | OG | SER | H | 106 | 15.976 | −66.790 | −35.220 | 1.00 | 87.86 | MOL3 | O |
| ATOM | 11137 | C | SER | H | 106 | 14.516 | −65.709 | −33.135 | 1.00 | 76.13 | MOL3 | C |
| ATOM | 11138 | O | SER | H | 106 | 13.424 | −66.194 | −32.874 | 1.00 | 74.49 | MOL3 | O |

TABLE 1-continued

The atomic coordinates of IL17F in complex with 496 Fab
(H32; a = 189.4; b = 189.4; c = 490.9, α, β = 90°; γ = 120°)

| ATOM | 11139 | N | ILE | H | 107 | 15.595 | −65.862 | −32.368 | 1.00 | 70.79 | MOL3 | N |
|---|---|---|---|---|---|---|---|---|---|---|---|---|
| ATOM | 11140 | CA | ILE | H | 107 | 15.648 | −66.599 | −31.103 | 1.00 | 65.83 | MOL3 | C |
| ATOM | 11141 | CB | ILE | H | 107 | 16.545 | −65.844 | −30.114 | 1.00 | 57.68 | MOL3 | C |
| ATOM | 11142 | CG2 | ILE | H | 107 | 16.497 | −66.513 | −28.753 | 1.00 | 52.02 | MOL3 | C |
| ATOM | 11143 | CG1 | ILE | H | 107 | 17.965 | −65.767 | −30.680 | 1.00 | 53.71 | MOL3 | C |
| ATOM | 11144 | CD1 | ILE | H | 107 | 18.924 | −64.891 | −29.897 | 1.00 | 51.07 | MOL3 | C |
| ATOM | 11145 | C | ILE | H | 107 | 14.305 | −66.864 | −30.423 | 1.00 | 71.45 | MOL3 | C |
| ATOM | 11146 | O | ILE | H | 107 | 13.680 | −65.946 | −29.897 | 1.00 | 75.63 | MOL3 | O |
| ATOM | 11147 | N | TYR | H | 108 | 13.877 | −68.122 | −30.395 | 1.00 | 72.70 | MOL3 | N |
| ATOM | 11148 | CA | TYR | H | 108 | 12.590 | −68.453 | −29.788 | 1.00 | 70.96 | MOL3 | C |
| ATOM | 11149 | CB | TYR | H | 108 | 12.095 | −69.821 | −30.276 | 1.00 | 75.57 | MOL3 | C |
| ATOM | 11150 | CG | TYR | H | 108 | 10.795 | −70.266 | −29.633 | 1.00 | 76.72 | MOL3 | C |
| ATOM | 11151 | CD1 | TYR | H | 108 | 9.587 | −69.672 | −29.968 | 1.00 | 79.87 | MOL3 | C |
| ATOM | 11152 | CE1 | TYR | H | 108 | 8.398 | −70.052 | −29.342 | 1.00 | 84.10 | MOL3 | C |
| ATOM | 11153 | CD2 | TYR | H | 108 | 10.785 | −71.254 | −28.658 | 1.00 | 79.63 | MOL3 | C |
| ATOM | 11154 | CE2 | TYR | H | 108 | 9.607 | −71.638 | −28.026 | 1.00 | 84.89 | MOL3 | C |
| ATOM | 11155 | CZ | TYR | H | 108 | 8.418 | −71.033 | −28.367 | 1.00 | 85.99 | MOL3 | C |
| ATOM | 11156 | OH | TYR | H | 108 | 7.262 | −71.382 | −27.698 | 1.00 | 85.76 | MOL3 | O |
| ATOM | 11157 | C | TYR | H | 108 | 12.582 | −68.447 | −28.269 | 1.00 | 66.39 | MOL3 | C |
| ATOM | 11158 | O | TYR | H | 108 | 11.756 | −67.763 | −27.662 | 1.00 | 66.11 | MOL3 | O |
| ATOM | 11159 | N | ARG | H | 109 | 13.501 | −69.210 | −27.672 | 1.00 | 60.68 | MOL3 | N |
| ATOM | 11160 | CA | ARG | H | 109 | 13.622 | −69.367 | −26.212 | 1.00 | 57.47 | MOL3 | C |
| ATOM | 11161 | CB | ARG | H | 109 | 14.825 | −70.256 | −25.877 | 1.00 | 64.22 | MOL3 | C |
| ATOM | 11162 | CG | ARG | H | 109 | 14.804 | −71.664 | −26.449 | 1.00 | 77.26 | MOL3 | C |
| ATOM | 11163 | CD | ARG | H | 109 | 13.703 | −72.498 | −25.832 | 1.00 | 86.22 | MOL3 | C |
| ATOM | 11164 | NE | ARG | H | 109 | 13.930 | −73.935 | −25.963 | 1.00 | 97.73 | MOL3 | N |
| ATOM | 11165 | CZ | ARG | H | 109 | 13.978 | −74.596 | −27.117 | 1.00 | 105.94 | MOL3 | C |
| ATOM | 11166 | NH1 | ARG | H | 109 | 13.820 | −73.958 | −28.272 | 1.00 | 107.40 | MOL3 | N |
| ATOM | 11167 | NH2 | ARG | H | 109 | 14.172 | −75.908 | −27.113 | 1.00 | 113.45 | MOL3 | N |
| ATOM | 11168 | C | ARG | H | 109 | 13.763 | −68.076 | −25.405 | 1.00 | 53.74 | MOL3 | C |
| ATOM | 11169 | O | ARG | H | 109 | 13.870 | −68.107 | −24.178 | 1.00 | 50.39 | MOL3 | O |
| ATOM | 11170 | N | LEU | H | 110 | 13.764 | −66.950 | −26.104 | 1.00 | 52.94 | MOL3 | N |
| ATOM | 11171 | CA | LEU | H | 110 | 13.920 | −65.620 | −25.516 | 1.00 | 44.20 | MOL3 | C |
| ATOM | 11172 | CB | LEU | H | 110 | 13.718 | −64.580 | −26.611 | 1.00 | 44.89 | MOL3 | C |
| ATOM | 11173 | CG | LEU | H | 110 | 14.757 | −63.476 | −26.691 | 1.00 | 42.03 | MOL3 | C |
| ATOM | 11174 | CD1 | LEU | H | 110 | 15.903 | −63.797 | −25.744 | 1.00 | 44.64 | MOL3 | C |
| ATOM | 11175 | CD2 | LEU | H | 110 | 15.237 | −63.363 | −28.118 | 1.00 | 27.69 | MOL3 | C |
| ATOM | 11176 | C | LEU | H | 110 | 12.999 | −65.288 | −24.367 | 1.00 | 40.38 | MOL3 | C |
| ATOM | 11177 | O | LEU | H | 110 | 11.781 | −65.399 | −24.491 | 1.00 | 43.05 | MOL3 | O |
| ATOM | 11178 | N | TRP | H | 111 | 13.580 | −64.844 | −23.259 | 1.00 | 41.21 | MOL3 | N |
| ATOM | 11179 | CA | TRP | H | 111 | 12.796 | −64.463 | −22.081 | 1.00 | 46.91 | MOL3 | C |
| ATOM | 11180 | CB | TRP | H | 111 | 13.723 | −64.172 | −20.927 | 1.00 | 44.02 | MOL3 | C |
| ATOM | 11181 | CG | TRP | H | 111 | 14.741 | −63.205 | −21.304 | 1.00 | 44.21 | MOL3 | C |
| ATOM | 11182 | CD2 | TRP | H | 111 | 15.962 | −63.484 | −21.974 | 1.00 | 46.92 | MOL3 | C |
| ATOM | 11183 | CE2 | TRP | H | 111 | 16.635 | −62.274 | −22.132 | 1.00 | 47.79 | MOL3 | C |
| ATOM | 11184 | CE3 | TRP | H | 111 | 16.554 | −64.646 | −22.454 | 1.00 | 56.76 | MOL3 | C |
| ATOM | 11185 | CD1 | TRP | H | 111 | 14.713 | −61.878 | −21.092 | 1.00 | 51.48 | MOL3 | C |
| ATOM | 11186 | NE1 | TRP | H | 111 | 15.854 | −61.298 | −21.584 | 1.00 | 55.01 | MOL3 | N |
| ATOM | 11187 | CZ2 | TRP | H | 111 | 17.865 | −62.190 | −22.744 | 1.00 | 57.38 | MOL3 | C |
| ATOM | 11188 | CZ3 | TRP | H | 111 | 17.783 | −64.560 | −23.063 | 1.00 | 56.79 | MOL3 | C |
| ATOM | 11189 | CH2 | TRP | H | 111 | 18.424 | −63.349 | −23.202 | 1.00 | 57.16 | MOL3 | C |
| ATOM | 11190 | C | TRP | H | 111 | 12.101 | −63.190 | −22.460 | 1.00 | 47.34 | MOL3 | C |
| ATOM | 11191 | O | TRP | H | 111 | 12.016 | −62.875 | −23.645 | 1.00 | 58.35 | MOL3 | O |
| ATOM | 11192 | N | PHE | H | 112 | 11.576 | −62.454 | −21.488 | 1.00 | 42.90 | MOL3 | N |
| ATOM | 11193 | CA | PHE | H | 112 | 10.974 | −61.191 | −21.876 | 1.00 | 50.92 | MOL3 | C |
| ATOM | 11194 | CB | PHE | H | 112 | 9.540 | −61.348 | −22.475 | 1.00 | 59.93 | MOL3 | C |
| ATOM | 11195 | CG | PHE | H | 112 | 8.655 | −62.430 | −21.854 | 1.00 | 57.20 | MOL3 | C |
| ATOM | 11196 | CD1 | PHE | H | 112 | 7.995 | −63.347 | −22.687 | 1.00 | 51.87 | MOL3 | C |
| ATOM | 11197 | CD2 | PHE | H | 112 | 8.422 | −62.496 | −20.500 | 1.00 | 52.26 | MOL3 | C |
| ATOM | 11198 | CE1 | PHE | H | 112 | 7.135 | −64.297 | −22.191 | 1.00 | 34.50 | MOL3 | C |
| ATOM | 11199 | CE2 | PHE | H | 112 | 7.551 | −63.459 | −20.001 | 1.00 | 55.87 | MOL3 | C |
| ATOM | 11200 | CZ | PHE | H | 112 | 6.911 | −64.359 | −20.860 | 1.00 | 43.50 | MOL3 | C |
| ATOM | 11201 | C | PHE | H | 112 | 10.988 | −60.016 | −20.927 | 1.00 | 48.47 | MOL3 | C |
| ATOM | 11202 | O | PHE | H | 112 | 10.466 | −60.088 | −19.814 | 1.00 | 42.85 | MOL3 | O |
| ATOM | 11203 | N | ALA | H | 113 | 11.630 | −58.941 | −21.397 | 1.00 | 47.44 | MOL3 | N |
| ATOM | 11204 | CA | ALA | H | 113 | 11.699 | −57.677 | −20.674 | 1.00 | 44.75 | MOL3 | C |
| ATOM | 11205 | CB | ALA | H | 113 | 12.964 | −56.955 | −20.977 | 1.00 | 43.44 | MOL3 | C |
| ATOM | 11206 | C | ALA | H | 113 | 10.540 | −56.950 | −21.298 | 1.00 | 45.85 | MOL3 | C |
| ATOM | 11207 | O | ALA | H | 113 | 10.031 | −57.385 | −22.323 | 1.00 | 53.70 | MOL3 | O |
| ATOM | 11208 | N | HIS | H | 114 | 10.101 | −55.856 | −20.706 | 1.00 | 44.73 | MOL3 | N |
| ATOM | 11209 | CA | HIS | H | 114 | 8.965 | −55.140 | −21.275 | 1.00 | 43.87 | MOL3 | C |
| ATOM | 11210 | CB | HIS | H | 114 | 9.236 | −54.796 | −22.734 | 1.00 | 47.49 | MOL3 | C |
| ATOM | 11211 | CG | HIS | H | 114 | 10.571 | −54.178 | −22.965 | 1.00 | 47.48 | MOL3 | C |
| ATOM | 11212 | CD2 | HIS | H | 114 | 11.557 | −54.489 | −23.837 | 1.00 | 47.60 | MOL3 | C |
| ATOM | 11213 | ND1 | HIS | H | 114 | 11.019 | −53.093 | −22.241 | 1.00 | 52.82 | MOL3 | N |
| ATOM | 11214 | CE1 | HIS | H | 114 | 12.229 | −52.764 | −22.657 | 1.00 | 59.40 | MOL3 | C |
| ATOM | 11215 | NE2 | HIS | H | 114 | 12.579 | −53.595 | −23.625 | 1.00 | 58.20 | MOL3 | N |

TABLE 1-continued

The atomic coordinates of IL17F in complex with 496 Fab
(H32; a = 189.4; b = 189.4; c = 490.9, α, β = 90°; γ = 120°)

| ATOM | 11216 | C | HIS | H | 114 | 7.645 | −55.916 | −21.195 | 1.00 | 40.81 | MOL3 | C |
|---|---|---|---|---|---|---|---|---|---|---|---|---|
| ATOM | 11217 | O | HIS | H | 114 | 7.375 | −56.835 | −21.978 | 1.00 | 35.72 | MOL3 | O |
| ATOM | 11218 | N | TRP | H | 115 | 6.832 | −55.519 | −20.228 | 1.00 | 41.79 | MOL3 | N |
| ATOM | 11219 | CA | TRP | H | 115 | 5.514 | −56.086 | −19.994 | 1.00 | 41.86 | MOL3 | C |
| ATOM | 11220 | CB | TRP | H | 115 | 5.393 | −56.663 | −18.576 | 1.00 | 38.41 | MOL3 | C |
| ATOM | 11221 | CG | TRP | H | 115 | 6.217 | −57.853 | −18.289 | 1.00 | 37.34 | MOL3 | C |
| ATOM | 11222 | CD2 | TRP | H | 115 | 5.746 | −59.155 | −17.909 | 1.00 | 43.06 | MOL3 | C |
| ATOM | 11223 | CE2 | TRP | H | 115 | 6.880 | −59.982 | −17.760 | 1.00 | 40.84 | MOL3 | C |
| ATOM | 11224 | CE3 | TRP | H | 115 | 4.477 | −59.703 | −17.688 | 1.00 | 39.73 | MOL3 | C |
| ATOM | 11225 | CD1 | TRP | H | 115 | 7.566 | −57.939 | −18.346 | 1.00 | 39.27 | MOL3 | C |
| ATOM | 11226 | NE1 | TRP | H | 115 | 7.980 | −59.215 | −18.032 | 1.00 | 41.55 | MOL3 | N |
| ATOM | 11227 | CZ2 | TRP | H | 115 | 6.786 | −61.326 | −17.400 | 1.00 | 35.42 | MOL3 | C |
| ATOM | 11228 | CZ3 | TRP | H | 115 | 4.386 | −61.033 | −17.335 | 1.00 | 37.87 | MOL3 | C |
| ATOM | 11229 | CH2 | TRP | H | 115 | 5.536 | −61.831 | −17.193 | 1.00 | 37.55 | MOL3 | C |
| ATOM | 11230 | C | TRP | H | 115 | 4.580 | −54.878 | −20.081 | 1.00 | 45.00 | MOL3 | C |
| ATOM | 11231 | O | TRP | H | 115 | 4.990 | −53.743 | −19.831 | 1.00 | 45.07 | MOL3 | O |
| ATOM | 11232 | N | GLY | H | 116 | 3.324 | −55.108 | −20.427 | 1.00 | 43.82 | MOL3 | N |
| ATOM | 11233 | CA | GLY | H | 116 | 2.408 | −53.992 | −20.479 | 1.00 | 47.62 | MOL3 | C |
| ATOM | 11234 | C | GLY | H | 116 | 1.920 | −53.792 | −19.064 | 1.00 | 50.34 | MOL3 | C |
| ATOM | 11235 | O | GLY | H | 116 | 2.449 | −54.402 | −18.154 | 1.00 | 45.88 | MOL3 | O |
| ATOM | 11236 | N | GLN | H | 117 | 0.928 | −52.937 | −18.857 | 1.00 | 58.66 | MOL3 | N |
| ATOM | 11237 | CA | GLN | H | 117 | 0.401 | −52.751 | −17.514 | 1.00 | 61.51 | MOL3 | C |
| ATOM | 11238 | CB | GLN | H | 117 | −0.203 | −51.349 | −17.354 | 1.00 | 70.43 | MOL3 | C |
| ATOM | 11239 | CG | GLN | H | 117 | −0.659 | −50.680 | −18.656 | 1.00 | 87.36 | MOL3 | C |
| ATOM | 11240 | CD | GLN | H | 117 | −1.991 | −51.204 | −19.170 | 1.00 | 92.80 | MOL3 | C |
| ATOM | 11241 | OE1 | GLN | H | 117 | −3.021 | −51.085 | −18.499 | 1.00 | 95.16 | MOL3 | O |
| ATOM | 11242 | NE2 | GLN | H | 117 | −1.978 | −51.780 | −20.368 | 1.00 | 92.67 | MOL3 | N |
| ATOM | 11243 | C | GLN | H | 117 | −0.640 | −53.844 | −17.261 | 1.00 | 59.17 | MOL3 | C |
| ATOM | 11244 | O | GLN | H | 117 | −0.942 | −54.172 | −16.121 | 1.00 | 60.38 | MOL3 | O |
| ATOM | 11245 | N | GLY | H | 118 | −1.172 | −54.415 | −18.338 | 1.00 | 58.73 | MOL3 | N |
| ATOM | 11246 | CA | GLY | H | 118 | −2.146 | −55.487 | −18.216 | 1.00 | 52.72 | MOL3 | C |
| ATOM | 11247 | C | GLY | H | 118 | −3.582 | −55.045 | −18.058 | 1.00 | 50.79 | MOL3 | C |
| ATOM | 11248 | O | GLY | H | 118 | −3.842 | −53.941 | −17.590 | 1.00 | 52.19 | MOL3 | O |
| ATOM | 11249 | N | THR | H | 119 | −4.515 | −55.903 | −18.465 | 1.00 | 51.53 | MOL3 | N |
| ATOM | 11250 | CA | THR | H | 119 | −5.944 | −55.609 | −18.339 | 1.00 | 52.25 | MOL3 | C |
| ATOM | 11251 | CB | THR | H | 119 | −6.646 | −55.514 | −19.675 | 1.00 | 51.94 | MOL3 | C |
| ATOM | 11252 | OG1 | THR | H | 119 | −6.441 | −56.736 | −20.390 | 1.00 | 46.45 | MOL3 | O |
| ATOM | 11253 | CG2 | THR | H | 119 | −6.125 | −54.334 | −20.460 | 1.00 | 58.58 | MOL3 | C |
| ATOM | 11254 | C | THR | H | 119 | −6.629 | −56.729 | −17.591 | 1.00 | 49.07 | MOL3 | C |
| ATOM | 11255 | O | THR | H | 119 | −6.326 | −57.904 | −17.787 | 1.00 | 42.26 | MOL3 | O |
| ATOM | 11256 | N | LEU | H | 120 | −7.577 | −56.356 | −16.748 | 1.00 | 50.02 | MOL3 | N |
| ATOM | 11257 | CA | LEU | H | 120 | −8.294 | −57.337 | −15.965 | 0.50 | 47.90 | MOL3 | C |
| ATOM | 11258 | CB | LEU | H | 120 | −8.811 | −56.699 | −14.694 | 1.00 | 47.04 | MOL3 | C |
| ATOM | 11259 | CG | LEU | H | 120 | −9.591 | −57.678 | −13.851 | 1.00 | 42.65 | MOL3 | C |
| ATOM | 11260 | CD1 | LEU | H | 120 | −8.945 | −59.043 | −13.898 | 1.00 | 42.81 | MOL3 | C |
| ATOM | 11261 | CD2 | LEU | H | 120 | −9.648 | −57.133 | −12.443 | 1.00 | 57.87 | MOL3 | C |
| ATOM | 11262 | C | LEU | H | 120 | −9.446 | −57.984 | −16.711 | 1.00 | 47.31 | MOL3 | C |
| ATOM | 11263 | O | LEU | H | 120 | −10.246 | −57.312 | −17.360 | 1.00 | 53.62 | MOL3 | O |
| ATOM | 11264 | N | VAL | H | 121 | −9.526 | −59.301 | −16.615 | 1.00 | 43.57 | MOL3 | N |
| ATOM | 11265 | CA | VAL | H | 121 | −10.585 | −60.048 | −17.274 | 1.00 | 46.90 | MOL3 | C |
| ATOM | 11266 | CB | VAL | H | 121 | −10.028 | −60.913 | −18.431 | 1.00 | 42.22 | MOL3 | C |
| ATOM | 11267 | CG1 | VAL | H | 121 | −11.013 | −61.946 | −18.860 | 1.00 | 35.72 | MOL3 | C |
| ATOM | 11268 | CG2 | VAL | H | 121 | −9.749 | −60.053 | −19.608 | 1.00 | 57.37 | MOL3 | C |
| ATOM | 11269 | C | VAL | H | 121 | −11.228 | −60.957 | −16.247 | 1.00 | 54.19 | MOL3 | C |
| ATOM | 11270 | O | VAL | H | 121 | −10.612 | −61.919 | −15.795 | 1.00 | 54.20 | MOL3 | O |
| ATOM | 11271 | N | THR | H | 122 | −12.459 | −60.648 | −15.855 | 1.00 | 61.64 | MOL3 | N |
| ATOM | 11272 | CA | THR | H | 122 | −13.143 | −61.485 | −14.879 | 1.00 | 64.37 | MOL3 | C |
| ATOM | 11273 | CB | THR | H | 122 | −13.480 | −60.709 | −13.556 | 1.00 | 64.21 | MOL3 | C |
| ATOM | 11274 | OG1 | THR | H | 122 | −14.752 | −61.149 | −13.063 | 1.00 | 63.64 | MOL3 | O |
| ATOM | 11275 | CG2 | THR | H | 122 | −13.478 | −59.192 | −13.769 | 1.00 | 58.83 | MOL3 | C |
| ATOM | 11276 | C | THR | H | 122 | −14.389 | −62.179 | −15.417 | 1.00 | 64.05 | MOL3 | C |
| ATOM | 11277 | O | THR | H | 122 | −15.403 | −61.563 | −15.746 | 1.00 | 64.50 | MOL3 | O |
| ATOM | 11278 | N | VAL | H | 123 | −14.281 | −63.491 | −15.514 | 1.00 | 66.51 | MOL3 | N |
| ATOM | 11279 | CA | VAL | H | 123 | −15.375 | −64.306 | −15.995 | 1.00 | 75.45 | MOL3 | C |
| ATOM | 11280 | CB | VAL | H | 123 | −14.827 | −65.500 | −16.821 | 1.00 | 76.15 | MOL3 | C |
| ATOM | 11281 | CG1 | VAL | H | 123 | −13.889 | −66.316 | −15.973 | 1.00 | 80.19 | MOL3 | C |
| ATOM | 11282 | CG2 | VAL | H | 123 | −15.958 | −66.356 | −17.343 | 1.00 | 75.45 | MOL3 | C |
| ATOM | 11283 | C | VAL | H | 123 | −16.220 | −64.801 | −14.809 | 1.00 | 77.76 | MOL3 | C |
| ATOM | 11284 | O | VAL | H | 123 | −15.848 | −65.743 | −14.101 | 1.00 | 76.11 | MOL3 | O |
| ATOM | 11285 | N | SER | H | 124 | −17.353 | −64.140 | −14.587 | 1.00 | 80.57 | MOL3 | N |
| ATOM | 11286 | CA | SER | H | 124 | −18.257 | −64.513 | −13.505 | 1.00 | 86.50 | MOL3 | C |
| ATOM | 11287 | CB | SER | H | 124 | −18.024 | −63.626 | −12.277 | 1.00 | 93.22 | MOL3 | C |
| ATOM | 11288 | OG | SER | H | 124 | −18.629 | −64.176 | −11.112 | 1.00 | 98.83 | MOL3 | O |
| ATOM | 11289 | C | SER | H | 124 | −19.701 | −64.392 | −13.971 | 1.00 | 87.68 | MOL3 | C |
| ATOM | 11290 | O | SER | H | 124 | −20.028 | −63.548 | −14.803 | 1.00 | 90.87 | MOL3 | O |
| ATOM | 11291 | N | SER | H | 125 | −20.561 | −65.248 | −13.432 | 1.00 | 89.63 | MOL3 | N |
| ATOM | 11292 | CA | SER | H | 125 | −21.977 | −65.265 | −13.791 | 1.00 | 92.13 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 11293 | CB  | SER | H | 125 | −22.540 | −66.674 | −13.572 | 1.00 | 96.84  | MOL3 | C |
|------|-------|-----|-----|---|-----|---------|---------|---------|------|--------|------|---|
| ATOM | 11294 | OG  | SER | H | 125 | −22.293 | −67.117 | −12.244 | 1.00 | 100.51 | MOL3 | O |
| ATOM | 11295 | C   | SER | H | 125 | −22.800 | −64.257 | −12.991 | 1.00 | 88.79  | MOL3 | C |
| ATOM | 11296 | O   | SER | H | 125 | −23.919 | −63.917 | −13.372 | 1.00 | 85.49  | MOL3 | O |
| ATOM | 11297 | N   | ALA | H | 126 | −22.237 | −63.790 | −11.883 | 1.00 | 86.00  | MOL3 | N |
| ATOM | 11298 | CA  | ALA | H | 126 | −22.907 | −62.832 | −11.016 | 1.00 | 84.53  | MOL3 | C |
| ATOM | 11299 | CB  | ALA | H | 126 | −21.996 | −62.442 | −9.881  | 1.00 | 88.38  | MOL3 | C |
| ATOM | 11300 | C   | ALA | H | 126 | −23.306 | −61.596 | −11.788 | 1.00 | 83.73  | MOL3 | C |
| ATOM | 11301 | O   | ALA | H | 126 | −22.737 | −61.307 | −12.833 | 1.00 | 81.09  | MOL3 | O |
| ATOM | 11302 | N   | LYS | H | 127 | −24.281 | −60.863 | −11.259 | 1.00 | 86.86  | MOL3 | N |
| ATOM | 11303 | CA  | LYS | H | 127 | −24.763 | −59.646 | −11.906 | 1.00 | 87.73  | MOL3 | C |
| ATOM | 11304 | CB  | LYS | H | 127 | −26.265 | −59.743 | −12.215 | 1.00 | 97.62  | MOL3 | C |
| ATOM | 11305 | CG  | LYS | H | 127 | −26.743 | −61.083 | −12.805 | 1.00 | 110.82 | MOL3 | C |
| ATOM | 11306 | CD  | LYS | H | 127 | −26.864 | −62.183 | −11.726 | 1.00 | 119.00 | MOL3 | C |
| ATOM | 11307 | CE  | LYS | H | 127 | −27.463 | −63.487 | −12.279 | 1.00 | 121.43 | MOL3 | C |
| ATOM | 11308 | NZ  | LYS | H | 127 | −27.600 | −64.559 | −11.240 | 1.00 | 119.53 | MOL3 | N |
| ATOM | 11309 | C   | LYS | H | 127 | −24.508 | −58.457 | −10.997 | 1.00 | 83.80  | MOL3 | C |
| ATOM | 11310 | O   | LYS | H | 127 | −24.482 | −58.591 | −9.773  | 1.00 | 88.07  | MOL3 | O |
| ATOM | 11311 | N   | THR | H | 128 | −24.325 | −57.289 | −11.593 | 1.00 | 77.90  | MOL3 | N |
| ATOM | 11312 | CA  | THR | H | 128 | −24.049 | −56.092 | −10.813 | 1.00 | 76.97  | MOL3 | C |
| ATOM | 11313 | CB  | THR | H | 128 | −23.952 | −54.860 | −11.731 | 1.00 | 74.21  | MOL3 | C |
| ATOM | 11314 | OG1 | THR | H | 128 | −22.834 | −55.017 | −12.615 | 1.00 | 70.27  | MOL3 | O |
| ATOM | 11315 | CG2 | THR | H | 128 | −23.762 | −53.599 | −10.915 | 1.00 | 72.38  | MOL3 | C |
| ATOM | 11316 | C   | THR | H | 128 | −25.057 | −55.836 | −9.686  | 1.00 | 77.21  | MOL3 | C |
| ATOM | 11317 | O   | THR | H | 128 | −26.250 | −55.648 | −9.930  | 1.00 | 85.96  | MOL3 | O |
| ATOM | 11318 | N   | THR | H | 129 | −24.572 | −55.848 | −8.448  | 1.00 | 69.74  | MOL3 | N |
| ATOM | 11319 | CA  | THR | H | 129 | −25.438 | −55.613 | −7.310  | 1.00 | 67.73  | MOL3 | C |
| ATOM | 11320 | CB  | THR | H | 129 | −25.731 | −56.929 | −6.519  | 1.00 | 69.81  | MOL3 | C |
| ATOM | 11321 | OG1 | THR | H | 129 | −24.634 | −57.234 | −5.656  | 1.00 | 76.97  | MOL3 | O |
| ATOM | 11322 | CG2 | THR | H | 129 | −25.943 | −58.103 | −7.461  | 1.00 | 65.64  | MOL3 | C |
| ATOM | 11323 | C   | THR | H | 129 | −24.797 | −54.596 | −6.378  | 1.00 | 67.68  | MOL3 | C |
| ATOM | 11324 | O   | THR | H | 129 | −23.605 | −54.657 | −6.103  | 1.00 | 71.46  | MOL3 | O |
| ATOM | 11325 | N   | PRO | H | 130 | −25.565 | −53.597 | −5.933  | 1.00 | 66.63  | MOL3 | N |
| ATOM | 11326 | CD  | PRO | H | 130 | −26.673 | −52.937 | −6.633  | 1.00 | 65.48  | MOL3 | C |
| ATOM | 11327 | CA  | PRO | H | 130 | −24.896 | −52.664 | −5.031  | 1.00 | 65.88  | MOL3 | C |
| ATOM | 11328 | CB  | PRO | H | 130 | −25.787 | −51.419 | −5.071  | 1.00 | 60.89  | MOL3 | C |
| ATOM | 11329 | CG  | PRO | H | 130 | −27.069 | −51.890 | −5.649  | 1.00 | 62.80  | MOL3 | C |
| ATOM | 11330 | C   | PRO | H | 130 | −24.710 | −53.295 | −3.652  | 1.00 | 69.90  | MOL3 | C |
| ATOM | 11331 | O   | PRO | H | 130 | −25.303 | −54.334 | −3.345  | 1.00 | 73.73  | MOL3 | O |
| ATOM | 11332 | N   | PRO | H | 131 | −23.857 | −52.689 | −2.817  | 1.00 | 70.45  | MOL3 | N |
| ATOM | 11333 | CD  | PRO | H | 131 | −23.104 | −51.471 | −3.161  | 1.00 | 65.90  | MOL3 | C |
| ATOM | 11334 | CA  | PRO | H | 131 | −23.512 | −53.127 | −1.465  | 1.00 | 73.01  | MOL3 | C |
| ATOM | 11335 | CB  | PRO | H | 131 | −22.194 | −52.427 | −1.231  | 1.00 | 70.44  | MOL3 | C |
| ATOM | 11336 | CG  | PRO | H | 131 | −22.474 | −51.095 | −1.841  | 1.00 | 64.04  | MOL3 | C |
| ATOM | 11337 | C   | PRO | H | 131 | −24.497 | −52.773 | −0.386  | 1.00 | 76.32  | MOL3 | C |
| ATOM | 11338 | O   | PRO | H | 131 | −25.164 | −51.748 | −0.462  | 1.00 | 76.84  | MOL3 | O |
| ATOM | 11339 | N   | SER | H | 132 | −24.582 | −53.634 | 0.619   | 1.00 | 77.23  | MOL3 | N |
| ATOM | 11340 | CA  | SER | H | 132 | −25.444 | −53.370 | 1.745   | 1.00 | 79.52  | MOL3 | C |
| ATOM | 11341 | CB  | SER | H | 132 | −26.223 | −54.626 | 2.136   | 1.00 | 79.39  | MOL3 | C |
| ATOM | 11342 | OG  | SER | H | 132 | −27.347 | −54.782 | 1.281   | 1.00 | 76.18  | MOL3 | O |
| ATOM | 11343 | C   | SER | H | 132 | −24.429 | −52.953 | 2.794   | 1.00 | 80.16  | MOL3 | C |
| ATOM | 11344 | O   | SER | H | 132 | −23.408 | −53.613 | 2.969   | 1.00 | 81.05  | MOL3 | O |
| ATOM | 11345 | N   | VAL | H | 133 | −24.678 | −51.833 | 3.462   | 1.00 | 80.73  | MOL3 | N |
| ATOM | 11346 | CA  | VAL | H | 133 | −23.729 | −51.354 | 4.456   | 1.00 | 77.55  | MOL3 | C |
| ATOM | 11347 | CB  | VAL | H | 133 | −23.234 | −49.961 | 4.068   | 1.00 | 74.70  | MOL3 | C |
| ATOM | 11348 | CG1 | VAL | H | 133 | −22.156 | −49.503 | 5.036   | 1.00 | 67.89  | MOL3 | C |
| ATOM | 11349 | CG2 | VAL | H | 133 | −22.724 | −49.992 | 2.636   | 1.00 | 67.06  | MOL3 | C |
| ATOM | 11350 | C   | VAL | H | 133 | −24.230 | −51.337 | 5.895   | 1.00 | 77.11  | MOL3 | C |
| ATOM | 11351 | O   | VAL | H | 133 | −25.209 | −50.671 | 6.229   | 1.00 | 79.78  | MOL3 | O |
| ATOM | 11352 | N   | TYR | H | 134 | −23.532 | −52.075 | 6.745   | 1.00 | 73.64  | MOL3 | N |
| ATOM | 11353 | CA  | TYR | H | 134 | −23.893 | −52.168 | 8.139   | 1.00 | 73.17  | MOL3 | C |
| ATOM | 11354 | CB  | TYR | H | 134 | −24.151 | −53.640 | 8.456   | 1.00 | 76.33  | MOL3 | C |
| ATOM | 11355 | CG  | TYR | H | 134 | −25.084 | −54.241 | 7.440   | 1.00 | 69.54  | MOL3 | C |
| ATOM | 11356 | CD1 | TYR | H | 134 | −26.348 | −53.716 | 7.255   | 1.00 | 70.76  | MOL3 | C |
| ATOM | 11357 | CE1 | TYR | H | 134 | −27.185 | −54.198 | 6.290   | 1.00 | 72.81  | MOL3 | C |
| ATOM | 11358 | CD2 | TYR | H | 134 | −24.685 | −55.279 | 6.628   | 1.00 | 67.53  | MOL3 | C |
| ATOM | 11359 | CE2 | TYR | H | 134 | −25.522 | −55.775 | 5.653   | 1.00 | 70.39  | MOL3 | C |
| ATOM | 11360 | CZ  | TYR | H | 134 | −26.774 | −55.229 | 5.487   | 1.00 | 71.99  | MOL3 | C |
| ATOM | 11361 | OH  | TYR | H | 134 | −27.635 | −55.711 | 4.521   | 1.00 | 73.51  | MOL3 | O |
| ATOM | 11362 | C   | TYR | H | 134 | −22.760 | −51.597 | 8.972   | 1.00 | 68.63  | MOL3 | C |
| ATOM | 11363 | O   | TYR | H | 134 | −21.594 | −51.752 | 8.631   | 1.00 | 65.24  | MOL3 | O |
| ATOM | 11364 | N   | PRO | H | 135 | −23.096 | −50.886 | 10.044  | 1.00 | 65.60  | MOL3 | N |
| ATOM | 11365 | CD  | PRO | H | 135 | −24.381 | −50.182 | 10.147  | 1.00 | 61.86  | MOL3 | C |
| ATOM | 11366 | CA  | PRO | H | 135 | −22.103 | −50.284 | 10.938  | 1.00 | 69.19  | MOL3 | C |
| ATOM | 11367 | CB  | PRO | H | 135 | −22.797 | −49.015 | 11.403  | 1.00 | 69.64  | MOL3 | C |
| ATOM | 11368 | CG  | PRO | H | 135 | −24.228 | −49.433 | 11.438  | 1.00 | 70.95  | MOL3 | C |
| ATOM | 11369 | C   | PRO | H | 135 | −21.665 | −51.172 | 12.099  | 1.00 | 70.59  | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 11370 | O | PRO | H | 135 | −22.488 | −51.757 | 12.802 | 1.00 | 78.60 | MOL3 | O |
|---|---|---|---|---|---|---|---|---|---|---|---|---|
| ATOM | 11371 | N | LEU | H | 136 | −20.359 | −51.267 | 12.296 | 1.00 | 65.79 | MOL3 | N |
| ATOM | 11372 | CA | LEU | H | 136 | −19.826 | −52.075 | 13.371 | 1.00 | 71.09 | MOL3 | C |
| ATOM | 11373 | CB | LEU | H | 136 | −18.494 | −52.678 | 12.937 | 1.00 | 68.96 | MOL3 | C |
| ATOM | 11374 | CG | LEU | H | 136 | −18.519 | −53.926 | 12.050 | 1.00 | 69.64 | MOL3 | C |
| ATOM | 11375 | CD1 | LEU | H | 136 | −19.863 | −54.060 | 11.356 | 1.00 | 72.74 | MOL3 | C |
| ATOM | 11376 | CD2 | LEU | H | 136 | −17.374 | −53.851 | 11.047 | 1.00 | 63.09 | MOL3 | C |
| ATOM | 11377 | C | LEU | H | 136 | −19.642 | −51.218 | 14.618 | 1.00 | 76.09 | MOL3 | C |
| ATOM | 11378 | O | LEU | H | 136 | −18.699 | −50.437 | 14.710 | 1.00 | 74.57 | MOL3 | O |
| ATOM | 11379 | N | ALA | H | 137 | −20.552 | −51.365 | 15.577 | 1.00 | 81.71 | MOL3 | N |
| ATOM | 11380 | CA | ALA | H | 137 | −20.484 | −50.606 | 16.817 | 1.00 | 84.93 | MOL3 | C |
| ATOM | 11381 | CB | ALA | H | 137 | −21.803 | −49.900 | 17.054 | 1.00 | 82.25 | MOL3 | C |
| ATOM | 11382 | C | ALA | H | 137 | −20.158 | −51.528 | 17.989 | 1.00 | 89.90 | MOL3 | C |
| ATOM | 11383 | O | ALA | H | 137 | −20.551 | −52.699 | 18.003 | 1.00 | 93.75 | MOL3 | O |
| ATOM | 11384 | N | PRO | H | 138 | −19.433 | −51.008 | 18.990 | 1.00 | 91.29 | MOL3 | N |
| ATOM | 11385 | CD | PRO | H | 138 | −18.930 | −49.624 | 19.015 | 1.00 | 85.59 | MOL3 | C |
| ATOM | 11386 | CA | PRO | H | 138 | −19.019 | −51.733 | 20.196 | 1.00 | 94.76 | MOL3 | C |
| ATOM | 11387 | CB | PRO | H | 138 | −18.372 | −50.638 | 21.038 | 1.00 | 89.04 | MOL3 | C |
| ATOM | 11388 | CG | PRO | H | 138 | −17.817 | −49.714 | 20.010 | 1.00 | 84.54 | MOL3 | C |
| ATOM | 11389 | C | PRO | H | 138 | −20.176 | −52.407 | 20.937 | 1.00 | 100.89 | MOL3 | C |
| ATOM | 11390 | O | PRO | H | 138 | −21.345 | −52.148 | 20.660 | 1.00 | 100.36 | MOL3 | O |
| ATOM | 11391 | N | GLY | H | 139 | −19.836 | −53.279 | 21.878 | 1.00 | 109.51 | MOL3 | N |
| ATOM | 11392 | CA | GLY | H | 139 | −20.853 | −53.941 | 22.670 | 1.00 | 120.98 | MOL3 | C |
| ATOM | 11393 | C | GLY | H | 139 | −20.971 | −53.181 | 23.978 | 1.00 | 128.74 | MOL3 | C |
| ATOM | 11394 | O | GLY | H | 139 | −20.295 | −52.169 | 24.177 | 1.00 | 128.54 | MOL3 | O |
| ATOM | 11395 | N | SER | H | 140 | −21.822 | −53.650 | 24.878 | 1.00 | 135.63 | MOL3 | N |
| ATOM | 11396 | CA | SER | H | 140 | −21.972 | −52.966 | 26.150 | 1.00 | 141.95 | MOL3 | C |
| ATOM | 11397 | CB | SER | H | 140 | −23.390 | −53.172 | 26.677 | 1.00 | 144.66 | MOL3 | C |
| ATOM | 11398 | OG | SER | H | 140 | −24.334 | −52.676 | 25.736 | 1.00 | 145.22 | MOL3 | O |
| ATOM | 11399 | C | SER | H | 140 | −20.926 | −53.468 | 27.140 | 1.00 | 145.89 | MOL3 | C |
| ATOM | 11400 | O | SER | H | 140 | −21.219 | −53.715 | 28.310 | 1.00 | 145.25 | MOL3 | O |
| ATOM | 11401 | N | ALA | H | 141 | −19.697 | −53.609 | 26.647 | 1.00 | 151.86 | MOL3 | N |
| ATOM | 11402 | CA | ALA | H | 141 | −18.571 | −54.078 | 27.451 | 1.00 | 157.16 | MOL3 | C |
| ATOM | 11403 | CB | ALA | H | 141 | −17.701 | −55.025 | 26.630 | 1.00 | 156.03 | MOL3 | C |
| ATOM | 11404 | C | ALA | H | 141 | −17.730 | −52.911 | 27.973 | 1.00 | 160.68 | MOL3 | C |
| ATOM | 11405 | O | ALA | H | 141 | −16.497 | −52.990 | 28.026 | 1.00 | 160.33 | MOL3 | O |
| ATOM | 11406 | N | ALA | H | 142 | −18.412 | −51.831 | 28.348 | 1.00 | 164.19 | MOL3 | N |
| ATOM | 11407 | CA | ALA | H | 142 | −17.776 | −50.631 | 28.893 | 1.00 | 166.64 | MOL3 | C |
| ATOM | 11408 | CB | ALA | H | 142 | −17.255 | −50.915 | 30.311 | 1.00 | 166.91 | MOL3 | C |
| ATOM | 11409 | C | ALA | H | 142 | −16.650 | −50.055 | 28.032 | 1.00 | 166.72 | MOL3 | C |
| ATOM | 11410 | O | ALA | H | 142 | −16.377 | −50.539 | 26.931 | 1.00 | 165.63 | MOL3 | O |
| ATOM | 11411 | N | GLN | H | 143 | −16.003 | −49.013 | 28.554 | 1.00 | 166.73 | MOL3 | N |
| ATOM | 11412 | CA | GLN | H | 143 | −14.907 | −48.341 | 27.859 | 1.00 | 164.95 | MOL3 | C |
| ATOM | 11413 | CB | GLN | H | 143 | −15.225 | −46.854 | 27.665 | 1.00 | 163.69 | MOL3 | C |
| ATOM | 11414 | CG | GLN | H | 143 | −15.857 | −46.513 | 26.323 | 1.00 | 161.37 | MOL3 | C |
| ATOM | 11415 | CD | GLN | H | 143 | −17.151 | −47.261 | 26.071 | 1.00 | 160.20 | MOL3 | C |
| ATOM | 11416 | OE1 | GLN | H | 143 | −18.101 | −47.162 | 26.851 | 1.00 | 159.41 | MOL3 | O |
| ATOM | 11417 | NE2 | GLN | H | 143 | −17.198 | −48.014 | 24.974 | 1.00 | 156.54 | MOL3 | N |
| ATOM | 11418 | C | GLN | H | 143 | −13.556 | −48.471 | 28.556 | 1.00 | 164.79 | MOL3 | C |
| ATOM | 11419 | O | GLN | H | 143 | −13.273 | −47.779 | 29.540 | 1.00 | 163.41 | MOL3 | O |
| ATOM | 11420 | N | THR | H | 144 | −12.724 | −49.365 | 28.034 | 1.00 | 164.54 | MOL3 | N |
| ATOM | 11421 | CA | THR | H | 144 | −11.390 | −49.570 | 28.578 | 1.00 | 163.56 | MOL3 | C |
| ATOM | 11422 | CB | THR | H | 144 | −11.071 | −51.078 | 28.775 | 1.00 | 165.35 | MOL3 | C |
| ATOM | 11423 | OG1 | THR | H | 144 | −12.120 | −51.698 | 29.532 | 1.00 | 165.87 | MOL3 | O |
| ATOM | 11424 | CG2 | THR | H | 144 | −9.750 | −51.250 | 29.533 | 1.00 | 164.82 | MOL3 | C |
| ATOM | 11425 | C | THR | H | 144 | −10.412 | −48.956 | 27.575 | 1.00 | 160.51 | MOL3 | C |
| ATOM | 11426 | O | THR | H | 144 | −10.699 | −48.883 | 26.377 | 1.00 | 157.79 | MOL3 | O |
| ATOM | 11427 | N | ASN | H | 145 | −9.266 | −48.505 | 28.078 | 1.00 | 157.51 | MOL3 | N |
| ATOM | 11428 | CA | ASN | H | 145 | −8.235 | −47.872 | 27.258 | 1.00 | 149.48 | MOL3 | C |
| ATOM | 11429 | CB | ASN | H | 145 | −7.789 | −48.795 | 26.115 | 1.00 | 149.22 | MOL3 | C |
| ATOM | 11430 | CG | ASN | H | 145 | −6.623 | −48.222 | 25.324 | 1.00 | 147.20 | MOL3 | C |
| ATOM | 11431 | OD1 | ASN | H | 145 | −5.591 | −47.849 | 25.889 | 1.00 | 147.24 | MOL3 | O |
| ATOM | 11432 | ND2 | ASN | H | 145 | −6.781 | −48.153 | 24.010 | 1.00 | 145.12 | MOL3 | N |
| ATOM | 11433 | C | ASN | H | 145 | −8.715 | −46.538 | 26.693 | 1.00 | 141.72 | MOL3 | C |
| ATOM | 11434 | O | ASN | H | 145 | −9.906 | −46.215 | 26.720 | 1.00 | 138.02 | MOL3 | O |
| ATOM | 11435 | N | SER | H | 146 | −7.766 | −45.771 | 26.178 | 1.00 | 133.95 | MOL3 | N |
| ATOM | 11436 | CA | SER | H | 146 | −8.045 | −44.461 | 25.629 | 1.00 | 128.86 | MOL3 | C |
| ATOM | 11437 | CB | SER | H | 146 | −6.769 | −43.621 | 25.683 | 1.00 | 132.13 | MOL3 | C |
| ATOM | 11438 | OG | SER | H | 146 | −6.175 | −43.688 | 26.971 | 1.00 | 137.19 | MOL3 | O |
| ATOM | 11439 | C | SER | H | 146 | −8.582 | −44.487 | 24.198 | 1.00 | 124.22 | MOL3 | C |
| ATOM | 11440 | O | SER | H | 146 | −9.107 | −43.486 | 23.714 | 1.00 | 124.12 | MOL3 | O |
| ATOM | 11441 | N | MET | H | 147 | −8.456 | −45.623 | 23.520 | 1.00 | 117.70 | MOL3 | N |
| ATOM | 11442 | CA | MET | H | 147 | −8.920 | −45.725 | 22.137 | 1.00 | 107.72 | MOL3 | C |
| ATOM | 11443 | CB | MET | H | 147 | −7.779 | −46.181 | 21.230 | 1.00 | 108.51 | MOL3 | C |
| ATOM | 11444 | CG | MET | H | 147 | −6.639 | −45.192 | 21.135 | 1.00 | 114.40 | MOL3 | C |
| ATOM | 11445 | SD | MET | H | 147 | −7.112 | −43.663 | 20.310 | 1.00 | 121.49 | MOL3 | S |
| ATOM | 11446 | CE | MET | H | 147 | −5.898 | −43.614 | 18.963 | 1.00 | 119.67 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 11447 | C | MET | H | 147 | −10.103 | −46.650 | 21.926 | 1.00 | 102.40 | MOL3 | C |
|---|---|---|---|---|---|---|---|---|---|---|---|---|
| ATOM | 11448 | O | MET | H | 147 | −10.288 | −47.627 | 22.645 | 1.00 | 103.99 | MOL3 | O |
| ATOM | 11449 | N | VAL | H | 148 | −10.895 | −46.335 | 20.910 | 1.00 | 97.82 | MOL3 | N |
| ATOM | 11450 | CA | VAL | H | 148 | −12.077 | −47.113 | 20.555 | 1.00 | 92.16 | MOL3 | C |
| ATOM | 11451 | CB | VAL | H | 148 | −13.377 | −46.307 | 20.788 | 1.00 | 86.31 | MOL3 | C |
| ATOM | 11452 | CG1 | VAL | H | 148 | −13.307 | −44.993 | 20.058 | 1.00 | 80.24 | MOL3 | C |
| ATOM | 11453 | CG2 | VAL | H | 148 | −14.570 | −47.084 | 20.279 | 1.00 | 81.35 | MOL3 | C |
| ATOM | 11454 | C | VAL | H | 148 | −12.029 | −47.470 | 19.075 | 1.00 | 90.39 | MOL3 | C |
| ATOM | 11455 | O | VAL | H | 148 | −11.738 | −46.616 | 18.238 | 1.00 | 85.60 | MOL3 | O |
| ATOM | 11456 | N | THR | H | 149 | −12.314 | −48.725 | 18.749 | 1.00 | 88.35 | MOL3 | N |
| ATOM | 11457 | CA | THR | H | 149 | −12.312 | −49.133 | 17.356 | 1.00 | 81.69 | MOL3 | C |
| ATOM | 11458 | CB | THR | H | 149 | −11.509 | −50.407 | 17.126 | 1.00 | 83.07 | MOL3 | C |
| ATOM | 11459 | OG1 | THR | H | 149 | −10.128 | −50.075 | 16.934 | 1.00 | 84.79 | MOL3 | O |
| ATOM | 11460 | CG2 | THR | H | 149 | −12.027 | −51.128 | 15.903 | 1.00 | 82.03 | MOL3 | C |
| ATOM | 11461 | C | THR | H | 149 | −13.715 | −49.371 | 16.858 | 1.00 | 77.72 | MOL3 | C |
| ATOM | 11462 | O | THR | H | 149 | −14.471 | −50.136 | 17.453 | 1.00 | 78.65 | MOL3 | O |
| ATOM | 11463 | N | LEU | H | 150 | −14.050 | −48.692 | 15.764 | 1.00 | 73.41 | MOL3 | N |
| ATOM | 11464 | CA | LEU | H | 150 | −15.356 | −48.794 | 15.117 | 1.00 | 69.81 | MOL3 | C |
| ATOM | 11465 | CB | LEU | H | 150 | −15.953 | −47.419 | 14.866 | 1.00 | 69.43 | MOL3 | C |
| ATOM | 11466 | CG | LEU | H | 150 | −16.775 | −46.808 | 15.985 | 1.00 | 71.83 | MOL3 | C |
| ATOM | 11467 | CD1 | LEU | H | 150 | −16.098 | −47.048 | 17.320 | 1.00 | 73.94 | MOL3 | C |
| ATOM | 11468 | CD2 | LEU | H | 150 | −16.953 | −45.330 | 15.697 | 1.00 | 73.90 | MOL3 | C |
| ATOM | 11469 | C | LEU | H | 150 | −15.176 | −49.456 | 13.778 | 1.00 | 66.09 | MOL3 | C |
| ATOM | 11470 | O | LEU | H | 150 | −14.083 | −49.450 | 13.220 | 1.00 | 63.47 | MOL3 | O |
| ATOM | 11471 | N | GLY | H | 151 | −16.259 | −49.998 | 13.244 | 1.00 | 65.92 | MOL3 | N |
| ATOM | 11472 | CA | GLY | H | 151 | −16.160 | −50.668 | 11.968 | 1.00 | 70.49 | MOL3 | C |
| ATOM | 11473 | C | GLY | H | 151 | −17.302 | −50.392 | 11.021 | 1.00 | 71.85 | MOL3 | C |
| ATOM | 11474 | O | GLY | H | 151 | −18.281 | −49.731 | 11.361 | 1.00 | 73.68 | MOL3 | O |
| ATOM | 11475 | N | CYS | H | 152 | −17.176 | −50.942 | 9.823 | 1.00 | 72.23 | MOL3 | N |
| ATOM | 11476 | CA | CYS | H | 152 | −18.170 | −50.746 | 8.788 | 1.00 | 73.94 | MOL3 | C |
| ATOM | 11477 | C | CYS | H | 152 | −18.171 | −51.956 | 7.841 | 1.00 | 67.77 | MOL3 | C |
| ATOM | 11478 | O | CYS | H | 152 | −17.260 | −52.119 | 7.043 | 1.00 | 61.88 | MOL3 | O |
| ATOM | 11479 | CB | CYS | H | 152 | −17.806 | −49.464 | 8.042 | 1.00 | 77.20 | MOL3 | C |
| ATOM | 11480 | SG | CYS | H | 152 | −18.839 | −49.053 | 6.611 | 1.00 | 89.22 | MOL3 | S |
| ATOM | 11481 | N | LEU | H | 153 | −19.192 | −52.802 | 7.933 | 1.00 | 64.17 | MOL3 | N |
| ATOM | 11482 | CA | LEU | H | 153 | −19.256 | −53.985 | 7.085 | 1.00 | 62.43 | MOL3 | C |
| ATOM | 11483 | CB | LEU | H | 153 | −19.968 | −55.131 | 7.799 | 1.00 | 67.70 | MOL3 | C |
| ATOM | 11484 | CG | LEU | H | 153 | −20.023 | −56.468 | 7.047 | 1.00 | 69.14 | MOL3 | C |
| ATOM | 11485 | CD1 | LEU | H | 153 | −18.611 | −56.889 | 6.620 | 1.00 | 66.63 | MOL3 | C |
| ATOM | 11486 | CD2 | LEU | H | 153 | −20.651 | −57.528 | 7.947 | 1.00 | 67.24 | MOL3 | C |
| ATOM | 11487 | C | LEU | H | 153 | −19.989 | −53.706 | 5.803 | 1.00 | 61.32 | MOL3 | C |
| ATOM | 11488 | O | LEU | H | 153 | −21.132 | −53.258 | 5.832 | 1.00 | 66.08 | MOL3 | O |
| ATOM | 11489 | N | VAL | H | 154 | −19.325 | −53.984 | 4.683 | 1.00 | 56.07 | MOL3 | N |
| ATOM | 11490 | CA | VAL | H | 154 | −19.893 | −53.792 | 3.348 | 1.00 | 51.90 | MOL3 | C |
| ATOM | 11491 | CB | VAL | H | 154 | −18.903 | −53.087 | 2.413 | 1.00 | 49.28 | MOL3 | C |
| ATOM | 11492 | CG1 | VAL | H | 154 | −19.519 | −52.892 | 1.049 | 1.00 | 46.64 | MOL3 | C |
| ATOM | 11493 | CG2 | VAL | H | 154 | −18.506 | −51.767 | 2.984 | 1.00 | 50.17 | MOL3 | C |
| ATOM | 11494 | C | VAL | H | 154 | −20.160 | −55.174 | 2.770 | 1.00 | 55.96 | MOL3 | C |
| ATOM | 11495 | O | VAL | H | 154 | −19.257 | −55.819 | 2.240 | 1.00 | 54.62 | MOL3 | O |
| ATOM | 11496 | N | LYS | H | 155 | −21.403 | −55.624 | 2.853 | 1.00 | 61.21 | MOL3 | N |
| ATOM | 11497 | CA | LYS | H | 155 | −21.742 | −56.954 | 2.378 | 1.00 | 59.99 | MOL3 | C |
| ATOM | 11498 | CB | LYS | H | 155 | −22.627 | −57.658 | 3.412 | 1.00 | 60.96 | MOL3 | C |
| ATOM | 11499 | CG | LYS | H | 155 | −22.704 | −59.164 | 3.253 | 1.00 | 70.31 | MOL3 | C |
| ATOM | 11500 | CD | LYS | H | 155 | −23.715 | −59.782 | 4.205 | 1.00 | 75.62 | MOL3 | C |
| ATOM | 11501 | CE | LYS | H | 155 | −23.523 | −61.286 | 4.285 | 1.00 | 78.29 | MOL3 | C |
| ATOM | 11502 | NZ | LYS | H | 155 | −22.140 | −61.628 | 4.748 | 1.00 | 76.71 | MOL3 | N |
| ATOM | 11503 | C | LYS | H | 155 | −22.408 | −57.020 | 1.012 | 1.00 | 60.38 | MOL3 | C |
| ATOM | 11504 | O | LYS | H | 155 | −22.966 | −56.040 | 0.508 | 1.00 | 53.20 | MOL3 | O |
| ATOM | 11505 | N | GLY | H | 156 | −22.309 | −58.212 | 0.433 | 1.00 | 66.29 | MOL3 | N |
| ATOM | 11506 | CA | GLY | H | 156 | −22.888 | −58.542 | −0.855 | 1.00 | 70.93 | MOL3 | C |
| ATOM | 11507 | C | GLY | H | 156 | −22.985 | −57.510 | −1.963 | 1.00 | 73.35 | MOL3 | C |
| ATOM | 11508 | O | GLY | H | 156 | −24.077 | −57.019 | −2.270 | 1.00 | 77.12 | MOL3 | O |
| ATOM | 11509 | N | TYR | H | 157 | −21.853 | −57.187 | −2.577 | 1.00 | 70.56 | MOL3 | N |
| ATOM | 11510 | CA | TYR | H | 157 | −21.847 | −56.244 | −3.687 | 1.00 | 66.66 | MOL3 | C |
| ATOM | 11511 | CB | TYR | H | 157 | −21.221 | −54.916 | −3.296 | 1.00 | 63.22 | MOL3 | C |
| ATOM | 11512 | CG | TYR | H | 157 | −19.734 | −54.992 | −3.142 | 1.00 | 60.83 | MOL3 | C |
| ATOM | 11513 | CD1 | TYR | H | 157 | −19.166 | −55.498 | −1.988 | 1.00 | 60.30 | MOL3 | C |
| ATOM | 11514 | CE1 | TYR | H | 157 | −17.799 | −55.579 | −1.846 | 1.00 | 57.35 | MOL3 | C |
| ATOM | 11515 | CD2 | TYR | H | 157 | −18.891 | −54.571 | −4.156 | 1.00 | 59.48 | MOL3 | C |
| ATOM | 11516 | CE2 | TYR | H | 157 | −17.522 | −54.652 | −4.019 | 1.00 | 56.34 | MOL3 | C |
| ATOM | 11517 | CZ | TYR | H | 157 | −16.989 | −55.155 | −2.862 | 1.00 | 51.94 | MOL3 | C |
| ATOM | 11518 | OH | TYR | H | 157 | −15.638 | −55.227 | −2.706 | 1.00 | 57.08 | MOL3 | O |
| ATOM | 11519 | C | TYR | H | 157 | −21.035 | −56.846 | −4.821 | 1.00 | 67.40 | MOL3 | C |
| ATOM | 11520 | O | TYR | H | 157 | −20.214 | −57.741 | −4.609 | 1.00 | 65.47 | MOL3 | O |
| ATOM | 11521 | N | PHE | H | 158 | −21.265 | −56.345 | −6.028 | 1.00 | 70.19 | MOL3 | N |
| ATOM | 11522 | CA | PHE | H | 158 | −20.562 | −56.839 | −7.205 | 1.00 | 74.83 | MOL3 | C |
| ATOM | 11523 | CB | PHE | H | 158 | −21.124 | −58.190 | −7.631 | 1.00 | 71.48 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 11524 | CG | PHE | H | 158 | −20.255 | −58.940 | −8.597 | 1.00 | 72.68 | MOL3 | C |
|---|---|---|---|---|---|---|---|---|---|---|---|---|
| ATOM | 11525 | CD1 | PHE | H | 158 | −19.269 | −59.804 | −8.138 | 1.00 | 74.53 | MOL3 | C |
| ATOM | 11526 | CD2 | PHE | H | 158 | −20.453 | −58.823 | −9.962 | 1.00 | 72.90 | MOL3 | C |
| ATOM | 11527 | CE1 | PHE | H | 158 | −18.500 | −60.546 | −9.024 | 1.00 | 73.17 | MOL3 | C |
| ATOM | 11528 | CE2 | PHE | H | 158 | −19.689 | −59.559 | −10.853 | 1.00 | 76.21 | MOL3 | C |
| ATOM | 11529 | CZ | PHE | H | 158 | −18.713 | −60.423 | −10.383 | 1.00 | 75.38 | MOL3 | C |
| ATOM | 11530 | C | PHE | H | 158 | −20.733 | −55.855 | −8.353 | 1.00 | 79.34 | MOL3 | C |
| ATOM | 11531 | O | PHE | H | 158 | −21.811 | −55.278 | −8.533 | 1.00 | 83.42 | MOL3 | O |
| ATOM | 11532 | N | PRO | H | 159 | −19.658 | −55.637 | −9.134 | 1.00 | 79.37 | MOL3 | N |
| ATOM | 11533 | CD | PRO | H | 159 | −19.671 | −55.048 | −10.487 | 1.00 | 75.33 | MOL3 | C |
| ATOM | 11534 | CA | PRO | H | 159 | −18.378 | −56.304 | −8.897 | 1.00 | 77.27 | MOL3 | C |
| ATOM | 11535 | CB | PRO | H | 159 | −17.912 | −56.619 | −10.301 | 1.00 | 70.82 | MOL3 | C |
| ATOM | 11536 | CG | PRO | H | 159 | −18.262 | −55.354 | −10.999 | 1.00 | 71.69 | MOL3 | C |
| ATOM | 11537 | C | PRO | H | 159 | −17.418 | −55.350 | −8.203 | 1.00 | 77.61 | MOL3 | C |
| ATOM | 11538 | O | PRO | H | 159 | −17.813 | −54.276 | −7.742 | 1.00 | 76.98 | MOL3 | O |
| ATOM | 11539 | N | GLU | H | 160 | −16.154 | −55.747 | −8.129 | 1.00 | 76.69 | MOL3 | N |
| ATOM | 11540 | CA | GLU | H | 160 | −15.153 | −54.899 | −7.523 | 1.00 | 79.57 | MOL3 | C |
| ATOM | 11541 | CB | GLU | H | 160 | −13.816 | −55.640 | −7.470 | 1.00 | 75.33 | MOL3 | C |
| ATOM | 11542 | CG | GLU | H | 160 | −13.705 | −56.694 | −6.357 | 1.00 | 80.58 | MOL3 | C |
| ATOM | 11543 | CD | GLU | H | 160 | −13.011 | −56.177 | −5.078 | 1.00 | 90.70 | MOL3 | C |
| ATOM | 11544 | OE1 | GLU | H | 160 | −13.417 | −55.118 | −4.537 | 1.00 | 89.63 | MOL3 | O |
| ATOM | 11545 | OE2 | GLU | H | 160 | −12.055 | −56.841 | −4.607 | 1.00 | 90.40 | MOL3 | O |
| ATOM | 11546 | C | GLU | H | 160 | −15.065 | −53.677 | −8.433 | 1.00 | 83.98 | MOL3 | C |
| ATOM | 11547 | O | GLU | H | 160 | −15.395 | −53.757 | −9.614 | 1.00 | 91.30 | MOL3 | O |
| ATOM | 11548 | N | PRO | H | 161 | −14.652 | −52.524 | −7.893 | 1.00 | 84.34 | MOL3 | N |
| ATOM | 11549 | CD | PRO | H | 161 | −13.856 | −51.590 | −8.710 | 1.00 | 81.86 | MOL3 | C |
| ATOM | 11550 | CA | PRO | H | 161 | −14.292 | −52.377 | −6.487 | 1.00 | 84.58 | MOL3 | C |
| ATOM | 11551 | CB | PRO | H | 161 | −12.863 | −51.880 | −6.568 | 1.00 | 82.05 | MOL3 | C |
| ATOM | 11552 | CG | PRO | H | 161 | −12.966 | −50.900 | −7.671 | 1.00 | 80.99 | MOL3 | C |
| ATOM | 11553 | C | PRO | H | 161 | −15.195 | −51.383 | −5.774 | 1.00 | 85.92 | MOL3 | C |
| ATOM | 11554 | O | PRO | H | 161 | −15.965 | −50.641 | −6.398 | 1.00 | 89.34 | MOL3 | O |
| ATOM | 11555 | N | VAL | H | 162 | −15.090 | −51.382 | −4.455 | 1.00 | 82.39 | MOL3 | N |
| ATOM | 11556 | CA | VAL | H | 162 | −15.858 | −50.475 | −3.642 | 1.00 | 78.67 | MOL3 | C |
| ATOM | 11557 | CB | VAL | H | 162 | −16.607 | −51.238 | −2.558 | 1.00 | 74.90 | MOL3 | C |
| ATOM | 11558 | CG1 | VAL | H | 162 | −15.645 | −52.113 | −1.794 | 1.00 | 72.98 | MOL3 | C |
| ATOM | 11559 | CG2 | VAL | H | 162 | −17.295 | −50.272 | −1.636 | 1.00 | 79.19 | MOL3 | C |
| ATOM | 11560 | C | VAL | H | 162 | −14.808 | −49.579 | −3.017 | 1.00 | 77.99 | MOL3 | C |
| ATOM | 11561 | O | VAL | H | 162 | −13.655 | −49.979 | −2.863 | 1.00 | 72.49 | MOL3 | O |
| ATOM | 11562 | N | THR | H | 163 | −15.178 | −48.354 | −2.693 | 1.00 | 80.25 | MOL3 | N |
| ATOM | 11563 | CA | THR | H | 163 | −14.214 | −47.474 | −2.070 | 1.00 | 82.23 | MOL3 | C |
| ATOM | 11564 | CB | THR | H | 163 | −13.816 | −46.332 | −3.017 | 1.00 | 86.16 | MOL3 | C |
| ATOM | 11565 | OG1 | THR | H | 163 | −12.847 | −46.830 | −3.954 | 1.00 | 77.67 | MOL3 | O |
| ATOM | 11566 | CG2 | THR | H | 163 | −13.230 | −45.153 | −2.240 | 1.00 | 89.23 | MOL3 | C |
| ATOM | 11567 | C | THR | H | 163 | −14.761 | −46.976 | −0.743 | 1.00 | 83.40 | MOL3 | C |
| ATOM | 11568 | O | THR | H | 163 | −15.849 | −46.384 | −0.658 | 1.00 | 86.29 | MOL3 | O |
| ATOM | 11569 | N | VAL | H | 164 | −13.993 | −47.261 | 0.300 | 1.00 | 78.21 | MOL3 | N |
| ATOM | 11570 | CA | VAL | H | 164 | −14.364 | −46.918 | 1.657 | 1.00 | 80.05 | MOL3 | C |
| ATOM | 11571 | CB | VAL | H | 164 | −14.114 | −48.113 | 2.575 | 1.00 | 78.14 | MOL3 | C |
| ATOM | 11572 | CG1 | VAL | H | 164 | −14.808 | −47.911 | 3.914 | 1.00 | 76.92 | MOL3 | C |
| ATOM | 11573 | CG2 | VAL | H | 164 | −14.579 | −49.374 | 1.892 | 1.00 | 77.40 | MOL3 | C |
| ATOM | 11574 | C | VAL | H | 164 | −13.541 | −45.762 | 2.169 | 1.00 | 82.24 | MOL3 | C |
| ATOM | 11575 | O | VAL | H | 164 | −12.367 | −45.641 | 1.834 | 1.00 | 83.12 | MOL3 | O |
| ATOM | 11576 | N | THR | H | 165 | −14.149 | −44.940 | 3.017 | 1.00 | 82.62 | MOL3 | N |
| ATOM | 11577 | CA | THR | H | 165 | −13.470 | −43.786 | 3.566 | 1.00 | 79.38 | MOL3 | C |
| ATOM | 11578 | CB | THR | H | 165 | −13.472 | −42.684 | 2.518 | 1.00 | 76.55 | MOL3 | C |
| ATOM | 11579 | OG1 | THR | H | 165 | −12.133 | −42.467 | 2.063 | 1.00 | 74.39 | MOL3 | O |
| ATOM | 11580 | CG2 | THR | H | 165 | −14.068 | −41.420 | 3.067 | 1.00 | 80.32 | MOL3 | C |
| ATOM | 11581 | C | THR | H | 165 | −14.174 | −43.334 | 4.835 | 1.00 | 82.23 | MOL3 | C |
| ATOM | 11582 | O | THR | H | 165 | −15.369 | −43.590 | 5.006 | 1.00 | 92.20 | MOL3 | O |
| ATOM | 11583 | N | TRP | H | 166 | −13.446 | −42.676 | 5.730 | 1.00 | 78.45 | MOL3 | N |
| ATOM | 11584 | CA | TRP | H | 166 | −14.053 | −42.227 | 6.974 | 1.00 | 83.57 | MOL3 | C |
| ATOM | 11585 | CB | TRP | H | 166 | −13.297 | −42.835 | 8.154 | 1.00 | 75.83 | MOL3 | C |
| ATOM | 11586 | CG | TRP | H | 166 | −13.359 | −44.331 | 8.178 | 1.00 | 61.73 | MOL3 | C |
| ATOM | 11587 | CD2 | TRP | H | 166 | −14.374 | −45.129 | 8.786 | 1.00 | 53.21 | MOL3 | C |
| ATOM | 11588 | CE2 | TRP | H | 166 | −14.078 | −46.473 | 8.497 | 1.00 | 50.56 | MOL3 | C |
| ATOM | 11589 | CE3 | TRP | H | 166 | −15.509 | −44.835 | 9.540 | 1.00 | 57.81 | MOL3 | C |
| ATOM | 11590 | CD1 | TRP | H | 166 | −12.507 | −45.196 | 7.565 | 1.00 | 56.26 | MOL3 | C |
| ATOM | 11591 | NE1 | TRP | H | 166 | −12.933 | −46.489 | 7.750 | 1.00 | 49.49 | MOL3 | N |
| ATOM | 11592 | CZ2 | TRP | H | 166 | −14.871 | −47.524 | 8.936 | 1.00 | 62.55 | MOL3 | C |
| ATOM | 11593 | CZ3 | TRP | H | 166 | −16.303 | −45.881 | 9.977 | 1.00 | 67.42 | MOL3 | C |
| ATOM | 11594 | CH2 | TRP | H | 166 | −15.981 | −47.211 | 9.674 | 1.00 | 69.04 | MOL3 | C |
| ATOM | 11595 | C | TRP | H | 166 | −14.110 | −40.707 | 7.103 | 1.00 | 90.73 | MOL3 | C |
| ATOM | 11596 | O | TRP | H | 166 | −13.101 | −40.024 | 6.953 | 1.00 | 90.08 | MOL3 | O |
| ATOM | 11597 | N | ASN | H | 167 | −15.299 | −40.182 | 7.387 | 1.00 | 100.29 | MOL3 | N |
| ATOM | 11598 | CA | ASN | H | 167 | −15.482 | −38.739 | 7.523 | 1.00 | 103.08 | MOL3 | C |
| ATOM | 11599 | CB | ASN | H | 167 | −14.688 | −38.216 | 8.717 | 1.00 | 104.70 | MOL3 | C |
| ATOM | 11600 | CG | ASN | H | 167 | −15.454 | −38.331 | 10.018 | 1.00 | 110.34 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 11601 | OD1 | ASN | H | 167 | −16.057 | −39.366 | 10.309 | 1.00 | 114.18 | MOL3 | O |
|------|-------|-----|-----|---|-----|---------|---------|--------|------|--------|------|---|
| ATOM | 11602 | ND2 | ASN | H | 167 | −15.431 | −37.266 | 10.815 | 1.00 | 114.51 | MOL3 | N |
| ATOM | 11603 | C | ASN | H | 167 | −15.037 | −38.025 | 6.261 | 1.00 | 101.78 | MOL3 | C |
| ATOM | 11604 | O | ASN | H | 167 | −14.484 | −36.930 | 6.315 | 1.00 | 99.40 | MOL3 | O |
| ATOM | 11605 | N | SER | H | 168 | −15.267 | −38.678 | 5.130 | 1.00 | 102.77 | MOL3 | N |
| ATOM | 11606 | CA | SER | H | 168 | −14.933 | −38.133 | 3.828 | 1.00 | 105.60 | MOL3 | C |
| ATOM | 11607 | CB | SER | H | 168 | −15.753 | −36.865 | 3.595 | 1.00 | 108.93 | MOL3 | C |
| ATOM | 11608 | OG | SER | H | 168 | −17.060 | −37.011 | 4.130 | 1.00 | 112.36 | MOL3 | O |
| ATOM | 11609 | C | SER | H | 168 | −13.448 | −37.825 | 3.656 | 1.00 | 105.78 | MOL3 | C |
| ATOM | 11610 | O | SER | H | 168 | −13.057 | −37.168 | 2.695 | 1.00 | 107.78 | MOL3 | O |
| ATOM | 11611 | N | GLY | H | 169 | −12.621 | −38.293 | 4.582 | 1.00 | 105.25 | MOL3 | N |
| ATOM | 11612 | CA | GLY | H | 169 | −11.197 | −38.041 | 4.468 | 1.00 | 104.83 | MOL3 | C |
| ATOM | 11613 | C | GLY | H | 169 | −10.615 | −37.471 | 5.740 | 1.00 | 106.28 | MOL3 | C |
| ATOM | 11614 | O | GLY | H | 169 | −9.393 | −37.402 | 5.897 | 1.00 | 103.08 | MOL3 | O |
| ATOM | 11615 | N | SER | H | 170 | −11.495 | −37.060 | 6.650 | 1.00 | 107.77 | MOL3 | N |
| ATOM | 11616 | CA | SER | H | 170 | −11.064 | −36.497 | 7.924 | 1.00 | 111.76 | MOL3 | C |
| ATOM | 11617 | CB | SER | H | 170 | −12.291 | −36.111 | 8.768 | 1.00 | 114.37 | MOL3 | C |
| ATOM | 11618 | OG | SER | H | 170 | −11.929 | −35.539 | 10.020 | 1.00 | 113.88 | MOL3 | O |
| ATOM | 11619 | C | SER | H | 170 | −10.186 | −37.510 | 8.676 | 1.00 | 112.11 | MOL3 | C |
| ATOM | 11620 | O | SER | H | 170 | −9.178 | −37.145 | 9.287 | 1.00 | 113.84 | MOL3 | O |
| ATOM | 11621 | N | LEU | H | 171 | −10.565 | −38.783 | 8.618 | 1.00 | 108.77 | MOL3 | N |
| ATOM | 11622 | CA | LEU | H | 171 | −9.811 | −39.833 | 9.289 | 1.00 | 103.21 | MOL3 | C |
| ATOM | 11623 | CB | LEU | H | 171 | −10.746 | −40.733 | 10.098 | 1.00 | 100.76 | MOL3 | C |
| ATOM | 11624 | CG | LEU | H | 171 | −11.514 | −40.137 | 11.281 | 1.00 | 97.25 | MOL3 | C |
| ATOM | 11625 | CD1 | LEU | H | 171 | −12.388 | −38.985 | 10.826 | 1.00 | 95.97 | MOL3 | C |
| ATOM | 11626 | CD2 | LEU | H | 171 | −12.369 | −41.218 | 11.909 | 1.00 | 94.50 | MOL3 | C |
| ATOM | 11627 | C | LEU | H | 171 | −9.070 | −40.670 | 8.262 | 1.00 | 102.49 | MOL3 | C |
| ATOM | 11628 | O | LEU | H | 171 | −9.686 | −41.390 | 7.478 | 1.00 | 103.13 | MOL3 | O |
| ATOM | 11629 | N | SER | H | 172 | −7.747 | −40.573 | 8.269 | 1.00 | 103.04 | MOL3 | N |
| ATOM | 11630 | CA | SER | H | 172 | −6.919 | −41.320 | 7.327 | 1.00 | 104.87 | MOL3 | C |
| ATOM | 11631 | CB | SER | H | 172 | −6.076 | −40.361 | 6.487 | 1.00 | 106.36 | MOL3 | C |
| ATOM | 11632 | OG | SER | H | 172 | −5.095 | −39.713 | 7.284 | 1.00 | 107.12 | MOL3 | O |
| ATOM | 11633 | C | SER | H | 172 | −5.986 | −42.257 | 8.068 | 1.00 | 105.79 | MOL3 | C |
| ATOM | 11634 | O | SER | H | 172 | −5.656 | −43.336 | 7.581 | 1.00 | 106.18 | MOL3 | O |
| ATOM | 11635 | N | SER | H | 173 | −5.556 | −41.822 | 9.247 | 1.00 | 107.31 | MOL3 | N |
| ATOM | 11636 | CA | SER | H | 173 | −4.646 | −42.595 | 10.081 | 1.00 | 104.81 | MOL3 | C |
| ATOM | 11637 | CB | SER | H | 173 | −3.729 | −41.646 | 10.866 | 1.00 | 105.83 | MOL3 | C |
| ATOM | 11638 | OG | SER | H | 173 | −4.461 | −40.605 | 11.499 | 1.00 | 98.57 | MOL3 | O |
| ATOM | 11639 | C | SER | H | 173 | −5.407 | −43.495 | 11.038 | 1.00 | 102.90 | MOL3 | C |
| ATOM | 11640 | O | SER | H | 173 | −6.477 | −43.128 | 11.525 | 1.00 | 104.60 | MOL3 | O |
| ATOM | 11641 | N | GLY | H | 174 | −4.853 | −44.674 | 11.303 | 1.00 | 98.71 | MOL3 | N |
| ATOM | 11642 | CA | GLY | H | 174 | −5.500 | −45.602 | 12.214 | 1.00 | 97.65 | MOL3 | C |
| ATOM | 11643 | C | GLY | H | 174 | −6.699 | −46.262 | 11.569 | 1.00 | 94.80 | MOL3 | C |
| ATOM | 11644 | O | GLY | H | 174 | −7.621 | −46.721 | 12.247 | 1.00 | 95.87 | MOL3 | O |
| ATOM | 11645 | N | VAL | H | 175 | −6.674 | −46.311 | 10.243 | 1.00 | 90.26 | MOL3 | N |
| ATOM | 11646 | CA | VAL | H | 175 | −7.754 | −46.900 | 9.461 | 1.00 | 85.11 | MOL3 | C |
| ATOM | 11647 | CB | VAL | H | 175 | −8.243 | −45.928 | 8.358 | 1.00 | 82.39 | MOL3 | C |
| ATOM | 11648 | CG1 | VAL | H | 175 | −9.044 | −46.689 | 7.310 | 1.00 | 76.61 | MOL3 | C |
| ATOM | 11649 | CG2 | VAL | H | 175 | −9.077 | −44.813 | 8.971 | 1.00 | 80.37 | MOL3 | C |
| ATOM | 11650 | C | VAL | H | 175 | −7.284 | −48.159 | 8.762 | 1.00 | 81.26 | MOL3 | C |
| ATOM | 11651 | O | VAL | H | 175 | −6.206 | −48.173 | 8.173 | 1.00 | 83.63 | MOL3 | O |
| ATOM | 11652 | N | HIS | H | 176 | −8.094 | −49.210 | 8.821 | 1.00 | 76.09 | MOL3 | N |
| ATOM | 11653 | CA | HIS | H | 176 | −7.762 | −50.467 | 8.158 | 1.00 | 68.75 | MOL3 | C |
| ATOM | 11654 | CB | HIS | H | 176 | −7.401 | −51.553 | 9.173 | 1.00 | 71.27 | MOL3 | C |
| ATOM | 11655 | CG | HIS | H | 176 | −5.962 | −51.564 | 9.588 | 1.00 | 71.42 | MOL3 | C |
| ATOM | 11656 | CD2 | HIS | H | 176 | −5.390 | −51.538 | 10.816 | 1.00 | 67.95 | MOL3 | C |
| ATOM | 11657 | ND1 | HIS | H | 176 | −4.927 | −51.688 | 8.685 | 1.00 | 74.70 | MOL3 | N |
| ATOM | 11658 | CE1 | HIS | H | 176 | −3.780 | −51.743 | 9.341 | 1.00 | 77.04 | MOL3 | C |
| ATOM | 11659 | NE2 | HIS | H | 176 | −4.034 | −51.656 | 10.635 | 1.00 | 69.41 | MOL3 | N |
| ATOM | 11660 | C | HIS | H | 176 | −8.952 | −50.951 | 7.351 | 1.00 | 64.01 | MOL3 | C |
| ATOM | 11661 | O | HIS | H | 176 | −9.948 | −51.410 | 7.910 | 1.00 | 65.62 | MOL3 | O |
| ATOM | 11662 | N | THR | H | 177 | −8.872 | −50.825 | 6.038 | 1.00 | 56.48 | MOL3 | N |
| ATOM | 11663 | CA | THR | H | 177 | −9.958 | −51.311 | 5.211 | 1.00 | 52.80 | MOL3 | C |
| ATOM | 11664 | CB | THR | H | 177 | −10.441 | −50.265 | 4.177 | 1.00 | 52.89 | MOL3 | C |
| ATOM | 11665 | OG1 | THR | H | 177 | −10.646 | −50.920 | 2.923 | 1.00 | 55.66 | MOL3 | O |
| ATOM | 11666 | CG2 | THR | H | 177 | −9.444 | −49.110 | 4.027 | 1.00 | 56.20 | MOL3 | C |
| ATOM | 11667 | C | THR | H | 177 | −9.420 | −52.564 | 4.539 | 1.00 | 47.84 | MOL3 | C |
| ATOM | 11668 | O | THR | H | 177 | −8.528 | −52.516 | 3.704 | 1.00 | 44.37 | MOL3 | O |
| ATOM | 11669 | N | PHE | H | 178 | −9.966 | −53.700 | 4.942 | 1.00 | 49.87 | MOL3 | N |
| ATOM | 11670 | CA | PHE | H | 178 | −9.516 | −54.994 | 4.453 | 1.00 | 50.15 | MOL3 | C |
| ATOM | 11671 | CB | PHE | H | 178 | −9.950 | −56.083 | 5.425 | 1.00 | 51.36 | MOL3 | C |
| ATOM | 11672 | CG | PHE | H | 178 | −9.513 | −55.833 | 6.833 | 1.00 | 50.93 | MOL3 | C |
| ATOM | 11673 | CD1 | PHE | H | 178 | −8.462 | −56.540 | 7.381 | 1.00 | 50.19 | MOL3 | C |
| ATOM | 11674 | CD2 | PHE | H | 178 | −10.120 | −54.849 | 7.591 | 1.00 | 49.49 | MOL3 | C |
| ATOM | 11675 | CE1 | PHE | H | 178 | −8.022 | −56.270 | 8.652 | 1.00 | 49.58 | MOL3 | C |
| ATOM | 11676 | CE2 | PHE | H | 178 | −9.683 | −54.574 | 8.861 | 1.00 | 51.26 | MOL3 | C |
| ATOM | 11677 | CZ | PHE | H | 178 | −8.631 | −55.285 | 9.393 | 1.00 | 52.32 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 11678 | C | PHE | H | 178 | −9.953 | −55.375 | 3.061 | 1.00 | 54.56 | MOL3 | C |
|---|---|---|---|---|---|---|---|---|---|---|---|---|
| ATOM | 11679 | O | PHE | H | 178 | −10.897 | −54.821 | 2.505 | 1.00 | 64.25 | MOL3 | O |
| ATOM | 11680 | N | PRO | H | 179 | −9.251 | −56.342 | 2.472 | 1.00 | 55.68 | MOL3 | N |
| ATOM | 11681 | CD | PRO | H | 179 | −8.011 | −56.902 | 3.031 | 1.00 | 57.16 | MOL3 | C |
| ATOM | 11682 | CA | PRO | H | 179 | −9.494 | −56.872 | 1.132 | 1.00 | 58.45 | MOL3 | C |
| ATOM | 11683 | CB | PRO | H | 179 | −8.380 | −57.903 | 0.959 | 1.00 | 53.58 | MOL3 | C |
| ATOM | 11684 | CG | PRO | H | 179 | −7.286 | −57.362 | 1.781 | 1.00 | 55.46 | MOL3 | C |
| ATOM | 11685 | C | PRO | H | 179 | −10.851 | −57.535 | 1.043 | 1.00 | 63.31 | MOL3 | C |
| ATOM | 11686 | O | PRO | H | 179 | −11.238 | −58.285 | 1.935 | 1.00 | 60.56 | MOL3 | O |
| ATOM | 11687 | N | ALA | H | 180 | −11.572 | −57.269 | −0.038 | 1.00 | 70.63 | MOL3 | N |
| ATOM | 11688 | CA | ALA | H | 180 | −12.874 | −57.889 | −0.222 | 1.00 | 71.32 | MOL3 | C |
| ATOM | 11689 | CB | ALA | H | 180 | −13.559 | −57.322 | −1.456 | 1.00 | 74.52 | MOL3 | C |
| ATOM | 11690 | C | ALA | H | 180 | −12.656 | −59.387 | −0.386 | 1.00 | 67.08 | MOL3 | C |
| ATOM | 11691 | O | ALA | H | 180 | −11.623 | −59.827 | −0.881 | 1.00 | 62.03 | MOL3 | O |
| ATOM | 11692 | N | VAL | H | 181 | −13.634 | −60.166 | 0.039 | 1.00 | 67.73 | MOL3 | N |
| ATOM | 11693 | CA | VAL | H | 181 | −13.546 | −61.607 | −0.064 | 1.00 | 71.50 | MOL3 | C |
| ATOM | 11694 | CB | VAL | H | 181 | −13.481 | −62.232 | 1.311 | 1.00 | 67.32 | MOL3 | C |
| ATOM | 11695 | CG1 | VAL | H | 181 | −14.678 | −61.799 | 2.120 | 1.00 | 70.09 | MOL3 | C |
| ATOM | 11696 | CG2 | VAL | H | 181 | −13.442 | −63.728 | 1.183 | 1.00 | 73.32 | MOL3 | C |
| ATOM | 11697 | C | VAL | H | 181 | −14.793 | −62.109 | −0.772 | 1.00 | 75.39 | MOL3 | C |
| ATOM | 11698 | O | VAL | H | 181 | −15.853 | −61.510 | −0.652 | 1.00 | 74.98 | MOL3 | O |
| ATOM | 11699 | N | LEU | H | 182 | −14.673 | −63.210 | −1.506 | 1.00 | 84.53 | MOL3 | N |
| ATOM | 11700 | CA | LEU | H | 182 | −15.817 | −63.741 | −2.239 | 1.00 | 93.08 | MOL3 | C |
| ATOM | 11701 | CB | LEU | H | 182 | −15.357 | −64.531 | −3.459 | 1.00 | 95.26 | MOL3 | C |
| ATOM | 11702 | CG | LEU | H | 182 | −16.452 | −64.746 | −4.503 | 1.00 | 94.65 | MOL3 | C |
| ATOM | 11703 | CD1 | LEU | H | 182 | −16.926 | −63.403 | −5.030 | 1.00 | 87.89 | MOL3 | C |
| ATOM | 11704 | CD2 | LEU | H | 182 | −15.907 | −65.600 | −5.638 | 1.00 | 99.72 | MOL3 | C |
| ATOM | 11705 | C | LEU | H | 182 | −16.718 | −64.621 | −1.394 | 1.00 | 98.95 | MOL3 | C |
| ATOM | 11706 | O | LEU | H | 182 | −16.340 | −65.727 | −1.011 | 1.00 | 100.71 | MOL3 | O |
| ATOM | 11707 | N | GLN | H | 183 | −17.919 | −64.120 | −1.119 | 1.00 | 104.61 | MOL3 | N |
| ATOM | 11708 | CA | GLN | H | 183 | −18.902 | −64.845 | −0.323 | 1.00 | 109.98 | MOL3 | C |
| ATOM | 11709 | CB | GLN | H | 183 | −19.488 | −63.922 | 0.745 | 1.00 | 115.13 | MOL3 | C |
| ATOM | 11710 | CG | GLN | H | 183 | −20.405 | −64.612 | 1.739 | 1.00 | 123.91 | MOL3 | C |
| ATOM | 11711 | CD | GLN | H | 183 | −20.898 | −63.669 | 2.828 | 1.00 | 127.70 | MOL3 | C |
| ATOM | 11712 | OE1 | GLN | H | 183 | −20.125 | −63.205 | 3.670 | 1.00 | 127.00 | MOL3 | O |
| ATOM | 11713 | NE2 | GLN | H | 183 | −22.193 | −63.378 | 2.810 | 1.00 | 131.46 | MOL3 | N |
| ATOM | 11714 | C | GLN | H | 183 | −20.009 | −65.357 | −1.239 | 1.00 | 111.46 | MOL3 | C |
| ATOM | 11715 | O | GLN | H | 183 | −21.092 | −64.765 | −1.333 | 1.00 | 107.91 | MOL3 | O |
| ATOM | 11716 | N | SER | H | 184 | −19.718 | −66.463 | −1.916 | 1.00 | 113.64 | MOL3 | N |
| ATOM | 11717 | CA | SER | H | 184 | −20.659 | −67.076 | −2.843 | 1.00 | 112.70 | MOL3 | C |
| ATOM | 11718 | CB | SER | H | 184 | −21.845 | −67.672 | −2.082 | 1.00 | 119.48 | MOL3 | C |
| ATOM | 11719 | OG | SER | H | 184 | −21.434 | −68.782 | −1.297 | 1.00 | 125.71 | MOL3 | O |
| ATOM | 11720 | C | SER | H | 184 | −21.151 | −66.077 | −3.880 | 1.00 | 107.75 | MOL3 | C |
| ATOM | 11721 | O | SER | H | 184 | −22.170 | −65.407 | −3.694 | 1.00 | 99.42 | MOL3 | O |
| ATOM | 11722 | N | ASP | H | 185 | −20.393 | −65.974 | −4.964 | 1.00 | 106.74 | MOL3 | N |
| ATOM | 11723 | CA | ASP | H | 185 | −20.723 | −65.089 | −6.068 | 1.00 | 104.66 | MOL3 | C |
| ATOM | 11724 | CB | ASP | H | 185 | −21.941 | −65.628 | −6.812 | 1.00 | 113.67 | MOL3 | C |
| ATOM | 11725 | CG | ASP | H | 185 | −21.725 | −67.025 | −7.340 | 1.00 | 121.58 | MOL3 | C |
| ATOM | 11726 | OD1 | ASP | H | 185 | −20.920 | −67.186 | −8.287 | 1.00 | 122.38 | MOL3 | O |
| ATOM | 11727 | OD2 | ASP | H | 185 | −22.361 | −67.958 | −6.798 | 1.00 | 126.77 | MOL3 | O |
| ATOM | 11728 | C | ASP | H | 185 | −21.015 | −63.662 | −5.650 | 1.00 | 99.48 | MOL3 | C |
| ATOM | 11729 | O | ASP | H | 185 | −21.866 | −63.016 | −6.251 | 1.00 | 97.47 | MOL3 | O |
| ATOM | 11730 | N | LEU | H | 186 | −20.336 | −63.175 | −4.618 | 1.00 | 93.59 | MOL3 | N |
| ATOM | 11731 | CA | LEU | H | 186 | −20.533 | −61.802 | −4.168 | 1.00 | 84.79 | MOL3 | C |
| ATOM | 11732 | CB | LEU | H | 186 | −21.903 | −61.626 | −3.510 | 1.00 | 82.33 | MOL3 | C |
| ATOM | 11733 | CG | LEU | H | 186 | −22.955 | −61.244 | −4.557 | 1.00 | 77.08 | MOL3 | C |
| ATOM | 11734 | CD1 | LEU | H | 186 | −24.166 | −60.555 | −3.938 | 1.00 | 73.45 | MOL3 | C |
| ATOM | 11735 | CD2 | LEU | H | 186 | −22.288 | −60.319 | −5.540 | 1.00 | 73.17 | MOL3 | C |
| ATOM | 11736 | C | LEU | H | 186 | −19.431 | −61.343 | −3.234 | 1.00 | 81.42 | MOL3 | C |
| ATOM | 11737 | O | LEU | H | 186 | −18.911 | −62.124 | −2.435 | 1.00 | 78.72 | MOL3 | O |
| ATOM | 11738 | N | TYR | H | 187 | −19.073 | −60.069 | −3.347 | 1.00 | 76.82 | MOL3 | N |
| ATOM | 11739 | CA | TYR | H | 187 | −18.006 | −59.521 | −2.531 | 1.00 | 75.32 | MOL3 | C |
| ATOM | 11740 | CB | TYR | H | 187 | −17.208 | −58.501 | −3.338 | 1.00 | 74.97 | MOL3 | C |
| ATOM | 11741 | CG | TYR | H | 187 | −16.436 | −59.113 | −4.485 | 1.00 | 80.55 | MOL3 | C |
| ATOM | 11742 | CD1 | TYR | H | 187 | −15.559 | −60.170 | −4.278 | 1.00 | 81.09 | MOL3 | C |
| ATOM | 11743 | CE1 | TYR | H | 187 | −14.826 | −60.716 | −5.334 | 1.00 | 83.98 | MOL3 | C |
| ATOM | 11744 | CD2 | TYR | H | 187 | −16.564 | −58.617 | −5.773 | 1.00 | 88.64 | MOL3 | C |
| ATOM | 11745 | CE2 | TYR | H | 187 | −15.833 | −59.154 | −6.834 | 1.00 | 90.45 | MOL3 | C |
| ATOM | 11746 | CZ | TYR | H | 187 | −14.967 | −60.199 | −6.608 | 1.00 | 86.86 | MOL3 | C |
| ATOM | 11747 | OH | TYR | H | 187 | −14.239 | −60.705 | −7.663 | 1.00 | 83.28 | MOL3 | O |
| ATOM | 11748 | C | TYR | H | 187 | −18.456 | −58.910 | −1.213 | 1.00 | 72.95 | MOL3 | C |
| ATOM | 11749 | O | TYR | H | 187 | −19.469 | −58.219 | −1.139 | 1.00 | 73.00 | MOL3 | O |
| ATOM | 11750 | N | THR | H | 188 | −17.687 | −59.190 | −0.170 | 1.00 | 70.13 | MOL3 | N |
| ATOM | 11751 | CA | THR | H | 188 | −17.957 | −58.678 | 1.159 | 1.00 | 69.86 | MOL3 | C |
| ATOM | 11752 | CB | THR | H | 188 | −18.489 | −59.749 | 2.095 | 1.00 | 71.98 | MOL3 | C |
| ATOM | 11753 | OG1 | THR | H | 188 | −19.758 | −60.210 | 1.626 | 1.00 | 81.84 | MOL3 | O |
| ATOM | 11754 | CG2 | THR | H | 188 | −18.627 | −59.190 | 3.500 | 1.00 | 71.01 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 11755 | C | THR | H | 188 | −16.653 | −58.216 | 1.755 | 1.00 | 71.41 | MOL3 | C |
|---|---|---|---|---|---|---|---|---|---|---|---|---|
| ATOM | 11756 | O | THR | H | 188 | −15.665 | −58.946 | 1.742 | 1.00 | 72.76 | MOL3 | O |
| ATOM | 11757 | N | LEU | H | 189 | −16.637 | −56.999 | 2.274 | 1.00 | 72.91 | MOL3 | N |
| ATOM | 11758 | CA | LEU | H | 189 | −15.428 | −56.497 | 2.901 | 1.00 | 69.76 | MOL3 | C |
| ATOM | 11759 | CB | LEU | H | 189 | −14.557 | −55.728 | 1.897 | 1.00 | 71.14 | MOL3 | C |
| ATOM | 11760 | CG | LEU | H | 189 | −14.614 | −54.206 | 1.799 | 1.00 | 70.24 | MOL3 | C |
| ATOM | 11761 | CD1 | LEU | H | 189 | −13.453 | −53.742 | 0.963 | 1.00 | 68.48 | MOL3 | C |
| ATOM | 11762 | CD2 | LEU | H | 189 | −15.911 | −53.755 | 1.185 | 1.00 | 73.49 | MOL3 | C |
| ATOM | 11763 | C | LEU | H | 189 | −15.781 | −55.637 | 4.106 | 1.00 | 65.92 | MOL3 | C |
| ATOM | 11764 | O | LEU | H | 189 | −16.892 | −55.114 | 4.230 | 1.00 | 62.95 | MOL3 | O |
| ATOM | 11765 | N | SER | H | 190 | −14.825 | −55.522 | 5.009 | 1.00 | 64.50 | MOL3 | N |
| ATOM | 11766 | CA | SER | H | 190 | −15.016 | −54.763 | 6.223 | 1.00 | 65.87 | MOL3 | C |
| ATOM | 11767 | CB | SER | H | 190 | −14.978 | −55.728 | 7.401 | 1.00 | 67.18 | MOL3 | C |
| ATOM | 11768 | OG | SER | H | 190 | −14.049 | −56.766 | 7.139 | 1.00 | 69.18 | MOL3 | O |
| ATOM | 11769 | C | SER | H | 190 | −13.930 | −53.706 | 6.364 | 1.00 | 63.60 | MOL3 | C |
| ATOM | 11770 | O | SER | H | 190 | −12.930 | −53.740 | 5.658 | 1.00 | 59.51 | MOL3 | O |
| ATOM | 11771 | N | SER | H | 191 | −14.138 | −52.746 | 7.255 | 1.00 | 62.63 | MOL3 | N |
| ATOM | 11772 | CA | SER | H | 191 | −13.134 | −51.720 | 7.478 | 1.00 | 61.36 | MOL3 | C |
| ATOM | 11773 | CB | SER | H | 191 | −13.231 | −50.600 | 6.447 | 1.00 | 60.89 | MOL3 | C |
| ATOM | 11774 | OG | SER | H | 191 | −12.151 | −49.692 | 6.610 | 1.00 | 57.18 | MOL3 | O |
| ATOM | 11775 | C | SER | H | 191 | −13.259 | −51.145 | 8.868 | 1.00 | 63.38 | MOL3 | C |
| ATOM | 11776 | O | SER | H | 191 | −14.319 | −50.661 | 9.269 | 1.00 | 66.85 | MOL3 | O |
| ATOM | 11777 | N | SER | H | 192 | −12.157 | −51.214 | 9.601 | 1.00 | 62.58 | MOL3 | N |
| ATOM | 11778 | CA | SER | H | 192 | −12.105 | −50.725 | 10.966 | 1.00 | 65.54 | MOL3 | C |
| ATOM | 11779 | CB | SER | H | 192 | −11.263 | −51.656 | 11.839 | 1.00 | 67.43 | MOL3 | C |
| ATOM | 11780 | OG | SER | H | 192 | −9.880 | −51.322 | 11.768 | 1.00 | 65.40 | MOL3 | O |
| ATOM | 11781 | C | SER | H | 192 | −11.463 | −49.358 | 11.011 | 1.00 | 66.13 | MOL3 | C |
| ATOM | 11782 | O | SER | H | 192 | −10.750 | −48.959 | 10.093 | 1.00 | 61.68 | MOL3 | O |
| ATOM | 11783 | N | VAL | H | 193 | −11.711 | −48.654 | 12.105 | 1.00 | 66.29 | MOL3 | N |
| ATOM | 11784 | CA | VAL | H | 193 | −11.132 | −47.347 | 12.308 | 1.00 | 66.18 | MOL3 | C |
| ATOM | 11785 | CB | VAL | H | 193 | −11.976 | −46.253 | 11.634 | 1.00 | 59.00 | MOL3 | C |
| ATOM | 11786 | CG1 | VAL | H | 193 | −13.341 | −46.189 | 12.248 | 1.00 | 58.84 | MOL3 | C |
| ATOM | 11787 | CG2 | VAL | H | 193 | −11.275 | −44.930 | 11.743 | 1.00 | 56.17 | MOL3 | C |
| ATOM | 11788 | C | VAL | H | 193 | −11.028 | −47.118 | 13.807 | 1.00 | 71.49 | MOL3 | C |
| ATOM | 11789 | O | VAL | H | 193 | −12.014 | −47.234 | 14.537 | 1.00 | 74.28 | MOL3 | O |
| ATOM | 11790 | N | THR | H | 194 | −9.815 | −46.834 | 14.266 | 1.00 | 75.90 | MOL3 | N |
| ATOM | 11791 | CA | THR | H | 194 | −9.570 | −46.597 | 15.676 | 1.00 | 81.76 | MOL3 | C |
| ATOM | 11792 | CB | THR | H | 194 | −8.189 | −47.107 | 16.078 | 1.00 | 85.55 | MOL3 | C |
| ATOM | 11793 | OG1 | THR | H | 194 | −7.636 | −47.885 | 15.008 | 1.00 | 91.67 | MOL3 | O |
| ATOM | 11794 | CG2 | THR | H | 194 | −8.297 | −47.973 | 17.321 | 1.00 | 90.42 | MOL3 | C |
| ATOM | 11795 | C | THR | H | 194 | −9.648 | −45.105 | 15.964 | 1.00 | 84.06 | MOL3 | C |
| ATOM | 11796 | O | THR | H | 194 | −9.429 | −44.275 | 15.082 | 1.00 | 83.35 | MOL3 | O |
| ATOM | 11797 | N | VAL | H | 195 | −9.963 | −44.761 | 17.203 | 1.00 | 85.63 | MOL3 | N |
| ATOM | 11798 | CA | VAL | H | 195 | −10.060 | −43.365 | 17.554 | 1.00 | 85.95 | MOL3 | C |
| ATOM | 11799 | CB | VAL | H | 195 | −11.229 | −42.722 | 16.805 | 1.00 | 85.68 | MOL3 | C |
| ATOM | 11800 | CG1 | VAL | H | 195 | −12.201 | −42.093 | 17.778 | 1.00 | 93.53 | MOL3 | C |
| ATOM | 11801 | CG2 | VAL | H | 195 | −10.685 | −41.702 | 15.817 | 1.00 | 84.12 | MOL3 | C |
| ATOM | 11802 | C | VAL | H | 195 | −10.181 | −43.173 | 19.059 | 1.00 | 86.70 | MOL3 | C |
| ATOM | 11803 | O | VAL | H | 195 | −10.650 | −44.052 | 19.778 | 1.00 | 89.05 | MOL3 | O |
| ATOM | 11804 | N | PRO | H | 196 | −9.711 | −42.028 | 19.556 | 1.00 | 85.09 | MOL3 | N |
| ATOM | 11805 | CD | PRO | H | 196 | −8.914 | −41.053 | 18.792 | 1.00 | 81.74 | MOL3 | C |
| ATOM | 11806 | CA | PRO | H | 196 | −9.741 | −41.684 | 20.975 | 1.00 | 87.98 | MOL3 | C |
| ATOM | 11807 | CB | PRO | H | 196 | −9.153 | −40.283 | 20.979 | 1.00 | 89.01 | MOL3 | C |
| ATOM | 11808 | CG | PRO | H | 196 | −8.128 | −40.370 | 19.868 | 1.00 | 81.01 | MOL3 | C |
| ATOM | 11809 | C | PRO | H | 196 | −11.137 | −41.754 | 21.589 | 1.00 | 91.71 | MOL3 | C |
| ATOM | 11810 | O | PRO | H | 196 | −12.067 | −41.134 | 21.090 | 1.00 | 87.25 | MOL3 | O |
| ATOM | 11811 | N | SER | H | 197 | −11.272 | −42.510 | 22.677 | 1.00 | 99.52 | MOL3 | N |
| ATOM | 11812 | CA | SER | H | 197 | −12.560 | −42.673 | 23.347 | 1.00 | 105.85 | MOL3 | C |
| ATOM | 11813 | CB | SER | H | 197 | −12.399 | −43.573 | 24.583 | 1.00 | 109.81 | MOL3 | C |
| ATOM | 11814 | OG | SER | H | 197 | −11.381 | −43.105 | 25.455 | 1.00 | 115.70 | MOL3 | O |
| ATOM | 11815 | C | SER | H | 197 | −13.215 | −41.343 | 23.727 | 1.00 | 107.60 | MOL3 | C |
| ATOM | 11816 | O | SER | H | 197 | −14.435 | −41.260 | 23.879 | 1.00 | 106.99 | MOL3 | O |
| ATOM | 11817 | N | SER | H | 198 | −12.400 | −40.303 | 23.866 | 1.00 | 110.77 | MOL3 | N |
| ATOM | 11818 | CA | SER | H | 198 | −12.899 | −38.978 | 24.212 | 1.00 | 114.47 | MOL3 | C |
| ATOM | 11819 | CB | SER | H | 198 | −11.738 | −38.098 | 24.702 | 1.00 | 116.99 | MOL3 | C |
| ATOM | 11820 | OG | SER | H | 198 | −10.649 | −38.104 | 23.787 | 1.00 | 113.97 | MOL3 | O |
| ATOM | 11821 | C | SER | H | 198 | −13.602 | −38.310 | 23.024 | 1.00 | 115.10 | MOL3 | C |
| ATOM | 11822 | O | SER | H | 198 | −14.495 | −37.478 | 23.210 | 1.00 | 115.84 | MOL3 | O |
| ATOM | 11823 | N | THR | H | 199 | −13.202 | −38.678 | 21.807 | 1.00 | 114.41 | MOL3 | N |
| ATOM | 11824 | CA | THR | H | 199 | −13.794 | −38.105 | 20.596 | 1.00 | 111.03 | MOL3 | C |
| ATOM | 11825 | CB | THR | H | 199 | −12.701 | −37.820 | 19.509 | 1.00 | 111.21 | MOL3 | C |
| ATOM | 11826 | OG1 | THR | H | 199 | −11.808 | −38.936 | 19.401 | 1.00 | 109.25 | MOL3 | O |
| ATOM | 11827 | CG2 | THR | H | 199 | −11.899 | −36.573 | 19.869 | 1.00 | 108.67 | MOL3 | C |
| ATOM | 11828 | C | THR | H | 199 | −14.911 | −38.974 | 20.001 | 1.00 | 107.63 | MOL3 | C |
| ATOM | 11829 | O | THR | H | 199 | −15.168 | −38.949 | 18.795 | 1.00 | 103.69 | MOL3 | O |
| ATOM | 11830 | N | TRP | H | 200 | −15.588 | −39.720 | 20.867 | 1.00 | 105.36 | MOL3 | N |
| ATOM | 11831 | CA | TRP | H | 200 | −16.668 | −40.593 | 20.442 | 1.00 | 105.42 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 11832 | CB  | TRP | H | 200 | −16.075 | −41.748 | 19.638 | 1.00 | 96.93  | MOL3 | C |
|------|-------|-----|-----|---|-----|---------|---------|--------|------|--------|------|---|
| ATOM | 11833 | CG  | TRP | H | 200 | −17.042 | −42.360 | 18.712 | 1.00 | 90.71  | MOL3 | C |
| ATOM | 11834 | CD2 | TRP | H | 200 | −17.876 | −43.490 | 18.973 | 1.00 | 85.74  | MOL3 | C |
| ATOM | 11835 | CE2 | TRP | H | 200 | −18.730 | −43.640 | 17.868 | 1.00 | 82.86  | MOL3 | C |
| ATOM | 11836 | CE3 | TRP | H | 200 | −17.988 | −44.386 | 20.038 | 1.00 | 83.28  | MOL3 | C |
| ATOM | 11837 | CD1 | TRP | H | 200 | −17.402 | −41.893 | 17.487 | 1.00 | 87.30  | MOL3 | C |
| ATOM | 11838 | NE1 | TRP | H | 200 | −18.418 | −42.653 | 16.971 | 1.00 | 81.12  | MOL3 | N |
| ATOM | 11839 | CZ2 | TRP | H | 200 | −19.688 | −44.647 | 17.798 | 1.00 | 81.11  | MOL3 | C |
| ATOM | 11840 | CZ3 | TRP | H | 200 | −18.937 | −45.383 | 19.966 | 1.00 | 80.41  | MOL3 | C |
| ATOM | 11841 | CH2 | TRP | H | 200 | −19.776 | −45.505 | 18.855 | 1.00 | 79.21  | MOL3 | C |
| ATOM | 11842 | C   | TRP | H | 200 | −17.400 | −41.125 | 21.679 | 1.00 | 112.10 | MOL3 | C |
| ATOM | 11843 | O   | TRP | H | 200 | −16.761 | −41.549 | 22.647 | 1.00 | 117.37 | MOL3 | O |
| ATOM | 11844 | N   | PRO | H | 201 | −18.747 | −41.110 | 21.669 | 1.00 | 115.94 | MOL3 | N |
| ATOM | 11845 | CD  | PRO | H | 201 | −19.546 | −41.871 | 22.643 | 1.00 | 119.58 | MOL3 | C |
| ATOM | 11846 | CA  | PRO | H | 201 | −19.605 | −40.629 | 20.580 | 1.00 | 115.85 | MOL3 | C |
| ATOM | 11847 | CB  | PRO | H | 201 | −20.974 | −41.219 | 20.918 | 1.00 | 116.63 | MOL3 | C |
| ATOM | 11848 | CG  | PRO | H | 201 | −20.650 | −42.406 | 21.773 | 1.00 | 119.92 | MOL3 | C |
| ATOM | 11849 | C   | PRO | H | 201 | −19.663 | −39.110 | 20.489 | 1.00 | 118.24 | MOL3 | C |
| ATOM | 11850 | O   | PRO | H | 201 | −20.463 | −38.567 | 19.728 | 1.00 | 117.69 | MOL3 | O |
| ATOM | 11851 | N   | SER | H | 202 | −18.823 | −38.431 | 21.268 | 1.00 | 122.15 | MOL3 | N |
| ATOM | 11852 | CA  | SER | H | 202 | −18.779 | −36.967 | 21.272 | 1.00 | 123.53 | MOL3 | C |
| ATOM | 11853 | CB  | SER | H | 202 | −17.489 | −36.472 | 21.945 | 1.00 | 127.01 | MOL3 | C |
| ATOM | 11854 | OG  | SER | H | 202 | −16.332 | −36.884 | 21.238 | 1.00 | 131.60 | MOL3 | O |
| ATOM | 11855 | C   | SER | H | 202 | −18.886 | −36.409 | 19.852 | 1.00 | 121.08 | MOL3 | C |
| ATOM | 11856 | O   | SER | H | 202 | −19.941 | −35.914 | 19.456 | 1.00 | 117.79 | MOL3 | O |
| ATOM | 11857 | N   | GLU | H | 203 | −17.796 | −36.485 | 19.094 | 1.00 | 121.18 | MOL3 | N |
| ATOM | 11858 | CA  | GLU | H | 203 | −17.798 | −36.009 | 17.718 | 1.00 | 123.42 | MOL3 | C |
| ATOM | 11859 | CB  | GLU | H | 203 | −16.361 | −35.814 | 17.220 | 1.00 | 122.49 | MOL3 | C |
| ATOM | 11860 | CG  | GLU | H | 203 | −15.491 | −34.967 | 18.151 | 1.00 | 124.92 | MOL3 | C |
| ATOM | 11861 | CD  | GLU | H | 203 | −14.166 | −34.537 | 17.521 | 1.00 | 127.78 | MOL3 | C |
| ATOM | 11862 | OE1 | GLU | H | 203 | −13.260 | −34.104 | 18.272 | 1.00 | 127.29 | MOL3 | O |
| ATOM | 11863 | OE2 | GLU | H | 203 | −14.032 | −34.618 | 16.279 | 1.00 | 125.44 | MOL3 | O |
| ATOM | 11864 | C   | GLU | H | 203 | −18.517 | −37.078 | 16.893 | 1.00 | 124.67 | MOL3 | C |
| ATOM | 11865 | O   | GLU | H | 203 | −19.105 | −38.000 | 17.461 | 1.00 | 126.60 | MOL3 | O |
| ATOM | 11866 | N   | THR | H | 204 | −18.470 | −36.970 | 15.567 | 1.00 | 124.07 | MOL3 | N |
| ATOM | 11867 | CA  | THR | H | 204 | −19.149 | −37.940 | 14.706 | 1.00 | 120.80 | MOL3 | C |
| ATOM | 11868 | CB  | THR | H | 204 | −20.148 | −37.250 | 13.752 | 1.00 | 123.11 | MOL3 | C |
| ATOM | 11869 | OG1 | THR | H | 204 | −19.461 | −36.838 | 12.560 | 1.00 | 121.90 | MOL3 | O |
| ATOM | 11870 | CG2 | THR | H | 204 | −20.766 | −36.019 | 14.418 | 1.00 | 126.15 | MOL3 | C |
| ATOM | 11871 | C   | THR | H | 204 | −18.199 | −38.740 | 13.826 | 1.00 | 115.81 | MOL3 | C |
| ATOM | 11872 | O   | THR | H | 204 | −17.145 | −38.251 | 13.422 | 1.00 | 115.78 | MOL3 | O |
| ATOM | 11873 | N   | VAL | H | 205 | −18.589 | −39.974 | 13.528 | 1.00 | 109.46 | MOL3 | N |
| ATOM | 11874 | CA  | VAL | H | 205 | −17.804 | −40.839 | 12.661 | 1.00 | 102.80 | MOL3 | C |
| ATOM | 11875 | CB  | VAL | H | 205 | −17.070 | −41.924 | 13.433 | 1.00 | 98.37  | MOL3 | C |
| ATOM | 11876 | CG1 | VAL | H | 205 | −16.167 | −42.689 | 12.492 | 1.00 | 94.03  | MOL3 | C |
| ATOM | 11877 | CG2 | VAL | H | 205 | −16.271 | −41.310 | 14.548 | 1.00 | 101.45 | MOL3 | C |
| ATOM | 11878 | C   | VAL | H | 205 | −18.760 | −41.507 | 11.691 | 1.00 | 103.28 | MOL3 | C |
| ATOM | 11879 | O   | VAL | H | 205 | −19.759 | −42.109 | 12.102 | 1.00 | 106.02 | MOL3 | O |
| ATOM | 11880 | N   | THR | H | 206 | −18.461 | −41.394 | 10.402 | 1.00 | 101.05 | MOL3 | N |
| ATOM | 11881 | CA  | THR | H | 206 | −19.324 | −41.978 | 9.385  | 1.00 | 98.75  | MOL3 | C |
| ATOM | 11882 | CB  | THR | H | 206 | −20.147 | −40.896 | 8.651  | 1.00 | 101.71 | MOL3 | C |
| ATOM | 11883 | OG1 | THR | H | 206 | −20.732 | −39.998 | 9.601  | 1.00 | 104.93 | MOL3 | O |
| ATOM | 11884 | CG2 | THR | H | 206 | −21.261 | −41.546 | 7.846  | 1.00 | 105.24 | MOL3 | C |
| ATOM | 11885 | C   | THR | H | 206 | −18.558 | −42.761 | 8.330  | 1.00 | 92.67  | MOL3 | C |
| ATOM | 11886 | O   | THR | H | 206 | −17.455 | −42.401 | 7.932  | 1.00 | 84.29  | MOL3 | O |
| ATOM | 11887 | N   | CYS | H | 207 | −19.166 | −43.843 | 7.876  | 1.00 | 90.17  | MOL3 | N |
| ATOM | 11888 | CA  | CYS | H | 207 | −18.561 | −44.670 | 6.863  | 1.00 | 85.84  | MOL3 | C |
| ATOM | 11889 | C   | CYS | H | 207 | −18.945 | −44.075 | 5.523  | 1.00 | 87.41  | MOL3 | C |
| ATOM | 11890 | O   | CYS | H | 207 | −20.063 | −43.574 | 5.358  | 1.00 | 93.47  | MOL3 | O |
| ATOM | 11891 | CB  | CYS | H | 207 | −19.093 | −46.079 | 6.974  | 1.00 | 84.82  | MOL3 | C |
| ATOM | 11892 | SG  | CYS | H | 207 | −18.122 | −47.253 | 6.011  | 1.00 | 91.88  | MOL3 | S |
| ATOM | 11893 | N   | ASN | H | 208 | −18.022 | −44.124 | 4.568  | 1.00 | 83.21  | MOL3 | N |
| ATOM | 11894 | CA  | ASN | H | 208 | −18.252 | −43.571 | 3.229  | 1.00 | 81.80  | MOL3 | C |
| ATOM | 11895 | CB  | ASN | H | 208 | −17.236 | −42.461 | 2.910  | 1.00 | 77.24  | MOL3 | C |
| ATOM | 11896 | CG  | ASN | H | 208 | −17.573 | −41.133 | 3.562  | 1.00 | 74.85  | MOL3 | C |
| ATOM | 11897 | OD1 | ASN | H | 208 | −18.664 | −40.600 | 3.388  | 1.00 | 76.94  | MOL3 | O |
| ATOM | 11898 | ND2 | ASN | H | 208 | −16.625 | −40.585 | 4.303  | 1.00 | 69.62  | MOL3 | N |
| ATOM | 11899 | C   | ASN | H | 208 | −18.094 | −44.635 | 2.156  | 1.00 | 81.06  | MOL3 | C |
| ATOM | 11900 | O   | ASN | H | 208 | −17.074 | −44.667 | 1.474  | 1.00 | 78.69  | MOL3 | O |
| ATOM | 11901 | N   | VAL | H | 209 | −19.087 | −45.496 | 1.981  | 1.00 | 83.28  | MOL3 | N |
| ATOM | 11902 | CA  | VAL | H | 209 | −18.958 | −46.533 | 0.966  | 1.00 | 80.87  | MOL3 | C |
| ATOM | 11903 | CB  | VAL | H | 209 | −19.731 | −47.810 | 1.351  | 1.00 | 85.63  | MOL3 | C |
| ATOM | 11904 | CG1 | VAL | H | 209 | −19.229 | −48.983 | 0.524  | 1.00 | 79.18  | MOL3 | C |
| ATOM | 11905 | CG2 | VAL | H | 209 | −19.563 | −48.093 | 2.842  | 1.00 | 82.07  | MOL3 | C |
| ATOM | 11906 | C   | VAL | H | 209 | −19.414 | −46.036 | −0.395 | 1.00 | 78.89  | MOL3 | C |
| ATOM | 11907 | O   | VAL | H | 209 | −20.415 | −45.318 | −0.518 | 1.00 | 81.76  | MOL3 | O |
| ATOM | 11908 | N   | ALA | H | 210 | −18.665 | −46.428 | −1.417 | 1.00 | 75.82  | MOL3 | N |

TABLE 1-continued

The atomic coordinates of IL17F in complex with 496 Fab
(H32; a = 189.4; b = 189.4; c = 490.9, α, β = 90°; γ = 120°)

| ATOM | 11909 | CA | ALA | H | 210 | −18.940 | −46.001 | −2.784 | 1.00 | 81.55 | MOL3 | C |
|---|---|---|---|---|---|---|---|---|---|---|---|---|
| ATOM | 11910 | CB | ALA | H | 210 | −17.986 | −44.886 | −3.147 | 1.00 | 78.92 | MOL3 | C |
| ATOM | 11911 | C | ALA | H | 210 | −18.810 | −47.121 | −3.815 | 1.00 | 83.84 | MOL3 | C |
| ATOM | 11912 | O | ALA | H | 210 | −17.757 | −47.752 | −3.906 | 1.00 | 80.91 | MOL3 | O |
| ATOM | 11913 | N | HIS | H | 211 | −19.862 | −47.360 | −4.601 | 1.00 | 86.08 | MOL3 | N |
| ATOM | 11914 | CA | HIS | H | 211 | −19.795 | −48.397 | −5.624 | 1.00 | 84.97 | MOL3 | C |
| ATOM | 11915 | CB | HIS | H | 211 | −20.796 | −49.509 | −5.405 | 1.00 | 80.26 | MOL3 | C |
| ATOM | 11916 | CG | HIS | H | 211 | −20.470 | −50.742 | −6.181 | 1.00 | 73.85 | MOL3 | C |
| ATOM | 11917 | CD2 | HIS | H | 211 | −19.278 | −51.271 | −6.540 | 1.00 | 72.72 | MOL3 | C |
| ATOM | 11918 | ND1 | HIS | H | 211 | −21.428 | −51.632 | −6.610 | 1.00 | 76.06 | MOL3 | N |
| ATOM | 11919 | CE1 | HIS | H | 211 | −20.841 | −52.662 | −7.193 | 1.00 | 70.05 | MOL3 | C |
| ATOM | 11920 | NE2 | HIS | H | 211 | −19.536 | −52.468 | −7.162 | 1.00 | 68.29 | MOL3 | N |
| ATOM | 11921 | C | HIS | H | 211 | −20.037 | −47.842 | −7.004 | 1.00 | 89.60 | MOL3 | C |
| ATOM | 11922 | O | HIS | H | 211 | −21.178 | −47.650 | −7.421 | 1.00 | 93.26 | MOL3 | O |
| ATOM | 11923 | N | PRO | H | 212 | −18.951 | −47.601 | −7.746 | 1.00 | 93.11 | MOL3 | N |
| ATOM | 11924 | CD | PRO | H | 212 | −17.573 | −47.920 | −7.339 | 1.00 | 92.68 | MOL3 | C |
| ATOM | 11925 | CA | PRO | H | 212 | −18.967 | −47.062 | −9.107 | 1.00 | 91.18 | MOL3 | C |
| ATOM | 11926 | CB | PRO | H | 212 | −17.500 | −47.090 | −9.509 | 1.00 | 87.71 | MOL3 | C |
| ATOM | 11927 | CG | PRO | H | 212 | −16.782 | −46.993 | −8.207 | 1.00 | 89.67 | MOL3 | C |
| ATOM | 11928 | C | PRO | H | 212 | −19.798 | −47.904 | −10.054 | 1.00 | 90.13 | MOL3 | C |
| ATOM | 11929 | O | PRO | H | 212 | −20.741 | −47.424 | −10.668 | 1.00 | 89.72 | MOL3 | O |
| ATOM | 11930 | N | ALA | H | 213 | −19.431 | −49.169 | −10.174 | 1.00 | 90.84 | MOL3 | N |
| ATOM | 11931 | CA | ALA | H | 213 | −20.136 | −50.076 | −11.062 | 1.00 | 92.12 | MOL3 | C |
| ATOM | 11932 | CB | ALA | H | 213 | −19.669 | −51.499 | −10.822 | 1.00 | 92.89 | MOL3 | C |
| ATOM | 11933 | C | ALA | H | 213 | −21.655 | −49.994 | −10.942 | 1.00 | 94.00 | MOL3 | C |
| ATOM | 11934 | O | ALA | H | 213 | −22.368 | −50.327 | −11.882 | 1.00 | 94.47 | MOL3 | O |
| ATOM | 11935 | N | SER | H | 214 | −22.145 | −49.544 | −9.791 | 1.00 | 95.58 | MOL3 | N |
| ATOM | 11936 | CA | SER | H | 214 | −23.580 | −49.427 | −9.553 | 1.00 | 93.94 | MOL3 | C |
| ATOM | 11937 | CB | SER | H | 214 | −23.965 | −50.266 | −8.343 | 1.00 | 93.75 | MOL3 | C |
| ATOM | 11938 | OG | SER | H | 214 | −23.219 | −49.865 | −7.205 | 1.00 | 89.83 | MOL3 | O |
| ATOM | 11939 | C | SER | H | 214 | −23.949 | −47.980 | −9.290 | 1.00 | 95.88 | MOL3 | C |
| ATOM | 11940 | O | SER | H | 214 | −25.095 | −47.665 | −8.984 | 1.00 | 100.11 | MOL3 | O |
| ATOM | 11941 | N | SER | H | 215 | −22.960 | −47.104 | −9.403 | 1.00 | 97.87 | MOL3 | N |
| ATOM | 11942 | CA | SER | H | 215 | −23.143 | −45.680 | −9.167 | 1.00 | 99.24 | MOL3 | C |
| ATOM | 11943 | CB | SER | H | 215 | −23.980 | −45.070 | −10.284 | 1.00 | 98.78 | MOL3 | C |
| ATOM | 11944 | OG | SER | H | 215 | −23.278 | −45.147 | −11.514 | 1.00 | 102.48 | MOL3 | O |
| ATOM | 11945 | C | SER | H | 215 | −23.767 | −45.381 | −7.812 | 1.00 | 99.58 | MOL3 | C |
| ATOM | 11946 | O | SER | H | 215 | −24.384 | −44.337 | −7.628 | 1.00 | 102.78 | MOL3 | O |
| ATOM | 11947 | N | THR | H | 216 | −23.587 | −46.300 | −6.867 | 1.00 | 97.10 | MOL3 | N |
| ATOM | 11948 | CA | THR | H | 216 | −24.111 | −46.145 | −5.520 | 1.00 | 93.31 | MOL3 | C |
| ATOM | 11949 | CB | THR | H | 216 | −24.374 | −47.504 | −4.881 | 1.00 | 92.04 | MOL3 | C |
| ATOM | 11950 | OG1 | THR | H | 216 | −24.966 | −48.378 | −5.846 | 1.00 | 88.94 | MOL3 | O |
| ATOM | 11951 | CG2 | THR | H | 216 | −25.316 | −47.360 | −3.698 | 1.00 | 97.81 | MOL3 | C |
| ATOM | 11952 | C | THR | H | 216 | −23.050 | −45.432 | −4.690 | 1.00 | 93.44 | MOL3 | C |
| ATOM | 11953 | O | THR | H | 216 | −21.868 | −45.500 | −5.008 | 1.00 | 89.78 | MOL3 | O |
| ATOM | 11954 | N | LYS | H | 217 | −23.469 | −44.742 | −3.634 | 1.00 | 93.38 | MOL3 | N |
| ATOM | 11955 | CA | LYS | H | 217 | −22.530 | −44.043 | −2.768 | 1.00 | 88.95 | MOL3 | C |
| ATOM | 11956 | CB | LYS | H | 217 | −22.073 | −42.741 | −3.428 | 1.00 | 85.95 | MOL3 | C |
| ATOM | 11957 | CG | LYS | H | 217 | −20.668 | −42.287 | −3.026 | 1.00 | 90.47 | MOL3 | C |
| ATOM | 11958 | CD | LYS | H | 217 | −20.061 | −41.264 | −4.023 | 1.00 | 95.55 | MOL3 | C |
| ATOM | 11959 | CE | LYS | H | 217 | −20.843 | −39.935 | −4.065 | 1.00 | 98.10 | MOL3 | C |
| ATOM | 11960 | NZ | LYS | H | 217 | −20.382 | −38.979 | −5.126 | 1.00 | 90.44 | MOL3 | N |
| ATOM | 11961 | C | LYS | H | 217 | −23.224 | −43.792 | −1.437 | 1.00 | 89.96 | MOL3 | C |
| ATOM | 11962 | O | LYS | H | 217 | −23.720 | −42.706 | −1.156 | 1.00 | 93.10 | MOL3 | O |
| ATOM | 11963 | N | VAL | H | 218 | −23.231 | −44.843 | −0.629 | 1.00 | 88.84 | MOL3 | N |
| ATOM | 11964 | CA | VAL | H | 218 | −23.858 | −44.902 | 0.688 | 1.00 | 87.90 | MOL3 | C |
| ATOM | 11965 | CB | VAL | H | 218 | −24.147 | −46.359 | 1.010 | 1.00 | 88.66 | MOL3 | C |
| ATOM | 11966 | CG1 | VAL | H | 218 | −25.423 | −46.487 | 1.817 | 1.00 | 95.34 | MOL3 | C |
| ATOM | 11967 | CG2 | VAL | H | 218 | −24.190 | −47.156 | −0.288 | 1.00 | 89.64 | MOL3 | C |
| ATOM | 11968 | C | VAL | H | 218 | −23.005 | −44.391 | 1.837 | 1.00 | 84.78 | MOL3 | C |
| ATOM | 11969 | O | VAL | H | 218 | −21.827 | −44.695 | 1.893 | 1.00 | 80.97 | MOL3 | O |
| ATOM | 11970 | N | ASP | H | 219 | −23.600 | −43.640 | 2.759 | 1.00 | 86.47 | MOL3 | N |
| ATOM | 11971 | CA | ASP | H | 219 | −22.878 | −43.158 | 3.935 | 1.00 | 90.23 | MOL3 | C |
| ATOM | 11972 | CB | ASP | H | 219 | −22.793 | −41.633 | 3.970 | 1.00 | 95.17 | MOL3 | C |
| ATOM | 11973 | CG | ASP | H | 219 | −21.793 | −41.082 | 2.968 | 1.00 | 102.60 | MOL3 | C |
| ATOM | 11974 | OD1 | ASP | H | 219 | −20.742 | −41.732 | 2.788 | 1.00 | 104.56 | MOL3 | O |
| ATOM | 11975 | OD2 | ASP | H | 219 | −22.043 | −40.004 | 2.373 | 1.00 | 102.34 | MOL3 | O |
| ATOM | 11976 | C | ASP | H | 219 | −23.655 | −43.651 | 5.132 | 1.00 | 92.51 | MOL3 | C |
| ATOM | 11977 | O | ASP | H | 219 | −24.871 | −43.495 | 5.180 | 1.00 | 99.15 | MOL3 | O |
| ATOM | 11978 | N | LYS | H | 220 | −22.962 | −44.261 | 6.089 | 1.00 | 92.41 | MOL3 | N |
| ATOM | 11979 | CA | LYS | H | 220 | −23.622 | −44.796 | 7.275 | 1.00 | 93.36 | MOL3 | C |
| ATOM | 11980 | CB | LYS | H | 220 | −23.543 | −46.333 | 7.260 | 1.00 | 84.54 | MOL3 | C |
| ATOM | 11981 | CG | LYS | H | 220 | −24.734 | −47.055 | 7.914 | 1.00 | 81.35 | MOL3 | C |
| ATOM | 11982 | CD | LYS | H | 220 | −25.977 | −47.143 | 7.015 | 1.00 | 75.68 | MOL3 | C |
| ATOM | 11983 | CE | LYS | H | 220 | −25.735 | −48.051 | 5.800 | 1.00 | 87.50 | MOL3 | C |
| ATOM | 11984 | NZ | LYS | H | 220 | −26.946 | −48.477 | 4.992 | 1.00 | 88.31 | MOL3 | N |
| ATOM | 11985 | C | LYS | H | 220 | −22.944 | −44.228 | 8.521 | 1.00 | 94.15 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 11986 | O   | LYS | H | 220 | −21.753 | −44.423 | 8.725   | 1.00 | 91.61  | MOL3 | O |
|------|-------|-----|-----|---|-----|---------|---------|---------|------|--------|------|---|
| ATOM | 11987 | N   | LYS | H | 221 | −23.693 | −43.500 | 9.343   | 1.00 | 96.99  | MOL3 | N |
| ATOM | 11988 | CA  | LYS | H | 221 | −23.106 | −42.934 | 10.545  | 1.00 | 95.18  | MOL3 | C |
| ATOM | 11989 | CB  | LYS | H | 221 | −23.928 | −41.739 | 11.040  | 1.00 | 98.20  | MOL3 | C |
| ATOM | 11990 | CG  | LYS | H | 221 | −23.304 | −41.018 | 12.223  | 1.00 | 101.59 | MOL3 | C |
| ATOM | 11991 | CD  | LYS | H | 221 | −24.228 | −39.946 | 12.803  | 1.00 | 105.32 | MOL3 | C |
| ATOM | 11992 | CE  | LYS | H | 221 | −24.359 | −38.736 | 11.884  | 1.00 | 107.02 | MOL3 | C |
| ATOM | 11993 | NZ  | LYS | H | 221 | −25.213 | −37.656 | 12.475  | 1.00 | 101.78 | MOL3 | N |
| ATOM | 11994 | C   | LYS | H | 221 | −23.036 | −44.027 | 11.600  | 1.00 | 93.02  | MOL3 | C |
| ATOM | 11995 | O   | LYS | H | 221 | −23.934 | −44.873 | 11.704  | 1.00 | 91.92  | MOL3 | O |
| ATOM | 11996 | N   | ILE | H | 222 | −21.955 | −44.022 | 12.368  | 1.00 | 89.58  | MOL3 | N |
| ATOM | 11997 | CA  | ILE | H | 222 | −21.774 | −45.030 | 13.400  | 1.00 | 88.34  | MOL3 | C |
| ATOM | 11998 | CB  | ILE | H | 222 | −20.288 | −45.415 | 13.580  | 1.00 | 83.38  | MOL3 | C |
| ATOM | 11999 | CG2 | ILE | H | 222 | −20.164 | −46.498 | 14.621  | 1.00 | 84.72  | MOL3 | C |
| ATOM | 12000 | CG1 | ILE | H | 222 | −19.715 | −45.965 | 12.280  | 1.00 | 78.50  | MOL3 | C |
| ATOM | 12001 | CD1 | ILE | H | 222 | −19.672 | −44.965 | 11.171  | 1.00 | 84.43  | MOL3 | C |
| ATOM | 12002 | C   | ILE | H | 222 | −22.311 | −44.550 | 14.734  | 1.00 | 86.50  | MOL3 | C |
| ATOM | 12003 | O   | ILE | H | 222 | −21.734 | −43.681 | 15.365  | 1.00 | 82.24  | MOL3 | O |
| ATOM | 12004 | N   | VAL | H | 223 | −23.432 | −45.113 | 15.156  | 1.00 | 90.57  | MOL3 | N |
| ATOM | 12005 | CA  | VAL | H | 223 | −24.008 | −44.728 | 16.427  | 1.00 | 95.46  | MOL3 | C |
| ATOM | 12006 | CB  | VAL | H | 223 | −25.396 | −44.102 | 16.256  | 1.00 | 91.96  | MOL3 | C |
| ATOM | 12007 | CG1 | VAL | H | 223 | −25.266 | −42.793 | 15.504  | 1.00 | 88.47  | MOL3 | C |
| ATOM | 12008 | CG2 | VAL | H | 223 | −26.318 | −45.063 | 15.529  | 1.00 | 92.22  | MOL3 | C |
| ATOM | 12009 | C   | VAL | H | 223 | −24.086 | −45.928 | 17.349  | 1.00 | 100.28 | MOL3 | C |
| ATOM | 12010 | O   | VAL | H | 223 | −24.399 | −47.046 | 16.928  | 1.00 | 105.28 | MOL3 | O |
| ATOM | 12011 | N   | PRO | H | 224 | −23.784 | −45.704 | 18.629  | 1.00 | 99.26  | MOL3 | N |
| ATOM | 12012 | CD  | PRO | H | 224 | −23.449 | −44.354 | 19.105  | 1.00 | 92.15  | MOL3 | C |
| ATOM | 12013 | CA  | PRO | H | 224 | −23.766 | −46.665 | 19.730  | 1.00 | 102.86 | MOL3 | C |
| ATOM | 12014 | CB  | PRO | H | 224 | −23.245 | −45.828 | 20.882  | 1.00 | 100.47 | MOL3 | C |
| ATOM | 12015 | CG  | PRO | H | 224 | −23.768 | −44.457 | 20.544  | 1.00 | 94.92  | MOL3 | C |
| ATOM | 12016 | C   | PRO | H | 224 | −25.101 | −47.313 | 20.057  | 1.00 | 109.86 | MOL3 | C |
| ATOM | 12017 | O   | PRO | H | 224 | −26.122 | −46.990 | 19.459  | 1.00 | 111.11 | MOL3 | O |
| ATOM | 12018 | N   | ARG | H | 225 | −25.080 | −48.245 | 21.002  | 1.00 | 119.34 | MOL3 | N |
| ATOM | 12019 | CA  | ARG | H | 225 | −26.306 | −48.904 | 21.437  | 1.00 | 129.90 | MOL3 | C |
| ATOM | 12020 | CB  | ARG | H | 225 | −26.143 | −50.422 | 21.468  | 1.00 | 127.38 | MOL3 | C |
| ATOM | 12021 | CG  | ARG | H | 225 | −26.052 | −51.065 | 20.101  | 1.00 | 117.97 | MOL3 | C |
| ATOM | 12022 | CD  | ARG | H | 225 | −24.671 | −50.923 | 19.513  | 1.00 | 107.99 | MOL3 | C |
| ATOM | 12023 | NE  | ARG | H | 225 | −24.461 | −51.902 | 18.450  | 1.00 | 107.59 | MOL3 | N |
| ATOM | 12024 | CZ  | ARG | H | 225 | −24.624 | −53.215 | 18.595  | 1.00 | 103.80 | MOL3 | C |
| ATOM | 12025 | NH1 | ARG | H | 225 | −24.405 | −54.031 | 17.570  | 1.00 | 101.69 | MOL3 | N |
| ATOM | 12026 | NH2 | ARG | H | 225 | −25.010 | −53.715 | 19.763  | 1.00 | 101.56 | MOL3 | N |
| ATOM | 12027 | C   | ARG | H | 225 | −26.687 | −48.382 | 22.825  | 1.00 | 138.98 | MOL3 | C |
| ATOM | 12028 | O   | ARG | H | 225 | −25.836 | −47.869 | 23.562  | 1.00 | 138.90 | MOL3 | O |
| ATOM | 12029 | N   | ASP | H | 226 | −27.964 | −48.513 | 23.176  | 1.00 | 148.18 | MOL3 | N |
| ATOM | 12030 | CA  | ASP | H | 226 | −28.457 | −48.017 | 24.461  | 1.00 | 156.78 | MOL3 | C |
| ATOM | 12031 | CB  | ASP | H | 226 | −29.974 | −47.765 | 24.378  | 1.00 | 157.84 | MOL3 | C |
| ATOM | 12032 | CG  | ASP | H | 226 | −30.340 | −46.675 | 23.370  | 1.00 | 158.63 | MOL3 | C |
| ATOM | 12033 | OD1 | ASP | H | 226 | −31.513 | −46.239 | 23.362  | 1.00 | 157.41 | MOL3 | O |
| ATOM | 12034 | OD2 | ASP | H | 226 | −29.461 | −46.256 | 22.584  | 1.00 | 157.97 | MOL3 | O |
| ATOM | 12035 | C   | ASP | H | 226 | −28.140 | −48.882 | 25.691  | 1.00 | 160.96 | MOL3 | C |
| ATOM | 12036 | O   | ASP | H | 226 | −27.022 | −48.852 | 26.213  | 1.00 | 160.25 | MOL3 | O |
| ATOM | 12037 | N   | CYS | H | 227 | −29.129 | −49.638 | 26.158  | 1.00 | 167.01 | MOL3 | N |
| ATOM | 12038 | CA  | CYS | H | 227 | −28.954 | −50.485 | 27.333  | 1.00 | 172.77 | MOL3 | C |
| ATOM | 12039 | CB  | CYS | H | 227 | −30.325 | −50.765 | 27.988  | 1.00 | 176.72 | MOL3 | C |
| ATOM | 12040 | SG  | CYS | H | 227 | −31.668 | −51.545 | 27.040  | 1.00 | 183.08 | MOL3 | S |
| ATOM | 12041 | C   | CYS | H | 227 | −28.199 | −51.789 | 27.059  | 1.00 | 174.15 | MOL3 | C |
| ATOM | 12042 | O   | CYS | H | 227 | −27.700 | −51.958 | 25.921  | 1.00 | 174.94 | MOL3 | O |
| ATOM | 12043 | OXT | CYS | H | 227 | −28.104 | −52.618 | 27.995  | 1.00 | 175.28 | MOL3 | O |
| ATOM | 12044 | CB  | GLU | I | 15  | 28.076  | −18.463 | −10.237 | 1.00 | 162.95 | MOL3 | C |
| ATOM | 12045 | CG  | GLU | I | 15  | 27.674  | −18.794 | −8.792  | 1.00 | 163.87 | MOL3 | C |
| ATOM | 12046 | CD  | GLU | I | 15  | 27.343  | −17.564 | −7.955  | 1.00 | 163.49 | MOL3 | C |
| ATOM | 12047 | OE1 | GLU | I | 15  | 28.222  | −16.684 | −7.824  | 1.00 | 162.41 | MOL3 | O |
| ATOM | 12048 | OE2 | GLU | I | 15  | 26.212  | −17.481 | −7.421  | 1.00 | 160.36 | MOL3 | O |
| ATOM | 12049 | C   | GLU | I | 15  | 26.323  | −16.749 | −10.849 | 1.00 | 163.75 | MOL3 | C |
| ATOM | 12050 | O   | GLU | I | 15  | 25.252  | −16.652 | −10.243 | 1.00 | 163.46 | MOL3 | O |
| ATOM | 12051 | N   | GLU | I | 15  | 27.404  | −18.150 | −12.598 | 1.00 | 161.12 | MOL3 | N |
| ATOM | 12052 | CA  | GLU | I | 15  | 26.915  | −18.125 | −11.188 | 1.00 | 163.21 | MOL3 | C |
| ATOM | 12053 | N   | SER | I | 16  | 27.020  | −15.693 | −11.262 | 1.00 | 163.58 | MOL3 | N |
| ATOM | 12054 | CA  | SER | I | 16  | 26.593  | −14.319 | −11.009 | 1.00 | 162.86 | MOL3 | C |
| ATOM | 12055 | CB  | SER | I | 16  | 27.451  | −13.714 | −9.892  | 1.00 | 160.63 | MOL3 | C |
| ATOM | 12056 | OG  | SER | I | 16  | 27.167  | −12.339 | −9.700  | 1.00 | 158.49 | MOL3 | O |
| ATOM | 12057 | C   | SER | I | 16  | 26.702  | −13.445 | −12.264 | 1.00 | 164.09 | MOL3 | C |
| ATOM | 12058 | O   | SER | I | 16  | 26.070  | −12.390 | −12.351 | 1.00 | 164.62 | MOL3 | O |
| ATOM | 12059 | N   | CYS | I | 17  | 27.503  | −13.895 | −13.229 | 1.00 | 165.88 | MOL3 | N |
| ATOM | 12060 | CA  | CYS | I | 17  | 27.723  | −13.155 | −14.476 | 1.00 | 168.09 | MOL3 | C |
| ATOM | 12061 | C   | CYS | I | 17  | 26.405  | −12.749 | −15.143 | 1.00 | 169.75 | MOL3 | C |
| ATOM | 12062 | O   | CYS | I | 17  | 25.363  | −13.364 | −14.911 | 1.00 | 168.23 | MOL3 | O |

TABLE 1-continued

The atomic coordinates of IL17F in complex with 496 Fab
(H32; a = 189.4; b = 189.4; c = 490.9, α, β = 90°; γ = 120°)

| ATOM | 12063 | CB  | CYS | I | 17 | 28.543 | −13.991 | −15.488 | 1.00 | 168.90 | MOL3 | C |
|------|-------|-----|-----|---|----|--------|---------|---------|------|--------|------|---|
| ATOM | 12064 | SG  | CYS | I | 17 | 29.769 | −15.216 | −14.875 | 1.00 | 172.29 | MOL3 | S |
| ATOM | 12065 | N   | PRO | I | 18 | 26.441 | −11.695 | −15.981 | 1.00 | 173.94 | MOL3 | N |
| ATOM | 12066 | CD  | PRO | I | 18 | 27.604 | −10.809 | −16.170 | 1.00 | 175.68 | MOL3 | C |
| ATOM | 12067 | CA  | PRO | I | 18 | 25.272 | −11.177 | −16.707 | 1.00 | 176.27 | MOL3 | C |
| ATOM | 12068 | CB  | PRO | I | 18 | 25.854 | −10.018 | −17.516 | 1.00 | 176.47 | MOL3 | C |
| ATOM | 12069 | CG  | PRO | I | 18 | 26.950 | −9.517  | −16.623 | 1.00 | 177.15 | MOL3 | C |
| ATOM | 12070 | C   | PRO | I | 18 | 24.671 | −12.262 | −17.602 | 1.00 | 177.65 | MOL3 | C |
| ATOM | 12071 | O   | PRO | I | 18 | 25.175 | −12.531 | −18.698 | 1.00 | 177.40 | MOL3 | O |
| ATOM | 12072 | N   | PRO | I | 19 | 23.573 | −12.885 | −17.144 | 1.00 | 178.76 | MOL3 | N |
| ATOM | 12073 | CD  | PRO | I | 19 | 22.801 | −12.395 | −15.989 | 1.00 | 178.22 | MOL3 | C |
| ATOM | 12074 | CA  | PRO | I | 19 | 22.842 | −13.957 | −17.833 | 1.00 | 179.21 | MOL3 | C |
| ATOM | 12075 | CB  | PRO | I | 19 | 21.534 | −14.056 | −17.037 | 1.00 | 179.55 | MOL3 | C |
| ATOM | 12076 | CG  | PRO | I | 19 | 21.391 | −12.689 | −16.414 | 1.00 | 179.46 | MOL3 | C |
| ATOM | 12077 | C   | PRO | I | 19 | 22.609 | −13.803 | −19.342 | 1.00 | 179.60 | MOL3 | C |
| ATOM | 12078 | O   | PRO | I | 19 | 22.938 | −12.779 | −19.950 | 1.00 | 179.12 | MOL3 | O |
| ATOM | 12079 | N   | VAL | I | 20 | 22.040 | −14.854 | −19.928 | 1.00 | 179.64 | MOL3 | N |
| ATOM | 12080 | CA  | VAL | I | 20 | 21.747 | −14.924 | −21.356 | 1.00 | 179.72 | MOL3 | C |
| ATOM | 12081 | CB  | VAL | I | 20 | 22.385 | −16.214 | −21.958 | 1.00 | 179.88 | MOL3 | C |
| ATOM | 12082 | CG1 | VAL | I | 20 | 21.393 | −17.369 | −21.888 | 1.00 | 178.65 | MOL3 | C |
| ATOM | 12083 | CG2 | VAL | I | 20 | 22.869 | −15.969 | −23.379 | 1.00 | 179.43 | MOL3 | C |
| ATOM | 12084 | C   | VAL | I | 20 | 20.221 | −14.982 | −21.506 | 1.00 | 179.53 | MOL3 | C |
| ATOM | 12085 | O   | VAL | I | 20 | 19.513 | −15.232 | −20.528 | 1.00 | 179.05 | MOL3 | O |
| ATOM | 12086 | N   | PRO | I | 21 | 19.695 | −14.742 | −22.723 | 1.00 | 179.95 | MOL3 | N |
| ATOM | 12087 | CD  | PRO | I | 21 | 20.392 | −14.285 | −23.942 | 1.00 | 179.35 | MOL3 | C |
| ATOM | 12088 | CA  | PRO | I | 21 | 18.247 | −14.781 | −22.949 | 1.00 | 180.09 | MOL3 | C |
| ATOM | 12089 | CB  | PRO | I | 21 | 18.151 | −14.857 | −24.465 | 1.00 | 179.29 | MOL3 | C |
| ATOM | 12090 | CG  | PRO | I | 21 | 19.237 | −13.907 | −24.870 | 1.00 | 180.07 | MOL3 | C |
| ATOM | 12091 | C   | PRO | I | 21 | 17.503 | −15.917 | −22.235 | 1.00 | 180.81 | MOL3 | C |
| ATOM | 12092 | O   | PRO | I | 21 | 16.366 | −15.731 | −21.794 | 1.00 | 179.87 | MOL3 | O |
| ATOM | 12093 | N   | GLY | I | 22 | 18.139 | −17.083 | −22.117 | 1.00 | 181.44 | MOL3 | N |
| ATOM | 12094 | CA  | GLY | I | 22 | 17.503 | −18.198 | −21.432 | 1.00 | 180.30 | MOL3 | C |
| ATOM | 12095 | C   | GLY | I | 22 | 17.641 | −19.565 | −22.081 | 1.00 | 179.20 | MOL3 | C |
| ATOM | 12096 | O   | GLY | I | 22 | 17.286 | −19.749 | −23.250 | 1.00 | 179.81 | MOL3 | O |
| ATOM | 12097 | N   | GLY | I | 23 | 18.151 | −20.527 | −21.314 | 1.00 | 177.37 | MOL3 | N |
| ATOM | 12098 | CA  | GLY | I | 23 | 18.321 | −21.882 | −21.815 | 1.00 | 174.20 | MOL3 | C |
| ATOM | 12099 | C   | GLY | I | 23 | 19.267 | −22.011 | −22.996 | 1.00 | 171.91 | MOL3 | C |
| ATOM | 12100 | O   | GLY | I | 23 | 18.878 | −22.495 | −24.062 | 1.00 | 173.02 | MOL3 | O |
| ATOM | 12101 | N   | SER | I | 24 | 20.512 | −21.584 | −22.807 | 1.00 | 167.31 | MOL3 | N |
| ATOM | 12102 | CA  | SER | I | 24 | 21.517 | −21.654 | −23.861 | 1.00 | 161.68 | MOL3 | C |
| ATOM | 12103 | CB  | SER | I | 24 | 21.215 | −20.606 | −24.941 | 1.00 | 161.88 | MOL3 | C |
| ATOM | 12104 | OG  | SER | I | 24 | 21.059 | −19.311 | −24.383 | 1.00 | 162.49 | MOL3 | O |
| ATOM | 12105 | C   | SER | I | 24 | 22.922 | −21.442 | −23.296 | 1.00 | 157.77 | MOL3 | C |
| ATOM | 12106 | O   | SER | I | 24 | 23.103 | −20.705 | −22.326 | 1.00 | 156.54 | MOL3 | O |
| ATOM | 12107 | N   | MET | I | 25 | 23.908 | −22.101 | −23.901 | 1.00 | 153.19 | MOL3 | N |
| ATOM | 12108 | CA  | MET | I | 25 | 25.298 | −21.980 | −23.470 | 1.00 | 147.19 | MOL3 | C |
| ATOM | 12109 | CB  | MET | I | 25 | 25.658 | −23.140 | −22.531 | 1.00 | 148.21 | MOL3 | C |
| ATOM | 12110 | CG  | MET | I | 25 | 24.828 | −23.180 | −21.241 | 1.00 | 149.84 | MOL3 | C |
| ATOM | 12111 | SD  | MET | I | 25 | 25.033 | −24.682 | −20.221 | 1.00 | 155.01 | MOL3 | S |
| ATOM | 12112 | CE  | MET | I | 25 | 26.088 | −24.076 | −18.866 | 1.00 | 151.08 | MOL3 | C |
| ATOM | 12113 | C   | MET | I | 25 | 26.236 | −21.943 | −24.686 | 1.00 | 143.35 | MOL3 | C |
| ATOM | 12114 | O   | MET | I | 25 | 25.825 | −22.221 | −25.815 | 1.00 | 142.51 | MOL3 | O |
| ATOM | 12115 | N   | LYS | I | 26 | 27.494 | −21.585 | −24.449 | 1.00 | 139.00 | MOL3 | N |
| ATOM | 12116 | CA  | LYS | I | 26 | 28.491 | −21.492 | −25.514 | 1.00 | 136.16 | MOL3 | C |
| ATOM | 12117 | CB  | LYS | I | 26 | 29.665 | −20.617 | −25.051 | 1.00 | 138.48 | MOL3 | C |
| ATOM | 12118 | CG  | LYS | I | 26 | 29.436 | −19.119 | −25.209 | 1.00 | 139.69 | MOL3 | C |
| ATOM | 12119 | CD  | LYS | I | 26 | 28.154 | −18.661 | −24.524 | 1.00 | 141.68 | MOL3 | C |
| ATOM | 12120 | CE  | LYS | I | 26 | 27.854 | −17.196 | −24.830 | 1.00 | 140.20 | MOL3 | C |
| ATOM | 12121 | NZ  | LYS | I | 26 | 26.570 | −16.747 | −24.225 | 1.00 | 138.85 | MOL3 | N |
| ATOM | 12122 | C   | LYS | I | 26 | 29.028 | −22.842 | −25.991 | 1.00 | 132.33 | MOL3 | C |
| ATOM | 12123 | O   | LYS | I | 26 | 29.700 | −23.552 | −25.245 | 1.00 | 130.87 | MOL3 | O |
| ATOM | 12124 | N   | LEU | I | 27 | 28.739 | −23.182 | −27.243 | 1.00 | 127.83 | MOL3 | N |
| ATOM | 12125 | CA  | LEU | I | 27 | 29.201 | −24.437 | −27.820 | 1.00 | 126.14 | MOL3 | C |
| ATOM | 12126 | CB  | LEU | I | 27 | 28.002 | −25.273 | −28.267 | 1.00 | 126.37 | MOL3 | C |
| ATOM | 12127 | CG  | LEU | I | 27 | 28.270 | −26.698 | −28.756 | 1.00 | 125.28 | MOL3 | C |
| ATOM | 12128 | CD1 | LEU | I | 27 | 28.778 | −27.539 | −27.596 | 1.00 | 123.34 | MOL3 | C |
| ATOM | 12129 | CD2 | LEU | I | 27 | 26.992 | −27.300 | −29.329 | 1.00 | 122.30 | MOL3 | C |
| ATOM | 12130 | C   | LEU | I | 27 | 30.089 | −24.138 | −29.022 | 1.00 | 126.93 | MOL3 | C |
| ATOM | 12131 | O   | LEU | I | 27 | 29.592 | −23.915 | −30.123 | 1.00 | 125.48 | MOL3 | O |
| ATOM | 12132 | N   | ASP | I | 28 | 31.400 | −24.133 | −28.814 | 1.00 | 130.16 | MOL3 | N |
| ATOM | 12133 | CA  | ASP | I | 28 | 32.329 | −23.848 | −29.899 | 1.00 | 133.88 | MOL3 | C |
| ATOM | 12134 | CB  | ASP | I | 28 | 33.775 | −23.863 | −29.384 | 1.00 | 139.45 | MOL3 | C |
| ATOM | 12135 | CG  | ASP | I | 28 | 34.040 | −22.776 | −28.349 | 1.00 | 142.85 | MOL3 | C |
| ATOM | 12136 | OD1 | ASP | I | 28 | 33.393 | −22.808 | −27.282 | 1.00 | 140.81 | MOL3 | O |
| ATOM | 12137 | OD2 | ASP | I | 28 | 34.891 | −21.890 | −28.602 | 1.00 | 145.07 | MOL3 | O |
| ATOM | 12138 | C   | ASP | I | 28 | 32.173 | −24.842 | −31.045 | 1.00 | 133.64 | MOL3 | C |
| ATOM | 12139 | O   | ASP | I | 28 | 31.911 | −26.026 | −30.831 | 1.00 | 131.79 | MOL3 | O |

TABLE 1-continued

The atomic coordinates of IL17F in complex with 496 Fab
(H32; a = 189.4; b = 189.4; c = 490.9, α, β = 90°; γ = 120°)

| ATOM | 12140 | N | ILE | I | 29 | 32.321 | −24.344 | −32.267 | 1.00 | 135.74 | MOL3 | N |
|---|---|---|---|---|---|---|---|---|---|---|---|---|
| ATOM | 12141 | CA | ILE | I | 29 | 32.214 | −25.190 | −33.447 | 1.00 | 138.15 | MOL3 | C |
| ATOM | 12142 | CB | ILE | I | 29 | 32.085 | −24.365 | −34.739 | 1.00 | 142.38 | MOL3 | C |
| ATOM | 12143 | CG2 | ILE | I | 29 | 30.785 | −23.569 | −34.717 | 1.00 | 144.15 | MOL3 | C |
| ATOM | 12144 | CG1 | ILE | I | 29 | 33.317 | −23.463 | −34.896 | 1.00 | 144.80 | MOL3 | C |
| ATOM | 12145 | CD1 | ILE | I | 29 | 33.425 | −22.759 | −36.238 | 1.00 | 144.70 | MOL3 | C |
| ATOM | 12146 | C | ILE | I | 29 | 33.486 | −26.012 | −33.554 | 1.00 | 136.65 | MOL3 | C |
| ATOM | 12147 | O | ILE | I | 29 | 34.481 | −25.727 | −32.883 | 1.00 | 136.50 | MOL3 | O |
| ATOM | 12148 | N | GLY | I | 30 | 33.455 | −27.027 | −34.407 | 1.00 | 133.72 | MOL3 | N |
| ATOM | 12149 | CA | GLY | I | 30 | 34.625 | −27.862 | −34.571 | 1.00 | 130.45 | MOL3 | C |
| ATOM | 12150 | C | GLY | I | 30 | 34.696 | −28.942 | −33.514 | 1.00 | 125.76 | MOL3 | C |
| ATOM | 12151 | O | GLY | I | 30 | 34.797 | −28.668 | −32.318 | 1.00 | 124.14 | MOL3 | O |
| ATOM | 12152 | N | ILE | I | 31 | 34.649 | −30.183 | −33.973 | 1.00 | 122.20 | MOL3 | N |
| ATOM | 12153 | CA | ILE | I | 31 | 34.699 | −31.334 | −33.095 | 1.00 | 117.41 | MOL3 | C |
| ATOM | 12154 | CB | ILE | I | 31 | 33.791 | −32.462 | −33.634 | 1.00 | 115.17 | MOL3 | C |
| ATOM | 12155 | CG2 | ILE | I | 31 | 33.610 | −33.530 | −32.575 | 1.00 | 115.99 | MOL3 | C |
| ATOM | 12156 | CG1 | ILE | I | 31 | 32.428 | −31.897 | −34.053 | 1.00 | 109.89 | MOL3 | C |
| ATOM | 12157 | CD1 | ILE | I | 31 | 32.432 | −31.169 | −35.386 | 1.00 | 106.19 | MOL3 | C |
| ATOM | 12158 | C | ILE | I | 31 | 36.134 | −31.849 | −33.004 | 1.00 | 116.13 | MOL3 | C |
| ATOM | 12159 | O | ILE | I | 31 | 36.793 | −32.045 | −34.022 | 1.00 | 115.05 | MOL3 | O |
| ATOM | 12160 | N | ILE | I | 32 | 36.611 | −32.064 | −31.785 | 1.00 | 116.20 | MOL3 | N |
| ATOM | 12161 | CA | ILE | I | 32 | 37.959 | −32.563 | −31.569 | 1.00 | 119.99 | MOL3 | C |
| ATOM | 12162 | CB | ILE | I | 32 | 38.343 | −32.472 | −30.084 | 1.00 | 121.62 | MOL3 | C |
| ATOM | 12163 | CG2 | ILE | I | 32 | 39.748 | −33.022 | −29.879 | 1.00 | 124.67 | MOL3 | C |
| ATOM | 12164 | CG1 | ILE | I | 32 | 38.249 | −31.020 | −29.607 | 1.00 | 121.53 | MOL3 | C |
| ATOM | 12165 | CD1 | ILE | I | 32 | 38.719 | −30.806 | −28.169 | 1.00 | 120.71 | MOL3 | C |
| ATOM | 12166 | C | ILE | I | 32 | 38.087 | −34.021 | −32.013 | 1.00 | 122.93 | MOL3 | C |
| ATOM | 12167 | O | ILE | I | 32 | 37.331 | −34.877 | −31.564 | 1.00 | 123.52 | MOL3 | O |
| ATOM | 12168 | N | ASN | I | 33 | 39.046 | −34.291 | −32.896 | 1.00 | 128.61 | MOL3 | N |
| ATOM | 12169 | CA | ASN | I | 33 | 39.295 | −35.640 | −33.410 | 1.00 | 134.25 | MOL3 | C |
| ATOM | 12170 | CB | ASN | I | 33 | 39.338 | −36.659 | −32.266 | 1.00 | 138.33 | MOL3 | C |
| ATOM | 12171 | CG | ASN | I | 33 | 40.529 | −36.467 | −31.350 | 1.00 | 143.66 | MOL3 | C |
| ATOM | 12172 | OD1 | ASN | I | 33 | 40.677 | −37.177 | −30.354 | 1.00 | 147.45 | MOL3 | O |
| ATOM | 12173 | ND2 | ASN | I | 33 | 41.387 | −35.508 | −31.682 | 1.00 | 147.64 | MOL3 | N |
| ATOM | 12174 | C | ASN | I | 33 | 38.268 | −36.109 | −34.434 | 1.00 | 136.93 | MOL3 | C |
| ATOM | 12175 | O | ASN | I | 33 | 38.037 | −37.307 | −34.572 | 1.00 | 137.56 | MOL3 | O |
| ATOM | 12176 | N | GLU | I | 34 | 37.661 | −35.171 | −35.151 | 1.00 | 141.98 | MOL3 | N |
| ATOM | 12177 | CA | GLU | I | 34 | 36.659 | −35.495 | −36.162 | 1.00 | 147.90 | MOL3 | C |
| ATOM | 12178 | CB | GLU | I | 34 | 36.202 | −34.206 | −36.851 | 1.00 | 149.63 | MOL3 | C |
| ATOM | 12179 | CG | GLU | I | 34 | 35.181 | −34.405 | −37.957 | 1.00 | 155.63 | MOL3 | C |
| ATOM | 12180 | CD | GLU | I | 34 | 34.739 | −33.094 | −38.585 | 1.00 | 157.32 | MOL3 | C |
| ATOM | 12181 | OE1 | GLU | I | 34 | 34.140 | −32.265 | −37.867 | 1.00 | 159.91 | MOL3 | O |
| ATOM | 12182 | OE2 | GLU | I | 34 | 34.993 | −32.894 | −39.794 | 1.00 | 156.42 | MOL3 | O |
| ATOM | 12183 | C | GLU | I | 34 | 37.199 | −36.483 | −37.198 | 1.00 | 152.50 | MOL3 | C |
| ATOM | 12184 | O | GLU | I | 34 | 36.446 | −37.034 | −38.005 | 1.00 | 150.94 | MOL3 | O |
| ATOM | 12185 | N | ASN | I | 35 | 38.506 | −36.718 | −37.162 | 1.00 | 160.08 | MOL3 | N |
| ATOM | 12186 | CA | ASN | I | 35 | 39.136 | −37.626 | −38.113 | 1.00 | 166.41 | MOL3 | C |
| ATOM | 12187 | CB | ASN | I | 35 | 40.524 | −37.093 | −38.495 | 1.00 | 169.05 | MOL3 | C |
| ATOM | 12188 | CG | ASN | I | 35 | 40.452 | −35.768 | −39.252 | 1.00 | 168.59 | MOL3 | C |
| ATOM | 12189 | OD1 | ASN | I | 35 | 39.841 | −35.678 | −40.319 | 1.00 | 166.12 | MOL3 | O |
| ATOM | 12190 | ND2 | ASN | I | 35 | 41.076 | −34.735 | −38.696 | 1.00 | 169.03 | MOL3 | N |
| ATOM | 12191 | C | ASN | I | 35 | 39.210 | −39.101 | −37.680 | 1.00 | 167.95 | MOL3 | C |
| ATOM | 12192 | O | ASN | I | 35 | 39.466 | −39.975 | −38.511 | 1.00 | 169.37 | MOL3 | O |
| ATOM | 12193 | N | GLN | I | 36 | 38.982 | −39.380 | −36.397 | 1.00 | 167.80 | MOL3 | N |
| ATOM | 12194 | CA | GLN | I | 36 | 38.996 | −40.760 | −35.906 | 1.00 | 169.12 | MOL3 | C |
| ATOM | 12195 | CB | GLN | I | 36 | 38.535 | −40.814 | −34.444 | 1.00 | 168.38 | MOL3 | C |
| ATOM | 12196 | CG | GLN | I | 36 | 39.615 | −40.555 | −33.393 | 1.00 | 167.52 | MOL3 | C |
| ATOM | 12197 | CD | GLN | I | 36 | 40.523 | −41.758 | −33.160 | 1.00 | 166.66 | MOL3 | C |
| ATOM | 12198 | OE1 | GLN | I | 36 | 41.340 | −41.765 | −32.237 | 1.00 | 163.74 | MOL3 | O |
| ATOM | 12199 | NE2 | GLN | I | 36 | 40.383 | −42.779 | −34.000 | 1.00 | 167.07 | MOL3 | N |
| ATOM | 12200 | C | GLN | I | 36 | 38.034 | −41.584 | −36.760 | 1.00 | 171.58 | MOL3 | C |
| ATOM | 12201 | O | GLN | I | 36 | 36.821 | −41.354 | −36.727 | 1.00 | 169.42 | MOL3 | O |
| ATOM | 12202 | N | ARG | I | 37 | 38.569 | −42.544 | −37.514 | 1.00 | 175.43 | MOL3 | N |
| ATOM | 12203 | CA | ARG | I | 37 | 37.741 | −43.376 | −38.385 | 1.00 | 178.58 | MOL3 | C |
| ATOM | 12204 | CB | ARG | I | 37 | 38.587 | −44.001 | −39.503 | 1.00 | 180.60 | MOL3 | C |
| ATOM | 12205 | CG | ARG | I | 37 | 37.771 | −44.812 | −40.517 | 1.00 | 180.87 | MOL3 | C |
| ATOM | 12206 | CD | ARG | I | 37 | 38.629 | −45.374 | −41.654 | 1.00 | 180.99 | MOL3 | C |
| ATOM | 12207 | NE | ARG | I | 37 | 38.691 | −44.504 | −42.830 | 1.00 | 180.13 | MOL3 | N |
| ATOM | 12208 | CZ | ARG | I | 37 | 39.248 | −43.295 | −42.859 | 1.00 | 179.27 | MOL3 | C |
| ATOM | 12209 | NH1 | ARG | I | 37 | 39.806 | −42.780 | −41.772 | 1.00 | 178.28 | MOL3 | N |
| ATOM | 12210 | NH2 | ARG | I | 37 | 39.253 | −42.599 | −43.989 | 1.00 | 178.79 | MOL3 | N |
| ATOM | 12211 | C | ARG | I | 37 | 36.966 | −44.474 | −37.661 | 1.00 | 179.06 | MOL3 | C |
| ATOM | 12212 | O | ARG | I | 37 | 37.439 | −45.049 | −36.676 | 1.00 | 177.51 | MOL3 | O |
| ATOM | 12213 | N | VAL | I | 38 | 35.767 | −44.749 | −38.174 | 1.00 | 180.94 | MOL3 | N |
| ATOM | 12214 | CA | VAL | I | 38 | 34.870 | −45.763 | −37.623 | 1.00 | 181.97 | MOL3 | C |
| ATOM | 12215 | CB | VAL | I | 38 | 33.609 | −45.946 | −38.515 | 1.00 | 182.48 | MOL3 | C |
| ATOM | 12216 | CG1 | VAL | I | 38 | 32.638 | −46.912 | −37.851 | 1.00 | 180.01 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 12217 | CG2 | VAL | I | 38 | 32.940 | −44.598 | −38.770 | 1.00 | 182.29 | MOL3 | C |
|---|---|---|---|---|---|---|---|---|---|---|---|---|
| ATOM | 12218 | C | VAL | I | 38 | 35.578 | −47.106 | −37.513 | 1.00 | 181.78 | MOL3 | C |
| ATOM | 12219 | O | VAL | I | 38 | 35.495 | −47.940 | −38.416 | 1.00 | 182.53 | MOL3 | O |
| ATOM | 12220 | N | SER | I | 39 | 36.272 | −47.314 | −36.402 | 1.00 | 180.64 | MOL3 | N |
| ATOM | 12221 | CA | SER | I | 39 | 36.995 | −48.557 | −36.198 | 1.00 | 180.27 | MOL3 | C |
| ATOM | 12222 | CB | SER | I | 39 | 37.880 | −48.450 | −34.954 | 1.00 | 182.42 | MOL3 | C |
| ATOM | 12223 | OG | SER | I | 39 | 38.805 | −49.523 | −34.890 | 1.00 | 184.31 | MOL3 | O |
| ATOM | 12224 | C | SER | I | 39 | 36.027 | −49.734 | −36.065 | 1.00 | 178.35 | MOL3 | C |
| ATOM | 12225 | O | SER | I | 39 | 35.590 | −50.080 | −34.965 | 1.00 | 177.64 | MOL3 | O |
| ATOM | 12226 | N | MET | I | 40 | 35.687 | −50.333 | −37.203 | 1.00 | 175.54 | MOL3 | N |
| ATOM | 12227 | CA | MET | I | 40 | 34.791 | −51.486 | −37.245 | 1.00 | 169.58 | MOL3 | C |
| ATOM | 12228 | CB | MET | I | 40 | 33.400 | −51.100 | −37.771 | 1.00 | 168.92 | MOL3 | C |
| ATOM | 12229 | CG | MET | I | 40 | 32.565 | −50.221 | −36.855 | 1.00 | 166.14 | MOL3 | C |
| ATOM | 12230 | SD | MET | I | 40 | 30.812 | −50.310 | −37.299 | 1.00 | 161.34 | MOL3 | S |
| ATOM | 12231 | CE | MET | I | 40 | 30.822 | −49.553 | −38.922 | 1.00 | 163.80 | MOL3 | C |
| ATOM | 12232 | C | MET | I | 40 | 35.373 | −52.562 | −38.159 | 1.00 | 164.34 | MOL3 | C |
| ATOM | 12233 | O | MET | I | 40 | 34.960 | −52.686 | −39.316 | 1.00 | 163.71 | MOL3 | O |
| ATOM | 12234 | N | SER | I | 41 | 36.339 | −53.323 | −37.649 | 1.00 | 156.31 | MOL3 | N |
| ATOM | 12235 | CA | SER | I | 41 | 36.942 | −54.392 | −38.435 | 1.00 | 148.84 | MOL3 | C |
| ATOM | 12236 | CB | SER | I | 41 | 37.887 | −55.236 | −37.578 | 1.00 | 147.06 | MOL3 | C |
| ATOM | 12237 | OG | SER | I | 41 | 38.952 | −54.454 | −37.077 | 1.00 | 143.09 | MOL3 | O |
| ATOM | 12238 | C | SER | I | 41 | 35.789 | −55.249 | −38.925 | 1.00 | 145.37 | MOL3 | C |
| ATOM | 12239 | O | SER | I | 41 | 35.267 | −56.089 | −38.198 | 1.00 | 146.63 | MOL3 | O |
| ATOM | 12240 | N | ARG | I | 42 | 35.389 | −55.020 | −40.165 | 1.00 | 140.97 | MOL3 | N |
| ATOM | 12241 | CA | ARG | I | 42 | 34.274 | −55.735 | −40.760 | 1.00 | 135.24 | MOL3 | C |
| ATOM | 12242 | CB | ARG | I | 42 | 34.191 | −55.397 | −42.251 | 1.00 | 138.21 | MOL3 | C |
| ATOM | 12243 | CG | ARG | I | 42 | 32.791 | −55.444 | −42.836 | 1.00 | 142.33 | MOL3 | C |
| ATOM | 12244 | CD | ARG | I | 42 | 32.624 | −54.362 | −43.900 | 1.00 | 147.22 | MOL3 | C |
| ATOM | 12245 | NE | ARG | I | 42 | 32.913 | −53.033 | −43.356 | 1.00 | 151.01 | MOL3 | N |
| ATOM | 12246 | CZ | ARG | I | 42 | 32.777 | −51.891 | −44.027 | 1.00 | 151.43 | MOL3 | C |
| ATOM | 12247 | NH1 | ARG | I | 42 | 32.350 | −51.895 | −45.284 | 1.00 | 151.19 | MOL3 | N |
| ATOM | 12248 | NH2 | ARG | I | 42 | 33.074 | −50.739 | −43.440 | 1.00 | 152.19 | MOL3 | N |
| ATOM | 12249 | C | ARG | I | 42 | 34.294 | −57.249 | −40.567 | 1.00 | 128.50 | MOL3 | C |
| ATOM | 12250 | O | ARG | I | 42 | 35.346 | −57.878 | −40.420 | 1.00 | 126.72 | MOL3 | O |
| ATOM | 12251 | N | ASN | I | 43 | 33.090 | −57.805 | −40.553 | 1.00 | 121.76 | MOL3 | N |
| ATOM | 12252 | CA | ASN | I | 43 | 32.846 | −59.229 | −40.405 | 1.00 | 114.72 | MOL3 | C |
| ATOM | 12253 | CB | ASN | I | 43 | 33.385 | −59.960 | −41.628 | 1.00 | 121.20 | MOL3 | C |
| ATOM | 12254 | CG | ASN | I | 43 | 32.607 | −59.614 | −42.881 | 1.00 | 126.99 | MOL3 | C |
| ATOM | 12255 | OD1 | ASN | I | 43 | 32.585 | −58.458 | −43.308 | 1.00 | 131.03 | MOL3 | O |
| ATOM | 12256 | ND2 | ASN | I | 43 | 31.947 | −60.608 | −43.467 | 1.00 | 128.09 | MOL3 | N |
| ATOM | 12257 | C | ASN | I | 43 | 33.274 | −59.943 | −39.129 | 1.00 | 106.15 | MOL3 | C |
| ATOM | 12258 | O | ASN | I | 43 | 32.968 | −61.125 | −38.971 | 1.00 | 109.43 | MOL3 | O |
| ATOM | 12259 | N | ILE | I | 44 | 33.953 | −59.262 | −38.206 | 1.00 | 92.33 | MOL3 | N |
| ATOM | 12260 | CA | ILE | I | 44 | 34.334 | −59.945 | −36.968 | 1.00 | 78.29 | MOL3 | C |
| ATOM | 12261 | CB | ILE | I | 44 | 35.195 | −59.098 | −36.010 | 1.00 | 71.39 | MOL3 | C |
| ATOM | 12262 | CG2 | ILE | I | 44 | 36.374 | −58.488 | −36.736 | 1.00 | 77.24 | MOL3 | C |
| ATOM | 12263 | CG1 | ILE | I | 44 | 34.335 | −58.031 | −35.359 | 1.00 | 62.95 | MOL3 | C |
| ATOM | 12264 | CD1 | ILE | I | 44 | 35.046 | −57.323 | −34.262 | 1.00 | 60.82 | MOL3 | C |
| ATOM | 12265 | C | ILE | I | 44 | 33.052 | −60.237 | −36.227 | 1.00 | 72.52 | MOL3 | C |
| ATOM | 12266 | O | ILE | I | 44 | 33.018 | −61.063 | −35.328 | 1.00 | 69.19 | MOL3 | O |
| ATOM | 12267 | N | GLU | I | 45 | 31.995 | −59.535 | −36.607 | 1.00 | 71.23 | MOL3 | N |
| ATOM | 12268 | CA | GLU | I | 45 | 30.699 | −59.722 | −35.985 | 1.00 | 72.96 | MOL3 | C |
| ATOM | 12269 | CB | GLU | I | 45 | 29.681 | −58.728 | −36.539 | 1.00 | 75.42 | MOL3 | C |
| ATOM | 12270 | CG | GLU | I | 45 | 30.258 | −57.695 | −37.494 | 1.00 | 92.67 | MOL3 | C |
| ATOM | 12271 | CD | GLU | I | 45 | 29.653 | −57.785 | −38.895 | 1.00 | 103.60 | MOL3 | C |
| ATOM | 12272 | OE1 | GLU | I | 45 | 28.517 | −58.303 | −39.013 | 1.00 | 106.90 | MOL3 | O |
| ATOM | 12273 | OE2 | GLU | I | 45 | 30.302 | −57.325 | −39.871 | 1.00 | 104.63 | MOL3 | O |
| ATOM | 12274 | C | GLU | I | 45 | 30.226 | −61.127 | −36.290 | 1.00 | 70.37 | MOL3 | C |
| ATOM | 12275 | O | GLU | I | 45 | 29.288 | −61.625 | −35.674 | 1.00 | 75.71 | MOL3 | O |
| ATOM | 12276 | N | SER | I | 46 | 30.871 | −61.772 | −37.250 | 1.00 | 66.05 | MOL3 | N |
| ATOM | 12277 | CA | SER | I | 46 | 30.482 | −63.127 | −37.604 | 1.00 | 67.53 | MOL3 | C |
| ATOM | 12278 | CB | SER | I | 46 | 30.000 | −63.188 | −39.055 | 1.00 | 66.91 | MOL3 | C |
| ATOM | 12279 | OG | SER | I | 46 | 30.684 | −62.251 | −39.865 | 1.00 | 70.73 | MOL3 | O |
| ATOM | 12280 | C | SER | I | 46 | 31.582 | −64.150 | −37.367 | 1.00 | 66.95 | MOL3 | C |
| ATOM | 12281 | O | SER | I | 46 | 31.358 | −65.353 | −37.503 | 1.00 | 68.04 | MOL3 | O |
| ATOM | 12282 | N | ARG | I | 47 | 32.765 | −63.671 | −36.999 | 1.00 | 64.16 | MOL3 | N |
| ATOM | 12283 | CA | ARG | I | 47 | 33.884 | −64.558 | −36.724 | 1.00 | 62.29 | MOL3 | C |
| ATOM | 12284 | CB | ARG | I | 47 | 35.204 | −63.917 | −37.163 | 1.00 | 59.57 | MOL3 | C |
| ATOM | 12285 | CG | ARG | I | 47 | 35.200 | −63.317 | −38.550 | 1.00 | 56.22 | MOL3 | C |
| ATOM | 12286 | CD | ARG | I | 47 | 36.607 | −63.280 | −39.127 | 1.00 | 60.55 | MOL3 | C |
| ATOM | 12287 | NE | ARG | I | 47 | 37.637 | −62.948 | −38.140 | 1.00 | 64.99 | MOL3 | N |
| ATOM | 12288 | CZ | ARG | I | 47 | 38.135 | −61.730 | −37.925 | 1.00 | 70.18 | MOL3 | C |
| ATOM | 12289 | NH1 | ARG | I | 47 | 37.702 | −60.681 | −38.629 | 1.00 | 68.79 | MOL3 | N |
| ATOM | 12290 | NH2 | ARG | I | 47 | 39.090 | −61.566 | −37.013 | 1.00 | 65.99 | MOL3 | N |
| ATOM | 12291 | C | ARG | I | 47 | 33.948 | −64.853 | −35.224 | 1.00 | 63.25 | MOL3 | C |
| ATOM | 12292 | O | ARG | I | 47 | 34.722 | −65.697 | −34.783 | 1.00 | 69.03 | MOL3 | O |
| ATOM | 12293 | N | SER | I | 48 | 33.133 | −64.154 | −34.444 | 1.00 | 57.25 | MOL3 | N |

TABLE 1-continued

The atomic coordinates of IL17F in complex with 496 Fab
(H32; a = 189.4; b = 189.4; c = 490.9, α, β = 90°; γ = 120°)

| ATOM | 12294 | CA | SER | I | 48 | 33.121 | −64.332 | −33.002 | 1.00 | 55.05 | MOL3 | C |
|---|---|---|---|---|---|---|---|---|---|---|---|---|
| ATOM | 12295 | CB | SER | I | 48 | 32.484 | −63.107 | −32.334 | 1.00 | 57.41 | MOL3 | C |
| ATOM | 12296 | OG | SER | I | 48 | 32.431 | −63.231 | −30.919 | 1.00 | 60.15 | MOL3 | O |
| ATOM | 12297 | C | SER | I | 48 | 32.368 | −65.581 | −32.586 | 1.00 | 56.43 | MOL3 | C |
| ATOM | 12298 | O | SER | I | 48 | 31.442 | −66.016 | −33.265 | 1.00 | 53.09 | MOL3 | O |
| ATOM | 12299 | N | THR | I | 49 | 32.783 | −66.151 | −31.460 | 1.00 | 57.82 | MOL3 | N |
| ATOM | 12300 | CA | THR | I | 49 | 32.155 | −67.338 | −30.904 | 1.00 | 58.63 | MOL3 | C |
| ATOM | 12301 | CB | THR | I | 49 | 32.918 | −67.825 | −29.677 | 1.00 | 61.95 | MOL3 | C |
| ATOM | 12302 | OG1 | THR | I | 49 | 32.690 | −66.924 | −28.585 | 1.00 | 63.24 | MOL3 | O |
| ATOM | 12303 | CG2 | THR | I | 49 | 34.398 | −67.863 | −29.971 | 1.00 | 69.51 | MOL3 | C |
| ATOM | 12304 | C | THR | I | 49 | 30.768 | −66.928 | −30.443 | 1.00 | 58.47 | MOL3 | C |
| ATOM | 12305 | O | THR | I | 49 | 29.925 | −67.775 | −30.149 | 1.00 | 65.64 | MOL3 | O |
| ATOM | 12306 | N | SER | I | 50 | 30.557 | −65.619 | −30.352 | 1.00 | 51.66 | MOL3 | N |
| ATOM | 12307 | CA | SER | I | 50 | 29.283 | −65.054 | −29.931 | 1.00 | 45.28 | MOL3 | C |
| ATOM | 12308 | CB | SER | I | 50 | 29.392 | −64.456 | −28.519 | 1.00 | 47.18 | MOL3 | C |
| ATOM | 12309 | OG | SER | I | 50 | 30.412 | −63.477 | −28.395 | 1.00 | 40.37 | MOL3 | O |
| ATOM | 12310 | C | SER | I | 50 | 28.953 | −63.980 | −30.942 | 1.00 | 44.20 | MOL3 | C |
| ATOM | 12311 | O | SER | I | 50 | 29.090 | −62.797 | −30.676 | 1.00 | 47.70 | MOL3 | O |
| ATOM | 12312 | N | PRO | I | 51 | 28.509 | −64.395 | −32.127 | 1.00 | 45.21 | MOL3 | N |
| ATOM | 12313 | CD | PRO | I | 51 | 28.056 | −65.785 | −32.242 | 1.00 | 46.36 | MOL3 | C |
| ATOM | 12314 | CA | PRO | I | 51 | 28.115 | −63.618 | −33.314 | 1.00 | 43.94 | MOL3 | C |
| ATOM | 12315 | CB | PRO | I | 51 | 27.623 | −64.678 | −34.291 | 1.00 | 46.00 | MOL3 | C |
| ATOM | 12316 | CG | PRO | I | 51 | 28.124 | −65.997 | −33.710 | 1.00 | 53.03 | MOL3 | C |
| ATOM | 12317 | C | PRO | I | 51 | 27.015 | −62.633 | −33.027 | 1.00 | 42.77 | MOL3 | C |
| ATOM | 12318 | O | PRO | I | 51 | 26.266 | −62.804 | −32.079 | 1.00 | 50.02 | MOL3 | O |
| ATOM | 12319 | N | TRP | I | 52 | 26.886 | −61.625 | −33.871 | 1.00 | 42.01 | MOL3 | N |
| ATOM | 12320 | CA | TRP | I | 52 | 25.842 | −60.631 | −33.676 | 1.00 | 43.72 | MOL3 | C |
| ATOM | 12321 | CB | TRP | I | 52 | 26.248 | −59.690 | −32.561 | 1.00 | 41.79 | MOL3 | C |
| ATOM | 12322 | CG | TRP | I | 52 | 27.348 | −58.743 | −32.939 | 1.00 | 47.86 | MOL3 | C |
| ATOM | 12323 | CD2 | TRP | I | 52 | 28.725 | −58.830 | −32.554 | 1.00 | 45.17 | MOL3 | C |
| ATOM | 12324 | CE2 | TRP | I | 52 | 29.362 | −57.675 | −33.024 | 1.00 | 41.06 | MOL3 | C |
| ATOM | 12325 | CE3 | TRP | I | 52 | 29.475 | −59.771 | −31.848 | 1.00 | 52.60 | MOL3 | C |
| ATOM | 12326 | CD1 | TRP | I | 52 | 27.219 | −57.576 | −33.629 | 1.00 | 45.22 | MOL3 | C |
| ATOM | 12327 | NE1 | TRP | I | 52 | 28.423 | −56.926 | −33.679 | 1.00 | 44.52 | MOL3 | N |
| ATOM | 12328 | CZ2 | TRP | I | 52 | 30.706 | −57.431 | −32.809 | 1.00 | 42.81 | MOL3 | C |
| ATOM | 12329 | CZ3 | TRP | I | 52 | 30.812 | −59.525 | −31.634 | 1.00 | 54.69 | MOL3 | C |
| ATOM | 12330 | CH2 | TRP | I | 52 | 31.413 | −58.364 | −32.112 | 1.00 | 50.64 | MOL3 | C |
| ATOM | 12331 | C | TRP | I | 52 | 25.559 | −59.825 | −34.937 | 1.00 | 47.78 | MOL3 | C |
| ATOM | 12332 | O | TRP | I | 52 | 26.452 | −59.611 | −35.751 | 1.00 | 57.91 | MOL3 | O |
| ATOM | 12333 | N | ASN | I | 53 | 24.318 | −59.379 | −35.102 | 1.00 | 47.44 | MOL3 | N |
| ATOM | 12334 | CA | ASN | I | 53 | 23.940 | −58.581 | −36.266 | 1.00 | 52.67 | MOL3 | C |
| ATOM | 12335 | CB | ASN | I | 53 | 22.504 | −58.853 | −36.697 | 1.00 | 59.42 | MOL3 | C |
| ATOM | 12336 | CG | ASN | I | 53 | 22.321 | −60.215 | −37.296 | 1.00 | 72.49 | MOL3 | C |
| ATOM | 12337 | OD1 | ASN | I | 53 | 21.503 | −61.011 | −36.818 | 1.00 | 80.15 | MOL3 | O |
| ATOM | 12338 | ND2 | ASN | I | 53 | 23.068 | −60.500 | −38.360 | 1.00 | 76.42 | MOL3 | N |
| ATOM | 12339 | C | ASN | I | 53 | 24.022 | −57.114 | −35.917 | 1.00 | 55.36 | MOL3 | C |
| ATOM | 12340 | O | ASN | I | 53 | 24.062 | −56.747 | −34.745 | 1.00 | 56.59 | MOL3 | O |
| ATOM | 12341 | N | TYR | I | 54 | 24.036 | −56.274 | −36.945 | 1.00 | 59.30 | MOL3 | N |
| ATOM | 12342 | CA | TYR | I | 54 | 24.083 | −54.827 | −36.763 | 1.00 | 60.15 | MOL3 | C |
| ATOM | 12343 | CB | TYR | I | 54 | 25.236 | −54.194 | −37.549 | 1.00 | 67.64 | MOL3 | C |
| ATOM | 12344 | CG | TYR | I | 54 | 26.588 | −54.204 | −36.862 | 1.00 | 73.74 | MOL3 | C |
| ATOM | 12345 | CD1 | TYR | I | 54 | 27.695 | −54.760 | −37.479 | 1.00 | 79.03 | MOL3 | C |
| ATOM | 12346 | CE1 | TYR | I | 54 | 28.954 | −54.712 | −36.888 | 1.00 | 85.47 | MOL3 | C |
| ATOM | 12347 | CD2 | TYR | I | 54 | 26.770 | −53.603 | −35.627 | 1.00 | 80.28 | MOL3 | C |
| ATOM | 12348 | CE2 | TYR | I | 54 | 28.027 | −53.551 | −35.026 | 1.00 | 85.95 | MOL3 | C |
| ATOM | 12349 | CZ | TYR | I | 54 | 29.116 | −54.106 | −35.665 | 1.00 | 85.84 | MOL3 | C |
| ATOM | 12350 | OH | TYR | I | 54 | 30.374 | −54.042 | −35.095 | 1.00 | 89.54 | MOL3 | O |
| ATOM | 12351 | C | TYR | I | 54 | 22.781 | −54.287 | −37.299 | 1.00 | 58.45 | MOL3 | C |
| ATOM | 12352 | O | TYR | I | 54 | 22.101 | −54.940 | −38.082 | 1.00 | 64.52 | MOL3 | O |
| ATOM | 12353 | N | THR | I | 55 | 22.432 | −53.089 | −36.872 | 1.00 | 59.53 | MOL3 | N |
| ATOM | 12354 | CA | THR | I | 55 | 21.201 | −52.449 | −37.312 | 1.00 | 64.27 | MOL3 | C |
| ATOM | 12355 | CB | THR | I | 55 | 20.052 | −52.673 | −36.344 | 1.00 | 62.30 | MOL3 | C |
| ATOM | 12356 | OG1 | THR | I | 55 | 19.817 | −54.074 | −36.188 | 1.00 | 66.33 | MOL3 | O |
| ATOM | 12357 | CG2 | THR | I | 55 | 18.810 | −52.003 | −36.869 | 1.00 | 62.90 | MOL3 | C |
| ATOM | 12358 | C | THR | I | 55 | 21.491 | −50.975 | −37.279 | 1.00 | 68.03 | MOL3 | C |
| ATOM | 12359 | O | THR | I | 55 | 21.766 | −50.431 | −36.212 | 1.00 | 72.64 | MOL3 | O |
| ATOM | 12360 | N | VAL | I | 56 | 21.423 | −50.318 | −38.428 | 1.00 | 68.68 | MOL3 | N |
| ATOM | 12361 | CA | VAL | I | 56 | 21.721 | −48.896 | −38.473 | 1.00 | 66.68 | MOL3 | C |
| ATOM | 12362 | CB | VAL | I | 56 | 22.607 | −48.547 | −39.683 | 1.00 | 65.22 | MOL3 | C |
| ATOM | 12363 | CG1 | VAL | I | 56 | 23.143 | −47.126 | −39.538 | 1.00 | 64.85 | MOL3 | C |
| ATOM | 12364 | CG2 | VAL | I | 56 | 23.734 | −49.553 | −39.818 | 1.00 | 70.15 | MOL3 | C |
| ATOM | 12365 | C | VAL | I | 56 | 20.494 | −48.006 | −38.564 | 1.00 | 65.12 | MOL3 | C |
| ATOM | 12366 | O | VAL | I | 56 | 19.517 | −48.338 | −39.224 | 1.00 | 68.43 | MOL3 | O |
| ATOM | 12367 | N | THR | I | 57 | 20.540 | −46.873 | −37.882 | 1.00 | 63.18 | MOL3 | N |
| ATOM | 12368 | CA | THR | I | 57 | 19.450 | −45.922 | −37.985 | 1.00 | 65.41 | MOL3 | C |
| ATOM | 12369 | CB | THR | I | 57 | 18.649 | −45.749 | −36.682 | 1.00 | 64.42 | MOL3 | C |
| ATOM | 12370 | OG1 | THR | I | 57 | 19.343 | −44.880 | −35.778 | 1.00 | 62.37 | MOL3 | O |

TABLE 1-continued

The atomic coordinates of IL17F in complex with 496 Fab
(H32; a = 189.4; b = 189.4; c = 490.9, α, β = 90°; γ = 120°)

| ATOM | 12371 | CG2 | THR | I | 57 | 18.436 | −47.086 | −36.043 | 1.00 | 67.87 | MOL3 | C |
|---|---|---|---|---|---|---|---|---|---|---|---|---|
| ATOM | 12372 | C | THR | I | 57 | 20.100 | −44.604 | −38.370 | 1.00 | 69.15 | MOL3 | C |
| ATOM | 12373 | O | THR | I | 57 | 21.212 | −44.273 | −37.913 | 1.00 | 68.91 | MOL3 | O |
| ATOM | 12374 | N | TRP | I | 58 | 19.421 | −43.867 | −39.243 | 1.00 | 66.81 | MOL3 | N |
| ATOM | 12375 | CA | TRP | I | 58 | 19.950 | −42.598 | −39.706 | 1.00 | 65.75 | MOL3 | C |
| ATOM | 12376 | CB | TRP | I | 58 | 20.240 | −42.632 | −41.218 | 1.00 | 69.27 | MOL3 | C |
| ATOM | 12377 | CG | TRP | I | 58 | 20.671 | −41.296 | −41.743 | 1.00 | 68.80 | MOL3 | C |
| ATOM | 12378 | CD2 | TRP | I | 58 | 19.861 | −40.368 | −42.469 | 1.00 | 72.41 | MOL3 | C |
| ATOM | 12379 | CE2 | TRP | I | 58 | 20.612 | −39.180 | −42.610 | 1.00 | 73.32 | MOL3 | C |
| ATOM | 12380 | CE3 | TRP | I | 58 | 18.570 | −40.422 | −43.007 | 1.00 | 73.79 | MOL3 | C |
| ATOM | 12381 | CD1 | TRP | I | 58 | 21.857 | −40.659 | −41.496 | 1.00 | 67.42 | MOL3 | C |
| ATOM | 12382 | NE1 | TRP | I | 58 | 21.826 | −39.386 | −42.008 | 1.00 | 72.38 | MOL3 | N |
| ATOM | 12383 | CZ2 | TRP | I | 58 | 20.112 | −38.056 | −43.266 | 1.00 | 72.82 | MOL3 | C |
| ATOM | 12384 | CZ3 | TRP | I | 58 | 18.076 | −39.306 | −43.657 | 1.00 | 76.30 | MOL3 | C |
| ATOM | 12385 | CH2 | TRP | I | 58 | 18.845 | −38.139 | −43.780 | 1.00 | 77.05 | MOL3 | C |
| ATOM | 12386 | C | TRP | I | 58 | 18.999 | −41.463 | −39.429 | 1.00 | 61.07 | MOL3 | C |
| ATOM | 12387 | O | TRP | I | 58 | 17.832 | −41.524 | −39.787 | 1.00 | 60.74 | MOL3 | O |
| ATOM | 12388 | N | ASP | I | 59 | 19.500 | −40.431 | −38.770 | 1.00 | 60.51 | MOL3 | N |
| ATOM | 12389 | CA | ASP | I | 59 | 18.696 | −39.254 | −38.500 | 1.00 | 62.88 | MOL3 | C |
| ATOM | 12390 | CB | ASP | I | 59 | 18.256 | −39.172 | −37.045 | 1.00 | 68.73 | MOL3 | C |
| ATOM | 12391 | CG | ASP | I | 59 | 17.528 | −37.871 | −36.733 | 1.00 | 72.79 | MOL3 | C |
| ATOM | 12392 | OD1 | ASP | I | 59 | 16.982 | −37.731 | −35.617 | 1.00 | 72.88 | MOL3 | O |
| ATOM | 12393 | OD2 | ASP | I | 59 | 17.507 | −36.979 | −37.605 | 1.00 | 73.48 | MOL3 | O |
| ATOM | 12394 | C | ASP | I | 59 | 19.530 | −38.040 | −38.834 | 1.00 | 69.37 | MOL3 | C |
| ATOM | 12395 | O | ASP | I | 59 | 20.581 | −37.792 | −38.228 | 1.00 | 70.12 | MOL3 | O |
| ATOM | 12396 | N | PRO | I | 60 | 19.053 | −37.254 | −39.803 | 1.00 | 72.10 | MOL3 | N |
| ATOM | 12397 | CD | PRO | I | 60 | 17.643 | −37.400 | −40.203 | 1.00 | 68.92 | MOL3 | C |
| ATOM | 12398 | CA | PRO | I | 60 | 19.614 | −36.019 | −40.363 | 1.00 | 73.74 | MOL3 | C |
| ATOM | 12399 | CB | PRO | I | 60 | 18.524 | −35.580 | −41.318 | 1.00 | 75.30 | MOL3 | C |
| ATOM | 12400 | CG | PRO | I | 60 | 17.280 | −35.993 | −40.566 | 1.00 | 67.02 | MOL3 | C |
| ATOM | 12401 | C | PRO | I | 60 | 19.875 | −34.937 | −39.323 | 1.00 | 74.13 | MOL3 | C |
| ATOM | 12402 | O | PRO | I | 60 | 20.772 | −34.097 | −39.487 | 1.00 | 74.87 | MOL3 | O |
| ATOM | 12403 | N | ASN | I | 61 | 19.055 | −34.951 | −38.275 | 1.00 | 71.15 | MOL3 | N |
| ATOM | 12404 | CA | ASN | I | 61 | 19.146 | −33.980 | −37.191 | 1.00 | 70.87 | MOL3 | C |
| ATOM | 12405 | CB | ASN | I | 61 | 17.750 | −33.541 | −36.765 | 1.00 | 73.60 | MOL3 | C |
| ATOM | 12406 | CG | ASN | I | 61 | 17.078 | −32.679 | −37.794 | 1.00 | 80.65 | MOL3 | C |
| ATOM | 12407 | OD1 | ASN | I | 61 | 17.360 | −32.791 | −38.986 | 1.00 | 81.99 | MOL3 | O |
| ATOM | 12408 | ND2 | ASN | I | 61 | 16.170 | −31.815 | −37.346 | 1.00 | 85.54 | MOL3 | N |
| ATOM | 12409 | C | ASN | I | 61 | 19.850 | −34.551 | −35.981 | 1.00 | 69.03 | MOL3 | C |
| ATOM | 12410 | O | ASN | I | 61 | 19.536 | −34.189 | −34.853 | 1.00 | 67.81 | MOL3 | O |
| ATOM | 12411 | N | ARG | I | 62 | 20.787 | −35.458 | −36.206 | 1.00 | 69.56 | MOL3 | N |
| ATOM | 12412 | CA | ARG | I | 62 | 21.519 | −36.048 | −35.102 | 1.00 | 69.21 | MOL3 | C |
| ATOM | 12413 | CB | ARG | I | 62 | 20.895 | −37.376 | −34.682 | 1.00 | 74.15 | MOL3 | C |
| ATOM | 12414 | CG | ARG | I | 62 | 21.690 | −38.108 | −33.600 | 1.00 | 76.69 | MOL3 | C |
| ATOM | 12415 | CD | ARG | I | 62 | 21.008 | −39.410 | −33.214 | 1.00 | 75.30 | MOL3 | C |
| ATOM | 12416 | NE | ARG | I | 62 | 20.958 | −40.346 | −34.329 | 1.00 | 71.91 | MOL3 | N |
| ATOM | 12417 | CZ | ARG | I | 62 | 20.201 | −41.436 | −34.355 | 1.00 | 76.00 | MOL3 | C |
| ATOM | 12418 | NH1 | ARG | I | 62 | 19.418 | −41.727 | −33.320 | 1.00 | 82.17 | MOL3 | N |
| ATOM | 12419 | NH2 | ARG | I | 62 | 20.236 | −42.243 | −35.410 | 1.00 | 76.17 | MOL3 | N |
| ATOM | 12420 | C | ARG | I | 62 | 22.967 | −36.269 | −35.466 | 1.00 | 66.94 | MOL3 | C |
| ATOM | 12421 | O | ARG | I | 62 | 23.287 | −36.763 | −36.555 | 1.00 | 70.53 | MOL3 | O |
| ATOM | 12422 | N | TYR | I | 63 | 23.847 | −35.897 | −34.552 | 1.00 | 59.41 | MOL3 | N |
| ATOM | 12423 | CA | TYR | I | 63 | 25.255 | −36.077 | −34.802 | 1.00 | 60.87 | MOL3 | C |
| ATOM | 12424 | CB | TYR | I | 63 | 25.951 | −34.718 | −34.900 | 1.00 | 64.40 | MOL3 | C |
| ATOM | 12425 | CG | TYR | I | 63 | 27.435 | −34.834 | −35.112 | 1.00 | 60.52 | MOL3 | C |
| ATOM | 12426 | CD1 | TYR | I | 63 | 28.307 | −34.775 | −34.041 | 1.00 | 60.25 | MOL3 | C |
| ATOM | 12427 | CE1 | TYR | I | 63 | 29.645 | −34.968 | −34.205 | 1.00 | 64.80 | MOL3 | C |
| ATOM | 12428 | CD2 | TYR | I | 63 | 27.953 | −35.083 | −36.368 | 1.00 | 61.44 | MOL3 | C |
| ATOM | 12429 | CE2 | TYR | I | 63 | 29.298 | −35.280 | −36.546 | 1.00 | 70.48 | MOL3 | C |
| ATOM | 12430 | CZ | TYR | I | 63 | 30.142 | −35.226 | −35.455 | 1.00 | 70.11 | MOL3 | C |
| ATOM | 12431 | OH | TYR | I | 63 | 31.491 | −35.467 | −35.605 | 1.00 | 81.28 | MOL3 | O |
| ATOM | 12432 | C | TYR | I | 63 | 25.851 | −36.918 | −33.697 | 1.00 | 57.17 | MOL3 | C |
| ATOM | 12433 | O | TYR | I | 63 | 25.805 | −36.549 | −32.529 | 1.00 | 59.51 | MOL3 | O |
| ATOM | 12434 | N | PRO | I | 64 | 26.399 | −38.081 | −34.052 | 1.00 | 54.16 | MOL3 | N |
| ATOM | 12435 | CD | PRO | I | 64 | 27.073 | −39.001 | −33.124 | 1.00 | 60.20 | MOL3 | C |
| ATOM | 12436 | CA | PRO | I | 64 | 26.456 | −38.585 | −35.423 | 1.00 | 56.37 | MOL3 | C |
| ATOM | 12437 | CB | PRO | I | 64 | 27.402 | −39.777 | −35.309 | 1.00 | 62.30 | MOL3 | C |
| ATOM | 12438 | CG | PRO | I | 64 | 27.140 | −40.277 | −33.933 | 1.00 | 62.78 | MOL3 | C |
| ATOM | 12439 | C | PRO | I | 64 | 25.081 | −38.973 | −35.959 | 1.00 | 56.35 | MOL3 | C |
| ATOM | 12440 | O | PRO | I | 64 | 24.187 | −39.324 | −35.189 | 1.00 | 47.16 | MOL3 | O |
| ATOM | 12441 | N | SER | I | 65 | 24.925 | −38.902 | −37.282 | 1.00 | 58.87 | MOL3 | N |
| ATOM | 12442 | CA | SER | I | 65 | 23.662 | −39.223 | −37.935 | 1.00 | 58.52 | MOL3 | C |
| ATOM | 12443 | CB | SER | I | 65 | 23.677 | −38.729 | −39.372 | 1.00 | 61.77 | MOL3 | C |
| ATOM | 12444 | OG | SER | I | 65 | 24.803 | −39.262 | −40.056 | 1.00 | 78.46 | MOL3 | O |
| ATOM | 12445 | C | SER | I | 65 | 23.354 | −40.710 | −37.908 | 1.00 | 60.17 | MOL3 | C |
| ATOM | 12446 | O | SER | I | 65 | 22.210 | −41.098 | −37.696 | 1.00 | 61.52 | MOL3 | O |
| ATOM | 12447 | N | GLU | I | 66 | 24.355 | −41.552 | −38.135 | 1.00 | 62.60 | MOL3 | N |

TABLE 1-continued

The atomic coordinates of IL17F in complex with 496 Fab
(H32; a = 189.4; b = 189.4; c = 490.9, α, β = 90°; γ = 120°)

| ATOM | 12448 | CA | GLU | I | 66 | 24.111 | −42.987 | −38.092 | 1.00 | 60.91 | MOL3 | C |
|---|---|---|---|---|---|---|---|---|---|---|---|---|
| ATOM | 12449 | CB | GLU | I | 66 | 24.940 | −43.722 | −39.148 | 1.00 | 69.71 | MOL3 | C |
| ATOM | 12450 | CG | GLU | I | 66 | 24.199 | −43.996 | −40.438 | 1.00 | 87.37 | MOL3 | C |
| ATOM | 12451 | CD | GLU | I | 66 | 25.015 | −44.826 | −41.420 | 1.00 | 101.15 | MOL3 | C |
| ATOM | 12452 | OE1 | GLU | I | 66 | 24.461 | −45.203 | −42.482 | 1.00 | 106.35 | MOL3 | O |
| ATOM | 12453 | OE2 | GLU | I | 66 | 26.207 | −45.099 | −41.131 | 1.00 | 102.75 | MOL3 | O |
| ATOM | 12454 | C | GLU | I | 66 | 24.449 | −43.529 | −36.715 | 1.00 | 57.38 | MOL3 | C |
| ATOM | 12455 | O | GLU | I | 66 | 25.476 | −43.172 | −36.121 | 1.00 | 57.75 | MOL3 | O |
| ATOM | 12456 | N | VAL | I | 67 | 23.562 | −44.366 | −36.192 | 1.00 | 50.57 | MOL3 | N |
| ATOM | 12457 | CA | VAL | I | 67 | 23.791 | −44.995 | −34.896 | 1.00 | 52.97 | MOL3 | C |
| ATOM | 12458 | CB | VAL | I | 67 | 22.824 | −44.501 | −33.808 | 1.00 | 49.35 | MOL3 | C |
| ATOM | 12459 | CG1 | VAL | I | 67 | 23.160 | −45.182 | −32.498 | 1.00 | 45.91 | MOL3 | C |
| ATOM | 12460 | CG2 | VAL | I | 67 | 22.947 | −43.010 | −33.634 | 1.00 | 51.36 | MOL3 | C |
| ATOM | 12461 | C | VAL | I | 67 | 23.585 | −46.489 | −35.074 | 1.00 | 51.44 | MOL3 | C |
| ATOM | 12462 | O | VAL | I | 67 | 22.486 | −46.940 | −35.371 | 1.00 | 41.82 | MOL3 | O |
| ATOM | 12463 | N | VAL | I | 68 | 24.648 | −47.251 | −34.878 | 1.00 | 52.20 | MOL3 | N |
| ATOM | 12464 | CA | VAL | I | 68 | 24.579 | −48.676 | −35.072 | 1.00 | 52.82 | MOL3 | C |
| ATOM | 12465 | CB | VAL | I | 68 | 25.814 | −49.132 | −35.834 | 1.00 | 54.27 | MOL3 | C |
| ATOM | 12466 | CG1 | VAL | I | 68 | 25.583 | −50.485 | −36.462 | 1.00 | 57.06 | MOL3 | C |
| ATOM | 12467 | CG2 | VAL | I | 68 | 26.162 | −48.097 | −36.865 | 1.00 | 53.35 | MOL3 | C |
| ATOM | 12468 | C | VAL | I | 68 | 24.478 | −49.449 | −33.768 | 1.00 | 55.29 | MOL3 | C |
| ATOM | 12469 | O | VAL | I | 68 | 25.310 | −49.277 | −32.867 | 1.00 | 57.52 | MOL3 | O |
| ATOM | 12470 | N | GLN | I | 69 | 23.456 | −50.305 | −33.696 | 1.00 | 51.88 | MOL3 | N |
| ATOM | 12471 | CA | GLN | I | 69 | 23.185 | −51.160 | −32.541 | 1.00 | 46.59 | MOL3 | C |
| ATOM | 12472 | CB | GLN | I | 69 | 21.748 | −50.962 | −32.073 | 1.00 | 37.10 | MOL3 | C |
| ATOM | 12473 | CG | GLN | I | 69 | 21.416 | −49.586 | −31.518 | 1.00 | 40.21 | MOL3 | C |
| ATOM | 12474 | CD | GLN | I | 69 | 21.661 | −49.476 | −30.031 | 1.00 | 45.80 | MOL3 | C |
| ATOM | 12475 | OE1 | GLN | I | 69 | 21.584 | −50.467 | −29.305 | 1.00 | 62.60 | MOL3 | O |
| ATOM | 12476 | NE2 | GLN | I | 69 | 21.930 | −48.268 | −29.561 | 1.00 | 41.98 | MOL3 | N |
| ATOM | 12477 | C | GLN | I | 69 | 23.381 | −52.628 | −32.929 | 1.00 | 48.53 | MOL3 | C |
| ATOM | 12478 | O | GLN | I | 69 | 22.961 | −53.053 | −34.001 | 1.00 | 51.42 | MOL3 | O |
| ATOM | 12479 | N | ALA | I | 70 | 24.012 | −53.398 | −32.050 | 1.00 | 49.34 | MOL3 | N |
| ATOM | 12480 | CA | ALA | I | 70 | 24.258 | −54.813 | −32.301 | 1.00 | 50.49 | MOL3 | C |
| ATOM | 12481 | CB | ALA | I | 70 | 25.625 | −55.183 | −31.774 | 1.00 | 48.62 | MOL3 | C |
| ATOM | 12482 | C | ALA | I | 70 | 23.193 | −55.664 | −31.614 | 1.00 | 53.01 | MOL3 | C |
| ATOM | 12483 | O | ALA | I | 70 | 22.481 | −55.171 | −30.751 | 1.00 | 62.67 | MOL3 | O |
| ATOM | 12484 | N | GLN | I | 71 | 23.088 | −56.938 | −31.986 | 1.00 | 49.41 | MOL3 | N |
| ATOM | 12485 | CA | GLN | I | 71 | 22.113 | −57.850 | −31.383 | 1.00 | 40.42 | MOL3 | C |
| ATOM | 12486 | CB | GLN | I | 71 | 20.849 | −57.890 | −32.222 | 1.00 | 39.93 | MOL3 | C |
| ATOM | 12487 | CG | GLN | I | 71 | 20.362 | −56.569 | −32.754 | 1.00 | 58.72 | MOL3 | C |
| ATOM | 12488 | CD | GLN | I | 71 | 19.086 | −56.745 | −33.573 | 1.00 | 78.54 | MOL3 | C |
| ATOM | 12489 | OE1 | GLN | I | 71 | 19.117 | −57.265 | −34.696 | 1.00 | 83.05 | MOL3 | O |
| ATOM | 12490 | NE2 | GLN | I | 71 | 17.950 | −56.333 | −33.002 | 1.00 | 85.90 | MOL3 | N |
| ATOM | 12491 | C | GLN | I | 71 | 22.694 | −59.258 | −31.376 | 1.00 | 38.43 | MOL3 | C |
| ATOM | 12492 | O | GLN | I | 71 | 22.920 | −59.810 | −32.438 | 1.00 | 42.21 | MOL3 | O |
| ATOM | 12493 | N | CYS | I | 72 | 22.919 | −59.860 | −30.213 | 1.00 | 33.54 | MOL3 | N |
| ATOM | 12494 | CA | CYS | I | 72 | 23.493 | −61.200 | −30.200 | 1.00 | 36.75 | MOL3 | C |
| ATOM | 12495 | C | CYS | I | 72 | 22.672 | −62.169 | −31.069 | 1.00 | 43.44 | MOL3 | C |
| ATOM | 12496 | O | CYS | I | 72 | 21.465 | −62.270 | −30.915 | 1.00 | 43.06 | MOL3 | O |
| ATOM | 12497 | CB | CYS | I | 72 | 23.594 | −61.693 | −28.762 | 1.00 | 38.34 | MOL3 | C |
| ATOM | 12498 | SG | CYS | I | 72 | 24.419 | −60.497 | −27.654 | 1.00 | 51.35 | MOL3 | S |
| ATOM | 12499 | N | ARG | I | 73 | 23.328 | −62.877 | −31.988 | 1.00 | 51.34 | MOL3 | N |
| ATOM | 12500 | CA | ARG | I | 73 | 22.626 | −63.796 | −32.875 | 1.00 | 52.99 | MOL3 | C |
| ATOM | 12501 | CB | ARG | I | 73 | 23.491 | −64.095 | −34.099 | 1.00 | 53.47 | MOL3 | C |
| ATOM | 12502 | CG | ARG | I | 73 | 23.371 | −63.034 | −35.193 | 1.00 | 60.70 | MOL3 | C |
| ATOM | 12503 | CD | ARG | I | 73 | 24.257 | −63.334 | −36.405 | 1.00 | 74.71 | MOL3 | C |
| ATOM | 12504 | NE | ARG | I | 73 | 23.847 | −64.525 | −37.149 | 1.00 | 86.48 | MOL3 | N |
| ATOM | 12505 | CZ | ARG | I | 73 | 22.843 | −64.563 | −38.024 | 1.00 | 93.95 | MOL3 | C |
| ATOM | 12506 | NH1 | ARG | I | 73 | 22.134 | −63.468 | −38.273 | 1.00 | 93.66 | MOL3 | N |
| ATOM | 12507 | NH2 | ARG | I | 73 | 22.548 | −65.698 | −38.654 | 1.00 | 97.47 | MOL3 | N |
| ATOM | 12508 | C | ARG | I | 73 | 22.102 | −65.096 | −32.251 | 1.00 | 57.97 | MOL3 | C |
| ATOM | 12509 | O | ARG | I | 73 | 21.099 | −65.649 | −32.725 | 1.00 | 58.89 | MOL3 | O |
| ATOM | 12510 | N | ASN | I | 74 | 22.752 | −65.582 | −31.195 | 1.00 | 59.16 | MOL3 | N |
| ATOM | 12511 | CA | ASN | I | 74 | 22.302 | −66.808 | −30.534 | 1.00 | 61.20 | MOL3 | C |
| ATOM | 12512 | CB | ASN | I | 74 | 23.227 | −67.983 | −30.874 | 1.00 | 63.33 | MOL3 | C |
| ATOM | 12513 | CG | ASN | I | 74 | 23.230 | −68.319 | −32.355 | 1.00 | 71.09 | MOL3 | C |
| ATOM | 12514 | OD1 | ASN | I | 74 | 24.001 | −67.757 | −33.132 | 1.00 | 76.52 | MOL3 | O |
| ATOM | 12515 | ND2 | ASN | I | 74 | 22.353 | −69.233 | −32.756 | 1.00 | 79.30 | MOL3 | N |
| ATOM | 12516 | C | ASN | I | 74 | 22.258 | −66.640 | −29.023 | 1.00 | 61.32 | MOL3 | C |
| ATOM | 12517 | O | ASN | I | 74 | 22.634 | −65.597 | −28.500 | 1.00 | 63.19 | MOL3 | O |
| ATOM | 12518 | N | LEU | I | 75 | 21.794 | −67.660 | −28.314 | 1.00 | 59.20 | MOL3 | N |
| ATOM | 12519 | CA | LEU | I | 75 | 21.755 | −67.563 | −26.870 | 1.00 | 58.57 | MOL3 | C |
| ATOM | 12520 | CB | LEU | I | 75 | 20.537 | −68.281 | −26.320 | 1.00 | 61.07 | MOL3 | C |
| ATOM | 12521 | CG | LEU | I | 75 | 19.208 | −67.574 | −26.554 | 1.00 | 62.75 | MOL3 | C |
| ATOM | 12522 | CD1 | LEU | I | 75 | 18.094 | −68.272 | −25.784 | 1.00 | 63.42 | MOL3 | C |
| ATOM | 12523 | CD2 | LEU | I | 75 | 19.336 | −66.145 | −26.088 | 1.00 | 69.62 | MOL3 | C |
| ATOM | 12524 | C | LEU | I | 75 | 23.028 | −68.151 | −26.284 | 1.00 | 65.13 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 12525 | O   | LEU | I | 75 | 23.575 | −67.620 | −25.324 | 1.00 | 64.76  | MOL3 | O |
|------|-------|-----|-----|---|----|--------|---------|---------|------|--------|------|---|
| ATOM | 12526 | N   | GLY | I | 76 | 23.502 | −69.251 | −26.863 | 1.00 | 69.53  | MOL3 | N |
| ATOM | 12527 | CA  | GLY | I | 76 | 24.730 | −69.860 | −26.377 | 1.00 | 75.95  | MOL3 | C |
| ATOM | 12528 | C   | GLY | I | 76 | 25.887 | −69.348 | −27.218 | 1.00 | 78.77  | MOL3 | C |
| ATOM | 12529 | O   | GLY | I | 76 | 25.741 | −68.340 | −27.899 | 1.00 | 80.97  | MOL3 | O |
| ATOM | 12530 | N   | CYS | I | 77 | 27.037 | −70.017 | −27.170 | 1.00 | 80.93  | MOL3 | N |
| ATOM | 12531 | CA  | CYS | I | 77 | 28.182 | −69.603 | −27.977 | 1.00 | 80.29  | MOL3 | C |
| ATOM | 12532 | C   | CYS | I | 77 | 28.372 | −70.666 | −29.036 | 1.00 | 82.30  | MOL3 | C |
| ATOM | 12533 | O   | CYS | I | 77 | 27.714 | −71.702 | −29.005 | 1.00 | 85.65  | MOL3 | O |
| ATOM | 12534 | CB  | CYS | I | 77 | 29.436 | −69.457 | −27.114 | 1.00 | 76.04  | MOL3 | C |
| ATOM | 12535 | SG  | CYS | I | 77 | 29.104 | −68.363 | −25.697 | 1.00 | 92.75  | MOL3 | S |
| ATOM | 12536 | N   | ILE | I | 78 | 29.269 | −70.413 | −29.975 | 1.00 | 86.64  | MOL3 | N |
| ATOM | 12537 | CA  | ILE | I | 78 | 29.518 | −71.349 | −31.060 | 1.00 | 91.28  | MOL3 | C |
| ATOM | 12538 | CB  | ILE | I | 78 | 29.297 | −70.624 | −32.385 | 1.00 | 83.06  | MOL3 | C |
| ATOM | 12539 | CG2 | ILE | I | 78 | 29.815 | −71.450 | −33.536 | 1.00 | 81.37  | MOL3 | C |
| ATOM | 12540 | CG1 | ILE | I | 78 | 27.815 | −70.282 | −32.515 | 1.00 | 75.71  | MOL3 | C |
| ATOM | 12541 | CD1 | ILE | I | 78 | 27.472 | −69.576 | −33.795 | 1.00 | 79.68  | MOL3 | C |
| ATOM | 12542 | C   | ILE | I | 78 | 30.921 | −71.973 | −31.023 | 1.00 | 100.86 | MOL3 | C |
| ATOM | 12543 | O   | ILE | I | 78 | 31.894 | −71.298 | −30.694 | 1.00 | 102.48 | MOL3 | O |
| ATOM | 12544 | N   | ASN | I | 79 | 31.018 | −73.262 | −31.351 | 1.00 | 111.20 | MOL3 | N |
| ATOM | 12545 | CA  | ASN | I | 79 | 32.303 | −73.962 | −31.356 | 1.00 | 121.64 | MOL3 | C |
| ATOM | 12546 | CB  | ASN | I | 79 | 32.139 | −75.397 | −30.839 | 1.00 | 129.98 | MOL3 | C |
| ATOM | 12547 | CG  | ASN | I | 79 | 32.170 | −75.485 | −29.314 | 1.00 | 139.44 | MOL3 | C |
| ATOM | 12548 | OD1 | ASN | I | 79 | 33.107 | −75.005 | −28.667 | 1.00 | 142.26 | MOL3 | O |
| ATOM | 12549 | ND2 | ASN | I | 79 | 31.148 | −76.111 | −28.737 | 1.00 | 142.57 | MOL3 | N |
| ATOM | 12550 | C   | ASN | I | 79 | 32.934 | −74.003 | −32.746 | 1.00 | 123.95 | MOL3 | C |
| ATOM | 12551 | O   | ASN | I | 79 | 32.720 | −73.106 | −33.562 | 1.00 | 123.14 | MOL3 | O |
| ATOM | 12552 | N   | ALA | I | 80 | 33.724 | −75.044 | −32.997 | 1.00 | 127.12 | MOL3 | N |
| ATOM | 12553 | CA  | ALA | I | 80 | 34.384 | −75.220 | −34.285 | 1.00 | 131.19 | MOL3 | C |
| ATOM | 12554 | CB  | ALA | I | 80 | 35.306 | −76.430 | −34.238 | 1.00 | 130.77 | MOL3 | C |
| ATOM | 12555 | C   | ALA | I | 80 | 33.308 | −75.412 | −35.348 | 1.00 | 133.79 | MOL3 | C |
| ATOM | 12556 | O   | ALA | I | 80 | 33.173 | −76.490 | −35.933 | 1.00 | 130.81 | MOL3 | O |
| ATOM | 12557 | N   | GLN | I | 81 | 32.546 | −74.347 | −35.582 | 1.00 | 137.91 | MOL3 | N |
| ATOM | 12558 | CA  | GLN | I | 81 | 31.453 | −74.349 | −36.545 | 1.00 | 141.10 | MOL3 | C |
| ATOM | 12559 | CB  | GLN | I | 81 | 31.984 | −74.637 | −37.957 | 1.00 | 144.01 | MOL3 | C |
| ATOM | 12560 | CG  | GLN | I | 81 | 32.170 | −73.385 | −38.827 | 1.00 | 146.30 | MOL3 | C |
| ATOM | 12561 | CD  | GLN | I | 81 | 33.159 | −72.368 | −38.252 | 1.00 | 148.19 | MOL3 | C |
| ATOM | 12562 | OE1 | GLN | I | 81 | 33.254 | −71.239 | −38.741 | 1.00 | 147.01 | MOL3 | O |
| ATOM | 12563 | NE2 | GLN | I | 81 | 33.900 | −72.767 | −37.221 | 1.00 | 146.34 | MOL3 | N |
| ATOM | 12564 | C   | GLN | I | 81 | 30.416 | −75.388 | −36.130 | 1.00 | 139.64 | MOL3 | C |
| ATOM | 12565 | O   | GLN | I | 81 | 29.576 | −75.802 | −36.927 | 1.00 | 140.30 | MOL3 | O |
| ATOM | 12566 | N   | GLY | I | 82 | 30.473 | −75.783 | −34.861 | 1.00 | 137.81 | MOL3 | N |
| ATOM | 12567 | CA  | GLY | I | 82 | 29.551 | −76.784 | −34.354 | 1.00 | 135.11 | MOL3 | C |
| ATOM | 12568 | C   | GLY | I | 82 | 28.377 | −76.274 | −33.539 | 1.00 | 129.16 | MOL3 | C |
| ATOM | 12569 | O   | GLY | I | 82 | 28.085 | −76.804 | −32.471 | 1.00 | 130.23 | MOL3 | O |
| ATOM | 12570 | N   | LYS | I | 83 | 27.694 | −75.258 | −34.050 | 1.00 | 122.11 | MOL3 | N |
| ATOM | 12571 | CA  | LYS | I | 83 | 26.539 | −74.677 | −33.375 | 1.00 | 117.25 | MOL3 | C |
| ATOM | 12572 | CB  | LYS | I | 83 | 25.254 | −75.436 | −33.743 | 1.00 | 121.48 | MOL3 | C |
| ATOM | 12573 | CG  | LYS | I | 83 | 24.451 | −74.758 | −34.864 | 1.00 | 128.67 | MOL3 | C |
| ATOM | 12574 | CD  | LYS | I | 83 | 23.099 | −75.426 | −35.132 | 1.00 | 129.79 | MOL3 | C |
| ATOM | 12575 | CE  | LYS | I | 83 | 22.257 | −74.616 | −36.129 | 1.00 | 128.95 | MOL3 | C |
| ATOM | 12576 | NZ  | LYS | I | 83 | 21.875 | −73.259 | −35.619 | 1.00 | 124.03 | MOL3 | N |
| ATOM | 12577 | C   | LYS | I | 83 | 26.619 | −74.518 | −31.856 | 1.00 | 112.18 | MOL3 | C |
| ATOM | 12578 | O   | LYS | I | 83 | 27.612 | −74.877 | −31.215 | 1.00 | 106.52 | MOL3 | O |
| ATOM | 12579 | N   | GLU | I | 84 | 25.539 | −73.963 | −31.308 | 1.00 | 108.47 | MOL3 | N |
| ATOM | 12580 | CA  | GLU | I | 84 | 25.384 | −73.651 | −29.889 | 1.00 | 102.61 | MOL3 | C |
| ATOM | 12581 | CB  | GLU | I | 84 | 23.899 | −73.403 | −29.565 | 1.00 | 104.06 | MOL3 | C |
| ATOM | 12582 | CG  | GLU | I | 84 | 23.277 | −72.227 | −30.315 | 1.00 | 110.83 | MOL3 | C |
| ATOM | 12583 | CD  | GLU | I | 84 | 21.986 | −71.716 | −29.684 | 1.00 | 115.94 | MOL3 | C |
| ATOM | 12584 | OE1 | GLU | I | 84 | 22.013 | −71.322 | −28.499 | 1.00 | 114.28 | MOL3 | O |
| ATOM | 12585 | OE2 | GLU | I | 84 | 20.945 | −71.696 | −30.376 | 1.00 | 122.04 | MOL3 | O |
| ATOM | 12586 | C   | GLU | I | 84 | 25.945 | −74.621 | −28.867 | 1.00 | 97.07  | MOL3 | C |
| ATOM | 12587 | O   | GLU | I | 84 | 26.056 | −75.816 | −29.115 | 1.00 | 101.79 | MOL3 | O |
| ATOM | 12588 | N   | ASP | I | 85 | 26.291 | −74.075 | −27.709 | 1.00 | 86.77  | MOL3 | N |
| ATOM | 12589 | CA  | ASP | I | 85 | 26.805 | −74.843 | −26.594 | 1.00 | 80.76  | MOL3 | C |
| ATOM | 12590 | CB  | ASP | I | 85 | 28.328 | −74.821 | −26.583 | 1.00 | 88.70  | MOL3 | C |
| ATOM | 12591 | CG  | ASP | I | 85 | 28.916 | −75.526 | −25.363 | 1.00 | 100.36 | MOL3 | C |
| ATOM | 12592 | OD1 | ASP | I | 85 | 30.156 | −75.709 | −25.315 | 1.00 | 105.99 | MOL3 | O |
| ATOM | 12593 | OD2 | ASP | I | 85 | 28.141 | −75.894 | −24.451 | 1.00 | 101.76 | MOL3 | O |
| ATOM | 12594 | C   | ASP | I | 85 | 26.270 | −74.110 | −25.389 | 1.00 | 76.14  | MOL3 | C |
| ATOM | 12595 | O   | ASP | I | 85 | 27.017 | −73.467 | −24.671 | 1.00 | 76.99  | MOL3 | O |
| ATOM | 12596 | N   | ILE | I | 86 | 24.969 | −74.212 | −25.161 | 1.00 | 73.75  | MOL3 | N |
| ATOM | 12597 | CA  | ILE | I | 86 | 24.359 | −73.487 | −24.060 | 1.00 | 72.05  | MOL3 | C |
| ATOM | 12598 | CB  | ILE | I | 86 | 22.878 | −73.808 | −23.919 | 1.00 | 74.81  | MOL3 | C |
| ATOM | 12599 | CG2 | ILE | I | 86 | 22.090 | −72.495 | −24.005 | 1.00 | 65.53  | MOL3 | C |
| ATOM | 12600 | CG1 | ILE | I | 86 | 22.437 | −74.793 | −25.013 | 1.00 | 78.50  | MOL3 | C |
| ATOM | 12601 | CD1 | ILE | I | 86 | 21.899 | −74.141 | −26.301 | 1.00 | 81.27  | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 12602 | C | ILE | I | 86 | 25.025 | −73.598 | −22.698 | 1.00 | 71.80 | MOL3 | C |
|---|---|---|---|---|---|---|---|---|---|---|---|---|
| ATOM | 12603 | O | ILE | I | 86 | 24.589 | −72.958 | −21.741 | 1.00 | 67.43 | MOL3 | O |
| ATOM | 12604 | N | SER | I | 87 | 26.083 | −74.397 | −22.610 | 1.00 | 73.02 | MOL3 | N |
| ATOM | 12605 | CA | SER | I | 87 | 26.836 | −74.532 | −21.368 | 1.00 | 73.89 | MOL3 | C |
| ATOM | 12606 | CB | SER | I | 87 | 28.135 | −75.314 | −21.632 | 1.00 | 74.46 | MOL3 | C |
| ATOM | 12607 | OG | SER | I | 87 | 28.957 | −75.400 | −20.477 | 1.00 | 81.93 | MOL3 | O |
| ATOM | 12608 | C | SER | I | 87 | 27.163 | −73.103 | −20.929 | 1.00 | 73.31 | MOL3 | C |
| ATOM | 12609 | O | SER | I | 87 | 27.107 | −72.767 | −19.743 | 1.00 | 72.96 | MOL3 | O |
| ATOM | 12610 | N | MET | I | 88 | 27.505 | −72.276 | −21.919 | 1.00 | 74.81 | MOL3 | N |
| ATOM | 12611 | CA | MET | I | 88 | 27.844 | −70.857 | −21.741 | 1.00 | 70.38 | MOL3 | C |
| ATOM | 12612 | CB | MET | I | 88 | 29.305 | −70.574 | −22.080 | 1.00 | 74.17 | MOL3 | C |
| ATOM | 12613 | CG | MET | I | 88 | 30.330 | −71.152 | −21.147 | 1.00 | 81.15 | MOL3 | C |
| ATOM | 12614 | SD | MET | I | 88 | 31.915 | −71.043 | −21.968 | 1.00 | 89.06 | MOL3 | S |
| ATOM | 12615 | CE | MET | I | 88 | 31.469 | −71.803 | −23.597 | 1.00 | 70.24 | MOL3 | C |
| ATOM | 12616 | C | MET | I | 88 | 27.018 | −70.075 | −22.740 | 1.00 | 64.86 | MOL3 | C |
| ATOM | 12617 | O | MET | I | 88 | 26.720 | −70.569 | −23.825 | 1.00 | 63.49 | MOL3 | O |
| ATOM | 12618 | N | ASN | I | 89 | 26.661 | −68.848 | −22.397 | 1.00 | 58.50 | MOL3 | N |
| ATOM | 12619 | CA | ASN | I | 89 | 25.880 | −68.057 | −23.325 | 1.00 | 55.53 | MOL3 | C |
| ATOM | 12620 | CB | ASN | I | 89 | 24.555 | −67.628 | −22.706 | 1.00 | 53.36 | MOL3 | C |
| ATOM | 12621 | CG | ASN | I | 89 | 24.358 | −68.176 | −21.329 | 1.00 | 60.59 | MOL3 | C |
| ATOM | 12622 | OD1 | ASN | I | 89 | 24.825 | −67.608 | −20.328 | 1.00 | 66.90 | MOL3 | O |
| ATOM | 12623 | ND2 | ASN | I | 89 | 23.668 | −69.301 | −21.257 | 1.00 | 62.81 | MOL3 | N |
| ATOM | 12624 | C | ASN | I | 89 | 26.624 | −66.827 | −23.783 | 1.00 | 53.09 | MOL3 | C |
| ATOM | 12625 | O | ASN | I | 89 | 27.581 | −66.389 | −23.149 | 1.00 | 53.14 | MOL3 | O |
| ATOM | 12626 | N | SER | I | 90 | 26.162 | −66.284 | −24.902 | 1.00 | 49.09 | MOL3 | N |
| ATOM | 12627 | CA | SER | I | 90 | 26.725 | −65.083 | −25.485 | 1.00 | 45.65 | MOL3 | C |
| ATOM | 12628 | CB | SER | I | 90 | 26.618 | −65.145 | −26.997 | 1.00 | 47.24 | MOL3 | C |
| ATOM | 12629 | OG | SER | I | 90 | 25.265 | −65.214 | −27.378 | 1.00 | 52.52 | MOL3 | O |
| ATOM | 12630 | C | SER | I | 90 | 25.903 | −63.917 | −24.986 | 1.00 | 42.91 | MOL3 | C |
| ATOM | 12631 | O | SER | I | 90 | 24.685 | −63.965 | −25.010 | 1.00 | 42.52 | MOL3 | O |
| ATOM | 12632 | N | VAL | I | 91 | 26.563 | −62.861 | −24.543 | 1.00 | 47.63 | MOL3 | N |
| ATOM | 12633 | CA | VAL | I | 91 | 25.847 | −61.697 | −24.037 | 1.00 | 50.80 | MOL3 | C |
| ATOM | 12634 | CB | VAL | I | 91 | 25.992 | −61.626 | −22.520 | 1.00 | 50.09 | MOL3 | C |
| ATOM | 12635 | CG1 | VAL | I | 91 | 25.693 | −62.988 | −21.937 | 1.00 | 52.59 | MOL3 | C |
| ATOM | 12636 | CG2 | VAL | I | 91 | 27.388 | −61.185 | −22.150 | 1.00 | 49.22 | MOL3 | C |
| ATOM | 12637 | C | VAL | I | 91 | 26.295 | −60.369 | −24.668 | 1.00 | 48.91 | MOL3 | C |
| ATOM | 12638 | O | VAL | I | 91 | 27.444 | −60.208 | −25.076 | 1.00 | 48.59 | MOL3 | O |
| ATOM | 12639 | N | PRO | I | 92 | 25.382 | −59.393 | −24.738 | 1.00 | 47.27 | MOL3 | N |
| ATOM | 12640 | CD | PRO | I | 92 | 24.039 | −59.367 | −24.130 | 1.00 | 50.11 | MOL3 | C |
| ATOM | 12641 | CA | PRO | I | 92 | 25.686 | −58.093 | −25.320 | 1.00 | 47.17 | MOL3 | C |
| ATOM | 12642 | CB | PRO | I | 92 | 24.312 | −57.459 | −25.445 | 1.00 | 43.77 | MOL3 | C |
| ATOM | 12643 | CG | PRO | I | 92 | 23.671 | −57.885 | −24.194 | 1.00 | 41.60 | MOL3 | C |
| ATOM | 12644 | C | PRO | I | 92 | 26.580 | −57.252 | −24.442 | 1.00 | 47.20 | MOL3 | C |
| ATOM | 12645 | O | PRO | I | 92 | 26.537 | −57.365 | −23.220 | 1.00 | 36.30 | MOL3 | O |
| ATOM | 12646 | N | ILE | I | 93 | 27.379 | −56.407 | −25.092 | 1.00 | 54.33 | MOL3 | N |
| ATOM | 12647 | CA | ILE | I | 93 | 28.262 | −55.461 | −24.416 | 1.00 | 58.28 | MOL3 | C |
| ATOM | 12648 | CB | ILE | I | 93 | 29.698 | −55.563 | −24.892 | 1.00 | 59.93 | MOL3 | C |
| ATOM | 12649 | CG2 | ILE | I | 93 | 30.502 | −54.448 | −24.287 | 1.00 | 60.89 | MOL3 | C |
| ATOM | 12650 | CG1 | ILE | I | 93 | 30.290 | −56.893 | −24.456 | 1.00 | 63.13 | MOL3 | C |
| ATOM | 12651 | CD1 | ILE | I | 93 | 31.745 | −57.019 | −24.789 | 1.00 | 73.89 | MOL3 | C |
| ATOM | 12652 | C | ILE | I | 93 | 27.724 | −54.087 | −24.795 | 1.00 | 54.71 | MOL3 | C |
| ATOM | 12653 | O | ILE | I | 93 | 27.652 | −53.741 | −25.975 | 1.00 | 48.66 | MOL3 | O |
| ATOM | 12654 | N | GLN | I | 94 | 27.340 | −53.308 | −23.794 | 1.00 | 50.70 | MOL3 | N |
| ATOM | 12655 | CA | GLN | I | 94 | 26.762 | −52.009 | −24.069 | 1.00 | 54.91 | MOL3 | C |
| ATOM | 12656 | CB | GLN | I | 94 | 25.367 | −51.937 | −23.464 | 1.00 | 50.69 | MOL3 | C |
| ATOM | 12657 | CG | GLN | I | 94 | 24.405 | −52.955 | −24.040 | 1.00 | 49.22 | MOL3 | C |
| ATOM | 12658 | CD | GLN | I | 94 | 23.249 | −53.248 | −23.107 | 1.00 | 50.77 | MOL3 | C |
| ATOM | 12659 | OE1 | GLN | I | 94 | 22.247 | −53.833 | −23.508 | 1.00 | 57.54 | MOL3 | O |
| ATOM | 12660 | NE2 | GLN | I | 94 | 23.390 | −52.854 | −21.850 | 1.00 | 48.35 | MOL3 | N |
| ATOM | 12661 | C | GLN | I | 94 | 27.598 | −50.854 | −23.566 | 1.00 | 60.57 | MOL3 | C |
| ATOM | 12662 | O | GLN | I | 94 | 28.312 | −50.972 | −22.573 | 1.00 | 69.65 | MOL3 | O |
| ATOM | 12663 | N | GLN | I | 95 | 27.503 | −49.730 | −24.264 | 1.00 | 60.06 | MOL3 | N |
| ATOM | 12664 | CA | GLN | I | 95 | 28.251 | −48.539 | −23.905 | 1.00 | 60.79 | MOL3 | C |
| ATOM | 12665 | CB | GLN | I | 95 | 29.437 | −48.361 | −24.856 | 1.00 | 66.04 | MOL3 | C |
| ATOM | 12666 | CG | GLN | I | 95 | 30.196 | −47.060 | −24.673 | 1.00 | 83.53 | MOL3 | C |
| ATOM | 12667 | CD | GLN | I | 95 | 30.731 | −46.903 | −23.258 | 1.00 | 95.07 | MOL3 | C |
| ATOM | 12668 | OE1 | GLN | I | 95 | 31.208 | −45.828 | −22.868 | 1.00 | 96.45 | MOL3 | O |
| ATOM | 12669 | NE2 | GLN | I | 95 | 30.658 | −47.981 | −22.480 | 1.00 | 98.63 | MOL3 | N |
| ATOM | 12670 | C | GLN | I | 95 | 27.332 | −47.339 | −24.011 | 1.00 | 61.87 | MOL3 | C |
| ATOM | 12671 | O | GLN | I | 95 | 26.599 | −47.206 | −24.995 | 1.00 | 57.72 | MOL3 | O |
| ATOM | 12672 | N | GLU | I | 96 | 27.349 | −46.478 | −22.997 | 1.00 | 61.98 | MOL3 | N |
| ATOM | 12673 | CA | GLU | I | 96 | 26.510 | −45.292 | −23.039 | 1.00 | 65.81 | MOL3 | C |
| ATOM | 12674 | CB | GLU | I | 96 | 26.145 | −44.818 | −21.625 | 1.00 | 78.65 | MOL3 | C |
| ATOM | 12675 | CG | GLU | I | 96 | 27.317 | −44.392 | −20.736 | 1.00 | 102.84 | MOL3 | C |
| ATOM | 12676 | CD | GLU | I | 96 | 27.760 | −42.943 | −20.959 | 1.00 | 111.84 | MOL3 | C |
| ATOM | 12677 | OE1 | GLU | I | 96 | 28.603 | −42.446 | −20.171 | 1.00 | 115.81 | MOL3 | O |
| ATOM | 12678 | OE2 | GLU | I | 96 | 27.270 | −42.303 | −21.918 | 1.00 | 114.58 | MOL3 | O |

TABLE 1-continued

The atomic coordinates of IL17F in complex with 496 Fab
(H32; a = 189.4; b = 189.4; c = 490.9, α, β = 90°; γ = 120°)

| ATOM | 12679 | C | GLU | I | 96 | 27.291 | −44.234 | −23.797 | 1.00 | 59.47 | MOL3 | C |
| ATOM | 12680 | O | GLU | I | 96 | 28.472 | −44.014 | −23.545 | 1.00 | 52.75 | MOL3 | O |
| ATOM | 12681 | N | THR | I | 97 | 26.630 | −43.600 | −24.754 | 1.00 | 57.04 | MOL3 | N |
| ATOM | 12682 | CA | THR | I | 97 | 27.271 | −42.586 | −25.563 | 1.00 | 59.66 | MOL3 | C |
| ATOM | 12683 | CB | THR | I | 97 | 27.456 | −43.061 | −27.012 | 1.00 | 63.08 | MOL3 | C |
| ATOM | 12684 | OG1 | THR | I | 97 | 27.994 | −41.991 | −27.807 | 1.00 | 75.09 | MOL3 | O |
| ATOM | 12685 | CG2 | THR | I | 97 | 26.132 | −43.476 | −27.600 | 1.00 | 50.30 | MOL3 | C |
| ATOM | 12686 | C | THR | I | 97 | 26.451 | −41.318 | −25.619 | 1.00 | 60.19 | MOL3 | C |
| ATOM | 12687 | O | THR | I | 97 | 25.284 | −41.305 | −25.246 | 1.00 | 59.18 | MOL3 | O |
| ATOM | 12688 | N | LEU | I | 98 | 27.074 | −40.256 | −26.114 | 1.00 | 58.80 | MOL3 | N |
| ATOM | 12689 | CA | LEU | I | 98 | 26.417 | −38.976 | −26.254 | 1.00 | 52.73 | MOL3 | C |
| ATOM | 12690 | CB | LEU | I | 98 | 27.294 | −37.890 | −25.671 | 1.00 | 54.84 | MOL3 | C |
| ATOM | 12691 | CG | LEU | I | 98 | 26.509 | −36.935 | −24.800 | 1.00 | 56.72 | MOL3 | C |
| ATOM | 12692 | CD1 | LEU | I | 98 | 25.325 | −37.702 | −24.277 | 1.00 | 60.24 | MOL3 | C |
| ATOM | 12693 | CD2 | LEU | I | 98 | 27.382 | −36.386 | −23.660 | 1.00 | 47.65 | MOL3 | C |
| ATOM | 12694 | C | LEU | I | 98 | 26.195 | −38.698 | −27.721 | 1.00 | 56.10 | MOL3 | C |
| ATOM | 12695 | O | LEU | I | 98 | 26.981 | −39.116 | −28.576 | 1.00 | 61.32 | MOL3 | O |
| ATOM | 12696 | N | VAL | I | 99 | 25.108 | −38.008 | −28.016 | 1.00 | 55.60 | MOL3 | N |
| ATOM | 12697 | CA | VAL | I | 99 | 24.800 | −37.643 | −29.393 | 1.00 | 59.48 | MOL3 | C |
| ATOM | 12698 | CB | VAL | I | 99 | 23.783 | −38.589 | −30.029 | 1.00 | 52.31 | MOL3 | C |
| ATOM | 12699 | CG1 | VAL | I | 99 | 24.341 | −39.985 | −30.065 | 1.00 | 46.88 | MOL3 | C |
| ATOM | 12700 | CG2 | VAL | I | 99 | 22.475 | −38.512 | −29.267 | 1.00 | 43.72 | MOL3 | C |
| ATOM | 12701 | C | VAL | I | 99 | 24.180 | −36.263 | −29.306 | 1.00 | 63.19 | MOL3 | C |
| ATOM | 12702 | O | VAL | I | 99 | 23.772 | −35.841 | −28.229 | 1.00 | 64.00 | MOL3 | O |
| ATOM | 12703 | N | VAL | I | 100 | 24.113 | −35.544 | −30.417 | 1.00 | 64.84 | MOL3 | N |
| ATOM | 12704 | CA | VAL | I | 100 | 23.516 | −34.230 | −30.349 | 1.00 | 64.62 | MOL3 | C |
| ATOM | 12705 | CB | VAL | I | 100 | 24.520 | −33.140 | −30.701 | 1.00 | 66.60 | MOL3 | C |
| ATOM | 12706 | CG1 | VAL | I | 100 | 23.852 | −31.780 | −30.594 | 1.00 | 59.29 | MOL3 | C |
| ATOM | 12707 | CG2 | VAL | I | 100 | 25.724 | −33.234 | −29.767 | 1.00 | 65.89 | MOL3 | C |
| ATOM | 12708 | C | VAL | I | 100 | 22.319 | −34.126 | −31.259 | 1.00 | 69.08 | MOL3 | C |
| ATOM | 12709 | O | VAL | I | 100 | 22.312 | −34.691 | −32.364 | 1.00 | 68.87 | MOL3 | O |
| ATOM | 12710 | N | ARG | I | 101 | 21.295 | −33.429 | −30.763 | 1.00 | 71.73 | MOL3 | N |
| ATOM | 12711 | CA | ARG | I | 101 | 20.058 | −33.213 | −31.508 | 1.00 | 79.13 | MOL3 | C |
| ATOM | 12712 | CB | ARG | I | 101 | 18.830 | −33.495 | −30.651 | 1.00 | 73.61 | MOL3 | C |
| ATOM | 12713 | CG | ARG | I | 101 | 18.430 | −34.937 | −30.677 | 1.00 | 82.98 | MOL3 | C |
| ATOM | 12714 | CD | ARG | I | 101 | 16.944 | −35.123 | −30.463 | 1.00 | 92.97 | MOL3 | C |
| ATOM | 12715 | NE | ARG | I | 101 | 16.550 | −36.484 | −30.810 | 1.00 | 103.33 | MOL3 | N |
| ATOM | 12716 | CZ | ARG | I | 101 | 16.804 | −37.055 | −31.986 | 1.00 | 108.63 | MOL3 | C |
| ATOM | 12717 | NH1 | ARG | I | 101 | 17.448 | −36.379 | −32.931 | 1.00 | 110.19 | MOL3 | N |
| ATOM | 12718 | NH2 | ARG | I | 101 | 16.426 | −38.308 | −32.219 | 1.00 | 113.00 | MOL3 | N |
| ATOM | 12719 | C | ARG | I | 101 | 19.978 | −31.789 | −32.004 | 1.00 | 84.87 | MOL3 | C |
| ATOM | 12720 | O | ARG | I | 101 | 20.271 | −30.854 | −31.267 | 1.00 | 84.77 | MOL3 | O |
| ATOM | 12721 | N | ARG | I | 102 | 19.580 | −31.638 | −33.261 | 1.00 | 91.94 | MOL3 | N |
| ATOM | 12722 | CA | ARG | I | 102 | 19.451 | −30.335 | −33.890 | 1.00 | 99.79 | MOL3 | C |
| ATOM | 12723 | CB | ARG | I | 102 | 19.955 | −30.409 | −35.339 | 1.00 | 104.81 | MOL3 | C |
| ATOM | 12724 | CG | ARG | I | 102 | 19.914 | −29.096 | −36.111 | 1.00 | 112.01 | MOL3 | C |
| ATOM | 12725 | CD | ARG | I | 102 | 20.666 | −29.184 | −37.445 | 1.00 | 118.63 | MOL3 | C |
| ATOM | 12726 | NE | ARG | I | 102 | 19.903 | −29.846 | −38.504 | 1.00 | 127.04 | MOL3 | N |
| ATOM | 12727 | CZ | ARG | I | 102 | 20.370 | −30.068 | −39.732 | 1.00 | 131.04 | MOL3 | C |
| ATOM | 12728 | NH1 | ARG | I | 102 | 21.601 | −29.683 | −40.051 | 1.00 | 133.41 | MOL3 | N |
| ATOM | 12729 | NH2 | ARG | I | 102 | 19.609 | −30.664 | −40.646 | 1.00 | 128.01 | MOL3 | N |
| ATOM | 12730 | C | ARG | I | 102 | 17.976 | −29.971 | −33.864 | 1.00 | 105.49 | MOL3 | C |
| ATOM | 12731 | O | ARG | I | 102 | 17.241 | −30.310 | −34.788 | 1.00 | 109.22 | MOL3 | O |
| ATOM | 12732 | N | LYS | I | 103 | 17.545 | −29.291 | −32.802 | 1.00 | 111.48 | MOL3 | N |
| ATOM | 12733 | CA | LYS | I | 103 | 16.146 | −28.885 | −32.643 | 1.00 | 117.54 | MOL3 | C |
| ATOM | 12734 | CB | LYS | I | 103 | 15.833 | −28.638 | −31.160 | 1.00 | 114.22 | MOL3 | C |
| ATOM | 12735 | CG | LYS | I | 103 | 15.448 | −29.891 | −30.377 | 1.00 | 117.65 | MOL3 | C |
| ATOM | 12736 | CD | LYS | I | 103 | 15.551 | −29.689 | −28.866 | 1.00 | 120.97 | MOL3 | C |
| ATOM | 12737 | CE | LYS | I | 103 | 14.681 | −28.538 | −28.376 | 1.00 | 128.40 | MOL3 | C |
| ATOM | 12738 | NZ | LYS | I | 103 | 14.856 | −28.264 | −26.912 | 1.00 | 132.06 | MOL3 | N |
| ATOM | 12739 | C | LYS | I | 103 | 15.766 | −27.644 | −33.451 | 1.00 | 123.80 | MOL3 | C |
| ATOM | 12740 | O | LYS | I | 103 | 16.535 | −26.684 | −33.532 | 1.00 | 123.83 | MOL3 | O |
| ATOM | 12741 | N | HIS | I | 104 | 14.571 | −27.673 | −34.041 | 1.00 | 130.52 | MOL3 | N |
| ATOM | 12742 | CA | HIS | I | 104 | 14.047 | −26.564 | −34.845 | 1.00 | 134.60 | MOL3 | C |
| ATOM | 12743 | CB | HIS | I | 104 | 14.198 | −25.242 | −34.097 | 1.00 | 130.27 | MOL3 | C |
| ATOM | 12744 | CG | HIS | I | 104 | 13.721 | −25.292 | −32.684 | 1.00 | 128.01 | MOL3 | C |
| ATOM | 12745 | CD2 | HIS | I | 104 | 12.613 | −25.843 | −32.136 | 1.00 | 128.00 | MOL3 | C |
| ATOM | 12746 | ND1 | HIS | I | 104 | 14.426 | −24.728 | −31.644 | 1.00 | 128.90 | MOL3 | N |
| ATOM | 12747 | CE1 | HIS | I | 104 | 13.774 | −24.931 | −30.513 | 1.00 | 129.69 | MOL3 | C |
| ATOM | 12748 | NE2 | HIS | I | 104 | 12.670 | −25.605 | −30.784 | 1.00 | 129.66 | MOL3 | N |
| ATOM | 12749 | C | HIS | I | 104 | 14.737 | −26.432 | −36.199 | 1.00 | 139.28 | MOL3 | C |
| ATOM | 12750 | O | HIS | I | 104 | 15.706 | −27.138 | −36.492 | 1.00 | 139.83 | MOL3 | O |
| ATOM | 12751 | N | GLN | I | 105 | 14.238 | −25.501 | −37.011 | 1.00 | 142.80 | MOL3 | N |
| ATOM | 12752 | CA | GLN | I | 105 | 14.777 | −25.262 | −38.347 | 1.00 | 145.64 | MOL3 | C |
| ATOM | 12753 | CB | GLN | I | 105 | 13.723 | −25.624 | −39.406 | 1.00 | 147.69 | MOL3 | C |
| ATOM | 12754 | CG | GLN | I | 105 | 13.031 | −26.985 | −39.232 | 1.00 | 151.62 | MOL3 | C |
| ATOM | 12755 | CD | GLN | I | 105 | 11.997 | −27.015 | −38.106 | 1.00 | 152.19 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 12756 | OE1 | GLN | I | 105 | 11.128 | −26.144 | −38.018 | 1.00 | 153.16 | MOL3 | O |
|---|---|---|---|---|---|---|---|---|---|---|---|---|
| ATOM | 12757 | NE2 | GLN | I | 105 | 12.078 | −28.035 | −37.251 | 1.00 | 150.44 | MOL3 | N |
| ATOM | 12758 | C | GLN | I | 105 | 15.187 | −23.799 | −38.550 | 1.00 | 145.76 | MOL3 | C |
| ATOM | 12759 | O | GLN | I | 105 | 14.914 | −22.940 | −37.708 | 1.00 | 145.60 | MOL3 | O |
| ATOM | 12760 | N | GLY | I | 106 | 15.839 | −23.529 | −39.679 | 1.00 | 145.04 | MOL3 | N |
| ATOM | 12761 | CA | GLY | I | 106 | 16.251 | −22.174 | −40.002 | 1.00 | 144.36 | MOL3 | C |
| ATOM | 12762 | C | GLY | I | 106 | 17.161 | −21.468 | −39.013 | 1.00 | 143.06 | MOL3 | C |
| ATOM | 12763 | O | GLY | I | 106 | 18.148 | −22.034 | −38.552 | 1.00 | 142.81 | MOL3 | O |
| ATOM | 12764 | N | CYS | I | 107 | 16.815 | −20.221 | −38.699 | 1.00 | 142.79 | MOL3 | N |
| ATOM | 12765 | CA | CYS | I | 107 | 17.573 | −19.367 | −37.780 | 1.00 | 143.20 | MOL3 | C |
| ATOM | 12766 | C | CYS | I | 107 | 17.387 | −19.764 | −36.331 | 1.00 | 140.21 | MOL3 | C |
| ATOM | 12767 | O | CYS | I | 107 | 18.243 | −19.505 | −35.482 | 1.00 | 138.31 | MOL3 | O |
| ATOM | 12768 | CB | CYS | I | 107 | 17.098 | −17.915 | −37.891 | 1.00 | 148.55 | MOL3 | C |
| ATOM | 12769 | SG | CYS | I | 107 | 17.213 | −17.129 | −39.526 | 1.00 | 155.31 | MOL3 | S |
| ATOM | 12770 | N | SER | I | 108 | 16.234 | −20.351 | −36.050 | 1.00 | 138.28 | MOL3 | N |
| ATOM | 12771 | CA | SER | I | 108 | 15.896 | −20.757 | −34.694 | 1.00 | 138.03 | MOL3 | C |
| ATOM | 12772 | CB | SER | I | 108 | 14.376 | −20.692 | −34.511 | 1.00 | 138.19 | MOL3 | C |
| ATOM | 12773 | OG | SER | I | 108 | 13.704 | −21.114 | −35.689 | 1.00 | 138.08 | MOL3 | O |
| ATOM | 12774 | C | SER | I | 108 | 16.422 | −22.147 | −34.338 | 1.00 | 136.26 | MOL3 | C |
| ATOM | 12775 | O | SER | I | 108 | 15.731 | −22.939 | −33.695 | 1.00 | 137.24 | MOL3 | O |
| ATOM | 12776 | N | VAL | I | 109 | 17.661 | −22.422 | −34.734 | 1.00 | 132.37 | MOL3 | N |
| ATOM | 12777 | CA | VAL | I | 109 | 18.282 | −23.717 | −34.484 | 1.00 | 126.45 | MOL3 | C |
| ATOM | 12778 | CB | VAL | I | 109 | 19.198 | −24.112 | −35.670 | 1.00 | 125.21 | MOL3 | C |
| ATOM | 12779 | CG1 | VAL | I | 109 | 20.443 | −23.251 | −35.675 | 1.00 | 126.29 | MOL3 | C |
| ATOM | 12780 | CG2 | VAL | I | 109 | 19.562 | −25.574 | −35.588 | 1.00 | 127.65 | MOL3 | C |
| ATOM | 12781 | C | VAL | I | 109 | 19.085 | −23.796 | −33.179 | 1.00 | 123.63 | MOL3 | C |
| ATOM | 12782 | O | VAL | I | 109 | 19.935 | −22.946 | −32.890 | 1.00 | 120.91 | MOL3 | O |
| ATOM | 12783 | N | SER | I | 110 | 18.796 | −24.832 | −32.395 | 1.00 | 119.29 | MOL3 | N |
| ATOM | 12784 | CA | SER | I | 110 | 19.472 | −25.071 | −31.125 | 1.00 | 112.29 | MOL3 | C |
| ATOM | 12785 | CB | SER | I | 110 | 18.498 | −24.893 | −29.965 | 1.00 | 112.58 | MOL3 | C |
| ATOM | 12786 | OG | SER | I | 110 | 17.440 | −25.831 | −30.066 | 1.00 | 113.59 | MOL3 | O |
| ATOM | 12787 | C | SER | I | 110 | 19.986 | −26.500 | −31.121 | 1.00 | 107.33 | MOL3 | C |
| ATOM | 12788 | O | SER | I | 110 | 19.546 | −27.326 | −31.921 | 1.00 | 108.34 | MOL3 | O |
| ATOM | 12789 | N | PHE | I | 111 | 20.911 | −26.793 | −30.216 | 1.00 | 98.83 | MOL3 | N |
| ATOM | 12790 | CA | PHE | I | 111 | 21.464 | −28.130 | −30.125 | 1.00 | 91.59 | MOL3 | C |
| ATOM | 12791 | CB | PHE | I | 111 | 22.898 | −28.120 | −30.609 | 1.00 | 88.41 | MOL3 | C |
| ATOM | 12792 | CG | PHE | I | 111 | 23.027 | −27.698 | −32.027 | 1.00 | 88.39 | MOL3 | C |
| ATOM | 12793 | CD1 | PHE | I | 111 | 22.015 | −27.971 | −32.925 | 1.00 | 87.43 | MOL3 | C |
| ATOM | 12794 | CD2 | PHE | I | 111 | 24.159 | −27.059 | −32.478 | 1.00 | 91.02 | MOL3 | C |
| ATOM | 12795 | CE1 | PHE | I | 111 | 22.124 | −27.620 | −34.242 | 1.00 | 87.09 | MOL3 | C |
| ATOM | 12796 | CE2 | PHE | I | 111 | 24.276 | −26.703 | −33.805 | 1.00 | 94.27 | MOL3 | C |
| ATOM | 12797 | CZ | PHE | I | 111 | 23.255 | −26.985 | −34.688 | 1.00 | 92.34 | MOL3 | C |
| ATOM | 12798 | C | PHE | I | 111 | 21.392 | −28.668 | −28.716 | 1.00 | 89.67 | MOL3 | C |
| ATOM | 12799 | O | PHE | I | 111 | 21.721 | −27.966 | −27.768 | 1.00 | 89.13 | MOL3 | O |
| ATOM | 12800 | N | GLN | I | 112 | 20.948 | −29.913 | −28.576 | 1.00 | 88.62 | MOL3 | N |
| ATOM | 12801 | CA | GLN | I | 112 | 20.847 | −30.521 | −27.257 | 1.00 | 85.20 | MOL3 | C |
| ATOM | 12802 | CB | GLN | I | 112 | 19.372 | −30.648 | −26.857 | 1.00 | 82.76 | MOL3 | C |
| ATOM | 12803 | CG | GLN | I | 112 | 19.162 | −30.717 | −25.349 | 1.00 | 88.40 | MOL3 | C |
| ATOM | 12804 | CD | GLN | I | 112 | 17.699 | −30.676 | −24.935 | 1.00 | 88.82 | MOL3 | C |
| ATOM | 12805 | OE1 | GLN | I | 112 | 17.387 | −30.631 | −23.742 | 1.00 | 88.63 | MOL3 | O |
| ATOM | 12806 | NE2 | GLN | I | 112 | 16.797 | −30.693 | −25.913 | 1.00 | 86.67 | MOL3 | N |
| ATOM | 12807 | C | GLN | I | 112 | 21.569 | −31.885 | −27.191 | 1.00 | 84.79 | MOL3 | C |
| ATOM | 12808 | O | GLN | I | 112 | 21.588 | −32.649 | −28.169 | 1.00 | 86.05 | MOL3 | O |
| ATOM | 12809 | N | LEU | I | 113 | 22.176 | −32.165 | −26.038 | 1.00 | 77.59 | MOL3 | N |
| ATOM | 12810 | CA | LEU | I | 113 | 22.919 | −33.406 | −25.806 | 1.00 | 74.68 | MOL3 | C |
| ATOM | 12811 | CB | LEU | I | 113 | 23.962 | −33.178 | −24.715 | 1.00 | 72.42 | MOL3 | C |
| ATOM | 12812 | CG | LEU | I | 113 | 25.416 | −33.002 | −25.129 | 1.00 | 71.48 | MOL3 | C |
| ATOM | 12813 | CD1 | LEU | I | 113 | 25.477 | −32.150 | −26.365 | 1.00 | 73.62 | MOL3 | C |
| ATOM | 12814 | CD2 | LEU | I | 113 | 26.203 | −32.377 | −23.994 | 1.00 | 66.43 | MOL3 | C |
| ATOM | 12815 | C | LEU | I | 113 | 22.063 | −34.597 | −25.384 | 1.00 | 74.82 | MOL3 | C |
| ATOM | 12816 | O | LEU | I | 113 | 21.606 | −34.647 | −24.251 | 1.00 | 75.69 | MOL3 | O |
| ATOM | 12817 | N | GLU | I | 114 | 21.864 | −35.564 | −26.275 | 1.00 | 77.60 | MOL3 | N |
| ATOM | 12818 | CA | GLU | I | 114 | 21.078 | −36.751 | −25.943 | 1.00 | 76.36 | MOL3 | C |
| ATOM | 12819 | CB | GLU | I | 114 | 20.248 | −37.208 | −27.150 | 1.00 | 82.69 | MOL3 | C |
| ATOM | 12820 | CG | GLU | I | 114 | 19.266 | −38.351 | −26.848 | 1.00 | 93.78 | MOL3 | C |
| ATOM | 12821 | CD | GLU | I | 114 | 18.228 | −38.572 | −27.959 | 1.00 | 99.06 | MOL3 | C |
| ATOM | 12822 | OE1 | GLU | I | 114 | 18.585 | −39.083 | −29.045 | 1.00 | 98.43 | MOL3 | O |
| ATOM | 12823 | OE2 | GLU | I | 114 | 17.045 | −38.224 | −27.741 | 1.00 | 103.13 | MOL3 | O |
| ATOM | 12824 | C | GLU | I | 114 | 22.028 | −37.864 | −25.521 | 1.00 | 73.47 | MOL3 | C |
| ATOM | 12825 | O | GLU | I | 114 | 23.185 | −37.906 | −25.961 | 1.00 | 73.93 | MOL3 | O |
| ATOM | 12826 | N | LYS | I | 115 | 21.541 | −38.761 | −24.670 | 1.00 | 66.56 | MOL3 | N |
| ATOM | 12827 | CA | LYS | I | 115 | 22.353 | −39.878 | −24.195 | 1.00 | 65.32 | MOL3 | C |
| ATOM | 12828 | CB | LYS | I | 115 | 22.391 | −39.872 | −22.669 | 1.00 | 60.03 | MOL3 | C |
| ATOM | 12829 | CG | LYS | I | 115 | 23.354 | −40.869 | −22.059 | 1.00 | 68.17 | MOL3 | C |
| ATOM | 12830 | CD | LYS | I | 115 | 24.048 | −40.283 | −20.821 | 1.00 | 73.57 | MOL3 | C |
| ATOM | 12831 | CE | LYS | I | 115 | 25.054 | −41.260 | −20.196 | 1.00 | 76.98 | MOL3 | C |
| ATOM | 12832 | NZ | LYS | I | 115 | 25.885 | −40.647 | −19.107 | 1.00 | 76.99 | MOL3 | N |

TABLE 1-continued

The atomic coordinates of IL17F in complex with 496 Fab
(H32; a = 189.4; b = 189.4; c = 490.9, α, β = 90°; γ = 120°)

| ATOM | 12833 | C   | LYS | I | 115 | 21.770 | −41.194 | −24.700 | 1.00 | 65.75 | MOL3 | C |
|------|-------|-----|-----|---|-----|--------|---------|---------|------|-------|------|---|
| ATOM | 12834 | O   | LYS | I | 115 | 20.613 | −41.495 | −24.433 | 1.00 | 73.64 | MOL3 | O |
| ATOM | 12835 | N   | VAL | I | 116 | 22.541 | −41.976 | −25.449 | 1.00 | 63.54 | MOL3 | N |
| ATOM | 12836 | CA  | VAL | I | 116 | 22.005 | −43.244 | −25.931 | 1.00 | 60.63 | MOL3 | C |
| ATOM | 12837 | CB  | VAL | I | 116 | 21.817 | −43.260 | −27.455 | 1.00 | 56.29 | MOL3 | C |
| ATOM | 12838 | CG1 | VAL | I | 116 | 20.851 | −42.186 | −27.852 | 1.00 | 58.71 | MOL3 | C |
| ATOM | 12839 | CG2 | VAL | I | 116 | 23.122 | −43.055 | −28.150 | 1.00 | 61.08 | MOL3 | C |
| ATOM | 12840 | C   | VAL | I | 116 | 22.843 | −44.434 | −25.521 | 1.00 | 61.46 | MOL3 | C |
| ATOM | 12841 | O   | VAL | I | 116 | 24.073 | −44.355 | −25.443 | 1.00 | 64.32 | MOL3 | O |
| ATOM | 12842 | N   | LEU | I | 117 | 22.160 | −45.534 | −25.230 | 1.00 | 59.90 | MOL3 | N |
| ATOM | 12843 | CA  | LEU | I | 117 | 22.843 | −46.747 | −24.827 | 1.00 | 59.20 | MOL3 | C |
| ATOM | 12844 | CB  | LEU | I | 117 | 22.076 | −47.484 | −23.743 | 1.00 | 59.79 | MOL3 | C |
| ATOM | 12845 | CG  | LEU | I | 117 | 23.098 | −48.056 | −22.763 | 1.00 | 64.44 | MOL3 | C |
| ATOM | 12846 | CD1 | LEU | I | 117 | 23.577 | −46.912 | −21.850 | 1.00 | 63.43 | MOL3 | C |
| ATOM | 12847 | CD2 | LEU | I | 117 | 22.502 | −49.200 | −21.964 | 1.00 | 60.66 | MOL3 | C |
| ATOM | 12848 | C   | LEU | I | 117 | 22.952 | −47.630 | −26.046 | 1.00 | 57.49 | MOL3 | C |
| ATOM | 12849 | O   | LEU | I | 117 | 21.944 | −47.996 | −26.653 | 1.00 | 55.99 | MOL3 | O |
| ATOM | 12850 | N   | VAL | I | 118 | 24.181 | −47.982 | −26.387 | 1.00 | 52.58 | MOL3 | N |
| ATOM | 12851 | CA  | VAL | I | 118 | 24.427 | −48.784 | −27.563 | 1.00 | 53.37 | MOL3 | C |
| ATOM | 12852 | CB  | VAL | I | 118 | 25.419 | −48.063 | −28.487 | 1.00 | 54.52 | MOL3 | C |
| ATOM | 12853 | CG1 | VAL | I | 118 | 25.492 | −48.767 | −29.825 | 1.00 | 60.80 | MOL3 | C |
| ATOM | 12854 | CG2 | VAL | I | 118 | 25.032 | −46.622 | −28.643 | 1.00 | 52.59 | MOL3 | C |
| ATOM | 12855 | C   | VAL | I | 118 | 25.001 | −50.160 | −27.289 | 1.00 | 53.89 | MOL3 | C |
| ATOM | 12856 | O   | VAL | I | 118 | 25.858 | −50.346 | −26.419 | 1.00 | 54.34 | MOL3 | O |
| ATOM | 12857 | N   | THR | I | 119 | 24.536 | −51.120 | −28.067 | 1.00 | 51.05 | MOL3 | N |
| ATOM | 12858 | CA  | THR | I | 119 | 25.013 | −52.472 | −27.956 | 1.00 | 54.15 | MOL3 | C |
| ATOM | 12859 | CB  | THR | I | 119 | 23.935 | −53.438 | −28.368 | 1.00 | 55.88 | MOL3 | C |
| ATOM | 12860 | OG1 | THR | I | 119 | 22.716 | −53.099 | −27.694 | 1.00 | 56.94 | MOL3 | O |
| ATOM | 12861 | CG2 | THR | I | 119 | 24.356 | −54.845 | −28.021 | 1.00 | 60.72 | MOL3 | C |
| ATOM | 12862 | C   | THR | I | 119 | 26.137 | −52.552 | −28.966 | 1.00 | 54.71 | MOL3 | C |
| ATOM | 12863 | O   | THR | I | 119 | 25.888 | −52.667 | −30.167 | 1.00 | 56.60 | MOL3 | O |
| ATOM | 12864 | N   | VAL | I | 120 | 27.373 | −52.488 | −28.492 | 1.00 | 52.53 | MOL3 | N |
| ATOM | 12865 | CA  | VAL | I | 120 | 28.488 | −52.538 | −29.408 | 1.00 | 48.66 | MOL3 | C |
| ATOM | 12866 | CB  | VAL | I | 120 | 29.710 | −51.959 | −28.760 | 1.00 | 44.49 | MOL3 | C |
| ATOM | 12867 | CG1 | VAL | I | 120 | 30.676 | −51.549 | −29.819 | 1.00 | 56.06 | MOL3 | C |
| ATOM | 12868 | CG2 | VAL | I | 120 | 29.325 | −50.775 | −27.933 | 1.00 | 34.75 | MOL3 | C |
| ATOM | 12869 | C   | VAL | I | 120 | 28.790 | −53.929 | −29.967 | 1.00 | 52.06 | MOL3 | C |
| ATOM | 12870 | O   | VAL | I | 120 | 29.355 | −54.041 | −31.055 | 1.00 | 53.88 | MOL3 | O |
| ATOM | 12871 | N   | GLY | I | 121 | 28.400 | −54.979 | −29.237 | 1.00 | 58.06 | MOL3 | N |
| ATOM | 12872 | CA  | GLY | I | 121 | 28.622 | −56.350 | −29.692 | 1.00 | 56.05 | MOL3 | C |
| ATOM | 12873 | C   | GLY | I | 121 | 28.391 | −57.392 | −28.610 | 1.00 | 53.74 | MOL3 | C |
| ATOM | 12874 | O   | GLY | I | 121 | 27.944 | −57.068 | −27.511 | 1.00 | 54.78 | MOL3 | O |
| ATOM | 12875 | N   | CYS | I | 122 | 28.702 | −58.648 | −28.901 | 1.00 | 48.59 | MOL3 | N |
| ATOM | 12876 | CA  | CYS | I | 122 | 28.511 | −59.690 | −27.909 | 1.00 | 48.40 | MOL3 | C |
| ATOM | 12877 | C   | CYS | I | 122 | 29.792 | −60.428 | −27.578 | 1.00 | 50.48 | MOL3 | C |
| ATOM | 12878 | O   | CYS | I | 122 | 30.716 | −60.498 | −28.380 | 1.00 | 56.16 | MOL3 | O |
| ATOM | 12879 | CB  | CYS | I | 122 | 27.431 | −60.652 | −28.381 | 1.00 | 49.75 | MOL3 | C |
| ATOM | 12880 | SG  | CYS | I | 122 | 25.924 | −59.722 | −28.788 | 1.00 | 53.34 | MOL3 | S |
| ATOM | 12881 | N   | THR | I | 123 | 29.847 | −60.958 | −26.369 | 1.00 | 50.67 | MOL3 | N |
| ATOM | 12882 | CA  | THR | I | 123 | 31.010 | −61.679 | −25.905 | 1.00 | 50.35 | MOL3 | C |
| ATOM | 12883 | CB  | THR | I | 123 | 31.755 | −60.859 | −24.858 | 1.00 | 48.34 | MOL3 | C |
| ATOM | 12884 | OG1 | THR | I | 123 | 32.900 | −61.583 | −24.393 | 1.00 | 58.31 | MOL3 | O |
| ATOM | 12885 | CG2 | THR | I | 123 | 30.845 | −60.575 | −23.699 | 1.00 | 43.06 | MOL3 | C |
| ATOM | 12886 | C   | THR | I | 123 | 30.494 | −62.953 | −25.272 | 1.00 | 52.98 | MOL3 | C |
| ATOM | 12887 | O   | THR | I | 123 | 29.433 | −62.957 | −24.659 | 1.00 | 49.33 | MOL3 | O |
| ATOM | 12888 | N   | CYS | I | 124 | 31.242 | −64.038 | −25.418 | 1.00 | 58.71 | MOL3 | N |
| ATOM | 12889 | CA  | CYS | I | 124 | 30.816 | −65.302 | −24.850 | 1.00 | 61.53 | MOL3 | C |
| ATOM | 12890 | C   | CYS | I | 124 | 31.202 | −65.460 | −23.391 | 1.00 | 59.84 | MOL3 | C |
| ATOM | 12891 | O   | CYS | I | 124 | 32.380 | −65.512 | −23.071 | 1.00 | 63.22 | MOL3 | O |
| ATOM | 12892 | CB  | CYS | I | 124 | 31.410 | −66.450 | −25.631 | 1.00 | 66.83 | MOL3 | C |
| ATOM | 12893 | SG  | CYS | I | 124 | 30.908 | −67.986 | −24.839 | 1.00 | 78.44 | MOL3 | S |
| ATOM | 12894 | N   | VAL | I | 125 | 30.216 | −65.547 | −22.507 | 1.00 | 61.41 | MOL3 | N |
| ATOM | 12895 | CA  | VAL | I | 125 | 30.498 | −65.695 | −21.084 | 1.00 | 61.67 | MOL3 | C |
| ATOM | 12896 | CB  | VAL | I | 125 | 29.886 | −64.548 | −20.263 | 1.00 | 58.41 | MOL3 | C |
| ATOM | 12897 | CG1 | VAL | I | 125 | 30.311 | −64.662 | −18.819 | 1.00 | 61.93 | MOL3 | C |
| ATOM | 12898 | CG2 | VAL | I | 125 | 30.320 | −63.240 | −20.812 | 1.00 | 58.88 | MOL3 | C |
| ATOM | 12899 | C   | VAL | I | 125 | 29.987 | −67.007 | −20.491 | 1.00 | 62.73 | MOL3 | C |
| ATOM | 12900 | O   | VAL | I | 125 | 29.107 | −67.670 | −21.046 | 1.00 | 62.50 | MOL3 | O |
| ATOM | 12901 | N   | THR | I | 126 | 30.566 | −67.372 | −19.356 | 1.00 | 61.71 | MOL3 | N |
| ATOM | 12902 | CA  | THR | I | 126 | 30.190 | −68.573 | −18.649 | 1.00 | 65.19 | MOL3 | C |
| ATOM | 12903 | CB  | THR | I | 126 | 31.439 | −69.374 | −18.196 | 1.00 | 70.00 | MOL3 | C |
| ATOM | 12904 | OG1 | THR | I | 126 | 31.059 | −70.336 | −17.204 | 1.00 | 78.86 | MOL3 | O |
| ATOM | 12905 | CG2 | THR | I | 126 | 32.493 | −68.448 | −17.609 | 1.00 | 74.14 | MOL3 | C |
| ATOM | 12906 | C   | THR | I | 126 | 29.394 | −68.127 | −17.433 | 1.00 | 61.85 | MOL3 | C |
| ATOM | 12907 | O   | THR | I | 126 | 29.855 | −67.309 | −16.639 | 1.00 | 58.44 | MOL3 | O |
| ATOM | 12908 | N   | PRO | I | 127 | 28.169 | −68.642 | −17.288 | 1.00 | 61.14 | MOL3 | N |
| ATOM | 12909 | CD  | PRO | I | 127 | 27.499 | −69.689 | −18.074 | 1.00 | 58.06 | MOL3 | C |

TABLE 1-continued

The atomic coordinates of IL17F in complex with 496 Fab
(H32; a = 189.4; b = 189.4; c = 490.9, α, β = 90°; γ = 120°)

| ATOM | 12910 | CA  | PRO | I | 127 | 27.360 | −68.252 | −16.139 | 1.00 | 61.92  | MOL3 | C |
|------|-------|-----|-----|---|-----|--------|---------|---------|------|--------|------|---|
| ATOM | 12911 | CB  | PRO | I | 127 | 26.121 | −69.131 | −16.279 | 1.00 | 61.05  | MOL3 | C |
| ATOM | 12912 | CG  | PRO | I | 127 | 26.625 | −70.320 | −17.045 | 1.00 | 59.93  | MOL3 | C |
| ATOM | 12913 | C   | PRO | I | 127 | 28.122 | −68.496 | −14.851 | 1.00 | 63.96  | MOL3 | C |
| ATOM | 12914 | O   | PRO | I | 127 | 29.046 | −69.310 | −14.813 | 1.00 | 63.82  | MOL3 | O |
| ATOM | 12915 | N   | VAL | I | 128 | 27.760 | −67.765 | −13.803 | 1.00 | 67.46  | MOL3 | N |
| ATOM | 12916 | CA  | VAL | I | 128 | 28.418 | −67.942 | −12.517 | 1.00 | 74.09  | MOL3 | C |
| ATOM | 12917 | CB  | VAL | I | 128 | 28.223 | −66.690 | −11.592 | 1.00 | 67.87  | MOL3 | C |
| ATOM | 12918 | CG1 | VAL | I | 128 | 26.783 | −66.274 | −11.554 | 1.00 | 69.54  | MOL3 | C |
| ATOM | 12919 | CG2 | VAL | I | 128 | 28.694 | −66.985 | −10.198 | 1.00 | 62.25  | MOL3 | C |
| ATOM | 12920 | C   | VAL | I | 128 | 27.841 | −69.204 | −11.880 | 1.00 | 84.32  | MOL3 | C |
| ATOM | 12921 | O   | VAL | I | 128 | 26.761 | −69.187 | −11.293 | 1.00 | 88.97  | MOL3 | O |
| ATOM | 12922 | N   | ILE | I | 129 | 28.555 | −70.315 | −12.030 | 1.00 | 94.72  | MOL3 | N |
| ATOM | 12923 | CA  | ILE | I | 129 | 28.099 | −71.587 | −11.479 | 1.00 | 103.85 | MOL3 | C |
| ATOM | 12924 | CB  | ILE | I | 129 | 28.755 | −72.784 | −12.216 | 1.00 | 102.83 | MOL3 | C |
| ATOM | 12925 | CG2 | ILE | I | 129 | 28.240 | −74.096 | −11.640 | 1.00 | 102.03 | MOL3 | C |
| ATOM | 12926 | CG1 | ILE | I | 129 | 28.453 | −72.704 | −13.721 | 1.00 | 103.88 | MOL3 | C |
| ATOM | 12927 | CD1 | ILE | I | 129 | 29.165 | −73.757 | −14.581 | 1.00 | 99.35  | MOL3 | C |
| ATOM | 12928 | C   | ILE | I | 129 | 28.439 | −71.665 | −9.995  | 1.00 | 111.48 | MOL3 | C |
| ATOM | 12929 | O   | ILE | I | 129 | 27.850 | −72.457 | −9.256  | 1.00 | 113.95 | MOL3 | O |
| ATOM | 12930 | N   | HIS | I | 130 | 29.373 | −70.817 | −9.566  | 1.00 | 118.09 | MOL3 | N |
| ATOM | 12931 | CA  | HIS | I | 130 | 29.833 | −70.772 | −8.179  | 1.00 | 123.91 | MOL3 | C |
| ATOM | 12932 | CB  | HIS | I | 130 | 30.581 | −69.464 | −7.923  | 1.00 | 124.74 | MOL3 | C |
| ATOM | 12933 | CG  | HIS | I | 130 | 31.614 | −69.160 | −8.961  | 1.00 | 125.86 | MOL3 | C |
| ATOM | 12934 | CD2 | HIS | I | 130 | 32.190 | −67.994 | −9.336  | 1.00 | 126.62 | MOL3 | C |
| ATOM | 12935 | ND1 | HIS | I | 130 | 32.167 | −70.136 | −9.763  | 1.00 | 125.37 | MOL3 | N |
| ATOM | 12936 | CE1 | HIS | I | 130 | 33.036 | −69.583 | −10.589 | 1.00 | 127.54 | MOL3 | C |
| ATOM | 12937 | NE2 | HIS | I | 130 | 33.069 | −68.284 | −10.351 | 1.00 | 129.23 | MOL3 | N |
| ATOM | 12938 | C   | HIS | I | 130 | 28.733 | −70.954 | −7.144  | 1.00 | 127.61 | MOL3 | C |
| ATOM | 12939 | O   | HIS | I | 130 | 28.085 | −69.987 | −6.725  | 1.00 | 123.05 | MOL3 | O |
| ATOM | 12940 | N   | HIS | I | 131 | 28.554 | −72.215 | −6.744  | 1.00 | 134.09 | MOL3 | N |
| ATOM | 12941 | CA  | HIS | I | 131 | 27.558 | −72.646 | −5.761  | 1.00 | 139.89 | MOL3 | C |
| ATOM | 12942 | CB  | HIS | I | 131 | 28.219 | −72.781 | −4.381  | 1.00 | 142.14 | MOL3 | C |
| ATOM | 12943 | CG  | HIS | I | 131 | 27.313 | −73.340 | −3.326  | 1.00 | 146.96 | MOL3 | C |
| ATOM | 12944 | CD2 | HIS | I | 131 | 27.059 | −72.932 | −2.060  | 1.00 | 148.14 | MOL3 | C |
| ATOM | 12945 | ND1 | HIS | I | 131 | 26.543 | −74.466 | −3.527  | 1.00 | 148.76 | MOL3 | N |
| ATOM | 12946 | CE1 | HIS | I | 131 | 25.854 | −74.728 | −2.430  | 1.00 | 148.98 | MOL3 | C |
| ATOM | 12947 | NE2 | HIS | I | 131 | 26.149 | −73.812 | −1.525  | 1.00 | 149.64 | MOL3 | N |
| ATOM | 12948 | C   | HIS | I | 131 | 26.328 | −71.737 | −5.674  | 1.00 | 141.32 | MOL3 | C |
| ATOM | 12949 | O   | HIS | I | 131 | 25.507 | −71.683 | −6.597  | 1.00 | 141.72 | MOL3 | O |
| ATOM | 12950 | N   | VAL | I | 132 | 26.201 | −71.037 | −4.552  | 1.00 | 139.78 | MOL3 | N |
| ATOM | 12951 | CA  | VAL | I | 132 | 25.090 | −70.126 | −4.335  | 1.00 | 137.25 | MOL3 | C |
| ATOM | 12952 | CB  | VAL | I | 132 | 24.201 | −70.599 | −3.158  | 1.00 | 136.71 | MOL3 | C |
| ATOM | 12953 | CG1 | VAL | I | 132 | 23.127 | −69.569 | −2.861  | 1.00 | 136.10 | MOL3 | C |
| ATOM | 12954 | CG2 | VAL | I | 132 | 23.550 | −71.934 | −3.507  | 1.00 | 135.48 | MOL3 | C |
| ATOM | 12955 | C   | VAL | I | 132 | 25.675 | −68.750 | −4.041  | 1.00 | 136.90 | MOL3 | C |
| ATOM | 12956 | O   | VAL | I | 132 | 25.031 | −67.730 | −4.281  | 1.00 | 140.65 | MOL3 | O |
| ATOM | 12957 | N   | GLN | I | 133 | 26.904 | −68.727 | −3.528  | 1.00 | 134.50 | MOL3 | N |
| ATOM | 12958 | CA  | GLN | I | 133 | 27.590 | −67.470 | −3.236  | 1.00 | 131.12 | MOL3 | C |
| ATOM | 12959 | CB  | GLN | I | 133 | 28.826 | −67.713 | −2.347  | 1.00 | 127.09 | MOL3 | C |
| ATOM | 12960 | CG  | GLN | I | 133 | 29.634 | −68.970 | −2.689  | 1.00 | 122.98 | MOL3 | C |
| ATOM | 12961 | CD  | GLN | I | 133 | 31.021 | −68.986 | −2.056  | 1.00 | 118.67 | MOL3 | C |
| ATOM | 12962 | OE1 | GLN | I | 133 | 31.950 | −68.339 | −2.548  | 1.00 | 114.83 | MOL3 | O |
| ATOM | 12963 | NE2 | GLN | I | 133 | 31.165 | −69.724 | −0.956  | 1.00 | 114.69 | MOL3 | N |
| ATOM | 12964 | C   | GLN | I | 133 | 28.006 | −66.794 | −4.551  | 1.00 | 131.31 | MOL3 | C |
| ATOM | 12965 | O   | GLN | I | 133 | 27.812 | −65.561 | −4.667  | 1.00 | 130.65 | MOL3 | O |
| ATOM | 12966 | OXT | GLN | I | 133 | 28.520 | −67.505 | −5.451  | 1.00 | 129.17 | MOL3 | O |
| END  |       |     |     |   |     |        |         |         |      |        |      |   |

In further aspect there is provided a crystal structure comprising an epitope as defined herein.

Also provided is a method of generating a three dimensional computer representation employing 10, 20, 30, 40, 50, 60, 70, 80, 90 or 100% of co-ordinates listed in Table 1.

In one embodiment there is provided a machine readable mediume having stored thereon data comprising 10, 20, 30, 40, 50, 60, 70, 80, 90 or 100% of co-ordinates listed in Table 1.

It will of course be understood that the present invention has been described by way of example only, is in no way meant to be limiting, and that modifications of detail can be made within the scope of the claims hereinafter. Preferred features of each embodiment of the invention are as for each of the other embodiments mutatis mutandis. All publications, including but not limited to patents and patent applications, cited in this specification are herein incorporated by reference as if each individual publication were specifically and individually indicated to be incorporated by reference herein as though fully set forth.

The invention claimed is:

1. A method of treating inflammation associated with an IL-17A mediated pathological condition in a mammal comprising the step of administering to the mammal an effective amount of a pharmaceutical composition comprising a monoclonal antibody that specifically binds an epitope of human IL-17A, wherein the epitope comprises residues TYR44, ASN45, TRP51, ASN52 and ASP84 of SEQ ID NO: 21, and wherein the monoclonal antibody additionally binds human IL-17F.

2. A method of treating inflammation associated with an IL-17A mediated pathological condition in a mammal comprising administering to the mammal an effective amount of a pharmaceutical composition comprising a chimeric or humanized antibody that specifically binds an epitope of human IL-17A, wherein the epitope comprises residues TYR44, ASN45, TRP51, ASN52, and ASP84 of SEQ ID NO: 21, and wherein the chimeric or humanized antibody additionally binds human IL-17F.

3. The method of claim 2, wherein the epitope further comprises one or more of the residues selected from the group consisting of SER41, ARG46, HIS54, ARG72, HIS73, HIS86, VAL128, HIS129 and VAL131 of SEQ ID NO: 21.

4. The method of claim 2, wherein the epitope does not comprise one or more of the amino acid residues selected from the group consisting of ASP80, GLY81 and ASN82 of SEQ ID NO:21.

5. The method of claim 2, wherein the antibody has a binding affinity for human IL-17A of better than 500 pM.

6. The method of claim 2, wherein the pharmaceutical composition further comprises one or more of pharmaceutically acceptable excipients, diluents or carriers.

7. The method of claim 2, wherein inflammation associated with an IL-17A mediated pathological condition is reduced, wherein the IL-17A mediated pathological condition is selected from the group consisting of arthritis, rheumatoid arthritis, asthma, pelvic inflammatory disease, Crohn's disease, inflammatory bowel disease, ulcerative colitis, Peyronie's disease, coeliac disease, gallbladder disease, Pilonidal disease, peritonitis, psoriasis, vasculitis, surgical adhesions, stroke, Type I Diabetes, lyme arthritis, multiple sclerosis, Guillain-Barr syndrome, pancreatitis, trauma associated with surgery, graft-versus-host disease, transplant rejection, myocardial-infarction, atherosclerosis, intravascular coagulation, bone resorption, osteoporosis, periodontitis, hypochlorhydia, pain, inflammatory disease and autoimmune disease.

\* \* \* \* \*

SEQUENCE LISTING

<160> NUMBER OF SEQ ID NOS: 24

<210> SEQ ID NO 1
<211> LENGTH: 10
<212> TYPE: PRT
<213> ORGANISM: Artificial sequence
<220> FEATURE:
<223> OTHER INFORMATION: derived from Rattus

<400> SEQUENCE: 1

Gly Phe Thr Phe Ser Asp Tyr Asn Met Ala
1               5                   10

<210> SEQ ID NO 2
<211> LENGTH: 17
<212> TYPE: PRT
<213> ORGANISM: Artificial sequence
<220> FEATURE:
<223> OTHER INFORMATION: derived from Rattus

<400> SEQUENCE: 2

Thr Ile Thr Tyr Glu Gly Arg Asn Thr Tyr Tyr Arg Asp Ser Val Lys
1               5                   10                  15

Gly

<210> SEQ ID NO 3
<211> LENGTH: 16
<212> TYPE: PRT
<213> ORGANISM: Artificial sequence
<220> FEATURE:
<223> OTHER INFORMATION: derived from Rattus

<400> SEQUENCE: 3

Pro Pro Gln Tyr Tyr Glu Gly Ser Ile Tyr Arg Leu Trp Phe Ala His
1               5                   10                  15

<210> SEQ ID NO 4
<211> LENGTH: 11
<212> TYPE: PRT
<213> ORGANISM: Artificial sequence
<220> FEATURE:
<223> OTHER INFORMATION: derived from Rattus

<400> SEQUENCE: 4

Arg Ala Asp Glu Ser Val Thr Thr Leu Met His
1               5                   10

<210> SEQ ID NO 5
<211> LENGTH: 7
<212> TYPE: PRT
<213> ORGANISM: Artificial sequence
<220> FEATURE:
<223> OTHER INFORMATION: derived from Rattus

<400> SEQUENCE: 5

Leu Val Ser Asn Arg Glu Ser
1               5

<210> SEQ ID NO 6
<211> LENGTH: 9
<212> TYPE: PRT
<213> ORGANISM: Artificial sequence
<220> FEATURE:
<223> OTHER INFORMATION: derived from Rattus

<400> SEQUENCE: 6

```
Gln Gln Thr Trp Ser Asp Pro Trp Thr
1               5
```

<210> SEQ ID NO 7
<211> LENGTH: 108
<212> TYPE: PRT
<213> ORGANISM: Artificial sequence
<220> FEATURE:
<223> OTHER INFORMATION: CDRs derived from Rattus

<400> SEQUENCE: 7

```
Ala Ile Gln Leu Thr Gln Ser Pro Ser Ser Leu Ser Ala Ser Val Gly
1               5                   10                  15

Asp Arg Val Thr Ile Thr Cys Arg Ala Asp Glu Ser Val Thr Thr Leu
            20                  25                  30

Met His Trp Tyr Gln Gln Lys Pro Gly Lys Ala Pro Lys Leu Leu Ile
        35                  40                  45

Tyr Leu Val Ser Asn Arg Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Trp Ser Asp Pro Trp
                85                  90                  95

Thr Phe Gly Gln Gly Thr Lys Val Glu Ile Lys Arg
            100                 105
```

<210> SEQ ID NO 8
<211> LENGTH: 4
<212> TYPE: PRT
<213> ORGANISM: Artificial sequence
<220> FEATURE:
<223> OTHER INFORMATION: derived from IL-17

<400> SEQUENCE: 8

```
Ser Met Ser Arg
1
```

<210> SEQ ID NO 9
<211> LENGTH: 125
<212> TYPE: PRT
<213> ORGANISM: Artificial sequence
<220> FEATURE:
<223> OTHER INFORMATION: CDRs derived from Rattus

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asn Met Ala Trp Val Arg Gln Ala Pro Gly Lys Gly Leu Glu Trp Val
        35                  40                  45

Ala Thr Ile Thr Tyr Glu Gly Arg Asn Thr Tyr Tyr Arg Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Pro Gln Tyr Tyr Glu Gly Ser Ile Tyr Arg Leu Trp Phe
            100                 105                 110

Ala His Trp Gly Gln Gly Thr Leu Val Thr Val Ser Ser
        115                 120                 125
```

<210> SEQ ID NO 10
<211> LENGTH: 4
<212> TYPE: PRT
<213> ORGANISM: Artificial seqence
<220> FEATURE:
<223> OTHER INFORMATION: derived from IL-17

<400> SEQUENCE: 10

Cys Arg Asn Leu
1

<210> SEQ ID NO 11
<211> LENGTH: 214
<212> TYPE: PRT
<213> ORGANISM: Artificial sequence
<220> FEATURE:
<223> OTHER INFORMATION: derive from at least from Rattus

<400> SEQUENCE: 11

Ala Ile Gln Leu Thr Gln Ser Pro Ser Ser Leu Ser Ala Ser Val Gly
1               5                   10                  15

Asp Arg Val Thr Ile Thr Cys Arg Ala Asp Glu Ser Val Thr Thr Leu
            20                  25                  30

Met His Trp Tyr Gln Gln Lys Pro Gly Lys Ala Pro Lys Leu Leu Ile
        35                  40                  45

Tyr Leu Val Ser Asn Arg Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Trp Ser Asp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 10
<212> TYPE: PRT
<213> ORGANISM: Artificial sequence
<220> FEATURE:
<223> OTHER INFORMATION: derived from IL-17

<400> SEQUENCE: 12

Lys Glu Asp Ile Ser Met Asn Ser Val Pro
1               5                   10

<210> SEQ ID NO 13
<211> LENGTH: 4
<212> TYPE: PRT
<213> ORGANISM: Artificial sequence
<220> FEATURE:
<223> OTHER INFORMATION: derived from IL-17

<400> SEQUENCE: 13

Val Thr Pro Val
1

<210> SEQ ID NO 14
<211> LENGTH: 705
<212> TYPE: DNA
<213> ORGANISM: Artificial sequence
<220> FEATURE:
<223> OTHER INFORMATION: CDRs encoded derived from Rattus

<400> SEQUENCE: 14

```
atgtcagttc ccacacaggt gctgggcctg cttctgttgt ggctcaccga tgctaggtgt      60
gccatccagc tgacccagag cccttcctct ctcagcgcca gtgtcggaga cagagtgact     120
attacctgca gggctgacga aagcgtgacc acattgatgc actggtacca acagaagcct    180
ggcaaagccc ccaagctcct gatctatctg gtttccaatc gggagtctgg agtccccagc    240
aggttcagcg gcagtgggtc tggaactgac tttaccctga caatctcctc actccagccc    300
gaagatttcg ccacctacta ttgccagcag acttggagcg acccttggac atttggacag    360
ggcacaaaag tggagatcaa gcgtacggta gcggccccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gttag                    705
```

<210> SEQ ID NO 15
<211> LENGTH: 452
<212> TYPE: PRT
<213> ORGANISM: Artificial sequence
<220> FEATURE:
<223> OTHER INFORMATION: derived from at least Rattus

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asn Met Ala Trp Val Arg Gln Ala Pro Gly Lys Gly Leu Glu Trp Val
        35                  40                  45

Ala Thr Ile Thr Tyr Glu Gly Arg Asn Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Pro Gln Tyr Tyr Glu Gly Ser Ile Tyr Arg Leu Trp Phe
            100                 105                 110

```
Ala His Trp Gly Gln Gly Thr Leu Val Thr Val Ser Ala Ser Thr
        115                 120                 125

Lys Gly Pro Ser Val Phe Pro Leu Ala Pro Cys Ser Arg Ser Thr
130                 135                 140

Ser Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                    165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val Glu
        210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
                    295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 16

<400> SEQUENCE: 16

000

<210> SEQ ID NO 17

<400> SEQUENCE: 17

000
```

<210> SEQ ID NO 18
<211> LENGTH: 2020
<212> TYPE: DNA
<213> ORGANISM: Artificial sequence
<220> FEATURE:
<223> OTHER INFORMATION: CDRs encoded derived from Rattus

<400> SEQUENCE: 18

| | | | | | |
|---|---|---|---|---|---|
| atggaatggt | cctgggtctt | cctgttttc | ctttctgtca | caaccggggt | gcacagcgag | 60 |
| gttcagctcg | ttgaatccgg | aggcggactc | gtgcagcctg | ggggctcctt | gcggctgagc | 120 |
| tgcgctgcca | gtggcttcac | tttcagcgat | tacaatatgg | cctgggtgcg | ccaggcccca | 180 |
| ggcaagggtc | tggagtgggt | ggccacaatt | acctatgagg | cagaaacac | ttattaccgg | 240 |
| gattcagtga | aagggcgatt | taccatcagc | agggataatg | caaagaacag | tctgtacctg | 300 |
| cagatgaact | ctctgagagc | tgaggacacc | gctgtctact | attgtgcaag | cccaccccag | 360 |
| tactatgagg | gctcaatcta | cagattgtgg | tttgcccatt | ggggccaggg | aacactggtg | 420 |
| accgtctcga | gcgcttctac | aaagggccca | tccgtcttcc | ccctggcgcc | ctgctccagg | 480 |
| agcacctccg | agagcacagc | cgccctgggc | tgcctggtca | aggactactt | ccccgaaccg | 540 |
| gtgacggtgt | cgtggaactc | aggcgccctg | accagcggcg | tgcacacctt | cccggctgtc | 600 |
| ctacagtcct | caggactcta | ctccctcagc | agcgtggtga | ccgtgccctc | agcagcttg | 660 |
| ggcacgaaga | cctacacctg | caacgtagat | cacaagccca | gcaacaccaa | ggtggacaag | 720 |
| agagttggtg | agaggccagc | acaggggaggg | agggtgtctg | ctggaagcca | ggctcagccc | 780 |
| tcctgcctgg | acgcaccccg | gctgtgcagc | cccagcccag | ggcagcaagg | catgccccat | 840 |
| ctgtctcctc | acccggaggc | ctctgaccac | cccactcatg | cccagggaga | gggtcttctg | 900 |
| gatttttcca | ccaggctccg | ggcagccaca | ggctggatgc | cctaccccca | ggccctgcgc | 960 |
| atacaggggc | aggtgctgcg | ctcagacctg | ccaagagcca | tatccgggag | gaccctgccc | 1020 |
| ctgacctaag | cccacccaa | aggccaaact | ctccactccc | tcagctcaga | caccttctct | 1080 |
| cctcccagat | ctgagtaact | cccaatcttc | tctctgcaga | gtccaaatat | ggtccccat | 1140 |
| gcccaccatg | cccaggtaag | ccaacccagg | cctcgccctc | cagctcaagg | cgggacaggt | 1200 |
| gccctagagt | agcctgcatc | cagggacagg | cccagccgg | gtgctgacgc | atccacctcc | 1260 |
| atctcttcct | cagcacctga | gttcctgggg | ggaccatcag | tcttcctgtt | cccccaaaa | 1320 |
| cccaaggaca | ctctcatgat | ctcccggacc | cctgaggtca | cgtgcgtggt | ggtggacgtg | 1380 |
| agccaggaag | accccgaggt | ccagttcaac | tggtacgtgg | atggcgtgga | ggtgcataat | 1440 |
| gccaagacaa | agccgcggga | ggagcagttc | aacagcacgt | accgtgtggt | cagcgtcctc | 1500 |
| accgtcctgc | accaggactg | gctgaacggc | aaggagtaca | agtgcaaggt | ctccaacaaa | 1560 |
| ggcctcccgt | cctccatcga | gaaaaccatc | tccaaagcca | aggtgggac | ccacggggtg | 1620 |
| cgagggccac | atggacagag | gtcagctcgg | cccacccctct | gccctgggag | tgaccgctgt | 1680 |
| gccaacctct | gtccctacag | ggcagccccg | agagccacag | gtgtacaccc | tgcccccatc | 1740 |
| ccaggaggag | atgaccaaga | accaggtcag | cctgacctgc | ctggtcaaag | gcttctaccc | 1800 |
| cagcgacatc | gccgtggagt | gggagagcaa | tgggcagccg | gagaacaact | acaagaccac | 1860 |
| gcctcccgtg | ctggactccg | acggctcctt | cttcctctac | agcaggctaa | ccgtggacaa | 1920 |
| gagcaggtgg | caggaggga | atgtcttctc | atgctccgtg | atgcatgagg | ctctgcacaa | 1980 |
| ccactacaca | cagaagagcc | tctccctgtc | tctgggtaaa | | | 2020 |

<210> SEQ ID NO 19
<211> LENGTH: 286
<212> TYPE: PRT
<213> ORGANISM: Artificial sequence
<220> FEATURE:
<223> OTHER INFORMATION: Recombinant IL-17A/F heterodimer was produced by linking IL-17A and IL-17F using a GS linker.

<400> SEQUENCE: 19

Met Gly Ile Thr Ile Pro Arg Asn Pro Gly Cys Pro Asn Ser Glu Asp
1               5                   10                  15

Lys Asn Phe Pro Arg Thr Val Met Val Asn Leu Asn Ile His Asn Arg
            20                  25                  30

Asn Thr Asn Thr Asn Pro Lys Arg Ser Ser Asp Tyr Tyr Asn Arg Ser
        35                  40                  45

Thr Ser Pro Trp Asn Leu His Arg Asn Glu Asp Pro Glu Arg Tyr Pro
    50                  55                  60

Ser Val Ile Trp Glu Ala Lys Cys Arg His Leu Gly Cys Ile Asn Ala
65                  70                  75                  80

Asp Gly Asn Val Asp Tyr His Met Asn Ser Val Pro Ile Gln Gln Glu
                85                  90                  95

Ile Leu Val Leu Arg Arg Glu Pro Pro His Cys Pro Asn Ser Phe Arg
            100                 105                 110

Leu Glu Lys Ile Leu Val Ser Val Gly Cys Thr Cys Val Thr Pro Ile
        115                 120                 125

Val His His Val Ala Gly Gly Gly Ser Gly Gly Gly Ser Gly
    130                 135                 140

Gly Gly Ser Gly Gly Gly Ser Arg Lys Ile Pro Lys Val Gly
145                 150                 155                 160

His Thr Phe Phe Gln Lys Pro Glu Ser Cys Pro Pro Val Pro Gly Gly
                165                 170                 175

Ser Met Lys Leu Asp Ile Gly Ile Ile Asn Glu Asn Gln Arg Val Ser
            180                 185                 190

Met Ser Arg Asn Ile Glu Ser Arg Ser Thr Ser Pro Trp Asn Tyr Thr
        195                 200                 205

Val Thr Trp Asp Pro Asn Arg Tyr Pro Ser Glu Val Val Gln Ala Gln
    210                 215                 220

Cys Arg Asn Leu Gly Cys Ile Asn Ala Gln Gly Lys Glu Asp Ile Ser
225                 230                 235                 240

Met Asn Ser Val Pro Ile Gln Gln Glu Thr Leu Val Val Arg Arg Lys
                245                 250                 255

His Gln Gly Cys Ser Val Ser Phe Gln Leu Glu Lys Val Leu Val Thr
            260                 265                 270

Val Gly Cys Thr Cys Val Thr Pro Val Ile His His Val Gln
        275                 280                 285

<210> SEQ ID NO 20
<211> LENGTH: 134
<212> TYPE: PRT
<213> ORGANISM: Artificial sequence
<220> FEATURE:
<223> OTHER INFORMATION: Recombinant cynomolgus IL-17F

<400> SEQUENCE: 20

Met Arg Lys Ile Pro Lys Val Gly His Thr Phe Phe Gln Lys Pro Glu
1               5                   10                  15

Ser Cys Pro Pro Val Pro Glu Gly Ser Met Lys Leu Asp Thr Gly Ile

```
                    20                  25                  30

Ile Asn Glu Asn Gln Arg Val Ser Met Ser Arg Asn Ile Glu Ser Arg
                35                  40                  45

Ser Thr Ser Pro Trp Asn Tyr Thr Val Thr Trp Asp Pro Asn Arg Tyr
 50                  55                  60

Pro Ser Glu Val Val Gln Ala Gln Cys Lys His Leu Gly Cys Ile Asn
 65                  70                  75                  80

Ala Gln Gly Lys Glu Asp Ile Ser Met Asn Ser Val Pro Ile Gln Gln
                85                  90                  95

Glu Thr Leu Val Leu Arg Arg Lys His Gln Gly Cys Ser Val Ser Phe
                100                 105                 110

Gln Leu Glu Lys Val Leu Val Thr Val Gly Cys Thr Cys Val Thr Pro
                115                 120                 125

Val Ile His His Val Gln
                130

<210> SEQ ID NO 21
<211> LENGTH: 132
<212> TYPE: PRT
<213> ORGANISM: Homo sapiens

<400> SEQUENCE: 21

Gly Ile Thr Ile Pro Arg Asn Pro Gly Cys Pro Asn Ser Glu Asp Lys
 1               5                  10                  15

Asn Phe Pro Arg Thr Val Met Val Asn Leu Asn Ile His Asn Arg Asn
                20                  25                  30

Thr Asn Thr Asn Pro Lys Arg Ser Ser Asp Tyr Tyr Asn Arg Ser Thr
                35                  40                  45

Ser Pro Trp Asn Leu His Arg Asn Glu Asp Pro Glu Arg Tyr Pro Ser
 50                  55                  60

Val Ile Trp Glu Ala Lys Cys Arg His Leu Gly Cys Ile Asn Ala Asp
 65                  70                  75                  80

Gly Asn Val Asp Tyr His Met Asn Ser Val Pro Ile Gln Gln Glu Ile
                85                  90                  95

Leu Val Leu Arg Arg Glu Pro Pro His Cys Pro Asn Ser Phe Arg Leu
                100                 105                 110

Glu Lys Ile Leu Val Ser Val Gly Cys Thr Cys Val Thr Pro Ile Val
                115                 120                 125

His His Val Ala
                130

<210> SEQ ID NO 22
<211> LENGTH: 133
<212> TYPE: PRT
<213> ORGANISM: Homo sapiens

<400> SEQUENCE: 22

Arg Lys Ile Pro Lys Val Gly His Thr Phe Phe Gln Lys Pro Glu Ser
 1               5                  10                  15

Cys Pro Pro Val Pro Gly Gly Ser Met Lys Leu Asp Ile Gly Ile Ile
                20                  25                  30

Asn Glu Asn Gln Arg Val Ser Met Ser Arg Asn Ile Glu Ser Arg Ser
                35                  40                  45

Thr Ser Pro Trp Asn Tyr Thr Val Thr Trp Asp Pro Asn Arg Tyr Pro
 50                  55                  60

Ser Glu Val Val Gln Ala Gln Cys Arg Asn Leu Gly Cys Ile Asn Ala
```

```
                    65                  70                  75                  80

Gln Gly Lys Glu Asp Ile Ser Met Asn Ser Val Pro Ile Gln Gln Glu
                85                  90                  95

Thr Leu Val Val Arg Arg Lys His Gln Gly Cys Ser Val Ser Phe Gln
            100                 105                 110

Leu Glu Lys Val Leu Val Thr Val Gly Cys Thr Cys Val Thr Pro Val
        115                 120                 125

Ile His His Val Gln
    130

<210> SEQ ID NO 23
<211> LENGTH: 445
<212> TYPE: PRT
<213> ORGANISM: Artificial sequence
<220> FEATURE:
<223> OTHER INFORMATION: derived from at least Rattus and Murine origin

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asn Met Ala Trp Val Arg Gln Ala Pro Gly Lys Gly Leu Glu Trp Val
        35                  40                  45

Ala Thr Ile Thr Tyr Glu Gly Arg Asn Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Pro Gln Tyr Tyr Glu Gly Ser Ile Tyr Arg Leu Trp Phe
            100                 105                 110

Ala His Trp Gly Gln Gly Thr Leu Val Thr Val Ser Ser Ala Lys Thr
        115                 120                 125

Thr Pro Pro Ser Val Tyr Pro Leu Ala Pro Gly Ser Ala Ala Gln Thr
    130                 135                 140

Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Pro Ser Ser Thr Trp Pro Ser Glu Thr Val Thr Cys Asn
        195                 200                 205

Val Ala His Pro Ala Ser Ser Thr Lys Val Asp Lys Lys Ile Val Pro
    210                 215                 220

Arg Asp Cys Gly Cys Ala Ala Ala Ile Gln Leu Thr Gln Ser Pro Ser
225                 230                 235                 240

Ser Leu Ser Ala Ser Val Gly Asp Arg Val Thr Ile Thr Cys Arg Ala
                245                 250                 255

Asp Glu Ser Val Thr Thr Leu Met His Trp Tyr Gln Gln Lys Pro Gly
            260                 265                 270

Lys Ala Pro Lys Leu Leu Ile Tyr Leu Val Ser Asn Arg Glu Ser Gly
        275                 280                 285

Val Pro Ser Arg Phe Ser Gly Ser Gly Ser Gly Thr Asp Phe Thr Leu
```

```
                290                 295                 300
Thr Ile Ser Ser Leu Gln Pro Glu Asp Phe Ala Thr Tyr Tyr Cys Gln
305                 310                 315                 320

Gln Thr Trp Ser Asp Pro Trp Thr Phe Gly Gln Gly Thr Lys Val Glu
                325                 330                 335

Ile Lys Arg Thr Asp Ala Ala Pro Thr Val Ser Ile Phe Pro Pro Ser
                340                 345                 350

Ser Glu Gln Leu Thr Ser Gly Gly Ala Ser Val Val Cys Phe Leu Asn
                355                 360                 365

Asn Phe Tyr Pro Lys Asp Ile Asn Val Lys Trp Lys Ile Asp Gly Ser
                370                 375                 380

Glu Arg Gln Asn Gly Val Leu Asn Ser Trp Thr Asp Gln Asp Ser Lys
385                 390                 395                 400

Asp Ser Thr Tyr Ser Met Ser Ser Thr Leu Thr Leu Thr Lys Asp Glu
                405                 410                 415

Tyr Glu Arg His Asn Ser Tyr Thr Cys Glu Ala Thr His Lys Thr Ser
                420                 425                 430

Thr Ser Pro Ile Val Lys Ser Phe Asn Arg Asn Glu Cys
                435                 440                 445

<210> SEQ ID NO 24
<211> LENGTH: 107
<212> TYPE: PRT
<213> ORGANISM: Artificial sequence
<220> FEATURE:
<223> OTHER INFORMATION: derived from at least Rattus and Murine

<400> SEQUENCE: 24

Ala Ile Gln Leu Thr Gln Ser Pro Ser Ser Leu Ser Ala Ser Val Gly
1               5                   10                  15

Asp Arg Val Thr Ile Thr Cys Arg Ala Asp Glu Ser Val Thr Thr Leu
                20                  25                  30

Met His Trp Tyr Gln Gln Lys Pro Gly Lys Ala Pro Lys Leu Leu Ile
                35                  40                  45

Tyr Leu Val Ser Asn Arg Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Trp Ser Asp Pro Trp
                85                  90                  95

Thr Phe Gly Gln Gly Thr Lys Val Glu Ile Lys
                100                 105
```